United States Patent
Lv et al.

(10) Patent No.: US 11,459,327 B1
(45) Date of Patent: Oct. 4, 2022

(54) CYCLOALKYL AND HETERO-CYCLOALKYL INHIBITORS, PREPARATION METHODS THEREFOR, AND USE THEREOF

(71) Applicants: Suzhou Zelgen Biopharmaceuticals Co., Ltd., Jiangsu (CN); Shanghai Zelgen Pharma.Tech Co., Ltd., Shanghai (CN)

(72) Inventors: Binhua Lv, Shanghai (CN); Dawei Cui, Shanghai (CN); Lianjun Liu, Shanghai (CN); Tao Han, Shanghai (CN); Runqing Wang, Shanghai (CN); Peizhong Ni, Shanghai (CN); Zelin Sheng, Shanghai (CN)

(73) Assignees: Suzhou Zelgen Biopharmaceuticals Co., Ltd., Jiangsu (CN); Shanghai Zelgen Pharma.Tech Co., Ltd., Shanghai (CN)

( * ) Notice: Subject to any disclaimer, the term of this patent is extended or adjusted under 35 U.S.C. 154(b) by 2 days.

(21) Appl. No.: 17/303,762

(22) Filed: Jun. 7, 2021

Related U.S. Application Data

(63) Continuation of application No. PCT/CN2020/138142, filed on Dec. 21, 2020.

(30) Foreign Application Priority Data

| Oct. 23, 2019 | (CN) | ......................... 201911013680.X |
| Dec. 20, 2019 | (CN) | ......................... 201911330659.2 |

(51) Int. Cl.
C07D 471/04 (2006.01)

(52) U.S. Cl.
CPC .................................. *C07D 471/04* (2013.01)

(58) Field of Classification Search
CPC .................................................. C07D 471/04
USPC .................................................. 514/210.21
See application file for complete search history.

(56) References Cited

U.S. PATENT DOCUMENTS

| 10,125,134 B2 * | 11/2018 | Blake ....................... A61P 43/00 |
| 2018/0072723 A1 | 3/2018 | Blake et al. |
| 2019/0144444 A1 | 5/2019 | Blake et al. |

FOREIGN PATENT DOCUMENTS

| CN | 109843856 A | 6/2019 |
| CN | 112174950 A | 1/2021 |
| WO | 2017201161 | * 11/2017 |
| WO | 2019099524 A1 | 5/2019 |
| WO | 2019150305 | * 8/2019 |
| WO | 2020055756 | * 3/2020 |
| WO | 2020055756 A1 | 3/2020 |
| WO | 2020118066 A1 | 6/2020 |
| WO | 2020238791 A1 | 12/2020 |

OTHER PUBLICATIONS

Lu et al., ACS Catalysis (2019), 9(8), 7188-7196.*
International Search Report (Form PCT/ISA/210) for International Patent Application No. PCT/CN2020/138142, issued from the International Searching Authority, dated Mar. 22, 2021, with English-language translation, 6 pages.
Written Opinion of the International Searching Authority (Form PCT/ISA/237) for International Patent Application No. PCT/CN2020/138142, issued from the International Searching Authority, dated Mar. 22, 2021, 6 pages.
Fell, Jay Bradford et al., "Discovery of tetrahydropyridopyrimidines as irreversible covalent inhibitors of KRAS-G12C with in vivo activity," ACS Medical Chemistry Letters, vol. 9, issue 12, pp. 1230-1234.
Fell, Jay Bradford et al., "Identification of the clinical development candidate MRTX849, a covalent KRASG12C inhibitor for the treatment of cancer," Journal of Medical Chemistry, vol. 63, Issue 13, 2020; pp. 6679-6693.

* cited by examiner

*Primary Examiner* — Niloofar Rahmani
(74) *Attorney, Agent, or Firm* — Ice Miller LLP

(57) ABSTRACT

Cycloalkyl and hetero-cycloalkyl inhibitors, preparation methods therefor, and the use thereof are described. Compounds of the present invention have a structure represented by formula (I). Further disclosed are preparation methods for said compounds, and the use of said compounds as $KRAS^{G12C}$ inhibitors. The compounds have an excellent ability to selectively inhibit $KRAS^{G12C}$, improved pharmacodynamic and pharmacokinetic performance, and reduced toxic side effects.

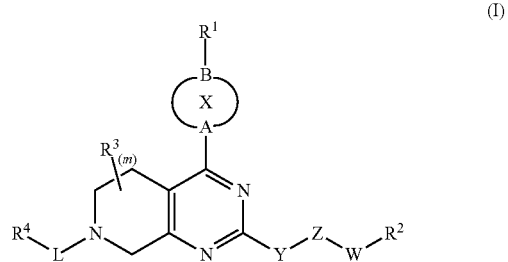

6 Claims, 2 Drawing Sheets

CYCLOALKYL AND HETERO-CYCLOALKYL INHIBITORS, PREPARATION METHODS THEREFOR, AND USE THEREOF

CROSS-REFERENCE TO RELATED APPLICATIONS

This application is continuation of International Application No. PCT/CN2020/138142 filed Dec. 21, 2020, which was published in the Chinese language Apr. 29, 2021, under International Publication No. WO 2021/078312 A1, which claims priority to Chinese Patent Application Nos 201911013680.X filed Oct. 23, 2019, and 201911330659.2, filed Dec. 20, 2019, the disclosures of which are incorporated herein by reference in their entireties.

TECHNICAL FIELD

The invention belongs to the field of pharmaceutical, and more particularly to cycloalkyl and hetero-cycloalkyl inhibitors, preparation method therefor, and use thereof.

BACKGROUND OF THE INVENTION

Lung cancer is one of the important causes of human cancer death. According to cell type, lung cancer can be divided into small cell lung cancer (SCLC) and non-small cell lung cancer (NSCLC), of which NSCLC accounts for 85% of all lung cancer patients. According to statistics, the global NSCLC market was approximately $20.9 billion in 2016, of which the US market occupied half, followed by Japan, Germany and China. Based on current trends, the non-small cell lung cancer market continues to grow and is expected to reach $54 billion worldwide by 2023 (Nature, 2018; 553(7689):446-454).

At present, the main therapeutic drugs for NSCLC include chemotherapy drugs, molecular targeting drugs, and tumor immunotherapy, etc. Among them, chemotherapy drugs mainly include gemcitabine, paclitaxel, and platinum drugs, but these drugs generally have poor selectivity and high toxicity, leading to relatively strong toxic and side effects. In recent years, the molecular targeted drugs have gradually become a research hotspot due to their obvious advantages such as high selectivity, relatively small toxic and side effects, and the ability to achieve precision therapy. Existing molecular targeting agents for NSCLC include EGFR inhibitors (such as Afatinib, Gefitinib, Erlotinib, Lapatinib, Dacomitinib, Icotinib, Pyrotinib, Rociletinib, Osimertinib, etc.), ALK inhibitors (such as Ceritinib, Alectinib, Brigatinib, Lorlatinib, ocatinib, etc.), and VEGFR inhibitors (Sorafenib, Regorafenib, Cabozantinib, Sunitinib, Donafenib, etc.) (Current Medicinal Chemistry, 2019, 26, 1-39).

In the patients with lung cancer, KRAS mutation is often detected, accounting for about 32% of all carcinogenic mutations. The $KRAS^{G12C}$ mutation accounted for 44% of all carcinogenic mutations in NSCLC. So far, there is still no drug for $KRAS^{G12C}$ mutations on the market.

Since $KRAS^{G12C}$ target protein is related to a variety of diseases in pathology, novel $KRAS^{G12C}$ inhibitors are currently needed for clinical treatment. Highly selective and active $KRAS^{G12C}$ inhibitors have a more urgent clinical need for more effective treatment of $KRAS^{G12C}$ mutation-induced cancers and other diseases, as well as the potential to reduce off-target effects.

SUMMARY OF THE INVENTION

The object of the present invention is to provide a new class of compounds with selective inhibition of $KRAS^{G12C}$ and/or better pharmacodynamic properties and the use thereof.

In the first aspect of the invention, cycloalkyl and hetero-cycloalkyl compounds of formula (I), stereoisomer, tautomer, crystal form, pharmaceutically acceptable salt, hydrate, solvate or prodrug thereof are provided:

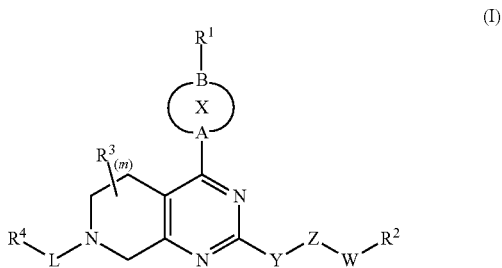

(I)

wherein:

A and B are the same or different, independently selected from CH or N;

X is selected from 4-14 membered saturated or unsaturated cycloalkyl or heterocyclyl, $C_6$-$C_{14}$ aryl or 5-14 membered heteroaryl, wherein said saturated or unsaturated cycloalkyl or heterocyclyl, aryl or heteroaryl may optionally be substituted by one or more $R^8$;

Y is selected from the group consisting of bond, O, S, NH, $NR^5$, $CR^5R^6$, CONH, $CONR^5$, $SO_2NH$, $SO_2NR^5$, NHCO, $NR^5CO$, $NHSO_2$, $NR^5SO_2$;

Z is selected from the group consisting of bond, $C_1$-$C_{18}$ alkylene, deuterated $C_1$-$C_{18}$ alkylene, $C_1$-$C_{18}$ haloalkylene, $C_3$-$C_{20}$ cycloalkylene, $C_4$-$C_{20}$ heterocyclylene, $C_1$-$C_{18}$ alkyleneoxy, deuterated $C_1$-$C_{18}$ alkyleneoxy, $C_1$-$C_{18}$ haloalkyleneoxy;

W is selected from the group consisting of bond, O, NH, $NR^5$, CONH, $CONR^5$, $SO_2NH$, $SO_2NR^5$, NHCO, $NHSO_2$, NHCONH, $NR^5CONH$, $NHCONR^5$, $NR^5CONR^6$, $NHSO_2NH$, $NR^5SO_2NH$, $NHSO_2NR^5$ and $NR^5SO_2NR^6$;

$R^1$ is selected from the group consisting of —C(O)C($R^4$)═C($R^B$)$_p$ and —S(O)$_2$C($R^4$)═C($R^B$)$_p$;

$R^2$ is selected from the group consisting of —(CH$_2$)$_n R^7$, —(CH$_2$)$_n$O(CH$_2$)$_q R^7$, —(CH$_2$)$_n$SR$^7$, —(CH$_2$)$_n$COR$^7$, —(CH$_2$)$_n$C(O)OR$^7$, —(CH$_2$)$_n$S(O)$_q R^7$, —(CH$_2$)$_n$NR$^5 R^7$, —(CH$_2$)$_n$C(O)NR$^5 R^7$, —(CH$_2$)$_n$NR$^5$C(O)R$^7$, —(CH$_2$)$_n$NR$^5$C(O)NR$^5 R^7$, —(CH$_2$)$_n$S(O)$_q$NR$^5 R^7$, —(CH$_2$)$_n$NR$^5$S(O)$_q R^7$ and —(CH$_2$)$_n$NR$^5$S(O)$_q$NR$^5 R^7$, wherein H in CH$_2$ can be substituted;

$R^3$ is independently selected from the group consisting of hydrogen, deuterium, oxygen, $C_1$-$C_3$ alkyl and $C_1$-$C_3$ haloalkyl;

L is selected from the group consisting of bond, —C(O)— and $C_1$-$C_3$ alkylene;

$R^4$ is selected from the substituted or unsubstituted group consisting of hydrogen, deuterium, $C_1$-$C_{18}$ alkyl, deuterated $C_1$-$C_{18}$ alkyl, $C_1$-$C_{18}$ haloalkyl, $C_3$-$C_{20}$ cycloalkyl, $C_1$-$C_{18}$ alkoxy, deuterated $C_1$-$C_{18}$ alkoxy, $C_1$-$C_{18}$ haloalkoxy, amino, hydroxy, 4-20 membered heterocyclyl, $C_6$-$C_{14}$ aryl and 5-14 membered heteroaryl;

$R^5$ and $R^6$ are the same or different, and each independently selected from substituted or unsubstituted group consisting of hydrogen, deuterium, $C_1$-$C_{18}$ alkyl, deuterated $C_1$-$C_{18}$ alkyl, $C_1$-$C_{18}$ haloalkyl, $C_3$-$C_{20}$ cycloalkyl, $C_1$-$C_{18}$ alkoxy, deuterated $C_1$-$C_{18}$ alkoxy, $C_1$-$C_{18}$ haloalkoxy, amino, hydroxyl, 4-20 membered heterocyclyl, $C_6$-$C_{14}$ aryl and 5-14 membered heteroaryl;

$R^7$ is selected from substituted or unsubstituted $C_1$-$C_{18}$ alkyl, $C_3$-$C_{20}$ cycloalkyl or 4-20 membered heterocyclyl;

$R^8$ is independently selected from the substituted or unsubstituted group consisting of hydrogen, deuterium, $C_1$-$C_{18}$ alkyl, deuterated $C_1$-$C_{18}$ alkyl, $C_1$-$C_{18}$ haloalkyl, $C_3$-$C_{20}$ cycloalkyl, $C_1$-$C_{18}$ alkoxy, deuterated $C_1$-$C_{18}$ alkoxy, $C_1$-$C_{18}$ haloalkoxy, amino, hydroxyl, 4-20 membered heterocyclyl, $C_6$-$C_{14}$ aryl, 5-14 membered heteroaryl;

wherein, the "substituted" refers to be substituted with one or more groups selected from the group consisting of hydrogen, deuterium, $C_1$-$C_{18}$ alkyl, deuterated $C_1$-$C_{18}$ alkyl, $C_1$-$C_{18}$ haloalkyl, $C_3$-$C_{20}$ cycloalkyl, $C_1$-$C_{18}$ alkoxy, deuterated $C_1$-$C_{18}$ alkoxy, $C_1$-$C_{18}$ haloalkoxy, $C_6$-$C_{14}$ aryl, 5-14 membered heteroaryl, 4-20 membered heterocyclyl, halogen, nitro, hydroxy, cyano, ester, amino, amido, sulfonamido and ureido;

"═" can be a double bond ""═"" or a triple bond ""≡"";

$R^A$ is absent, or is independently selected from hydrogen, deuterium, fluorine, cyano or $C_1$-$C_3$ alkyl;

$R^B$ is independently selected from hydrogen, deuterium, cyano or $C_1$-$C_3$ alkyl;

wherein the "alkyl" can be substituted with one or more substituents selected from the group consisting of deuterium, halogen, cyano, amino, $C_3$-$C_7$ cycloalkyl, 4-7 membered heterocyclyl, $NHR^9$ and $NR^9R^{10}$;

$R^9$ and $R^{10}$ are each independently selected from $C_1$-$C_3$ alkyl;

m is an integer of 0, 1, 2 or 3;

n is an integer of 0, 1, 2, 3, 4 or 5;

p is an integer of 1 or 2;

q is an integer of 0, 1, 2, 3, 4 or 5;

with the proviso that when both A and B are N, and X is 4-14 membered heterocyclyl, Y is selected from the group consisting of bond, O, S, NH and $NR^5$, and $R^5$ is $C_1$-$C_{18}$ alkyl, then Z is substituted or unsubstituted $C_3$-$C_{20}$ cycloalkylene;

or, when both A and B are N, and X is 4-14 membered heterocyclyl, Y is selected from the group consisting of bond, O, S, NH and $NR^5$, W is bond, and $R^5$ is $C_1$-$C_{18}$ alkyl, then $R^7$ is substituted or unsubstituted $C_3$-$C_{20}$ cycloalkyl;

or, when both A and B are N, and X is 4-14 membered heterocyclyl, Y is selected from the group consisting of bond, O, S, NH and $NR^5$, W is selected from the group consisting of NH and $NR^5$, and $R^5$ is $C_1$-$C_{18}$ alkyl, then $R^7$ is substituted or unsubstituted $C_3$-$C_{20}$ cycloalkyl or substituted or unsubstituted 4-20 membered heterocyclyl.

In another preferred embodiment, cycloalkyl and heterocycloalkyl compounds of formula (I), the stereoisomer, tautomer, crystal form, pharmaceutically acceptable salt, hydrate, solvate or prodrug thereof have a structure represented by general formula (II-A) or (II-B):

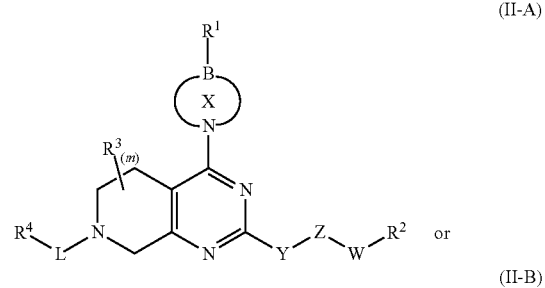
(II-A)

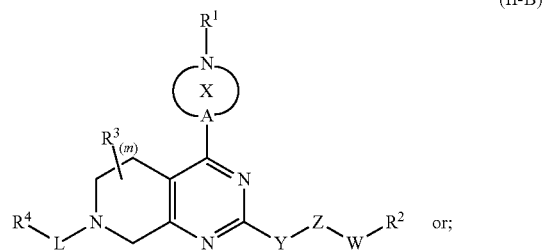
(II-B)

wherein:
$R^1$, $R^2$, $R^3$, $R^4$, A, B, X, Y, Z, L, W and m are as defined above.

In another preferred embodiment, cycloalkyl and heterocycloalkyl compounds of formula (I), the stereoisomer, tautomer, crystal form, pharmaceutically acceptable salt, hydrate, solvate or prodrug have a structure represented by general formula (III):

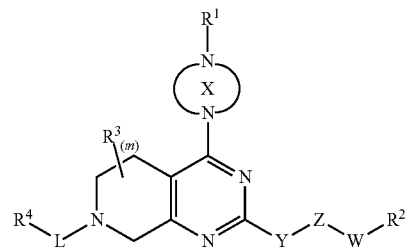
(III)

wherein, $R^1$, $R^2$, $R^3$, $R^4$, X, Y, Z, L, W and m are as defined above.

In another preferred embodiment, cycloalkyl and heterocycloalkyl compounds of formula (I), the stereoisomer, tautomer, crystal form, pharmaceutically acceptable salt, hydrate, solvate or prodrug thereof have a structure represented by general formula (IV):

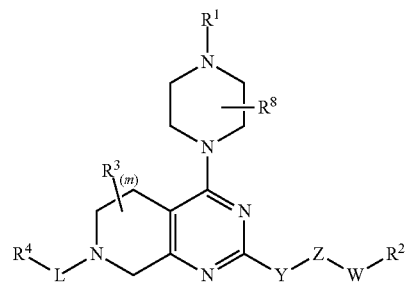
(IV)

wherein:
$R^1$, $R^2$, $R^3$, $R^4$, $R^8$, Y, Z, L, W and m are as defined above.

In another preferred embodiment, cycloalkyl and heterocycloalkyl compounds of formula (I), the stereoisomer, tautomer, crystal form, pharmaceutically acceptable salt, hydrate, solvate or prodrug thereof have a structure represented by general formula (V):

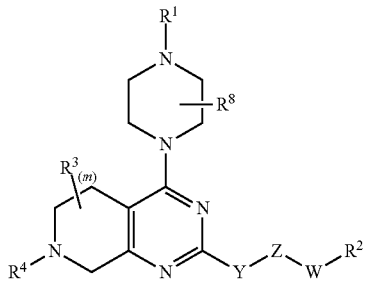

(V)

wherein:
$R^1$, $R^2$, $R^3$, $R^4$, $R^8$, Y, Z, W and m are as defined above.

In another preferred embodiment, cycloalkyl and heterocycloalkyl compounds of formula (I), the stereoisomer, tautomer, crystal form, pharmaceutically acceptable salt, hydrate, solvate or prodrug thereof have a structure represented by general formula (VI):

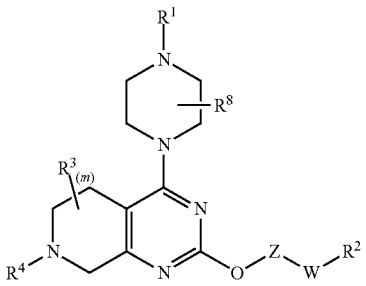

(VI)

wherein:
$R^1$, $R^2$, $R^3$, $R^4$, $R^8$, Z, W and m are as defined above.

In another preferred embodiment, cycloalkyl and heterocycloalkyl compounds of formula (I), the stereoisomer, tautomer, crystal form, pharmaceutically acceptable salt, hydrate, solvate or prodrug thereof have a structure represented by general formula (VII-A) or (VII-B):

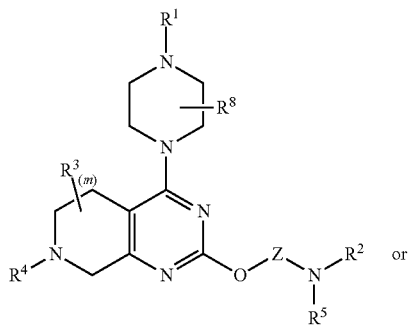

(VII-A)

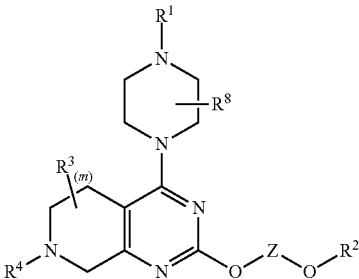

(VII-B)

wherein:
$R^1$, $R^2$, $R^3$, $R^4$, $R^5$, $R^8$, Z and m are as defined above.

In another preferred embodiment, the compound described in the formula I-VI, the stereoisomer, tautomer, crystal form, pharmaceutically acceptable salt, hydrate, solvate or prodrug thereof,
wherein:
Z is bond;
W is bond;
$R^2$ is —$(CH_2)_nR^7$, where H in $CH_2$ can be substituted;
$R^7$ is selected from substituted or unsubstituted $C_3$-$C_{20}$ cycloalkyl or 4-20 membered heterocyclyl; wherein the "substituted" refers to be substituted with one or more groups selected from the group consisting of $C_1$-$C_{18}$ alkyl and deuterated $C_1$-$C_{18}$ alkyl; and the alkyl can be substituted by one or more substituents selected from the group consisting of deuterium, halogen, cyano, amino, $C_3$-$C_7$ cycloalkyl, 4-7 membered heterocyclyl, $NHR^9$ and $NR^9R^{10}$; $R^9$ and $R^{10}$ are each independently $C_1$-$C_3$ alkyl;
n is 1, 2, or 3;
$R^1$, $R^3$, $R^4$, $R^8$ and m are as defined above.

In another preferred embodiment, the compound is shown in the formula VI, and wherein:
Z is bond;
W is bond;
$R^2$ is —$(CH_2)_nR^7$;
$R^7$ is selected from substituted or unsubstituted $C_3$-$C_8$ cycloalkyl; wherein the "substituted" refers to be substituted by one or more groups selected from the group consisting of $C_1$-$C_6$ alkyl, deuterated $C_1$-$C_6$ alkyl; and the alkyl can be substituted by one or more substituents selected from the group consisting of 4-7 membered heterocyclyl, $NHR^9$ and $NR^9R^{10}$; $R^9$ and $R^{10}$ are each independently $C_1$-$C_3$ alkyl;
n is 1 or 2;
$R^1$, $R^3$, $R^4$, $R^8$ and m are as defined above.

In another preferred embodiment, the compound is shown in the formula VI, and wherein:
Z is bond;
W is bond;
$R^2$ is —$(CH_2)_nR^7$;
$R^7$ is substituted or unsubstituted $C_3$-$C_6$ cycloalkyl; wherein the "substituted" refers to be substituted by one or more groups selected from the group consisting of $C_1$-$C_3$ alkyl, deuterated $C_1$-$C_3$ alkyl; and the alkyl can be substituted by one or more substituents selected from the group consisting of 4-7 membered heterocyclyl, $NHR^9$ and $NR^9R^{10}$; $R^9$ and $R^{10}$ are each independently $C_1$-$C_3$ alkyl;
n is 1 or 2;
$R^1$, $R^3$, $R^4$, $R^8$ and m are as defined above.

In another preferred embodiment, the compound described in the formula I-VI, the stereoisomer, tautomer, crystal form, pharmaceutically acceptable salt, hydrate, solvate or prodrug thereof has a structure represented by general formula (VIII):

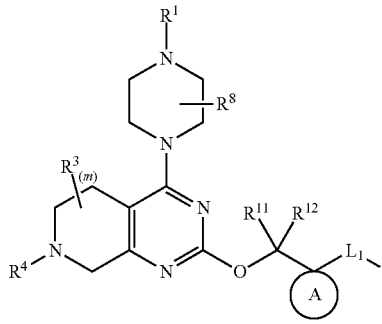

(VIII)

$R^{11}$ and $R^{12}$ are the same or different, and each independently selected from hydrogen, deuterium, $C_1$-$C_{18}$ alkyl, deuterated $C_1$-$C_{18}$ alkyl;

ring A is a substituted or unsubstituted $C_3$-$C_{20}$ cycloalkyl or 4-20 membered heterocyclyl;

$L_1$ is $C_1$-$C_{18}$ alkyl, deuterated $C_1$-$C_{18}$ alkyl;

Q is $C_3$-$C_7$ cycloalkyl, 4-7 membered heterocyclyl, $NHR^9$ or $NR^9R^{10}$; $R^9$ and $R^{10}$ are each independently $C_1$-$C_3$ alkyl.

In another preferred embodiment, the compound described in the formula I-VI, the stereoisomer, tautomer, crystal form, pharmaceutically acceptable salt, hydrate, solvate or prodrug thereof, wherein, Z is $C_1$-$C_{18}$ alkylene $C_3$-$C_{20}$ cycloalkylene;

W is bond;

$R^2$ is —$(CH_2)_nNR^5R^7$; where H in $CH_2$ can be substituted;

n is an integer of 0, 1, 2, 3, 4 or 5;

$R^5$ is selected from the substituted or unsubstituted group consisting of hydrogen, deuterium, $C_1$-$C_{18}$ alkyl, deuterated $C_1$-$C_{18}$ alkyl, $C_1$-$C_{18}$ haloalkyl, $C_3$-$C_{20}$ cycloalkyl, $C_1$-$C_{18}$ alkoxy, deuterated $C_1$-$C_{18}$ alkoxy, $C_1$-$C_{18}$ haloalkoxy, amino, hydroxyl, 4-20 membered heterocyclyl, $C_6$-$C_{14}$ aryl, 5-14 membered heteroaryl;

$R^7$ is selected from substituted or unsubstituted $C_1$-$C_{18}$ alkyl, $C_3$-$C_{20}$ cycloalkyl or 4-20 membered heterocyclyl;

wherein the "alkyl" can be substituted with one or more substituents selected from the group consisting of deuterium, halogen, cyano, amino, $C_3$-$C_7$ cycloalkyl, 4-7 membered heterocyclyl, $NHR^9$ and $NR^9R^{10}$;

$R^9$ and $R^{10}$ are each independently $C_1$-$C_3$ alkyl;

wherein, the "substituted" refers to be substituted by one or more groups selected from the group consisting of hydrogen, deuterium, $C_1$-$C_{18}$ alkyl, deuterated $C_1$-$C_{18}$ alkyl, $C_1$-$C_{18}$ haloalkyl, $C_3$-$C_{20}$ cycloalkyl, $C_1$-$C_{18}$ alkoxy, deuterated $C_1$-$C_{18}$ alkoxy, $C_1$-$C_{18}$ haloalkoxy, $C_6$-$C_{14}$ aryl, 5-14 membered heteroaryl, 4-20 membered heterocyclyl, halogen, nitro, hydroxy, cyano, ester, amino, amido, sulfonamido and ureido.

In another preferred embodiment, the compound is shown in the formula VI, and wherein:

Z is $CH_2C_3$-$C_6$cycloalkylene;

W is bond;

$R^2$ is —$(CH_2)_nR^7$;

$R^7$ is selected from substituted or unsubstituted $C_3$-$C_8$ cycloalkyl; wherein the "substituted" refers to be substituted by one or more groups selected from the group consisting of $C_1$-$C_6$ alkyl, deuterated $C_1$-$C_6$ alkyl; and the alkyl can be substituted by one or more substituents selected from the group consisting of 4-7 membered heterocyclyl, $NHR^9$ and $NR^9R^{10}$; $R^9$ and $R^{10}$ are each independently $C_1$-$C_3$ alkyl;

n is 1 or 2;

$R^1$, $R^3$, $R^4$, $R^8$ and m are as defined above.

In another preferred embodiment, the compound is shown in the formula VI, and wherein:

Z is $CH_2C_3$-$C_6$cycloalkylene;

W is bond;

$R^2$ is —$(CH_2)_nR^7$;

$R^7$ is substituted or unsubstituted $C_3$-$C_6$ cycloalkyl; wherein the "substituted" refers to be substituted by one or more groups selected from the group consisting of $C_1$-$C_3$ alkyl, deuterated $C_1$-$C_3$ alkyl; and the alkyl can be substituted by one or more substituents selected from the group consisting of 4-7 membered heterocyclyl, $NHR^9$ and $NR^9R^{10}$; $R^9$ and $R^{10}$ are each independently $C_1$-$C_3$ alkyl;

n is 1 or 2;

$R^1$, $R^3$, $R^4$, $R^8$ and m are as defined above.

In another preferred embodiment, $R^1$, $R^2$, $R^3$, $R^4$, $R^{11}$, $R^{12}$, A, B, L, $L_1$, X, Y, Z, W, Q, ring A and m in formula (I) are the specific groups corresponding to each specific compound in the examples.

In another preferred embodiment, the cycloalkyl and heterocycloalkyl compounds of formula (I), the stereoisomer, tautomer, crystal form, pharmaceutically acceptable salt, hydrate, solvate or prodrug thereof, and the compounds are selected from the group consisting of:

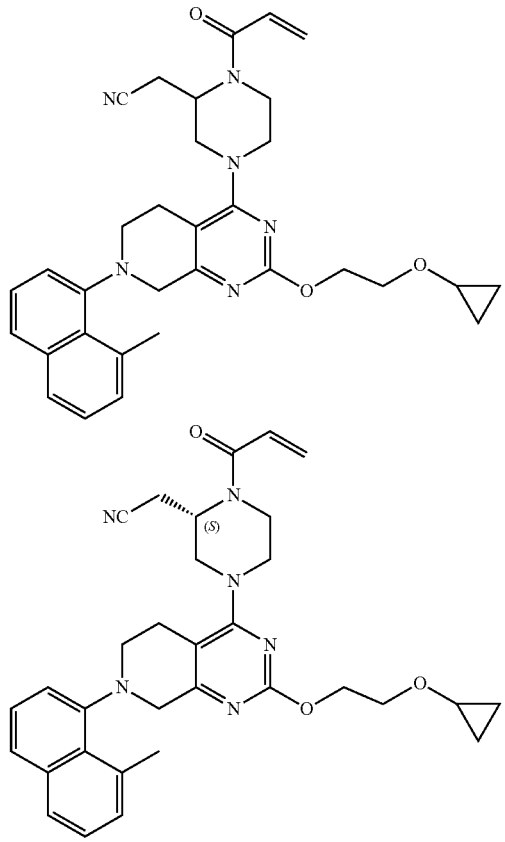

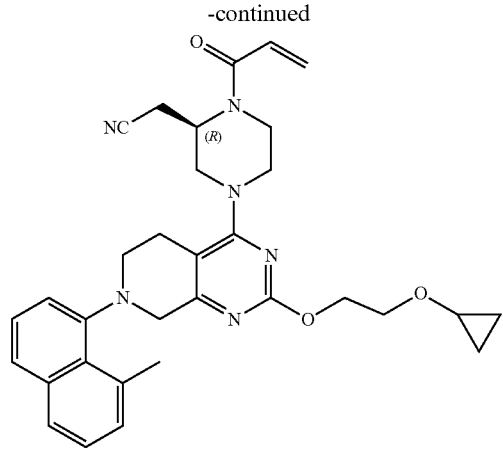
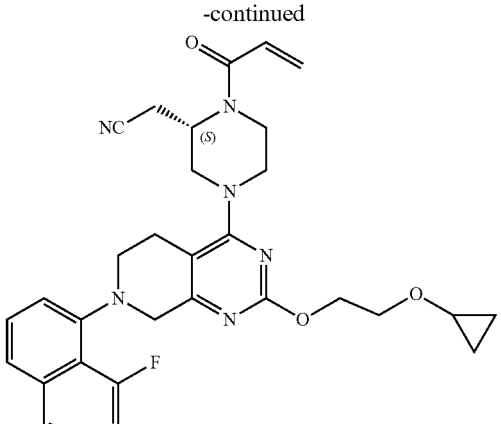
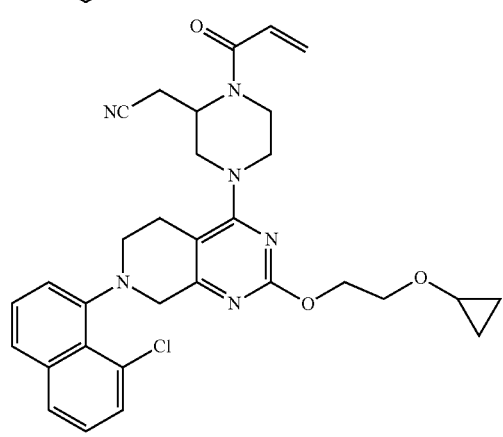
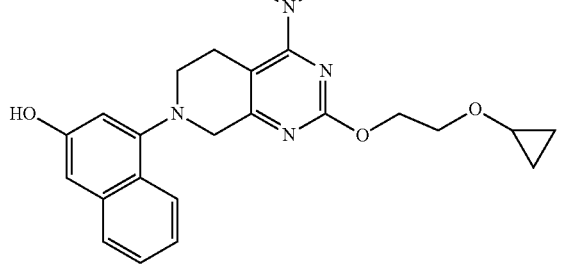
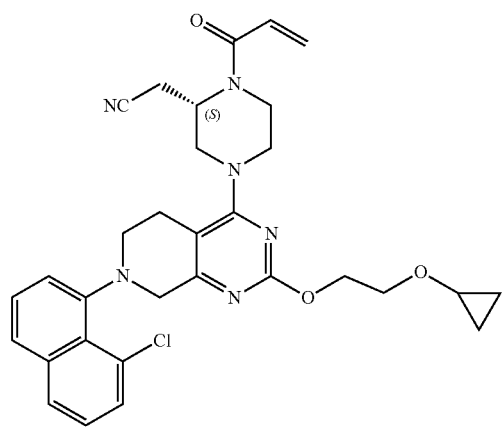
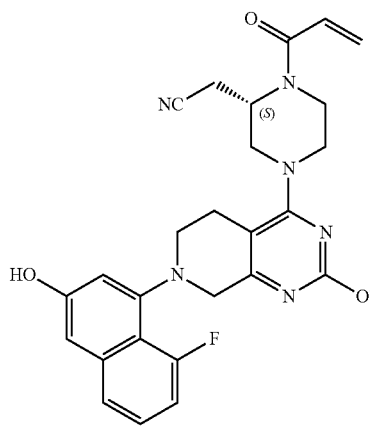
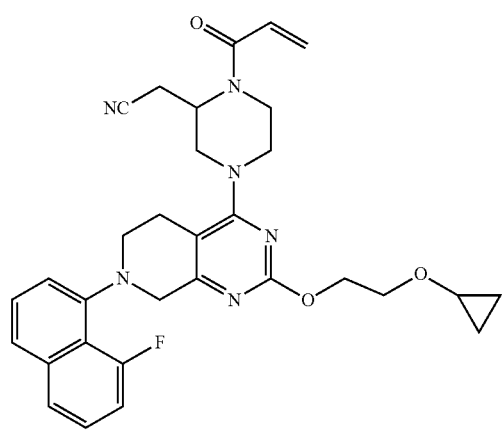
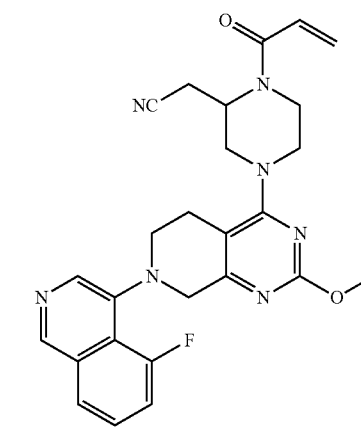

-continued
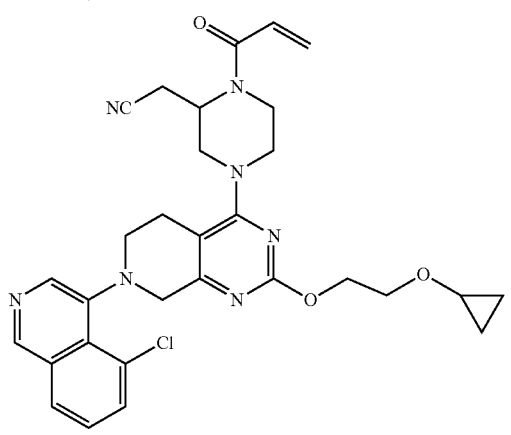
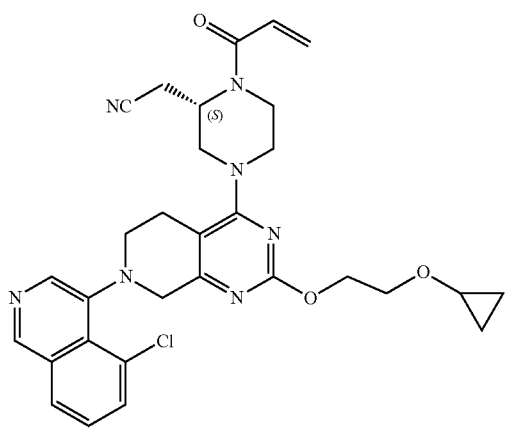
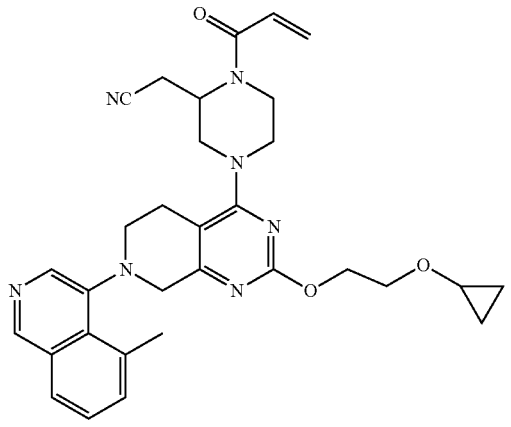
-continued
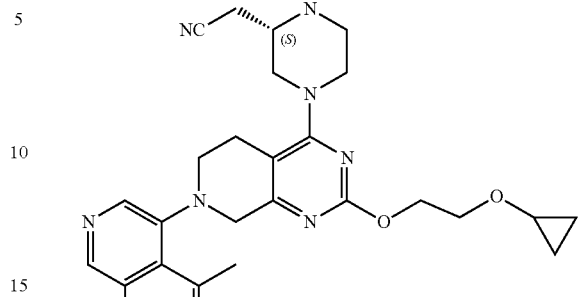
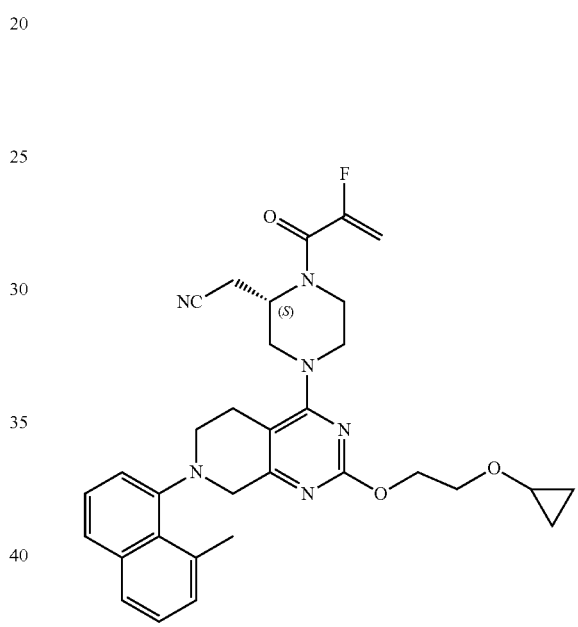
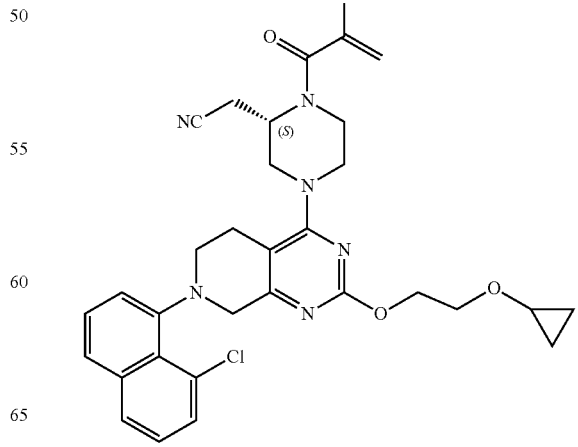

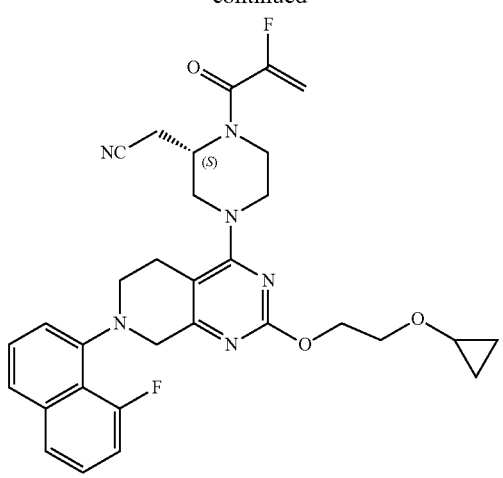
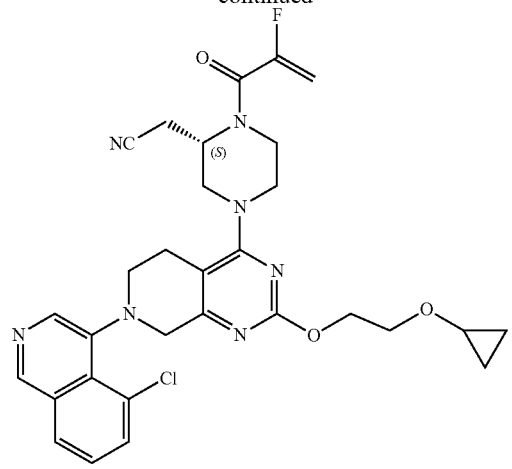
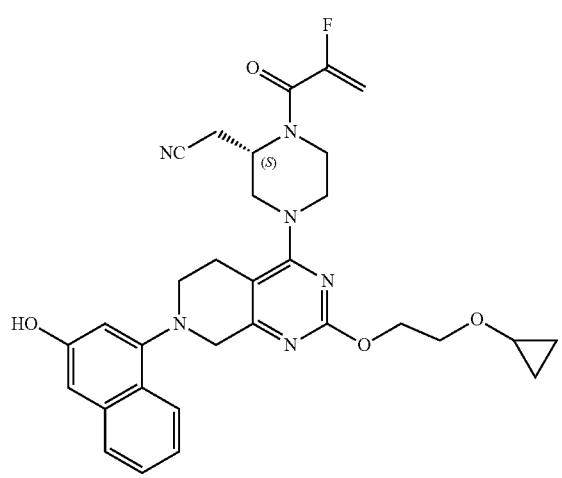
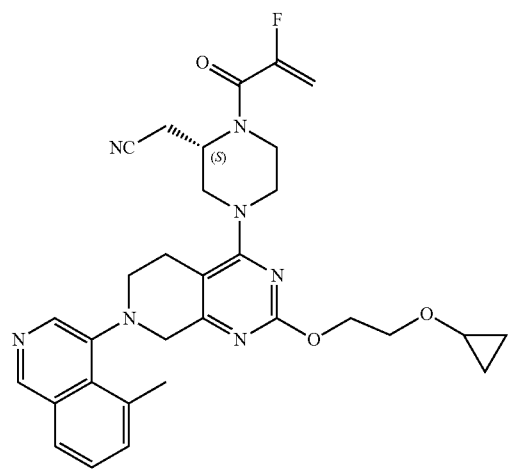
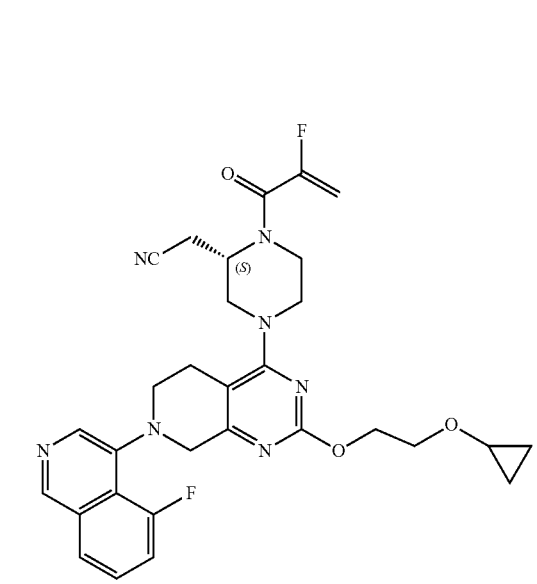
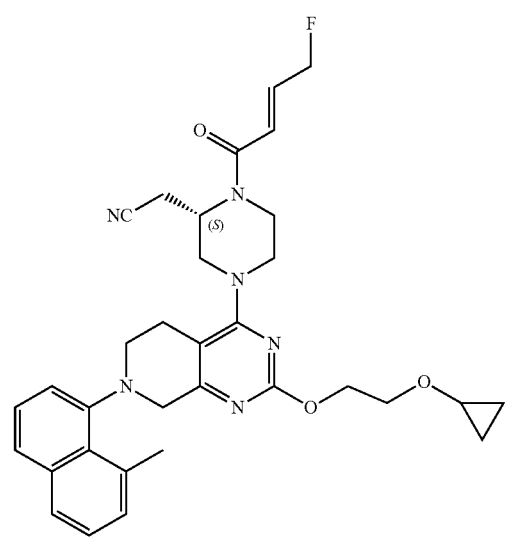

15
-continued
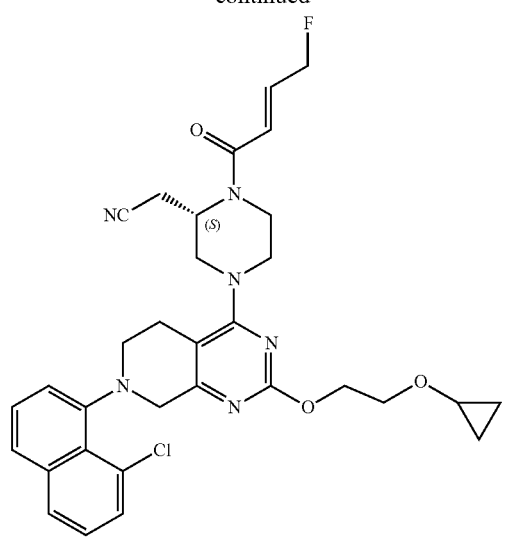
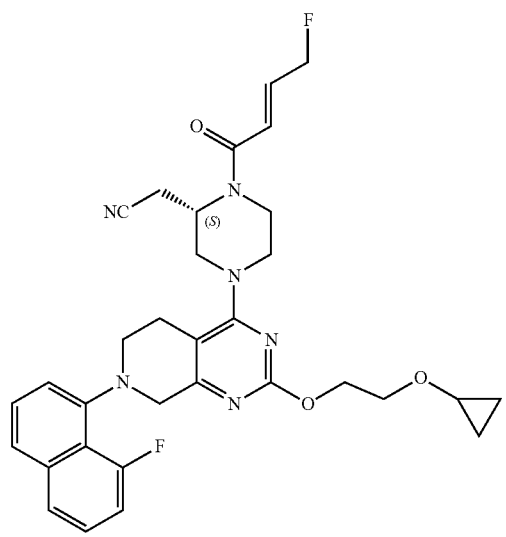
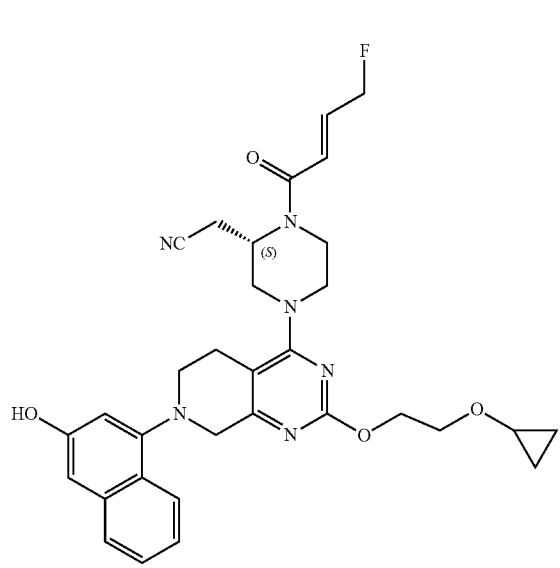
16
-continued
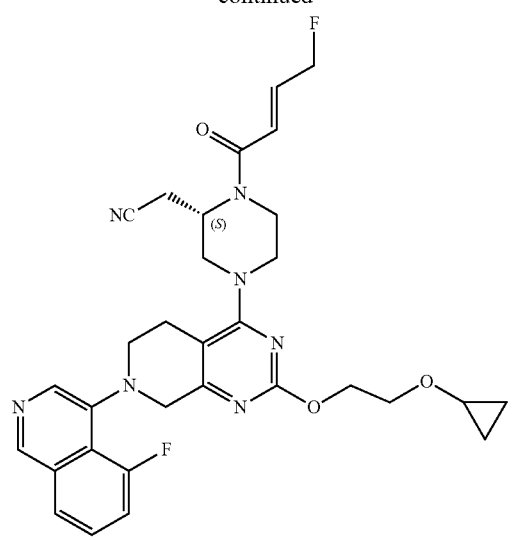
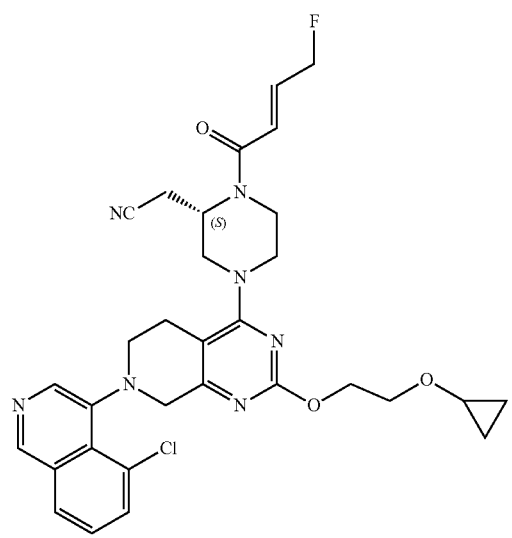
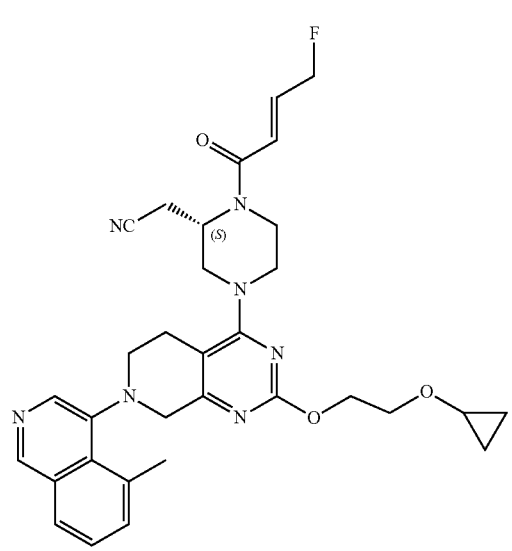

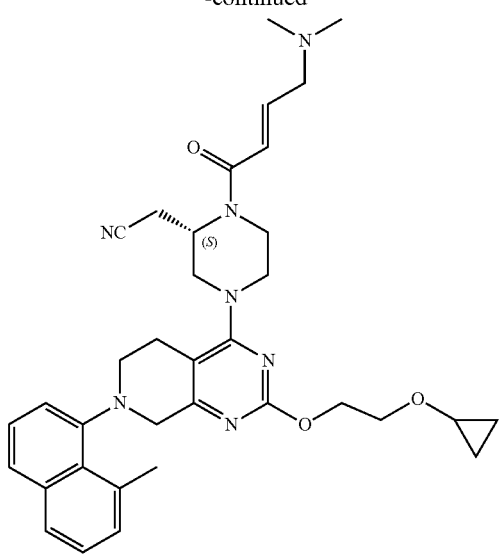
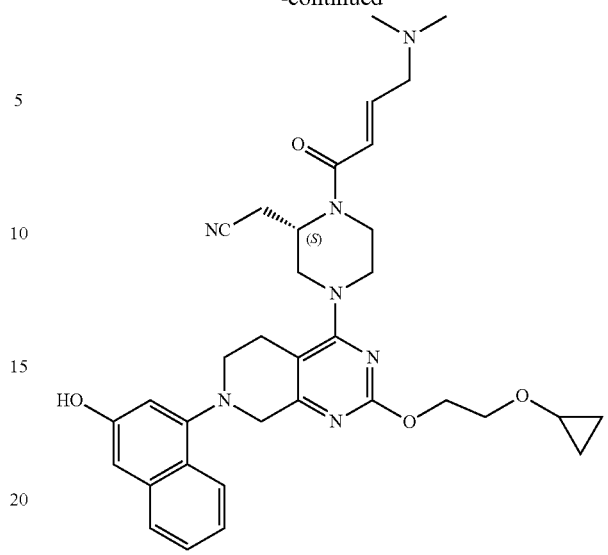

19
-continued
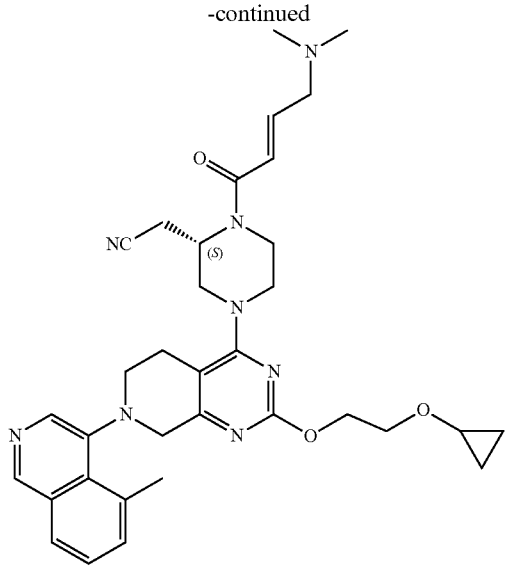
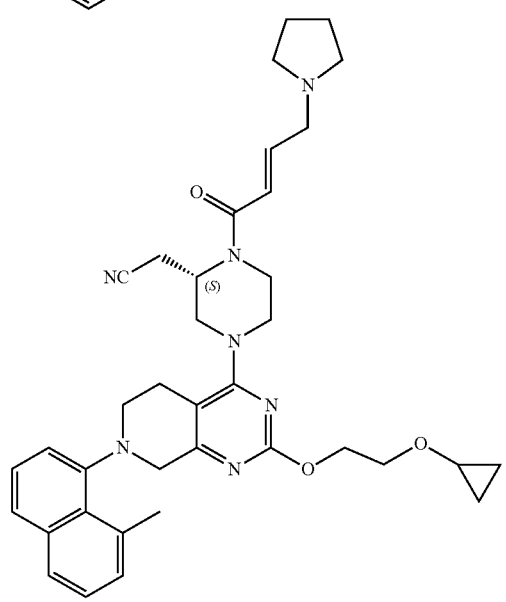
20
-continued
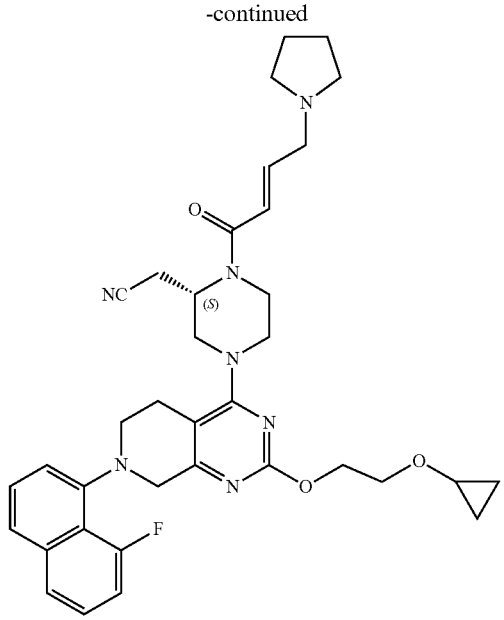
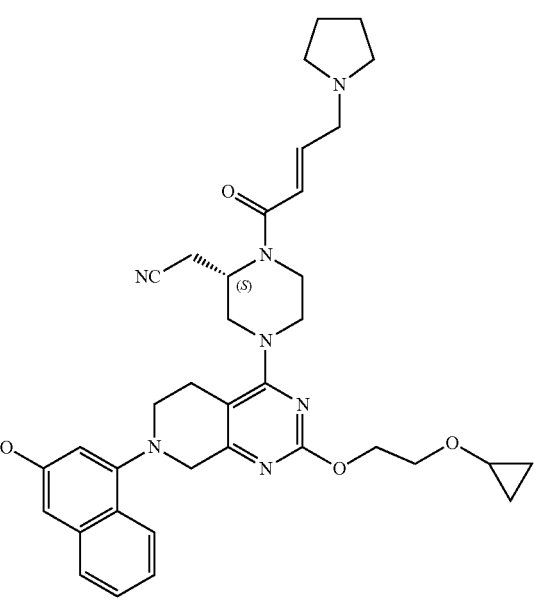

21
-continued
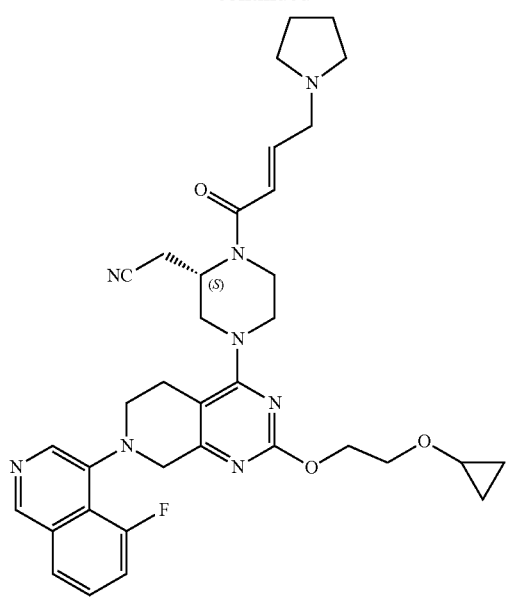
22
-continued
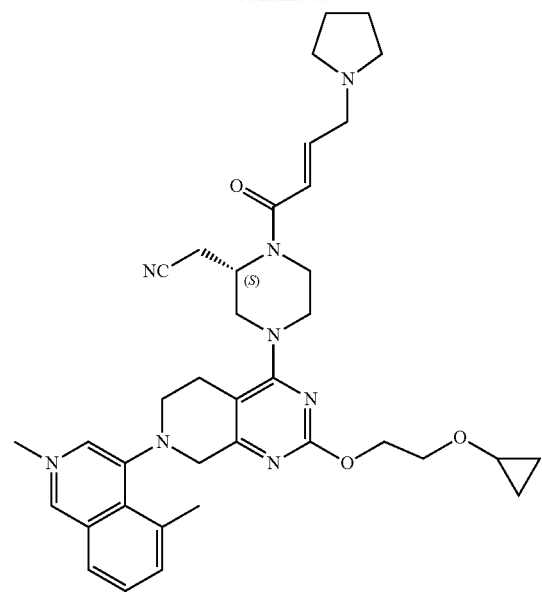
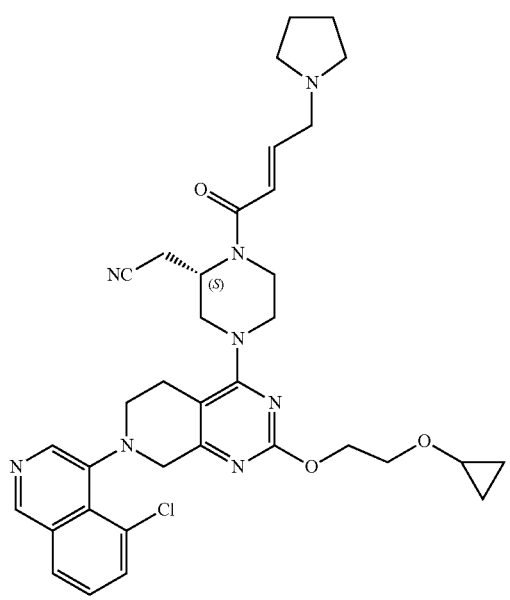
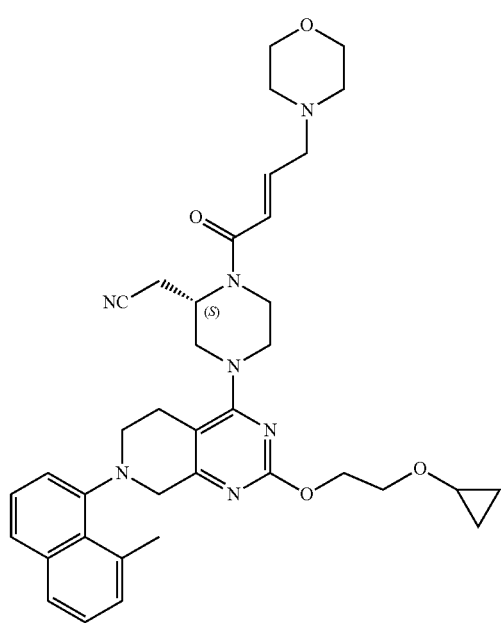

23
-continued
24
-continued
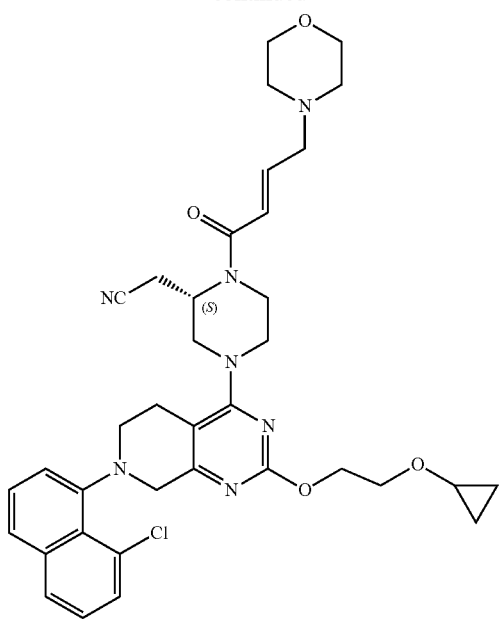
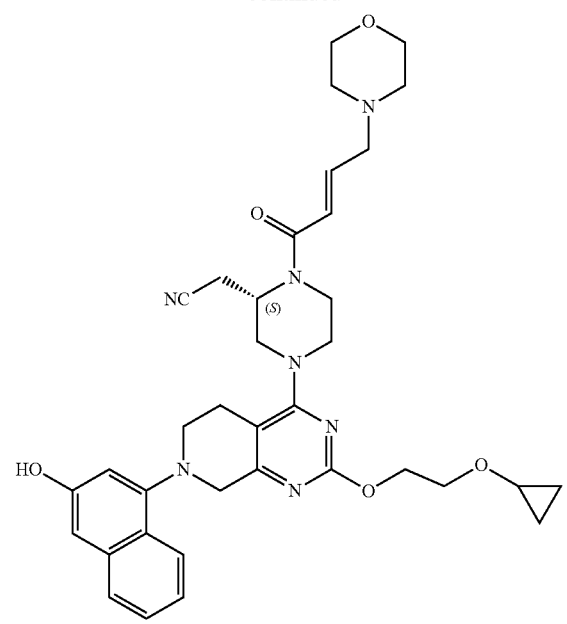

25
-continued
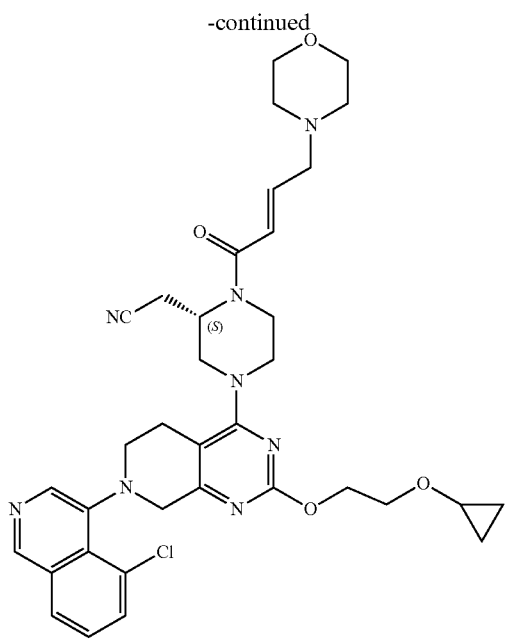
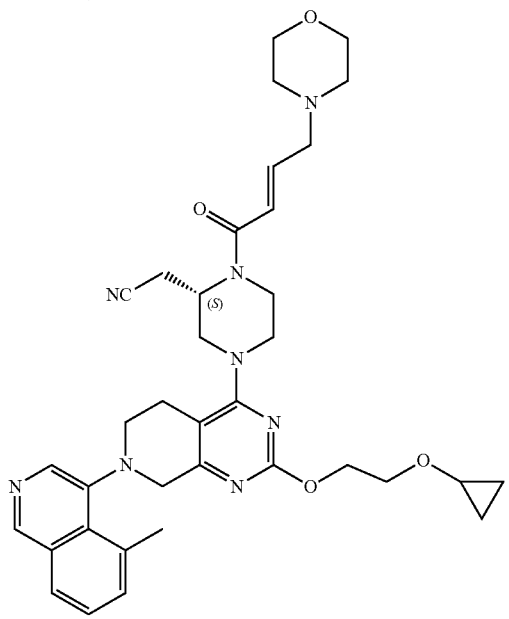
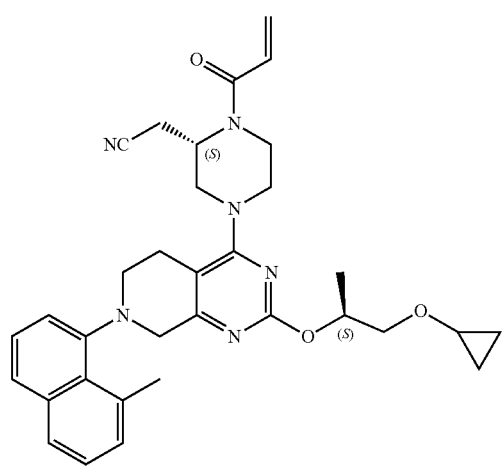
26
-continued
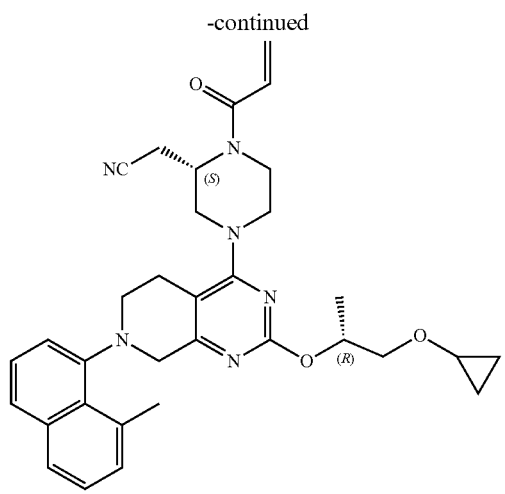
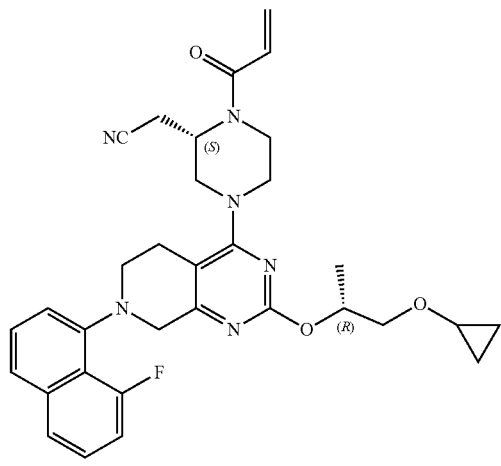

27
-continued
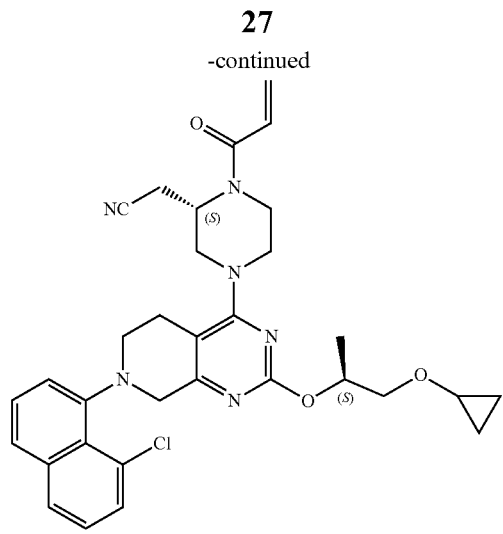
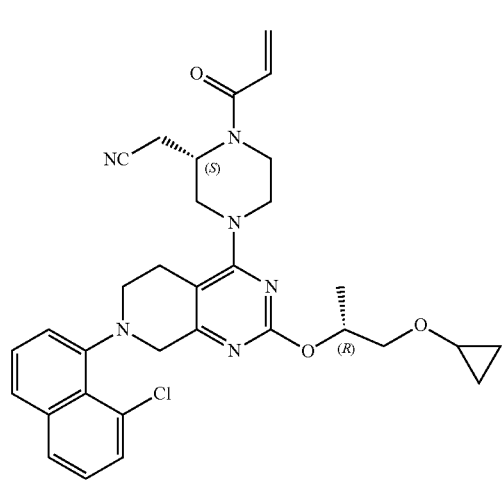
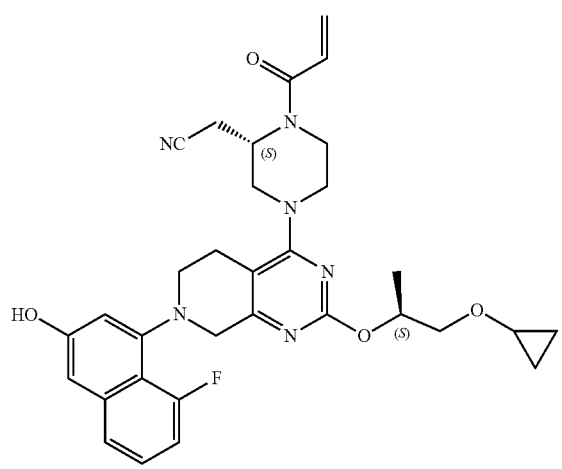
28
-continued
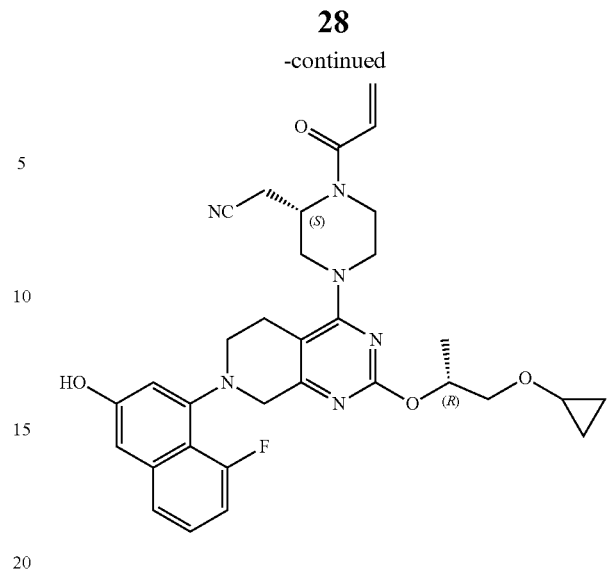
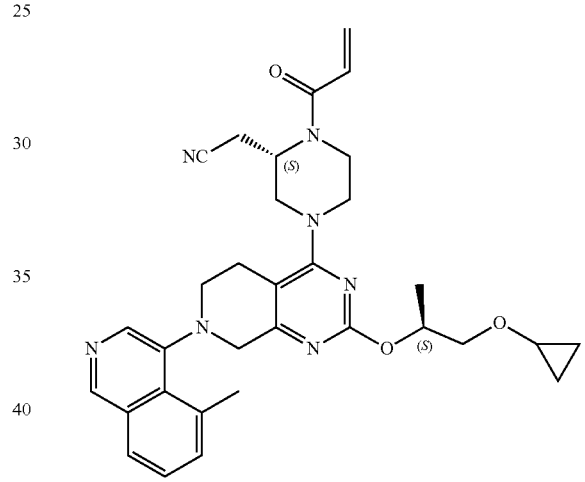
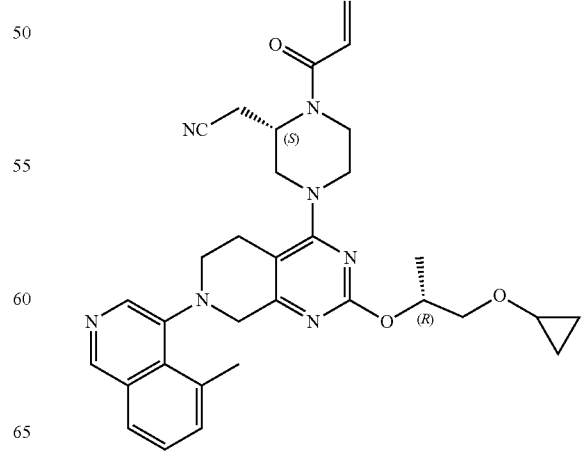

29
-continued
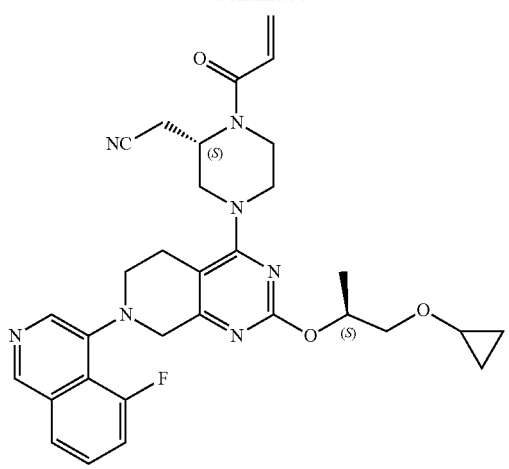
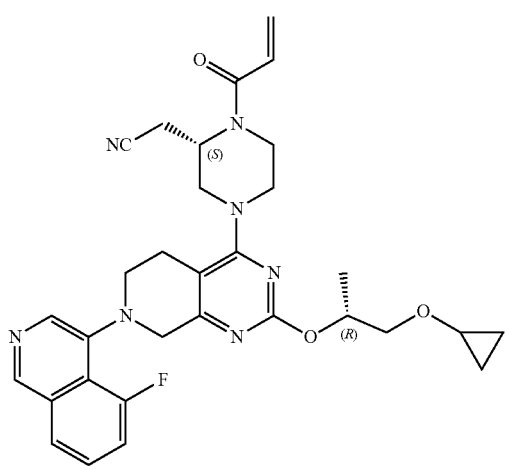
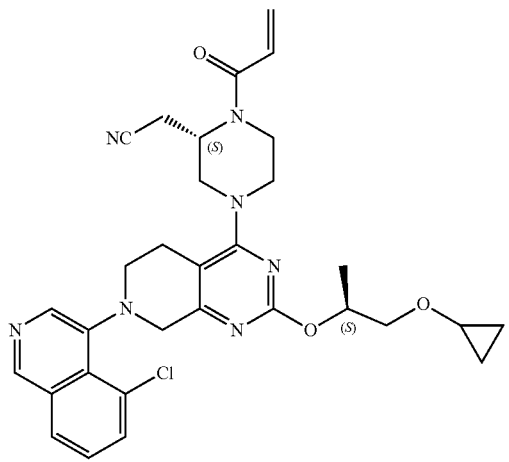
30
-continued
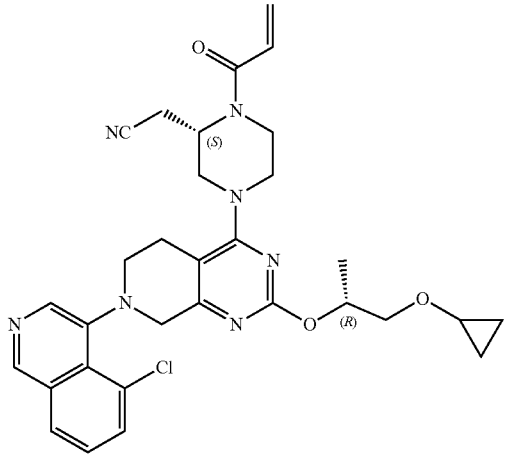
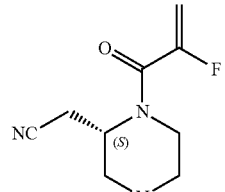
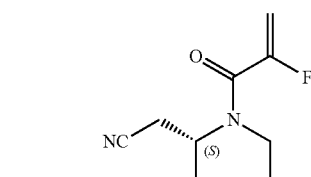
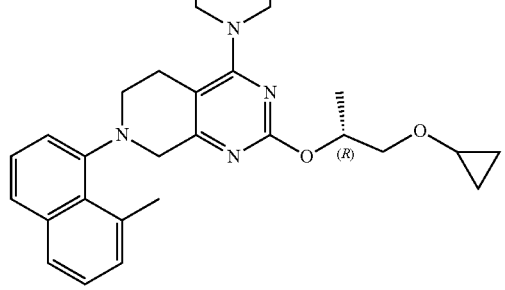

31
-continued
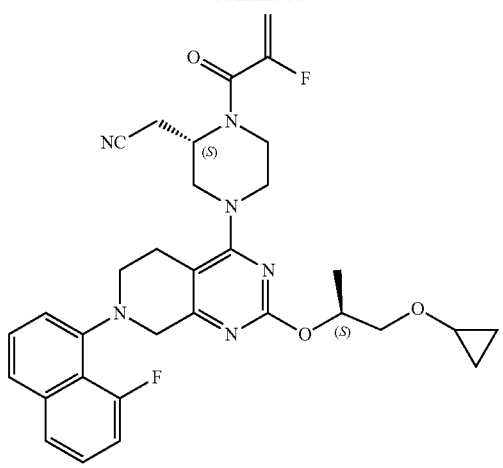
32
-continued
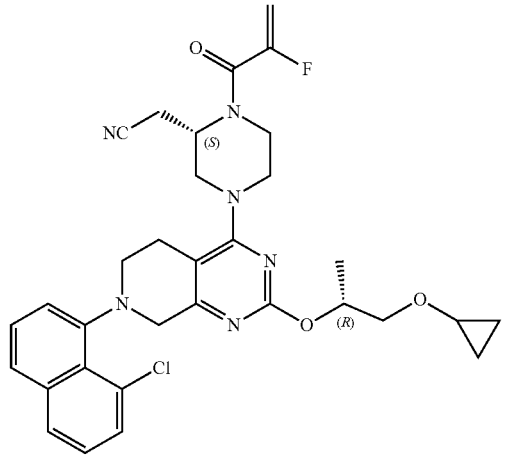
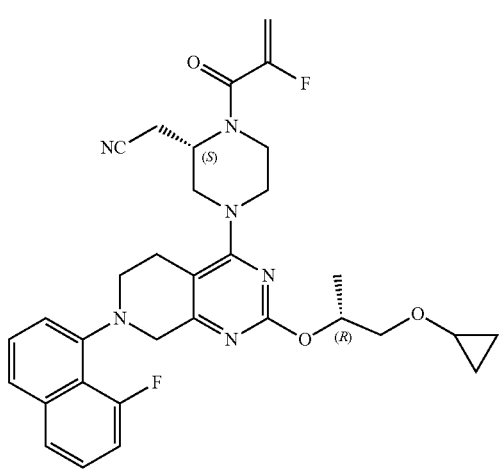
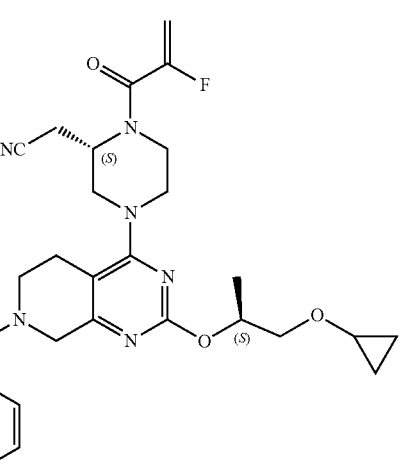
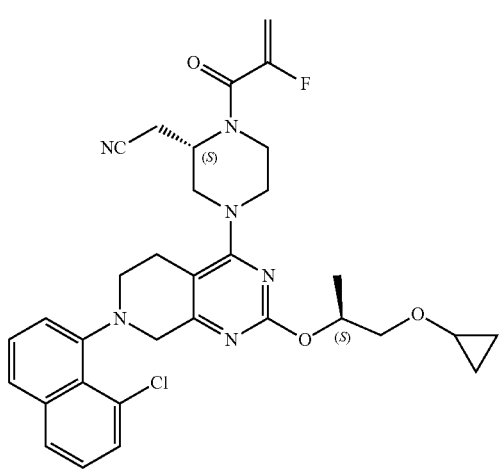
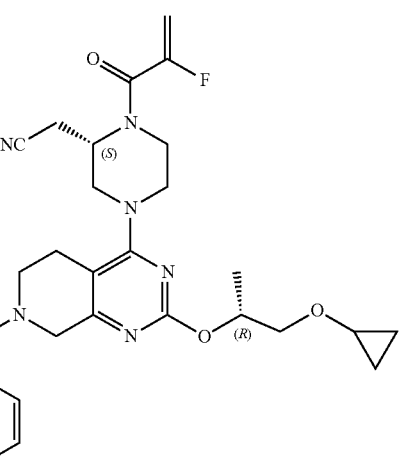

33
-continued
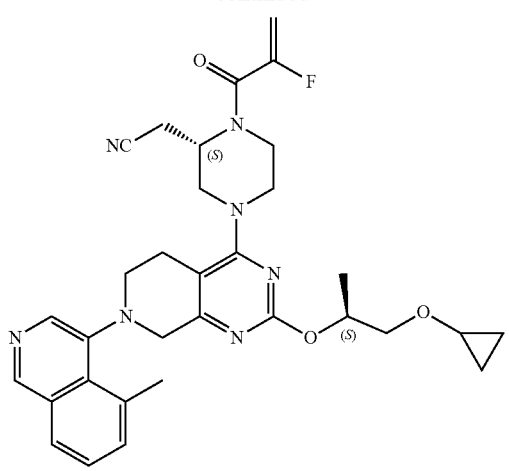
34
-continued
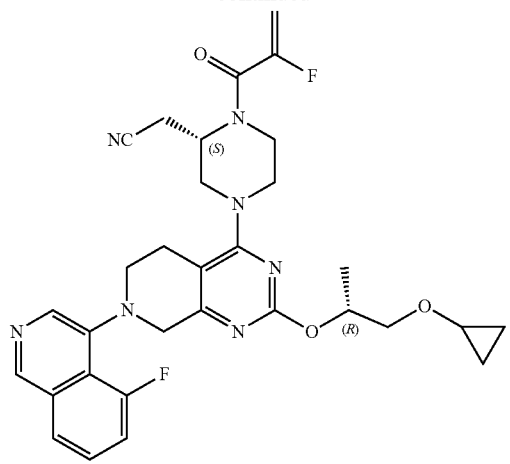
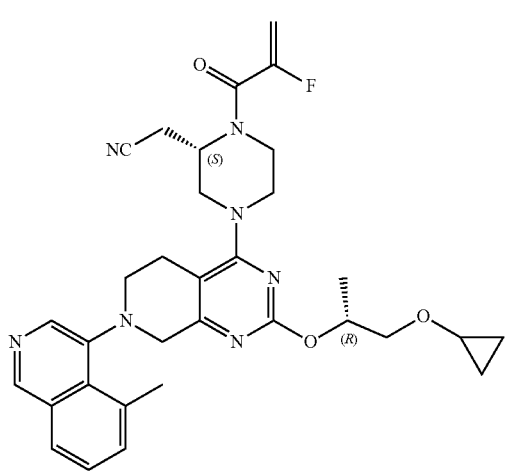
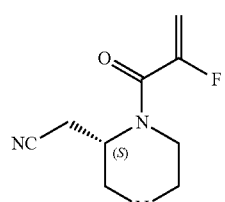
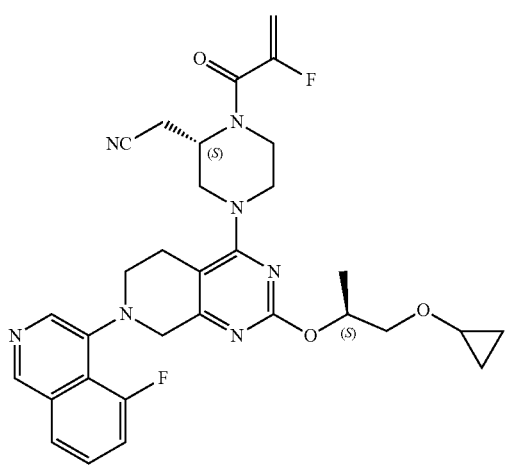
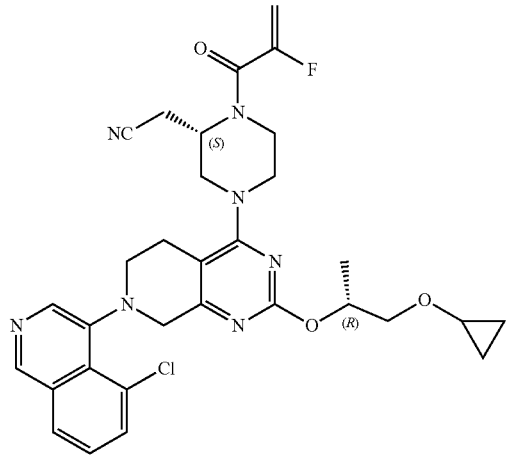

35
-continued
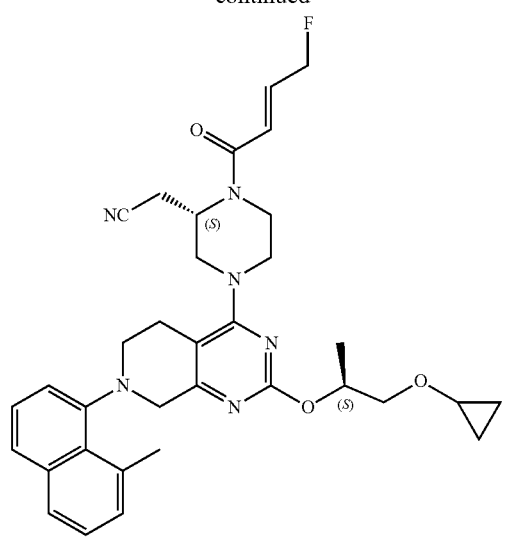
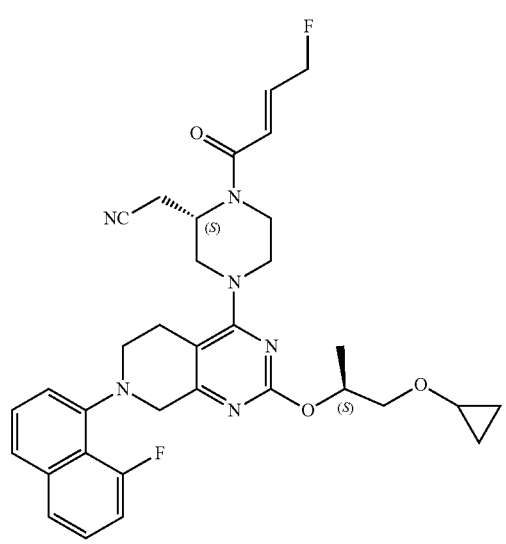
36
-continued
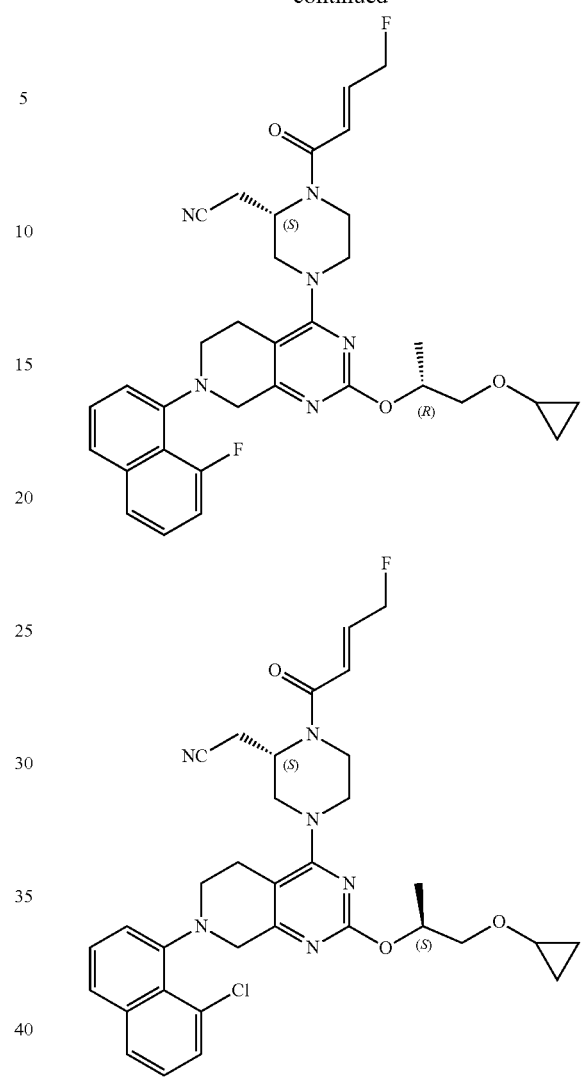
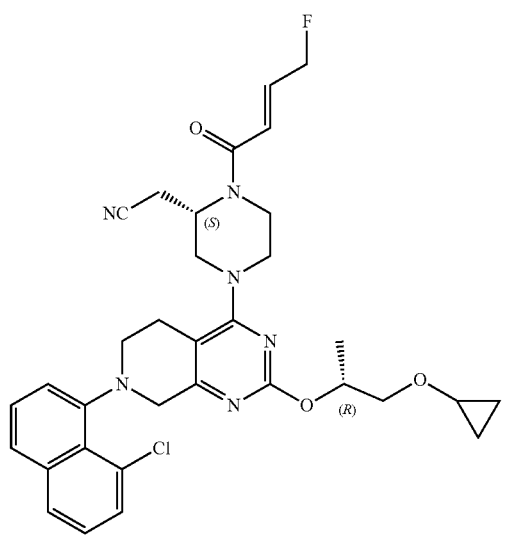

37
-continued
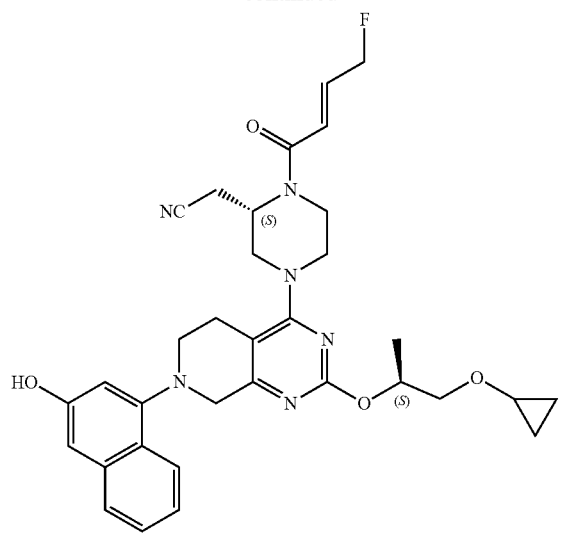
38
-continued
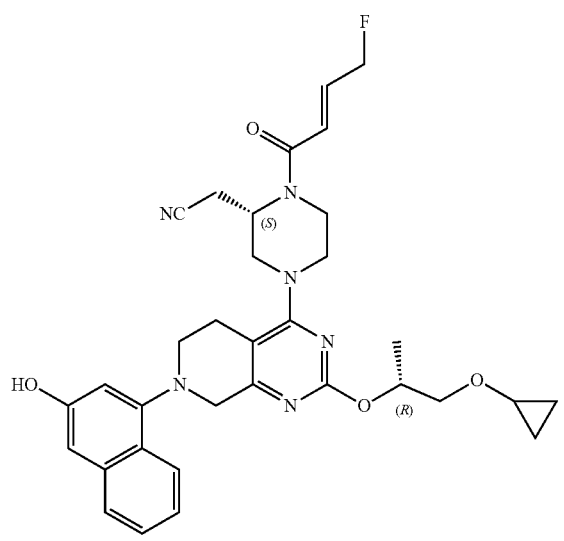
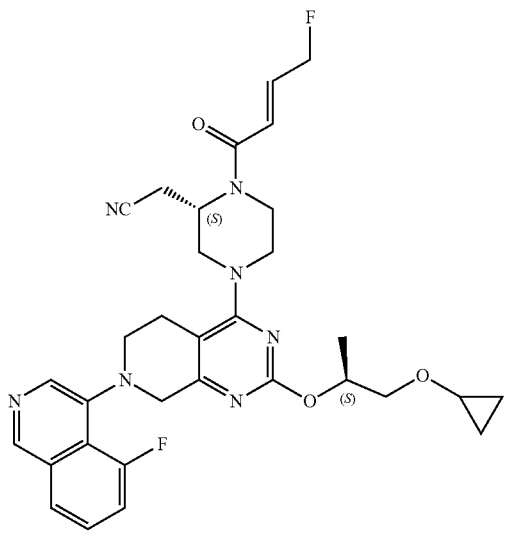
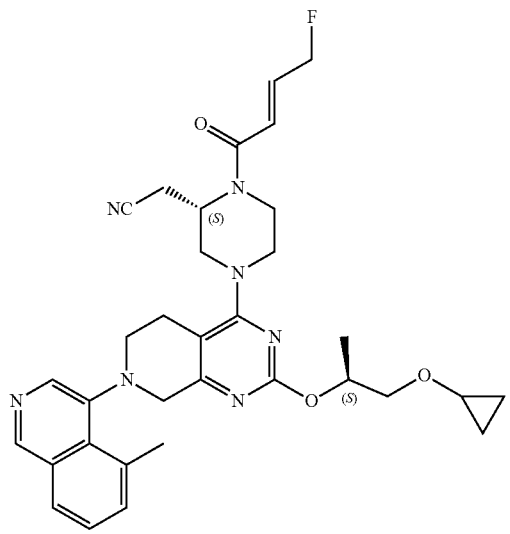
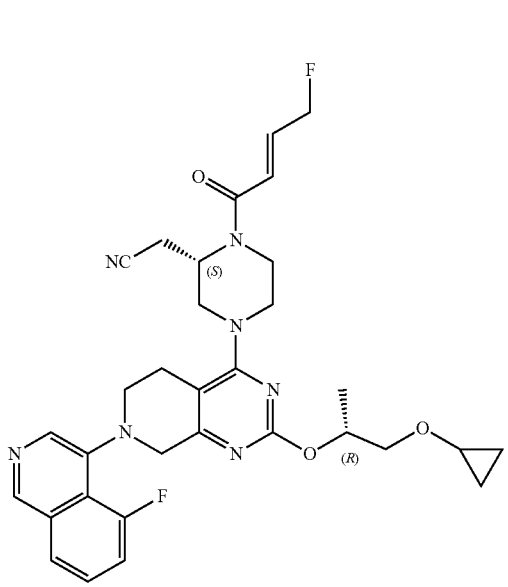

39
-continued
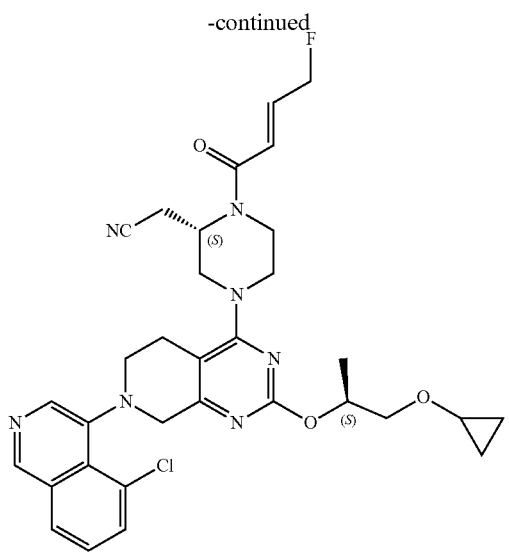
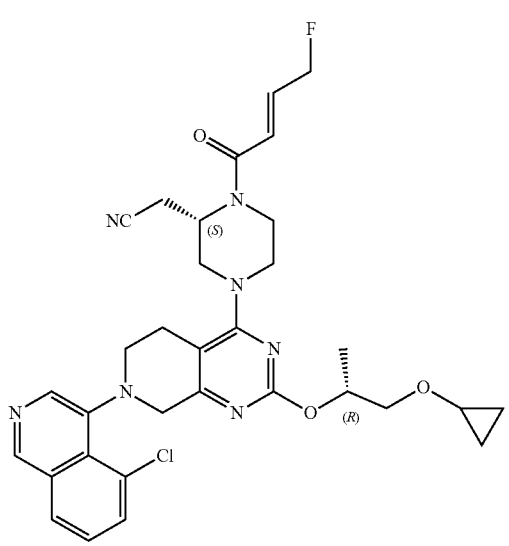
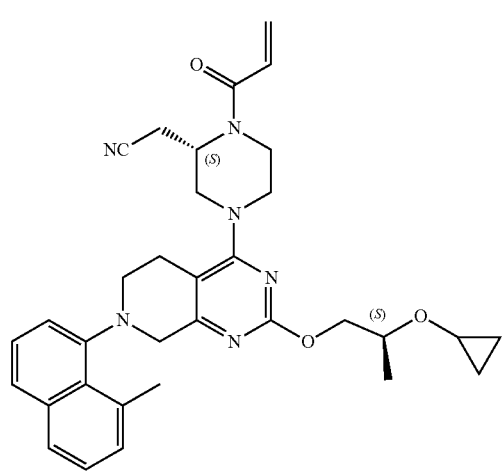
40
-continued
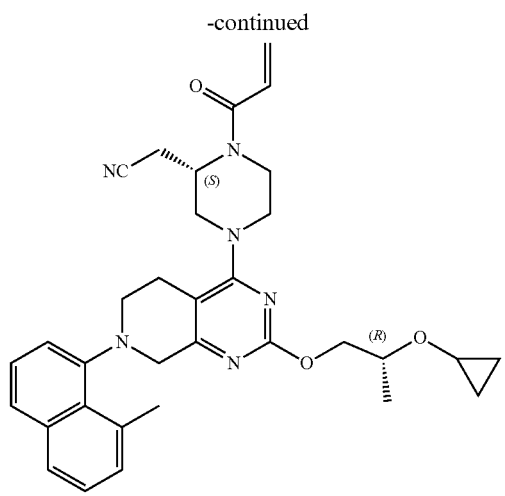
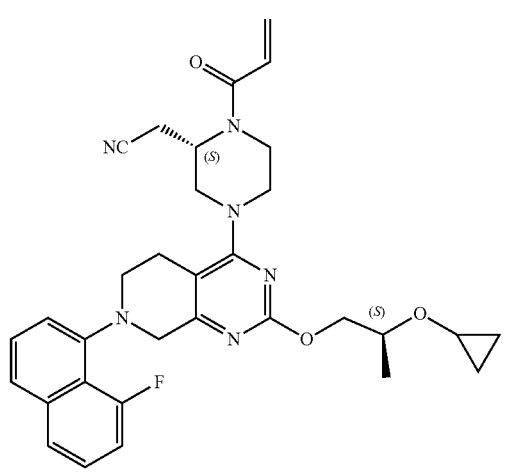
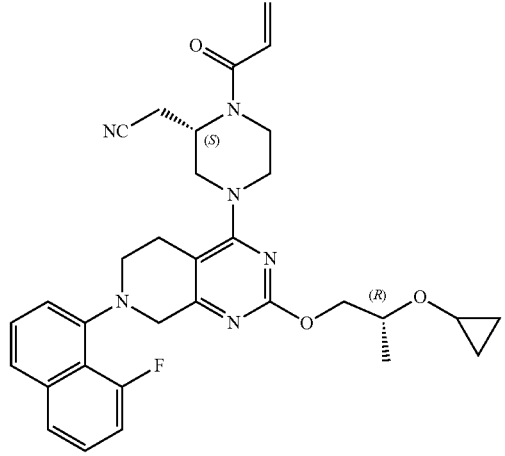

41
-continued
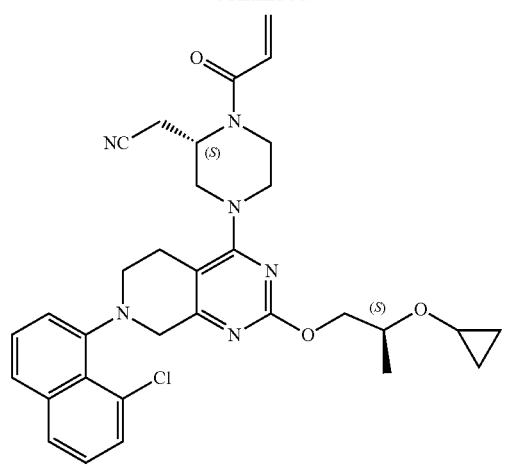
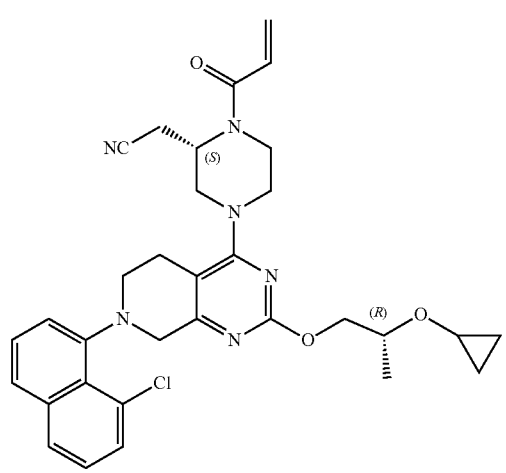
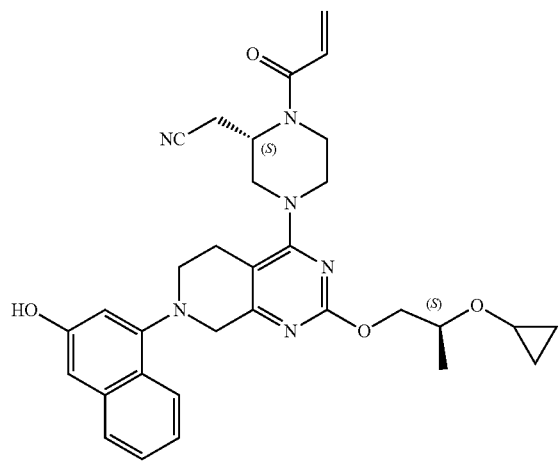
42
-continued
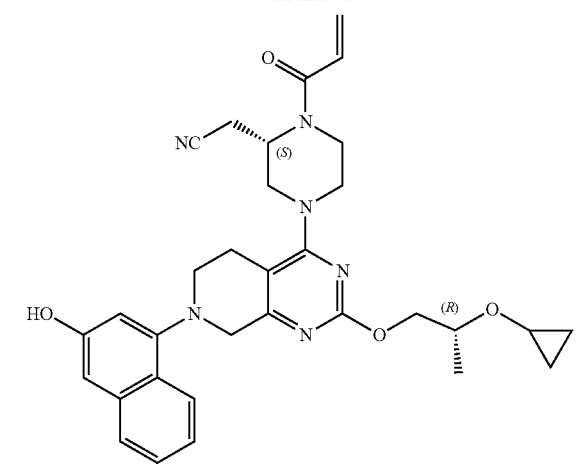
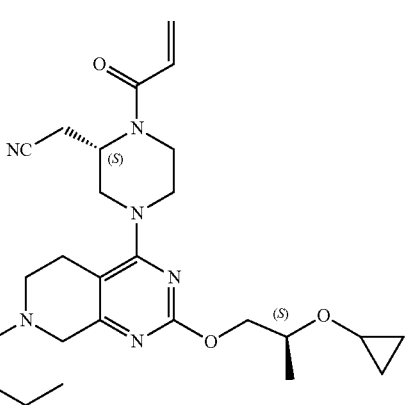
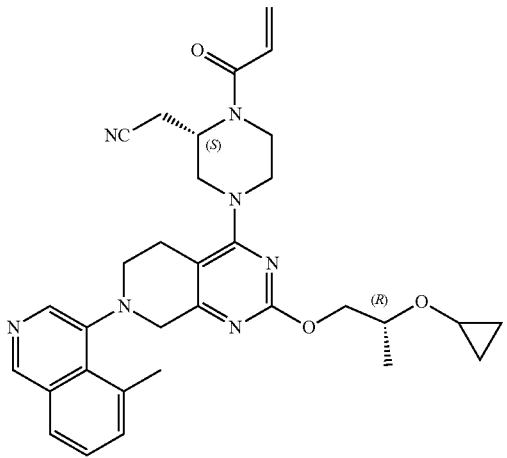

43
-continued
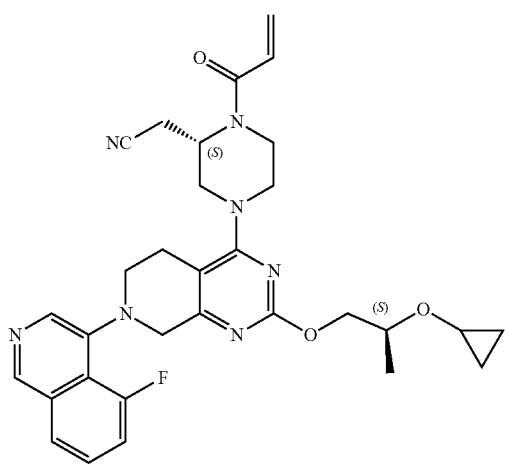
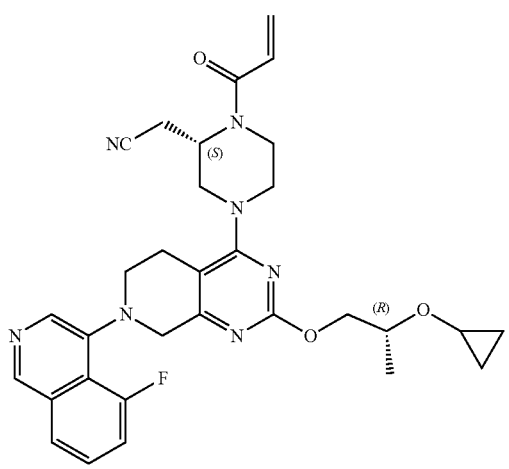
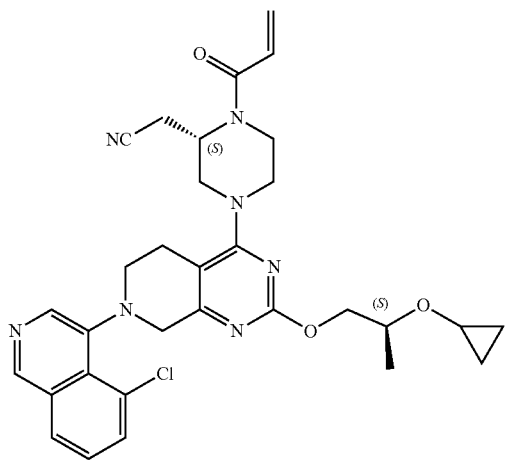
44
-continued
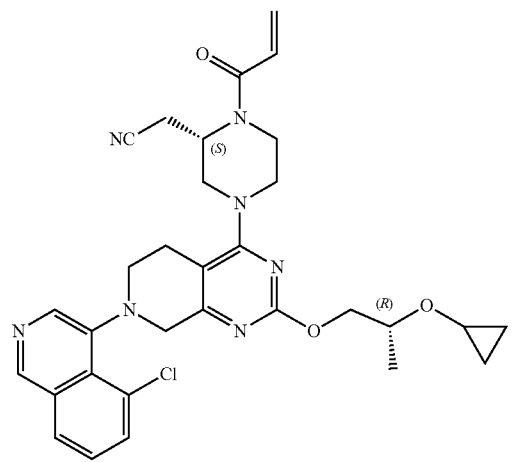
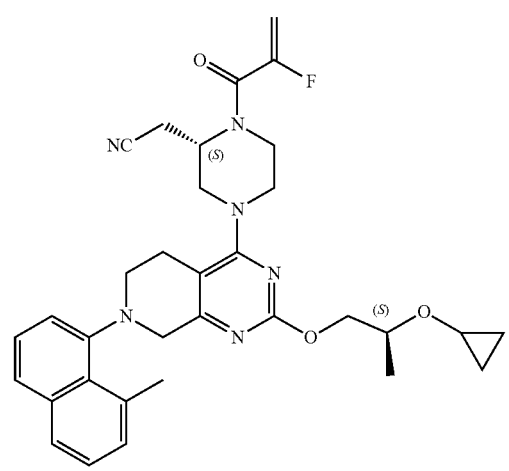
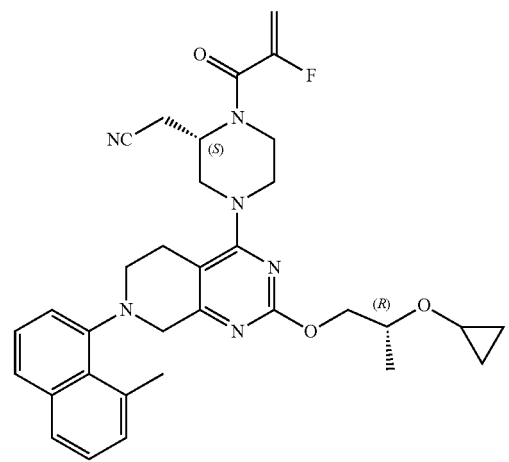

-continued
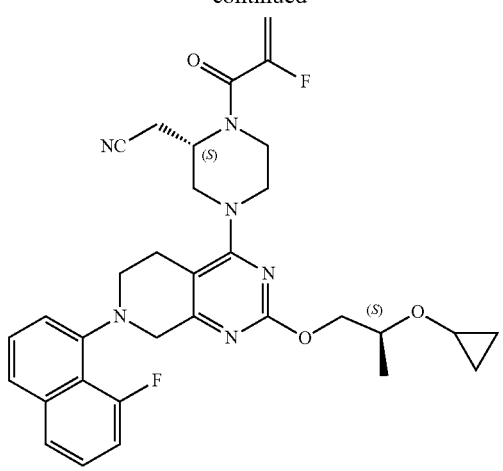
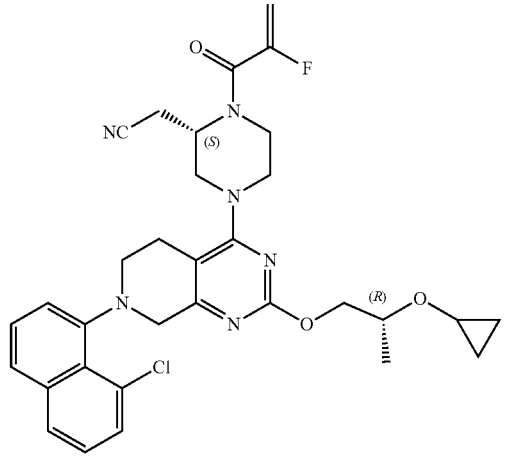
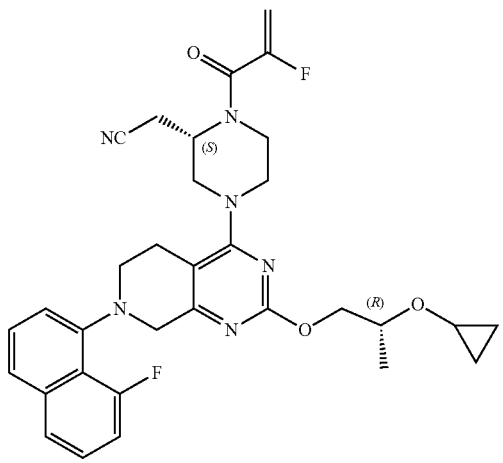
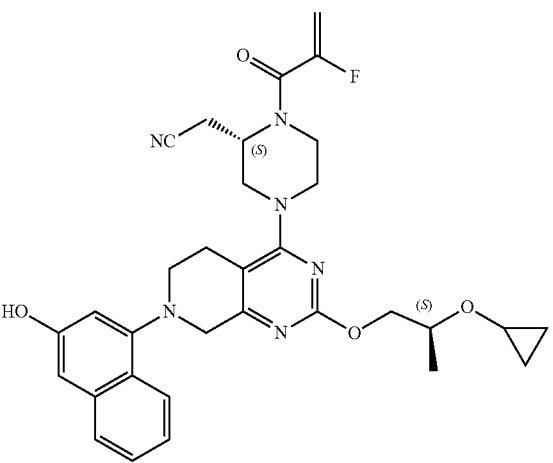
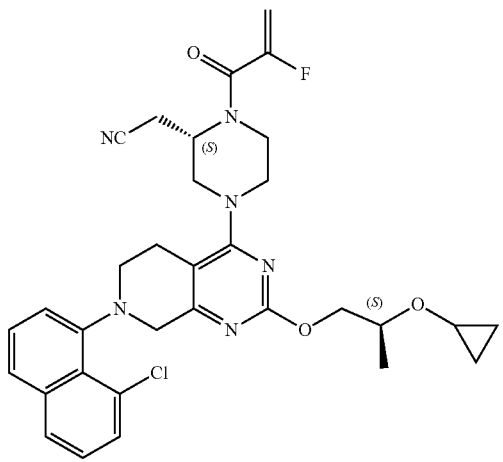
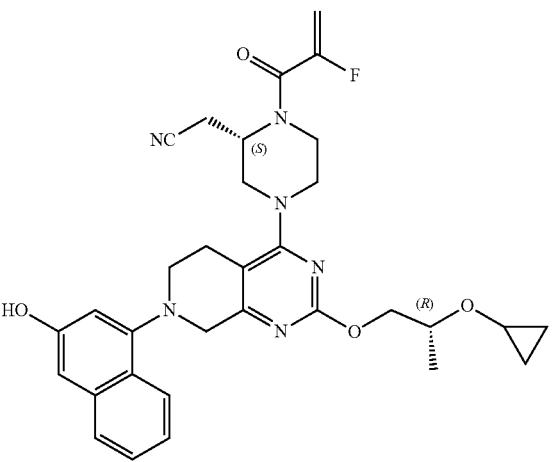

47
-continued
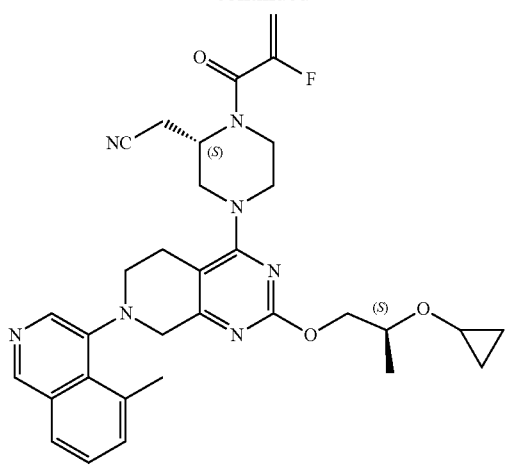
48
-continued
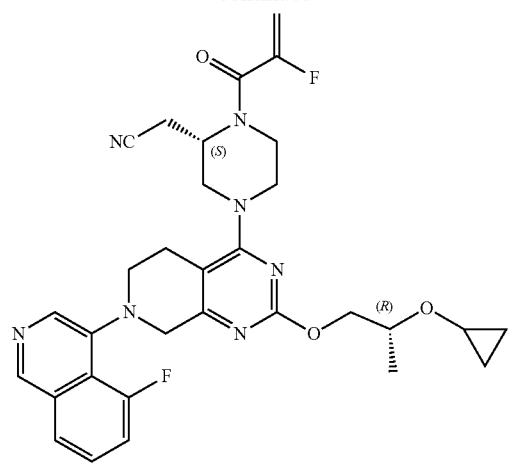
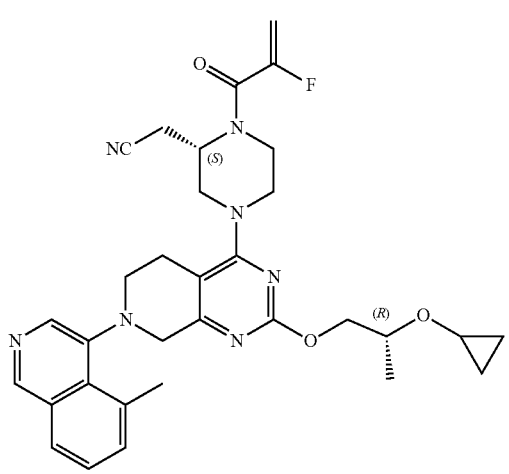
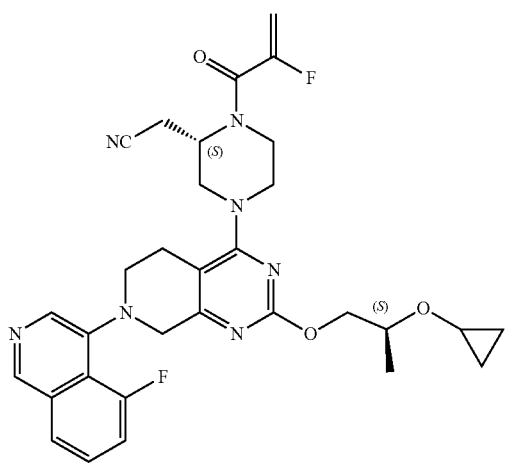
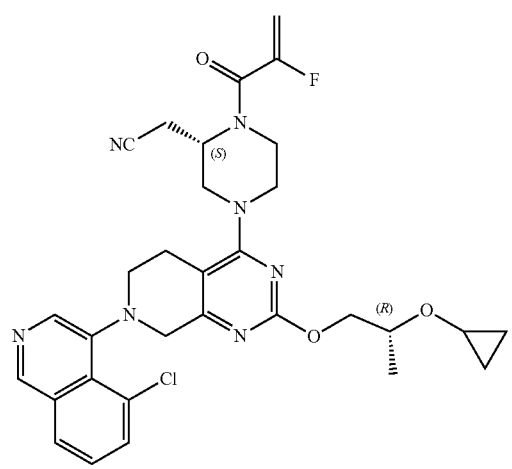

49
-continued
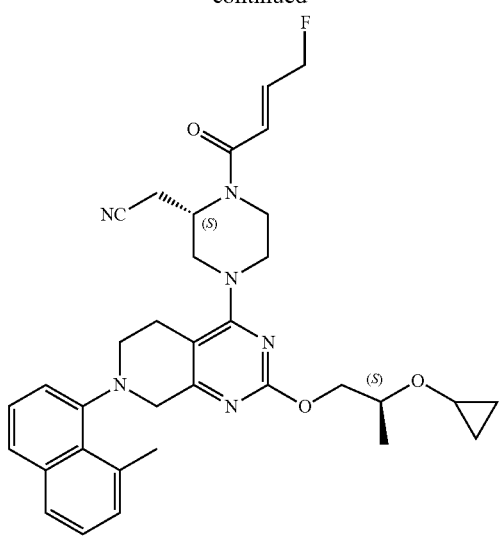
50
-continued
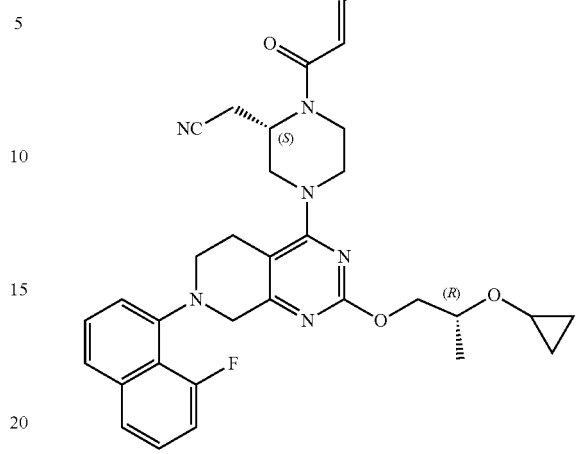
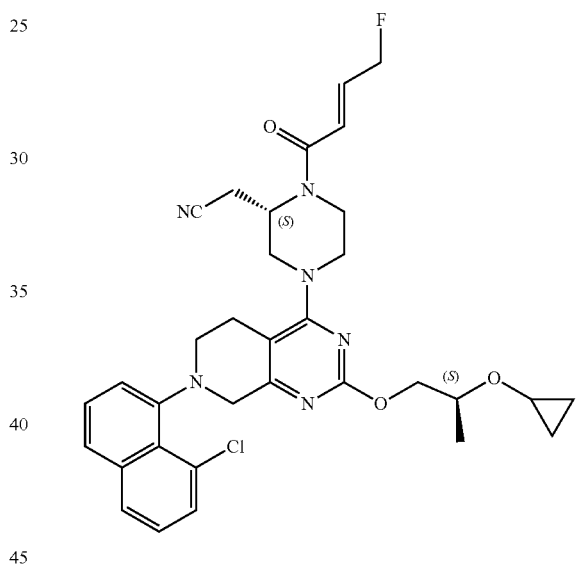
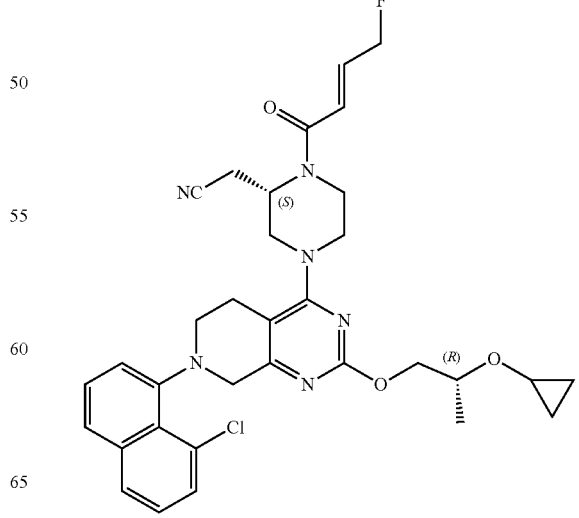

51
-continued
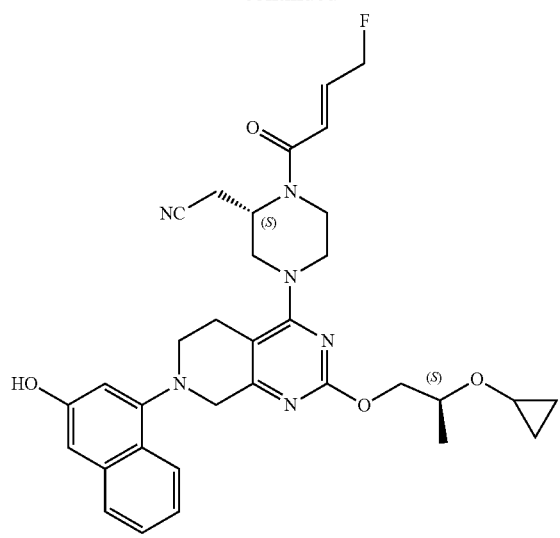
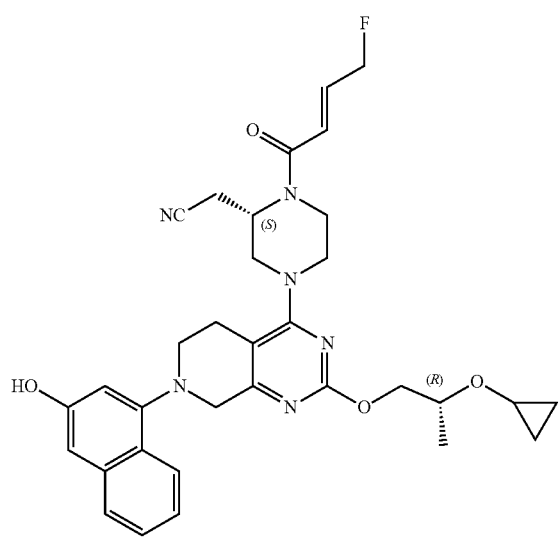
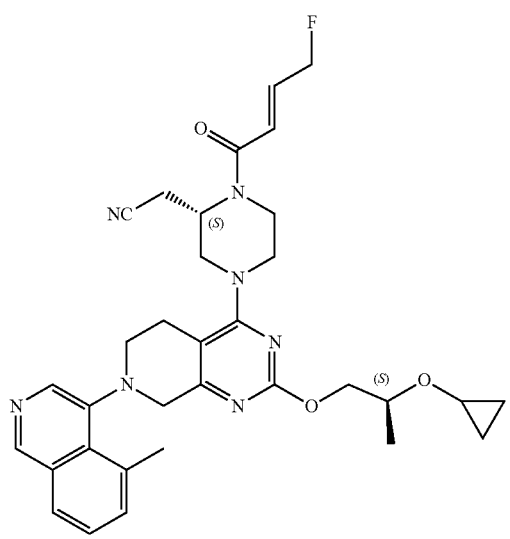
52
-continued
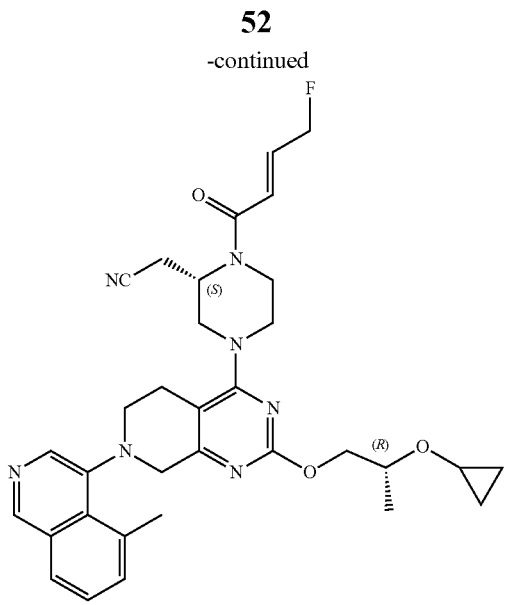
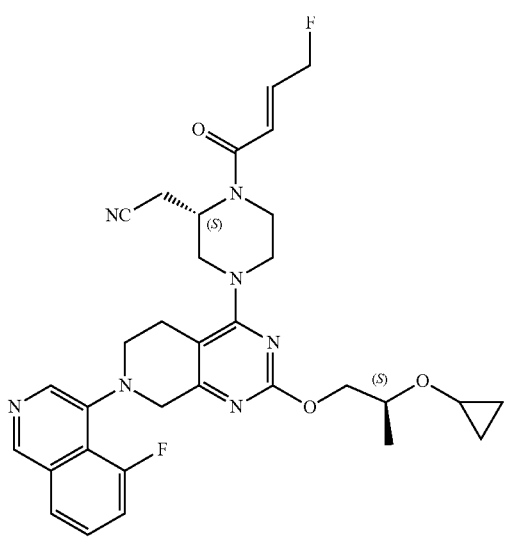
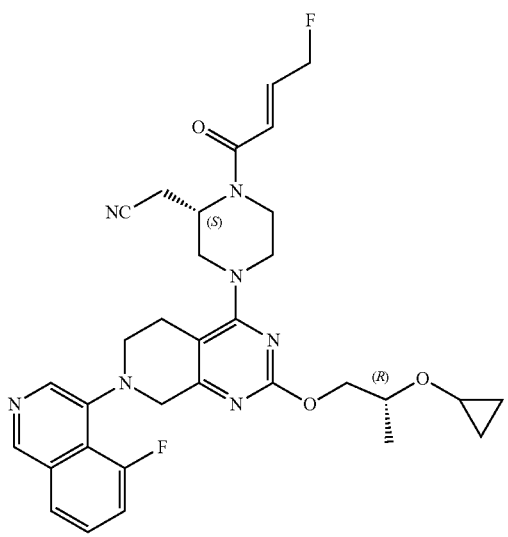

53
-continued
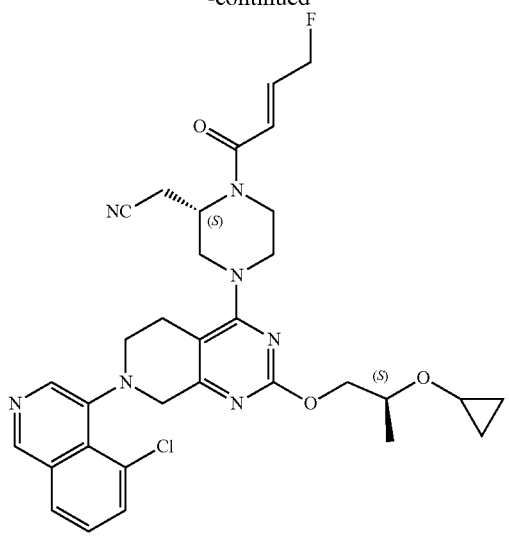
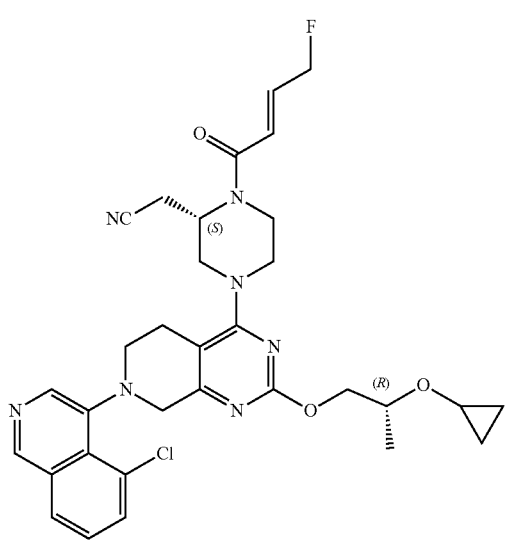
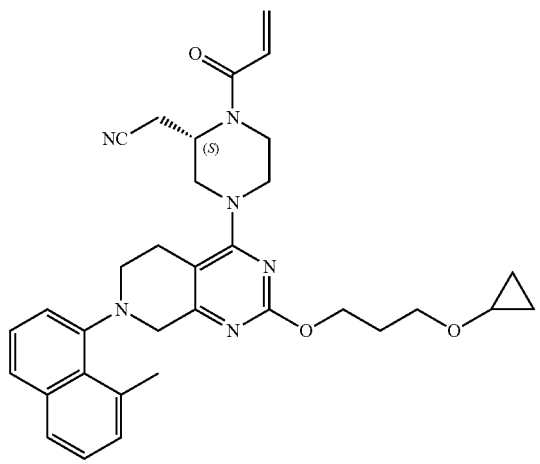
54
-continued
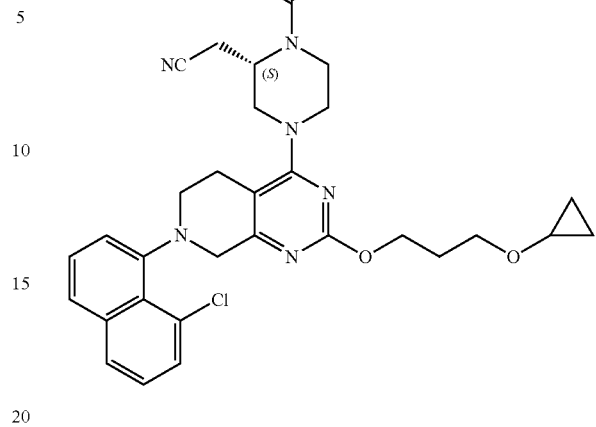
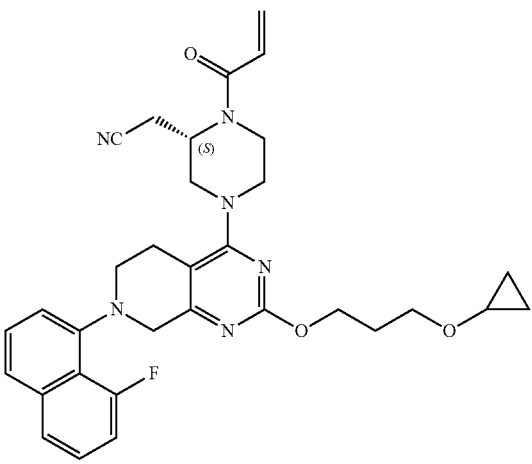
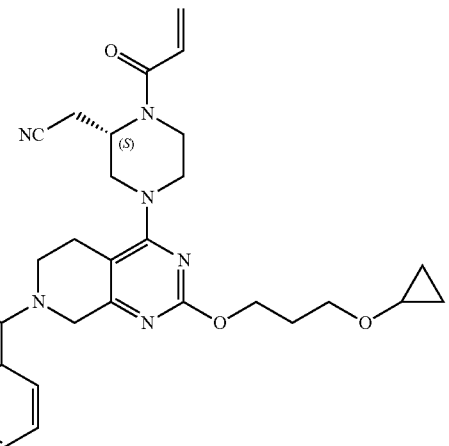

55
-continued
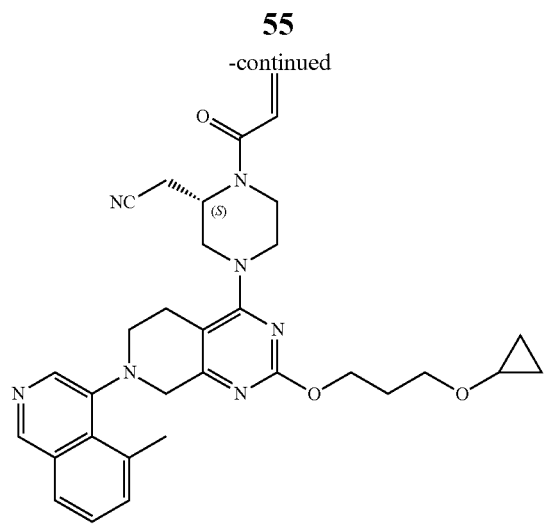
56
-continued
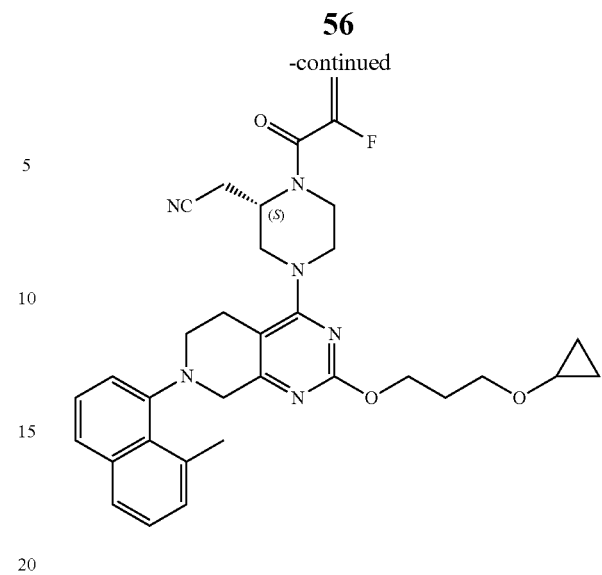
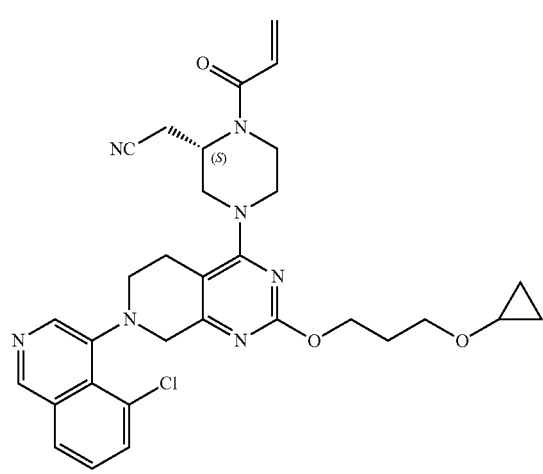
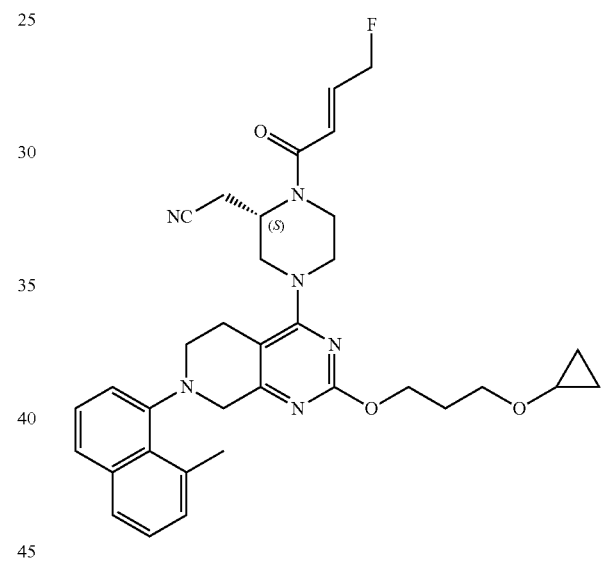
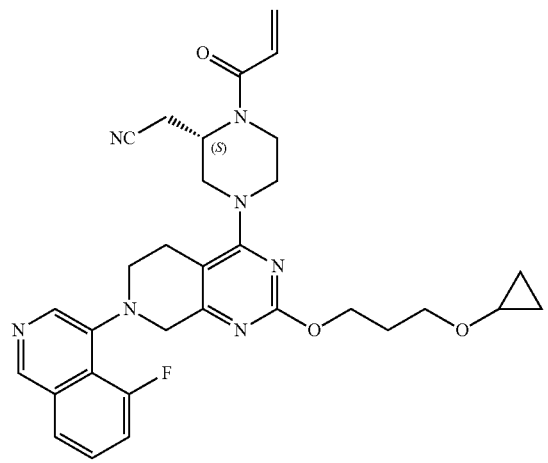
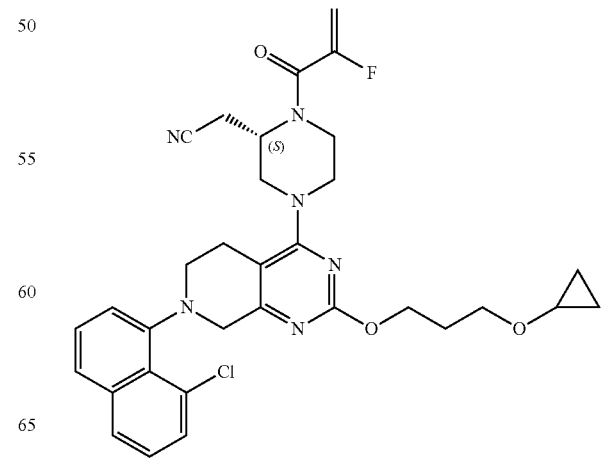

57
-continued
58
-continued
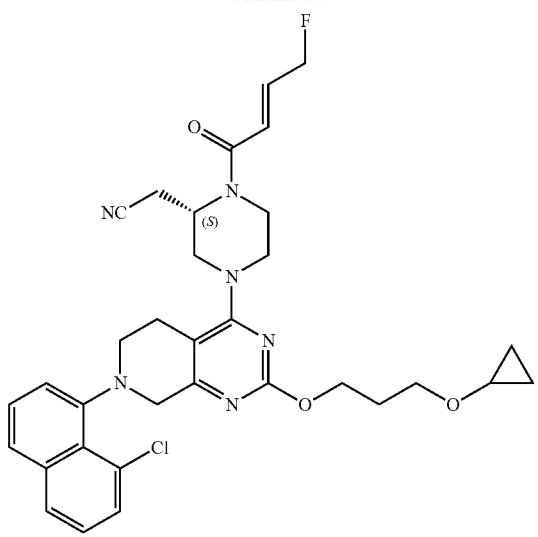
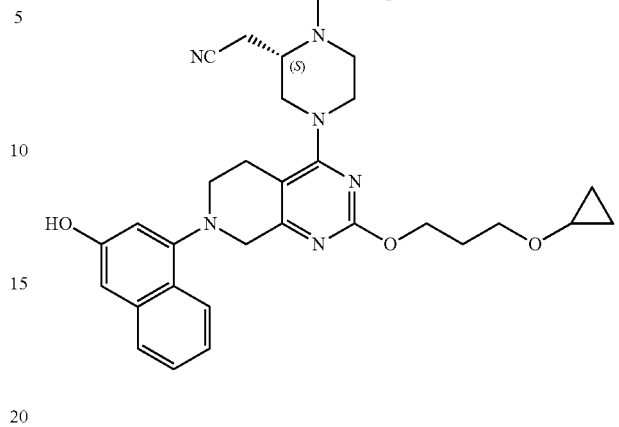

59
-continued
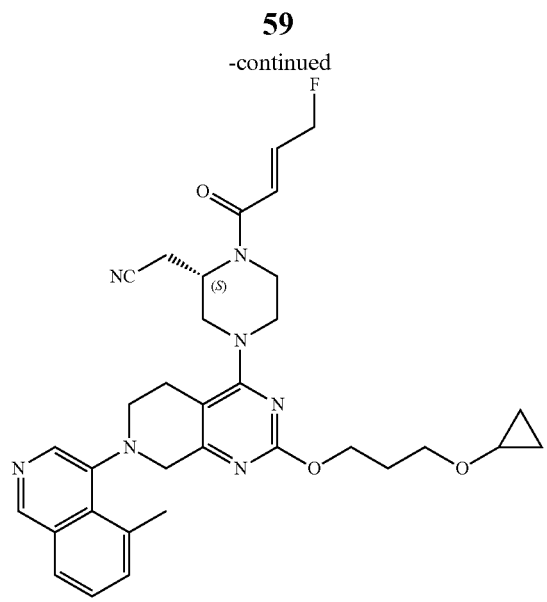
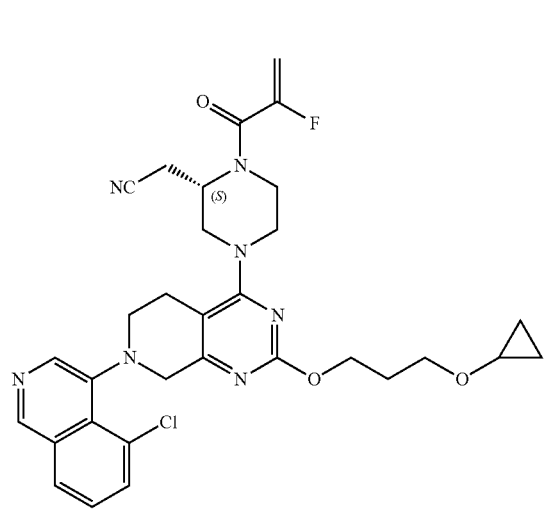
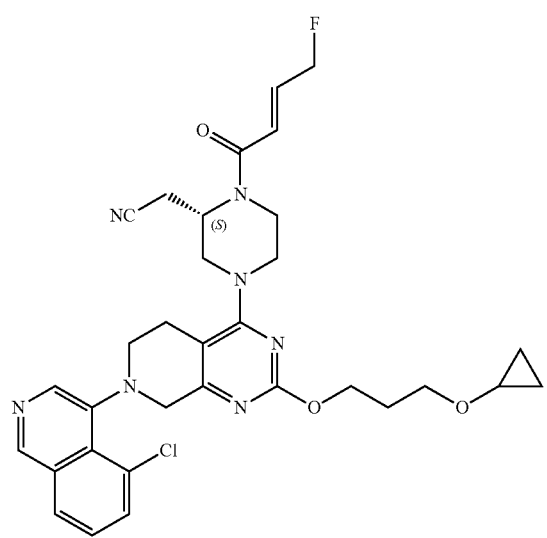
60
-continued
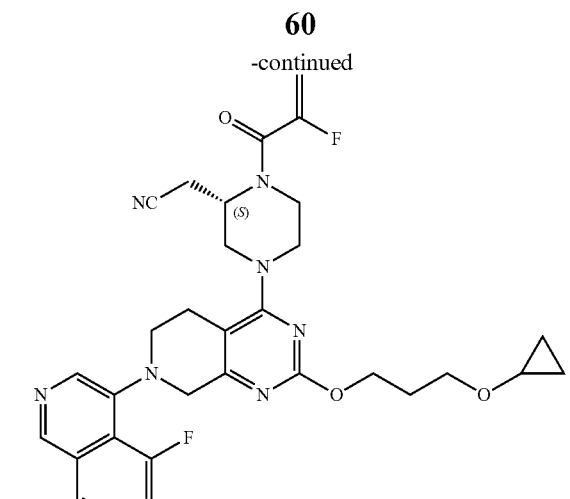
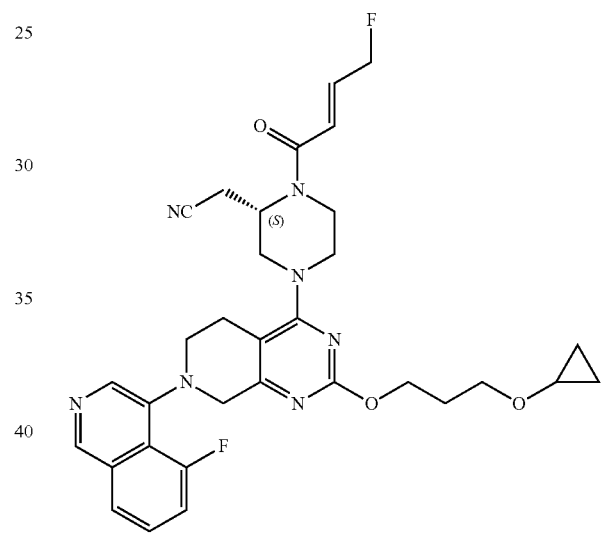
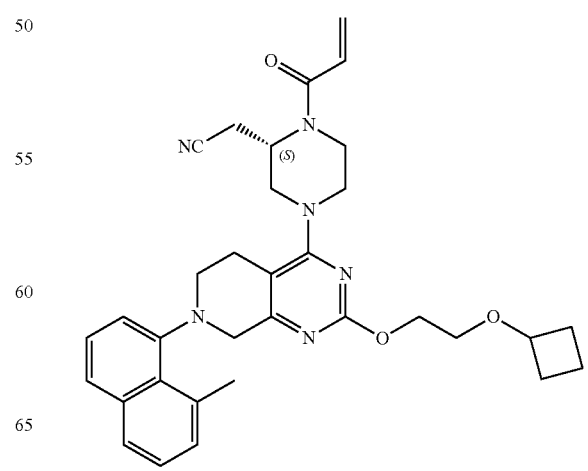

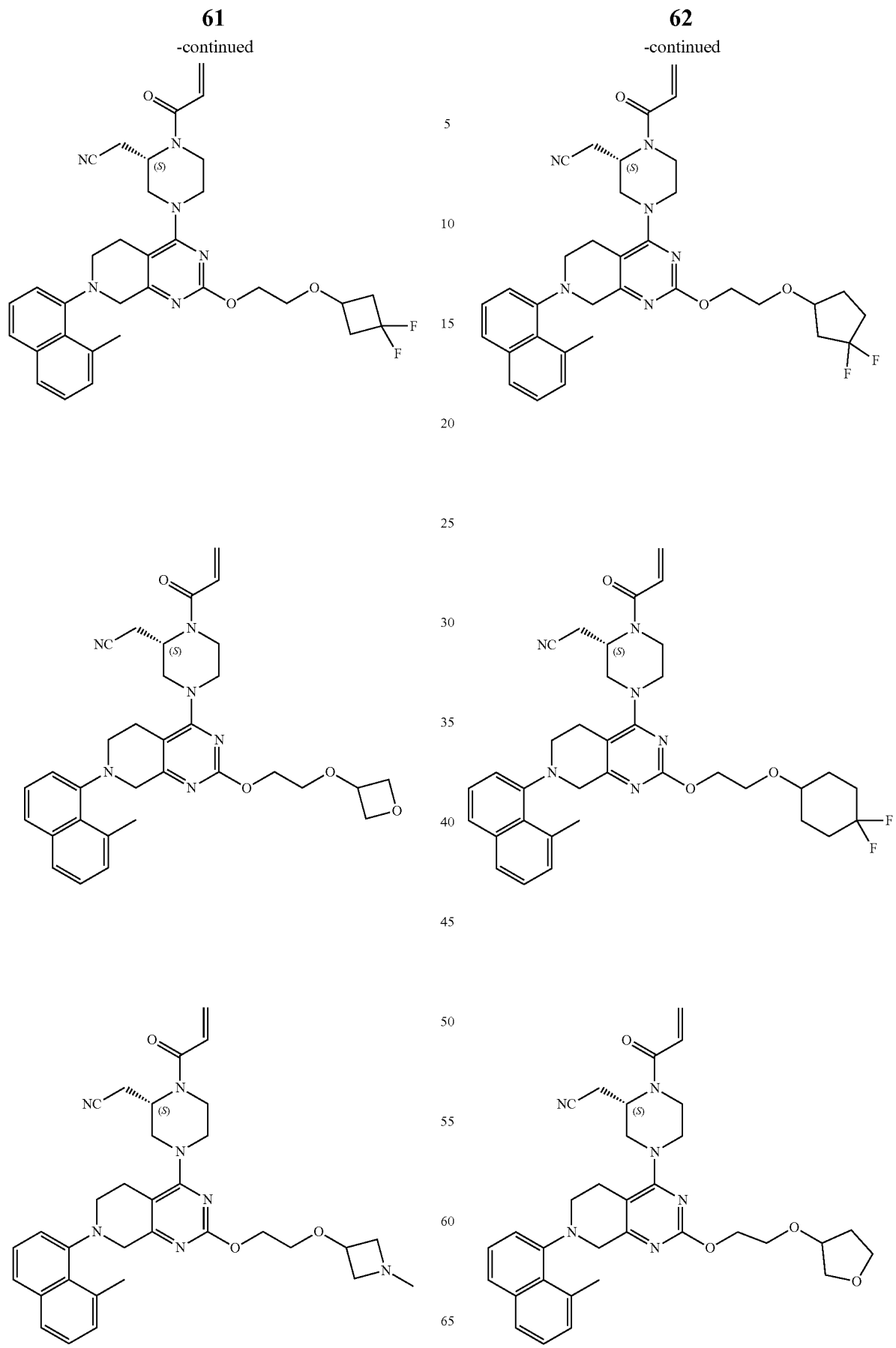

63
-continued
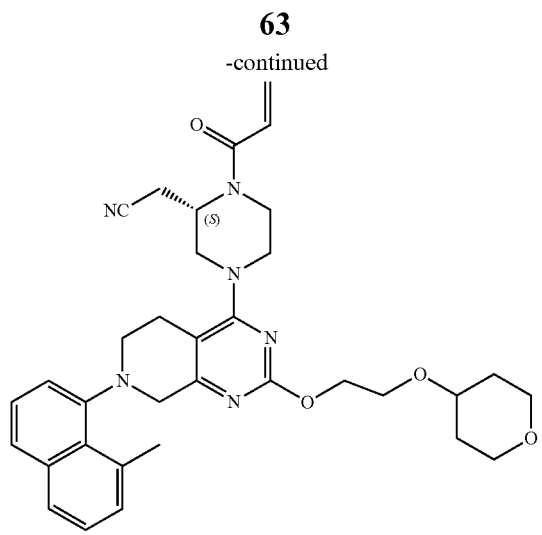
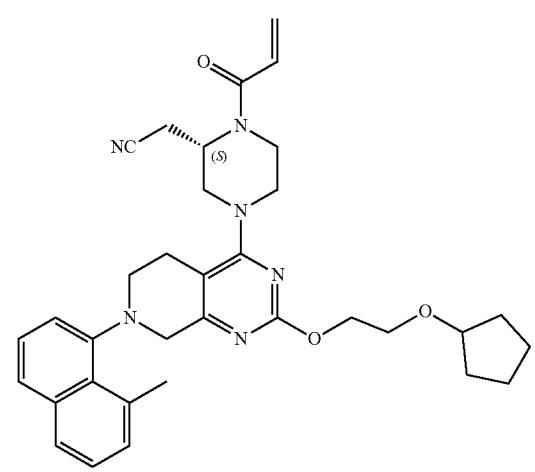
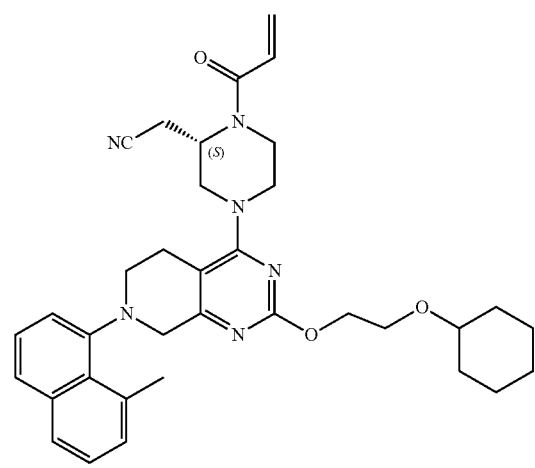
64
-continued
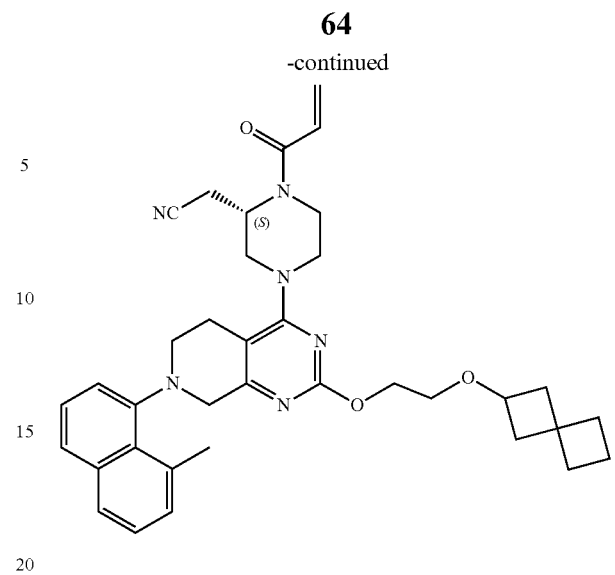
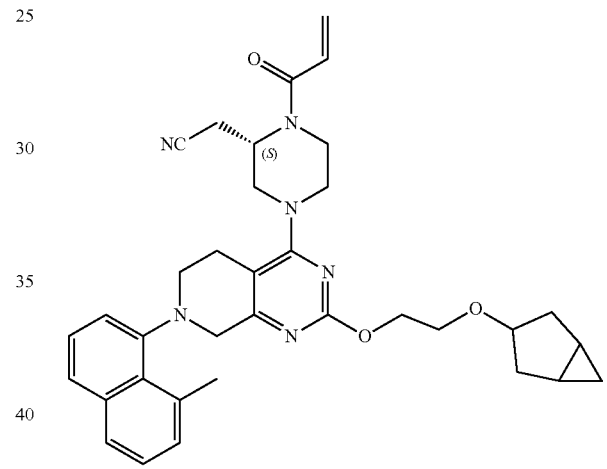
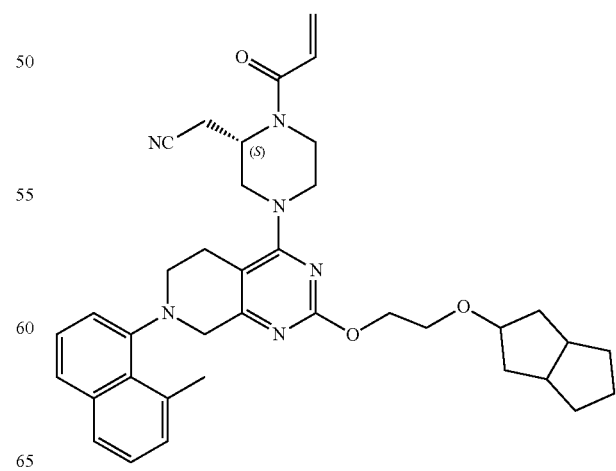

65
-continued
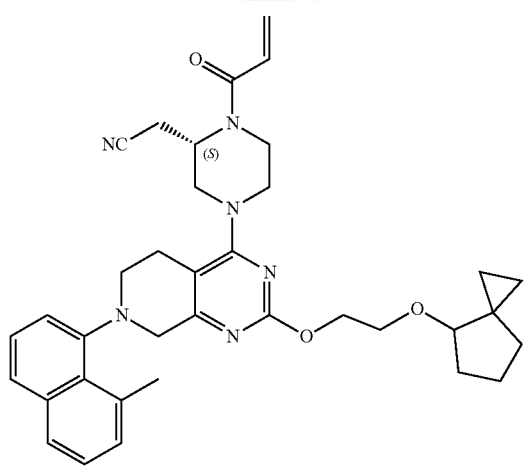
66
-continued
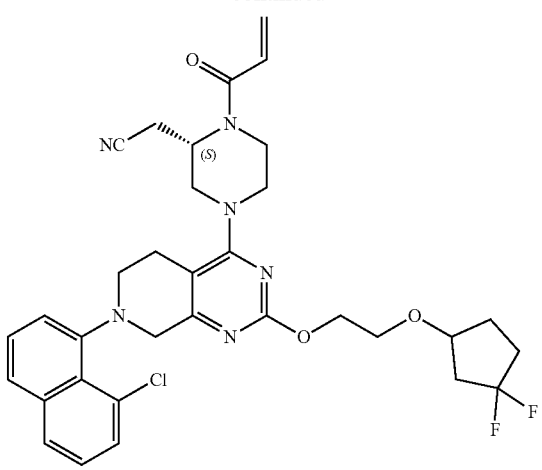
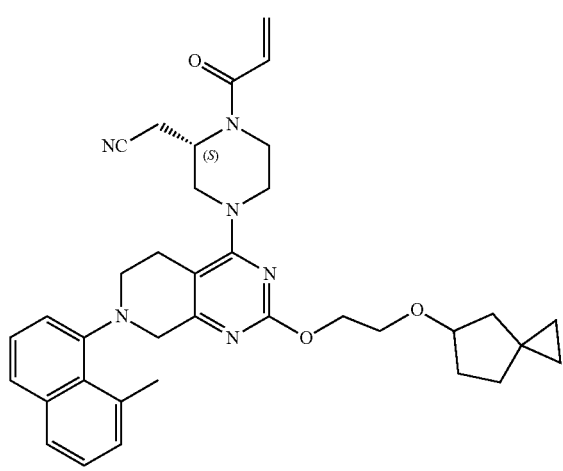
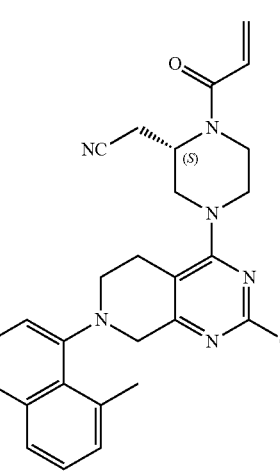
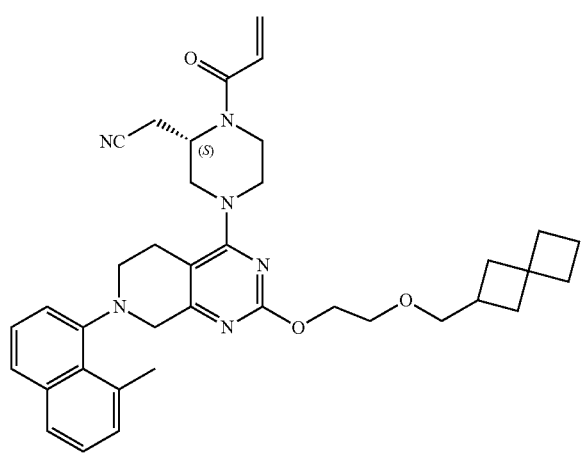
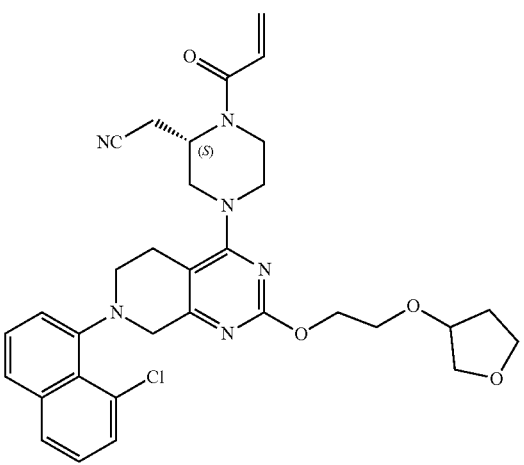

67
-continued
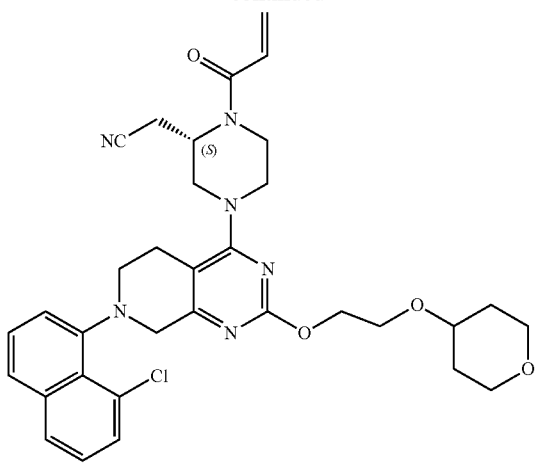
68
-continued
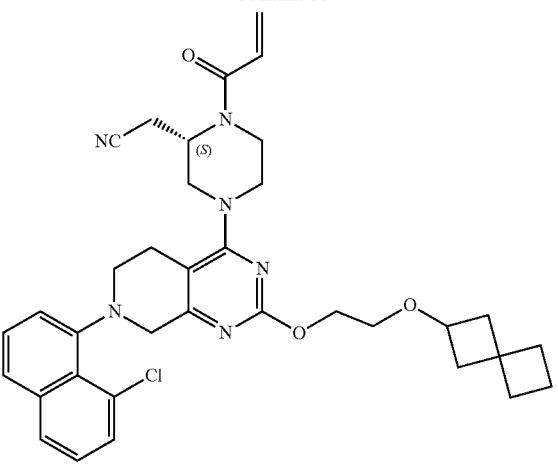
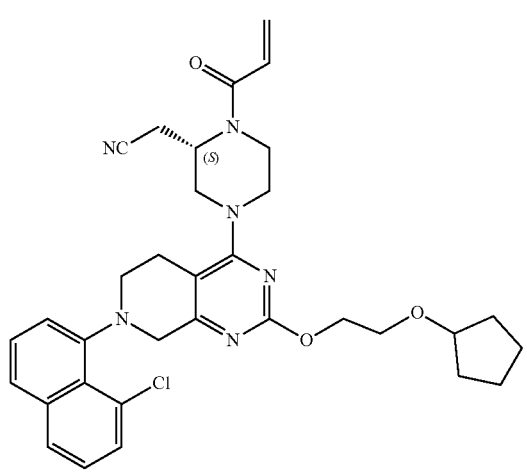
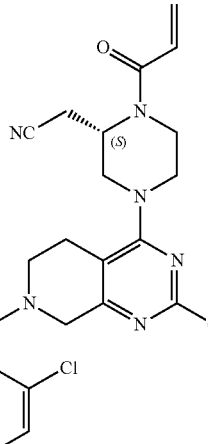
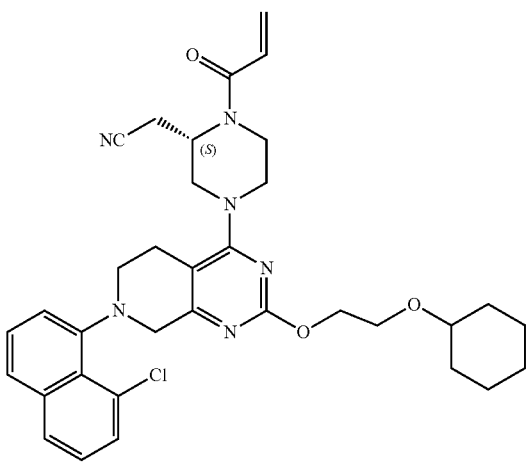
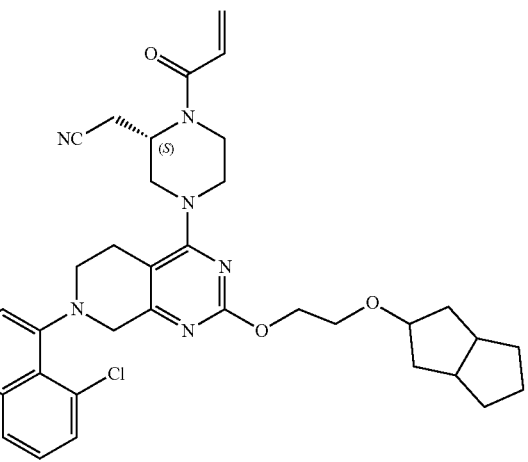

69
-continued
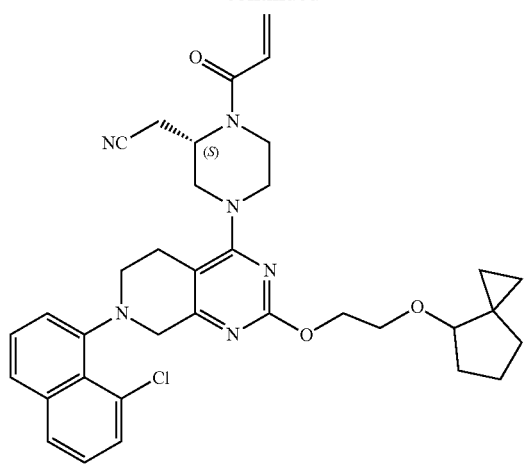
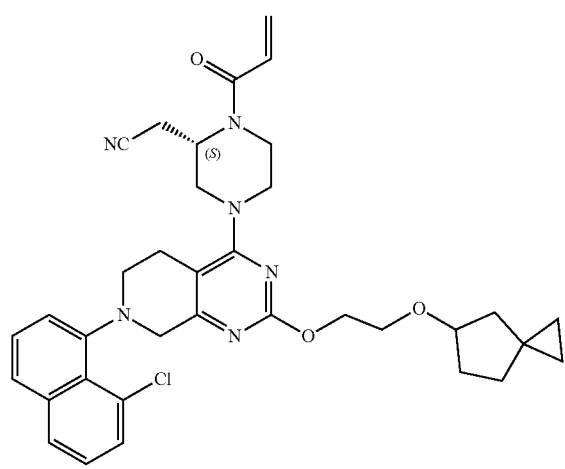
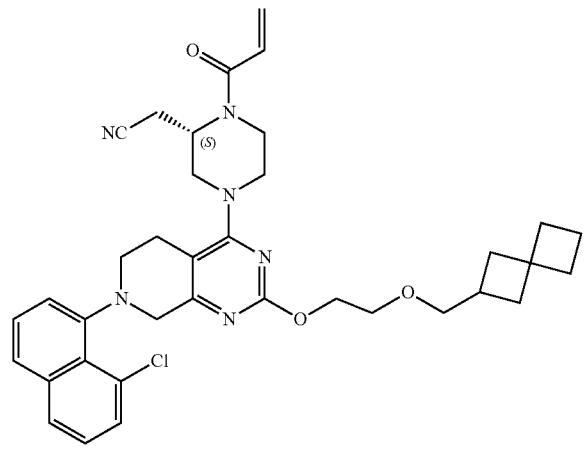
70
-continued
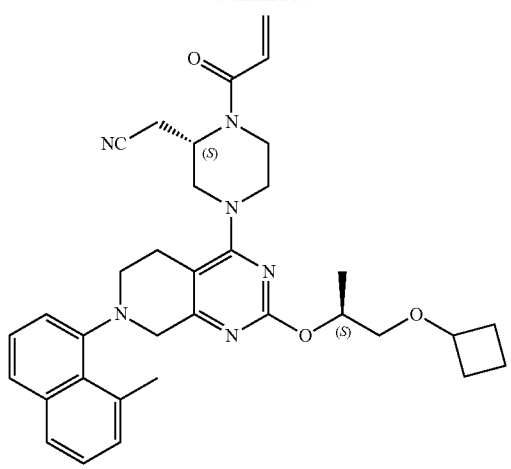
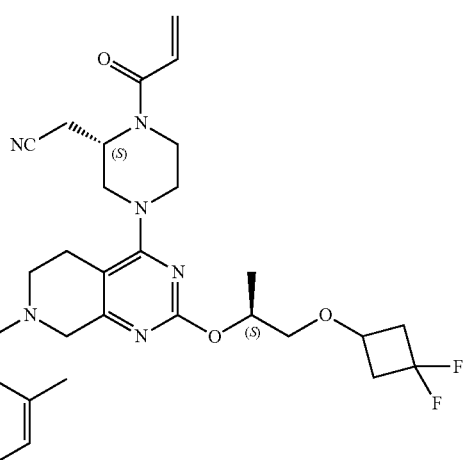
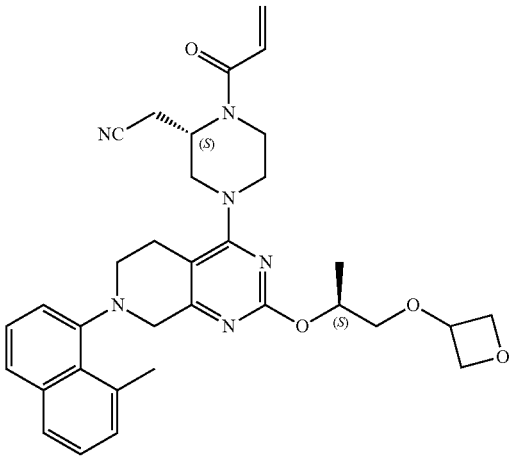

71
-continued
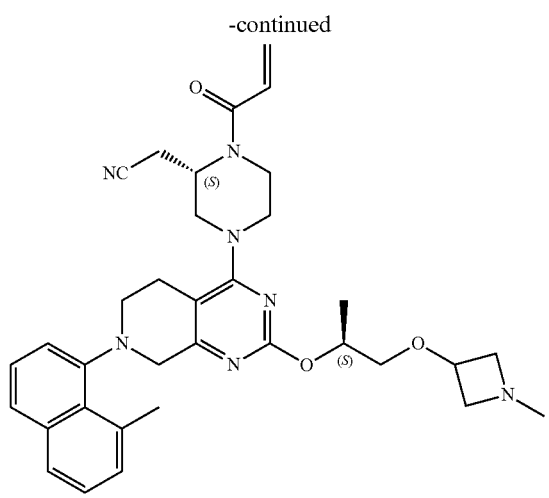
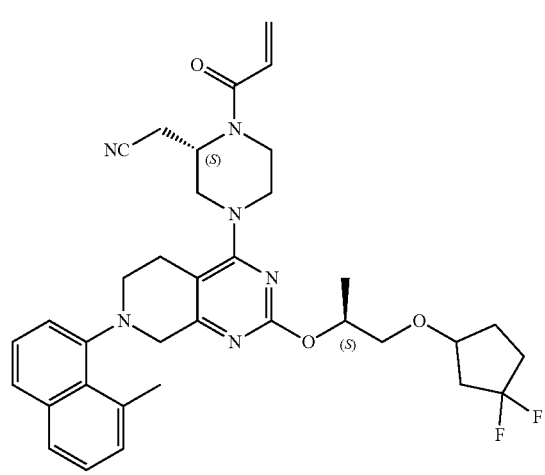
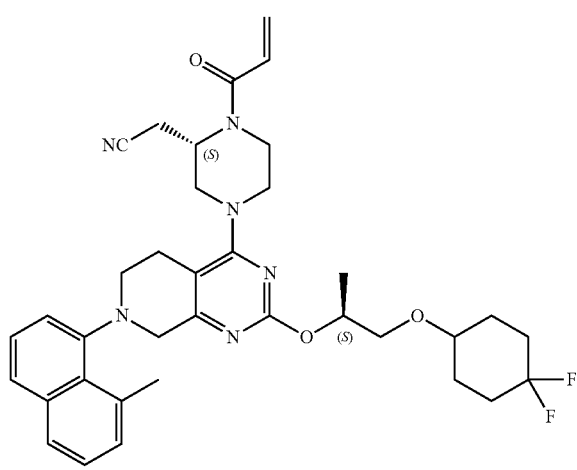
72
-continued
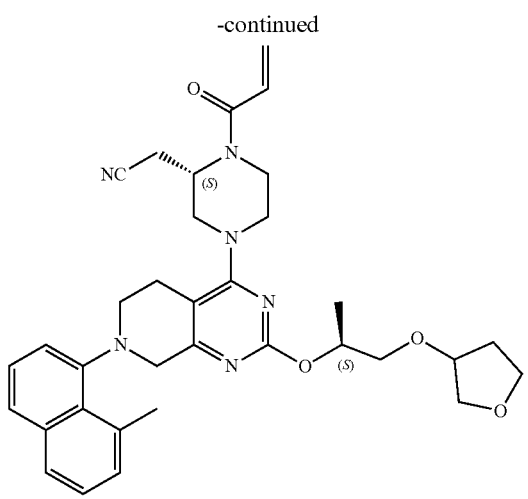
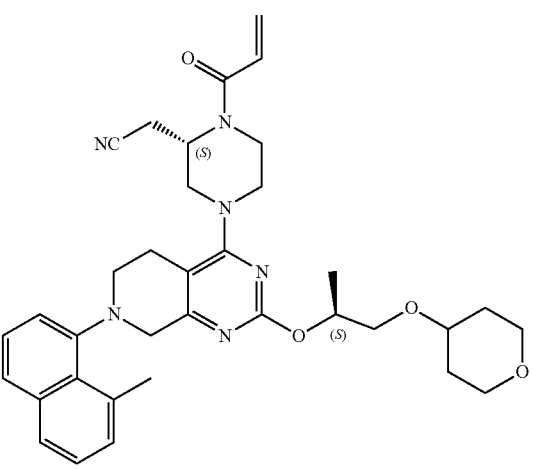
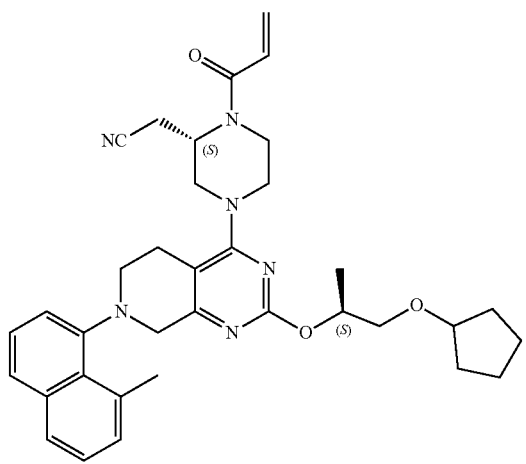

73
-continued
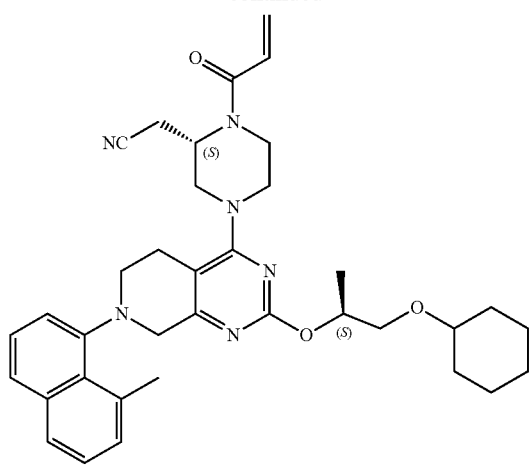
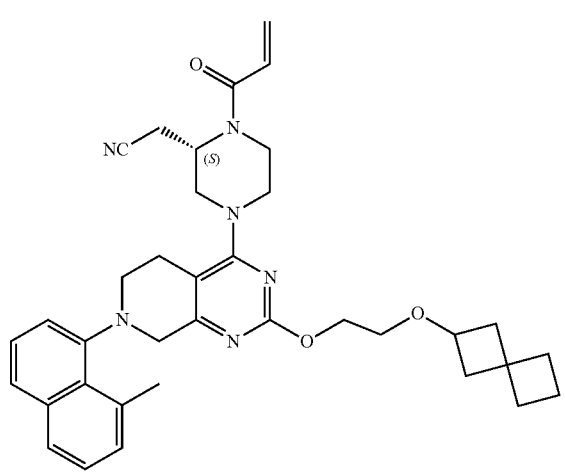
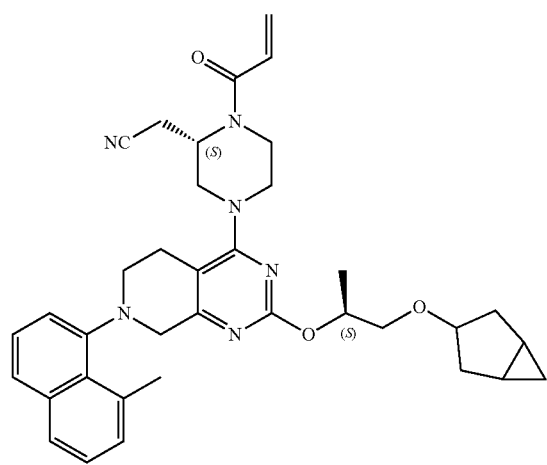
74
-continued
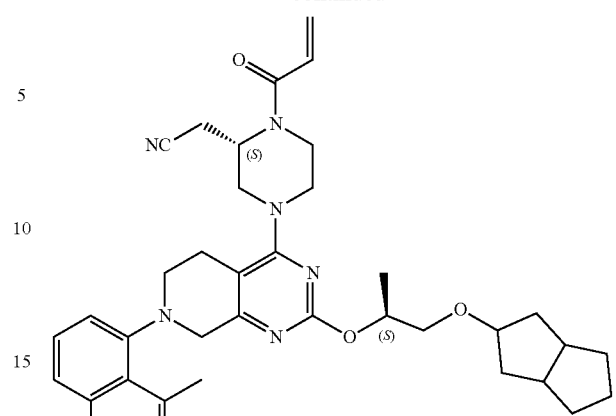
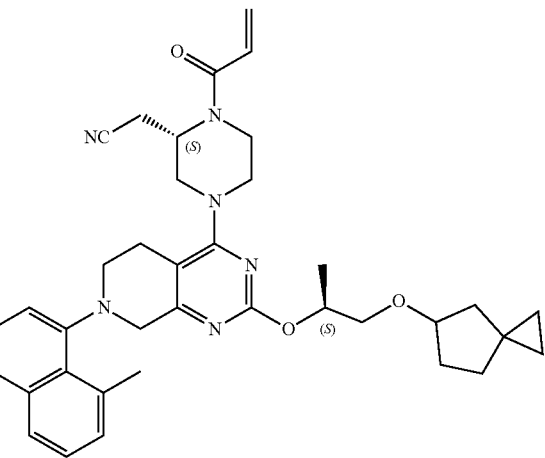

75
-continued
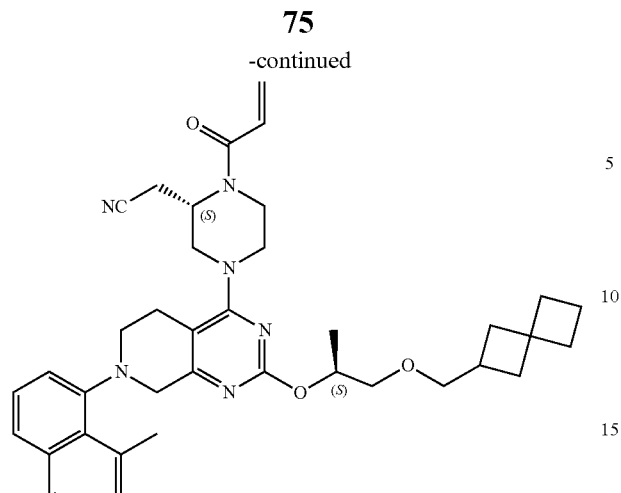
76
-continued
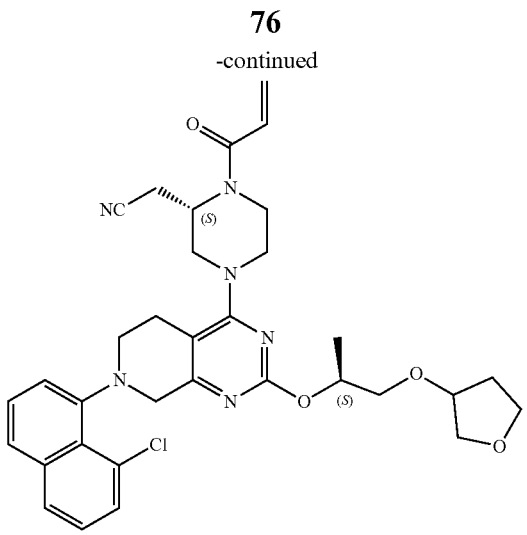
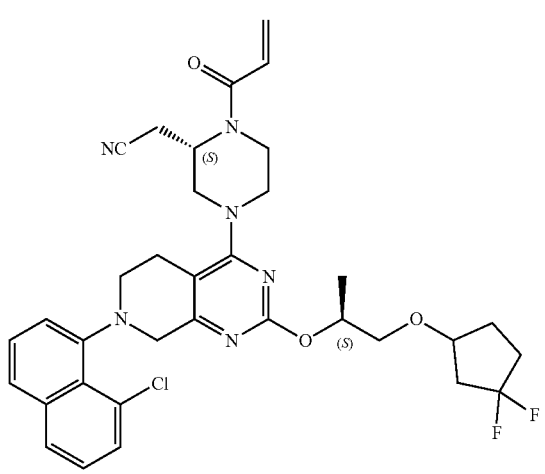
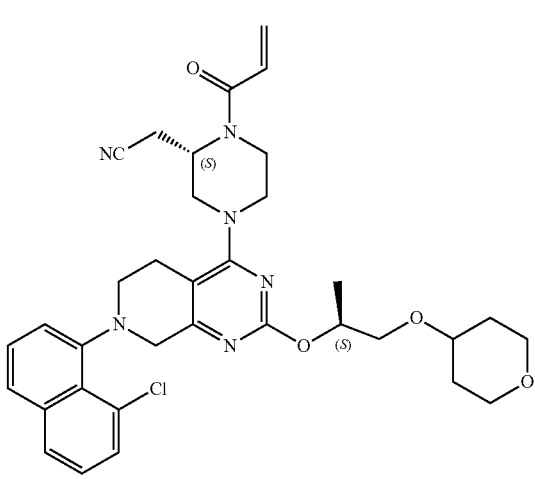
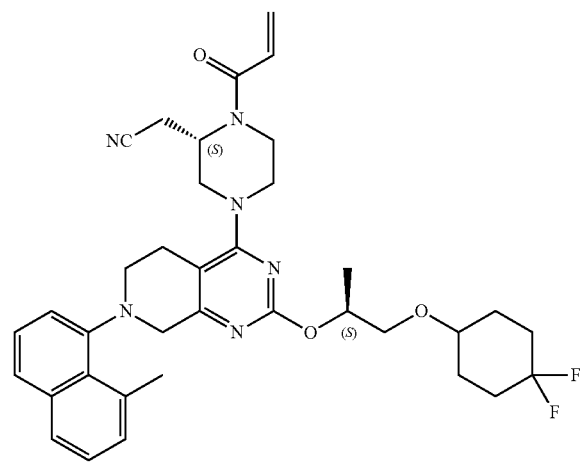
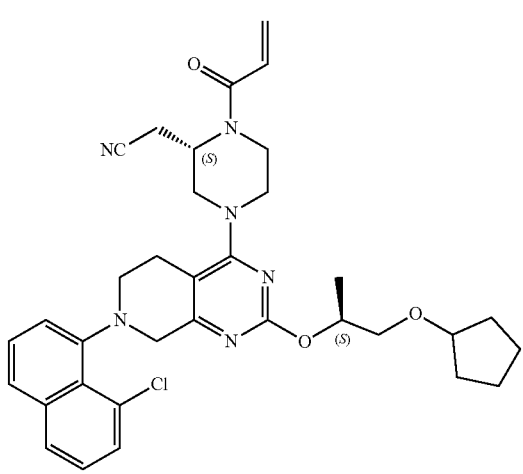

77
-continued
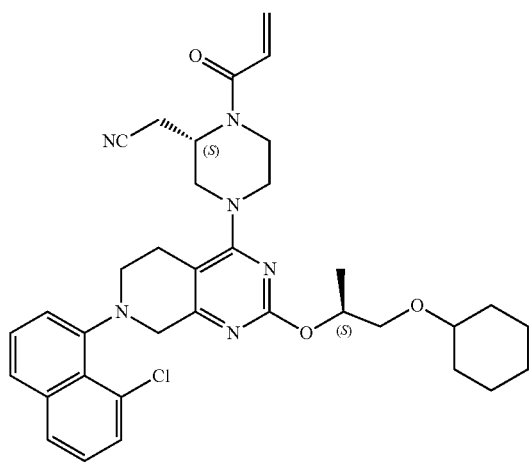
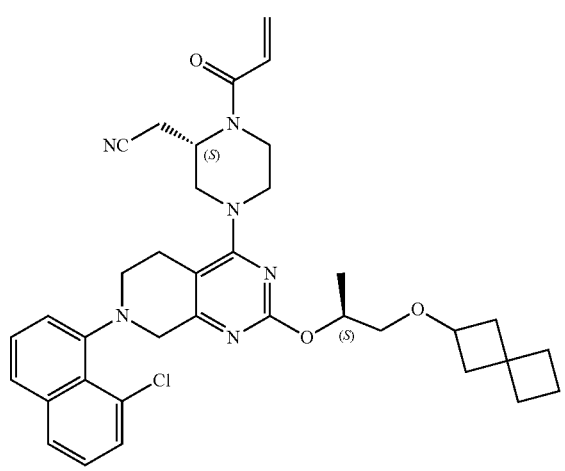
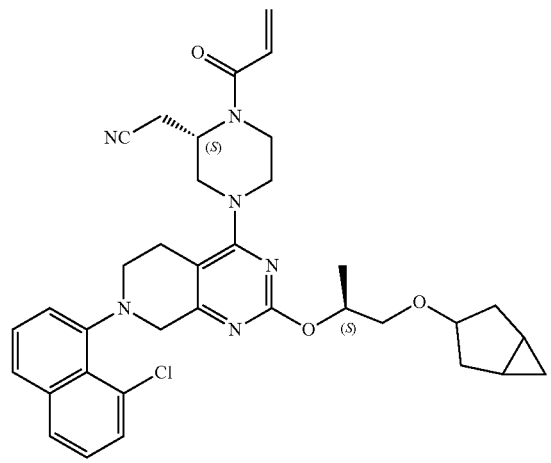
78
-continued
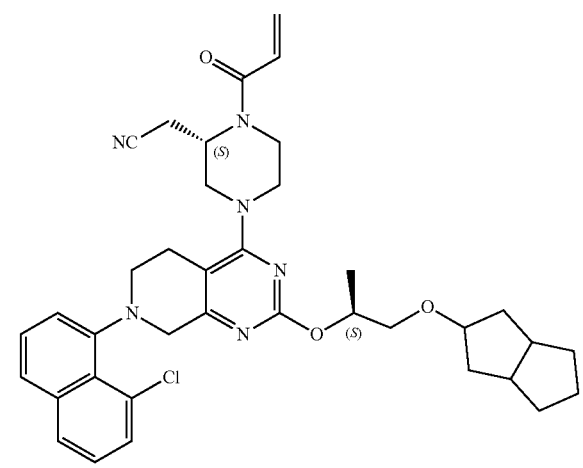
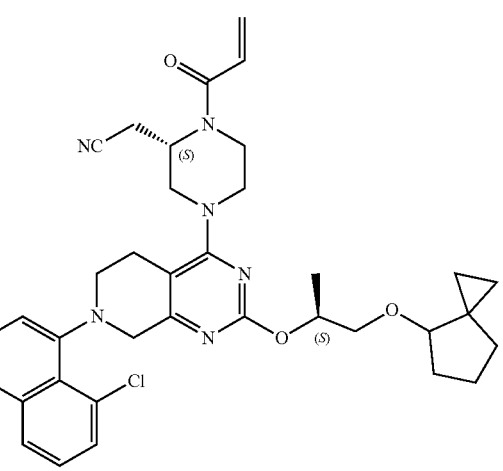
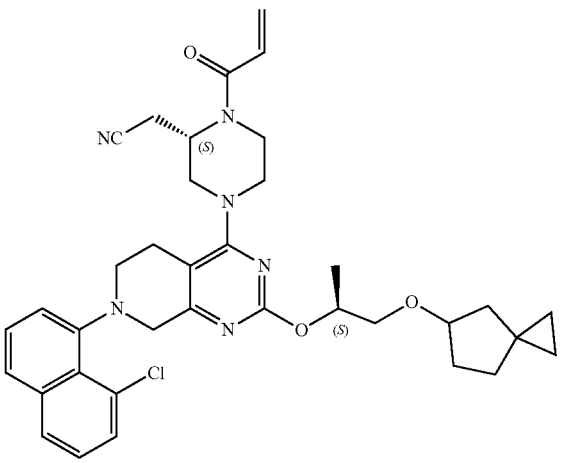

79
-continued
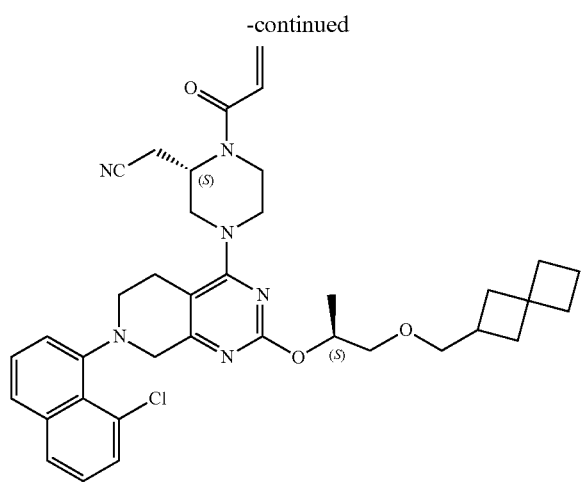
80
-continued
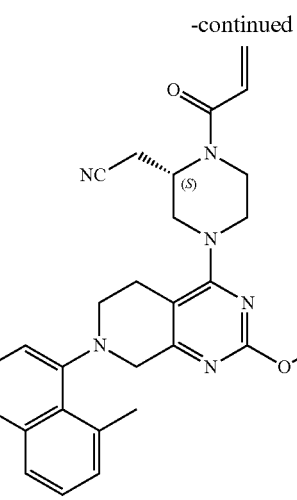
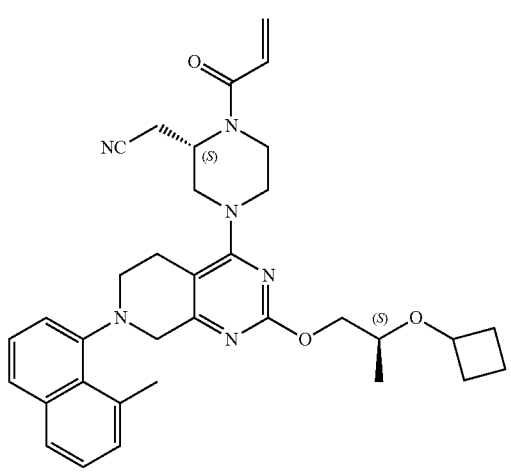
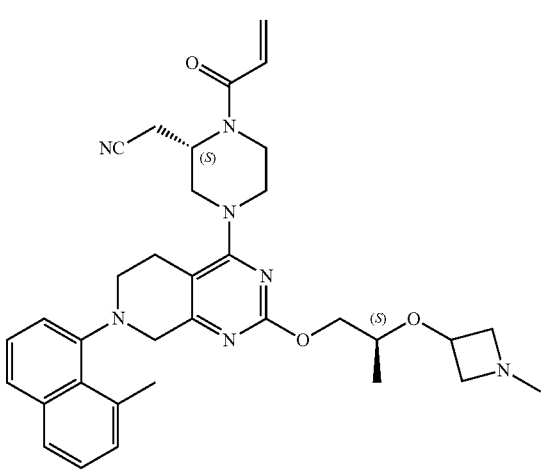
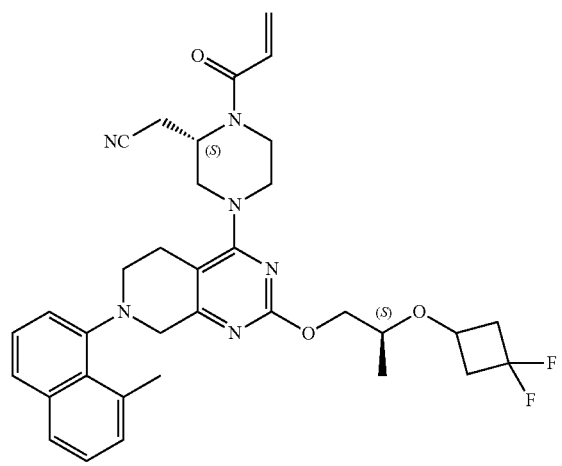
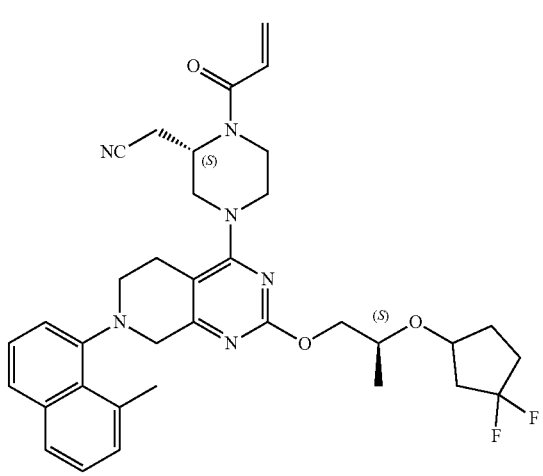

81
-continued
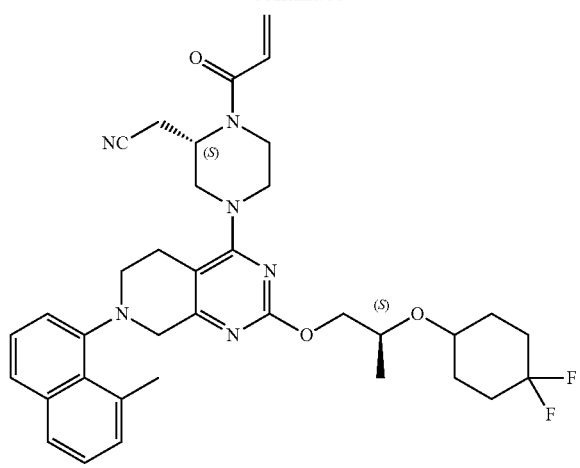
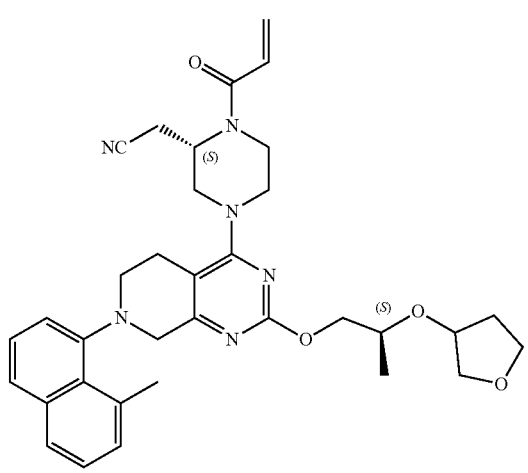
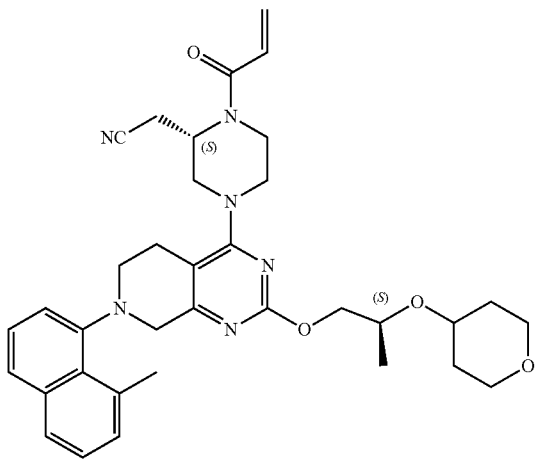
82
-continued
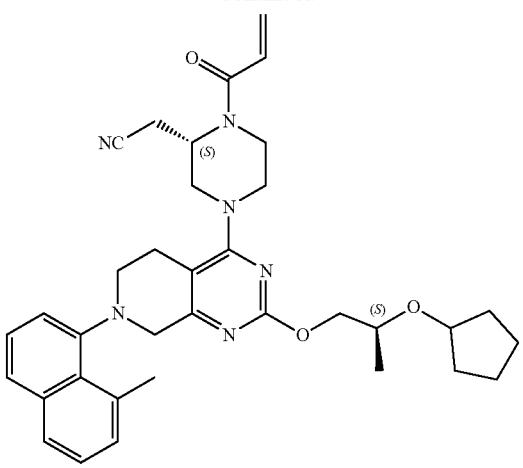
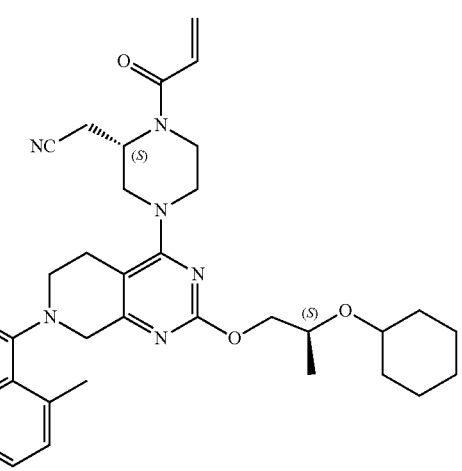
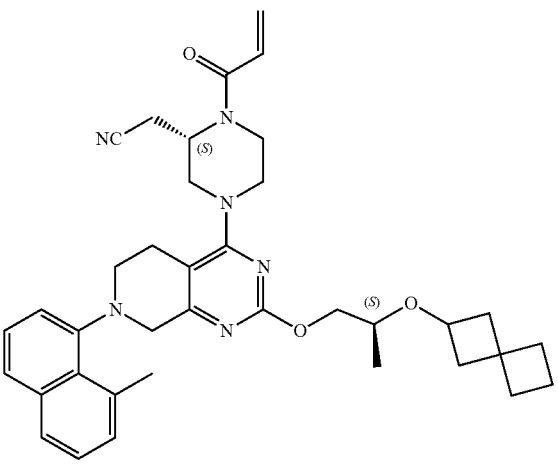

83
-continued
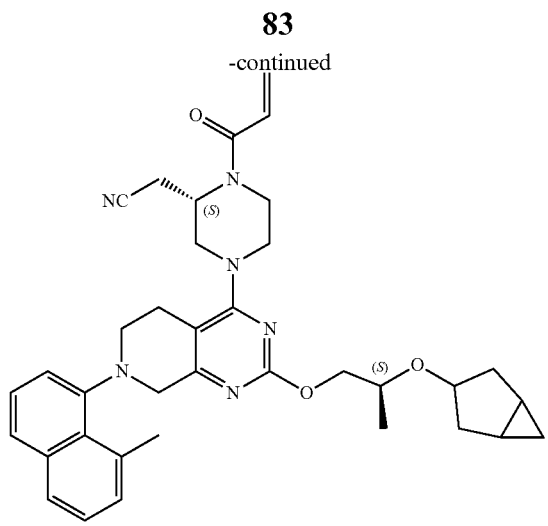
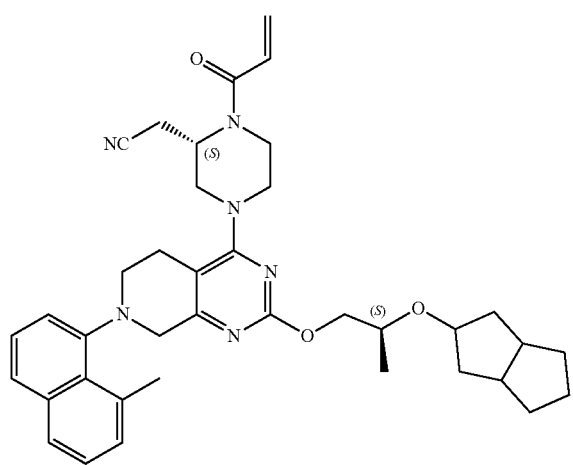
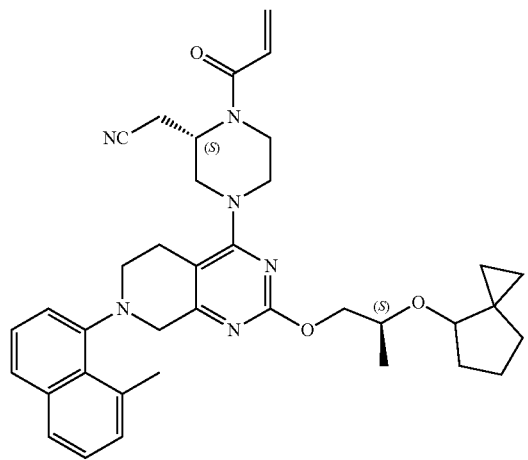
84
-continued
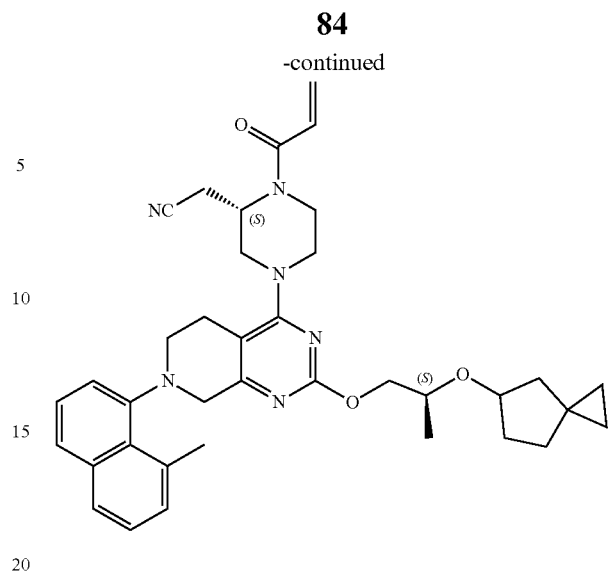
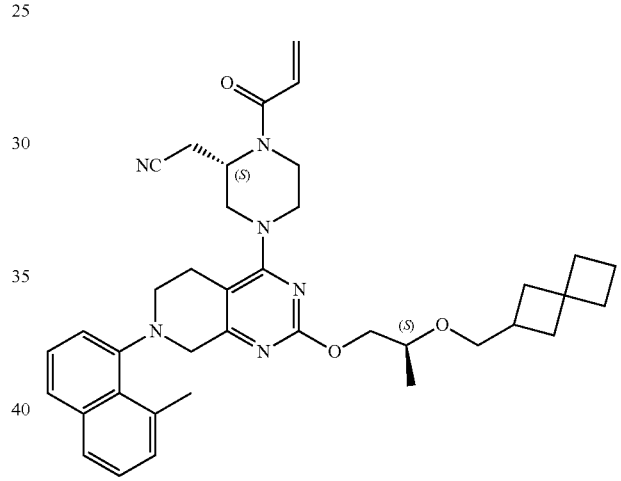
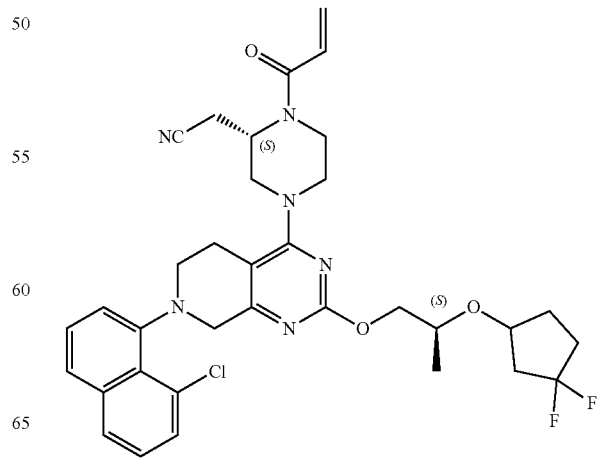

-continued
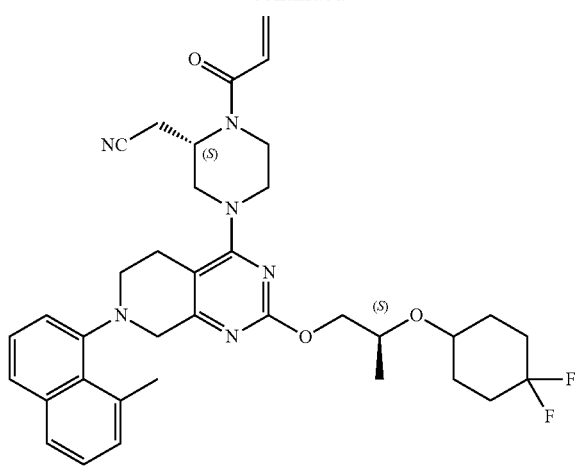
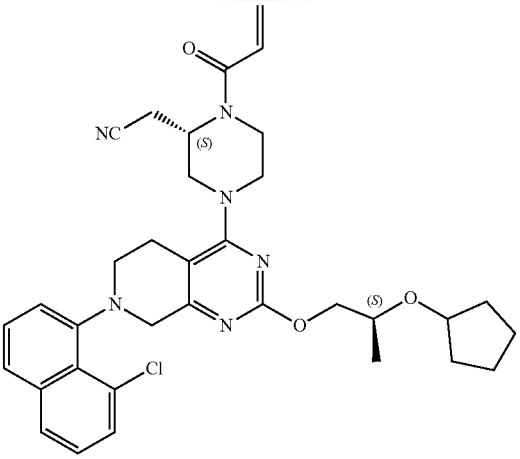
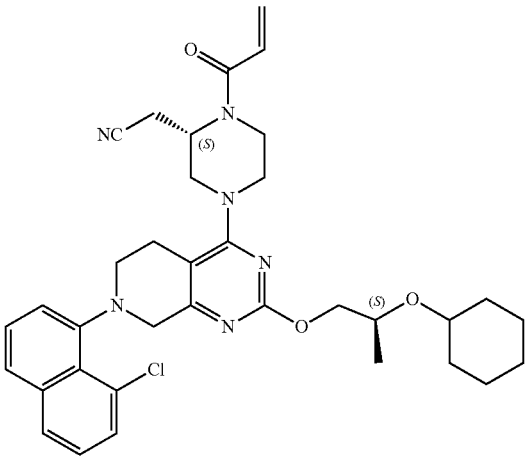
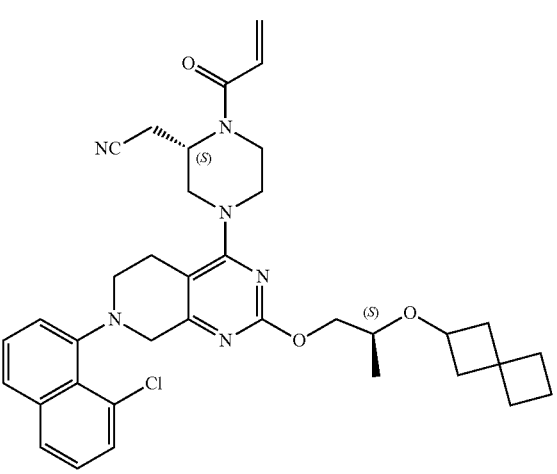

87
-continued
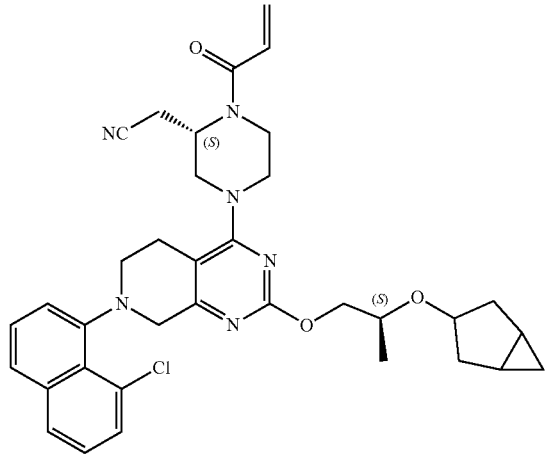
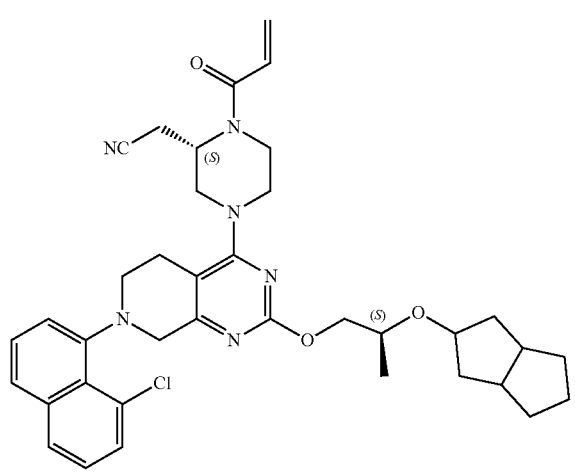
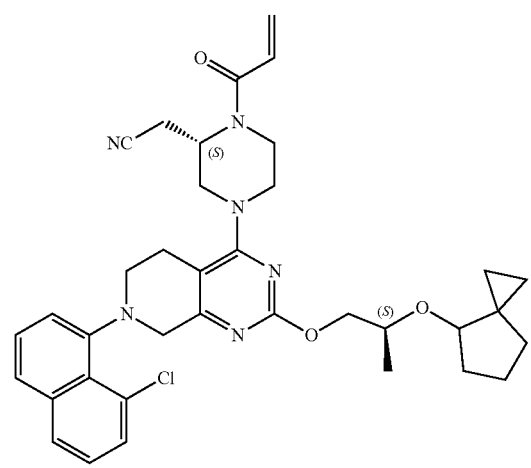
88
-continued
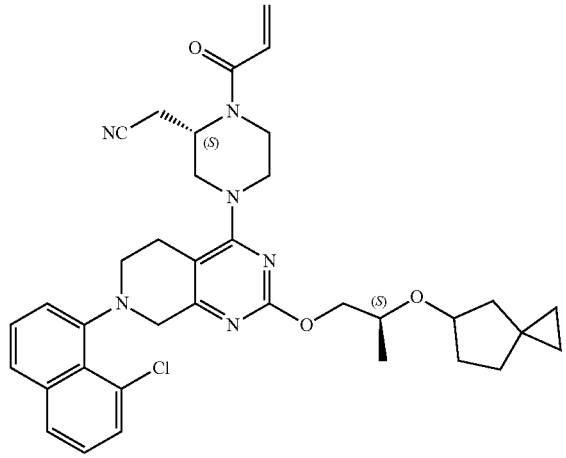
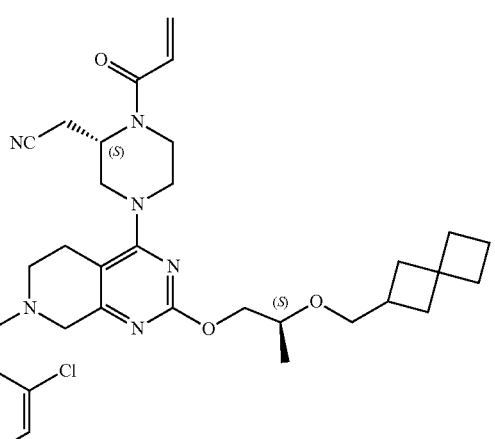
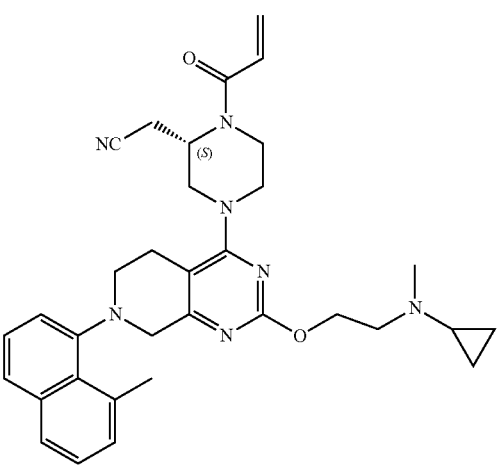

89
-continued
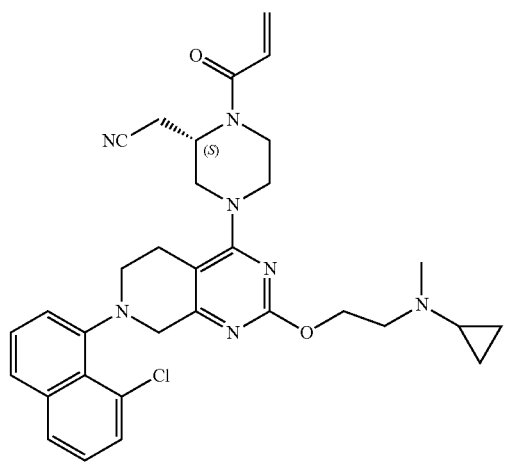
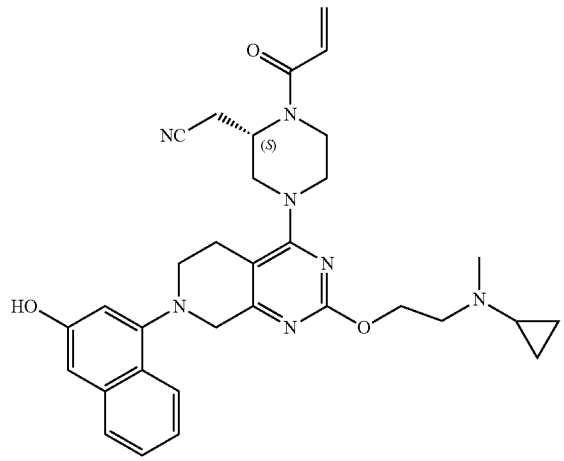
90
-continued

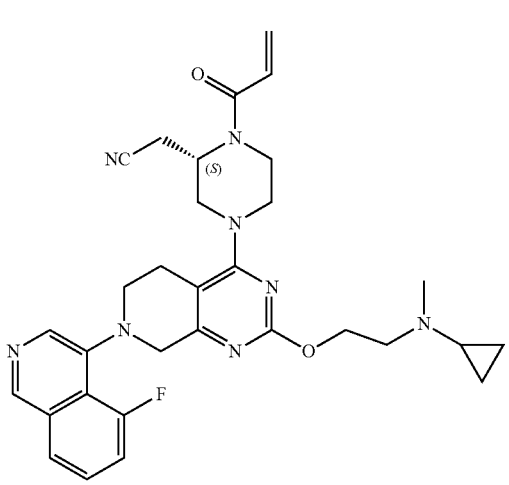
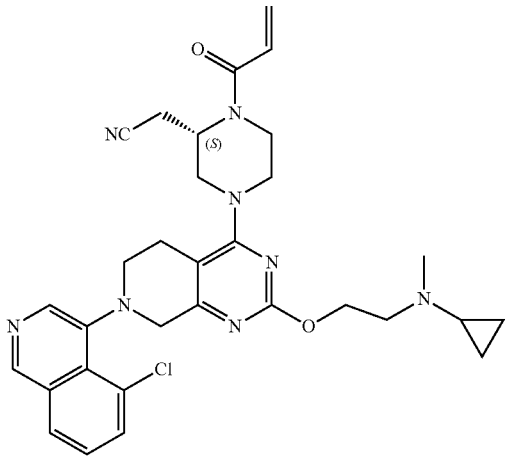

91
-continued
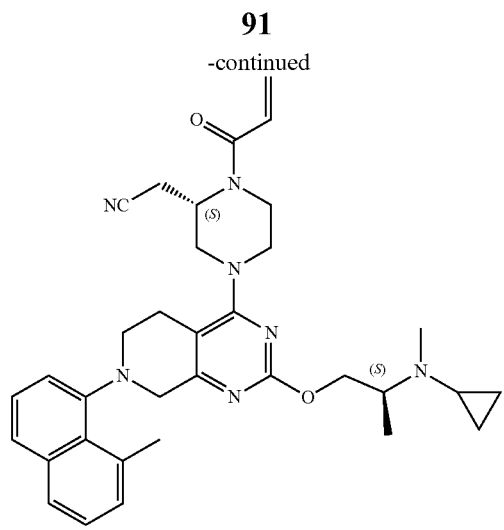
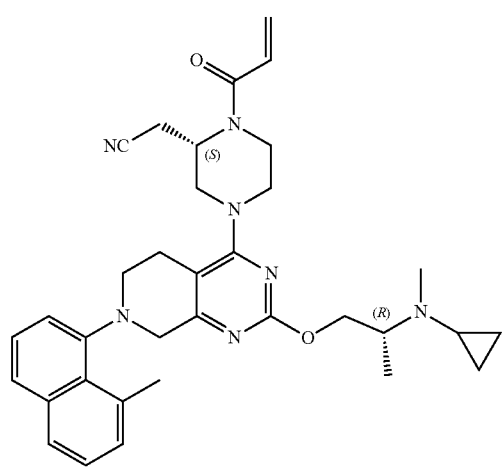
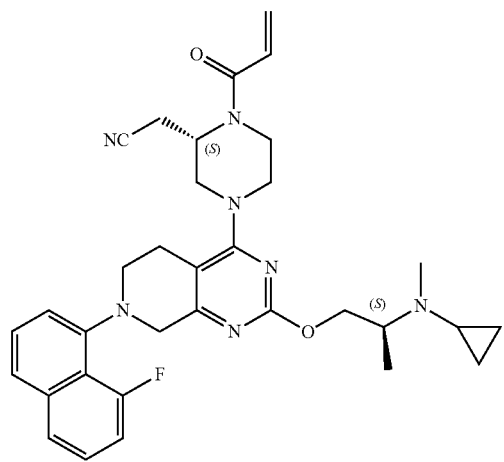
92
-continued
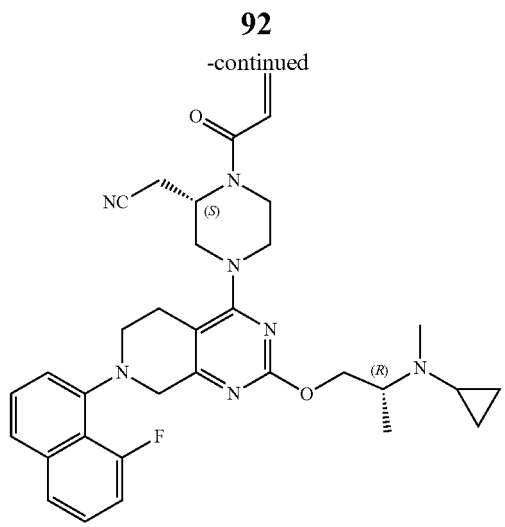
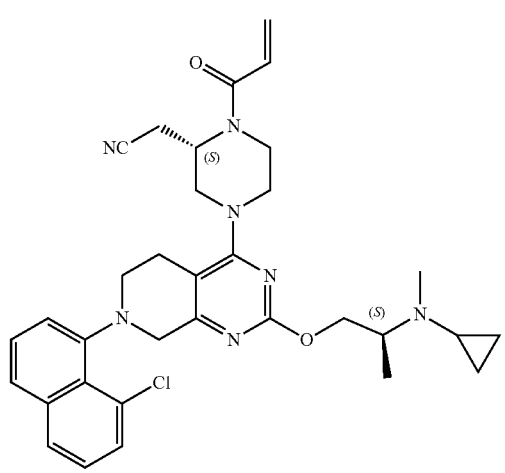
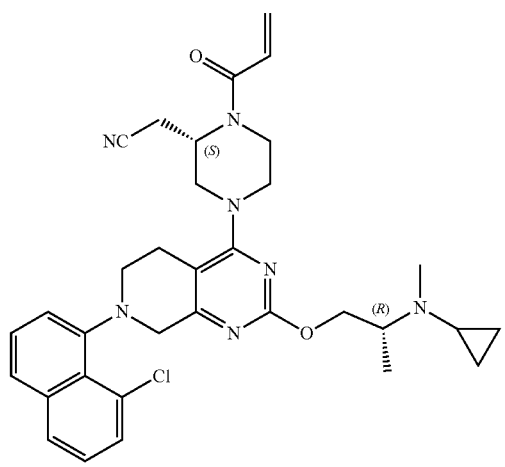

93
-continued
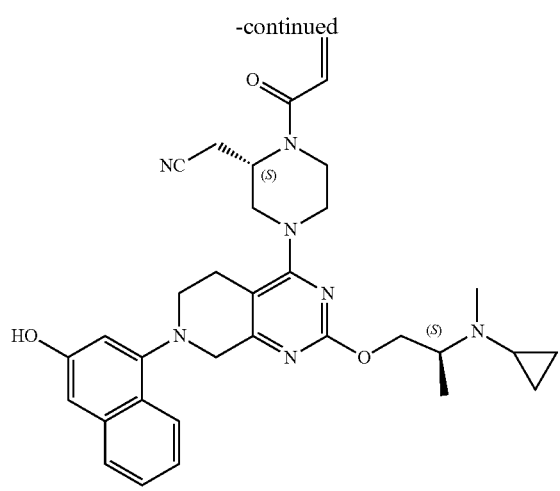
94
-continued
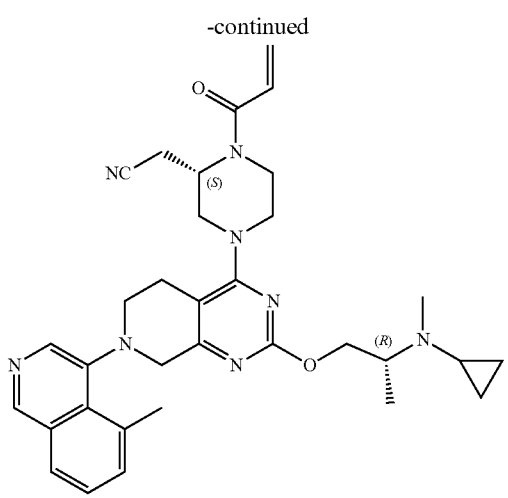
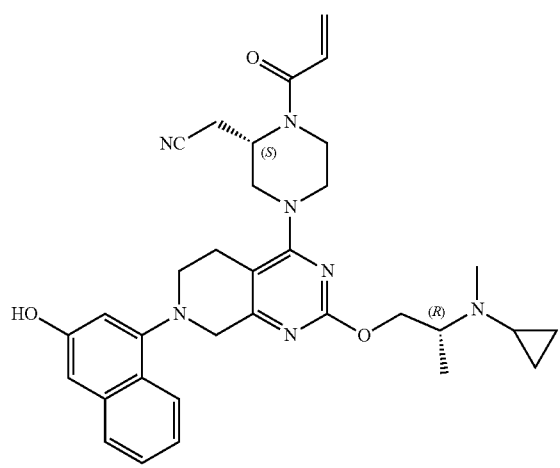
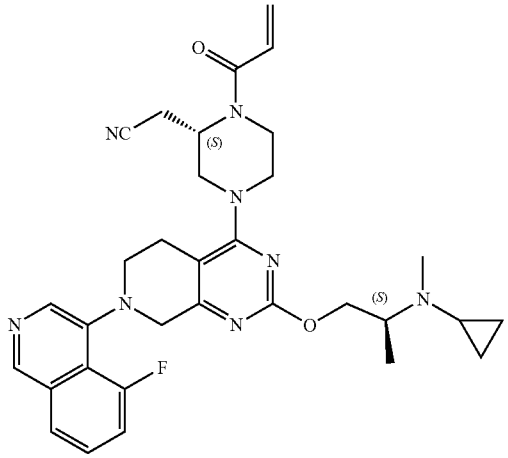
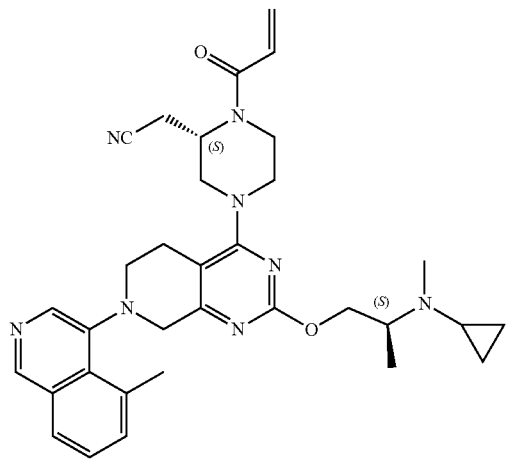
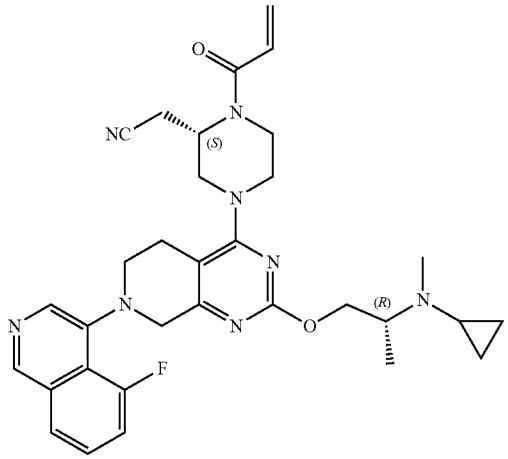

95
-continued
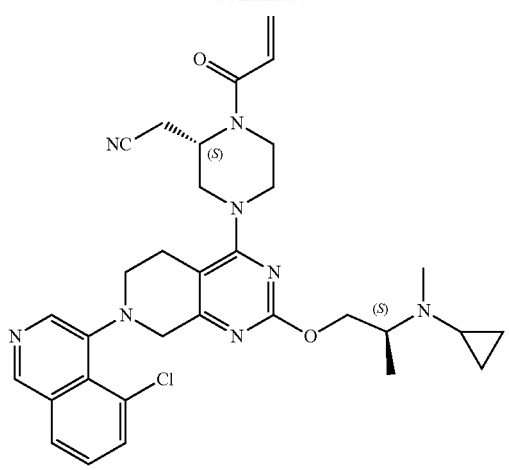
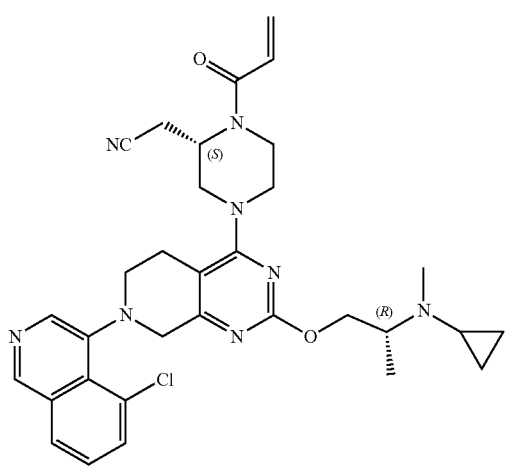
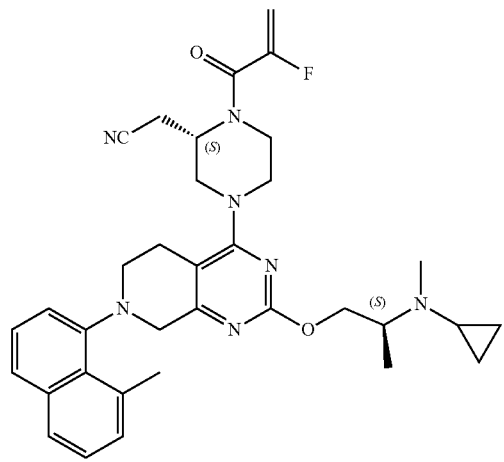
96
-continued
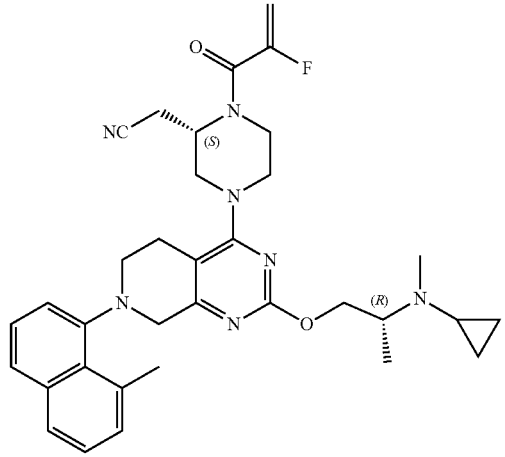
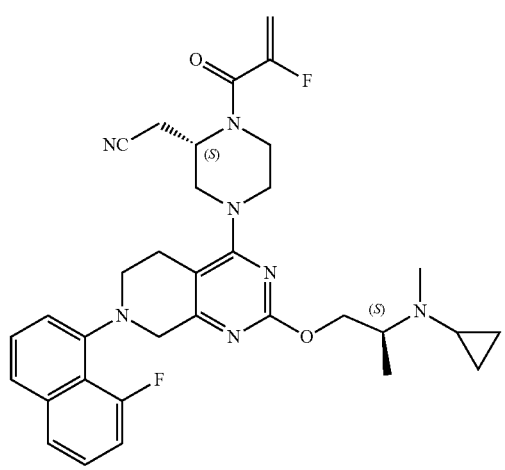

97
-continued
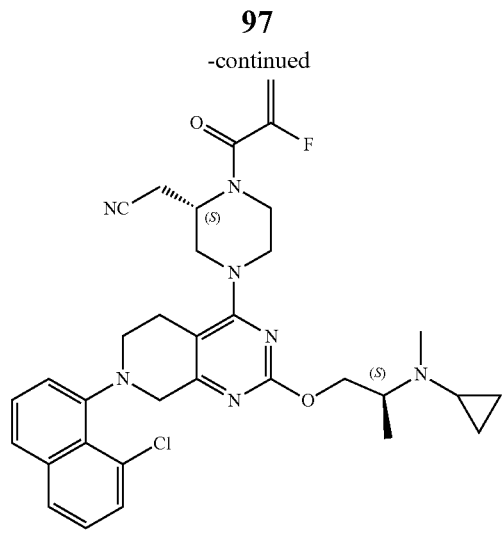
98
-continued
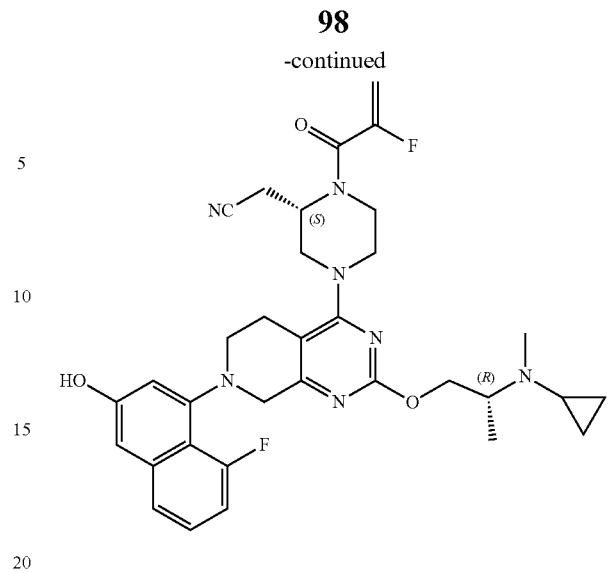
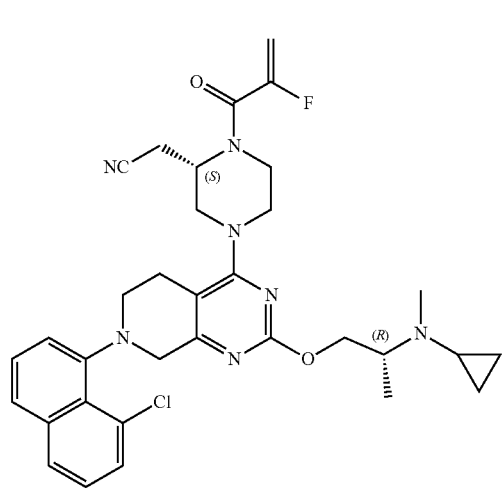
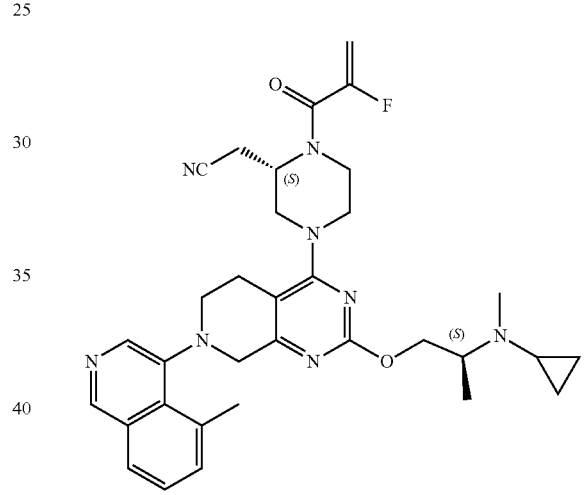
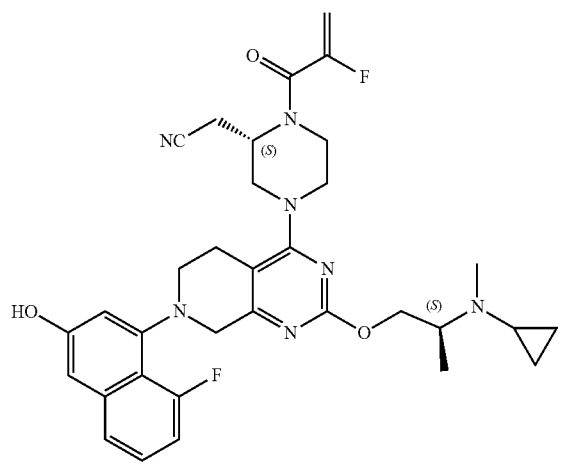
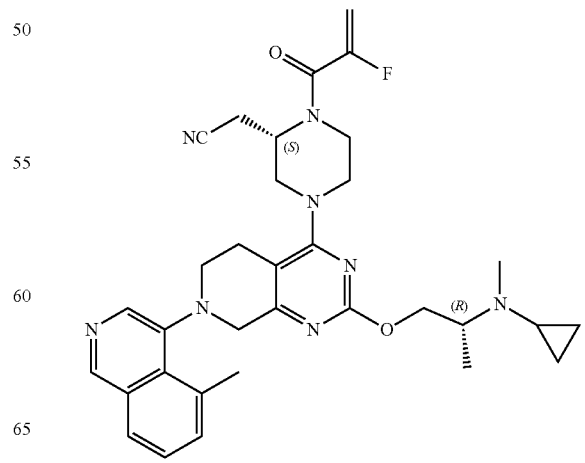

99
-continued
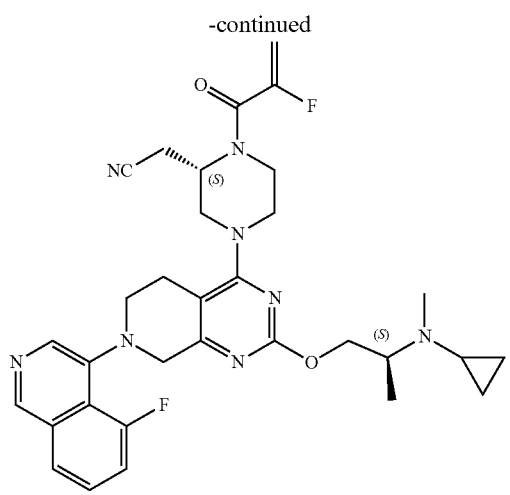
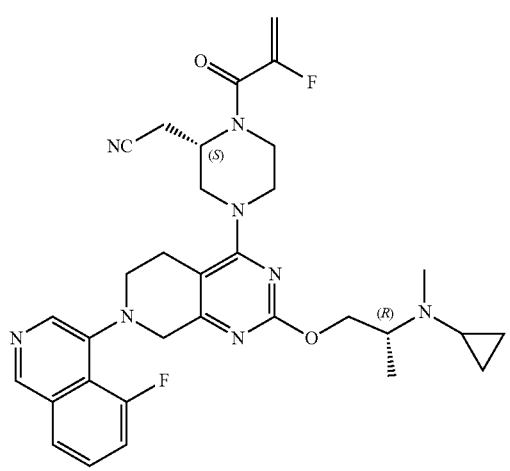
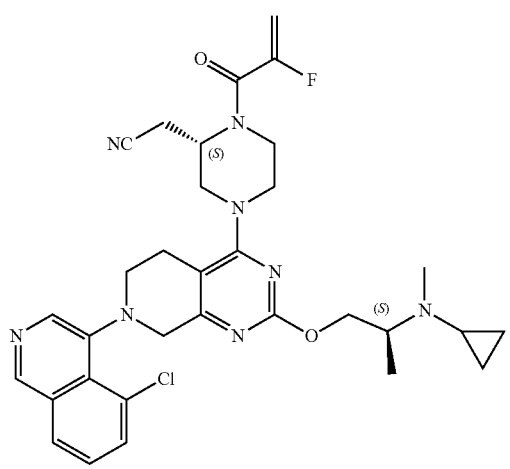
100
-continued
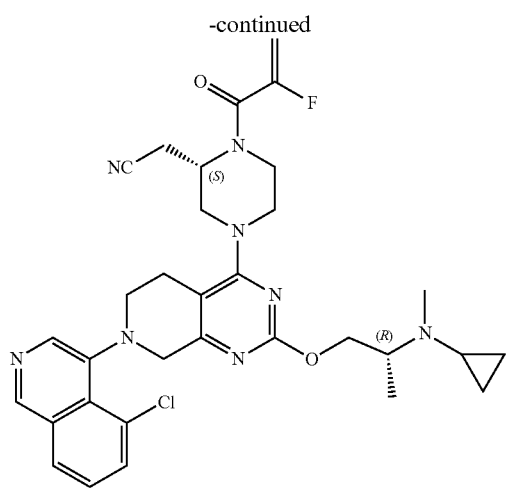
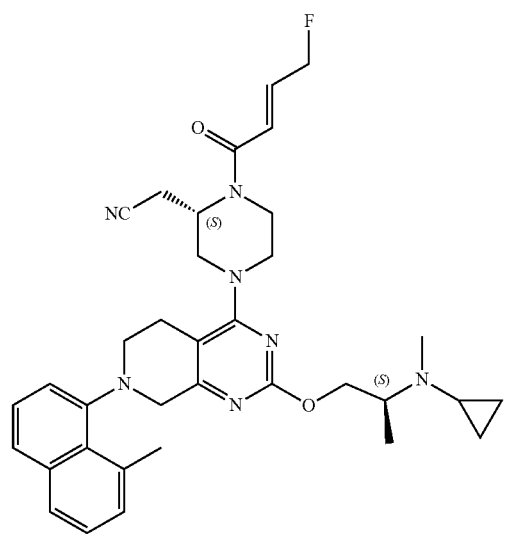
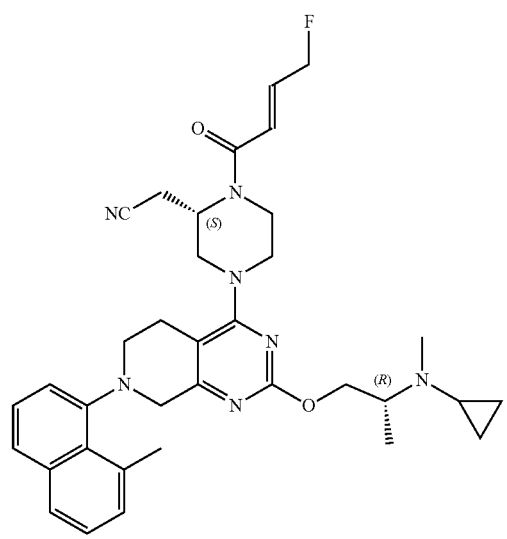

101
-continued
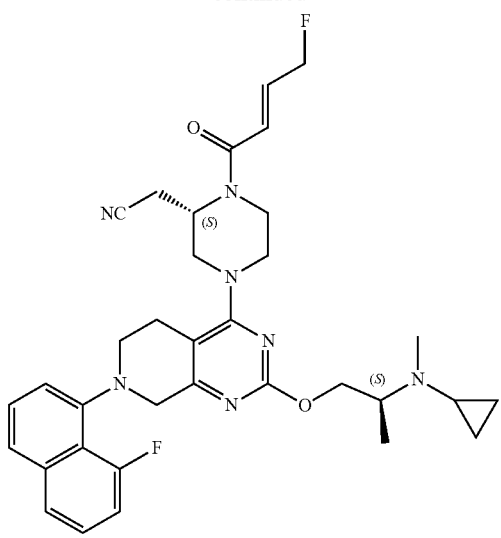
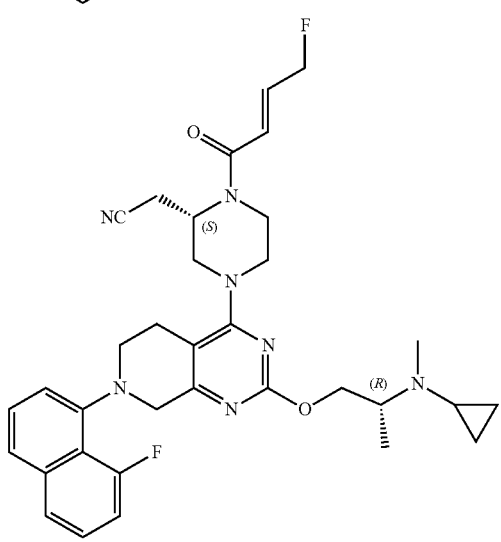
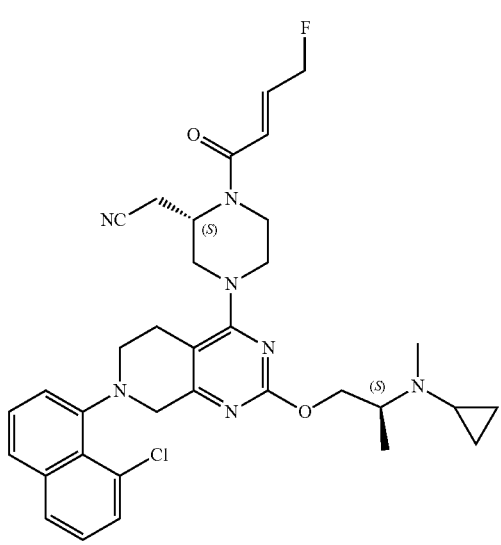
102
-continued
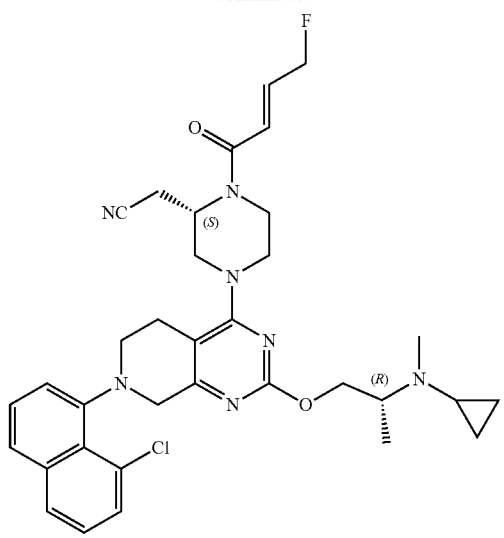
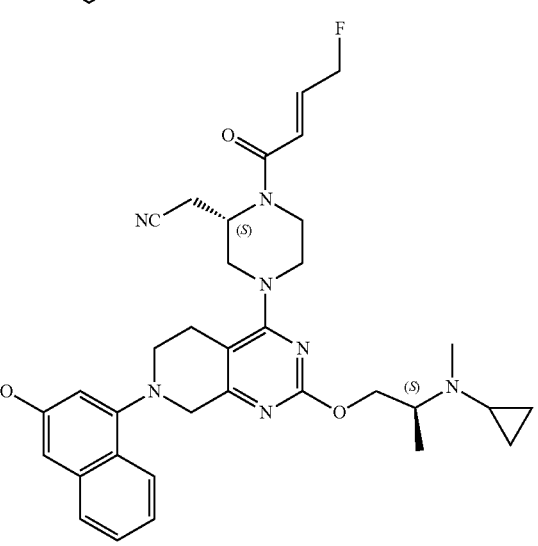
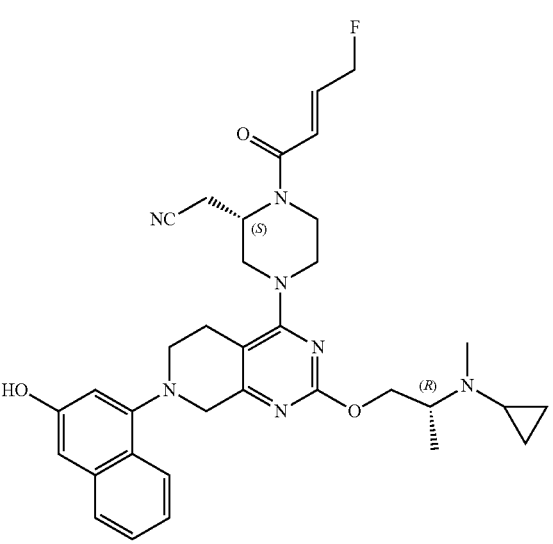

103
-continued
104
-continued
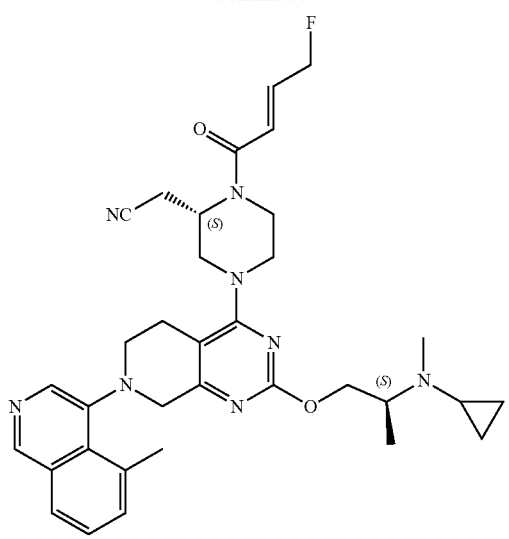
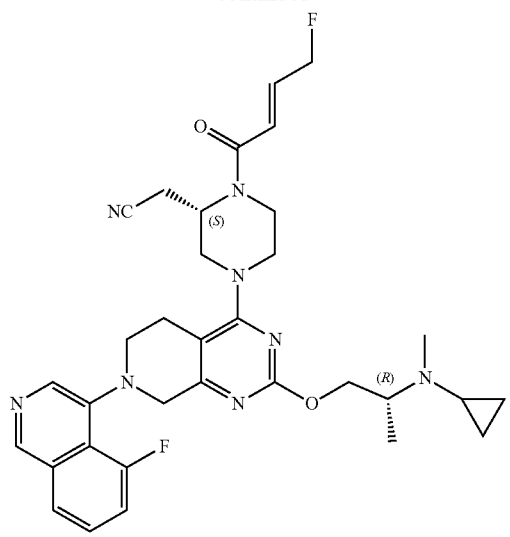
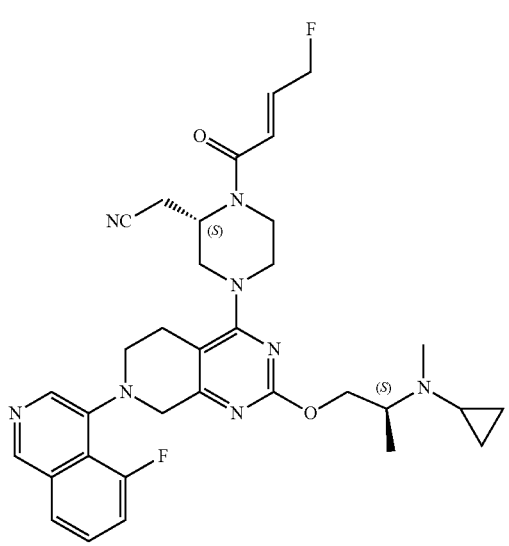

105
-continued
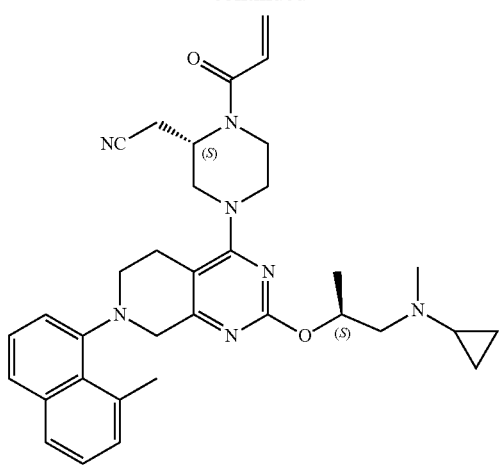
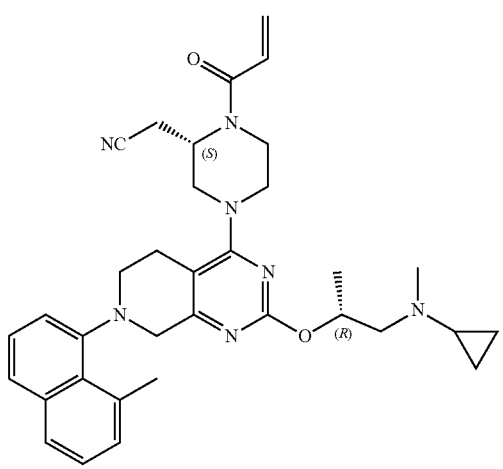
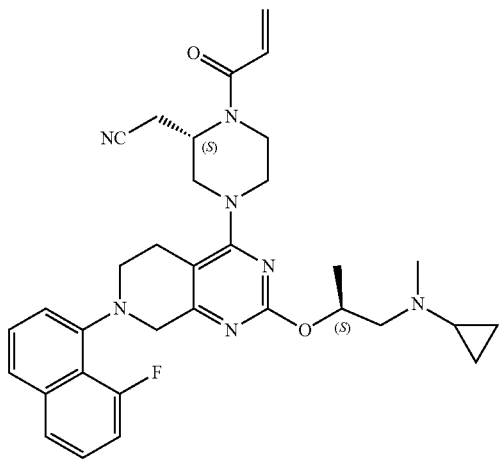
106
-continued
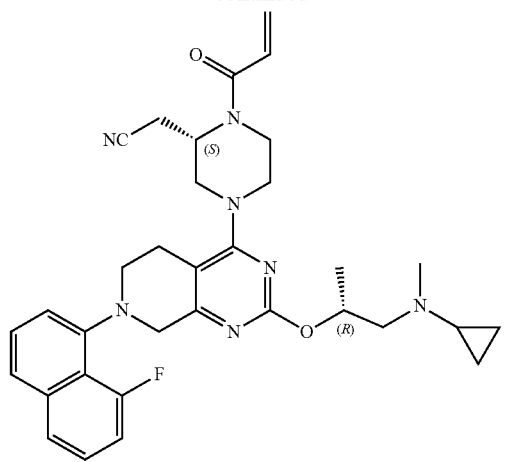
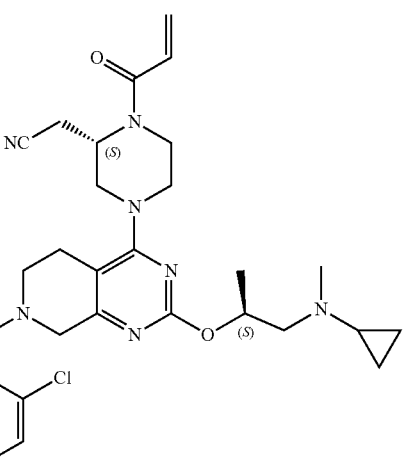
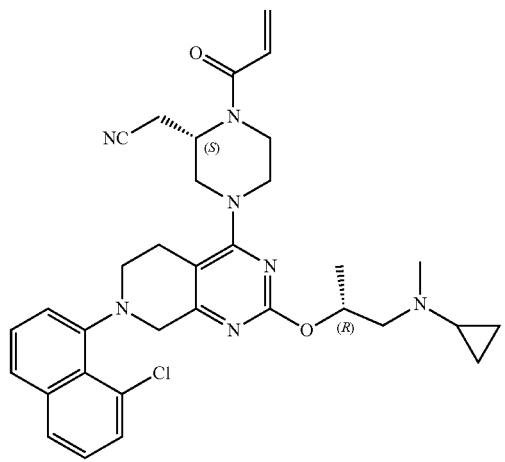

107
-continued
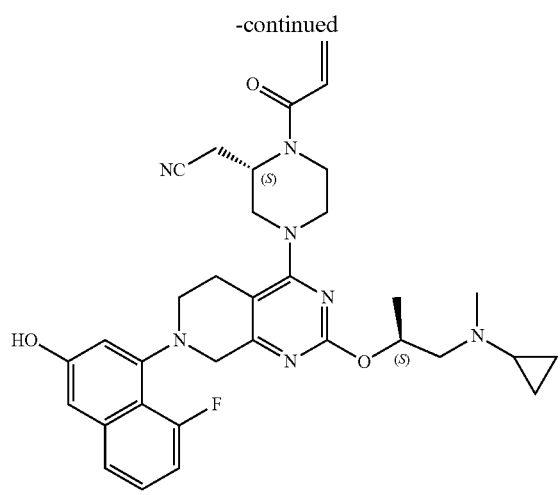
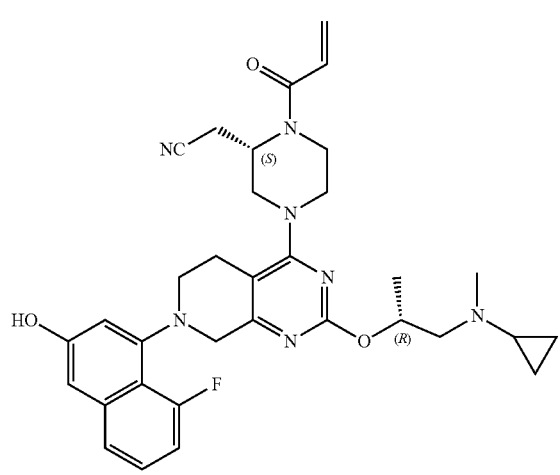
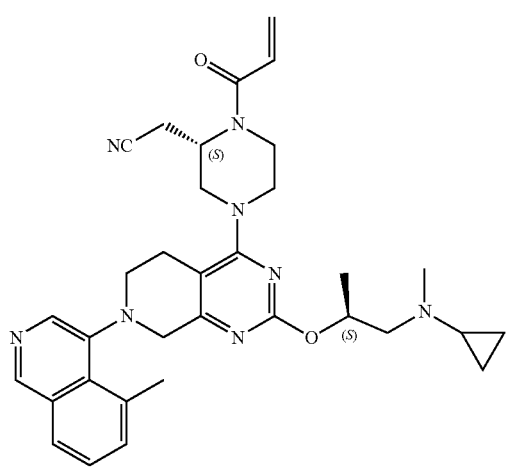
108
-continued
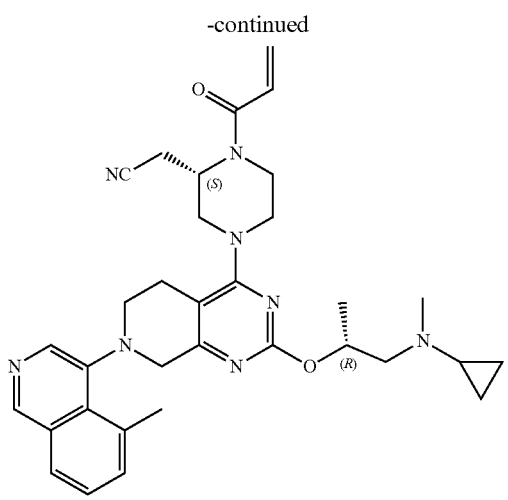
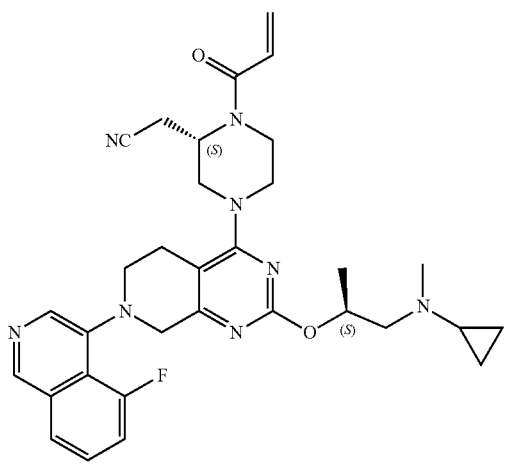
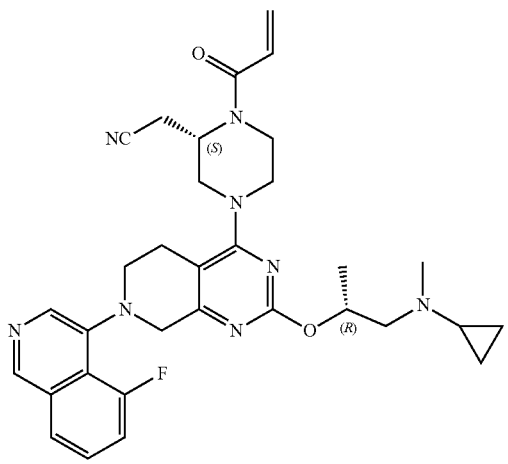

109 -continued
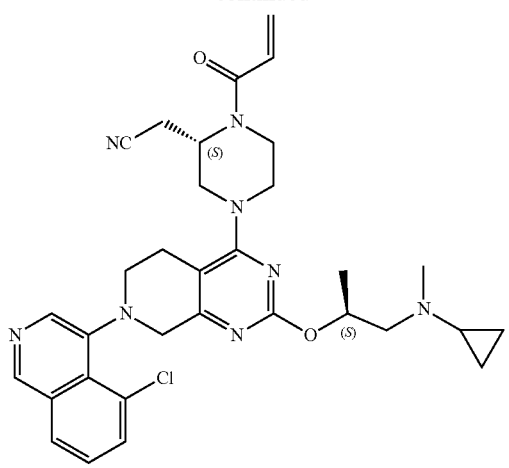
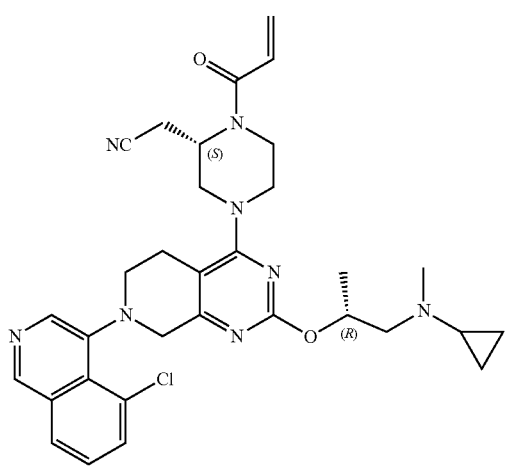
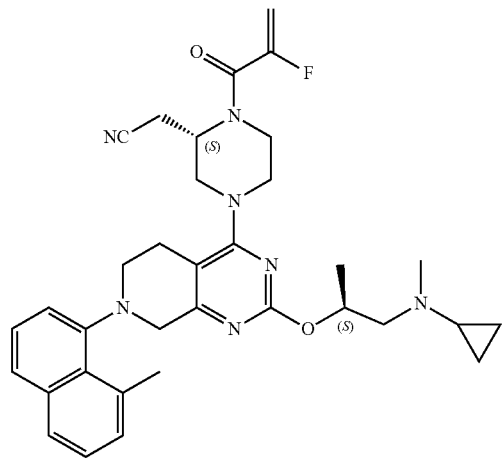
110 -continued
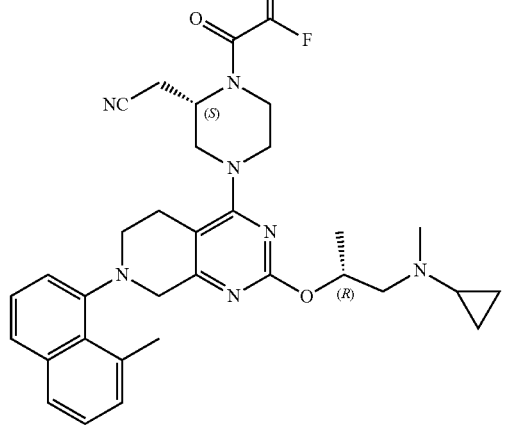
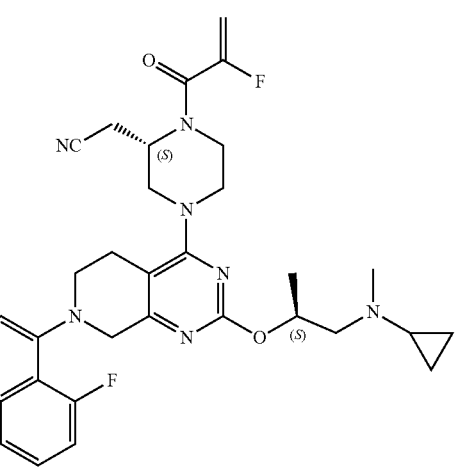
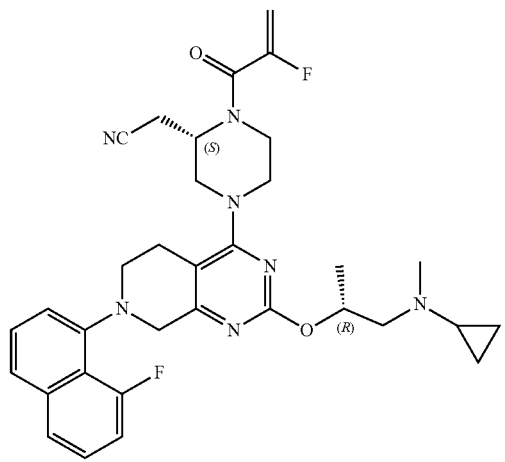

111
-continued
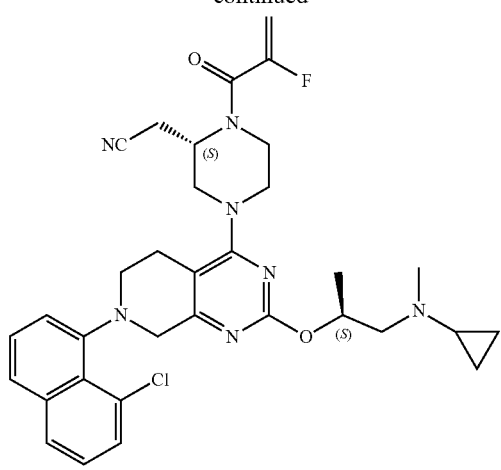
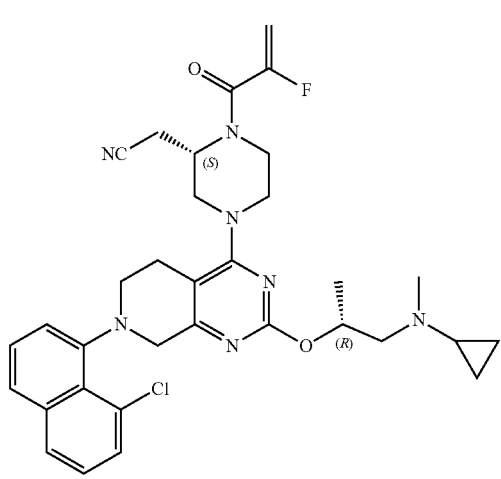
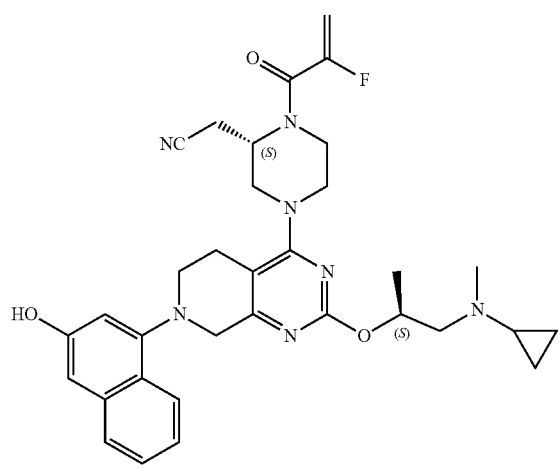
112
-continued
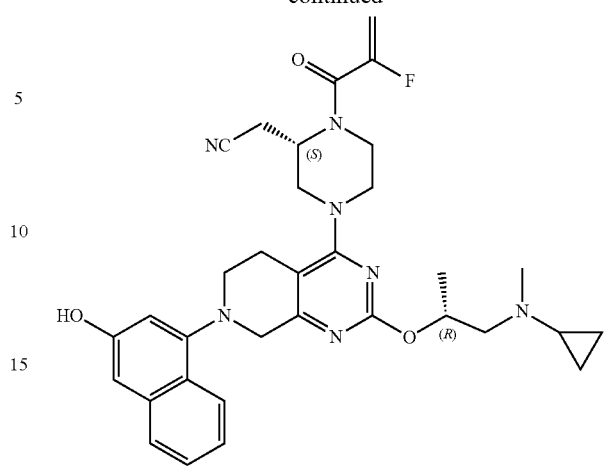
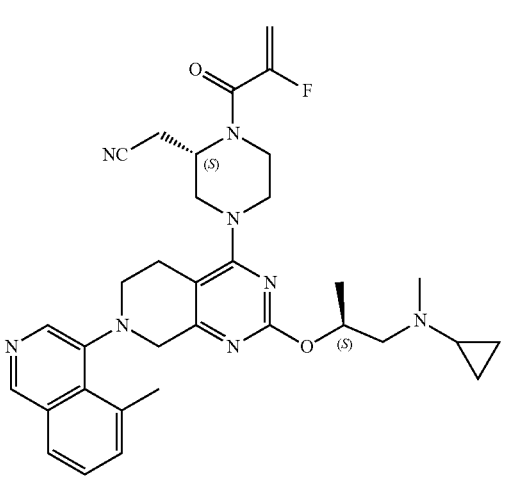
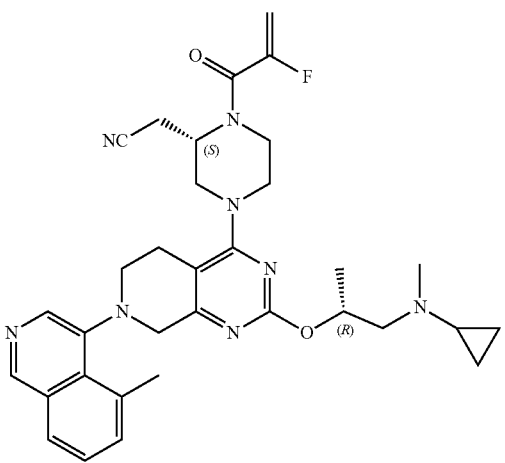

113
-continued
114
-continued
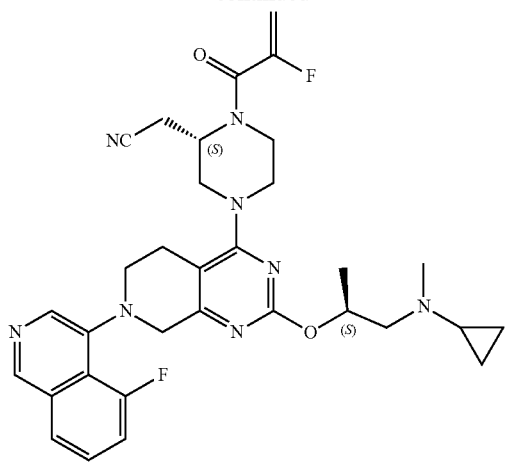
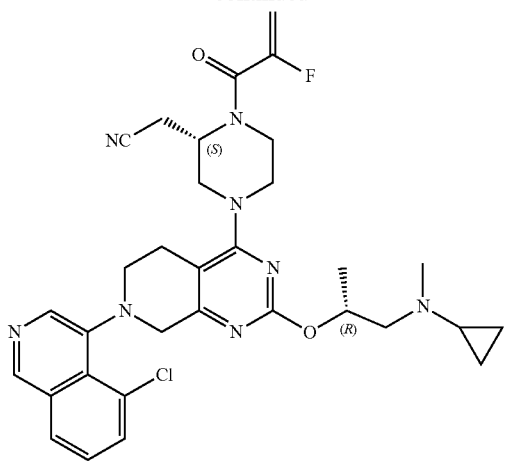

115
-continued
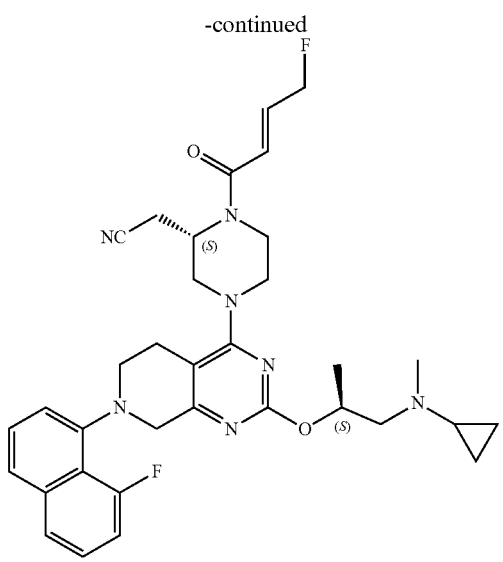
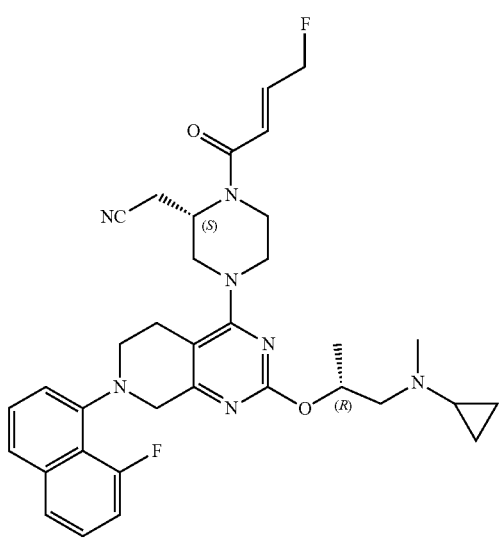
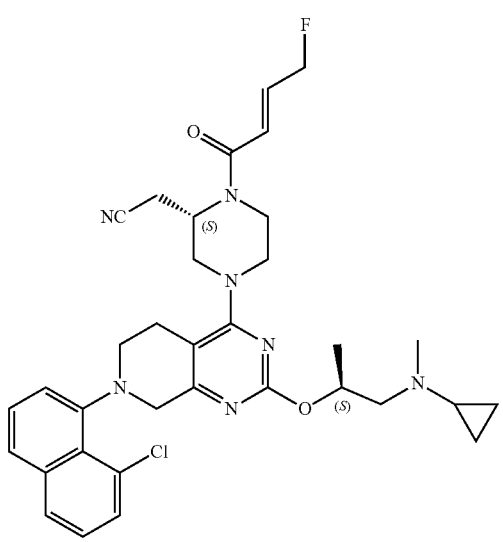
116
-continued
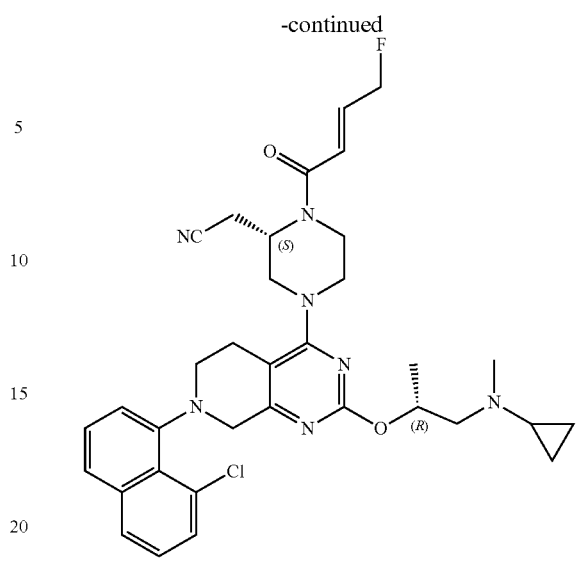
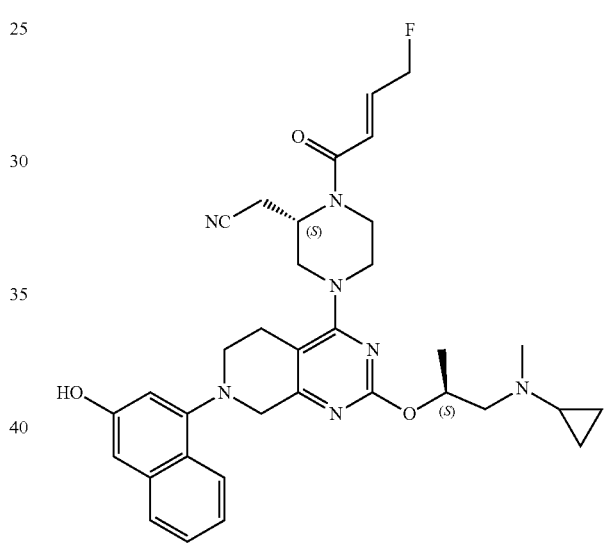
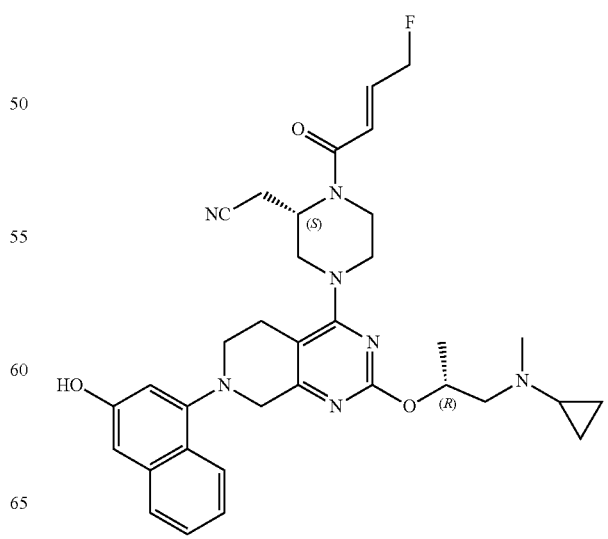

117
-continued
118
-continued
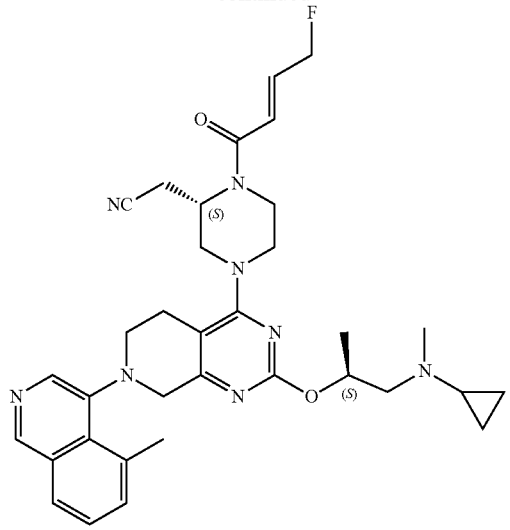
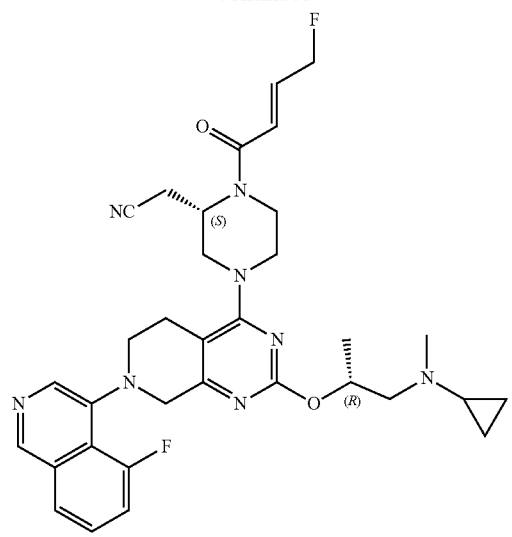

119
-continued
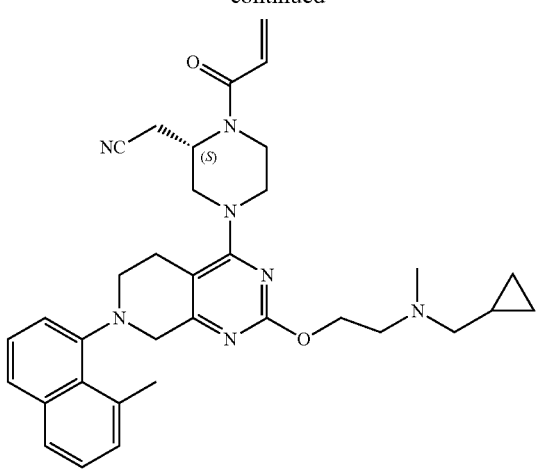
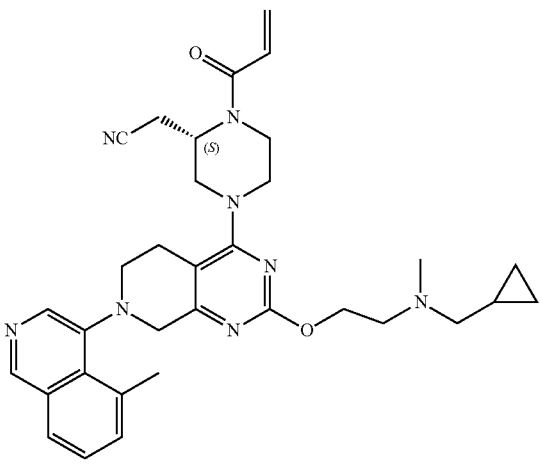
120
-continued
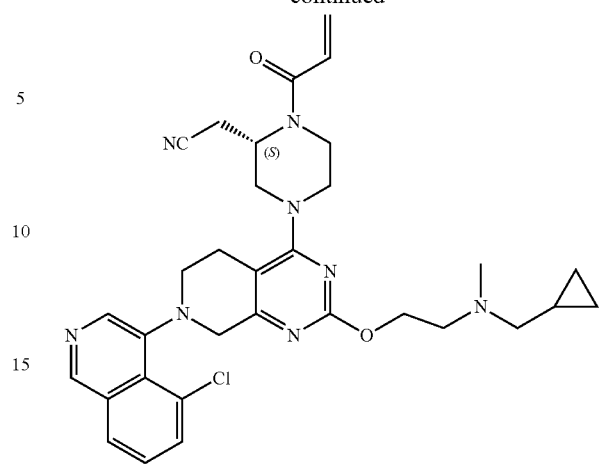
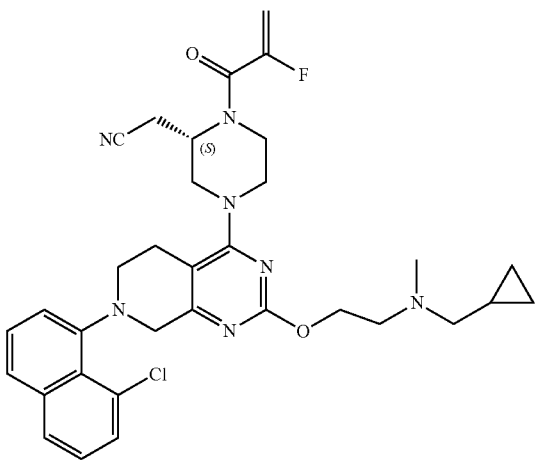

121
-continued
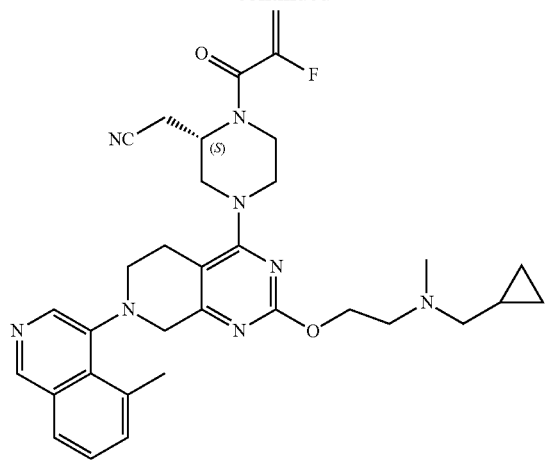
122
-continued
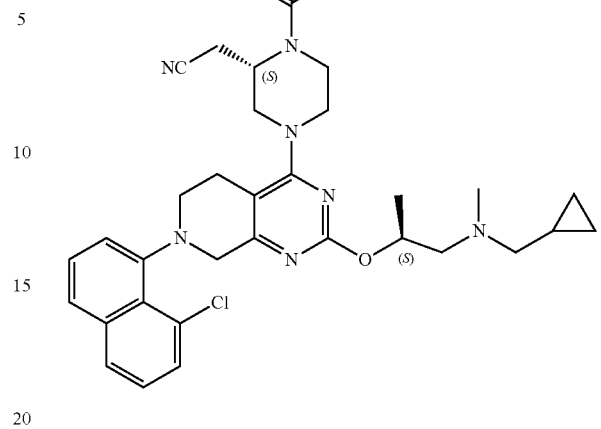
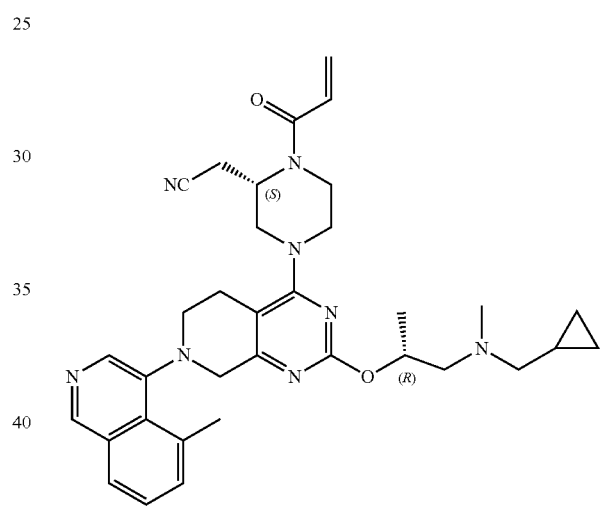
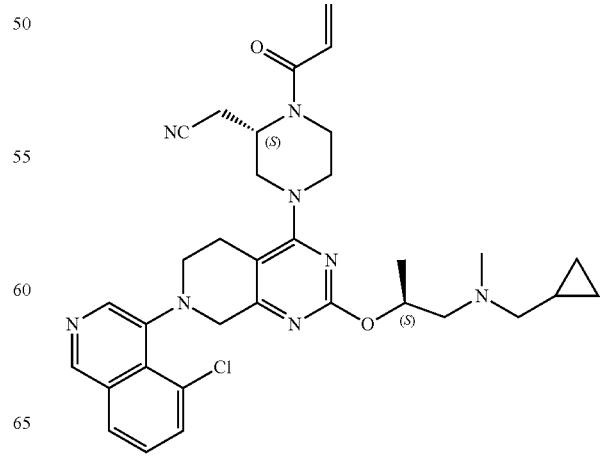

123
-continued
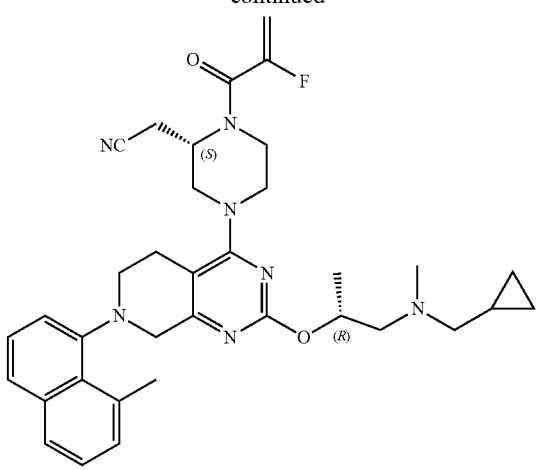
124
-continued
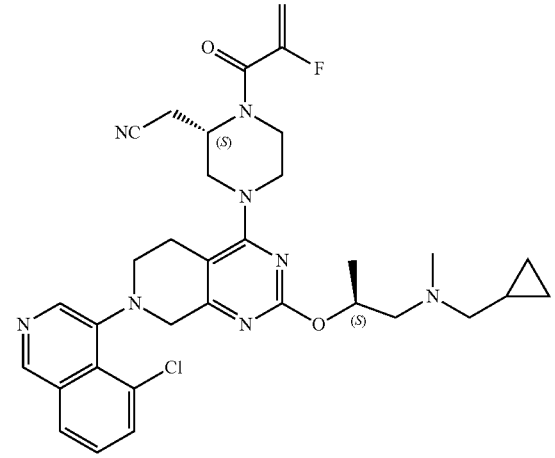
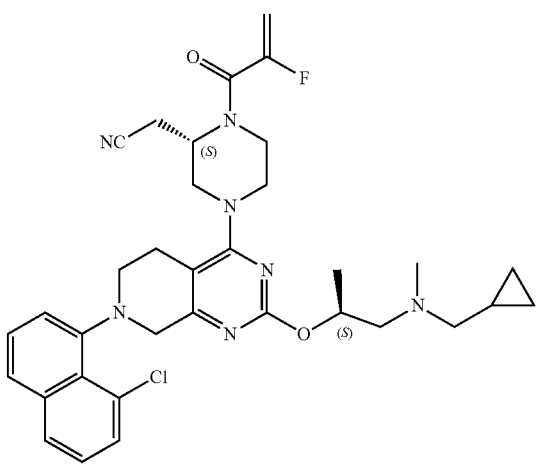
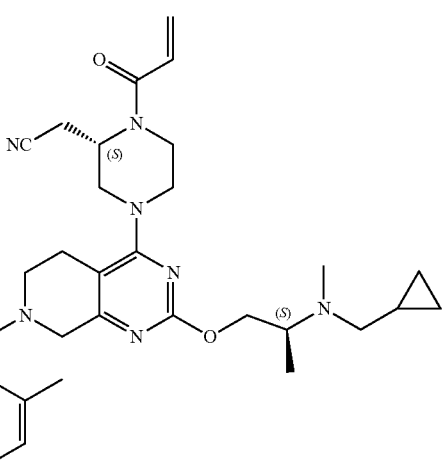
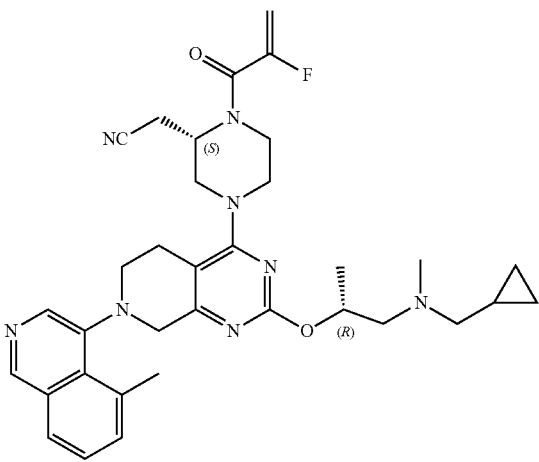
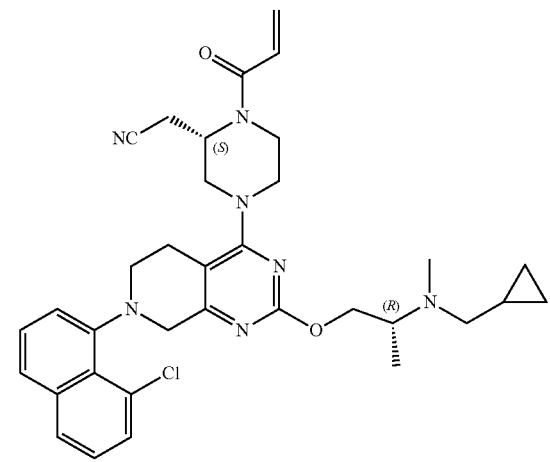

125
-continued
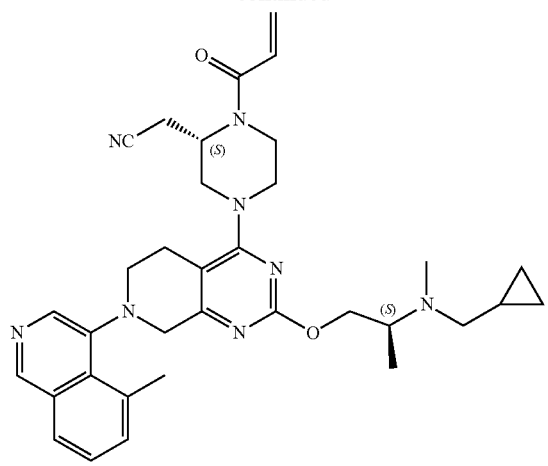
126
-continued
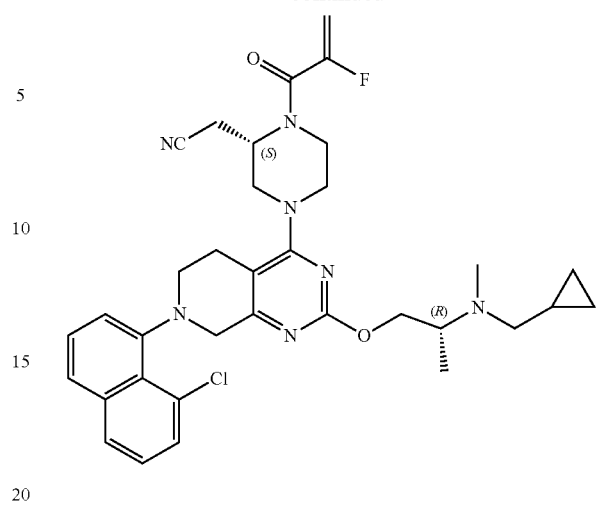
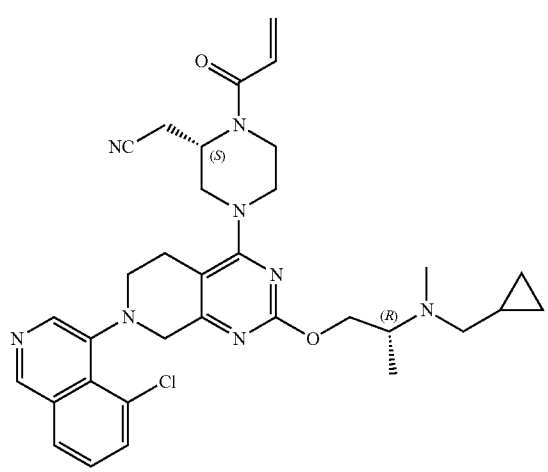
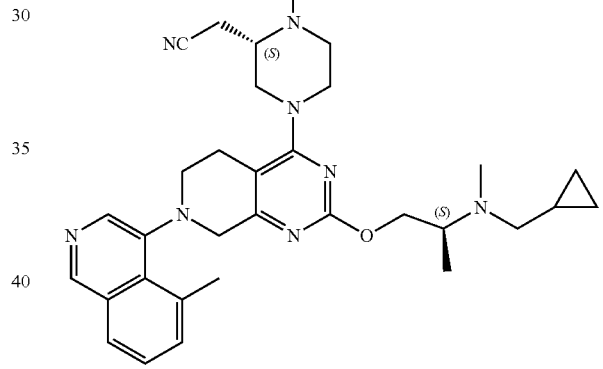
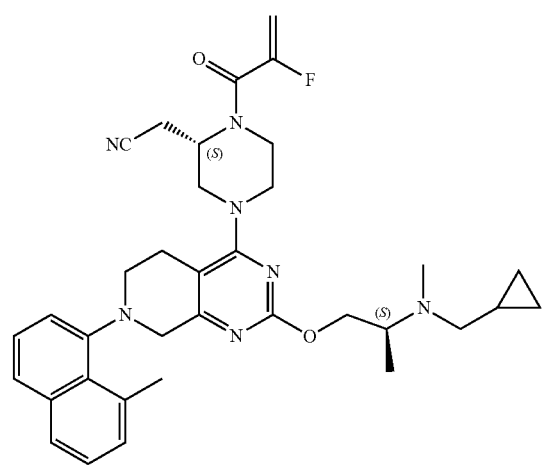
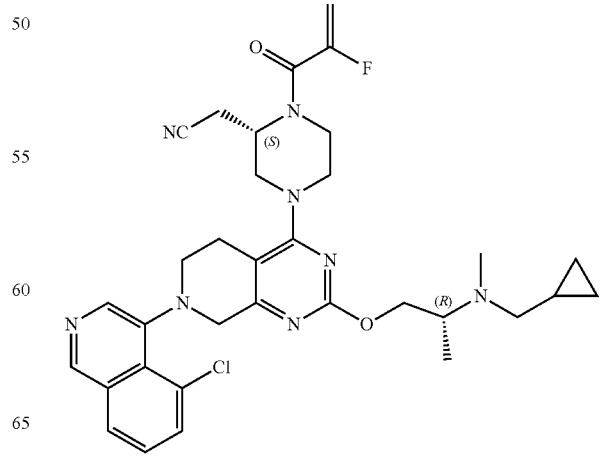

127
-continued
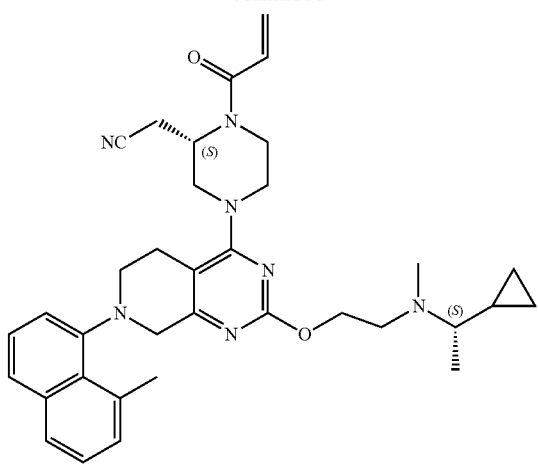
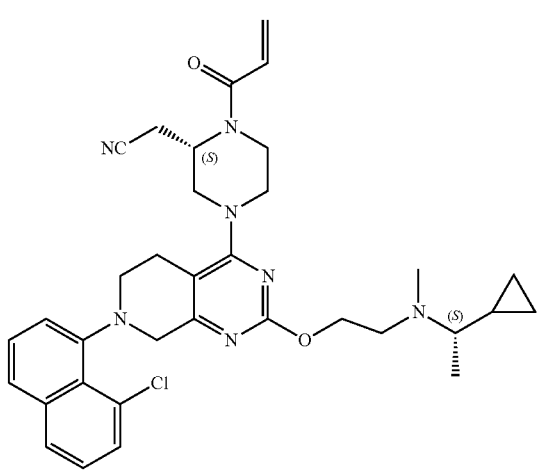
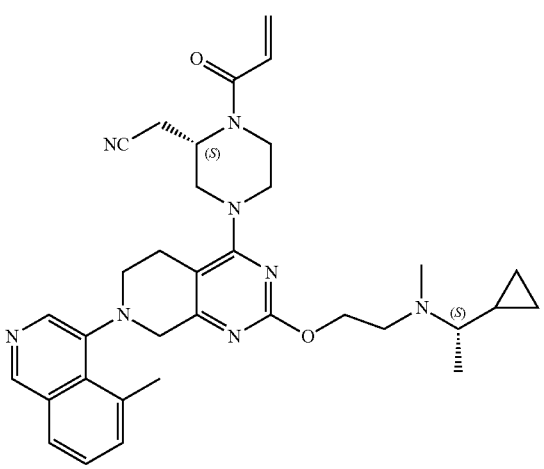
128
-continued
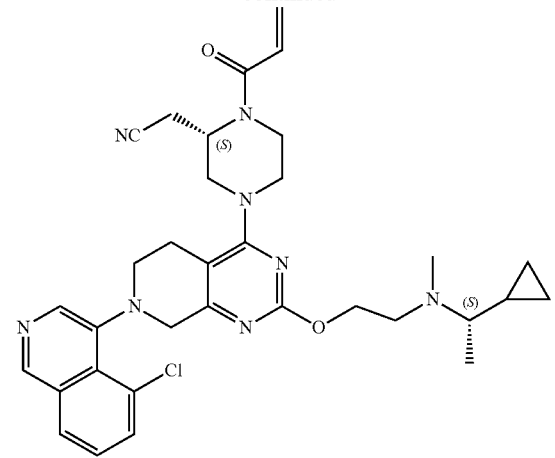
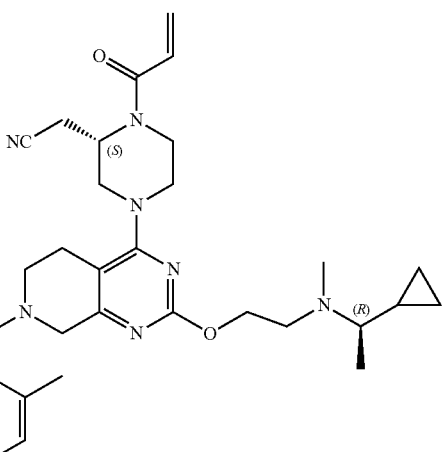
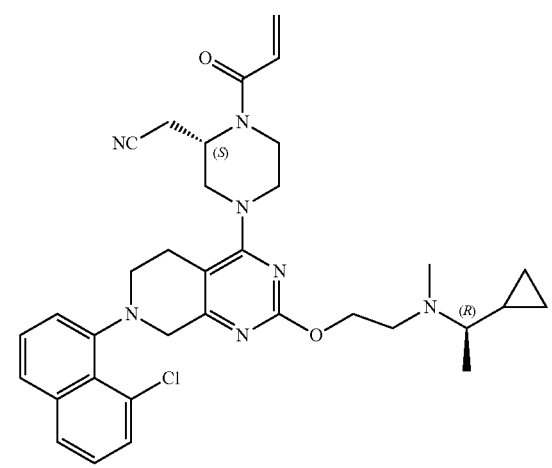

129
-continued
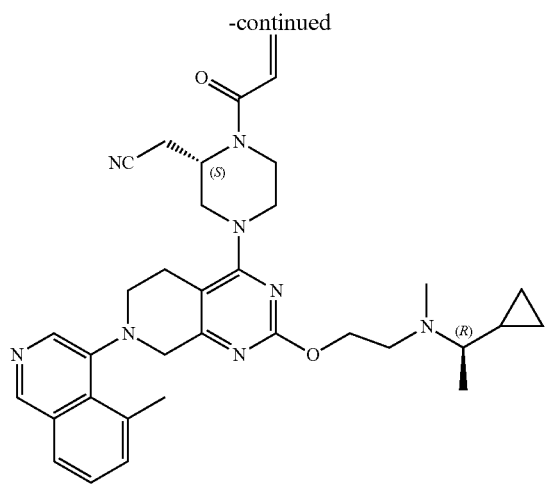
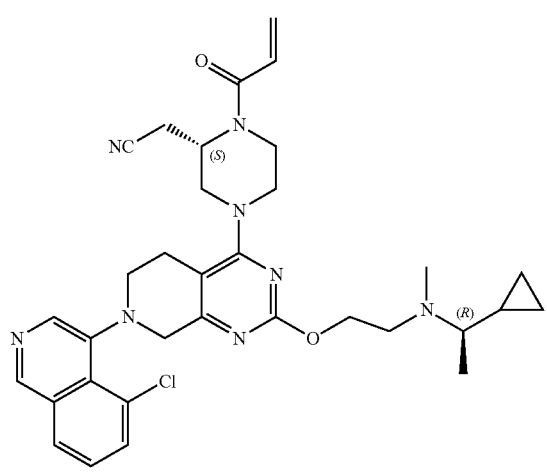
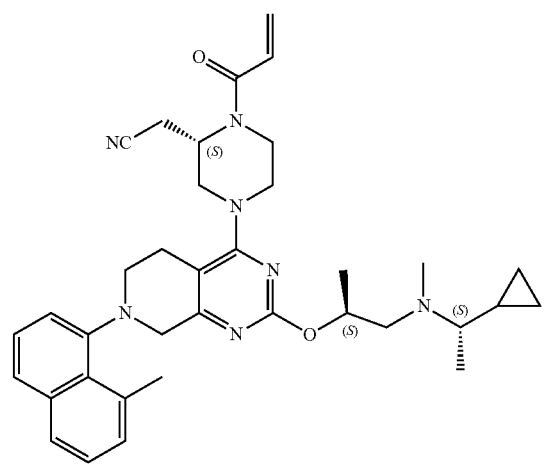
130
-continued
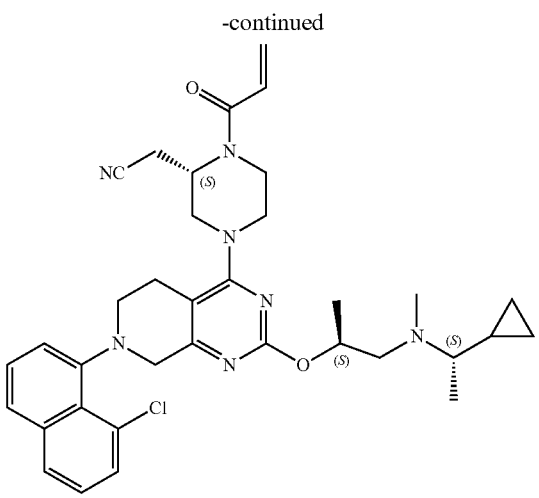
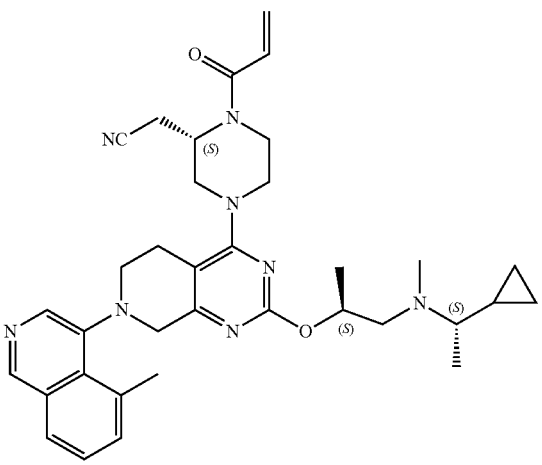
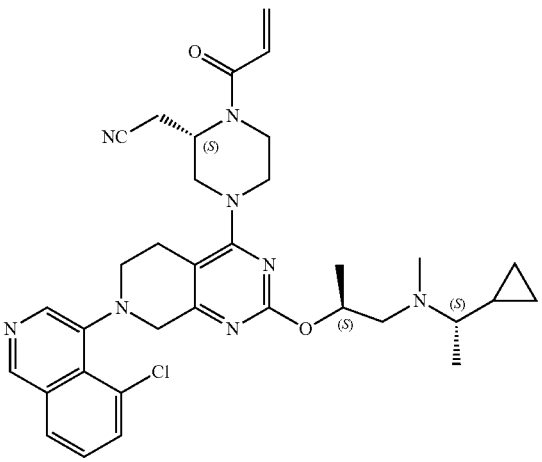

131
-continued
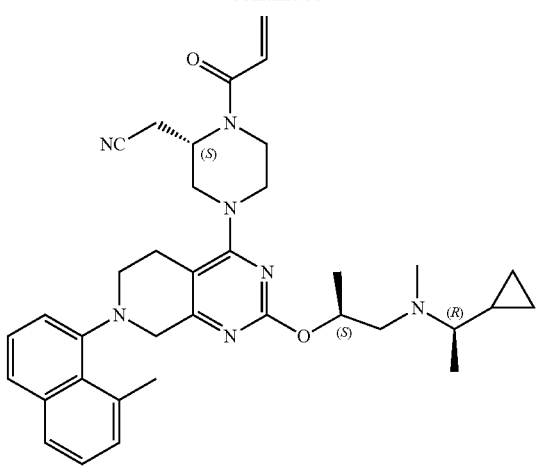
132
-continued
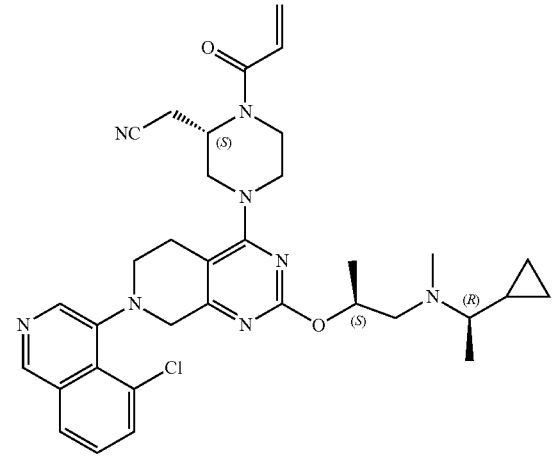
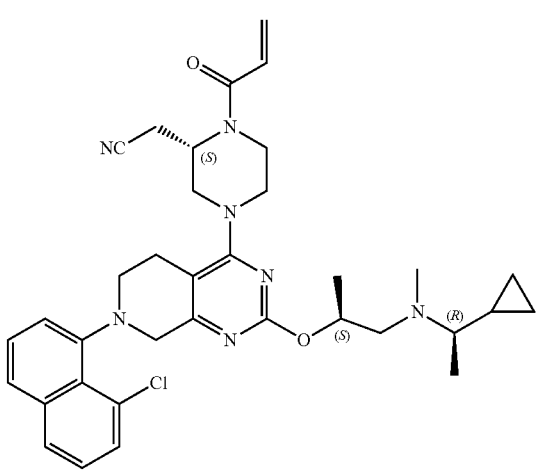
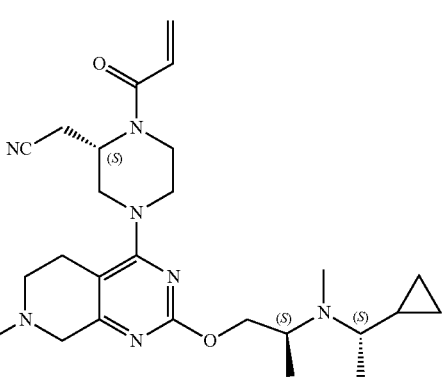
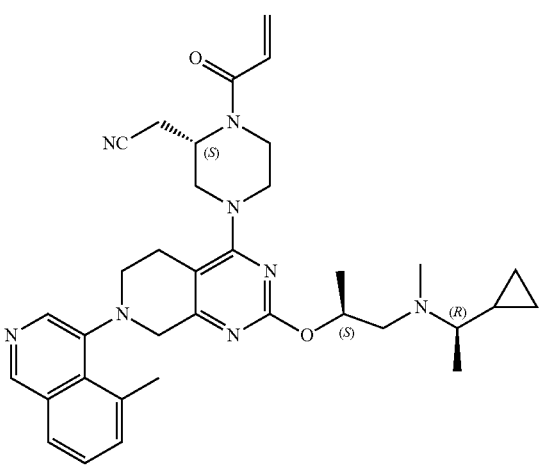
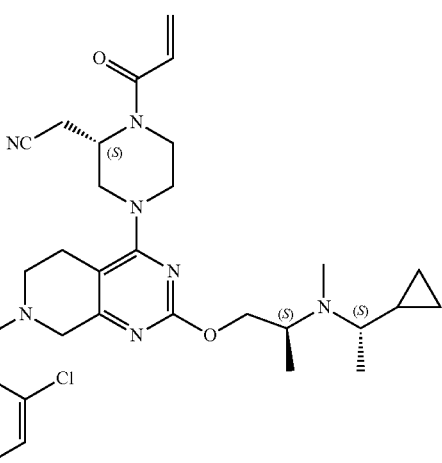

-continued
133
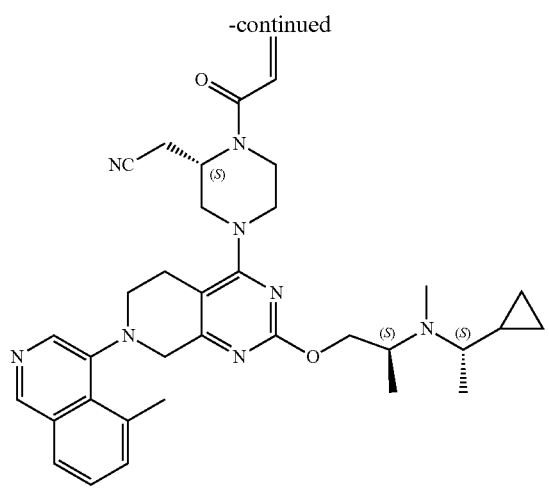
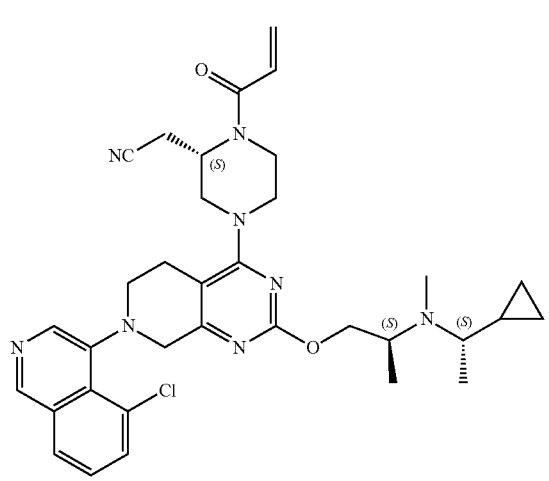
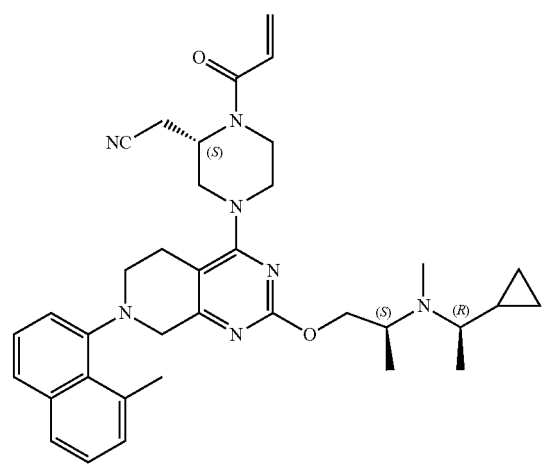
-continued
134
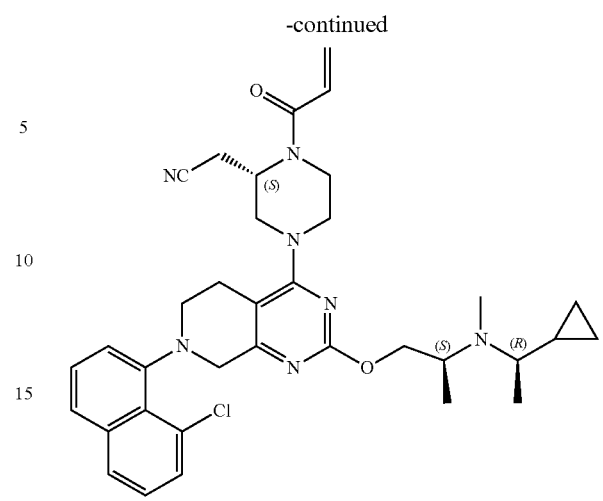
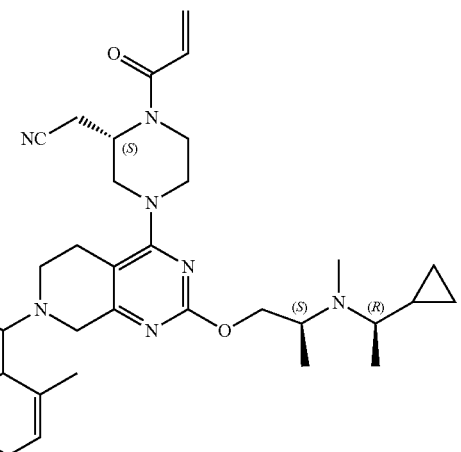
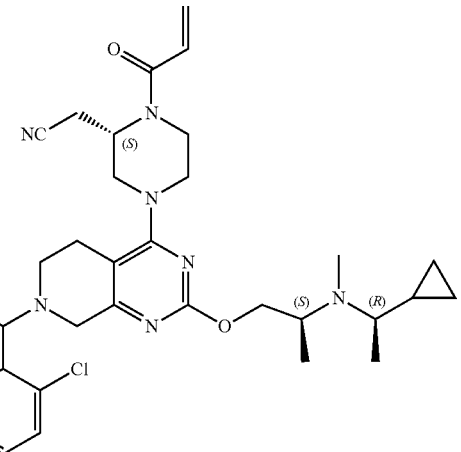

135
-continued
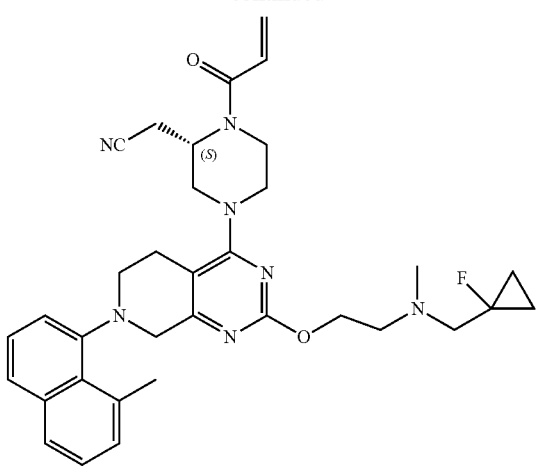
136
-continued
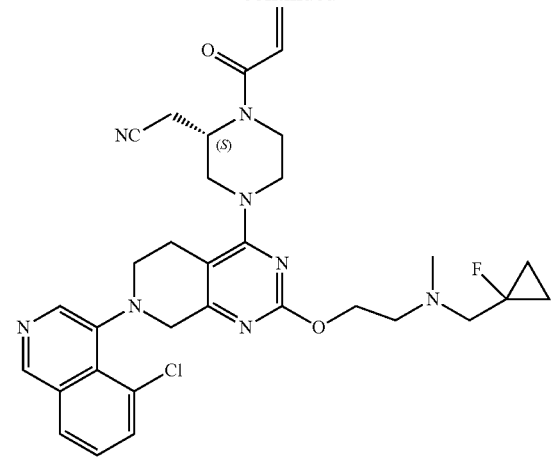
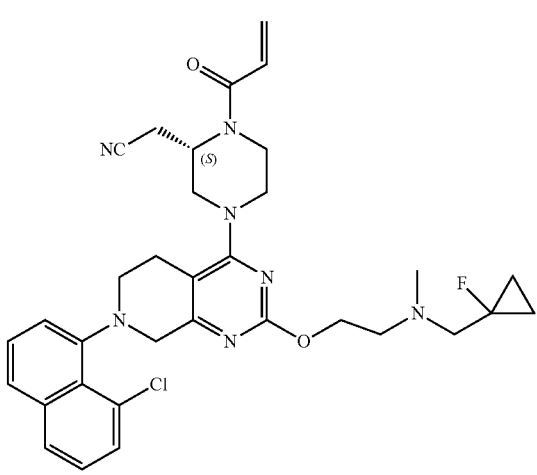
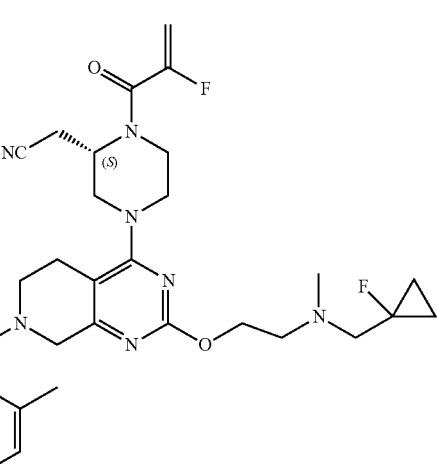
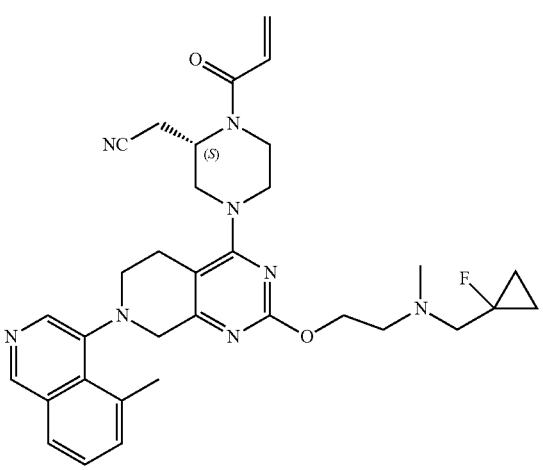
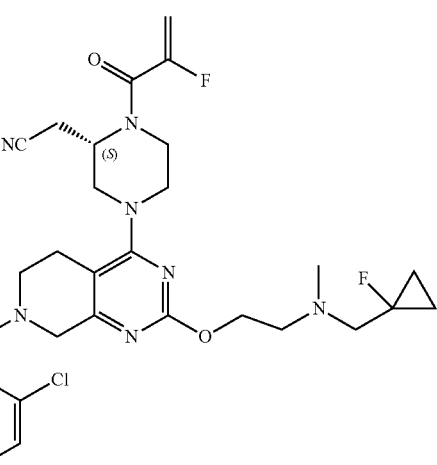

137
-continued
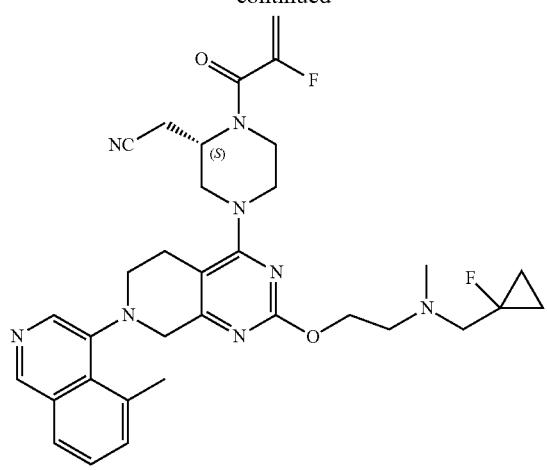
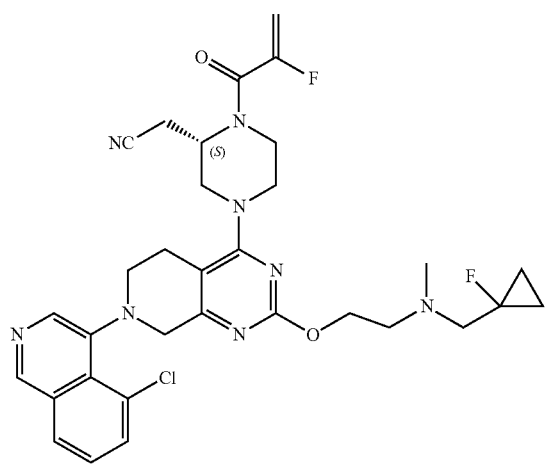
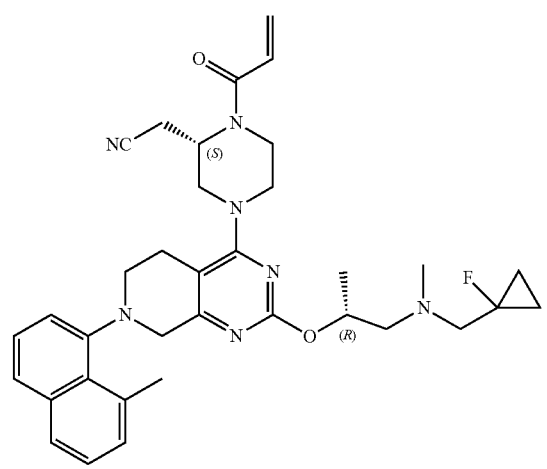
138
-continued
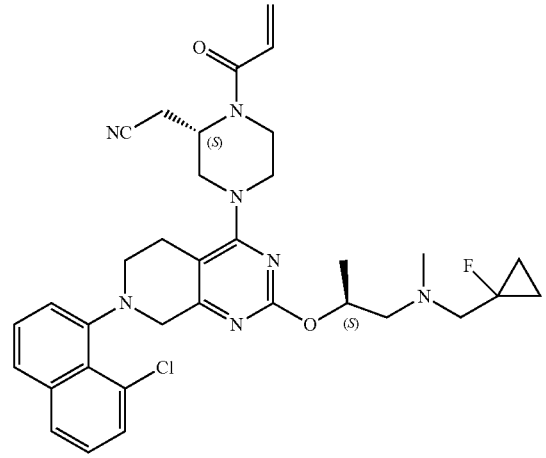
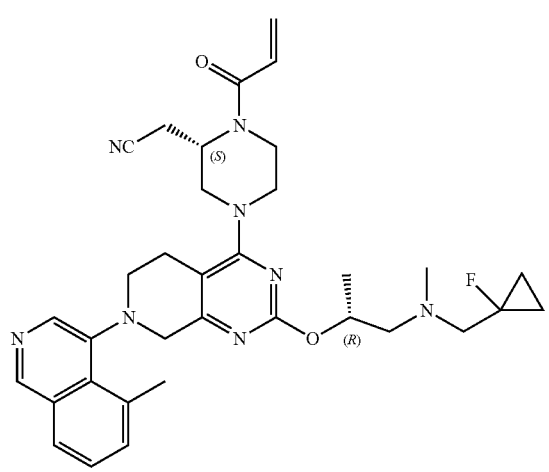
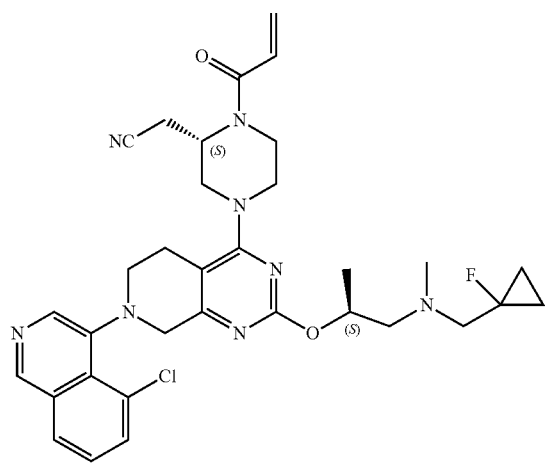

139
-continued
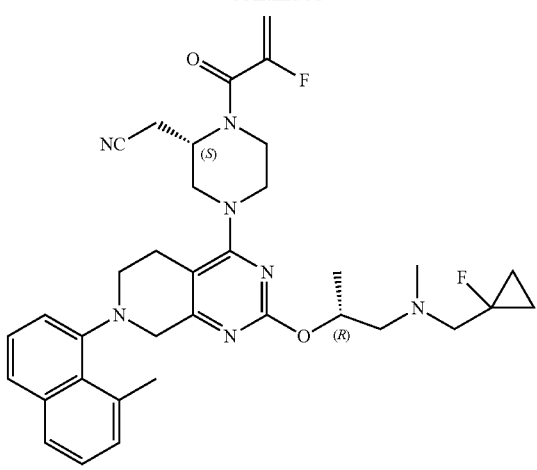
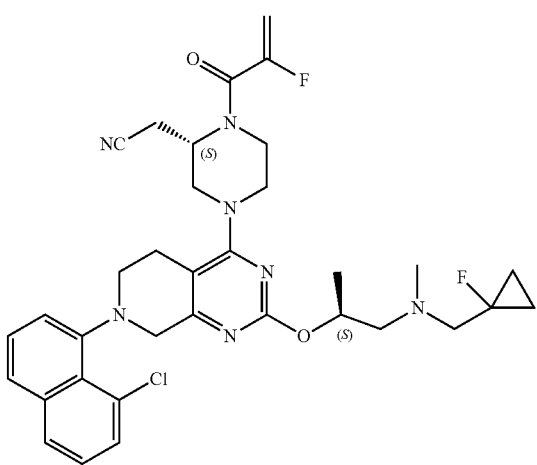
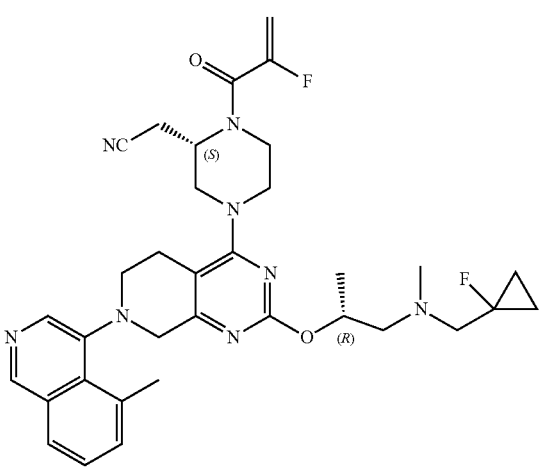
140
-continued
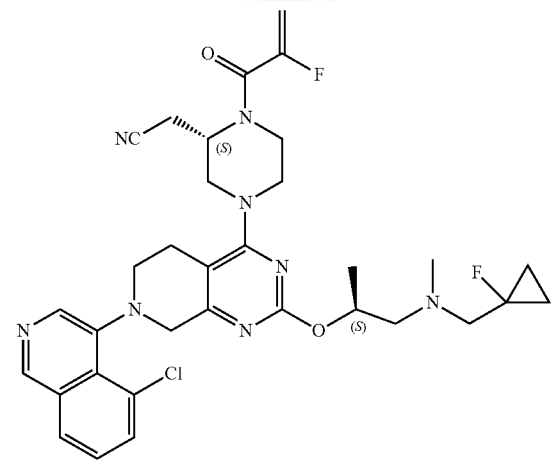
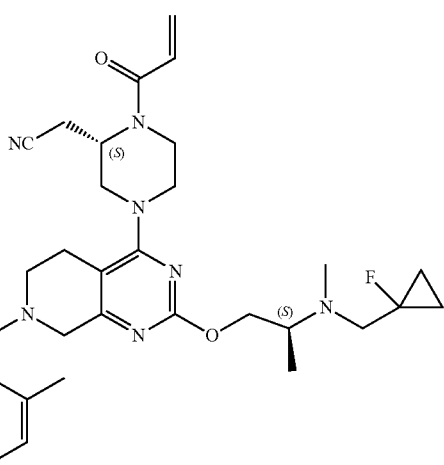
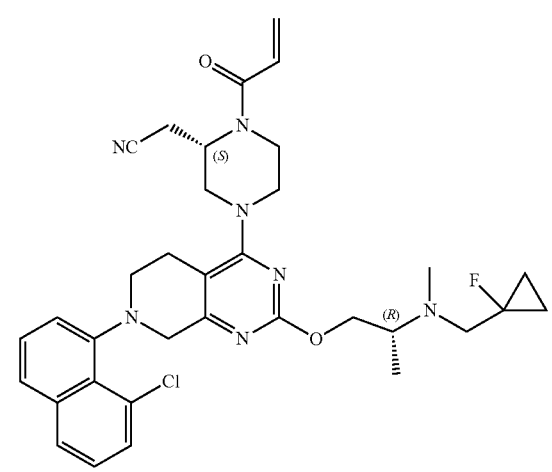

141
-continued
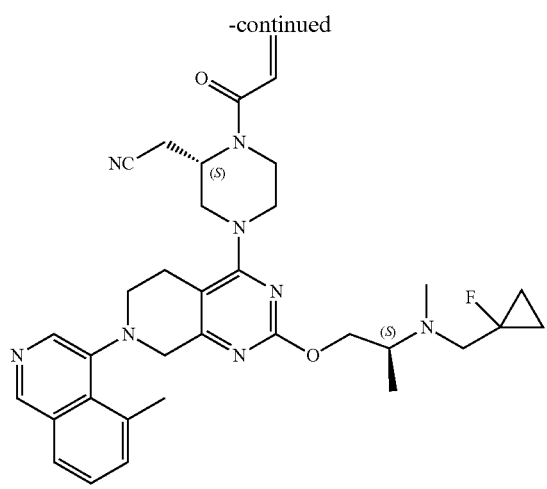
142
-continued
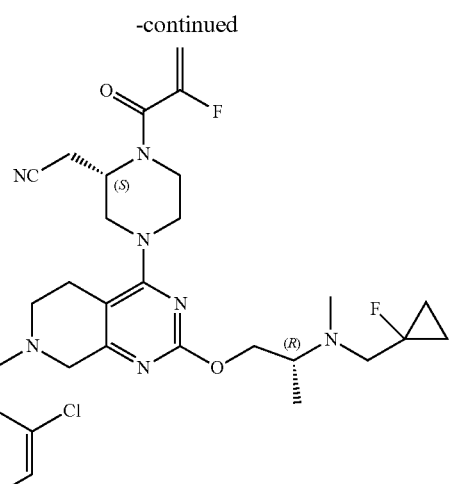
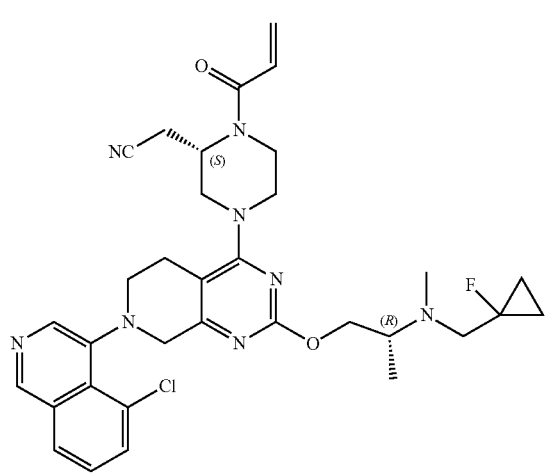
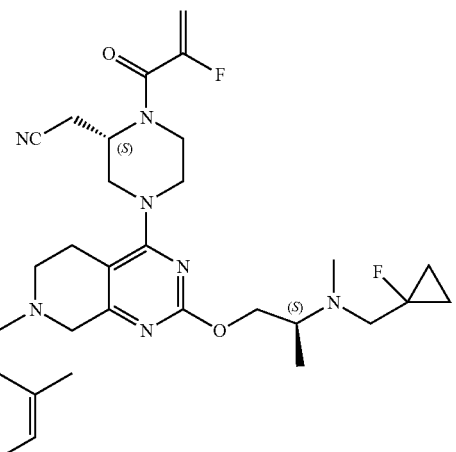
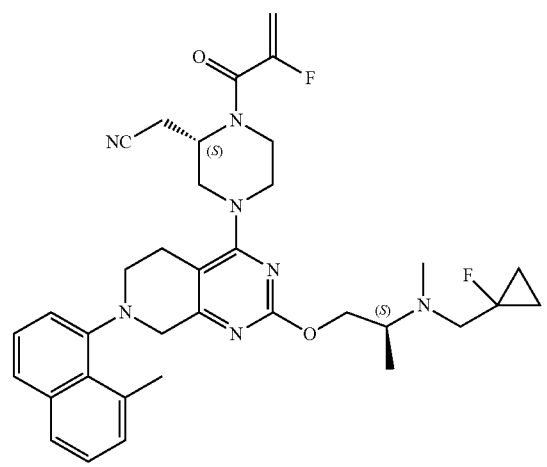
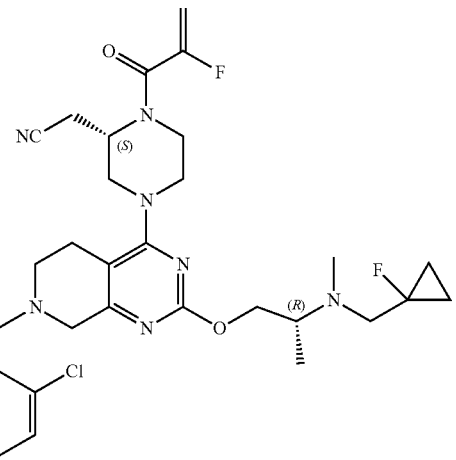

143
-continued
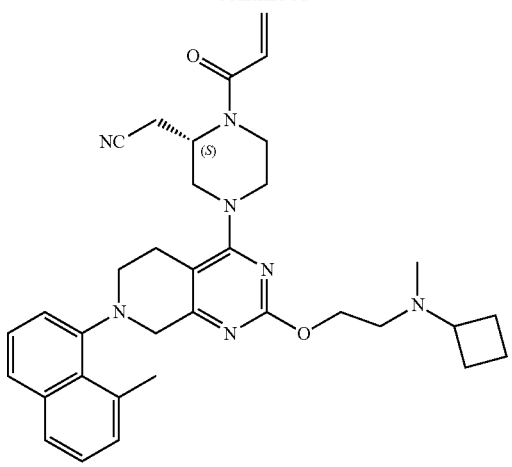
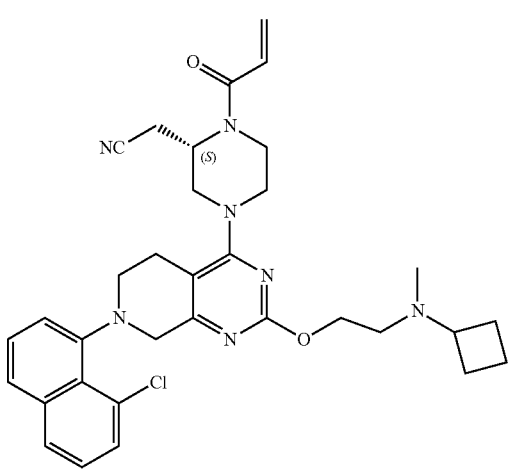
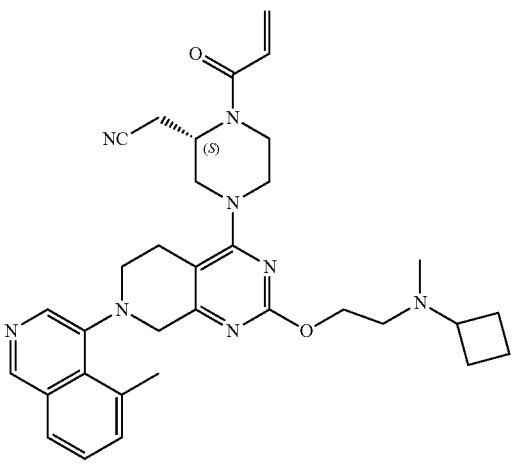
144
-continued
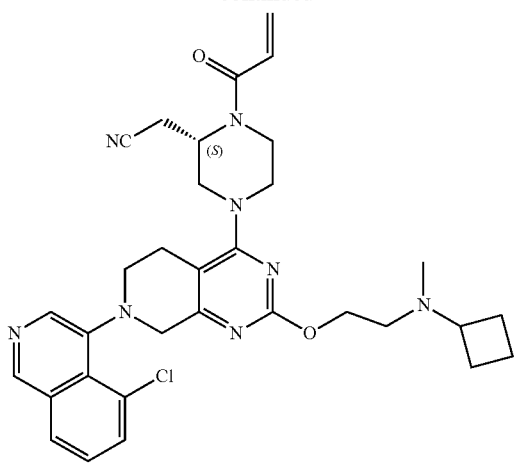
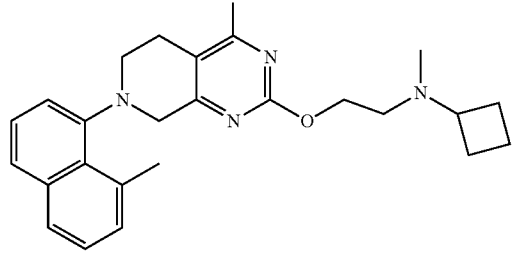
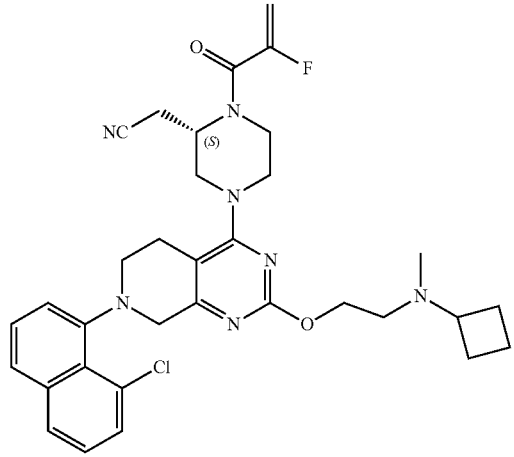

145
-continued
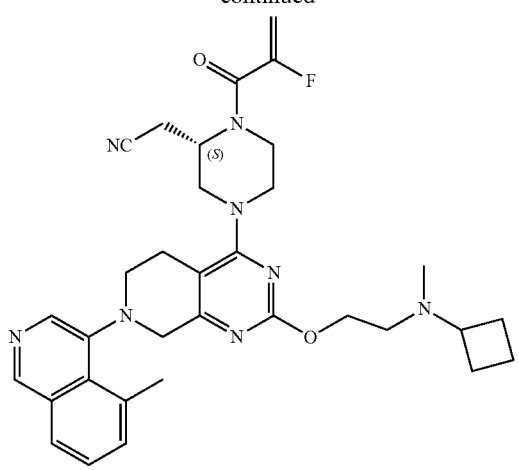
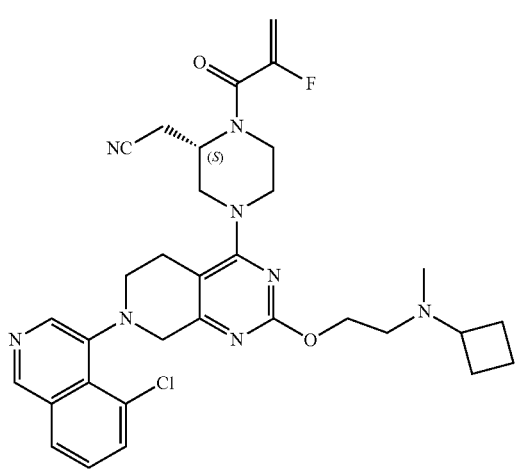
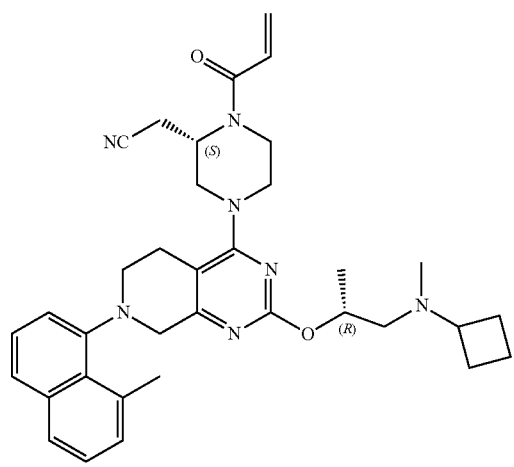
146
-continued
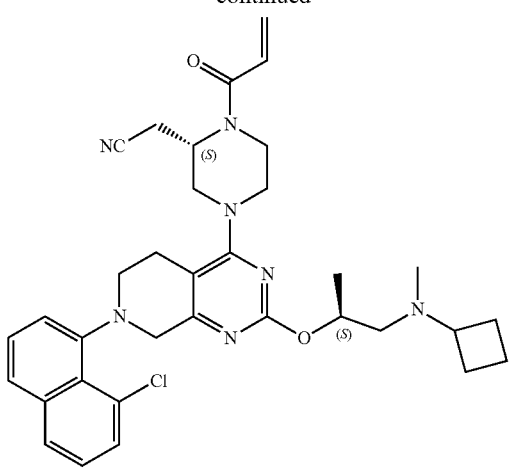
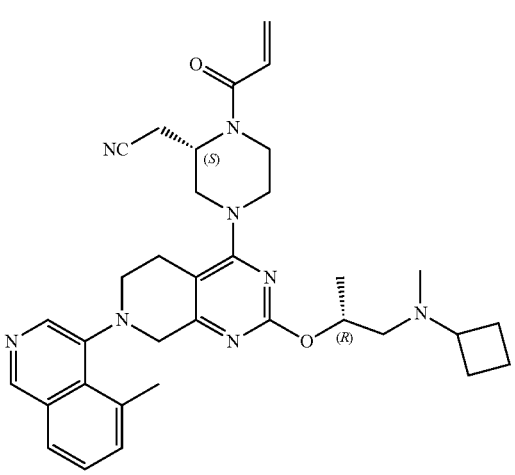
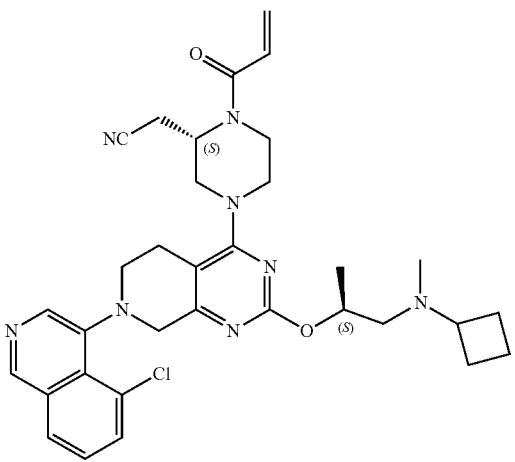

147
-continued
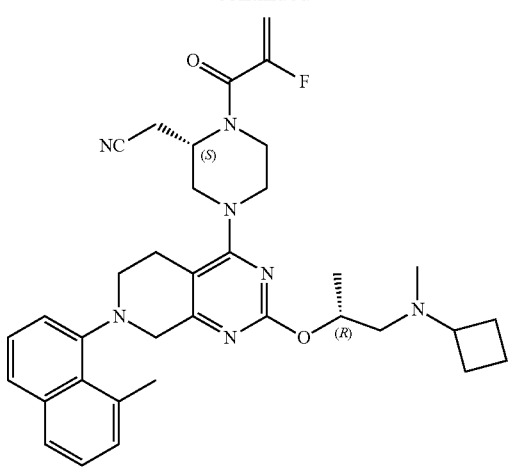
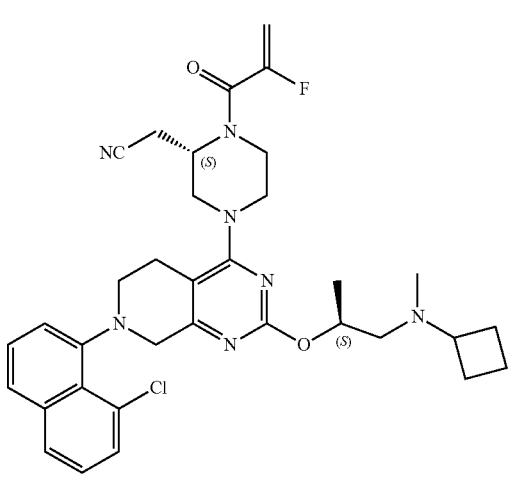
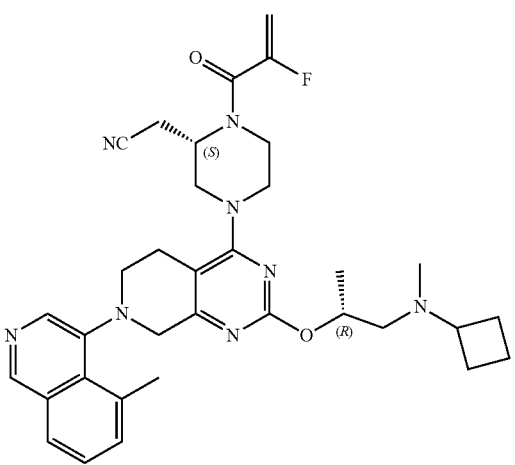
148
-continued
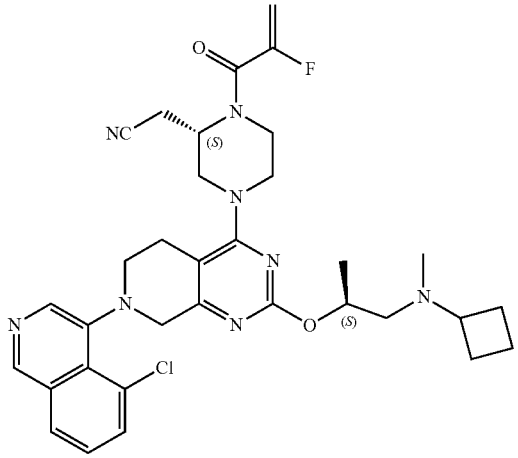
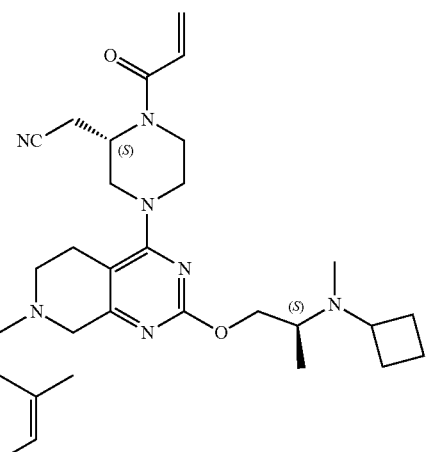
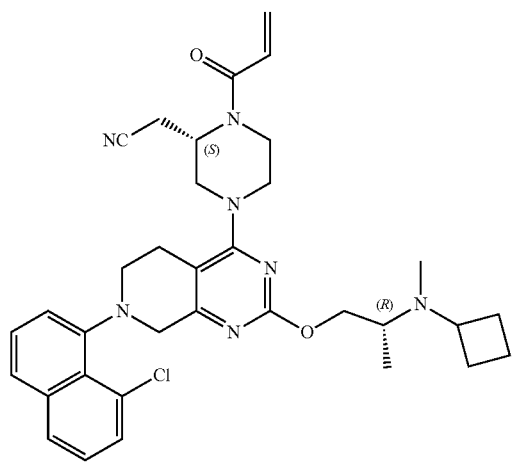

149
-continued
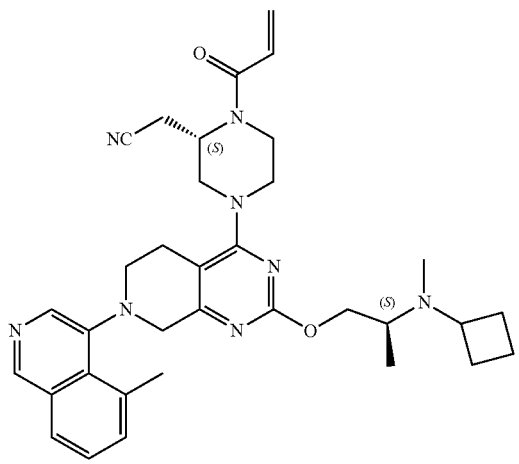
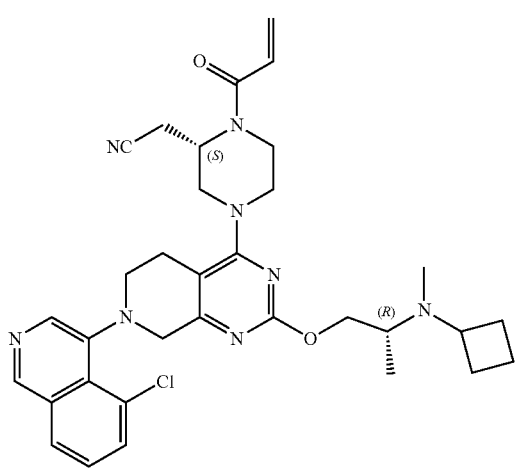
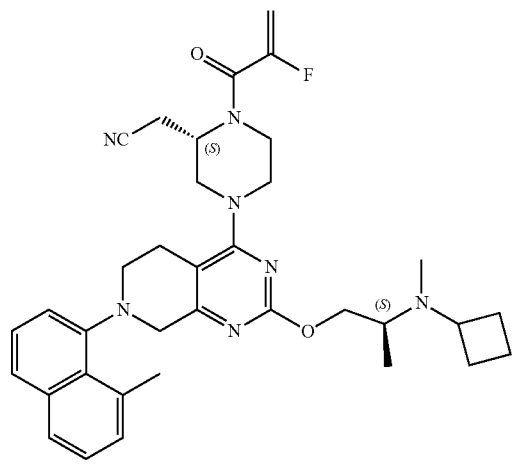
150
-continued
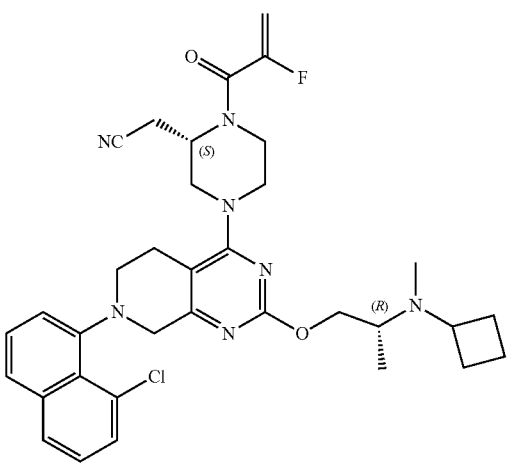
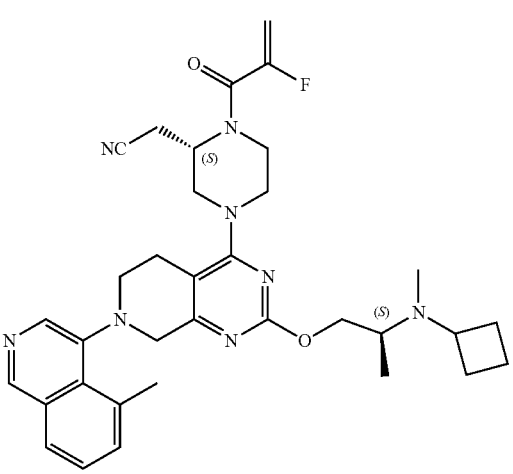
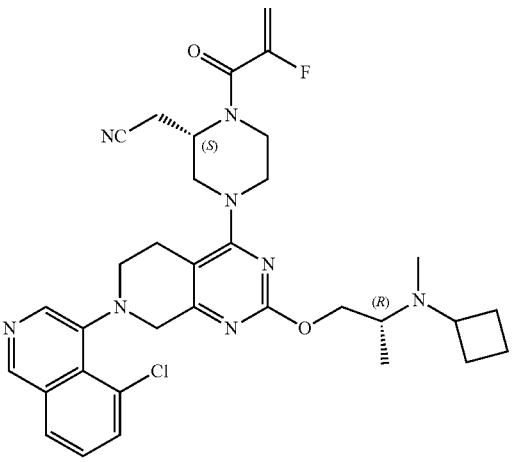

151
-continued
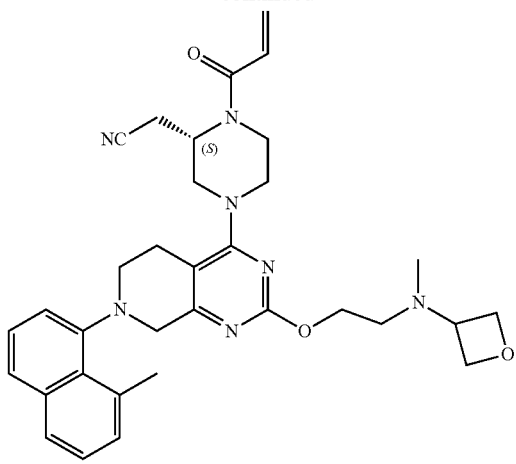
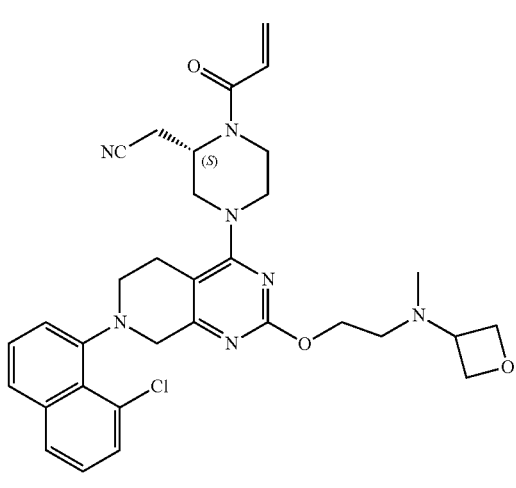 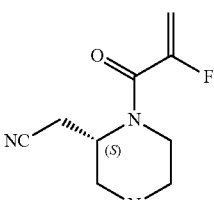
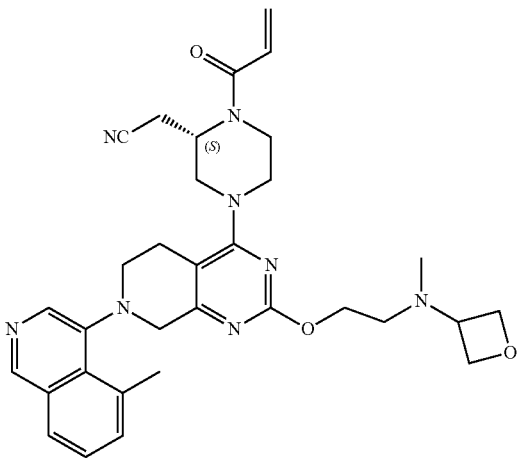
152
-continued
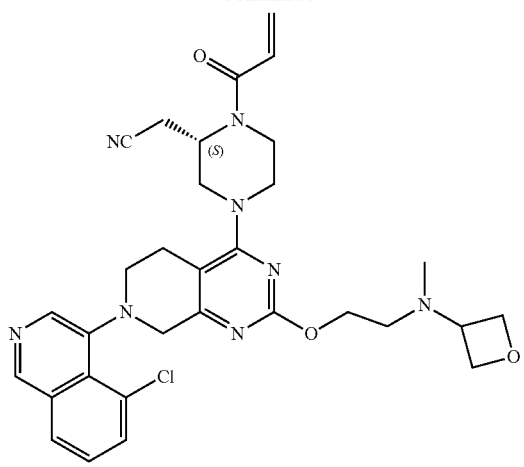
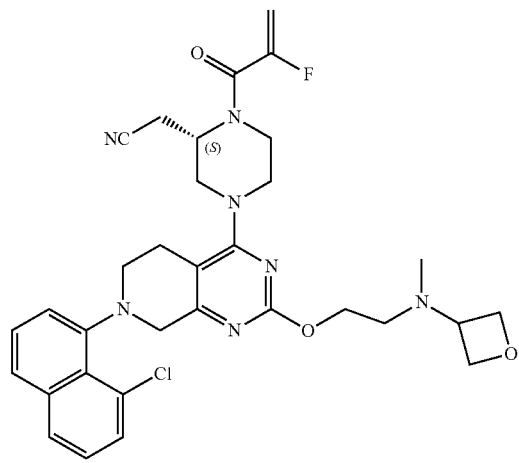

153
-continued
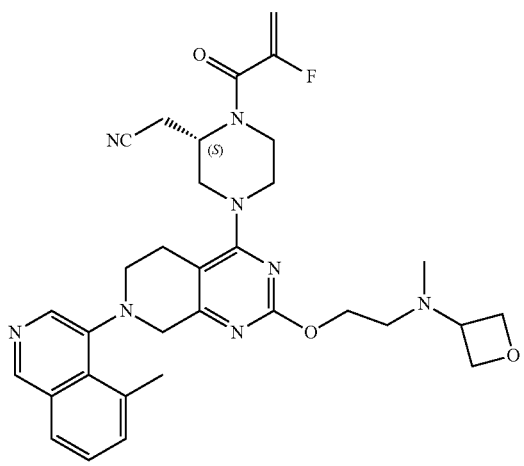
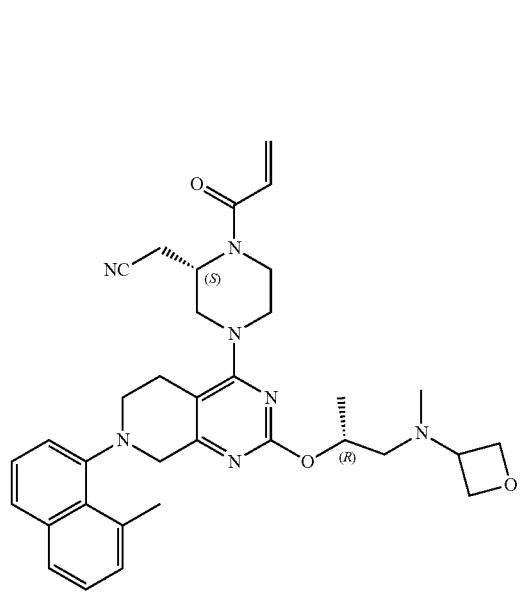
154
-continued
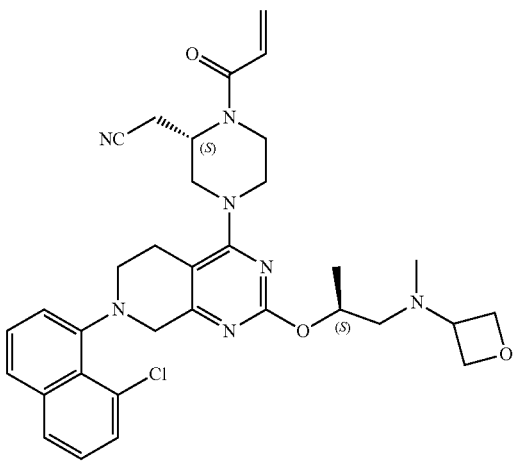
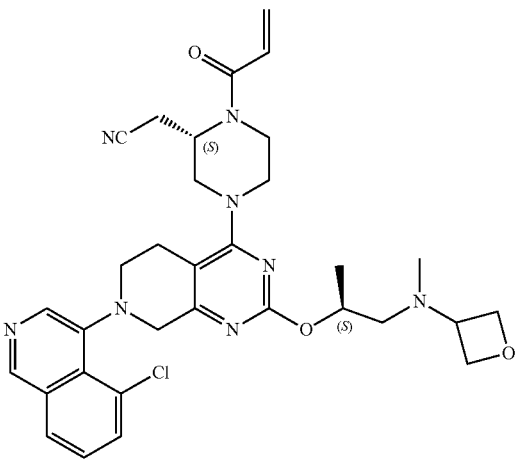

155
-continued
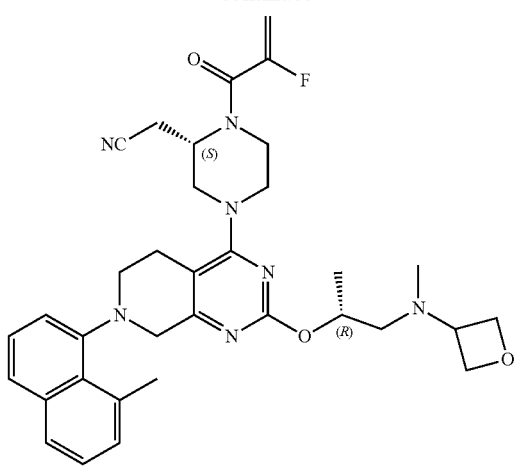
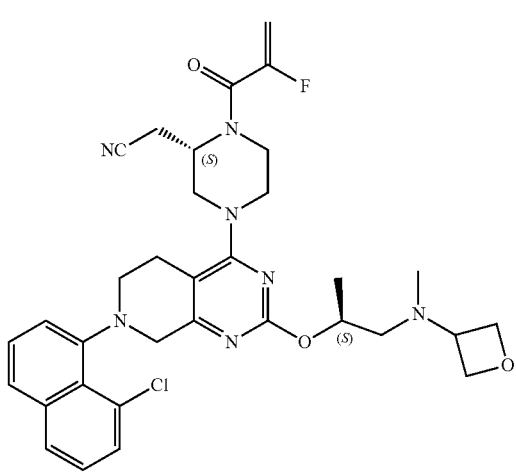
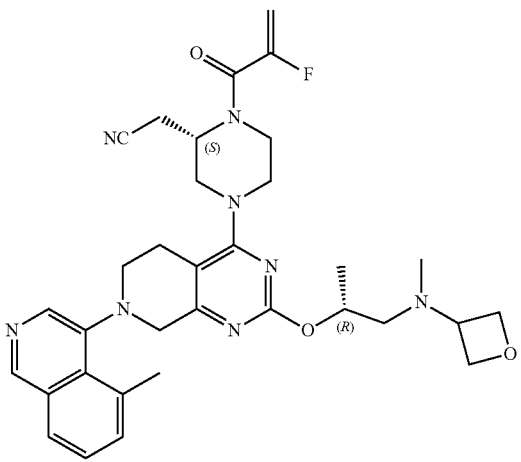
156
-continued
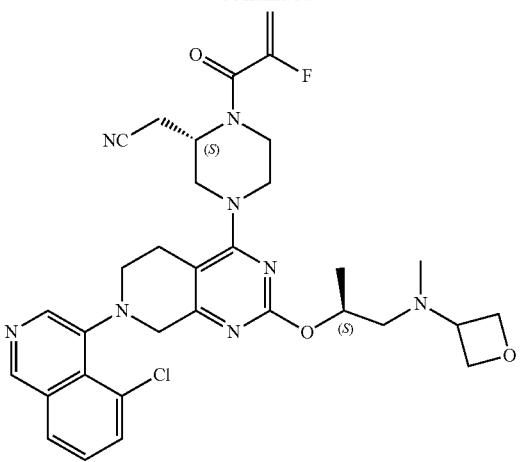
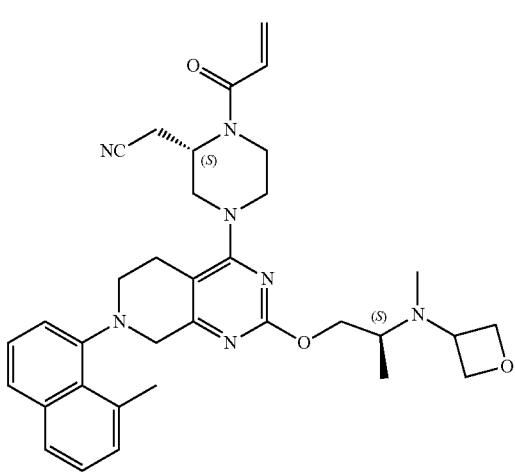

157
-continued
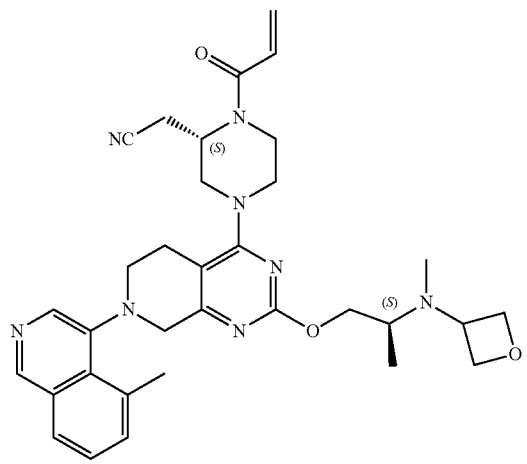
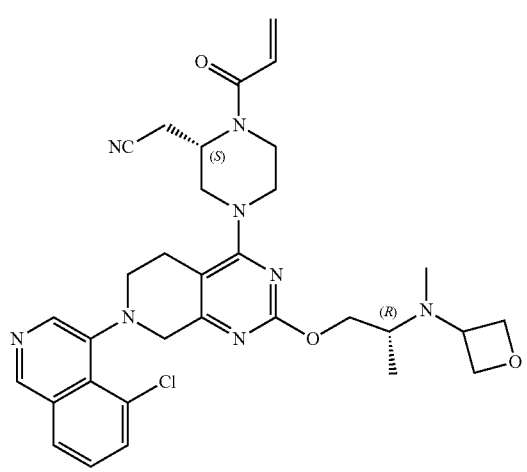
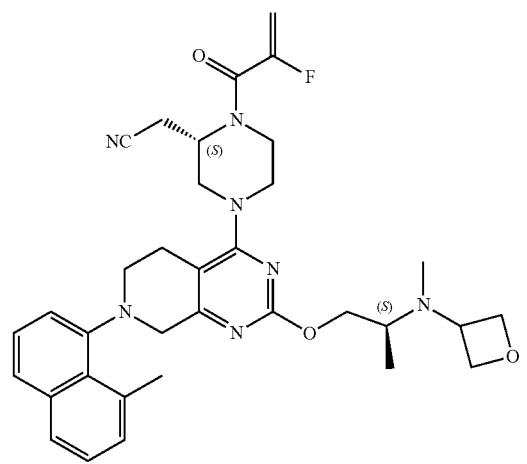
158
-continued
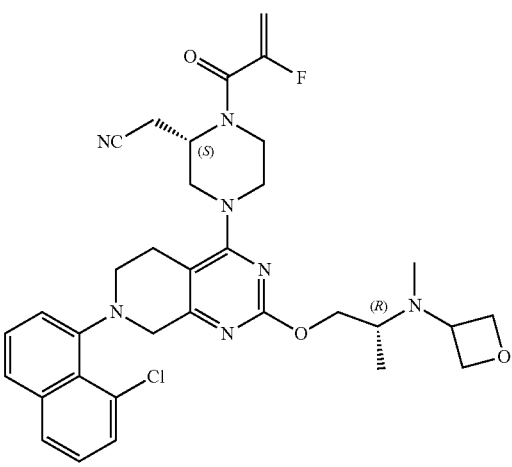
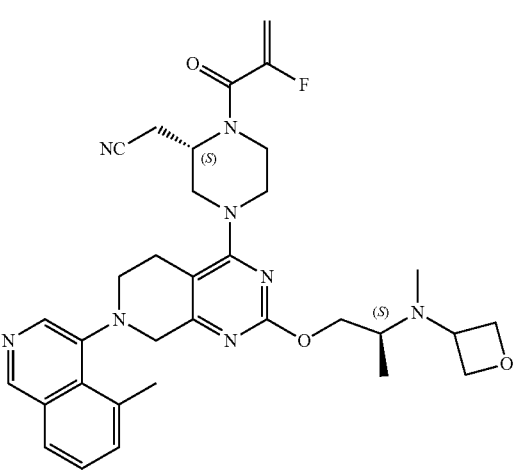
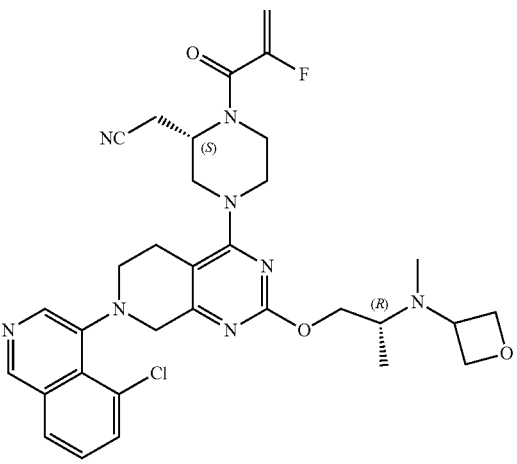

159
-continued
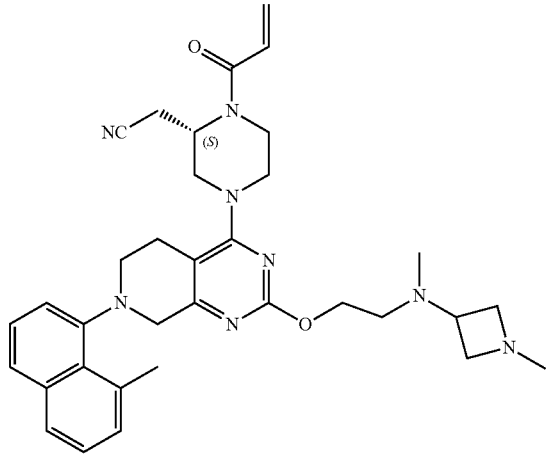
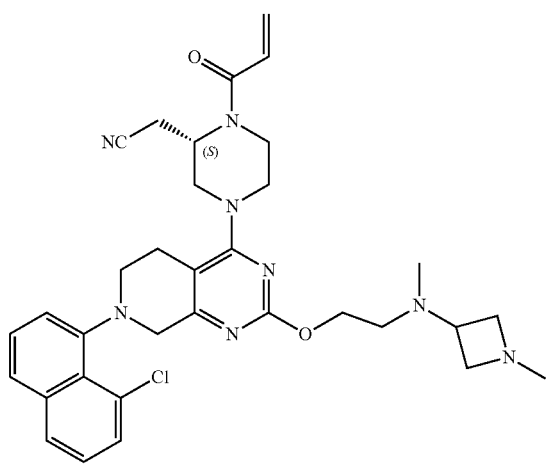
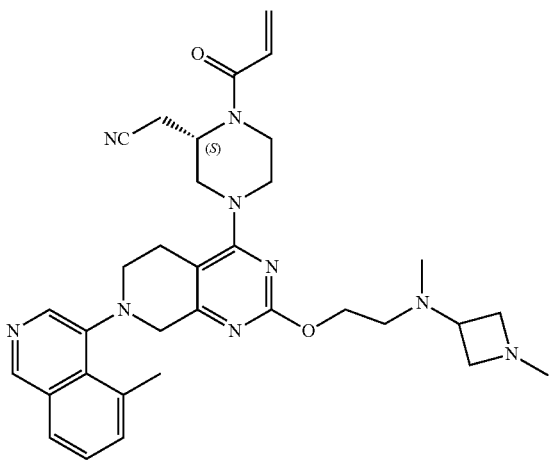
160
-continued
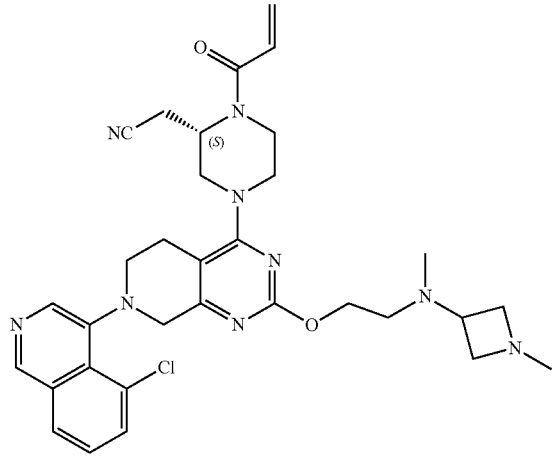
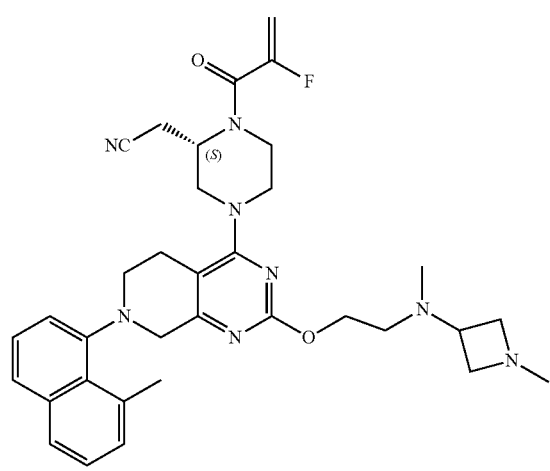
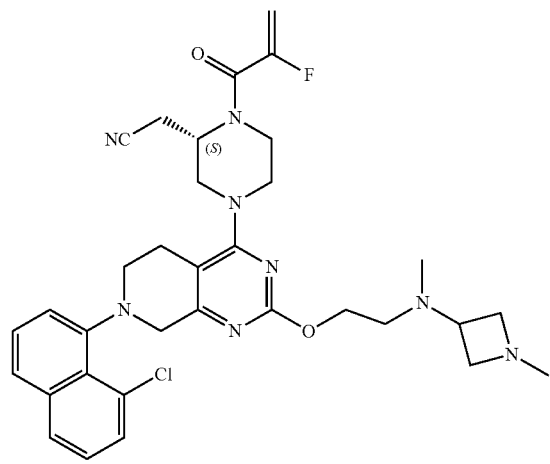

161
-continued
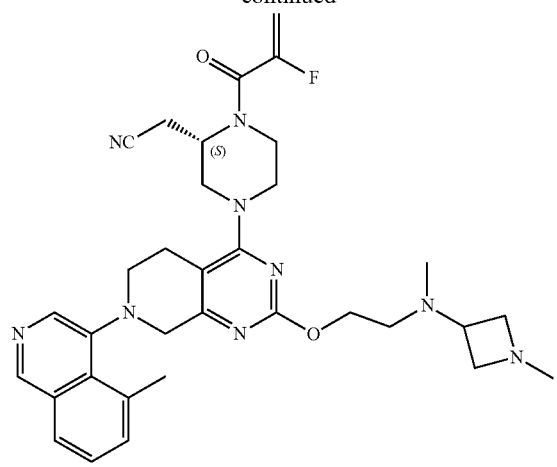
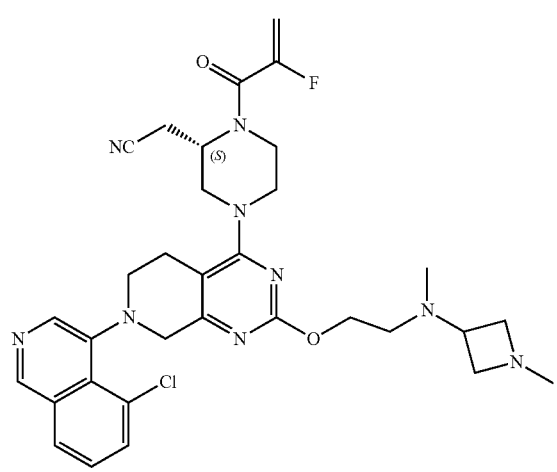
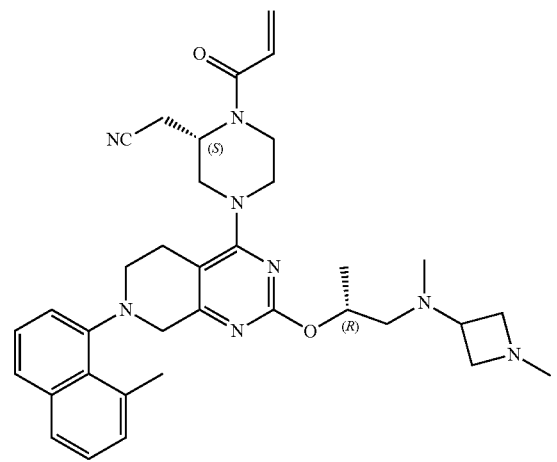
162
-continued
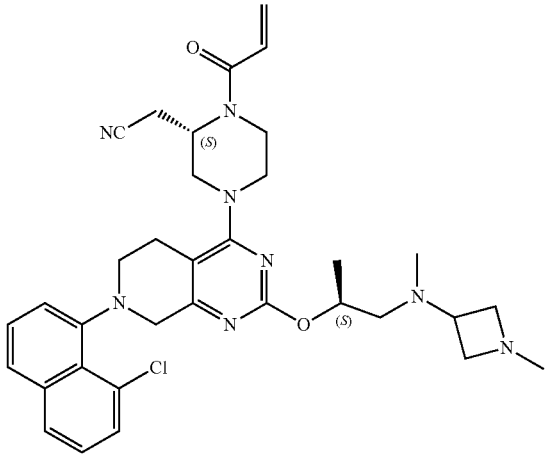
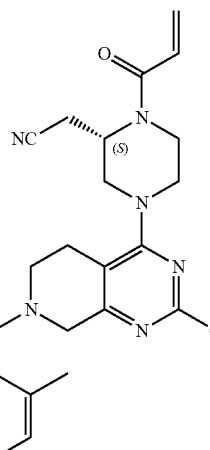
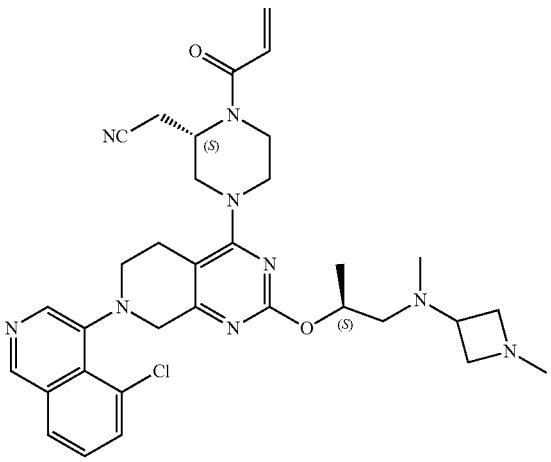

163
-continued
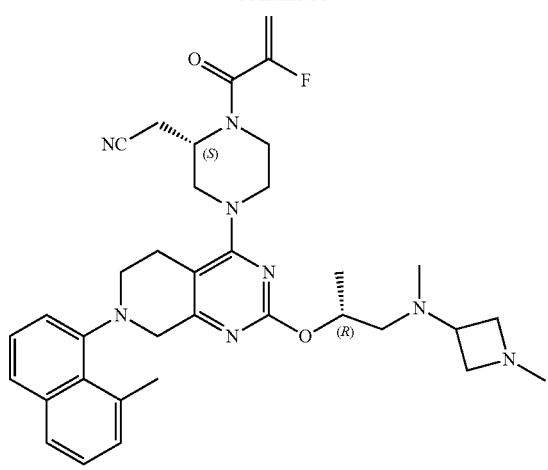
164
-continued
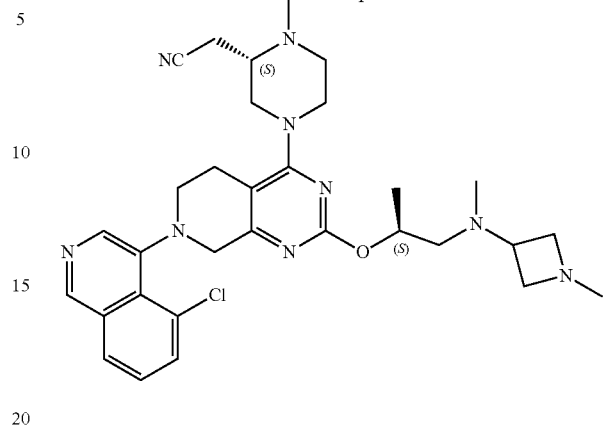
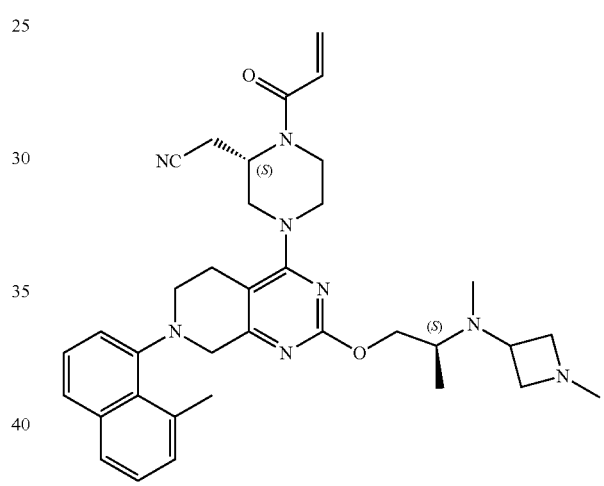
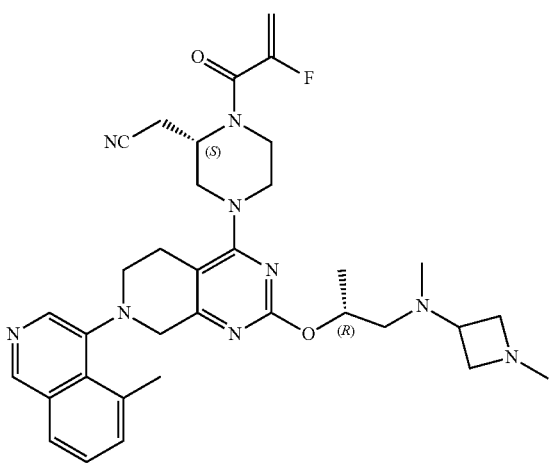
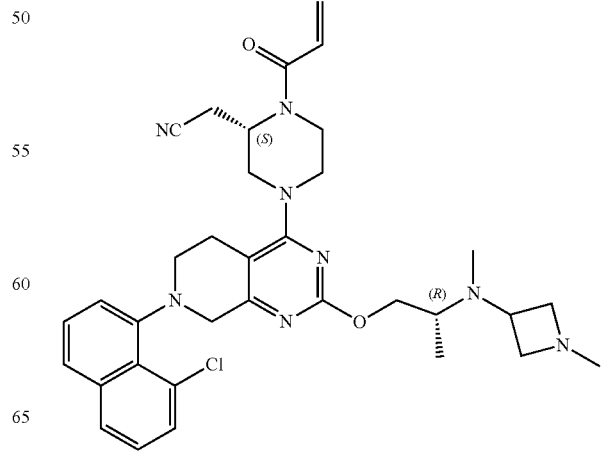

165
-continued
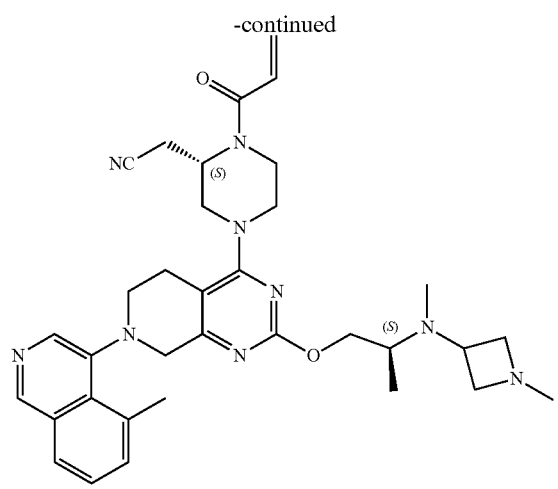
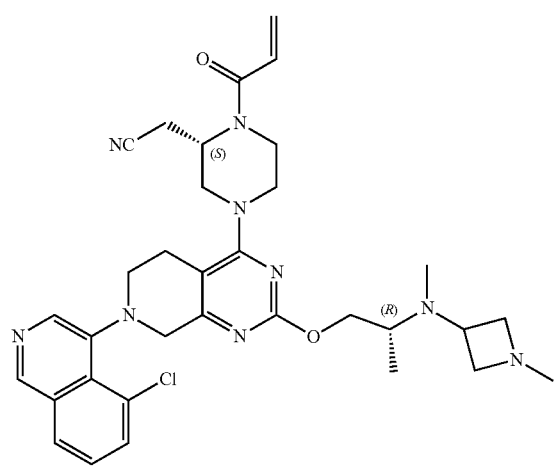
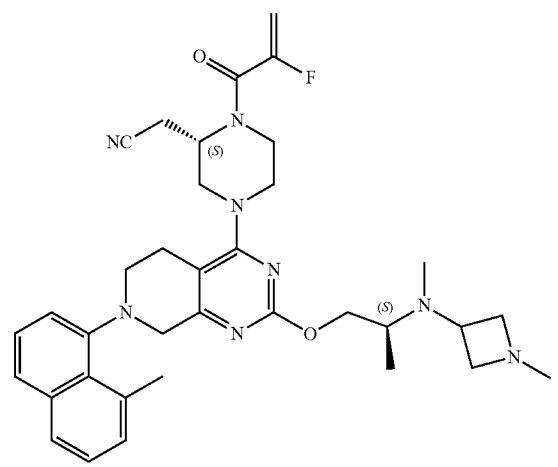
166
-continued
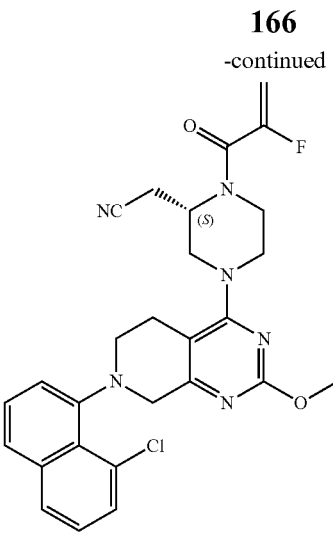
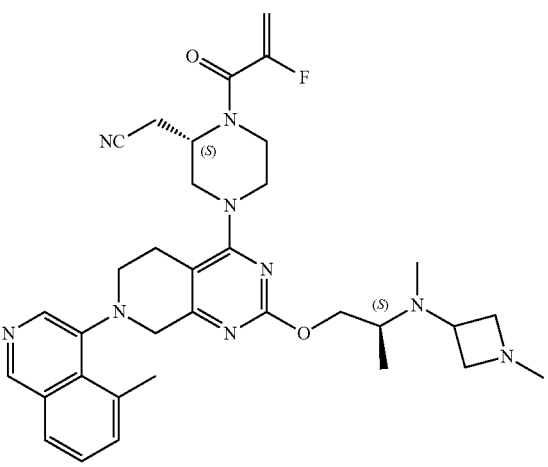
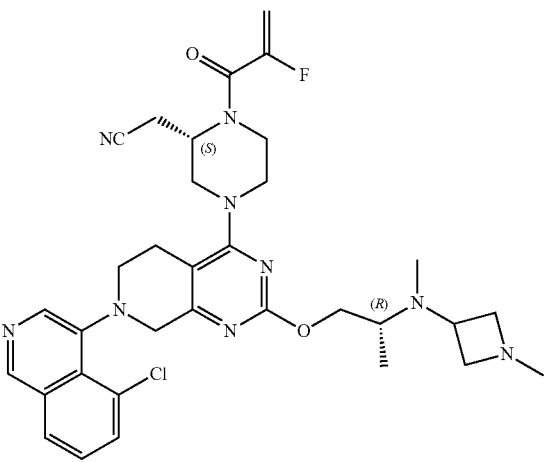

167
-continued
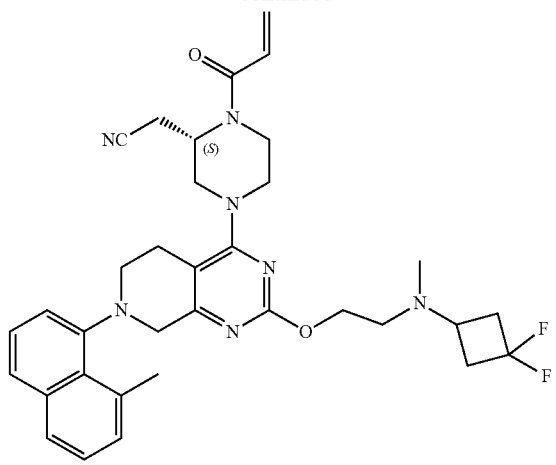
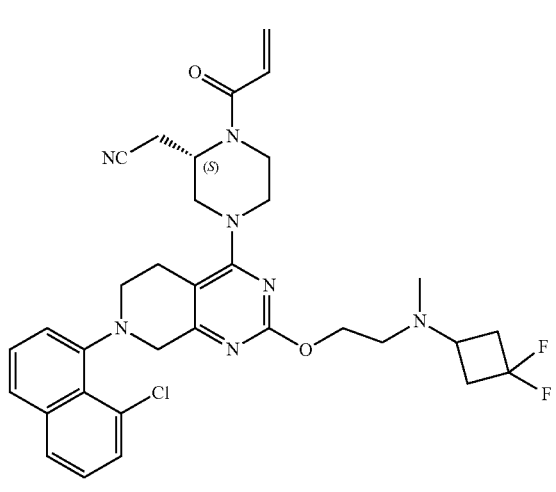
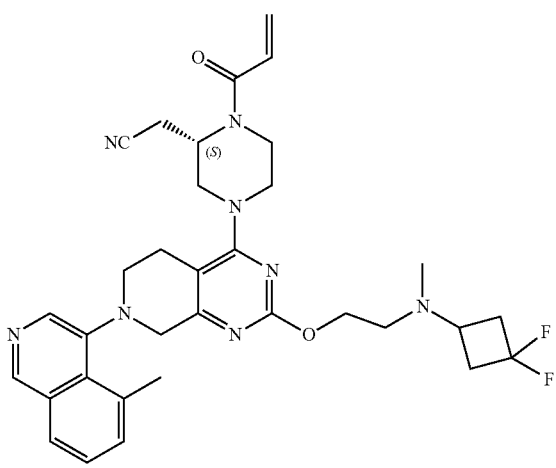
168
-continued
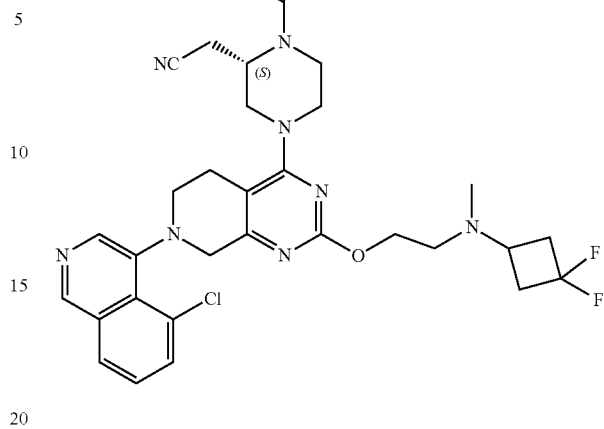
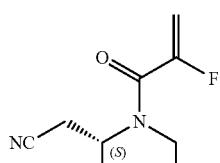
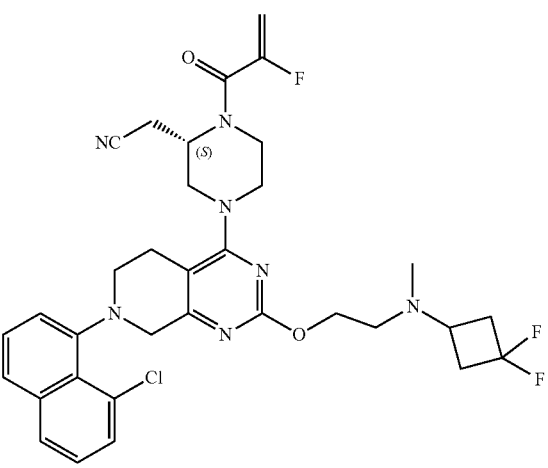

169
-continued
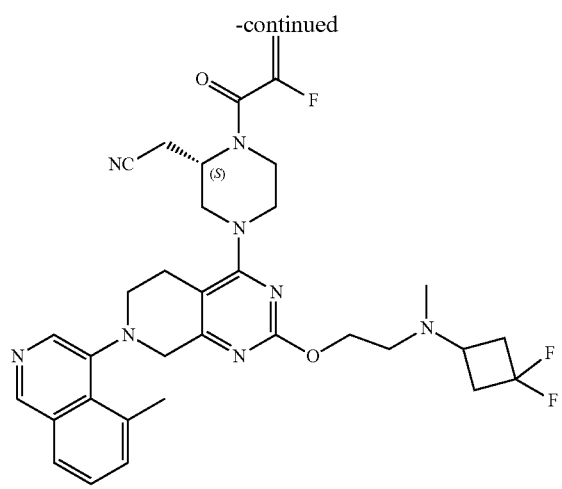
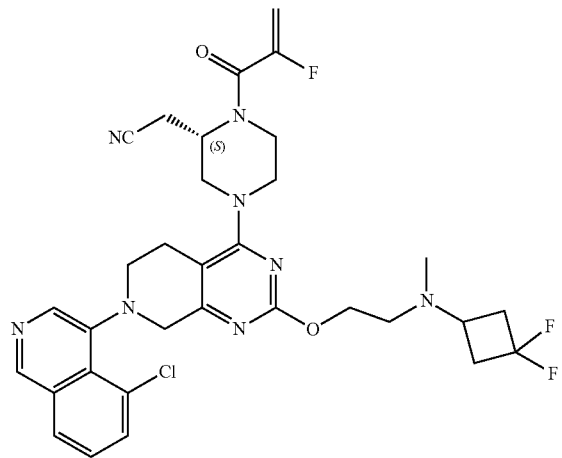
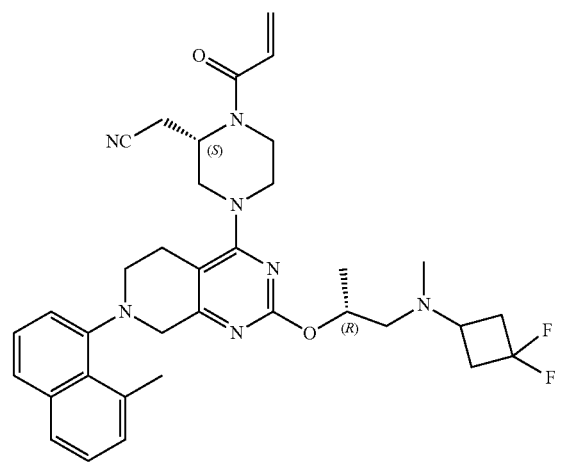
170
-continued
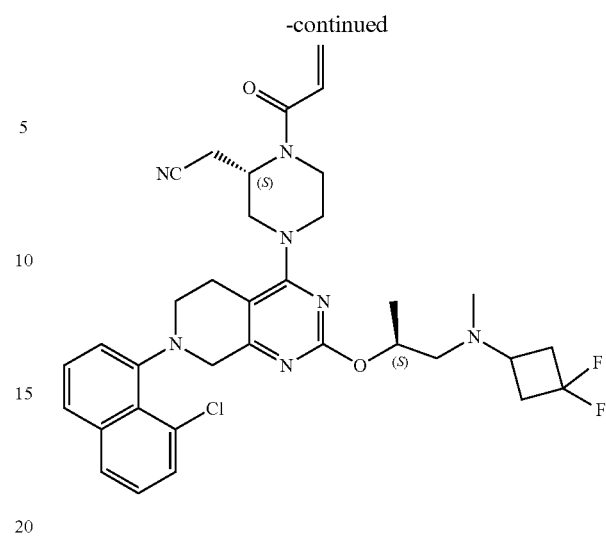
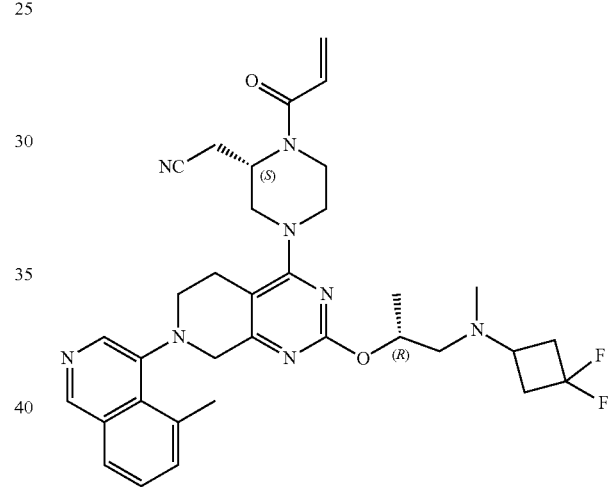
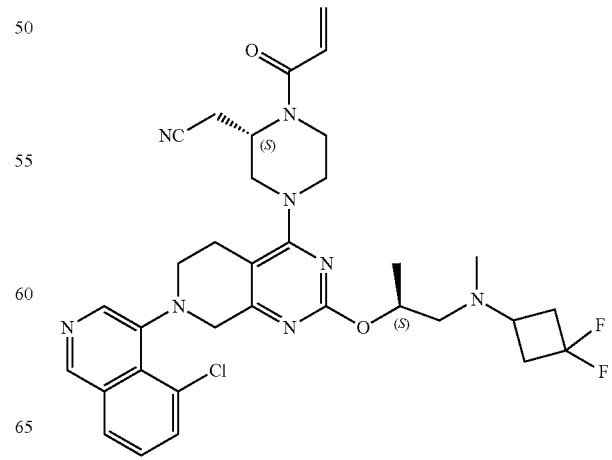

171
-continued
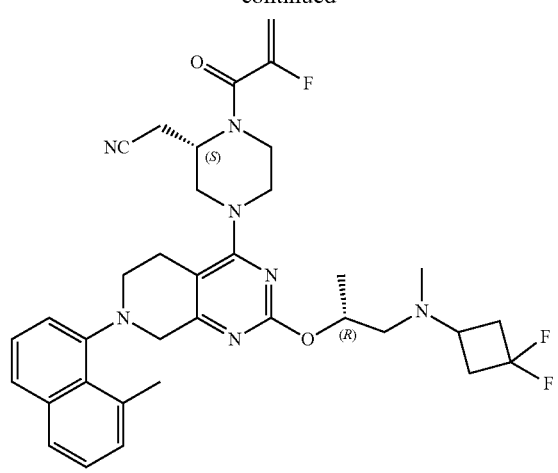
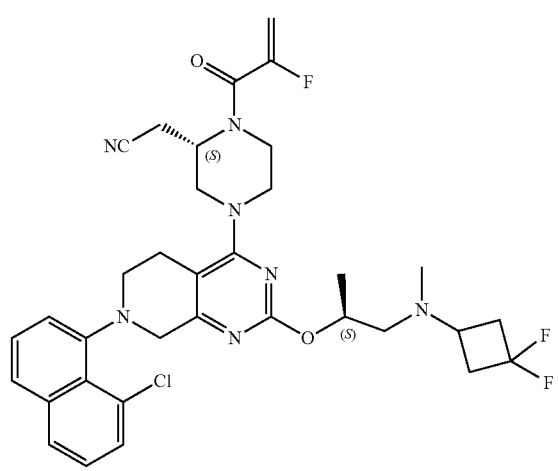
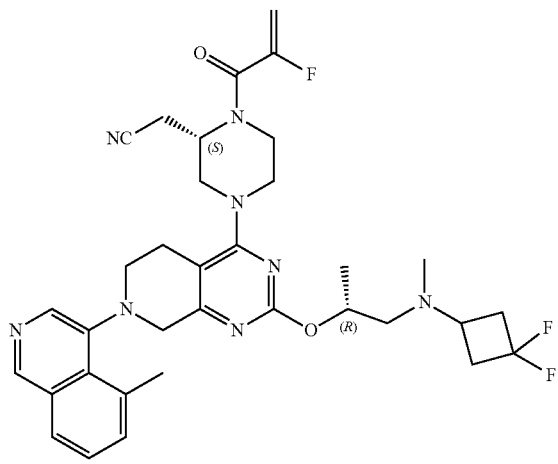
172
-continued
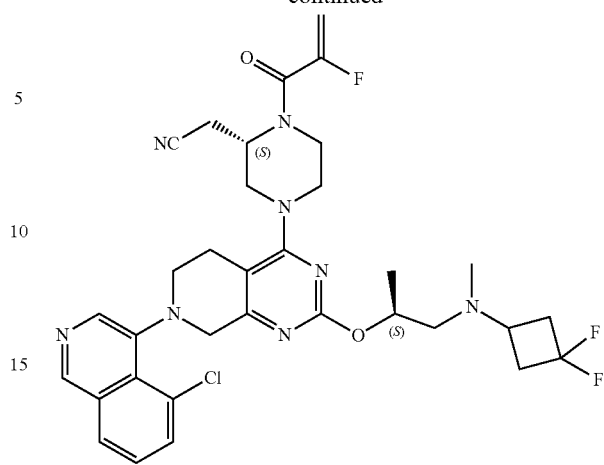
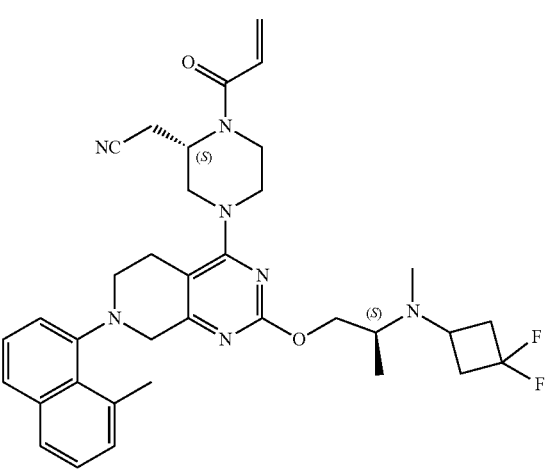
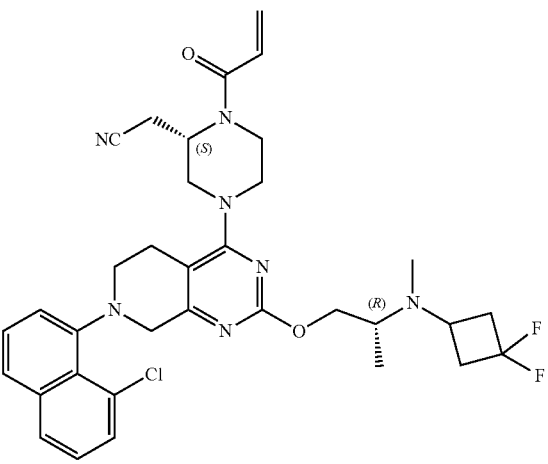

173
-continued
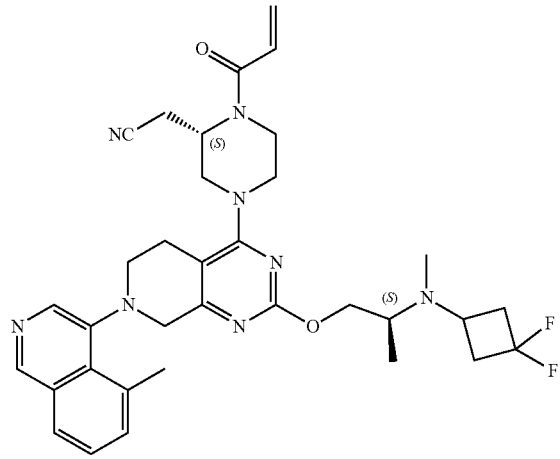
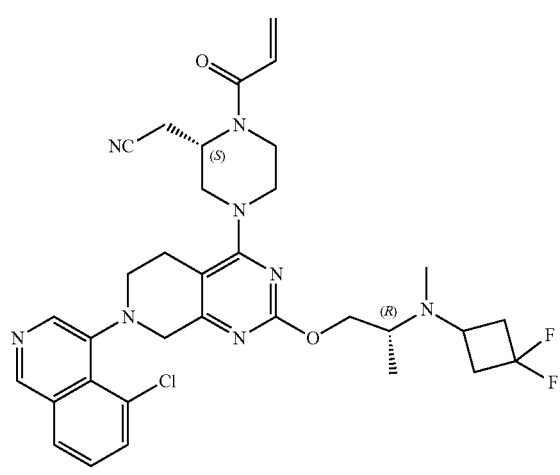
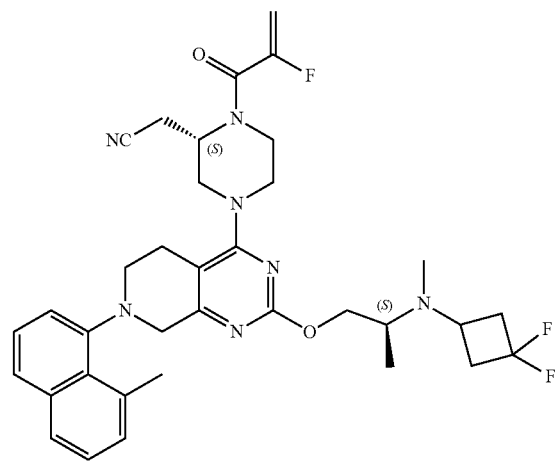
174
-continued
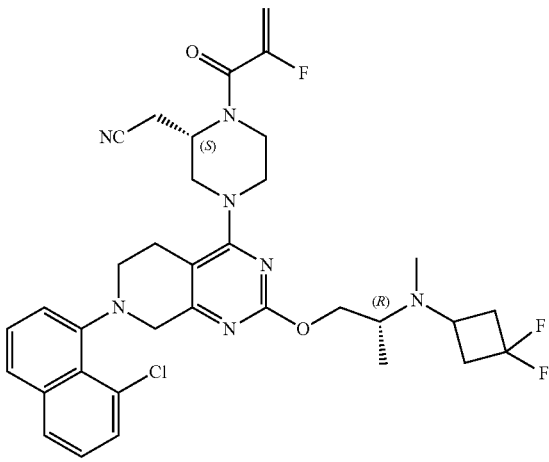
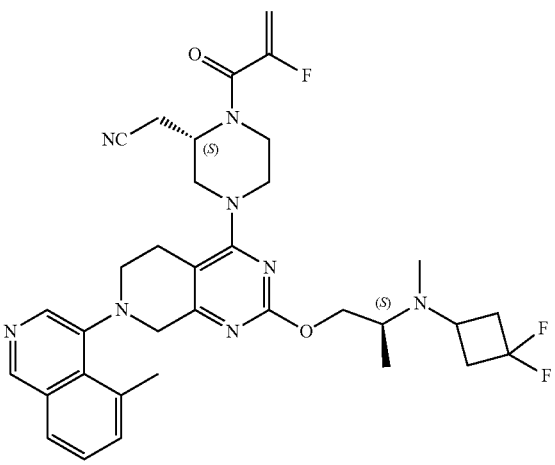
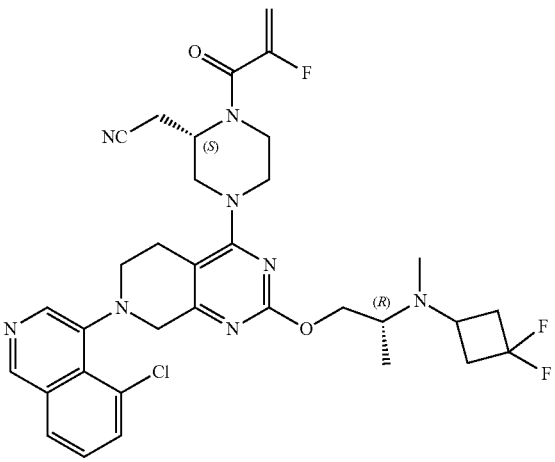

175
-continued
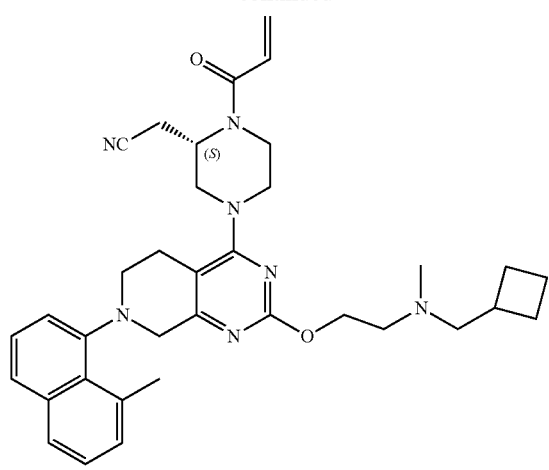
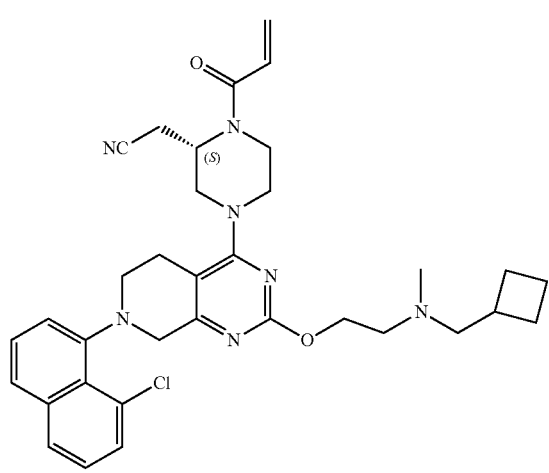
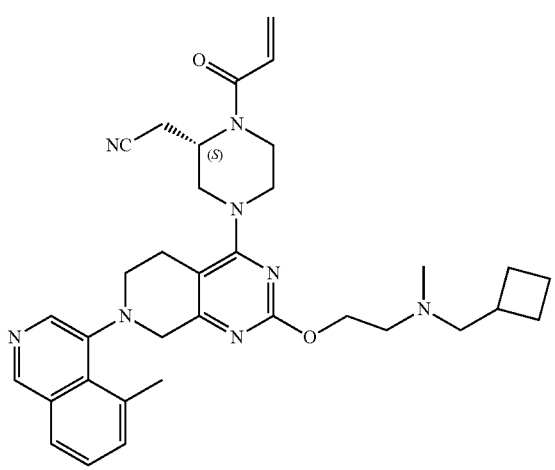
176
-continued
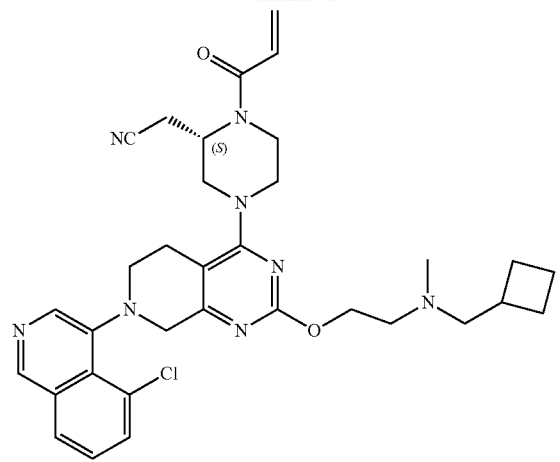
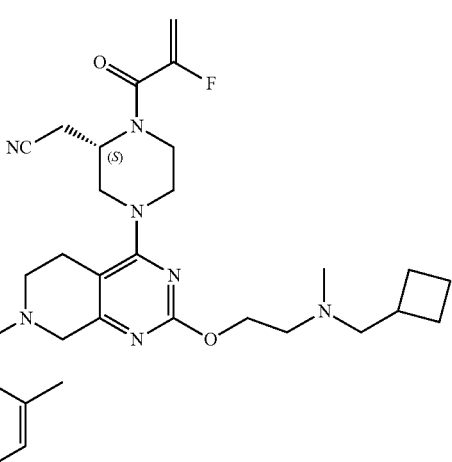
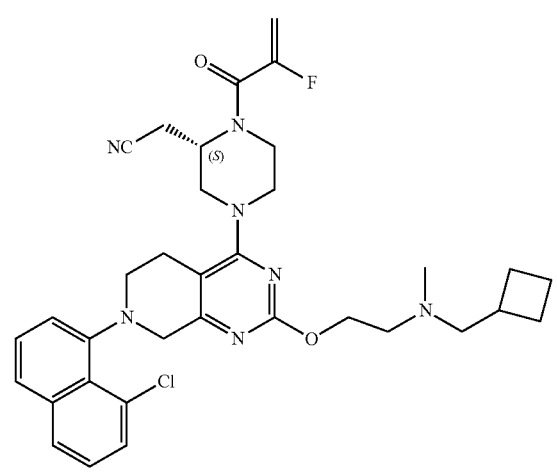

177
-continued
178
-continued
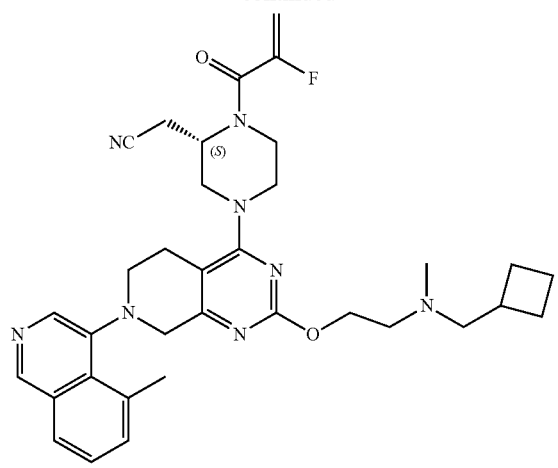
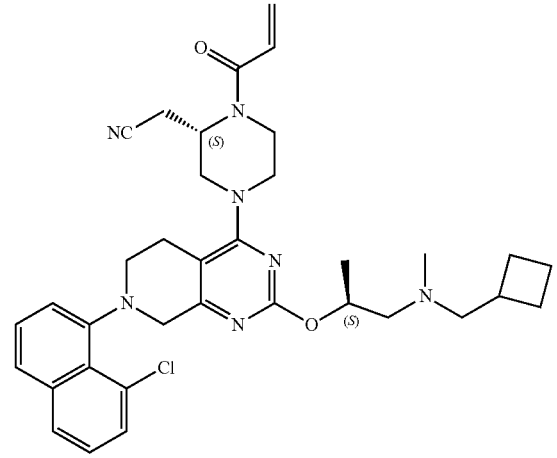
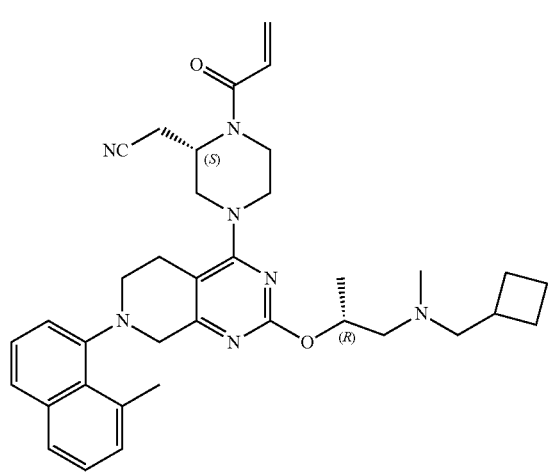

| 179 | 180 |
|---|---|
| -continued | -continued |
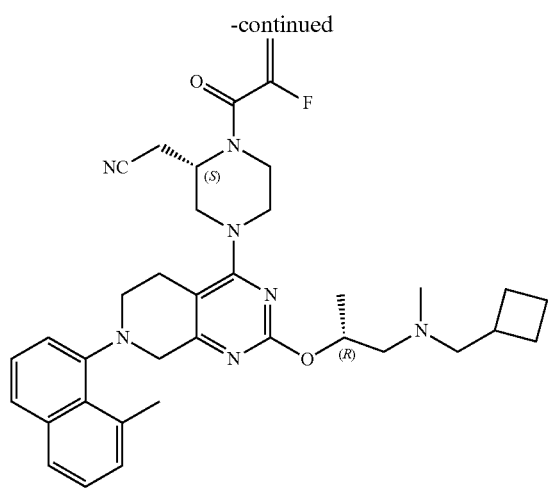
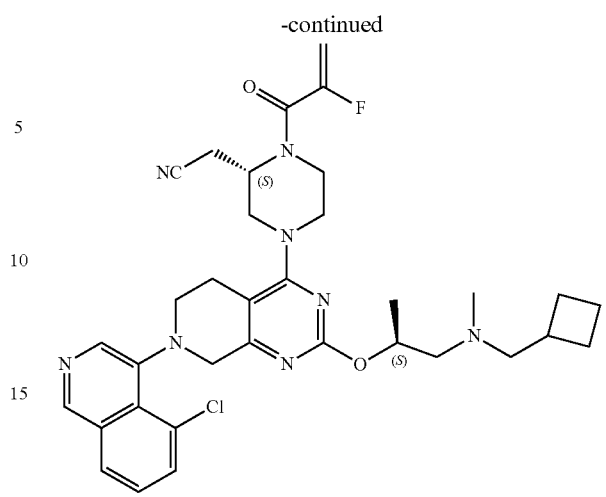
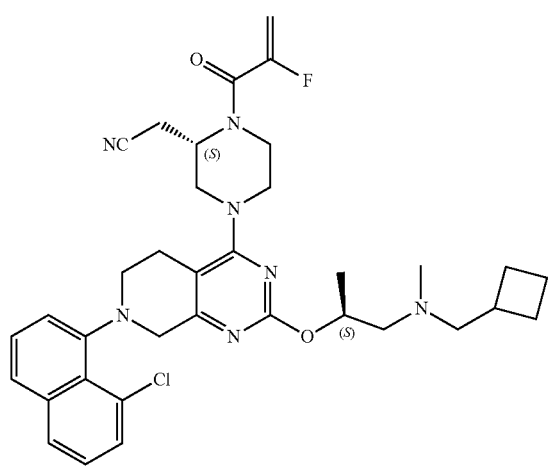
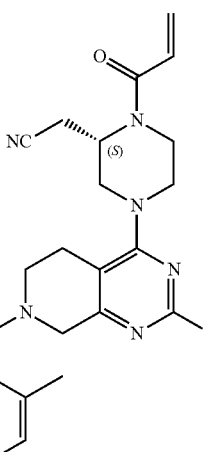
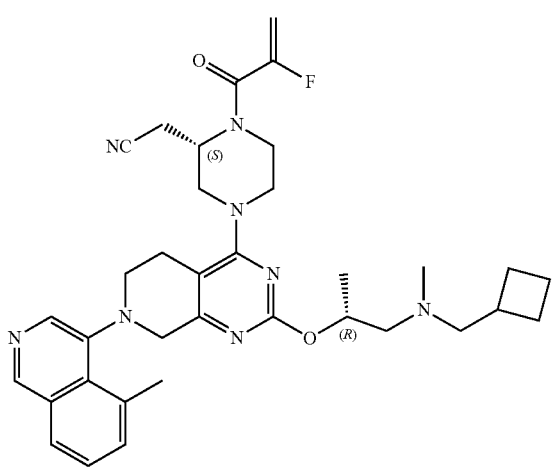
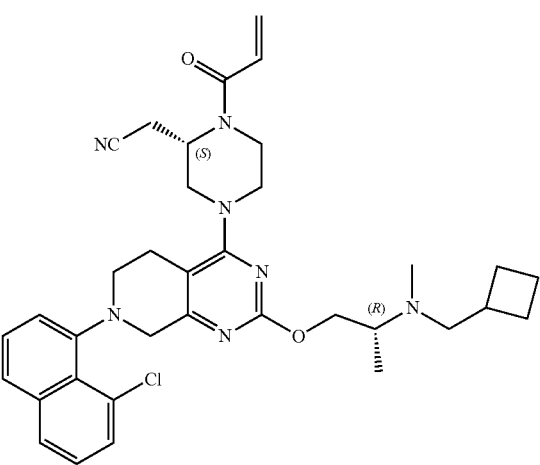

181
-continued
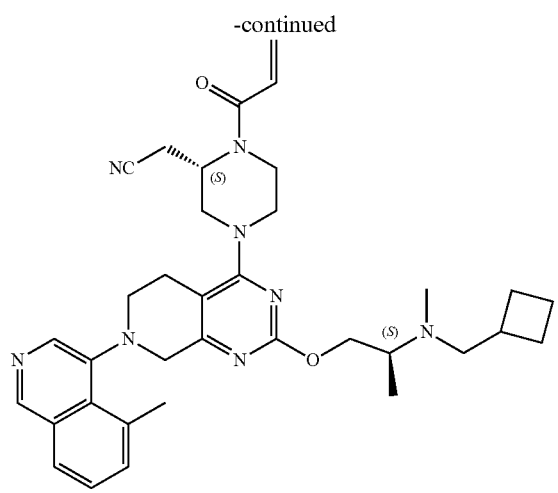
182
-continued
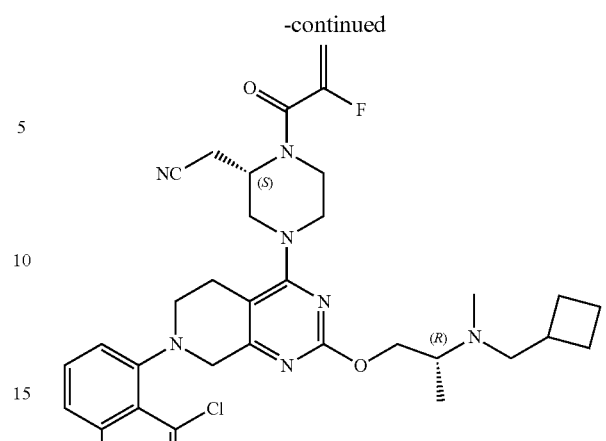
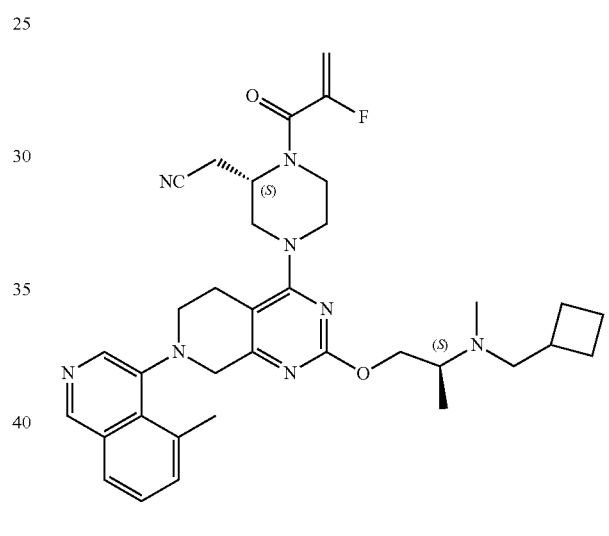
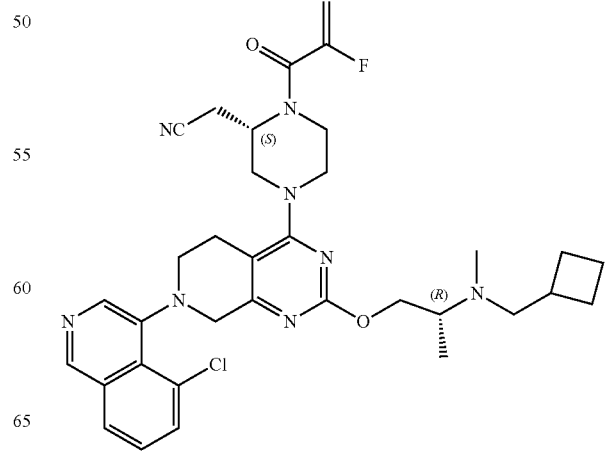

183
-continued
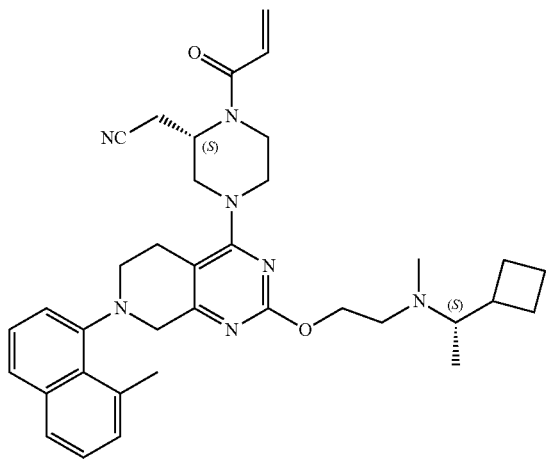
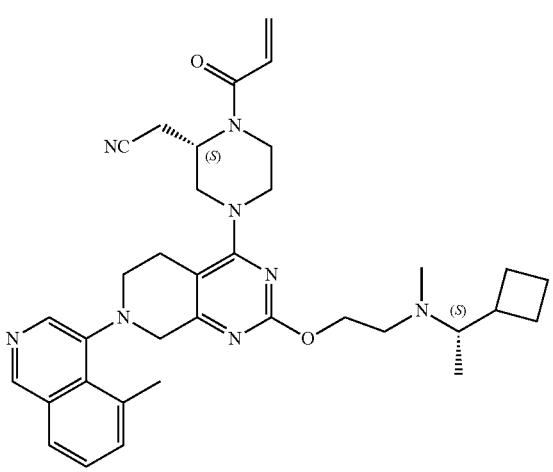
184
-continued
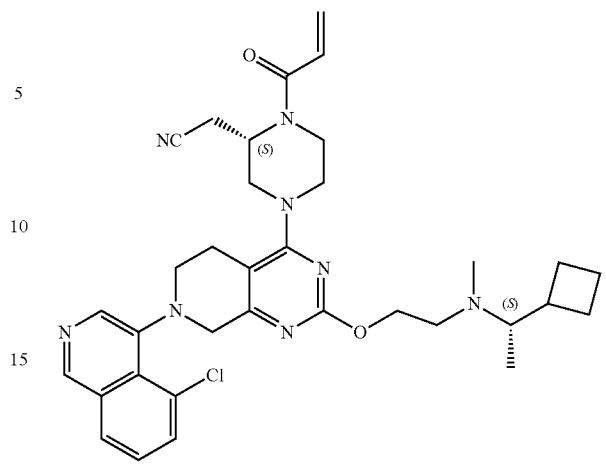
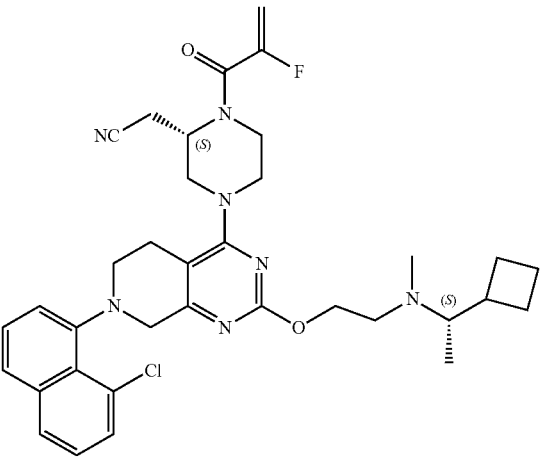

185
-continued
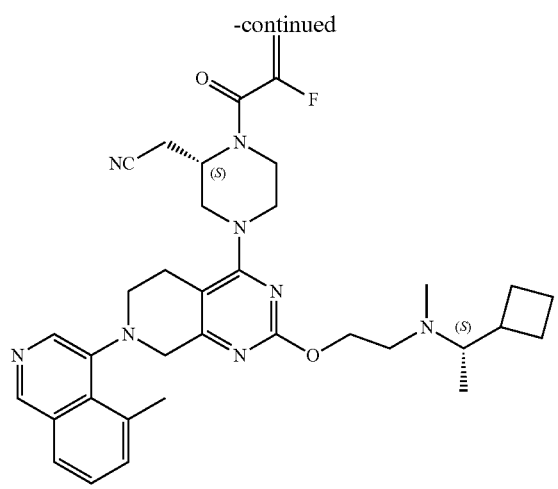
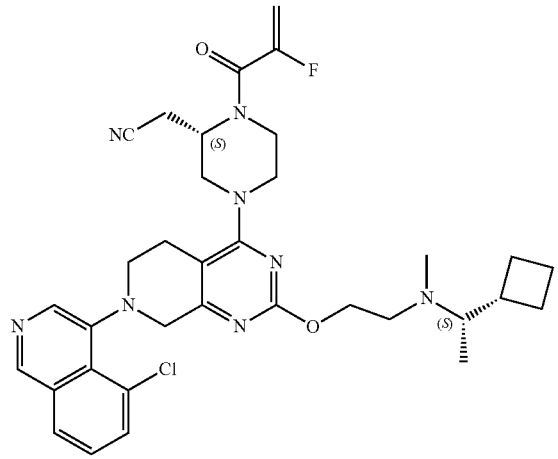
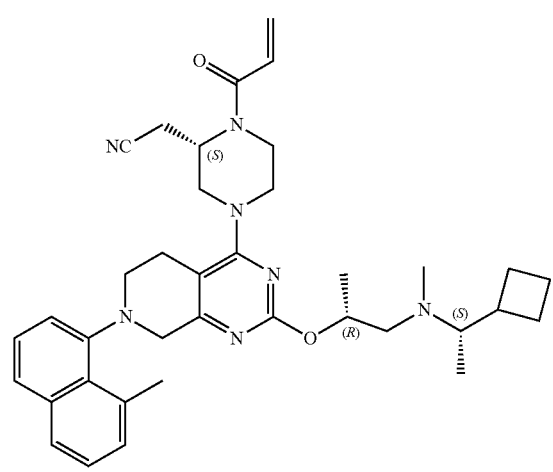
186
-continued
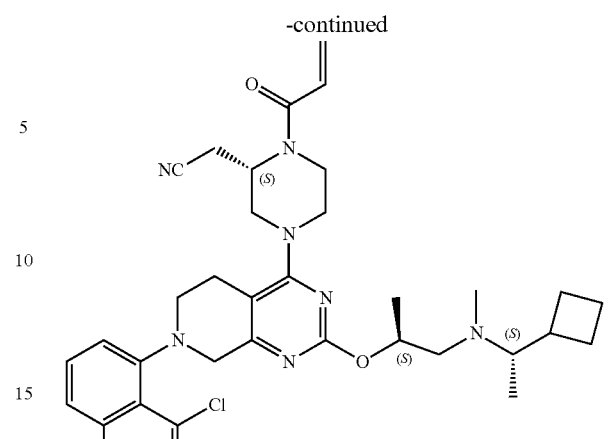
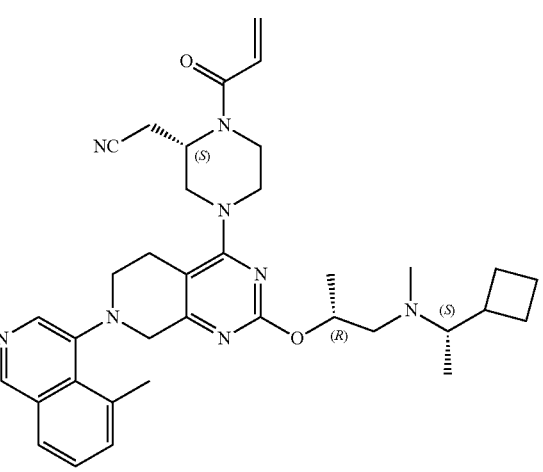
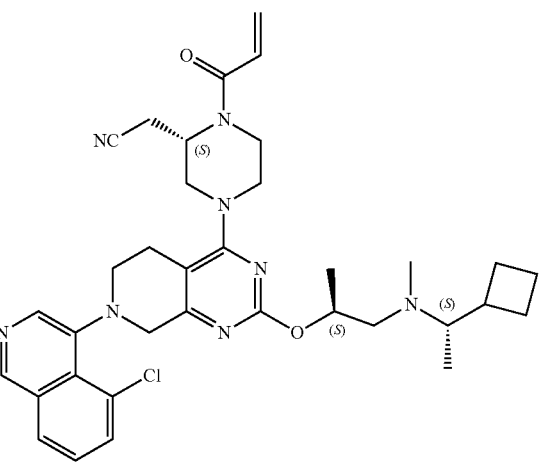

187
-continued
188
-continued
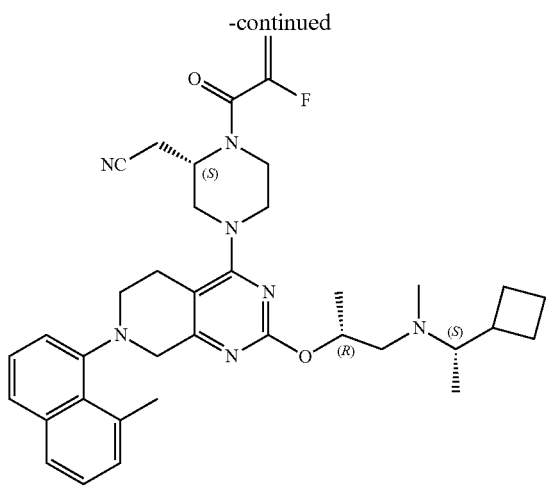
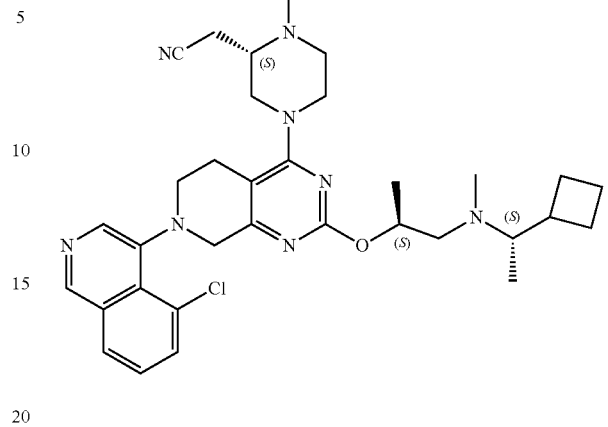
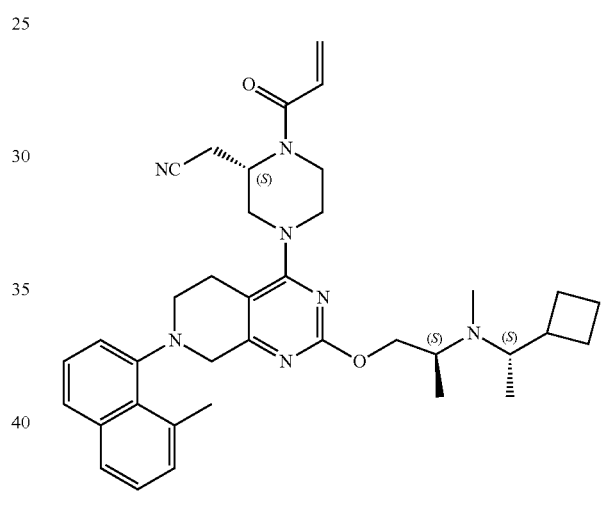
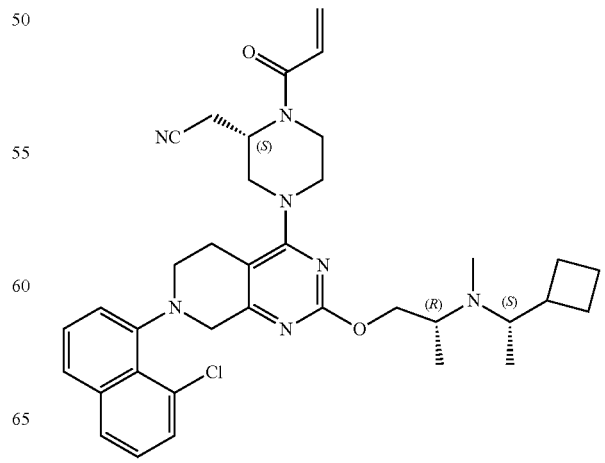

189
-continued
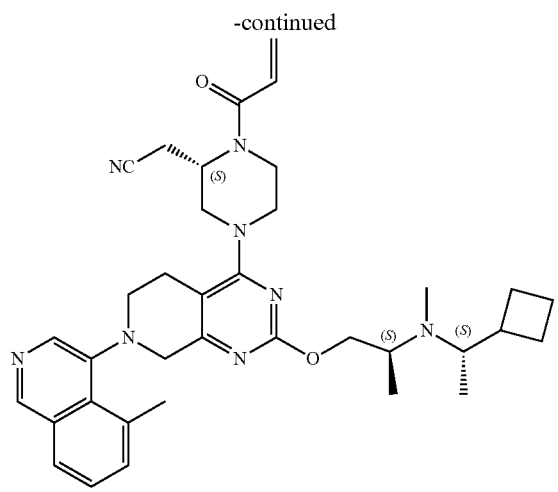
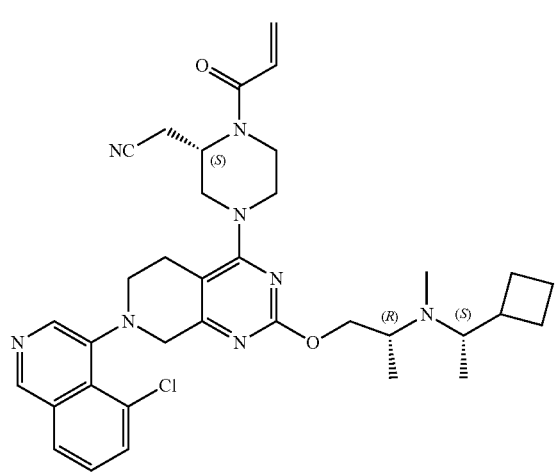
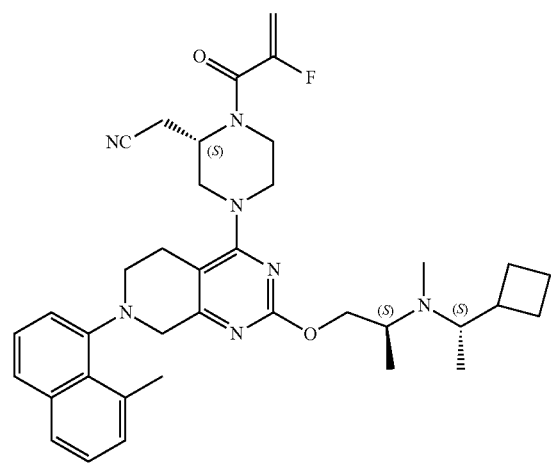
190
-continued
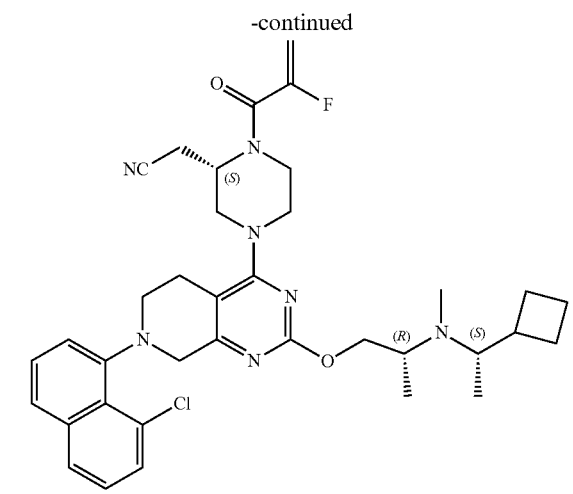
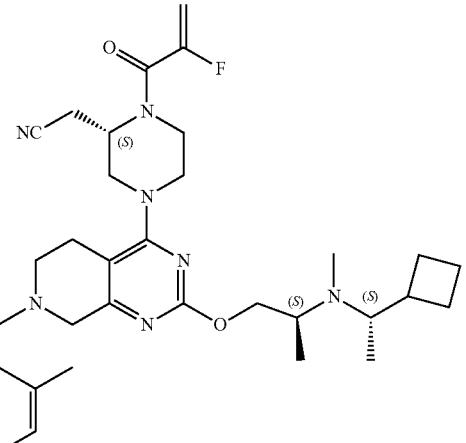
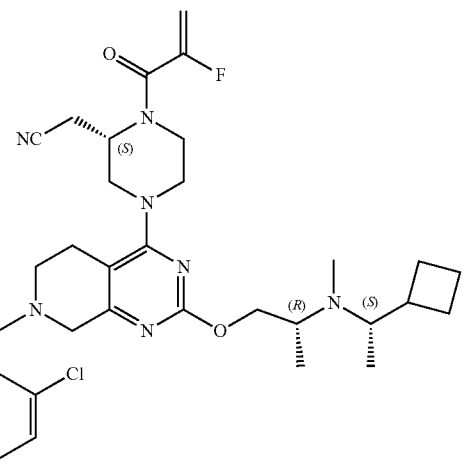

-continued

191

192

193
-continued
194
-continued
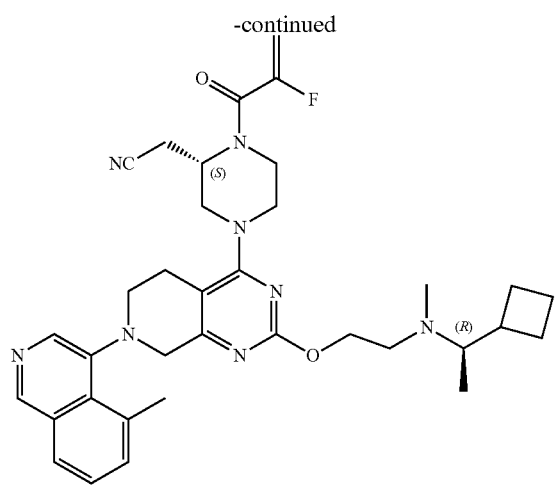
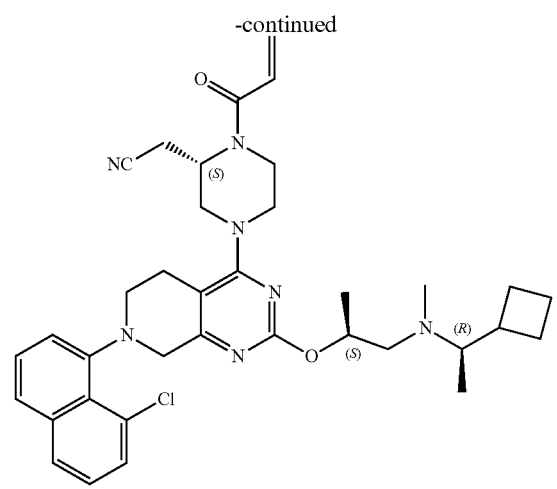
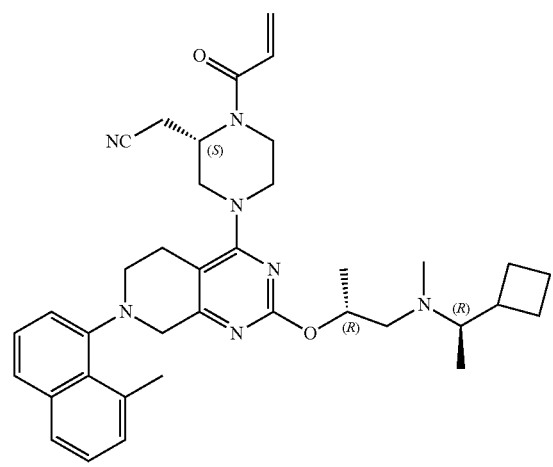

195
-continued
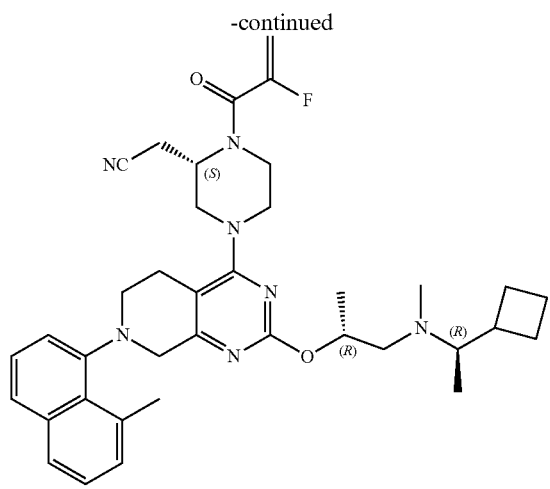
196
-continued
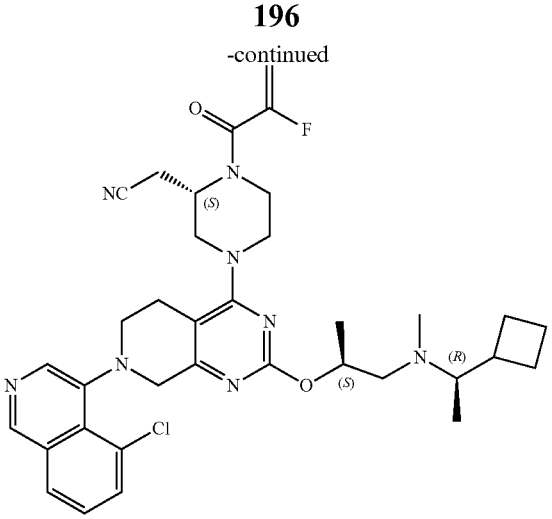
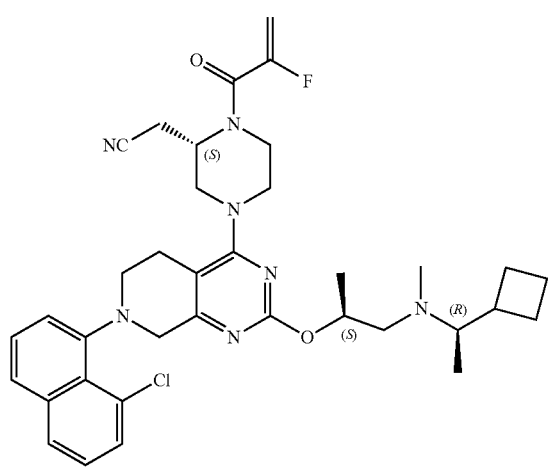
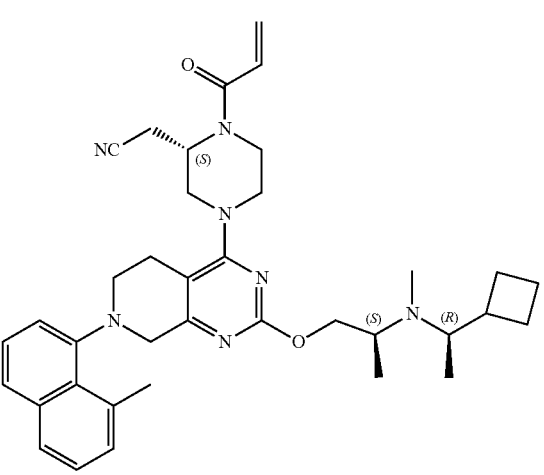
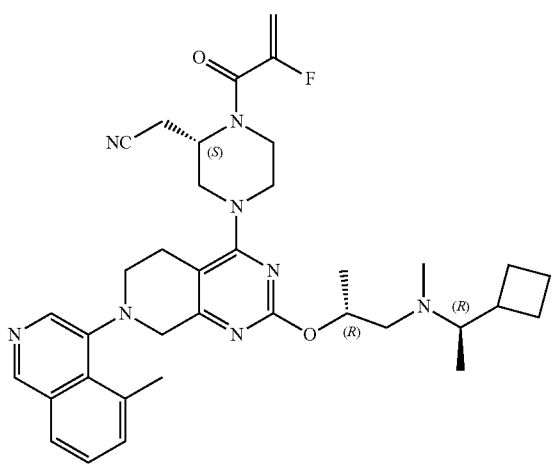
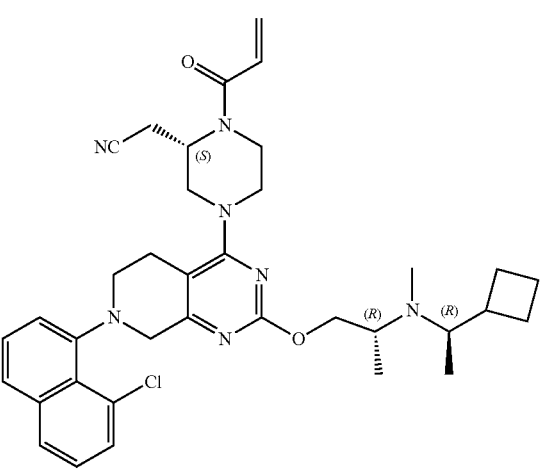

197
-continued
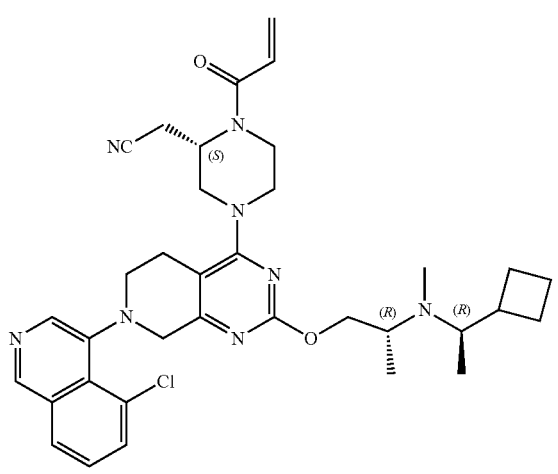
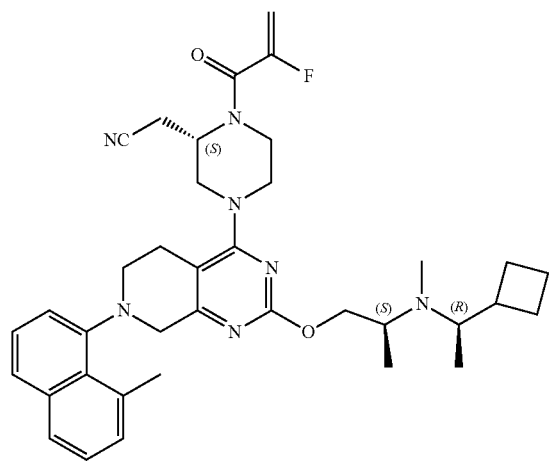
198
-continued

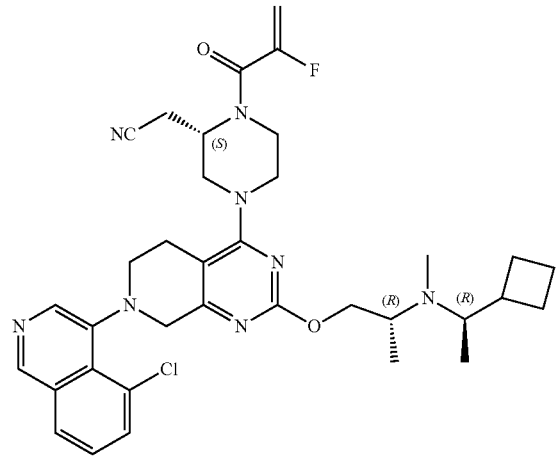

199
-continued
200
-continued
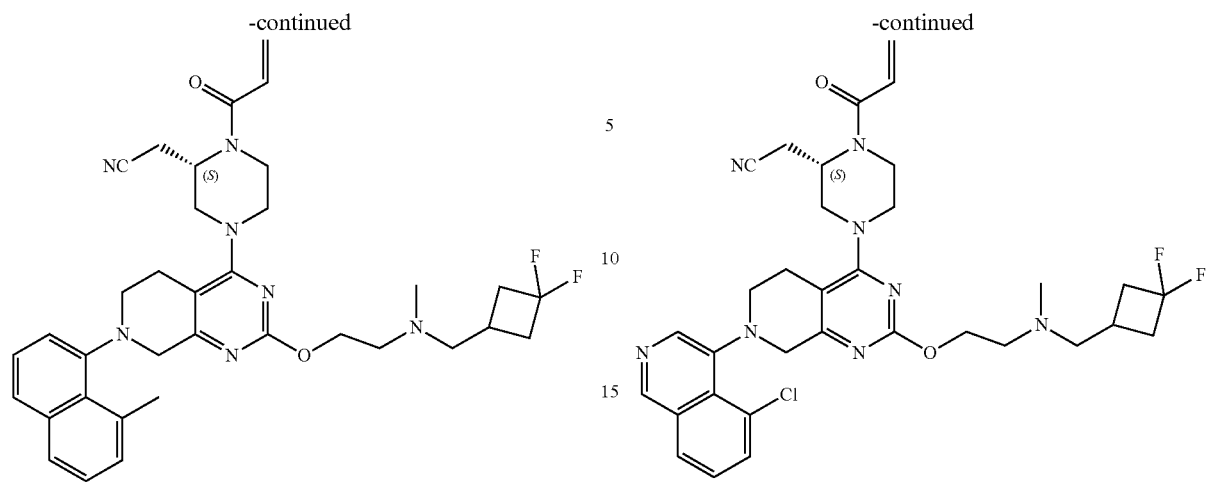
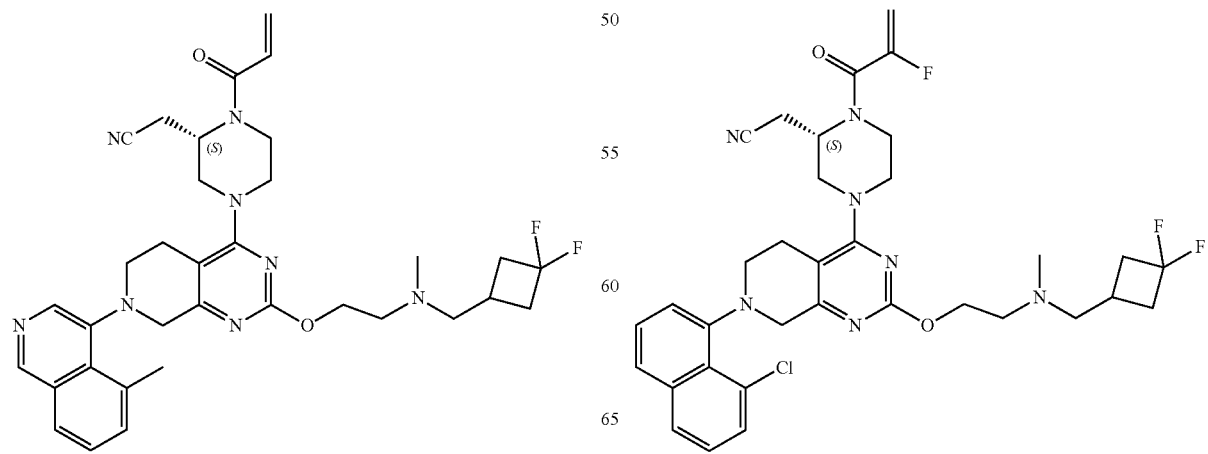

201
-continued
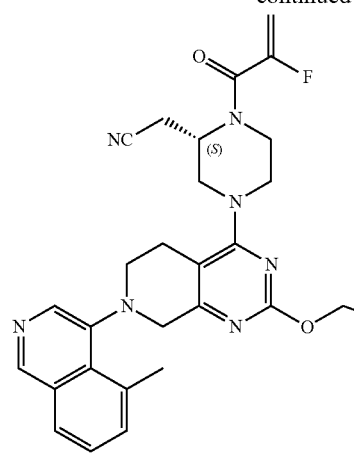
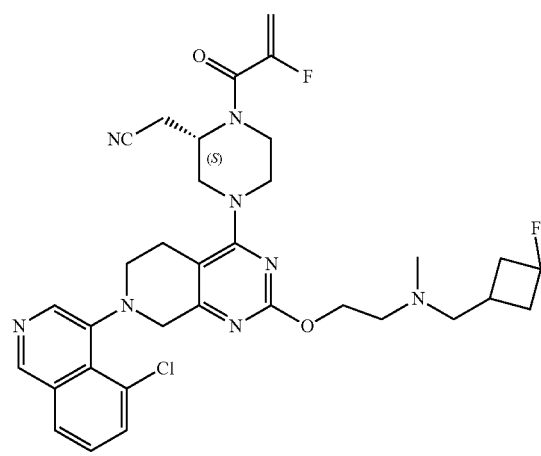
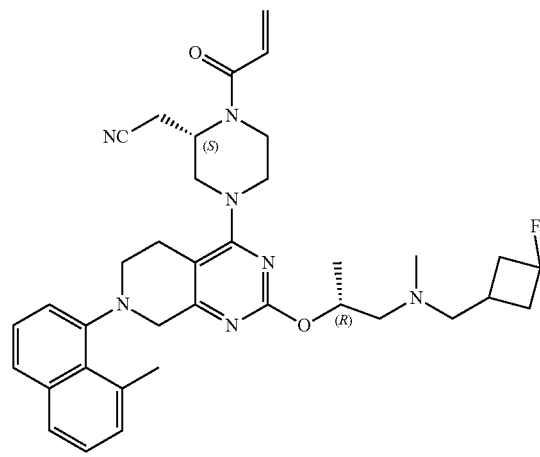
202
-continued
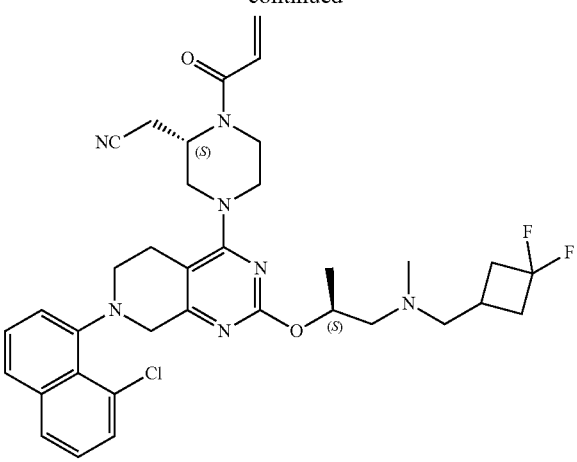
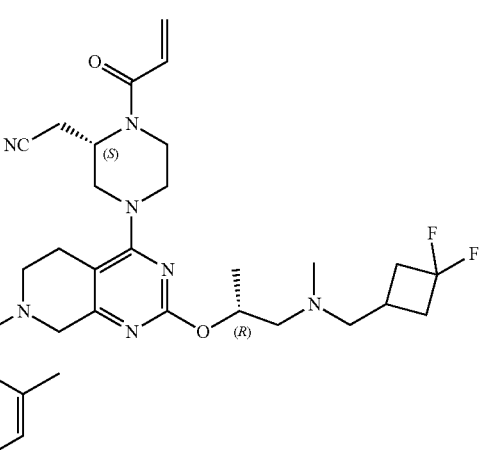
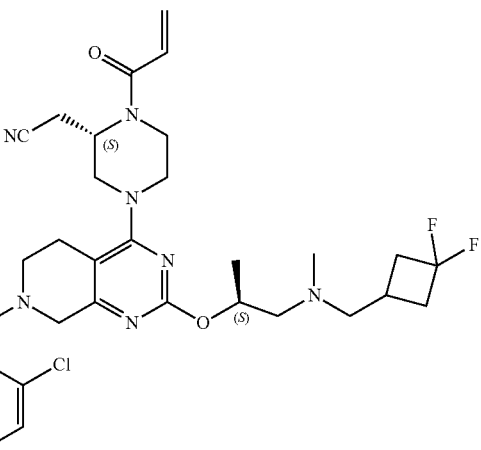

203
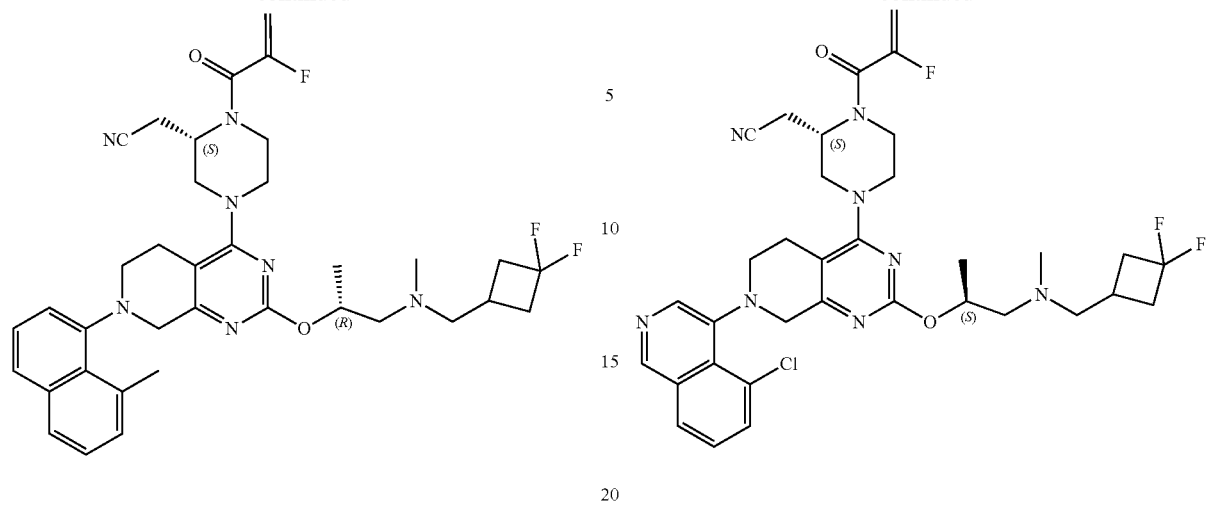
204
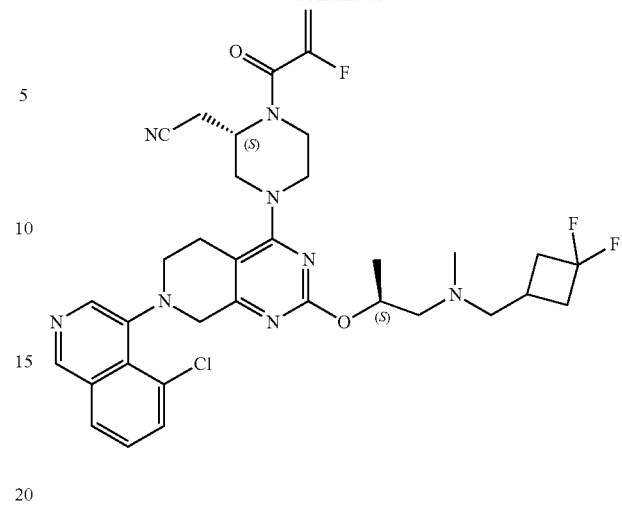

205
-continued
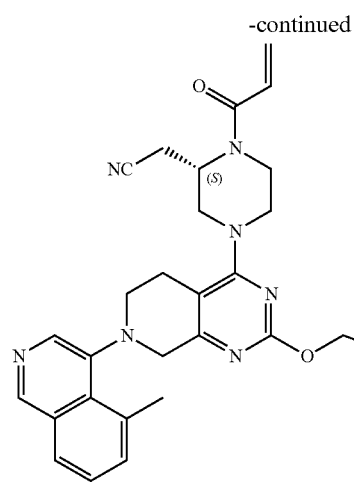
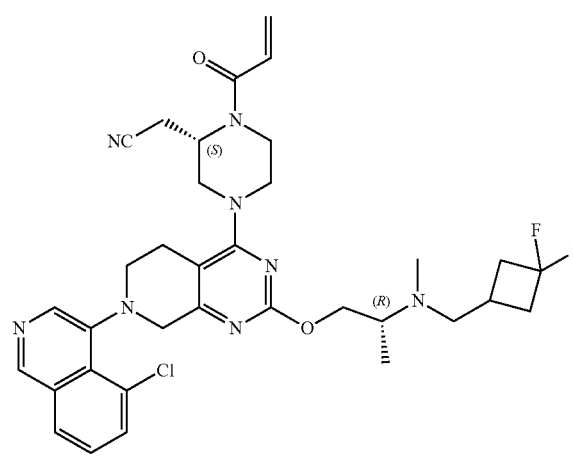
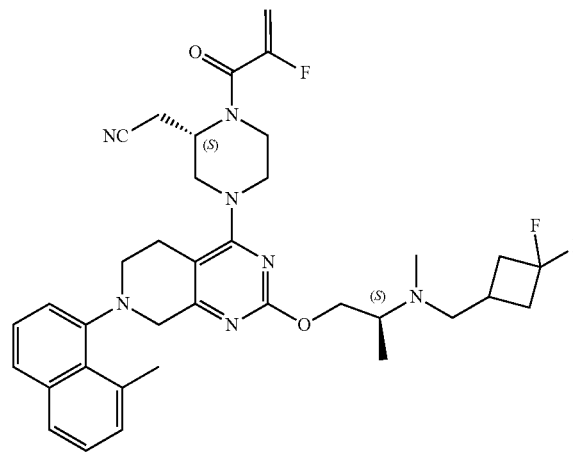
206
-continued
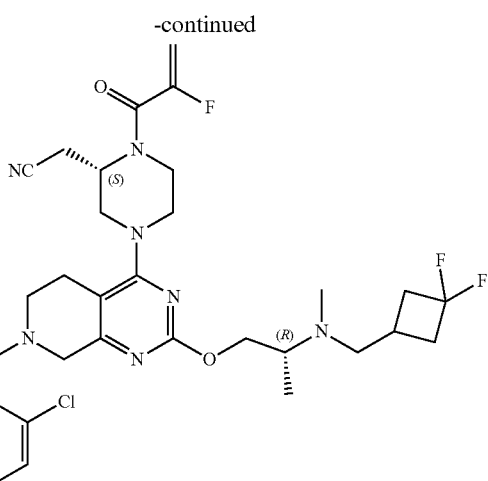
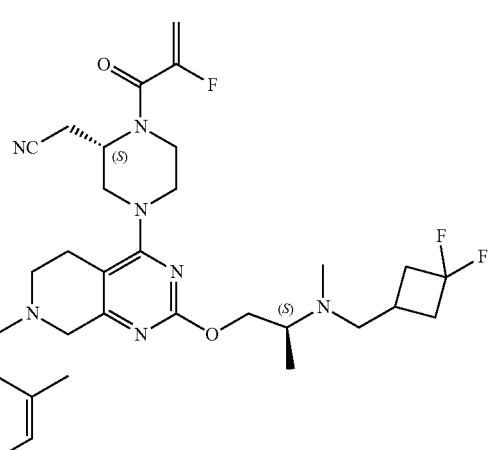
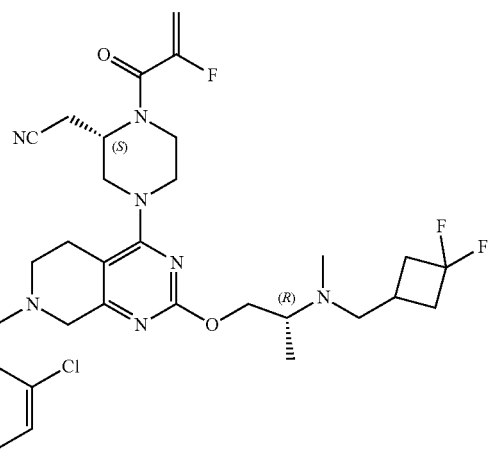

207
-continued
208
-continued
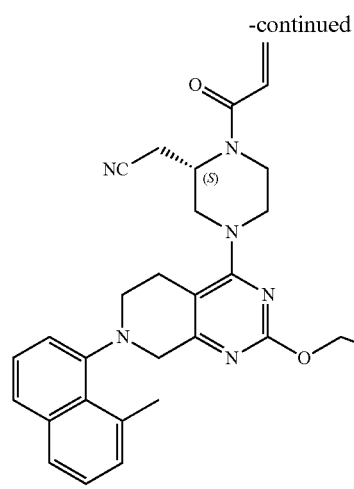
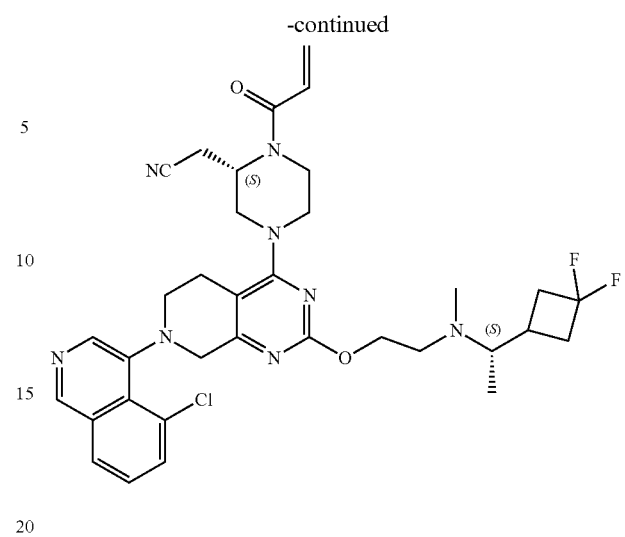
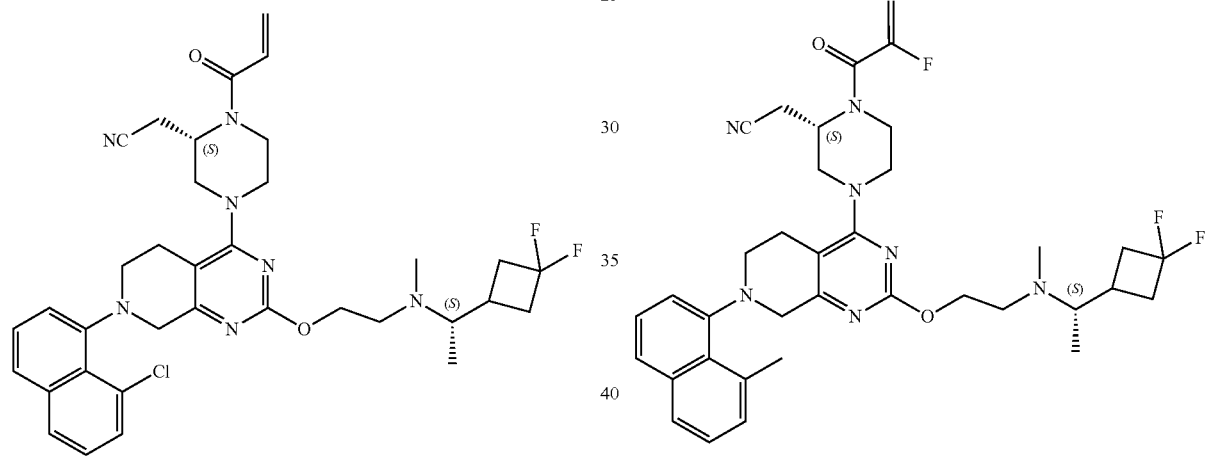
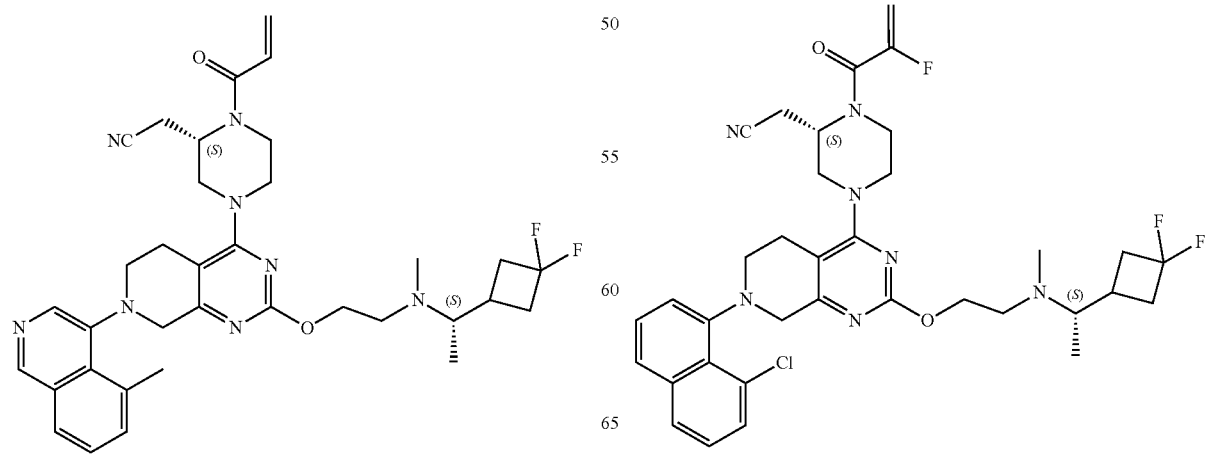

209
-continued
210
-continued

211
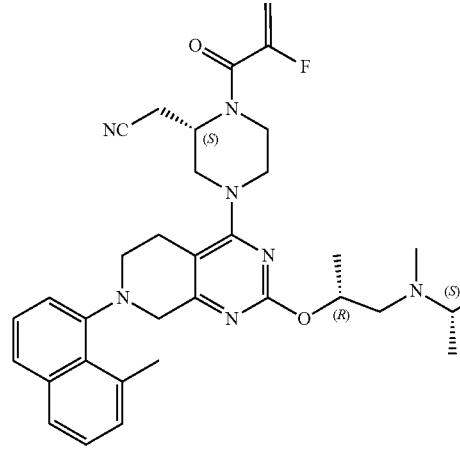
212
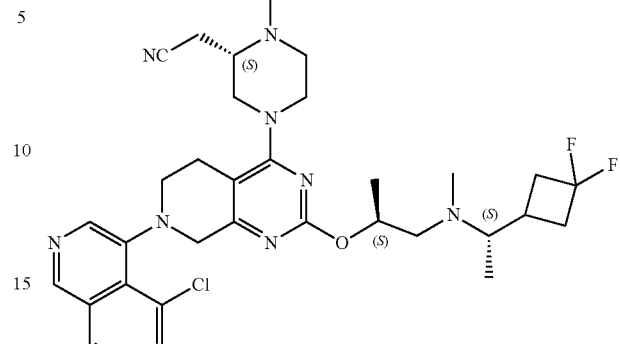
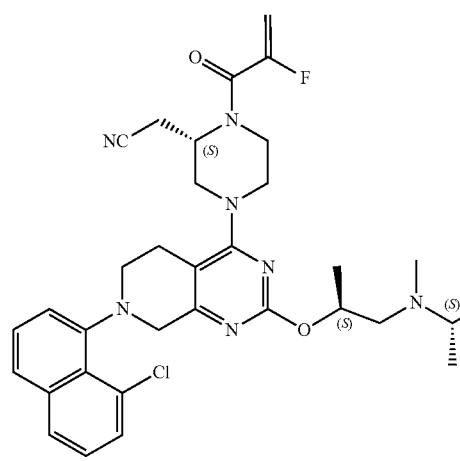
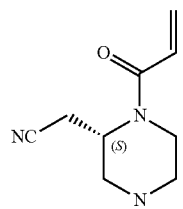
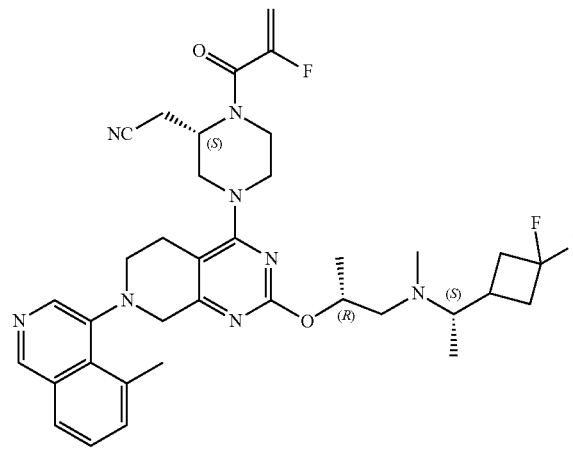
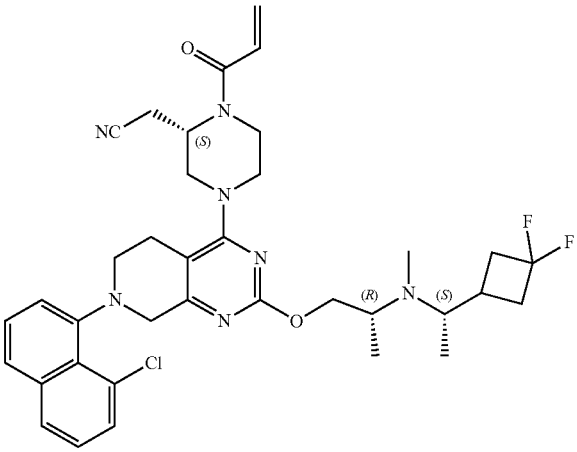

213
-continued
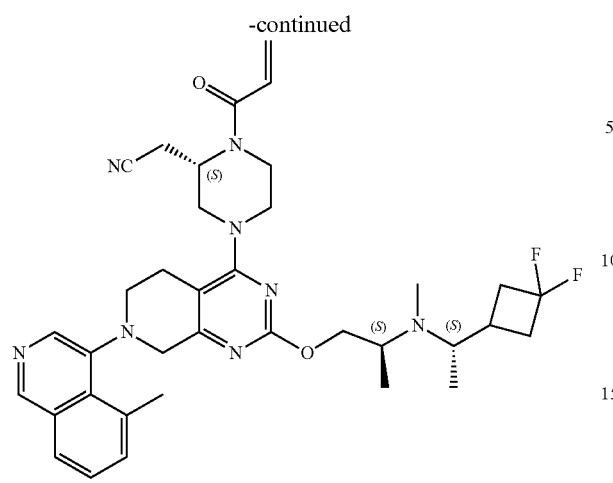
214
-continued
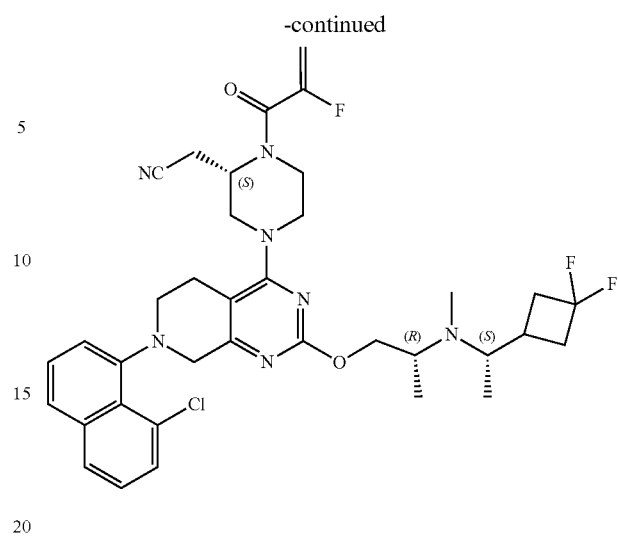
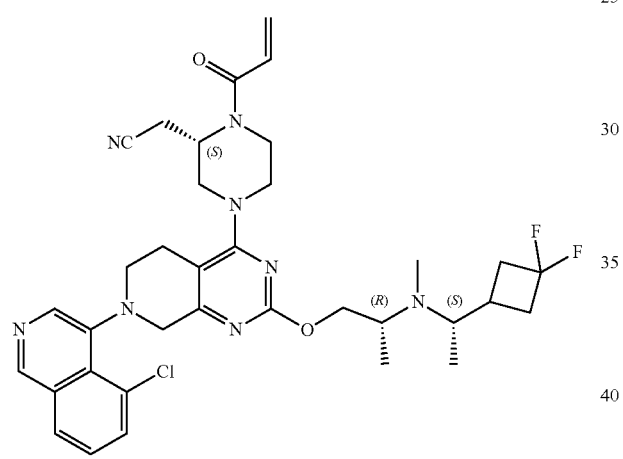
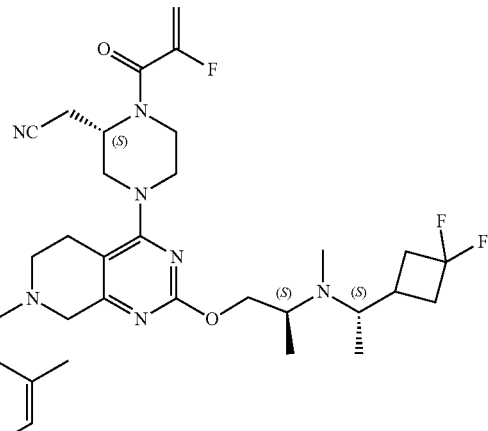
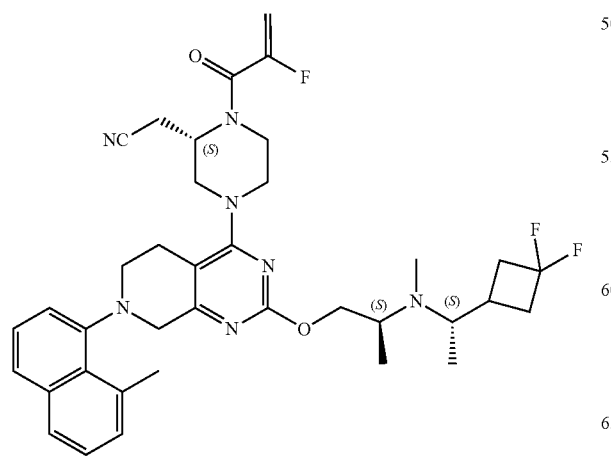
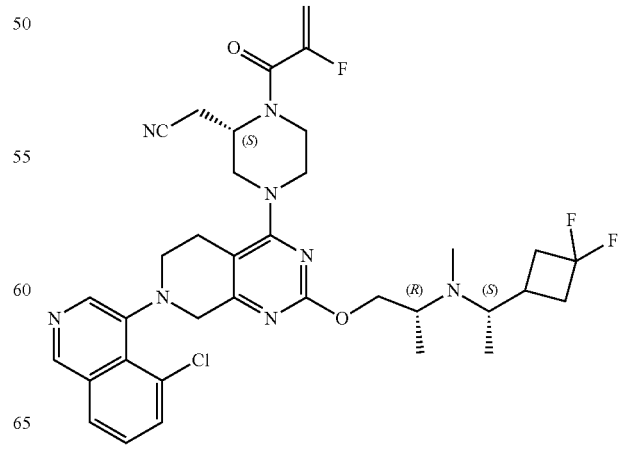

215
-continued
216
-continued
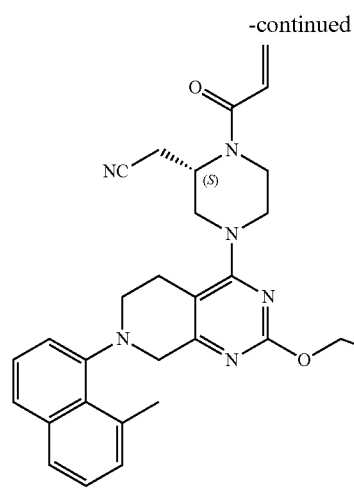
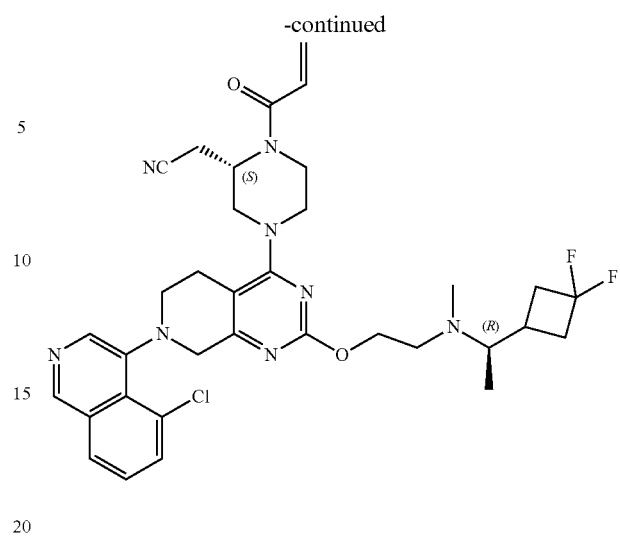
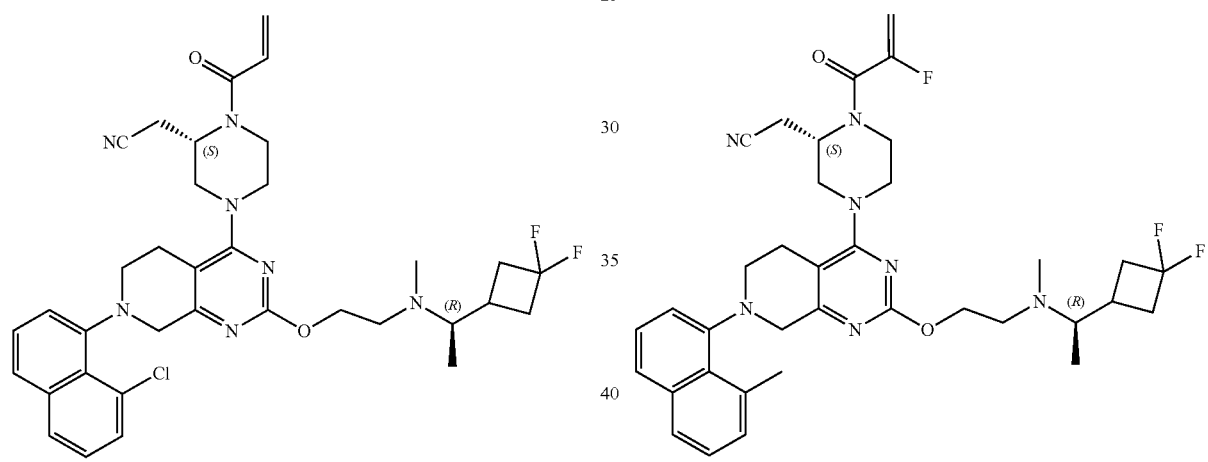
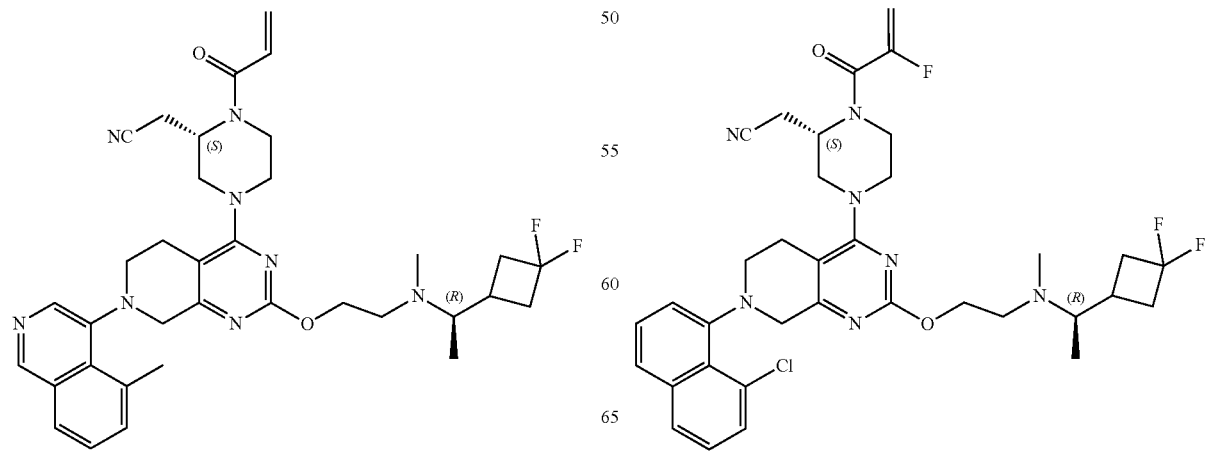

217
-continued
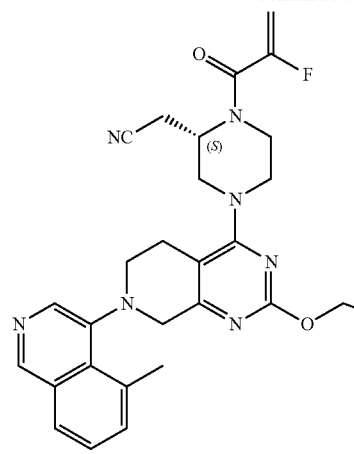
218
-continued
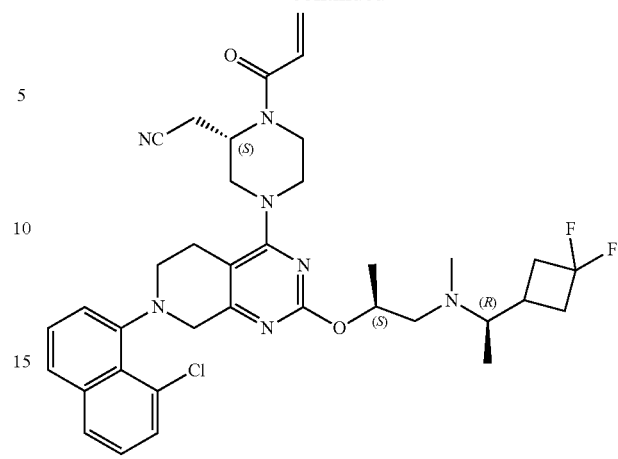
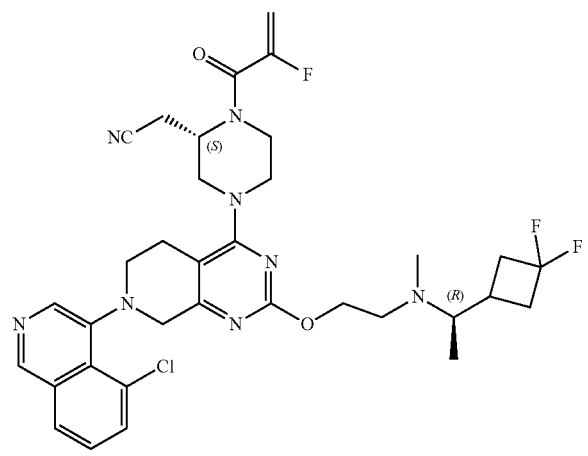
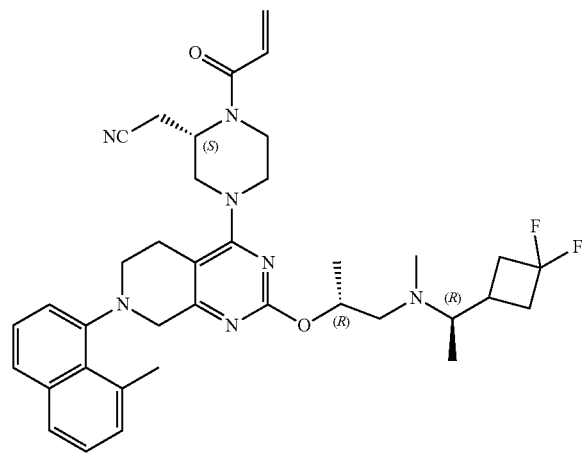
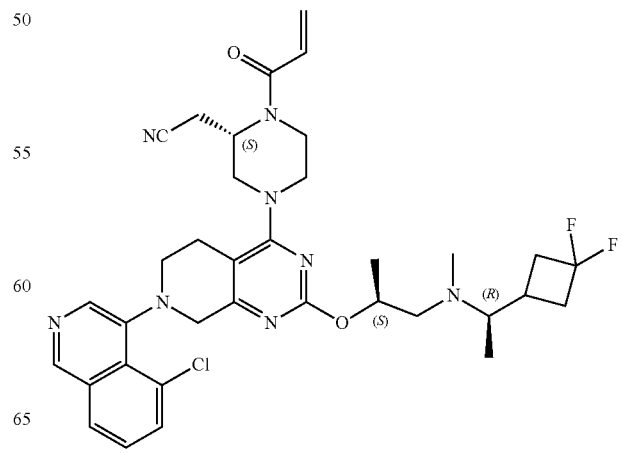

219
-continued
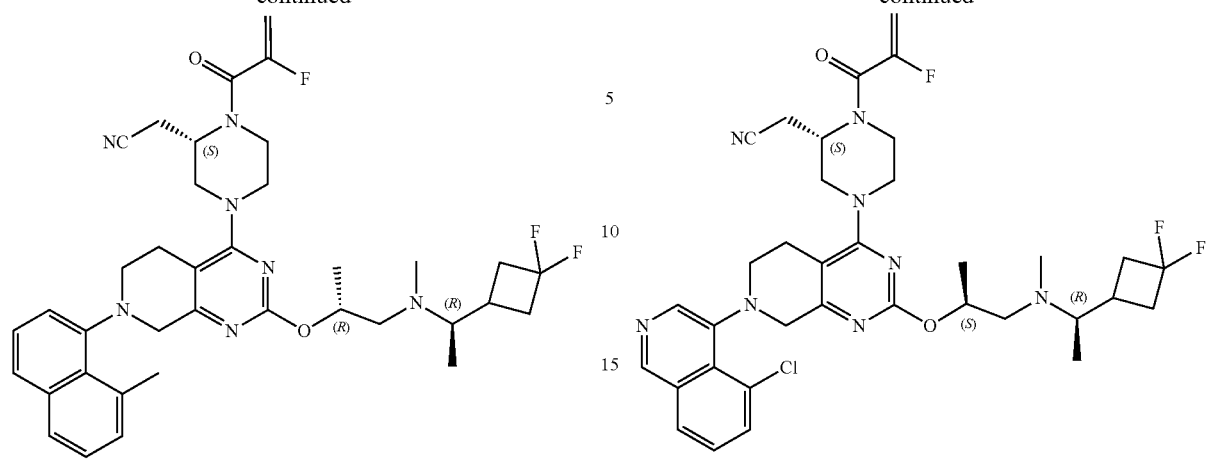
220
-continued
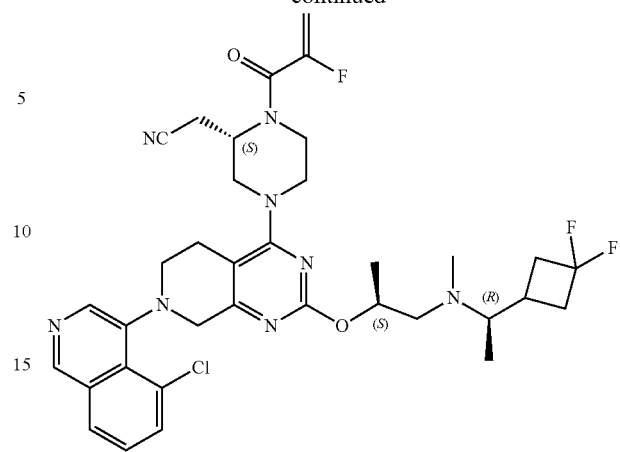
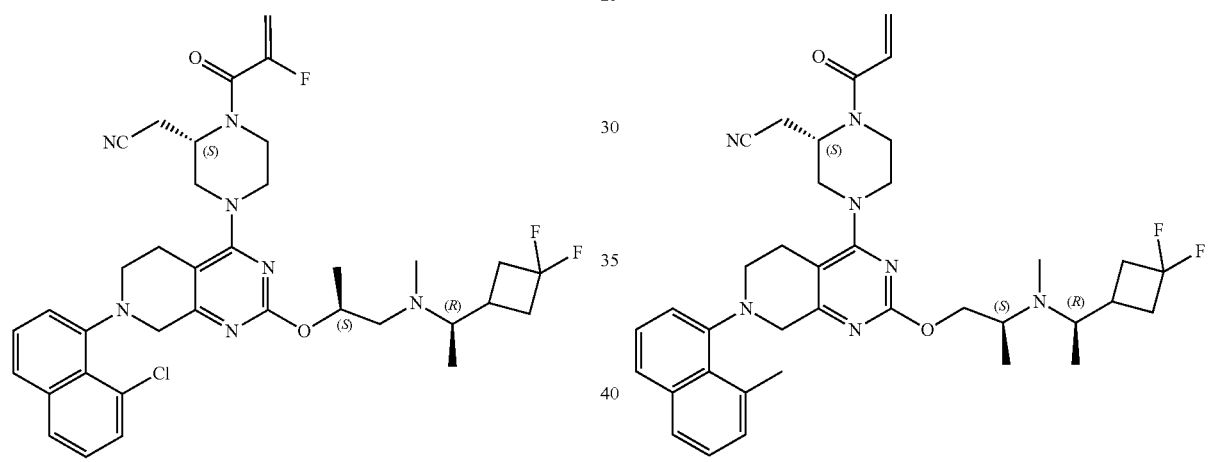

221
-continued
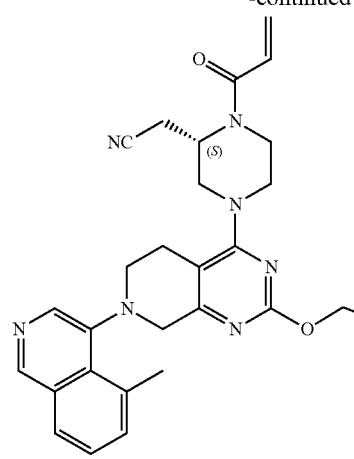
222
-continued
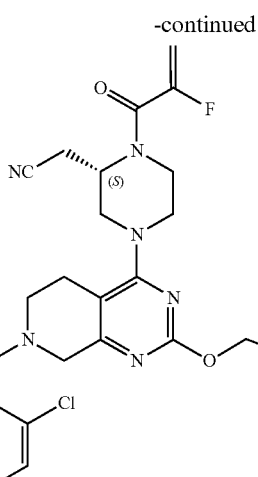
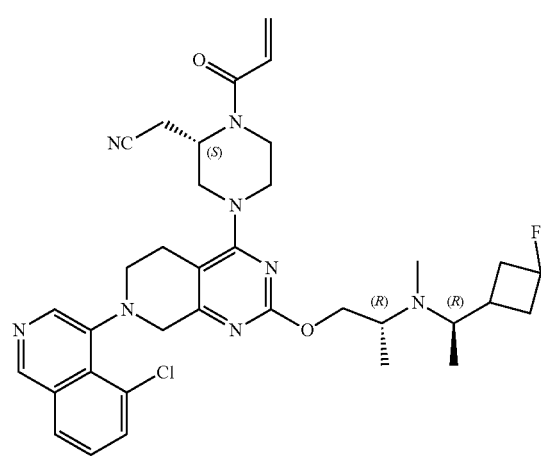
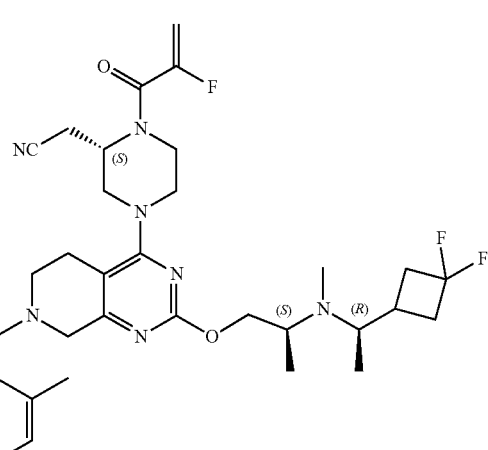
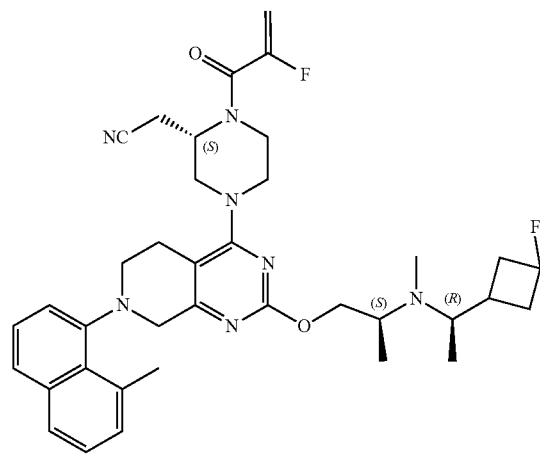
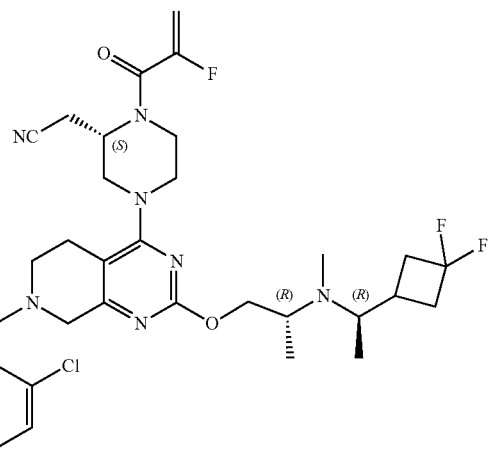

223
-continued
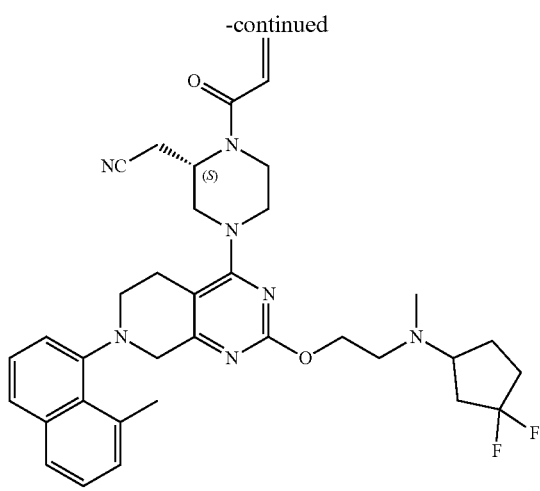
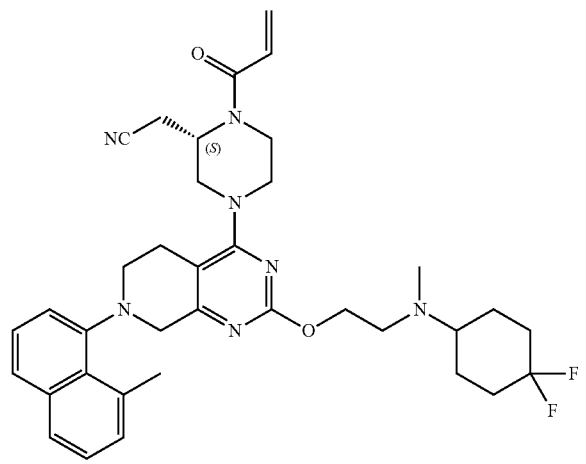
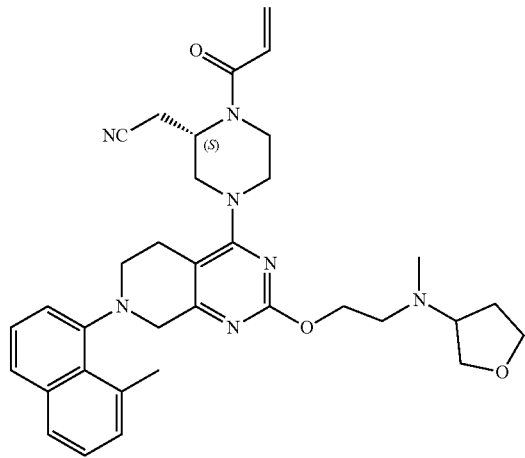
224
-continued
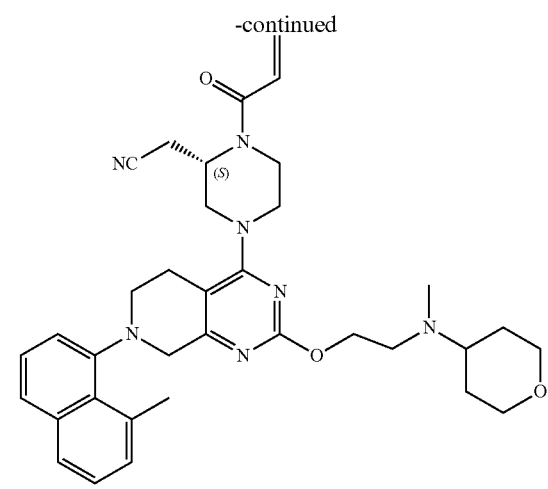
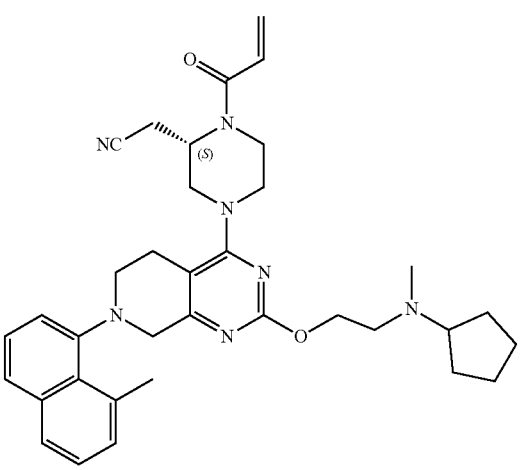
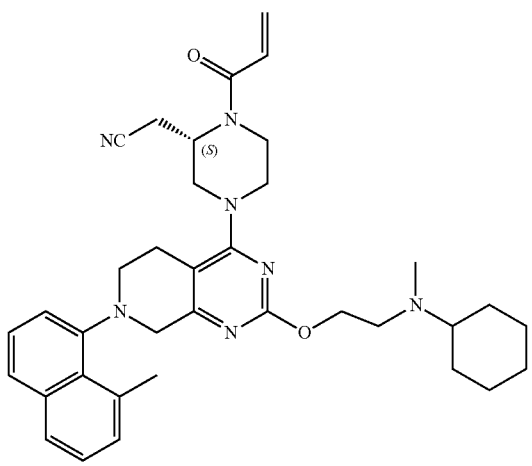

225
-continued
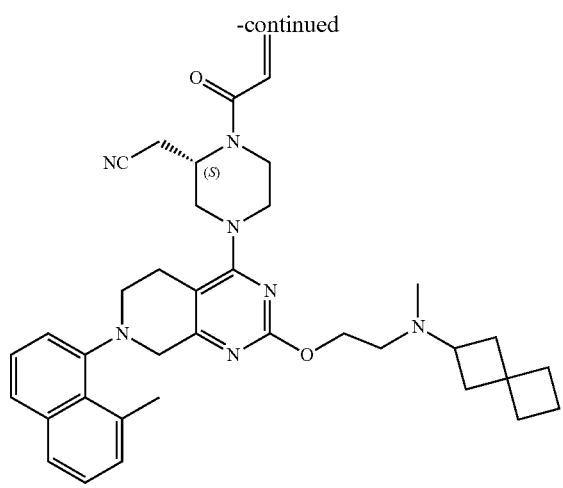
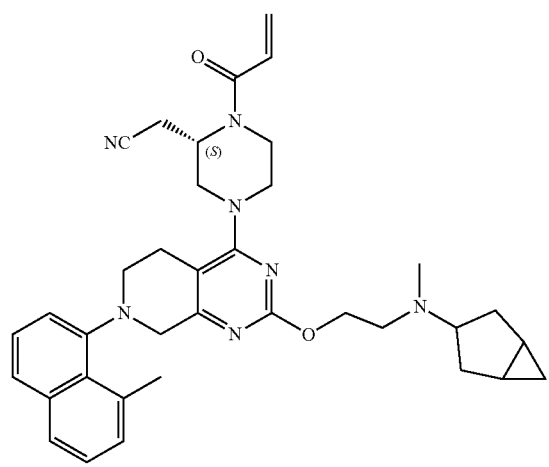
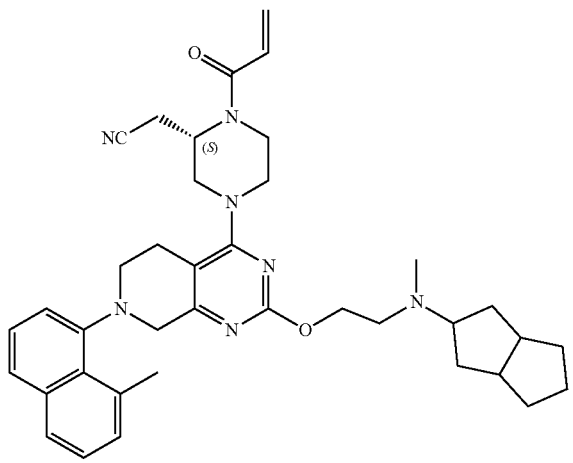
226
-continued
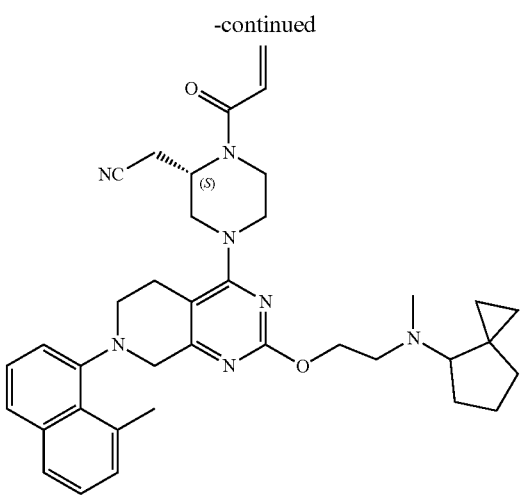
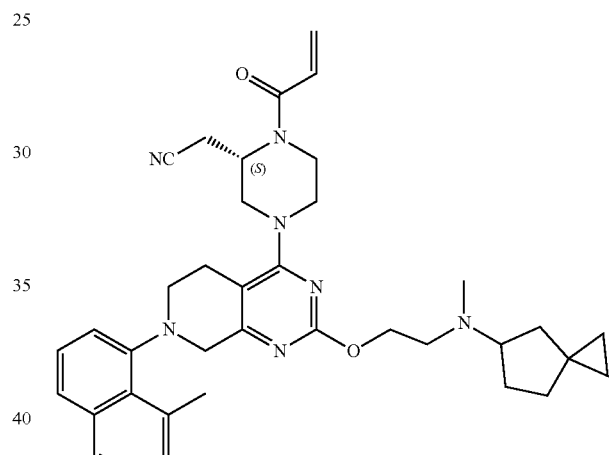
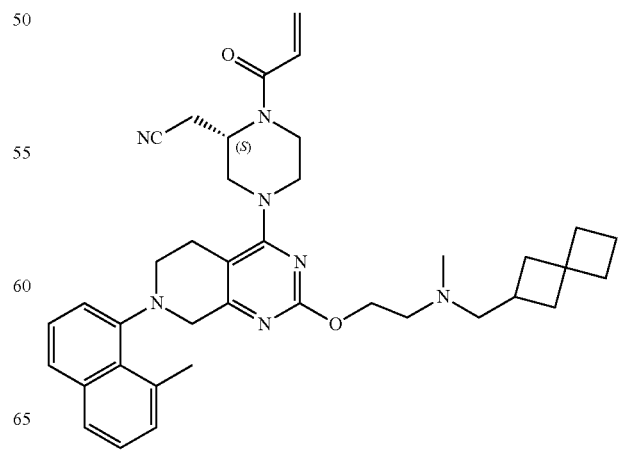

227
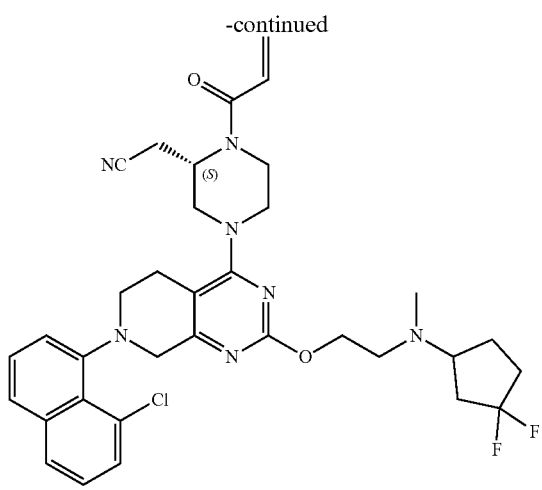
228
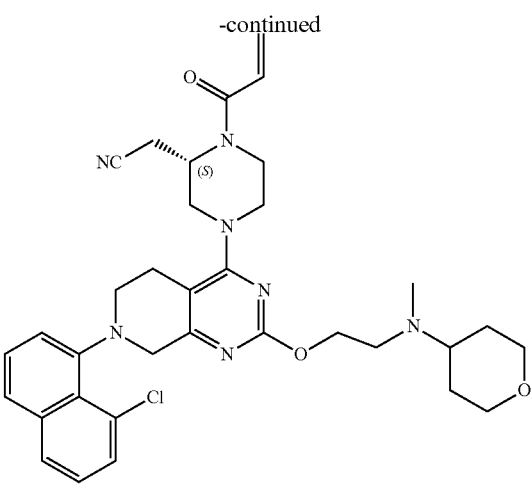
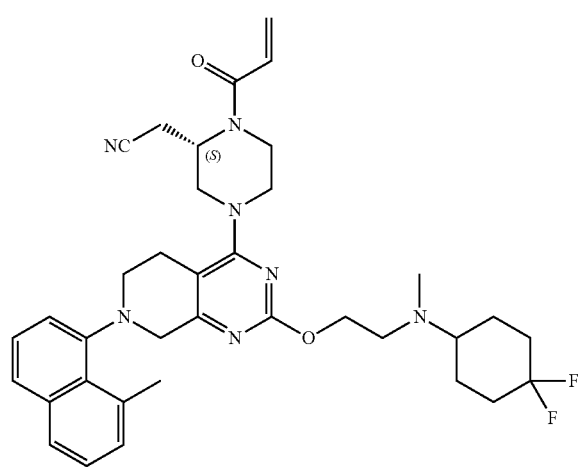
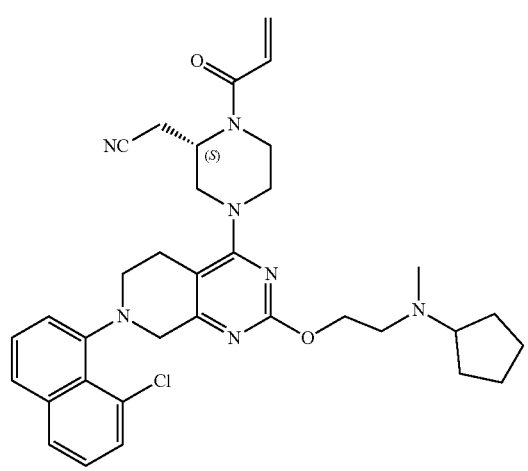
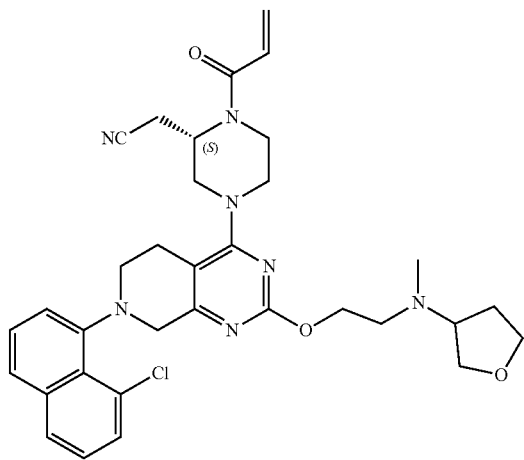

229
-continued
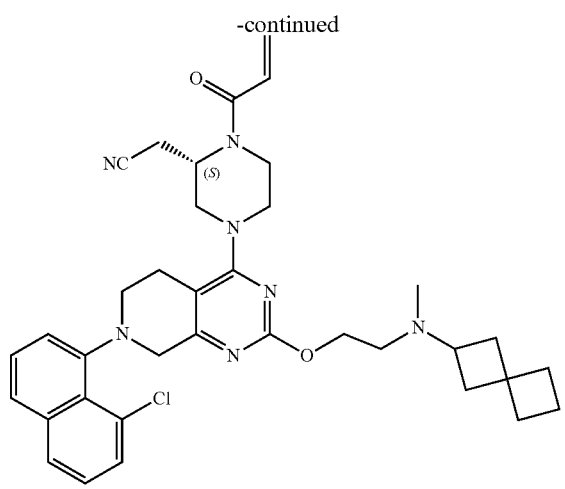
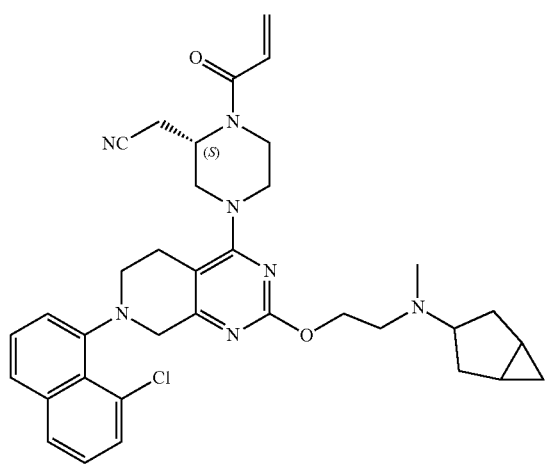
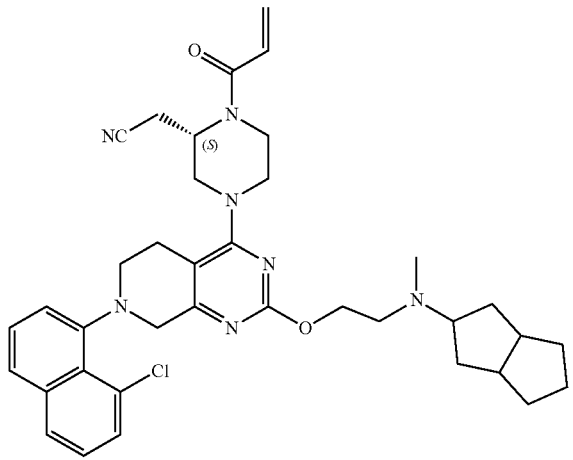
230
-continued
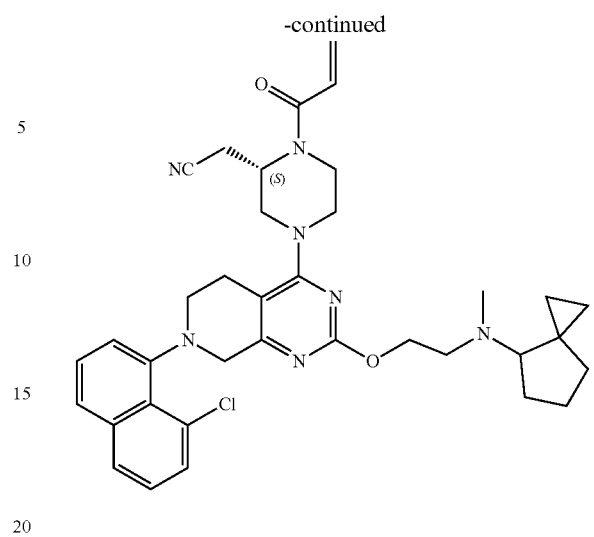
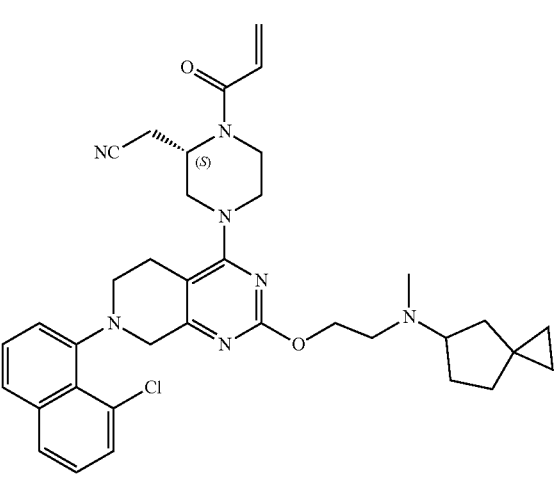
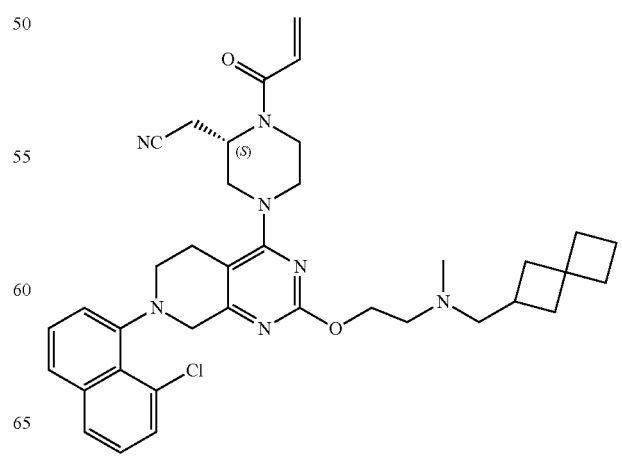

231
-continued
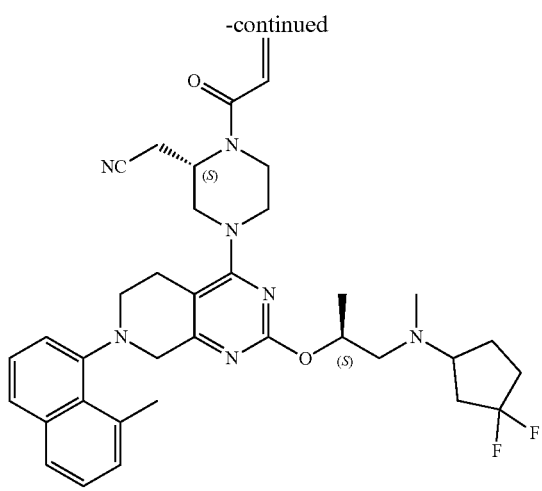
232
-continued
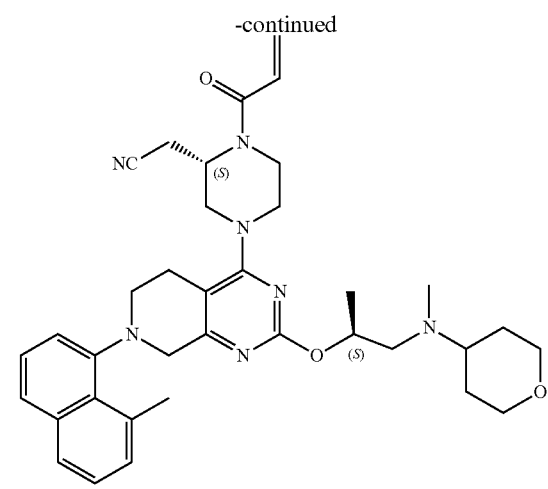
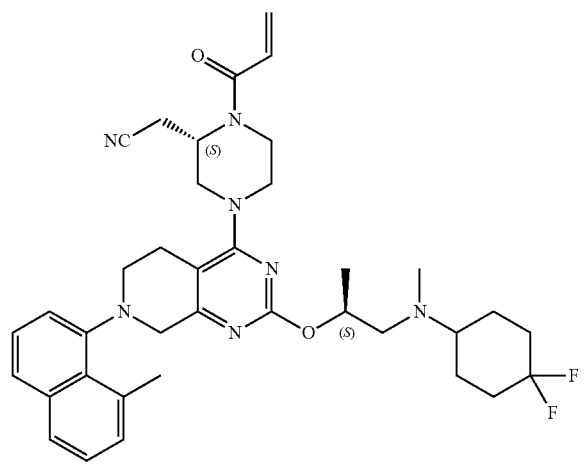
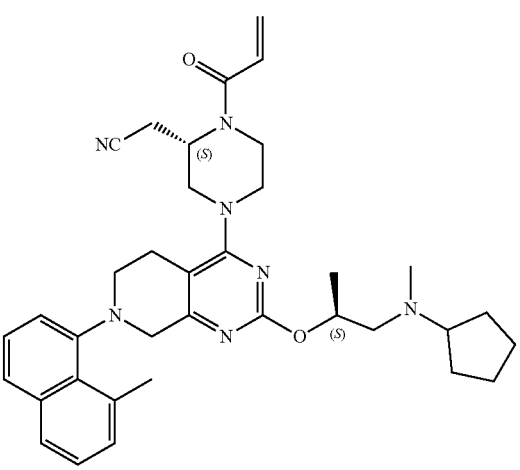
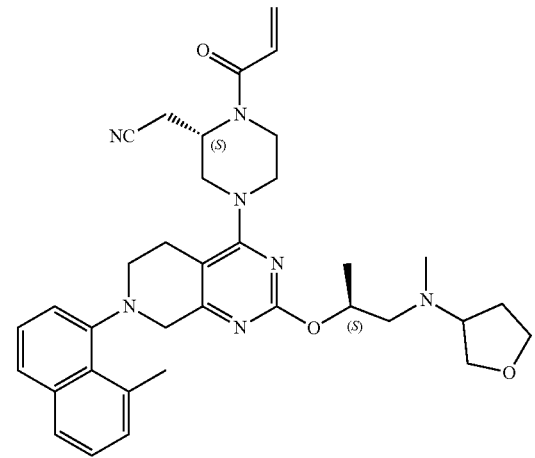
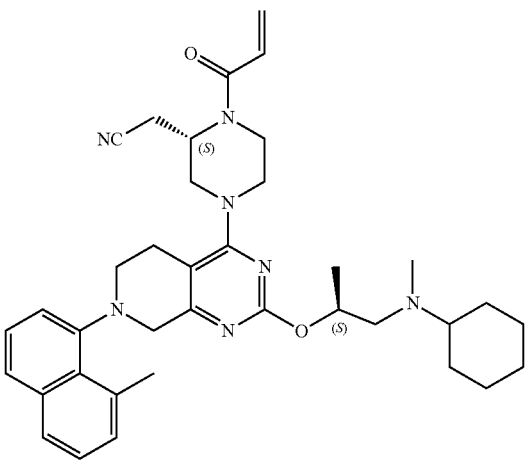

233
-continued
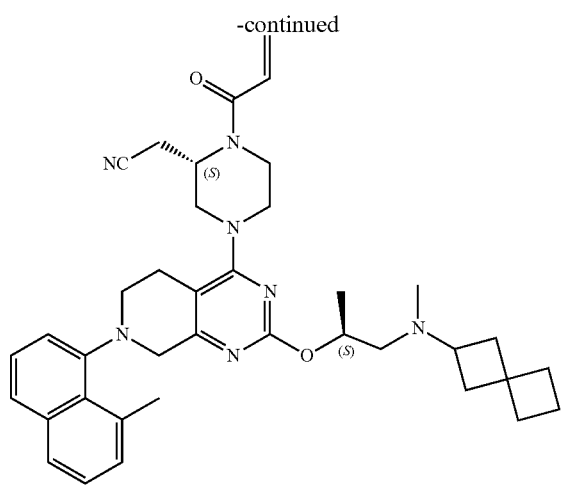
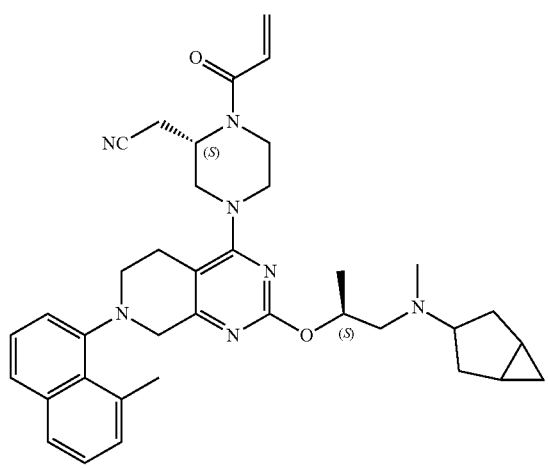
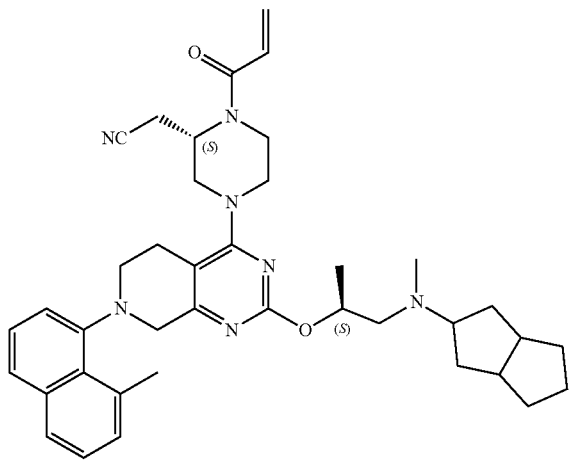
234
-continued
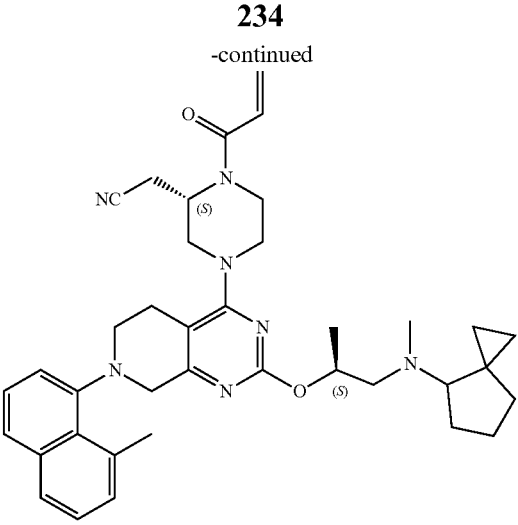
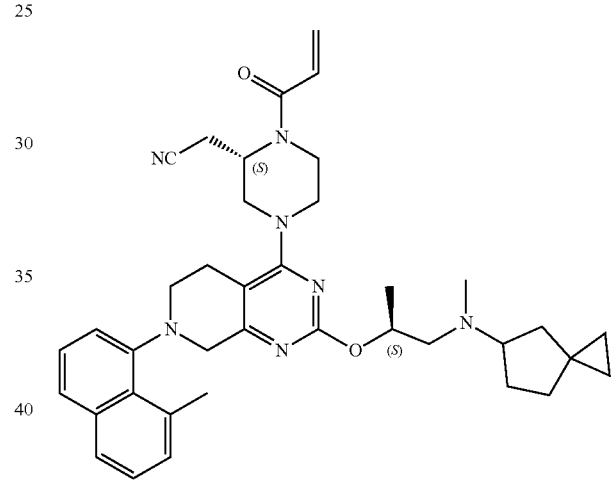
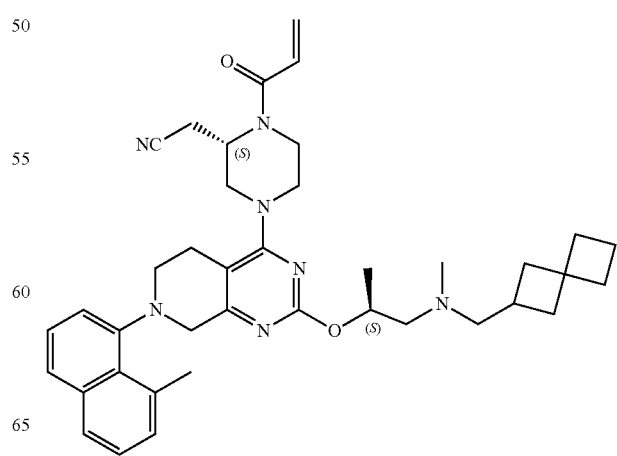

235
-continued
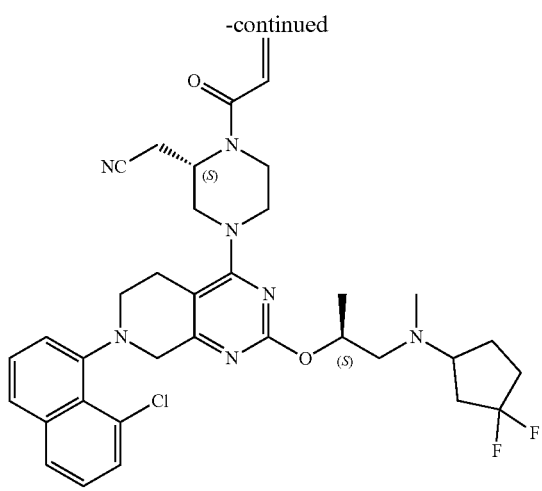
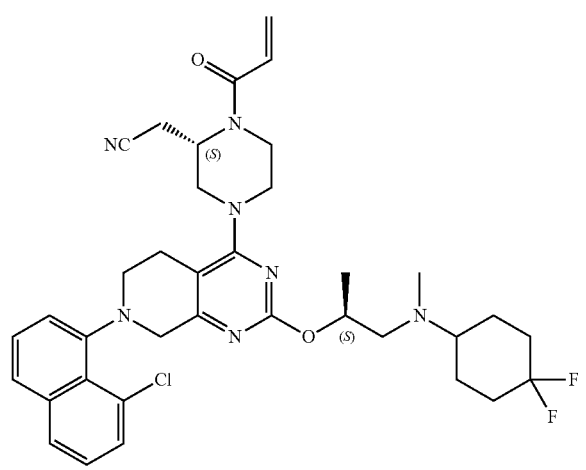
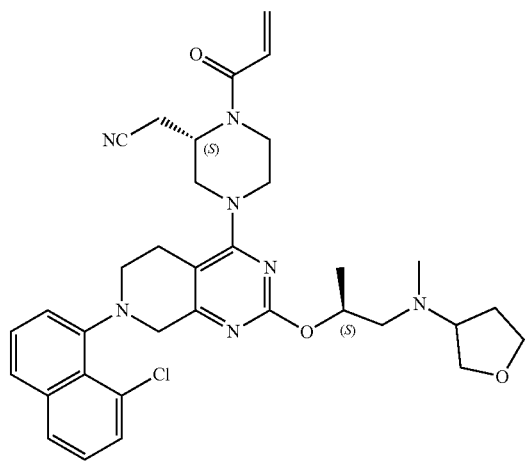
236
-continued
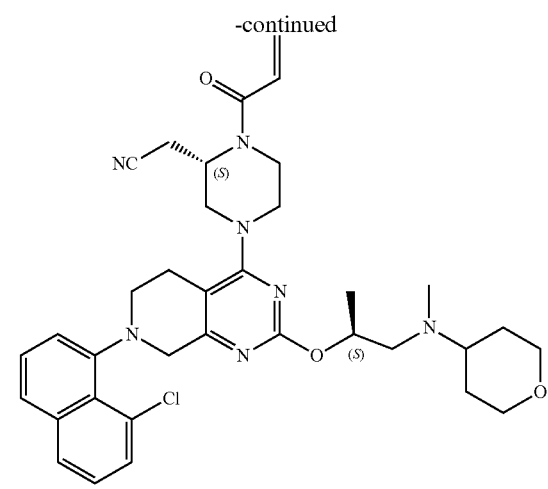
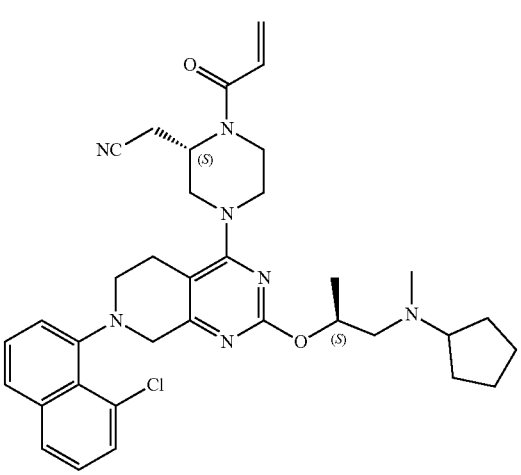
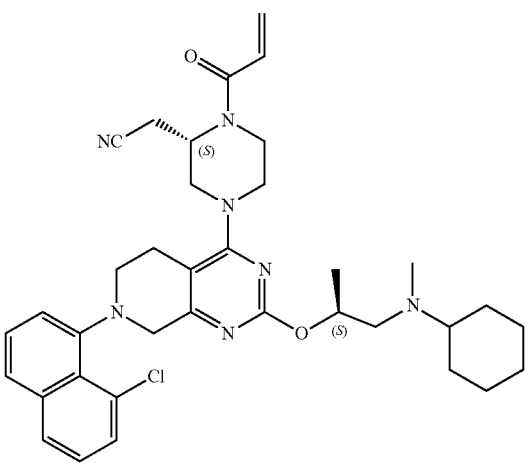

237
-continued
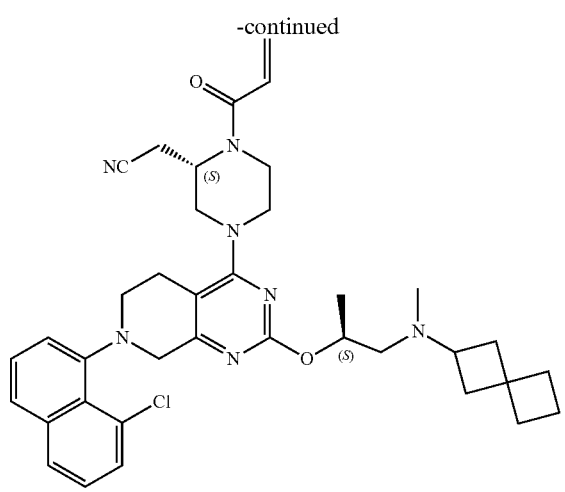
238
-continued
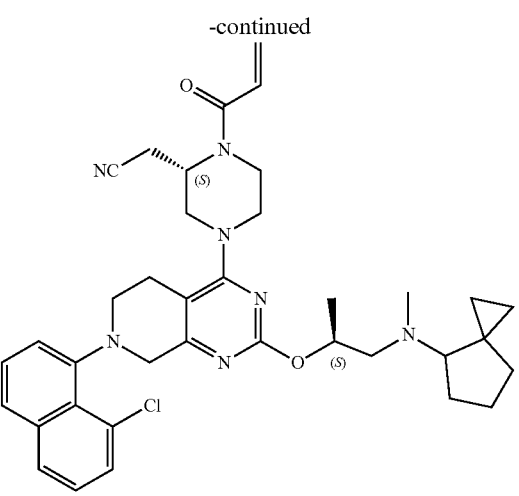
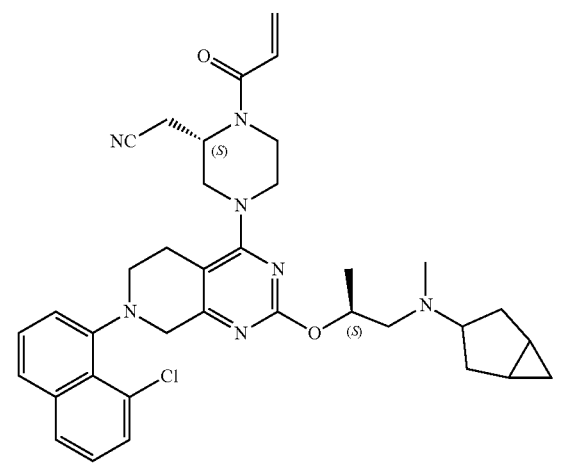
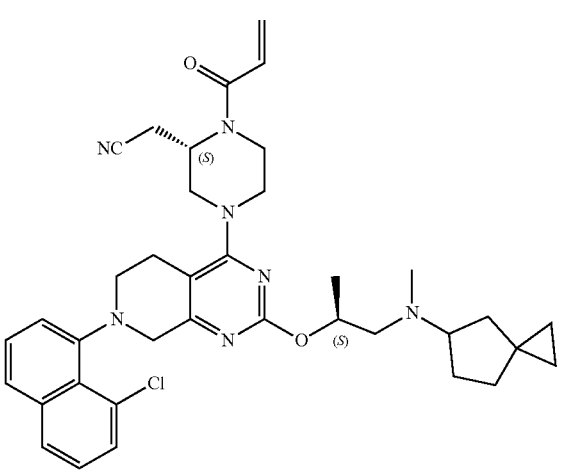
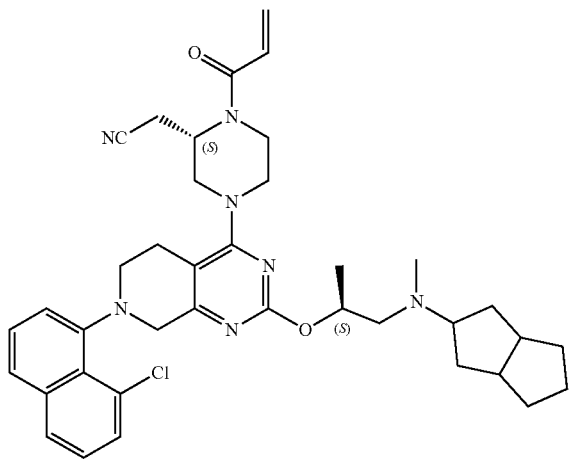
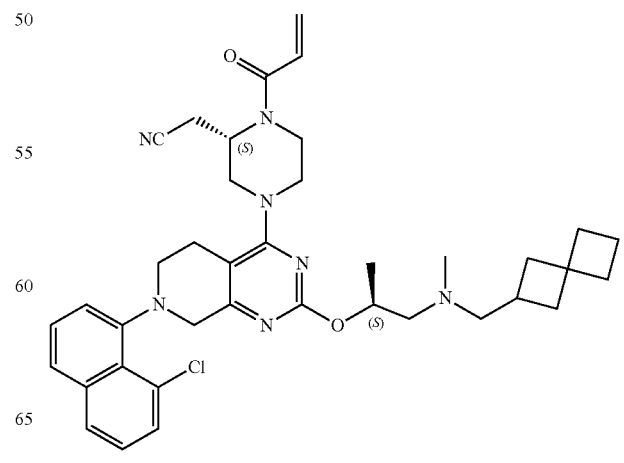

239
-continued
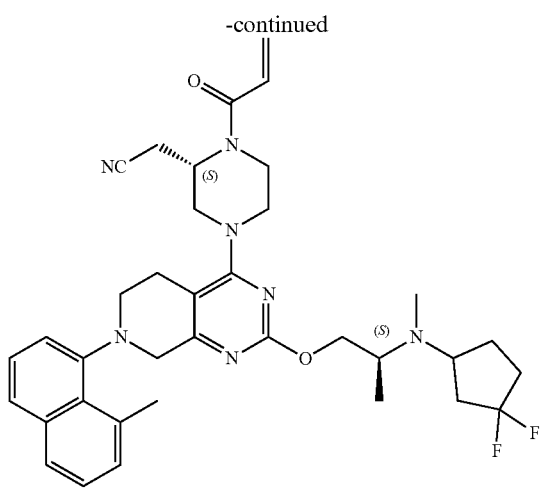
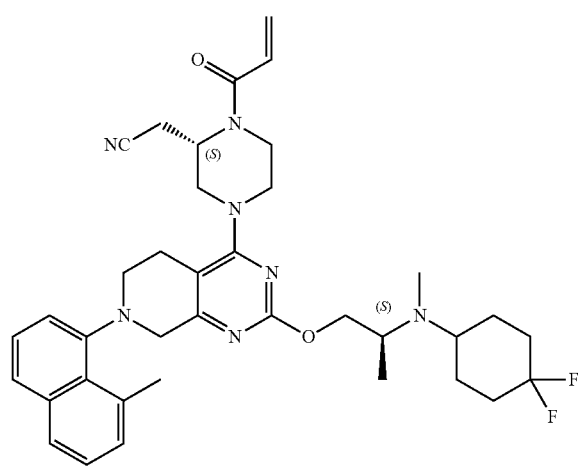
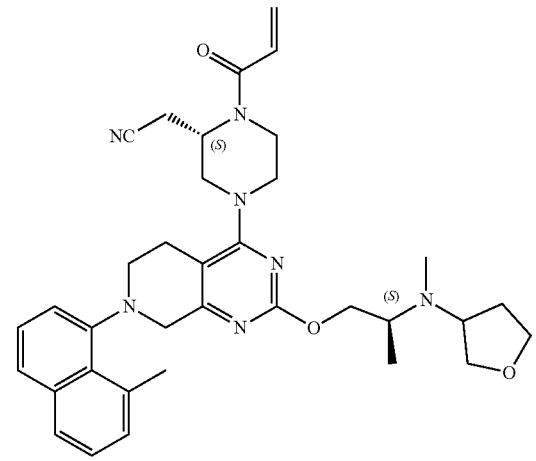
240
-continued
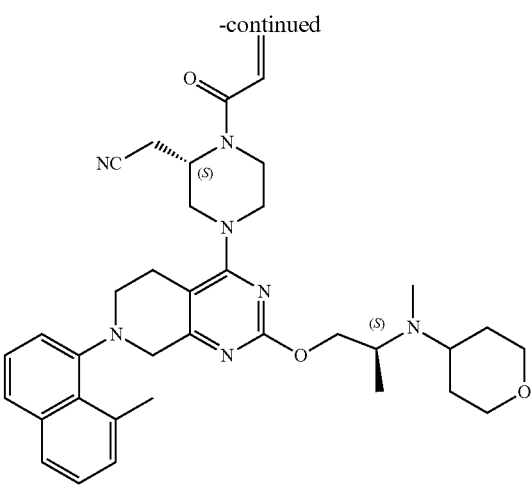
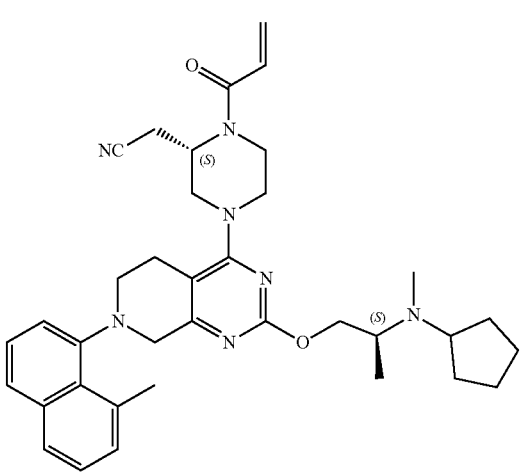
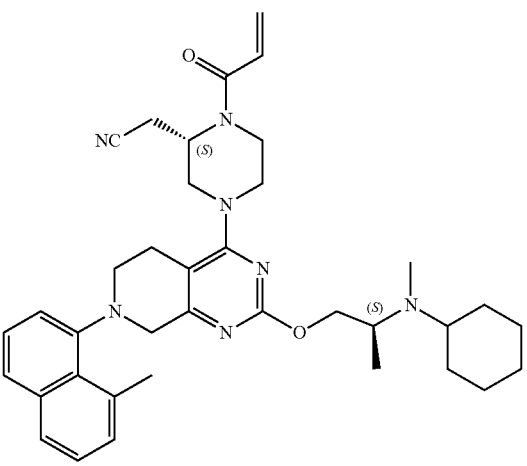

241
-continued
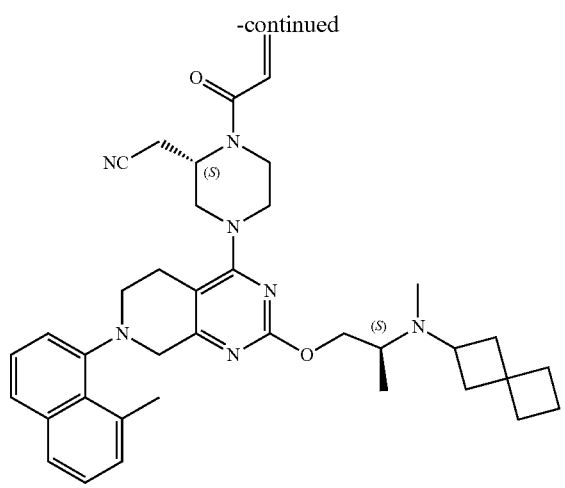
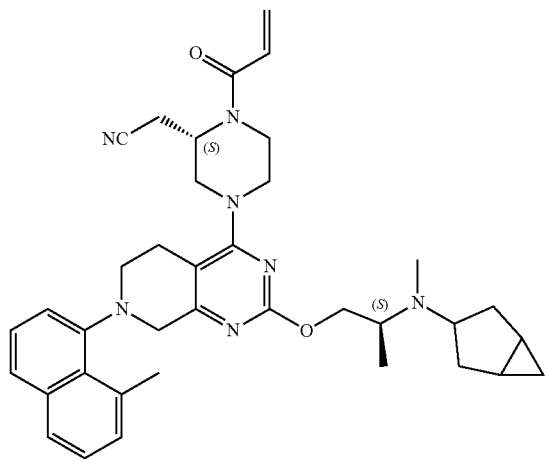
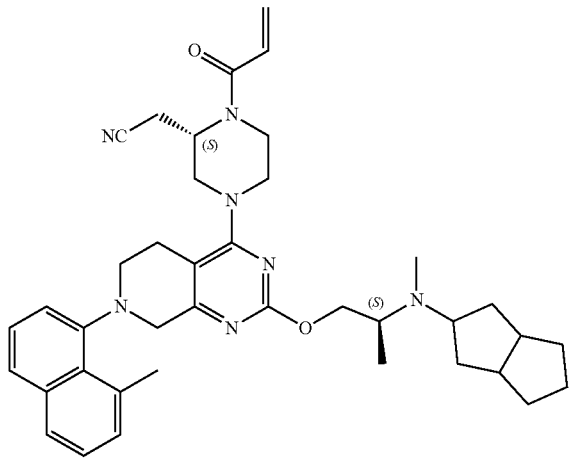
242
-continued
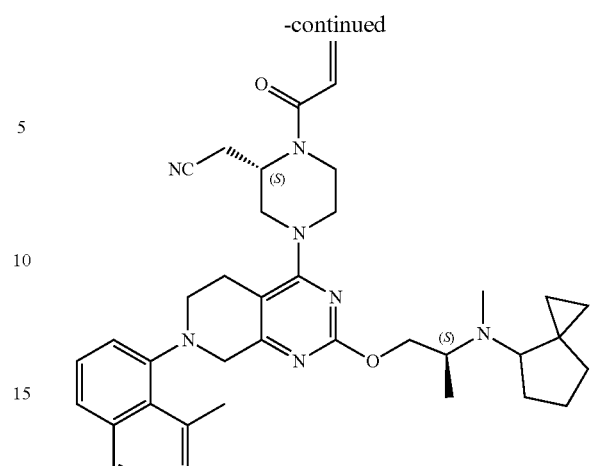
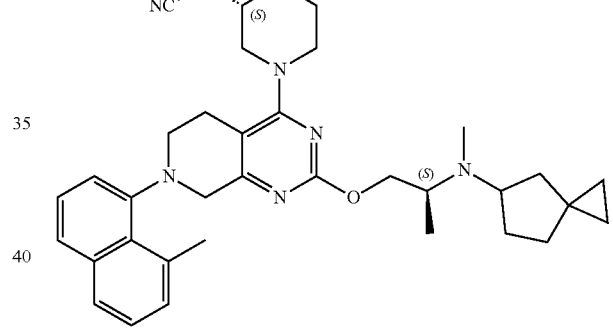
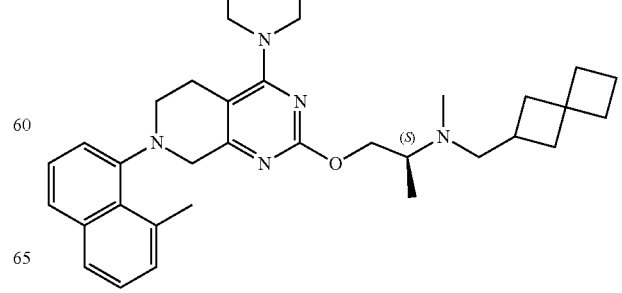

243
-continued
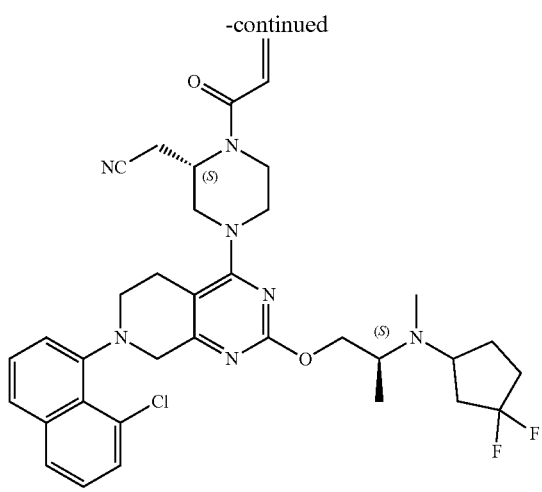
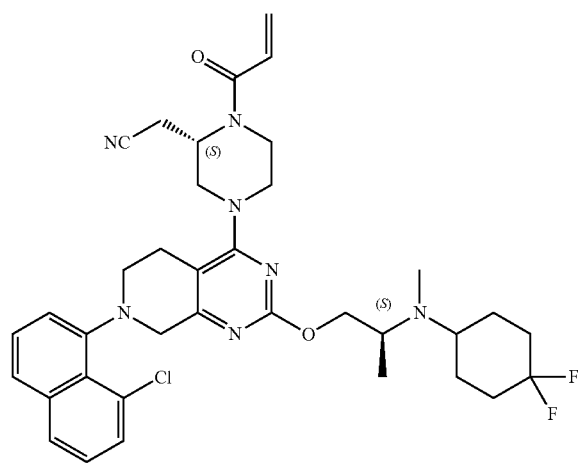
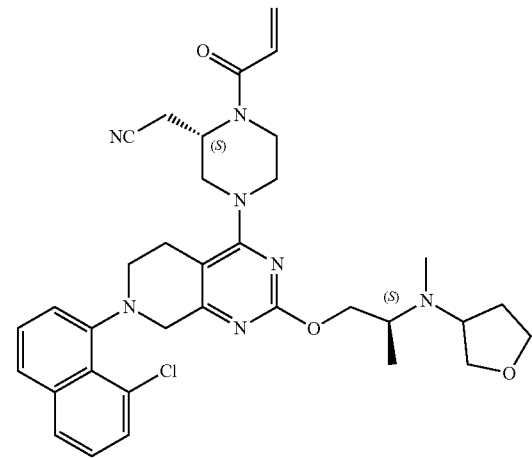
244
-continued
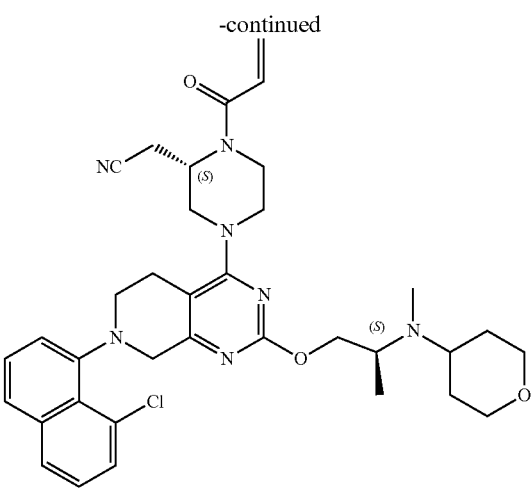
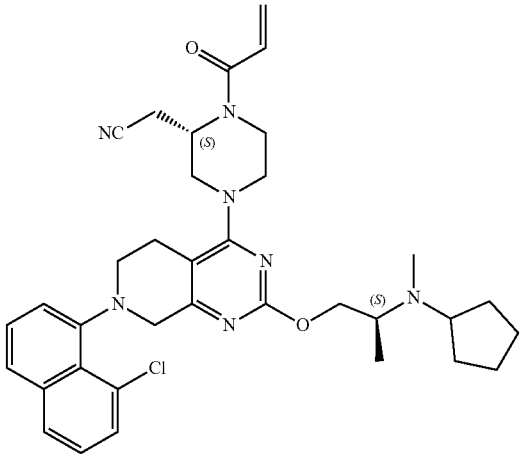
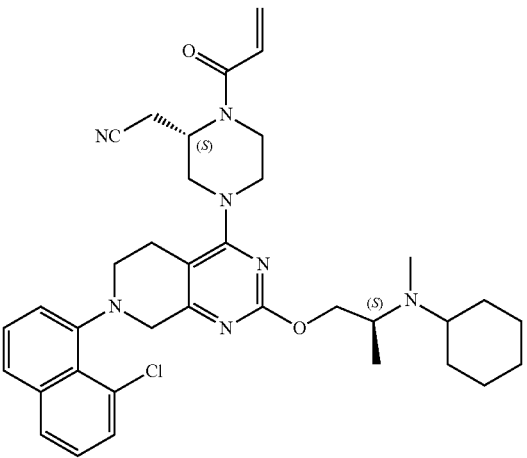

245
-continued
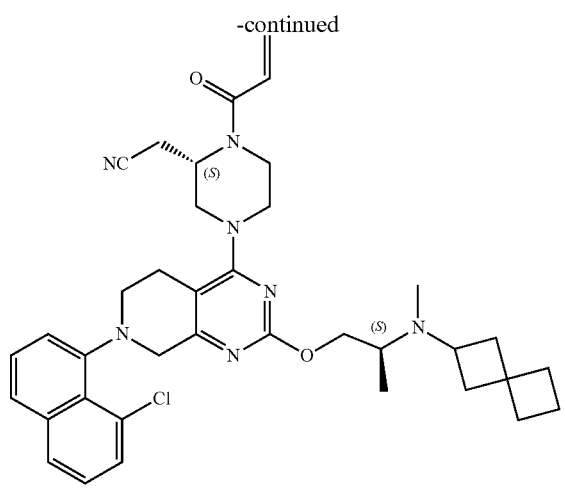
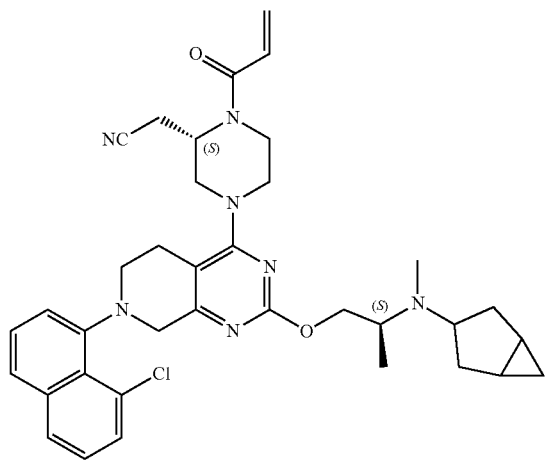
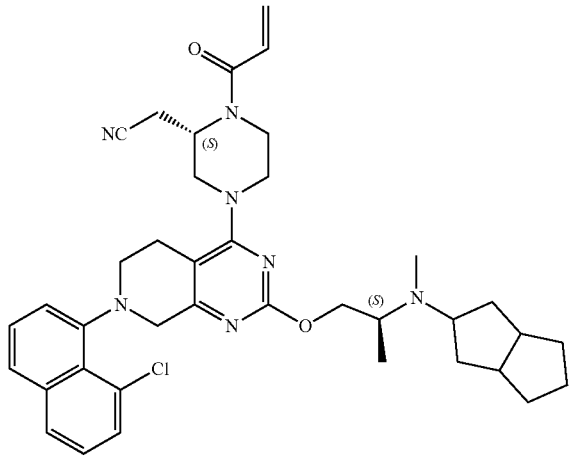
246
-continued
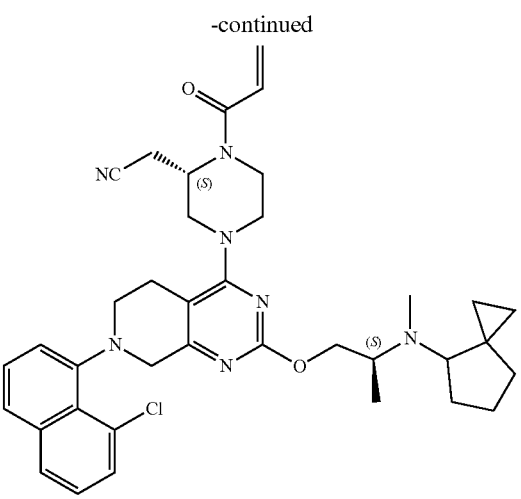
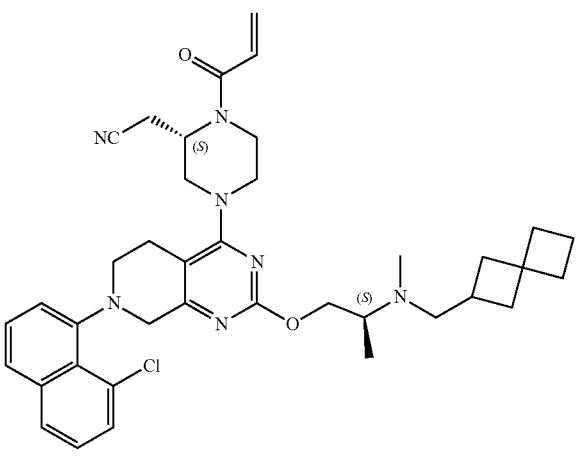

247
-continued
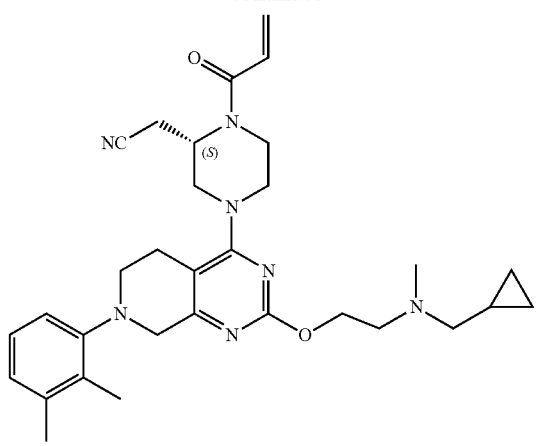
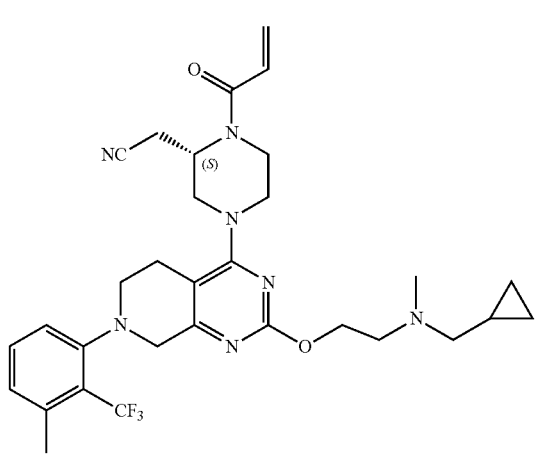
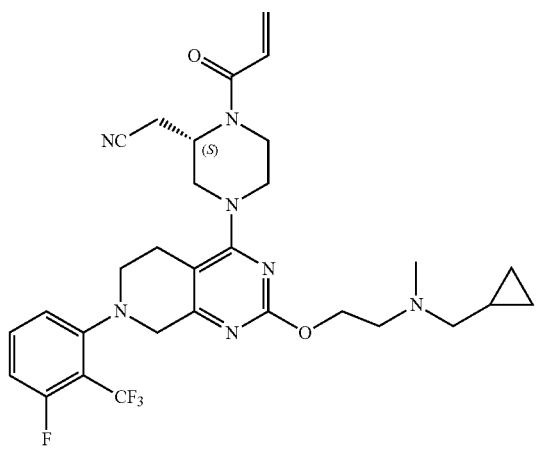
248
-continued
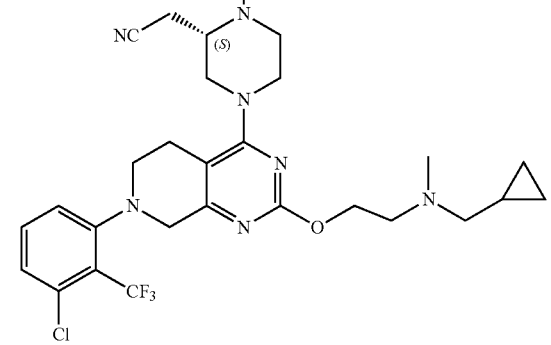
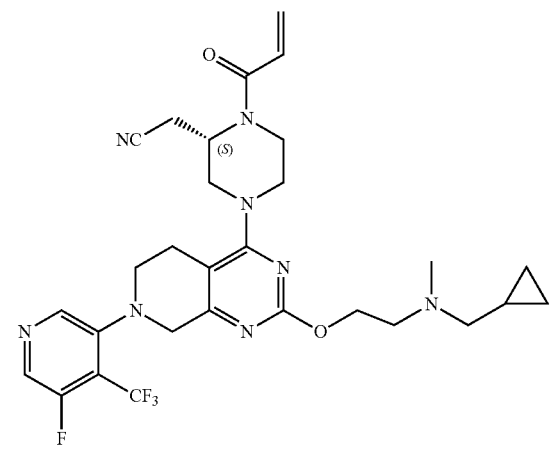
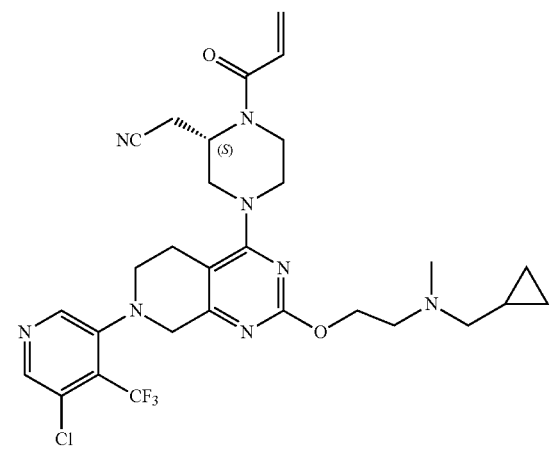

249
-continued
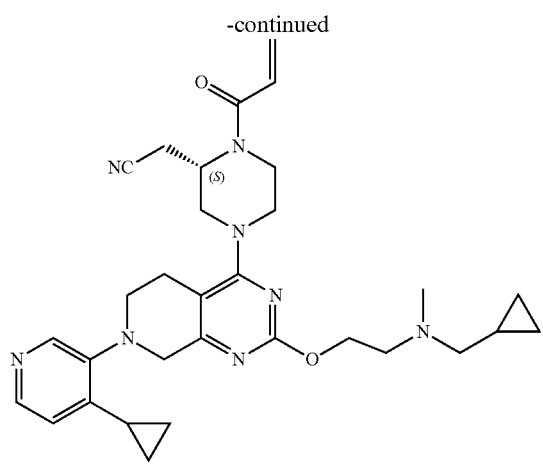
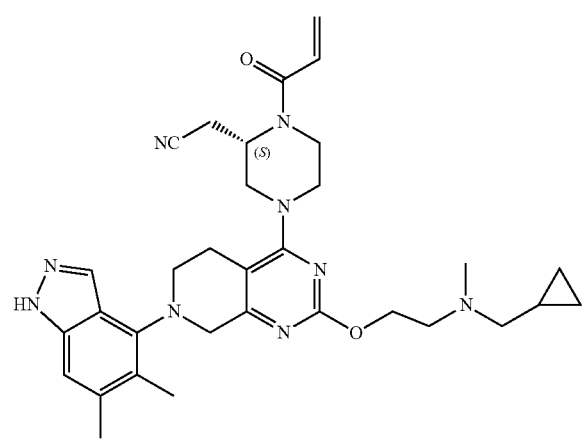
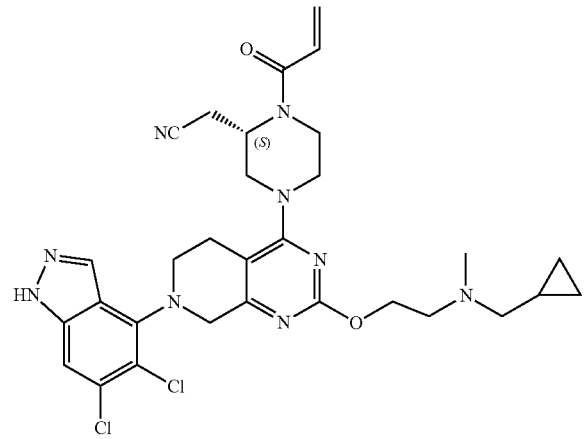
250
-continued
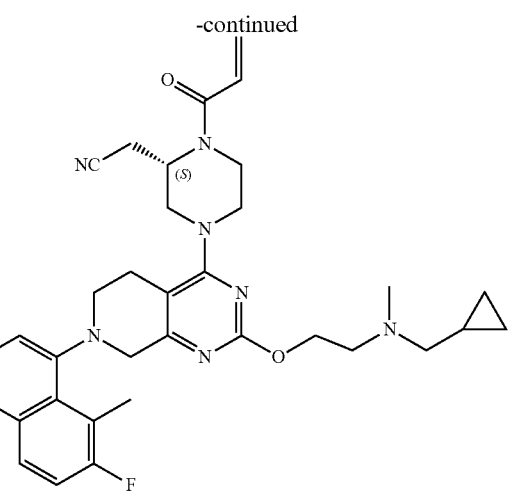
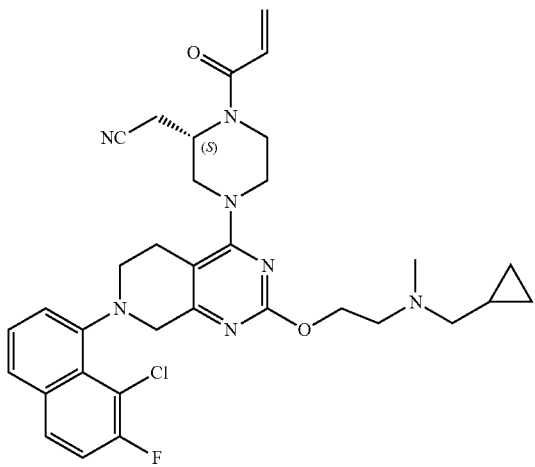
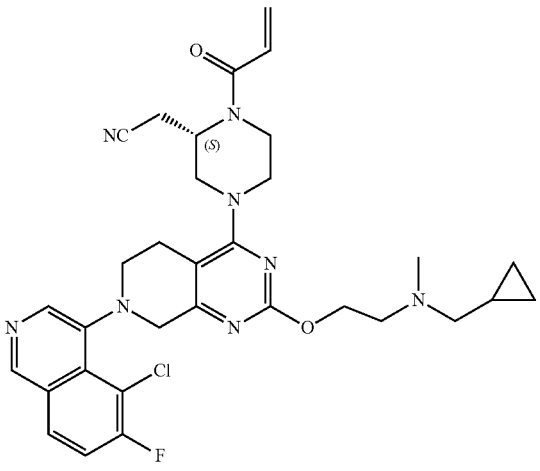

251
-continued
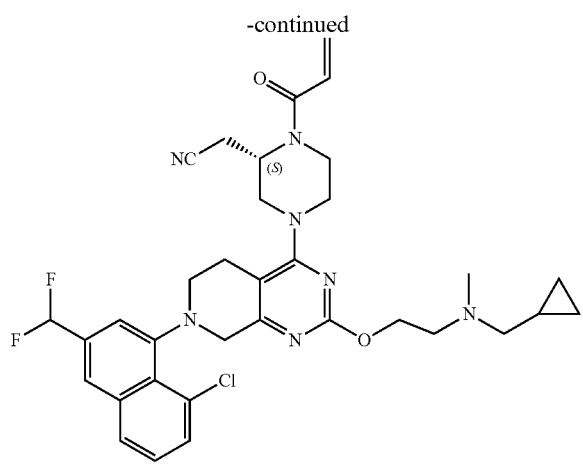
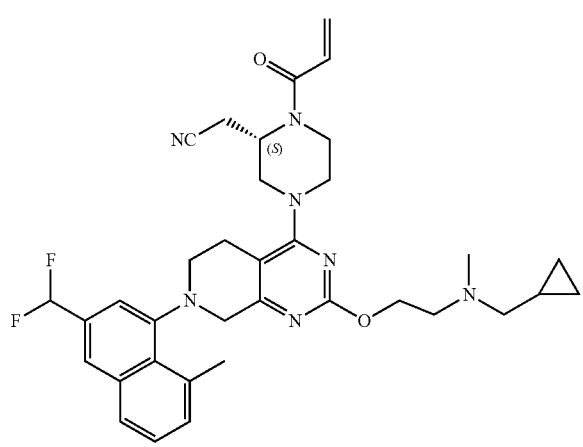
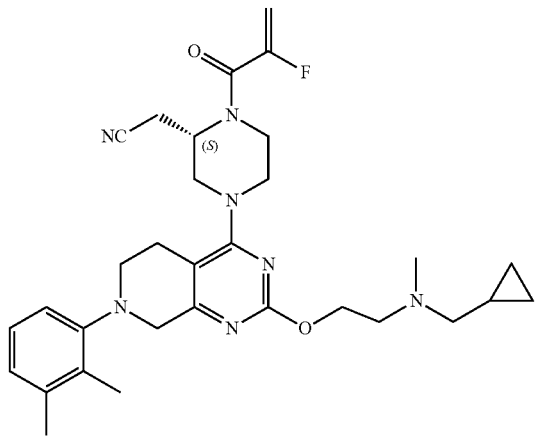
252
-continued
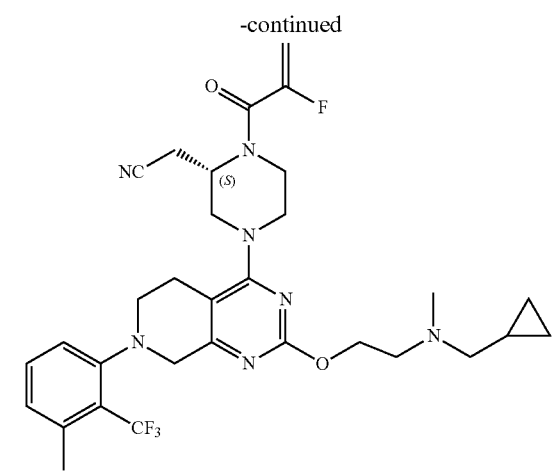
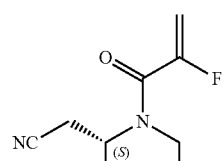
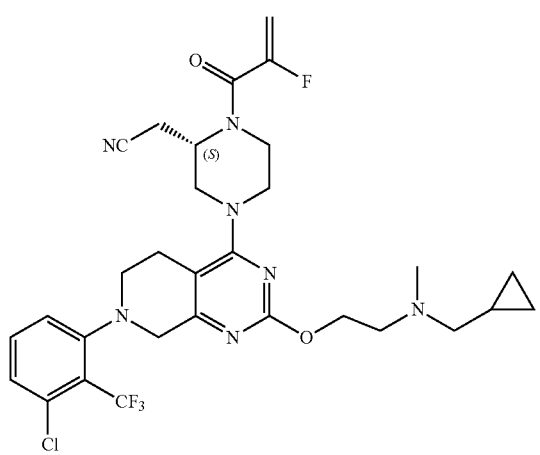

253
-continued
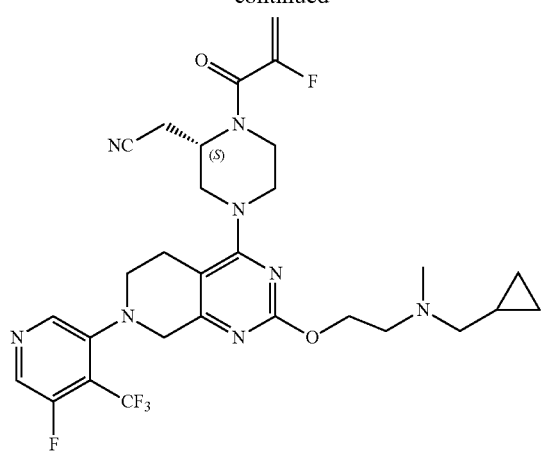
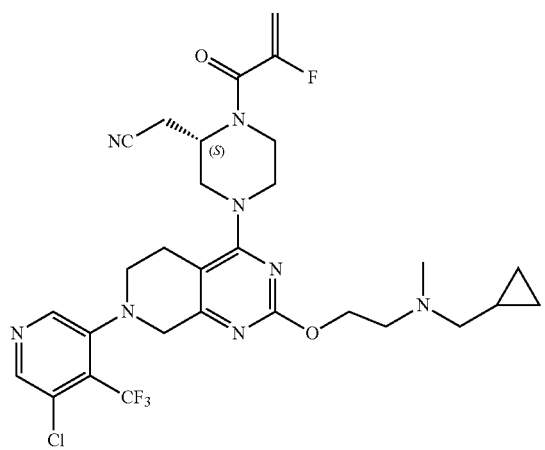
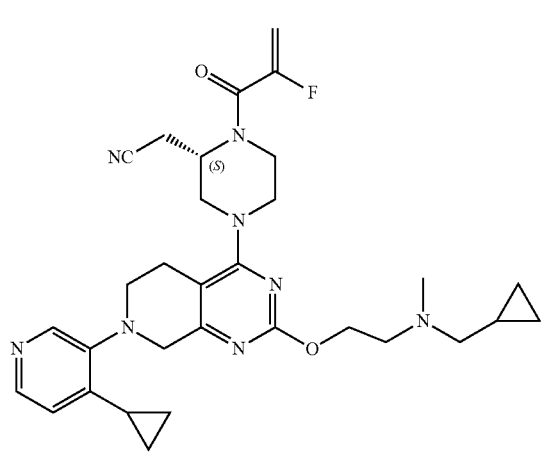
254
-continued
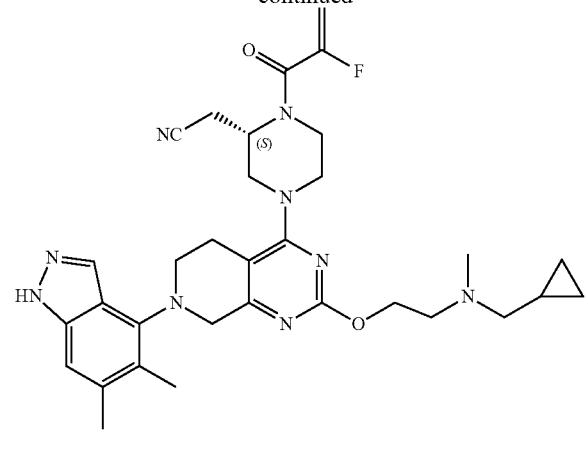
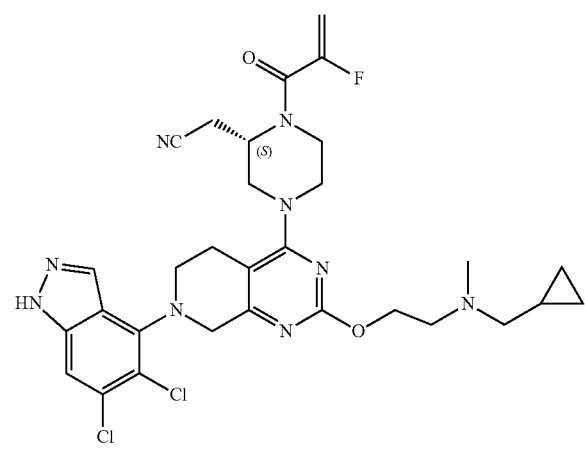
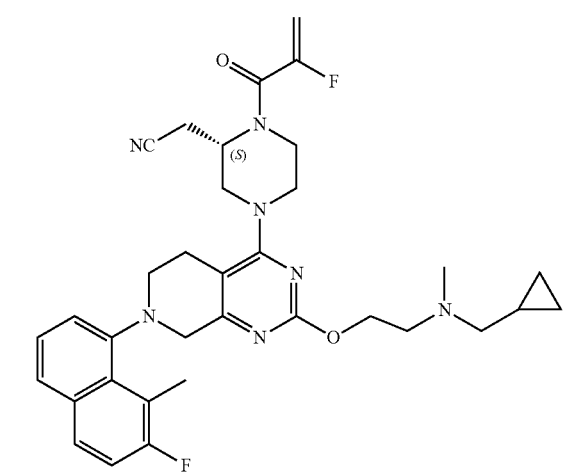

255
-continued
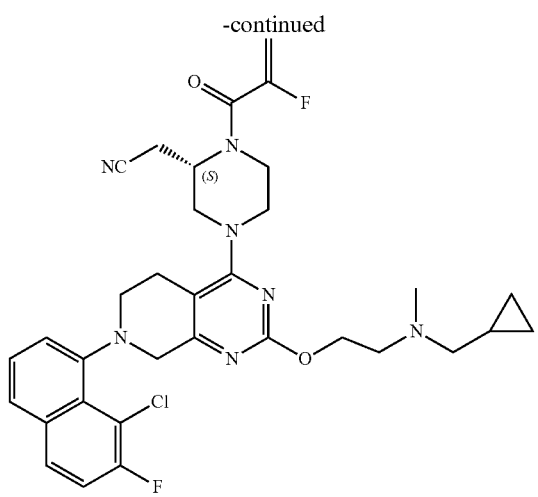
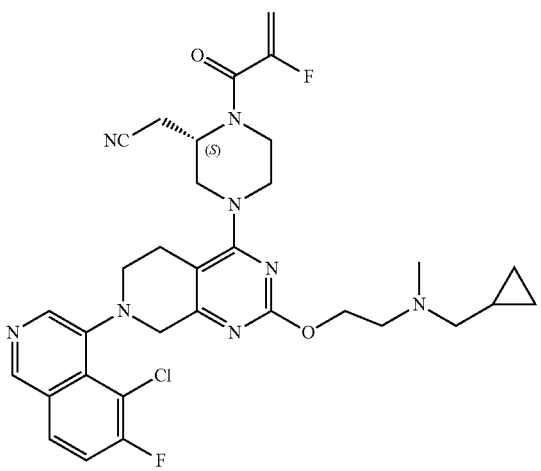
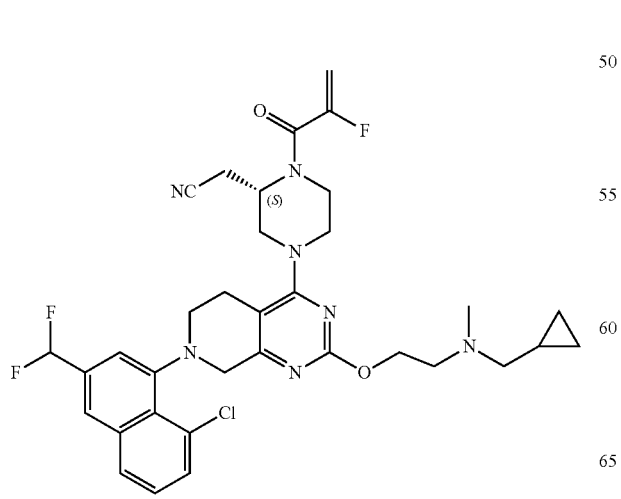
256
-continued
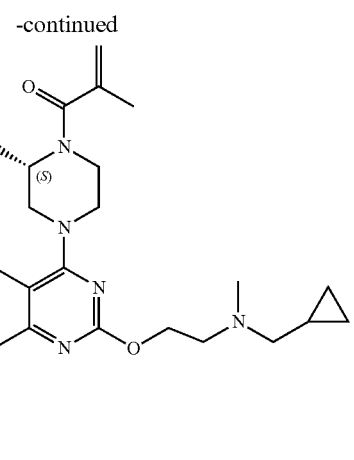
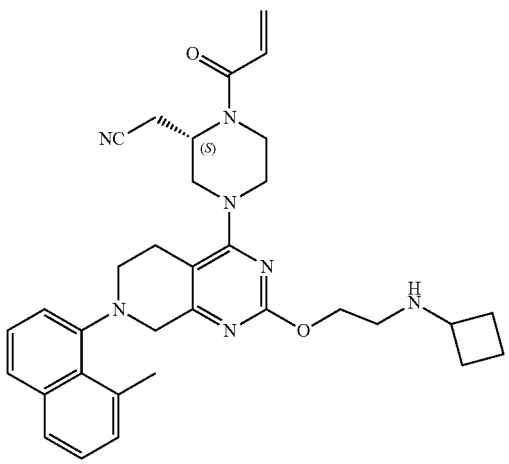
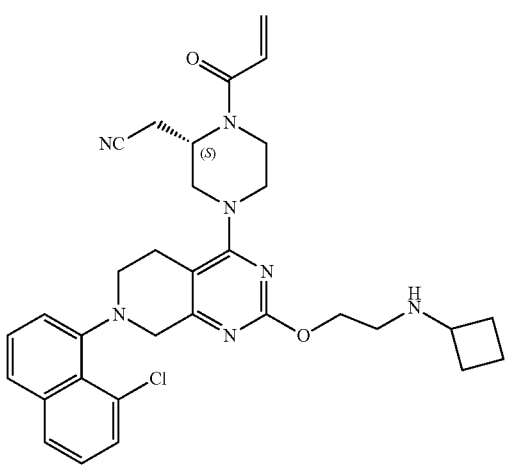

257
-continued
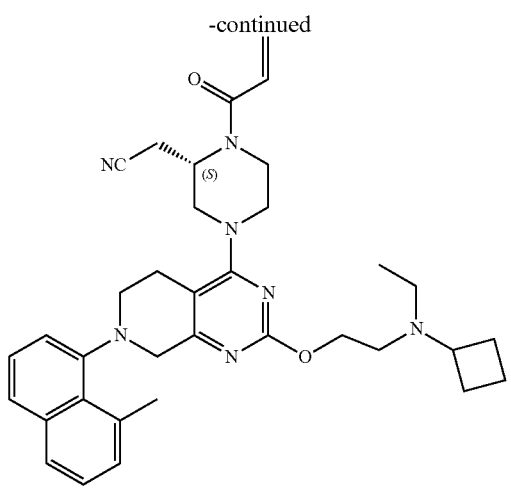
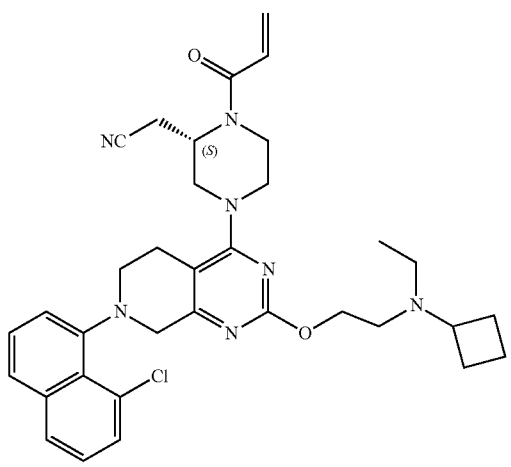
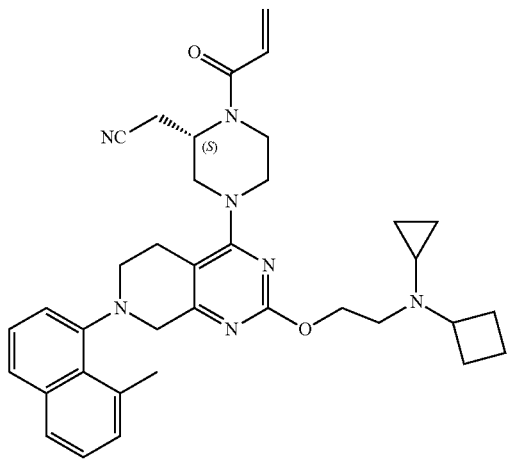
258
-continued
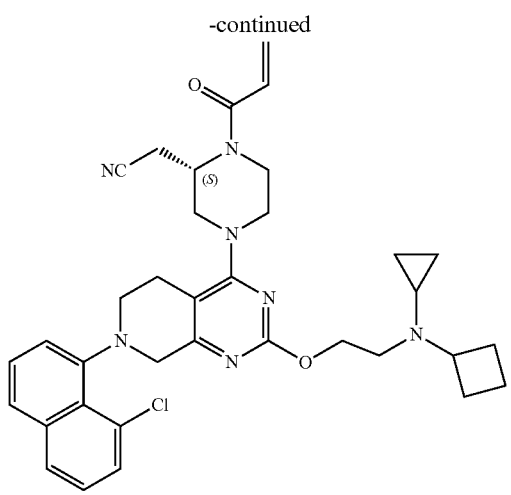
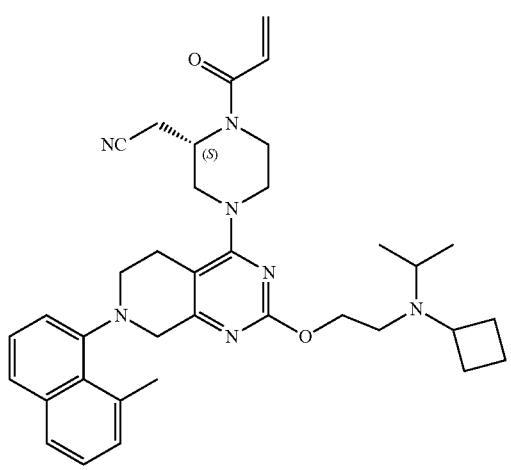
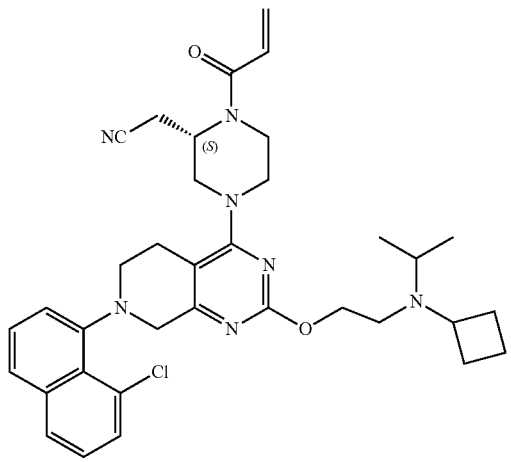

259
-continued
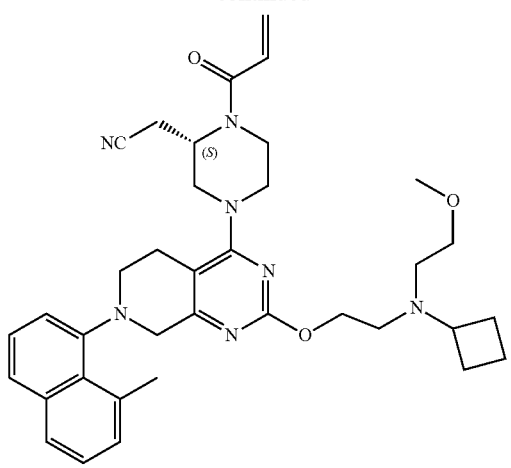
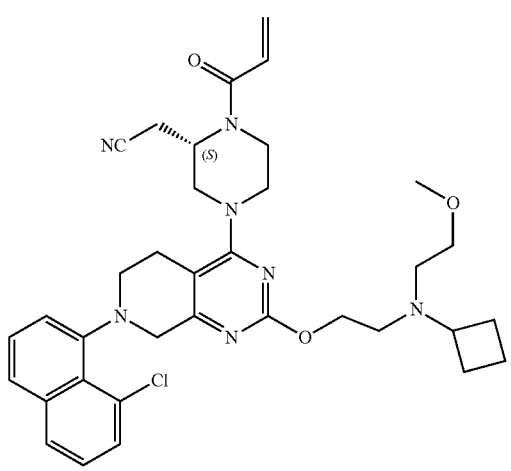
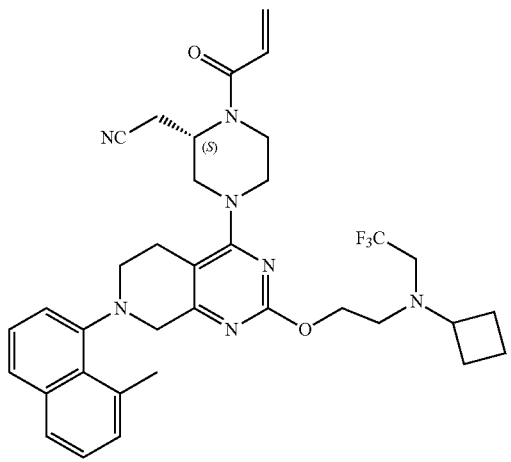
260
-continued
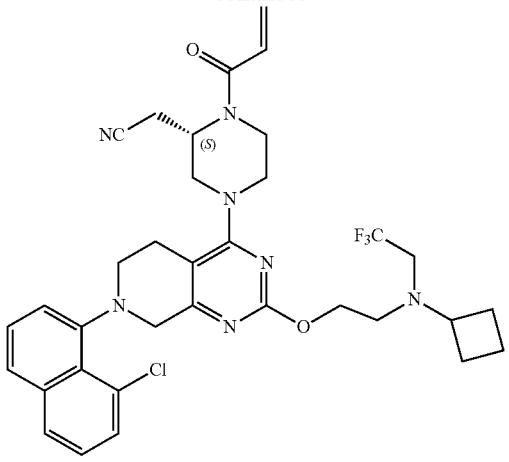
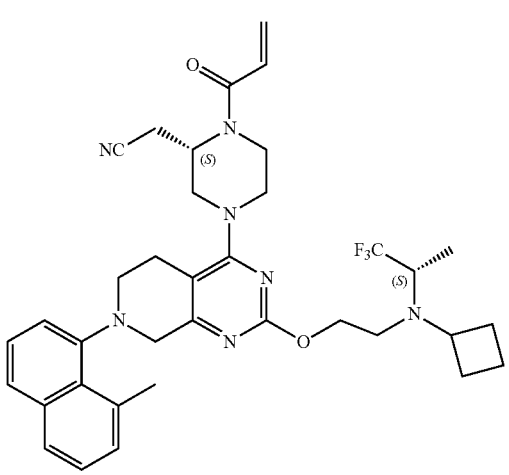
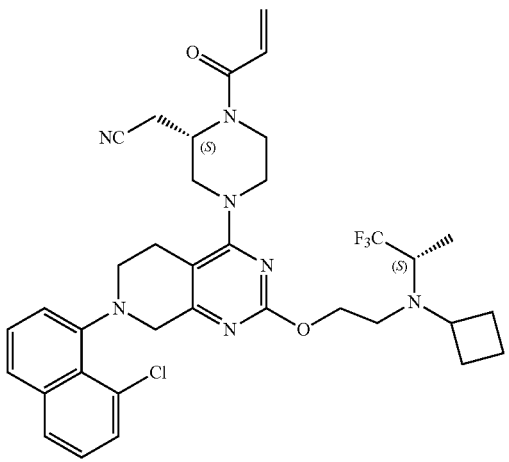

261
-continued
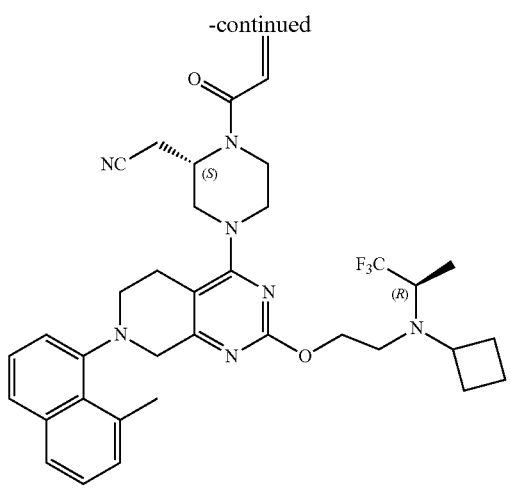
262
-continued
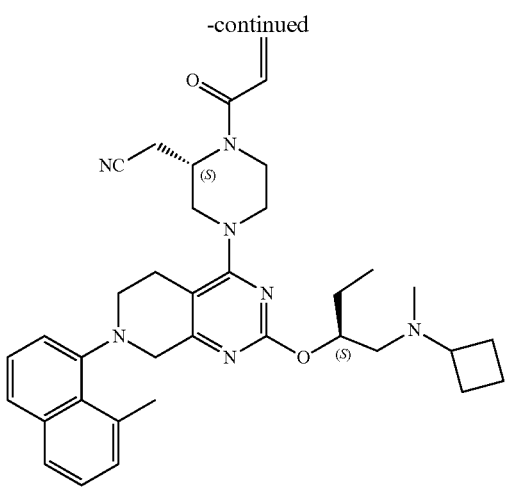
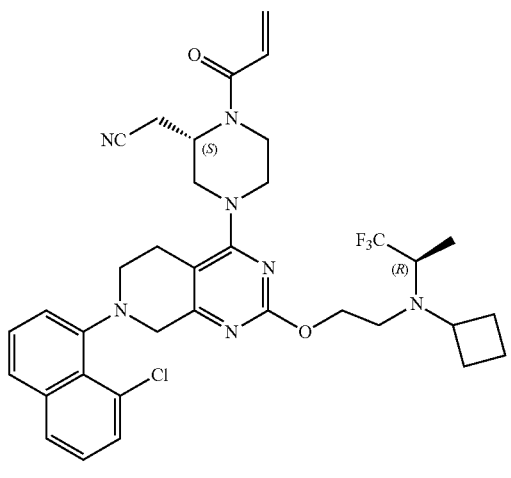
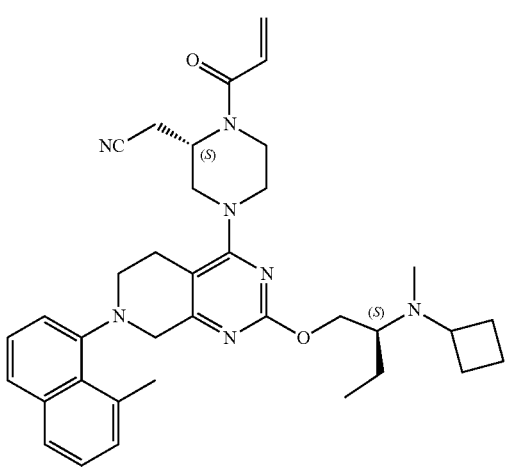
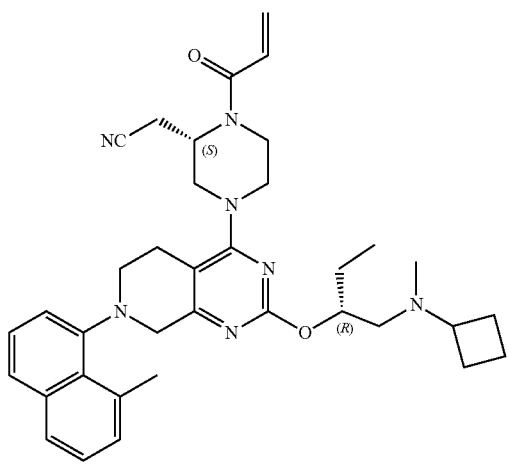
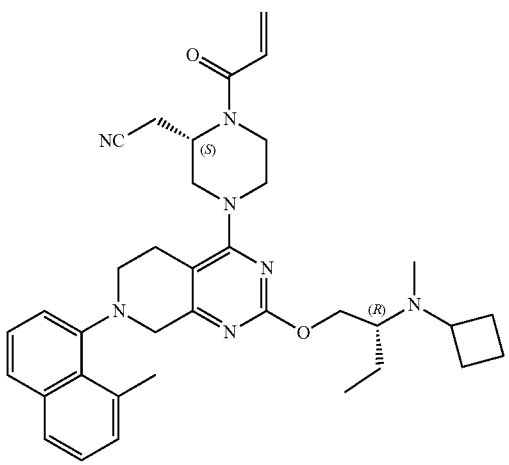

263
-continued
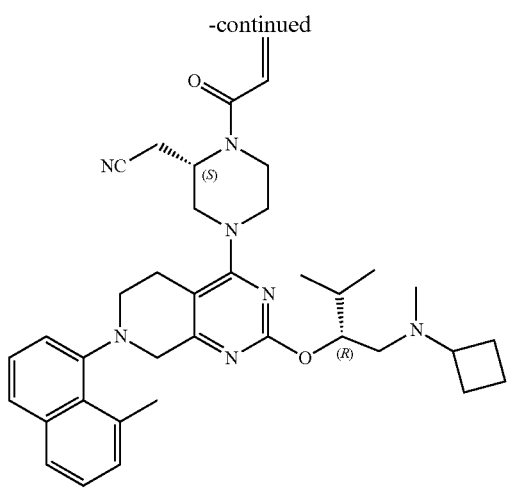
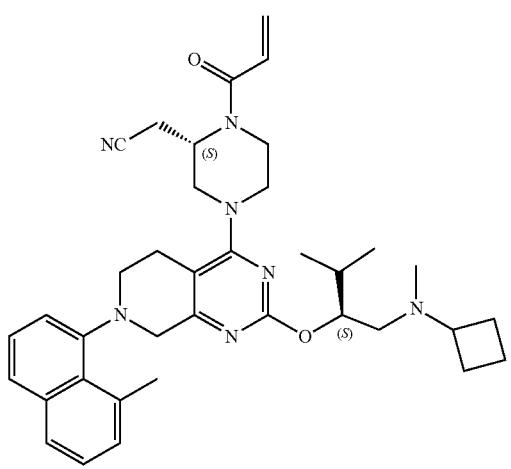
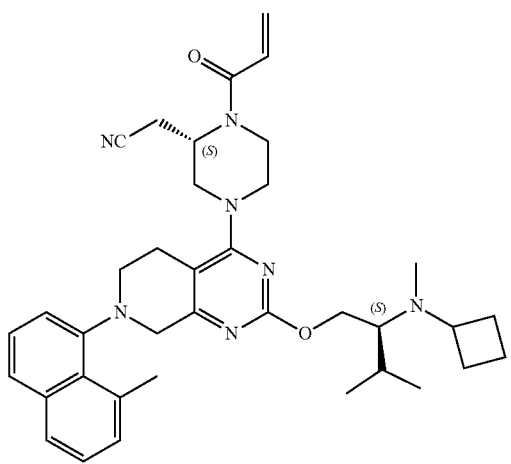
264
-continued
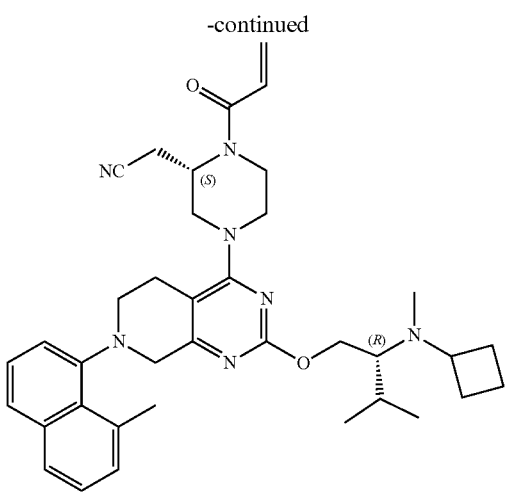
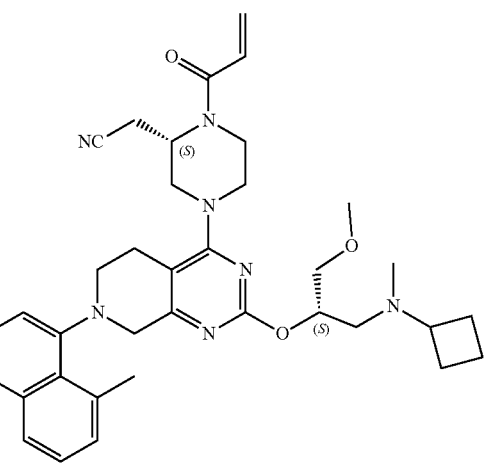
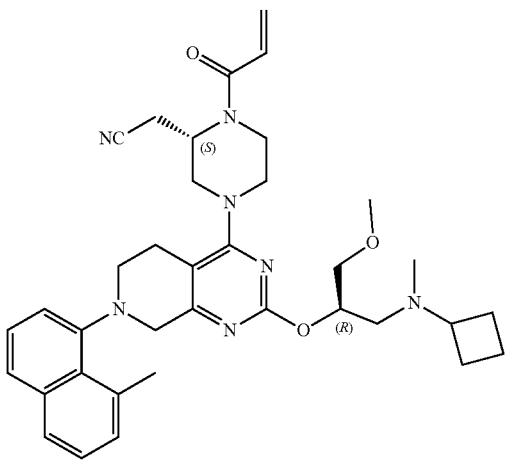

265
-continued
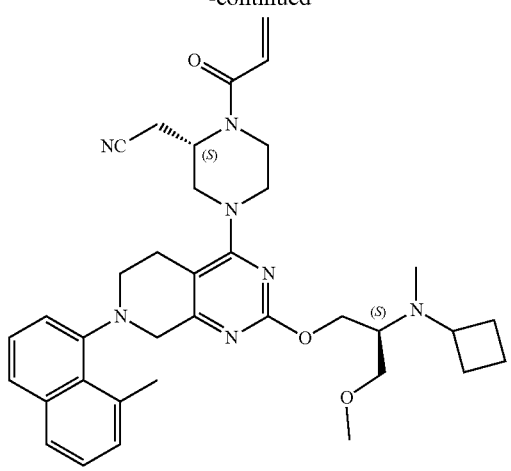
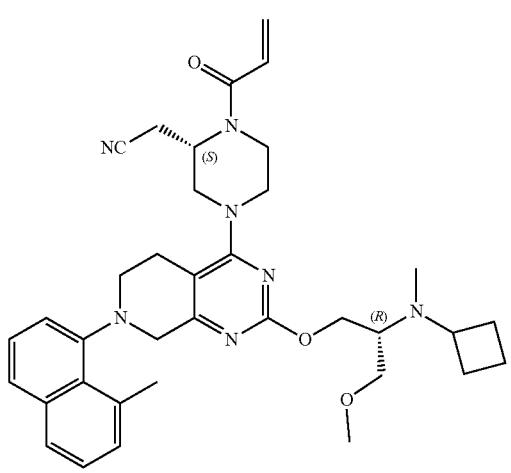
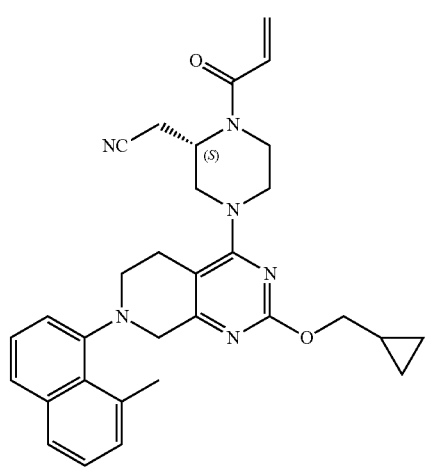
266
-continued
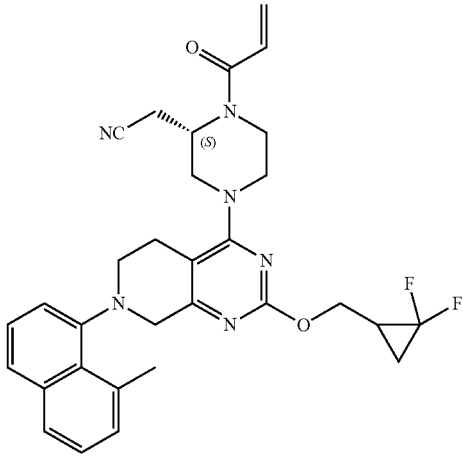
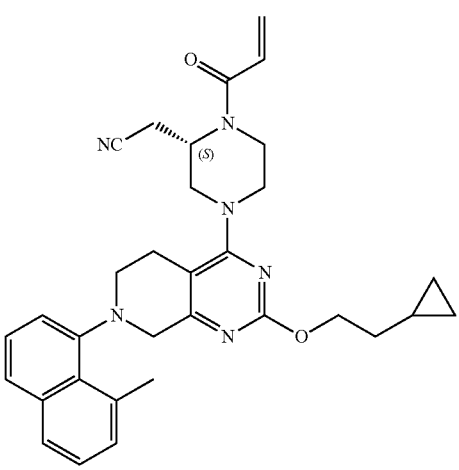
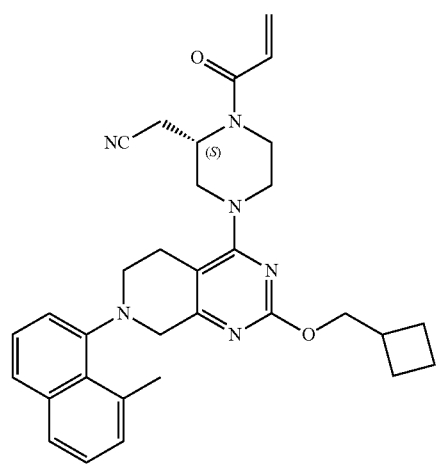

267
-continued
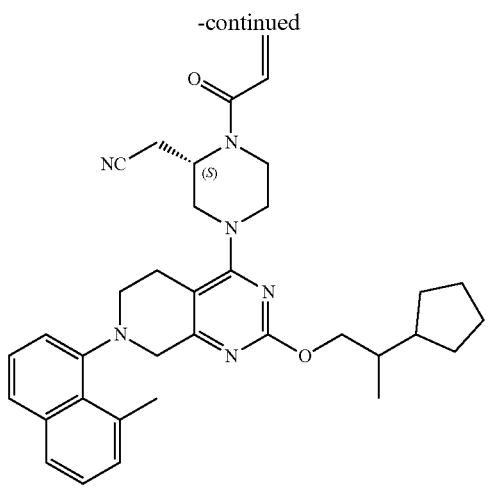
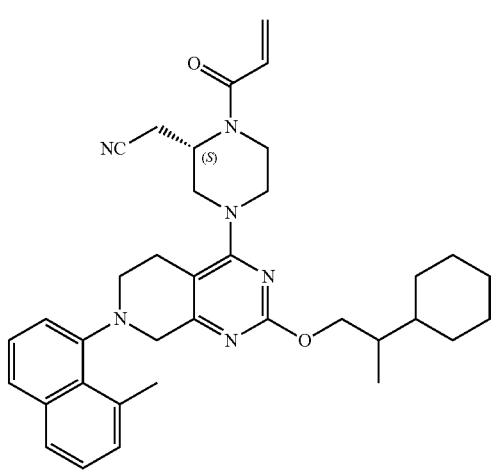
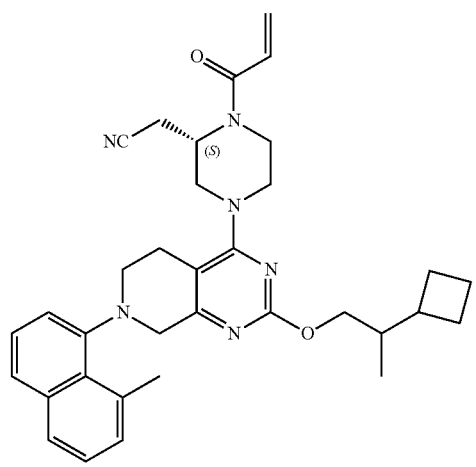
268
-continued
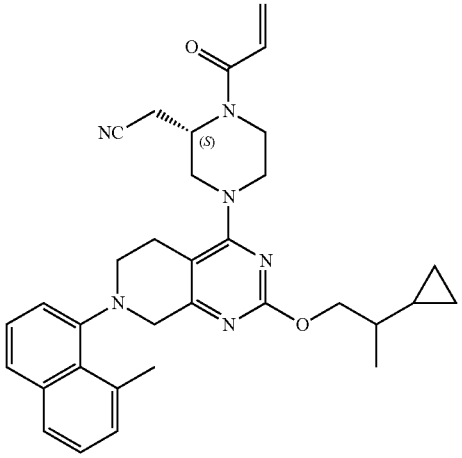
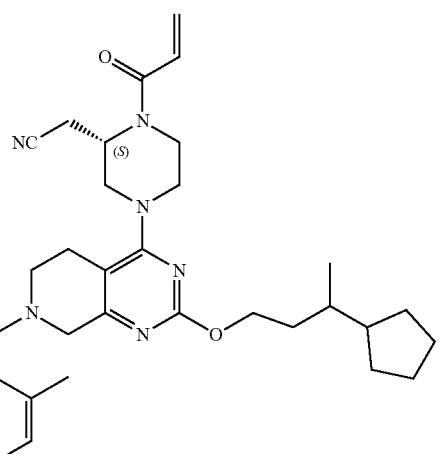
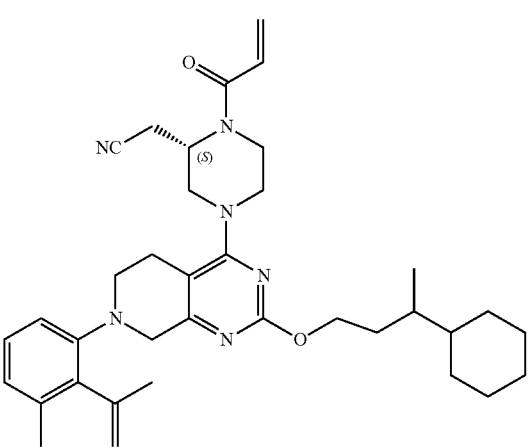

269
-continued
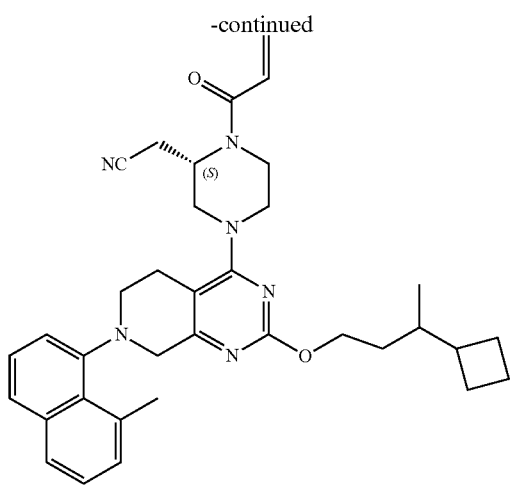
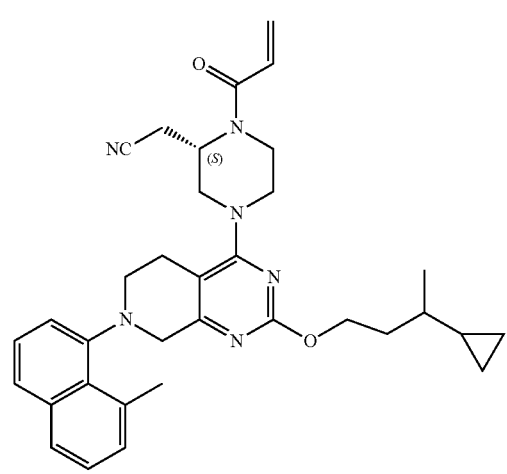
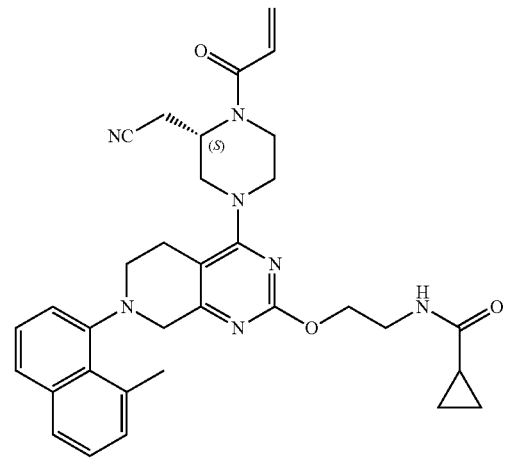
270
-continued
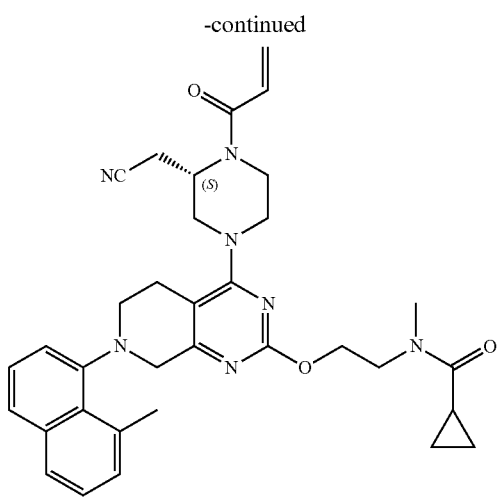
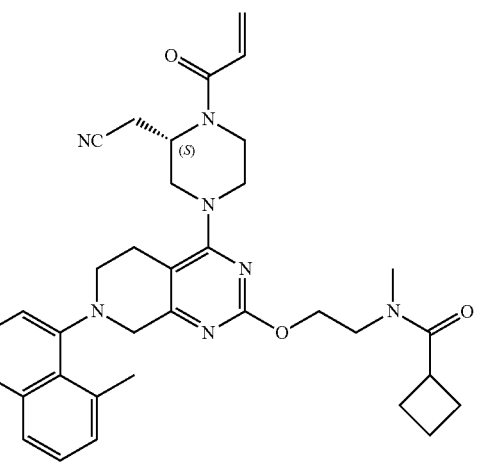
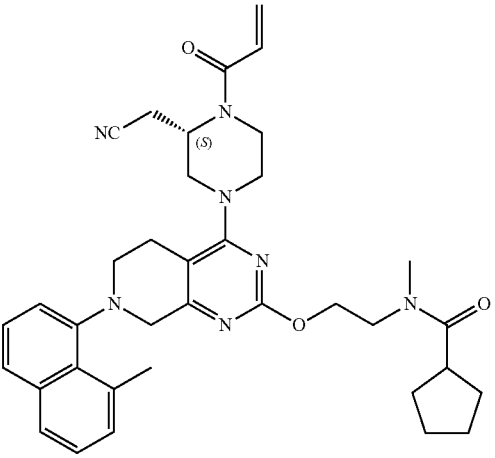

271
-continued
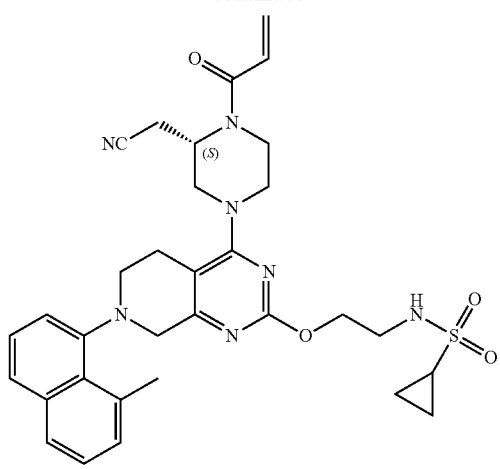
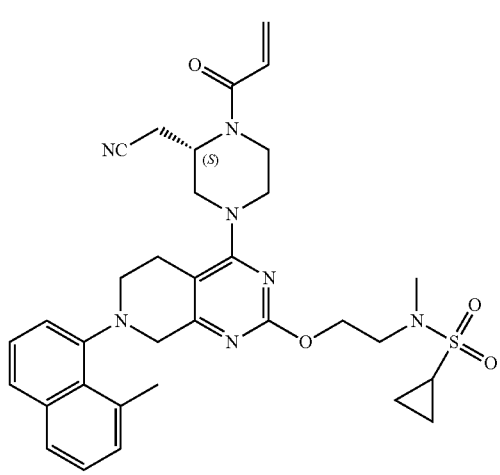
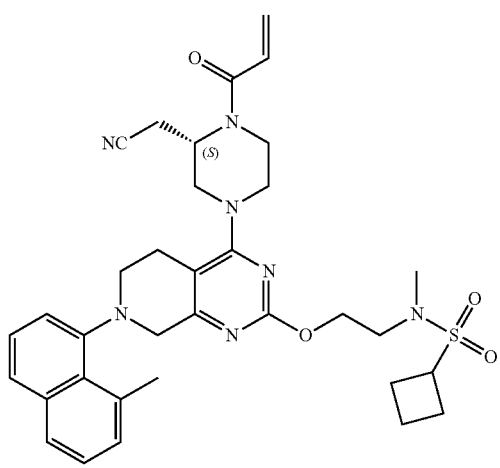
272
-continued
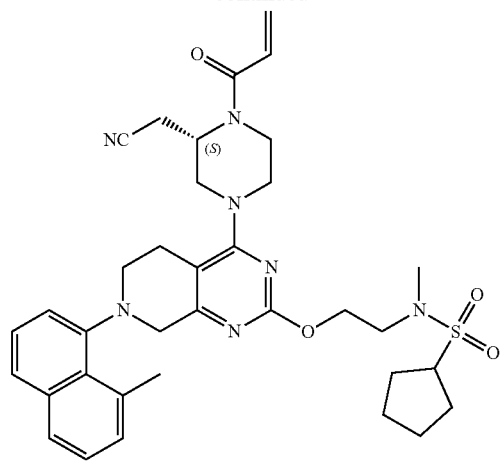
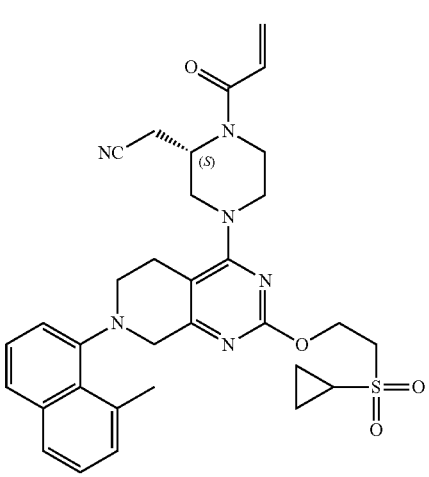
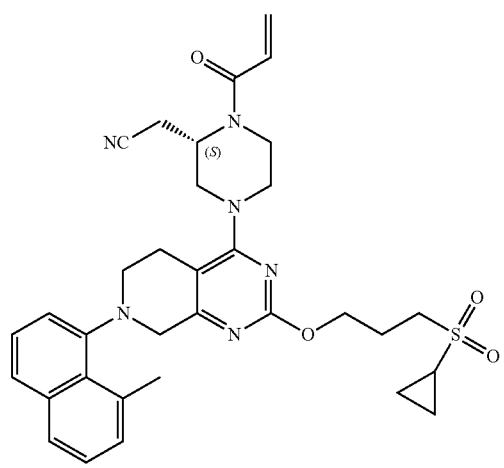

273
-continued
274
-continued
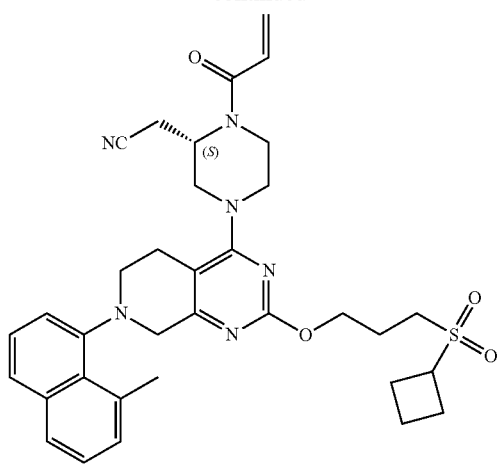
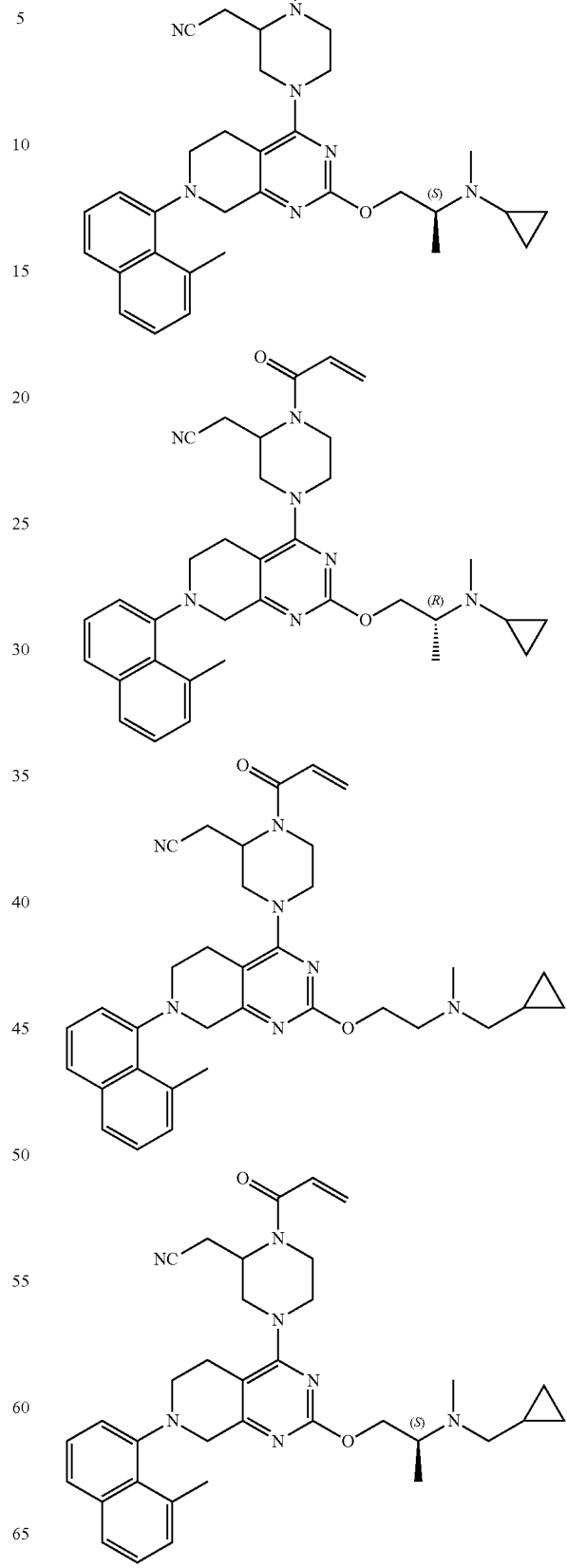

275
-continued
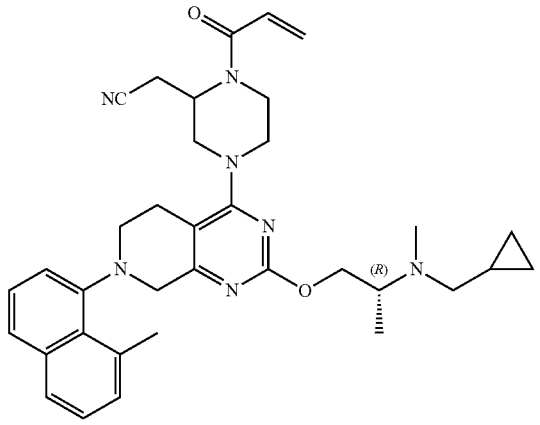
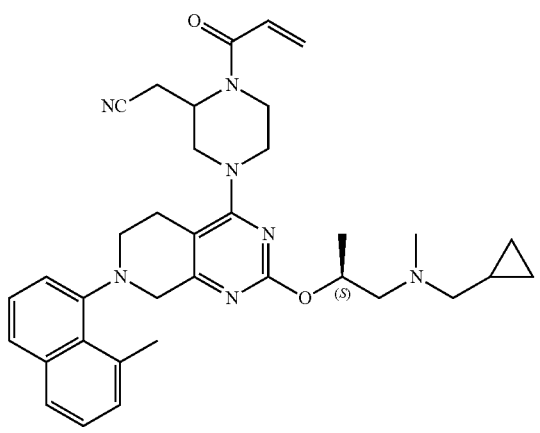
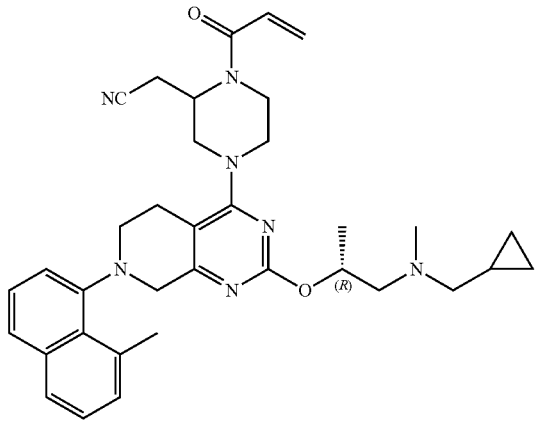
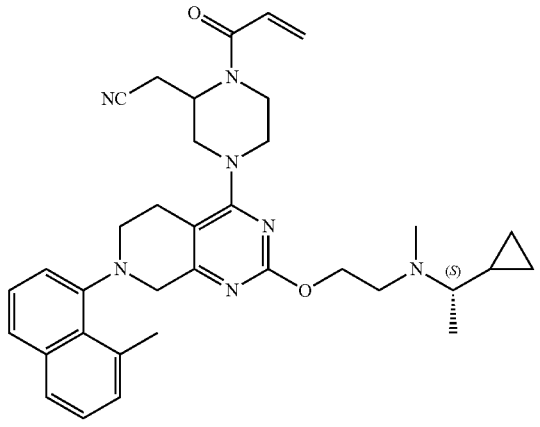
276
-continued
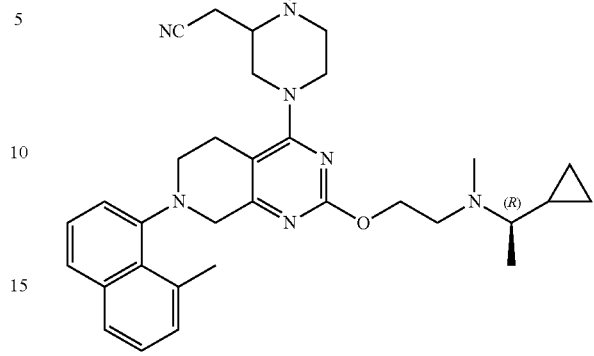
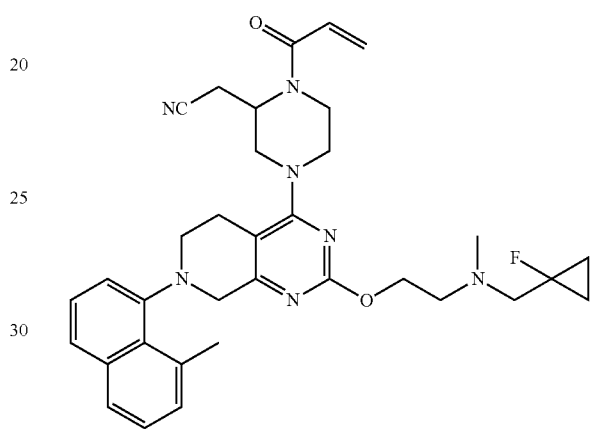
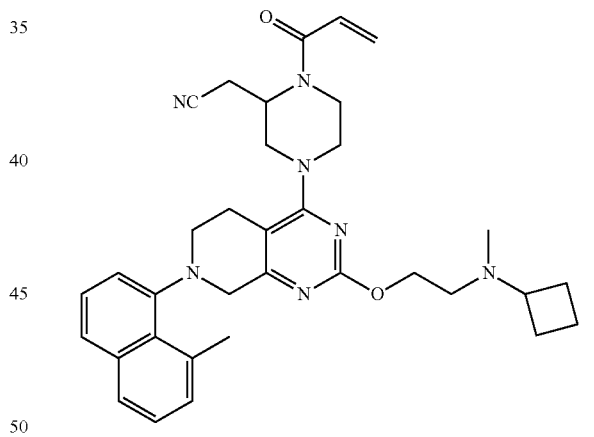
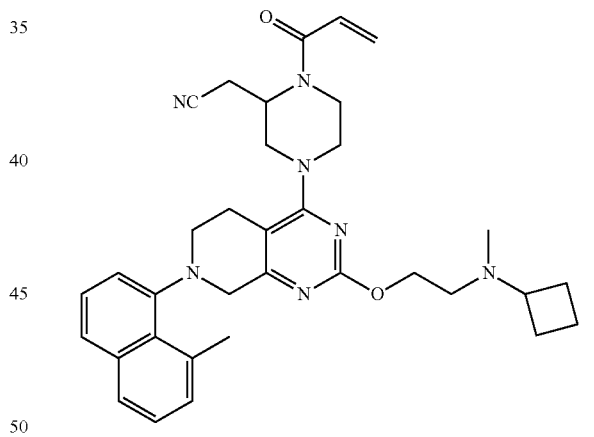

277
-continued
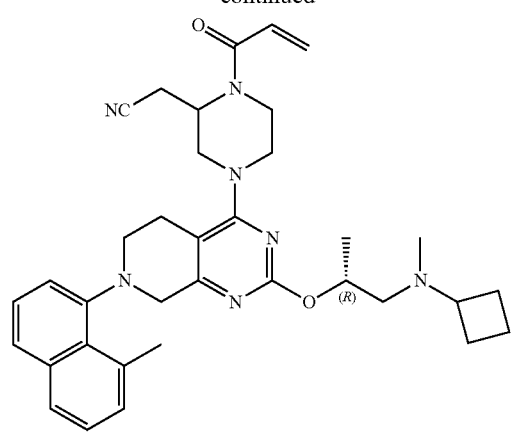
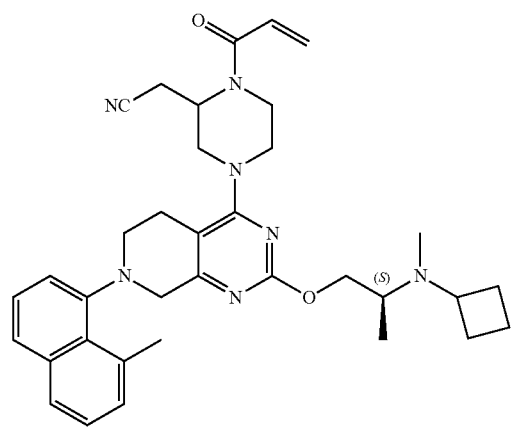
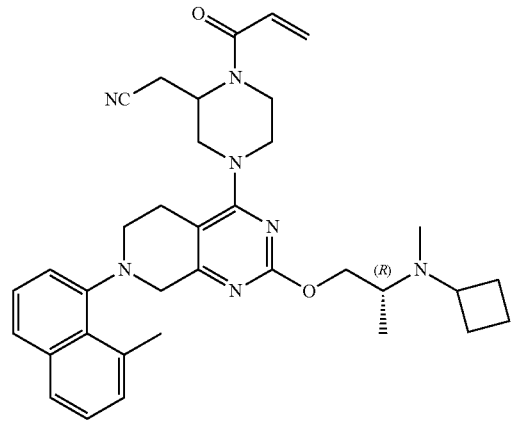
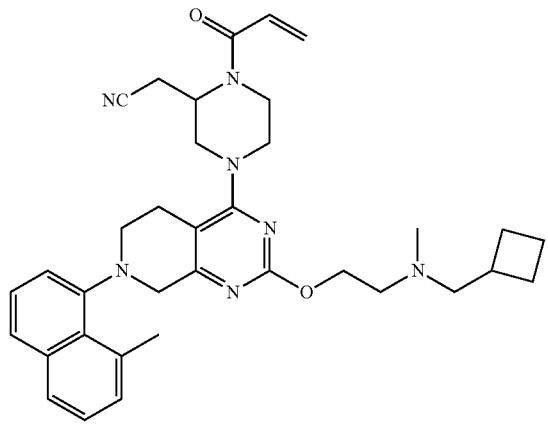
278
-continued
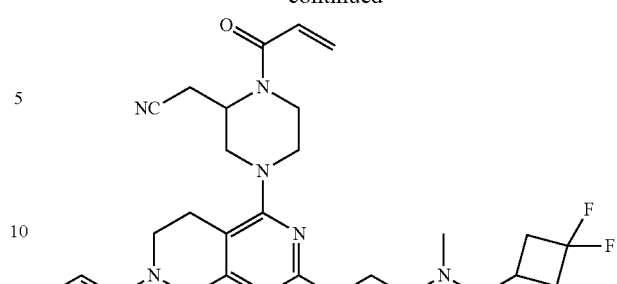
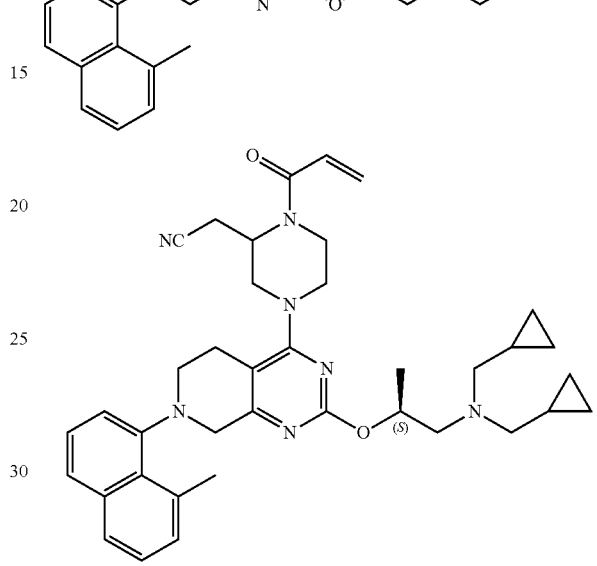
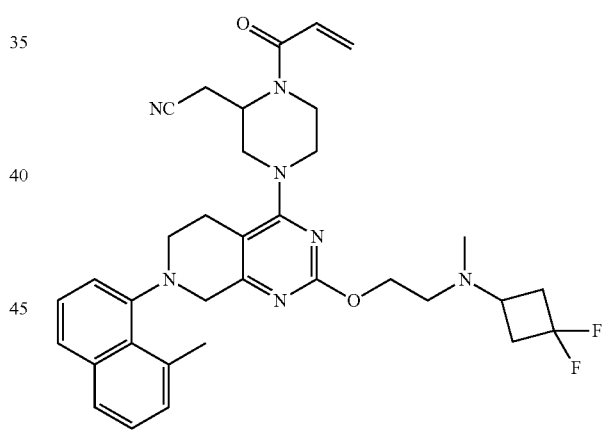
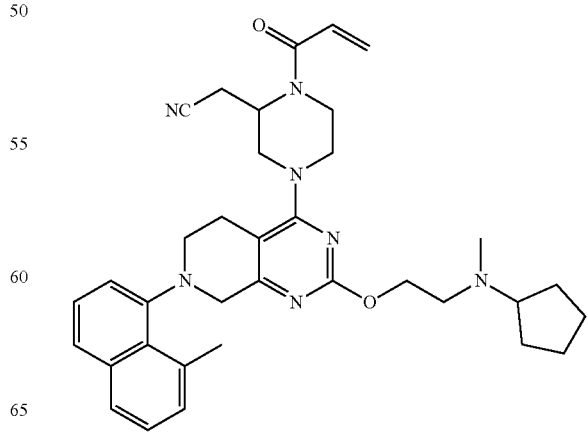

279
-continued
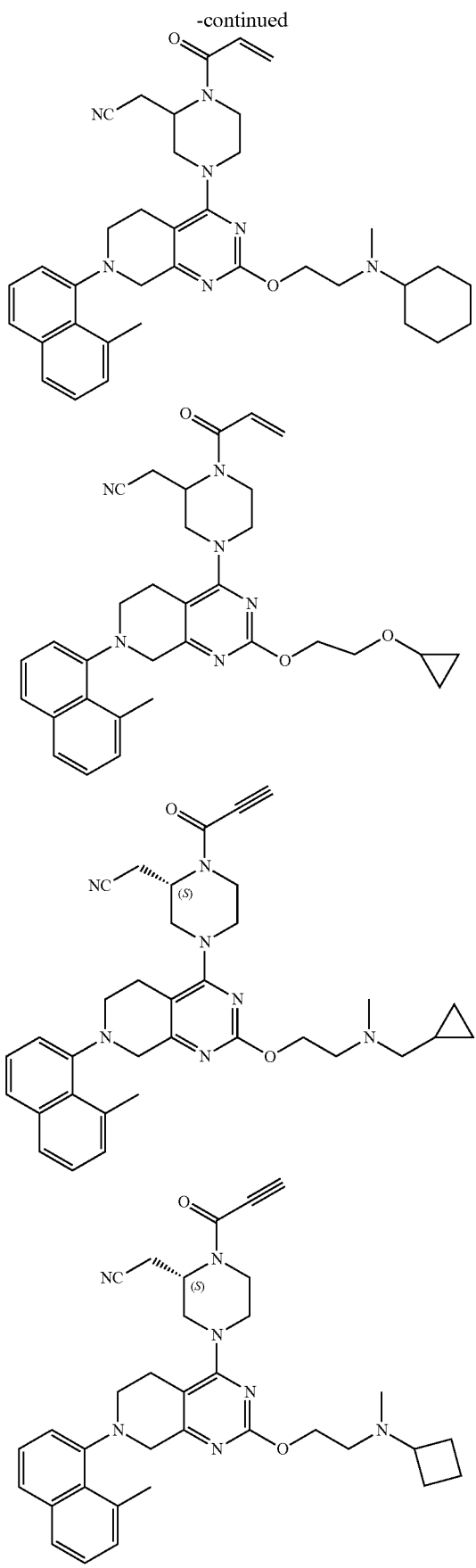
280
-continued
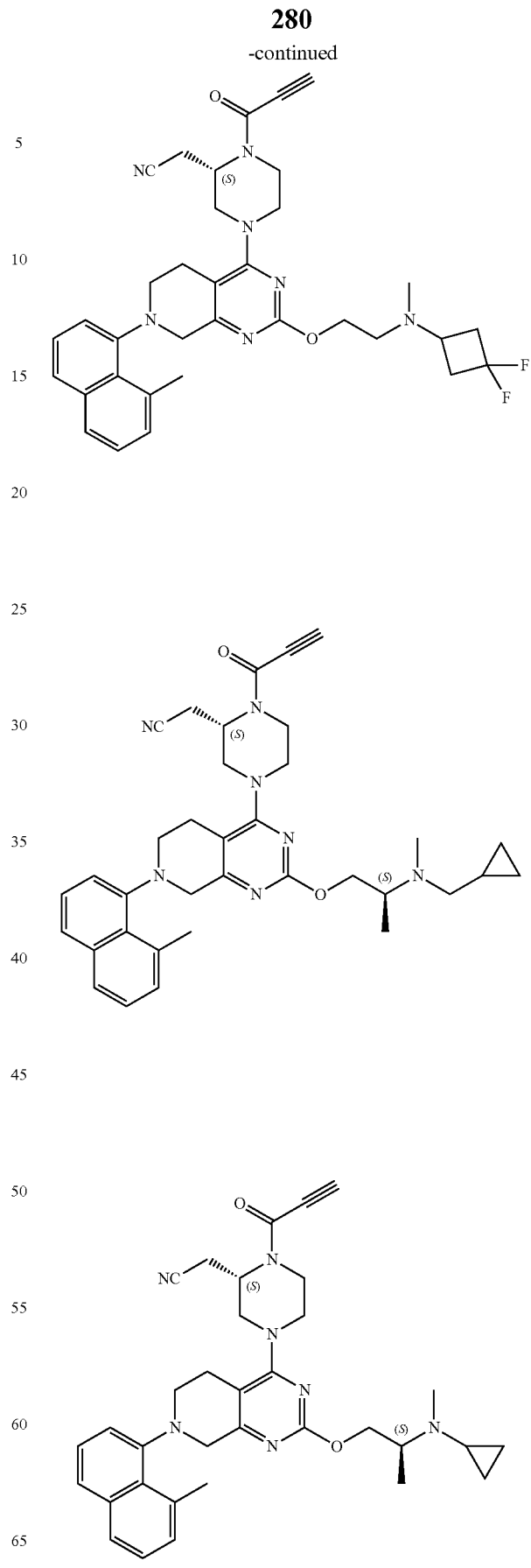

281
-continued
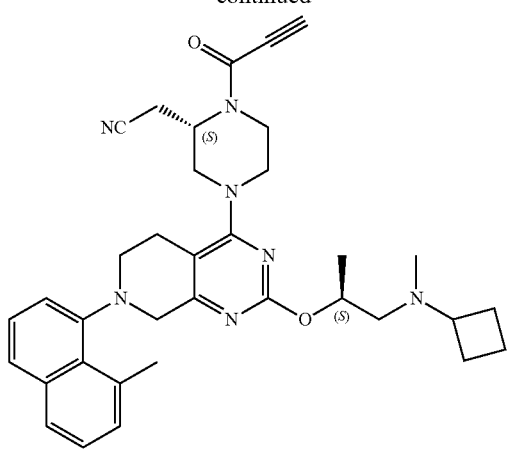
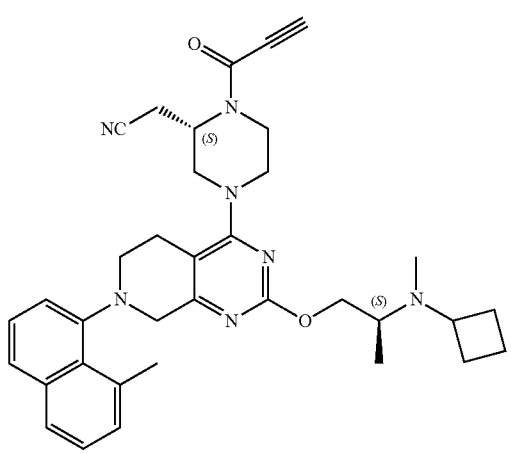
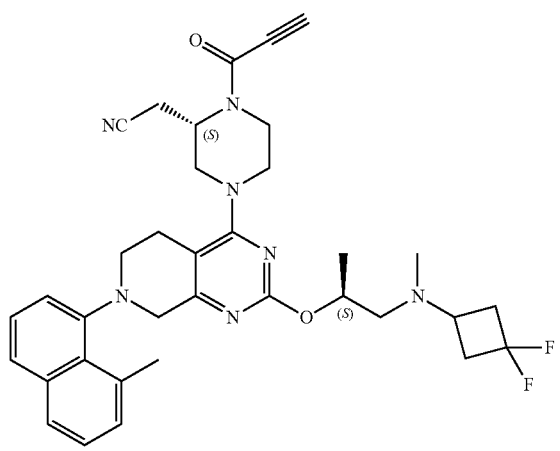
282
-continued
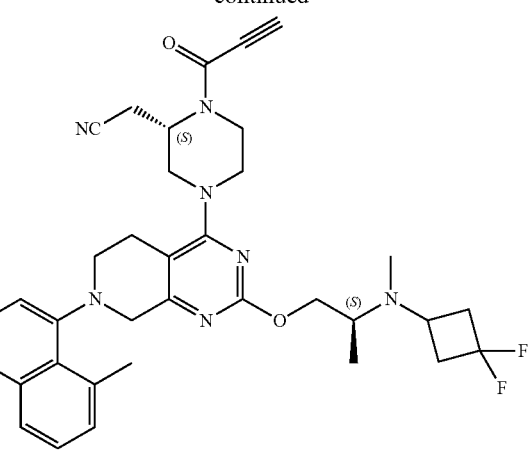
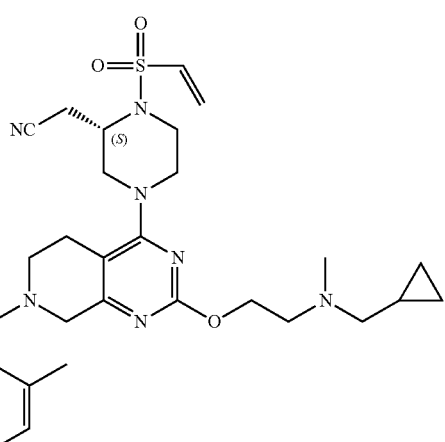
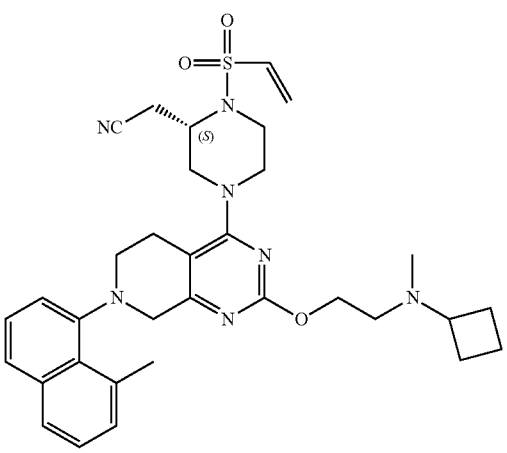

283
-continued
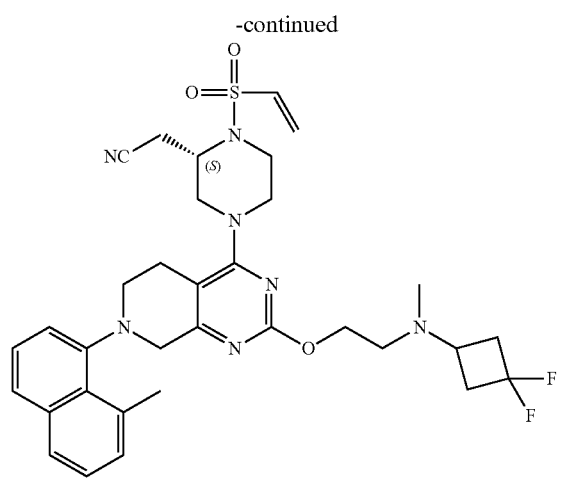
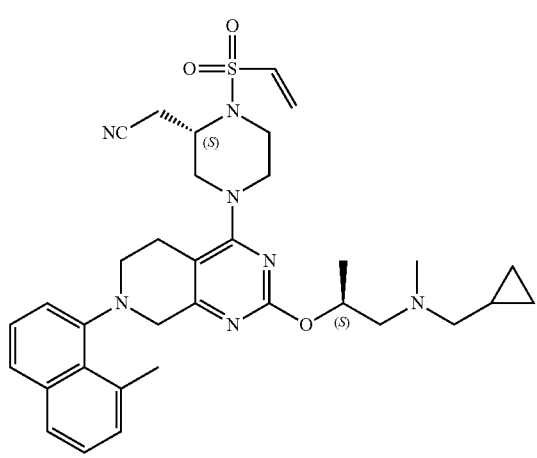
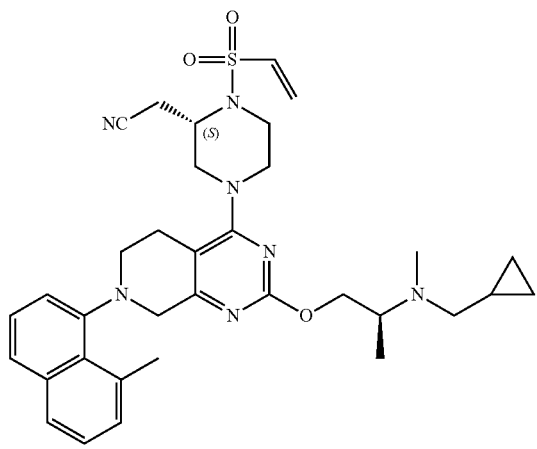
284
-continued
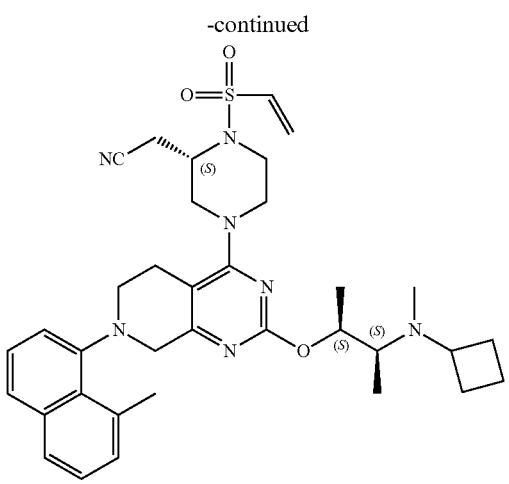
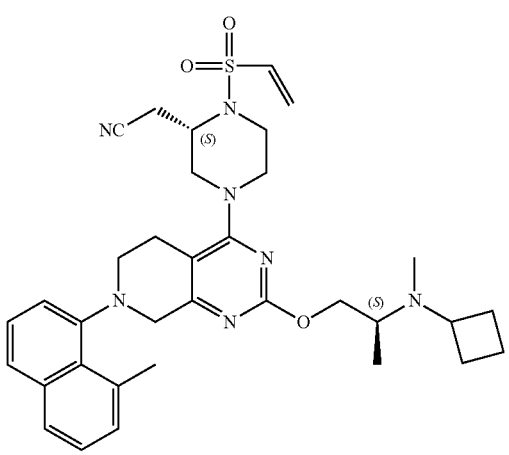
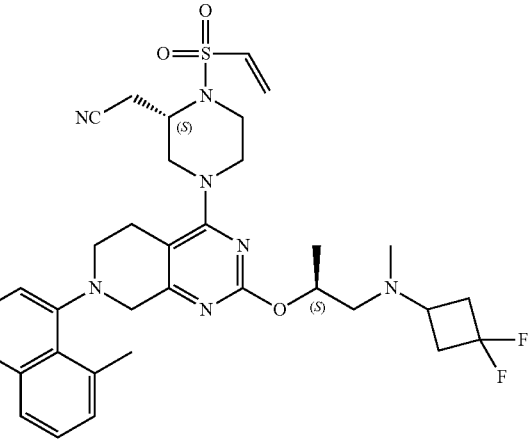

285
-continued
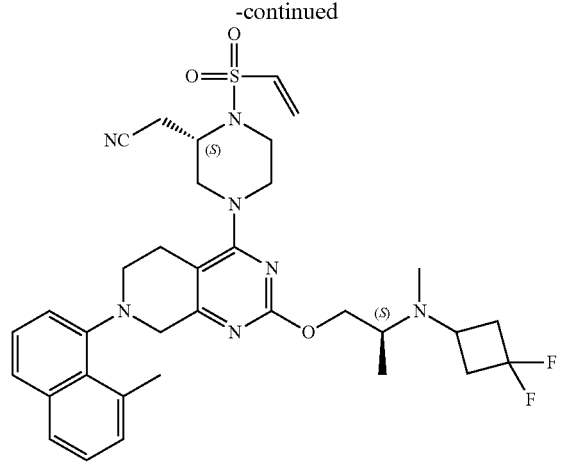
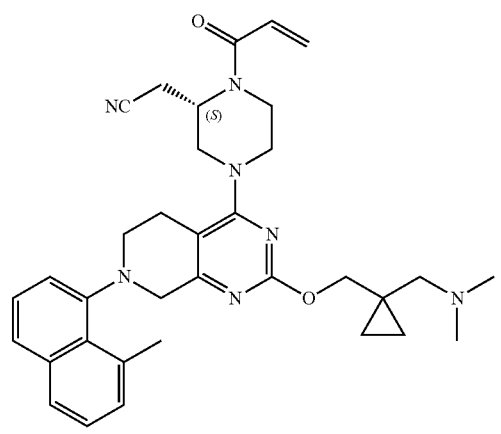
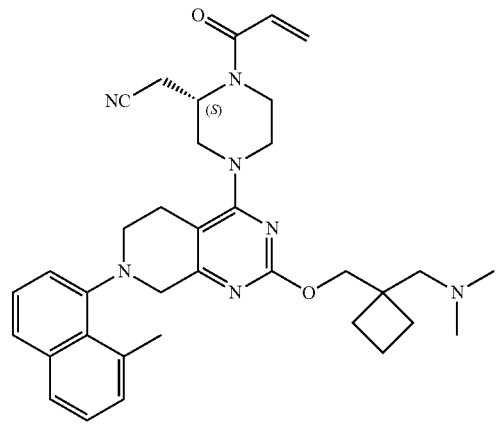
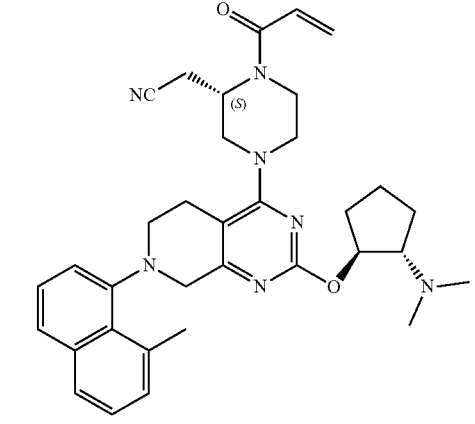
286
-continued
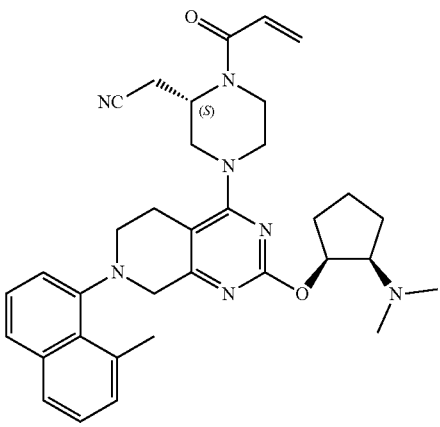
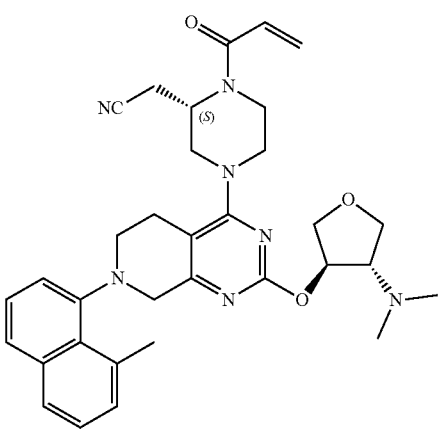
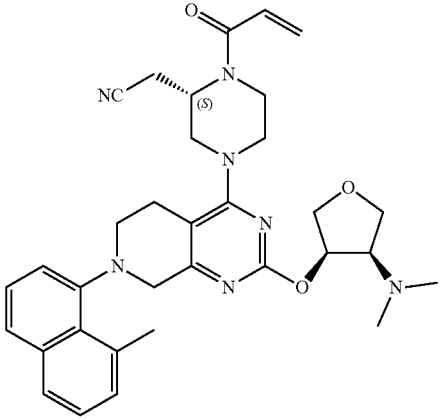
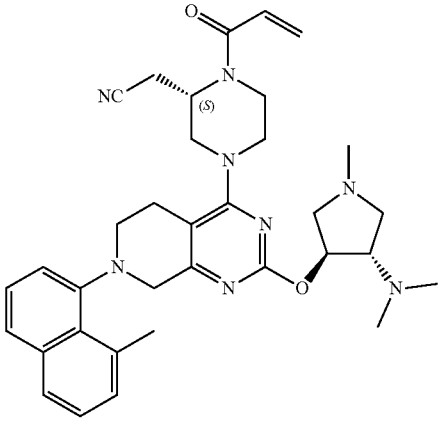

287
-continued
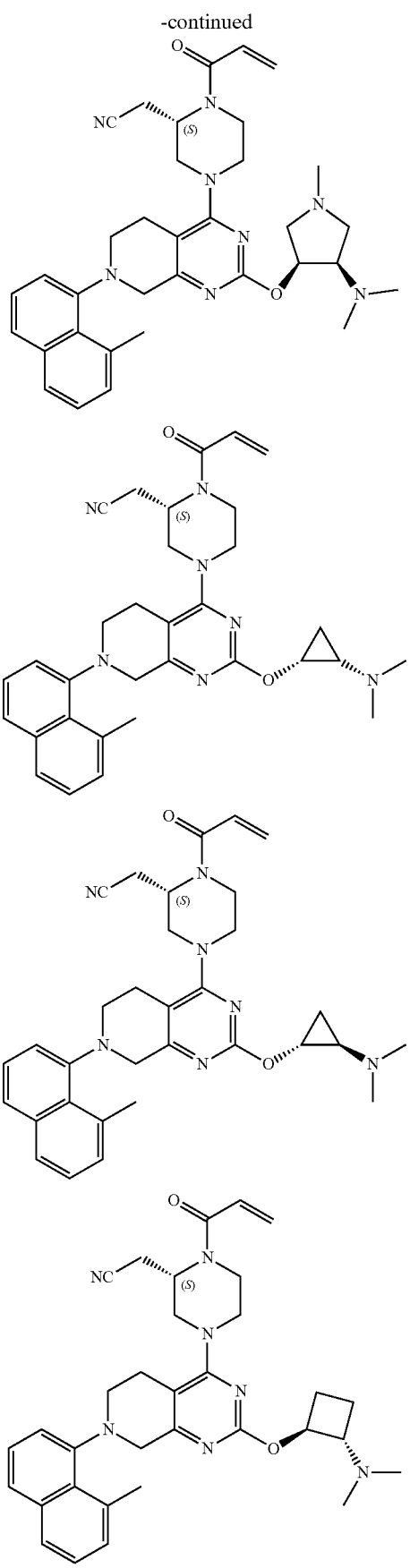
288
-continued
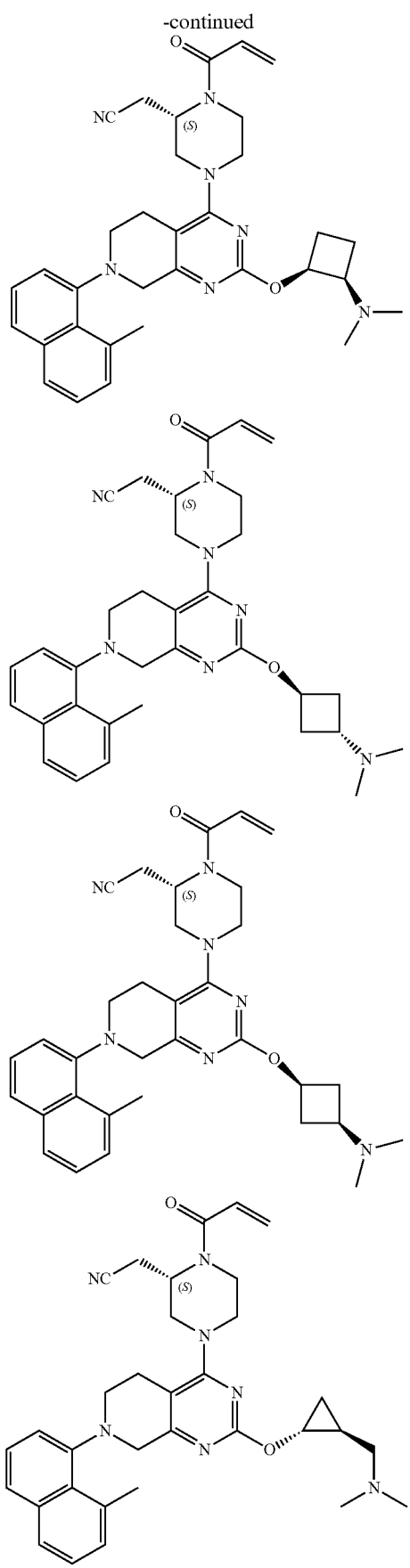

289
-continued
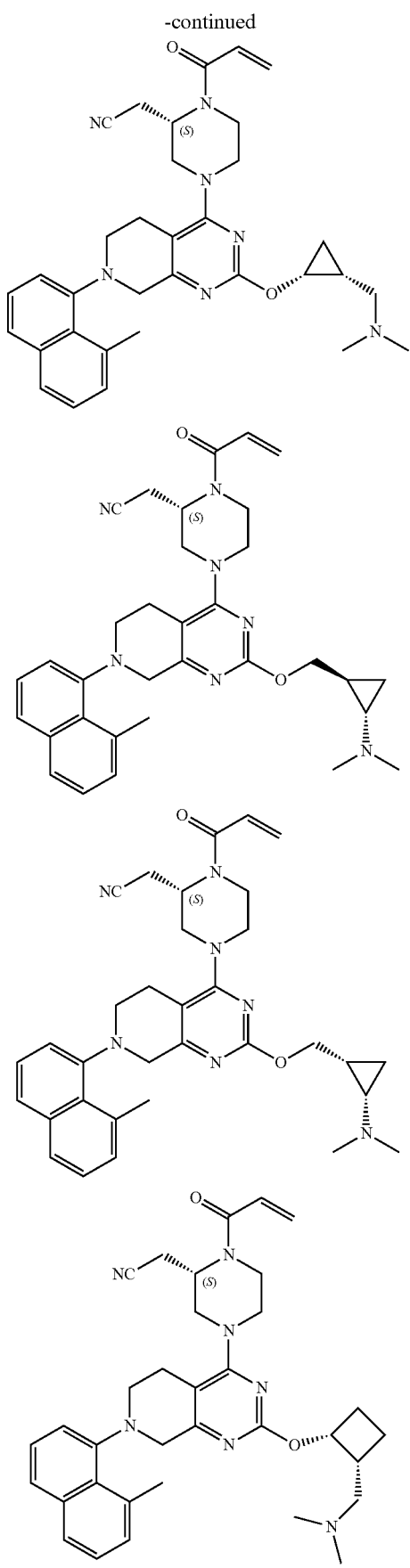
290
-continued
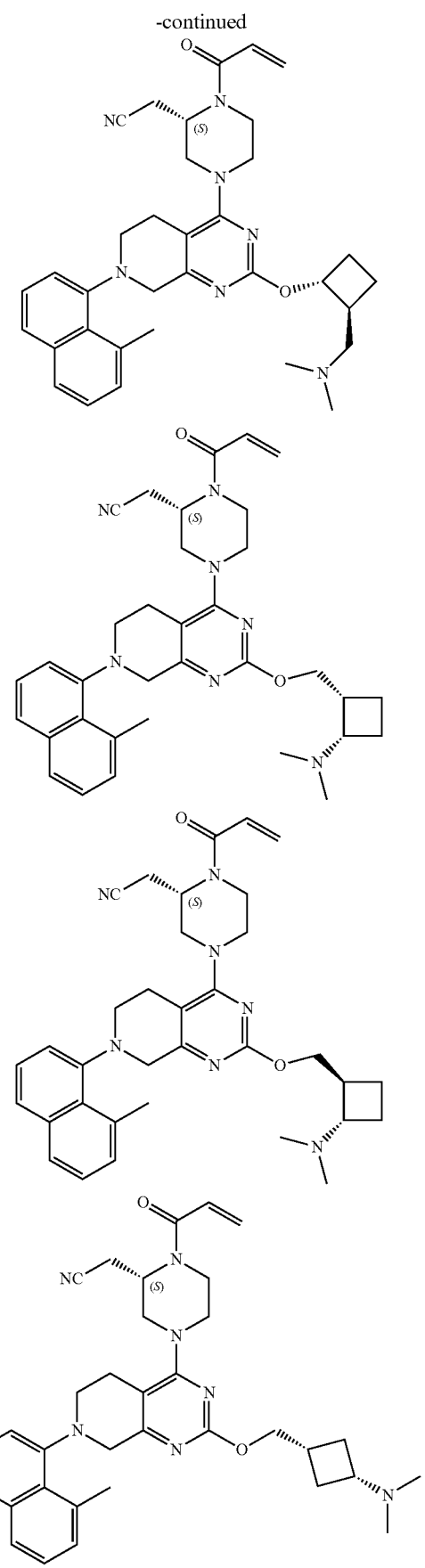

291
-continued
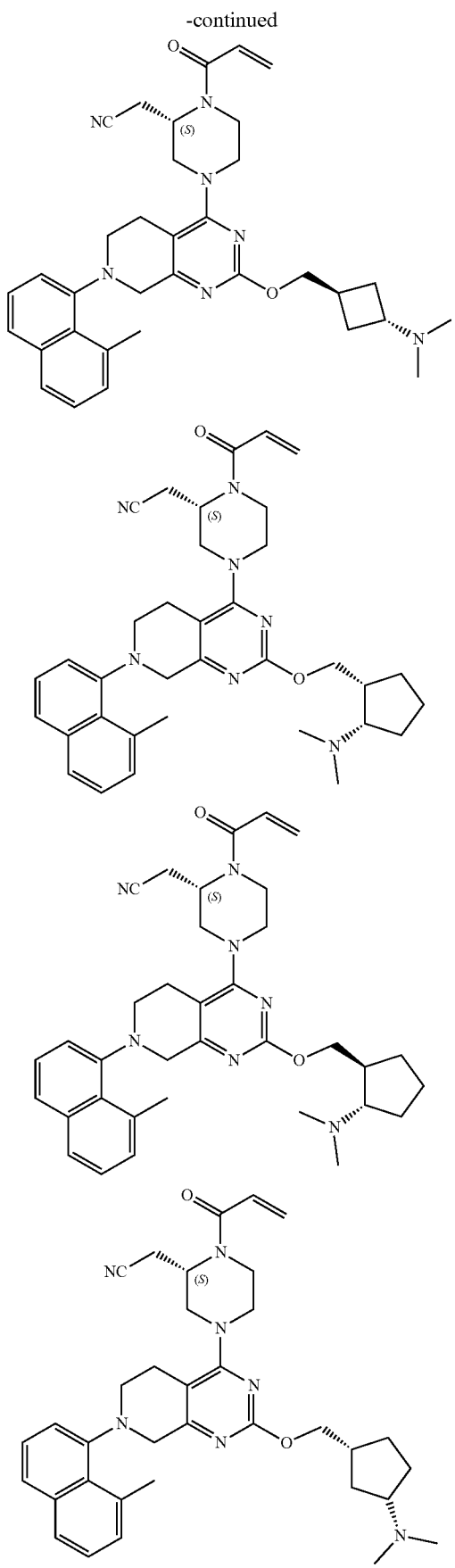
292
-continued
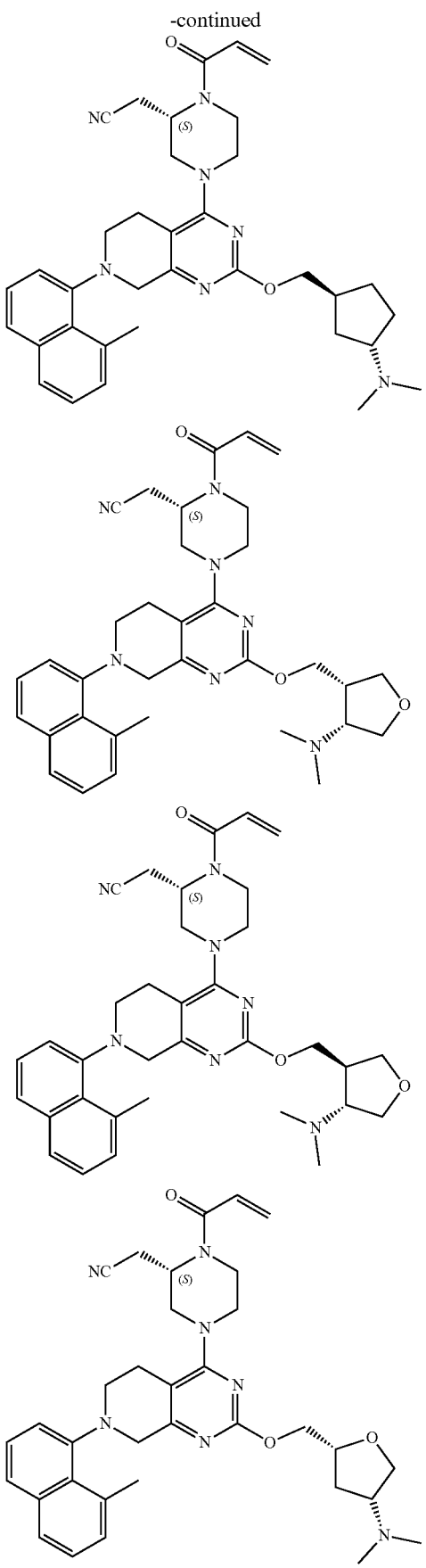

293
-continued
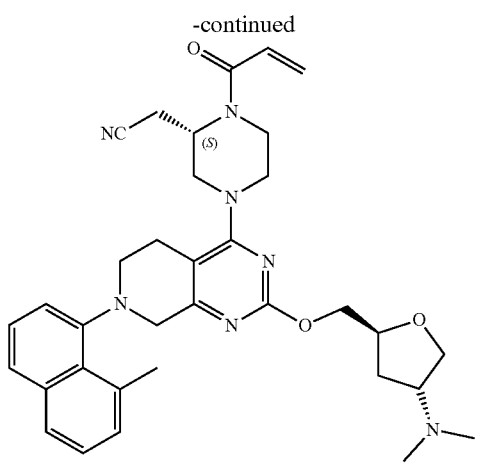
294
-continued
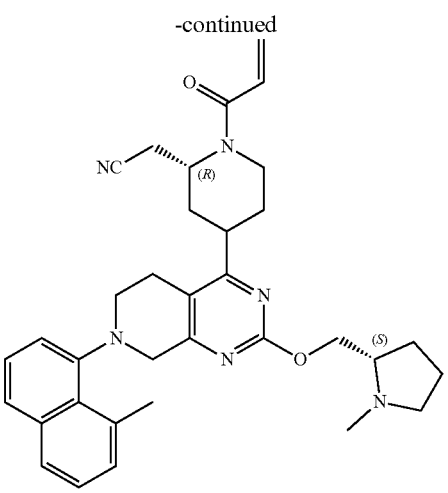
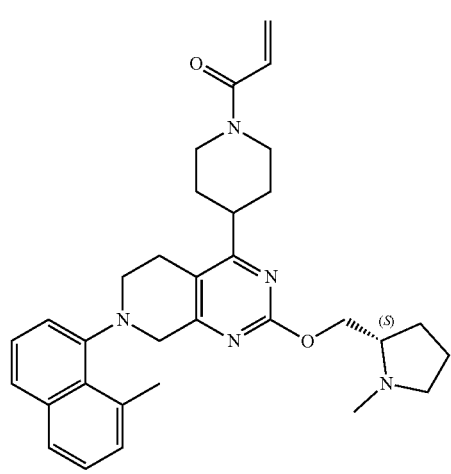
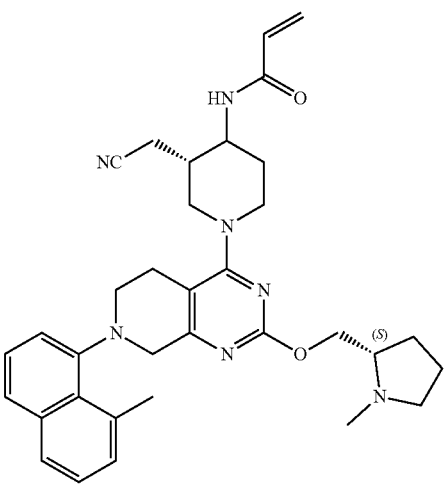
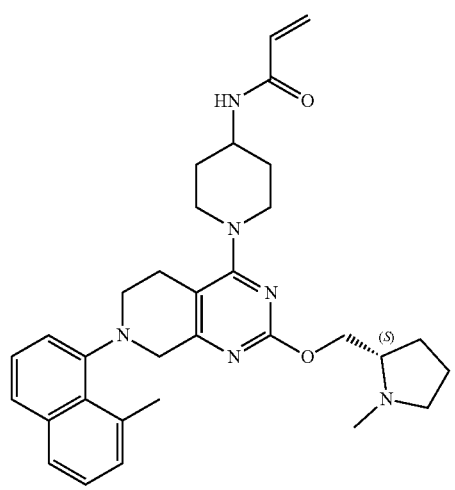
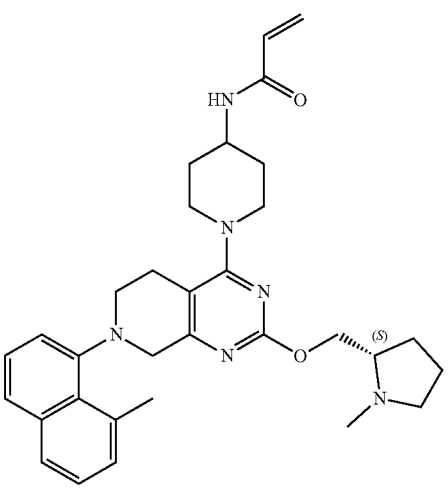

295
-continued
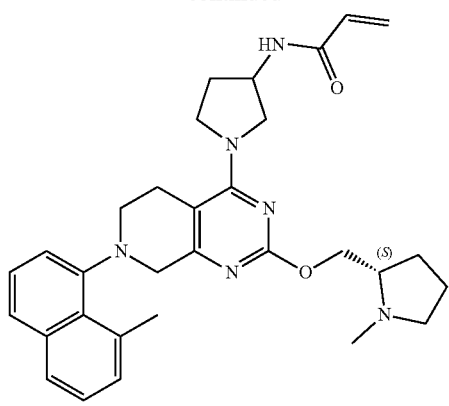
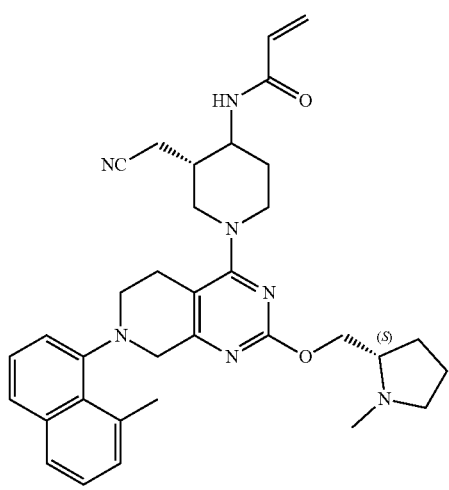
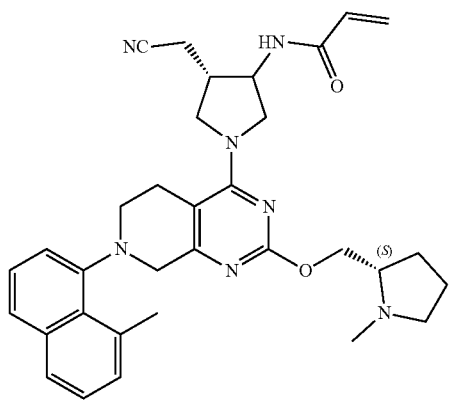
296
-continued
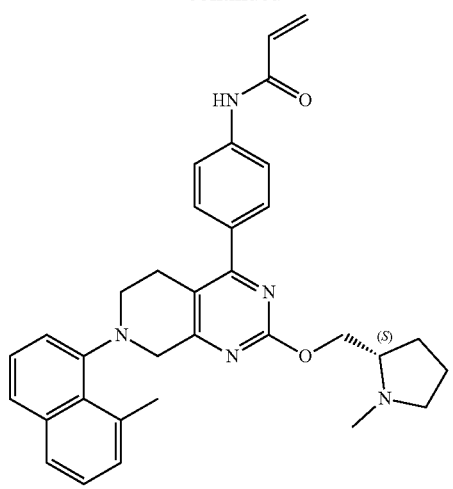
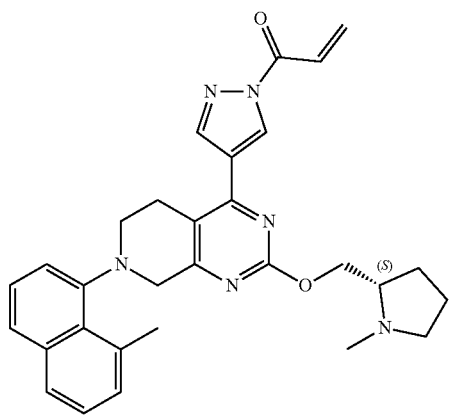

297
-continued
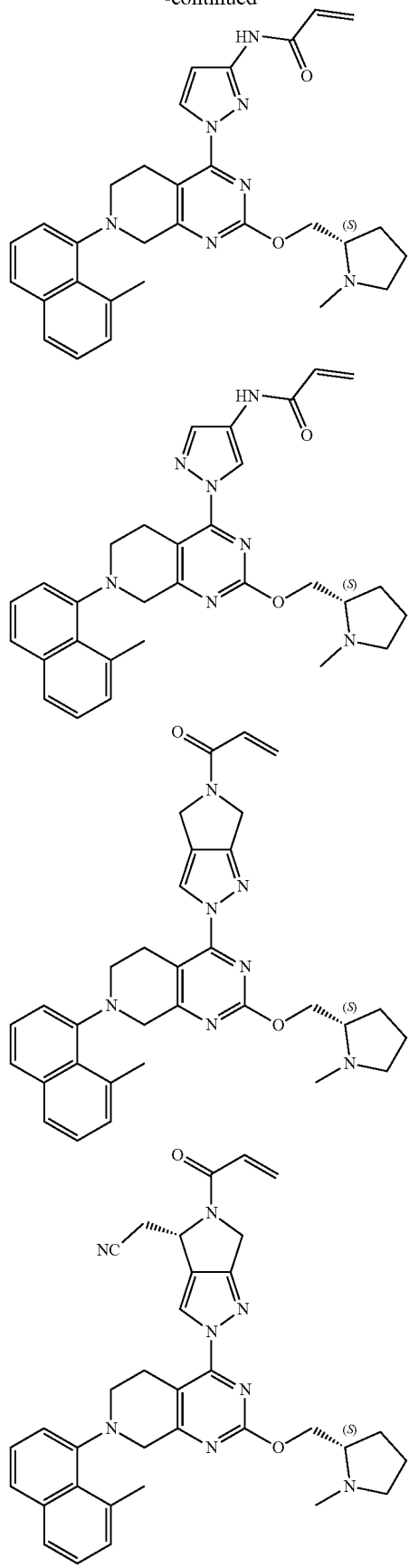
298
-continued
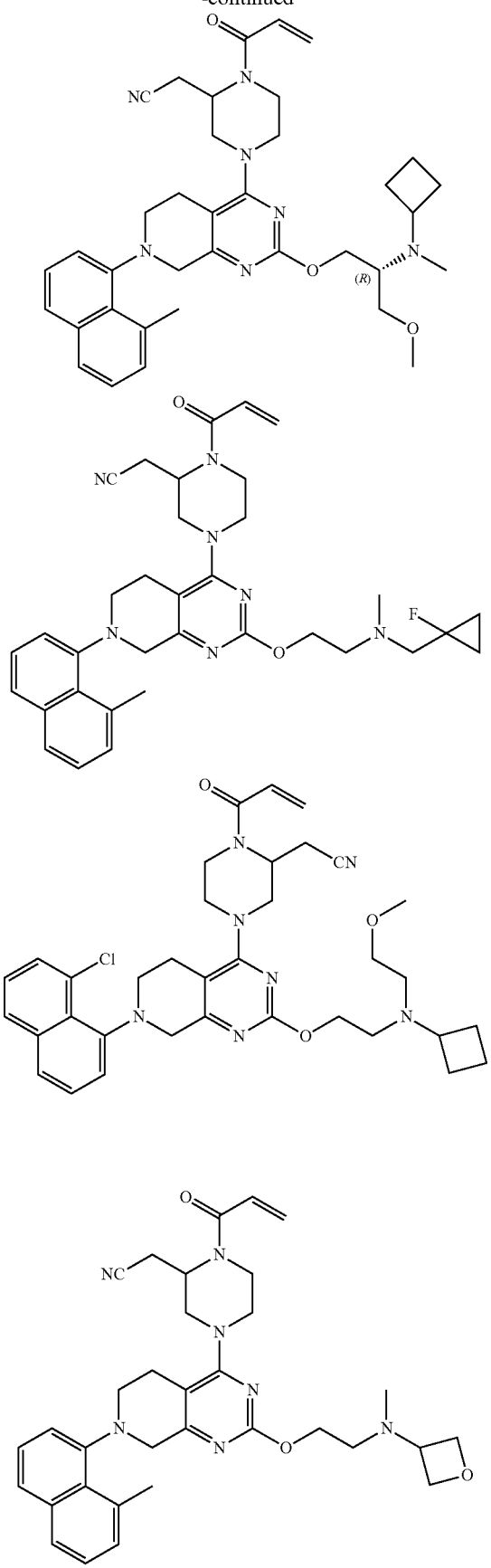

299
-continued
300
-continued
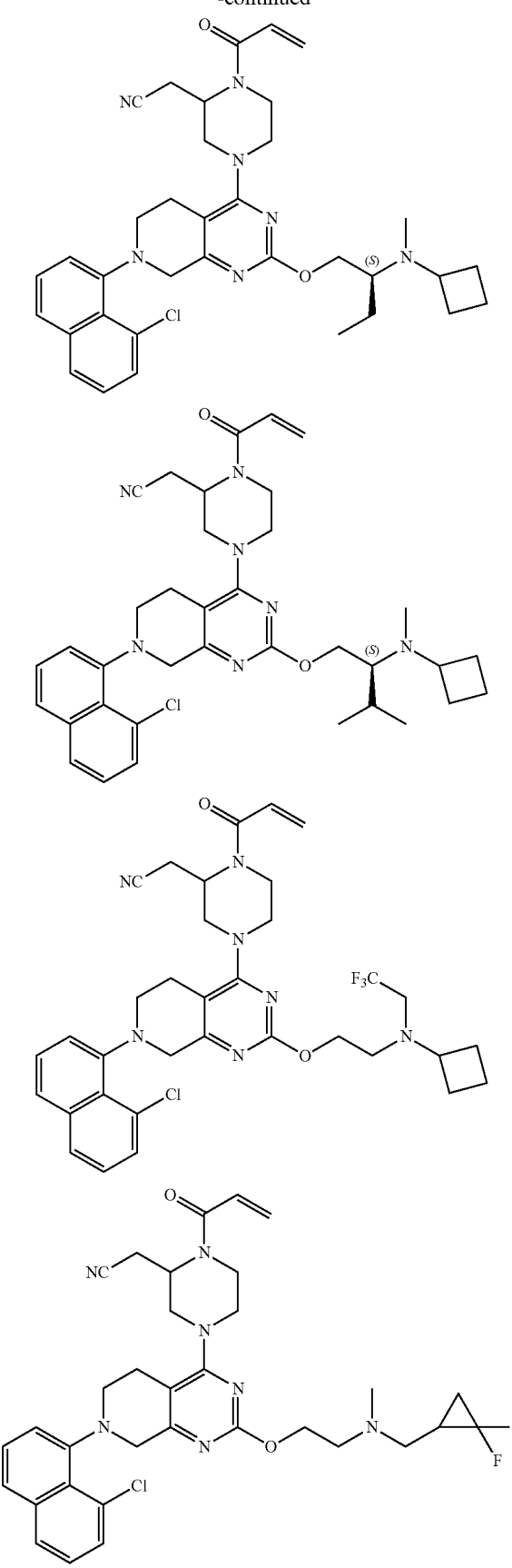
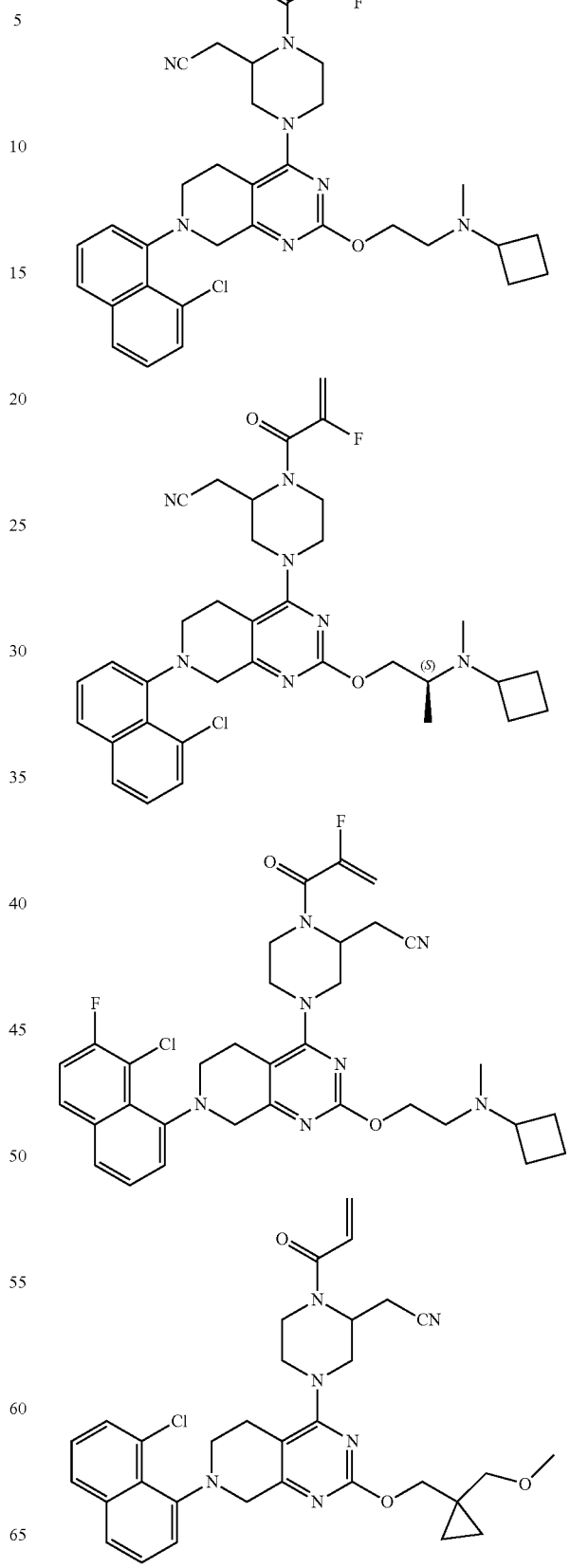

301
-continued
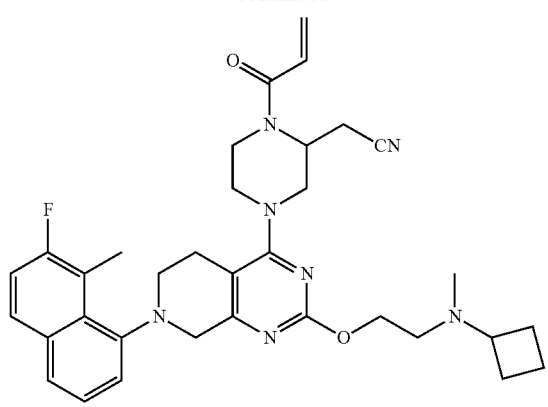
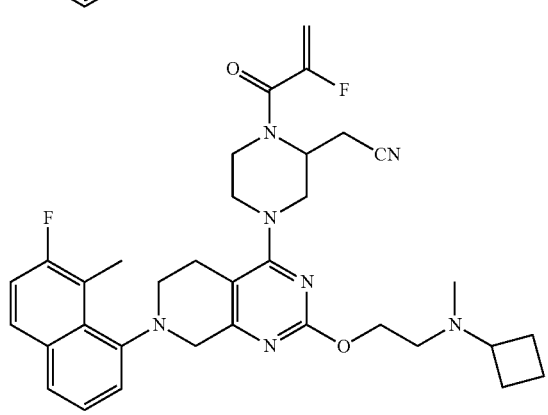
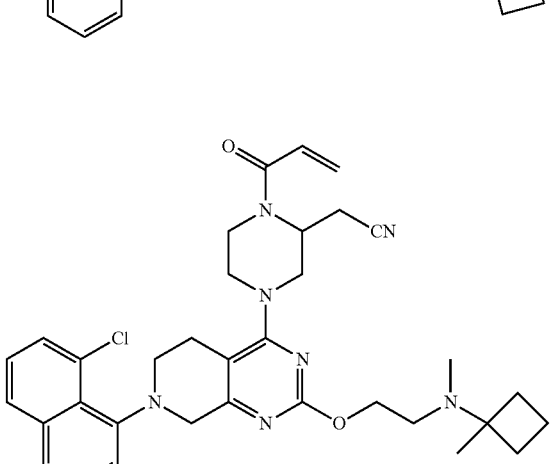
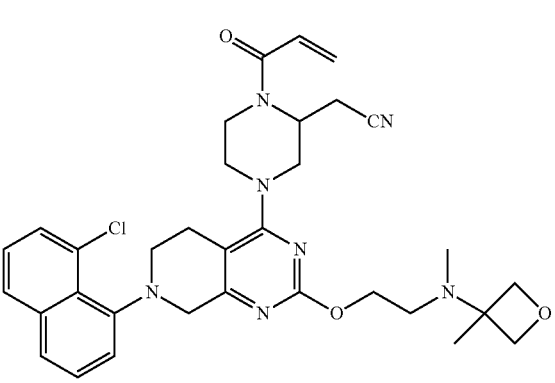
302
-continued
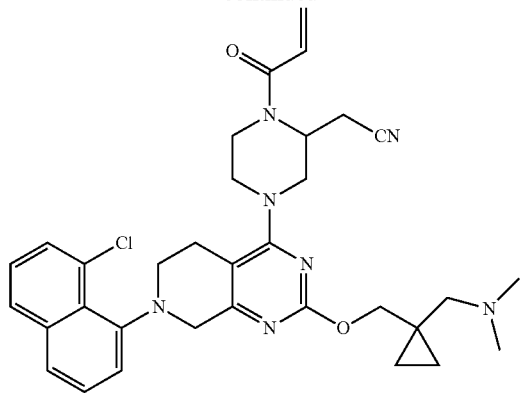
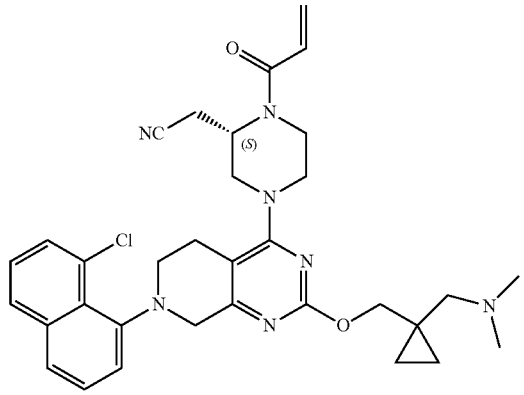
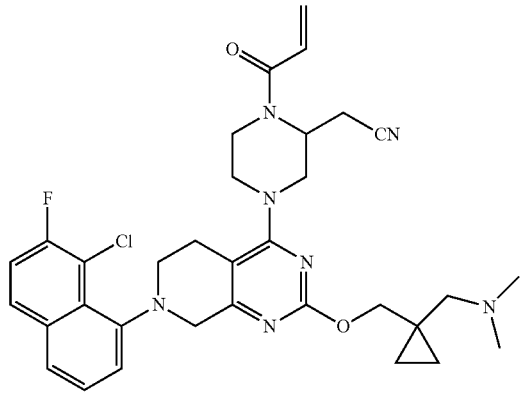
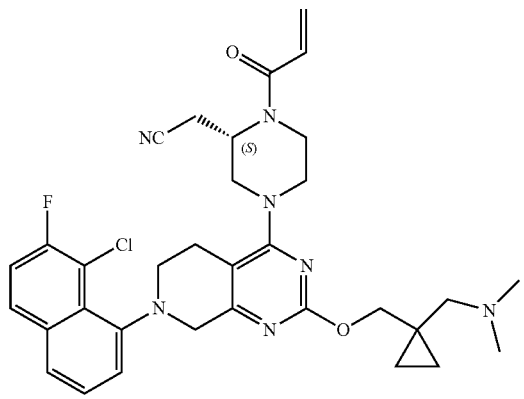

303
-continued
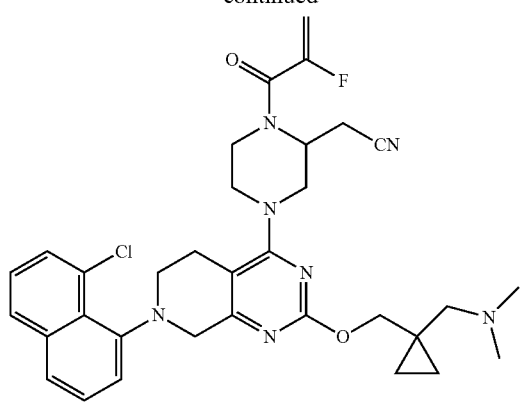
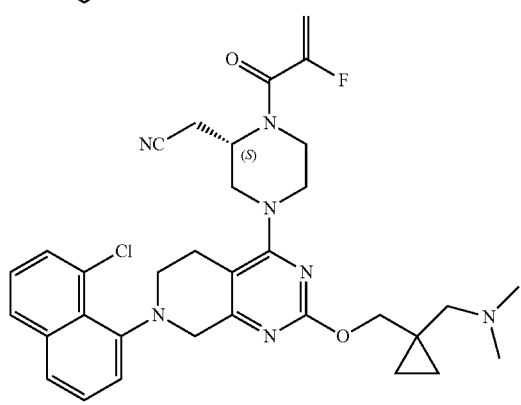
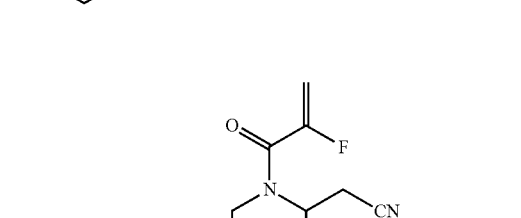
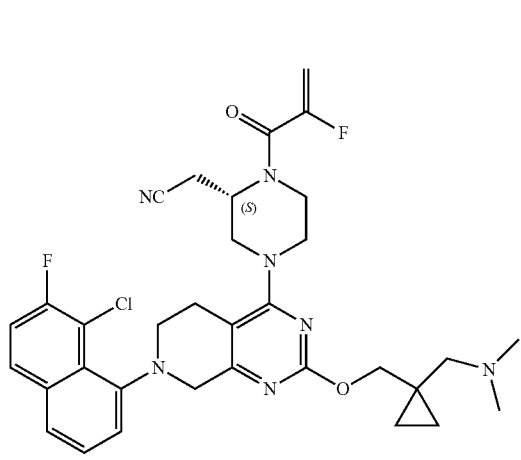
304
-continued
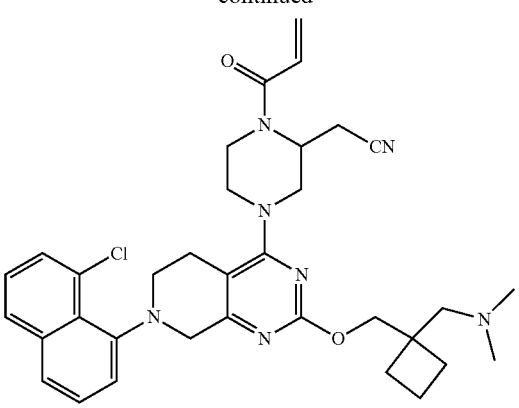
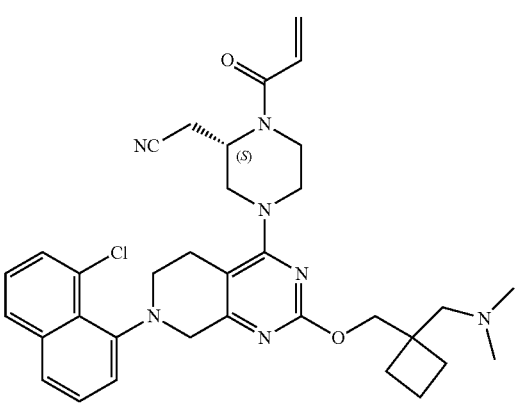

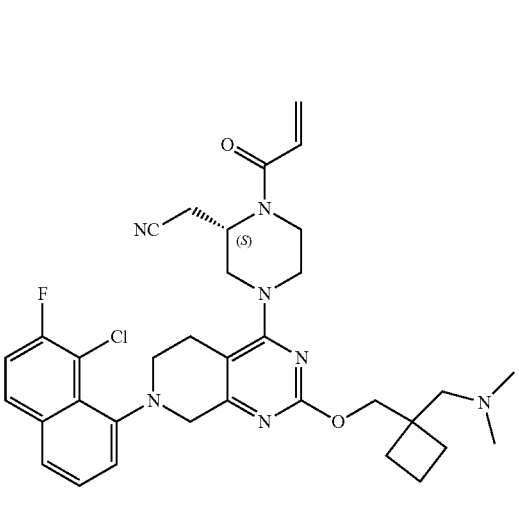

305
-continued
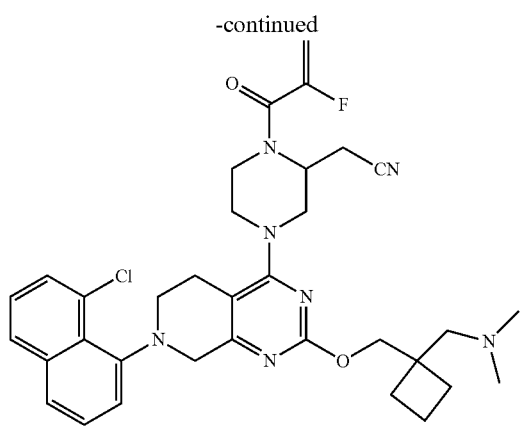
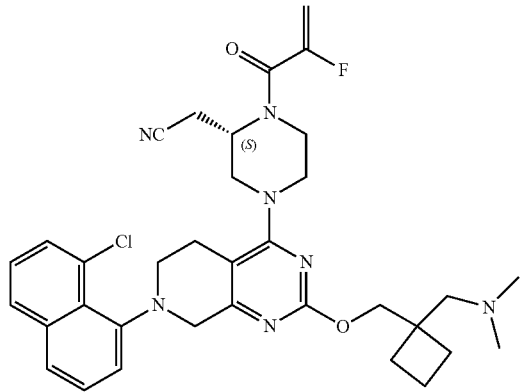
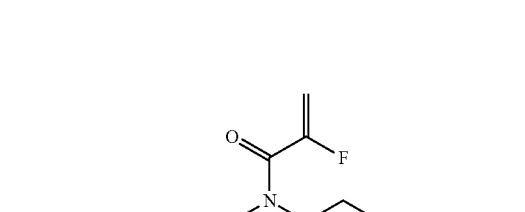
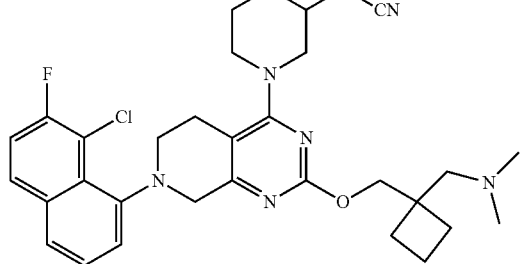
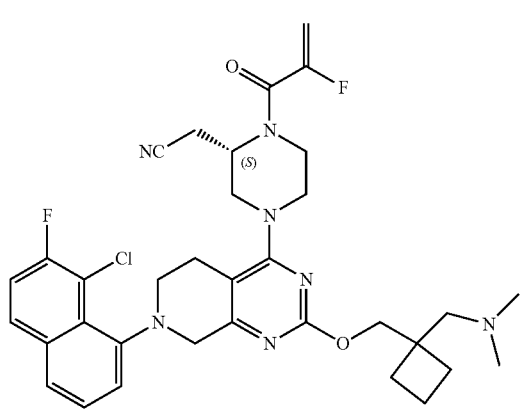
306
-continued
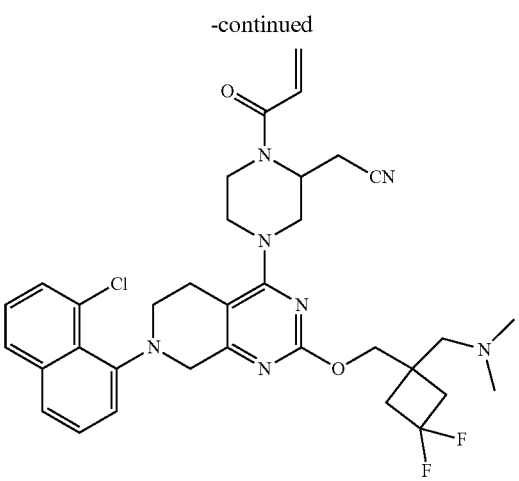
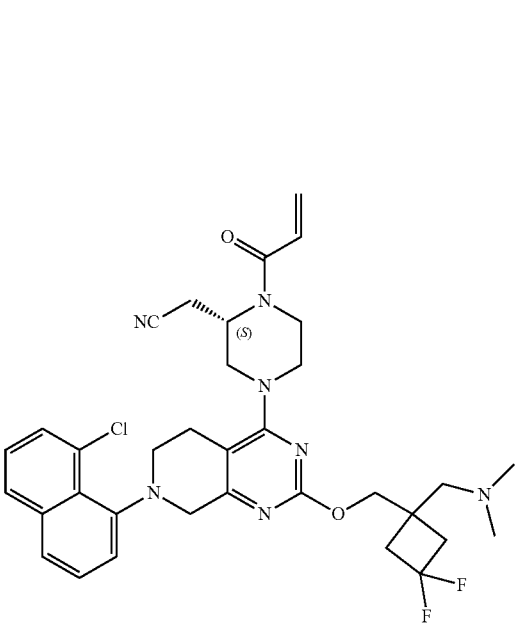
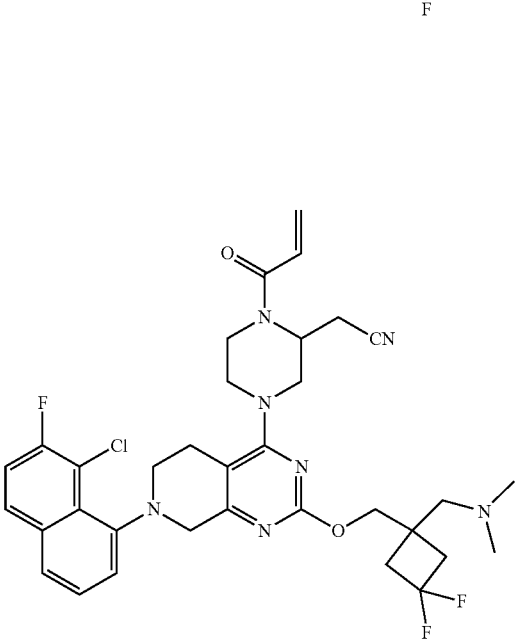

307
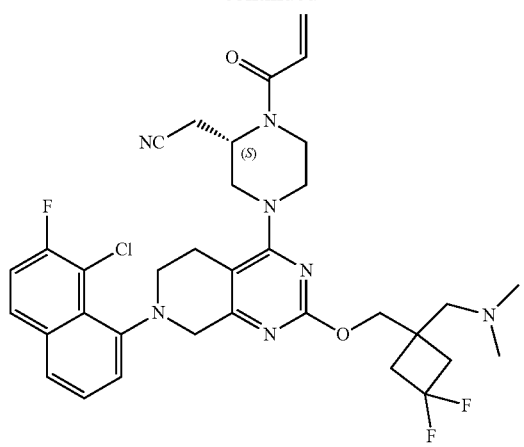
308
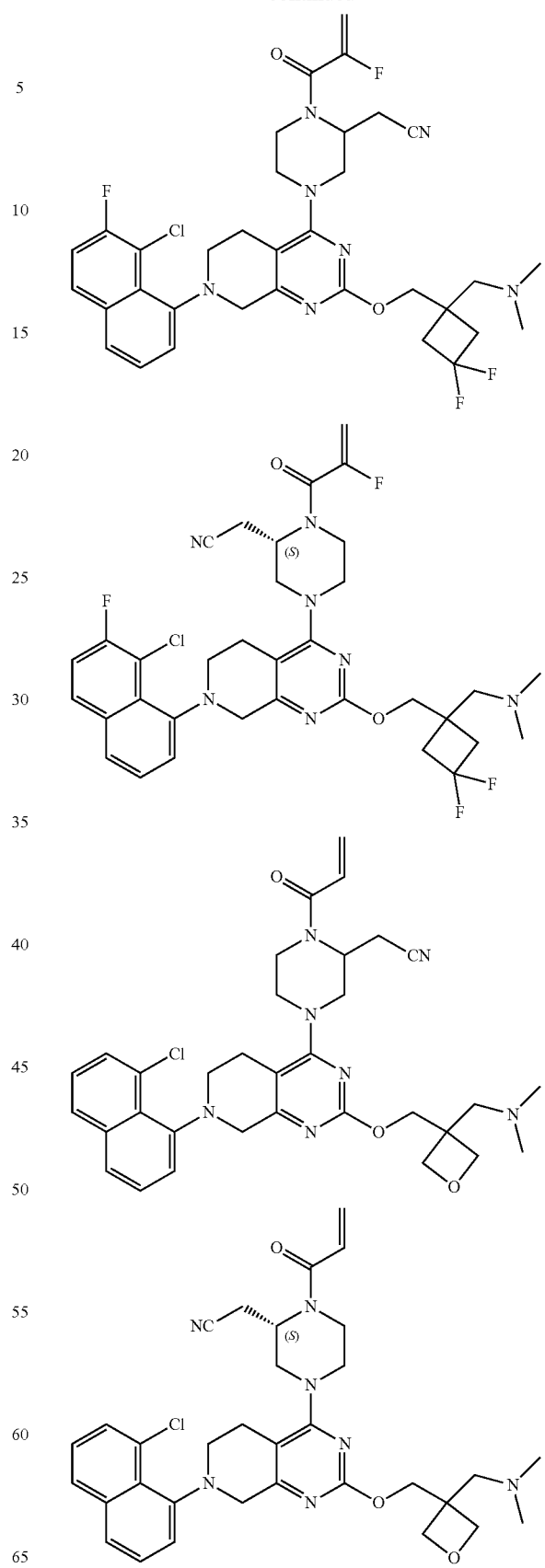

309
-continued
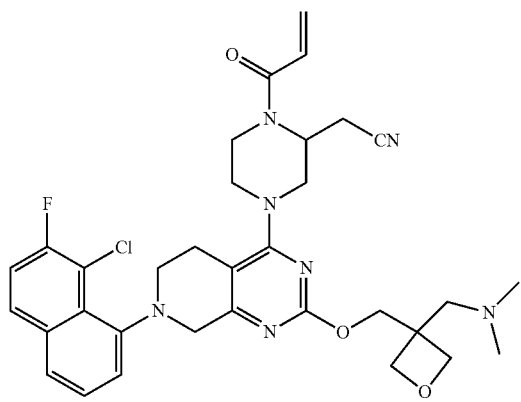
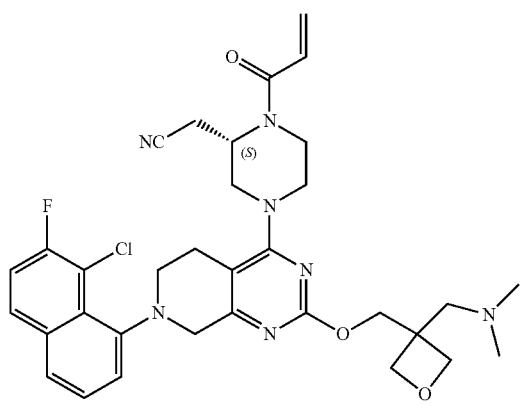
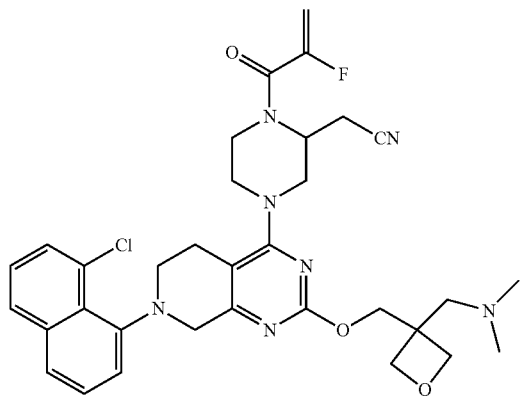
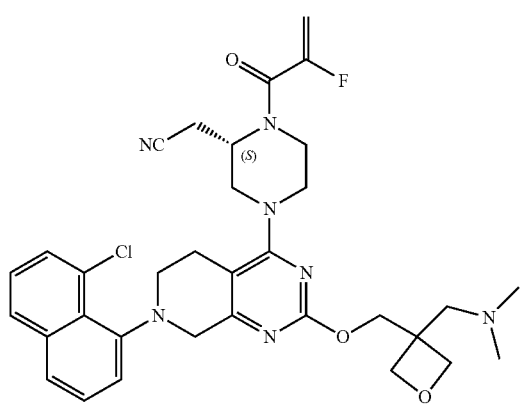
310
-continued
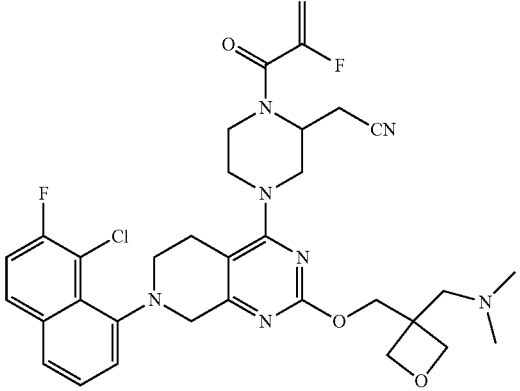
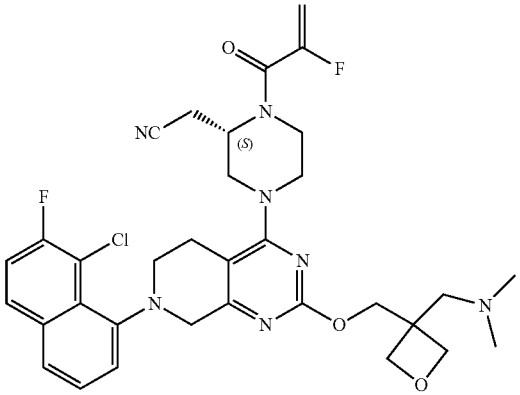
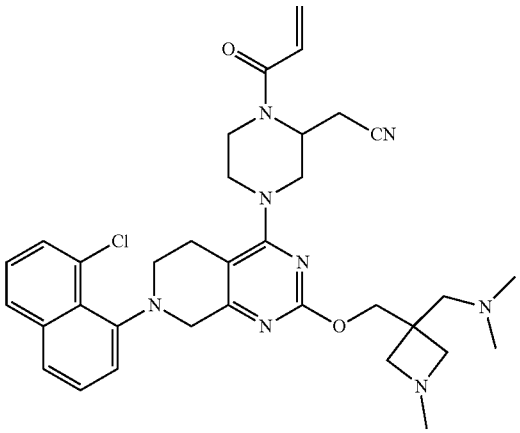
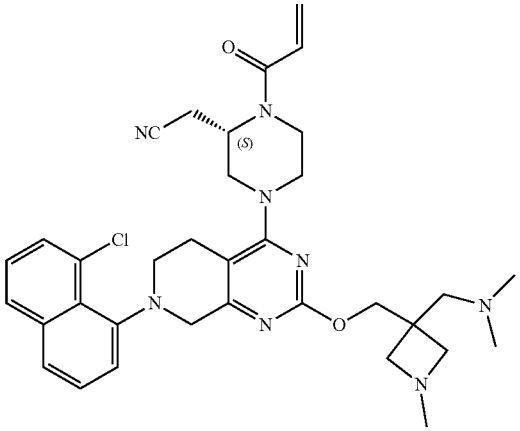

311
-continued

312
-continued

313
-continued
314
-continued
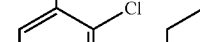

315
-continued
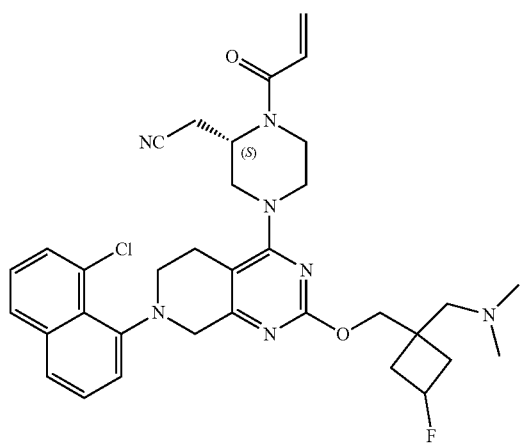
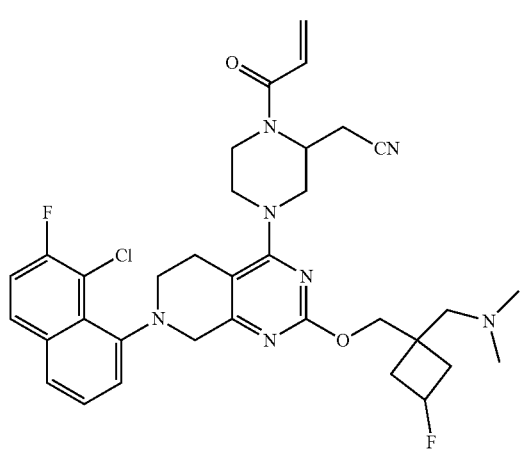
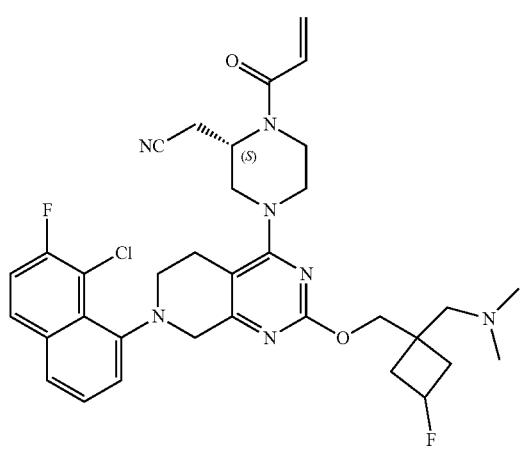
316
-continued
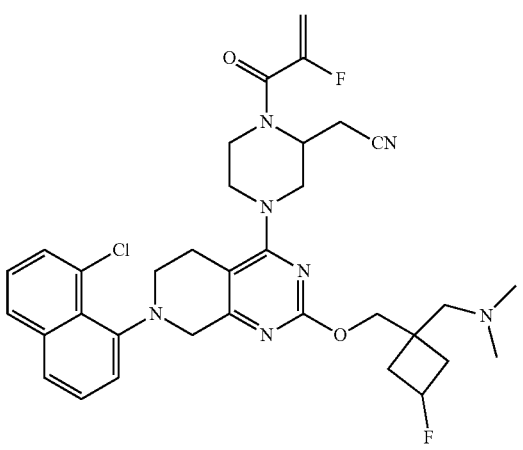
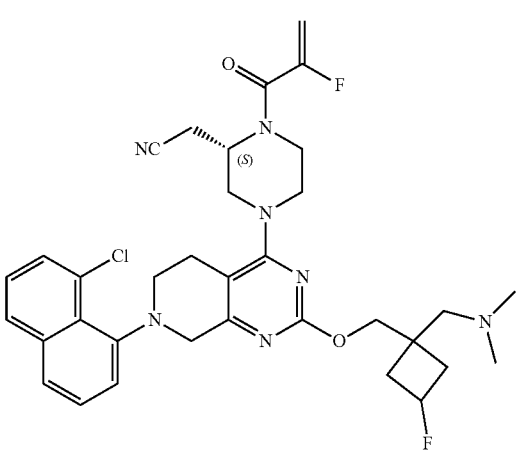
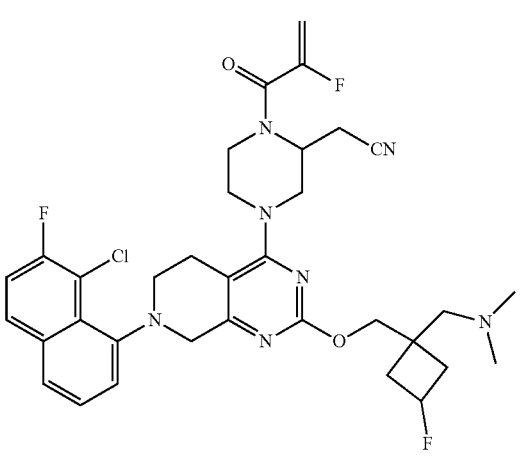

317
-continued
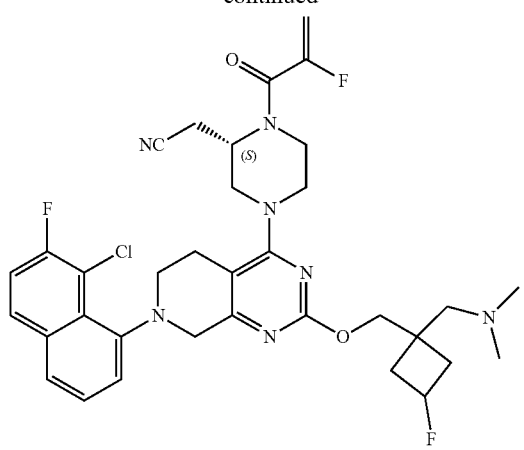
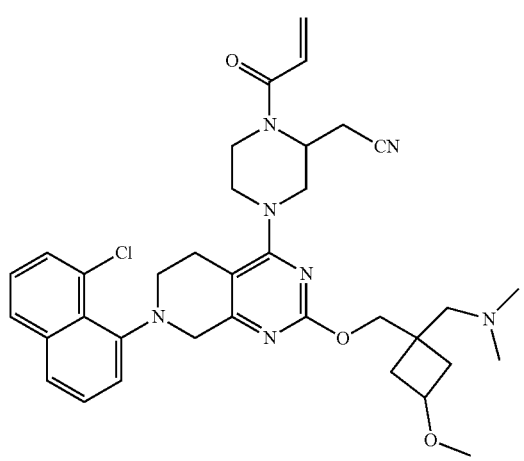
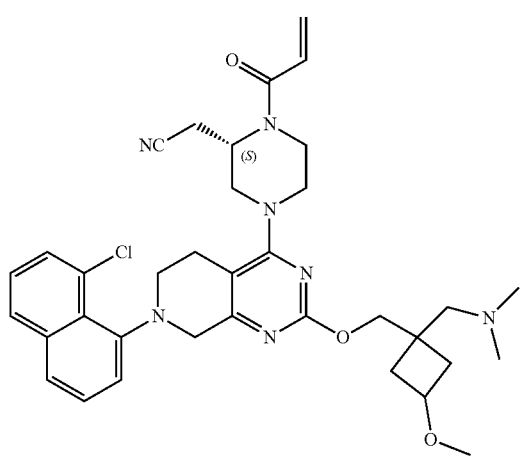
318
-continued
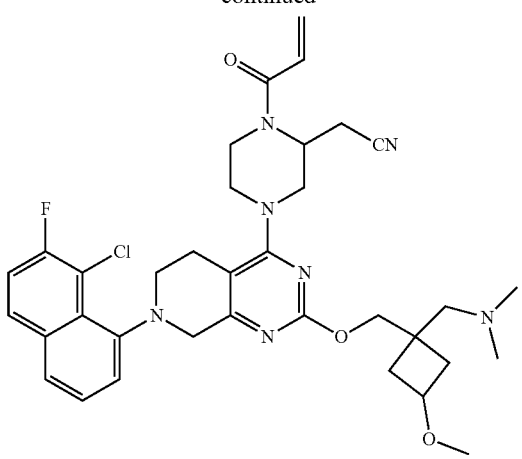
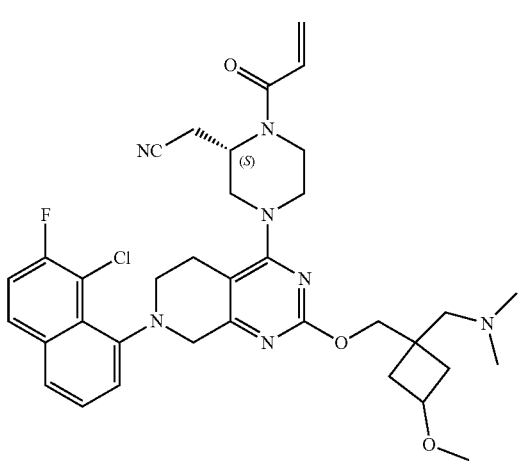
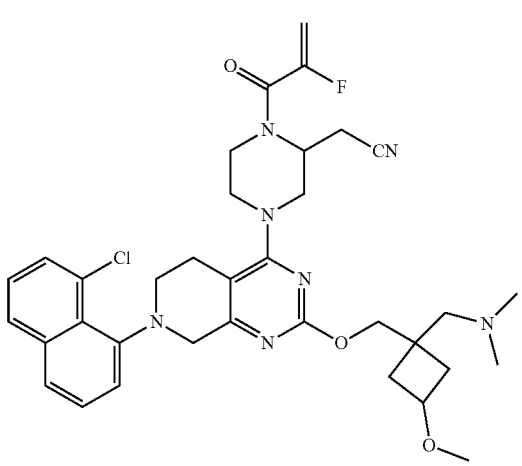

319
-continued
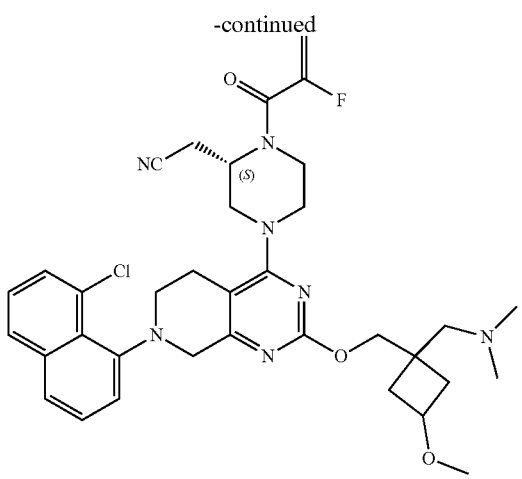
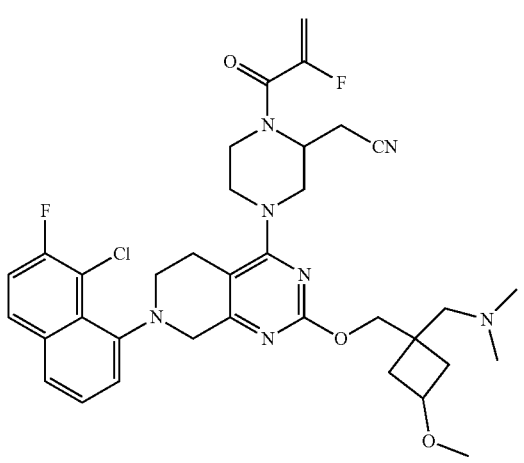
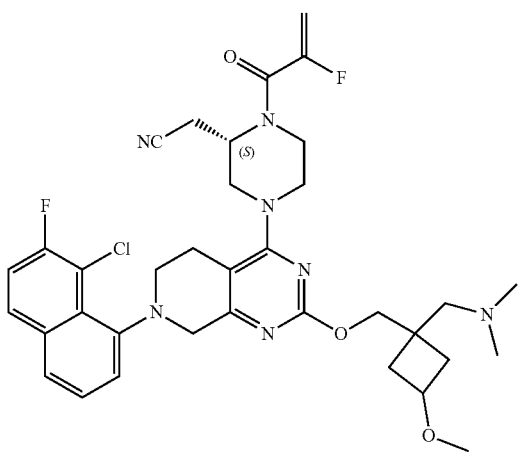
320
-continued
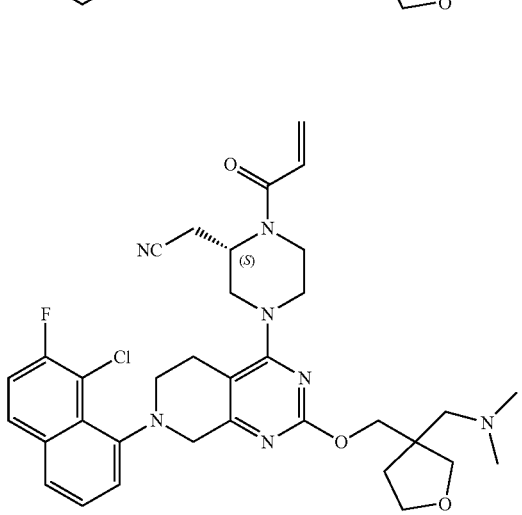

321
-continued
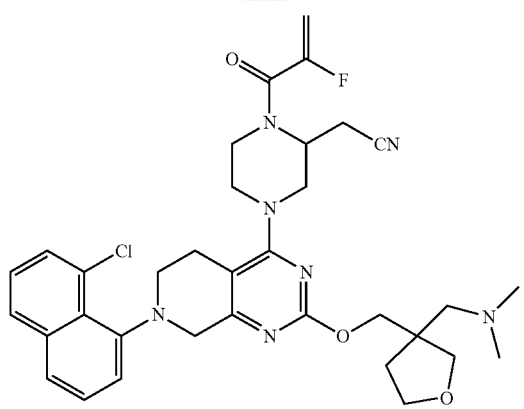
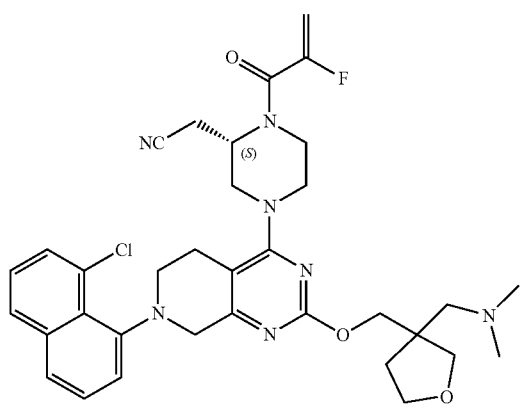
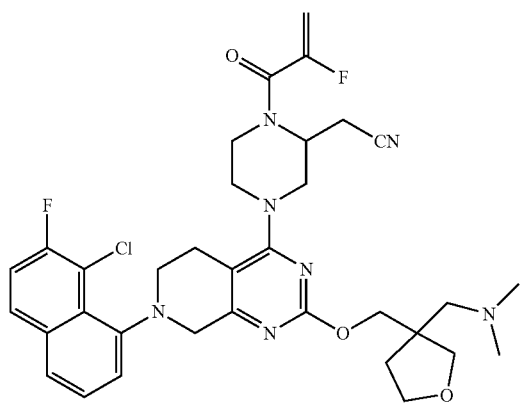
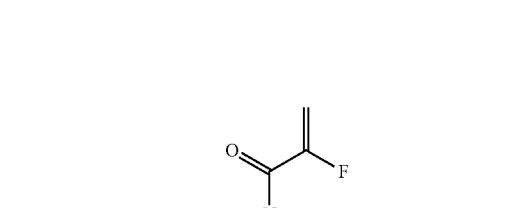
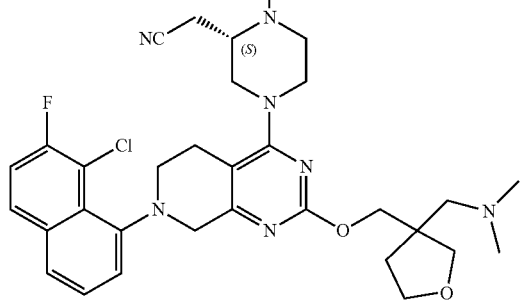
322
-continued
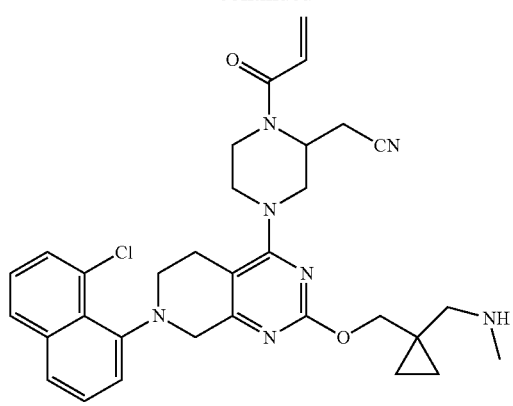
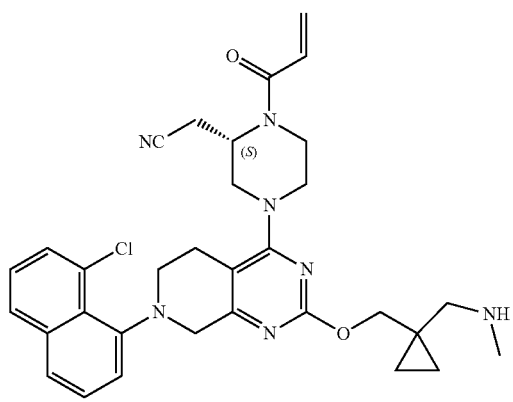
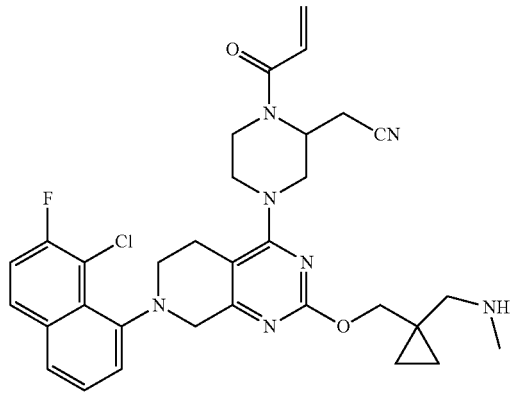
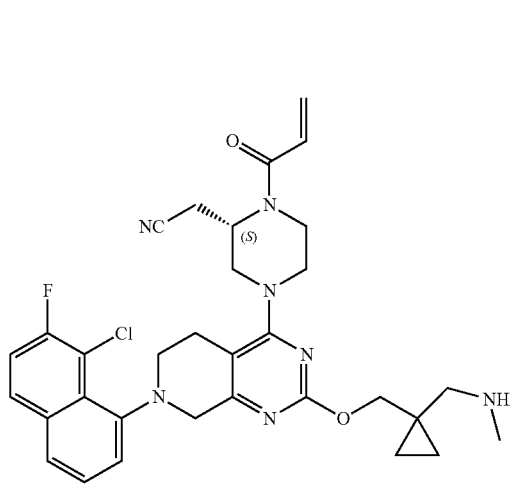

323
-continued
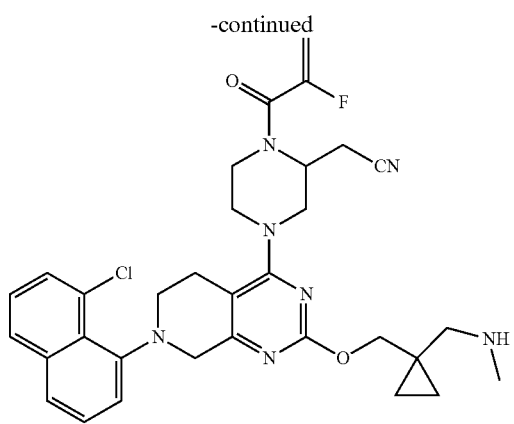
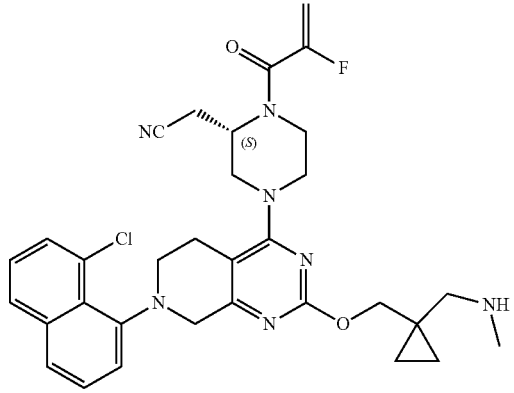
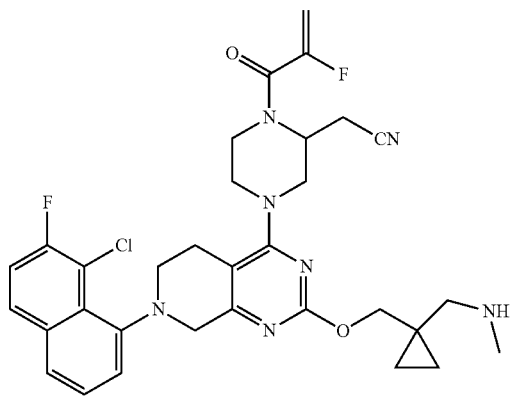
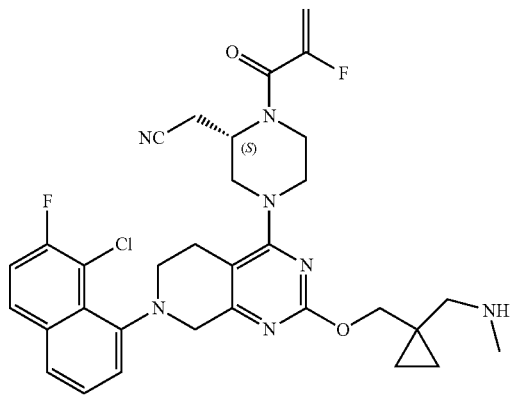
324
-continued
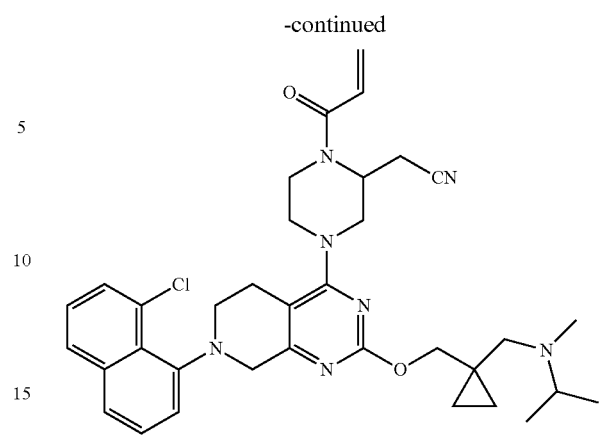
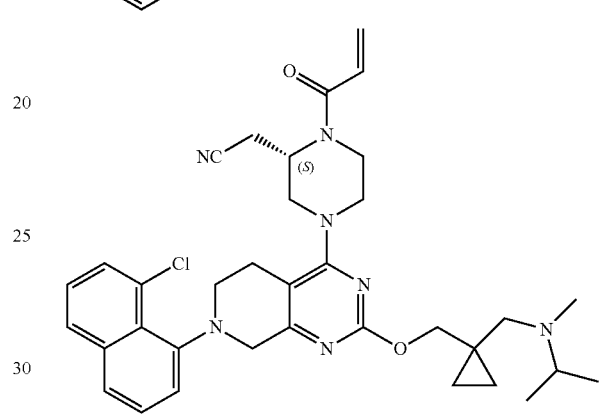
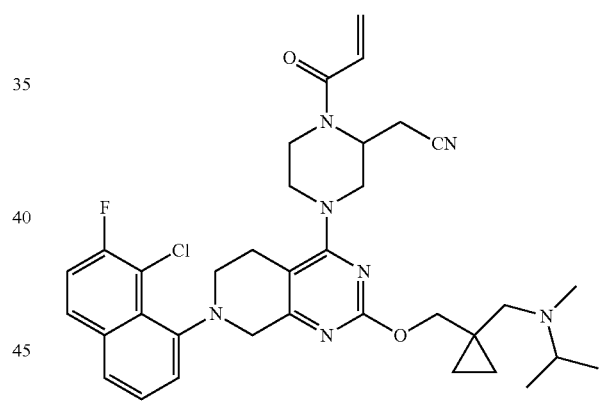
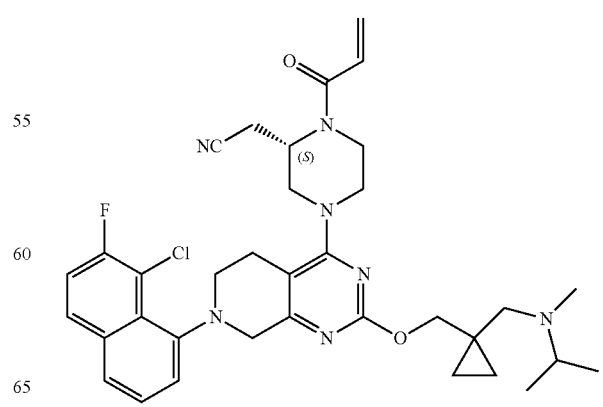

325
-continued
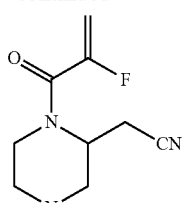
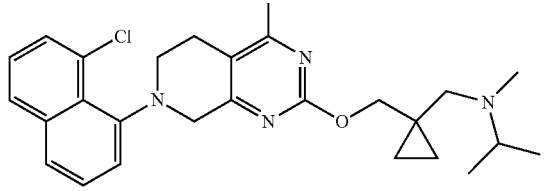
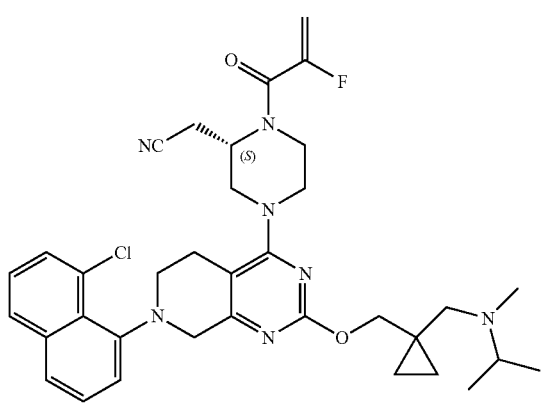
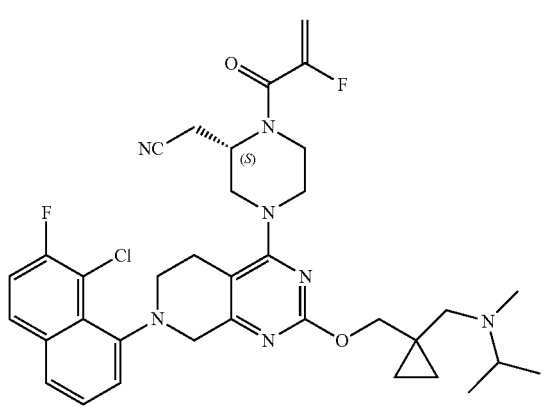
326
-continued
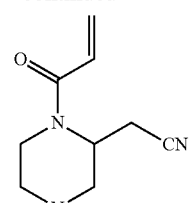
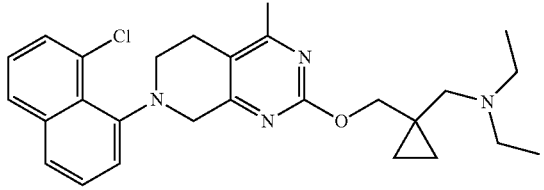
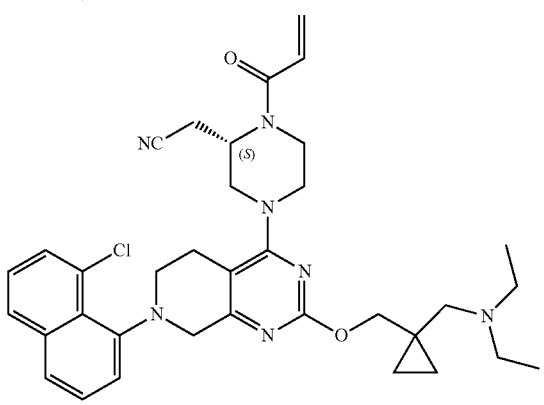
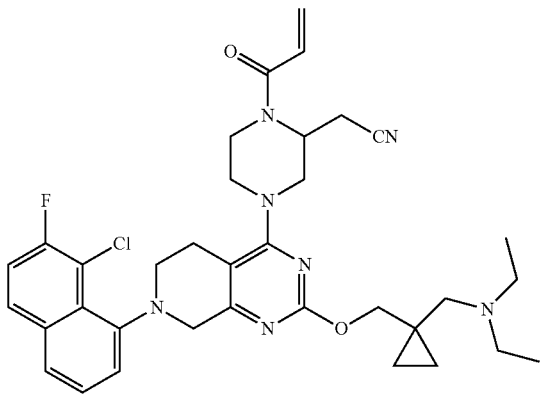
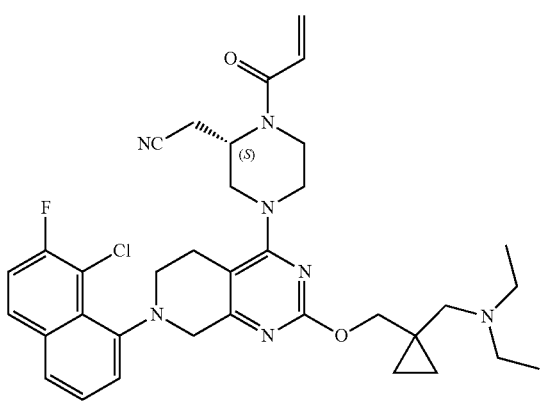
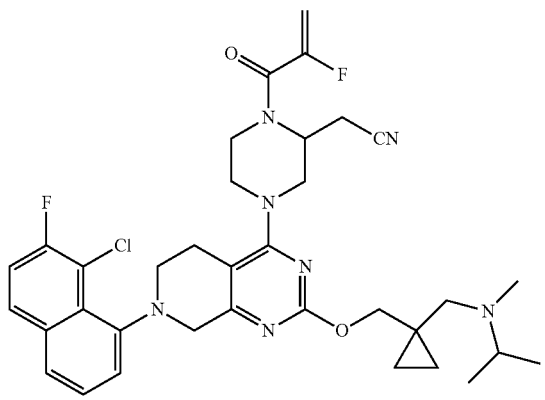

327
-continued
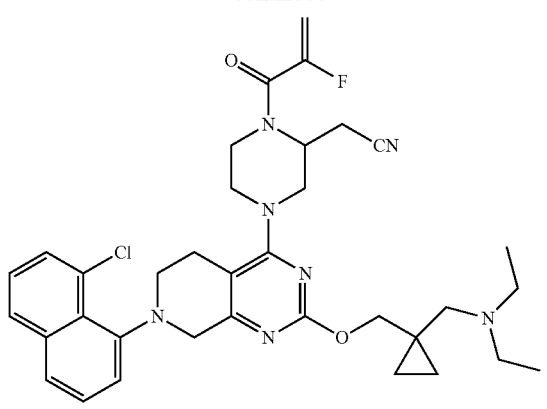
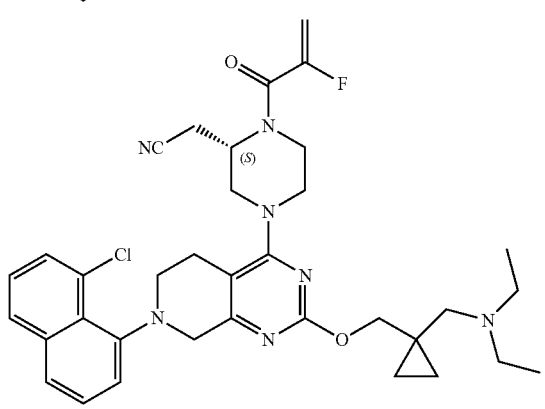
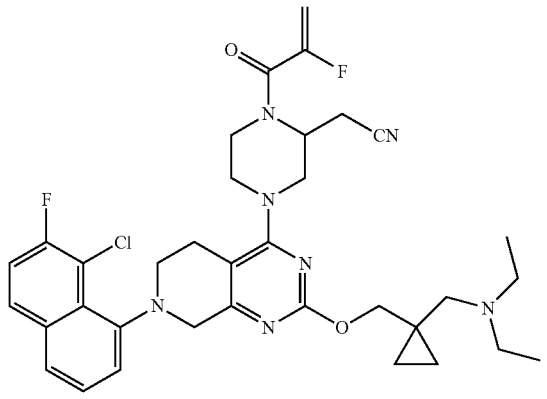
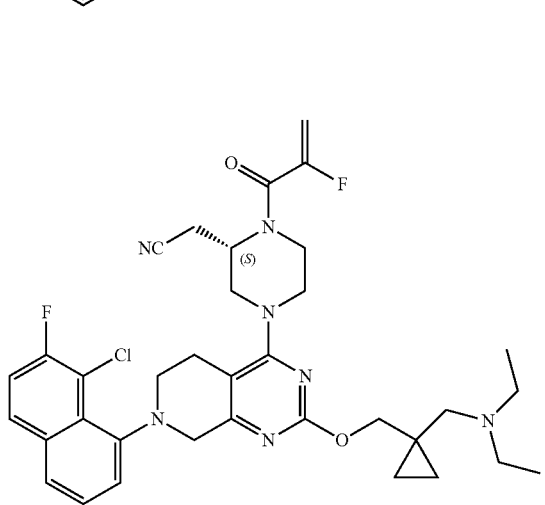
328
-continued
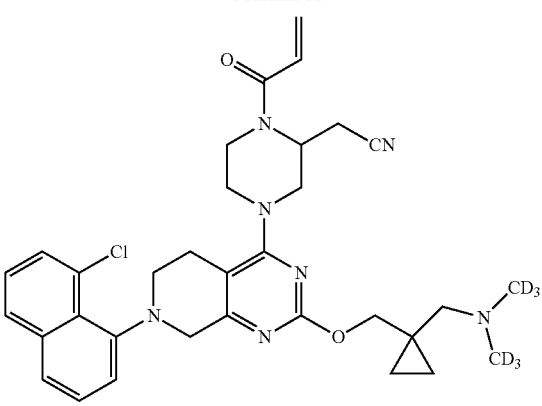
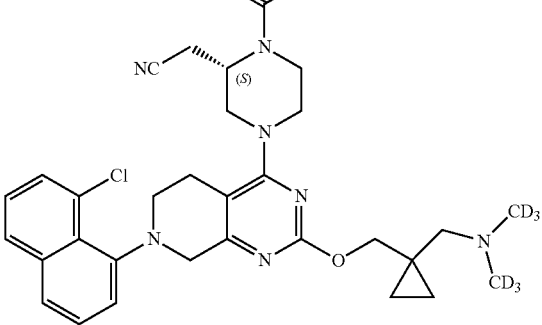
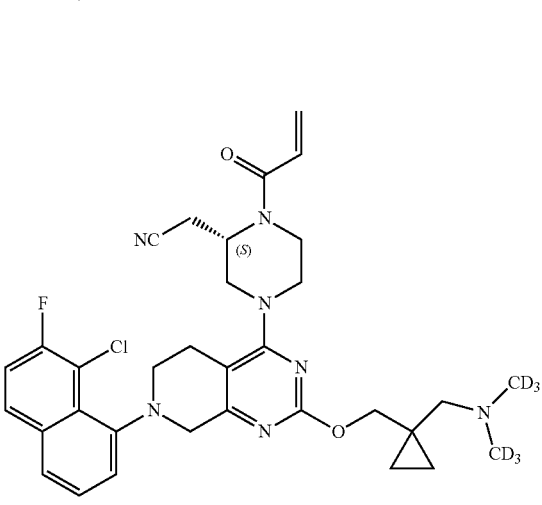

329
-continued
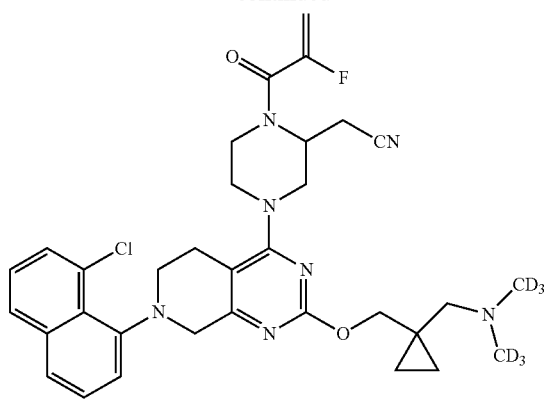
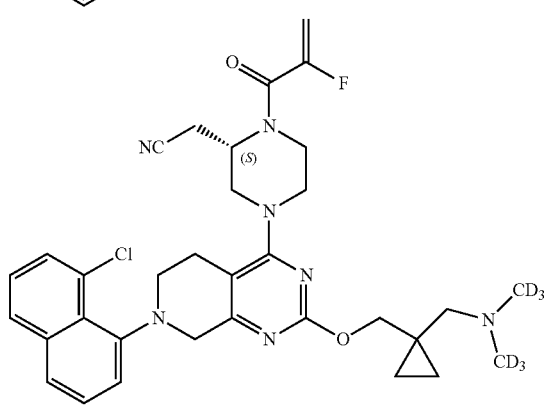
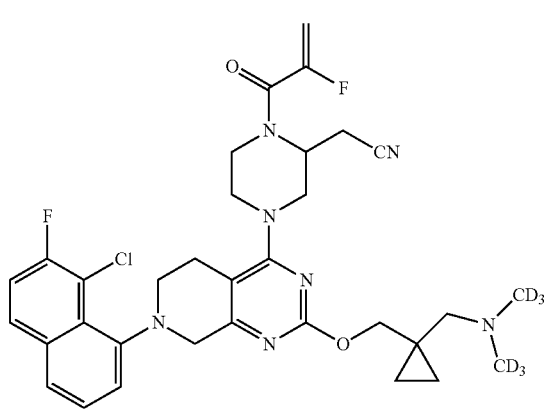
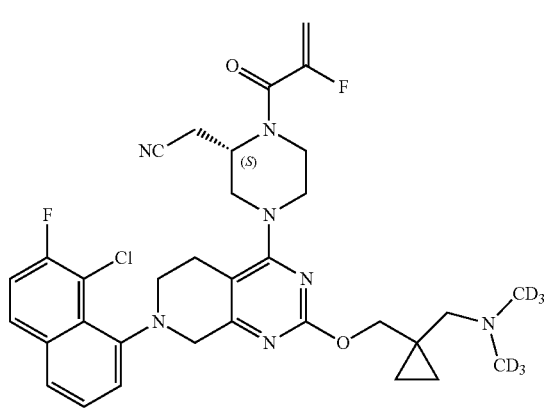
330
-continued
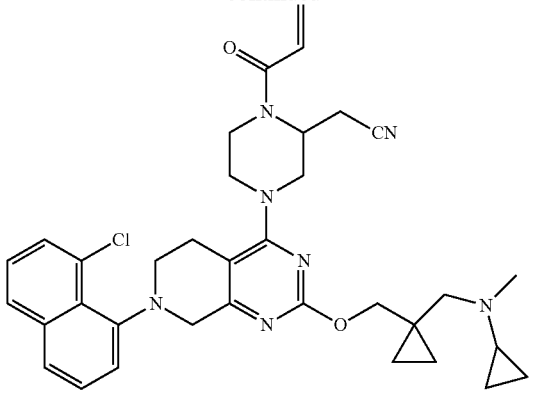
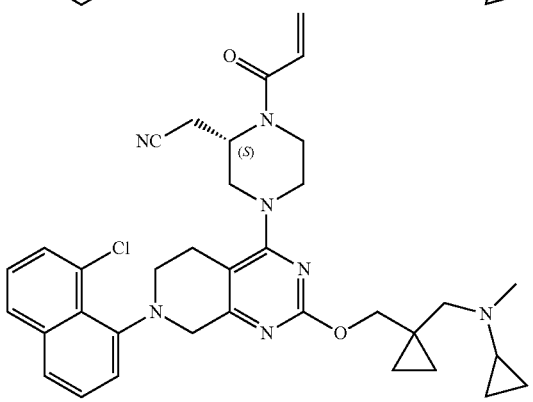
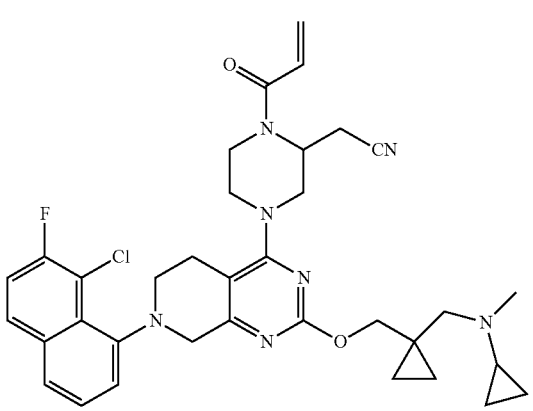
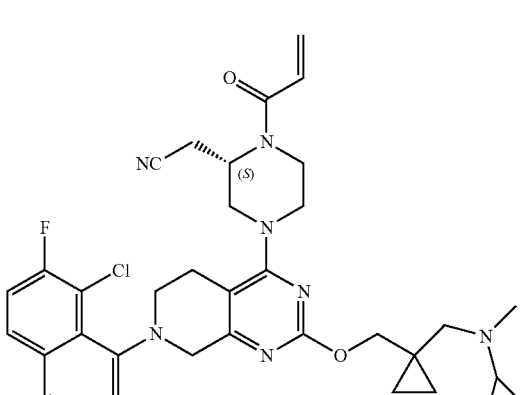

331
-continued
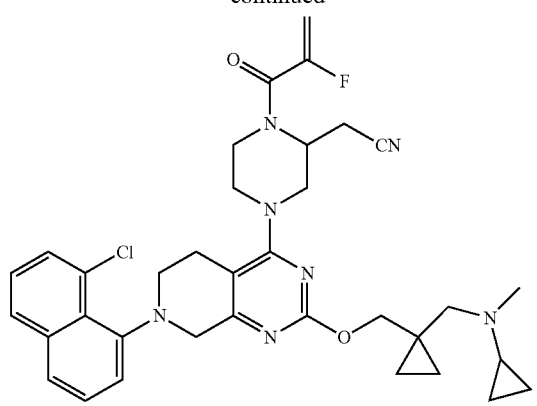
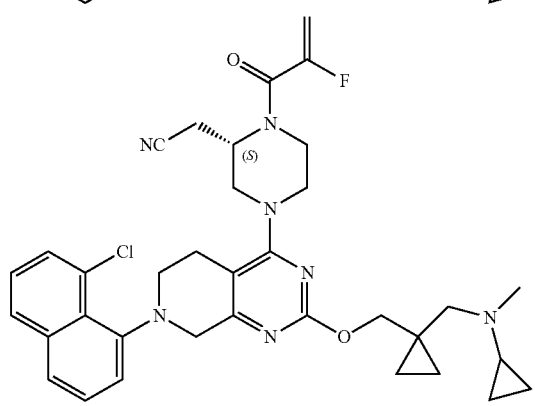
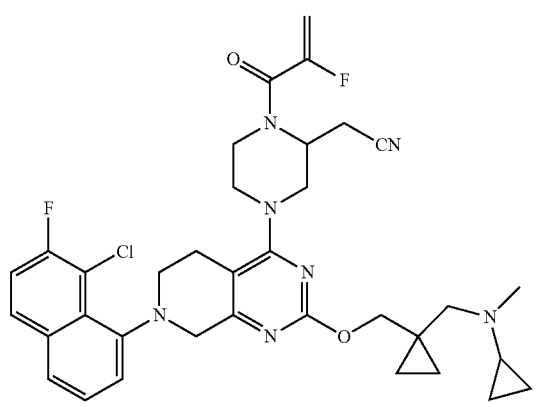
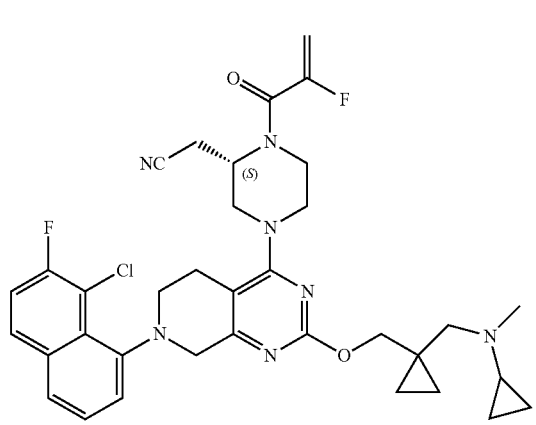
332
-continued
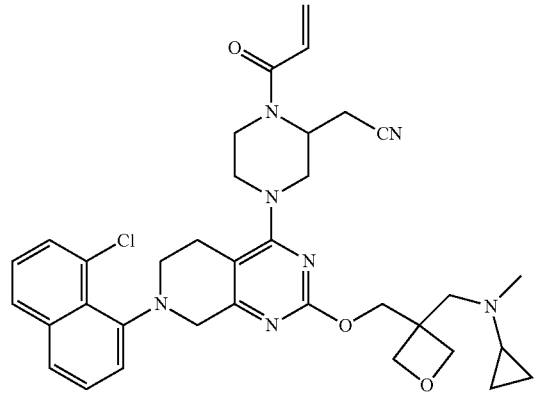
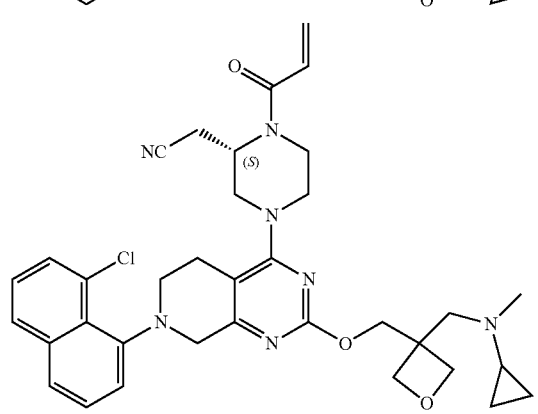
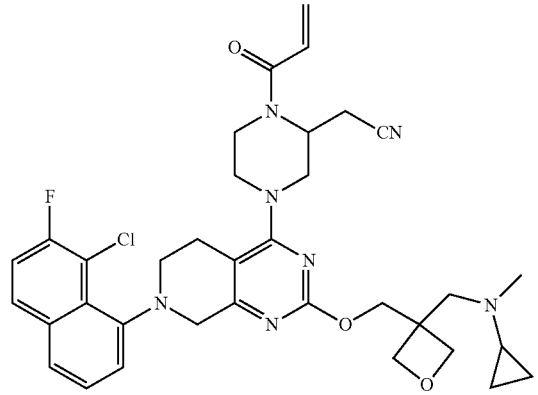
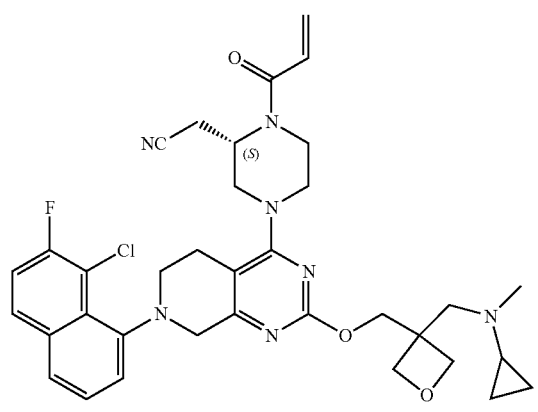

333
-continued
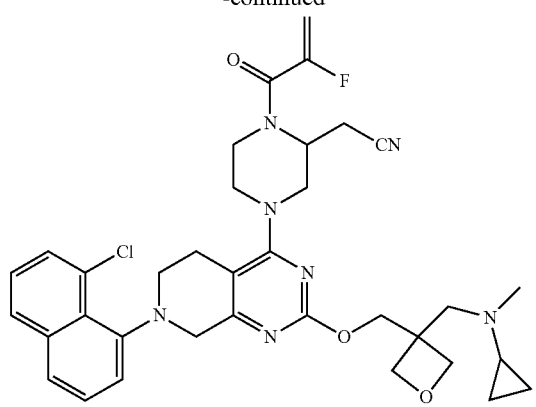
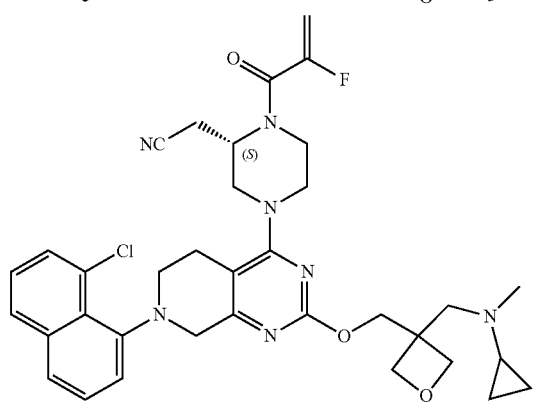
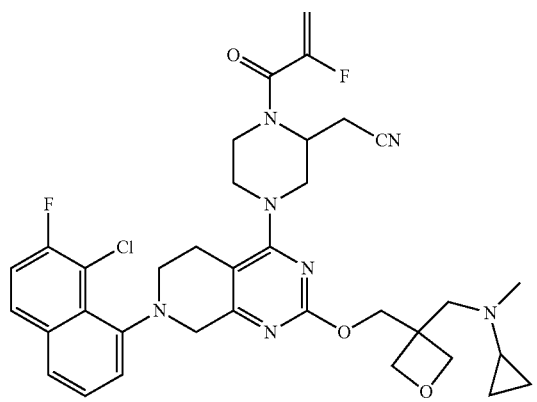
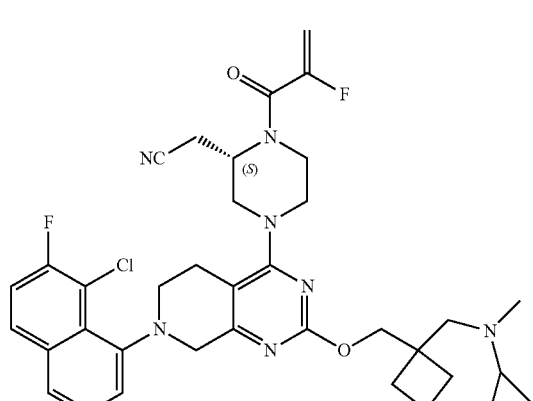
334
-continued
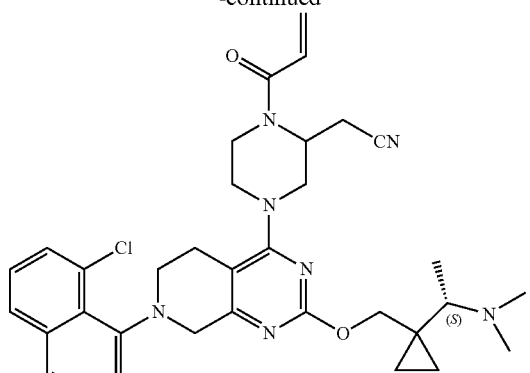
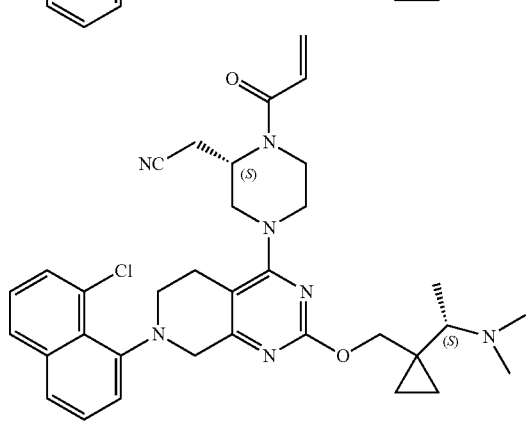
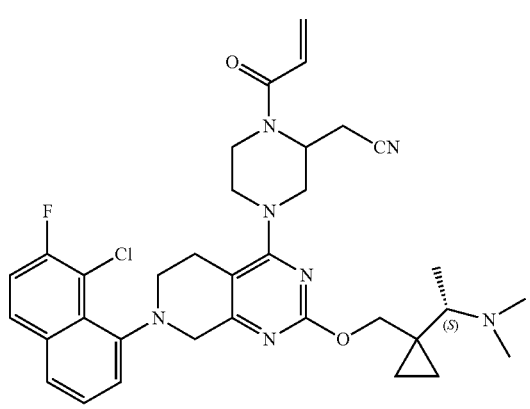
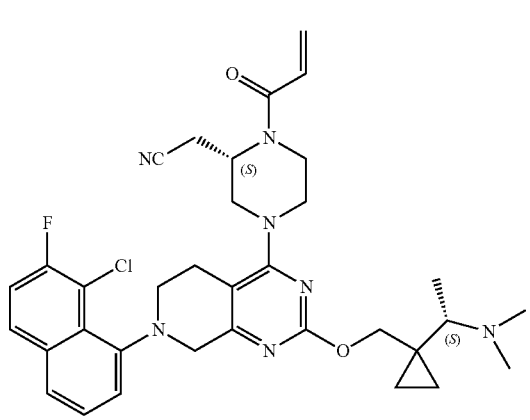

335
-continued
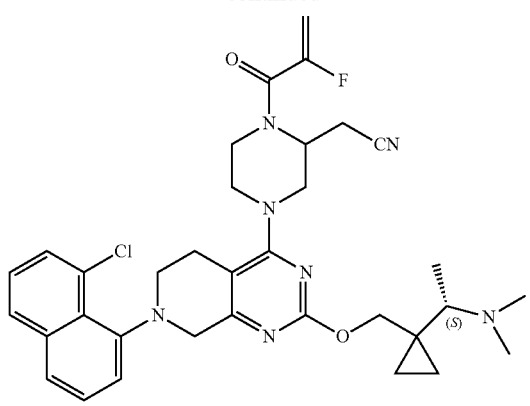
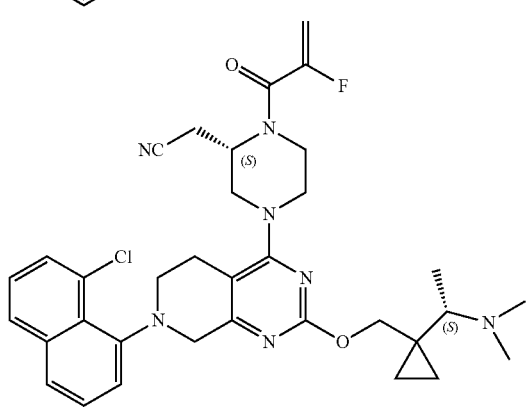
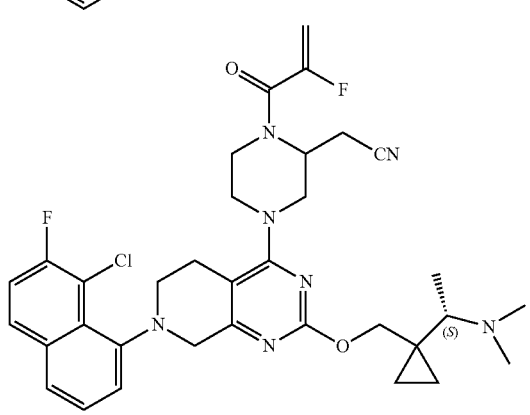
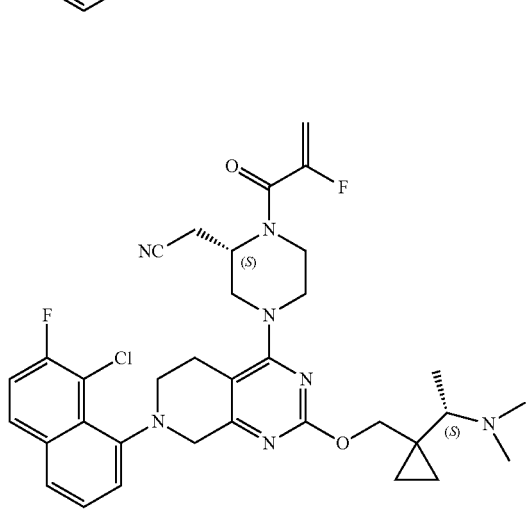
336
-continued
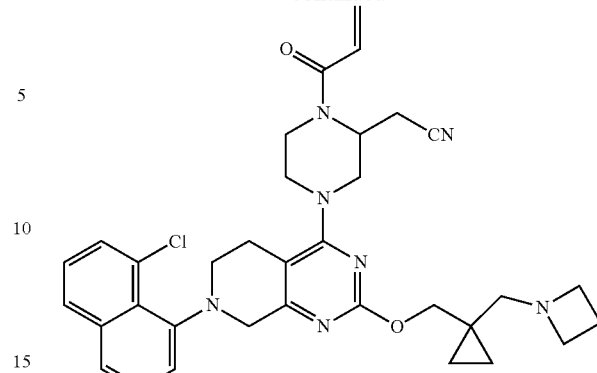
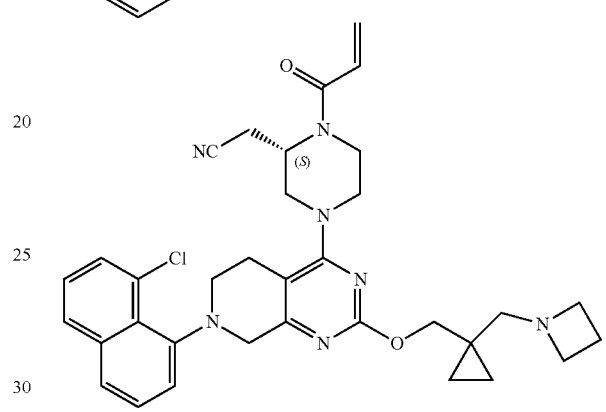
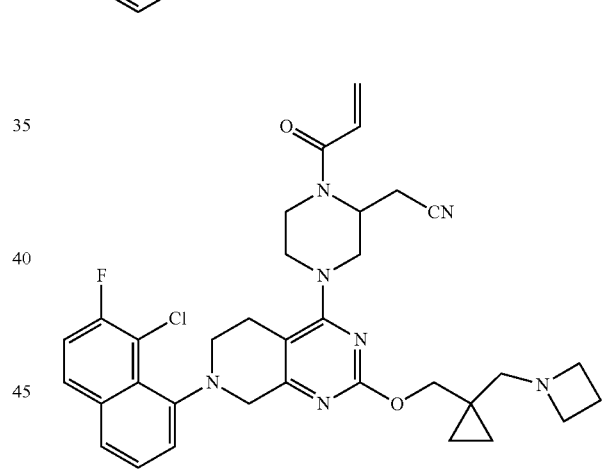
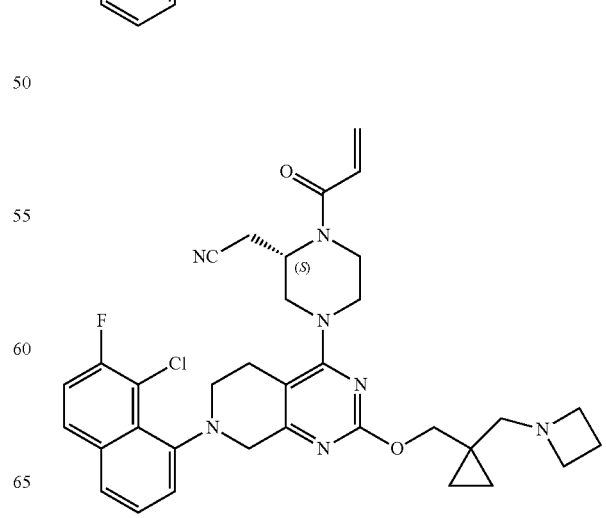

337
-continued
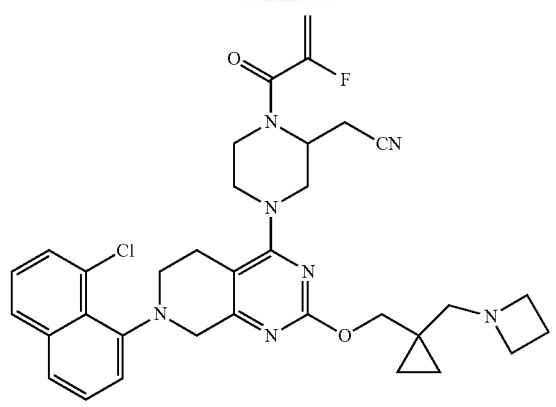
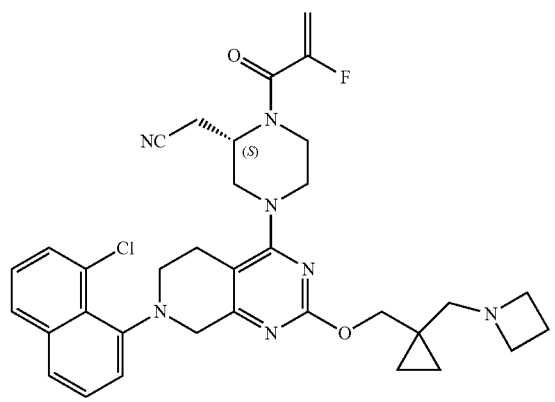
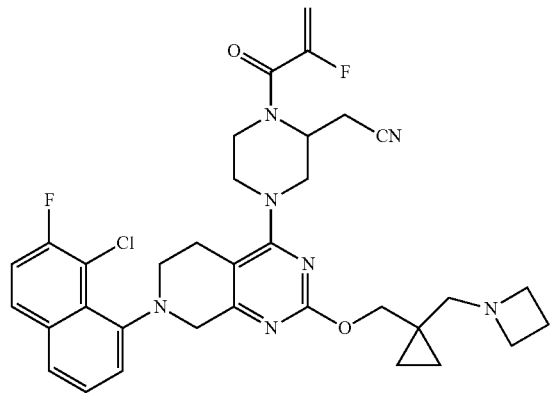
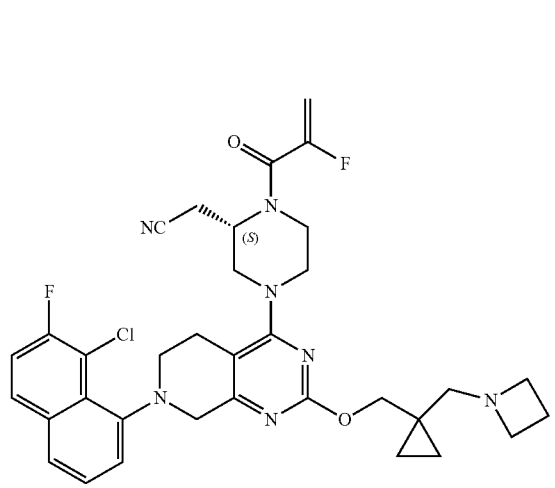
338
-continued
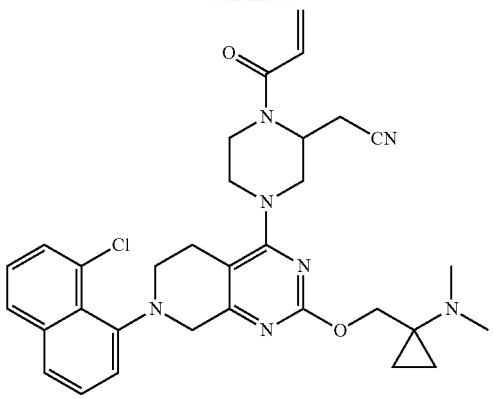
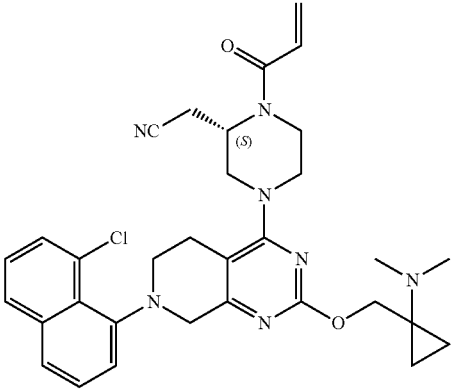
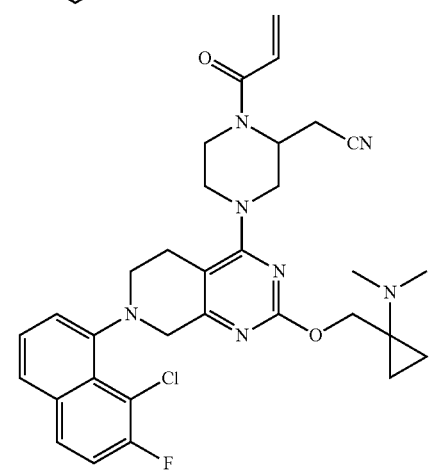
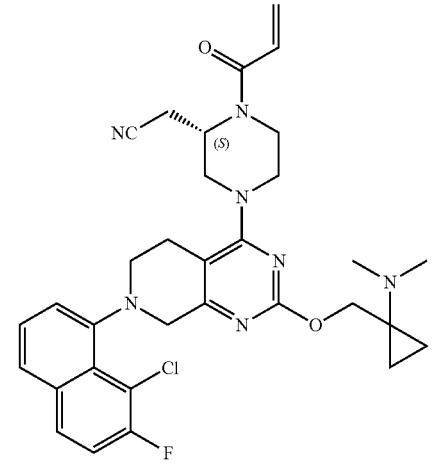

339
-continued
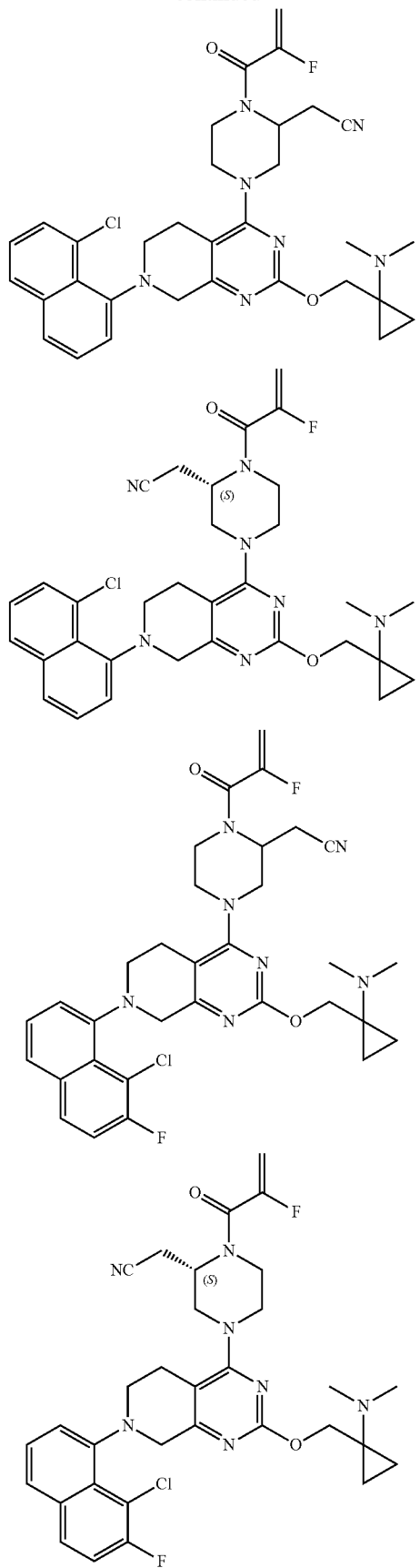
340
-continued
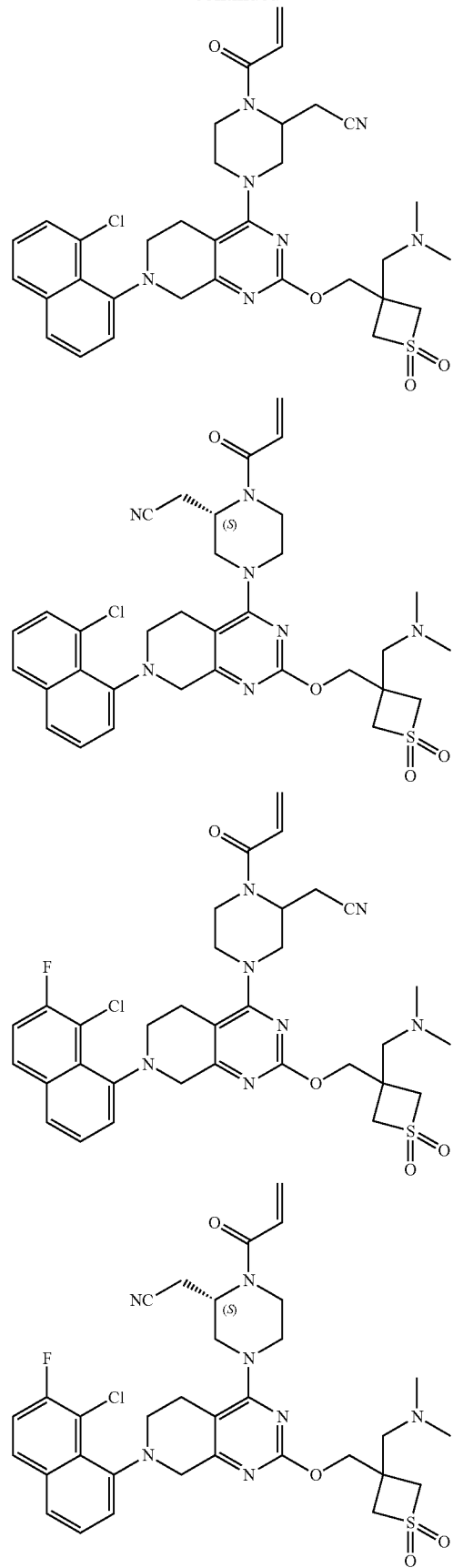

| 341 -continued | 342 -continued |
|---|---|
| 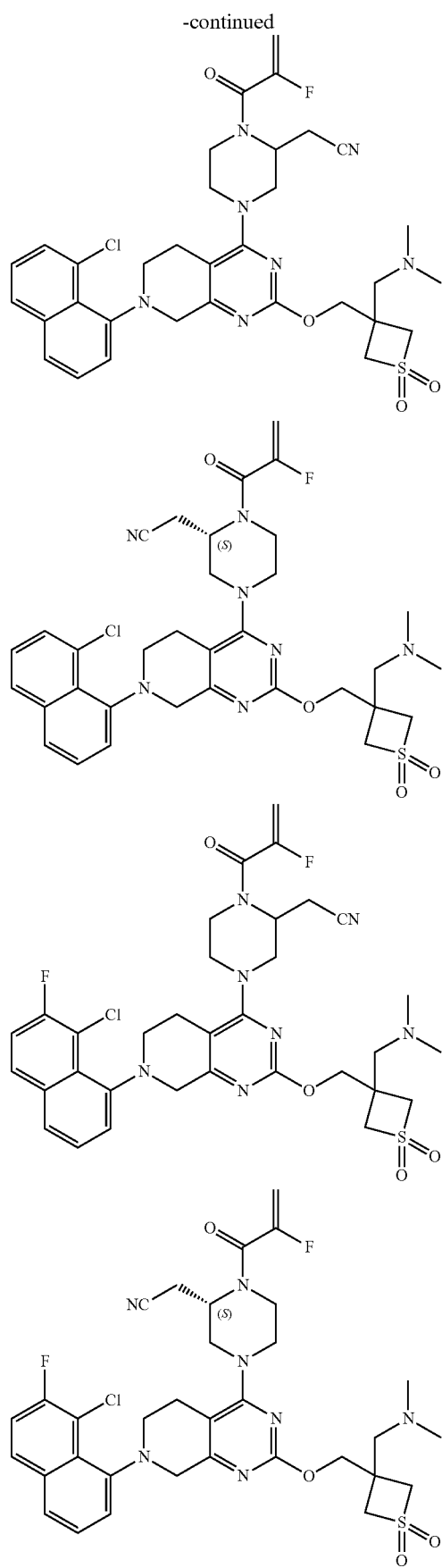 | 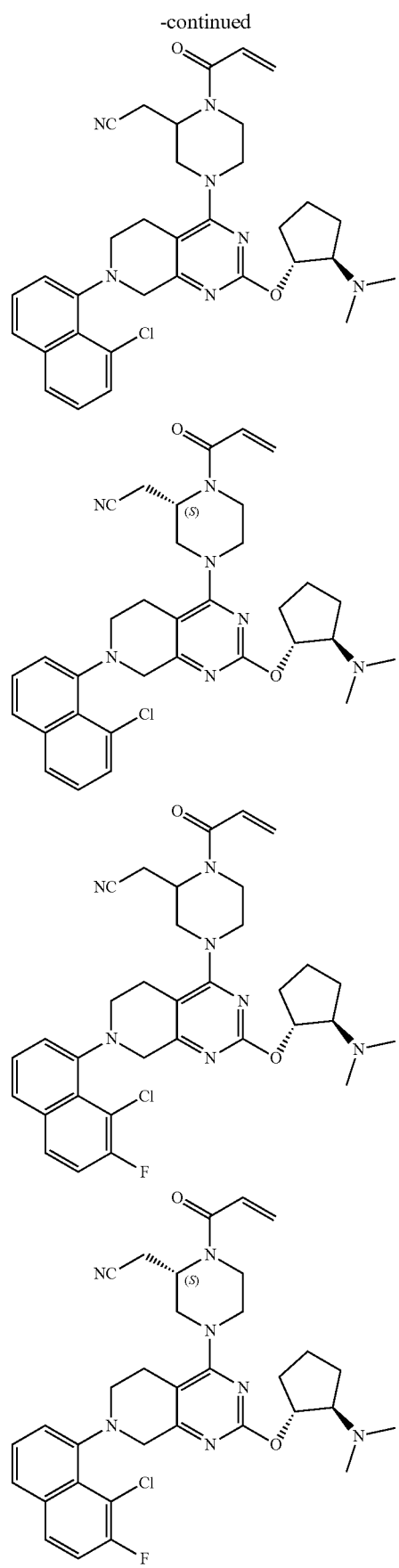 |

343
-continued
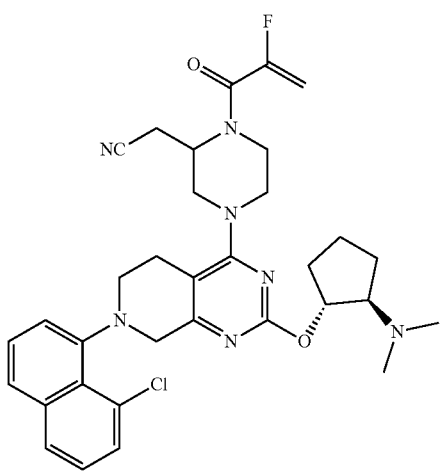
344
-continued
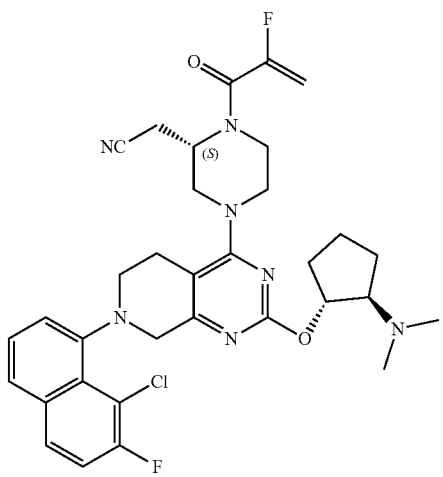
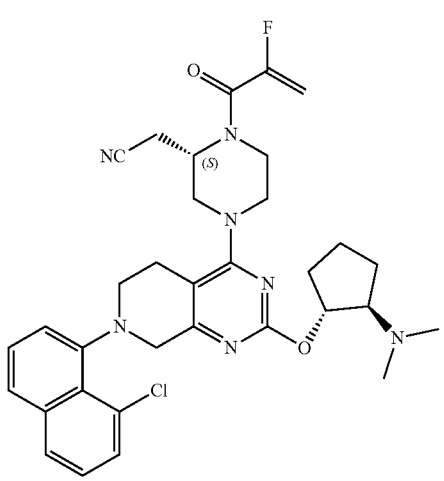
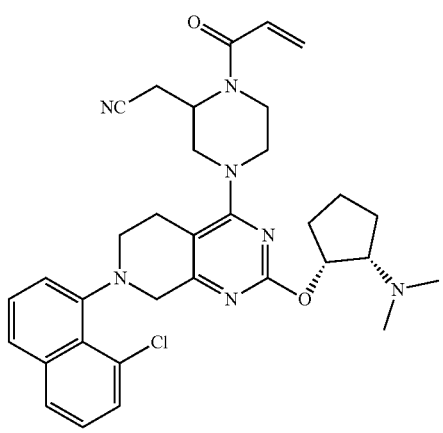
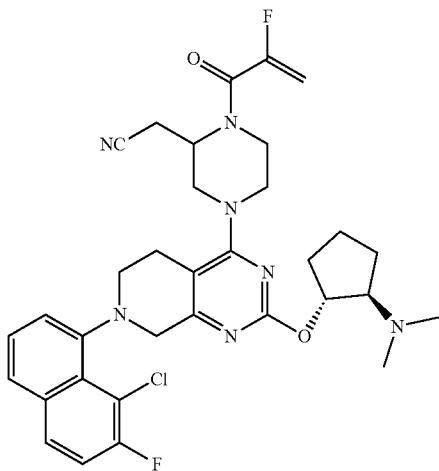
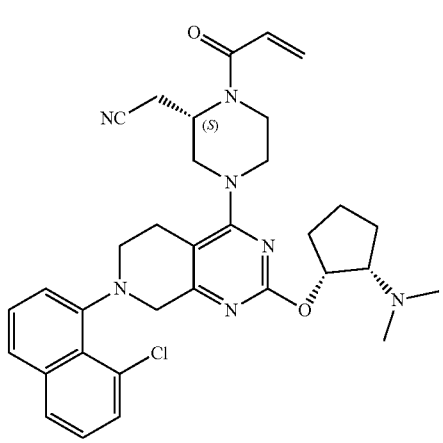

345
-continued
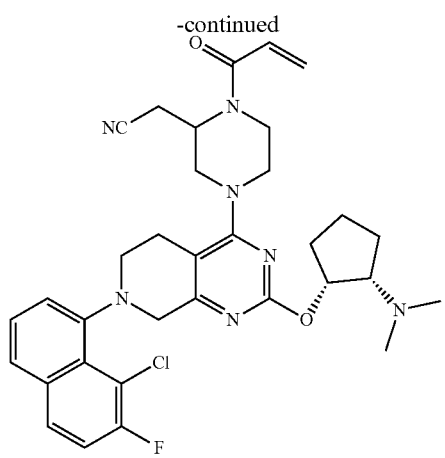
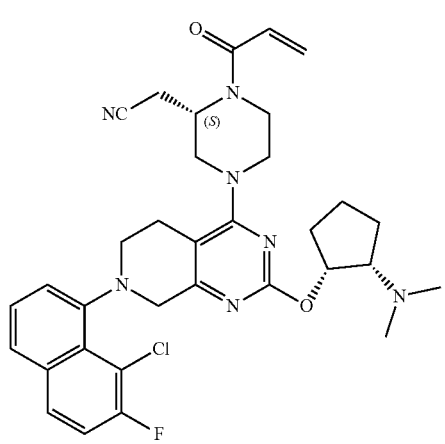
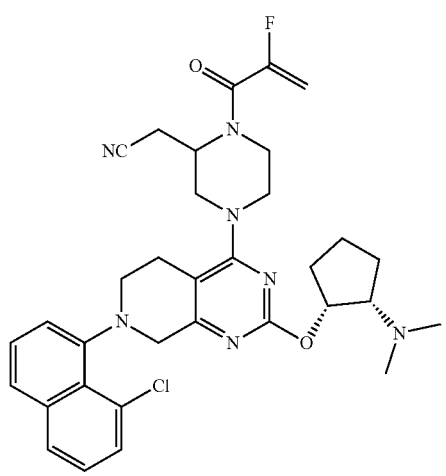
346
-continued
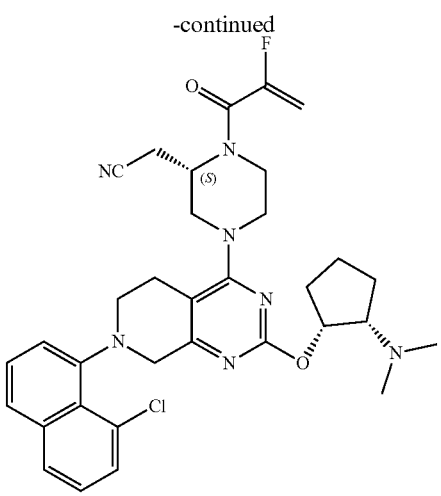
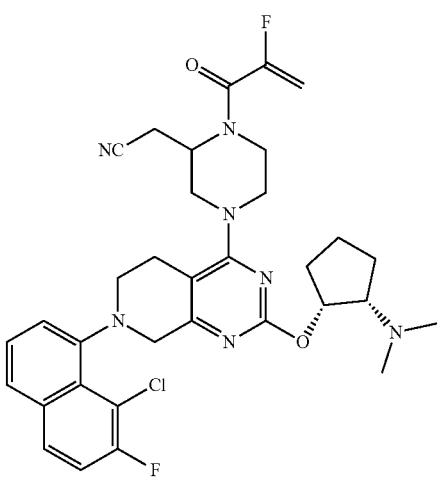
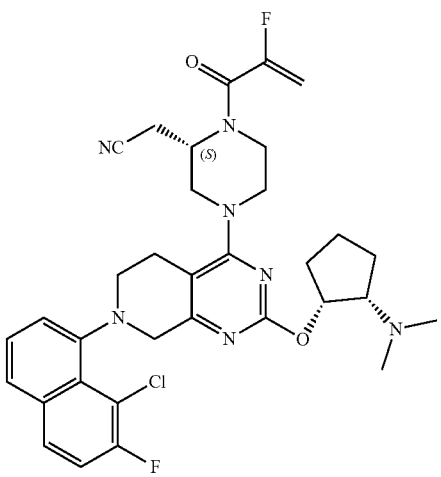

347
-continued
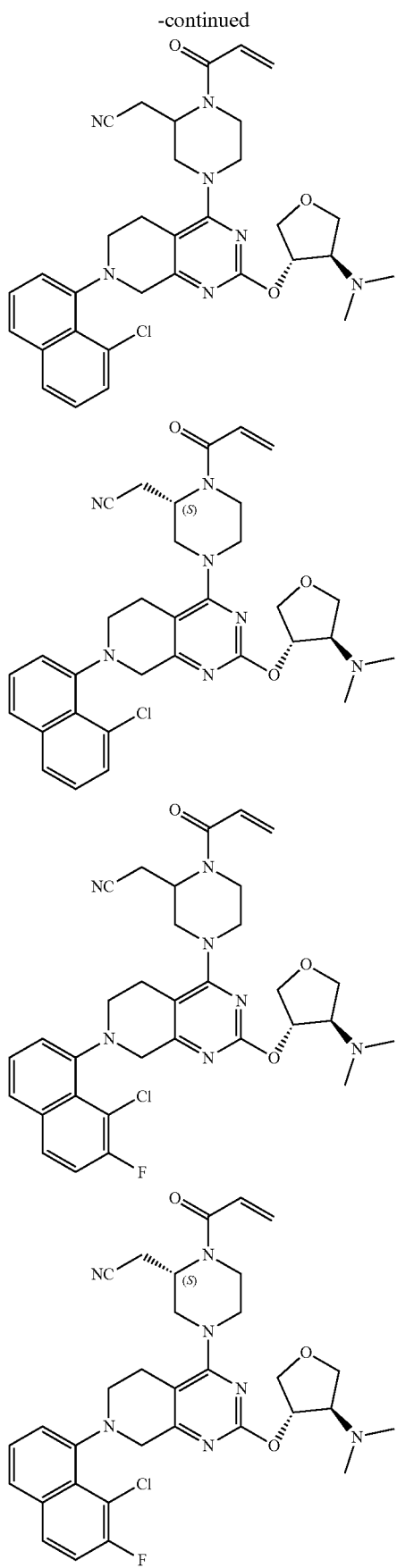
348
-continued
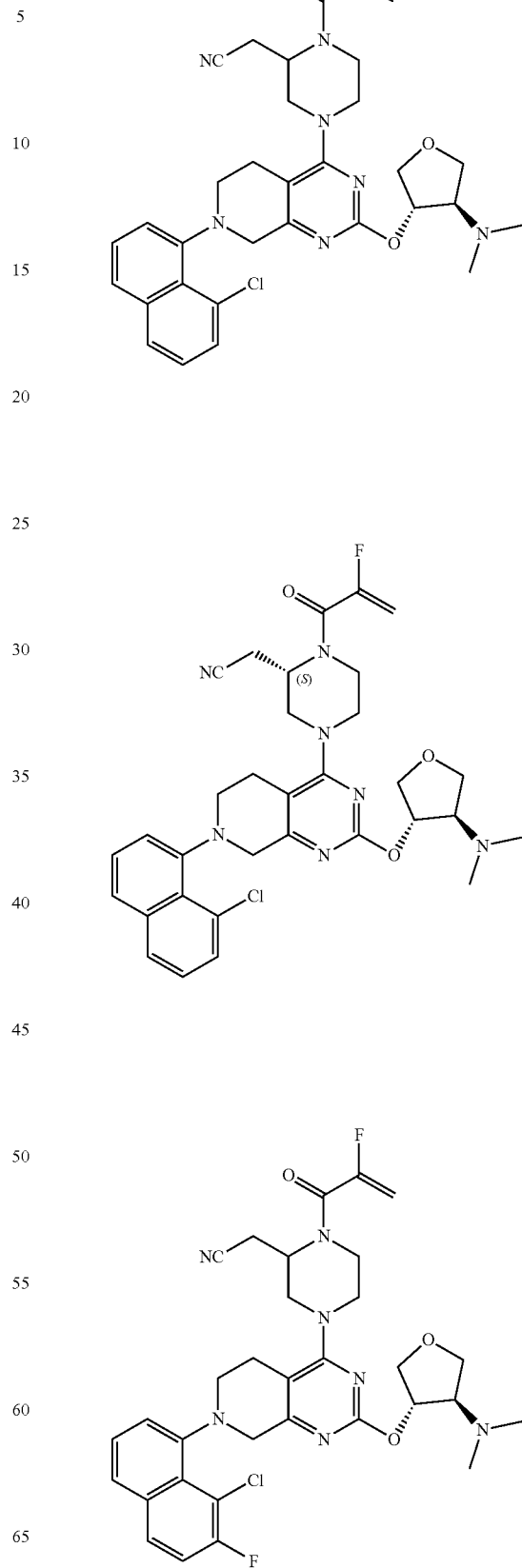

349
-continued
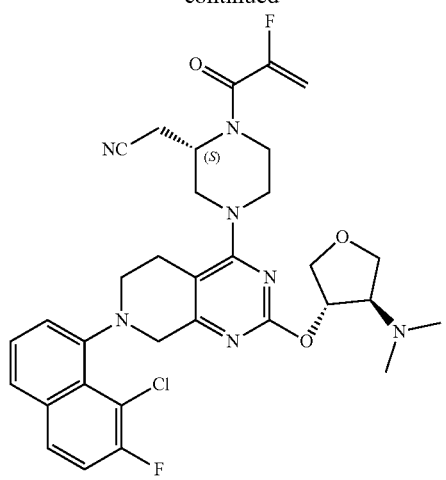
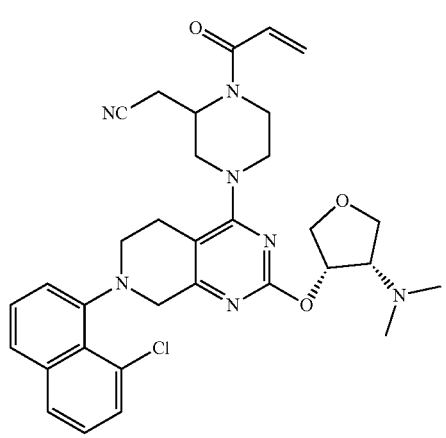
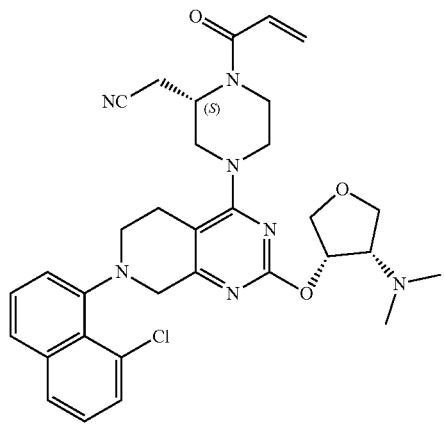
350
-continued
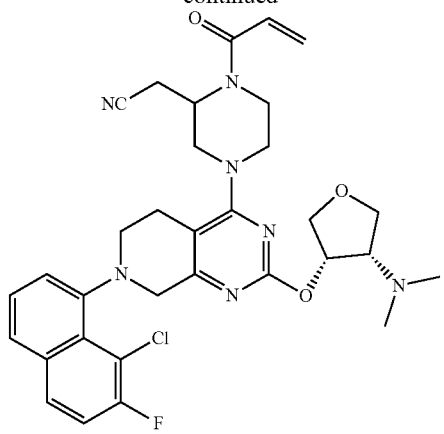
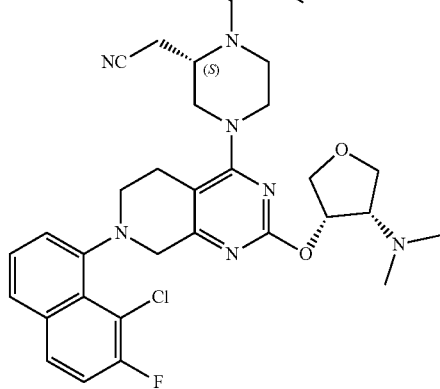
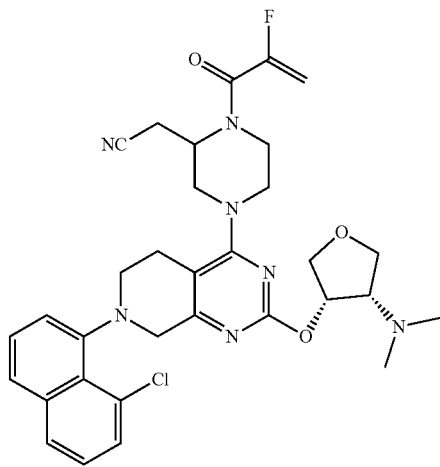

351
-continued
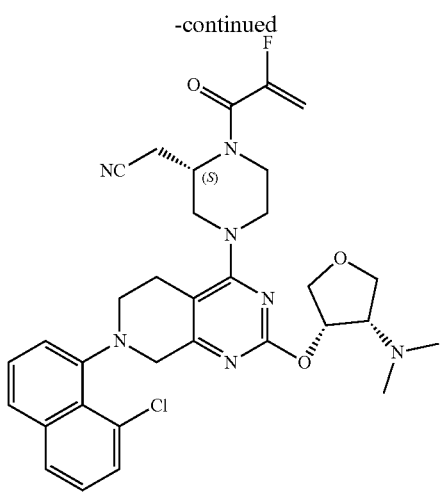
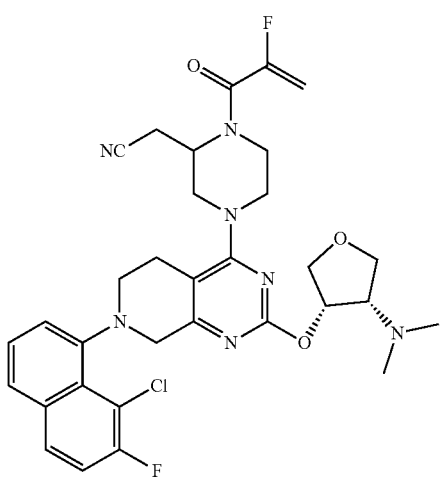
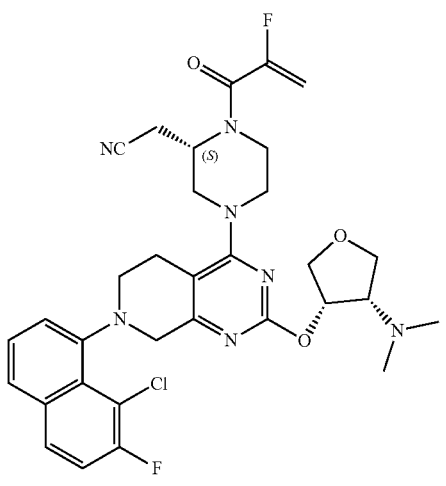
352
-continued
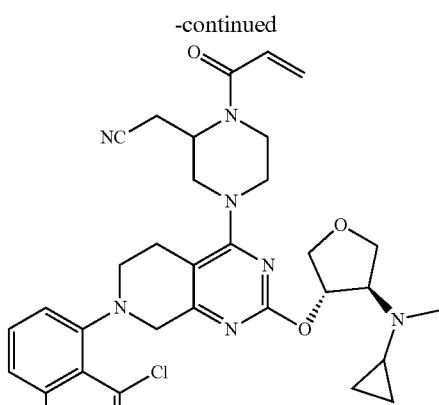
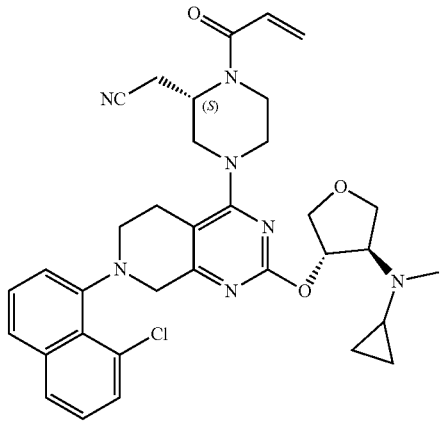
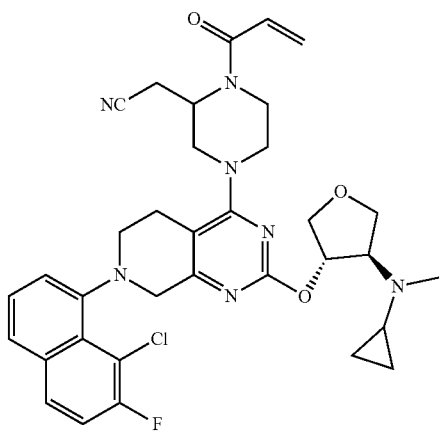
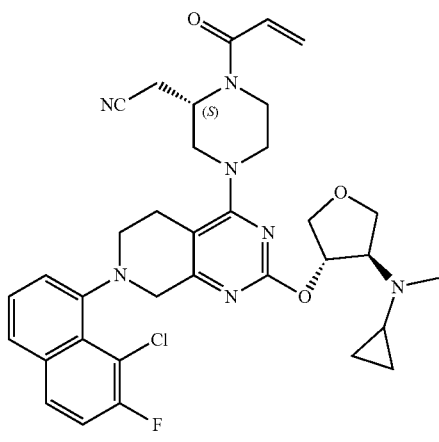

353
-continued
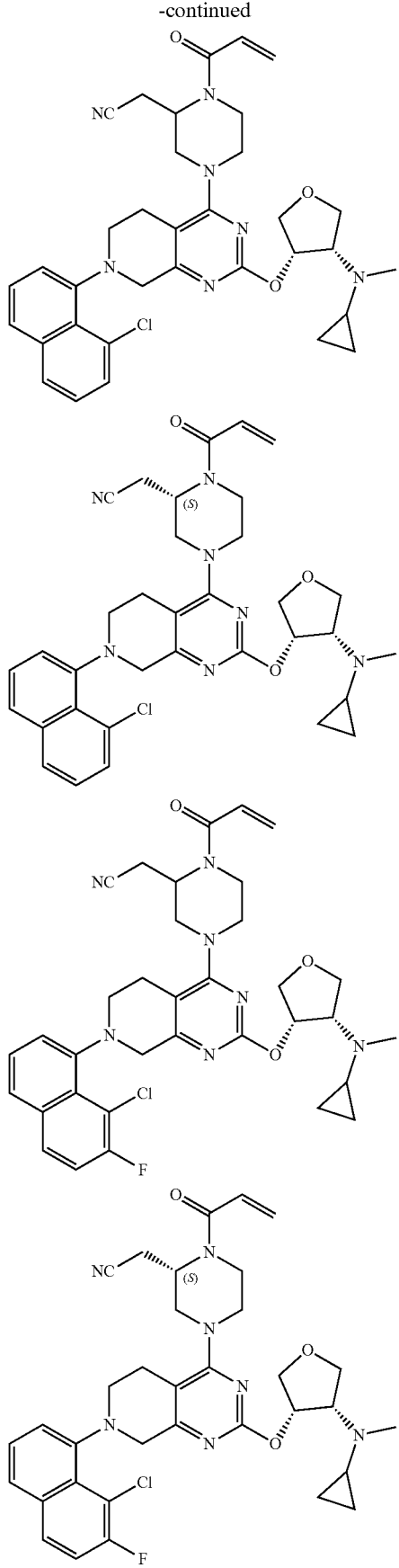
354
-continued
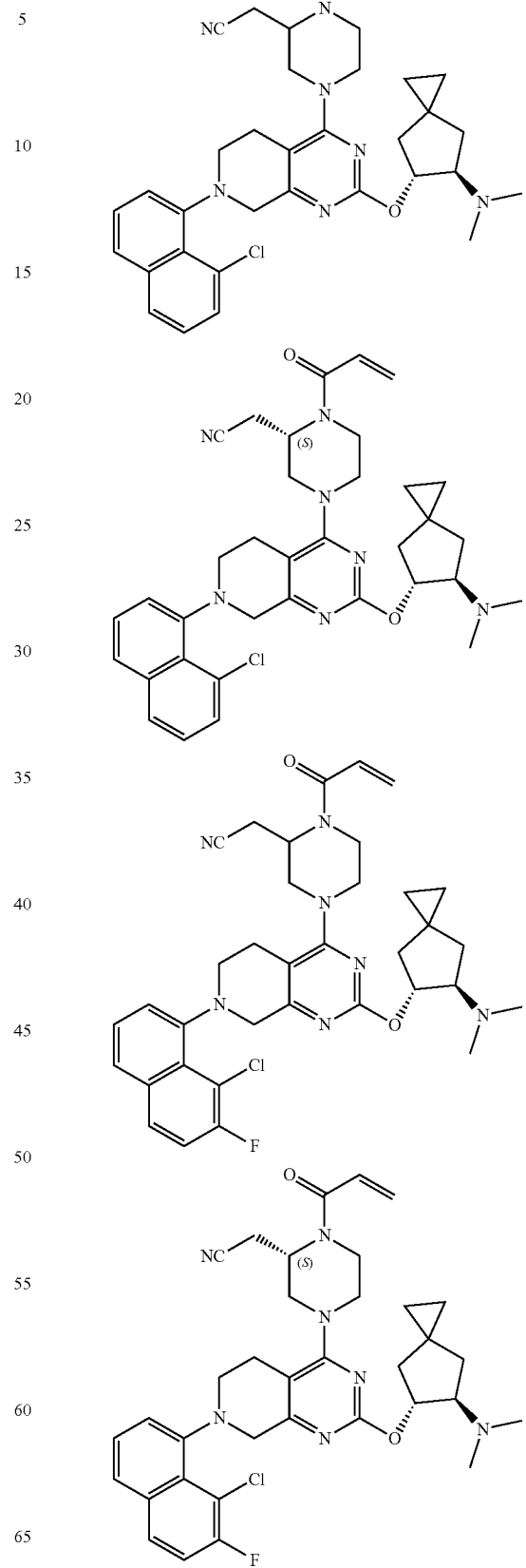

355
-continued
356
-continued
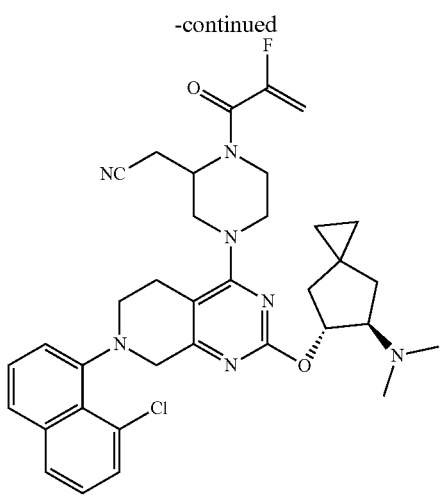
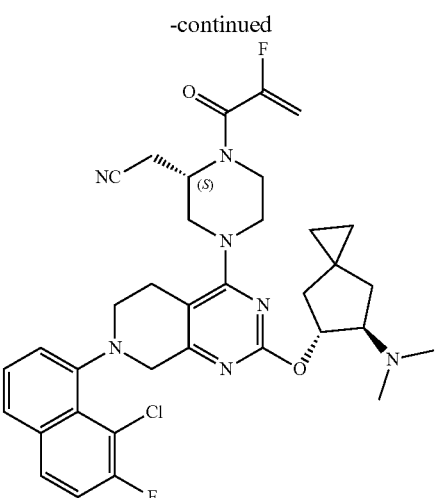
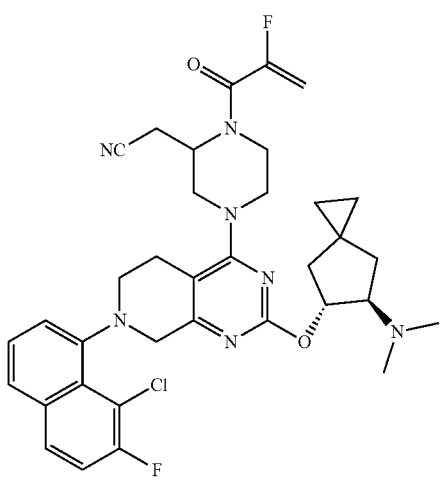

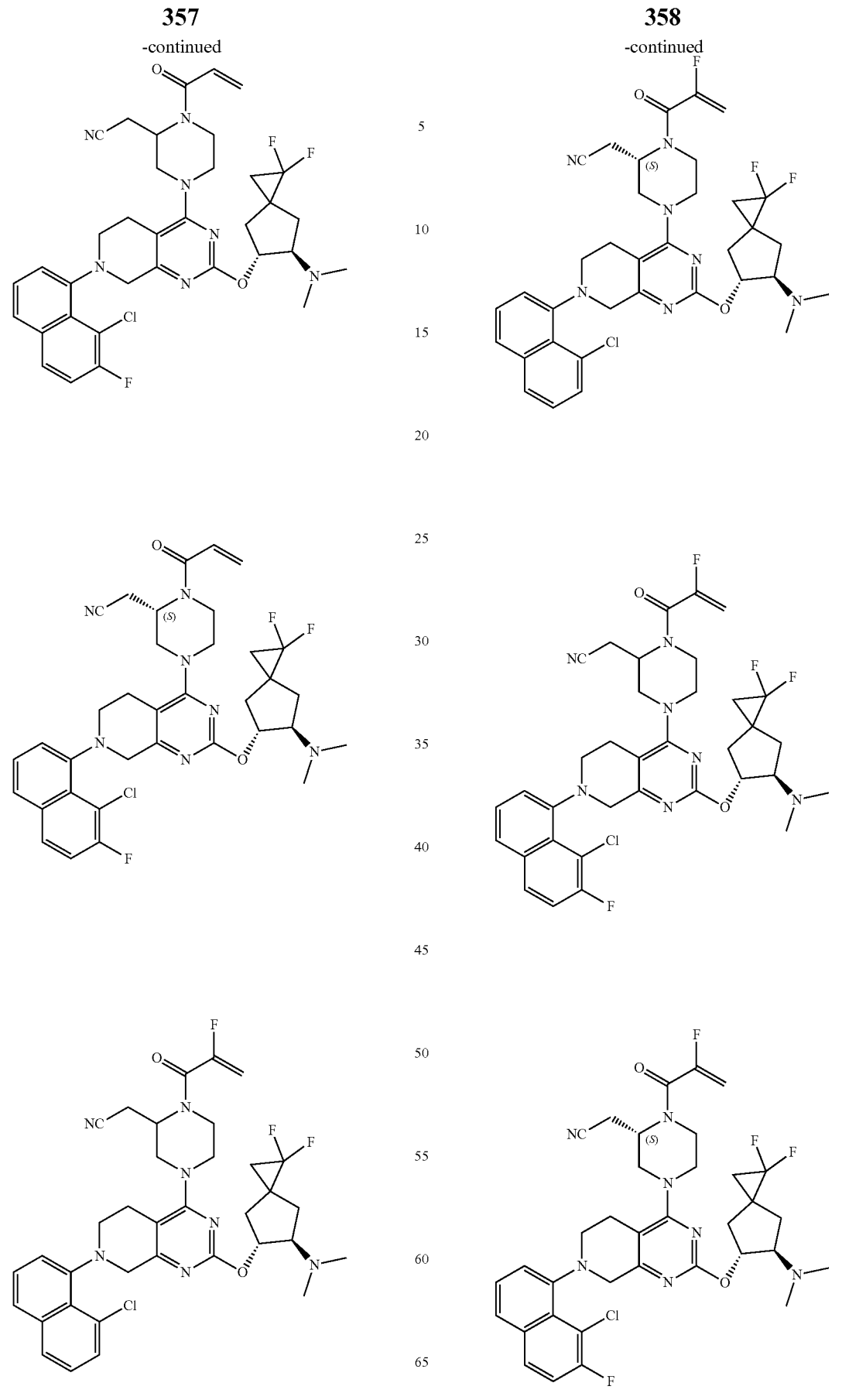

357

-continued

358

-continued

359
-continued
360
-continued
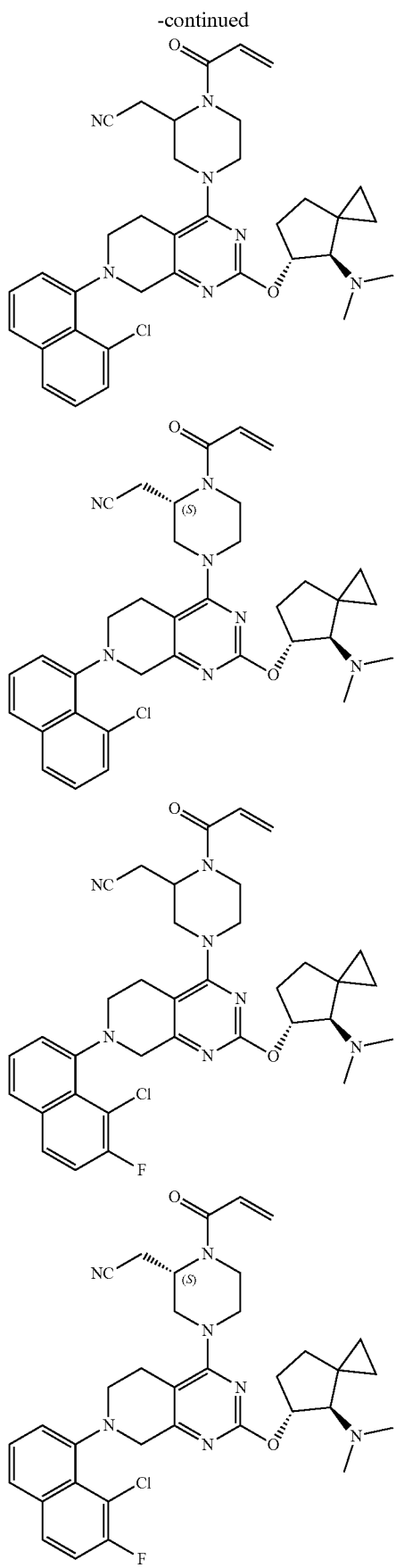
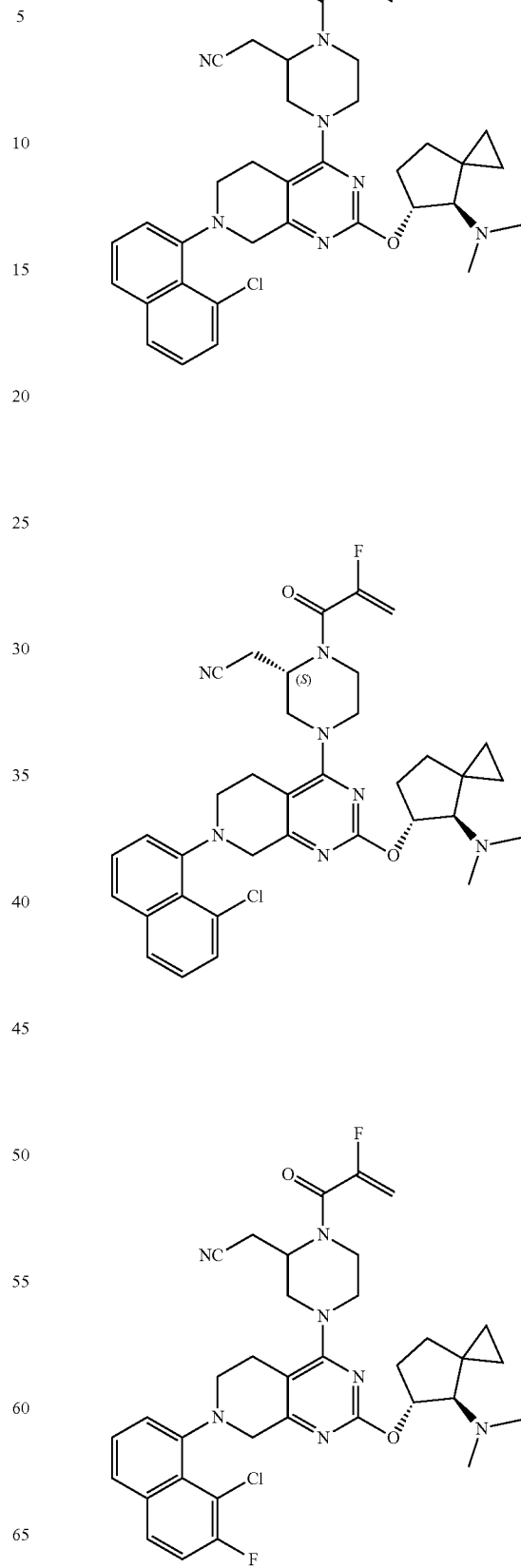

361
-continued
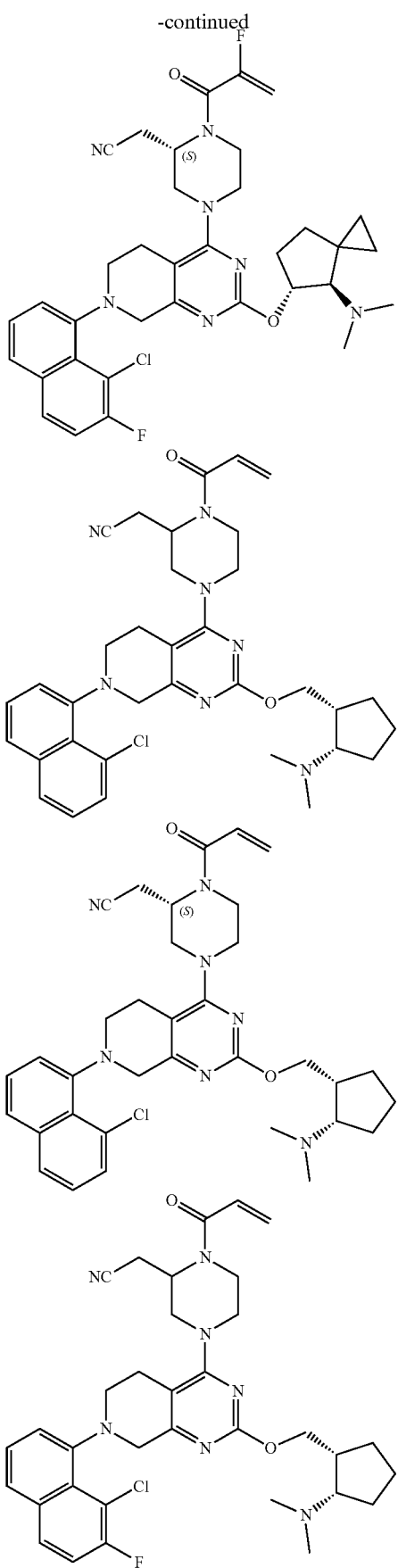
362
-continued
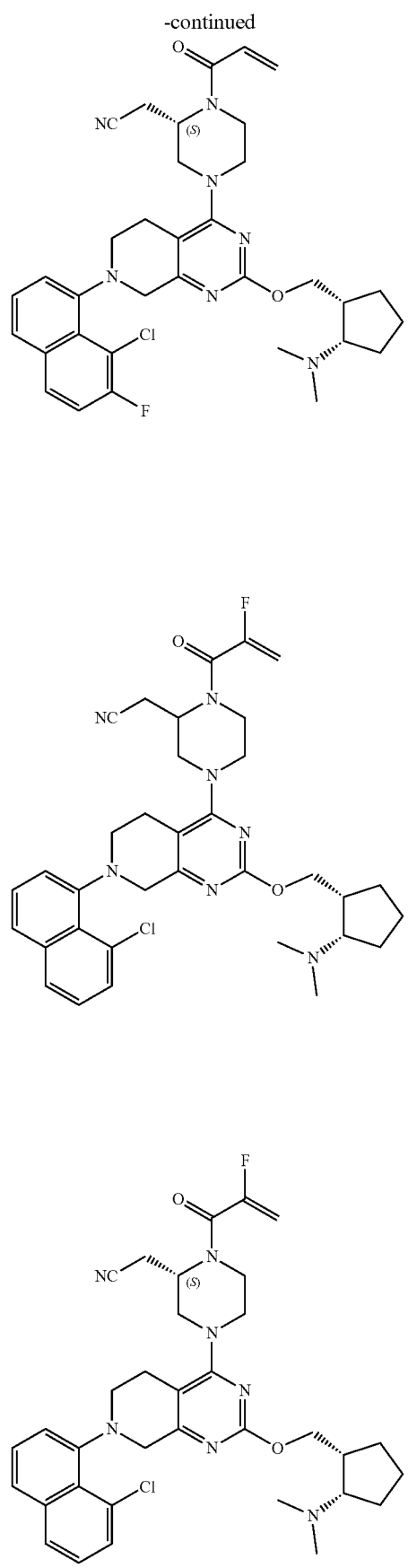

363
-continued
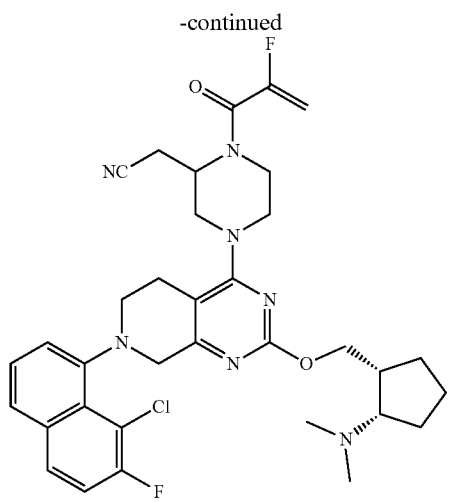
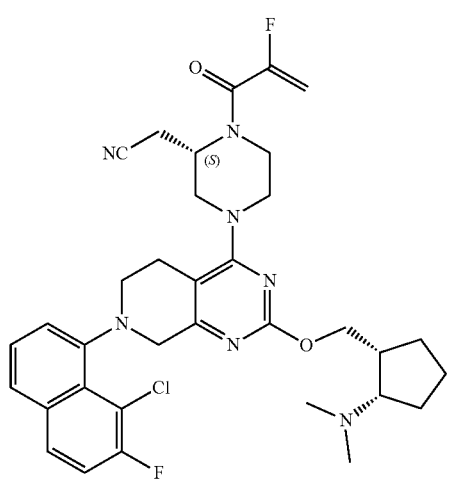
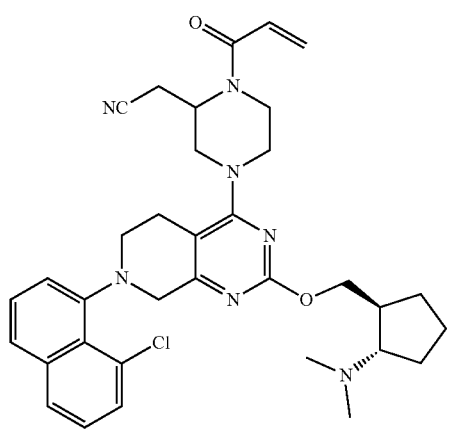
364
-continued
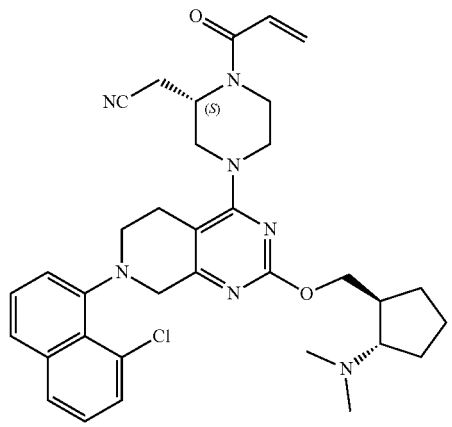
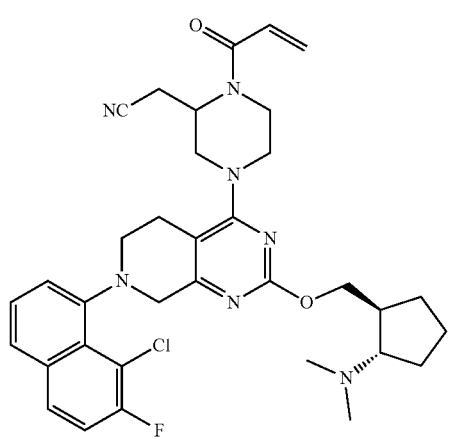
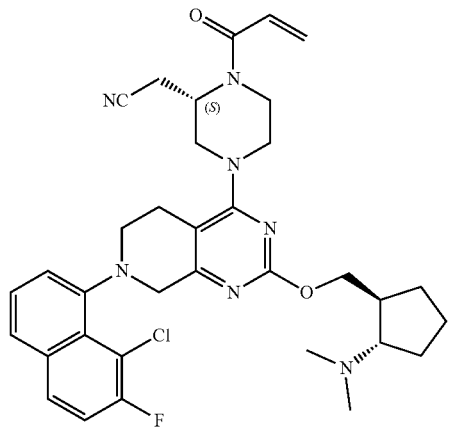

365
-continued
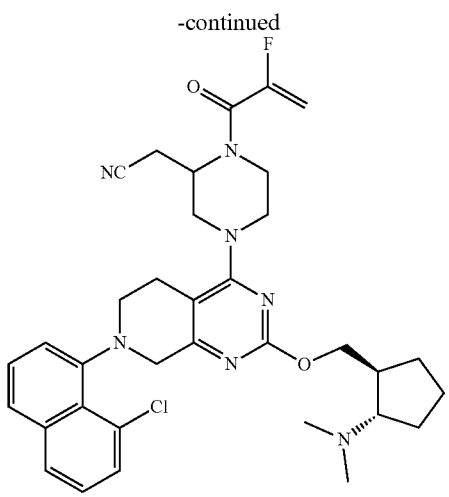
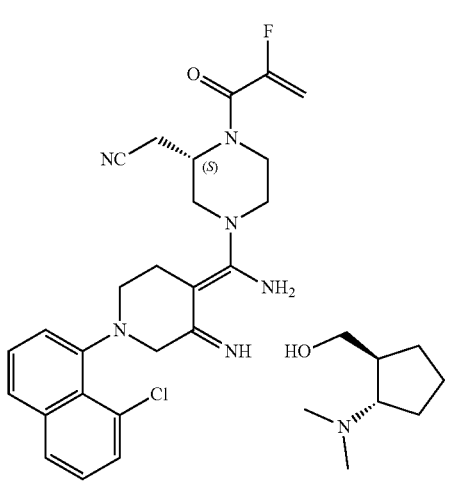
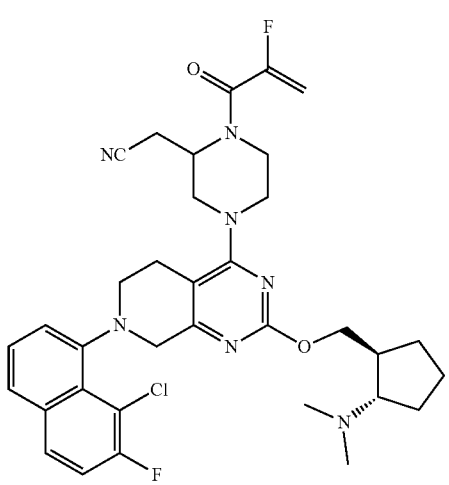
366
-continued
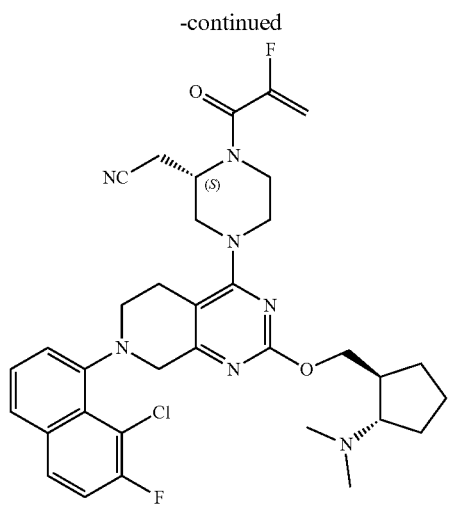
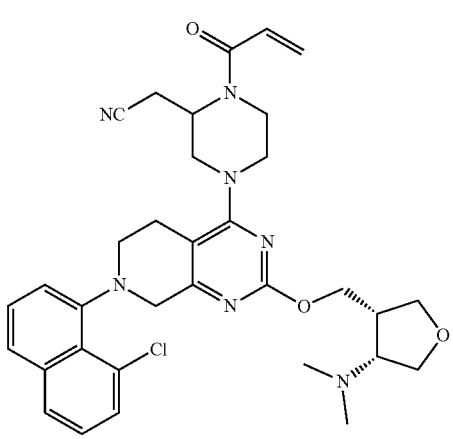
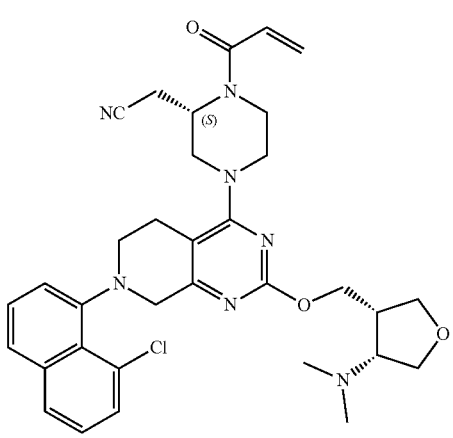

367
-continued
368
-continued
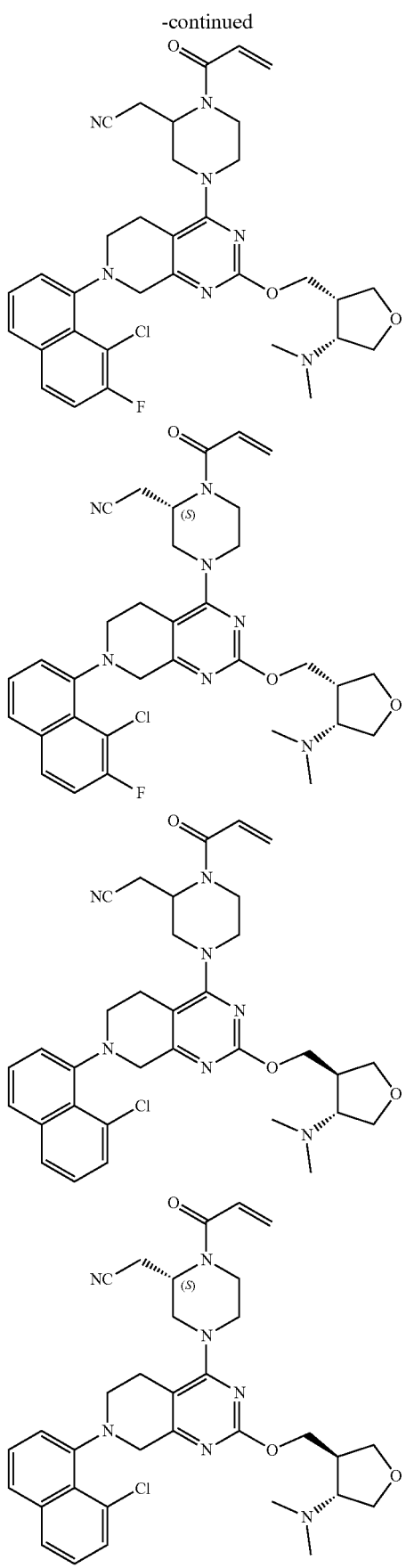
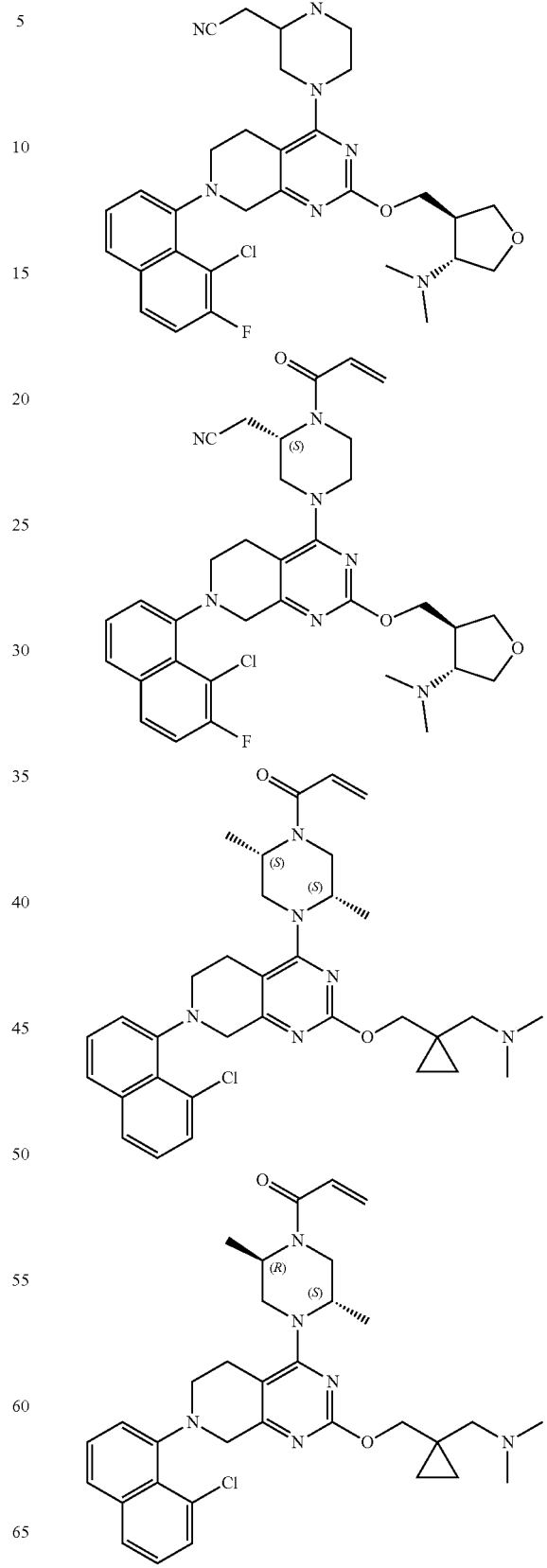

369
-continued
370
-continued
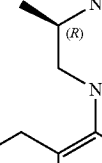
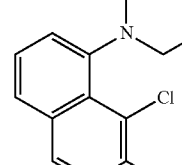
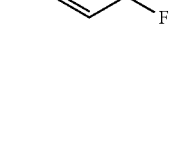
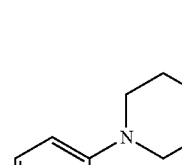
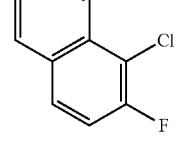
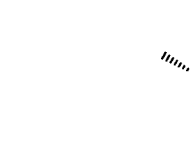
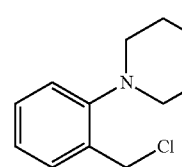
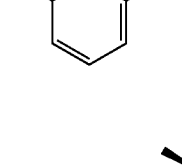

371
-continued

372
-continued

373
-continued

374
-continued

375
-continued
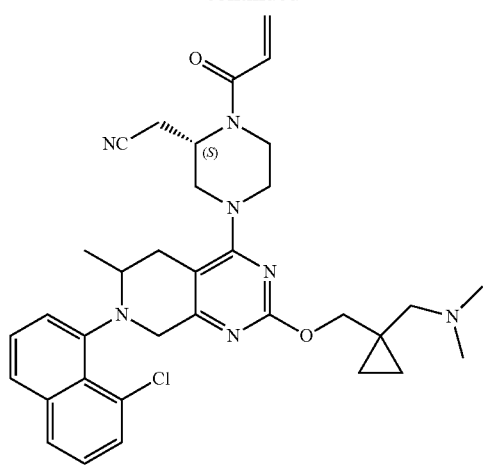
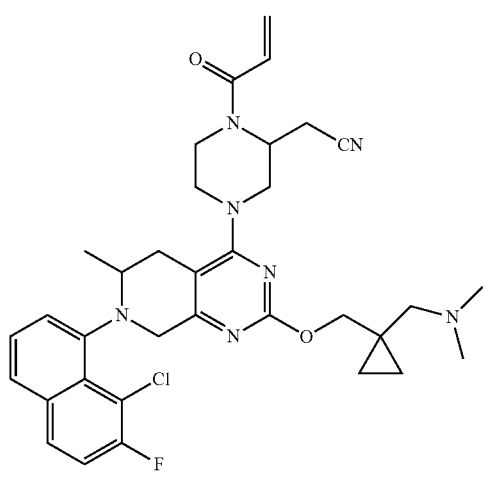
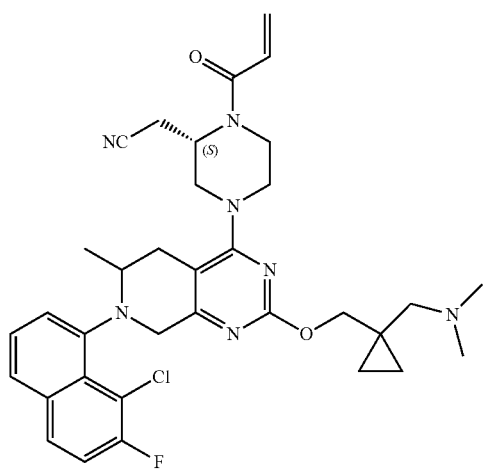
376
-continued
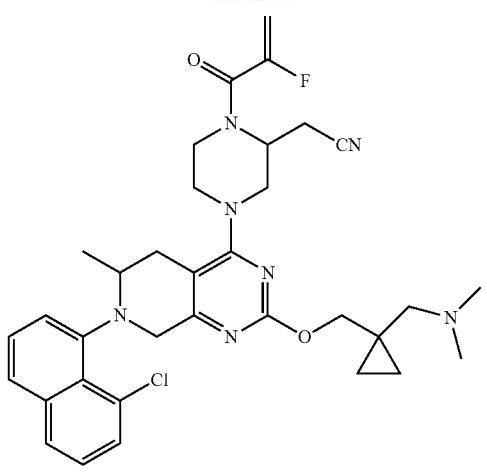
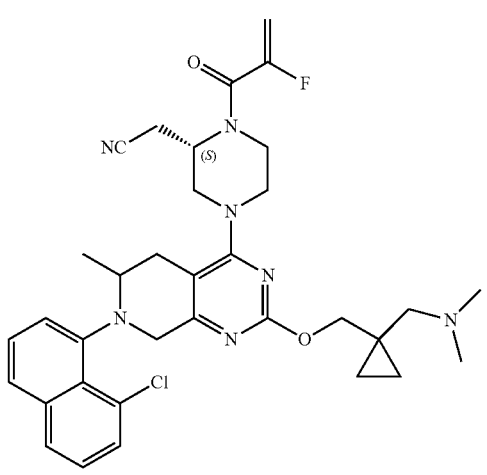
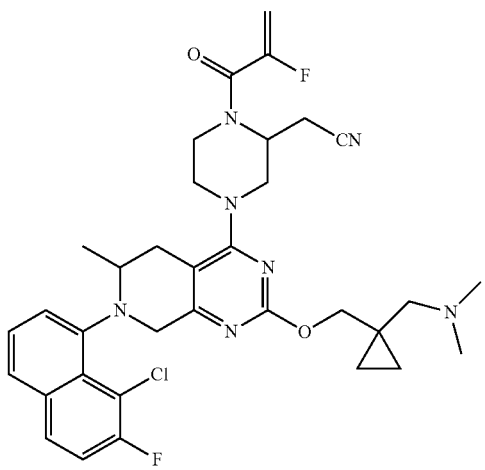

377
-continued
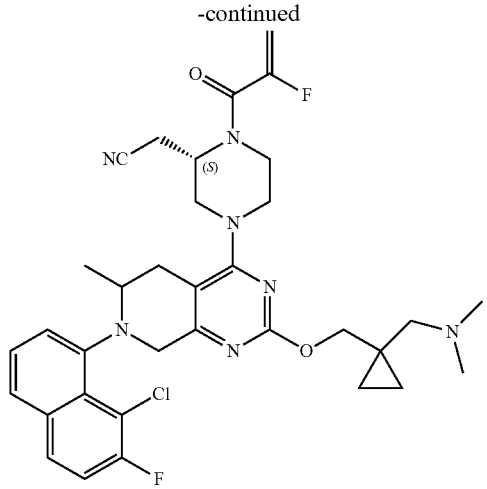
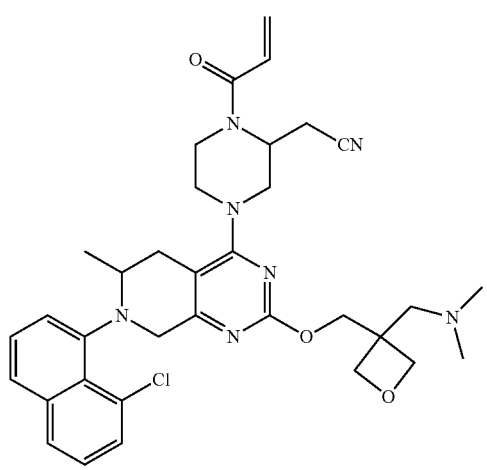
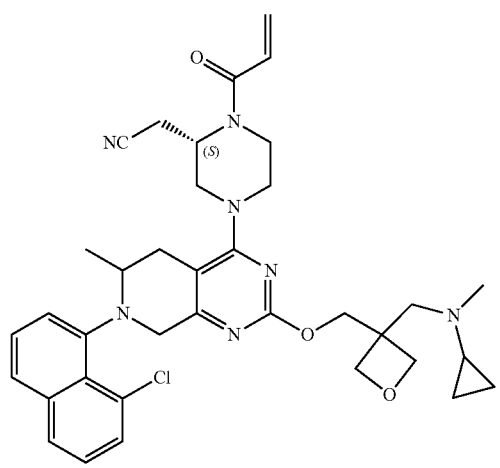
378
-continued
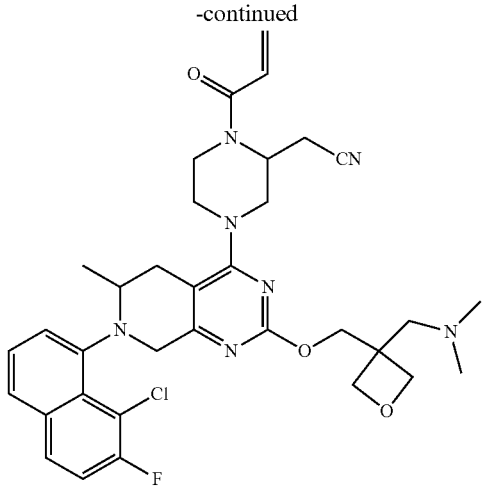
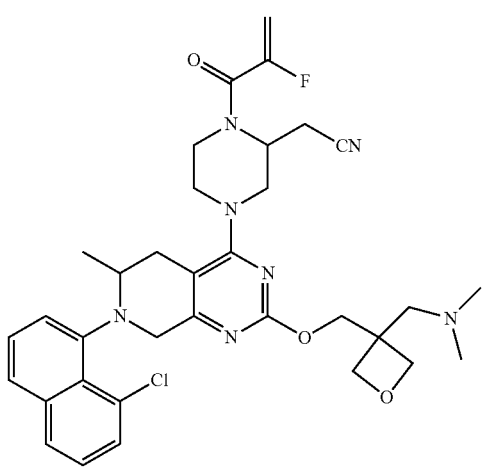

379
-continued
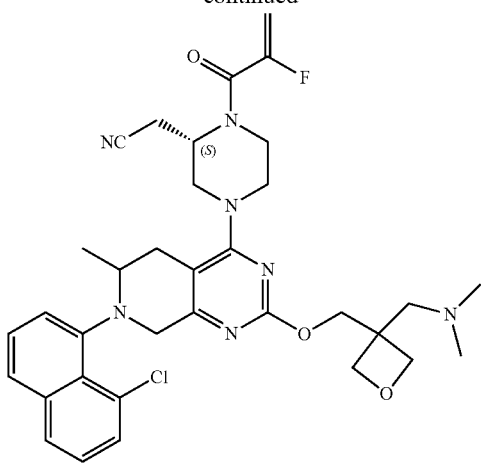
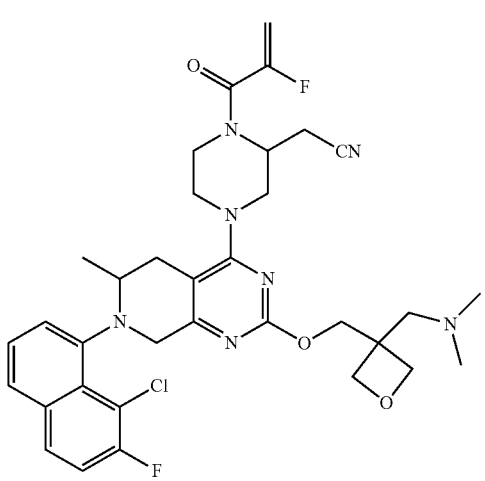
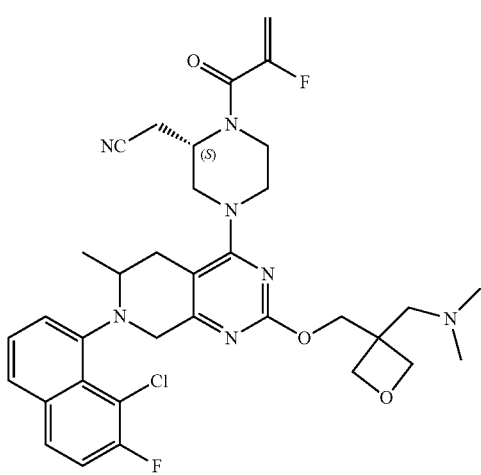
380
-continued
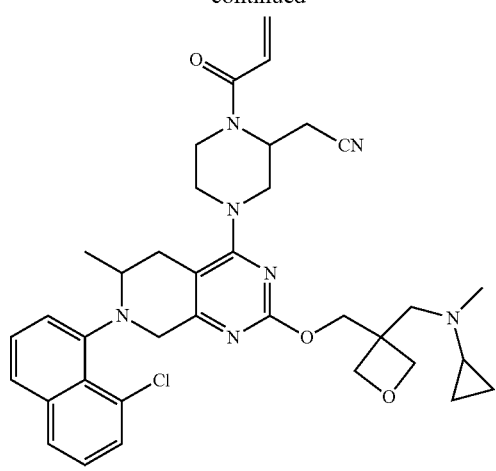
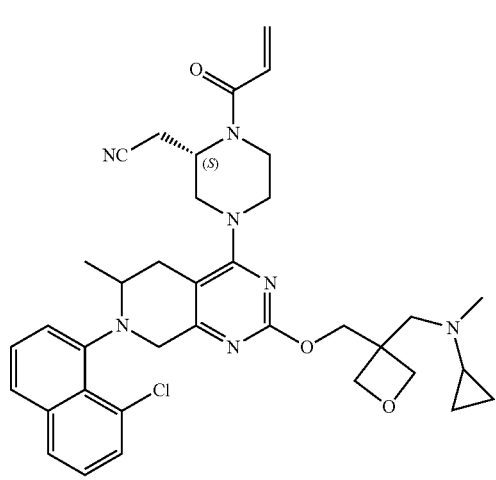
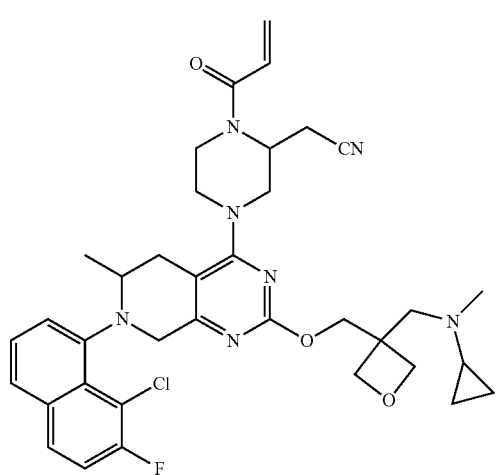

-continued
381
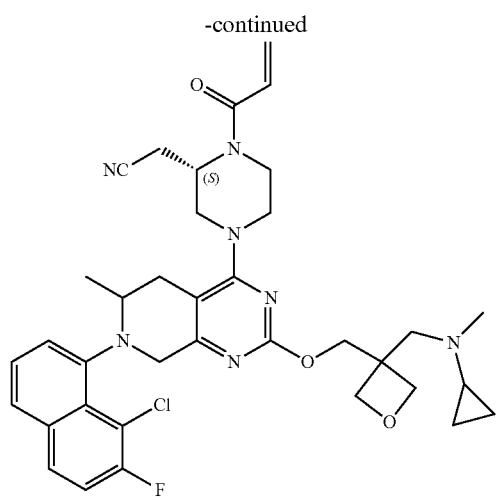
382
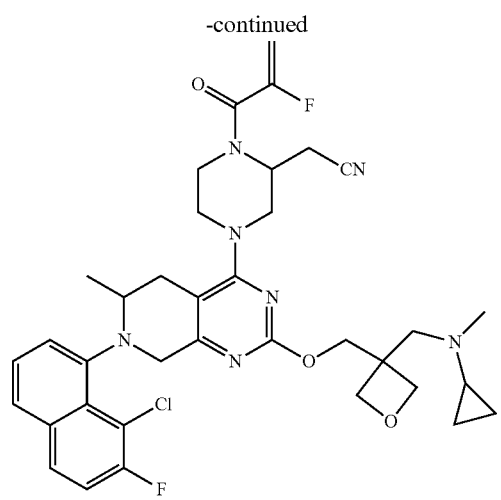
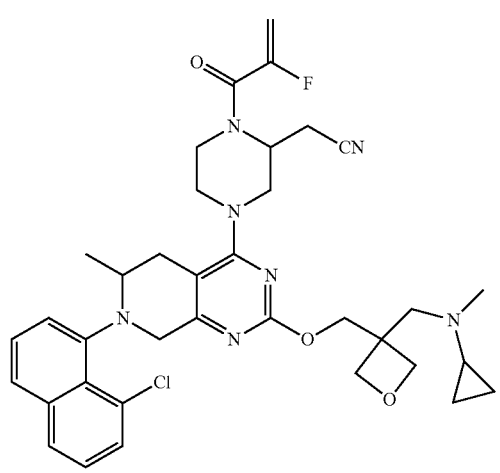
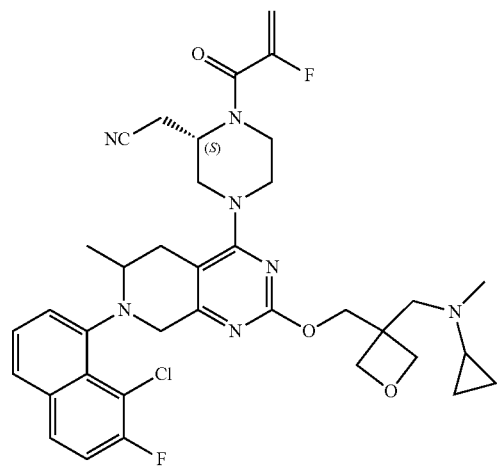
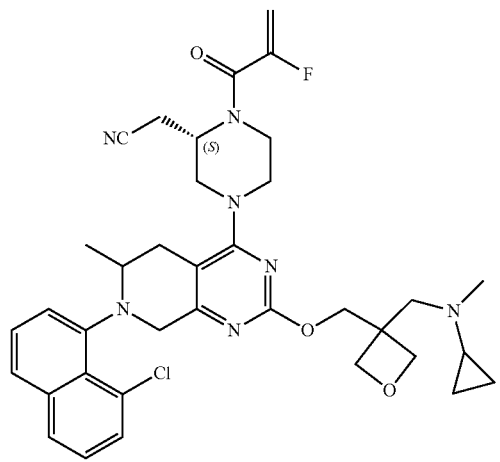
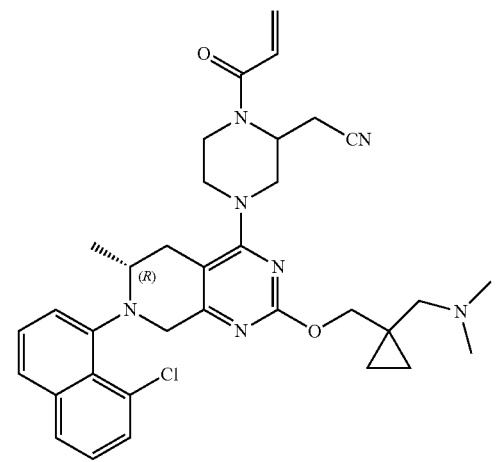

383
-continued
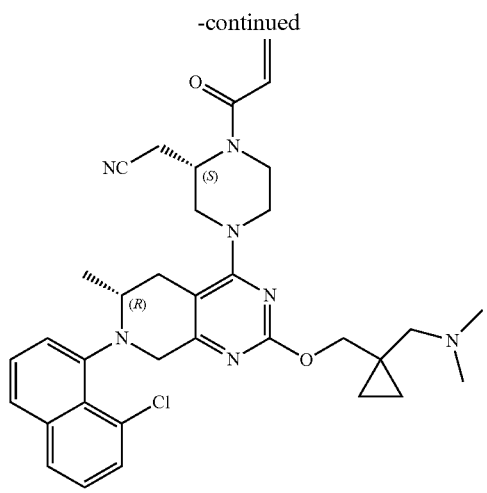
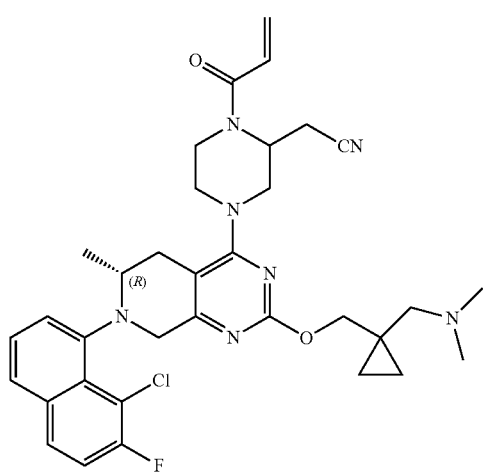
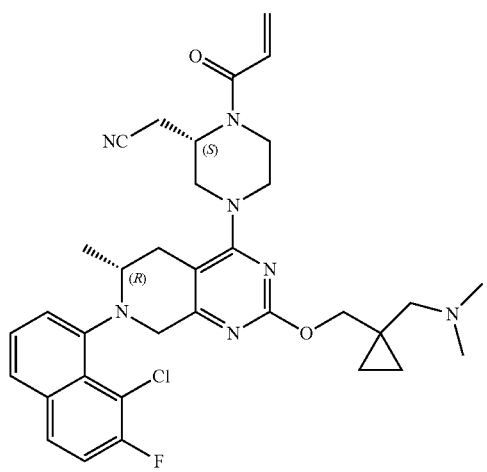
384
-continued
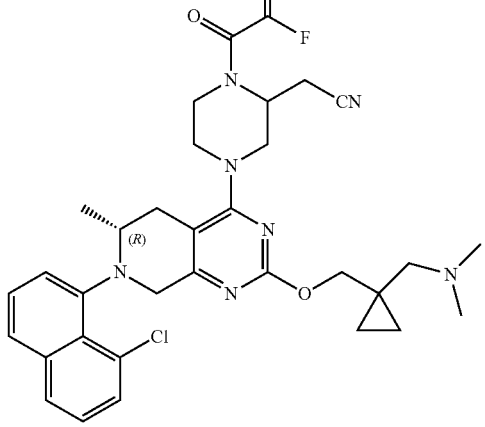
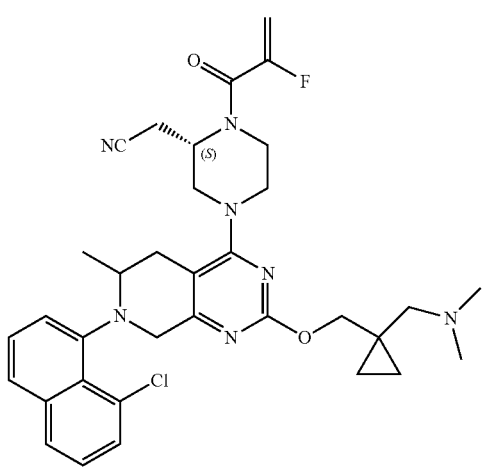
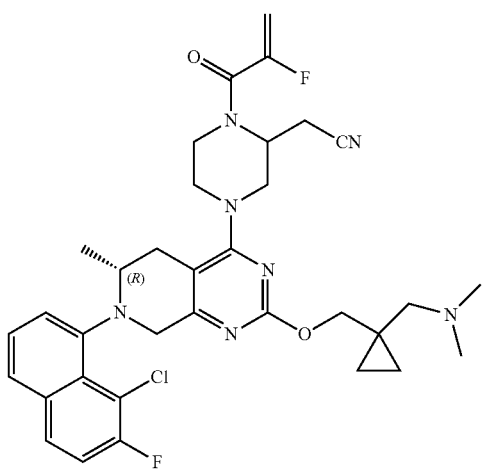

385
-continued
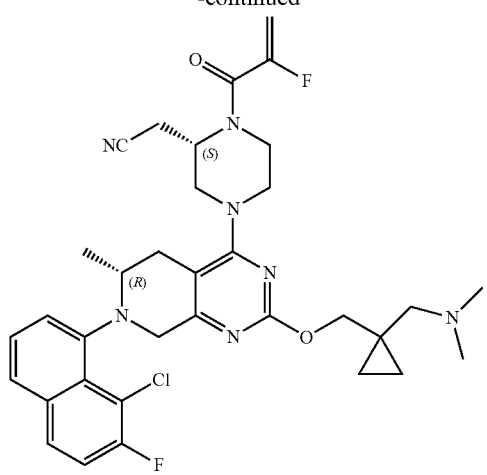
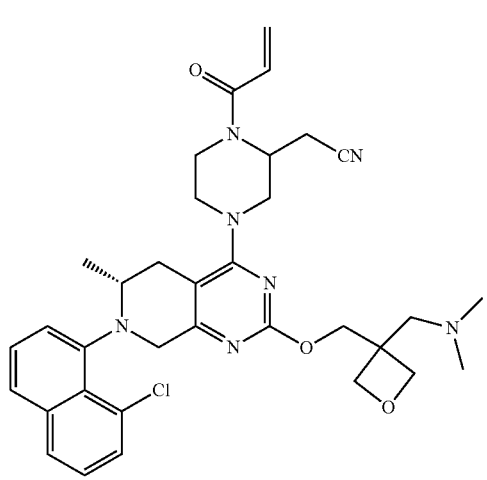
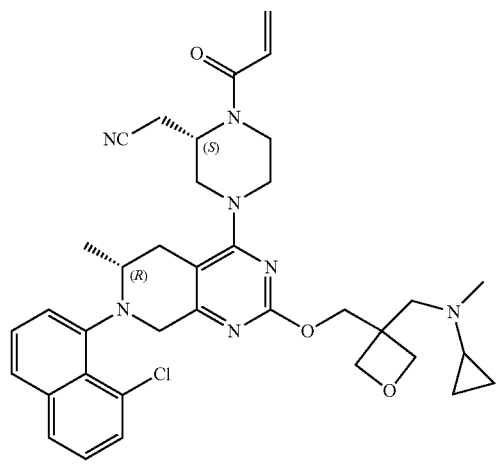
386
-continued
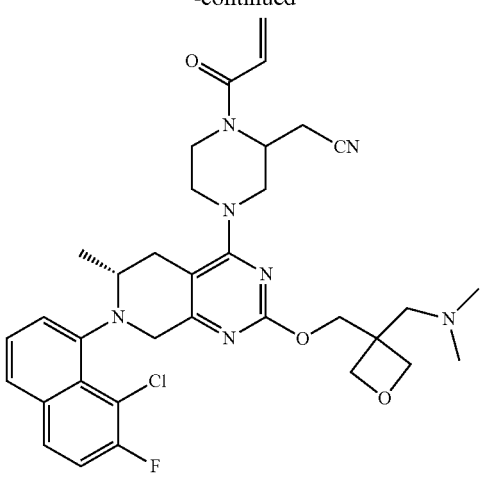
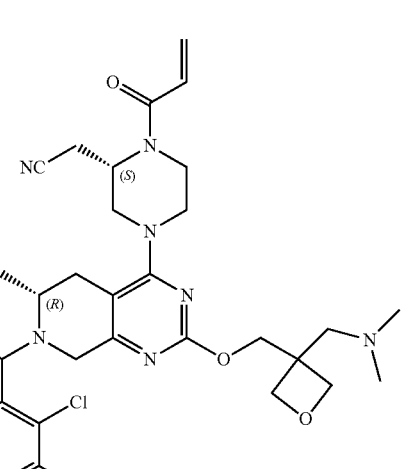
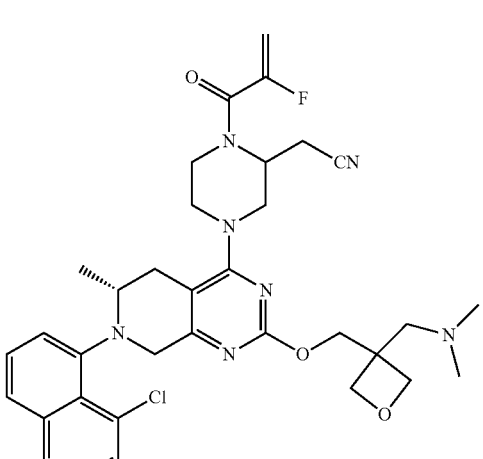

387
-continued
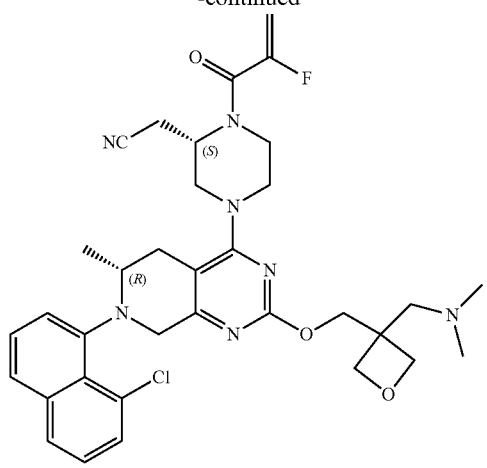
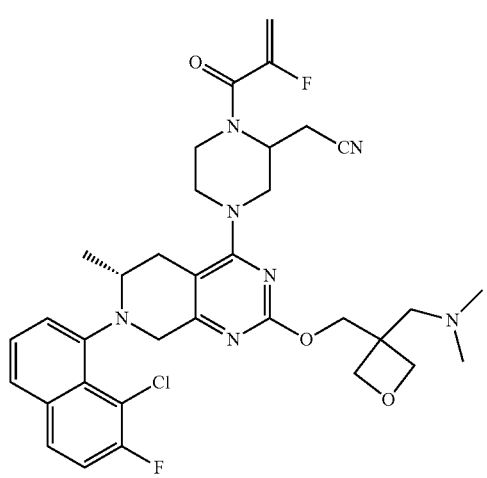
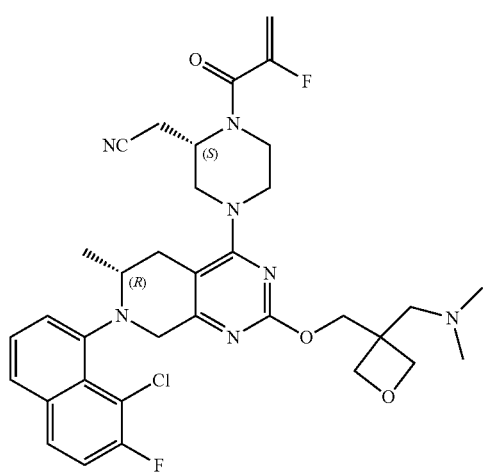
388
-continued
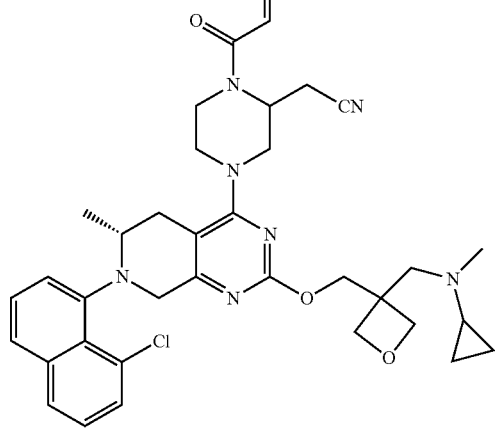
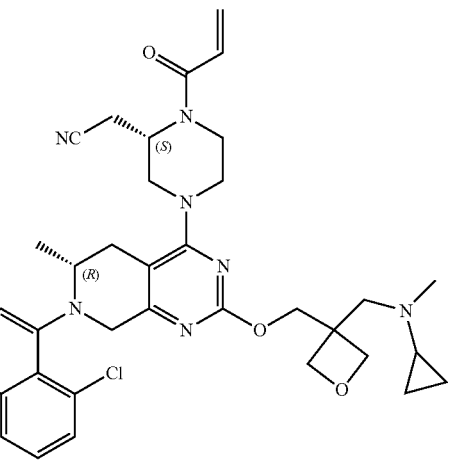
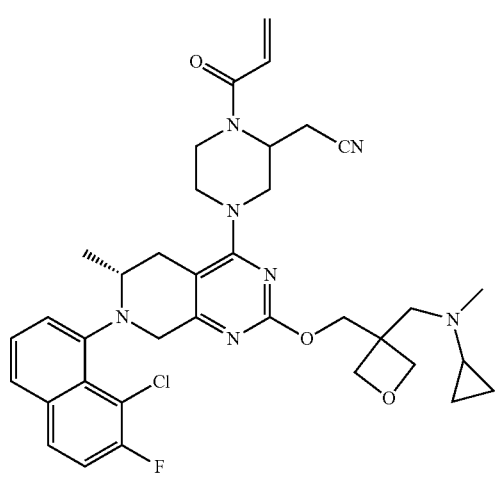

389
-continued
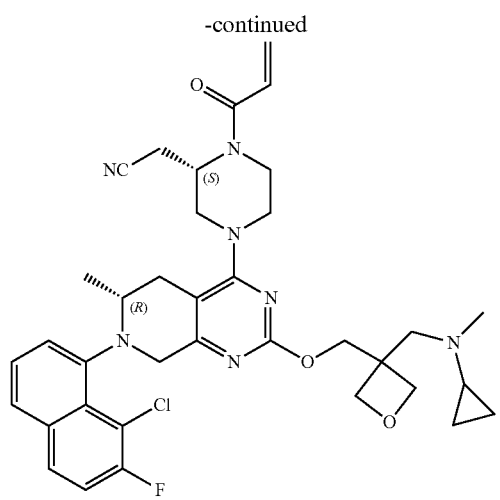
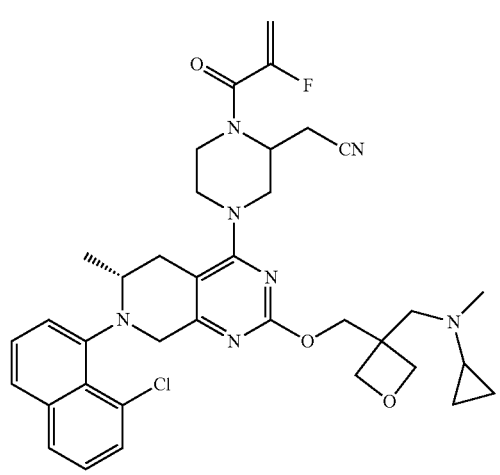
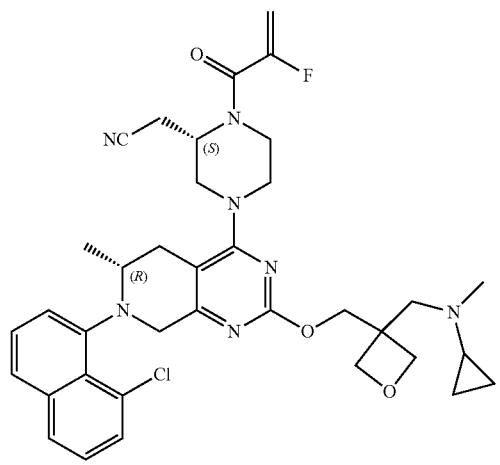
390
-continued
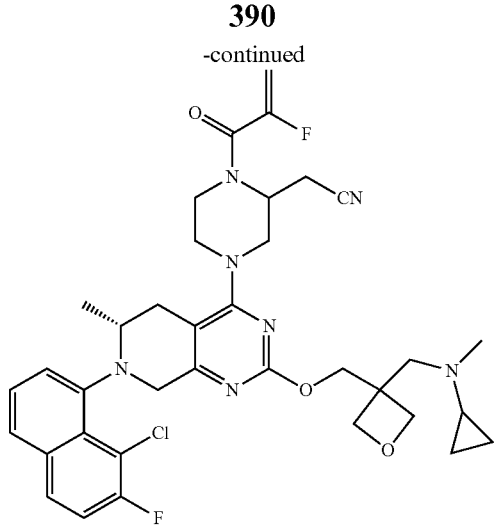
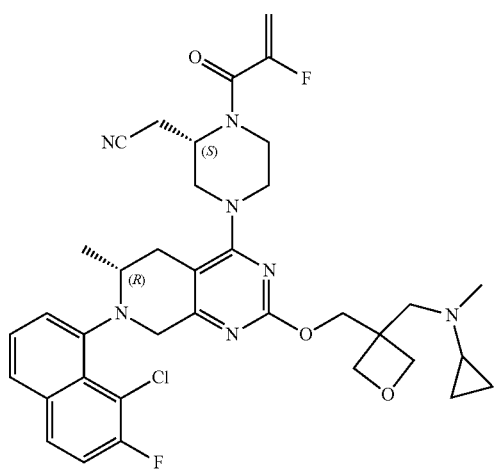
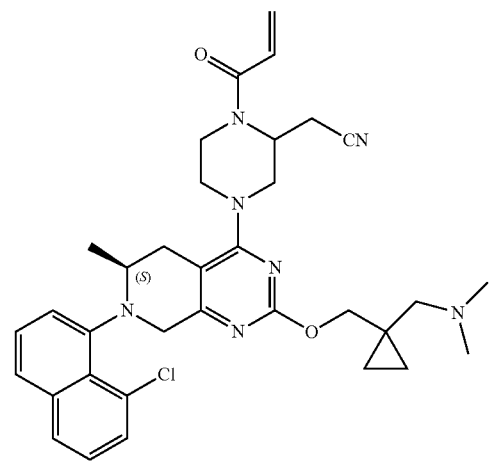

391
-continued
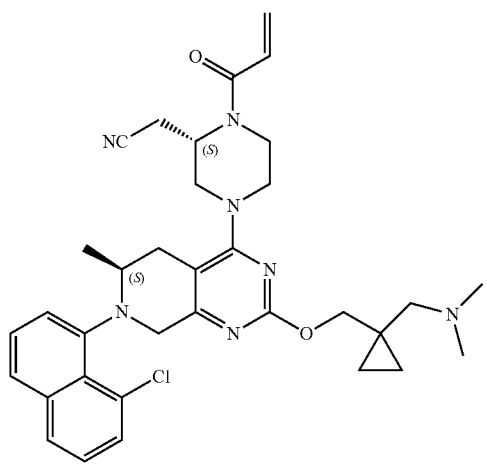
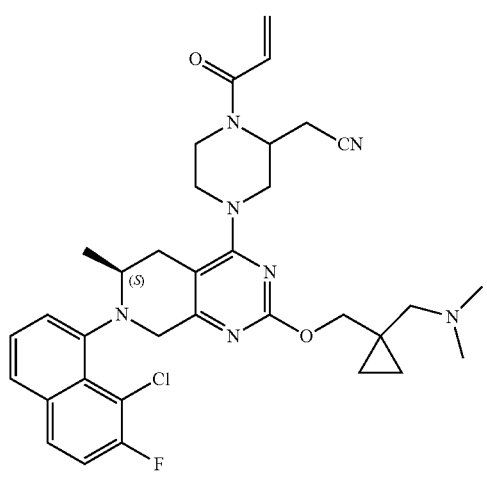
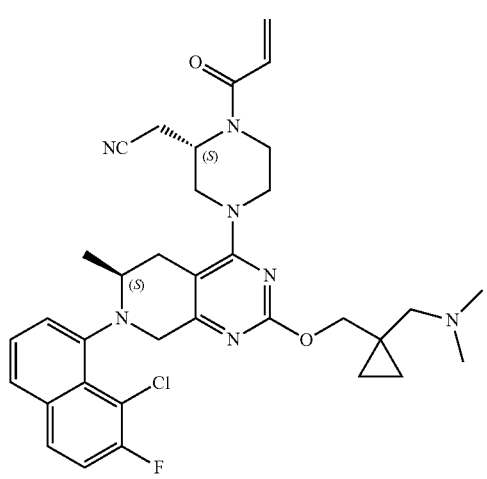
392
-continued
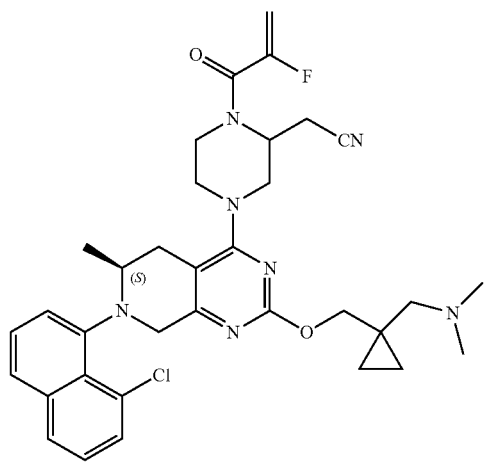
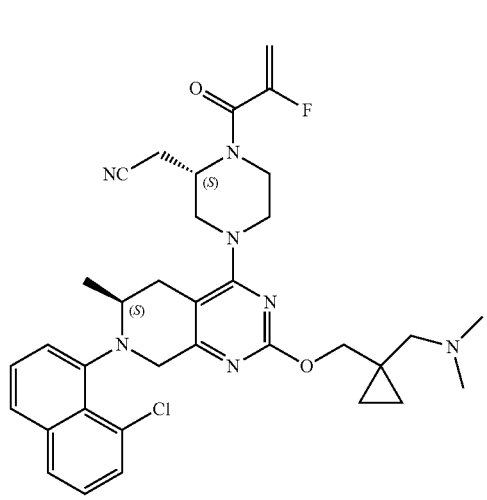
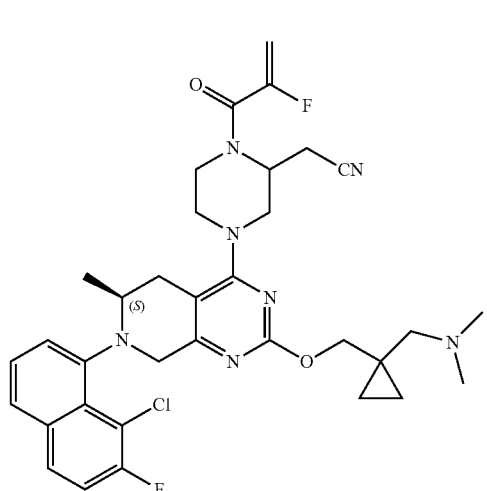

393
-continued
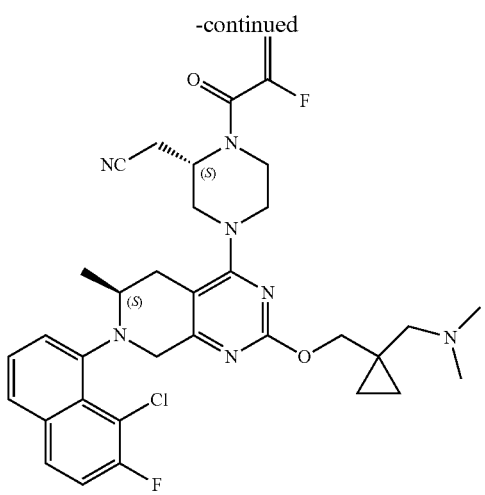
394
-continued
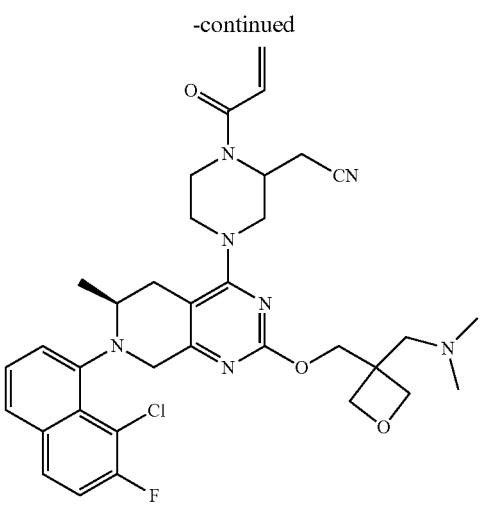
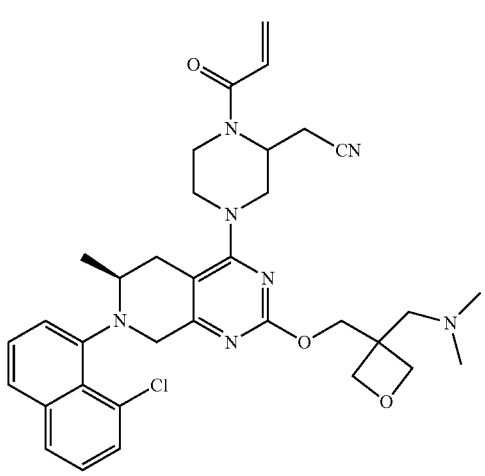
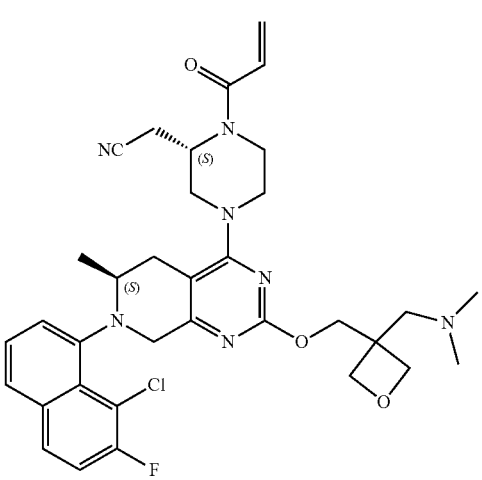
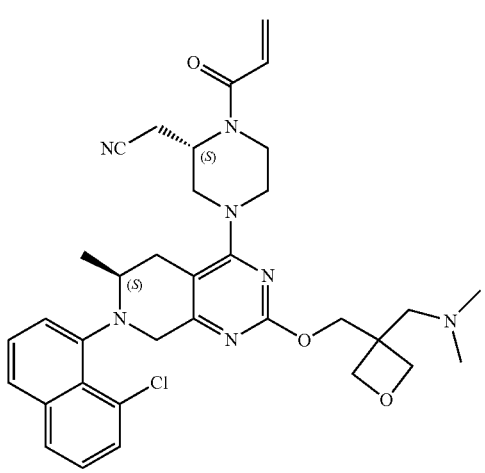
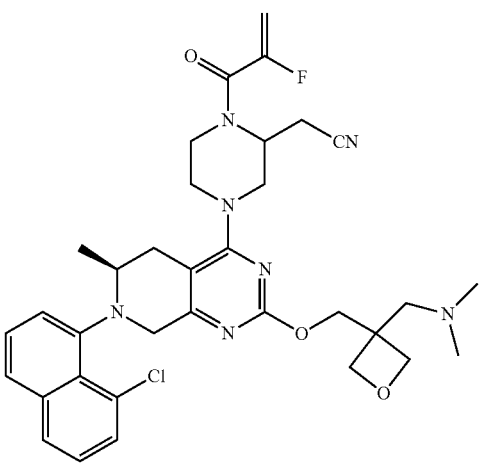

395
-continued
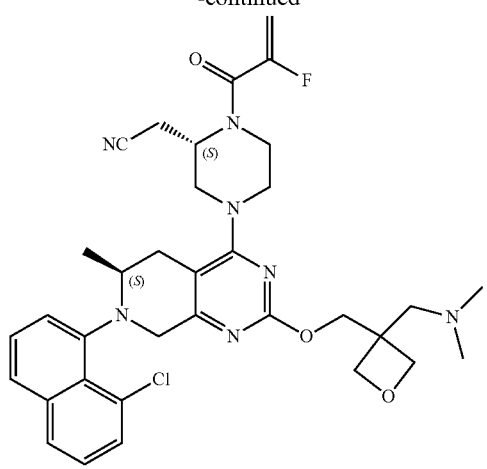
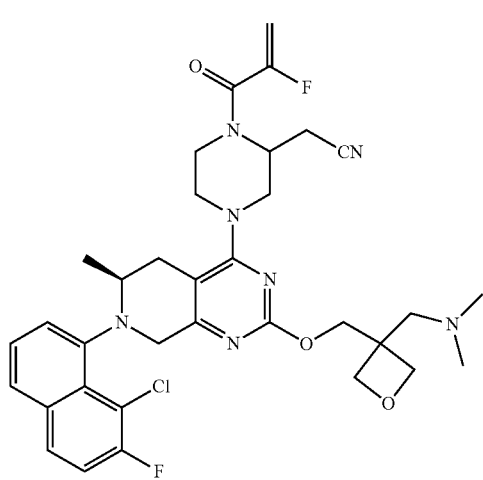
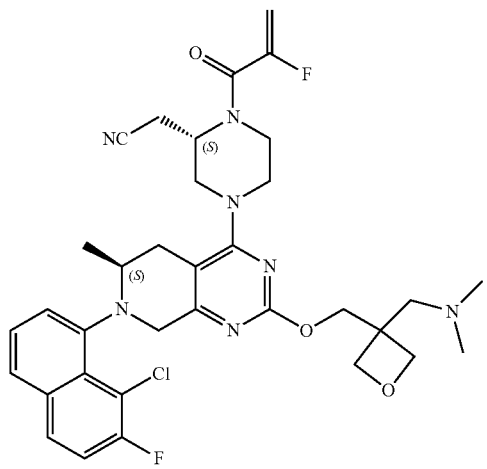
396
-continued
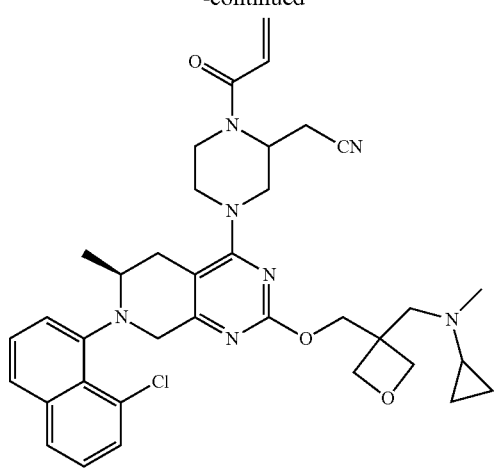
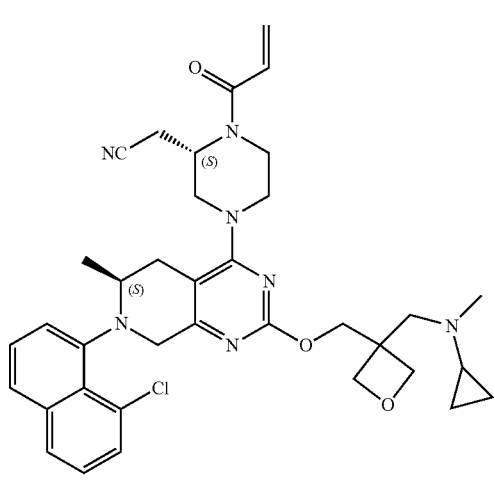
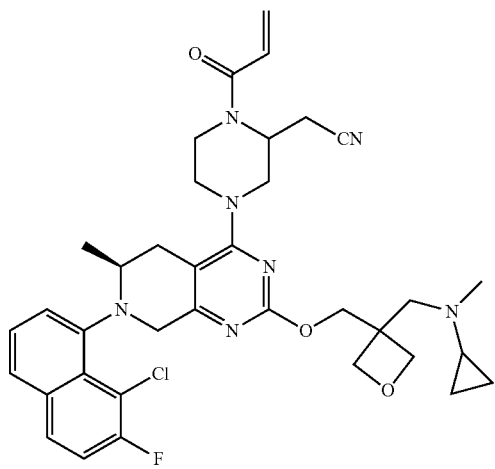

397
-continued

398
-continued

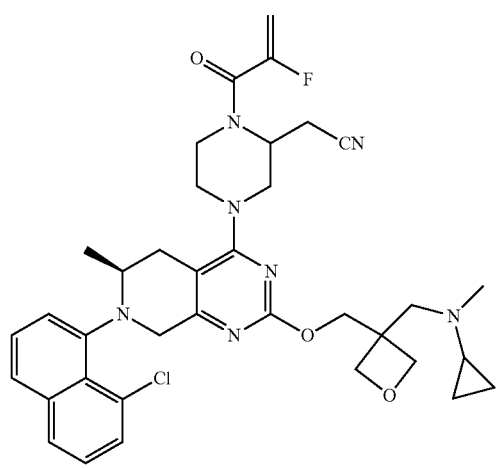
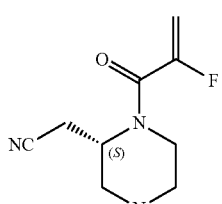
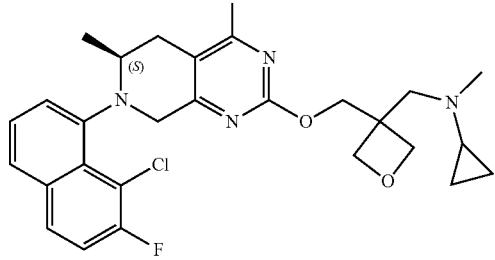
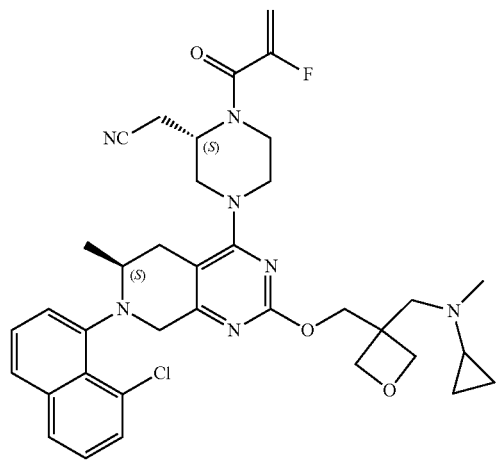
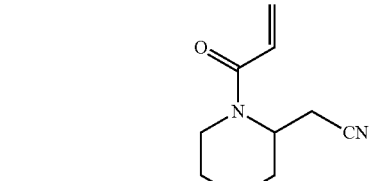
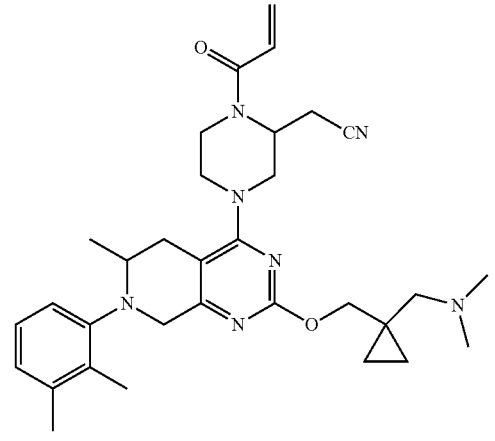

399
-continued
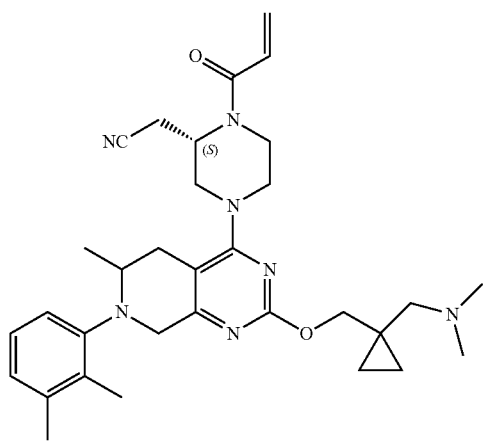
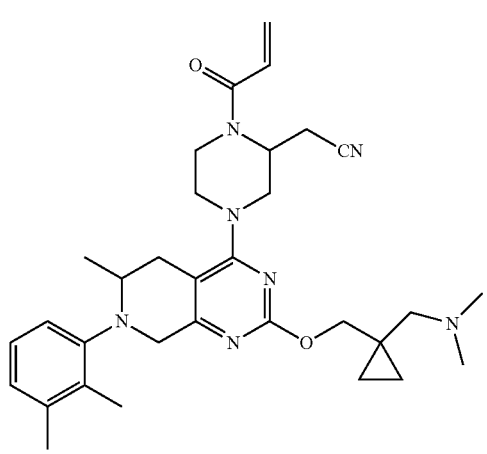
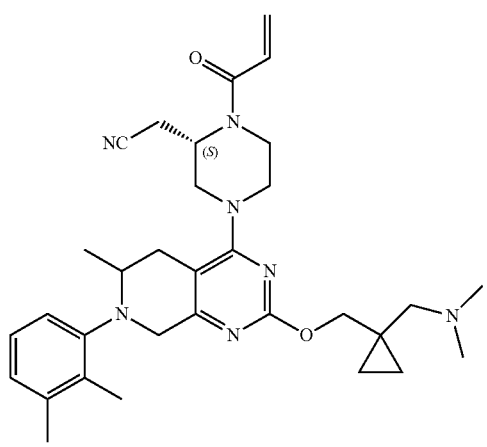
400
-continued
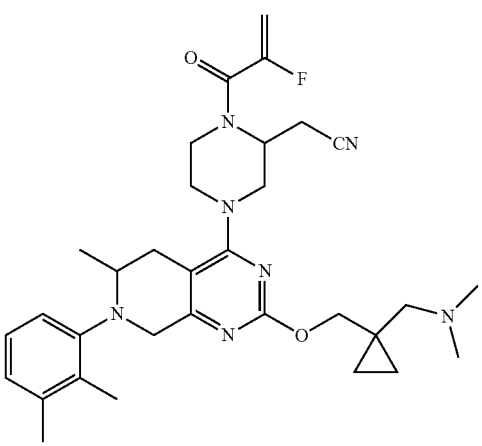
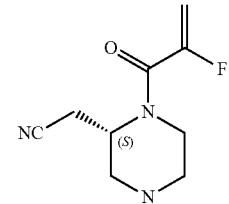
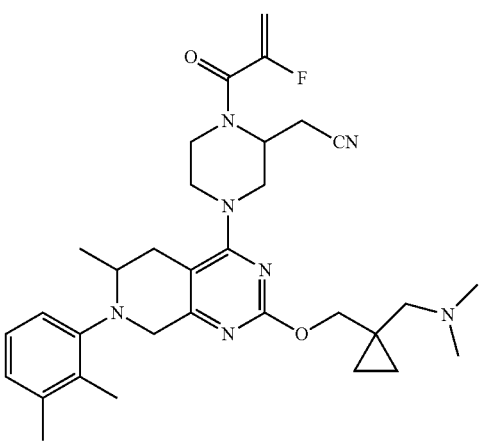

401
-continued
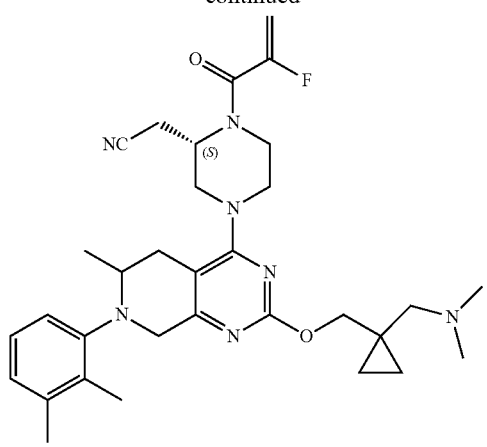
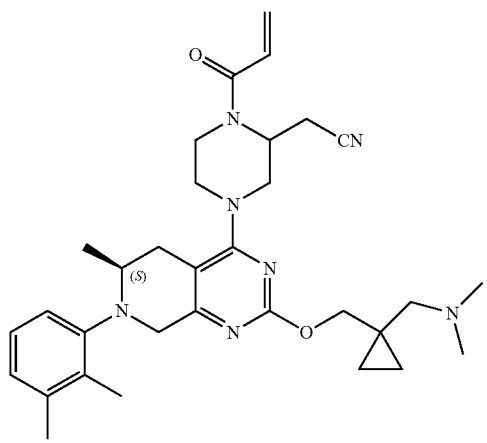
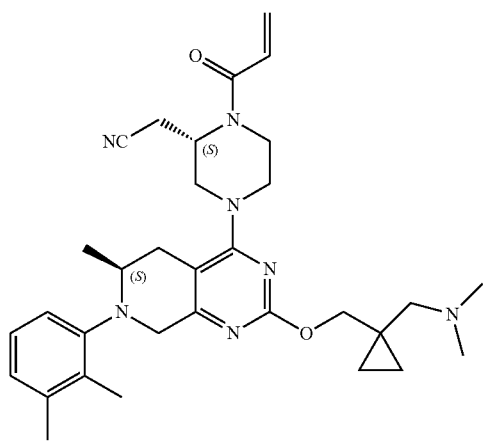
402
-continued
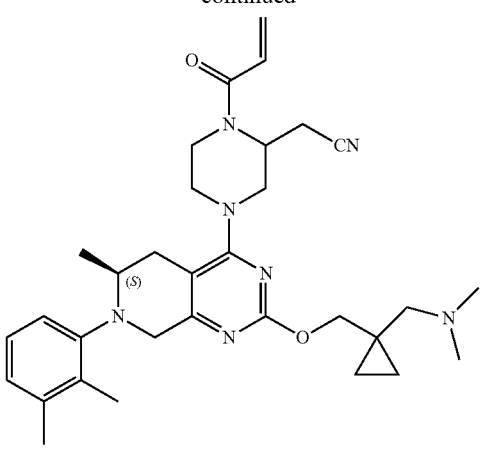
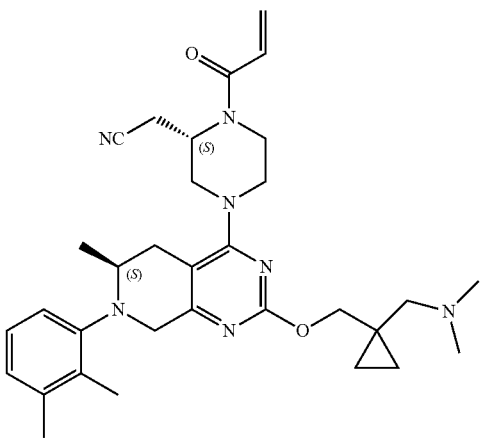
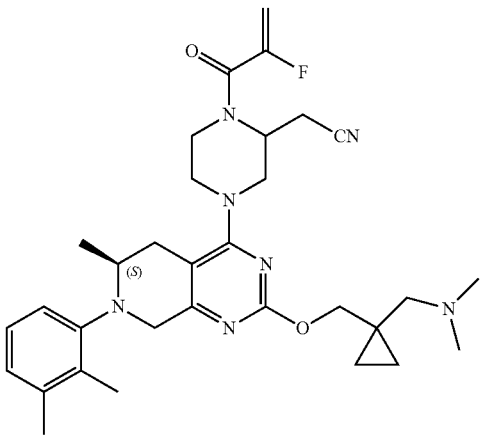

403
-continued
404
-continued
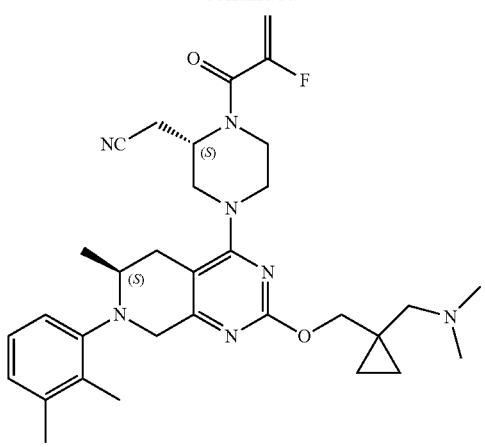
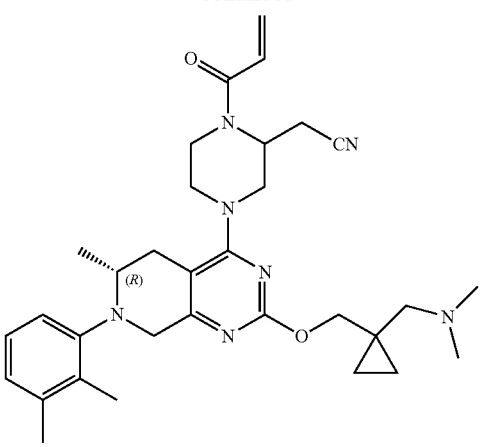

405
-continued
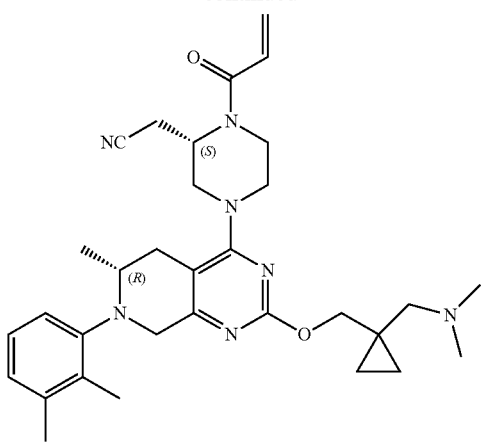
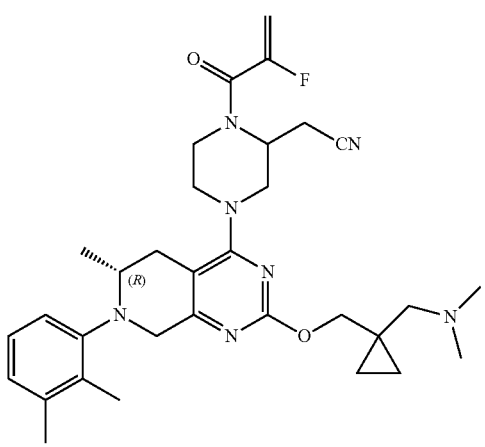
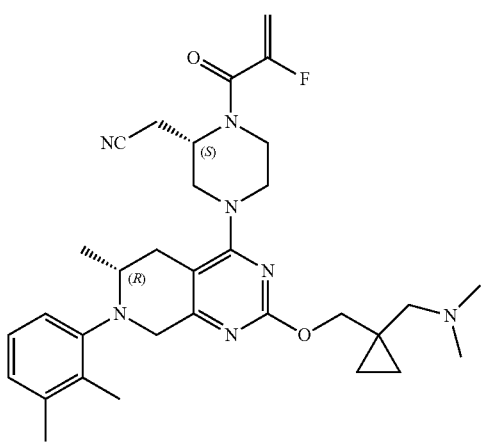
406
-continued
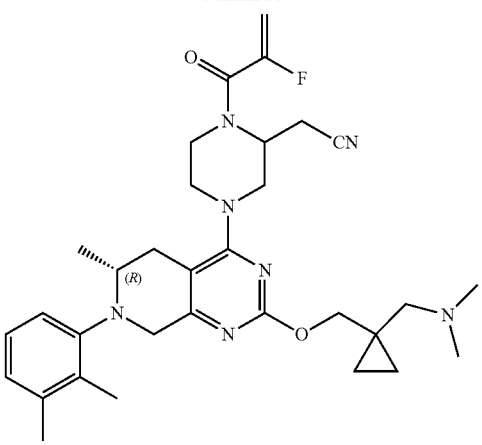
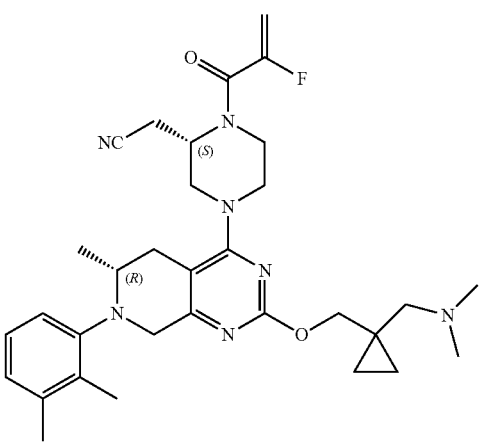
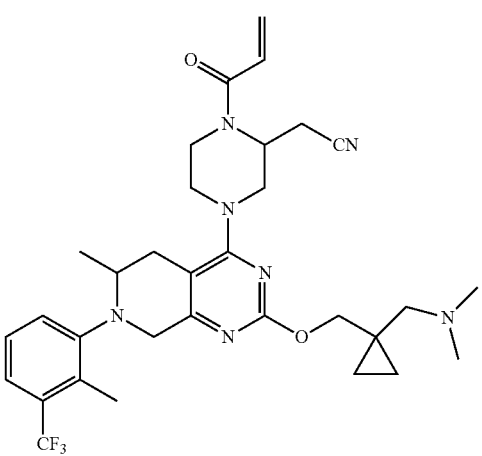

407
-continued
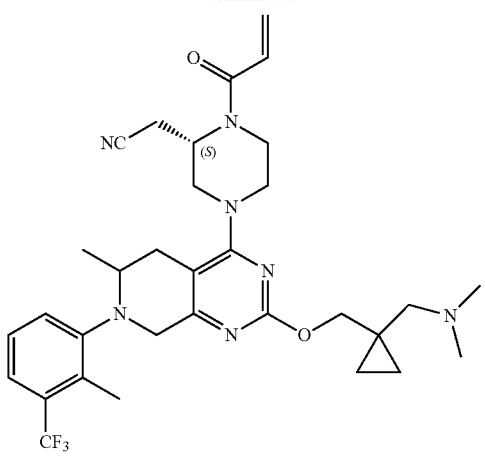
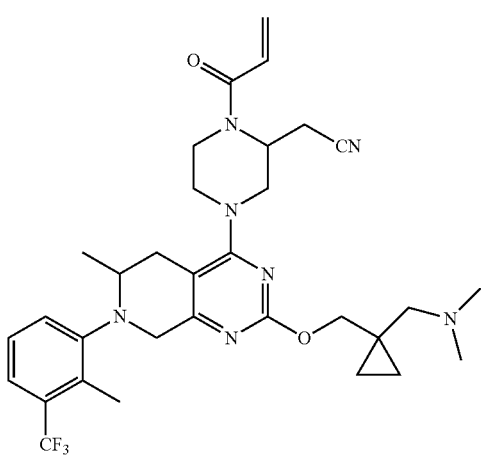
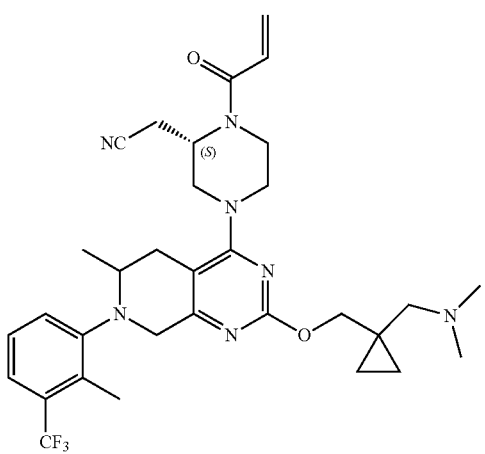
408
-continued
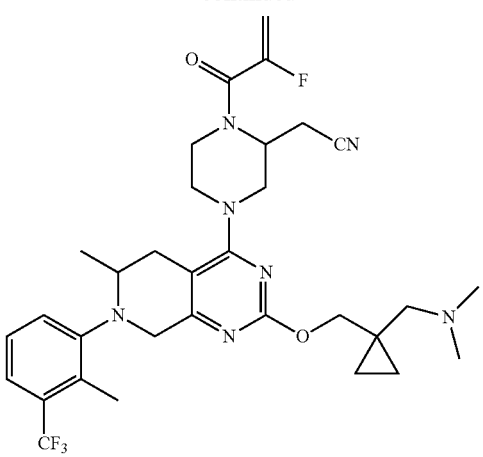
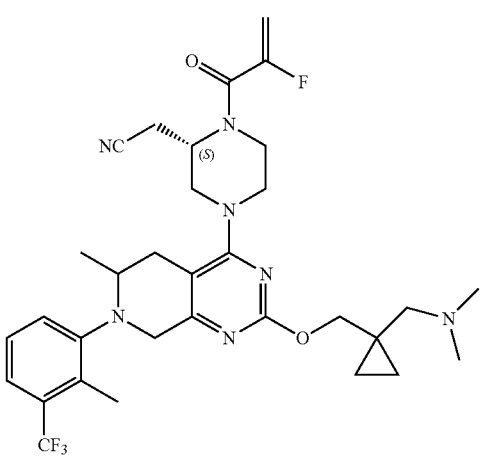
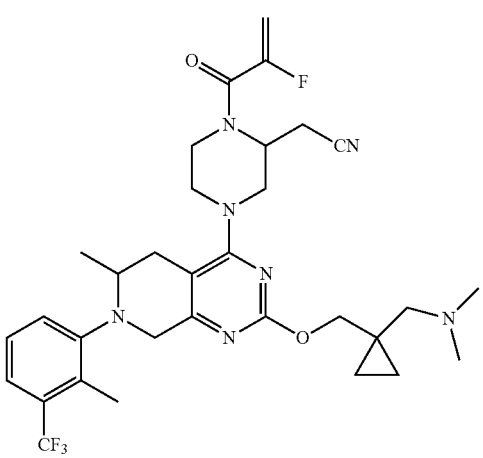

409
-continued
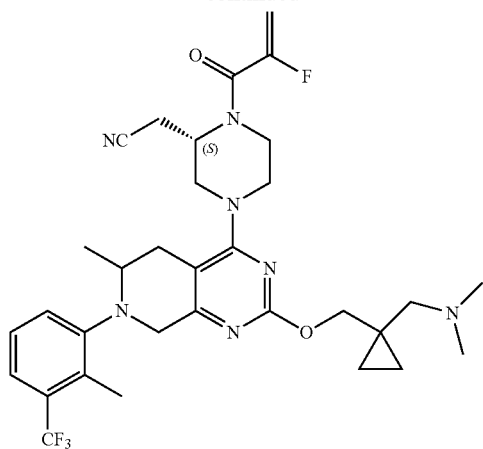
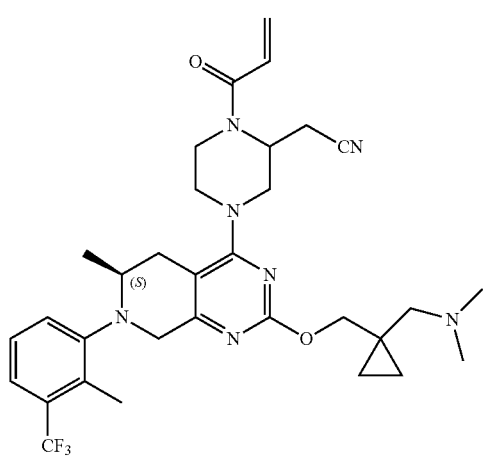
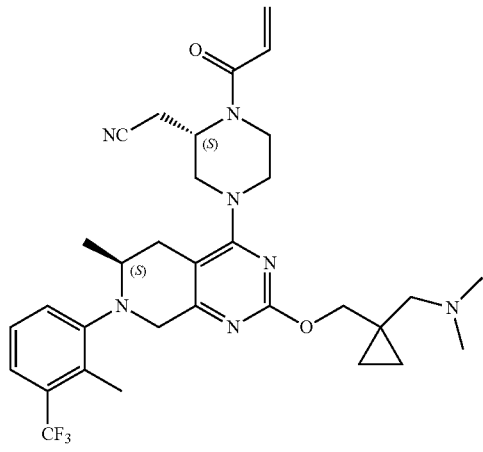
410
-continued
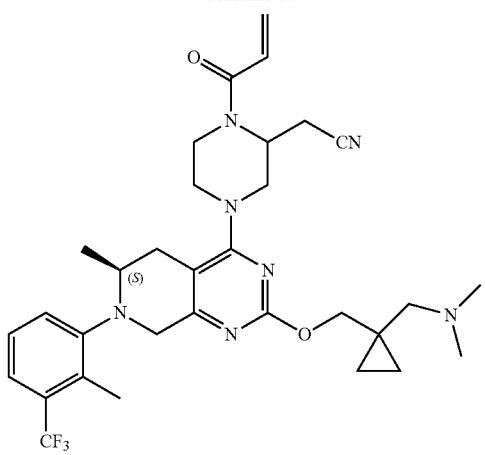
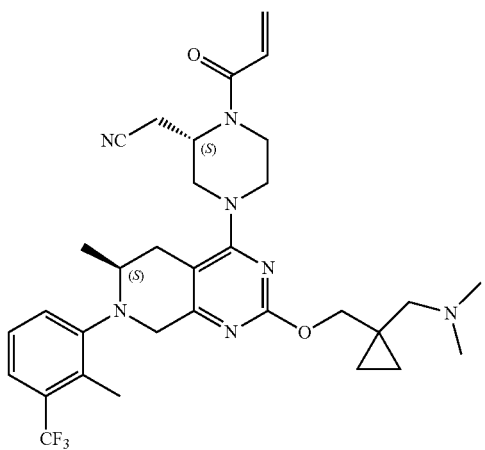
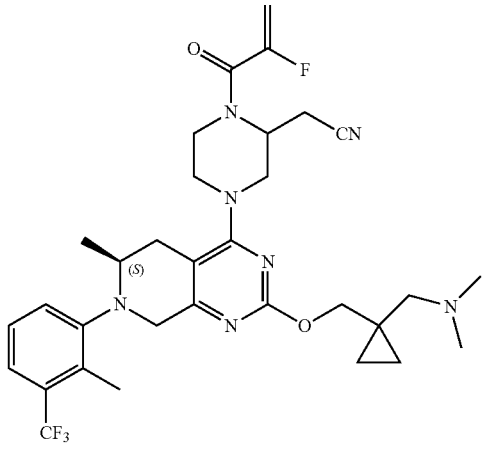

411
-continued
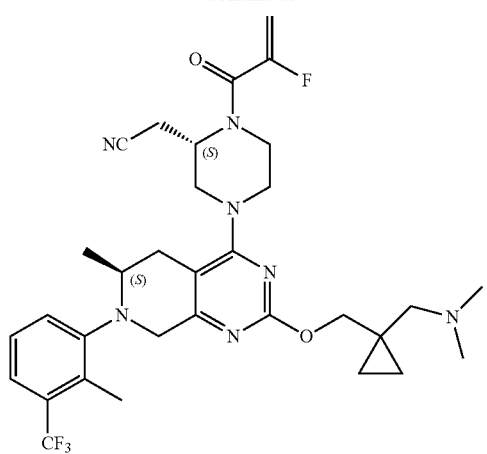
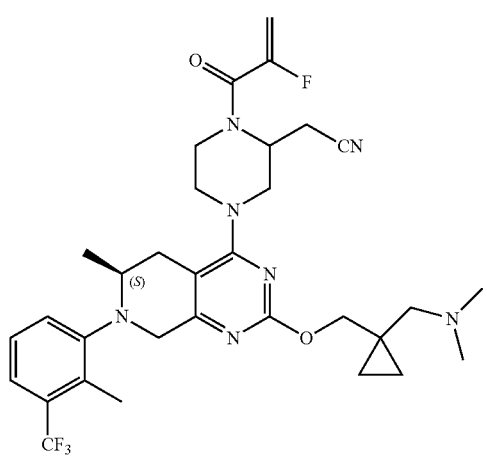
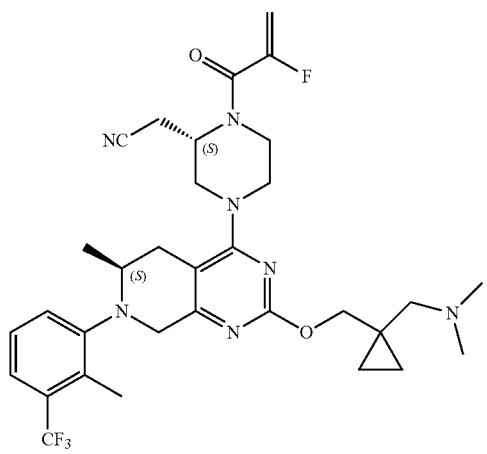
412
-continued
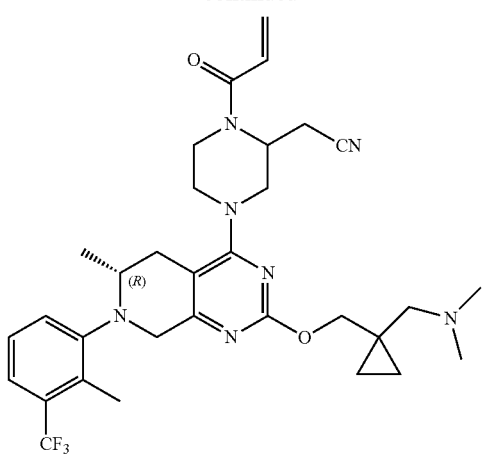
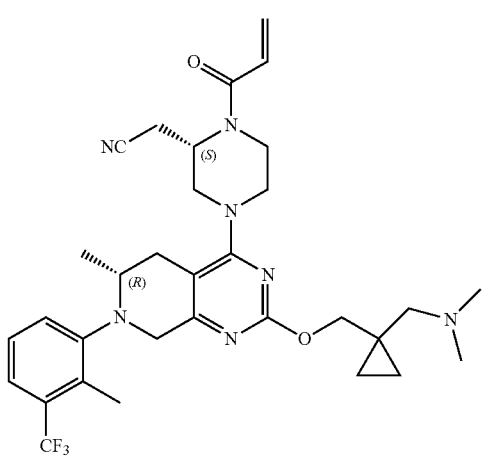
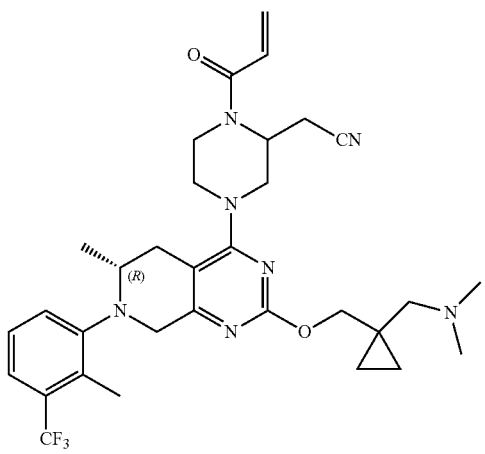

413
-continued
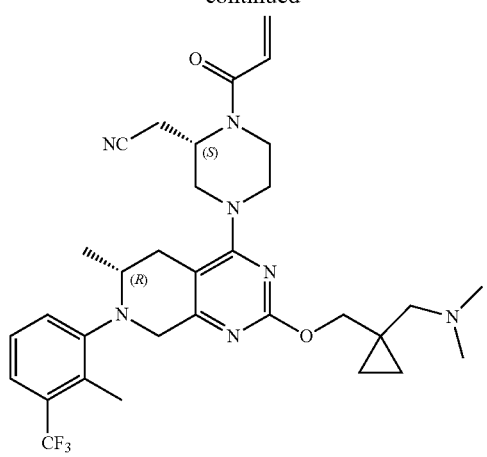
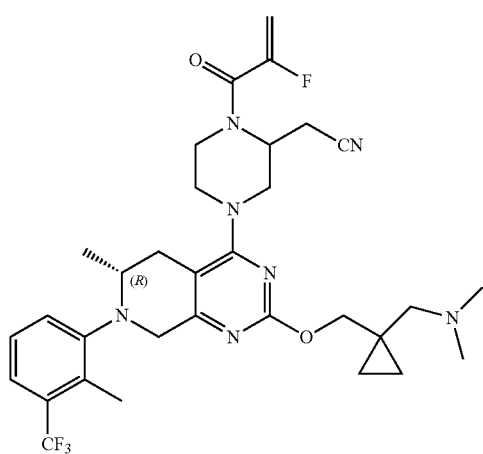
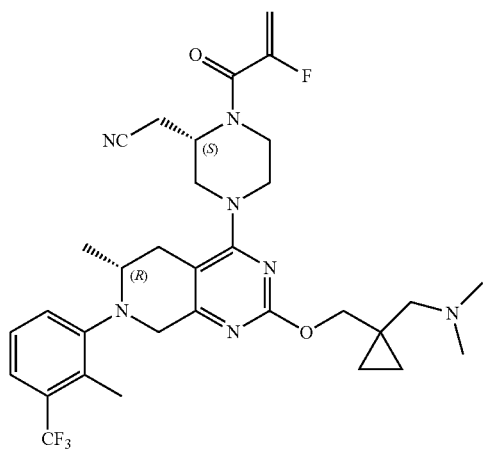
414
-continued
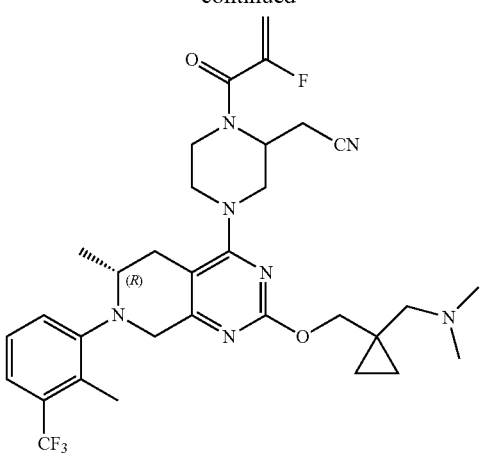
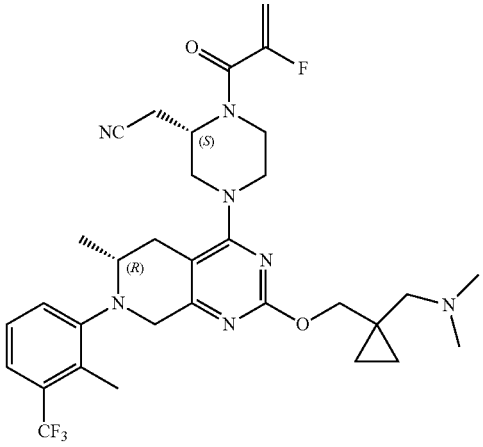
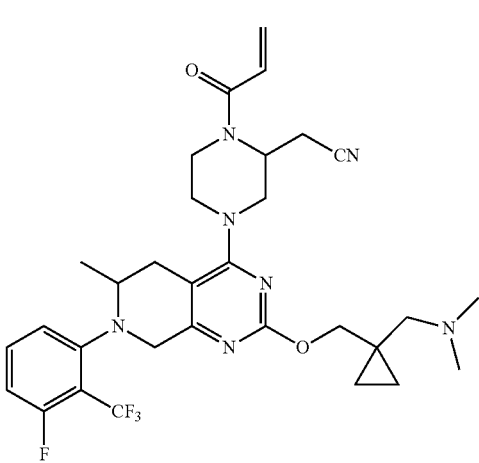

415
-continued
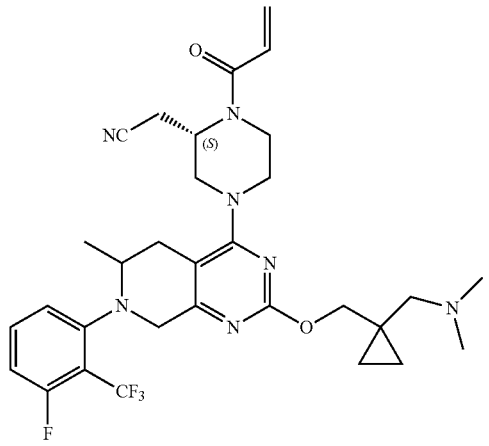
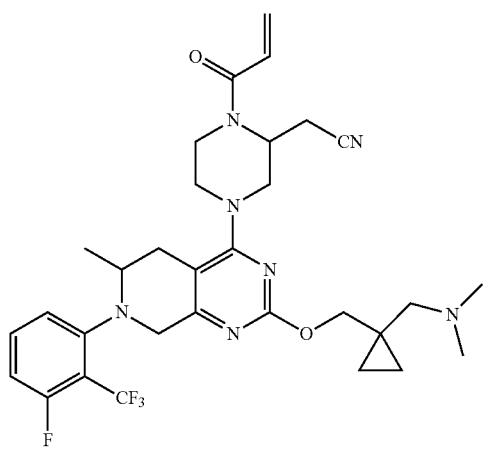
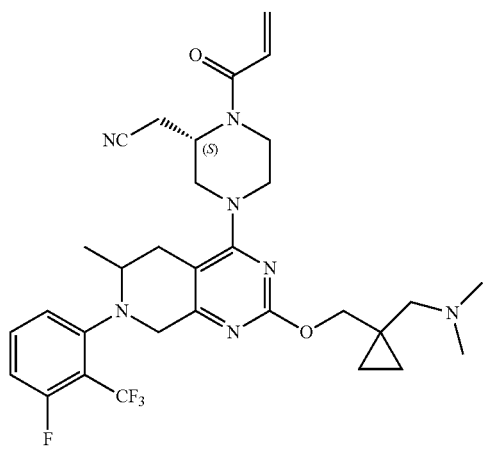
416
-continued
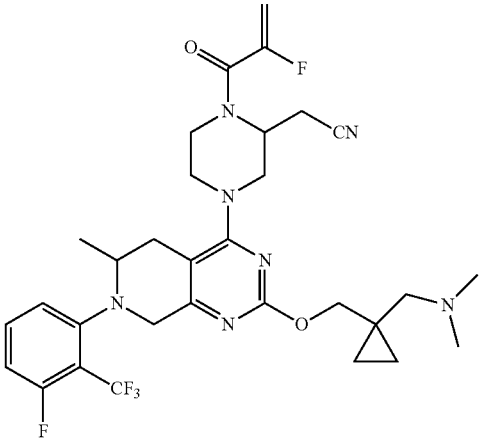
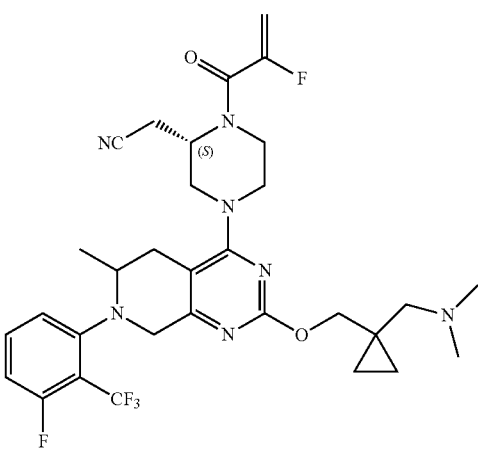
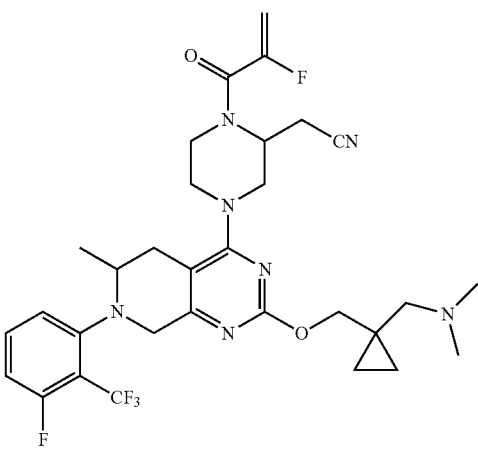

417
-continued
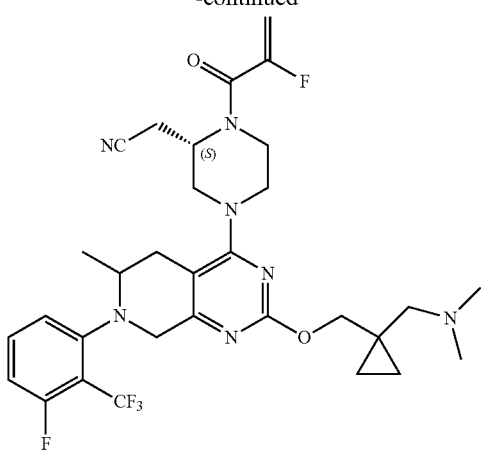
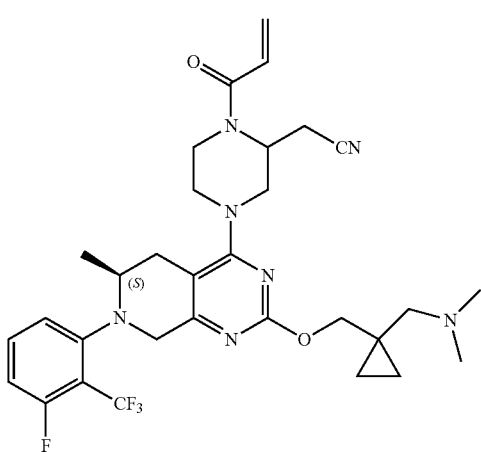
418
-continued
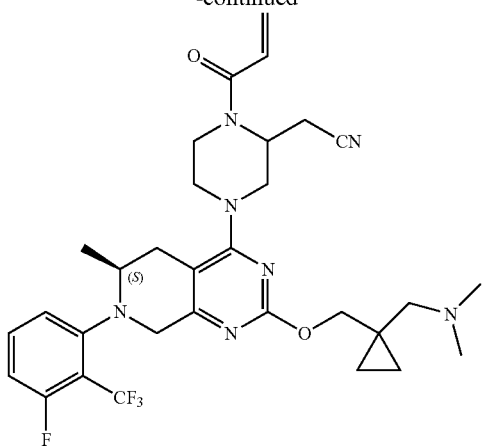
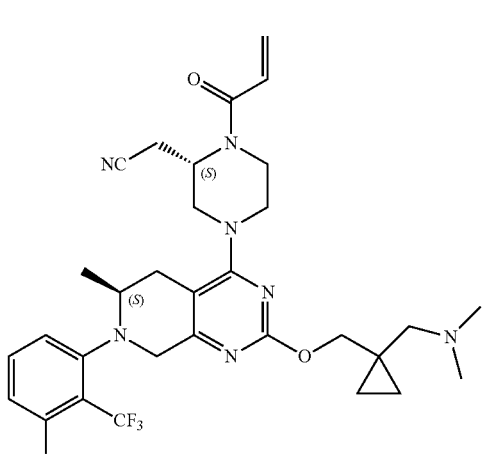
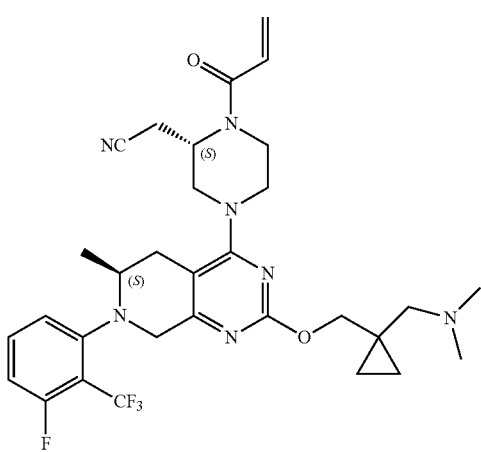
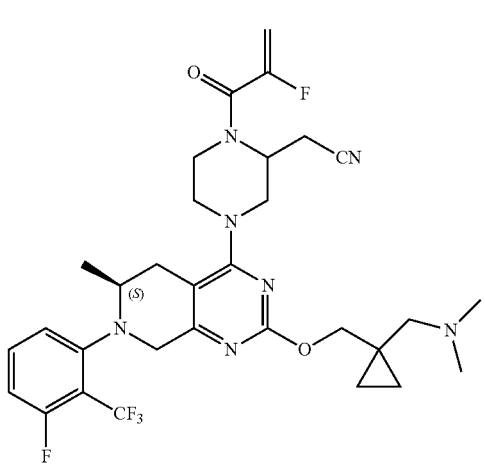

419
-continued
420
-continued
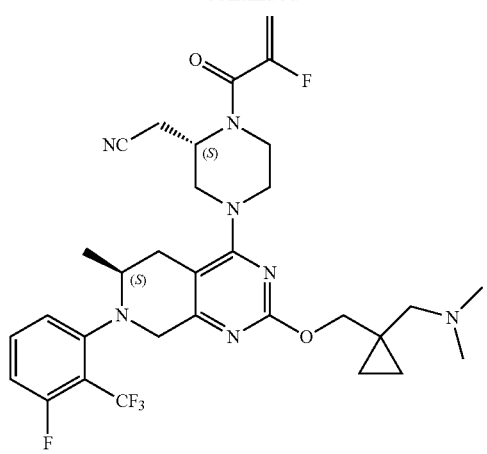
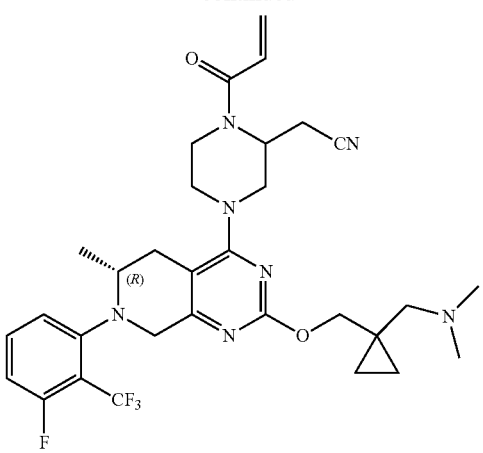
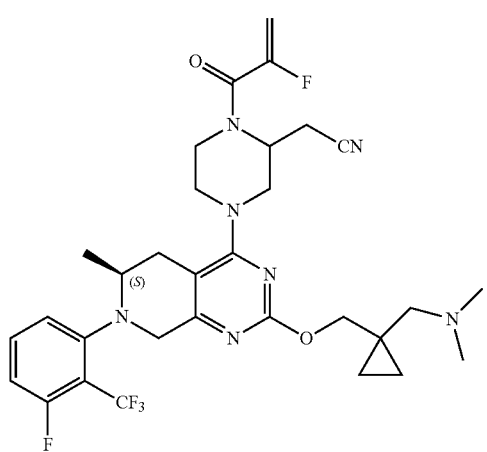
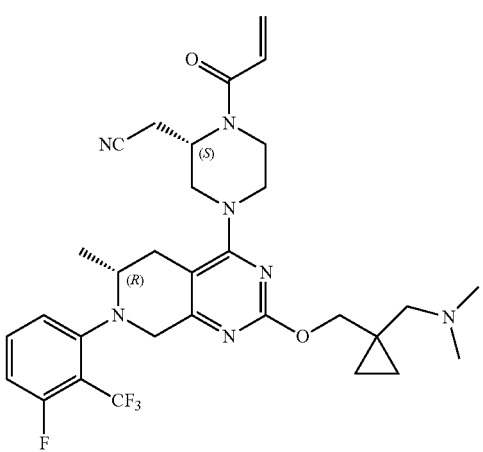
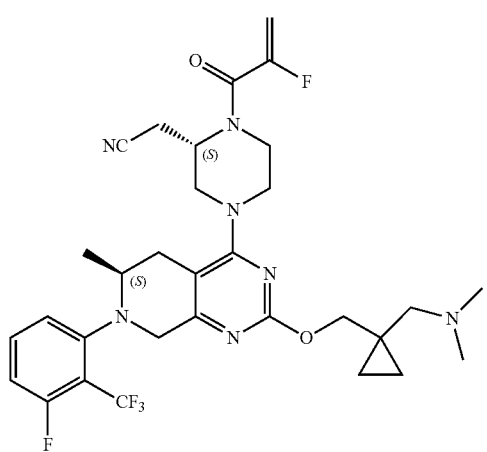
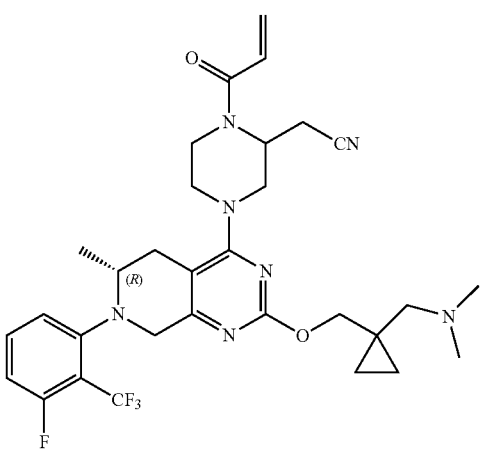

421
-continued
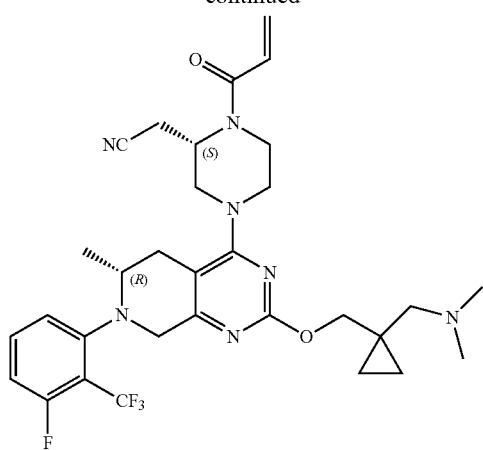
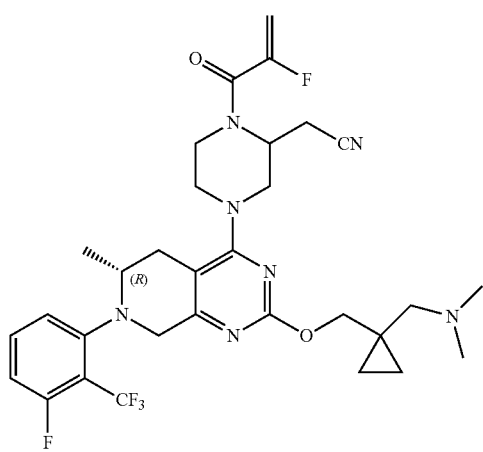
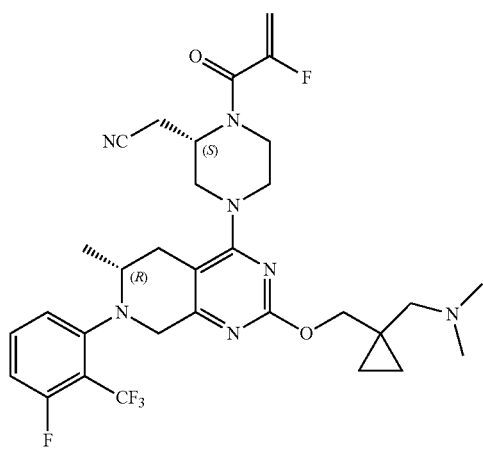
422
-continued
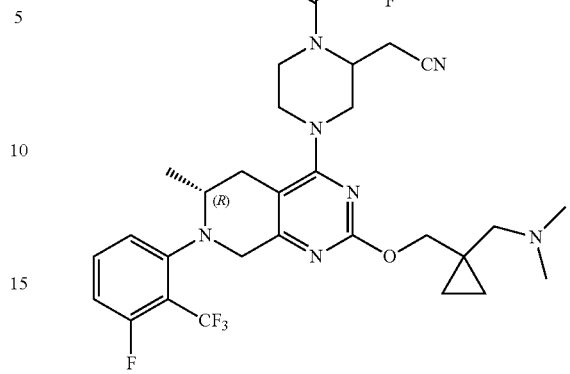
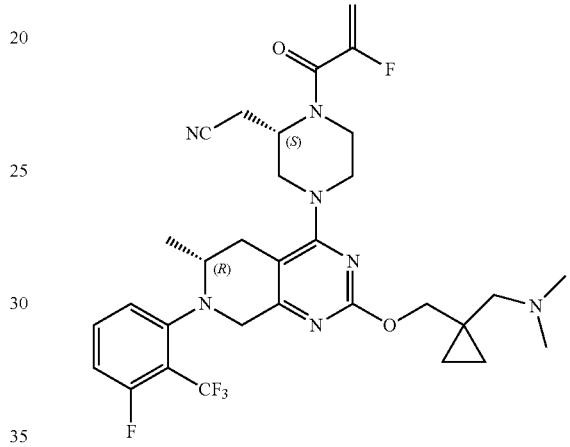
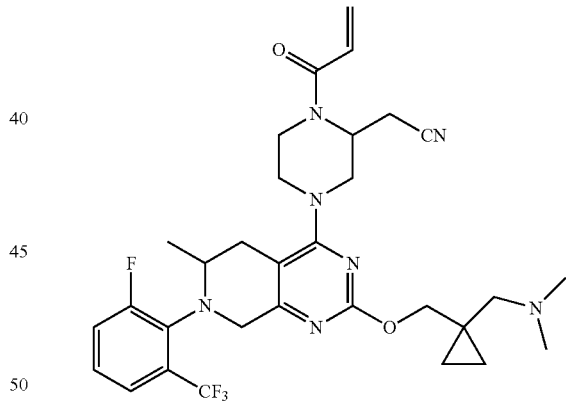
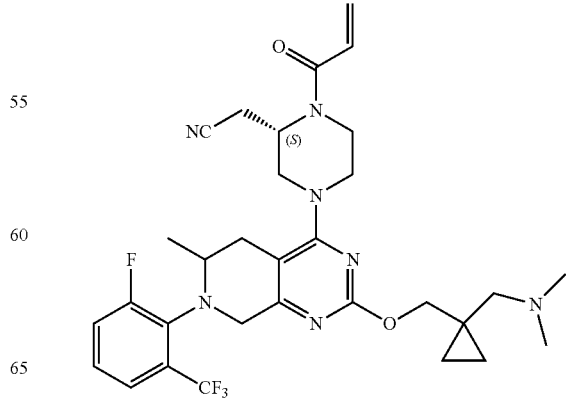

423 -continued
424 -continued
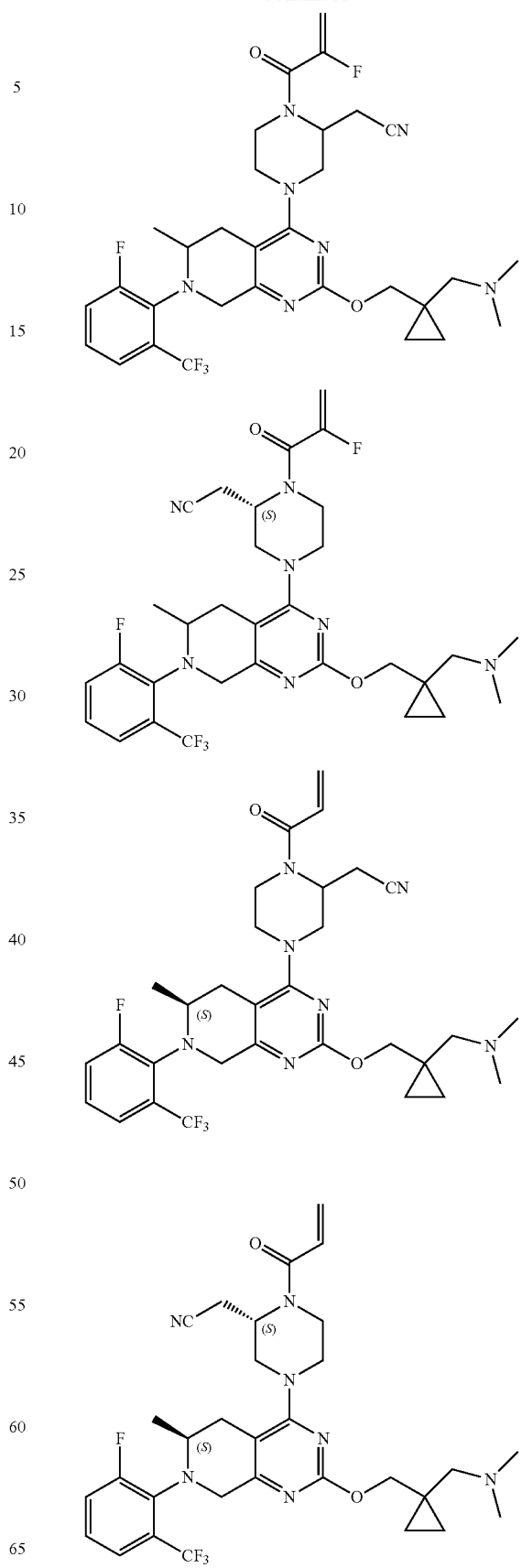

425
-continued
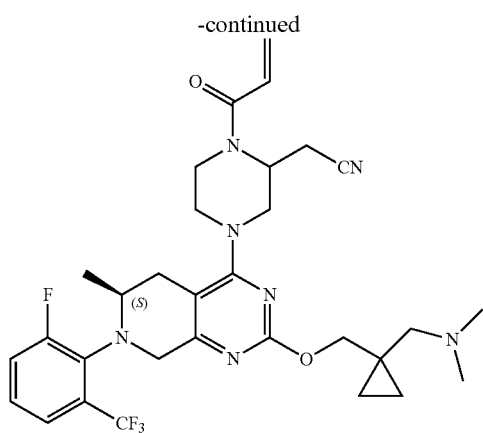
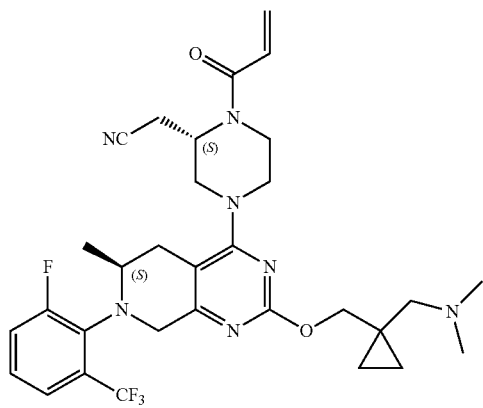
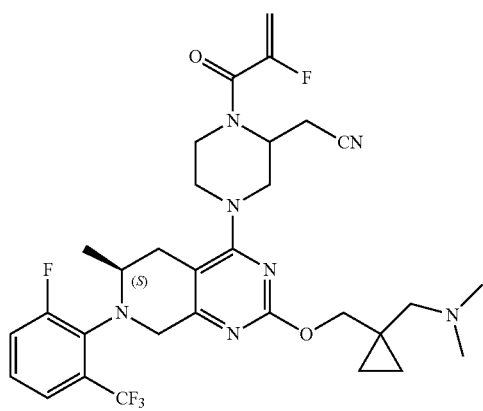
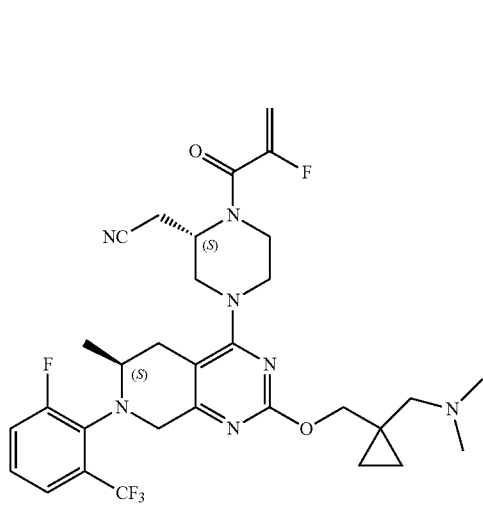
426
-continued
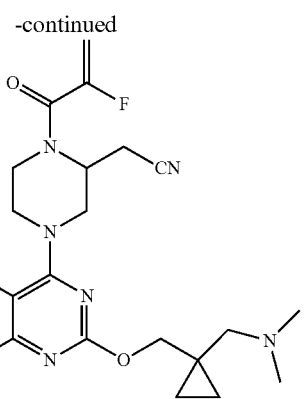
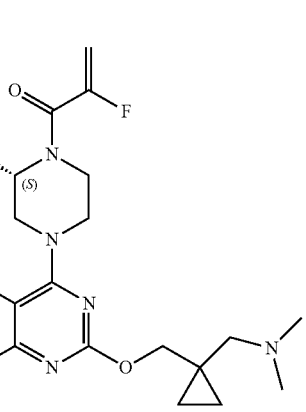
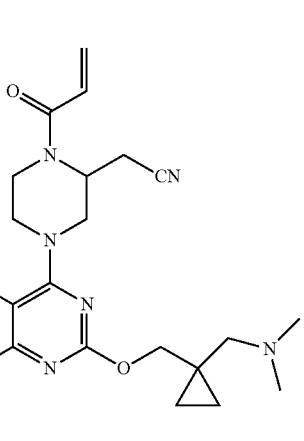
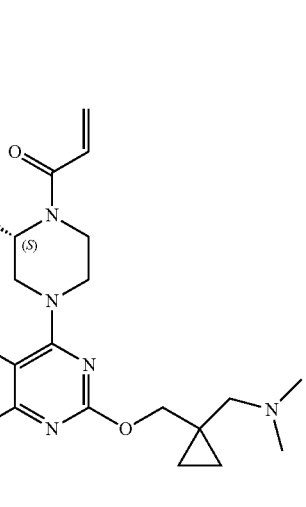

427
-continued
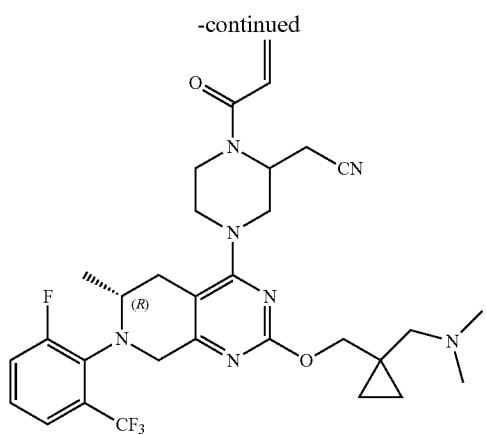
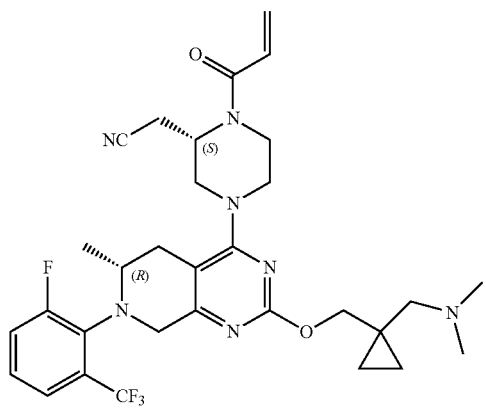
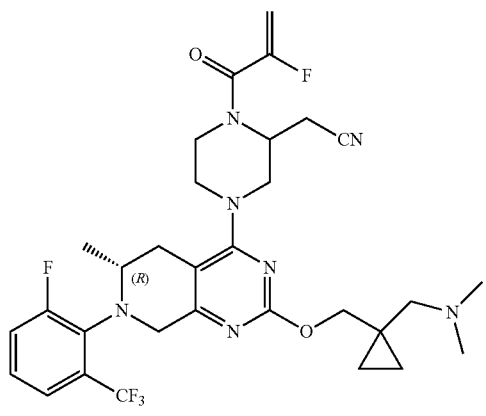
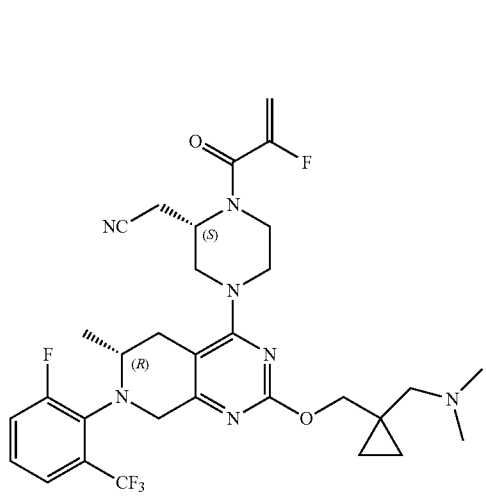
428
-continued
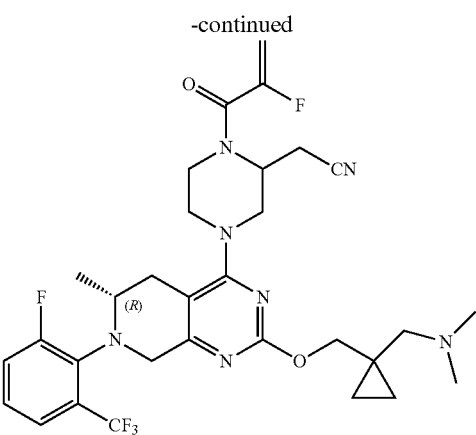
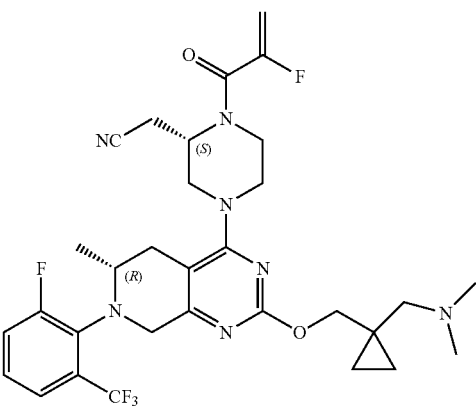
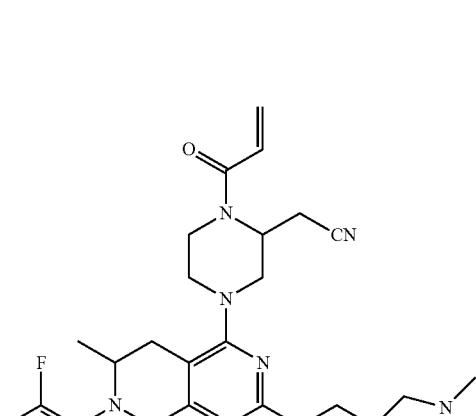
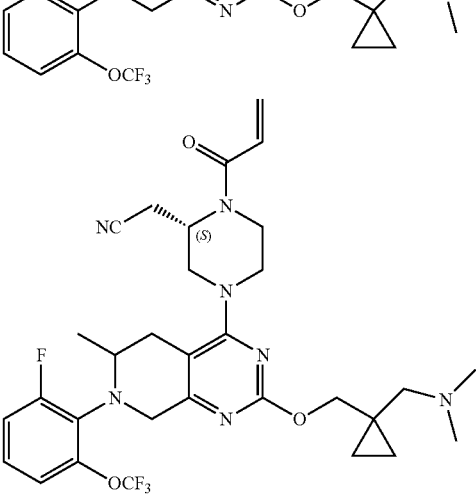

429
-continued

430
-continued

431
-continued
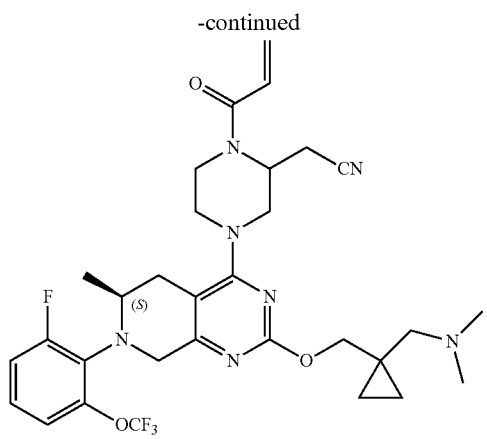
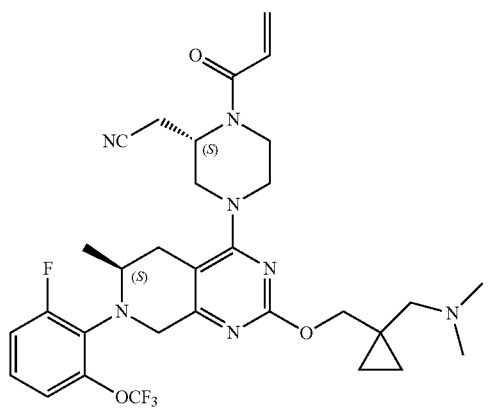
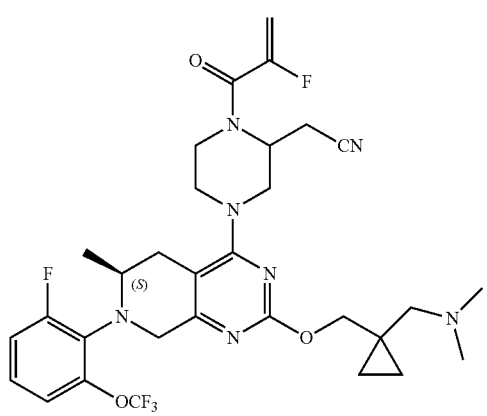
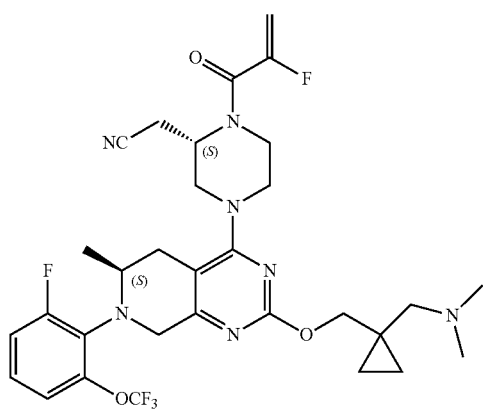
432
-continued
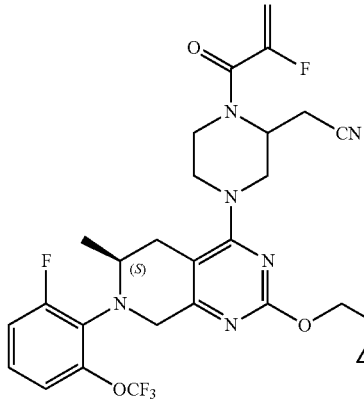
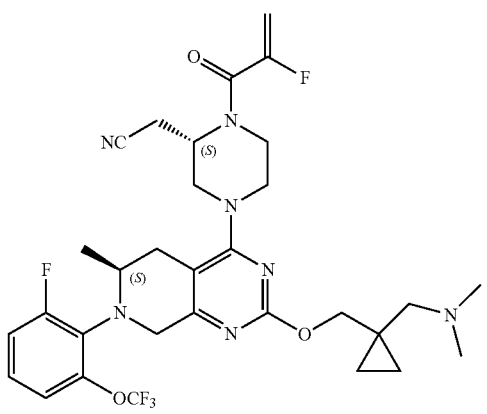
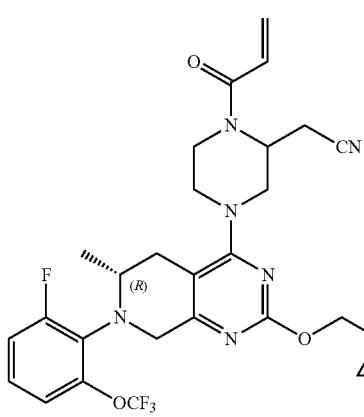
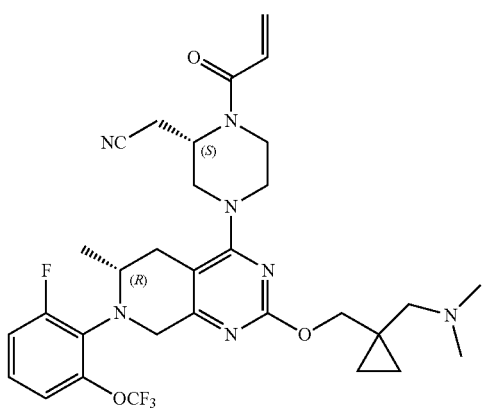

433
-continued
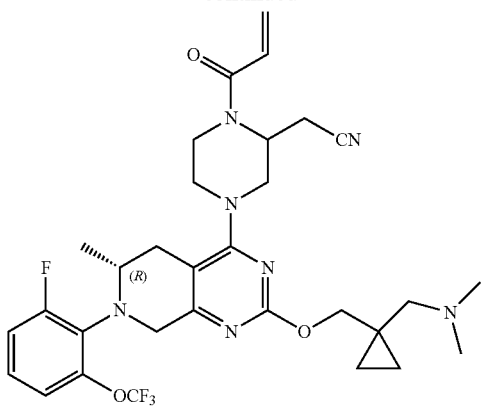
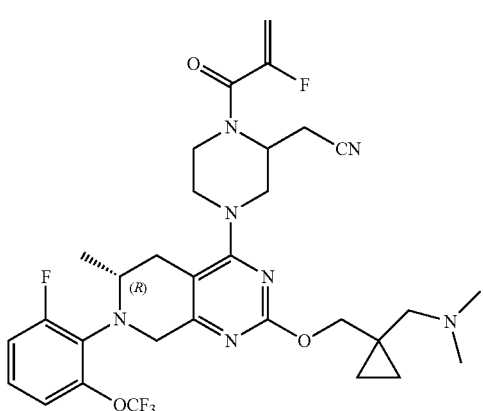
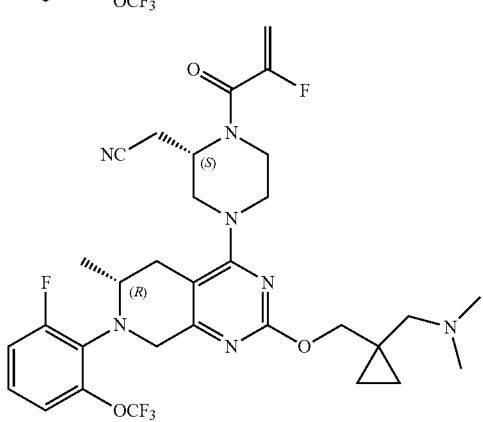
434
-continued
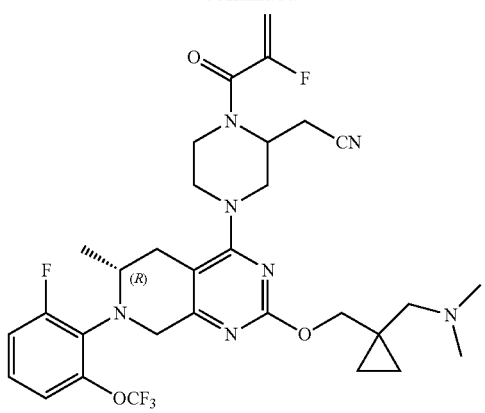
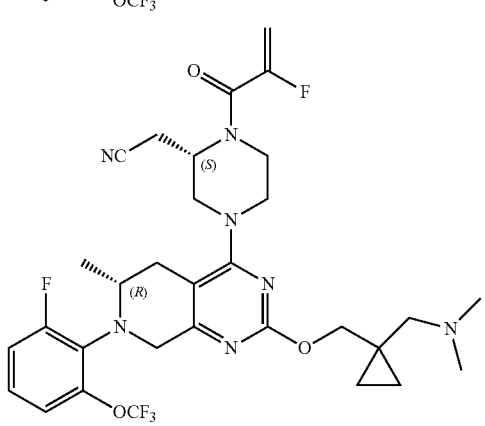
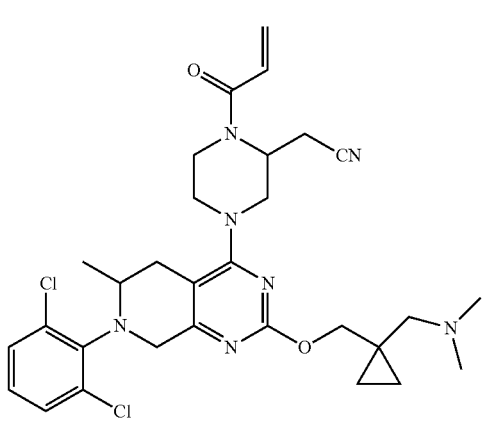
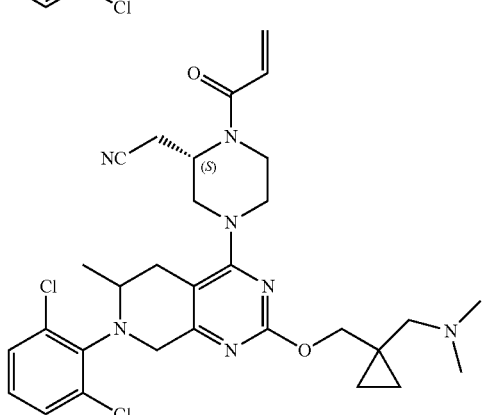

435
-continued
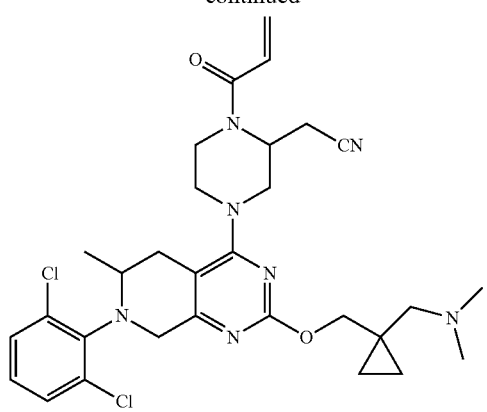
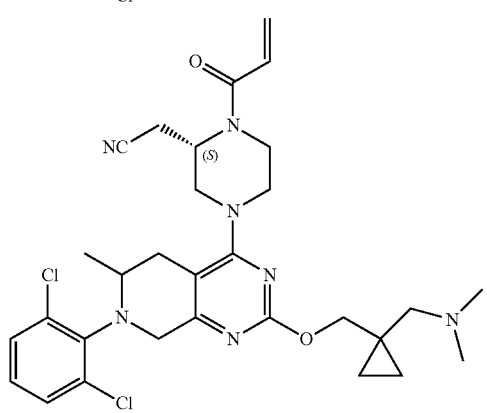
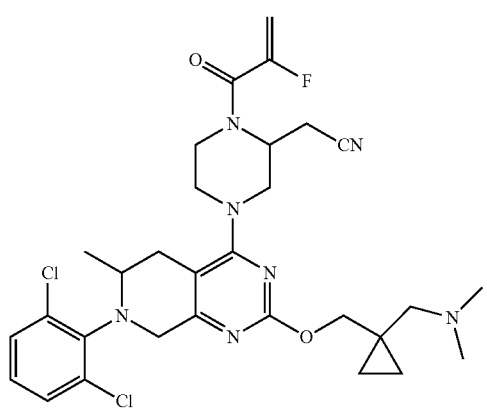
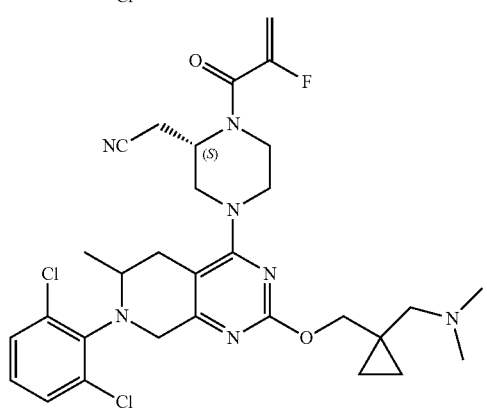
436
-continued
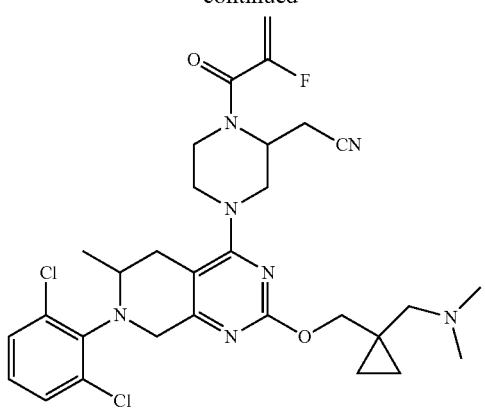
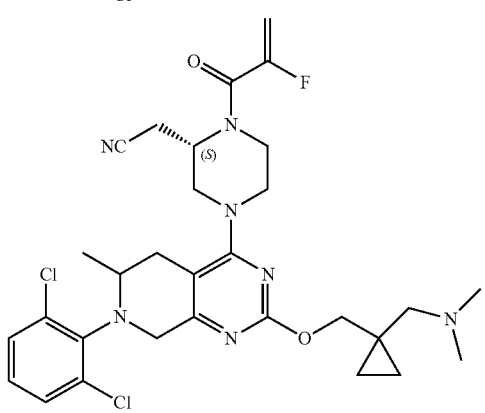
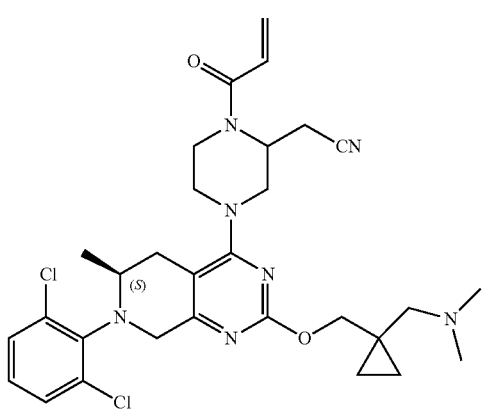
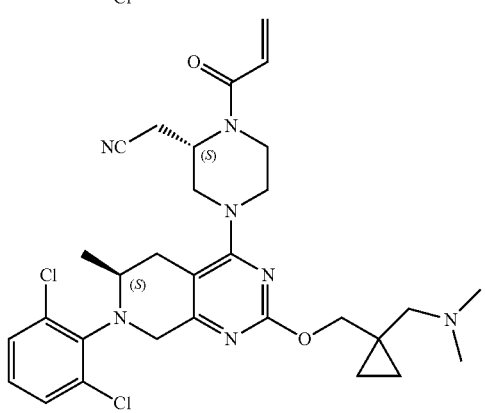

437
-continued
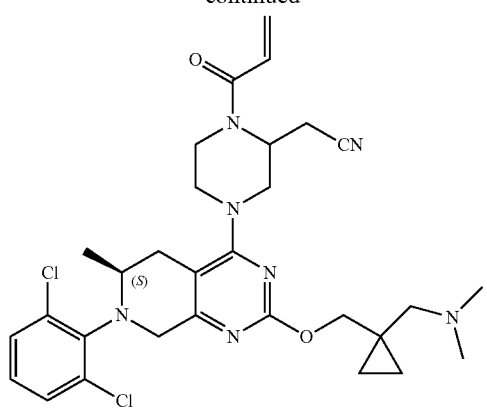
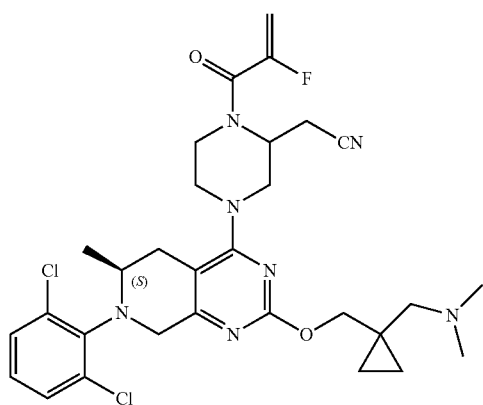
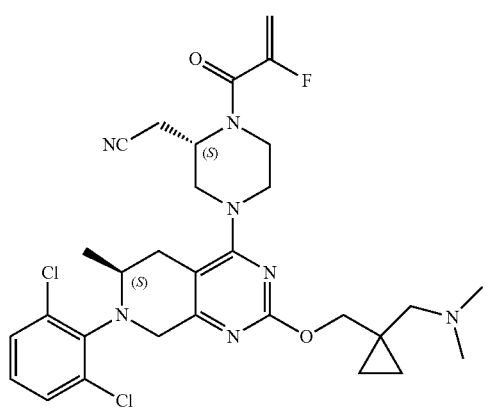
438
-continued
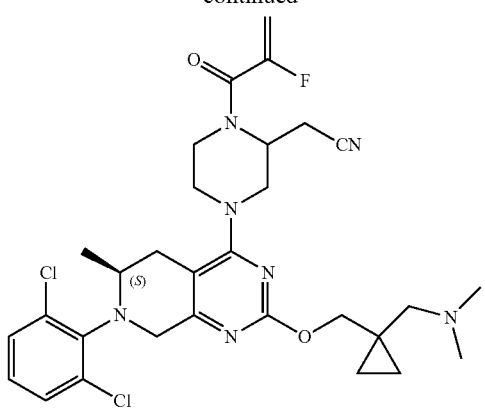
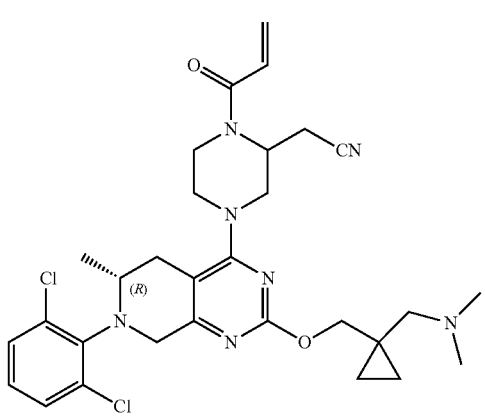
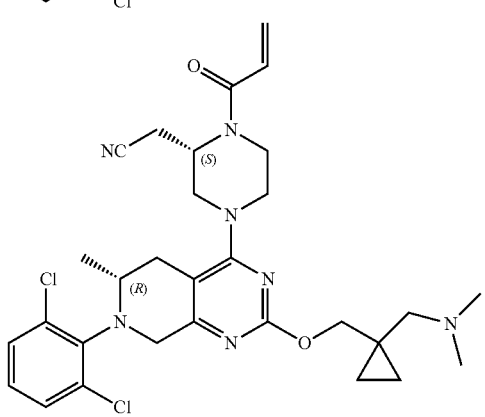

439
-continued
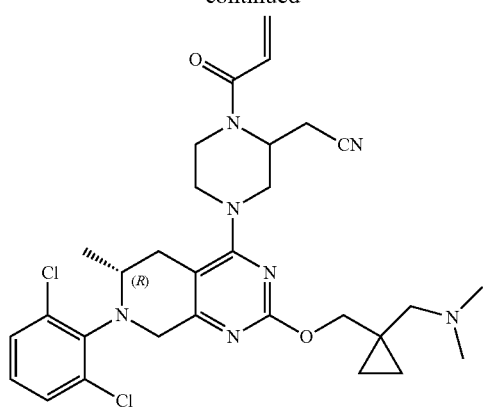
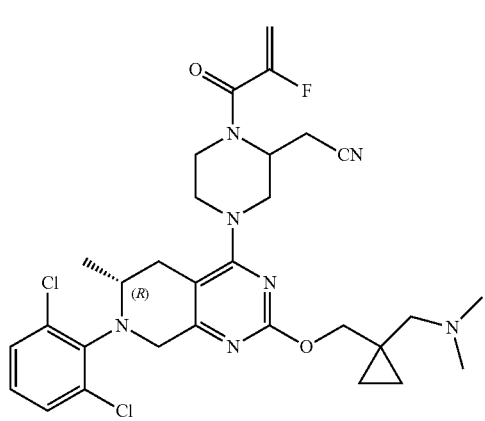
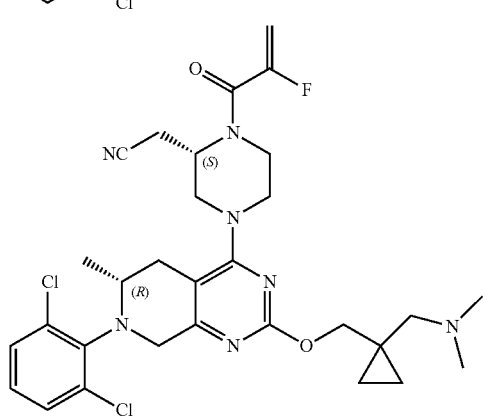
440
-continued
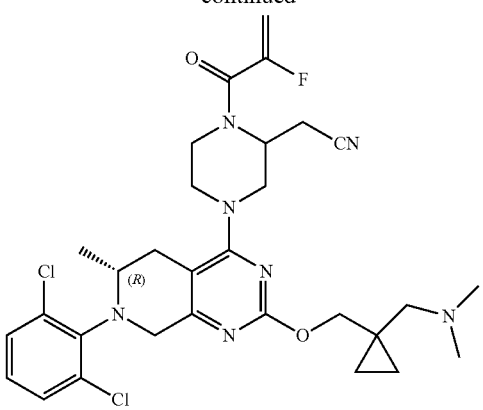
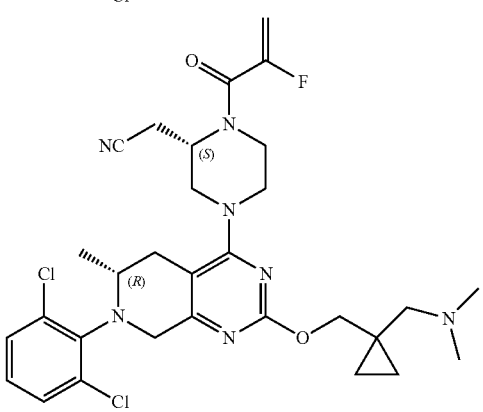
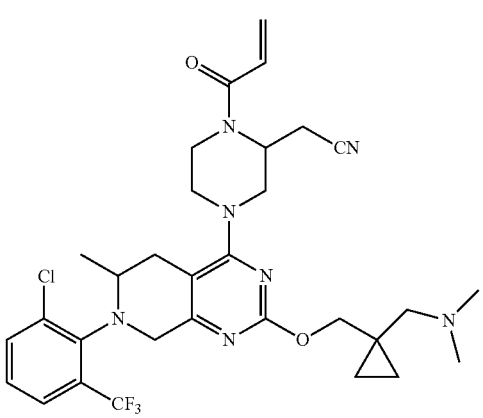
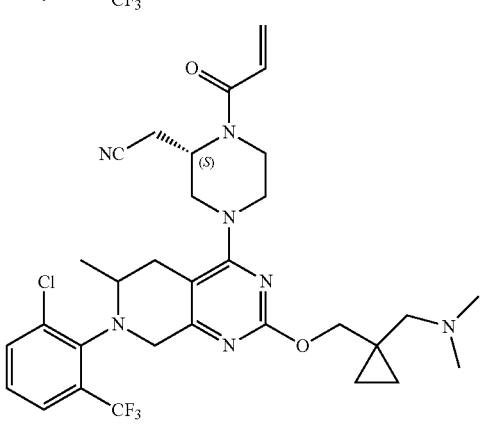

441
-continued
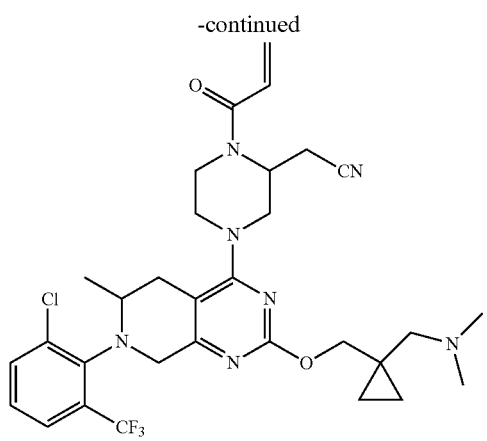
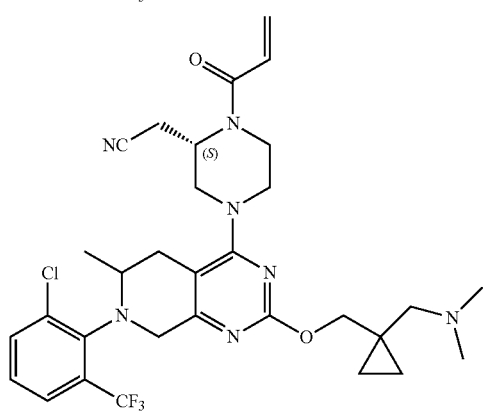
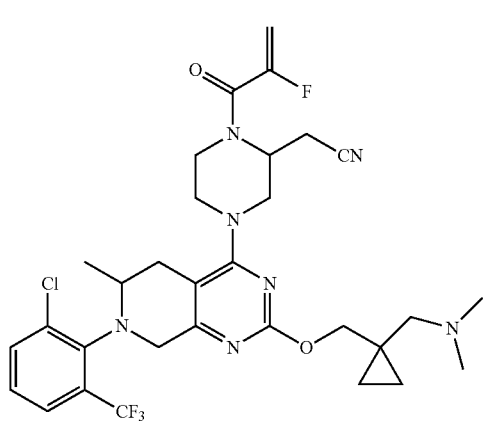
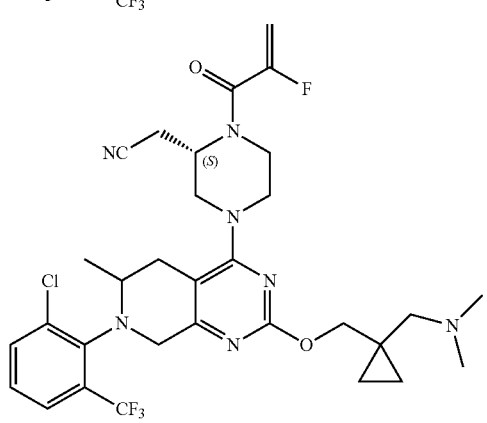
442
-continued
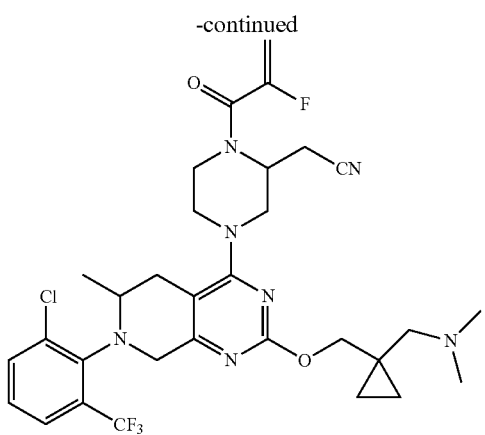
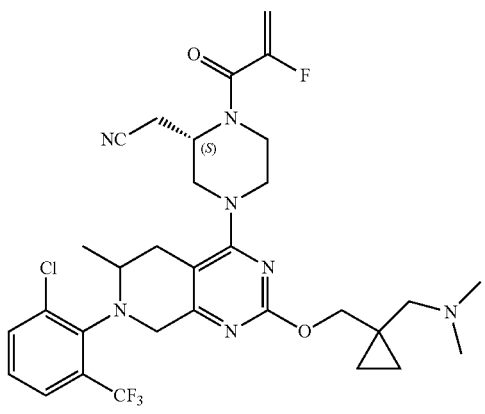
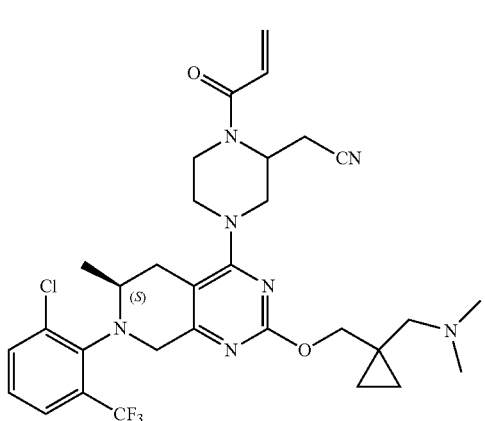
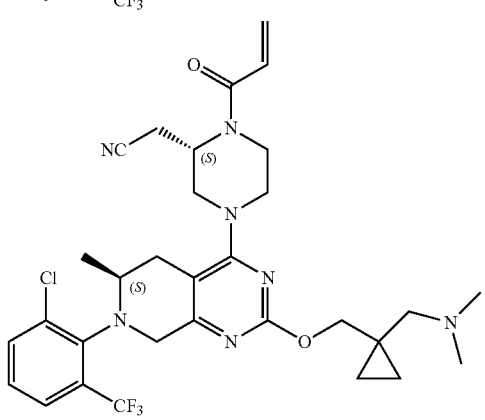

443
-continued
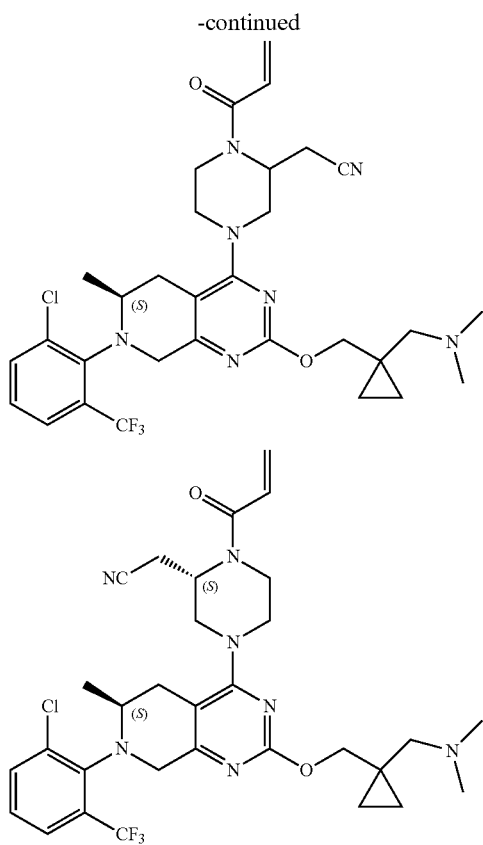
444
-continued
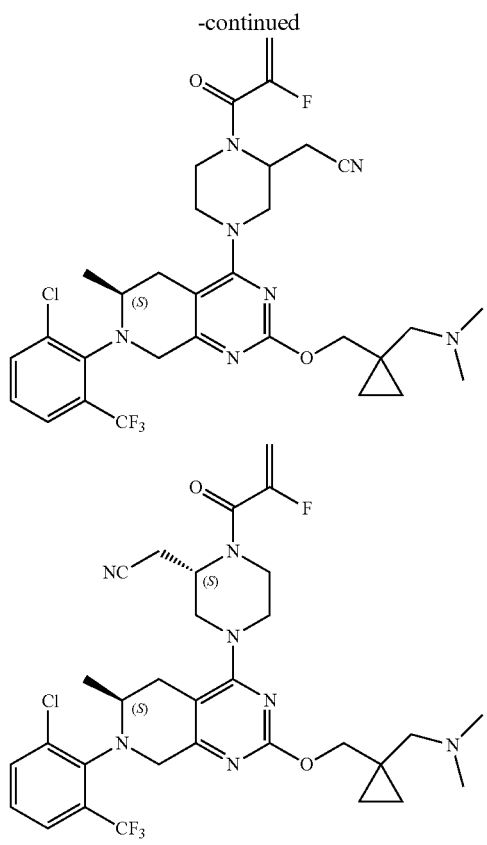
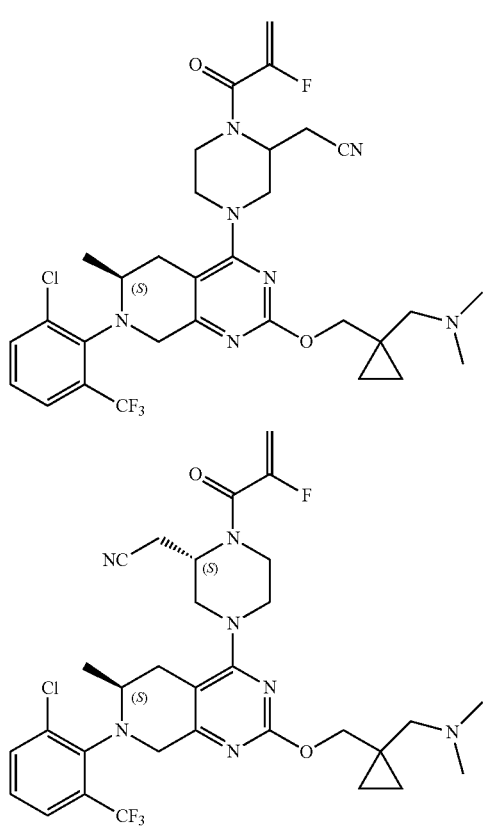
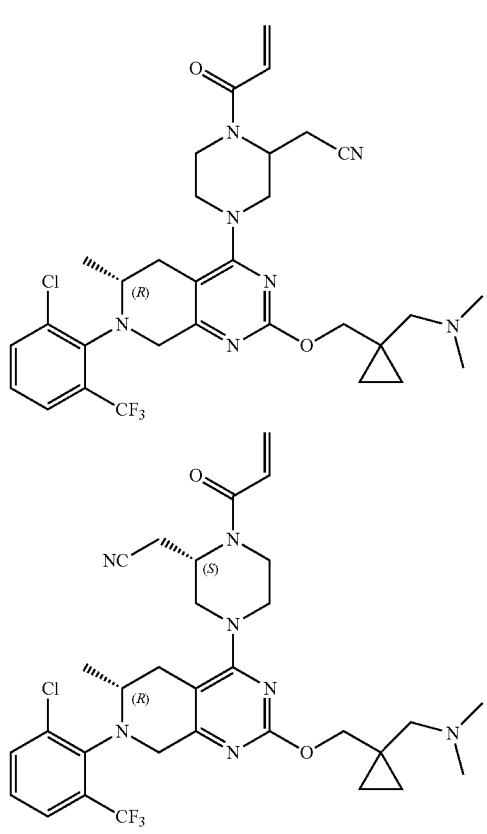

445
-continued
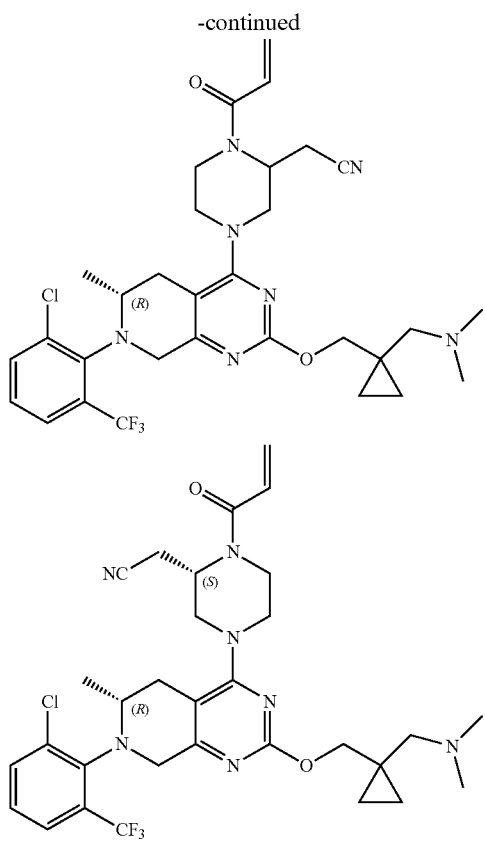
446
-continued
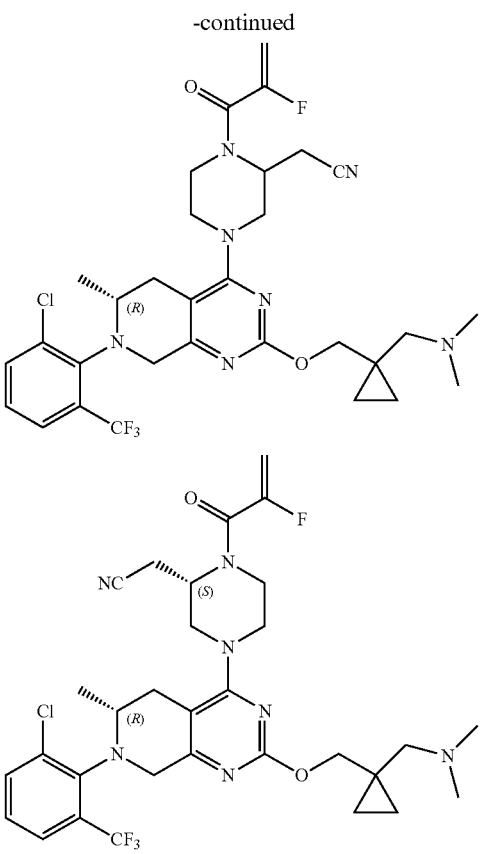
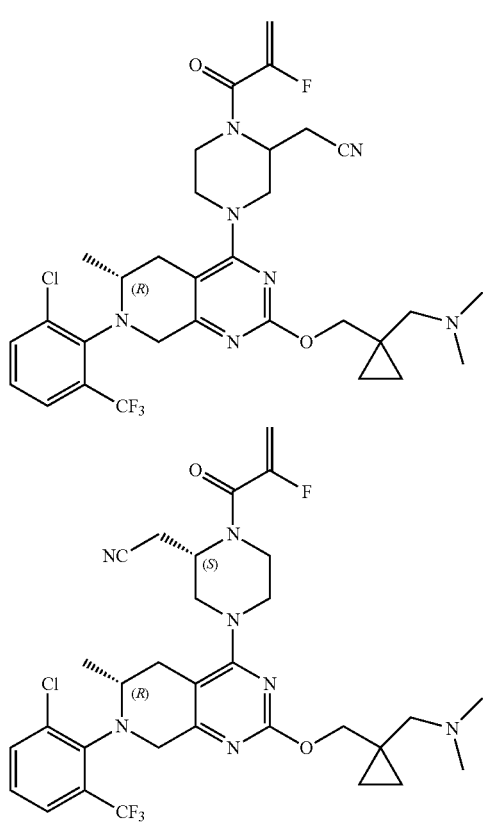
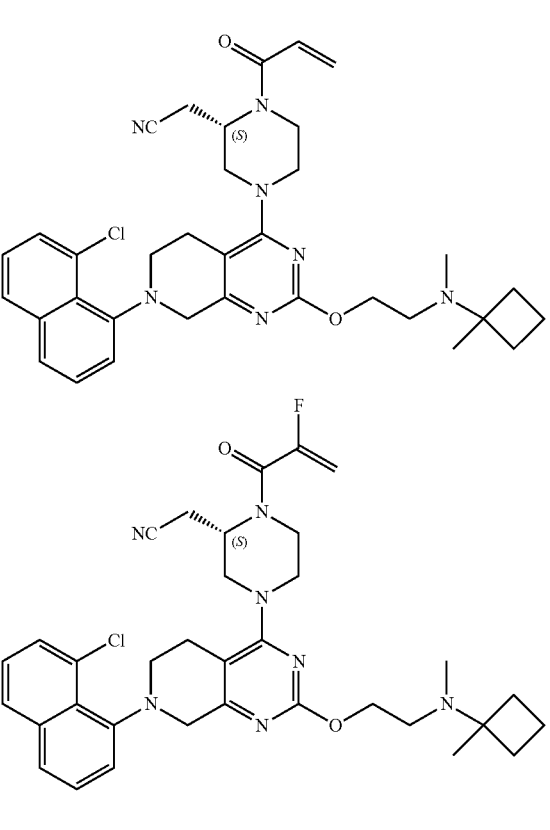

447
-continued
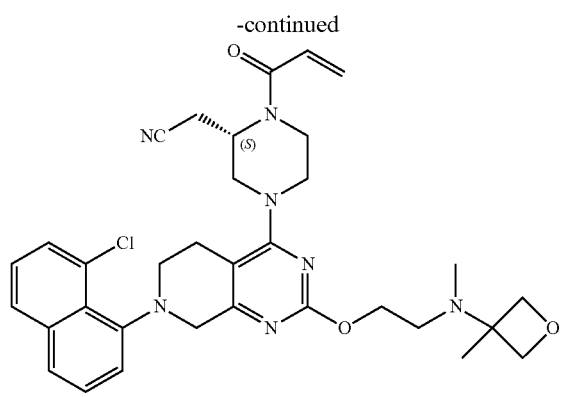
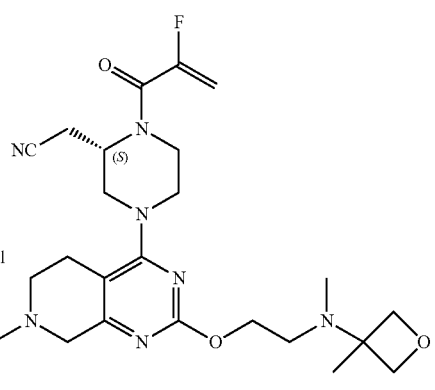
448
-continued
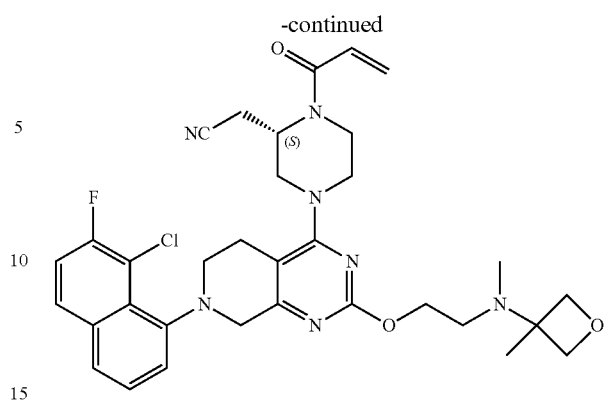
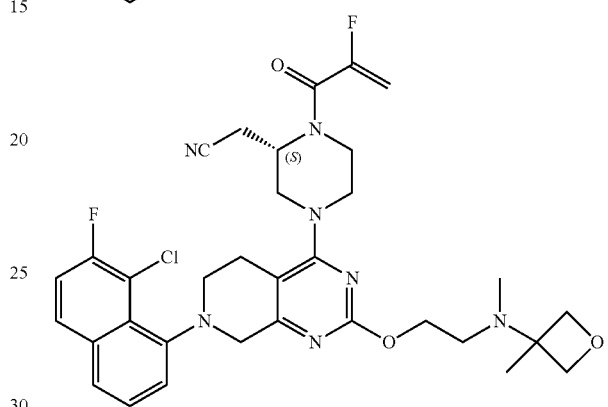
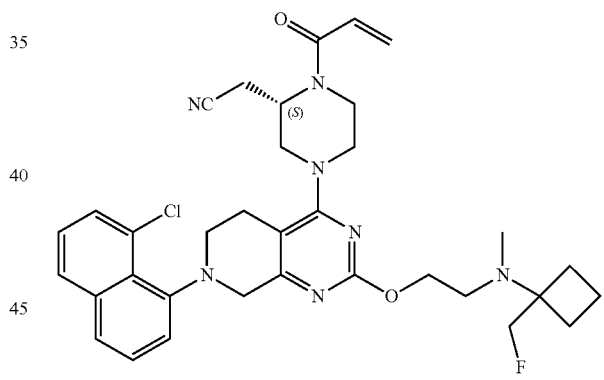
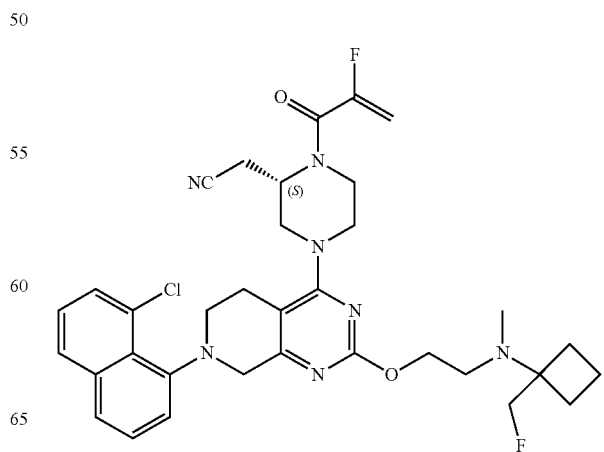

449
-continued
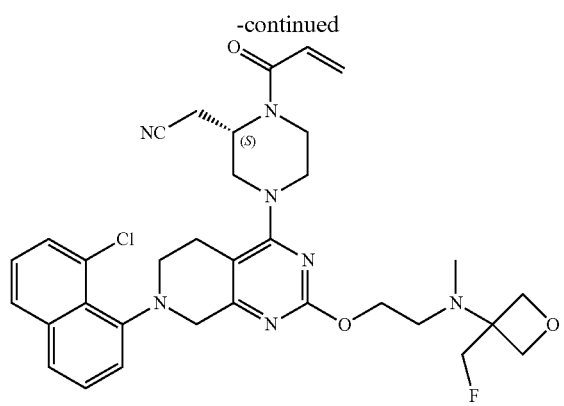
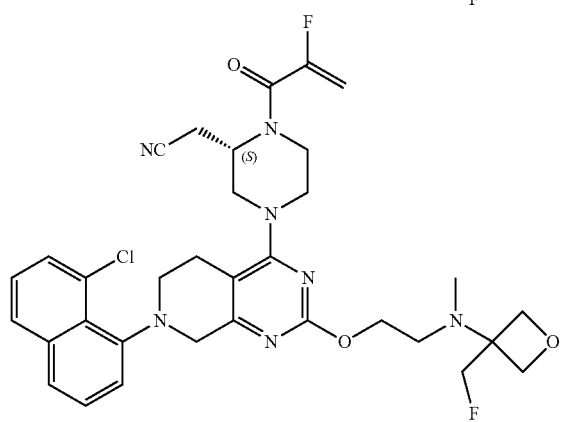
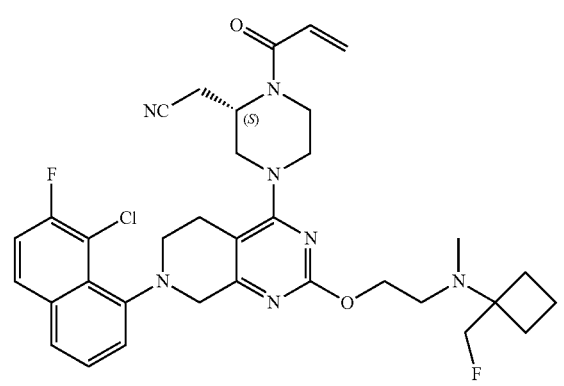
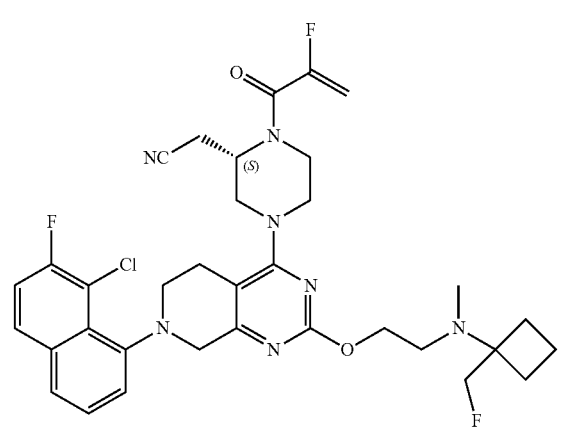
450
-continued
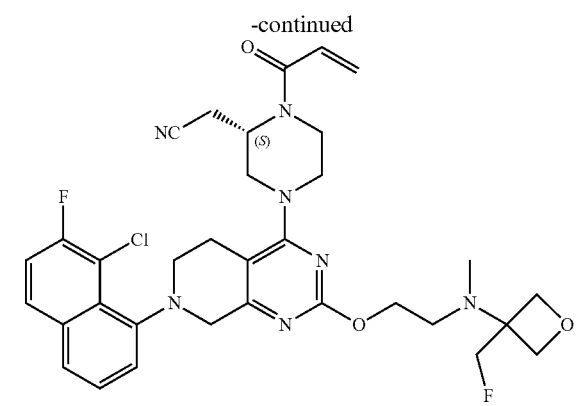
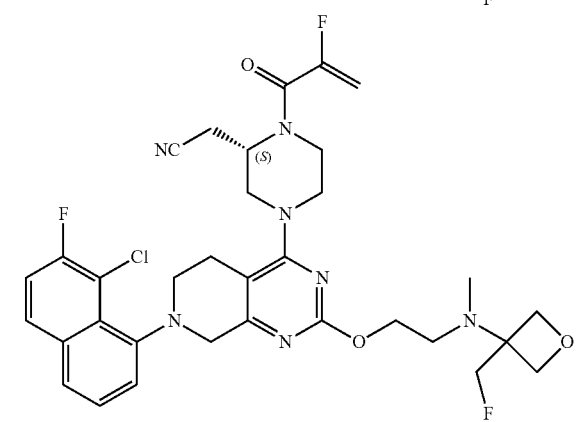
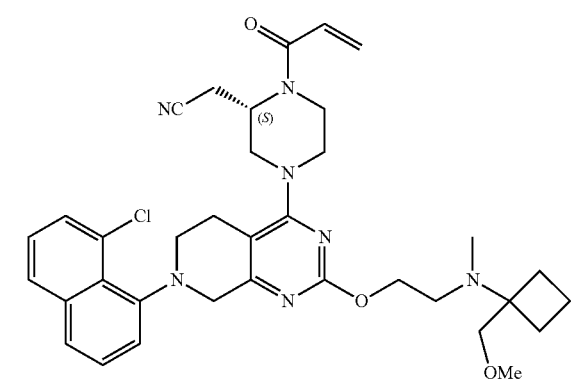
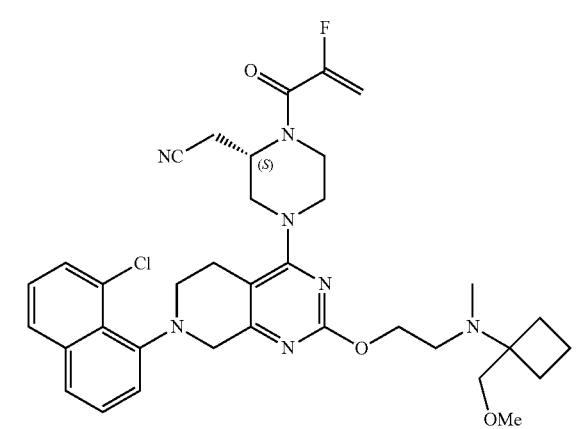

| 451 | 452 |
|---|---|
| -continued | -continued |
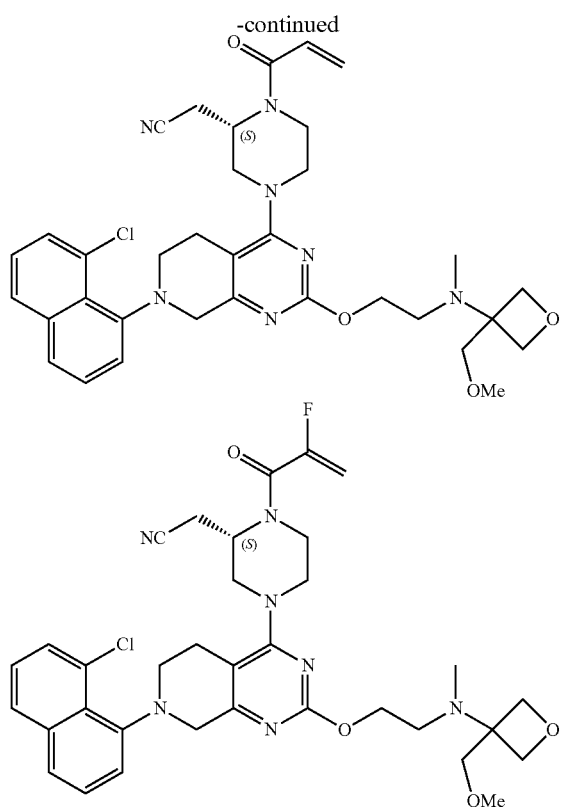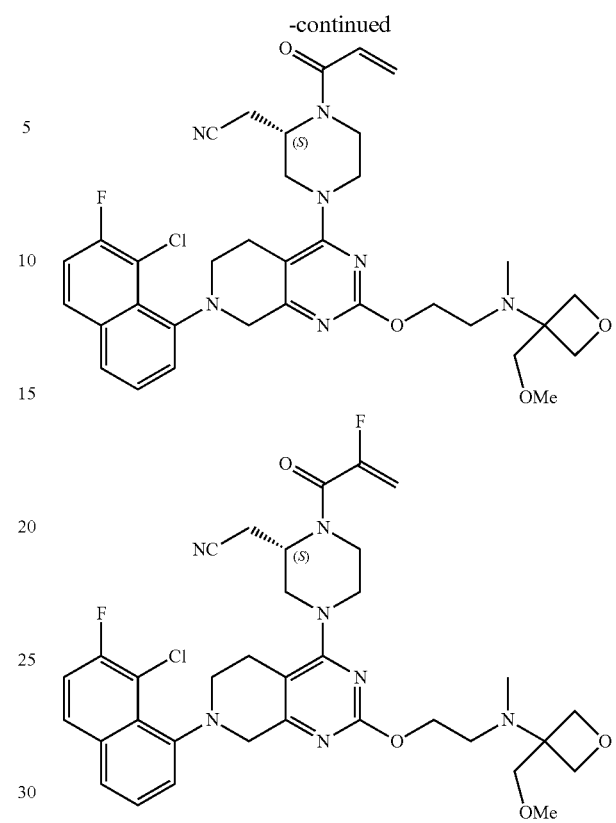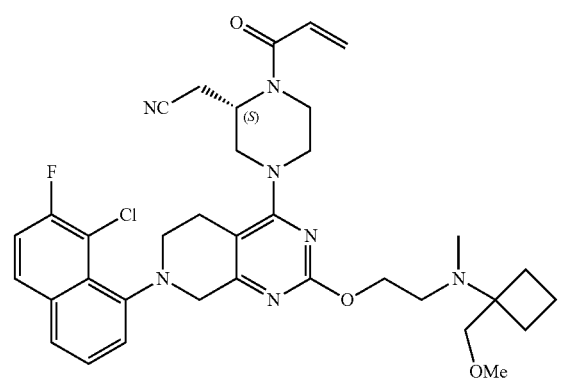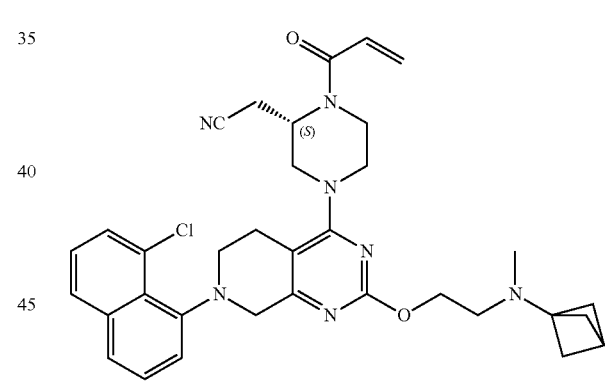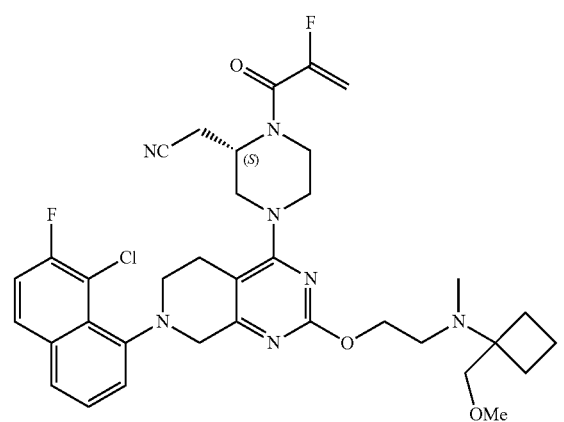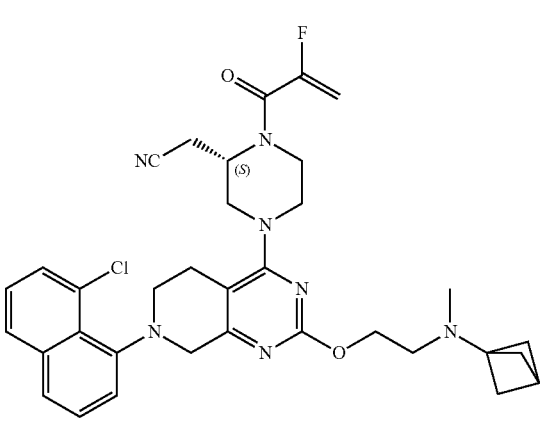

453
-continued
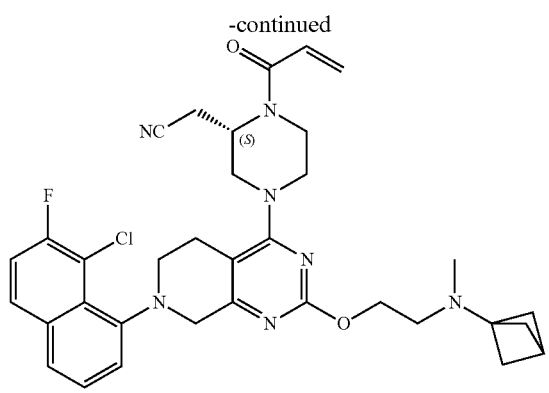
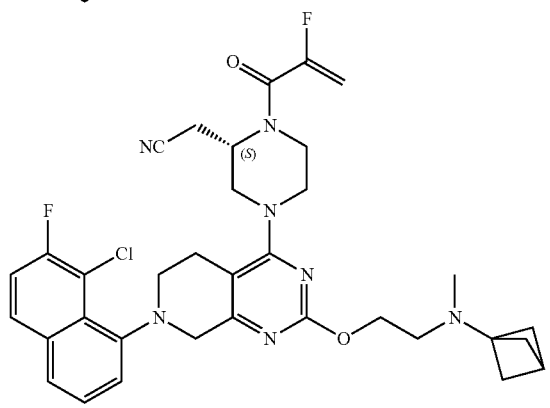
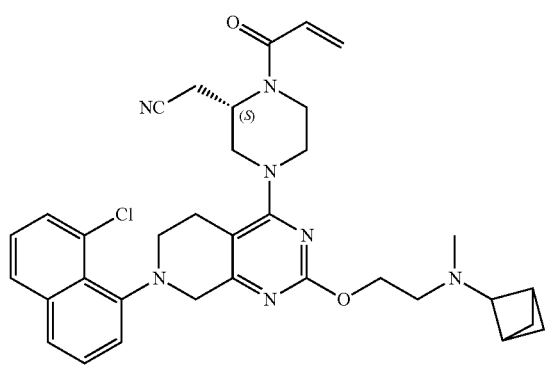
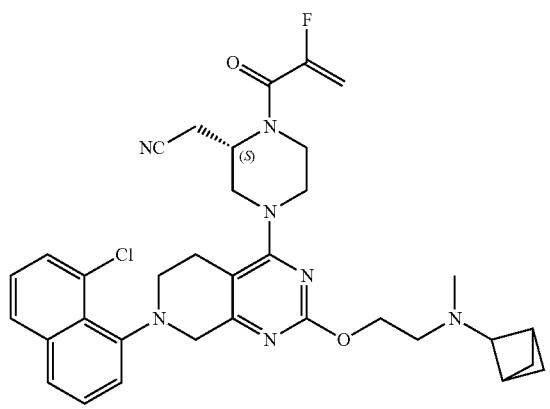
454
-continued
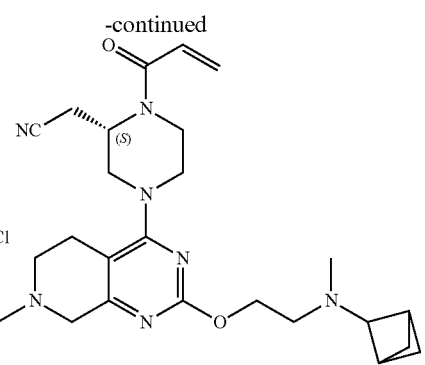
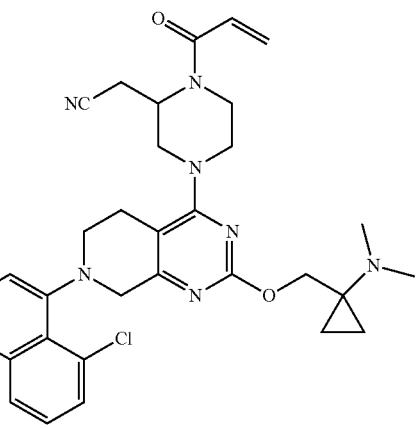
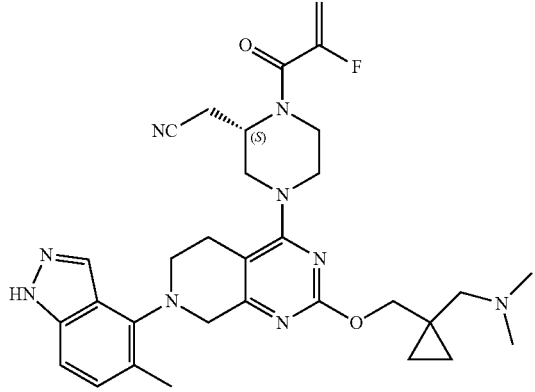

455
-continued
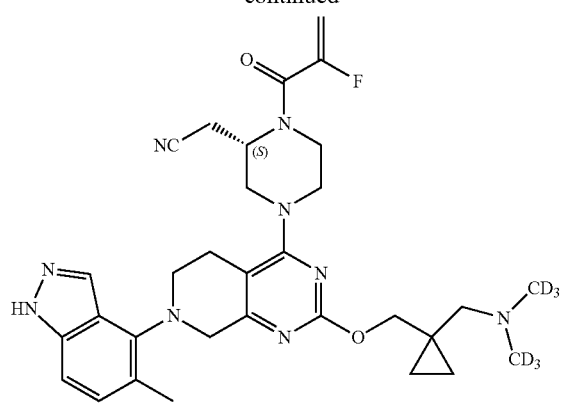
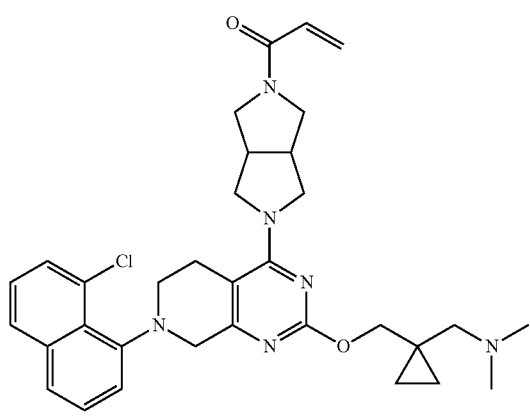
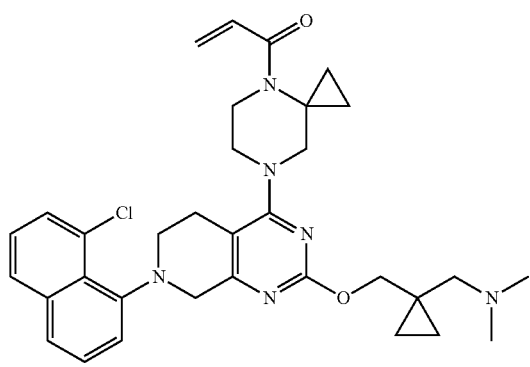
456
-continued
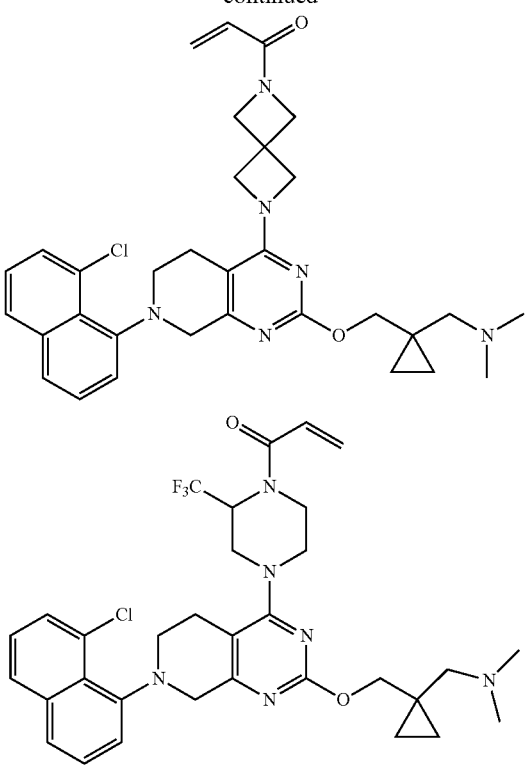
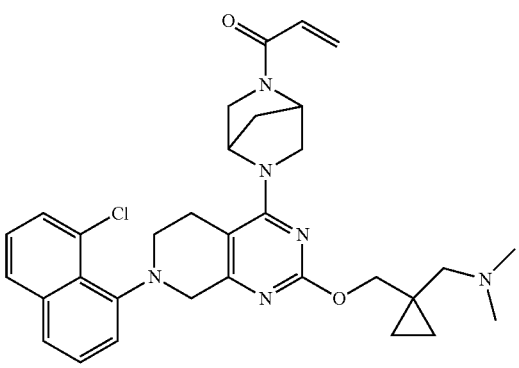
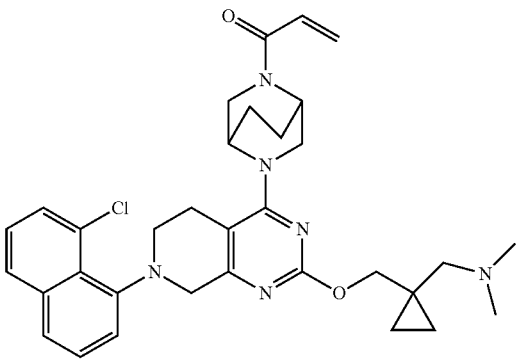

457
-continued
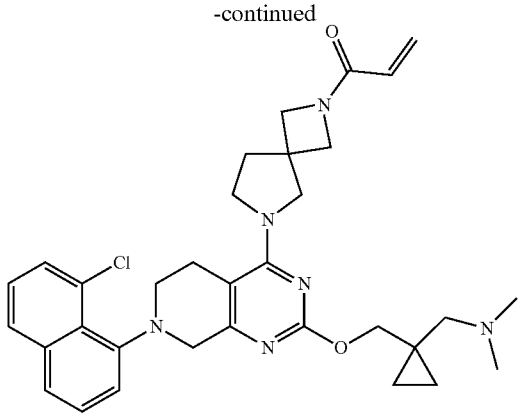
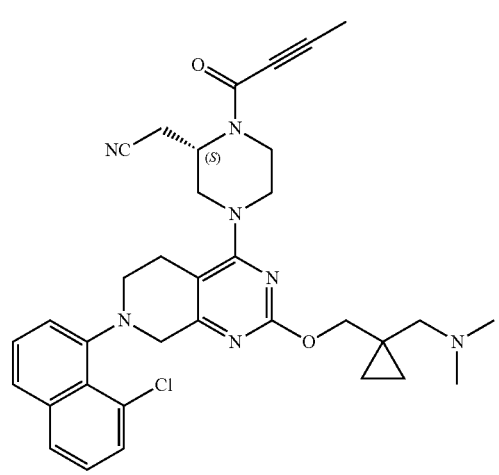
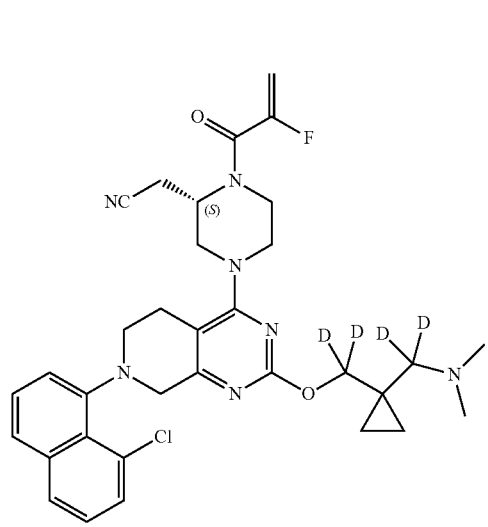
458
-continued
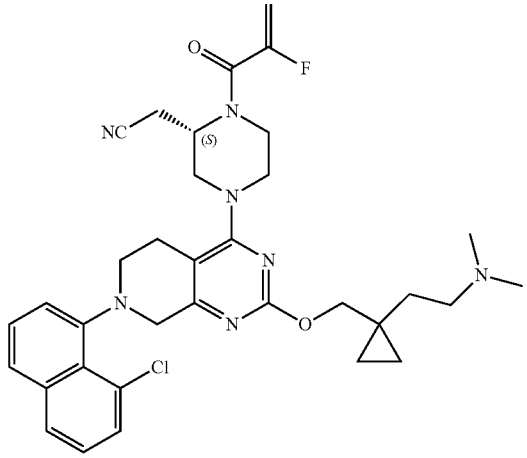
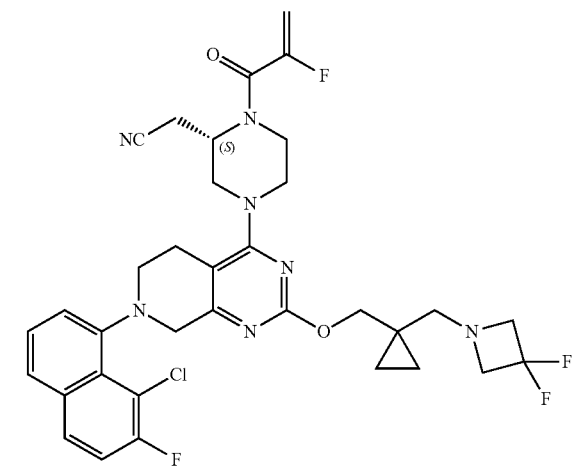

459
-continued

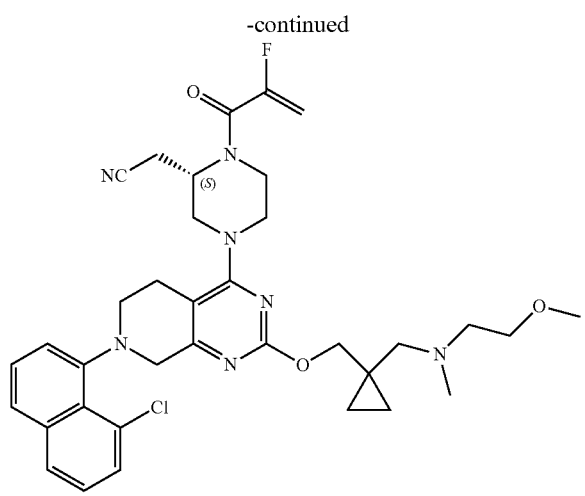

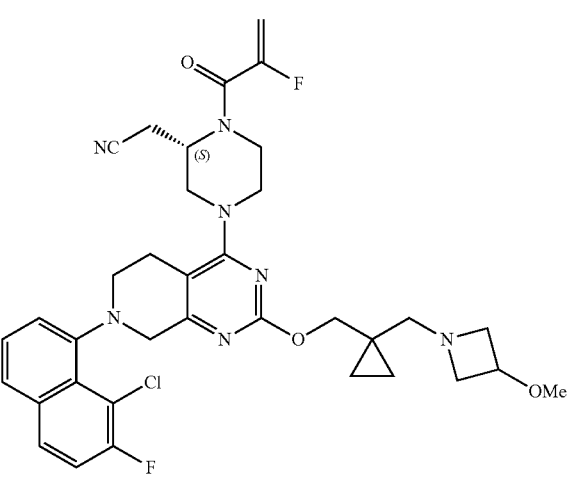

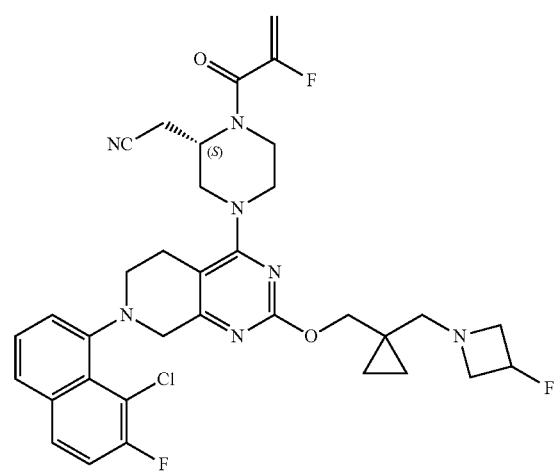

460
-continued

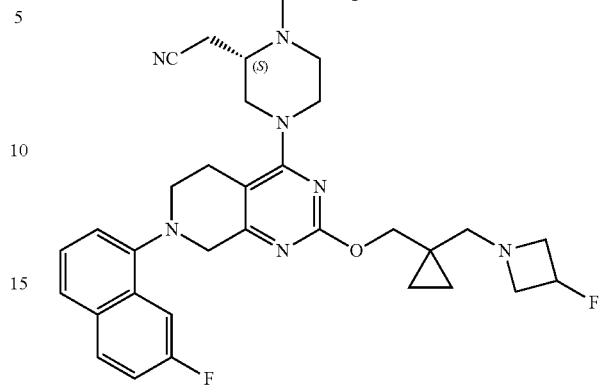

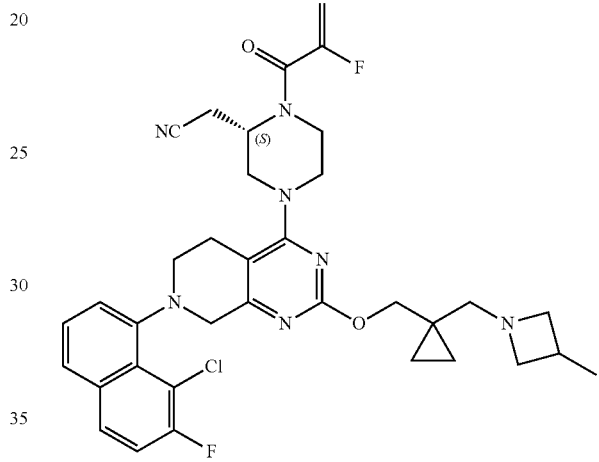

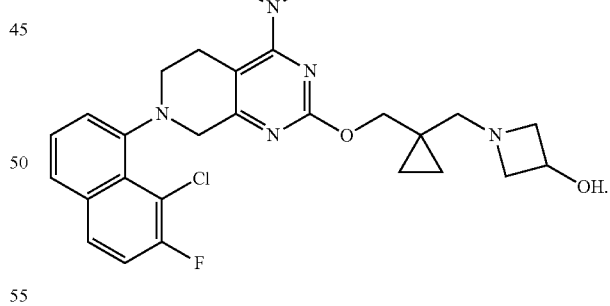

In another preferred embodiment, the compound of formula I is selected from the group consisting of the compounds shown in the Examples.

In the second aspect of the invention, a preparation method for cycloalkyl and heterocycloalkyl compounds of formula (I), the stereoisomer, tautomer, crystal form, pharmaceutically acceptable salt, hydrate, solvate or prodrug thereof is provided, comprising steps:

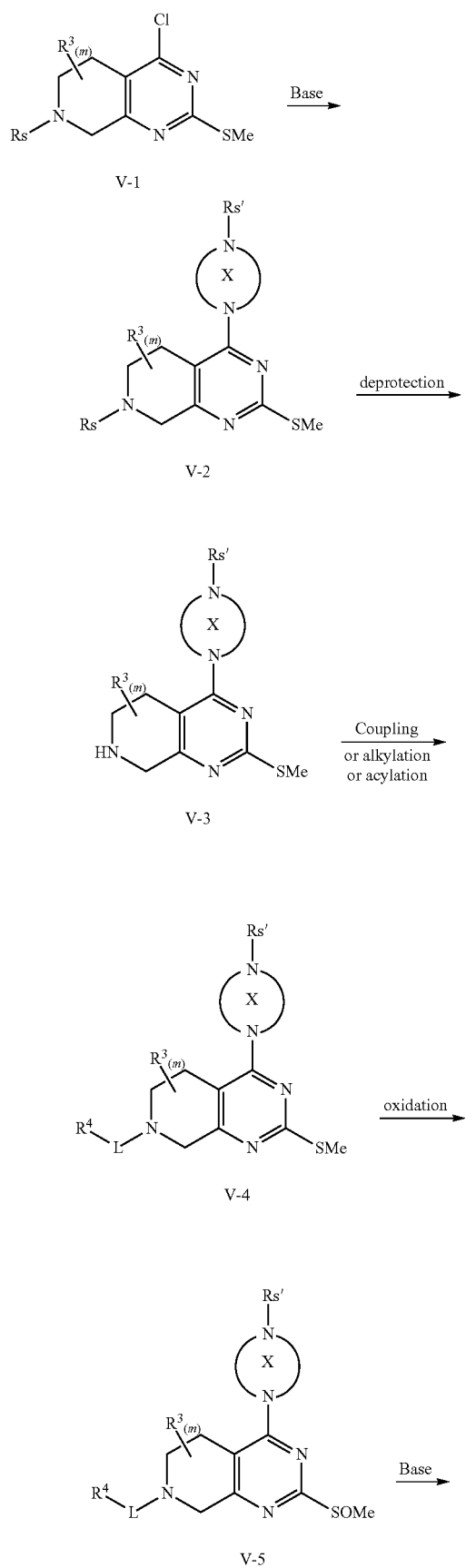
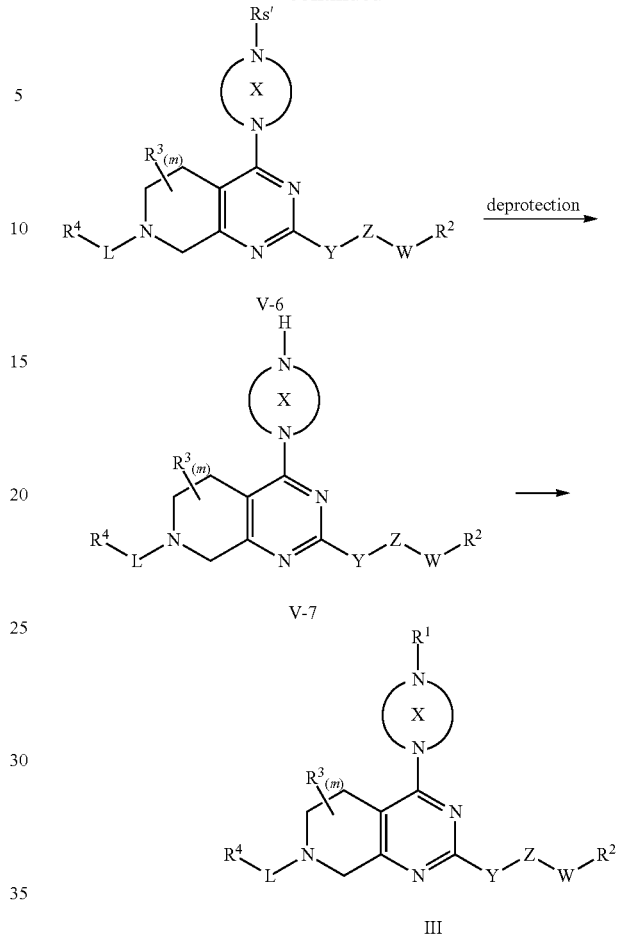

(i) in the presence of base, compound of formula V-1 is reacted with one amino in diamino compound, and then reacted with amino protectant, and compound of formula V-2 is obtained;

(ii) in the presence of deprotectant, the compound of formula V-2 is deprotected, and the compound of formula V-3 is obtained;

(iii) the compound of formula V-3 undergoes coupling, substitution or acylation reaction, and then compound of formula V-4 is obtained;

(iv) the compound of formula V-4 is reacted with oxidant, and the compound of formula V-5 is obtained;

(v) in the presence of base, the compound of formula V-5 is reacted, and the compound of formula V-6 is obtained;

(vi) in the presence of acid, the compound of formula V-6 is deprotected, and the compound of formula V-7 is obtained;

(vii) the compound of formula V-7 undergoes substitution or acylation reaction, and the compound of formula (III) is obtained;

wherein,

Rs and Rs' are protective group of amino, and the protective group is selected from Boc, Bn, Cbz or Fmoc;

$R^1$, $R^2$, $R^3$, $R^4$, L, X, Y, Z, W and m are as defined above.

In another preferred embodiment, the base is TEA or DIPEA in the step (i).

In another preferred embodiment, the amino protectant in the step (i) is selected from the group consisting of $(Boc)_2O$, benzyl chloroformate, di-tert-butyl dicarbonate, o-phthaloyl dichloride, benzyl chloride, triphenylchloromethane, 9-fluorenylmethyl chloroformate, allyl chloroformate.

In another preferred embodiment, the deprotectant is 1-chloroethyl chloroformate in the step (ii).

In another preferred embodiment, the oxidant is mCPBA in the step (iv).

In another preferred embodiment, in the step (v), the base is sodium alcoholate, potassium alcoholate, NaH or LiHNMDS, preferably sodium tert-butoxide or potassium tert-butoxide.

In another preferred embodiment, in the step (vi), the acid is TFA.

In the third aspect of the invention, a pharmaceutical composition is provided, and the pharmaceutical composition comprises one or more compounds of the formula (I), the stereoisomer, tautomer, crystal form, pharmaceutically acceptable salt, hydrate, solvate or prodrug thereof of the first aspect; and pharmaceutically acceptable carrier.

In another preferred embodiment, the pharmaceutical composition further comprises a drug selected from the group consisting of:

PD-1 inhibitor (such as nivolumab, pembrolizumab, pidilizumab, cemiplimab, JS-001, SHR-120, BGB-A317, IBI-308, GLS-010, GB-226, STW204, HX008, HLX10, BAT 1306, AK105, LZM 009 or the biological analogue thereof, etc.), PD-L1 inhibitor (such as durvalumab, atezolizumab, avelumab, CS1001, KN035, HLX20, SHR-1316, BGB-A333, JS003, CS1003, KL-A167, F 520, GR1405, MSB2311 or the biological analogue thereof, etc.), CD20 antibody (such as rituximab, obinutuzumab, ofatumumab, veltuzumab, tositumomab, 131I-tositumomab, ibritumomab, 90Y-ibritumomab, 90In-ibritumomab, ibritumomab tiuxetan, etc.), CD47 antibody (such as Hu5F9-G4, CC-90002, TTI-621, TTI-622, OSE-172, SRF-231, AlX-148, NI-1701, SHR-1603, IBI188, IMM01), ALK inhibitor (such as Ceritinib, Alectinib, Brigatinib, Lorlatinib, ocatinib, etc.), PI3K inhibitor (such as Idelalisib, Duvelisib, Dactolisib, Taselisib, Bimiralisib, Omipalisib, Buparlisib, etc.), BTK inhibitor (such as Ibrutinib, Tirabrutinib, Acalabrutinib, Zanubrutinib, Vecabrutinib, etc.), EGFR inhibitor (such as Afatinib, Gefitinib, Erlotinib, Lapatinib, Dacomitinib, Icotinib, Canertinib, Sapitinib, Naquotinib, Pyrotinib, Rociletinib, Osimertinib, etc.), VEGFR inhibitor (such as Sorafenib, Pazopanib, Regorafenib, Sitravatinib, Ningetinib, Cabozantinib, Sunitinib, Donafenib, etc.), HDAC inhibitor (such as Givinostat, Tucidinostat, Vorinostat, Fimepinostat, Droxinostat, Entinostat, Dacinostat, Quisinostat, Tacedinaline, etc.), CDK inhibitor (such as Palbociclib, Ribociclib, Abemaciclib, Milciclib, Trilaciclib, Lerociclib, etc.), MEK inhibitor (such as Selumetinib (AZD6244), Trametinib (GSK1120212), PD0325901, U0126, Pimasertib (AS-703026), PD184352 (CI-1040), etc.), mTOR inhibitor (such as Vistusertib, etc.), SHP2 inhibitor (such as RMC-4630, JAB-3068, TNO 155, etc.) or combinations thereof.

In another preferred embodiment, a method for preparing the pharmaceutical composition is provided, and the method comprises the step of mixing a pharmaceutically acceptable carrier with the compound of formula I, the stereoisomer, tautomer, crystal form, pharmaceutically acceptable salt, hydrate, solvate or prodrug thereof, thereby forming the pharmaceutical composition.

In the fourth aspect of the invention, a use of the cycloalkyl and heterocycloalkyl compounds of formula (I), the stereoisomer, tautomer, crystal form, pharmaceutically acceptable salt, hydrate, solvate or prodrug thereof of the first aspect, or the pharmaceutical composition of the third aspect for preparing a medicant for preventing and/or treating the disease related to the activity or expression of $KRAS^{G12C}$ is provided.

In another preferred embodiment, the disease is tumor or dysfunctional disease.

In another preferred embodiment, the disease is selected from the group consisting of lung cancer, breast cancer, prostate cancer, esophageal cancer, colorectal cancer, bone cancer, kidney cancer, gastric cancer, liver cancer, colon cancer, melanoma, lymphoma, leukemia, brain tumor, myeloma, soft tissue sarcoma, pancreatic cancer, skin cancer.

In the fifth aspect of the invention, a non-diagnostic and non-therapeutic method for inhibiting $KRAS^{G12C}$ is provided, and the method comprises the step of administrating an effective amount of the compound of the formula (I), the stereoisomer, tautomer, crystal form, pharmaceutically acceptable salt, hydrate, solvate or prodrug thereof of the first aspect or the pharmaceutical composition of the third aspect to the subject in need thereof.

In another preferred embodiment, the compound is preferably the compound prepared in the Examples.

It should be understood that in the present invention, any of the technical features specifically described above and below (such as in the Example) can be combined with each other, thereby constituting new or preferred technical solutions which will not redundantly be described one by one herein.

DETAILED DESCRIPTION OF THE INVENTION

Figure 1:
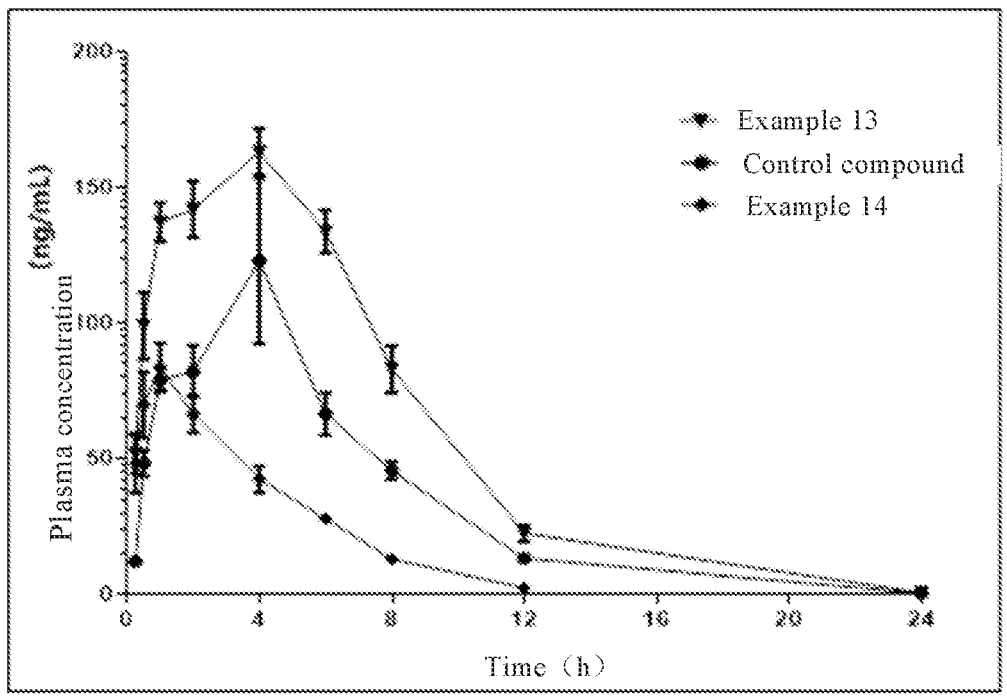
FIG. 1 shows the plasma concentration-time curve.

After a long and intensive study, the inventor had accidentally prepared a new class of compounds with selective inhibition and/or better pharmacodynamic properties of $KRAS^{G12C}$. On this basis, the inventor has completed the present invention.

Term

In the present invention, unless otherwise specified, the terms used have the general meanings known to those skilled in the art.

The term "alkyl" refers to a linear or branched or cyclic alkane group comprising 1-20 carbon atoms, such as 1-18 carbon atoms, particularly referred to 1-18 carbon atoms, preferably comprising 1-10 carbon atoms, more preferably comprising 1-6 carbon atoms. Typical "alkyl" includes methyl, ethyl, propyl, isopropyl, n-butyl, tert-butyl, isobutyl,

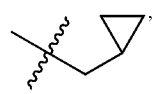

pentyl, isopentyl, heptyl, 4,4-dimethylpentyl, octyl, 2,2,4-trimethylpentyl, nonyl, decyl, undecyl, dodecyl, and the like.

The term "$C_1$-$C_{18}$ alkyl" refers to a linear or branched or cyclic alkyl, including 1, 2, 3, 4, 5, 6, 7, 8, 9, 10, 11, 12, 13, 14, 15, 16, 17 or 18 carbon atoms, such as methyl, ethyl, propyl, isopropyl

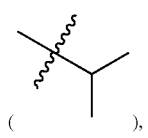

n-butyl, tert-butyl, isobutyl (such as

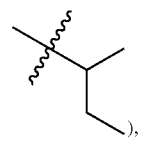

n-pentyl, isopentyl, n-hexyl, isohexyl, n-heptyl, isoheptyl. In the present invention, the alkyl further comprises substituted alkyl. "Substituted alkyl" refers to one or more positions in the alkyl are substituted, especially 1-4 substituents, which can be substituted at any position. Typically substituents include, but are not limited to one or more of the following groups: such as hydrogen, deuterium, halogen (such as monohalogenated substituent or polyhalogenated substituents, and the latter such as trifluoromethyl or alkyl containing $Cl_3$), cyano, nitro, oxo (=O), trifluoromethyl, trifluoromethoxy, cycloalkyl, alkenyl, cycloalkenyl, alkynyl, heterocycle, aromatic ring, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_e$, $NR_aC(=O)NR_bR_c$, $NR_aS(=O)_2NR_bR_c$, $NR_aP(=O)_2NR_bR_c$, $NR_bC(=O)R_a$ or $NR_bP(=O)_2R_e$, wherein $R_a$ can independently represent hydrogen, deuterium, $C_1$-$C_6$ alkyl, $C_3$-$C_8$ cycloalkyl, $C_2$-$C_6$ alkenyl, $C_3$-$C_6$ cycloalkenyl, $C_2$-$C_6$ alkynyl, 5-14 membered heterocycle or $C_6$-$C_{14}$ aromatic ring, $R_b$, $R_c$ and $R_d$ can independently represent hydrogen, deuterium, $C_1$-$C_6$ alkyl, $C_3$-$C_8$ cycloalkyl, 5-14 membered heterocycle or $C_6$-$C_{14}$ aromatic ring, or $R_b$ and $R_c$ together with the N atom form a heterocycle; $R_e$ can independently represent hydrogen, $C_1$-$C_6$ alkyl, $C_3$-$C_8$ cycloalkyl, $C_2$-$C_6$ alkenyl, $C_3$-$C_6$ cycloalkenyl, $C_2$-$C_6$ alkynyl, 5-14 membered heterocycle or $C_6$-$C_{14}$ aromatic ring. The above typical substituents, such as alkyl, cycloalkyl, alkenyl, cycloalkenyl, alkynyl, heterocyclic or aromatic ring can be optionally substituted.

The term "alkylene" refers to a group formed by "alkyl or substituted alkyl" removing a hydrogen atom, such as methylene, ethylene, propylene, and isopropylene (such as

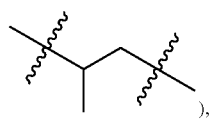 [SMILES: *CC(*)C]

butylene (such as or

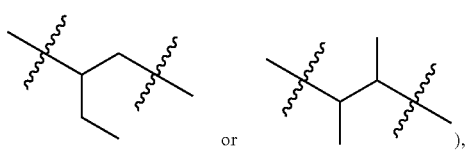

pentylidene such as

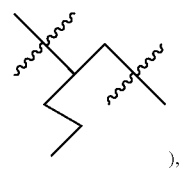 [SMILES: *CC(*)CCC]

hexylidene (such as

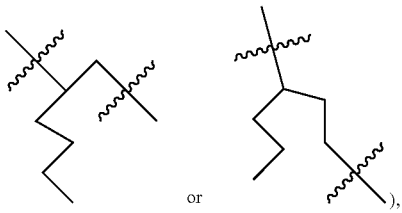

heptylene (such as

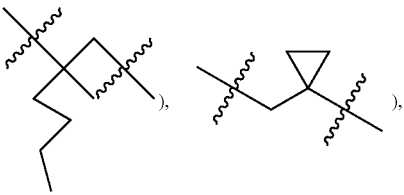

etc. Furthermore, the term also includes alkylene (e.g., a C1-C18 alkylene) wherein one methylene is substituted by cycloalkylene (e.g., C3-C20 cycloalkylene), such as "C1-C18 alkylene C3-C20 cycloalkylene" or "C3-C20 cycloalkylene C1-C18 alkylene". The term "C1-C18 alkylene C3-C20 cycloalkylene" or "C3-C20 cycloalkylene C1-C18 alkylene" has the same meaning, which refers to the group formed by the removal of two hydrogen atoms from cycloalkylalkyl or alkylcycloalkyl, such as

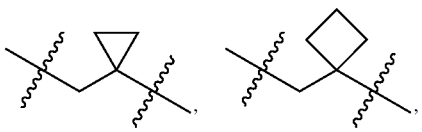

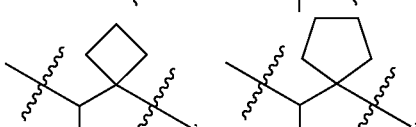

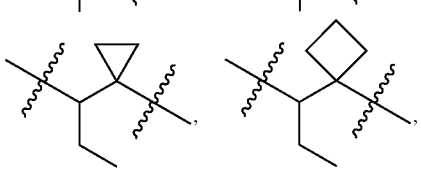

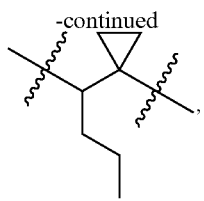

etc.

The term "cycloalkyl" refers to a completely saturated ring of hydrocarbon group containing 3, 4, 5, 6, 7, 8, 9, 10, 11, 12, 13, 14, 15, 16, 17, 18, 19 or 20 carbon atoms, consisting of 1-4 rings, each containing 3-8 carbon atoms. Preferably $C_3$-$C_{20}$ cycloalkyl, more preferably $C_3$-$C_{18}$ cycloalkyl, more preferably $C_3$-$C_{10}$ cycloalkyl, more preferably $C_3$-$C_6$ cycloalkyl. "Substituted cycloalkyl" refers to one or more positions in the cycloalkyl are substituted, especially 1-4 substituents, which can be substituted at any position. In the present invention, "cycloalkyl" comprises substituted cycloalkyl, typically substituents include, but are not limited to one or more of the following groups: such as hydrogen, deuterium, halogen (such as monohalogenated substituent or polyhalogenated substituents, and the latter such as trifluoromethyl or alkyl containing $Cl_3$), cyano, nitro, oxo (=O), trifluoromethyl, trifluoromethoxy, cycloalkyl, alkenyl, cycloalkenyl, alkynyl, heterocycle, aromatic ring, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_e$, $NR_aC(=O)NR_bR_c$, $NR_aS(=O)_2NR_bR_c$, $NR_aP(=O)_2NR_bR_c$, $NR_bC(=O)R_a$ or $NR_bP(=O)_2R_e$, wherein $R_a$ can independently represent hydrogen, deuterium, alkyl, cycloalkyl, alkenyl, cycloalkenyl, alkynyl, heterocycle or aromatic ring, $R_b$, $R_e$ and $R_d$ can independently represent hydrogen, deuterium, alkyl, cycloalkyl, heterocycle or aromatic ring, or $R_b$ and $R_e$ together with the N atom form a heterocycle, $R_e$ can independently represent hydrogen, deuterium, alkyl, cycloalkyl, alkenyl, cycloalkenyl, alkynyl, heterocycle or aromatic ring. The above typical substituents can be optionally substituted. Typical substituent also includes spiro, bridged or fused ring, especially spiro cycloalkyl, spiro cycloalkenyl, spiro heterocyclyl (excluding heteroaryl ring), bridged cycloalkyl, bridged cycloalkenyl, bridged heterocyclyl (excluding heteroaryl ring), fused cycloalkyl, fused cycloalkenyl, fused heterocyclyl or fused aryl, the above cycloalkyl, cycloalkenyl, heterocyclyl and aryl can be optionally substituted.

The term "$C_3$-$C_{20}$ cycloalkylene" refers to the group formed by the removal of two hydrogen atoms from cycloalkyl, such as

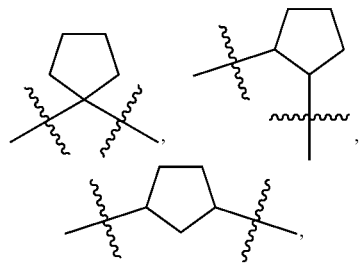

etc.

The term "heterocyclyl" refers to completely saturated or partially unsaturated ring group containing 3, 4, 5, 6, 7, 8, 9, 10, 11, 12, 13, 14, 15, 16, 17, 18, 19 or 20 ring atoms (including, but not limited to, such as 3-7 membered mono ring, 4-7 membered mono ring, 6-11 membered bicyclo, or 8-16 membered tricyclic system) in which at least one heteroatom exists in a ring containing at least one carbon atom. Each heterocyclyl containing heteroatom can have 1, 2, 3, or 4 heteroatoms, and these heteroatoms are selected from nitrogen atom, oxygen atom or sulfur atom, wherein the nitrogen atom or sulfur atom can be oxidized, and the nitrogen atom can also be quaternized. The heterocyclyl can be attached to the residue of any heteroatom or carbon atom of the ring or ring molecule, preferably N or C atom on the ring or ring molecule. Typical monocyclic heterocyclyls include, but are not limited to azetidinyl, pyrrolidyl, oxetanyl, pyrazolinyl, imidazolinyl, imidazolidinyl, oxazolidinyl, isoxazolidinyl, thiazolidinyl, isothiazolidinyl, tetrahydrofuryl, piperidyl, piperazinyl, 2-oxoppiperazinyl, 2-oxopiperidyl, 2-oxopyrrolidyl, hexahydroazepinyl, 4-piperidinone, tetrahydropyranyl, morpholinyl, thiomorpholinyl, thiomorpholinylsulfoxide, thiomorpholinylsulfone, 1,3-dioxane and tetrahydro-1,1-dioxythienyl, etc. The polycyclic heterocyclyl includes spiro, fused, and bridged heterocyclyls; the spiro, fused, and bridged heterocyclyls involved are optionally connected with other groups by single bond, or are further fused with other cycloalkyl, heterocyclyl, aryl and heteroaryl by any two or more atoms of the ring. The heterocyclyl may be substituted or unsubstituted, when substituted, the substituent is preferably one or more of the following groups, independently selected from alkyl, deuterated alkyl, haloalkyl, alkoxy, haloalkoxy, alkenyl, alkynyl, alkylthio, alkylamino, halogen, amino, nitro, hydroxy, thiol, cyano, cycloalkyl, heterocyclyl, aryl, heteroaryl, cycloalkylthio, oxo, carboxy, and carboxylate.

The term "C4-C20 (4-20 membered) heterocyclylene" refers to the group formed by the removal of two hydrogen atoms from heterocyclyl, such as

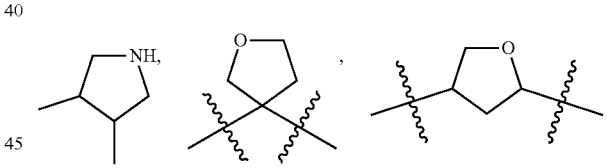

etc.

The term "aryl" refers to an aromatic ring of hydrocarbon group containing 6, 7, 8, 9, 10, 11, 12, 13 or 14 ring carbon atoms having 1-5 rings, particularly monocyclic and bicyclic groups such as phenyl, biphenyl or naphthyl. Any aromatic ring having two or more aromatic rings (bicyclic, etc.), the aromatic rings of aryl may be connected by single bond (such as biphenyl) or fused (such as naphthalene, anthracene, etc.). "Substituted aryl" refers to one or more positions in the aryl are substituted, especially 1-3 substituents, which can be substituted at any position. Typical substituents include, but are not limited to one or more of the following groups: such as hydrogen, deuterium, halogen (such as monohalogenated substituent or polyhalogenated substituents, and the latter such as trifluoromethyl or alkyl containing $Cl_3$), cyano, nitro, oxo (=O), trifluoromethyl, trifluoromethoxy, cycloalkyl, alkenyl, cycloalkenyl, alkynyl, heterocycle, aromatic ring, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, C(=O)OR$_a$, C(=O)R$_a$, C(=O)NR$_b$R$_c$, OC(=O)R$_a$, OC(=O)NR$_b$R$_c$, NR$_b$C(=O)OR$_e$, NR$_a$C(=O)NR$_b$R$_c$, NR$_a$S(=O)$_2$NR$_b$R$_c$, NR$_a$P(=O)$_2$NR$_b$R$_c$, NR$_b$C(=O)R$_a$ or NR$_b$P(=O)$_2$R$_e$, wherein R$_a$ can independently represent hydrogen, deuterium, alkyl, cycloalkyl, alkenyl, cycloalkenyl, alkynyl, heterocycle or aromatic ring, R$_b$, R$_c$ and R$_d$ can independently represent hydrogen, deuterium, alkyl, cycloalkyl, heterocycle or aromatic ring, or R$_b$ and R$_c$ together with the N atom form a heterocycle, R$_e$ can independently represent hydrogen, deuterium, alkyl, cycloalkyl, alkenyl, cycloalkenyl, alkynyl, heterocycle or aromatic ring. The above typical substituents can be optionally substituted. Typical substituent also includes fused ring, especially fused cycloalkyl, fused cycloalkenyl, fused heterocyclyl or fused aryl, the above cycloalkyl, cycloalkenyl, heterocyclyl and heterocyclic aryl can be optionally substituted.

The term "heteroaryl" refers to a heteroaromatic system containing 1-4 heteroatoms, 5-14 ring atoms, wherein the heteroatom is selected from oxygen, nitrogen and sulfur. The heteroaryl is preferably 5 to 10 membered ring, more preferably 5 or 6 membered, such as pyrryl, pyrazolyl, imidazolyl, oxazolyl, isoxazolyl, thiazoly, thiadiazolyl, isothiazolyl, furanyl, pyridyl, pyrazinyl, pyrimidyl, pyridazinyl, triazinyl, triazolyl, and tetrazolyl, etc. The "heteroaryl" may be substituted or unsubstituted, when substituted, the substituent is preferably one or more of the following groups, independently selected from alkyl, deuterated alkyl, haloalkyl, alkoxy, haloalkoxy, alkenyl, alkynyl, alkylthio, alkylamino, halogen, amino, nitro, hydroxy, thiol, cyano, cycloalkyl, heterocyclyl, aryl, heteroaryl, cycloalkylthio, oxo, carboxy, and carboxylate.

The term "C1-C18 alkoxy" refers to a straight or branched or cyclic alkoxy with 1-18 carbon atoms including C1-C18 alkyl-O—, —C1-C6 alkyl-O—C1-C6 alkyl, and unrestrictedly including methoxy, ethoxy, propoxy, isopropoxy, and butoxyl, etc. Preferably C1-C8 alkoxy, more preferably C$_1$-C$_6$ alkoxy.

The term "C1-C18 alkyleneoxy" refers to the group formed by the removal of one hydrogen atom from "C1-C18 alkoxy".

The term "4-7 membered heterocyclyl" refers to heterocyclic group having 1, 2, 3 or 4 (preferably 1, 2 or 3, more preferably 1 or 2) heteroatoms selected from N, O and S. Preferably, the 4-7 membered heterocyclyl contains at least one N-heteroatom, more preferably 4-7 membered heterocyclyl connects other moieties through N atom or C atom in the ring.

The term "halogen" or "halo" is chlorine, bromine, fluorine, and iodine.

The term "halogenated (halo)" refers to substituted by halogen.

The term "deuterated" refers to substituted by deuterium.

The term "hydroxy" refers to a group with a structure of OH.

The term "nitro" refers to a group with a structure of NO$_2$.

The term "cyano" refers to a group with a structure of CN.

The term "ester" refers to a group with a structure of —COOR, wherein R represents hydrogen, alkyl or substituted alkyl, cycloalkyl or substituted cycloalkyl, cycloalkeny or substituted cycloalkenyl, aryl or substituted aryl, heterocycle or substituted heterocycle.

The term "amino" refers to a group with a structure of —NRR', wherein R and R' independently represent hydrogen, alkyl or substituted alkyl, cycloalkyl or substituted cycloalkyl, cycloalkenyl or substituted cycloalkenyl, aryl or substituted aryl, heterocycle or substituted heterocycle, as defined above. R and R' may be the same or different in the dialkylamine segment.

The term "amido" refers to a group with a structure of —CONRR', wherein R and R' independently represent hydrogen, alkyl or substituted alkyl, cycloalkyl or substituted cycloalkyl, cycloalkenyl or substituted cycloalkenyl, aryl or substituted aryl, heterocycle or substituted heterocycle, as defined above. R and R' may be the same or different in the dialkylamine segments.

The term "sulfonamido" refers to a group with a structure of —SO$_2$NRR', wherein R and R' independently represent hydrogen, alkyl or substituted alkyl, cycloalkyl or substituted cycloalkyl, cycloalkenyl or substituted cycloalkenyl, aryl or substituted aryl, heterocycle or substituted heterocycle, as defined above. R and R' may be the same or different in the dialkylamine segment.

The term "ureido" refers to a group with a structure of —NRCONR'R", wherein R, R' and R" independently represent hydrogen, alkyl or substituted alkyl, cycloalkyl or substituted cycloalkyl, cycloalkenyl or substituted cycloalkenyl, aryl or substituted aryl, heterocycle or substituted heterocycle, as defined above. R, R' and R" may be the same or different in the dialkylamine segment.

The term "alkylaminealkyl" refers to a group with a structure of —RNHR', wherein R and R' independently represent hydrogen, alkyl or substituted alkyl, cycloalkyl or substituted cycloalkyl, cycloalkenyl or substituted cycloalkenyl, aryl or substituted aryl, heterocycle or substituted heterocycle, as defined above. R and R' can be the same or different.

The term "dialkylaminealkyl" refers to a group with a structure of —RNR'R", wherein R, R' and R" independently represent hydrogen, alkyl or substituted alkyl, cycloalkyl or substituted cycloalkyl, cycloalkenyl or substituted cycloalkenyl, aryl or substituted aryl, heterocycle or substituted heterocycle, as defined above. R, R' and R" may be the same or different in the dialkylamine segment.

The term "heterocyclylalkyl" refers to a group with a structure of —RR', wherein R can independently represent alkyl or substituted alkyl, cycloalkyl or substituted cycloalkyl, cycloalkenyl or substituted cycloalkenyl, aryl or substituted aryl; R' represents heterocycle or substituted heterocycle.

In the present invention, the term "substituted" refers to the substitution of one or more hydrogen atoms on a specific group by specific substituent. The specific substituents are those described in the preceding paragraph or those present in each Example. Unless otherwise specified, a substituted group may have a substituent selected from a specific group at any substitutable position of the group, and the substituent may be the same or different in each position. Those skilled in the art should understand that the combinations of substituents contemplated by the present invention are those that are stable or chemically achievable. The substituent is such as (but is not limited to): halogen, hydroxy, cyano, carboxy (—COOH), C1-C6 alkyl, C2-C6 alkenyl, C2-C6 alkynyl, C3-C8 cycloalkyl, 3- to 12 membered heterocyclyl, aryl, heteroaryl, C1-C8 aldehyde, C2-C10 acyl, C2-C10 ester, amino, C1-C6 alkoxy, C1-C10 sulfonyl, and C1-C6 ureido, etc.

Unless otherwise stated, it is assumed that any heteroatom with a lower valence state has enough hydrogen atoms to replenish its valence state.

When the substituent is a non-end substituent, it is a subunit of the corresponding substituent, such as alkyl corresponding to alkylene, cycloalkyl corresponding to cycloalkylene, heterocyclyl corresponding to heterocyclylene, alkoxy corresponding to alkyleneoxy, etc.

Active Ingredient

As used herein, "the compound of the present invention" refers to the compound represented by the formula I, and further comprises the stereoisomer or optical isomer, pharmaceutically acceptable salt, prodrug or solvate of the compound of formula I.

The compound of formula I has the following structure:

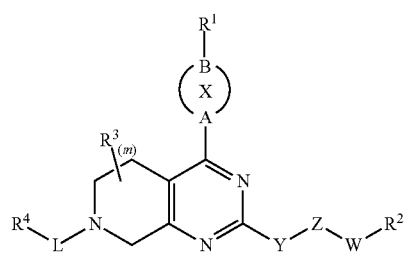
(I)

wherein, $R^1$, $R^2$, $R^3$, $R^4$, A, B, L, X, Y, Z, W and m are as defined above.

Preferably, the compound of formula I has the structure of formula (II-A) or (II-B):

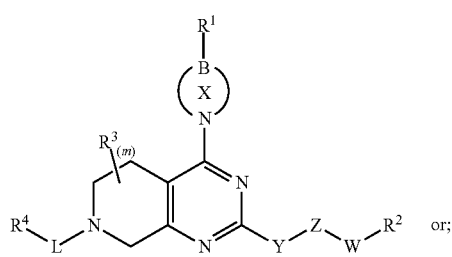
(II-A)

(II-B)

wherein:

$R^1$, $R^2$, $R^3$, $R^4$, A, B, X, Y, Z, L, W, and m are as defined above.

Preferably, the compound of formula I has the structure of formula (III):

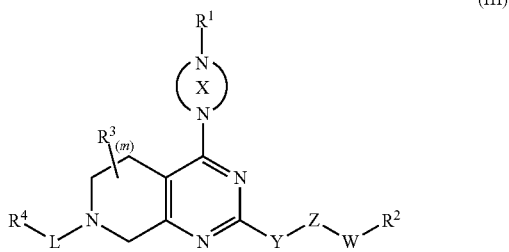
(III)

wherein, $R^1$, $R^2$, $R^3$, $R^4$, X, Y, Z, L, W, and m are as defined above.

Preferably, the compound of formula I has the structure of formula (IV):

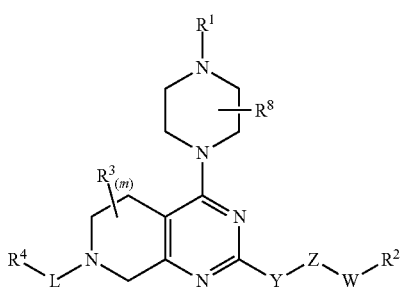
(IV)

wherein:

$R^1$, $R^2$, $R^3$, $R^4$, R, Y, Z, L, W, and m are as defined above.

Preferably, the compound of formula I has the structure of formula (V):

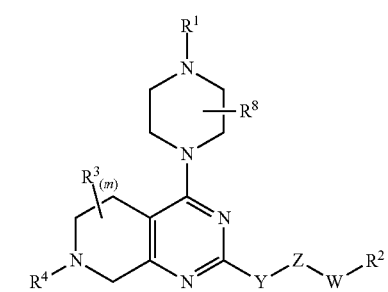
(V)

wherein:

$R^1$, $R^2$, $R^3$, $R^4$, $R^8$, Y, Z, W and m are as defined above.

Preferably, the compound of formula I has the structure of formula (VI):

(VI)

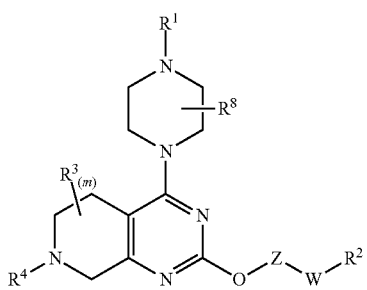

wherein:

R¹, R², R³, R⁴, R, Z, W and m are as defined above.

Preferably, the compound of formula I has the structure of formula (VII-A) or (VII-B):

(VII-A)

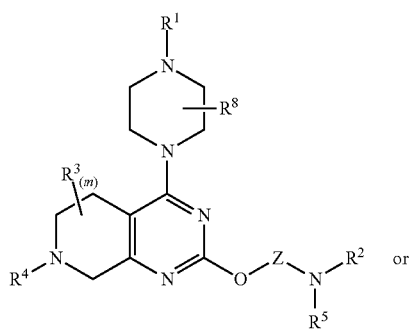

or (VII-B)

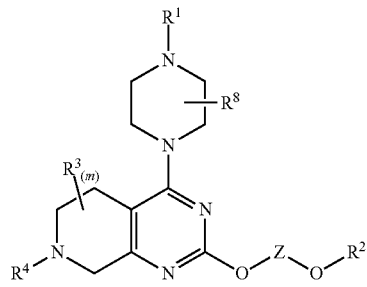

wherein:

R¹, R², R³, R⁴, R⁵, R⁸, Z and m are as defined above.

Preferably, in the above formulas, R¹ is —C(O)C(R$^A$)═C(R$^B$)$_p$, wherein the "═" is double bond "—"; ; R$^A$ is selected from: hydrogen, deuterium, fluorine, cyano or $C_1$-$C_3$ alkyl;

R$^B$ is selected from: hydrogen, deuterium, cyano or $C_1$-$C_3$ alkyl;

wherein the "alkyl" can be substituted by one or more substituents selected from the group consisting of deuterium, halogen, cyano, amino, $C_3$-$C_7$ cycloalkyl, 4-7 membered heterocyclyl, NHR⁹ and NR⁹R¹⁰; wherein, R⁹ and R¹⁰ are each independently $C_1$-$C_3$ alkyl.

Preferably, in above formula, Z is $C_1$-$C_{18}$ alkylene $C_3$-$C_{20}$ cycloalkylene, preferably $CH_2C_3$-$C_{20}$ cycloalkylene, more preferably a $CH_2C_3$-$C_6$ cycloalkylene.

Preferably, in above formula, Z is bond or $C_1$-$C_{18}$ alkylene $C_3$-$C_{20}$ cycloalkylene, W is bond; R² is —(CH₂)R⁷ or —(CH₂)$_n$NR⁵R⁷; n is 1, 2 or 3, preferably 1 or 2;

R⁵ and R⁷ are as defined above.

Preferably, in above formula, Z is bond or a $CH_2C_3$-$C_6$ cycloalkylene, W is bond; R² is —(CH₂)$_n$R⁷ or —(CH₂)$_n$NR⁵R⁷; n is 1, 2 or 3, preferably 1 or 2;

R⁵ is selected from the substituted or unsubstituted group consisting of $C_1$-$C_6$ alkyl, deuterated $C_1$-$C_6$ alkyl, $C_1$-$C_6$ haloalkyl, $C_3$-$C_6$ cycloalkyl, $C_1$-$C_6$ alkoxy, deuterated $C_1$-$C_6$ alkoxy, $C_1$-$C_6$ haloalkoxy, amino, hydroxyl, 3-7 membered heterocyclyl, $C_6$-$C_{14}$ aryl, 5-14 membered heteroaryl;

R⁷ is selected from substituted or unsubstituted $C_1$-$C_6$ alkyl, $C_3$-$C_6$ cycloalkyl or 4-7 membered heterocyclyl;

wherein, the "substituted" refers to be substituted by one or more substituents selected from the group consisting of deuterium, $C_1$-$C_{18}$ alkyl, deuterated $C_1$-$C_{18}$ alkyl, $C_1$-$C_{18}$ haloalkyl, $C_1$-$C_{18}$ alkoxy, deuterated $C_1$-$C_{18}$ alkoxy, $C_1$-$C_{18}$ haloalkoxy, halogen, nitro, hydroxy, cyano, ester, amino, amido, sulfonamido and ureido.

Preferably, the compound of formula I has the structure of formula (VIII):

(VIII)

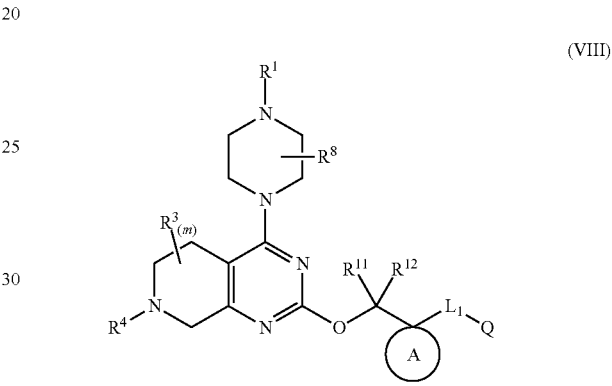

R¹, R⁴, R⁸, R¹¹, R¹², Ring A, L₁, Q, and m are as defined above.

Preferably, in the formula (VIII), ring A is substituted or unsubstituted group consisting of $C_3$-$C_6$ cycloalkyl or 4-6 membered heterocyclyl, wherein, the "substituted" refers to be substituted by one or more substituents selected from the group consisting of deuterium, $C_1$-$C_{18}$ alkyl, deuterated $C_1$-$C_{18}$ alkyl, $C_1$-$C_{18}$ haloalkyl, $C_1$-$C_{18}$ alkoxy, deuterated $C_1$-$C_{18}$ alkoxy, $C_1$-$C_{18}$ haloalkoxy, halogen, nitro, hydroxy, cyano, ester, amino, amido, sulfonamido and ureido.

Preferably, in the formula (VIII), Q is 4-7 membered heterocyclyl, NHR⁹ or NR⁹R¹⁰; more preferably Q is NR⁹R¹⁰; R⁹ and R¹⁰ are each independently $C_1$-$C_3$ alkyl.

Preferably, in above formulas, R⁸ is independently selected from substituted or unsubstituted group consisting of hydrogen, deuterium, $C_1$-$C_6$ alkyl, deuterated $C_1$-$C_6$ alkyl, $C_1$-$C_6$ haloalkyl, $C_1$-$C_6$ alkoxy, deuterated $C_1$-$C_6$ alkoxy, $C_1$-$C_6$ haloalkoxy, amino, hydroxyl; wherein the "substituted" refers to be substituted by one or more substituents selected from the group consisting of hydrogen, deuterium, $C_1$-$C_6$ alkyl, deuterated $C_1$-$C_6$ alkyl, $C_1$-$C_6$ haloalkyl, $C_1$-$C_6$ alkoxy, deuterated $C_1$-$C_6$ alkoxy, $C_1$-$C_6$ haloalkoxy, halogen, nitro, hydroxy, cyano, ester, amino, amido, sulfonamido and ureido; preferably R⁸ is CNCH₂—.

Preferably, in above formulas, Z is selected from the group consisting of $C_1$-$C_6$ alkylene, deuterated $C_1$-$C_6$ alkylene, $C_1$-$C_6$ haloalkylene, $C_3$-$C_8$ cycloalkylene, 4-8 membered heterocyclylene, $C_1$-$C_6$ alkyleneoxy, deuterated $C_1$-$C_6$ alkyleneoxy, $C_1$-$C_6$ haloalkyleneoxy.

The salt of the compound in the present invention may be formed which are also within the scope of the present invention. Unless otherwise stated, the compound in the present invention is understood to include its salt. The term "salt" as used herein refers to a salt formed in the form of acid or base from inorganic or organic acid and base. Further, when the compound in the present invention contains a base fragment which includes, but is not limited to pyridine or imidazole, when contains an acid segment which includes, but is not limited to carboxylic acid. The zwitterion that may form "inner salt" is included within the range of the term "salt". Pharmaceutically acceptable (i.e., non-toxic, physiologically acceptable) salt is preferred, although other salts are also useful and may be used, for example, in the separation or purification steps of the preparation process. The compound of the present invention may form a salt, for example, compound I is reacted with a certain amount (such as an equivalent amount) of an acid or base, and precipitated in a medium, or freeze-dried in aqueous solution.

The compounds in the present invention containing base fragment which includes but is not limited to amines or pyridine or imidazole rings, may form salt with organic or inorganic acid. Typical acids that form salts include acetate (such as acetate or trihalogenated acetic acid, such as trifluoroacetic acid), adipate, alginate, ascorbate, aspartate, benzoate, benzene sulfonate, disulfate, borate, butyrate, citrate, camphorate, camphor sulfonate, cyclopentane propionate, diethylene glycolate, lauryl sulfate, ethanesulphonate, fumarate, gluceptate, glycerophosphate, hemisulphate, enanthate, caproate, hydrochloride, hydrobromide, hydriodate, isethionate (e.g., 2-hydroxy-ethesulfonate), lactate, maleate, mesylate, naphthalenesulfonate (e.g., 2-naphthalenesulfonate), nicotinate, nitrate, oxalate, pectate, persulfate, phenylpropionate (e.g., 3-phenylpropionate), phosphate, picrate, pivalate, propionate, salicylate, succinate, sulfate (e.g., formed with sulfuric acid), sulfonate, tartrate, thiocyanate, toluenesulfonate (e.g., tosilate), dodecanoate, etc.

Some compounds of the invention may contain acidic fragments including, but not limited to carboxylic acid may form salts with various organic or inorganic bases. Salt formed by typical base includes ammonium salt, alkali metal salt (such as sodium, lithium and potassium salts), alkaline earth metal salt (such as calcium and magnesium salts), and salt formed by organic bases (such as organic amines), such as benzathine, dicyclohexylamine, hydrabamine (salt formed with N,N-bis(dehydroabietyl) ethylenediamine), N-methyl-D-glucanamine, N-methyl-D-glucoamide, tert-butyllamine, and the salt formed with amino acids such as arginine, lysine, etc. Basic nitrogen-containing groups can form quaternary ammonium salts with halides, such as small molecular alkyl halides (such as chlorides, bromides and iodides of methyl, ethyl, propyl and butyl), dialkyl sulfate (such as dimethyl, diethyl, dibutyl, and dipentyl sulfates), long chain halides (such as such as chlorides, bromides and iodides of decyl, dodecyl, tetradecyl, and tetradecyl), aralkyl halides (such as bromides of benzyl and phenyl), etc.

The prodrug and solvate of the compound in the present invention are also included within the scope of the present invention. The term "prodrug" herein refers to a compound resulting from the chemical transformation of a metabolic or chemical process to produce a compound, salt, or solvate in the present invention for the treatment of an associated disease. The compounds of the invention include solvates such as hydrates.

Compound, salt or solvate in the present invention, may be present in tautomeric forms such as amide and imino ether. All of these tautomers are part of the present invention.

Stereisomers of all compounds (e.g., those asymmetric carbon atoms that may be present due to various substitutions), including their enantiomeric forms and non-enantiomer forms, all belong to the protection scope of the present invention. The independent stereoisomer in the present invention may not coexist with other isomers (e.g., as a pure or substantially pure optical isomer with special activity), or may be a mixture (e.g., racemate), or a mixture formed with all other stereoisomers or a part thereof. The chiral center of the present invention has two configurations of S or R, which is defined by International Union of Pure and Applied Chemistry (IUPAC) founded in 1974. The racemization form can be solved by physical methods, such as fractional crystallization, or separation crystallization by derivation into diastereomers, or separation by chiral column chromatography. Individual optical isomer can be obtained from racemate by appropriate methods, including but not limited to conventional methods, such as recrystallization after salting with optically active acids.

Weight content of compound in the present invention obtained by preparation, separation and purification in turn is equal to or greater than 90%, such as equal to or greater than 95%, equal to or greater than 99% ("very pure" compound), and listed in the description of the text. In addition, the "very pure" compound of the present invention is also part of the present invention.

All configuration isomers of the compound of the present invention are within the scope, whether in mixture, pure or very pure form. The definition of the compound of the present invention comprises cis (Z) and trans (E) olefin isomers, and cis and trans isomers of carbocyclic and heterocyclic.

In the entire specification, the groups and substituents can be selected to provide stable fragments and compounds.

Specific functional groups and chemical term definitions are described in detail. For the purposes of the present invention, the chemical elements are consistent with Periodic Table of the Elements, CAS version, *Handbook of Chemistry and Physics,* $75^{th}$ Ed. The definition of a particular functional group is also described. In addition, the basic principles of Organic Chemistry as well as specific functional groups and reactivity described in "Organic Chemistry", Thomas Sorrell, University Science Books, Sausalito: 1999, the entire content of which is incorporated herein by reference.

Some compounds of the present invention may exist in specific geometric or stereoisomer forms. The present invention covers all compounds, including their cis and trans isomers, R and S enantiomers, diastereomers, (D) type isomers, (L) type isomers, racemic mixtures and other mixtures. In addition, asymmetric carbon atom can represent substituent, such as alkyl. All isomers and mixtures thereof are included in the present invention.

According to the invention, mixtures of isomers may contain a variety ratios of isomers. For example, mixtures with only two isomers may have the following combinations: 50:50, 60:40, 70:30, 80:20, 90:10, 95:5, 96:4, 97:3, 98:2, 99:1, or 100:0, all ratios of the isomers are within the scope of the present invention. Similar ratio and the ratio of mixtures of more complex isomers, which are readily understood by general skill of the art are also within the scope of the invention.

The present invention also includes the isotope labeled compound, which is equivalent to the original compound herein. However, in fact, the substitution of one or more atoms by an atom with a different atomic weight or mass number usually occurs. Examples of compound isotopes that may be listed in the present invention include hydrogen, carbon, nitrogen, oxygen, phosphorus, sulfur, fluorine, and chlorine isotopes such as $^2H$, $^3H$, $^{13}C$, $^{11}C$, $^{14}C$, $^{15}N$, $^{18}O$, $^{17}O$, $^{31}P$, $^{32}P$, $^{35}S$, $^{18}F$ and $^{36}Cl$, respectively. Compound, or enantiomer, diastereomer, isomer, or pharmaceutically acceptable salt or solvate, the above compound containing isotopes or other isotope atoms are all within the scope of the invention. Some isotope-labeled compounds in the present invention, such as the radioactive isotopes of $^3H$ and $^{14}C$, are also included and are useful in experiments on the tissue distribution of drugs and substrates. Tritium (3H) and Carbon-14 ($^{14}C$), which are relatively easy to prepare and detect. Which are the preferred choice. In addition, heavier isotope substitutions such as deuterium, i.e. $^2H$, have advantages in certain therapies due to their good metabolic stability, such as increased half-life or reduced dosage in vivo, and thus may be preferred in certain situations. Isotope-labeled compounds can be prepared by conventional methods through replacing readily available isotope-labeled reagents with non-isotopic reagents that can be prepared using the disclosed scheme shown in the Example.

If the synthesis of the compound of the invention is to be designed, it can be prepared by asymmetric synthesis, or derivatized with chiral auxiliary reagent, separating the resulting diastereomeric mixture and removing the chiral adjunct to obtain a pure enantiomer. In addition, if a molecule contains a basic functional group, such as an amino acid, or an acidic functional group, such as a carboxyl group, a diastereomer can be formed with a salt of suitable optically active acids or bases, which can be separated by conventional means, such as crystallization or chromatography, to obtain a pure enantiomer.

As described herein, the compound in the present invention may be substituted with any number of substituents or functional groups to extend its scope. In general, whether the term "substituted" appears before or after the term "optional", the general formula that includes substituents in the compound of the present invention means the substitution of a specified structural substituent for a hydrogen radical. When multiple locations in a particular structure are replaced by multiple specific substituents, each location of the substituents can be the same or different. The term "substituted" as used herein includes all substitution that allows organic compounds to be substituted. Broadly speaking, the allowable substituents include non-annular, cyclic, branched, non-branched, carbocyclic and heterocyclic, aromatic ring and non-aromatic organic compounds. In the present invention, such as heteroatomic nitrogen, its valence state may be supplemented by a hydrogen substituent or by any permitted organic compound described above. Furthermore, the invention is unintentionally limited to the substituted organic compounds. The present invention considers that a combination of substituents and variable groups is good for the treatment of diseases (such as infectious or hypertrophic diseases) in the form of stable compounds. The term "stable" herein refers to a stable compound which is sufficient for maintaining the integrity of the compound structure within a sufficiently long time, preferably in a sufficiently long time, which is hereby used for the above purposes.

The metabolite of the compounds of the present application and their pharmaceutically acceptable salts, and prodrugs that can be converted into the compounds of the present application and their pharmaceutically acceptable salts in vivo, also included in the claims.

Preparation Method

The preparation method of the compound of the formula (I) of the present invention is more specifically described below, but these specific methods do not constitute any limitation of the invention. The compound of the invention may also optionally be conveniently prepared by combining the various synthetic methods described in this specification or known in the art, such a combination may be easily performed by a skilled person in the art to which the invention belongs.

Typically, the preparation process for the compounds of the present invention is as follows, in which the raw materials and reagents used may be commercially purchased unless otherwise specified.

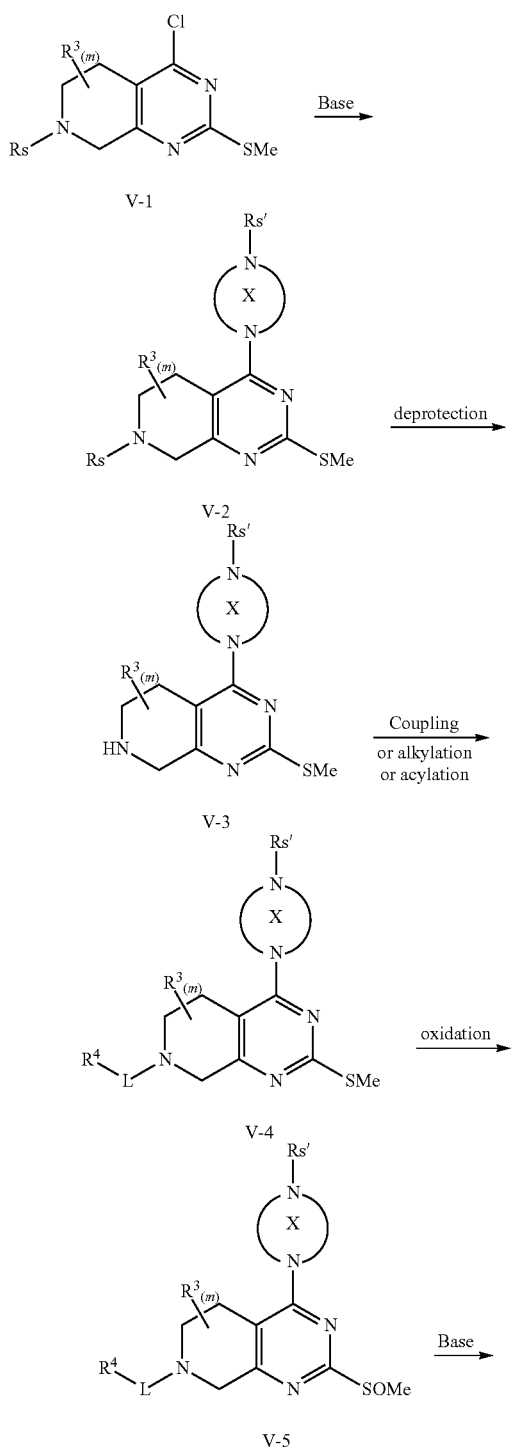

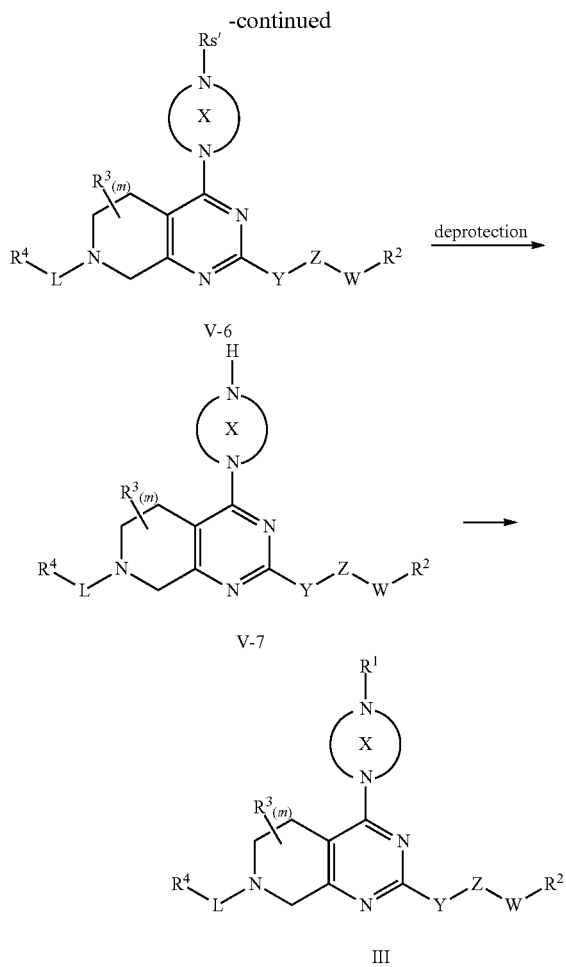

The compound of the formula (V-1) generates an intermediate (V-2) under an action of base (such as TEA or DIPEA), then deprotected to generate an intermediate (V-3). Intermediate (V-4) is obtained by coupling or substitution or acylation reaction of compound (V-3), then intermediate (V-5) is obtained under oxidizing agent (e.g., mCPBA). Compound (V-5) generates intermediate (V-6) under an action of base (such as NaH, LiHNMDS or tBuOK). Compound (V-6) is deprotected to form an intermediate (V-7), and then the target product formula (III) is obtained by substitution or acylation reaction; wherein $R^1$, $R^2$, $R^3$, $R^4$, L, X, Y, Z, W and m are as described above; Rs and Rs' are amino protecting groups (such as Boc, Bn, Cbz or Fmoc).

Pharmaceutical Composition and Method of Administration

The pharmaceutical compositions of the present invention are used to prevent and/or treat the following diseases: inflammation, cancer, cardiovascular disease, infection, immunological disease, metabolic disease.

The compounds of the formula (I) may be used in combination with other drugs known to treat or improve similar conditions. When administered in combination, the original administration for the drug can remain unchanged, while compound of formula I may be administered simultaneously or subsequently. Pharmaceutical composition containing one or more known drugs and the compound of formula I may be preferred when administered in combination with one or more other drugs. The drug combination also includes administering the compound of formula I and other one or more known drugs at overlapping time. When the compound of formula I is combined with other one or more drugs, the dose of the compound or known drug may be lower than that of their individual use.

The drug or active ingredients that can be used in pharmaceutical use with the compounds of the formula (I) include, but are not limited to PD-1 inhibitor (nivolumab, pembrolizumab, pidilizumab, cemiplimab, JS-001, SHR-120, BGB-A317, IBI-308, GLS-010, GB-226, STW204, HX008, HLX10, BAT 1306, AK105, LZM 009 or the biological analogue thereof, etc.), PD-L1 inhibitor (such as durvalumab, atezolizumab, avelumab, CS1001, KN035, HLX20, SHR-1316, BGB-A333, JS003, CS1003, KL-A167, F 520, GR1405, MSB2311 or the biological analogue thereof, etc.), CD20 antibody (such as rituximab, obinutuzumab, ofatumumab, veltuzumab, tositumomab, 131I-tositumomab, ibritumomab, 90Y-ibritumomab, 90In-ibritumomab, ibritumomab tiuxetan, etc.), CD47 antibody (such as Hu5F9-G4, CC-90002, TTI-621, TTI-622, OSE-172, SRF-231, AlX-148, NI-1701, SHR-1603, IBI188, IMM01), ALK inhibitor (such as Ceritinib, Alectinib, Brigatinib, Lorlatinib, ocatinib, etc.), PI3K inhibitor (such as Idelalisib, Duvelisib, Dactolisib, Taselisib, Bimiralisib, Omipalisib, Buparlisib, etc.), BTK inhibitor (such as Ibrutinib, Tirabrutinib, Acalabrutinib, Zanubrutinib, Vecabrutinib, etc.), EGFR inhibitor (such as Afatinib, Gefitinib, Erlotinib, Lapatinib, Dacomitinib, Icotinib, Canertinib, Sapitinib, Naquotinib, Pyrotinib, Rociletinib, Osimertinib, etc.), VEGFR inhibitor (such as Sorafenib, Pazopanib, Regorafenib, Sitravatinib, Ningetinib, Cabozantinib, Sunitinib, Donafenib, etc.), HDAC inhibitor (such as Givinostat, Tucidinostat, Vorinostat, Fimepinostat, Droxinostat, Entinostat, Dacinostat, Quisinostat, Tacedinaline, etc.), CDK inhibitor (such as Palbociclib, Ribociclib, Abemaciclib, Milciclib, Trilaciclib, Lerociclib, etc.), MEK inhibitor (such as Selumetinib (AZD6244), Trametinib (GSK1120212), PD0325901, U0126, Pimasertib (AS-703026), PD184352 (CI-1040), etc.), mTOR inhibitor (such as Vistusertib, etc.), SHP2 inhibitor (such as RMC-4630, JAB-3068, TNO 155, etc.) or the combination thereof.

The dosage forms of the pharmaceutical composition of the present invention include (but are not limited to): injection, tablet, capsule, aerosol, suppository, pellicle, pill, liniment for external use, controlled release or sustained-release or nano formulation.

The pharmaceutical composition of the present invention comprises a compound of the present invention or a pharmaceutically acceptable salt and a pharmaceutically acceptable excipient or carrier with safe and effective amount. wherein "safe and effective amount" refers to the amount of compound is sufficient to significantly improve the condition, not to produce severe side effects. Typically, the pharmaceutical composition contains 1-2000 mg of the compound/dosage of the present invention, and preferrably contains 10-1000 mg of the compound/dosage of the present invention. Preferably, "one dosage" is a capsule or a pill.

"Pharmaceutically acceptable carrier" refers to one or more compatible solid or liquid filler or gel substances, which are suitable for human use, and must be sufficiently pure and of sufficiently low toxicity. "Compatible" herein refers to ability of each component of a composition can be mixed with the compound of the present invention and can be mixed with each other without appreciably reducing the efficacy of the compound. Examples of pharmaceutically acceptable carrier include cellulose and derivatives thereof (such as sodium carboxymethylcellulose, sodium ethylcellulose, cellulose acetate, etc.), gelatin, talc, solid lubricant (such as stearic acid, magnesium stearate), calcium sulfate, vegetable oil (such as soybean oil, sesame oil, peanut oil, olive oil, etc.), polyol (such as propylene glycol, glycerol, mannitol, sorbitol, etc.), emulsifier (such as Tween®), wetting agent (such as lauryl sodium sulfate), colorant, flavoring, stabilizer, antioxidant, preservative, pyrogen-free water, etc.

There is no special limitation of administration mode for the compound or pharmaceutical compositions of the present invention, and the representative administration mode includes (but is not limited to): oral, intratumorally, rectal, parenteral (intravenous, intramuscular or subcutaneous), and topical administration.

Solid dosage forms for oral administration include capsules, tablets, pills, powders and granules. In these solid dosage forms, the active compounds are mixed with at least one conventional inert excipient (or carrier), such as sodium citrate or dicalcium phosphate, or mixed with any of the following components: (a) fillers or compatibilizer, such as starch, lactose, sucrose, glucose, mannitol and silicic acid; (b) binders, such as hydroxymethyl cellulose, alginate, gelatin, polyvinylpyrrolidone, sucrose and arabic gum; (c) humectant, such as, glycerol; (d) disintegrating agent, such as agar, calcium carbonate, potato starch or tapioca starch, alginic acid, certain composite silicates, and sodium carbonate; (e) dissolution-retarding agents, such as paraffin; (f) absorption accelerators, such as quaternary ammonium compounds; (g) wetting agents, such as cetyl alcohol and glyceryl monostearate; (h) adsorbents, for example, kaolin; and (i) lubricants such as talc, stearin calcium, magnesium stearate, solid polyethylene glycol, lauryl sodium sulfate, or the mixtures thereof. In capsules, tablets and pills, the dosage forms may also contain buffering agents.

The solid dosage forms such as tablets, sugar pills, capsules, pills and granules can be prepared by using coating and shell materials, such as enteric coatings and any other materials known in the art. They can contain an opaque agent. The release of the active compounds or compounds in the compositions can be released in a delayed mode in a given portion of the digestive tract. Examples of the embedding components include polymers and waxes. If necessary, the active compounds and one or more above excipients can form microcapsules.

Liquid dosage forms for oral administration include pharmaceutically acceptable emulsions, solutions, suspensions, syrups or tinctures. In addition to the active compounds, the liquid dosage forms may contain any conventional inert diluents known in the art such as water or other solvents, solubilizers and emulsifiers, such as ethanol, isopropanol, ethyl carbonate, ethyl acetate, propylene glycol, 1,3-butanediol, dimethyl formamide, as well as oil, in particular, cottonseed oil, peanut oil, corn germ oil, olive oil, castor oil and sesame oil, or the combination thereof.

Besides these inert diluents, the composition may also contain additives such as wetting agents, emulsifiers, and suspending agent, sweetener, flavoring agents and perfume.

In addition to the active compounds, the suspension may contain suspending agent, for example, ethoxylated isooctadecanol, polyoxyethylene sorbitol and sorbitan esters, microcrystalline cellulose, methanol aluminum and agar, or the combination thereof.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and any suitable mixtures thereof.

The dosage forms for topical administration of compounds of the invention include ointments, powders, patches, aerosol, and inhalants. The active ingredients are mixed with physiologically acceptable carriers and any preservatives, buffers, or propellant if necessary, under sterile conditions.

Compounds of the present invention can be administrated alone, or in combination with any other pharmaceutically acceptable compounds.

When the pharmaceutical compositions are used, a safe and effective amount of compound of the present invention is administrated to a mammal (such as human) in need thereof, wherein the dose of administration is a pharmaceutically effective dose. For a person weighed 60 kg, the daily dose is usually 1-2000 mg, preferably 50-1000 mg. Of course, the particular dose should also depend on various factors, such as the route of administration, patient healthy status, which are well within the skills of an experienced physician.

The present invention also provides a preparation method of pharmaceutical composition comprising the step of mixing a pharmaceutically acceptable carrier with the compound of formula (I) or crystal form, pharmaceutically acceptable salt, hydrate or solvate thereof of the present invention.

The invention also provides a treatment method comprising the step of administering the compound of formula (I), or its crystalline form, pharmaceutically acceptable salt, hydrate or solvate thereof, or the pharmaceutical composition of the invention to a subject in need thereof to selectively inhibit $KRAS^{G12C}$.

Compared with the prior art, the present invention has the following main advantages:

(1) The compound has a good selective inhibition on $KRAS^{G12C}$.

(2) The compound has better pharmacodynamics, pharmacokinetic properties and lower toxic and side effects.

The present invention will be further illustrated below with reference to the specific examples. It should be understood that these examples are only to illustrate the invention but not to limit the scope of the invention. The experimental methods without specific conditions in the following examples usually follow conventional conditions, such as Sambrook et al., Molecular Cloning: Laboratory Manual (New York: Cold Spring Harbor Laboratory Press, 1989), or according to the conditions recommended by the manufacturer. Unless otherwise stated, percentage and parts are calculated by weight.

All major and scientific terms used herein are the same as those familiar to those skilled in the art, unless otherwise defined. In addition, any method or material which is similar or equal to the recorded content may be applied to the method of the present invention. The preferred methods and materials described herein are described only for demonstration purposes.

The compound structure of the present invention was determined by nuclear magnetic resonance (NMR) and Liquid-mass chromatography (LC-MS).

NMR was detected by the Bruker AVANCE-400 NMR instrument, and the solvent included $DMSO-d_6$, $CD_3COCD_3$, $CDCl_3$ and $CD_3OD$, etc. The internal standard was tetramethylsilane (TMS), and the chemical shift was measured in percent per million (ppm).

LC-MS was detected by using Waters SQD2 mass spectrometry. HPLC was detected by using Agilent 1100 high voltage chromatograph (Microsorb 5 micron C18 100×3.0 mm column).

Qingdao GF254 silica gel plate was used for thin layer chromatography, 0.15-0.20 mm was used for TLC, and 0.4 mm-0.5 mm was used for preparative thin layer chromatography. Generally, Qingdao silica gel 200-300 mesh silica gel was used as carrier in column chromatography.

The starting materials in the Example of the present invention are known and commercially available, or may be synthesized by or in accordance with the literature reported in the art.

Unless otherwise specified, all reactions in the present invention are carried out by continuous magnetic stirring under the protection of dry inert gas (such as nitrogen or argon), and the reaction temperature is Celsius.

EXAMPLE

Preparation of Intermediate 1 2-(piperazin-2-yl) acetonitrile dihydrochloride

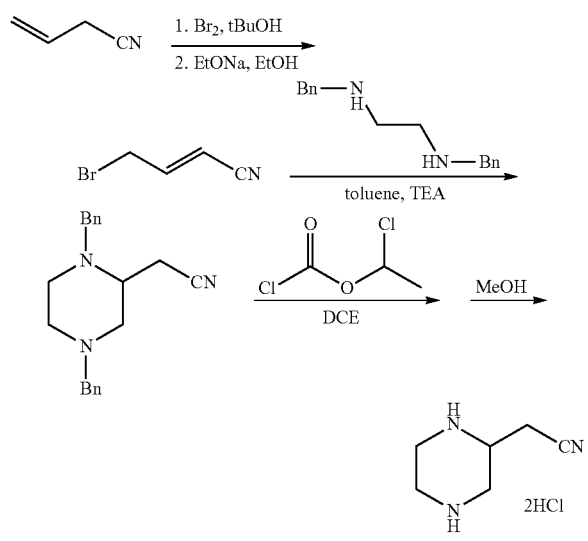

Step 1: Preparation of 4-bromine-but-2-enonitrile

The solution of bromin (119.2 g, 0.745 mol, 1.0 eq) and tert-butanol (75 mL) was added dropwise to the mixed solution of allyl cyanide (50 g, 0.745 mol, 1.0 eq) in t-butanol (75 mL) and petroleum ether (250 mL) at 10° C. After the addition, the reaction mixture was stirred for 30 min, followed by adding a solution of sodium ethanol (50.7 g, 0.745 mol, 1.0 eq) in ethanol (250 mL). The resulting mixture was reacted at room temperature for 2 h and then filtered. The filtrate was concentrated, and the residue was separated by silica gel column chromatography to obtain the target product (72.7 g, yield 67%).

Step 2: Preparation of 2-(1,4-diphenylpiperazin-2-yl) acetonitrile 4-bromo-but-2-enonitrile (58.16 g, 0.4 mol, 1.0 eq) was added dropwise to the solution of N,N'-dibenzylethylenediamine (95.9 g, 0.4 mol, 1.0 eq) and triethylamine (80.9 g, 0.8 mol, 2.0 eq) in toluene (360 mL) at 0° C. The resulting mixture was reacted at room temperature overnight, then filtered. The filtrate was concentrated, and the residue was separated by silica gel column chromatography to obtain the target product (65.3 g, yield 54%).

LC-MS: M/Z 306 (M+H)$^+$.

Step 3: Preparation of 2-(piperazin-2-yl) acetonitrile dihydrochloride 1-chloroethyl chloroformate (142 g, 1.096 mol, 6.0 eq) was added to 2-(1,4-diphenylpiperazin-2-yl) acetonitrile (55.8 g, 0.1827 mol, 1.0 eq) in 1,2-dichloroethane (250 mL) at 0° C. After the addition, the reaction mixture was reacted at 90° C. for 50 h, then concentrated under reduced pressure. Methanol (550 mL) was added to the residue, and the resulting mixture was reacted at 80° C. for 1 h, then concentrated under reduced pressure. The residue was slurried with methyl tert-butyl ether and filtered to obtain the target product (36 g, quantitative yield).

LC-MS: M/Z 126 (M+H)$^+$. $^1$H NMR (400 MHz, D$_2$O) δ 4.01-3.96 (m, 1H), 3.81-3.67 (m, 3H), 3.09 (D, J=6.0 Hz, 2H).

Preparation of Intermediate 2 tert-butyl 2-(cyanomethyl)-4-(7-(8-methylnaphthalen-1-yl)-2-(methyl sulfoxide)-5, 6, 7, 8-tetrahydropyrido[3,4-d]pyrimidin-4-yl)piperazine-1-formate

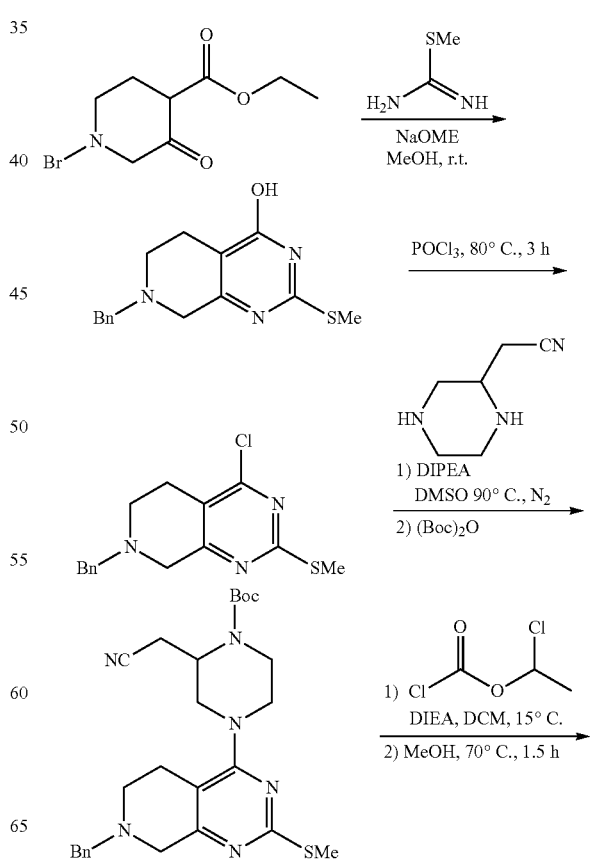

-continued

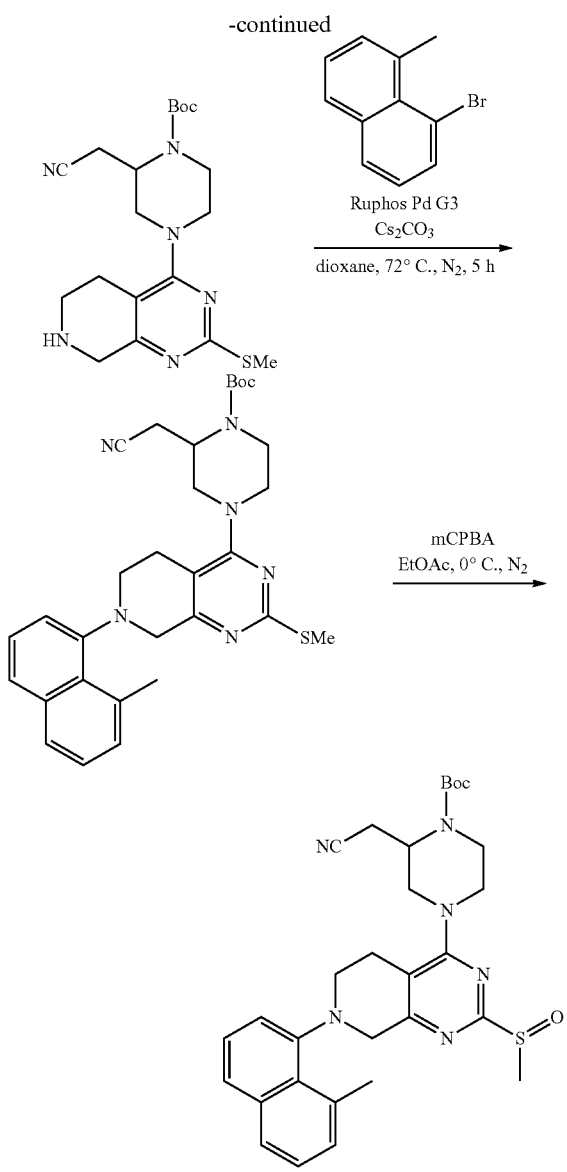

Step 1: Preparation of 7-benzyl-2-(methylthio)-5,6,7,8-tetrahydropyrido[3,4-d]pyrimidin-4-ol The metal sodium (11.0 g, 478.35 mmol) was added to methanol (500 mL) in batches. After cooling under an ice water bath and dissolved clarification under stirring, ethyl 1-benzyl-3-oxopiperidine-4-carboxylate (25.0 g, 95.67 mmol) and S-methylisothiourea sulfate (47.9 g, 172.2 mmol) were added successively. The resulting mixture was stirred at room temperature for 16 h under nitrogen protection. After completion of the reaction, the pH of the reaction solution was adjusted to 6 with 2M hydrochloric acid aqueous solution. The resulting mixture was concentrated under reduced pressure to remove methanol. 100 ml of water was added to the residue, and then filtered. The filter cake was successively washed with water (50 mL) and ethyl acetate (50 mL) for one time, and then vacuum dried at 50° C. to obtain the target product (25.68 g, yield 93%).

LC-MS: M/Z 288 (M+H)+.

Step 2: Preparation of 7-benzyl-4-chloro-2-(methylthio)-5,6,7,8-tetrahydropyrido[3,4-d]pyrimidine 7-benzyl-2-(methylthio)-5,6,7,8-tetrahydropyrido[3,4-d] pyrimidin-4-ol (25.68 g, 89.36 mmol) was added to phosphoryl chloride (310 mL). The resulting reaction solution was stirred at 80° C. for 3 h. After the completion of the reaction, the reaction solution was concentrated under reduced pressure to remove most of the phosphoryl chloride, then ethyl acetate (500 mL) was added. The resulting mixture was adjusted to a pH of 6 with a saturated sodium bicarbonate aqueous solution. After the aqueous phase was separated, extracted with ethyl acetate (3×100 mL). After all organic phases were combined, washed with saturated sodium chloride and then dried over anhydrous sodium sulfate and filtered. The filtrate was concentrated under reduced pressure, and the obtained residue was separated by silica gel column to obtain the target product (13.3 g, yield 49%).

LC-MS: M/Z 306 (M+H)<.

Step 3: Preparation of tert-butyl 4-(7-benzyl-2-(methylthio)-5,6,7,8-tetrahydropyrido[3,4-d]pyrimidin-4-yl)-2-(cyanomethyl) piperazin-1-formate 7-benzyl-4-chloro-2-(methylthio)-5,6,7,8-tetrahydropyrido[3,4-d]pyrimidine (7.0 g, 22.89 mmol), 2-(piperazin-2-yl) acetonitrile dihydrochloride (5.44 g, 27.47 mmol), N,N-diisopropylethylamine (22.8 mL, 137.34 mmol) and DMSO were added to the reaction flask. The reaction solution was heated to 80° C. and stirred for 3 h under the protection of nitrogen, and then dit-butyl dicarbonate (26.3 mL, 114.45 mmol) was added. After the completion of the reaction, the reaction solution was quenched with water and then extracted with ethyl acetate (3×100 mL). After all organic phases were combined, washed with saturated sodium chloride once and then dried over anhydrous sodium sulfate and filtered. The filtrate was concentrated under reduced pressure, and the residue was separated by silica gel column to obtain the target product (8.21 g, yield 73%).

LC-MS: M/Z 495 (M+H)+.

Step 4: Preparation of tert-butyl 2-(cyanomethyl)-4-(2-(methylthio)-5, 6, 7, 8-tetrahydropyrido[3,4-d] pyrimidin-4-yl) piperazine-1-formate tert-butyl 4-(7-benzyl-2-(methylthio)-5,6,7,8-tetrahydropyrido[3,4-d]pyrimidin-4-yl)-2-(cyanomethyl) piperazin-1-formate (8.21 g, 16.6 mmol) was added to dichloromethane (160 mL), followed by adding 1-chloroethyl chloroformate (3.58 mL, 33.2 mmol) at 0° C. After the addition, the reaction solution was stirred at 15° C. for 3 h. The resulting mixture was concentrated under reduced pressure to remove the solvent and then methanol (160 mL) was added. The resulting mixture was stirred at 70° C. for 1.5 h, then cooled to room temperature, followed by adding saturated sodium bicarbonate solution (300 mL). The resulting mixture was extracted with ethyl acetate (3×100 mL). After all organic phases were combined, washed with saturated sodium chloride once and then dried over anhydrous sodium sulfate and filtered. The filtrate was concentrated under reduced pressure, and the residue was separated by silica gel column (eluent: DCM/MeOH=100/1 to 30/1) to obtain the target product (4.9 g, yield 73%).

LC-MS: M/Z 405 (M+H)+. $^1$HNMR (400M, CDCl$_3$) 4.52 (s, 1H), 3.93 (m, 2H), 3.78 (d, J=12.4 Hz, 1H), 3.34 (m, 1H), 3.24 (m, 3H), 2.73 (m, 5H), 2.42 (s, 3H), 1.43 (s, 9H).

Step 5: Preparation of tert-butyl 2-(cyanomethyl)-4-(7-(8-methylnaphthalen-1-yl)-2-(methylthio)-5,6,7,8-tetrahydropyrido[3,4-d]pyrimidin-4-yl)piperazine-1-formate Tert-butyl 2-(cyanomethyl)-4-(2-(methylthio)-5, 6, 7, 8-tetrahydropyrido[3,4-d]pyrimidin-4-yl)piperazine-1-formate (2 g, 4.94 mmol), 1-bromo-8-methylnaphthalene (2.73 g, 12.35 mmol), cesium carbonate (4.83 g, 14.82 mmol) and dioxane (80 mL) were added to the reaction flask, then replaced with nitrogen three times, and Ruphos Pd G3 (1.24 g, 1.48 mmol) was added. The resulting mixture was replaced by nitrogen for three times and heated to 72° C., stirred for 16 h. The resulting mixture was added to water (100 mL) and then extracted with ethyl acetate (3×100 mL). After all organic phases were combined, washed with saturated sodium chloride once and then dried over anhydrous sodium sulfate and filtered. The filtrate was concentrated under reduced pressure, and the residue was separated by silica gel column (eluent: PE/EA=1/0 to 5/1) to obtain the target product (863 mg, yield 32%).

LC-MS: M/Z 545 (M+H)$^+$. 1HNMR (400M, CD$_3$OD) 7.54 (m, 2H), 7.28 (m, 1H), 7.17 (m, 3H), 4.55 (s, 1H), 4.48 (s, 1H), 3.98 (m, 4H), 3.56 (m, 1H), 3.38 (m, 1H), 3.27 (m, 1H), 3.02 (m, 3H), 2.86 (s, 1H), 2.79 (s, 3H), 2.57 (m, 2H), 2.40 (s, 3H), 1.41 (s, 9H).

Step 6: Preparation of tert-butyl 2-(cyanomethyl)-4-(7-(8-methylnaphthalen-1-yl)-2-(methyl sulfoxide)-5, 6, 7, 8-tetrahydropyrido[3,4-d]pyrimidin-4-yl) piperazine-1-formate Tert-butyl 2-(cyanomethyl)-4-(7-(8-methylnaphthalen-1-yl)-2-(methylthio)-5,6,7,8-tetrahydropyrido[3,4-d]pyrimidin-4-yl) piperazine-1-formate (340 mg, 0.62 mmol) was dissolved in ethyl acetate (6 mL), then cooled to 0° C. under ice-salt baths. Then the solution of meta-Chloroperoxybenzoic acid (216 mg, 1.25 mmol) in ethyl acetate (3 mL) was added. After the addition, the reaction solution was stirred at 0° C. for 10 min, and then quenched with a low sodium sulfite solution (50 mL). The resulting mixture was added to water (30 mL) and then extracted with ethyl acetate (3×30 mL). After all organic phases were combined, washed with saturated sodium chloride once and then dried over anhydrous sodium sulfate and filtered. The filtrate was concentrated under reduced pressure, and the residue was separated by silica gel column (eluent: PE:EA=1:0 to 0:1) to obtain the target product (186 mg, yield 53%).

LC-MS: M/Z 561 (M+H)$^+$. $^1$HNMR (400M, CDCl$_3$) δ 7.61 (m, 2H), 7.32 (m, 2H), 7.17 (m, 2H), 4.53 (s, 1H), 3.97 (m, 5H), 3.68 (m, 1H), 3.24 (m, 6H), 2.84 (m, 6H), 2.64 (m, 2H), 1.44 (s, 9H).

Preparation of Intermediate 3 2-(methyl (oxetan-3-yl) amino)ethanol

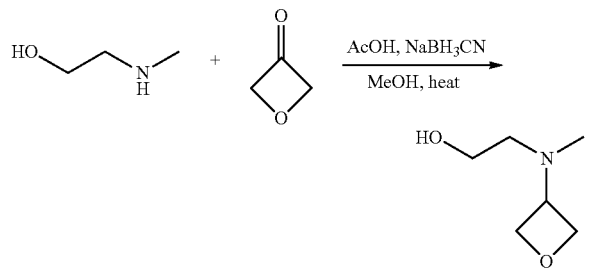

2-(methylamino) ethanol (5 g, 67 mmol) was added to methanol (50 mL), and then 3-oxetanone 2 (5.8 g, 80 mmol), sodium cyanoborohydride (12.6 g, 200 mmol) and acetic acid (1 mL) were added. Then the reaction solution was heated at 60° C., stirred for 2 hours, cooled down, poured into the saturated potassium carbonate aqueous solution, and then extracted with ethyl acetate (50 mL×2). The organic phase was dried, concentrated, and silica gel column chromatography was performed (eluent: DCM/MeOH=20/1) to obtain the target product (6.7 g, yield: 77%).

$^1$H NMR (400 MHz, CDCl$_3$) δ 4.67 (t, J=6.8 Hz, 2H), 4.60-4.56 (m, 2H), 3.70-3.60 (m, 3H), 2.41 (t, J=5.6 Hz, 2H), 2.16 (s, 3H).

Preparation of Intermediate 4 2-(methyl (1-methylazetidine-3-yl) amino ethanol

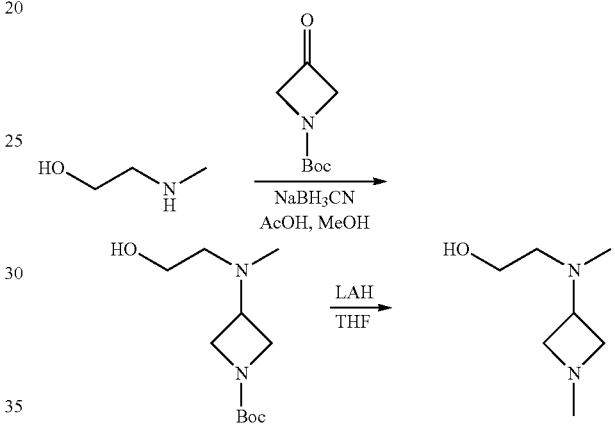

Step 1: Preparation of tert-butyl 3-((2-hydroxyethyl)(methyl)amino) azetidine-1-formate 2-(methylamino)ethanol (5 g, 67 mmol) was added to methanol (50 mL), and then 1-t-butyloxycarboryl-3-oxetanone (11.4 g, 67 mmol), sodium cyanoborohydride (12.6 g, 200 mmol) and acetic acid (1 mL) were added. Then the reaction solution was heated at 60° C., stirred for 2 hours, cooled down, poured into the saturated potassium carbonate solution, and then extracted with ethyl acetate (50 mL×2). The organic phase was dried, concentrated, and silica gel column chromatography was performed (eluent: DCM/MeOH=20/1) to obtain the target product (8 g, yield: 53%).

Step 2: Preparation of 2-(methyl(1-methylazetidine-3-yl)amino)ethanol

Tert-butyl 3-((2-hydroxyethyl) (methyl) amino) azetidine-1-formate (4 g, 17 mmol) was added to tetrahydrofuran (50 mL), and then lithium aluminium hydride (2.6 g, 70 mmol) was added. Then the reaction solution was heated and stirred overnight with reflux, cooled down, quenched with sodium sulfate decahydrate, filtered and concentrated, and silica gel column chromatography was performed (eluent: DCM/MeOH=10/1) to obtain the target product (600 mg, yield: 24%).

$^1$H NMR (400 MHz, CDCl$_3$) δ 3.71-3.67 (m, 2H), 3.59 (t, J=5.2 Hz, 2H), 3.23-3.17 (m, 1H), 3.08-3.04 (m, 2H), 2.49 (s, 3H), 2.41 (t, J=5.2 Hz, 2H), 2.14 (s, 3H).

489

Preparation of Intermediate 5 (R)-2-((cyclobutylm-ethyl)(methyl)amino)propano-1-ol

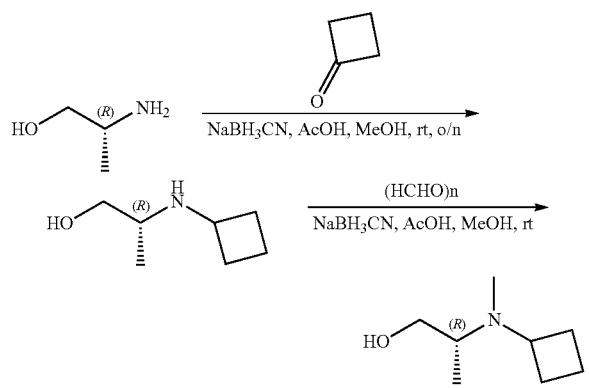

Step 1: Preparation of (R)-2-((cyclobutylmethyl)amino)propano-1-ol (R)-2-aminopropano-1-ol (3 g, 40 mmol), cyclobutanone (2.8 g, 40 mmol) and acetic acid (240 mg, 4 mmol) were added to methanol (25 mL), and stirred for half an hour under room temperature. Then the reaction solution was cooled to 0° C., and sodium cyanoborohydride (7.56 g, 120 mmol) was slowly added. The reaction solution was stirred overnight at room temperature, and TLC showed new spots. The reaction solution was concentrated to remove methanol to give crude product. The crude product was diluted with saturated potassium carbonate solution, extracted with ethyl acetate 3 times, combined organic phases and concentrated, silica gel column chromatography was performed (eluent: dichloromethane/methanol=10/1) to obtain target product (4.3 g, yield 56%).

LCMS: m/z 129.9 (M+H)$^+$.

Step 2: Preparation of (R)-2-((cyclobutylmethyl)(methyl)amino)propano-1-ol (R)-2-((cyclobutyl methyl)amino)propano-1-ol (2.9 g, 22.48 mmol), paraformaldehyde (2.02 g, 67.44 mmol) and acetic acid (138 mg, 2.3 mmol) were added to methanol (40 mL), and stirred for half an hour under room temperature. Then the reaction solution was cooled to 0° C., and sodium cyanoborohydride (12.6 g, 200 mmol) was slowly added. The reaction solution was stirred overnight at room temperature, and TLC showed new spots. The reaction solution was concentrated to remove methanol to give crude product. The crude product was diluted with saturated potassium carbonate solution, extracted with ethyl acetate 3 times, combined organic phases and concentrated, silica gel column chromatography was performed (eluent: dichloromethane/methanol=10/1) to obtain target product (1.6 g, yield 50%).

$^1$H NMR (400 MHz, CDCl$_3$) δ 3.37-3.33 (m, 2H), 3.25 (t, J=10.0 Hz, 1H), 3.14-3.10 (m, 1H), 2.89-2.85 (m, 1H), 2.06-1.98 (m, 5H), 1.86-1.73 (m, 2H), 1.69-1.61 (m, 2H), 0.80 (d, J=6.8 Hz, 3H).

490

Preparation of Intermediate 6 trans-2-(dimethylamino)cyclopentanol

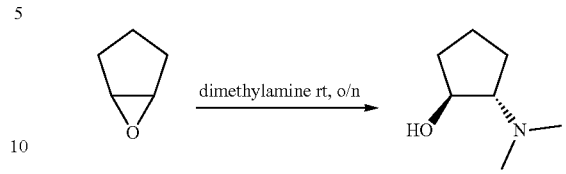

Step 1: (S)-2-((1-cyclopropylethyl)amino)ethan-1-ol 6-oxazole[3.1.0]hexane (2 g, 23.8 mmol) was added to the dimethylamine aqueous solution (content greater than 33%, 10 mL), and the resulting reaction solution was stirred overnight at room temperature. The reaction solution was concentrated, and the residue was separated by silica gel column (eluent: dichloromethane/methanol=20/1) to obtain the target product (1.63 g, yield: 53%).

Preparation of Intermediate 31 cis-2-(dimethylamino) cyclopentanol

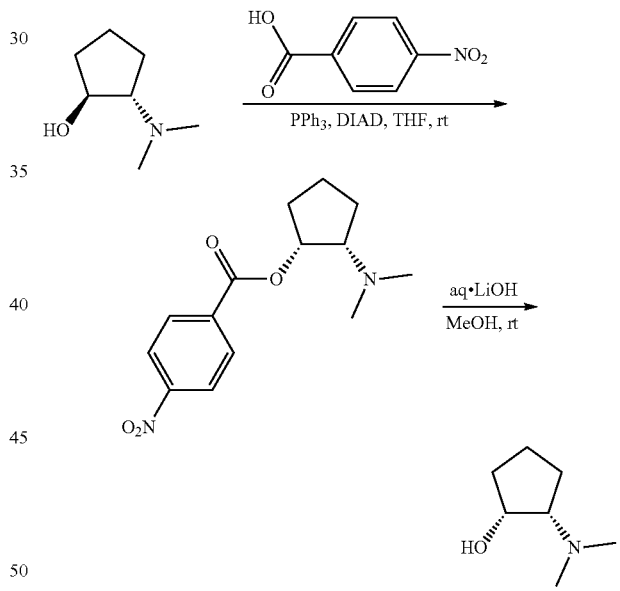

Step 1: Preparation of cis-2-(dimethylamino) cyclopentyl-4-nitrobenzoate

Trans-2-(dimethylamino) cyclopentanol (3.0 g, 23.3 mmol), 4-nitrobenzoic acid (4.66 g, 27.9 mmol) and triphenylphosphine (7.9 g, 30.2 mmol) were suspended in 50 ml of anhydrous tetrahydrofuran, replaced with nitrogen 3 times, cooled to 0° C. Diisopropyl azodicarboxylate (6.1 g, 30.2 mmol) was slowly added dropwise to the mixture, and the temperature should not more than 10° C. during the dropwise. The reaction solution was stirred at room temperature for 16 hours, spin-dried, separated by silica gel column (eluent: dichloromethane/methanol=30/1) to obtain the target product (crude).

Step 2: Preparation of cis-2-(dimethylamino) cyclopentanol

The cis-2-(dimethylamino) cyclopentyl-4-nitrobenzoate 2 (crude) was dissolved in 50 ml of methanol, and the solution of lithium hydroxide monohydrate (1.95 g, 46.52 mmol) in water (10 mL) was added. The reaction solution was stirred at room temperature for 16 hours, then concentrated to remove methanol, diluted with 50 ml of water, extracted 2 times with 50 ml of ethyl acetate, combined the organic layer, concentrated, and separated by silica gel column (dichloromethane:methanol=50:1 to 10):1) to obtain the target product (2 g), two-step yield: 67%.

$^1$H NMR (400 MHz, CDCl$_3$) δ 4.30-4.27 (m, 1H), 2.91-2.87 (m, 1H), 2.53 (s, 6H) 2.03-1.93 (m, 2H), 1.77-1.60 (m, 4H).

Preparation of Intermediate 7
trans-4-(dimethylamino) tetrahydrofuran-3-ol

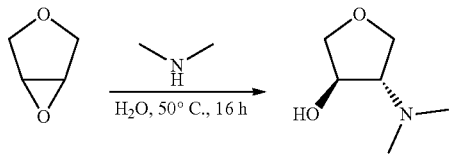

The dimethylamine aqueous solution (content greater than 33%, 20 mL) was heated and stirred at 50° C., and 3,4-epoxy tetrahydrofuran (5 g, 58 mmol) was added dropwise. Then the reaction solution was stirred at 50° C. for 16 hours. The reaction solution was spin-dried, separated by silica gel column (eluent: dichloromethane/methanol=10/1, supplemented with 1‰ ammonia water) to obtain the target product (7 g, yield: 92%).

$^1$H NMR (400 MHz, CDCl$_3$) δ 4.33-4.29 (m, 1H), 4.04 (dd, J=9.6 Hz, 6.8 Hz, 1H), 3.95 (dd, J=10.0 Hz, 5.6 Hz, 1H), 3.70 (dd, J=10.0 Hz, 3.2 Hz, 1H), 3.65 (dd, J=9.6 Hz, 6.8 Hz, 1H), 2.76-2.71 (m, 1H), 2.29 (s, 6H).

Preparation of Intermediate 8 cis-4-(dimethylamino) tetrahydrofuran-3-ol

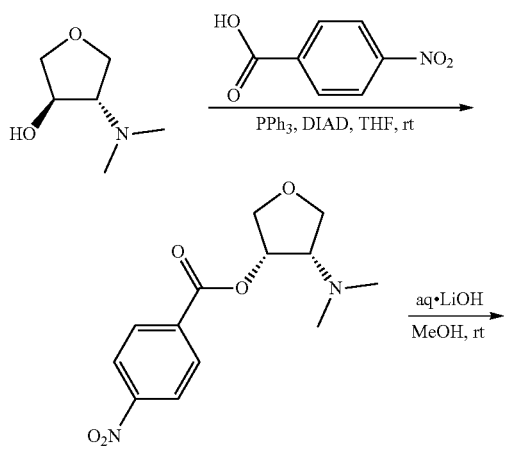

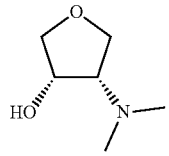

Step 1: Preparation of cis-4-(dimethylamino) tetrahydrofuran-3-yl-4-nitrobenzoate Trans-4-(dimethylamino) tetrahydrofuran-3-ol (3.0 g, 22.9 mmol), 4-nitrobenzoic acid (4.6 g, 27.5 mmol) and triphenylphosphine (7.8 g, 29.8 mmol) were suspended in 60 ml of anhydrous tetrahydrofuran, replaced with nitrogen 3 times, cooled to 0° C. Diisopropyl azodicarboxylate (6.0 g, 29.8 mmol) was slowly added dropwise to the mixture, and the temperature should not more than 10° C. during the dropwise. The reaction solution was stirred at room temperature for 16 hours, spin-dried, separated by silica gel column (eluent: dichloromethane/methanol=30/1) to obtain the target product (crude).

Step 2: Preparation of cis-4-(dimethylamino) tetrahydrofuran-3-ol

The cis-4-(dimethylamino) tetrahydrofuran-3-yl-4-nitrobenzoate (crude) was dissolved in 150 ml of methanol, and the solution of lithium hydroxide monohydrate (5.6 g, 133.6 mmol) in water (50 mL) was added. The reaction solution was stirred at room temperature for 16 hours, then concentrated to remove the methanol, diluted with 100 ml of water, and adjusted to pH 2 with 6 mol of hydrochloric acid. The mixture was washed twice with 200 ml of ethyl acetate, and the pH of aqueous phase was adjusted to greater than 12 with solid potassium carbonate. The mixture was then extracted with dichloromethane/isopropanol (10:1, 150 mL) for 10 times. Combined dichloromethane phase, concentrated, separated by silica gel column (eluent: dichloromethane/methanol=50/1 to 10/1) to obtain the target product (1.8 g, two step yield: 51%).

$^1$H NMR (400 MHz, CDCl$_3$) δ 4.33-4.30 (m, 1H), 4.07-4.02 (m, 1H), 3.95 (dd, J=10.0 Hz, 5.6 Hz, 1H), 3.71 (dd, J=10.0 Hz, 2.8 Hz, 1H), 3.64 (dd, J=9.2 Hz, 6.4 Hz, 1H), 2.75-2.70 (m, 1H), 2.29 (s, 6H).

Preparation of Intermediate 9
(S)-2-(cyclobutylmethylamine)-3-methoxy-1-propanol

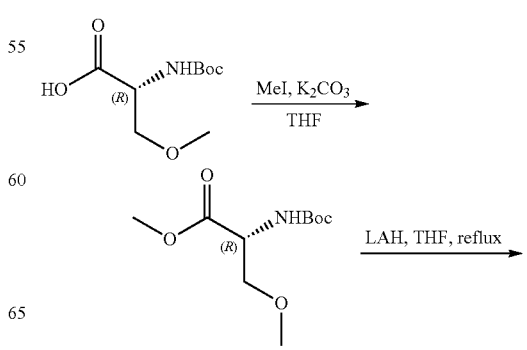

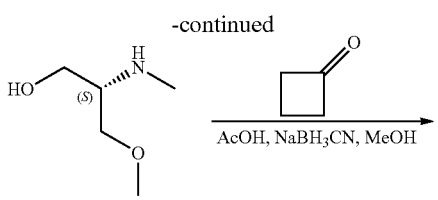

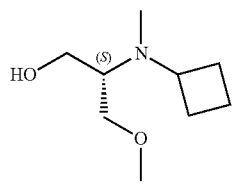

Step 1: Preparation of methyl (R)-2-tert-butoxycarbonylamino-3-methoxypropionate (R)-2-tert-butoxycarbonylamino-3-methoxypropionic acid (9 g, 41.1 mol) was dissolved in anhydrous tetrahydrofuran (90 mL), and potassium carbonate (8.5 g, 61.7 mol) and iodomethane (8.8 g, 61.7 mol) were added under ice bath. After the addition, the reaction was stirred overnight at room temperature. Ethyl acetate (400 mL) and water (300 mL) were added to the reaction solution to quench the reaction, and the organic phase was washed twice with water (200 mL), washed once with saturated brine (100 mL), dried over anhydrous sodium sulfate, filtered, spin-dried, to obtain the yellow oil target product (9.9 g), yield 93%.

LCMS: m/z 256 (M+H)$^+$.

Step 2: Preparation of (S)-3-methoxy-2-methylamino-1-ol

Methyl (R)-2-tert-butoxycarbonylamino-3-methoxypropionate (8.9 g, 38.2 mmol) was dissolved in anhydrous tetrahydrofuran (150 mL), lithium aluminum hydrogen (5.8 g, 153 mmol) was added in batches under ice bath. After the addition, the reaction was refluxed overnight. Sodium sulfate decahydrate (15 g) was slowly added to the reaction solution under ice bath to quench the reaction, filtered, and the filtrate was dried and separated by silica gel column (eluent: dichloromethane/methanol=15/1) to obtain the target product, 56%.

LCMS: m/z 120 (M+H)$^+$.

Step 3: Preparation of (S)-2-(cyclobutylmethylamine)-3-methoxy-1-propanol (S)-3-methoxy-2-methylamino-1-ol (2.5 g, 21 mmol), cyclobutanone (2.2 g, 31.5 mmol) and acetic acid (1.3 g, 21 mmol) were added to methanol (50 mL), the reaction solution was cooled to 0° C., and sodium cyanoborohydride (3.3 g, 52.5 mmol) was slowly added. The reaction solution was then stirred overnight at room temperature, and the LCMS showed that the raw material disappeared and the product was formed. The reaction solution was concentrated to remove methanol to obtain the crude, and the crude was adjusted to weakly alkaline with 1 mol/L potassium carbonate aqueous solution and extracted twice with ethyl acetate (200 mL). Combined the organic phase, washed once with saturated brine (100 mL), dried over anhydrous sodium sulfate, spin-dried, separated by silica gel column (eluent: dichloromethane/methanol=15/1) to obtain the target product (700 mg, yield: 19%).

$^1$H NMR (400 MHz, CDCl$_3$) δ 3.52-3.44 (m, 2H), 3.33-3.23 (m, 5H), 3.22-3.15 (m, 1H), 2.96-2.86 (m, 1H), 2.12 (s, 3H), 2.08-1.98 (m, 2H), 1.85-1.75 (m, 2H), 1.68-1.54 (m, 2H).

Preparation of Intermediate 10 (1-((dimethylamino)methyl) cyclopropyl) methanol

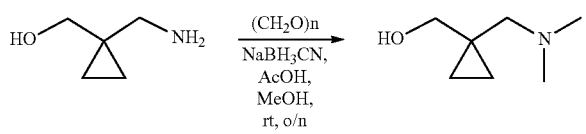

1-(amino methyl) cyclopropyl)methanol (800 mg, 7.92 mmol), paraformaldehyde (1.43 g, 47.52 mmol) and acetic acid (48 mg, 0.8 mmol) were added to methanol (10 mL), and stirred for half an hour under room temperature. The reaction solution was cooled to 0° C., and sodium cyanoborohydride (3.0 g, 47.52 mmol) was slowly added. The reaction solution was stirred overnight at room temperature, and TLC showed new spots. The reaction solution was concentrated to remove methanol to give crude product. The crude product was diluted with saturated potassium carbonate solution, extracted with ethyl acetate 3 times, combined organic phases, dried, and concentrated, and silica gel column chromatography was performed (eluent: dichloromethane/methanol=10/1) to obtain target product (273 mg), yield 27%.

LCMS: m/z 130 (M+H)$^+$.

$^1$H NMR (400 MHz, CDCl$_3$) δ 4.76 (brs, 1H), 3.53 (d, J=6.0 Hz 2H), 2.42 (s, 2H), 2.31 (s, 6H), 0.51-0.48 (m, 2H), 0.37-0.34 (m, 2H).

The following compounds were synthesized from different starting materials in the same manner as intermediate 10:

Preparation of Intermediate 11 (1-(dimethylamino)methyl) cyclobutyl) methanol

LCMS: m/z 144 (M+H)$^+$. $^1$H NMR (400 MHz, CDCl$_3$) δ 4.90 (brs, 1H), 3.79 (s, 2H), 2.50 (s, 2H), 2.24 (s, 6H), 1.83-1.80 (m, 6H).

Preparation of Intermediate 12 (3-(dimethylamino)methyl)oxetan-3-yl) methanol

LCMS: m/z 146 (M+H)$^+$. $^1$H NMR (400 MHz, CDCl$_3$) δ 5.20 (brs, 1H), 4.50-4.48 (m, 2H), 4.41-4.39 (m, 2H), 4.07 (s, 2H), 2.77 (s, 2H), 2.24 (s, 6H).

Preparation of Intermediate 13 2-(cyclobutyl (2-methoxyethyl) amino) ethanol

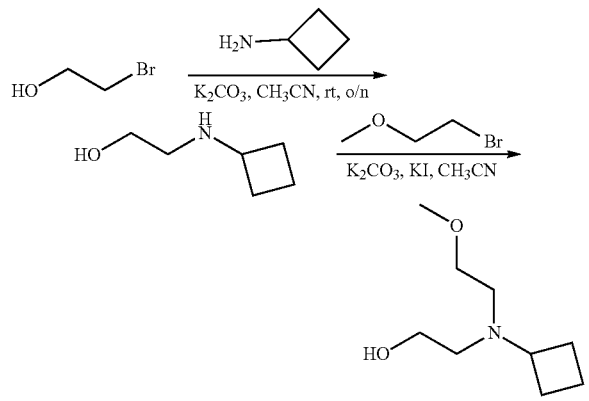

Step 1 Preparation of 2-(cyclobutylamino) ethanol 2-bromine ethanol (10 g, 57.14 mmol), cyclobutamine (4.06 g, 57.14 mmol) and potassium carbonate (11.83 g, 85.71 mmol) were added to acetonitrile (500 mL). The reaction solution was stirred overnight at room temperature, and TLC showed new spots. The reaction solution was filtered, the filtrate was concentrated, separated by silica gel column (eluent: dichloromethane/methanol=10/1) to obtain the target product (1.5 g, yield: 23%).
MS: m/z 116 (M+H)+.

Step 2. Preparation of (2-(cyclobutyl(2-methoxyethyl)amino)ethanol 2-(cyclobutylamino) ethanol (500 mg, 4.34 mmol), potassium carbonate (1.2 g, 8.69 mmol) and potassium iodide (71 mg, 0.43 mmol) were added to acetonitrile (20 mL), then 1-bromine-2-methoxyethane (725 mg, 5.22 mmol) was added to the reaction solution, and the reaction solution was stirred at room temperature overnight. TLC showed new spots. The reaction solution was filtered, the filtrate was concentrated, separated by silica gel column (eluent: dichloromethane/methanol=10/1) to obtain the target product (618 mg, yield: 86%).
MS: m/z 174 (M+H)+. $^1$H NMR (400 MHz, CDCl$_3$) δ 3.58 (t, J=5.6 Hz, 2H), 3.46 (t, J=6.0 Hz, 2H), 3.39-3.25 (m, 5H), 2.73-2.64 (m, 4H), 2.09-1.92 (m, 4H), 1.70-1.57 (m, 2H).

Intermediate 14 2-[(2,2-difluoro-cyclopropylmethyl)-methylamino]-ethanol

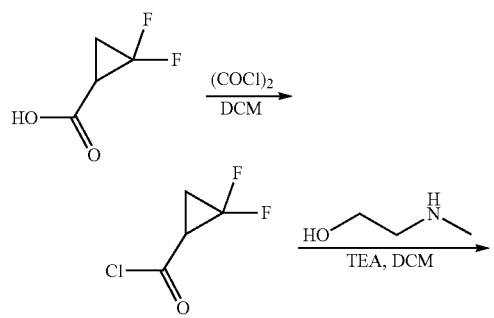

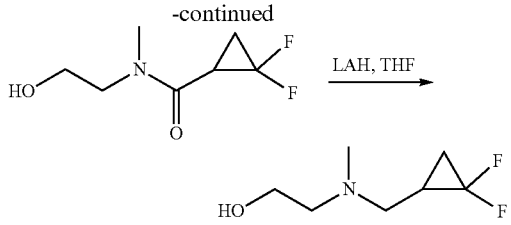

Step 1: Preparation of 2,2-difluorocyclopropanecarbonyl chloride 2,2-difluorocyclopropanecarboxylic acid (2.5 g, 20.5 mmol) was dissolved in anhydrous dichloromethane (25 mL), oxalyl chloride (2.1 mL, 24.6 mmol) and N,N-dimethylformamide (5 drops) were slowly added under ice bath. After the addition, the reaction was stirred for two hours at room temperature. The reaction solution was directly used for the next reaction.

Step 2: Preparation of 2,2-difluorocyclopropanecarboxylic Acid (2-hydroxyethyl)-formamide 2-methylamino ethanol (2.3 g, 31 mmol) was dissolved in dichloromethane (28 mL), and triethylamine (10.5 g, 102 mmol) and the reaction solution from first step were added under ice bath. After the addition, the reaction was reacted overnight at room temperature. Then, the dichloromethane was concentrated and removed. The organic phase was separated by adding ethyl acetate (200 mL) and water (100 mL) to the residue, washed once with saturated brine (50 mL), dried over anhydrous sodium sulfate, spin-dried, separated by silica gel column (eluent: petroleum ether/ethyl acetate=2/1) to obtain the target product (2.0 g, yield 38%).
MS: m/z 180 (M+H)>.

Step 3: Preparation of 2-[(2,2-difluoro-cyclopropylmethyl)-methylamino]-ethanol 2,2-difluorocyclopropanecarboxylic acid (2-hydroxyethyl)-formamide (1.9 g, 10.6 mmol) was dissolved in anhydrous tetrahydrofuran (30 mL), lithium aluminum hydrogen was added in batches under ice bath (0.8 g, 21.2 mmol). After the addition, the mixture was reacted at room temperature overnight. Sodium sulfate decahydrate (3 g) was slowly added to the reaction solution under ice bath to quench the reaction, filtered, spin-dried and separated by silica gel column (eluent: dichloromethane/methanol=20/1) to obtain the target product (750 mg, yield 43%).
$^1$H NMR (400 MHz, CDCl$_3$) δ 3.60 (t, J=5.2 Hz, 2H), 2.76-2.67 (m, 1H), 2.66-2.43 (m, 4H), 2.32 (s, 3H), 1.76-1.62 (m, 1H), 1.52-1.40 (m, 1H), 1.05-0.95 (m, 1H).

Preparation of Intermediate 15 (S)-2-(cyclobutylmethylamine)-3-methylbutanol

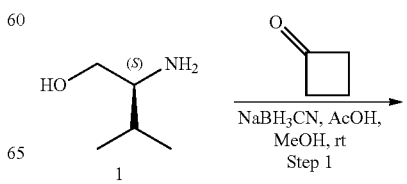

-continued

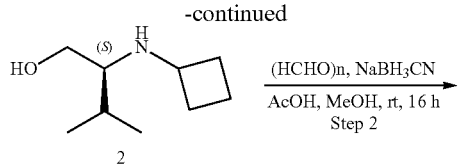

Step 1: (S)-2-cyclobutamine-3-methylbutanol (S)-2-amino-3-methyl-butanol 1 (3.1 g, 30 mmol), cyclobutanone (2.7 g, 39 mmol) and acetic acid (0.18 g, 0.1 mmol) were added to methanol (100 mL), the reaction solution was cooled to 0° C., and sodium cyanoborohydride (5.7 g, 90 mmol) was slowly added. The reaction solution was then stirred overnight at room temperature, and the LCMS showed that the raw material disappeared and the product was formed. The reaction solution was concentrated to remove methanol to obtain the crude, and the crude was adjusted to weakly alkaline with 1 mol/L potassium carbonate aqueous solution and extracted twice with ethyl acetate (200 mL). Combined the organic phase, washed once with saturated brine (100 mL), dried over anhydrous sodium sulfate, spin-dried, separated by silica gel column (eluent: petroleum ether/ethyl acetate=2/1) to obtain the target product (1.4 g, yield: 30%).

MS: m/z 158 (M+H)>.

Step 2: Preparation of (S)-2-(cyclobutylmethylamine)-3-methylbutanol (S)-2-cyclobutylamine-3-methyl-butanol 2 (1.2 g, 7.6 mmol), paraformaldehyde (0.69 g, 22.9 mmol) and acetic acid (46 mg, 0.76 mmol) were added to methanol (25 mL), the reaction solution was cooled to 0° C., and sodium cyanoborohydride (1.4 g, 22.9 mmol) was slowly added. The reaction solution was then stirred overnight at room temperature, and the LCMS showed that the raw material disappeared and the product was formed. The reaction solution was concentrated to remove methanol to obtain the crude, and the crude was adjusted to weakly alkaline with 1 mol/L potassium carbonate aqueous solution and extracted twice with ethyl acetate (200 mL). Combined the organic phase, washed once with saturated brine (100 mL), dried over anhydrous sodium sulfate, spin-dried, separated by silica gel column (eluent: petroleum ether/ethyl acetate=2/1) to obtain the target product (1.1 g, yield: 74%).

$^1$H NMR (400 MHz, CDCl$_3$) δ 3.52-3.47 (m, 1H), 3.45-3.34 (m, 1H), 3.12 (t, J=10.0 Hz, 1H), 2.43-2.34 (m, 1H), 2.17 (s, 3H), 2.12-1.95 (m, 2H), 1.86-1.50 (m, 5H), 0.96 (d, J=6.4 Hz, 3H), 0.81 (d, J=7.2 Hz, 3H).

Preparation of Intermediate 16 (S)-2-(cyclobutyl (methyl)amino)butan-1-ol

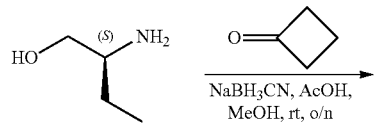

-continued

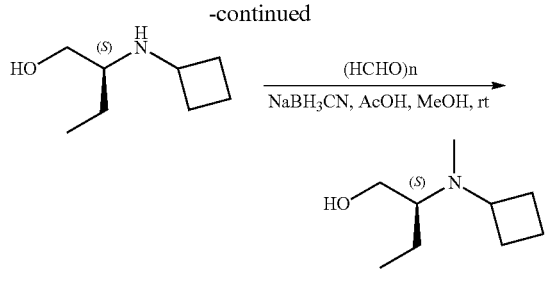

Step 1: Preparation of (S)-2-(cyclobutylamino)butan-1-ol (S)-2-aminobutan-1-ol (3 g, 33.7 mmol), cyclobutanone (2.83 g, 40.45 mmol) and acetic acid (204 mg, 3.4 mmol) were added to methanol (30 mL), and stirred for half an hour under room temperature. Then the reaction solution was cooled to 0° C., and sodium cyanoborohydride (6.37 g, 101.1 mmol) was slowly added. The reaction solution was stirred overnight at room temperature, and TLC showed new spots. The reaction solution was concentrated to remove methanol to give crude product. The crude product was diluted with saturated potassium carbonate solution, extracted with ethyl acetate 3 times, combined organic phases, dried, and concentrated, and silica gel column chromatography was performed (eluent: dichloromethane/methanol=10/1) to obtain target product (2.4 g, yield 50%).

MS: m/z 144 (M+H)>.

Step 2: Preparation of (S)-2-(cyclobutyl (methyl)amino)butan-1-ol (S)-2-(cyclobutylamino) butan-1-ol (2.4 g, 16.78 mmol), paraformaldehyde (1.5 g, 50.35 mmol) and acetic acid (102 mg, 1.7 mmol) were added to methanol (30 mL), and stirred for half an hour under room temperature. Then the reaction solution was cooled to 0° C., and sodium cyanoborohydride (3.17 g, 50.35 mmol) was slowly added. The reaction solution was stirred overnight at room temperature, and TLC showed new spots. The reaction solution was concentrated to remove methanol to give crude product. The crude product was diluted with saturated potassium carbonate solution, extracted with ethyl acetate 3 times, combined organic phases, dried, and concentrated, and silica gel column chromatography was performed (eluent: dichloromethane/methanol=10/1) to obtain target product (1.66 g, yield 63%).

$^1$H NMR (400 MHz, CDCl$_3$) δ 3.83 (s, 1H), 3.55-3.51 (m, 1H), 3.28-3.17 (m, 2H), 2.66-2.59 (m, 1H), 2.07-2.00 (m, 5H), 1.87-1.77 (m, 2H), 1.71-1.50 (m, 3H), 1.16-1.08 (m, 1H), 0.80 (t, J=8.0 Hz, 3H).

Preparation of Intermediate 17 2-(cyclobutyl(2,2,2-trifluoroethyl)amino)ethanol

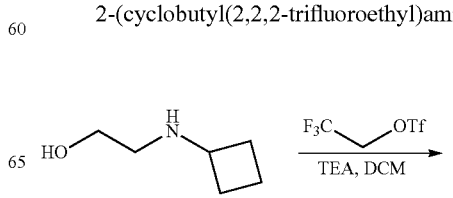

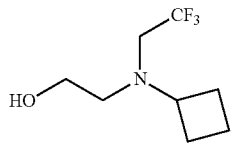

2-(cyclobutylamino) ethanol (450 mg, 3.9 mmol) and triethylamine (788 mg, 7.8 mmol) were added to dichloromethane (10 mL), then 2,2,2-trifluoroethyl trifluoromethesulfonate (1.09 g, 4.7 mmol) was added to the reaction solution, which was stirred overnight at room temperature. TLC showed new spots. The reaction solution was concentrated, separated by silica gel column (eluent: dichloromethane/methanol=10/1) to obtain the target product (555 mg, yield: 72%).

MS: m/z 198 (M+H)$^+$. $^1$H NMR (400 MHz, CDCl$_3$) δ 3.59 (d, J=4.8 Hz, 2H), 3.39-3.35 (m, 1H), 3.13-3.06 (m, 2H), 2.77 (t, J=5.6 Hz, 2H), 2.38 (s, 1H), 2.11-2.04 (m, 2H), 1.89-1.84 (m, 2H), 1.69-1.58 (m, 2H).

Preparation of Intermediate 18
N-(2-hydroxyethyl)-N-methylacetamide

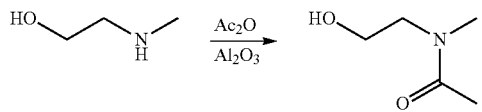

2-(methylamino) ethanol (10 g, 130 mmol) was added to alumina (20 g, 200 mmol), and then acetic anhydride (15 g, 150 mmol) was added. Then the reaction solution was stirred at room temperature for 0.5 hours, filtered, silica gel column chromatography (DCM:MeOH=20:1) was performed to obtain the target product (11 g, yield: 70%).

$^1$H NMR (400 MHz, CDCl$_3$) δ 4.00 (brs, 1H), 3.78-3.75 (m, 2H), 3.55-3.44 (m, 2H), 3.08-2.95 (m, 3H), 2.15-2.05 (m, 3 h).

Preparation of Intermediate 19 2-(methyl (1-methylcyclobutyl)amino)ethanol

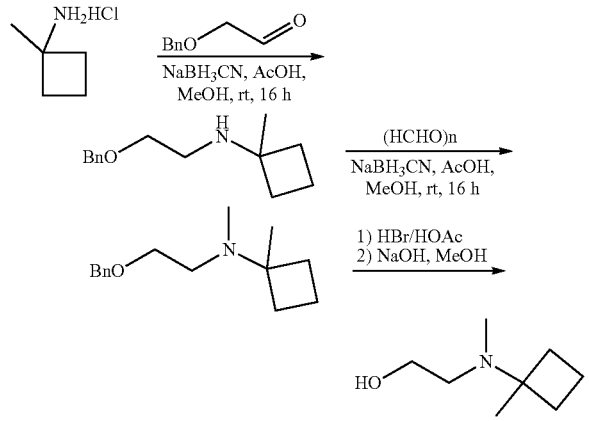

Step 1. Preparation of N-(2-(benzyloxy) ethyl)-1-methylcyclobutanamine 2-(benzoxy) acetaldehyde (717 mg, 4.78 mmol), 1-methyl cyclobutylamine hydrochloride (530 mg, 4.34 mmol) and acetic acid (24 mg, 0.4 mmol) were added to methanol (10 mL), and stirred for half an hour under room temperature. Then the reaction solution was cooled to 0° C., and sodium cyanoborohydride (820 mg, 13.02 mmol) was slowly added. The reaction solution was stirred overnight at room temperature. The reaction solution was concentrated to remove methanol to give the crude product. The crude product was diluted with a saturated potassium carbonate solution (40 mL), and extracted with ethyl acetate (40 mL) 2 times, and the organic phase was dried, concentrated. The residue was separated by silica gel column (eluent: dichloromethane/methanol=10/1) to obtain the target product (610 mg, yield: 58%).

MS: m/z 220 (M+H)$^+$.

Step 2. Preparation of N-(2-(benzyloxy) ethyl)-N,1-dimethylcyclobutylamine

N-(2-(benzoxy)ethyl)-1-methylcyclobutylamine (890 mg, 4.06 mmol), paraformaldehyde (244 mg, 8.13 mmol) and acetic acid (24 mg, 0.4 mmol) were added to methanol (10 mL), and stirred for half an hour under room temperature. Then the reaction solution was cooled to 0° C., and sodium cyanoborohydride (767 mg, 12.18 mmol) was slowly added. Then the reaction was stirred overnight at room temperature. The reaction solution was concentrated to remove methanol to give the crude product. The crude product was diluted with a saturated potassium carbonate solution (40 mL), and extracted with ethyl acetate (40 mL) 3 times, and the organic phase was dried, concentrated. The residue was separated by silica gel column (eluent: dichloromethane/methanol=10/1) to obtain the target product (800 mg, yield: 84%).

MS: m/z 234 (M+H)$^+$.

Step 3. Preparation of 2-(methyl (1-methylcyclobutyl) amino) ethanol

N-(2-(benzyloxy) ethyl)-N,1-dimethylcyclobutylamine (700 mg, 3 mmol) was added to the solution of hydrobromic acid (30%) in acetic acid (10 ml), and stirred overnight at room temperature. The reaction solution was concentrated to remove acetic acid, and then diluted with 2M sodium hydroxide solution (pH>10), extracted with ethyl acetate (40 mL) for 3 times, combined organic phase and concentrated, then diluted with methanol (10 ml), sodium hydroxide (240 mg) was added, stirred at room temperature for 30 minutes, and concentrated to remove methanol to obtain crude product. The crude product was diluted with a saturated potassium carbonate solution (40 mL), and extracted with ethyl acetate (40 mL) 2 times, and the organic phase was dried, and concentrated. The residue was separated by silica gel column (eluent: dichloromethane/methanol=10/1) to obtain the target product (100 mg, yield: 23%).

MS: m/z 144 (M+H)>. $^1$H NMR (400 MHz, CDCl$_3$) δ 3.53 (t, J=5.6 Hz, 2H), 3.0 (brs, 1H), 2.39 (t, J=5.6 Hz, 2H), 2.07 (s, 3H), 1.96-1.88 (m, 2H), 1.77-1.68 (m, 4H), 1.11 (s, 3H).

Intermediate 20 was synthesized from different starting materials according to the method of intermediate 19:

Preparation of Intermediate 20 2-(methyl(3-methyloxacyclobutane-3-yl)amino)ethan-1-ol

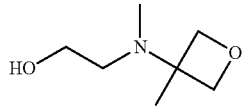

MS: m/z 146 (M+H)+. 1H NMR (400 MHz, CD3OD) δ 3.84-3.76 (m, 1H), 3.75-3.62 (m, 3H), 3.52-3.42 (m, 2H), 2.85-2.77 (m, 1H), 2.75-2.67 (m, 1H), 2.40 (s, 3H), 1.10 (s, 3H).

Preparation of Intermediate 3-1 2-(cyclopropyl(methyl)amino)ethan-1-ol

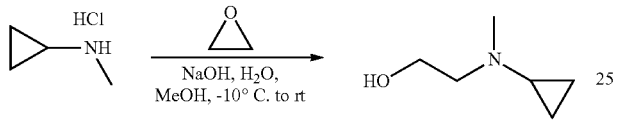

Step 1: Preparation of 2-(cyclopropyl(methyl)amino)ethan-1-ol

N-methylcyclopropylamine hydrochloride (3.2 g, 29.6 mmol) was dissolved in methanol (60 mL), water (1.1 mL, 59.1 mmol) and sodium hydroxide (2.4 g, 59.1 mmol) were added under stirring. The mixture was placed in an ice salt bath and a tetrahydrofuran solution of ethylene oxide (3 mol/L, 30 mL, 90.0 mmol) was added. The reaction solution was slowly raised to room temperature, stirred for 16 hours, and then concentrated in vacuum to remove the solvent. Water (30 mL) and potassium carbonate (5 g) were added to the residue, then extracted with ethyl acetate (30 mL×4). After the organic phases were combined and dried, it was filtered and concentrated in vacuo. The residue was purified by silica gel column (eluent: dichloromethane/methanol=100/1 to 50/1, supplemented with 1‰ ammonia water) to obtain the target product (1 g, yield: 29%).

1H NMR (400 MHz, CDCl3) δ 3.59 (t, J=5.6 Hz, 2H), 2.71 (t, J=5.6 Hz, 2H), 2.51 (brs, 1H), 2.34 (s, 3H), 1.76-1.70 (m, 1H), 0.50-0.46 (m, 2H), 0.42-0.38 (m, 2H).

Preparation of Intermediate 4-1 2-(cyclobutyl(methyl)amino)ethan-1-ol

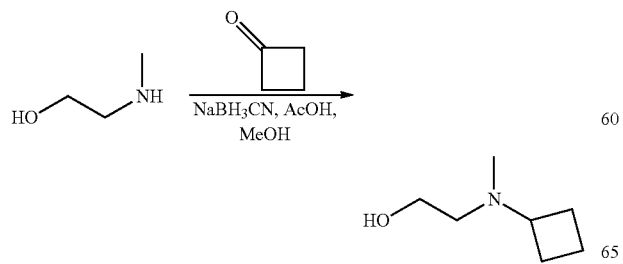

Step 1: Preparation of 2-(cyclobutyl(methyl)amino)ethan-1-ol 2-methylaminoethanol (1.2 g, 16 mmol), cyclobutanone (1.68 g, 24 mmol) and acetic acid (96 mg, 1.6 mmol) were added to methanol (12 mL), and then the solution was cooled to 0° C., and sodium cyanoborohydride (5.04 g, 80 mmol) was slowly added. The resulting reaction solution was stirred overnight at room temperature, and then concentrated to remove methanol to obtain the crude product. The crude product was diluted with a potassium carbonate solution (1 M), then extracted with ethyl acetate 5 times. The organic phase was combined and dried and concentrated, and the residue was purified by silica gel column (eluent: dichloromethane/methanol=5/1, Rf=0.3) to obtain the target product (838 mg, yield: 41%).

MS: m/z 130 (M+H)+. 1H NMR (400 MHz, CDCL3) δ 3.62-3.60 (m, 2H), 3.00-2.91 (m, 1H), 2.45 (T, J=5.2 Hz, 2H), 2.10-2.04 (m, 2H), 1.91-1.86 (m, 2H), 1.72-1.62 (m, 2H).

The following compounds were synthesized from different starting materials in the same manner as intermediate 5:

Preparation of Intermediate 5-1 2-(cyclopentyl(methyl)amino)ethan-1-ol

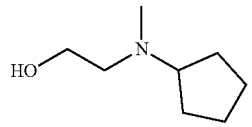

MS: m/z 144 (M+H)+. 1H NMR (400 MHz, CDCl3) δ 3.74 (t, J=5.6 Hz), 3.15-3.11 (m, 1H), 2.83 (t, J=4.2 Hz, 2H), 2.49 (s, 3H), 1.96-1.92 (m, 2H), 1.77-1.70 (m, 2H), 1.64-1.54 (m, 4H).

Preparation of Intermediate 6-1 2-(cyclohexyl(methyl)amino)ethan-1-ol

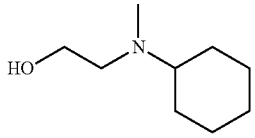

MS: m/z 158 (M+H)+. 1H NMR (400 MHz, CDCl3) δ 3.72 (t, J=4.2 Hz, 2H), 2.87 (t, J=4.2 Hz, 2H), 2.78-2.72 (m, 1H), 2.51 (s, 3H), 1.90-1.85 (m, 4H), 1.69-1.66 (m, 1H), 1.29-1.24 (m, 4H), 1.13-1.11 (m, 1H).

Intermediate 7-1 2-(cyclobutyl(ethyl)amino)ethan-1-ol

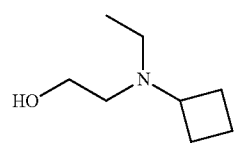

MS: m/z 144 (M+H)⁺. ¹H NMR (400 MHz, CDCl₃) δ 3.52 (t, J=5.6 Hz, 2H), 3.15 (m, 1H), 2.86 (brs, 1H), 2.57-2.53 (m, 4H), 2.04-1.99 (m, 2H), 1.88-1.83 (m, 2H), 1.65-1.58 (m, 2H), 0.97 (t, J=7.2 Hz, 3H).

Preparation of Intermediate 8-1 2-(cyclobutylmethyl (methyl)amino)ethan-1-ol

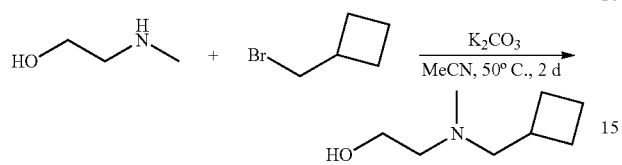

Step 1: Preparation of 2-(cyclobutylmethyl(methyl)amino)ethan-1-ol

Acetonitrile (30 mL) was added to the sealed tube, followed by 2-(methylamino) ethanol (5 g, 67 mmol) and bromomethylcyclobutane (5 g, 33.5 mmol), followed by K₂CO₃ (5 g, 37 mmol). The resulting mixture was heated to 45 to 50° C., stirred for 48 h. The system was cooled to room temperature, and ethyl acetate (100 mL) and water (100 mL) were added to stratify. The aqueous layer was separated and extracted twice with ethyl acetate (30 mL). The combined organic layers were successively washed with water (50 mL×2) and saturated sodium chloride (50 mL×2), then dried with anhydrous Na₂SO₄ and filtered. The filtrate was concentrated in vacuum to obtain the target product (3.7 g, yield: 78%).

MS: m/z 144 (M+H)⁺. ¹H NMR (400 MHz, CDCl₃) δ 3.56 (t, J=4.8 Hz, 2H), 2.56-2.46 (m, 3H), 2.42 (d, J=7.2 Hz, 2H), 2.21 (s, 3H), 2.09-2.02 (m, 2H), 1.94-1.78 (m, 2H), 1.70-1.63 (m, 2H).

The following compounds were synthesized from different starting materials in the same manner as intermediate 8:

Preparation of Intermediate 9-1 2-(cyclopropylmethyl (methyl)amino)ethan-1-ol

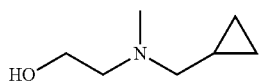

MS: m/z 130 (M+H)⁺. ¹H NMR (400 MHz, CDCl₃) δ 3.49 (t, J=5.4 Hz, 2H), 2.90 (brs, 1H), 2.48 (t, J=5.4 Hz, 2H), 2.27-2.14 (m, 5H), 0.84-0.64 (m, 1H), 0.49-0.32 (m, 2H), 0.01 (q, J=4.7 Hz, 2H).

Preparation of Intermediate 10-1 (S)-2-((cyclopropyl methyl)(methyl)amino)propano-1-ol

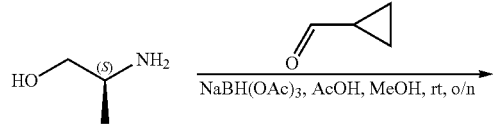

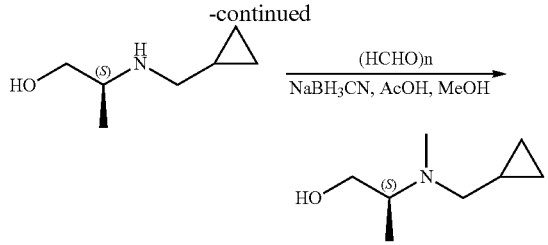

Step 1: Preparation of (S)-2-((cyclopropylmethyl) amino) propano-1-ol (S)-2-aminopropano-1-ol (10 g, 126.6 mmol), cyclopropanecarbaldehyde (9.3 g, 132.9 mmol) and acetic acid (760 mg, 12.6 mmol) were added to methanol (500 mL), and then the solution was cooled to 0° C., and sodium acetate borohydride (53.7 g, 253.2 mmol) was slowly added. The reaction solution was stirred overnight at room temperature, and then vacuum concentrated to remove methanol. The resulting crude product was subjected to silica gel column chromatography (eluent: dichloromethane/methanol=5/1, Rf=0.3) to obtain the target product (6.9 g), yield: 42%.

MS: m/z 130 (M+H)⁺.

Step 2: Preparation of (S)-2-((cyclopropyl methyl) (methyl)amino)propano-1-ol (S)-2-((cyclopropyl methyl) amino) propano-1-ol (2.35 g, 18.2 mmol), paraformldehyde (1.1 g, 36.4 mmol) and acetic acid (110 mg, 1.82 mmol) were added to m ethanol (45 mL). The reaction solution was cooled to 0° C., then sodium cyanoborohydride (3.45 g, 54.6 mmol) was slowly added. The reaction solution was stirred overnight at room temperature, and then concentrated under reduced pressure to remove methanol. The resulting crude product was subjected to silica gel column chromatography (eluent: dichloromethane/methanol=5/1, Rf=0.3) to obtain the target product (937 mg, yield: 37%).

MS: m/z 144 (M+H)⁺. ¹H NMR (400 MHz, CDCl₃) δ 3.73-3.69 (m, 1H), 3.58-3.53 (m, 1H), 3.45-3.41 (m, 1H), 2.82-3.2.77 (m, 1H), 2.65-2.60 (m, 1H), 2.57 (s, 3H), 1.08-1.02 (m, 4H), 0.70-0.67 (m, 2H), 0.34-0.26 (m, 2H).

The following compounds were synthesized from different starting materials in the same manner as intermediate 10:

Preparation of Intermediate 11-1 (R)-2-((cyclopropyl methyl) (methyl) amino) propano-1-ol

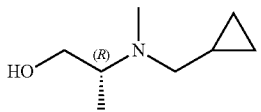

MS: m/z 144 (M+H)⁺. ¹H NMR (400 MHz, CDCl₃) δ 3.65-3.61 (m, 1H), 3.51-3.41 (m, 1H), 3.33-3.29 (m, 1H), 2.70-2.65 (m, 1H), 2.55-2.49 (m, 4H), 1.02-1.00 (m, 4H), 0.66-0.62 (m, 2H), 0.29-0.21 (m, 2H).

Intermediate 12-1 (S)-2-(cyclobutyl(methyl) amino)propano-1-ol

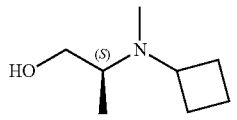

MS: m/z 144 (M+H)⁺. $^1$H NMR (400 MHz, CDCl$_3$) δ 3.47-3.43 (m, 1H), 3.35-3.30 (m, 1H), 3.25-3.22 (m, 1H), 3.02-2.97 (m, 1H), 2.13 (s, 3H), 2.10-2.05 (m, 2H), 1.99-1.87 (m, 2H), 1.74-1.64 (m, 2H), 089 (d, J=6.4 Hz, 3H).

Intermediate 13-1 (R)-2-(cyclobutyl(methyl) amino)propano-1-ol

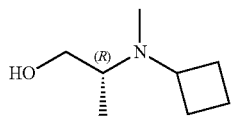

MS: m/z 144 (M+H)⁺.

Preparation of Intermediate 14-1 (S)-1-((cyclopropylmethyl)(methyl)amino)propano-2-ol

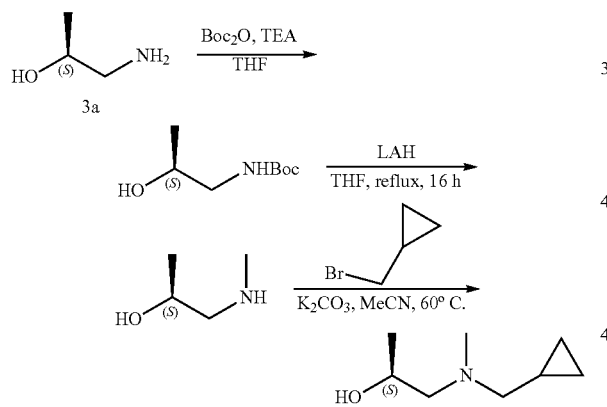

Step 1: Preparation of tert-butyl (S)-(2-hydroxypropyl)formate (S)-1-aminopropyl-2-ol (10 g, 0.13 mol) and triethylamine (26.9 g, 0.27 mol) were dissolved in anhydrous tetrahydrofuran (150 mL). Di-tert-butyl dicarbonate (34.8 g, 0.16 mol) was slowly added under ice bath. After the addition, the reaction solution was stirred at room temperature, and reacted overnight, then concentrated under reduced pressure. The residue was purified by silica gel column (eluent: petroleum ether/ethyl acetate=1/1) to obtain the target product (21.7 g, yield 93%).

Step 2: Preparation of (S)-1-(methylamino)propano-2-ol

Tert-butyl (S)-(2-hydroxypropyl) formate (21.7 g, 0.12 mol) was dissolved in anhydrous tetrahydrofuran (300 mL), lithium aluminum hydrogen (9.4 g, 0.25 mol) was added in batches under ice bath. After the addition, the reaction solution refluxed overnight. Sodium sulfate decahydrate (40 g) was slowly added to the resulting reaction solution under ice bath to quench the reaction, and then filtered. The filtrate was spin-dried, and the residue was purified by silica gel column (eluent: dichloromethane/methanol=5/1) to obtain the target product (6 g, yield 54%).

$^1$H NMR (400 MHz, CDCl$_3$) δ 3.90-3.80 (m, 1H), 2.66 (dd, J=12.0 Hz, 3.2 Hz, 1H), 2.51-2.43 (m, 4H), 1.17 (d, J=6.0 Hz, 3H).

Step 3: Preparation of (S)-1-((cyclopropyl methyl)(methyl)amino)propano-2-ol (S)-1-(methylamino) propano-2-ol (3 g, 33.7 mmol) was dissolved in acetonitrile (100 mL), and potassium carbonate (5.6 g, 40.5 mmol) and bromomethyl cyclopropane (4.6 g, 33.7 mmol) were added at room temperature. After the addition, the reaction solution was heated to 60° C. for 2 h. The resulting reaction solution was cooled to room temperature, ethyl acetate (150 mL) and water (100 mL) were added to quench the reaction. After the organic phase was collected, it was washed with water (100 mL) for two times and saturated salt water (50 mL) for one time successively. Then, it was dried with anhydrous sodium sulfate and filtered. The filtrate was concentrated in vacuo to obtain the target product (2 g, yield 42%).

MS: m/z 144 (M+H)⁺. $^1$H NMR (400 MHz, CDCl$_3$) δ 3.81-3.73 (m, 1H), 2.40-2.21 (m, 7H), 1.12 (d, J=6.0 Hz, 3H), 0.90-0.81 (m, 1H), 0.56-0.45 (m, 2H), 0.14-0.06 (m, 2H).

The following compounds were synthesized from different starting materials in the same manner as intermediate 14-1:

Preparation of Intermediate 15-1 (R)-1-((cyclopropyl methyl) (methyl) amino) propano-2-ol

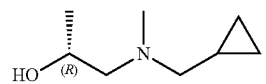

MS: m/z 144 (M+H)⁺. $^1$H NMR (400 MHz, CDCl$_3$) δ 3.81-3.73 (m, 1H), 2.40-2.21 (m, 7H), 1.12 (d, J=6.4 Hz, 3H), 0.90-0.81 (m, 1H), 0.56-0.45 (m, 2H), 0.14-0.06 (m, 2H).

Intermediate 16-1 (S)-1-(cyclobutyl(methyl) amino)propano-2-ol

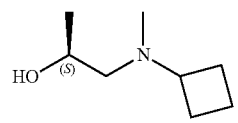

MS: m/z 144 (M+H)⁺. $^1$H NMR (400 MHz, CDCl$_3$) δ 3.78-3.76 (m, 1H), 2.89-2.85 (m, 1H), 2.27-2.23 (m, 1H), 2.21 (s, 3H), 2.10-1.95 (m, 3H), 1.83-1.76 (m, 2H), 1.68-1.59 (m, 2H), 1.11 (d, J=6.4 Hz, 3H).

Intermediate 17-1 (R)-1-(cyclobutyl (methyl) amino) propano-2-ol

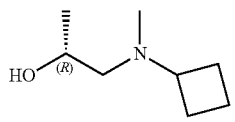

MS: m/z 144 (M+H)+. 1H NMR (400 MHz, CDCl3) δ 3.77-3.76 (m, 1H), 2.89-2.85 (m, 1H), 2.27-2.22 (m, 1H), 2.21 (s, 3H), 2.05-1.95 (m, 3H), 1.84-1.79 (m, 2H), 1.69-1.60 (m, 2H), 1.11 (d, J=6.4 Hz, 3H).

Preparation of Intermediate 18-1 2,2'-(cyclopropylazanediyl) bis (ethan-1-ol)

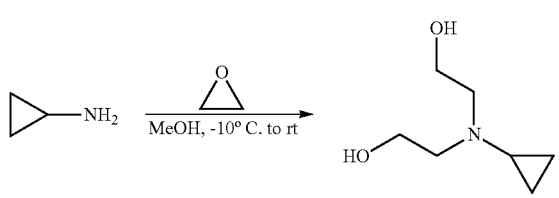

Step 1: Preparation of 2, 2'-(cyclopropylazanediyl) bis (ethan-1-ol)

Cyclopropylamine (550 mg, 9.7 mmol) was dissolved in methanol (20 mL), and a tetrahydrofuran solution of ethylene oxide (3 mol/L, 19.3 mL, 57.9 mmol) was added and stirred under ice salt bath. The reaction solution was slowly raised to room temperature, stirred for 16 h. The resulting reaction solution was concentrated to remove the solvent, and the residue was purified by silica gel column (eluent: dichloromethane/methanol=100/1 to 80/1, and supplemented with 1‰ ammonia water in the eluent) to obtain the target compound (700 mg, yield: 50%).

MS: m/z 146 (M+H)+. 1H NMR (400 MHz, CDCl3) δ 3.68 (t, J=5.6 Hz, 4H), 2.82 (t, J=5.6 Hz, 4H), 1.91-1.85 (m, 1H), 0.56-0.49 (m, 2H), 0.48-0.43 (m, 2H).

Preparation of Intermediate 19-1 (S)-1-(bis(cyclopropyl methyl)amino) propano-2-ol

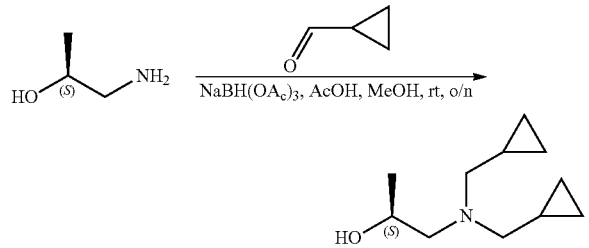

(S)-1-aminopropano-2-ol 9a (2 g, 26.7 mmol), cyclopropanecarbaldehyde (4.1 g, 58.7 mmol) and acetic acid (162 mg, 2.7 mmol) were added to methanol (80 mL), and then the solution was cooled to 0° C., and sodium acetate borohydride (17 g, 80.1 mmol) was added in batches. After the addition, the reaction solution was stirred at room temperature overnight. The reaction solution was concentrated in vacuum, and the crude product obtained was purified by silica gel column (eluent: dichloromethane/methanol=10/1) to obtain the target product (2.3 g, yield: 47%).

MS: m/z 184 (M+H)+. 1H NMR (400 MHz, CDCl3) δ 3.80-3.68 (m, 1H), 2.53-2.35 (m, 6H), 1.12 (d, J=6.4 Hz, 3H), 0.93-0.80 (m, 2H), 0.58-0.41 (m, 4H), 0.16-0.05 (m, 4H).

Preparation of Intermediate 20-1 2-(((3,3-difluorocyclobutyl) methyl) (methyl) amino) ethan-1-ol

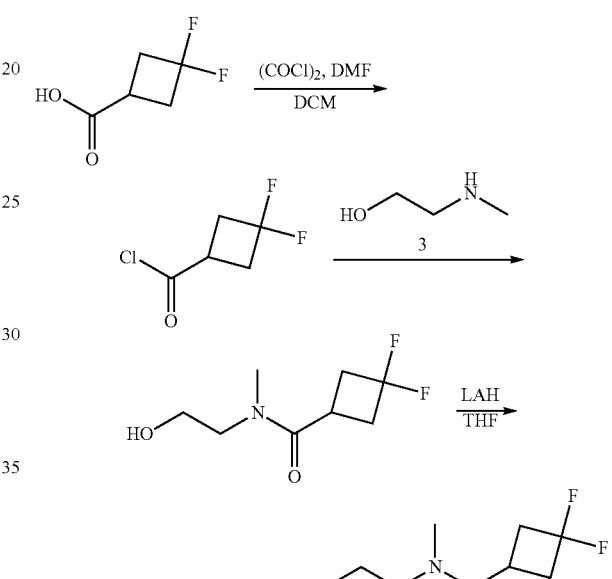

Step 1: Preparation of 3,3-difluorocyclobutane-1-formyl chloride 3,3-difluorocyclobutane-1-formic acid (4 g, 29.4 mmol) was dissolved in anhydrous dichloromethane (50 mL), oxalyl chloride (4.5 g, 35.3 mmol) and N,N-dimethylformamide (5 drops) were slowly added under ice bath. After the addition, the reaction solution was stirred at room temperature for 2 h and then directly used for the next reaction.

Step 2: Preparation of 3,3-difluoro-N-(2-hydroxyethyl)-N-methylcyclobutane-1-formamide 2-methylamino ethan-1-ol (3.3 g, 44.1 mmol) was dissolved in dichloromethane (50 mL), and triethylamine (14.7 g, 147 mmol) and the reaction solution obtained from first step were added under ice bath. After the addition, the reaction solution was reacted at room temperature overnight, then concentrated under reduced pressure to remove dichloromethane. Ethyl acetate (200 mL) and water (100 mL) were added to the residue. The organic phase was separated, and then washed once with saturated brine (50 mL), and then dried over anhydrous sodium sulfate, and filtered. The filtrate was concentrated under reduced pressure, and the residue was purified by silica gel column chromatography (eluent: dichloromethane/methanol=20/1) to obtain the target product (3.9 g, yield 68%).

MS: m/z 194 (M+H)+.

Step 3: Preparation of 2-(((3,3-difluorocyclobutyl) methyl) (methyl) amino) ethan-1-ol 3,3-difluoro-N-(2-hydroxyethyl)-N-methyl cyclobutane-1-formamide (3.9 g, 20.2 mmol) was dissolved in anhydrous tetrahydrofuran (60 mL), lithium aluminum hydrogen (2.2 g, 60.9 mmol) was added in batches under ice bath. After the addition, the mixture was reacted at room temperature overnight. Sodium sulfate decahydrate (4 g) was slowly added to the resulting mixture under ice bath to quench the reaction, and then filtered. The filtrate was concentrated under reduced pressure to obtain the target product (3.1 g, yield 86%).

MS: m/z 184 (M+H)+. 1H NMR (400 MHz, CDCl3) δ 3.58 (t, J=5.2 Hz, 2H), 2.73-2.60 (m, 2H), 2.56-2.50 (m, 4H), 2.40-2.13 (m, 7H).

Preparation of Intermediate 21-1 (S)-2-(cyclopropyl (methyl) amino) propano-1-ol

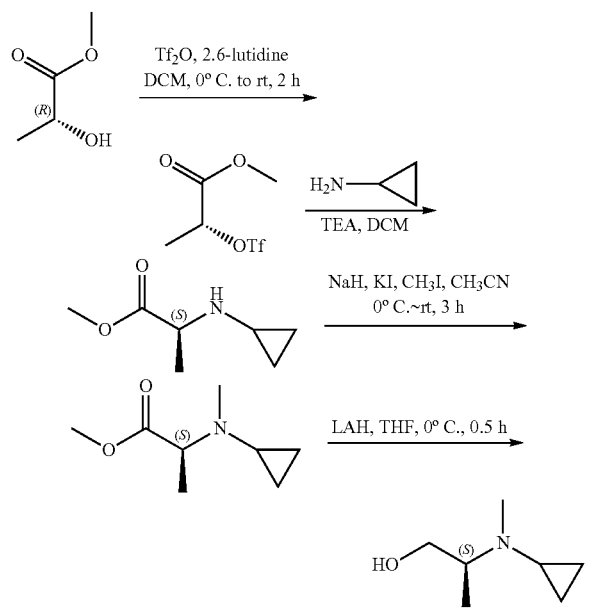

Step 1: Preparation of methyl (R)-2-((trifluoromethyl) sulfonyl)oxy)propionate Methyl (R)-2-hydroxypropionate (20.8 g, 0.2 mol) was added to anhydrous dichloromethane (800 mL). The reaction solution was cooled to 0° C., trifluoromethanesulfonic anhydride (35.3 mL, 0.21 mol) and 2,6-dimethylpyridine (24.4 mL, 0.21 mmol) were added under nitrogen protection, then stirred for 20 min at 0° C. The resulting mixture was concentrated under reduced pressure. The residue was purified by silica gel column (eluent: dichloromethane) to obtain the target product (42.3 g, yield 89%).

Step 2: Preparation of methyl (S)-2-(cyclopropylamino) propionate

Cyclopropylamine (9.3 g, 0.163 mol) and triethylamine (49.4 g, 0.489 mol) were added to dichloromethane solution (400 mL). The mixture was stirred at 0° C. for 10 min, then methyl (R)-2-((trifluoromethyl)sulfonyl)oxy)propionate (42.3 g, 0.179 mol) was added. The reaction mixture was stirred at room temperature for 2 h, then the reaction was quenched with saturated sodium bicarbonate (200 mL). The resulting mixture was extracted with dichloromethane (2×100 mL). The combined organic phase was dried over anhydrous sodium sulfate, and filtered. The filtrate was concentrated under reduced pressure, and the resulting residue was purified by silica gel column chromatography (eluent: petroleum ether/ethyl acetate=2/1) to obtain the target product (17.5 g, yield 75%).

Step 3: Preparation of methyl (S)-2-(cyclopropyl (methyl) amino) propionate

Compound methyl (S)-2-(cyclopropylamino) propionate (11.9 g, 83.22 mmol) was dissolved in acetonitrile (200 mL), and sodium hydrogen (60% wt, 5.0 g, 124.83 mmol) and potassium iodide (138 mg, 0.832 mmol) were added at 0° C. The reaction solution was stirred at 0° C. for 30 min, then methyl iodide (12.4 g, 87.38 mmol) was added. The resulting mixture was raised to room temperature and stirred for 4 hours and then quenched with water (100 mL) and then extracted with dichloromethane (200 mL). The combined organic phase was dried over anhydrous sodium sulfate, and filtered. The filtrate was concentrated under reduced pressure, and the resulting residue was purified by silica gel column chromatography (eluent: petroleum ether/ethyl acetate=2/1) to obtain the target product (4.3 g, yield 33%).

Step 4: Preparation of (S)-2-(cyclopropyl (methyl)amino)propano-1-ol

Lithium aluminum hydride (2.08 g, 54.78 mmol) was suspended to tetrahydrofuran (50 mL), cooled to 0° C., then a solution of methyl (S)-2-(cyclopropyl (methyl) amino) propionate (4.3 g, 27.39 mmol) in tetrahydrofuran (30 mL) was slowly added dropwise. The reaction solution was stirred at 0° C. for 30 min. Then 2 mL water, 2 mL 15% sodium hydroxide solution and 6 mL water were successively added at 0° C. The resulting mixture was stirred for 30 min and then filtered. After the filtrate was dried, it was concentrated under reduced pressure to give the target product (1.97 g, yield 56%).

MS: m/z 130 (M+H)+. 1H NMR (400 MHz, CDCl3) δ 3.35-3.31 (m, 1H), 3.24 (t, J=10.4 Hz, 1H), 3.02-2.96 (m, 1H), 2.74 (brs, 1H), 2.22 (s, 3H), 1.94-1.90 (m, 1H), 0.94 (d, J=6.4 Hz, 3H), 0.52-0.32 (m, 3H), 0.31-0.27 (m, 1H).

The following compounds were synthesized from different starting materials in the same manner as intermediate 21:

Preparation of Intermediate 22-1 (R)-2-(cyclopropyl (methyl) amino) propano-1-ol

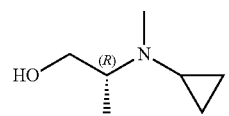

MS: m/z 130 (M+H)+. 1H NMR (400 MHz, CDCl3) δ 3.34-3.30 (m, 1H), 3.23 (t, J=10 Hz, 1H), 3.02-2.95 (m, 1H), 2.81 (brs, 1H), 2.20 (s, 3H), 1.94-1.89 (m, 1H), 0.93 (d, J=6.8 Hz, 3H), 0.51-0.31 (m, 3H), 0.30-0.25 (m, 1H).

Preparation of Intermediate 23-1 2-((1-fluorocyclopropyl) methyl) (methyl) amino) ethan-1-ol

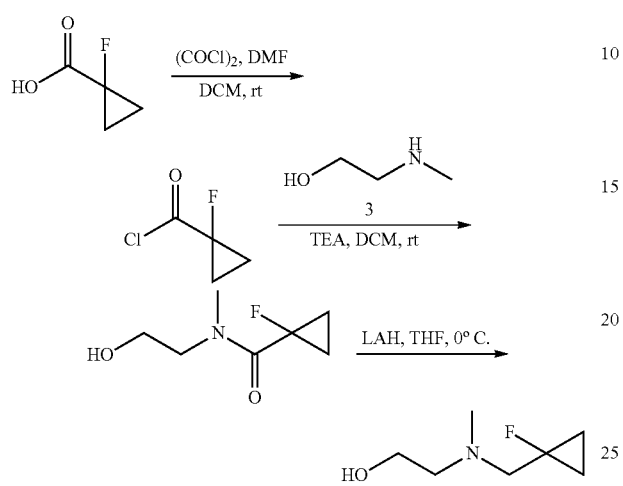

Step 1: Preparation of 1-fluorocyclopropane-1-formyl chloride 1-fluorocyclopropane-1-formic acid (1.7 g, 16.3 mmol) was dissolved in anhydrous dichloromethane (30 mL), oxalyl chloride (2.5 g, 19.6 mmol) and N,N-dimethylformamide (5 drops) were slowly added under ice bath. After the addition, the reaction solution was stirred at room temperature for 2 h and then directly used for the next reaction.

Step 2: Preparation of 1-fluoro-N-(2-hydroxyethyl)-N-methylcyclopropane-1-formamide 2-methylamino ethan-1-ol (1.8 g, 24.5 mmol) was dissolved in dichloromethane (40 mL), and triethylamine (8 g, 81.5 mmol) and the reaction solution obtained from first step were added under ice bath. After the addition, the reaction solution was stirred at room temperature, and reacted overnight, then concentrated under reduced pressure to remove dichloromethane. Ethyl acetate (200 mL) and water (100 mL) were added to the residue. The organic phase was separated, and then washed once with saturated brine (50 mL), and then dried over anhydrous sodium sulfate, and filtered. The filtrate was concentrated under reduced pressure, and the residue was purified by silica gel column chromatography (eluent: dichloromethane/methanol=40/1) to obtain the target product (1.9 g, yield 73%).

MS: m/z 162 (M+H)$^+$.

Step 3: Preparation of 2-(((1-fluorocyclopropyl) methyl)(methyl)amino)ethan-1-ol 1-fluoro-N-(2-hydroxyethyl)-N-methyl cyclopropane-1-formamide (1.9 g, 11.8 mmol) was dissolved in anhydrous tetrahydrofuran (40 mL), lithium aluminum hydrogen (0.87 g, 23.6 mmol) was added in batches under ice bath. After the addition, the reaction solution was reacted at room temperature overnight, then sodium sulfate decahydrate (2 g) was slowly added to the resulting reaction solution under ice bath to quench the reaction, and then filtered. The filtrate was concentrated under reduced pressure, and the obtained residue was purified by silica gel column chromatography (eluent: dichloromethane/methanol=40/1) to obtain the target product (0.64 g, yield 38%).

MS: m/z 148 (M+H)$^+$. $^1$H NMR (400 MHz, CDCl$_3$) δ 3.61 (t, J=5.6 Hz, 2H), 2.82 (d, J=19.2 Hz, 2H), 2.70 (t, J=5.6 Hz, 2H), 2.43 (s, 3H), 1.13-1.02 (m, 2H), 0.65-0.57 (m, 2H).

Preparation of Intermediate 24-1 (S)-2-(1-cyclopropylethyl)(methyl)amino)ethan-1-ol

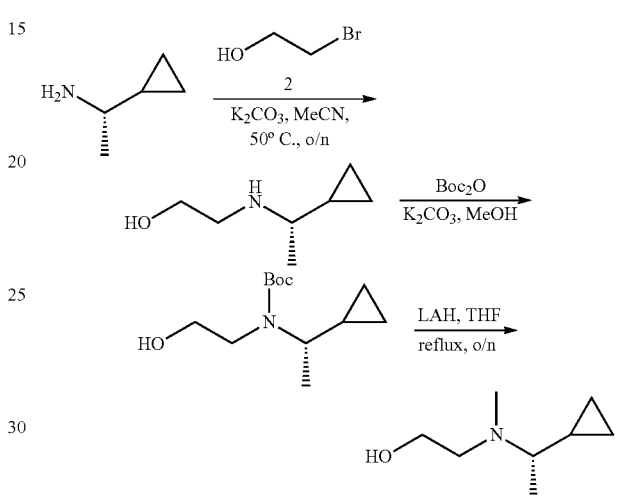

Step 1: (S)-2-((1-cyclopropylethyl)amino)ethan-1-ol (S)-1-cyclopropylethane-1-amine (3.4 g, 40 mmol), bromoethanol (5 g, 40 mmol) and potassium carbonate (8.3 g, 60 mmol) were added to acetonitrile (50 mL), then reaction was heated to 50° C. overnight. The resulting reaction mixture was directly used for the next step without purification.

Step 2: tert-butyl (S)-(1-cyclopropylethyl)(2-hydroxyethyl) carbamate

Di-tert-butyl dicarbonate (9.3 g, 43 mmol) and potassium carbonate (10.7 g, 78 mmol) were added to the previous reaction solution. The resulting reaction solution was stirred overnight at room temperature, and then filtered. The filtrate was concentrated under reduced pressure, and the obtained residue was purified by silica gel column chromatography to obtain the target product (1.9 g, yield 21%).

Step 3: Preparation of (S)-2-(1-cyclopropylethyl) (methyl)amino)ethan-1-ol tert-butyl (S)-(1-cyclopropylethyl) (2-hydroxyethyl) carbamate (1.9 g, 8.3 mmol) and lithium aluminium hydride (1.26 g, 33 mmol) were added to tetrahydrofuran. The obtained reaction solution was heated to reflux and stirred overnight, then cooled down, and quenched with sodium sulfate decahydrate. The resulting mixture was filtered and the filtrate was concentrated under reduced pressure. The residue was purified by silica gel column chromatography to obtain the target product (420 mg, yield 35%).

MS: m/z 144 (M+H)⁺. ¹H NMR (400 MHz, CDCl₃) δ 3.57 (t, J=4.8 Hz, 2H), 2.72-2.64 (m, 2H), 2.33 (s, 3H), 1.97-1.93 (m, 1H), 1.09 (d, J=6.8 Hz, 3H), 0.83-0.78 (m, 1H), 0.54-0.47 (m, 2H), 0.30-0.27 (m, 1H), 0.10-0.06 (m, 1H).

The following compounds were synthesized from different starting materials in the same manner as intermediate 24-1:

Preparation of Intermediate 25-1 (R)-2-(1-cyclopropylethyl)(methyl)amino)ethan-1-ol

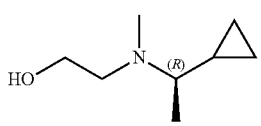

MS: m/z 144 (M+H)⁺. ¹H NMR (400 MHz, CDCl₃) δ 3.57 (t, J=4.8 Hz, 2H), 2.72-2.66 (m, 2H), 2.32 (s, 3H), 1.96-1.91 (m, 1H), 1.09 (d, J=6.8 Hz, 3H), 0.83-0.77 (m, 1H), 0.55-0.46 (m, 2H), 0.32-0.26 (m, 1H), 0.10-0.04 (m, 1H).

Preparation of Intermediate 26-1 2-((3,3-difluorocyclobutyl)(methyl)amino)ethan-1-ol

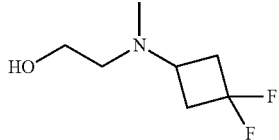

MS: m/z 166 (M+H)⁺. ¹H NMR (400 MHz, CDCl₃) δ (t, J=4.2 Hz, 2H), 2.87-2.85 (m, 1H), 2.73-2.65 (m, 2H), 2.48-2.33 (m, 4H), 2.18 (s, 3H).

Preparation of Intermediate 27-1 trans-2-(dimethylamino)cyclopentanol

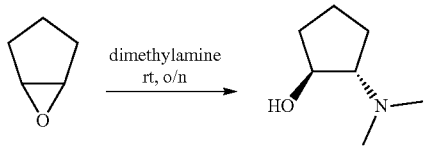

Step 1: (S)-2-((1-cyclopropylethyl) amino) ethan-1-ol 6-oxazole[3.1.0]hexane (2 g, 23.8 mmol) was added to the dimethylamine aqueous solution (content greater than 33%, 10 mL), and the resulting reaction solution was stirred overnight at room temperature. The reaction solution was concentrated, and the residue was purified by silica gel column (eluent: dichloromethane/methanol=20/1) to obtain the target product (1.63 g, yield: 53%).

Example 1 Preparation of 2-(1-acroloyl-4-(2-((R)-2-(cyclobutyl(methyl)amino)-3-methoxypropoxy)-7-(8-methylnaphthalen-1-yl)-5,6,7,8-tetrahydropyrido[3,4-d]pyrimidin-4-yl)piperazin-2-yl) acetonitrile

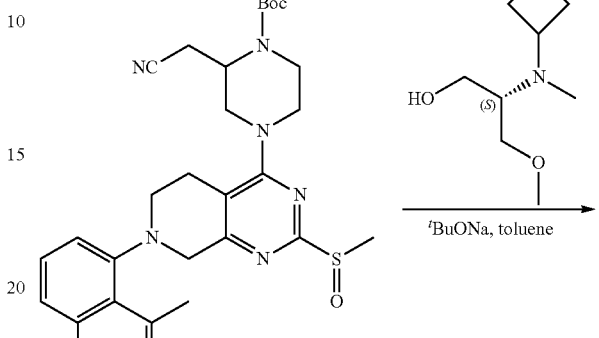

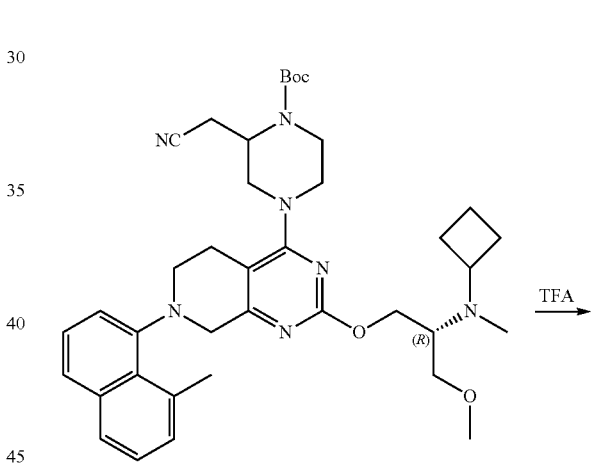

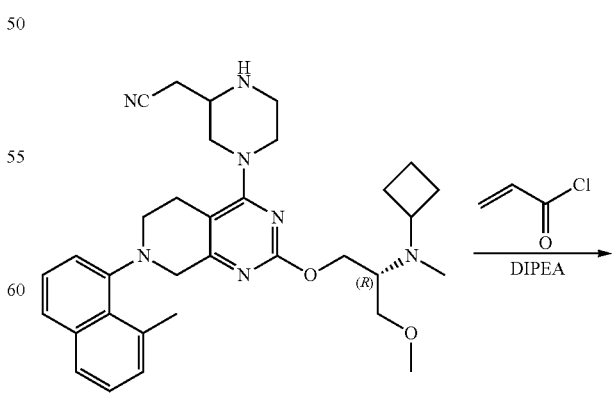

-continued

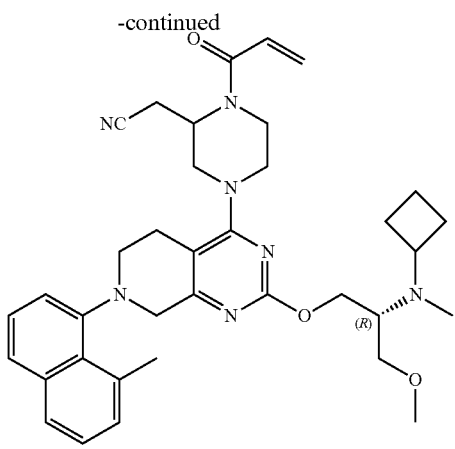

Step 1: Preparation of tert-butyl 2-(cyanomethyl)-4-(2-((R)-2-(cyclobutyl(meth yl)amino)-3-methoxy-propoxy)-7-(8-methylnaphthalen-1-yl)-5,6,7,8-tetrahydropyrido[3, 4-d]pyrimidin-4-yl) piperazine-1-formate Tert-butyl 2-(cyanomethyl)-4-(7-(8-methylnaphthalen-1-yl)-2-(methyl sulfoxide)-5, 6, 7, 8-tetrahydropyrido[3,4-d]pyrimidin-4-yl)piperazine-1-formate (72 mg, 0.128 mmol) was added to the reaction flask, and then toluene (0.8 mL), (S)-2-(cyclobutyl(methyl)amino)-3-methoxypropyl-1-ol (45 mg, 0.256 mmol) and sodium tert-butoxide (37 mg, 0.384 mmol) were successively added. The reaction solution was stirred for 0.5 h under ice water bath, then water (50 mL) was added, and extracted with ethyl acetate (3×30 mL). All organic phases were combined, washed once with saturated sodium chloride, and then dried over anhydrous sodium sulfate, and filtered. The filtrate was concentrated under reduced pressure, and the obtained residue was separated on preparative plate (eluent: DCM/MeOH=20/1) to obtain the target product (43 mg, yield 50%).
LC-MS: M/Z 670 (M+H)+.

Step 2: Preparation of 2-(4-(-(2-((R)-2-(cyclobutyl (methyl)amino)-3-methoxypropoxy)-7-(8-methyl-naphthalen-1-yl)-5,6,7,8-tetrahydropyrido[3,4-d]pyrimidin-4-yl)piperazin-2-yl) acetonitrile Tert-butyl 2-(cyanomethyl)-4-(2-((R)-2-(cyclobutyl (methyl)amino)-3-methoxypropoxy)-7-(8-methylnaphthalen-1-yl)-5,6,7,8-tetrahydropyrido[3,4-d]pyrimidin-4-yl) piperazine-1-formate (40 mg, 0.059 mmol) was dissolved in dichloromethane (1 mL), followed by trifluoroacetic acid (0.5 mL). The reaction solution was stirred at room temperature for 0.5 h and then concentrated until dry under reduced pressure to obtain the target product, then directly used for the next reaction.
LC-MS: m/z 570 (M+H)+.

Step 3: Preparation of 2-(1-acroloyl-4-(2-((R)-2-(cyclobutyl(methyl)amino)-3-methoxypropoxy)-7-(8-methylnaphthalen-1-yl)-5,6,7,8-tetrahydropyrido [3,4-d]pyrimidin-4-yl) piperazin-2-yl) acetonitrile 2-(4-(-(2-((R)-2-(cyclobutyl(methyl)amino)-3-methoxypropoxy)-7-(8-methylnaphthalen-1-yl)-5,6,7,8-tetrahydropyrido[3,4-d]pyrimidin-4-yl)piperazin-2-yl) acetonitrile obtained from the previous step was added to the solution of N,N-diisopropylethylamine (42 mg, 0.324 mmol) in dichloromethane (2 mL). The reaction solution was protected by nitrogen, and acroloyl chloride (10 mg, 0.108 mmol) was added dropwise at −40° C. After the addition, the reaction solution was stirred at room temperature for 1 h, then methanol (1 mL) was added to quench. The resulting mixture was concentrated, and the obtained residue was purified by preparative liquid phase to obtain the target product (13 mg, yield 35%).
LCMS: m/z 624 (M+H)+. $^1$HNMR (400 MHz, CDCl$_3$) δ 7.66 (m, 2H), 7.40 (m, 2H), 7.24 (m, 2H), 6.58 (m, 1H), 6.41 (d, J=16.8 Hz, 1H), 5.84 (d, J=10.4 Hz, 1H), 5.07 (brs, 0.5H), 4.60 (brs, 0.5H), 4.41 (m, 1H), 4.24 (m, 5H), 3.55 (m, 5H), 3.33 (m, 4H), 3.15 (m, 5H), 2.91 (s, 3H), 2.68 (m, 2H), 2.27 (s, 3H), 1.87 (m, 5H), 1.57 (m, 2H).

Examples 2-24 were synthesized from different starting materials according to the method of Example 1:

Example 2 2-(1-acroloyl-4-(7-(8-chloronaphthalen-1-yl)-2-((1-((dimethylamino) methyl)cyclopropyl) methoxyl)-5, 6, 7, 8-tetrahydropyrido[3,4-d]pyrimidin-4-yl)piperazin-2-yl) acetonitrile

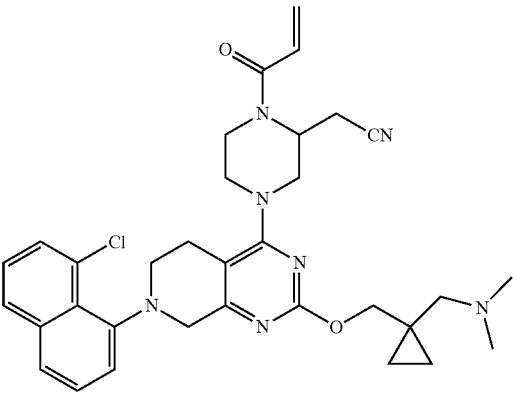

LCMS: m/z 600 (M+H)+. $^1$HNMR (400 MHz, CDCl$_3$) δ 7.76 (m, 1H), 7.62 (m, 1H), 7.52 (m, 1H), 7.44 (m, 1H), 7.33 (m, 1H), 7.23 (m, 1H), 6.58 (m, 1H), 6.41 (d, J=16.8 Hz, 1H), 5.84 (d, J=10.4 Hz, 1H), 5.08 (brs, 0.5H), 4.61 (brs, 0.5H), 4.41 (m, 1H), 4.05 (m, 6H), 3.56 (m, 1H), 3.42 (m, 1H), 3.14 (m, 4H), 2.40 (m, 11H), 0.72 (m, 2H), 0.54 (m, 2H).

Example 3 2-(1-acroloyl-4-(7-(8-chloronaphthalen-1-yl)-2-((1-((dimethylamino) methyl)cyclobutyl) methoxyl)-5, 6, 7, 8-tetrahydropyrido[3,4-d]pyrimidin-4-yl)piperazin-2-yl) acetonitrile

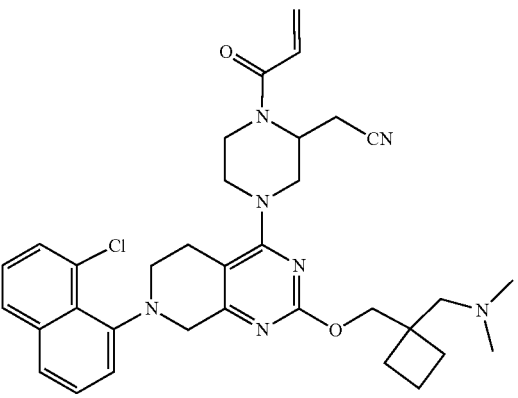 [SMILES: C=CC(=O)N1CCN(c2nc(OCC3(CN(C)C)CCC3)nc3c2CCN(c2cccc4cccc(Cl)c24)C3)CC1CC#N]

LCMS: m/z 614 (M+H)⁺. ¹H NMR (400 MHz, CDCl$_3$) δ 7.68 (d, J=8.0 Hz, 1H), 7.54 (dd, J=8.0, 3.2 Hz, 1H), 7.40 (m, 2H), 7.26 (t, J=7.8 Hz, 1H), 7.15 (m, 1H), 6.52 (brs, 1H), 6.31 (d, J=16.4 Hz, 1H), 5.74 (d, J=10.5 Hz, 1H), 5.00 (brs, 0.5H), 4.69 (m, 2.5H), 4.50-4.19 (m, 2H), 3.91 (m, 2H), 3.49 (m, 2H), 3.16 (m, 6H), 2.92 (m, 1H), 2.78 (m, 7H), 2.53 (m, 1H), 2.24-1.81 (m, 7H).

Example 4 2-(1-acroloyl-4-(2-(2-((1-fluorocyclopropyl)methyl)(methyl)amino)ethyoxyl)-7-(8-methylnaphthalen-1-yl)-5,6,7,8-tetrahydropyrido[3,4-d]pyrimidin-4-yl)piperazin-2-yl) acetonitrile

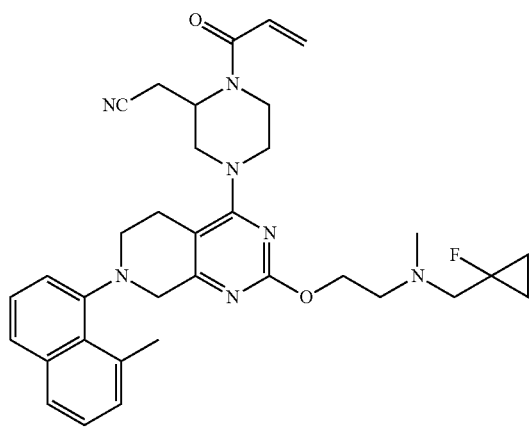 [SMILES: C=CC(=O)N1CCN(c2nc(OCCN(C)CC3(F)CC3)nc3c2CCN(c2cccc4cccc(C)c24)C3)CC1CC#N]

LCMS: m/z 598 (M+H)⁺. ¹HNMR (400 MHz, CDCl$_3$) δ 7.60 (m, 2H), 7.29 (m, 2H), 7.17 (m, 2H), 6.49 (m, 1H), 6.34 (d, J=17.2 Hz, 1H), 5.77 (d, J=10.0 Hz, 1H), 4.99 (brs, 0.5H), 4.59 (m, 2.5H), 2.88 (m, 5H), 3.46 (m, 2H), 3.09 (m, 8H), 2.84 (s, 3H), 2.69 (m, 6H), 1.12 (m, 2H), 0.81 (m, 2H).

Example 5 2-(1-acroloyl-4-(7-(8-chloronaphthalen-1-yl)-2-(cyclobutyl (2-methoxyethyl)amino)ethoxy)-5, 6, 7, 8-tetrahydropyrido[3,4-d]pyrimidin-4-yl) piperazin-2-yl) acetonitrile

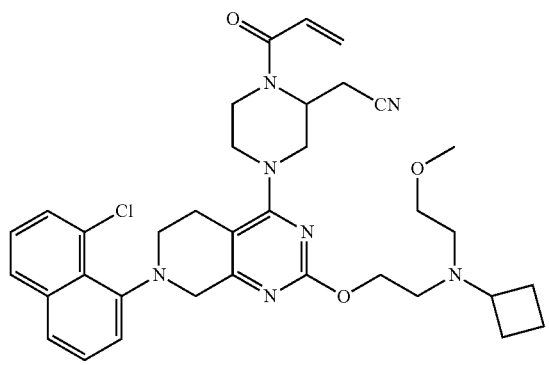 [SMILES: C=CC(=O)N1CCN(c2nc(OCCN(CCOC)C3CCC3)nc3c2CCN(c2cccc4cccc(Cl)c24)C3)CC1CC#N]

LCMS: m/z 644 (M+H)⁺. ¹HNMR (400 MHz, CDCl$_3$) δ 7.76 (m, 1H), 7.61 (m, 1H), 7.53 (m, 1H), 7.45 (m, 1H), 7.33 (m, 1H), 7.24 (m, 1H), 6.58 (m, 1H), 6.41 (d, J=16.8 Hz, 1H), 5.83 (d, J=10.4 Hz, 1H), 5.07 (brs, 0.5H), 4.62 (brs, 0.5H), 4.41 (m, 3H), 3.91 (m, 4H), 3.48 (m, 4H), 3.32 (m, 3H), 2.93 (m, 4H), 2.40 (m, 12H), 2.03 (m, 4H), 1.58 (m, 2H).

Example 6 2-(1-acroloyl-4-(7-(8-chloronaphthalen-1-yl)-2-(2-((2,2-difluorocyclopropyl)methyl) (methyl)amino)ethoxy)-5, 6, 7, 8-tetrahydropyrido [3,4-d]pyrimidin-4-yl) piperazin-2-yl) acetonitrile

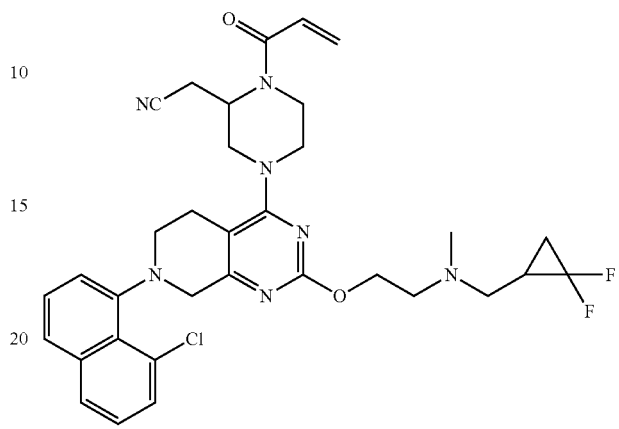

LCMS: m/z 636 (M+H)⁺. ¹HNMR (400 MHz, CDCl$_3$) δ 7.76 (m, 1H), 7.61 (m, 1H), 7.53 (m, 1H), 7.45 (m, 1H), 7.33 (m, 1H), 7.24 (m, 1H), 6.58 (m, 1H), 6.41 (d, J=16.8 Hz, 1H), 5.83 (d, J=10.4 Hz, 1H), 5.07 (brs, 0.5H), 4.61 (brs, 0.5H), 4.42 (m, 3H), 3.82 (m, 4H), 3.53 (m, 2H), 3.21 (m, 4H), 2.82 (m, 5H), 2.55 (m, 2H), 2.40 (s, 3H), 1.45 (m, 1H), 1.30 (m, 1H), 1.00 (m, 1H).

Example 7 2-(1-acroloyl-4-(2-(2-(methyl(cyclobutoxy-3-yl) amino)ethyoxyl)-7-(8-methylnaphthalen-1-yl)-5,6,7,8-tetrahydropyrido[3,4-d]pyrimidin-4-yl) piperazin-2-yl) acetonitrile

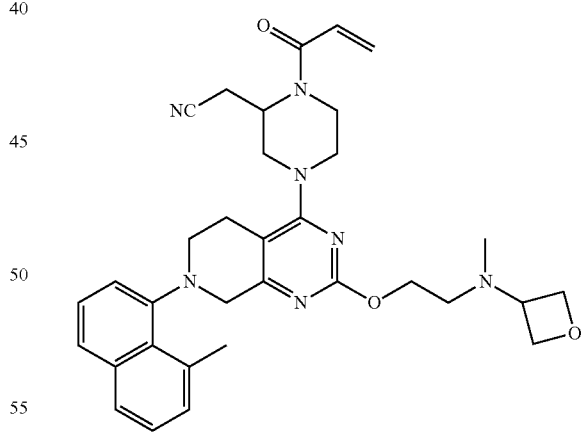

LC-MS: m/z 582 (M+H)⁺. ¹H NMR (400 MHz, CDCl$_3$) δ 7.71-7.63 (m, 2H), 7.44-7.32 (m, 2H), 7.25-7.19 (m, 2H), 6.62-6.55 (m, 1H), 6.42-6.38 (m, 1H), 5.83 (d, J=10.4 Hz, 1H), 5.11-4.99 (m, 0.5H), 4.67-4.63 (m, 4.5H), 4.44-4.37 (m, 2H), 4.27-4.06 (m, 3H), 3.92-3.84 (m, 1H), 3.78-3.68 (m, 2H), 3.56-3.42 (m, 2H), 3.22-2.97 (m, 4H), 2.91 (s, 3H), 2.86-2.60 (m, 5H), 2.28 (s, 3H).

Example 8 2-(1-acroloyl-4-(7-(8-chloronaphthalen-1-yl)-2-((S)-2-(cyclobutyl (methyl)amino)butyloxy)-5, 6, 7, 8-tetrahydropyrido[3,4-d]pyrimidin-4-yl)piperazin-2-yl) acetonitrile

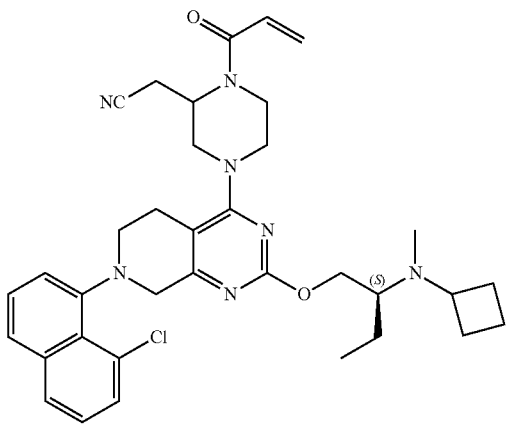

LC-MS: m/z 628 (M+H)+. ¹H NMR (400 MHz, CDCl₃) δ 7.73 (dd, J=14.4, 5.3 Hz, 1H), 7.61 (t, J=7.2 Hz, 1H), 7.52 (d, J=7.4 Hz, 1H), 7.44 (dt, J=12.1, 7.8 Hz, 1H), 7.33 (t, J=7.8 Hz, 1H), 7.26-7.17 (m, 1H), 6.59 (m, 1H), 6.39 (d, J=16.7 Hz, 1H), 5.82 (d, J=10.5 Hz, 1H), 5.08 (brs, 0.5H), 4.63 (brs, 0.5H), 4.50-3.76 (m, 7H), 3.75-2.47 (m, 12H), 2.22 (m, 3H), 2.00 (m, 3H), 1.67 (m, 4H), 0.97 (m, 3H).

Example 9 2-(1-acroloyl-4-(7-(8-chloronaphthalen-1-yl)-2-((S)-2-(cyclobutyl(methyl)amino)-3-methylbutyloxy)-5, 6, 7, 8-tetrahydropyrido[3,4-d]pyrimidin-4-yl)piperazin-2-yl) acetonitrile

LC-MS: m/z 642 (M+H)+. ¹H NMR (400 MHz, CDCl₃) δ 7.70 (d, J=7.7 Hz, 1H), 7.56 (m, 1H), 7.46 (d, J=7.3 Hz, 1H), 7.43-7.35 (m, 1H), 7.27 (t, J=7.8 Hz, 1H), 7.14 (d, J=7.4 Hz, 1H), 6.52 (m, 1H), 6.33 (d, J=16.5 Hz, 1H), 5.76 (d, J=10.0 Hz, 1H), 4.93 (brs, 0.5H), 4.65-4.20 (m, 3.5H), 4.17-3.63 (m, 4H), 3.61-2.90 (m, 8H), 2.63 (m, 7H), 2.25-1.79 (m, 4H), 1.29-1.00 (m, 8H).

Example 10 2-(1-acroloyl-4-(7-(8-chloronaphthalen-1-yl)-2-(2-(cyclobutyl(2,2,2-trifluoroethyl)amino)ethoxy)-5, 6, 7, 8-tetrahydropyrido[3,4-d]pyrimidin-4-yl)piperazin-2-yl) acetonitrile

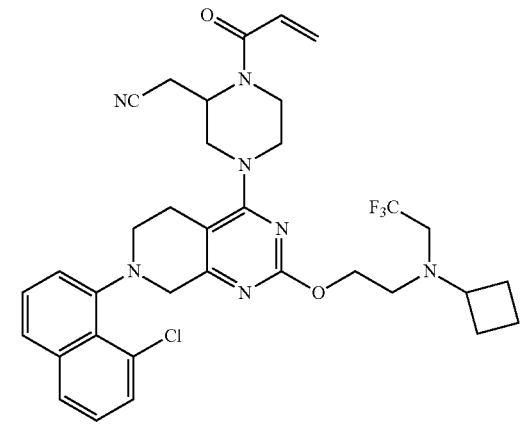 [SMILES: C=CC(=O)N1CCN(c2nc(OCCN(CC(F)(F)F)C3CCC3)nc3c2CCN(c2cccc4cccc(Cl)c24)C3)CC1CC#N]

LC-MS: m/z 668 (M+H)+. ¹H NMR (400 MHz, CDCl₃) δ 7.76 (d, J=8.0 Hz, 1H), 7.62 (t, J=6.4 Hz, 1H), 7.52 (d, J=7.2 Hz, 1H), 7.48-7.41 (m, 1H), 7.34 (t, J=8.0 Hz, 1H), 7.26-7.20 (m, 1H), 6.63-6.55 (m, 1H), 6.42-6.385 (m, 1H), 5.83 (d, J=10.4 Hz, 1H), 5.12-4.98 (m, 0.6H), 4.67-4.41 (m, 3.4H), 4.22-3.73 (m, 4H), 3.60-3.41 (m, 3H), 3.26-2.99 (m, 8H), 2.87-2.56 (m, 3H), 2.16-2.06 (m, 3H), 1.72-1.53 (m, 3H).

Example 11 2-(4-(7-(8-chloronaphthalen-1-yl)-2-(2-(cyclobutyl(methyl)amino)ethoxy)-5, 6, 7, 8-tetrahydropyrido[3,4-d]pyrimidin-4-yl)-1-(2-fluoroacroloyl)piperazin-2-yl) acetonitrile

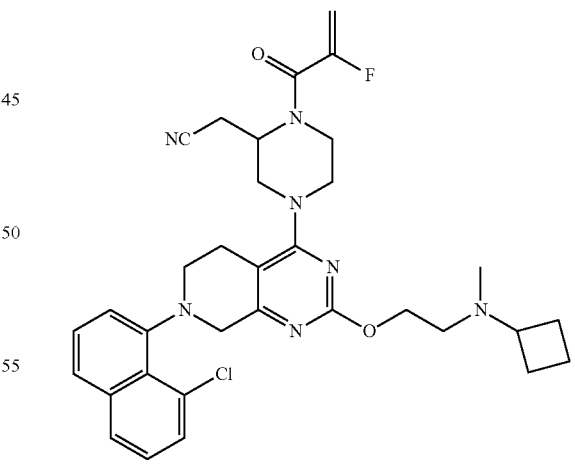

LC-MS: m/z 618 (M+H)+. ¹H NMR (400 MHz, CDCl₃) δ 7.69 (d, J=8.1 Hz, 1H), 7.59-7.51 (m, 1H), 7.45 (d, J=7.4 Hz, 1H), 7.38 (dd, J=17.3, 7.9 Hz, 1H), 7.27 (t, J=7.8 Hz, 1H), 7.19-7.11 (m, 1H), 5.34 (d, J=47.4 Hz, 1H), 5.24-5.12 (m, 1H), 4.74 (brs, 1H), 4.42-3.68 (m, 5H), 3.47 (d, J=32.7 Hz, 3H), 3.29-2.93 (m, 5H), 2.93-2.40 (m, 8H), 2.15 (m, 2H), 1.88 (m, 1H), 1.76-1.60 (m, 2H), 1.35-1.09 (m, 2H).

Example 12 2-(4-(7-(8-chloronaphthalen-1-yl)-2-((S)-2-(cyclopropyl(methyl)amino)propoxy)-5, 6, 7, 8-tetrahydropyrido[3,4-d]pyrimidin-4-yl)-1-(2-fluoroacroloyl)piperazin-2-yl) acetonitrile

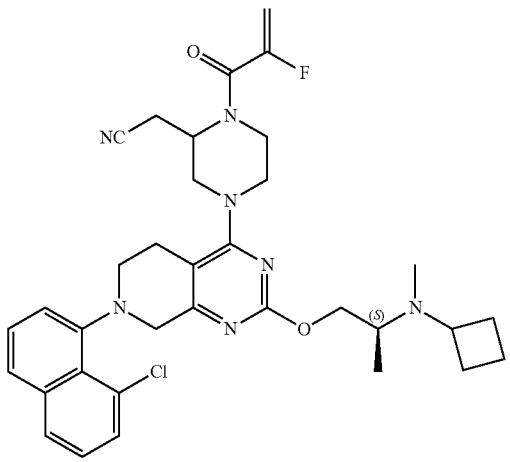

LC-MS: m/z 632 (M+H)+. 1H NMR (400 MHz, CDCl3) δ 7.69 (t, J=7.6 Hz, 1H), 7.56 (dd, J=12.8, 8.2 Hz, 1H), 7.45 (d, J=7.2 Hz, 1H), 7.42-7.33 (m, 1H), 7.27 (dd, J=14.4, 7.0 Hz, 1H), 7.19-7.09 (m, 1H), 5.35 (m, 1H), 5.17 (m, 1H), 4.65 (brs, 1H), 4.52-3.32 (m, 9H), 3.32-2.96 (m, 5H), 2.96-2.36 (m, 8H), 2.14 (d, J=7.5 Hz, 2H), 2.02-1.79 (m, 1H), 1.72-1.59 (m, 1H), 1.39 (d, J=6.2 Hz, 2H), 1.31-1.13 (m, 2H).

Example 13 2-(4-(7-(8-chloronaphthalen-1-yl)-2-((1-((dimethylamino)(methyl)cyclopropyl)methoxy)-5, 6, 7, 8-tetrahydropyrido[3,4-d]pyrimidin-4-yl)-1-(2-fluoroacroloyl)piperazin-2-yl) acetonitrile

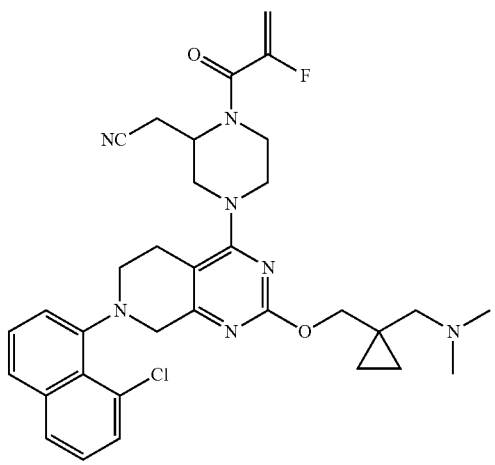 [SMILES: C=C(F)C(=O)N1CCN(c2nc(OCC3(CN(C)C)CC3)nc3c2CCN(c2cccc4cccc(Cl)c24)C3)CC1CC#N]

LC-MS: m/z 618 (M+H)+. 1H NMR (400 MHz, CDCl3) δ 7.68 (d, J=8.1 Hz, 1H), 7.57-7.51 (m, 1H), 7.44 (d, J=7.4 Hz, 1H), 7.37 (dt, J=10.3, 7.8 Hz, 1H), 7.26 (t, J=7.8 Hz, 1H), 7.18-7.11 (m, 1H), 5.32 (d, J=47.5 Hz, 1H), 5.16 (dd, J=16.9, 3.5 Hz, 1H), 4.75 (brs, 0.5H), 4.44-4.24 (m, 2.5H), 4.23-3.69 (m, 5H), 3.48 (m, 1H), 3.36 (m, 1H), 2.89 (m, 15H), 0.83 (m, 2H), 0.70 (m, 2H).

Example 14 2-(4-(7-(8-chloro-7-fluoronaphthalen-1-yl)-2-(2-(cyclobutyl(methyl) amino)ethoxy)-5, 6, 7, 8-tetrahydropyrido[3,4-d]pyrimidin-4-yl)-1-(2-fluoroacroloyl) piperazin-2-yl) acetonitrile

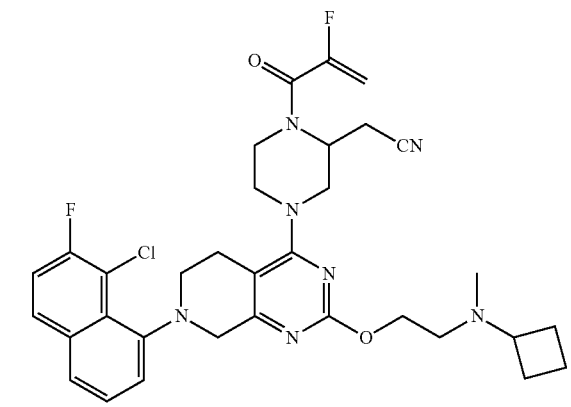 [SMILES: C=C(F)C(=O)N1CCN(c2nc(OCCN(C)C3CCC3)nc3c2CCN(c2cccc4ccc(F)c(Cl)c24)C3)CC1CC#N]

LCMS: m/z 636 (M+H)+. 1H NMR (400 MHz, CDCl3) δ 7.81-7.67 (m, 1H), 7.65-7.49 (m, 1H), 7.42 (dt, J=12.2, 7.8 Hz, 1H), 7.35-7.21 (m, 2H), 5.41 (m, 1H), 5.23 (m, 1H), 4.85 (brs, 1H), 4.36 (m, 3H), 4.23-3.97 (m, 2H), 3.96-3.73 (m, 1H), 3.50 (m, 2H), 3.13 (m, 3H), 3.00-2.51 (m, 5H), 2.24 (s, 3H), 2.02 (m, 5H), 1.80-1.55 (m, 2H), 1.29 (m, 2H).

Example 15 2-(1-acroloyl-4-(7-(8-chloronaphthalen-1-yl)-2-(((cis)-2-(dimethylamino)cyclopentyl)oxy)-5, 6, 7, 8-tetrahydropyrido[3,4-d]pyrimidin-4-yl) piperazin-2-yl) acetonitrile

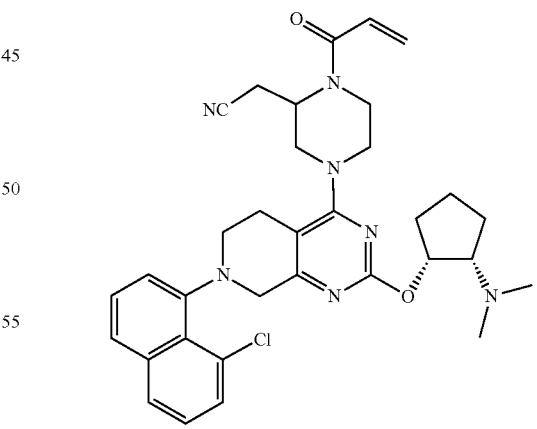

LCMS: m/z 600 (M+H)+. 1H NMR (400 MHz, CDCl3) δ 7.69 (d, J=8.1 Hz, 1H), 7.56 (t, J=7.6 Hz, 1H), 7.46 (d, J=7.4 Hz, 1H), 7.38 (dt, J=12.4, 7.7 Hz, 1H), 7.27 (t, J=7.8 Hz, 1H), 7.19-7.09 (m, 1H), 6.50 (m, 1H), 6.32 (d, J=16.7 Hz, 1H), 5.76 (d, J=10.6 Hz, 1H), 5.54 (m, 1H), 4.98 (brs, 0.5H), 4.59 (brs, 0.5H), 4.42-4.16 (m, 2H), 4.16-3.48 (m, 9H), 3.47-3.28 (m, 2H), 3.29-2.87 (m, 5H), 2.85-2.33 (m, 10H).

523

Example 16 2-(1-acroloyl-4-(7-(8-chloronaphthalen-1-yl)-2-(((trans)-2-(dimethyl amino)cyclopentyl)oxy)-5, 6, 7, 8-tetrahydropyrido[3,4-d]pyrimidin-4-yl)piperazin-2-yl) acetonitrile

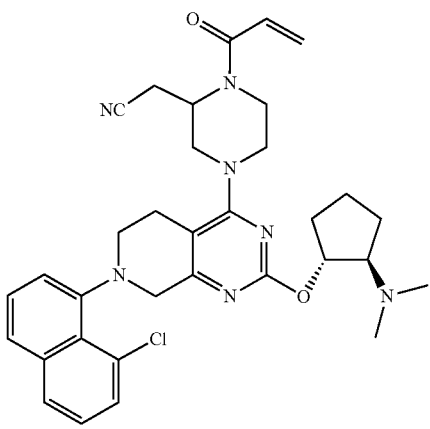 [SMILES: C=CC(=O)N1CCN(c2nc(O[C@@H]3CCC[C@H]3N(C)C)nc3c2CCN(c2cccc4cccc(Cl)c24)C3)CC1CC#N]

LCMS: m/z 600 (M+H)⁺.

Example 17 2-(1-acroloyl-4-(7-(8-chloronaphthalen-1-yl)-2-(((cis)-4-(dimethylamino)tetrahydrofuran-3-yl)oxy)-5, 6, 7, 8-tetrahydropyrido[3,4-d]pyrimidin-4-yl)piperazin-2-yl) acetonitrile

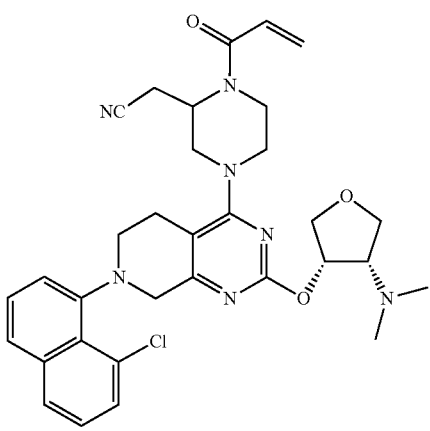 [SMILES: C=CC(=O)N1CCN(c2nc(O[C@@H]3COC[C@@H]3N(C)C)nc3c2CCN(c2cccc4cccc(Cl)c24)C3)CC1CC#N]

LCMS: m/z 602 (M+H)⁺.

524

Example 18 2-(1-acroloyl-4-(7-(8-chloronaphthalen-1-yl)-2-(((trans)-4-(dimethyl amino)tetrahydrofuran-3-yl)oxy)-5, 6, 7, 8-tetrahydropyrido[3,4-d]pyrimidin-4-yl)piperazin-2-yl) acetonitrile

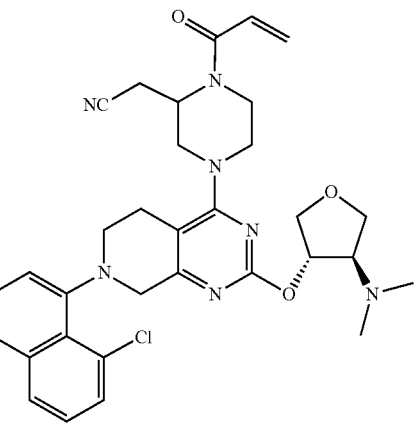

LCMS: m/z 602 (M+H)⁺.

Example 19 2-(1-acroloyl-4-(7-(8-chloronaphthalen-1-yl)-2-((3-((dimethylamino) methyl)oxetan-3-yl)methoxy)-5, 6, 7, 8-tetrahydropyrido[3,4-d]pyrimidin-4-yl)piperazin-2-yl) acetonitrile

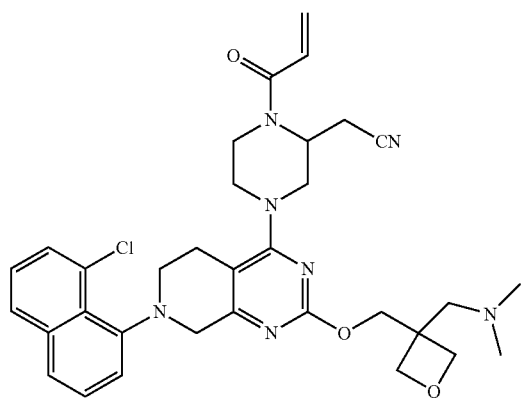

LCMS: m/z 616 (M+H)⁺. ¹H NMR (400 MHz, CDCl₃) δ 7.68 (d, J=8.1 Hz, 1H), 7.54 (dd, J=7.8, 4.8 Hz, 1H), 7.45 (d, J=7.4 Hz, 1H), 7.37 (dd, J=16.7, 8.0 Hz, 1H), 7.26 (t, J=7.8 Hz, 1H), 7.15 (dd, J=15.9, 7.3 Hz, 1H), 6.52 (m, 1H), 6.32 (d, J=16.7 Hz, 1H), 5.75 (d, J=10.6 Hz, 1H), 5.01 (brs, 0.5H), 4.79-4.44 (m, 6.5H), 4.35 (m, 1H), 4.29-3.70 (m, 4H), 3.47 (m, 2H), 3.29-2.88 (m, 6H), 2.89-2.60 (m, 2H), 2.48 (m, 7H).

Example 20 2-(1-acroloyl-4-(7-(8-chloronaphthalen-1-yl)-2-((1-(methoxymethyl) cyclopropyl) methoxyl)-5, 6, 7, 8-tetrahydropyrido[3,4-d]pyrimidin-4-yl)piperazin-2-yl) acetonitrile Example 22 2-(4-(2-(2-(cyclobutyl(methyl)amino) ethyoxyl)-7-(7-fluoro-8-methyl naphthalen-1-yl)-5,6,7,8-tetrahydropyrido[3,4-d]pyrimidin-4-yl)-1-(2-fluoroacroloyl)piperazin-2-yl) acetonitrile

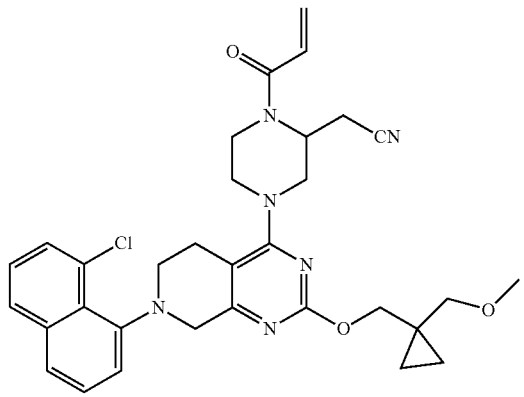 [SMILES: C=CC(=O)N1CCN(c2nc(OCC3(COC)CC3)nc3c2CCN(c2cccc4cccc(Cl)c24)C3)CC1CC#N]

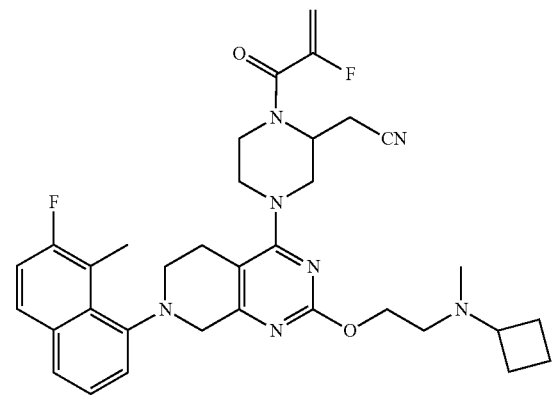

LCMS: m/z 587 (M+H)$^+$. $^1$H NMR (400 MHz, CDCl$_3$) δ 7.68 (d, J=8.2 Hz, 1H), 7.54 (t, J=7.1 Hz, 1H), 7.44 (d, J=7.4 Hz, 1H), 7.36 (dt, J=11.9, 7.8 Hz, 1H), 7.26 (t, J=7.8 Hz, 1H), 7.19-7.09 (m, 1H), 6.61-6.43 (m, 1H), 6.32 (d, J=16.7 Hz, 1H), 5.75 (d, J=10.7 Hz, 1H), 4.97 (brs, 0.5H), 4.80-4.32 (m, 1.5H), 4.23-3.97 (m, 4H), 3.85 (m, 2H), 3.71-3.25 (m, 8H), 3.23-2.86 (m, 4H), 2.77 (m, 1H), 2.53 (m, 1H), 0.65-0.44 (m, 4H).

LCMS: m/z 616 (M+H)$^+$. 1H NMR (400 MHz, CDCl$_3$) δ 7.77-7.46 (m, 3H), 7.36 (m, 1H), 7.24-7.18 (m, 1H), 5.42 (m, 1H), 5.24 (m, 1H), 4.61 (m, 2H), 4.07 (m, 5H), 3.53 (m, 2H), 3.35-2.73 (m, 11H), 2.71-2.05 (m, 5H), 1.71 (m, 3H), 1.44 (m, 1H), 1.30 (m, 3H).

Example 23 2-(1-acroloyl-4-(7-(8-chloronaphthalen-1-yl)-2-(2-(methyl(1-methylcyclobutyl)amino) ethoxy)-5, 6, 7, 8-tetrahydropyrido[3,4-d]pyrimidin-4-yl) piperazin-2-yl) acetonitrile Example 21 2-(1-acroloyl-4-(2-(2-(cyclobutyl (methyl)amino)ethyoxyl)-7-(7-fluoro-8-methylnaphthalen-1-yl)-5,6,7,8-tetrahydropyrido[3,4-d]pyrimidin-4-yl)piperazin-2-yl) acetonitrile

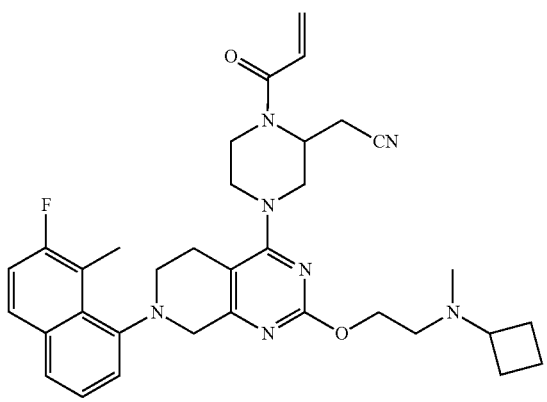 [SMILES: C=CC(=O)N1CCN(c2nc(OCCN(C)C3CCC3)nc3c2CCN(c2cccc4ccc(F)c(C)c24)C3)CC1CC#N]

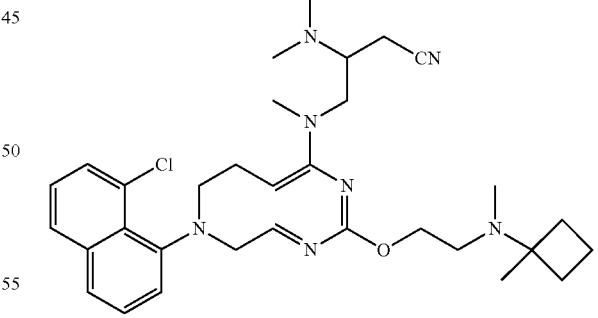

LCMS: m/z 598 (M+H)$^+$. $^1$H NMR (400 MHz, CDCl$_3$) δ 7.67 (m, 2H), 7.38 (m, 1H), 7.22 (m, 2H), 6.57 (m, 1H), 6.67 (m, 1H), 5.86 (d, J=12 Hz, 1H), 4.90 (m, 3H), 4.57 (m, 1H), 4.32 (m, 2H), 4.12-3.86 (m, 3H), 3.56 (m, 5H), 3.19 (m, 3H), 3.00-2.88 (m, 1H), 2.80-2.73 (m, 7H), 2.57 (m, 2H), 2.30 (m, 3H), 1.96-1.74 (m, 2H).

LCMS: m/z 614 (M+H)$^+$. $^1$H NMR (400 MHz, CDCl$_3$) δ 7.66 (t, J=11.3 Hz, 1H), 7.54 (t, J=7.3 Hz, 1H), 7.45 (d, J=7.3 Hz, 1H), 7.37 (dt, J=12.3, 7.8 Hz, 1H), 7.26 (t, J=7.8 Hz, 1H), 7.19-7.09 (m, 1H), 6.52 (m, 1H), 6.31 (d, J=16.7 Hz, 1H), 5.75 (d, J=10.5 Hz, 1H), 4.99 (brs, 0.5H), 4.70-4.20 (m, 3.5H), 4.17-3.58 (m, 4H), 3.57-3.27 (m, 2H), 3.27-2.45 (m, 10H), 2.45-2.08 (m, 4H), 1.88-1.48 (m, 5H), 1.16 (m, 2H).

527

Example 24 2-(1-acroloyl-4-(7-(8-chloronaphthalen-1-yl)-2-(2-(methyl(3-methyloxacyclobutan-3-yl)amino)ethoxy)-5, 6, 7, 8-tetrahydropyrido[3,4-d]pyrimidin-4-yl)piperazin-2-yl) acetonitrile

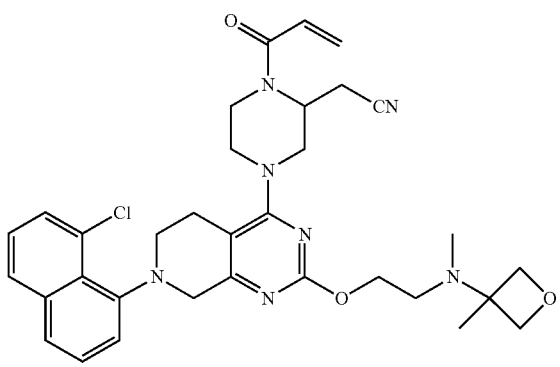 [SMILES: C=CC(=O)N1CCN(c2nc(OCCN(C)C3(C)COC3)nc3c2CCN(c2cccc4cccc(Cl)c24)C3)CC1CC#N]

LCMS: m/z 616 (M+H)$^+$.

Example 25 2-(4-(7-(8-chloronaphthalen-1-yl)-2-((3-((dimethylamino)methyl)oxetan-3-yl)methoxy)-5, 6, 7, 8-tetrahydropyrido[3,4-d]pyrimidin-4-yl)-1-(2-fluoroacroloyl)piperazin-2-yl) acetonitrile

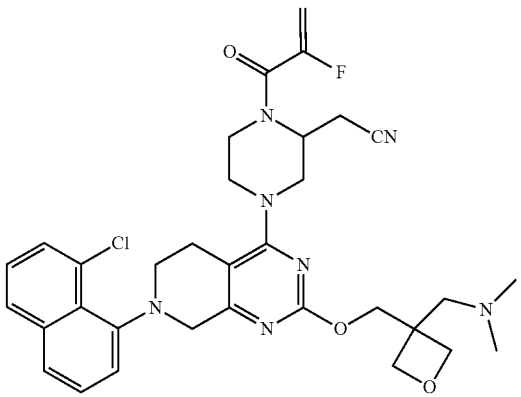 [SMILES: C=C(F)C(=O)N1CCN(c2nc(OCC3(CN(C)C)COC3)nc3c2CCN(c2cccc4cccc(Cl)c24)C3)CC1CC#N]

LCMS: m/z 634 (M+H)$^+$. H NMR (400 MHz, CDCl$_3$) δ 7.77 (d, J=8.1 Hz, 1H), 7.63 (dd, J=7.8, 5.0 Hz, 1H), 7.54 (d, J=7.3 Hz, 1H), 7.46 (dd, J=16.7, 8.1 Hz, 1H), 7.35 (t, J=7.8 Hz, 1H), 7.24 (dd, J=16.3, 7.5 Hz, 1H), 5.43 (m, 1H), 5.31-5.17 (m, 1H), 4.90 (brs, 0.5H), 4.80-4.51 (m, 6.5H), 4.50-4.24 (m, 2H), 4.20-3.79 (m, 3H), 3.55 (m, 2H), 3.35-2.75 (m, 8H), 2.59 (m, 1H), 2.30 (s, 6H).

528

Example 26 2-(1-acroloyl-4-(7-(8-chloronaphthalen-1-yl)-2-((1-((methylamino)methyl)cyclopropyl)methoxy)-5, 6, 7, 8-tetrahydropyrido[3,4-d]pyrimidin-4-yl) piperazin-2-yl) acetonitrile

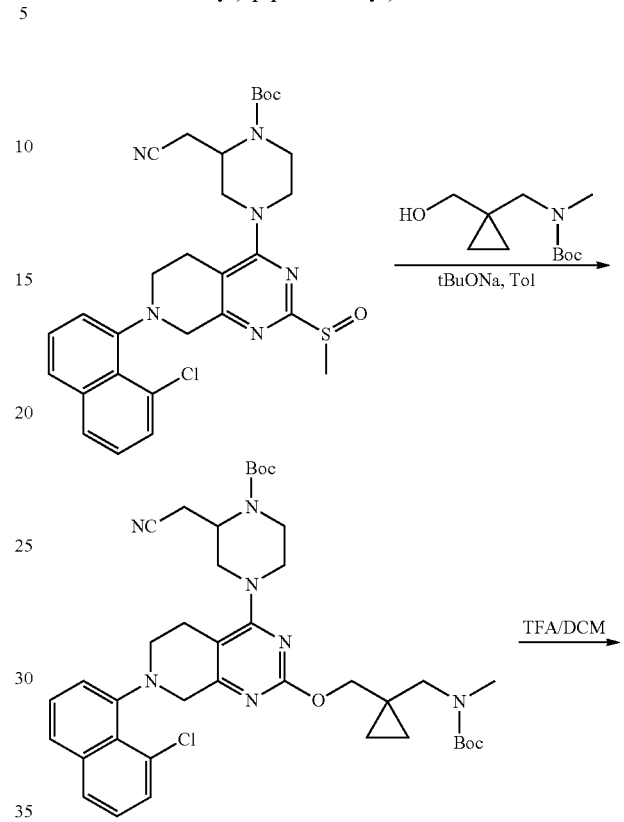

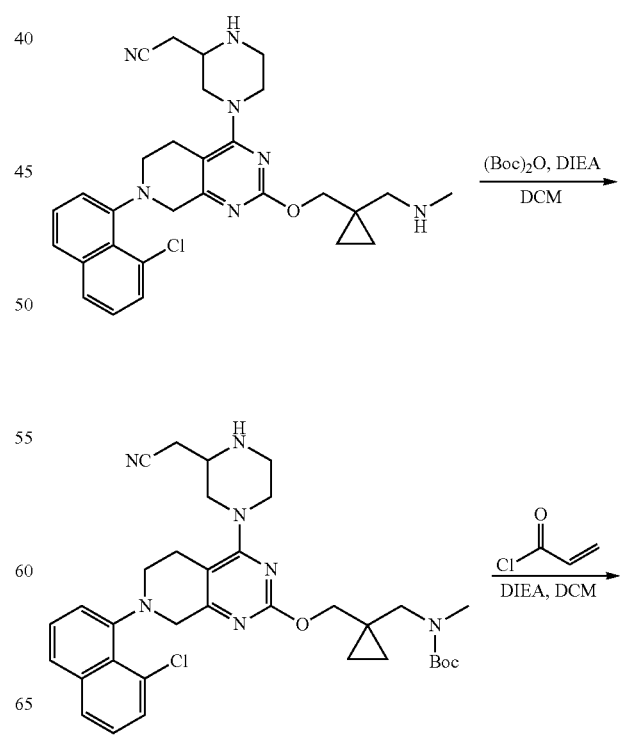

-continued

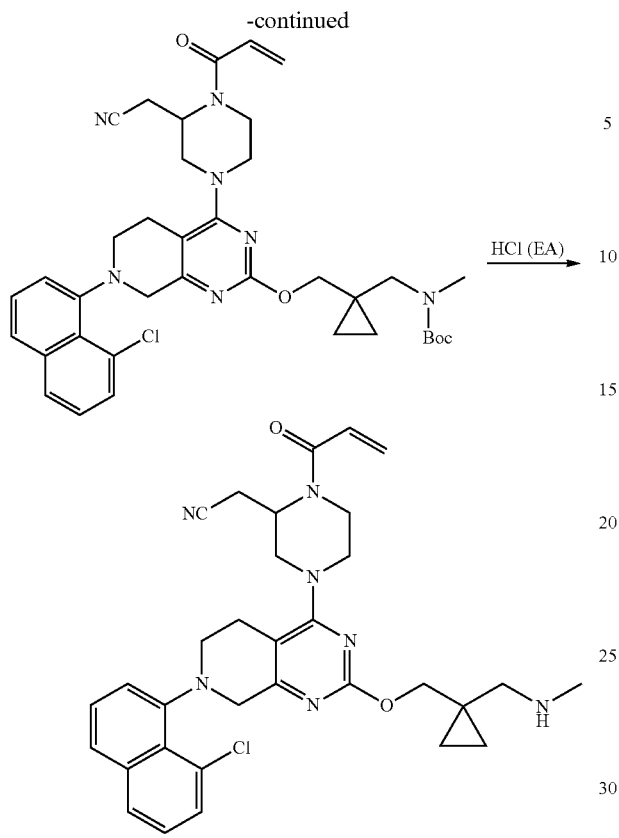

Step 1: Preparation of tert-butyl 4-(2-((1-(((t-butyloxycarboryl) (methyl)amino) methyl)cyclopropyl)methoxy)-7-(8-chloronaphthalen-1-yl)-5,6,7,8-tetrahydropyrido[3, 4-d]pyrimidin-4-yl)-2-(cyanomethyl) piperazin-1-carboxylate Tert-butyl 4-(7-(8-chloronaphthalen-1-yl)-2-(methyl sulfoxide)-5, 6, 7, 8-tetrahydropyrido[3,4-d]pyrimidin-4-yl)-2-(cyanomethyl) piperazin-1-carboxylate (155 mg, 0.267 mmol) was added to the reaction flask, and then toluene (1.5 mL), tert-butyl((1-(hydroxymethyl)cyclopropyl)methyl)(methyl) carbamate (115 mg, 0.533 mmol) and sodium tert-butoxide (77 mg, 0.800 mmol) were successively added. The reaction solution was stirred for 0.5 h under ice water bath, then water (50 mL) was added to quench, and extracted with ethyl acetate (30 mL×3). The combined organic phase was washed once with a saturated sodium chloride solution, and then dried over anhydrous sodium sulfate, then filtered. The filtrate was concentrated, then separated by TLC plate (eluent: EA/PE=1.5/1) to obtain the target compound (210 mg, yield 97%).
LC-MS: m/z 732.7 (M+H)$^+$.

Step 2: Preparation of 2-(4-(7-(8-chloronaphthalen-1-yl)-2-((1-((methylamino) methyl)cyclopropyl)methoxy)-5, 6, 7, 8-tetrahydropyrido[3,4-d]pyrimidin-4-yl) piperazin-2-yl) acetonitrile tert-butyl 4-(2-((1-(((t-butyloxycarboryl)(methyl)amino) methyl)cyclopropyl)methoxy)-7-(8-chloronaphthalen-1-yl)-5,6,7,8-tetrahydropyrido[3,4-d]pyrimidin-4-yl)-2-(cyanomethyl)piperazin-1-carboxylate (210 mg, 0.287 mmol) was dissolved in dichloromethane (4 mL) and trifluoroacetic acid (2 mL) was added. The reaction solution was stirred at room temperature for 0.5 h and then concentrated until dry to obtain the target product (crude product 150 mg), then directly used for the next reaction without purification.
LC-MS: m/z 532.4 (M+H)$^+$.

Step 3: Preparation of tert-butyl ((1-((7-(8-chloronaphthalen-1-yl)-4-(3-(cyanomethyl)piperazin-1-yl)-5, 6, 7, 8-tetrahydropyrido[3,4-d]pyrimidin-2-yl) oxy)meth yl) cyclopropyl) methyl) (methyl) carbamate 2-(4-(7-(8-chloronaphthalen-1-yl)-2-((1-((methylamino)methyl)cyclopropyl)methoxy)-5,6,7,8-tetrahydropyrido[3, 4-d]pyrimidin-4-yl) piperazin-2-yl) acetonitrile (150 mg) obtained from the previous step was added to the reaction flask, then dichloromethane (4 mL) and N, N-diisopropylethylamine (364 mg, 2.82 mmol) were added successively. The reaction solution was cooled to 0° C., and di-tert-butyl dicarbonate (49 mg, 0.226 mmol) was slowly added dropwise. The resulting mixture was stirred for 1 h under ice water bath, then water (50 mL) was added, and extracted with ethyl acetate (30 ml×3). The combined organic phase was washed once with a saturated sodium chloride solution, and then dried over anhydrous sodium sulfate, and filtered. The filtrate was concentrated and dried to obtain the target compound (crude product 150 mg), then directly used for the next reaction without purification.
LC-MS: m/z 632.6 (M+H)$^+$.

Step 4: Preparation of tert-butyl ((1-((4-(4-acroloyl-3-(cyanomethyl)piperazin-1-yl)-7-(8-chloronaphthalen-1-yl)-5, 6, 7, 8-tetrahydropyrido[3,4-d]pyrimidin-2-yl) oxy)methyl)cyclopropyl)methyl)(methyl) carbamate Dichloromethane (5 mL) and N, N-diisopropylethylamine (200 mg, 1.55 mmol) were added to tert-butyl ((1-((7-(8-chloronaphthalen-1-yl)-4-(3-(cyanomethyl)piperazin-1-yl)-5, 6, 7, 8-tetrahydropyrido[3,4-d]pyrimidin-2-yl)oxy) methyl)cyclopropyl) methyl) (methyl) carbamate (150 mg) obtained from the previous step. The reaction solution was protected by nitrogen, cooled to −40° C., and acroloyl chloride (60 mg, 0.663 m mol) was added dropwise. After the addition, the reaction solution was stirred at room temperature for 1 h, then methanol (1 mL) was added to quench. The resulting mixture was concentrated, then separated by TLC plate (eluent: EA/PE=3/2) to obtain the target compound (80 mg).
LC-MS: m/z 686.9 (M+H)$^+$.

Step 5: Preparation of 2-(1-acroloyl-4-(7-(8-chloronaphthalen-1-yl)-2-((1-((methylamino)methyl) cyclopropyl)methoxy)-5, 6, 7, 8-tetrahydropyrido[3, 4-d]pyrimidin-4-yl)piperazin-2-yl) acetonitrile Ethyl acetate (2 mL) and a solution of hydrochloric acid in ethyl acetate (4N, 4 mL) were added to tert-butyl ((1-((4-(4-acroloyl-3-(cyanomethyl)piperazin-1-yl)-7-(8-chloronaphthalen-1-yl)-5,6,7, 8-tetrahydropyrido[3,4-d]pyrimidin-2-yl)oxy)methyl) cyclopropyl) methyl) (methyl) carbamate (80 mg, 0.117 mmol). After the addition, the reaction solution was stirred for 0.5 h at room temperature, then saturated sodium bicarbonate solution (10 mL) was added to quench, and extracted with ethyl acetate (30 mL×3). The combined organic phase was washed once with a saturated sodium chloride solution, and then dried over anhydrous sodium sulfate, and filtered. The filtrate was concentrated and purified by preparative liquid phase to obtain the target product (20 mg, yield 29%).

LC-MS: m/z 586.6 (M+H)+. $^1$H NMR (400 MHz, CDCl$_3$) δ 7.76 (d, J=8.4 Hz, 1H), 7.62 (t, J=6.8 Hz, 1H), 7.52 (d, J=7.6 Hz, 1H), 7.48-7.41 (m, 1H), 7.33 (t, J=8.0 Hz, 1H), 7.24-7.19 (m, 1H), 6.64-6.53 (m, 1H), 6.41-6.37 (m, 1H), 5.82 (d, J=10.4 Hz, 1H), 5.11-4.96 (brs, 0.5H), 4.67-4.56 (brs, 0.5H), 4.39 (dd, J=15.2, 2.8 Hz, 1H), 4.28-4.20 (m, 2H), 4.12-3.78 (m, 4H), 3.61-3.57 (m, 1H), 3.48-3.35 (m, 1H), 3.26-3.01 (m, 4H), 2.88-2.73 (m, 4H), 2.62-2.50 (m, 5H), 0.71-0.60 (m, 4H).

Example 27 Preparation of (S)-2-(4-(7-(8-chloronaphthalen-1-yl)-2-((1-((dimethylamino)(methyl)cyclopropyl)methoxy)-5, 6, 7, 8-tetrahydropyrido[3,4-d]pyrimidin-4-yl)-1-(2-fluoroacroloyl)piperazin-2-yl) acetonitrile

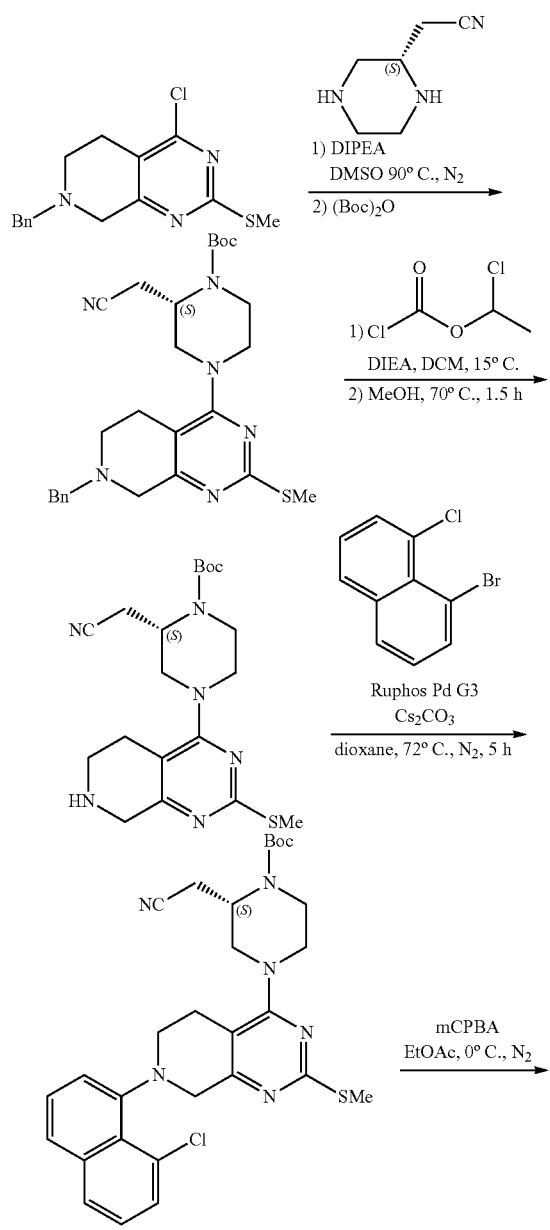

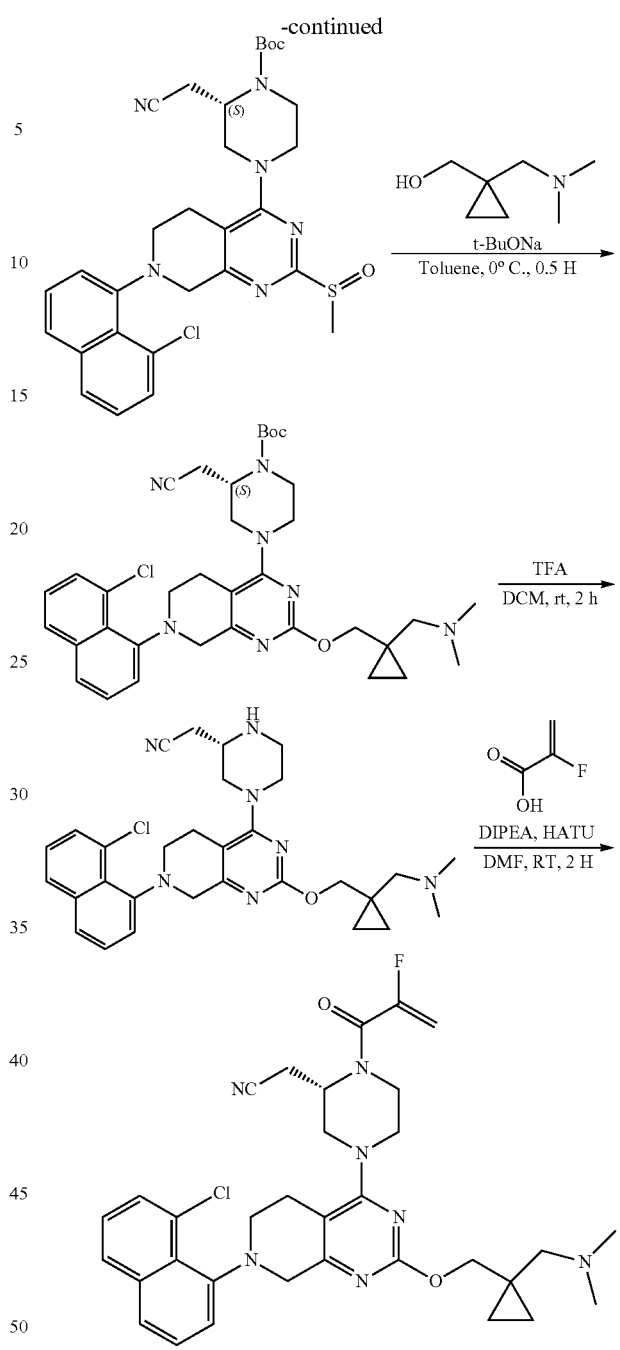

Step 1: Preparation of tert-butyl (S)-4-(7-benzyl-2-(methylthio)-5,6,7,8-tetrahydropyrido[3,4-d]pyrimidin-4-yl)-2-(cyanomethyl) piperazin-1-formate 7-benzyl-4-chloro-2-(methylthio)-5,6,7,8-tetrahydropyrido[3,4-d]pyrimidine (7.0 g, 22.89 mmol), (S)-2-(piperazin-2-yl) acetonitrile dihydrochloride (5.44 g, 27.47 mmol), N, N-diisopropylethylamine (22.8 mL, 137.34 mmol) and DMSO were added to the reaction flask. The reaction solution was heated to 80° C. and stirred for 3 h under the protection of nitrogen, and then dit-butyl dicarbonate (26.3 mL, 114.45 mmol) was added. After the completion of the reaction, the reaction solution was quenched with water and then extracted with ethyl acetate (3×100 mL). After all organic phases were combined, washed with saturated sodium chloride once and then dried over anhydrous sodium sulfate and filtered. The filtrate was concentrated under reduced pressure, and the residue was purified by silica gel column chromatography to obtain the target product (8.0 g, yield 71%).

LC-MS: m/z 495 (M+H)$^+$.

Step 2: Preparation of tert-butyl (S)-2-(cyanomethyl)-4-(2-(methylthio)-5, 6, 7, 8-tetrahydropyrido[3,4-d]pyrimidin-4-yl) piperazine-1-formate Tert-butyl (S)-4-(7-benzyl-2-(methylthio)-5,6,7,8-tetrahydropyrido[3,4-d]pyrimidin-4-yl)-2-(cyanomethyl) piperazin-1-formate (7.5 g, 15.2 mmol), DIPEA (5.9 g, 45.6 mmol) and dichloromethane (150 mL) were added to reaction flask, cooled down to 0° C., followed by adding 1-chloroethyl chloroformate (4.4 g, 30.4 mmol) dropwise. After the addition, the reaction solution was stirred for 3 h at 15° C. and then concentrated until dry under reduced pressure. The residue was added to methanol (150 mL), followed by stirring for 1.5 h at 70° C. After the completion of the reaction, the reaction solution was concentrated, then saturated sodium bicarbonate solution (50 mL) was added and extracted with ethyl acetate (3×25 mL). The combined organic phase was washed once with a saturated sodium chloride solution, and then dried over anhydrous sodium sulfate, then filtered. The filtrate was concentrated and separated by medium pressure preparative column to obtain the target product (2.25 g, yield 36.9%).

LC-MS: m/z 405 (M+H)$^+$.

Step 3: Preparation of tert-butyl (S)-4-(7-(8-chloronaphthalen-1-yl)-2-(methylthio)-5,6,7,8-tetrahydropyrido[3,4-d]pyrimidin-4-yl)-2-(cyanomethyl) piperazin-1-formate Tert-butyl (S)-2-(cyanomethyl)-4-(2-(methylthio)-5, 6, 7, 8-tetrahydropyrido[3,4-d]pyrimidin-4-yl)piperazine-1-formate (4.50 g, 11.12 mmol), 1-bromo-8-chloronaphthalene (3.22 g, 13.35 mmol), cesium carbonate (10.87 g, 33.36 mmol) and dioxane (90 mL) were added to the reaction flask, then replaced with nitrogen three times, and Rup hos G3 pd (2.79 g, 3.34 mmol) was added, and replaced with nitrogen three times again, then heated to 72° C. and stirred for 16 h. After the completion of the reaction, water (100 mL) was added, then extracted with ethyl acetate (3×100 mL). The combined organic phase was washed once with a saturated sodium chloride solution (100 mL), and dried over anhydrous sodium sulfate, then filtered. The filtrate was concentrated, and separated by column chromatography (EA/PE=0 to 20%) to obtain the target product (2.4 g, yield 38.7%).

LC-MS: m/z 565 (M+H)$^+$.

Step 4: Preparation of tert-butyl (2S)-4-(7-(8-chloronaphthalen-1-yl)-2-(methylsulfonyl)-5,6,7,8-tetrahydropyrido[3,4-d]pyrimidin-4-yl)-2-(cyanomethyl) piperazin-1-formate Tert-butyl (S)-4-(7-(8-chloronaphthalen-1-yl)-2-(methylthio)-5,6,7,8-tetrahydropyrido[3,4-d]pyrimidin-4-yl)-2-(cyanomethyl)-piperazine-1-formate (2.32 g, 4.12 mmol) was dissolved in ethyl acetate (45 mL), then cooled to 0° C. with ice-salt bath. Then the solution of meta-chloroperoxybenzoic acid (1.71 g, 9.89 mmol) in ethyl acetate (15 mL) was added. After the addition, the reaction solution was stirred at the temperature for 10 min, followed by quenching with saturated low sodium sulfite solution (100 mL), then water (50 mL) was added to dilute, extracted with ethyl acetate (3×50 mL). The combined organic phase was washed once with a saturated sodium chloride solution (50 mL), and dried over anhydrous sodium sulfate, then filtered. The filtrate was concentrated, and separated by column chromatography (EA/PE=0 to 100%) to obtain the target product (1.2 g, yield 51%).

LC-MS: m/z 581 (M+H)$^+$.

Step 5: Preparation of tert-butyl (S)-4-(7-(8-chloronaphthalen-1-yl)-2-((1-(dim ethylamino)methyl) cyclopropyl)methoxy)-5,6,7,8-tetrahydropyrido[3,4-d]pyrimidin-4-yl)-2-(cyanomethyl) piperazin-1-formate Tert-butyl (2S)-4-(7-(8-chloronaphthalen-1-yl)-2-(methylsulfonyl)-5, 6, 7, 8-tetrahydropyrido[3,4-d]pyrimidin-4-yl)-2-(cyanomethyl)piperazin-1-formate (1.16 g, 2.00 mmol) was added to the reaction flask, and then toluene (12 mL) and (1-((dimethylamino)methyl)cyclopropyl)methanol (517 mg, 4.00 mmol) were successively added, and followed by adding sodium tert-butoxide (577 mg, 6.00 mmol) under ice-water bath and stirring. The obtained reaction solution was stirred for 0.5 h under ice water bath, then water (100 mL) was added to quench, and extracted with ethyl acetate (3×50 mL). The combined organic phase was washed once with a saturated sodium chloride solution, and then dried over anhydrous sodium sulfate, then filtered. The filtrate was concentrated and purified by medium pressure preparative column to obtain the target product (730 mg, yield 60%).

LC-MS: m/z 646 (M+H)$^+$.

Step 6: Preparation of (S)-2-(4-(7-(8-chloronaphthalen-1-yl)-2-((1-((dimethylamino)methyl)cyclopropyl)methoxy)-5, 6, 7, 8-tetrahydropyrido[3,4-d]pyrimidin-4-yl) piperazin-2-yl) acetonitrile Tert-butyl (S)-4-(7-(8-chloronaphthalen-1-yl)-2-((1-(dimethylamino)methyl)cyclopropyl)methoxy)-5,6,7,8-tetrahydropyrido[3,4-d]pyrimidin-4-yl)-2-(cyanomethyl)piperazin-1-formate (678 mg, 1.05 mmol) was added into a reaction flask, then DCM (5 mL) and trifluoroacetic acid (5 mL) were added successively, and then stirred at room temperature for 2 h. After the completion of the reaction, the reaction solution was concentrated, then the pH was adjusted to 8 with a saturated sodium bicarbonate aqueous solution, and extracted with ethyl acetate (3×50 mL). The combined organic phase was washed once with a saturated sodium chloride aqueous solution, and then dried over anhydrous sodium sulfate, and filtered. The filtrate was concentrated until dry to obtain a crude product. It is directly used in the next step without further purification.

LC-MS: m/z 546 (M+H)$^+$.

Step 7: Preparation of (S)-2-(4-(7-(8-chloronaphthalen-1-yl)-2-((1-((dimethylamino)(methyl)cyclopropyl)methoxy)-5, 6, 7, 8-tetrahydropyrido[3,4-d]pyrimidin-4-yl)-1-(2-fluoroacroloyl)piperazin-2-yl) acetonitrile The crude product of (S)-2-(4-(7-(8-chloronaphthalen-1-yl)-2-((1-((dimethylamino) methyl)cyclopropyl)methoxy)-5,6,7,8-tetrahydropyrido[3,4-d]pyrimidin-4-yl)piperazin-2-yl) acetonitrile obtained from the previous step was added to DMF (12 mL), then DI PEA (1.40 g, 10.80 mmol), 2-fluoroacrylic acid (575 mg, 6.38 mmol) and HATU (2.05 g, 5.4 mmol) were added successively. The reaction solution was stirred for 0.5 h under the protection of nitrogen, then water (100 mL) was added to quench, and extracted with ethyl acetate (3×60 mL). The combined organic phase was washed 4 times with a saturated sodium chloride solution, and then dried over anhydrous sodium sulfate, and filtered. The filtrate was concentrated and purified by preparative chromatography to obtain the target product (162 mg, two-step yield 25%).

LC-MS: m/z 618 (M+H)+. 1H NMR (400 MHz, DMSO) δ 7.92 (d, J=8.1 Hz, 1H), 7.74 (dd, J=7.9, 3.3 Hz, 1H), 7.55 (m, 2H), 7.45 (t, J=7.8 Hz, 1H), 7.33 (m, 1H), 5.33 (m, 2H), 4.86 (brs, 1H), 4.26-3.65 (m, 8H), 3.57-3.43 (m, 2H), 3.26-2.60 (m, 7H), 2.37-2.05 (m, 7H), 0.58 (s, 2H), 0.39 (s, 2H).

Example 28 was synthesized from different starting materials according to the method of Example 27:

Example 28 Preparation of (S)-2-(4-(7-(8-chloro-7-fluoronaphthalen-1-yl)-2-((1-((dimethylamino)(methyl)cyclopropyl)methoxy)-tetrahydropyrido[3,4-d]pyrimidin-4-yl)-1-(2-fluoroacroloyl)piperazin-2-yl) acetonitrile

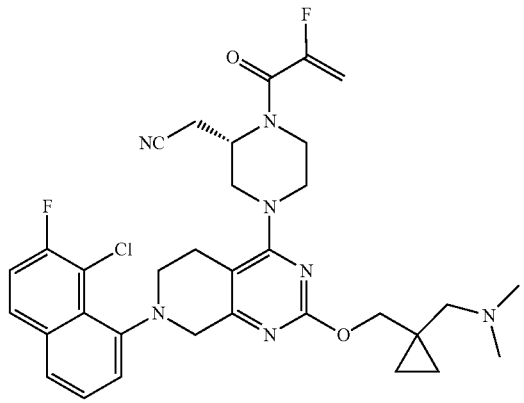 [SMILES: C=C(F)C(=O)N1CCN(c2nc(OCC3(CN(C)C)CC3)nc3c2CCN(c2cccc4ccc(F)c(Cl)c24)C3)C[C@@H]1CC#N]

LC-MS: m/z 636 (M+H)+. 1H NMR (400 MHz, DMSO) δ 8.02 (dd, J=8.9, 5.9 Hz, 1H), 7.79 (dd, J=7.8, 2.7 Hz, 1H), 7.65-7.49 (m, 2H), 7.42 (m, 1H), 5.50-5.16 (m, 2H), 4.87 (brs, 1H), 4.27-3.66 (m, 7H), 3.55-3.43 (m, 2H), 3.28-2.62 (m, 7H), 2.33-2.06 (m, 8H), 0.57 (s, 2H), 0.40 (s, 2H).

Example 29 Preparation of 2-(1-acroloyl-4-(7-(8-chloronaphthalen-1-yl)-2-((1-((dimethylamino)methyl)cyclopropyl)methoxyl)-6-methyl-5, 6, 7, 8-tetrahydropyrido [3,4-d]pyrimidin-4-yl)piperazin-2-yl) acetonitrile

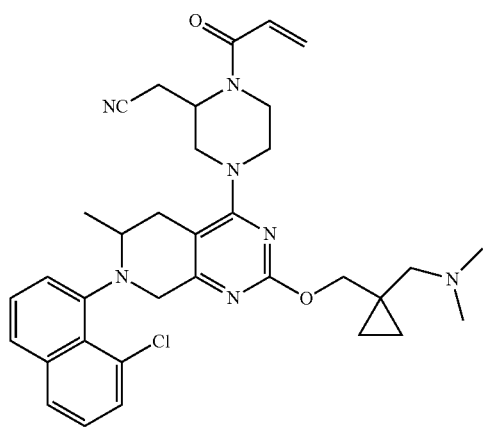 [SMILES: C=CC(=O)N1CCN(c2nc(OCC3(CN(C)C)CC3)nc3c2CC(C)N(c2cccc4cccc(Cl)c24)C3)CC1CC#N]

LC-MS: m/z 614 (M+H)+.

Example 29 Four isomer examples 29A, 29B, 29C and 29D were obtained by chiral resolution

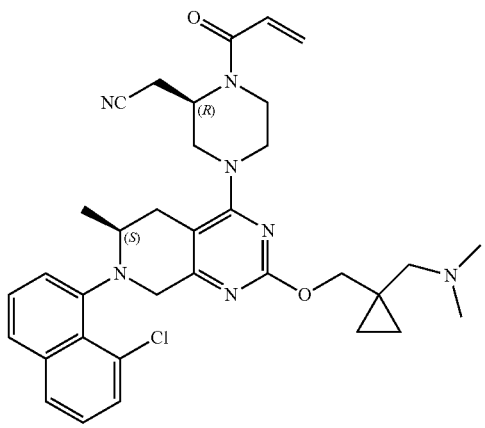

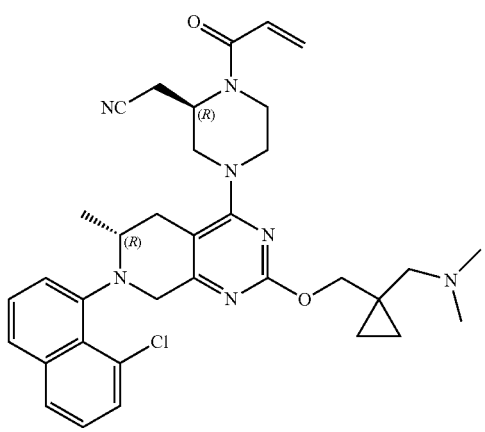

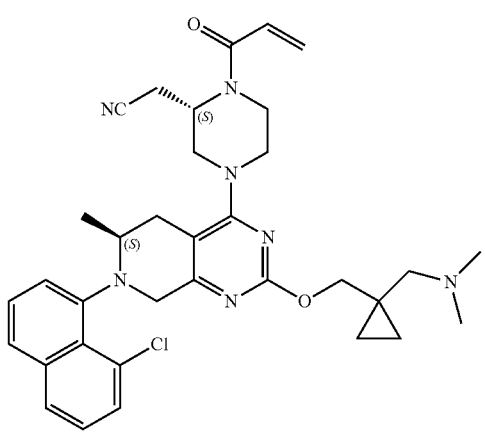

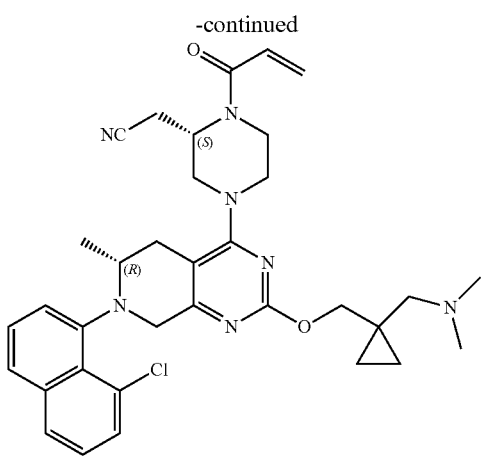

Isomer 29A: LC-MS: m/z 614 (M+H)+; 1HNMR (CDCl3) 7.76 (d, J=7.2 Hz, 1H), 7.70 (d, J=8.0 Hz, 0.6H), 7.58 (d, J=8.0 Hz, 0.4H), 7.54-7.42 (m, 2H), 7.34-7.31 (m, 2H), 6.66-6.53 (m, 1H), 6.41-6.36 (m, 1H), 5.83-5.80 (m, 1H), 5.13-5.02 (m, 0.5H), 4.66-4.50 (m, 0.5H), 4.36-4.32 (m, 1H), 4.21-4.13 (m, 2H), 4.05-3.87 (m, 3H), 3.68-3.62 (m, 1H), 3.45-2.97 (m, 4H), 2.87-2.76 (m, 2H), 2.60-2.56 (m, 1H), 2.35-2.20 (m, 9H), 1.08 (d, J=6.0 Hz, 2.5H), 0.80 (d, J=6.4 Hz, 0.5H), 0.69-0.59 (m, 2H), 0.47-0.41 (m, 2H).

Isomer 29B: LC-MS: m/z 614 (M+H)+; 1HNMR (CDCl3) 7.75 (d, J=8.4 Hz, 1H), 7.67 (d, J=8.0 Hz, 0.6H), 7.58 (d, J=8.0 Hz, 0.4H), 7.54-7.50 (m, 1H), 7.45 (t, J=7.6 Hz, 1H), 7.34-7.31 (m, 2H), 6.66-6.53 (m, 1H), 6.41-6.35 (m, 1H), 5.82-5.80 (m, 1H), 5.11-5.02 (m, 0.5H), 4.65-4.53 (m, 0.5H), 4.43-3.94 (m, 7H), 3.85-3.74 (m, 1H), 3.48-3.44 (m, 1H), 3.25-2.72 (m, 14H), 1.13 (d, J=6.4 Hz, 2H), 0.93-0.86 (m, 2H), 0.81-0.72 (m, 3H).

Isomer 29C: LC-MS: m/z 614 (M+H)+; 1HNMR (CDCl3) 7.75 (d, J=8.0 Hz, 1H), 7.68 (d, J=8.0 Hz, 1H), 7.58 (d, J=8.4 Hz, 0.4H), 7.54-7.49 (m, 1H), 7.44 (t, J=7.6 Hz, 1H), 7.33 (td, J=7.6, 2.0 Hz, 1H), 7.25-7.21 (m, 1H), 6.64-6.53 (m, 1H), 6.41-6.36 (m, 1H), 5.82-5.79 (m, 1H), 5.11-5.01 (m, 0.5H), 4.71-4.53 (m, 0.5H), 4.41-3.72 (m, 8H), 3.50-3.43 (m, 1H), 3.23-2.33 (m, 14H), 1.13 (d, J=6.4 Hz, 2.5H), 0.80-0.79 (m, 2.5H), 0.68-0.56 (m, 2H).

Isomer 29D: LC-MS: m/z 614 (M+H)+; 1HNMR (CDCl3) 7.76 (d, J=7.6 Hz, 1H), 7.70 (d, J=7.6 Hz, 1H), 7.58 (d, J=8.0 Hz, 1H), 7.54-7.42 (m, 2H), 7.34-7.30 (m, 2H), 6.56-6.54 (m, 1H), 6.39-6.35 (m, 1H), 5.79 (d, J=10.4 Hz, 1H), 5.15-5.07 (m, 0.5H), 4.69-4.59 (m, 0.5H), 4.43-3.93 (m, 8H), 3.72-3.65 (m, 1H), 3.44-2.76 (m, 13H), 2.62-2.58 (m, 1H), 1.09 (d, J=6.0 Hz, 2.5H), 0.96-0.90 (m, 2H), 20.83-0.75 (m, 2.5H).

Example 30 Preparation of 2-(1-acroloyl-4-(7-(8-chloronaphthalen-1-yl)-2-((1-((dimethylamino)cyclopropyl)methoxyl)-5, 6, 7, 8-tetrahydropyrido[3,4-d]pyrimidin-4-yl) piperazin-2-yl) acetonitrile

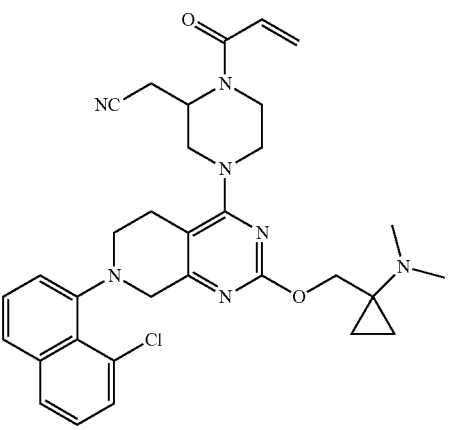 [SMILES: C=CC(=O)N1CCN(c2nc(OCC3(N(C)C)CC3)nc3c2CCN(c2cccc4cccc(Cl)c24)C3)CC1CC#N]

LC-MS: m/z 586 (M+H)+; 1H NMR (400 MHz, CDCl3) δ 7.69 (d, J=8.1 Hz, 1H), 7.55 (t, J=7.1 Hz, 1H), 7.47-7.33 (m, 2H), 7.26 (t, J=7.8 Hz, 1H), 7.18-7.09 (m, 1H), 6.50 (m, 1H), 6.32 (d, J=16.7 Hz, 1H), 5.75 (d, J=10.4 Hz, 1H), 5.01 (brs, 0.5H), 4.51 (brs, 0.5H), 4.33 (m, 3H), 4.21-3.69 (m, 4H), 3.67-2.86 (m, 7H), 2.76 (m, 2H), 2.54 (s, 6H), 0.90 (s, 2H), 0.75 (s, 2H).

Example 31 Preparation of 2-(acroloyl-4-(7-(8-chloronaphthalen-1-yl)-2-(2-((1-(methoxymethyl)cyclobutyl)(methyl)amino)ethoxy)-5, 6, 7, 8-tetrahydropyrido[3,4-d] pyrimidin-4-yl)piperazin-2-yl) acetonitrile

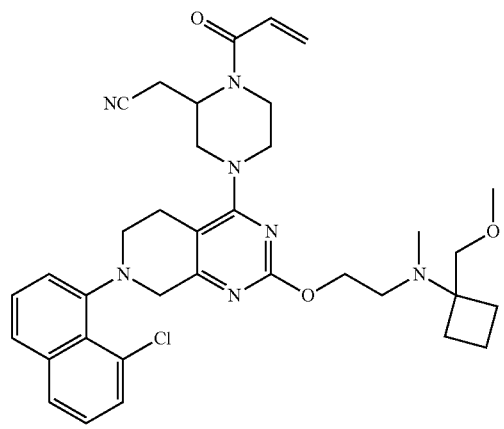 [SMILES: C=CC(=O)N1CCN(c2nc(OCCN(C)C3(COC)CCC3)nc3c2CCN(c2cccc4cccc(Cl)c24)C3)CC1CC#N]

LC-MS: m/z 644 (M+H)+; 1H NMR (400 MHz, CDCl3) δ 7.68 (d, J=8.1 Hz, 1H), 7.54 (t, J=7.2 Hz, 1H), 7.45 (d, J=7.4 Hz, 1H), 7.37 (m, 1H), 7.26 (t, J=7.8 Hz, 1H), 7.15 (m, 1H), 6.51 (m, 1H), 6.31 (d, J=16.7 Hz, 1H), 5.75 (d, J=10.4 Hz, 1H), 5.27 (brs, 0.5H), 4.99 (brs, 0.5H), 4.29 (m, 3H), 4.17-3.68 (m, 4H), 3.67-3.33 (m, 5H), 3.32-3.24 (m, 3H), 3.23-2.86 (m, 7H), 2.83-2.42 (m, 4H), 2.37 (m, 3H), 2.04 (m, 2H), 1.35 (t, J=8.6 Hz, 4H).

Example 32 Preparation of 2-(1-acroloyl-4-(7-(8-chloronaphthalen-1-yl)-2-((3-((cyclopropyl(methyl)amino)methyl)oxetan-3-yl)methoxyl)-5, 6, 7, 8-tetrahydropyrido[3,4-d]pyrimidin-4-yl) piperazin-2-yl) acetonitrile

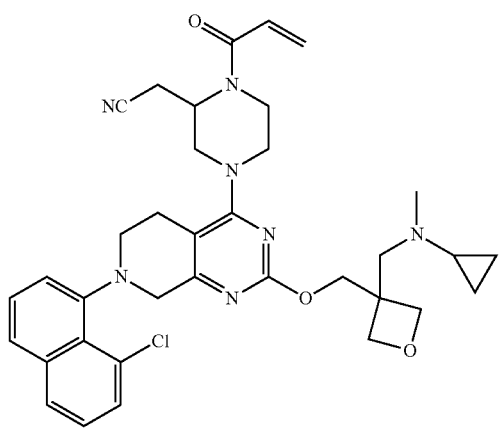 [SMILES: C=CC(=O)N1CCN(c2nc(OCC3(CN(C)C4CC4)COC3)nc3c2CCN(c2cccc4cccc(Cl)c24)C3)CC1CC#N]

LC-MS: m/z 642 (M+H)⁺; ¹H NMR (400 MHz, CDCl₃) δ 7.77 (d, J=8.2 Hz, 1H), 7.70-7.59 (m, 1H), 7.54 (d, J=7.4 Hz, 1H), 7.46 (dt, J=10.1, 7.8 Hz, 1H), 7.35 (t, J=7.8 Hz, 1H), 7.27-7.19 (m, 1H), 6.61 (m, 1H), 6.41 (d, J=16.7 Hz, 1H), 5.85 (d, J=10.4 Hz, 1H), 5.11 (brs, 0.5H), 4.78-4.35 (m, 7.5H), 4.30-3.81 (m, 4H), 3.81-3.36 (m, 3H), 3.18 (m, 7H), 2.74 (m, 3H), 2.24 (s, 2H), 0.40 (s, 2H), 0.27 (s, 2H).

Example 33 Preparation of 2-(4-(7-(8-chloro-7-fluoronaphthalen-1-yl)-2-(2-(methyl(1-methylcyclobutyl)amino)ethoxy)-5, 6, 7, 8-tetrahydropyrido[3,4-d]pyrimidin-4-yl)-1-(2-fluoroacroloyl)piperazin-2-yl) acetonitrile

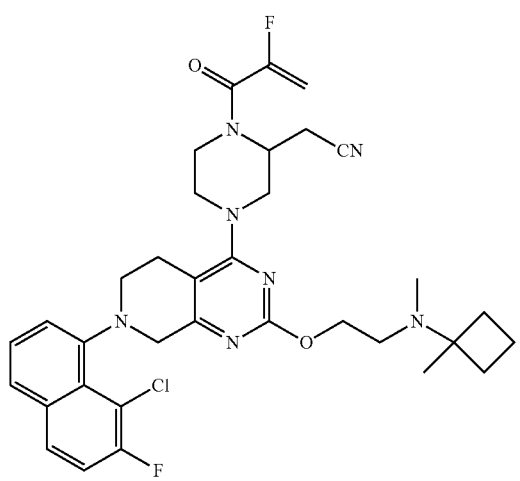 [SMILES: C=C(F)C(=O)N1CCN(c2nc(OCCN(C)C3(C)CCC3)nc3c2CCN(c2cccc4ccc(F)c(Cl)c24)C3)CC1CC#N]

LC-MS: m/z 650 (M+H)⁺; ¹H NMR (400 MHz, CDCl₃) δ 7.61 (m, 1H), 7.48 (t, J=7.2 Hz, 1H), 7.30 (m, 1H), 7.24-7.16 (m, 1H), 7.12 (d, J=7.5 Hz, 1H), 5.29 (d, J=47.3 Hz, 1H), 5.11 (dt, J=21.5, 10.7 Hz, 1H), 4.68 (brs, 0.5H), 4.24 (m, 3.5H), 4.11-3.61 (m, 4H), 3.52-3.21 (m, 2H), 3.19-2.83 (m, 4H), 2.82-2.35 (m, 5H), 2.20-1.91 (m, 5H), 1.57 (m, 4H), 1.03 (s, 3H).

Example 34 Preparation of 1-((2S,5R)-4-(7-(8-chloronaphthalen-1-yl)-2-((1-((dimethylamino)methyl)cyclopropyl)methoxyl)-5, 6, 7, 8-tetrahydropyrido[3,4-d]pyrimidin-4-yl)-2,5-dimethylpiperazin-1-yl) prop-2-ene-1-one

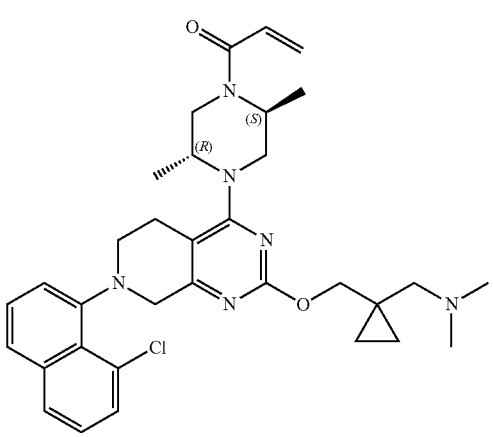

LC-MS: m/z 589 (M+H)⁺; ¹H NMR (400 MHz, DMSO) δ 9.46 (brs, 1H), 7.94 (d, J=8.2 Hz, 1H), 7.69 (m, 1H), 7.56 (m, 2H), 7.47 (t, J=7.8 Hz, 1H), 7.40-7.26 (m, 1H), 6.80 (m, 1H), 6.17 (m, 1H), 5.74 (m, 1H), 5.44-3.88 (m, 7H), 3.88-3.28 (m, 4H), 3.28-3.00 (m, 4H), 2.93-2.71 (m, 7H), 1.36-0.99 (m, 6H), 0.81 (m, 4H).

Example 35 Preparation of (S)-2-(4-(2-((1-((dimethylamino)methyl)cyclopropyl) methoxy-7-(5-methyl-1H-indazol-4-yl)-5, 6, 7, 8-tetrahydropyrido[3,4-d]pyrimidin-4-yl)-1-(2-fluoroacroloyl)piperazin-2-yl) acetonitrile

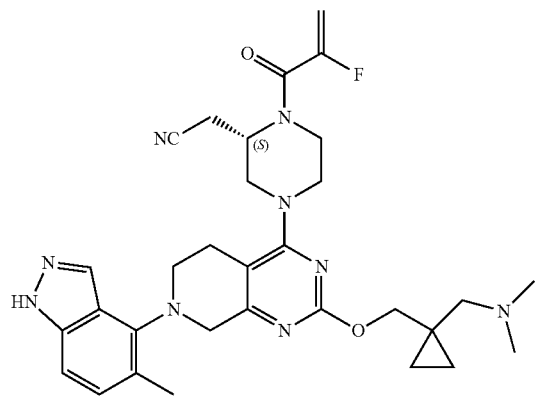

LC-MS: m/z 588 (M+H)⁺; ¹H NMR (400 MHz, CDCl₃) δ 10.50 (brs, 1H), 8.09 (s, 1H), 7.45-7.08 (m, 2H), 5.42 (d, J=47.6 Hz, 1H), 5.32-5.18 (m, 1H), 4.92 (brs, 1H), 4.30 (m, 4H), 4.20 (m, 1H), 3.99 (m, 1H), 3.53 (t, J=5.1 Hz, 2H), 3.33 (d, J=12.3 Hz, 1H), 3.21-2.94 (m, 2H), 2.81 (m, 4H), 2.71-2.30 (m, 11H), 0.77 (s, 2H), 0.59 (s, 2H).

Example 36 Preparation of (S)-2-(4-(2-((1-((bis(methyl-d3)amino)methyl)cyclopropyl)methoxy-7-(5-methyl-1H-indazol-4-yl)-5, 6, 7, 8-tetrahydropyrido[3,4-d]pyrimidin-4-yl)-1-(2-fluoroacroloyl)piperazin-2-yl) acetonitrile

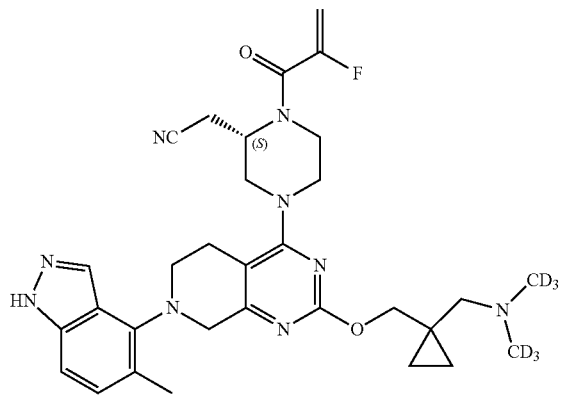

LC-MS: m/z 594 (M+H)+; 1H NMR (400 MHz, CDCl3) δ 10.35 (brs, 1H), 8.00 (d, J=13.6 Hz, 1H), 7.31-6.99 (m, 2H), 5.33 (d, J=46.7 Hz, 1H), 5.17 (dd, J=16.9, 3.5 Hz, 1H), 4.79 (brs, 1H), 4.33-3.82 (m, 8H), 3.42 (m, 2H), 3.25 (m, 1H), 2.98 (m, 2H), 2.85-2.45 (m, 5H), 2.33 (s, 3H), 0.72 (s, 2H), 0.54 (s, 2H).

Example 37 Preparation of 1-((1R,5S)-3-(7-(8-chloronaphthalen-1-yl)-2-((1-((dimethylamino)methyl)cyclopropyl)methoxyl)-5, 6, 7, 8-tetrahydropyrido[3,4-d]pyrimidin-4-yl)-3,8-diazabicyclo[3.2.1]octane-8-yl)prop-2-ene-1-one

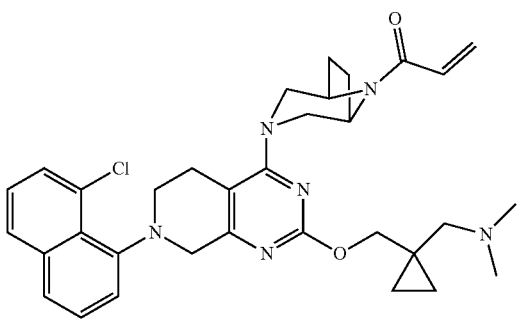 [SMILES: C=CC(=O)N1C2CCC1CN(c1nc(OCC3(CN(C)C)CC3)nc3c1CCN(c1cccc4cccc(Cl)c14)C3)C2]

LC-MS: m/z 587 (M+H)+; 1H NMR (400 MHz, DMSO) δ 7.92 (d, J=7.4 Hz, 1H), 7.74 (d, J=7.9 Hz, 1H), 7.58 (d, J=6.5 Hz, 1H), 7.53 (t, J=7.8 Hz, 1H), 7.45 (t, J=7.8 Hz, 1H), 7.33 (d, J=7.5 Hz, 1H), 6.83-6.69 (m, 1H), 6.21 (d, J=16.6 Hz, 1H), 5.73 (d, J=9.5 Hz, 1H), 4.65 (m, 2H), 4.11 (m, 4H), 3.80-3.61 (m, 2H), 3.48 (d, J=10.6 Hz, 1H), 3.28-2.78 (m, 3H), 1.97 (m, 6H), 1.26 (m, 8H), 0.58 (s, 2H), 0.39 (s, 2H).

Example 38 Preparation of 1-(5-(7-(8-chloronaphthalen-1-yl)-2-((1-((dimethylamino)methyl)cyclopropyl)methoxyl)-5, 6, 7, 8-tetrahydropyrido[3,4-d]pyrimidin-4-yl) hexahydropyrrolo[3,4-c]pyrrole-2(1H)-yl)prop-2-ene-1-one

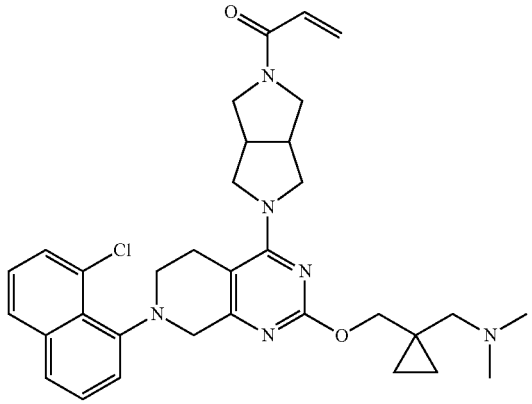 [SMILES: C=CC(=O)N1CC2CN(c3nc(OCC4(CN(C)C)CC4)nc4c3CCN(c3cccc5cccc(Cl)c35)C4)CC2C1]

LC-MS: m/z 587 (M+H)+; 1H NMR (400 MHz, DMSO) δ 7.91 (d, J=7.8 Hz, 1H), 7.72 (d, J=8.1 Hz, 1H), 7.61-7.49 (m, 2H), 7.44 (t, J=7.8 Hz, 1H), 7.31 (d, J=7.5 Hz, 1H), 6.56 (ddd, J=16.8, 10.3, 6.4 Hz, 1H), 6.13 (d, J=16.7 Hz, 1H), 5.66 (dd, J=12.5, 2.3 Hz, 1H), 4.14-3.41 (m, 11H), 3.24 (m, 2H), 3.09-2.75 (m, 5H), 2.12 (m, 8H), 0.55 (s, 2H), 0.35 (s, 2H).

Example 39 Preparation of 1-(7-(7-(8-chloronaphthalen-1-yl)-2-((1-((dimethylamino)methyl)cyclopropyl)methoxyl)-5, 6, 7, 8-tetrahydropyrido[3,4-d]pyrimidin-4-yl)-4,7-diazaspiro[2.5]octane-4-yl)prop-2-ene-1-one

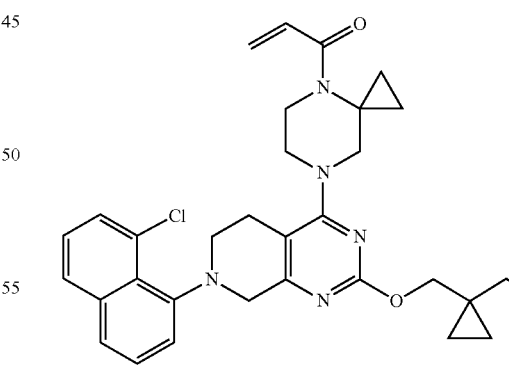

LC-MS: m/z 587 (M+H)+; 1H NMR (400 MHz, DMSO) δ 7.92 (d, J=7.4 Hz, 1H), 7.74 (d, J=7.9 Hz, 1H), 7.61-7.49 (m, 2H), 7.45 (t, J=7.8 Hz, 1H), 7.32 (d, J=7.0 Hz, 1H), 6.88 (m, 1H), 6.14 (dd, J=16.8, 2.2 Hz, 1H), 5.73 (d, J=10.4 Hz, 1H), 4.16 (d, J=17.4 Hz, 1H), 4.05 (s, 2H), 3.70 (m, 3H), 3.49 (m, 2H), 3.21-2.96 (m, 2H), 2.16 (m, 7H), 2.00 (m, 1H), 1.23 (m, 4H), 0.96 (m, 4H), 0.56 (t, J=4.7 Hz, 2H), 0.36 (t, J=4.9 Hz, 2H).

Example 40 Preparation of 1-(6-(7-(8-chloronaph-thalen-1-yl)-2-((1-(((dimethylamino)methyl)cyclopropyl)methoxyl)-5, 6, 7, 8-tetrahydropyrido[3,4-d]pyrimidin-4-yl)-2,6-diazaspiro[3.3]heptane-2-yl)prop-2-ene-1-one

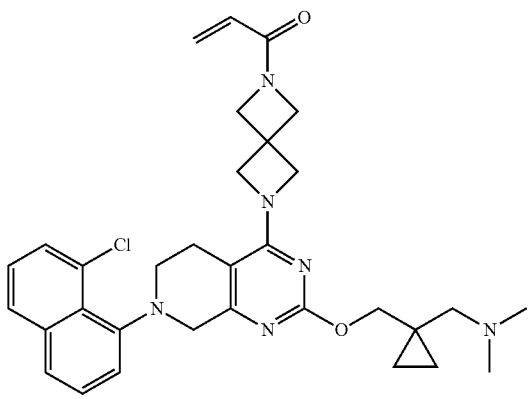 [SMILES: C=CC(=O)N1CC2(C1)CN(c1nc(OCC3(CN(C)C)CC3)nc3c1CCN(c1cccc4cccc(Cl)c14)C3)C2]

LC-MS: m/z 573 (M+H)+; 1H NMR (400 MHz, DMSO) δ 7.91 (d, J=7.4 Hz, 1H), 7.72 (d, J=7.9 Hz, 1H), 7.60-7.48 (m, 2H), 7.44 (t, J=7.8 Hz, 1H), 7.31 (d, J=7.2 Hz, 1H), 6.29 (dd, J=17.0, 10.3 Hz, 1H), 6.10 (dd, J=17.0, 2.2 Hz, 1H), 5.67 (dd, J=10.3, 2.2 Hz, 1H), 4.50-4.26 (m, 6H), 4.16-3.91 (m, 5H), 3.68 (d, J=16.8 Hz, 1H), 3.47 (d, J=10.6 Hz, 1H), 3.17-2.88 (m, 2H), 2.58 (d, J=14.9 Hz, 1H), 2.55-2.45 (m, 1H), 2.25-2.07 (m, 7H), 0.62-0.47 (m, 2H), 0.35 (t, J=4.9 Hz, 2H).

Example 41 Preparation of 1-(-4-(7-(8-chloronaph-thalen-1-yl)-2-((1-(((dimethylamino)methyl)cyclopropyl)methoxyl)-5, 6, 7, 8-tetrahydropyrido[3,4-d]pyrimidin-4-yl)-2-(trifluoromethyl)piperazin-1-yl)prop-2-ene-1-one

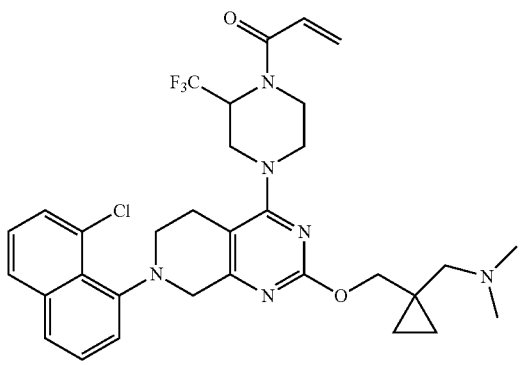 [SMILES: C=CC(=O)N1CCN(c2nc(OCC3(CN(C)C)CC3)nc3c2CCN(c2cccc4cccc(Cl)c24)C3)CC1C(F)(F)F]

LC-MS: m/z 629 (M+H)+; 1H NMR (400 MHz, DMSO) δ 7.92 (d, J=8.0 Hz, 1H), 7.74 (t, J=9.7 Hz, 1H), 7.61-7.23 (m, 4H), 6.88 (dd, J=16.8, 10.4 Hz, 1H), 6.25 (d, J=16.6 Hz, 1H), 5.90-5.77 (m, 1H), 5.49-5.15 (m, 1H), 4.57-3.39 (m, 9H), 2.94 (m, 5H), 2.24-2.06 (m, 8H), 0.57 (s, 2H), 0.37 (d, J=4.6 Hz, 2H).

Example 42 Preparation of 1-(5-(7-(8-chloronaph-thalen-1-yl)-2-((1-(((dimethylamino)methyl)cyclopropyl)methoxyl)-5, 6, 7, 8-tetrahydropyrido[3,4-d]pyrimidin-4-yl)-2,5-diazabicyclo[2.2.1]heptane-2-yl)prop-2-ene-1-one

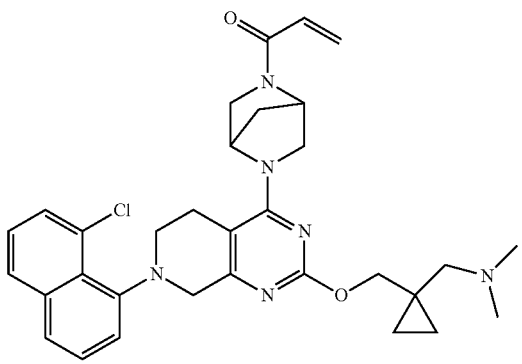 [SMILES: C=CC(=O)N1CC2CC1CN2c1nc(OCC2(CN(C)C)CC2)nc2c1CCN(c1cccc3cccc(Cl)c13)C2]

LC-MS: m/z 573 (M+H)+; 1H NMR (400 MHz, DMSO) δ 7.90 (dd, J=7.7, 4.1 Hz, 1H), 7.71 (dd, J=13.9, 8.1 Hz, 1H), 7.59-7.21 (m, 4H), 6.74 (dt, J=18.3, 9.2 Hz, 1H), 6.44 (m, 1H), 6.15 (dd, J=18.6, 1.9 Hz, 1H), 5.67 (dd, J=10.2, 2.3 Hz, 1H), 5.18-4.78 (m, 2H), 4.16-3.38 (m, 8H), 3.25-2.55 (m, 3H), 2.19 (m, 8H), 2.07-1.76 (m, 2H), 0.56 (s, 2H), 0.36 (s, 2H).

Example 43 Preparation of 1-(5-(7-(8-chloronaph-thalen-1-yl)-2-((1-(((dimethylamino)methyl)cyclopropyl)methoxyl)-5, 6, 7, 8-tetrahydropyrido[3,4-d]pyrimidin-4-yl)-2,5-diazabicyclo[2.2.2]octane-2-yl)prop-2-ene-1-one

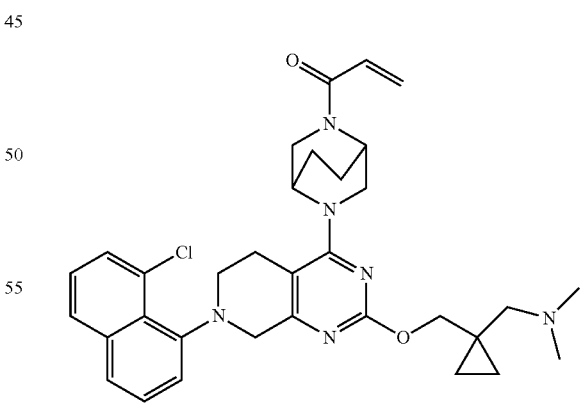

LC-MS: m/z 587 (M+H)+; 1H NMR (400 MHz, DMSO) δ 7.91 (d, J=8.1 Hz, 1H), 7.73 (d, J=8.0 Hz, 1H), 7.61-7.49 (m, 2H), 7.44 (td, J=7.8, 2.3 Hz, 1H), 7.32 (t, J=8.3 Hz, 1H), 6.85-6.53 (m, 1H), 6.27-6.06 (m, 1H), 5.71 (m, 1H), 4.60 (m, 2H), 4.20-3.38 (m, 8H), 2.97 (m, 5H), 2.01 (m, 8H), 0.54 (m, 4H).

Example 44 Preparation of 1-(6-(7-(8-chloronaphthalen-1-yl)-2-((1-(((dimethylamino)methyl)cyclopropyl)methoxyl)-5, 6, 7, 8-tetrahydropyrido[3,4-d]pyrimidin-4-yl)-2,6-diazaspiro[3.4]octane-2-yl)prop-2-ene-1-one

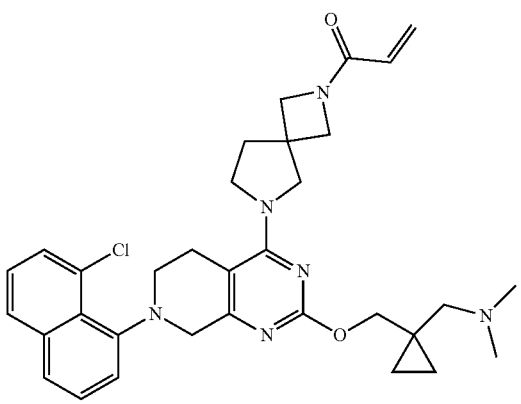 [SMILES: C=CC(=O)N1CC2(CCN(c3nc(OCC4(CN(C)C)CC4)nc4c3CCN(c3cccc5cccc(Cl)c35)C4)C2)C1]

LC-MS: m/z 587 (M+H)+; 1H NMR (400 MHz, DMSO) δ 7.91 (d, J=8.0 Hz, 1H), 7.72 (d, J=8.1 Hz, 1H), 7.60-7.38 (m, 3H), 7.32 (d, J=7.4 Hz, 1H), 6.31 (m, 1H), 6.11 (dd, J=17.0, 2.0 Hz, 1H), 5.67 (d, J=10.3 Hz, 1H), 4.36-3.80 (m, 9H), 3.80-3.59 (m, 3H), 3.46 (s, 1H), 3.24 (m, 1H), 3.04 (dm, 1H), 2.82 (m, 1H), 2.36-1.91 (m, 10H), 0.47 (m, 4H).

Example 45 Preparation of (S)-2-(4-(2-((1-(((bis(methyl-d3)amino)methyl)cyclo propyl)methoxy-7-(8-chloronaphthalen-1-yl)-5, 6, 7, 8-tetrahydro-pyrido[3,4-d]pyrimidin-4-yl)-1-(2-fluoroacroloyl)piperazin-2-yl) acetonitrile

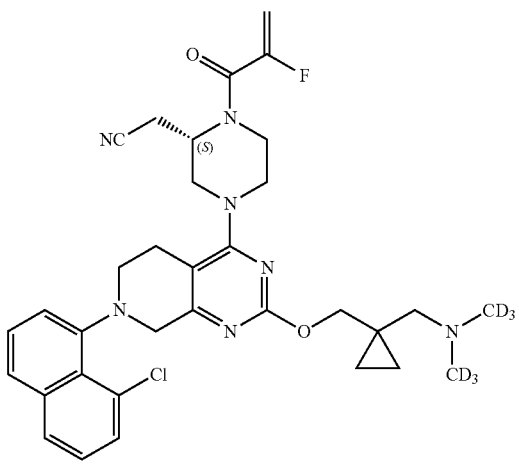

LC-MS: m/z 624 (M+H)+; 1H NMR (400 MHz, CDCl3) δ 7.68 (d, J=8.1 Hz, 1H), 7.54 (t, J=6.9 Hz, 1H), 7.44 (d, J=7.4 Hz, 1H), 7.37 (dt, J=11.2, 7.8 Hz, 1H), 7.26 (t, J=7.8 Hz, 1H), 7.14 (dd, J=19.3, 7.4 Hz, 1H), 5.33 (d, J=48.0 Hz, 1H), 5.15 (dt, J=24.2, 12.1 Hz, 1H), 4.84 (brs, 1H), 4.48-3.69 (m, 6H), 3.59-3.24 (m, 2H), 3.23-2.68 (m, 5H), 2.62-2.33 (m, 3H), 1.23 (m, 2H), 0.65 (s, 2H), 0.47 (s, 2H).

Example 46 Preparation of (S)-2-(4-(7-(8-chloronaphthalen-1-yl)-2-((3-((methoxymethyl)-1-methylazacyclobutylamine-3-yl)methoxy)-5, 6, 7, 8-tetrahydropyrido[3, 4-d]pyrimidin-4-yl)-1-(2-fluoroacroloyl)piperazin-2-yl) acetonitrile

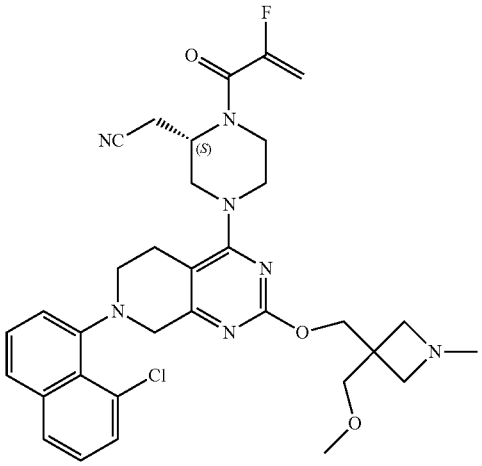

LC-MS: m/z 634 (M+H)+; 1H NMR (400 MHz, CDCl3) δ 7.68 (d, J=8.1 Hz, 1H), 7.55 (dd, J=7.8, 4.7 Hz, 1H), 7.45 (d, J=7.4 Hz, 1H), 7.37 (dd, J=17.0, 7.9 Hz, 1H), 7.26 (t, J=7.8 Hz, 1H), 7.15 (dd, J=16.1, 7.5 Hz, 1H), 5.34 (d, J=47.8 Hz, 1H), 5.18 (dd, J=16.8, 3.3 Hz, 1H), 4.80 (brs, 1H), 4.57-3.45 (m, 16H), 3.00 (m, 8H), 2.47 (m, 2H), 1.28-1.14 (m, 2H).

Example 47 Preparation of 2-((2S)-4-(7-(8-chloronaphthalen-1-yl)-2-((1-(1-(dim ethylamino)ethyl)cyclopropyl)methoxy)-5, 6, 7, 8-tetrahydropyrido[3, 4-d]pyrimidin-4-yl)-1-(2-fluoroacroloyl)piperazin-2-yl) acetonitrile

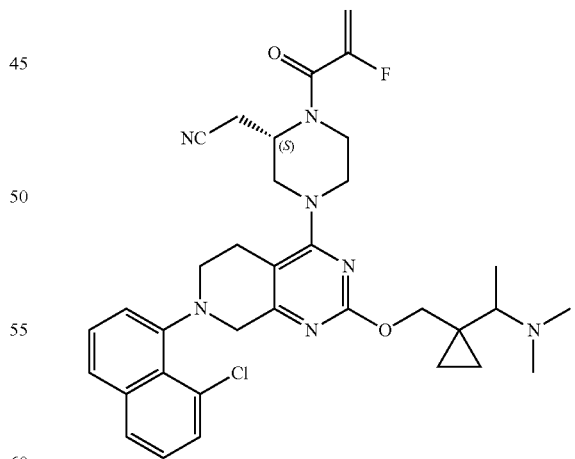

LC-MS: m/z 632 (M+H)+; 1H NMR (400 MHz, DMSO) δ 7.93 (d, J=8.1 Hz, 1H), 7.75 (dd, J=8.1, 3.0 Hz, 1H), 7.56 (m, 2H), 7.46 (t, J=7.8 Hz, 1H), 7.35 (dd, J=14.8, 7.4 Hz, 1H), 5.40 (m, 2H), 5.22 (brs, 1H), 4.97-4.45 (m, 2H), 4.33-3.40 (m, 7H), 3.01 (m, 8H), 2.20 (s, 6H), 1.28-0.92 (m, 3H), 0.70-0.34 (m, 4H).

Example 47 Two Isomer Examples 47A and 47B were Obtained by Chiral Resolution

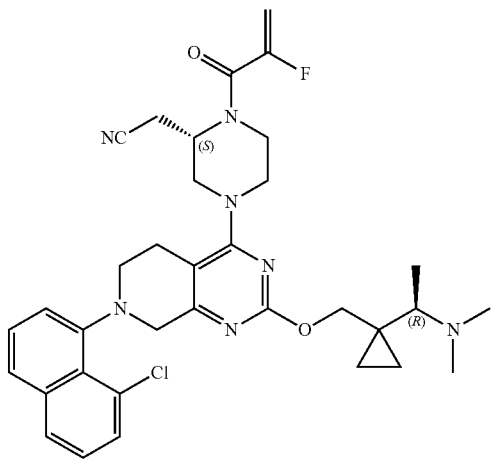

Example 48 Preparation of (S)-2-(4-(2-((1-(azacyclobutylamine-1-ylmethyl)cyclopropyl)methoxy-7-(8-chloronaphthalen-1-yl)-5, 6, 7, 8-tetrahydropyrido[3,4-d]pyrimidin-4-yl)-1-(2-fluoroacroloyl) piperazin-2-yl) acetonitrile

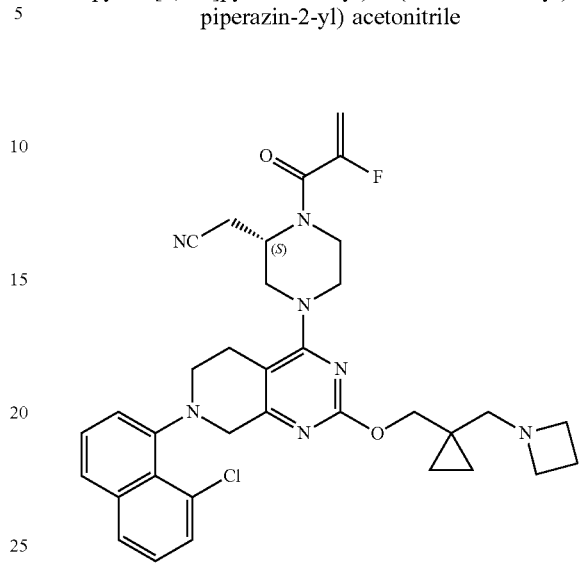

LC-MS: m/z 630 (M+H)$^+$; $^1$H NMR (400 MHz, CDCl$_3$) δ 7.68 (d, J=8.2 Hz, 1H), 7.54 (t, J=7.1 Hz, 1H), 7.44 (d, J=7.4 Hz, 1H), 7.37 (dt, J=11.9, 7.8 Hz, 1H), 7.26 (t, J=7.8 Hz, 1H), 7.15 (dd, J=20.9, 7.3 Hz, 1H), 5.34 (d, J=48.3 Hz, 1H), 5.16 (dt, J=23.4, 11.7 Hz, 1H), 4.81 (brs, 0.5H), 4.43-1.99 (m, 21.5H), 1.22 (m, 3H), 0.52 (m, 4H).

Example 49 (S)-2-(1-(but-2-ynoyl)-4-(7-(8-chloronaphthalen-1-yl)-2-((1-((dimethylamino)methyl) cyclopropyl)methoxyl)-5, 6, 7, 8-tetrahydropyrido[3,4-d]pyrimidin-4-yl) piperazin-2-yl) acetonitrile

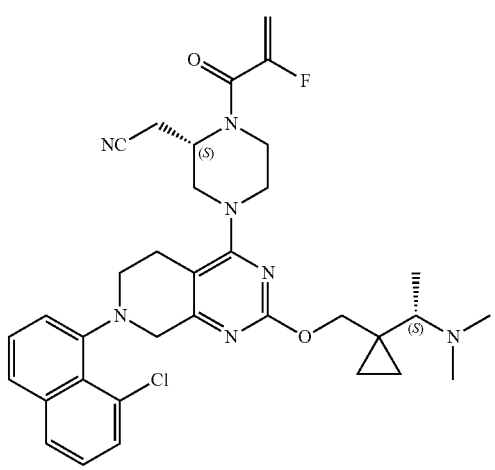

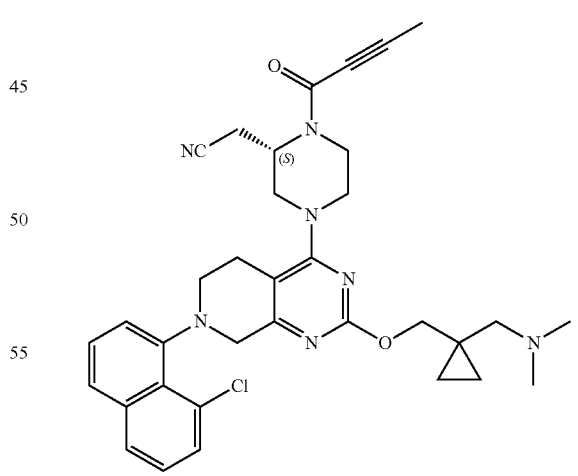

Example 47A: LC-MS: m/z 632 (M+H)$^+$; $^1$H NMR (400 MHz, DMSO) δ 7.92 (d, J=8.1 Hz, 1H), 7.74 (dd, J=7.9, 3.3 Hz, 1H), 7.62-7.49 (m, 2H), 7.45 (t, J=7.8 Hz, 1H), 7.34 (dd, J=14.8, 7.5 Hz, 1H), 5.51-5.11 (m, 2H), 4.86 (br s, 1H), 3.91 (m, 9H), 3.25-2.65 (m, 8H), 2.21 (s, 6H), 1.22 (m, 3H), 0.69-0.31 (m, 4H).

Example 47B: LC-MS: m/z 632 (M+H)$^+$; $^1$H NMR (400 MHz, DMSO) δ 7.92 (d, J=8.1 Hz, 1H), 7.74 (dd, J=8.0, 3.3 Hz, 1H), 7.55 (dt, J=22.4, 7.5 Hz, 2H), 7.45 (t, J=7.8 Hz, 1H), 7.34 (dd, J=14.9, 7.3 Hz, 1H), 5.34 (m, 2H), 4.86 (brs, 1H), 4.29-3.43 (m, 9H), 3.26-2.63 (m, 8H), 2.28 (s, 6H), 1.29-1.20 (m, 3H), 0.72-0.30 (m, 4H).

LC-MS: m/z 612 (M+H)$^+$; $^1$H NMR (400 MHz, DMSO) δ 7.93 (d, J=8.1 Hz, 1H), 7.75 (dd, J=7.9, 3.2 Hz, 1H), 7.62-7.50 (m, 2H), 7.46 (t, J=7.8 Hz, 1H), 7.34 (dd, J=14.5, 7.3 Hz, 1H), 4.89 (s, 1H), 4.38-3.43 (m, 9H), 3.26-2.64 (m, 8H), 2.23 (m, 7H), 2.13-1.96 (m, 3H), 0.59 (s, 2H), 0.40 (s, 2H).

Example 50 Preparation of (S)-1-(-4-(7-(8-chloronaphthalen-1-yl)-2-((1-((dimethylamino)methyl)cyclopropyl)methoxyl)-5, 6, 7, 8-tetrahydropyrido[3,4-d]pyrimidin-4-yl)-3-methylpiperazin-1-yl)prop-2-ene-1-one

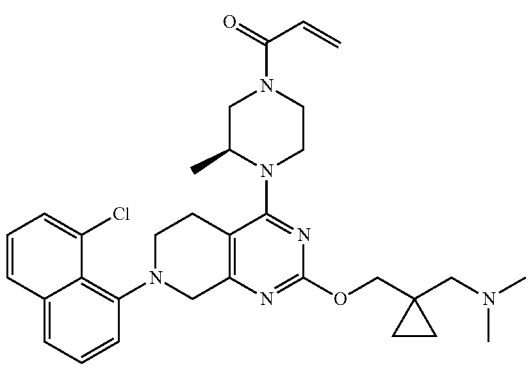 [SMILES: C=CC(=O)N1CCN(c2nc(OCC3(CN(C)C)CC3)nc3c2CCN(c2cccc4cccc(Cl)c24)C3)[C@@H](C)C1]

LC-MS: m/z 575 (M+H)⁺; ¹H NMR (400 MHz, DMSO) δ 7.92 (d, J=8.1 Hz, 1H), 7.74 (d, J=8.2 Hz, 1H), 7.62-7.51 (m, 2H), 7.45 (t, J=7.8 Hz, 1H), 7.33 (t, J=6.5 Hz, 1H), 6.95-6.74 (m, 1H), 6.17 (dd, J=16.5, 6.7 Hz, 1H), 5.73 (d, J=11.4 Hz, 1H), 4.49-3.41 (m, 10H), 3.28-2.80 (m, 4H), 2.17 (m, 8H), 1.34-1.15 (m, 2H), 1.13-0.93 (m, 2H), 0.57 (s, 2H), 0.39 (s, 2H).

Example 51 Preparation of (S)-2-(4-(7-(8-chloronaphthalen-1-yl)-2-((1-((dimethylaminomethyl)methyl-d2)cyclopropyl)methoxy-d2)-5, 6, 7, 8-tetrahydropyrido[3,4-d]pyrimidin-4-yl)-1-(2-fluoroacryloyl)piperazin-2-yl) acetonitrile

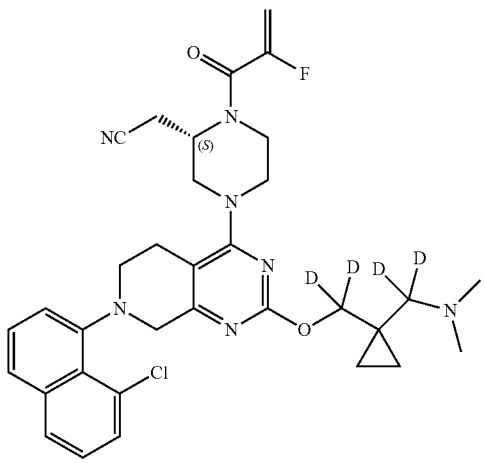

LC-MS: m/z 622 (M+H)⁺; ¹H NMR (400 MHz, DMSO) δ 7.91 (t, J=8.5 Hz, 1H), 7.74 (dd, J=7.8, 3.3 Hz, 1H), 7.62-7.40 (m, 3H), 7.33 (dd, J=15.0, 7.1 Hz, 1H), 5.46-5.16 (m, 2H), 4.86 (brs, 1H), 4.29-3.44 (m, 8H), 3.26-2.58 (m, 6H), 2.17 (s, 6H), 0.57 (s, 2H), 0.38 (s, 2H).

Example 52 Preparation of (S)-2-(4-(7-(8-chloronaphthalen-1-yl)-2-((1-(2-(dimethylamino)ethyl)cyclopropyl)methoxy)-5, 6, 7, 8-tetrahydropyrido[3, 4-d]pyrimidin-4-yl)-1-(2-fluoroacroloyl)piperazin-2-yl) acetonitrile

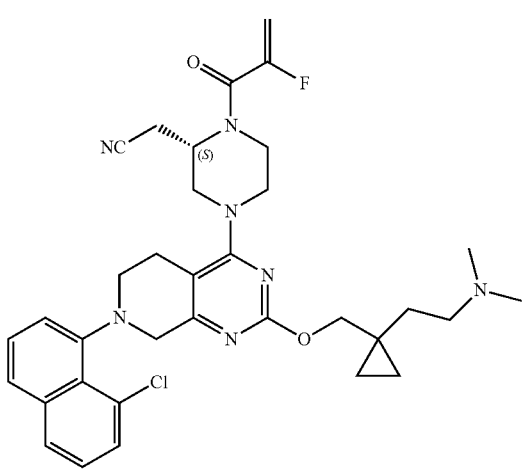

LC-MS: m/z 632 (M+H)⁺; ¹H NMR (400 MHz, DMSO) δ 7.92 (d, J=8.0 Hz, 1H), 7.74 (dd, J=7.9, 3.4 Hz, 1H), 7.54 (dt, J=21.4, 6.9 Hz, 2H), 7.45 (t, J=7.8 Hz, 1H), 7.34 (dd, J=14.5, 7.2 Hz, 1H), 5.49-5.12 (m, 2H), 4.84 (brs, 1H), 4.32-3.46 (m, 8H), 3.29-2.62 (m, 8H), 2.37 (m, 2H), 2.14 (s, 6H), 1.62-1.44 (m, 2H), 0.48 (s, 2H), 0.42 (s, 2H).

Example 53 Preparation of 2-((2S)-4-(7-(8-chloronaphthalen-1-yl)-2-(1-(1-((dimethylamino)ethyl)cyclopropyl)methoxy)-5, 6, 7, 8-tetrahydropyrido[3, 4-d]pyrimidin-4-yl)-1-(2-fluoroacroloyl)piperazin-2-yl) acetonitrile

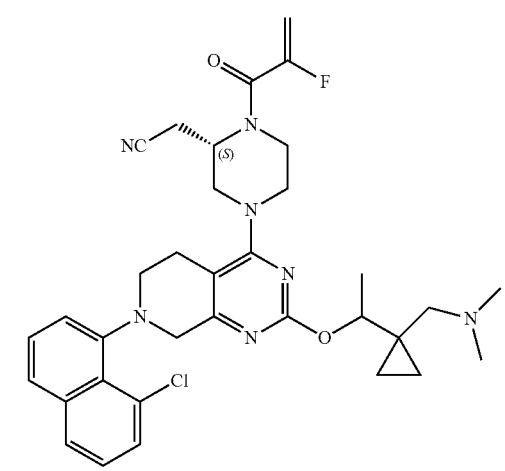

LC-MS: m/z 632 (M+H)⁺.

551

Example 53 Two Isomer Examples 53A and 53B were Obtained by Chiral Resolution

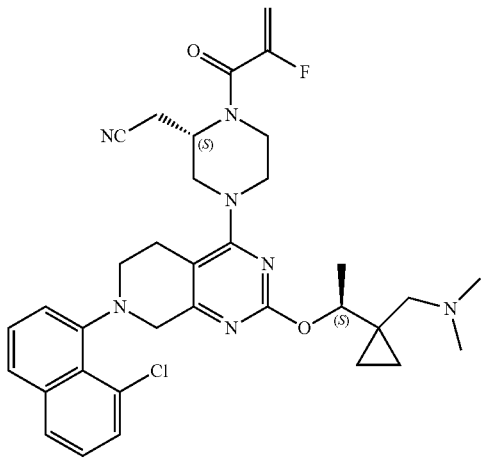

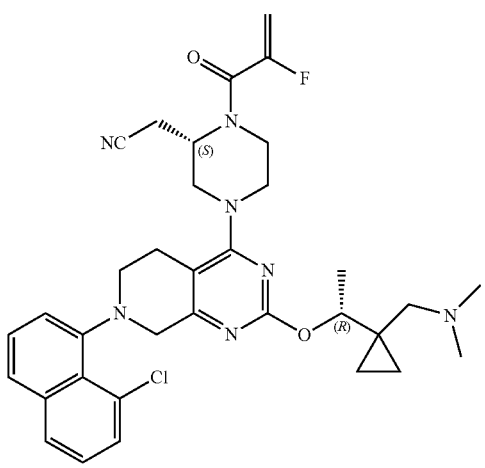

Example 53A LC-MS: m/z 632 (M+H); H NMR (400 MHz, DMSO) δ 7.93 (d, J=7.3 Hz, 1H), 7.75 (d, J=8.2 Hz, 1H), 7.48 (m, 4H), 5.45-5.18 (m, 3H), 4.87 (brs, 1H), 3.90 (m, 8H), 3.04 (m, 9H), 2.33-1.80 (m, 8H), 0.59 (d, J=6.1 Hz, 2H), 0.28 (m, 2H).

Example 53B LC-MS: m/z 632 (M+H)⁺; ¹H NMR (400 MHz, DMSO) 7.93 (d, J=8.2 Hz, 1H), 7.75 (dd, J=7.8, 5.0 Hz, 1H), 7.62-7.31 (m, 4H), 5.52-5.13 (m, 3H), 4.87 (brs, 1H), 4.31-3.44 (m, 8H), 3.27-2.60 (m, 9H), 2.40-1.91 (m, 8H), 0.63 (m, 2H), 0.33 (m, 2H).

552

Example 54 Preparation of (S)-2-(4-(7-(8-chloronaphthalen-1-yl)-2-((1-((ethyl (methyl)amino)methyl)cyclopropyl)methoxy)-5, 6, 7, 8-tetrahydropyrido[3,4-d]pyrimidin-4-yl)-1-(2-fluoroacroloyl)piperazin-2-yl) acetonitrile

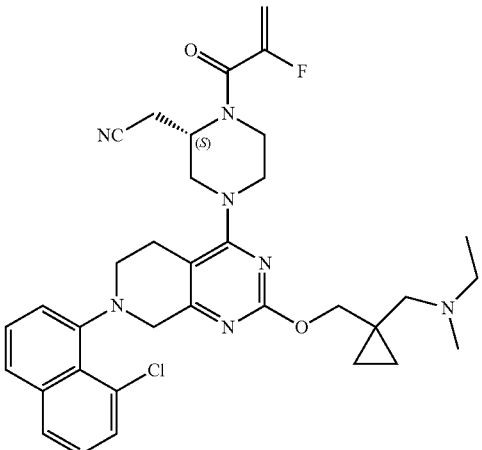

LC-MS: m/z 632 (M+H)⁺. ¹H NMR (400 MHz, DMSO) δ 7.92 (d, J=8.1 Hz, 1H), 7.74 (dd, J=7.8, 3.2 Hz, 1H), 7.55 (dt, J=22.3, 7.5 Hz, 2H), 7.45 (t, J=7.8 Hz, 1H), 7.34 (dd, J=14.6, 7.0 Hz, 1H), 5.39 (dd, J=18.0, 4.0 Hz, 1H), 5.35-5.13 (m, 1H), 4.86 (brs, 1H), 4.28-3.43 (m, 9H), 3.28-2.60 (m, 7H), 2.23 (m, 7H), 0.94 (m, 3H), 0.57 (s, 2H), 0.39 (s, 2H).

Example 55 Preparation of (S)-2-(4-(2-(2-bicyclo[1.1.1]pentane-1-yl(methyl)amino)ethoxy)-7-(8-chloronaphthalen-1-yl)-5, 6, 7, 8-tetrahydropyrido[3,4-d]pyrimidin-4-yl)-1-(2-fluoroacroloyl)piperazin-2-yl) acetonitrile

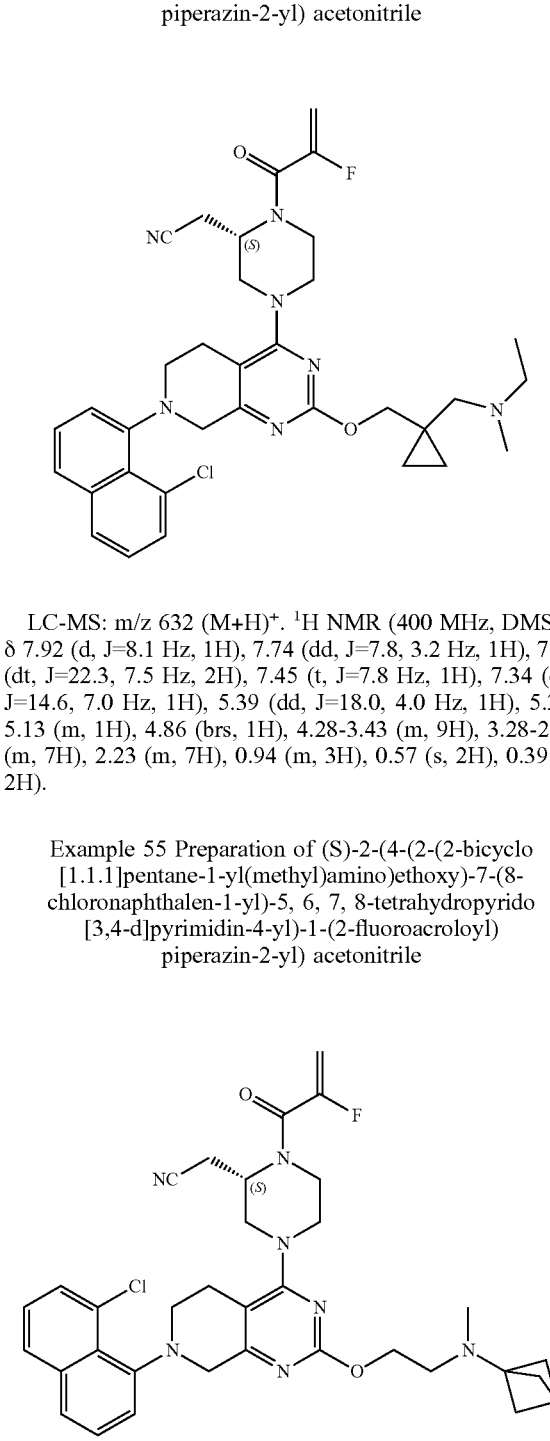

LC-MS: m/z 630 (M+H)⁺. ¹H NMR (400 MHz, DMSO) δ 7.92 (d, J=8.0 Hz, 1H), 7.74 (dd, J=7.9, 3.4 Hz, 1H), 7.55 (dt, J=15.1, 7.4 Hz, 2H), 7.45 (t, J=7.8 Hz, 1H), 7.34 (dd, J=15.0, 7.3 Hz, 1H), 5.39 (dd, J=18.0, 4.0 Hz, 1H), 5.28 (d, J=49.5 Hz, 1H), 4.86 (brs, 1H), 4.37-3.42 (m, 9H), 3.28-2.84 (m, 6H), 2.55-2.45 (m, 3H), 2.35 (s, 1H), 2.19 (s, 3H), 1.71 (s, 6H).

Example 56 Preparation of (S)-2-(4-(7-(8-chloronaphthalen-1-yl)-2-((1-(((isopropyl(methyl)amino)methyl)cyclopropyl)methoxy)-5, 6, 7, 8-tetrahydropyrido[3,4-d]pyrimidin-4-yl)-1-(2-fluoroacroloyl)piperazin-2-yl) acetonitrile

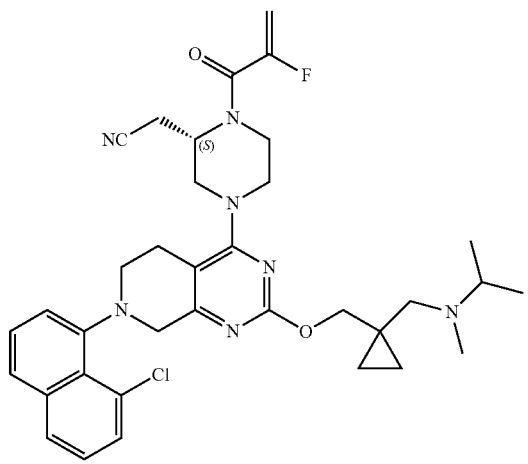

LC-MS: m/z 646 (M+H)$^+$. $^1$H NMR (400 MHz, DMSO) δ 7.92 (d, J=8.0 Hz, 1H), 7.74 (dd, J=7.9, 3.1 Hz, 1H), 7.55 (dt, J=14.5, 7.5 Hz, 2H), 7.45 (t, J=7.8 Hz, 1H), 7.34 (dd, J=14.1, 7.1 Hz, 1H), 5.38 (dt, J=10.1, 5.1 Hz, 1H), 5.27 (d, J=49.9 Hz, 1H), 4.86 (brs, 1H), 4.24-3.42 (m, 9H), 3.26-2.62 (m, 8H), 2.33 (s, 2H), 2.11 (m 3H), 0.89 (d, J=4.7 Hz, 6H), 0.54 (s, 2H), 0.37 (s, 2H).

Example 57 Preparation of (S)-2-(4-(7-(8-chloronaphthalen-1-yl)-2-((1-((methylsulfonyl)methyl)cyclopropyl)methoxy)-5, 6, 7, 8-tetrahydropyrido[3,4-d]pyrimidin-4-yl)-1-(2-fluoroacroloyl)piperazin-2-yl) acetonitrile

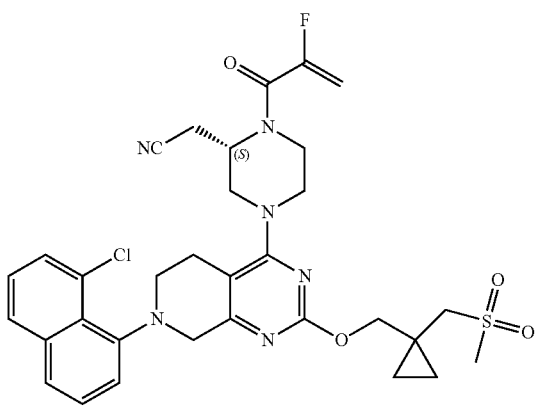

LC-MS: m/z 653 (M+H)$^+$. $^1$H NMR (400 MHz, DMSO) δ 7.92 (d, J=8.0 Hz, 1H), 7.74 (dd, J=7.9, 3.0 Hz, 1H), 7.62-7.50 (m, 2H), 7.44 (dd, J=17.1, 9.4 Hz, 1H), 7.34 (dd, J=14.3, 7.1 Hz, 1H), 5.39 (dd, J=18.0, 4.0 Hz, 1H), 5.34-5.16 (m, 1H), 4.85 (brs, 1H), 4.33-3.44 (m, 9H), 3.32-3.04 (m, 7H), 3.01 (d, J=10.2 Hz, 3H), 2.96-2.63 (m, 2H), 0.86-0.76 (m, 2H), 0.74 (s, 2H).

Example 58 Preparation of (S)-2-(4-(2-((1-(azetidin-1-ylmethyl)cyclopropyl)methoxy)-7-(8-chloro-7-fluoronaphthalen-1-yl)-5, 6, 7, 8-tetrahydropyrido[3,4-d]pyrimidin-4-yl)-1-(2-fluoroacroloyl)piperazin-2-yl) acetonitrile

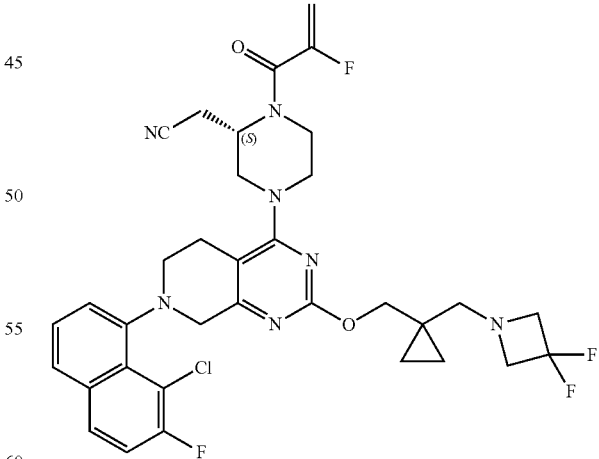

LC-MS: m/z 648 (M+H)$^+$. $^1$H NMR (400 MHz, DMSO) δ 8.02 (dd, J=9.0, 5.9 Hz, 1H), 7.79 (dd, J=7.9, 3.3 Hz, 1H), 7.65-7.49 (m, 2H), 7.42 (dd, J=16.5, 7.5 Hz, 1H), 5.39 (dd, J=18.0, 4.0 Hz, 1H), 5.34-5.16 (m, 1H), 4.87 (brs, 1H), 4.23-3.41 (m, 9H), 3.26-2.60 (m, 10H), 2.33 (s, 2H), 1.93 (p, J=6.4 Hz, 2H), 0.44 (s, 2H), 0.38 (s, 2H).

Example 59 Preparation of (S)-2-(4-(7-(8-chloro-7-fluoronaphthalen-1-yl)-2-((1-((3,3-difluoro-azetidin-1-ylmethyl)cyclopropyl)methoxy)-5, 6, 7, 8-tetrahydropyrido [3,4-d]pyrimidin-4-yl)-1-(2-fluoroacroloyl)piperazin-2-yl) acetonitrile LC-MS: m/z 684 (M+H)$^+$. $^1$H NMR (400 MHz, DMSO) δ 8.02 (dd, J=9.0, 5.9 Hz, 1H), 7.79 (dd, J=7.9, 3.3 Hz, 1H), 7.65-7.49 (m, 2H), 7.42 (dd, J=16.2, 7.6 Hz, 1H), 5.39 (dd, J=18.0, 4.0 Hz, 1H), 5.34-5.13 (m, 1H), 4.86 (brs, 1H), 4.35-3.40 (m, 14H), 3.28-2.60 (m, 7H), 1.16 (d, J=26.6 Hz, 1H), 0.47 (d, J=13.1 Hz, 4H).

Example 60 Preparation of (S)-2-(4-(7-(8-chloro-7-fluoronaphthalen-1-yl)-2-((1-((diethylamino)methyl)cyclopropyl)methoxy)-5, 6, 7, 8-tetrahydropyrido[3,4-d]pyrimidin-4-yl)-1-(2-fluoroacroloyl)piperazin-2-yl) acetonitrile

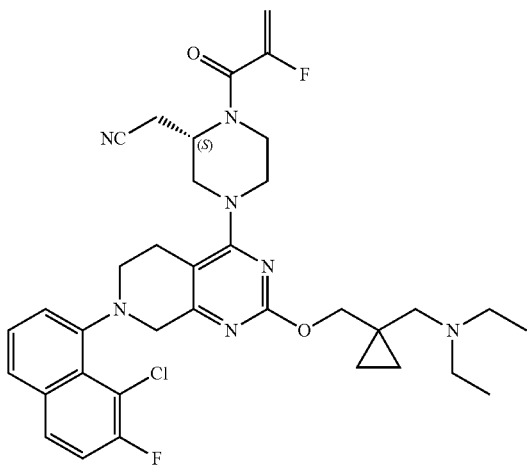

LC-MS: m/z 664 (M+H)+. 1H NMR (400 MHz, DMSO) δ 8.02 (dd, J=9.0, 5.9 Hz, 1H), 7.84-7.75 (m, 1H), 7.56 (dt, J=14.4, 8.2 Hz, 2H), 7.42 (dd, J=14.1, 7.6 Hz, 1H), 5.39 (dt, J=9.5, 4.8 Hz, 1H), 5.28 (d, J=50.1 Hz, 1H), 4.86 (brs, 1H), 4.35-3.69 (m, 11H), 3.30-2.64 (m, 10H), 1.21-1.06 (m, 1H), 1.05-0.79 (m, 6H), 0.57 (s, 2H), 0.43 (s, 2H).

Example 61 Preparation of (S)-2-(4-(7-(8-chloro-7-fluoronaphthalen-1-yl)-2-((1-((isopropyl(methyl)amino)methyl)cyclopropyl)methoxy)-5, 6, 7, 8-tetrahydropyrido [3,4-d]pyrimidin-4-yl)-1-(2-fluoroacroloyl)piperazin-2-yl) acetonitrile

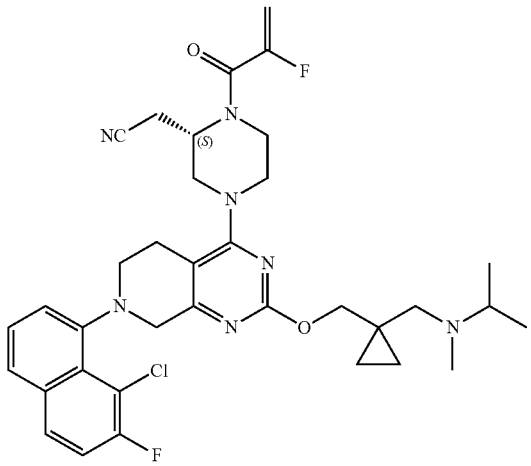

LC-MS: m/z 664 (M+H)+. 1H NMR (400 MHz, DMSO) δ 8.02 (dd, J=8.8, 5.9 Hz, 1H), 7.80 (d, J=7.9 Hz, 1H), 7.66-7.49 (m, 2H), 7.42 (dd, J=14.9, 7.5 Hz, 1H), 5.39 (dd, J=18.0, 3.8 Hz, 1H), 5.27 (d, J=50.3 Hz, 1H), 4.85 (brs, 1H), 4.26-3.46 (m, 9H), 3.27-2.61 (m, 8H), 2.13 (m, 5H), 0.90 (s, 6H), 0.55 (s, 2H), 0.39 (s, 2H).

Example 62 Preparation of (S)-2-(4-(7-(8-chloro-7-fluoronaphthalen-1-yl)-2-((1-((ethyl(methyl)amino)methyl)cyclopropyl)methoxy)-5, 6, 7, 8-tetrahydropyrido[3,4-d]pyrimidin-4-yl)-1-(2-fluoroacroloyl)piperazin-2-yl) acetonitrile

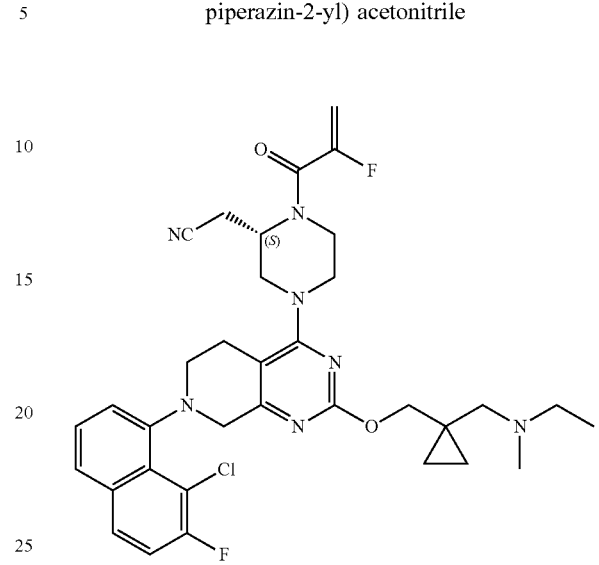

LC-MS: m/z 650 (M+H)+. 1H NMR (400 MHz, DMSO) δ 8.02 (dd, J=9.0, 5.9 Hz, 1H), 7.79 (dd, J=7.8, 3.0 Hz, 1H), 7.65-7.49 (m, 2H), 7.42 (dd, J=15.4, 7.5 Hz, 1H), 5.39 (dd, J=18.0, 4.0 Hz, 1H), 5.24 (d, J=21.3 Hz, 1H), 4.86 (brs, 1H), 4.29-3.68 (m, 8H), 3.56-3.39 (m, 1H), 3.28-2.62 (m, 7H), 2.45-2.24 (m, 4H), 2.12 (m, 3H), 1.00-0.85 (m, 3H), 0.54 (s, 2H), 0.40 (s, 2H).

Example 63 Preparation of (S)-2-(4-(2-((1-((bis(methyl-d3)amino)methyl)cyclopropyl)methoxy-7-(8-chloro-7-fluoronaphthalen-1-yl)-5, 6, 7, 8-tetrahydropyrido[3,4-d]pyrimidin-4-yl)-1-(2-fluoroacroloyl)piperazin-2-yl) acetonitrile

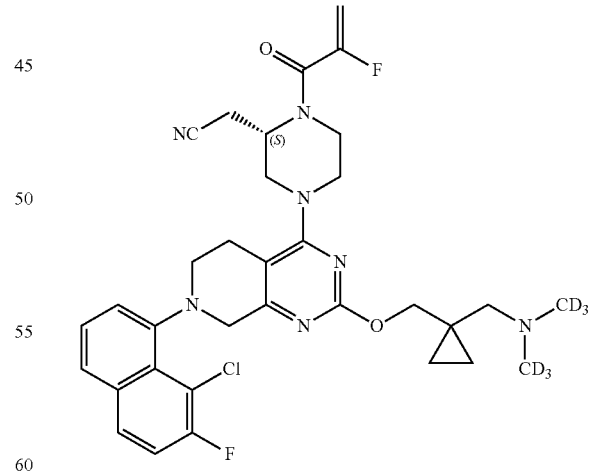

LC-MS: m/z 642 (M+H)+. 1H NMR (400 MHz, DMSO) δ 8.02 (dd, J=9.0, 5.9 Hz, 1H), 7.79 (dd, J=7.9, 3.2 Hz, 1H), 7.66-7.49 (m, 2H), 7.42 (dd, J=16.0, 7.5 Hz, 1H), 5.39 (dd, J=18.0, 4.0 Hz, 1H), 5.35-5.13 (m, 1H), 4.86 (brs, 1H), 4.30-3.65 (m, 7H), 3.47 (m, 2H), 3.27-2.59 (m, 7H), 2.24-2.13 (m, 2H), 0.54 (s, 2H), 0.37 (s, 2H).

Example 64 Preparation of (S)-2-(4-(7-(8-chloro-7-fluoronaphthalen-1-yl)-2-((1-((3-methoxy-azetidin-1-yl)methyl)cyclopropyl)methoxy)-5, 6, 7, 8-tetrahydropyrido [3,4-d]pyrimidin-4-yl)-1-(2-fluoroacroloyl)piperazin-2-yl) acetonitrile

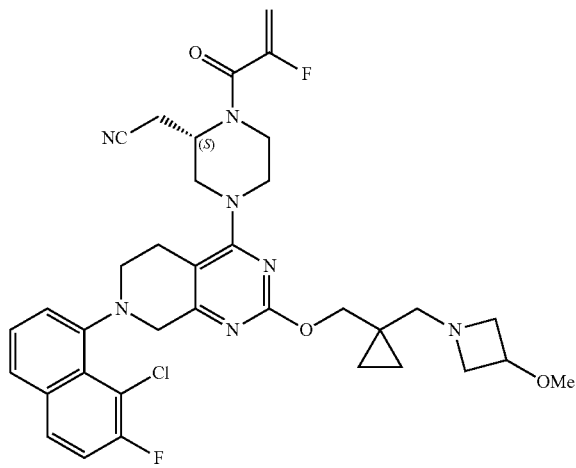

LC-MS: m/z 678 (M+H)⁺. ¹H NMR (400 MHz, DMSO) δ 8.02 (dd, J=9.0, 5.9 Hz, 1H), 7.79 (dd, J=7.9, 3.2 Hz, 1H), 7.66-7.51 (m, 2H), 7.46-7.34 (m, 1H), 5.40 (dd, J=18.0, 3.9 Hz, 1H), 5.36-5.18 (m, 1H), 4.86 (brs, 1H), 4.25-3.65 (m, 8H), 3.46 (m, 4H), 3.27-2.60 (m, 12H), 2.39 (s, 2H), 0.45 (s, 2H), 0.40 (s, 2H).

Example 65 Preparation of (S)-2-(4-(7-(8-chloro-7-fluoronaphthalen-1-yl)-2-((1-((3-fluoroazetidin-1-yl)methyl)cyclopropyl)methoxy)-5, 6, 7, 8-tetrahydro-pyrido[3,4-d]pyrimidin-4-yl)-1-(2-fluoroacroloyl)piperazin-2-yl) acetonitrile

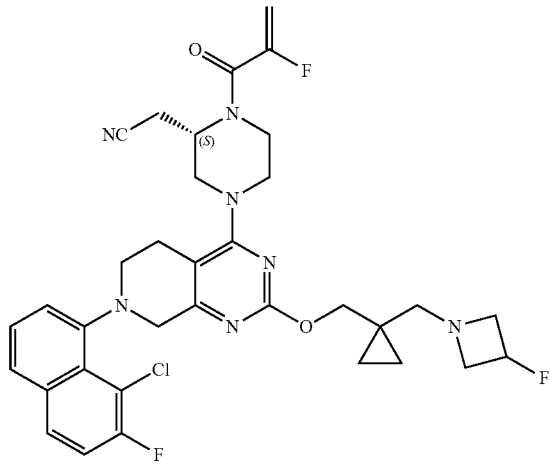

LC-MS: m/z 666 (M+H)⁺. ¹H NMR (400 MHz, DMSO) δ 8.02 (dd, J=8.9, 5.9 Hz, 1H), 7.79 (dd, J=7.8, 3.2 Hz, 1H), 7.66-7.49 (m, 2H), 7.42 (dd, J=16.5, 7.4 Hz, 1H), 5.48-4.98 (m, 3H), 4.85 (brs, 1H), 4.24-3.65 (m, 8H), 3.54 (m, 4H), 3.27-2.60 (m, 8H), 2.44 (s, 2H), 0.44 (m, 4H).

Example 66 Preparation of (S)-2-(1-(2-fluoroacroloyl)-4-(2-((1-((3-fluoroazetidin-1-yl)methyl)cyclopropyl)methoxy-7-(7-fluoronaphthalen-1-yl)-5, 6, 7, 8-tetrahydropyrido[3,4-d]pyrimidin-4-yl)-1-(2-fluoroacroloyl)piperazin-2-yl) acetonitrile

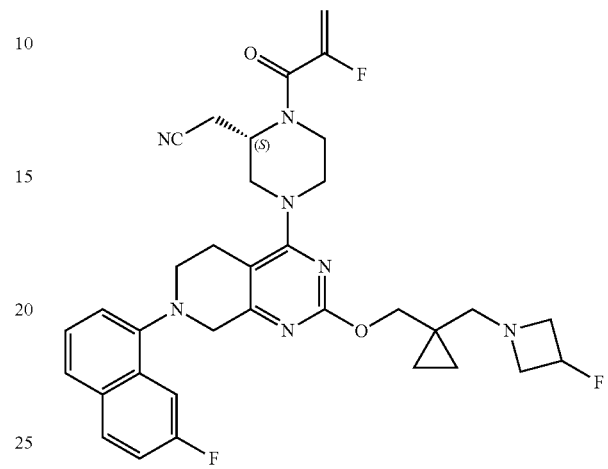

LC-MS: m/z 632 (M+H)⁺. ¹H NMR (400 MHz, DMSO) δ 8.04 (dd, J=9.0, 6.0 Hz, 1H), 7.80 (d, J=9.1 Hz, 1H), 7.71 (d, J=8.2 Hz, 1H), 7.46 (t, J=7.7 Hz, 2H), 7.31 (d, J=7.4 Hz, 1H), 5.49-4.99 (m, 3H), 4.87 (brs, 1H), 4.24-3.45 (m, 12H), 3.05 (m, 8H), 2.45 (s, 2H), 0.46 (m, 4H).

Example 67 Preparation of (S)-2-(4-(7-(8-chloro-7-fluoronaphthalen-1-yl)-2-((1-((3-methylazetidin-1-yl)methyl)cyclopropyl)methoxy)-5, 6, 7, 8-tetrahydropyrido[3, 4-d]pyrimidin-4-yl)-1-(2-fluoroacroloyl)piperazin-2-yl) acetonitrile

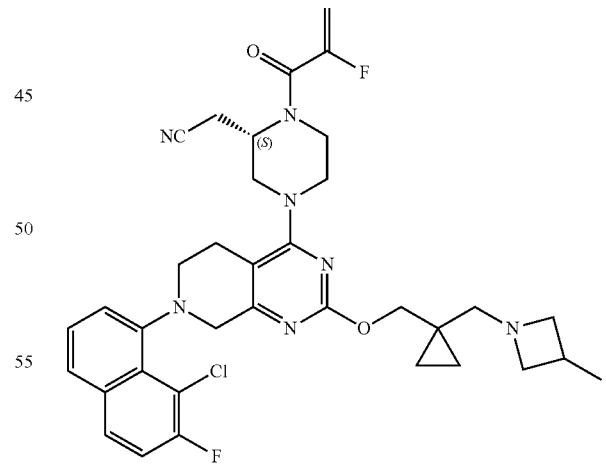

LC-MS: m/z 662 (M+H)⁺. ¹H NMR (400 MHz, DMSO) δ 8.02 (dd, J=8.9, 5.9 Hz, 1H), 7.79 (dd, J=7.9, 3.2 Hz, 1H), 7.66-7.49 (m, 2H), 7.42 (dd, J=16.3, 7.6 Hz, 1H), 5.39 (dt, J=9.5, 4.7 Hz, 1H), 5.35-5.15 (m, 1H), 4.85 (brs, 1H), 4.20-3.68 (m, 7H), 3.47 (m, 1H), 3.26-2.58 (m, 11H), 2.41 (m, 1H), 2.35 (m, 2H), 1.06 (d, J=6.6 Hz, 3H), 0.43 (s, 2H), 0.38 (s, 2H).

Example 68 Preparation of (S)-2-(4-(7-(8-chloro-7-fluoronaphthalen-1-yl)-2-((1-((3-hydroxyazetidin-1-yl)methyl)cyclopropyl)methoxy)-5, 6, 7, 8-tetrahydropyrido [3,4-d]pyrimidin-4-yl)-1-(2-fluoroacroloyl)piperazin-2-yl) acetonitrile

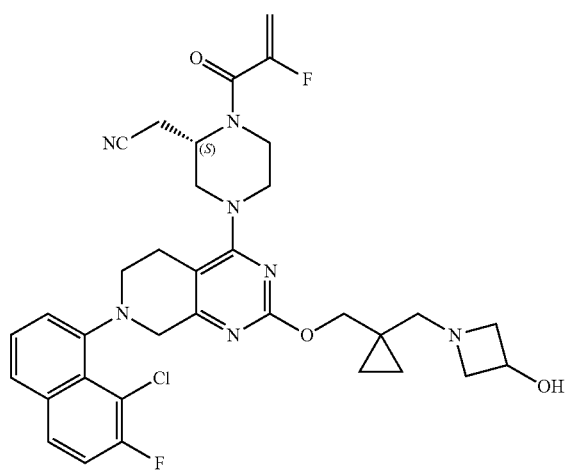

LC-MS: m/z 664 (M+H)⁺. ¹H NMR (400 MHz, DMSO) δ 8.02 (dd, J=8.9, 5.9 Hz, 1H), 7.79 (dd, J=7.9, 3.1 Hz, 1H), 7.66-7.49 (m, 2H), 7.42 (dd, J=16.3, 7.5 Hz, 1H), 5.47-5.10 (m, 3H), 4.85 (brs, 1H), 4.28-3.45 (m, 13H), 3.25-2.59 (m, 9H), 2.41 (s, 2H), 0.44 (s, 2H), 0.41 (s, 2H).

Example 69 Preparation of (S)-2-(4-(7-(8-chloro-7-fluoronaphthalen-1-yl)-2-((1-(((2-methoxyethyl(methyl)amino)methyl)cyclopropyl)methoxy)-5, 6, 7, 8-tetrahydropyrido[3,4-d]pyrimidin-4-yl)-1-(2-fluoroacroloyl)piperazin-2-yl) acetonitrile

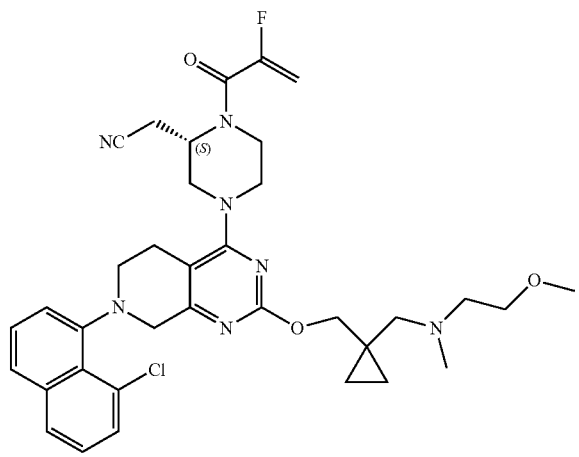

LC-MS: m/z 664 (M+H)⁺. ¹H NMR (400 MHz, CDCl₃) δ 7.77 (d, J=8.2 Hz, 1H), 7.67-7.60 (m, 1H), 7.57-7.51 (m, 1H), 7.46 (dt, J=11.3, 7.8 Hz, 1H), 7.35 (t, J=7.8 Hz, 1H), 7.24 (dd, J=19.2, 7.5 Hz, 1H), 5.43 (d, J=48.4 Hz, 1H), 5.27 (dd, J=16.8, 3.4 Hz, 1H), 4.92 (brs, 1H), 4.52-2.32 (m, 25H), 1.73 (m, 3H), 0.66 (m, 4H).

Example 70 Preparation of 2-(1-acroloyl-4-(2-(2-((cyclopropyl)(methyl)amino)ethoxy)-7-(8-methyl-naphthalen-1-yl)-5,6,7,8-tetrahydropyrido[3,4-d]pyrimidin-4-yl) piperazin-2-yl) acetonitrile

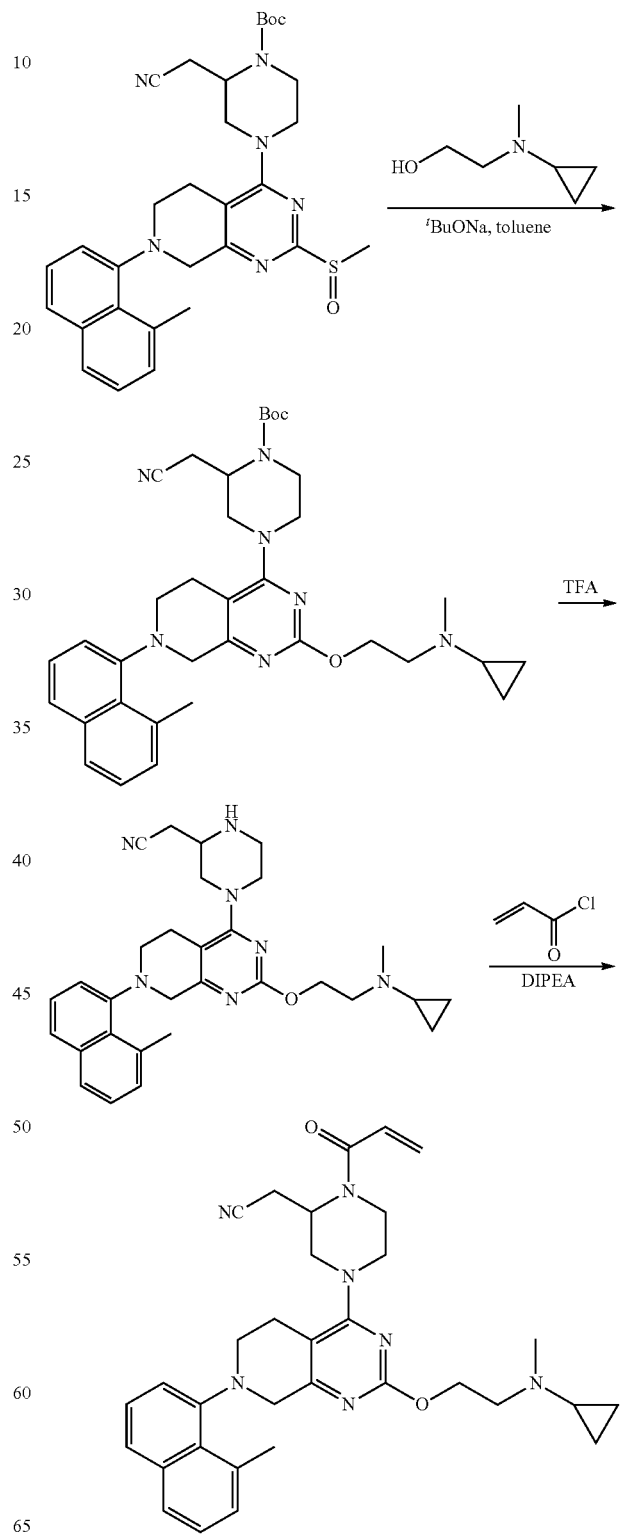

Step 1: Preparation of tert-butyl 2-(cyanomethyl)-4-(2-(cyclopropyl(methyl)amino)ethoxy)-7-(8-methyl-naphthalen-1-yl)-5,6,7,8-tetrahydropyrido[3,4-d]pyrimidin-4-yl)piperazine-1-formate Tert-butyl 2-(cyanomethyl)-4-(7-(8-methylnaphthalen-1-yl)-2-(methyl sulfoxide)-5, 6, 7, 8-tetrahydropyrido[3,4-d]pyrimidin-4-yl) piperazine-1-formate (72 mg, 0.128 m mol) was added to the reaction flask, and then toluene (0.8 mL), 2-(cyclopropyl(methyl) amino)ethan-1-ol (30 mg, 0.256 mmol) and sodium tert-butoxide (37 mg, 0.384 mmol) were successively added. The reaction solution was stirred for 0.5 h under ice water bath, then water (50 mL) was added, and extracted with ethyl acetate (3×30 mL). All organic phases were combined, washed once with saturated sodium chloride, and then dried over anhydrous sodium sulfate, and filtered. The filtrate was concentrated under reduced pressure, and the obtained residue was purified on preparative plate (eluent: DCM/MeOH=20/1) to obtain the target product (36 m g, yield 46%).

LC-MS: m/z 612 (M+H)$^+$.

Step 1: Preparation of 2-(4-(2-(2-(cyclopropyl (methyl) amino)-ethoxy)-7-(8-methylnaphthalen-1-yl)-5,6,7,8-tetrahydropyrido[3,4-d]pyrimidin-4-yl) piperazin-2-yl) acetonitrile Tert-butyl 2-(cyanomethyl)-4-(2-(cyclopropyl(methyl) amino)-ethoxy)-7-(8-methylnaphthalen-1-yl)-5,6,7,8-tetrahydropyrido[3,4-d]pyrimidin-4-yl)piperazine-1-formate (36 mg, 0.059 mmol) was dissolved in dichloromethane (1 mL), followed by adding trifluoroacetic acid (0.5 mL). The reaction solution was stirred at room temperature for 0.5 h and then concentrated until dry under reduced pressure to obtain the target pro duct (40 mg), then directly used for the next reaction without purification.

LC-MS: m/z 512 (M+H)$^+$.

Step 3: Preparation of 2-(1-acroloyl-4-(2-(2-((cyclopropyl)(methyl)amino)ethoxy)-7-(8-methylnaphthalen-1-yl)-5,6,7,8-tetrahydropyrido[3,4-d]pyrimidin-4-yl)piperazin-2-yl) acetonitrile A solution of N, N-diisopropylethylamine (42 mg, 0.324 mmol) in dichloromethane (2 mL) was added to 2-(4-(2-(2-(cyclopropyl(methyl)amino)ethoxy)-7-(8-methylnaphthalen-1-yl)-5,6,7,8-tetrahydropyrido[3,4-d]pyrimidin-4-yl) piperazin-2-yl) acetonitrile (40 mg, 0.054 mmol) obtained from the previous step. The reaction solution was protected by nitrogen, and acroloyl chloride (10 mg, 0.108 mmol) was added dropwise at −40° C. After the addition, the reaction solution was stirred at room temperature f or 1 h, then methanol (1 mL) was added to quench. The resulting mixture was concentrated, and the obtained residue was purified by reverse phase C18 column to obtain the target product (12 mg, yield 36%).

LC-MS: m/z 566 (M+H)$^+$. $^1$H NMR (400 MHz, CDCl$_3$) δ 7.66 (m, 2H), 7.38 (m, 2H), 7.24 (m, 2H), 6.56 (m, 1H), 6.41 (d, J=16.8 Hz, 1H), 5.84 (d, J=10.4 Hz, 1H), 5.06 (brs, 0.5H), 4.63 (brs, 0.5H), 4.44 (m, 2H), 4.01 (m, 5H), 3.52 (m, 2H), 3.08 (m, 6H), 2.91 (s, 3H), 2.70 (m, 3H), 2.45 (d, J=3.6 Hz, 3H), 1.77 (m, 1H), 0.48 (m, 4H).

The following compounds were synthesized from different starting materials according to the method of Example 70:

Example 71 Preparation of 2-(1-acroloyl-4-(2-((S)-2-(cyclopropyl(methyl)amino)propoxy)-7-(8-methyl-naphthalen-1-yl)-5,6,7,8-tetrahydropyrido[3,4-d]pyrimidin-4-yl) piperazin-2-yl) acetonitrile

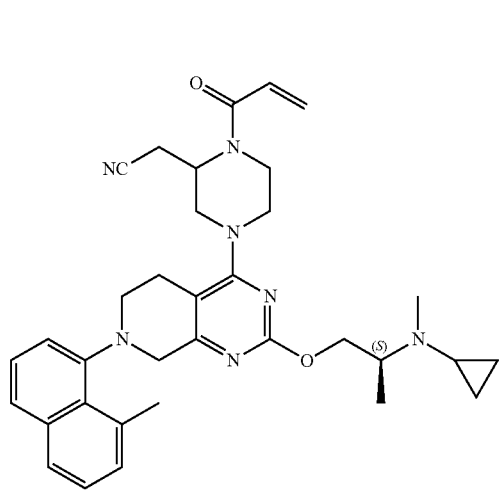

LC-MS: m/z 580 (M+H)$^+$. $^1$HNMR (400M, CDCl$_3$) δ 7.66 (m, 2H), 7.38 (m, 2H), 7.24 (m, 2H), 6.55 (m, 1H), 6.41 (d, J=16.8 Hz, 1H), 5.83 (d, J=10.0 Hz, 1H), 5.08 (brs, 0.5H), 4.63 (brs, 0.5H), 4.45 (m, 1H), 3.87 (m, 7H), 3.12 (m, 5H), 2.91 (s, 3H), 2.70 (m, 3H), 2.39 (s, 3H), 1.95 (s, 1H), 1.87 (s, 1H), 1.83 (m, 3H), 0.46 (m, 4H).

Example 72 Preparation of 2-(1-acroloyl-4-(2-((R)-2-(cyclopropyl(methyl)amino)propoxy)-7-(8-methyl-naphthalen-1-yl)-5,6,7,8-tetrahydropyrido[3,4-d]pyrimidin-4-yl) piperazin-2-yl) acetonitrile

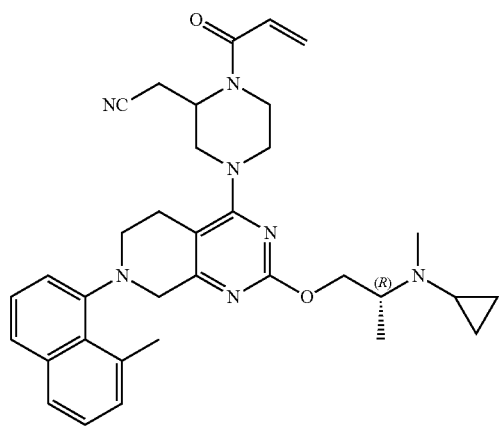

LC-MS: m/z 580 (M+H)$^+$. $^1$HNMR (400M, CDCl$_3$) δ 7.66 (m, 2H), 7.38 (m, 2H), 7.24 (m, 2H), 6.58 (m, 1H), 6.42 (d, J=16.4 Hz, 1H), 5.84 (d, J=10.4 Hz, 1H), 5.07 (brs, 0.5H), 4.63 (brs, 0.5H), 4.48 (m, 1H), 4.08 (m, 5H), 3.16 (m, 7H), 2.91 (s, 3H), 2.72 (m, 3H), 2.43 (s, 3H), 2.01 (m, 1H), 1.74 (m, 1H), 1.22 (s, 3H), 0.50 (s, 4H).

Example 73 Preparation of 2-(1-acroloyl-4-(2-2-((cyclopropylmethyl)(methyl)amino)ethoxy)-7-(8-methylnaphthalen-1-yl)-5,6,7,8-tetrahydropyrido[3,4-d]pyrimidin-4-yl)piperazin-2-yl) acetonitrile

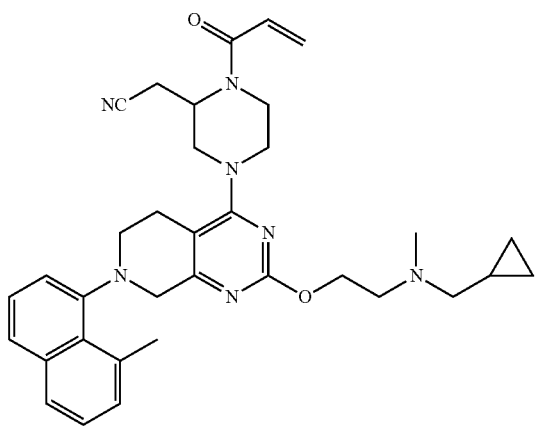 [SMILES: C=CC(=O)N1CCN(c2nc(OCCN(C)CC3CC3)nc3c2CCN(c2cccc4cccc(C)c24)C3)CC1CC#N]

LC-MS: m/z 580 (M+H)⁺. ¹HNMR (400M, CDCl₃) δ 7.66 (m, 2H), 7.38 (m, 2H), 7.24 (m, 2H), 6.58 (m, 1H), 6.41 (d, J=16.8 Hz, 1H), 5.84 (d, J=10.4 Hz, 1H), 5.05 (brs, 0.5H), 4.62 (brs, 0.5H), 4.44 (m, 2H), 4.08 (m, 5H), 3.52 (m, 2H), 2.91 (m, 12H), 2.43 (m, 5H), 0.90 (m, 1H), 0.52 (m, 2H), 0.14 (m, 2H).

Example 74 Preparation of 2-(1-acroloyl-4-(2-((S)-2-(cyclopropylmethyl)(methyl)amino)propoxy)-7-(8-methylnaphthalen-1-yl)-5,6,7,8-tetrahydropyrido[3,4-d]pyrimidin-4-yl)piperazin-2-yl) acetonitrile

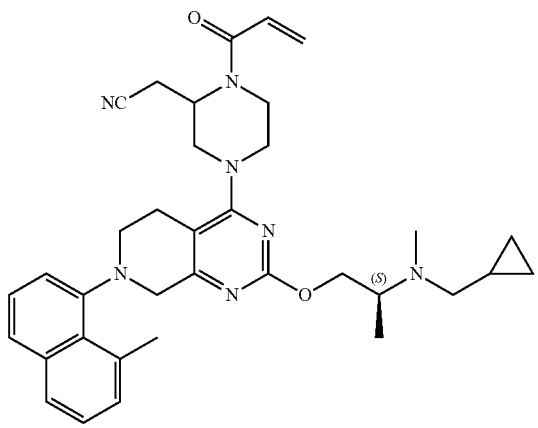

LC-MS: m/z 594 (M+H)⁺. ¹HNMR (400M, CDCl₃) δ 7.66 (m, 2H), 7.37 (m, 2H), 7.24 (m, 2H), 6.58 (m, 1H), 6.40 (m, 1H), 5.83 (d, J=10.4 Hz, 1H), 5.02 (brs, 0.5H), 4.60 (s, 0.5H), 4.42 (m, 1H), 4.07 (m, 6H), 3.29 (m, 7H), 2.91 (s, 3H), 2.75 (m, 3H), 2.40 (m, 5H), 1.13 (m, 3H), 0.86 (m, 1H), 0.50 (m, 2H), 0.12 (m, 2H).

Example 75 Preparation of 2-(1-acroloyl-4-(2-((R)-2-(cyclopropylmethyl)(methyl)amino)propoxy)-7-(8-methylnaphthalen-1-yl)-5,6,7,8-tetrahydropyrido[3,4-d]pyrimidin-4-yl)piperazin-2-yl) acetonitrile

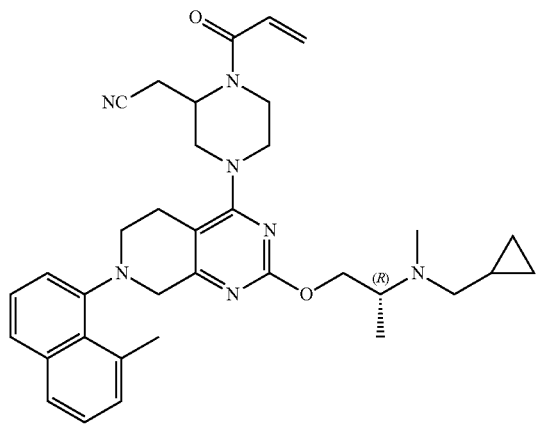

LC-MS: m/z 594 (M+H)⁺. ¹HNMR (400M, CDCl₃) δ 7.66 (m, 2H), 7.38 (m, 2H), 7.24 (m, 2H), 6.58 (m, 1H), 6.41 (d, J=16 Hz, 1H), 5.83 (d, J=8 Hz, 1H), 5.05 (brs, 0.5H), 4.63 (brs, 0.5H), 4.42 (m, 1H), 4.27-3.74 (m, 6H), 3.52 (m, 2H), 3.31 (brs, 1H), 3.20-2.94 (m, 4H), 2.91 (s, 3H), 2.84-2.59 (m, 3H), 2.41 (m, 5H), 1.13 (m, 3H), 0.88 (m, 1H), 0.53 (m, 2H), 0.12 (m, 2H).

Example 76 Preparation of 2-(1-acroloyl-4-(2-(((S)-1-((cyclopropylmethyl)(methyl)amino)propan-2-yl)oxy)-7-(8-methylnaphthalen-1-yl)-5,6,7,8-tetrahydropyrido[3,4-d]pyrimidin-4-yl)piperazin-2-yl) acetonitrile LC-MS: m/z 594 (M+H)⁺. ¹H NMR (400 MHz, CDCl₃) δ 7.79-7.58 (m, 2H), 7.50-7.32 (m, 2H), 7.29-7.18 (m, 2H), 6.61 (m, 1H), 6.41 (d, J=16.6 Hz, 1H), 5.84 (d, J=10.5 Hz, 1H), 5.08 (brs, 0.5H), 4.68 (brs, 0.5H), 4.34-3.65 (m, 5H), 3.65-2.38 (m, 20H), 1.42 (d, J=4.2 Hz, 3H), 1.08 (m, 1H), 0.66 (m, 2H), 0.28 (m, 2H).

Example 77 2-(1-acroloyl-4-(2-(((R)-1-((cyclopropylmethyl)(methyl)amino)propan-2-yl)oxy)-7-(8-methylnaphthalen-1-yl)-5,6,7,8-tetrahydropyrido[3,4-d]pyrimidin-4-yl) piperazin-2-yl) acetonitrile

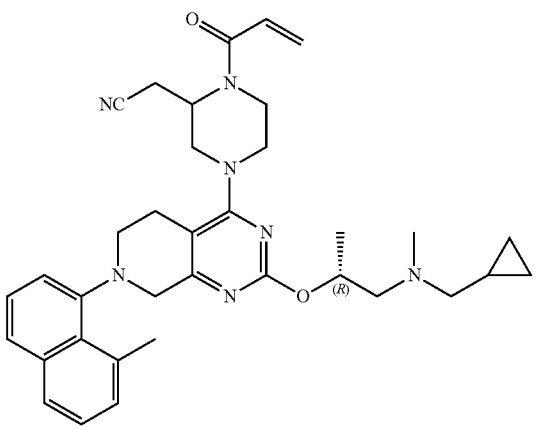

LC-MS: m/z 594 (M+H)+. 1H NMR (400 MHz, CDCl3) δ 7.78-7.58 (m, 2H), 7.49-7.31 (m, 2H), 7.26-7.13 (m, 2H), 6.57 (m, 1H), 6.39 (d, J=16.7 Hz, 1H), 5.82 (d, J=10.4 Hz, 1H), 5.07 (brs, 0.5H), 4.63 (brs, 0.5H), 4.35-3.81 (m, 4H), 3.81-2.88 (m, 11H), 2.73 (m, 5H), 2.39 (m, 5H), 1.34 (m, 3H), 0.87 (m, 1H), 0.50 (m, 2H), 0.10 (m, 2H).

Example 78 2-(1-acroloyl-4-(2-(2-(((S)-1-cyclopropylmethyl)(methyl)amino)ethoxy)-7-(8-methylnaphthalen-1-yl)-5,6,7,8-tetrahydropyrido[3,4-d]pyrimidin-4-yl)piperazin-2-yl) acetonitrile

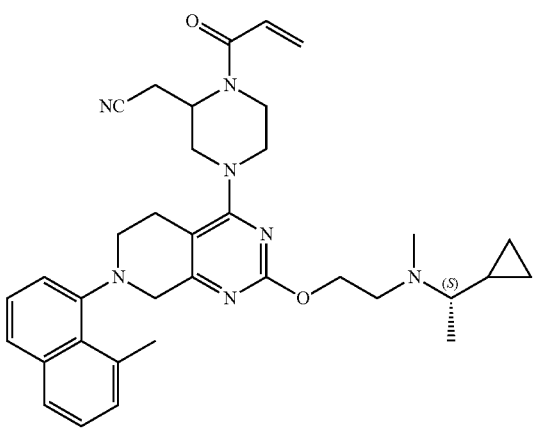

LC-MS: m/z 594 (M+H)+. 1HNMR (400M, CDCl3) δ 7.66 (m, 2H), 7.38 (m, 2H), 7.24 (m, 2H), 6.58 (m, 1H), 6.41 (d, J=16.8 Hz, 1H), 5.84 (d, J=10.8 Hz, 1H), 5.05 (brs, 0.5H), 4.65 (brs, 0.5H), 4.43 (m, 2H), 4.08 (m, 5H), 3.46 (m, 2H), 3.06 (m, 6H), 2.91 (s, 3H), 2.72 (m, 3H), 2.47 (m, 3H), 2.02 (m, 1H), 1.13 (m, 3H), 0.80 (s, 1H), 0.48 (m, 3H), 0.06 (m, 1H).

Example 79 2-(1-acroloyl-4-(2-(2-(((R)-1-cyclopropylmethyl)(methyl)amino)ethoxy)-7-(8-methylnaphthalen-1-yl)-5,6,7,8-tetrahydropyrido[3,4-d]pyrimidin-4-yl)piperazin-2-yl) acetonitrile

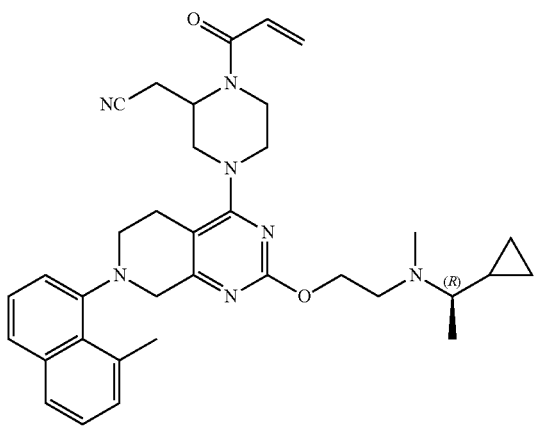

LC-MS: m/z 594 (M+H)+. 1H NMR (400 MHz, CDCl3) δ 7.66 (m, 2H), 7.38 (m, 2H), 7.24 (m, 2H), 6.58 (m, 1H), 6.41 (d, J=16 Hz, 1H), 5.83 (d, J=8 Hz, 1H), 5.06 (brs, 0.5H), 4.61 (brs, 0.5H), 4.38 (m, 2H), 4.27-3.76 (m, 5H), 3.52 (m, 2H), 3.20-2.94 (m, 6H), 2.91 (s, 3H), 2.84-2.63 (d, 3H), 2.43 (d, J=4 Hz, 3H), 1.96 (m, 1H), 1.10 (m, 3H), 0.78 (m, 1H), 0.53-0.43 (m, 2H), 0.30 (m, 1H), 0.04 (m, 1H).

Example 80 Preparation of 2-(1-acroloyl-4-(2-(2-(((1-fluorocyclopropyl)methyl) (methyl)amino) ethoxy)-7-(8-methylnaphthalen-1-yl)-5,6,7,8-tetrahydropyrido[3,4-d]pyrimidin-4-yl) piperazin-2-yl) acetonitrile

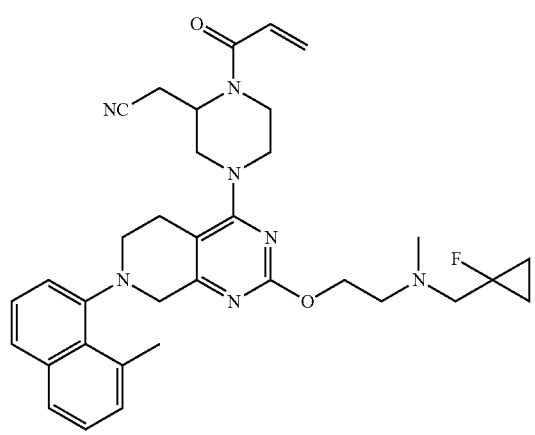 [SMILES: C=CC(=O)N1CCN(c2nc(OCCN(C)CC3(F)CC3)nc3c2CCN(c2cccc4cccc(C)c24)C3)CC1CC#N]

LC-MS: m/z 598 (M+H)+.

Example 81 Preparation of 2-(1-acroloyl-4-(2-(2-((cyclobutyl)(methyl)amino)ethoxy)-7-(8-methylnaphthalen-1-yl)-5,6,7,8-tetrahydropyrido[3,4-d]pyrimidin-4-yl)piperazin-2-yl) acetonitrile

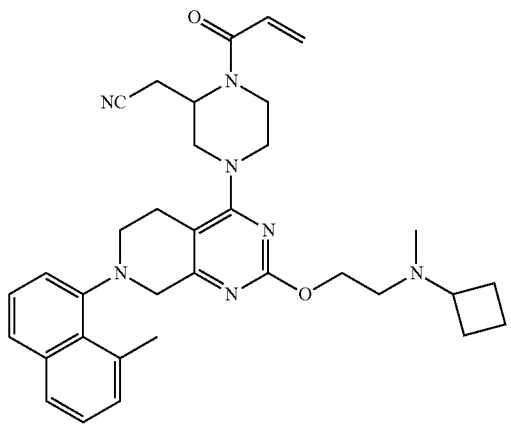 [SMILES: C=CC(=O)N1CCN(c2nc(OCCN(C)C3CCC3)nc3c2CCN(c2cccc4cccc(C)c24)C3)CC1CC#N]

LC-MS: m/z 580 (M+H)+. 1HNMR (400M, CDCl3) δ 7.66 (m, 2H), 7.38 (m, 2H), 7.24 (m, 2H), 6.56 (m, 1H), 6.41 (d, J=16.8 Hz, 1H), 5.84 (d, J=10.4 Hz, 1H), 5.06 (brs, 0.5H), 4.61 (brs, 0.5H), 4.38 (m, 2H), 4.08 (m, 5H), 3.16 (m, 6H), 2.91 (s, 3H), 2.70 (m, 5H), 2.21 (m, 3H), 2.05 (m, 2H), 1.90 (m, 3H), 1.63 (m, 2H).

Example 82 Preparation of 2-(1-acroloyl-4-(2-(2-((cyclobutylmethyl)(methyl)amino)ethoxy)-7-(8-methylnaphthalen-1-yl)-5,6,7,8-tetrahydropyrido[3,4-d]pyrimidin-4-yl)piperazin-2-yl) acetonitrile

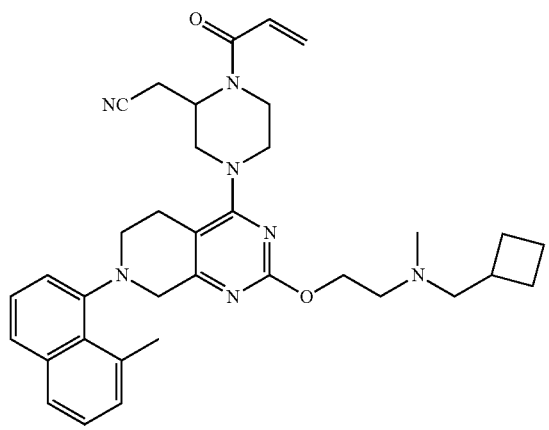 [SMILES: C=CC(=O)N1CCN(c2nc(OCCN(C)CC3CCC3)nc3c2CCN(c2cccc4cccc(C)c24)C3)CC1CC#N]

LC-MS: m/z 594 (M+H)+. 1HNMR (400M, CDCl3) δ 7.66 (m, 2H), 7.38 (m, 2H), 7.24 (m, 2H), 6.57 (m, 1H), 6.40 (d, J=16.4 Hz, 1H), 5.83 (d, J=10.4 Hz, 1H), 5.05 (brs, 0.5H), 4.58 (brs, 0.5H), 4.39 (m, 2H), 3.90 (m, 5H), 3.49 (m, 2H), 3.02 (m, 7H), 2.65 (m, 8H), 2.31 (m, 3H), 2.05 (m, 2H), 1.85 (m, 2H), 1.67 (m, 2H).

Example 83 Preparation of 2-(1-acroloyl-4-(2-(2-(((3,3-difluorocyclobutyl)methyl)(methyl)amino)ethoxy)-7-(8-methylnaphthalen-1-yl)-5,6,7,8-tetrahydropyrido[3,4-d]pyrimidin-4-yl)piperazin-2-yl) acetonitrile

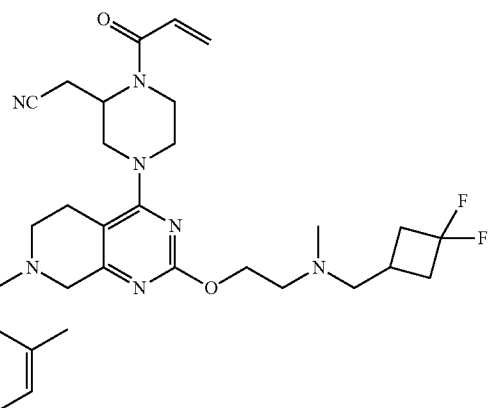

LC-MS: m/z 630 (M+H)+. 1H NMR (400 MHz, CDCl3) δ 7.76-7.59 (m, 2H), 7.37 (m, 2H), 7.26-7.14 (m, 2H), 6.70-6.49 (m, 1H), 6.39 (d, J=16.7 Hz, 1H), 5.82 (d, J=10.5 Hz, 1H), 5.06 (brs, 0.5H), 4.57 (brs, 0.5H), 4.39 (m, 2H), 4.32-4.00 (m, 3H), 3.80 (m, 2H), 3.62-2.96 (m, 7H), 2.92 (s, 3H), 2.87-2.74 (m, 3H), 2.72-2.51 (m, 5H), 2.33 (d, J=4.0 Hz, 4H), 2.26-2.13 (m, 2H).

Example 84 Preparation of 2-(1-acroloyl-4-(2-(((S)-1-(bis(cyclopropylmethyl)amino)propan-2-yl)oxy)-7-(8-methylnaphthalen-1-yl)-5,6,7,8-tetrahydropyrido[3,4-d]pyrimidin-4-yl)piperazin-2-yl) acetonitrile

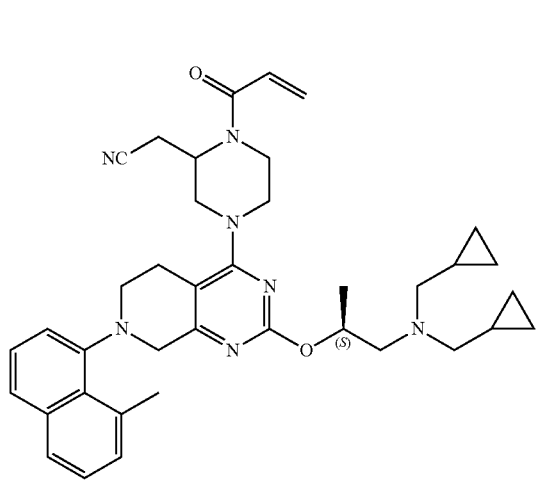

LC-MS: m/z 634 (M+H)+.

Example 85 Preparation of 2-(1-acroloyl-4-(2-(2-(((3,3-difluorocyclobutyl)(methyl)amino)ethoxy)-7-(8-methylnaphthalen-1-yl)-5,6,7,8-tetrahydropyrido[3,4-d]pyrimidin-4-yl)piperazin-2-yl) acetonitrile

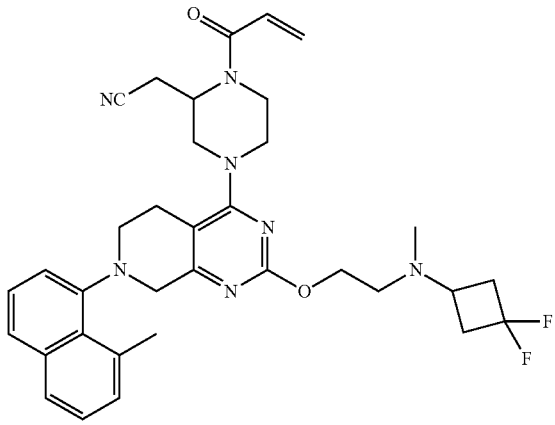 [SMILES: C=CC(=O)N1CCN(c2nc(OCCN(C)C3CC(F)(F)C3)nc3c2CCN(c2cccc4cccc(C)c24)C3)CC1CC#N]

LC-MS: m/z 616 (M+H)⁺.

Example 86 Preparation of 2-(1-acroloyl-4-(2-(2-((cyclopentyl)(methyl)amino)ethoxy)-7-(8-methylnaphthalen-1-yl)-5,6,7,8-tetrahydropyrido[3,4-d]pyrimidin-4-yl)piperazin-2-yl) acetonitrile

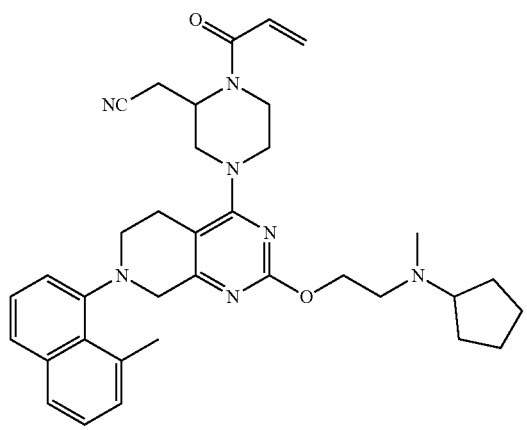 [SMILES: C=CC(=O)N1CCN(c2nc(OCCN(C)C3CCCC3)nc3c2CCN(c2cccc4cccc(C)c24)C3)CC1CC#N]

LC-MS: m/z 594 (M+H)⁺.

Example 87 Preparation of 2-(1-acroloyl-4-(2-(2-((cyclohexyl)(methyl)amino)ethoxy)-7-(8-methylnaphthalen-1-yl)-5,6,7,8-tetrahydropyrido[3,4-d]pyrimidin-4-yl)piperazin-2-yl) acetonitrile

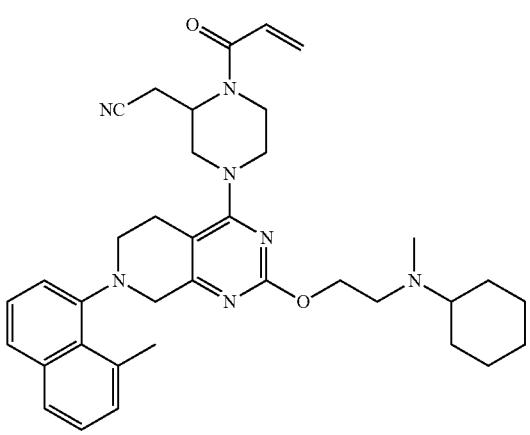 [SMILES: C=CC(=O)N1CCN(c2nc(OCCN(C)C3CCCCC3)nc3c2CCN(c2cccc4cccc(C)c24)C3)CC1CC#N]

LC-MS: m/z 608 (M+H)⁺. ¹H NMR (400 MHz, CDCl₃) δ 7.76-7.60 (m, 2H), 7.37 (m, 2H), 7.26-7.14 (m, 2H), 6.58 (s, 1H), 6.39 (d, J=16.7 Hz, 1H), 5.82 (d, J=10.5 Hz, 1H), 5.06 (brs, 0.5H), 4.61 (brs, 0.5H), 4.43 (m, 2H), 4.32-3.63 (m, 5H), 3.61-3.37 (m, 2H), 3.31-2.86 (m, 9H), 2.86-2.56 (m, 3H), 2.46 (d, J=36.3 Hz, 4H), 1.84 (d, J=33.8 Hz, 3H), 1.67-1.55 (m, 1H), 1.37-1.16 (m, 5H), 1.09 (m, 1H).

Example 88 Preparation of 2-(1-acroloyl-4-(2-(2-((cyclobutyl)(ethyl)amino)ethoxy)-7-(8-methylnaphthalen-1-yl)-5,6,7,8-tetrahydropyrido[3,4-d]pyrimidin-4-yl)piperazin-2-yl) acetonitrile

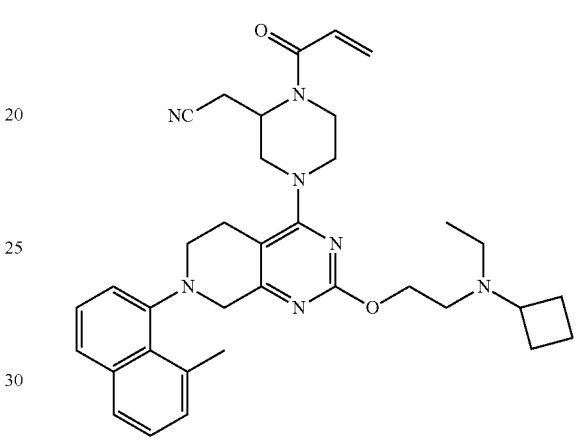

LC-MS: m/z 594 (M+H)⁺.

Example 89 Preparation of 2-(1-acroloyl-4-(2-(((S)-1-((cyclobutyl)(methyl)amino)propan-2-yl)oxy)-7-(8-methylnaphthalen-1-yl)-5,6,7,8-tetrahydropyrido[3,4-d]pyrimidin-4-yl)piperazin-2-yl) acetonitrile


LC-MS: m/z 594 (M+H)⁺.

Example 90 Preparation of 2-(1-acroloyl-4-(2-(((R)-1-((cyclobutyl)(methyl)amino)propan-2-yl)oxy)-7-(8-methylnaphthalen-1-yl)-5,6,7,8-tetrahydropyrido[3,4-d]pyrimidin-4-yl)piperazin-2-yl) acetonitrile

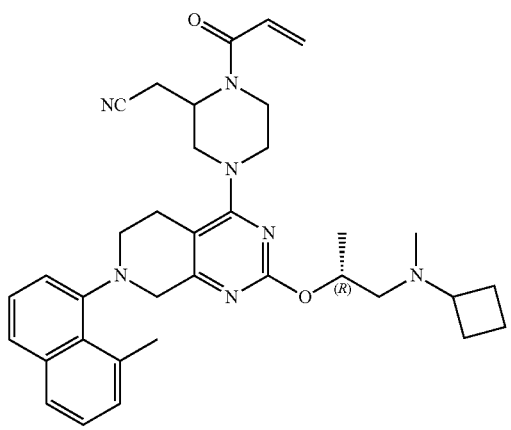

LC-MS: m/z 594 (M+H)⁺.

Example 91 Preparation of 2-(1-acroloyl-4-(2-((S)-2-(cyclobutyl(methyl)amino) propoxy)-7-(8-methyl-naphthalen-1-yl)-5,6,7,8-tetrahydropyrido[3,4-d] pyrimidin-4-yl) piperazin-2-yl) acetonitrile

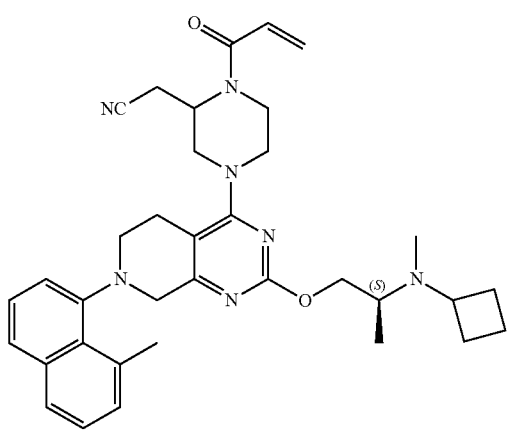

LC-MS: m/z 594 (M+H)⁺.

The compounds were separated by chiral preparation and 2-((S)-1-acroloyl-4-(2-((S)-2-(cyclobutyl(methyl)amino) propoxy)-7-(8-methylnaphthalen-1-yl)-5,6,7,8-tetrahydro-pyrido[3,4-d]pyrimidin-4-yl) piperazin-2-yl) acetonitrile (A) and 2-((R)-1-acroloyl-4-(2-((S)-2-(cyclobutyl(methyl) amino)propoxy)-7-(8-methylnaphthalen-1-yl)-5,6, 7,8-tetra-hydropyrido[3,4-d]pyrimidin-4-yl)piperazin-2-yl) acetonitrile (B) were obtained.

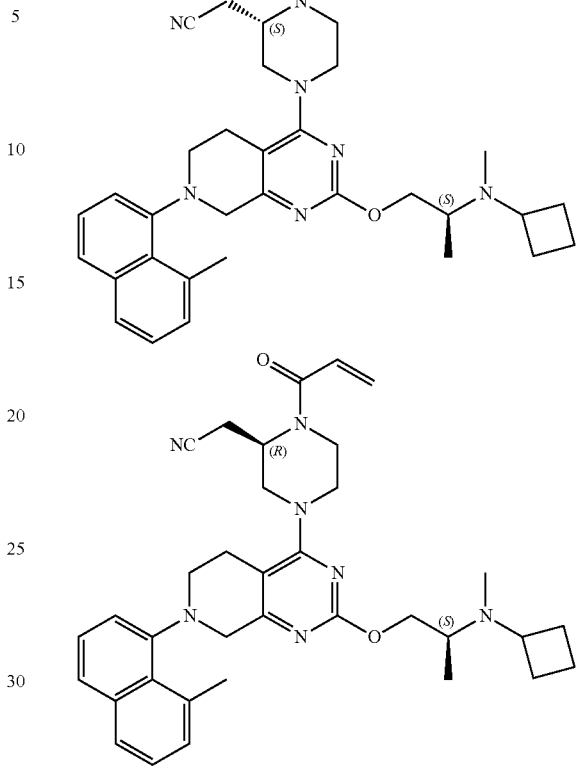

Isomer 91A
LC-MS: m/z 594 (M+H)⁺.
Isomer 91B
LC-MS: m/z 594 (M+H)⁺.

Example 92 Preparation of 2-(1-acroloyl-4-(2-((R)-2-(cyclobutyl(methyl)amino) propoxy)-7-(8-methyl-naphthalen-1-yl)-5,6,7,8-tetrahydropyrido[3,4-d] pyrimidin-4-yl) piperazin-2-yl) acetonitrile

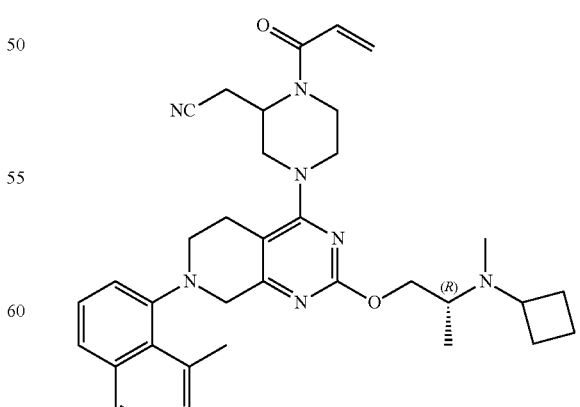

LC-MS: m/z 594 (M+H)⁺.

Example 93 Preparation of 2-(1-acroloyl-4-(2-(2-cyclopropoxyethyoxy)-7-(8-methylnaphthalen-1-yl)-5,6,7,8-tetrahydropyrido[3,4-d]pyrimidin-4-yl)piperazin-2-yl) acetonitrile

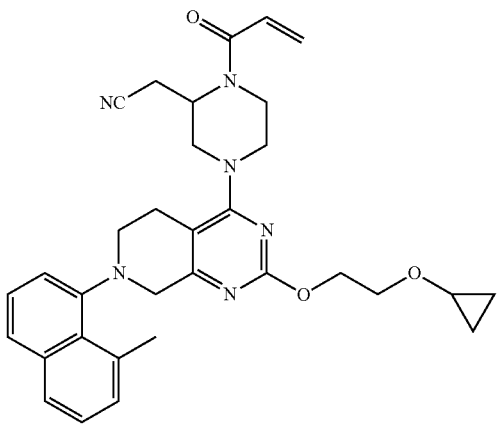 [SMILES: C=CC(=O)N1CCN(c2nc(OCCOC3CC3)nc3c2CCN(c2cccc4cccc(C)c24)C3)CC1CC#N]

LC-MS: m/z 553 (M+H)+. 1H NMR (400 MHz, CDCl3) δ 7.68-7.52 (m, 2H), 7.37-7.22 (m, 2H), 7.19-7.08 (m, 2H), 6.65-6.40 (m, 1H), 6.32 (d, J=16.7 Hz, 1H), 5.76 (d, J=10.5 Hz, 1H), 4.96 (brs, 0.5H), 4.54 (brs, 0.5H), 4.39 (m, 2H), 4.31-3.68 (m, 7H), 3.54-3.24 (m, 3H), 3.09 (s, 3H), 3.01-2.47 (m, 7H), 0.53 (m, 2H), 0.40 (m, 2H).

Example 94 Preparation of 2-(1-acroloyl-4-(2-(((trans)-2-(dimethylamino)cyclo pentyl)oxy)-7-(8-methylnaphthalen-1-yl)-5,6,7,8-tetrahydropyrido[3,4-d]pyrimidin-4-yl) piperazin-2-yl) acetonitrile

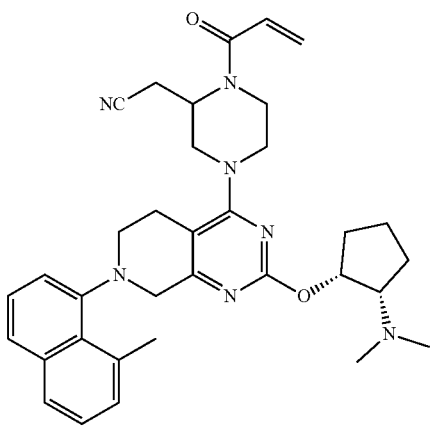 [SMILES: C=CC(=O)N1CCN(c2nc(O[C@@H]3CCC[C@@H]3N(C)C)nc3c2CCN(c2cccc4cccc(C)c24)C3)CC1CC#N]

LC-MS: m/z 580 (M+H)+.

Example 95 1-(4-(2-(2-((cyclopropylmethyl(methyl)amino)ethyoxyl)-7-(3-fluoro-2-(trifluoromethyl)phenyl)-5,6,7,8-tetrahydropyrido[3,4-d]pyrimidin-4-yl) piperazin-1-yl)prop-2-ene-1-one

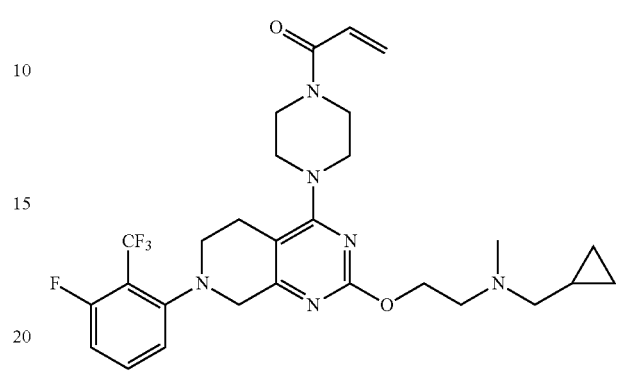

LC-MS: m/z 563 (M+H)+. 1H NMR (400 MHz, CDCl3) δ 7.27 (dd, J=14.4, 8.1 Hz, 1H), 6.86 (d, J=8.2 Hz, 1H), 6.80-6.67 (m, 1H), 6.39 (dd, J=16.8, 10.5 Hz, 1H), 6.14 (dd, J=16.8, 1.4 Hz, 1H), 5.55 (dd, J=10.5, 1.4 Hz, 1H), 4.30 (t, J=6.0 Hz, 2H), 3.88 (m, 2H), 3.52 (m, 2H), 3.50 (m, 2H), 3.37 (m, 3H), 2.99 (t, J=4.7 Hz, 2H), 2.84 (t, J=6.0 Hz, 3H), 2.54 (s, 2H), 2.33 (d, J=6.8 Hz, 5H), 0.75 (m, 1H), 0.38 (q, J=5.3 Hz, 2H), −0.01 (q, J=5.0 Hz, 2H).

Examples 96A and 96B were synthesized from different starting materials according to the method of Example 27:

2-((S)-4-((S)-7-(8-chloro-7-fluoronaphthalen-1-yl)-2-((1-((dimethylamino)methyl) cyclopropyl)methoxy)-6-methyl-5, 6, 7, 8-tetrahydropyrido[3,4-d]pyrimidin-4-yl)-1-(2-fluoroacroloyl)piperazin-2-yl) acetonitrile and 2-((S)-4-((R)-7-(8-chloro-7-fluoronaphthalen-1-yl)-2-((1-((dimethylamino)methyl)cyclopropyl)methoxy)-6-methyl-5, 6, 7, 8-tetrahydropyrido[3,4-d]pyrimidin-4-yl)-1-(2-fluoroacroloyl)piperazin-2-yl) acetonitrile

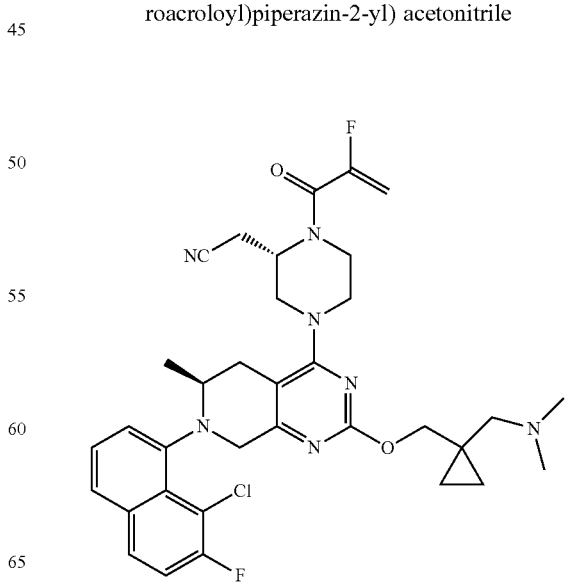

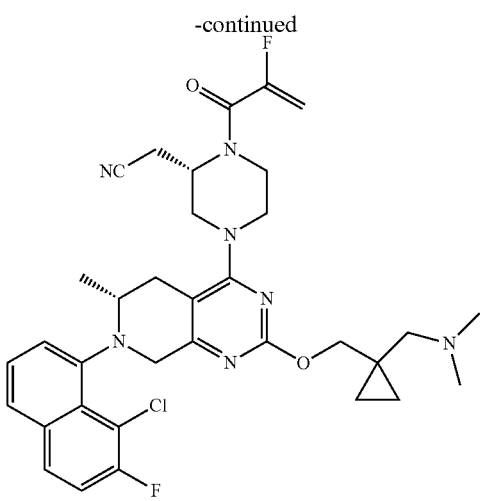

Example 96A (Isomer A)

LC-MS: m/z 650 (M+H)$^+$. $^1$HNMR (400M, DMSO-d$_6$): 8.02 (m, 1H), 7.87 (m, 0.68H), 7.75 (m, 0.32H), 7.55 (m, 3H), 5.37 (m, 2H), 4.82 (brs, 1H), 3.97 (m, 7H), 3.57 (m, 2H), 2.93 (m, 6H), 2.17 (m, 8H), 1.00 (d, J=8.0 Hz, 2.06H), 0.73 (d, J=8.0 Hz, 0.93H), 0.58 (m, 2H), 0.39 (m, 2H).

Example 96B (isomer B)

LC-MS: m/z 650 (M+H)$^+$. $^1$HNMR (400M, DMSO-d$_6$): 8.03 (m, 1H), 7.90 (m, 0.79H), 7.77 (m, 0.24H), 7.56 (m, 3H), 5.37 (m, 2H), 4.85 (brs, 1H), 3.98 (m, 7H), 3.53 (m, 2H), 2.94 (m, 6H), 2.15 (m, 8H), 1.00 (d, J=8.0 Hz, 2.3H), 0.73 (d, J=8.0 Hz, 0.66H), 0.57 (m, 2H), 0.38 (m, 2H).

Example 97 Biological Test Example

Biological Test Evaluation

The following biological test examples further describe the present invention, but these examples are not intended to limit the scope of the invention.

Cell assay of antiproliferative activity of compounds against NCI-H358(KRAS$^{G12C}$ mutation) and A549 (KRAS$^{G12S}$ mutation) cells.

Experimental Steps

40 μl phosphate buffer was added to the outer wells of the 384 microplate, and 40 μl cell suspension to be tested was added to the other wells. Then the microplate was incubated in a carbon dioxide incubator overnight.

The compounds to be tested were gradiently diluted, each compound was performed 10 concentration gradients (diluted from 50 μM to 0.003 μM) and added 100 nL to the corresponding wells in the microplate. After addition, 40 μl of phosphate buffer was added to each well in rows A and P and columns 1 and 24, and then the microplate was incubated in a carbon dioxide incubator for 5 days.

20 μL of Promega Celltiter-Glo reagent was added to each well of the microplate, and then the luminescence signal was stabilized by oscillating at room temperature for 10 min. Then PekinElmer Envision multi-label analyzer was used to read.

Finally, GraphPad Prism software was used to calculate the IC$_{50}$ value of the compound and the fitting curve was drawn.

Anti-proliferative activity of the compounds of the present invention against NCI-H358(KRAS$^{G12C}$ mutation) and A549(KRAS$^{G12S}$ mutation) cells were shown in Table 1.

TABLE 1

Anti-proliferative activity of the compound of the present invention

| IC$_{50}$ | NCI-H358 (μM) | A549 (μM) |
| --- | --- | --- |
| Example 1 | 0.22 | 7.1 |
| Example 2 | 0.0078 | 4.3 |
| Example 3 | 0.039 | 7.1 |
| Example 4 | 0.21 | 9.5 |
| Example 5 | 0.06 | 7.1 |
| Example 6 | 0.11 | 9.9 |
| Example 7 | 0.072 | 8.2 |
| Example 8 | 0.13 | 7.04 |
| Example 9 | 0.16 | 17.67 |
| Example 10 | 6.5 | 17.42 |
| Example 11 | 0.11 | 3.2 |
| Example 12 | 0.14 | 2.3 |
| Example 13 | 0.055 | 6.0 |
| Example 14 | 0.090 | 6.2 |
| Example 15 | 0.090 | 13.5 |
| Example 19 | 0.0046 | 8.9 |
| Example 20 | 0.87 | 7.7 |
| Example 21 | 0.027 | 7.8 |
| Example 22 | 0.091 | 2.2 |
| Example 23 | 0.013 | — |
| Example 25 | 0.059 | — |
| Example 26 | 0.062 | — |
| Example 27 | 0.014 | — |
| Example 28 | 0.008 | — |
| Example 29A | 0.36 | — |
| Example 29B | 0.053 | — |
| Example 29C | 0.1 | — |
| Example 29D | 0.006 | — |
| Example 30 | 0.041 | — |
| Example 31 | 0.073 | — |
| Example 32 | 0.12 | — |
| Example 33 | 0.066 | — |
| Example 34 | 1.9 | — |
| Example 35 | 0.31 | — |
| Example 36 | 0.25 | — |
| Example 37 | 1.4 | — |
| Example 38 | 4.9 | — |
| Example 39 | 2.5 | — |
| Example 40 | 0.30 | — |
| Example 41 | 1.4 | — |
| Example 42 | 5.5 | — |
| Example 43 | 0.83 | — |
| Example 44 | 3.3 | — |
| Example 45 | 0.049 | — |
| Example 46 | 0.037 | — |
| Example 47A | 0.1 | — |
| Example 47B | 0.071 | — |
| Example 48 | 0.065 | — |
| Example 49 | 0.043 | — |
| Example 50 | 0.30 | — |
| Example 52 | 0.54 | — |
| Example 53A | 1.4 | — |
| Example 53B | 1.3 | — |
| Example 54 | 0.047 | — |
| Example 55 | 0.87 | — |
| Example 56 | 0.061 | — |
| Example 57 | 1.3 | — |
| Example 58 | 0.065 | — |
| Example 59 | 0.81 | — |
| Example 60 | 0.092 | — |
| Example 61 | 0.11 | — |
| Example 62 | 0.036 | — |
| Example 63 | 0.007 | — |
| Example 65 | 0.045 | — |
| Example 66 | 0.18 | — |
| Example 67 | 0.051 | — |
| Example 68 | 0.086 | — |
| Example 69 | 0.059 | — |
| Example 70 | 0.17 | 11.5 |
| Example 71 | 0.15 | 11.5 |
| Example 72 | 0.18 | 10.6 |

TABLE 1-continued

Anti-proliferative activity of the compound of the present invention

| $IC_{50}$ | NCI-H358 (μM) | A549 (μM) |
|---|---|---|
| Example 73 | 0.06 | 3.7 |
| Example 74 | 0.08 | 2.6 |
| Example 75 | 0.09 | 2.8 |
| Example 76 | 0.86 | 3.5 |
| Example 77 | 1.80 | 2.7 |
| Example 78 | 0.05 | 2.8 |
| Example 79 | 0.04 | 3.1 |
| Example 80 | <0.1 | / |
| Example 81 | 0.04 | 7.5 |
| Example 82 | 0.16 | 6.6 |
| Example 85 | <0.1 | / |
| Example 91A | <0.03 | / |
| Example 91B | <1 | |
| Example 92 | <0.1 | / |
| Example 93 | 0.31 | 7.8 |
| Example 95 | 6.26 | / |
| Example 96A | 0.191 | / |
| Example 96B | 0.005 | / |

It can be seen from Table 1:

the compounds of the present invention showed good cell anti-proliferative activity for $KRAS^{G12C}$ mutant NCI-H358 cells, and weak anti-proliferation activity against $KRAS^{G12S}$ mutant A549 cells, showing high selectivity.

Pharmacokinetics Test Evaluation

Male SD rats, with a body weight of about 220 g, were given 15 mg/kg solution of the compound of the invention or the control compound by gavage after overnight fasting [10% cortisol (captisol) and 50 mM sodium citrate (pH 5) as vehicle]. Blood samples were collected at 0.5, 1.0, 2.0, 4.0, 6.0, 8.0, 12.0 and 24 hours after the compound was administrated, and the concentrations of the compound or the control compound in plasma were determined by LC/MS/MS.

The structure of the control compound is as follows:

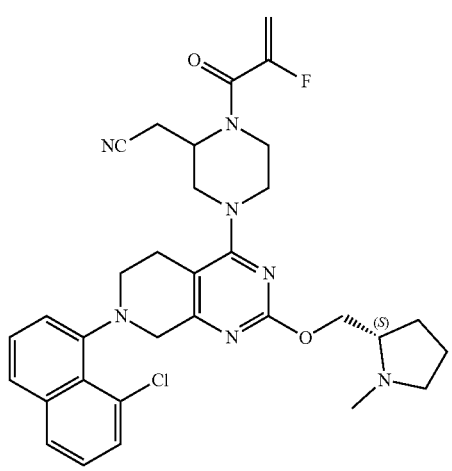

Pharmacokinetics Test Results

The plasma concentration-time curves of Examples 13 and 14 and control compounds were shown in FIG. 1, and the pharmacokinetics parameters were shown in Table 2:

TABLE 2

Summary of pharmacokinetics parameters: (n = 4, mean)

| parameter | unit | Control compound Dose 15 mg/kg | Example 13 Dose 15 mg/kg | Example 14 Dose 15 mg/kg |
|---|---|---|---|---|
| Tmax | Hours | 4.0 | 4.0 | 1.25 |
| Cmax | ng/mL | 123 | 163.3 | 85.1 |
| AUC | ng · h/mL | 830 | 1395 | 392 |
| $T_{1/2}$ | Hours | 2.47 | 2.33 | 1.69 |

In summary, it can be seen from Table 2 and FIG. 1 that compared with the control compound, Example 13 of the present invention showed better metabolic properties in rats, with higher maximum blood drug concentration (Cmax) and higher plasma exposure AUC. The results showed that Example 13 had excellent bioavailability and drug efficacy.

Pharmacodynamic Testing Evaluation of Anti-Tumor Activity (MIA PaCa-2 CDX Tumor Model)

Figure 2:
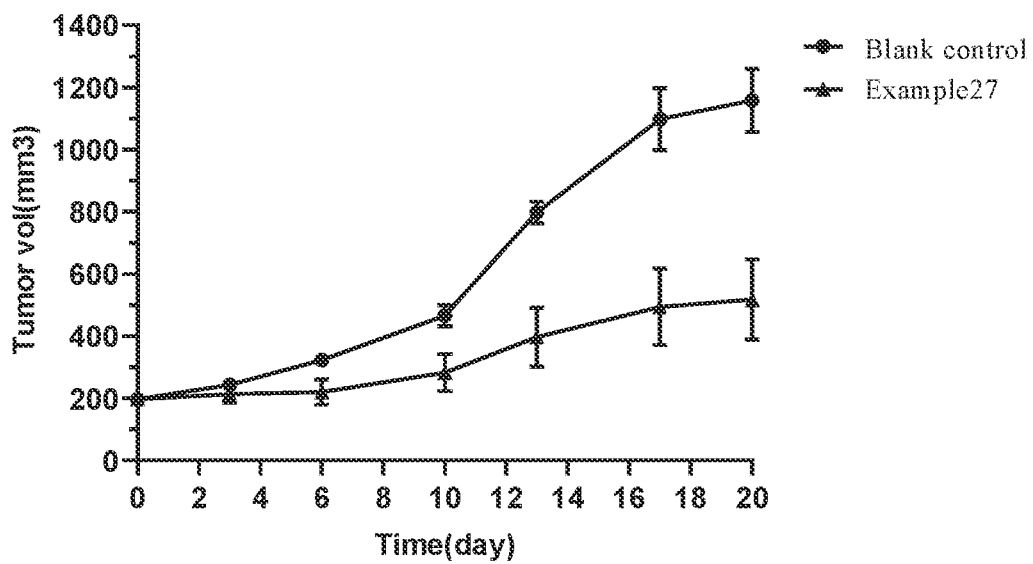
FIG. 2 shows the tumor volume-time curve in MIA PaCa-2 CDX tumor model.

100 uL suspension containing $5\times10^6$ MIA PaCa-2 tumor cells was subcutaneously injected into the right posterior abdomen of nude rats. The health of the rat was monitored daily. Measurements were started when the tumor grew palpable. The tumor volume calculation formula was adopted: $0.5\times L\times W^2$, where L and W represent tumor length and width, respectively. The tumor grew to ~200 mm³, the rats were randomly divided into groups. Rats were intragastrically administrated the corresponding dose (7.5 mg/Kg) of the compound's CMC-Na suspension every day, and their general status was monitored at the same time. The tumor was measured 3 times a week, and the weight was measured twice a week. The test results were shown in Table 3 and FIG. 2.

TABLE 3

Pharmacodynamic testing evaluation of anti-tumor activity

| Group | TV (mm³) Day 0 | TV (mm³) Day 20 | % Tumor Growth | % TGI |
|---|---|---|---|---|
| Blank control group | 197 | 1159 | 501.5 | — |
| Example 27 | 197 | 518 | 145.4 | 66.6 |

Pharmacodynamic Testing Evaluation of Anti-Tumor Activity (11358 CDX Tumor Model)

Figure 3:
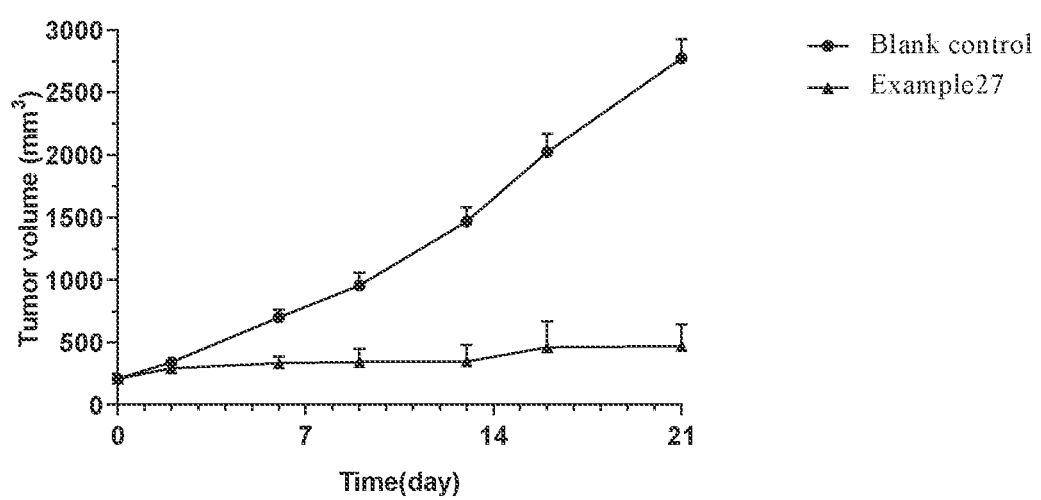
FIG. 3 shows the tumor volume-time curve in H358 CDX tumor model.

100 uL suspension containing $5\times10^6$ NCI-H358 tumor cells was subcutaneously injected into the right posterior back of nude rats. The health of the rat was monitored daily. Measurements were started when the tumor grew palpable. The tumor volume calculation formula was adopted: 0.5×L×W2, where L and W represent tumor length and width, respectively. The tumor grew to ~200 mm³, the rats were randomly divided into groups. Rats were intragastrically administrated the corresponding dose (30 mg/Kg) of the compound's solution every day, and their general status was monitored at the same time. The tumor was measured 2 times a week, and the weight was measured twice a week. The test results were shown in Table 4 and FIG. 3.

TABLE 4

| | Pharmacodynamic testing evaluation of anti-tumor activity | | | |
|---|---|---|---|---|
| Group | TV (mm³) Day 0 | TV (mm³) Day 20 | % Tumor Growth | % TGI |
| Blank control group | 209 | 2773 | 1326 | — |
| Example 27 | 209 | 471 | 182 | 89.8 |

The above test results showed that compared with the blank control, the compound of the invention can significantly reduce the tumor volume and had a good anti-tumor effect.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

The invention claimed is:

1. A compound of formula (I), and the stereoisomer, tautomer, crystal form, pharmaceutically acceptable salt, hydrate, solvate or prodrug thereof,

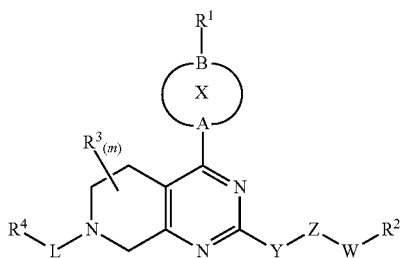

wherein:
A and B are N;
X is selected from 4-14 membered saturated or unsaturated heterocyclyl, wherein said saturated or unsaturated heterocyclyl may optionally be substituted by one or more $R^8$;
Y is O;
L is bond;
Z is bond;
W is bond;
$R^1$ is —C(O)C($R^A$)═C($R^B$)$_p$;
$R^A$ is absent, or is independently selected from hydrogen, deuterium, fluorine, cyano or $C_1$-$C_3$ alkyl;
$R^B$ is independently selected from hydrogen, deuterium, cyano or $C_1$-$C_3$ alkyl;
p is an integer of 1 or 2;
$R^2$ is —(CH$_2$)$_n$$R^7$, where H in CH$_2$ is optionally substituted;
$R^7$ is selected from substituted $C_3$-$C_{20}$ cycloalkyl or substituted 4-20 membered heterocyclyl; wherein "substituted" refers to substitution with one or more groups selected from the group consisting of $C_1$-$C_{18}$ alkyl, deuterated $C_1$-$C_{18}$ alkyl, and amino; and the $C_1$-$C_{18}$ alkyl or deuterated $C_1$-$C_{18}$ alkyl is substituted by one or more substituents selected from the group consisting of deuterium, halogen, cyano, amino, $C_3$-$C_7$ cycloalkyl, 4-7 membered heterocyclyl, NHR$^9$ and NR$^9$R$^{10}$; R$^9$ and R$^{10}$ are each independently $C_1$-$C_3$ alkyl;
n is 1, 2, or 3;
m is an integer of 0, 1, 2 or 3;
$R^3$ is independently selected from the group consisting of hydrogen, deuterium, oxygen, $C_1$-$C_3$ alkyl and $C_1$-$C_3$ haloalkyl;
$R^4$ is selected from group consisting of substituted or unsubstituted $C_6$-$C_{14}$ aryl and substituted or unsubstituted 5-14 membered heteroaryl;
$R^5$ is independently selected from substituted or unsubstituted group consisting of hydrogen, deuterium, $C_1$-$C_{18}$ alkyl, deuterated $C_1$-$C_{18}$ alkyl, $C_1$-$C_{18}$ haloalkyl, $C_3$-$C_{20}$ cycloalkyl, $C_1$-$C_{18}$ alkoxy, deuterated $C_1$-$C_{18}$ alkoxy, $C_1$-$C_{18}$ haloalkoxy, amino, hydroxyl, 4-20 membered heterocyclyl;
$R^8$ is independently selected from hydrogen, deuterium, $C_1$-$C_6$ alkyl, or CNCH$_2$—;
wherein, the above "substituted" refers to be substituted with one or more groups selected from the group consisting of hydrogen, deuterium, $C_1$-$C_{18}$ alkyl, deuterated $C_1$-$C_{18}$ alkyl, $C_1$-$C_{18}$ haloalkyl, $C_3$-$C_{20}$ cycloalkyl, $C_1$-$C_{18}$ alkoxy, deuterated $C_1$-$C_{18}$ alkoxy, $C_1$-$C_{18}$ haloalkoxy, $C_6$-$C_{14}$ aryl, 5-14 membered heteroaryl, 4-20 membered heterocyclyl, halogen, nitro, hydroxy, cyano, ester, amino, amido, sulfonamido and ureido.

2. The compound, and the stereoisomer, tautomer, crystal form, pharmaceutically acceptable salt, hydrate, solvate or prodrug thereof of claim 1, wherein it has a structure represented by formula (VIII):

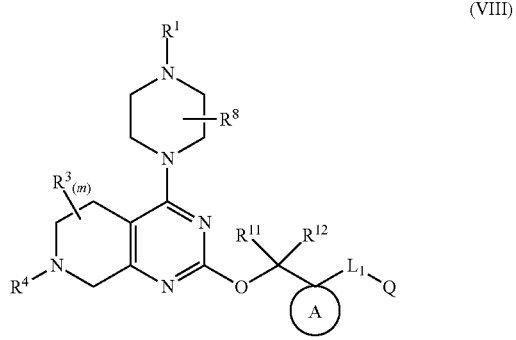

(VIII)

$R^{11}$ and $R^{12}$ are the same or different, and each independently selected from hydrogen, deuterium, $C_1$-$C_{18}$ alkyl, deuterated $C_1$-$C_{18}$ alkyl;
ring A is a substituted or unsubstituted $C_3$-$C_{20}$ cycloalkyl or a substituted or unsubstituted 4-20 membered heterocyclyl; and
$L_1$ is $C_1$-$C_{18}$ alkyl, or deuterated $C_1$-$C_{18}$ alkyl;
Q is $C_3$-$C_7$ cycloalkyl, 4-7 membered heterocyclyl, NHR$^9$ or NR$^9$R$^{10}$; R$^9$ and R$^{10}$ are each independently $C_1$-$C_3$ alkyl.

3. A compound is selected from the group consisting of:
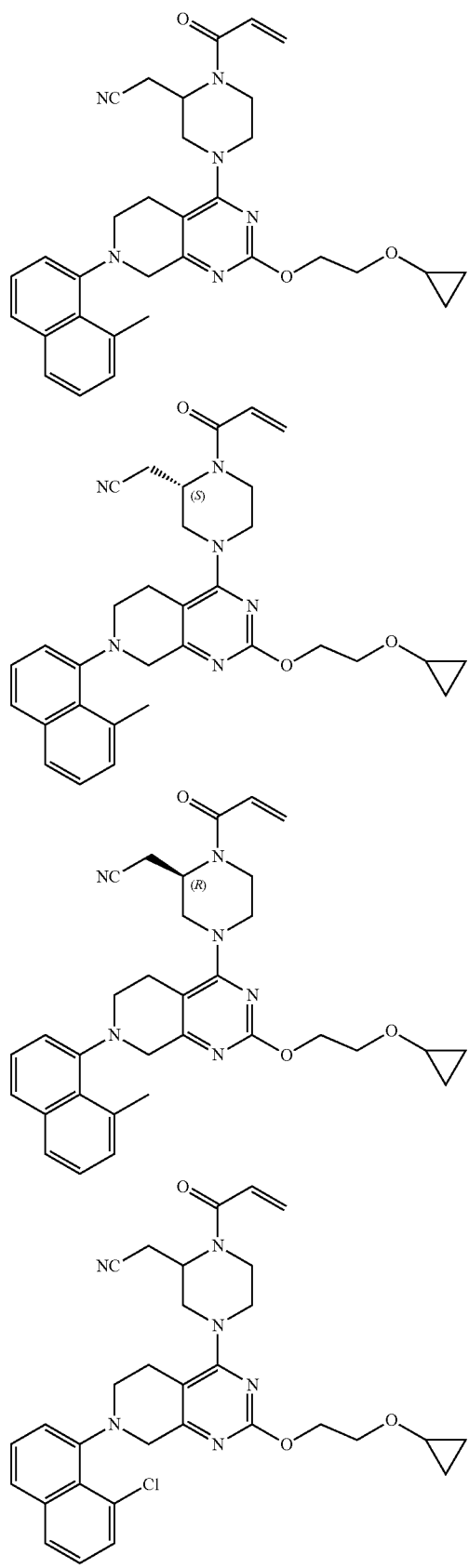
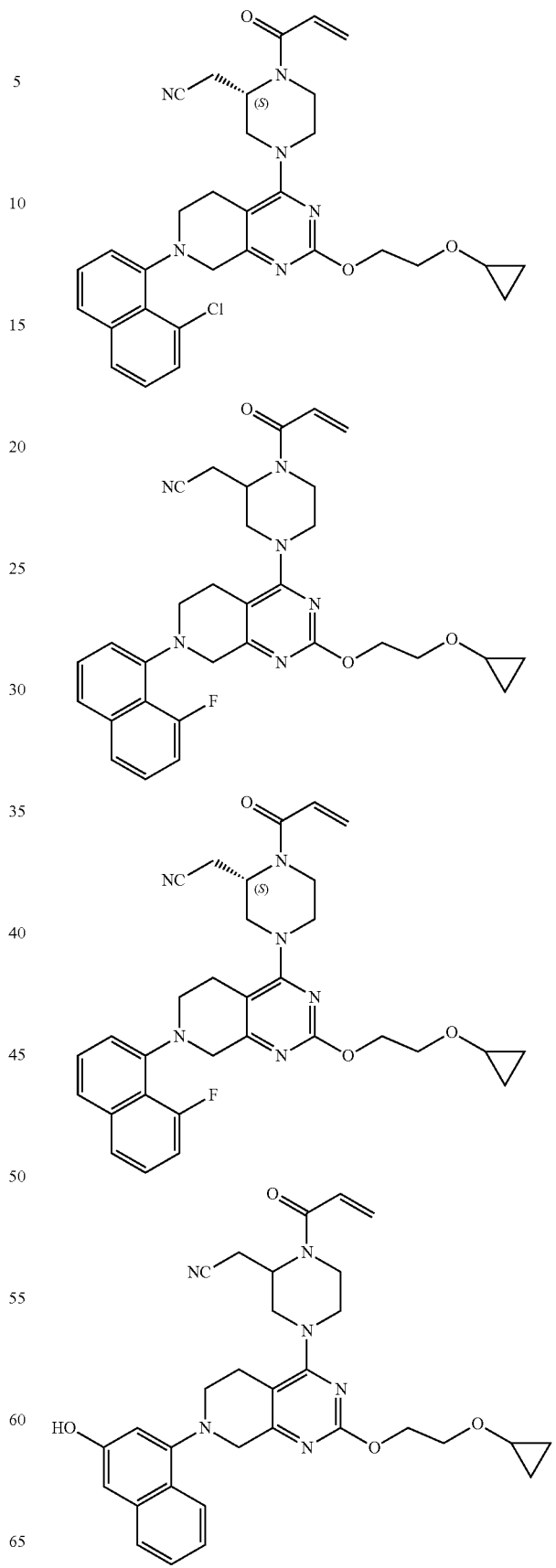

583
-continued
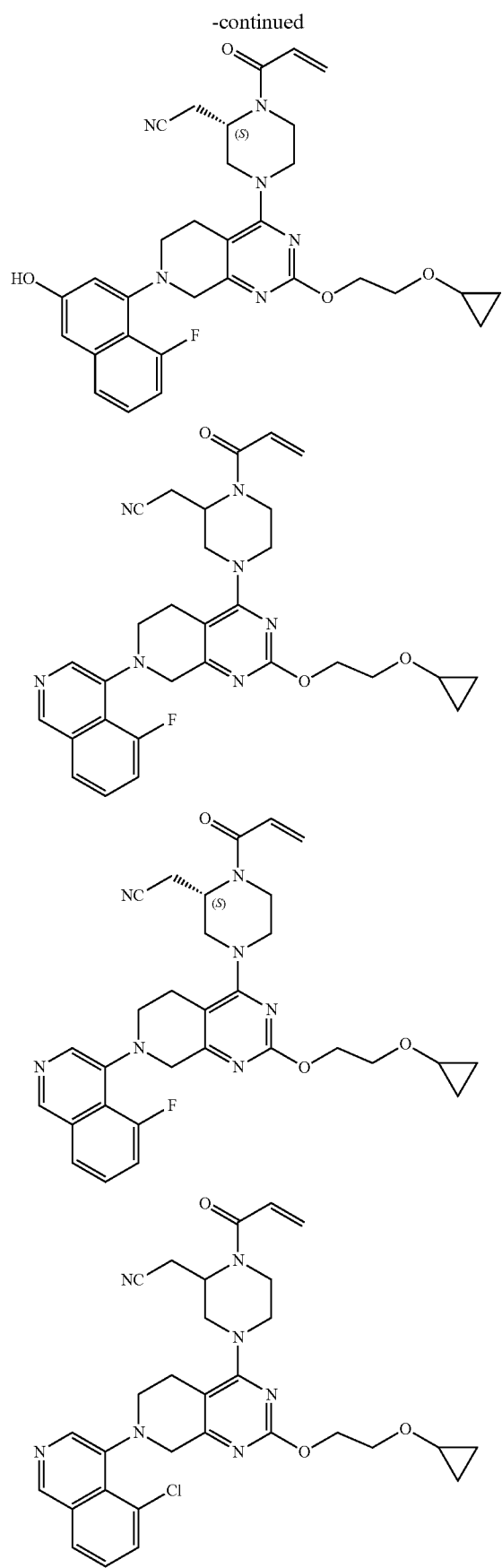
584
-continued
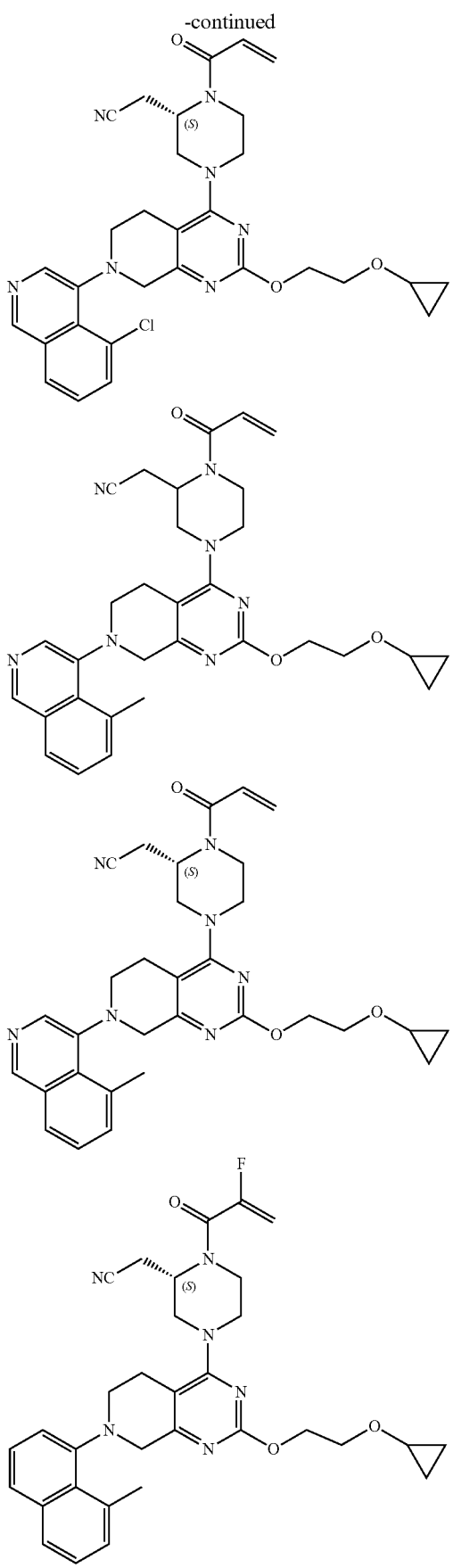

585
-continued
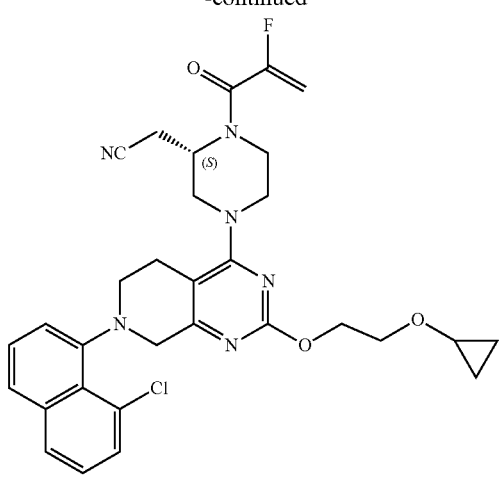
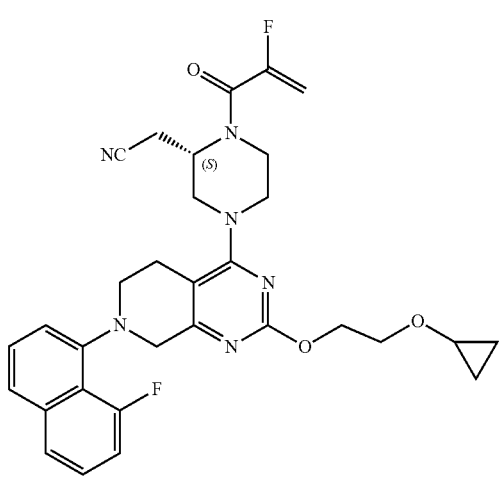
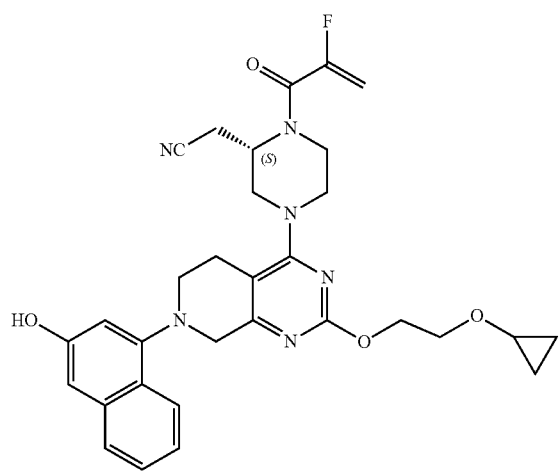
586
-continued
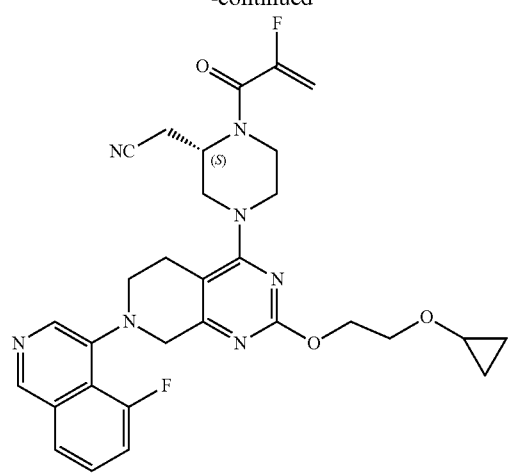
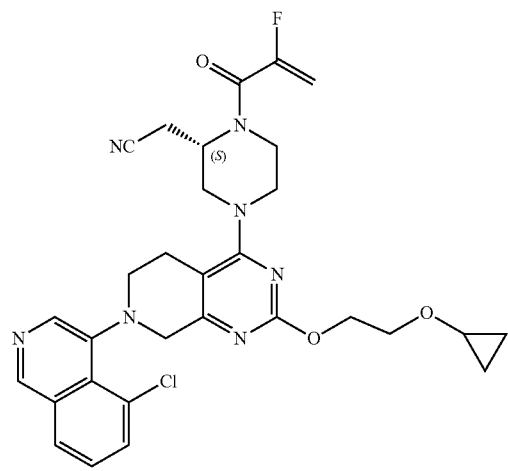
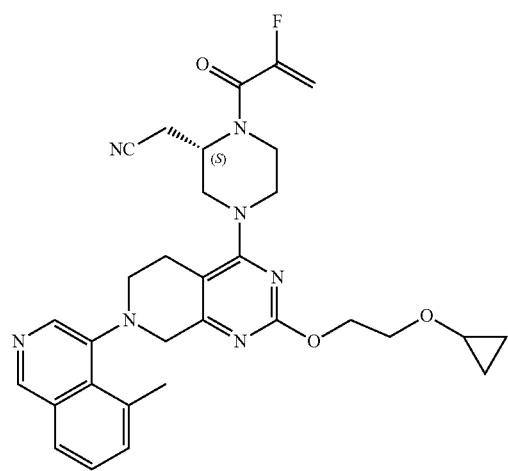

587
-continued
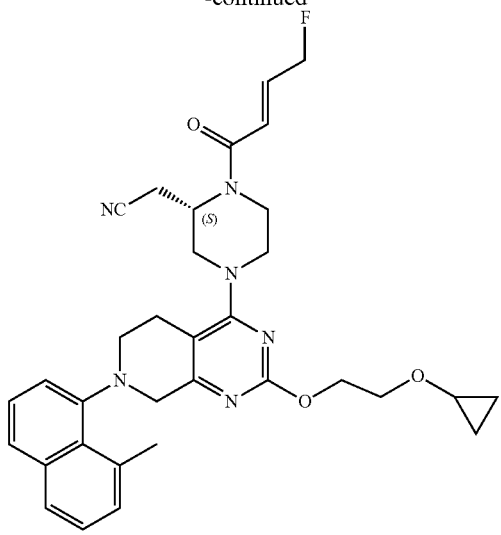
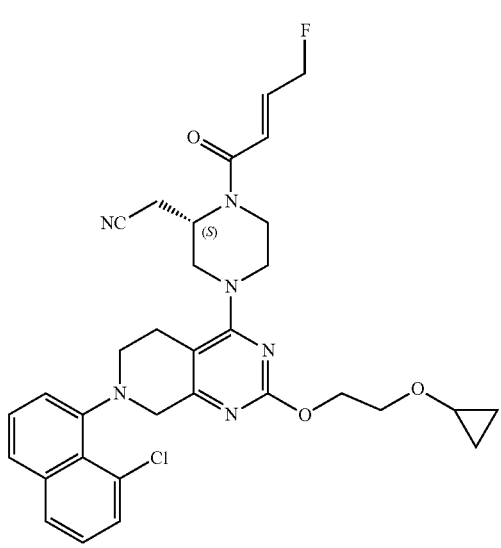
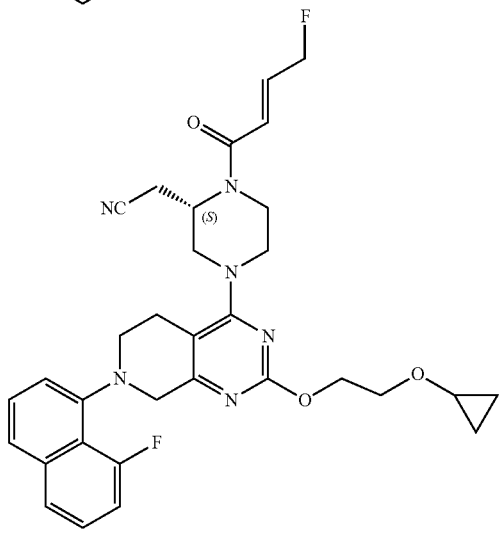
588
-continued
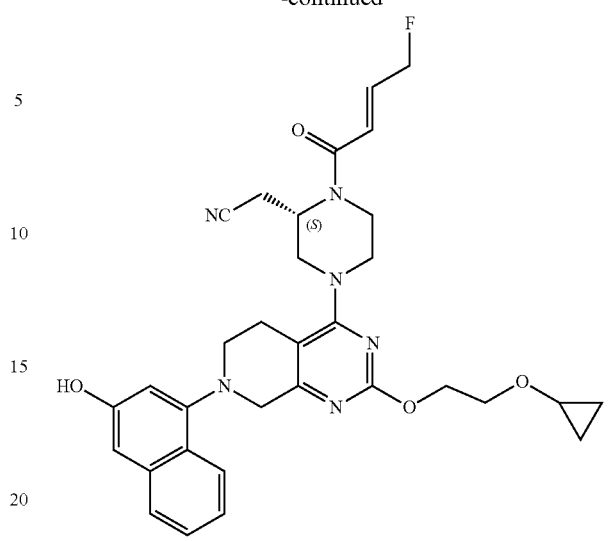
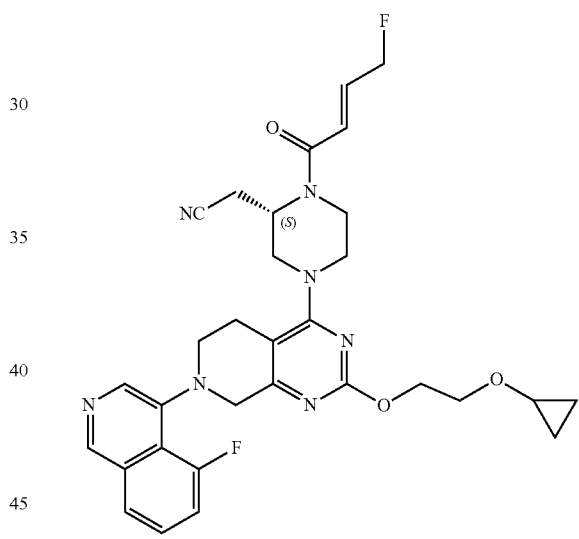
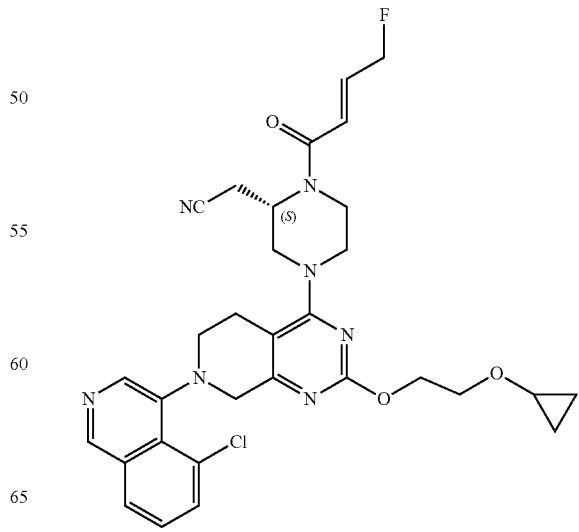

589
-continued
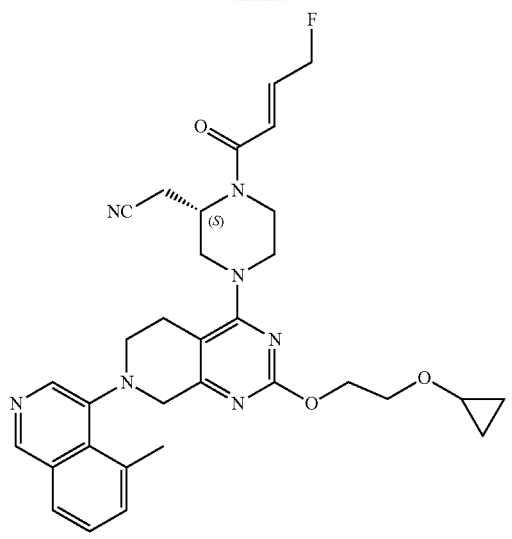
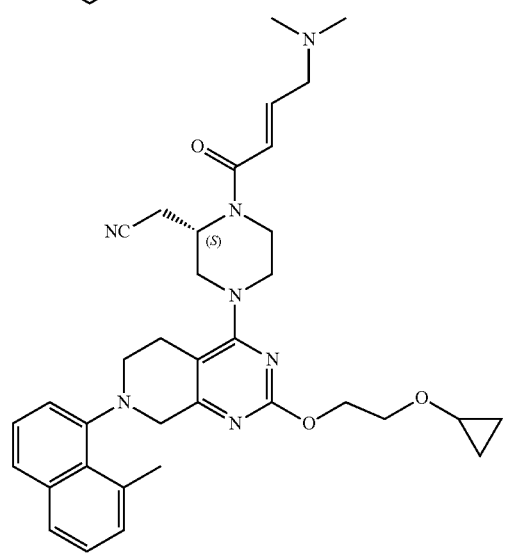
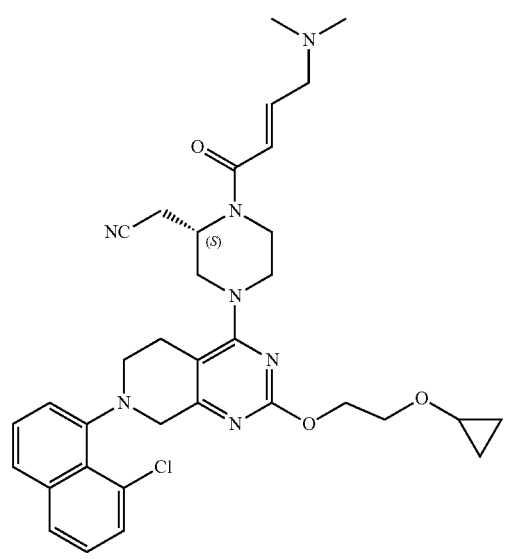
590
-continued

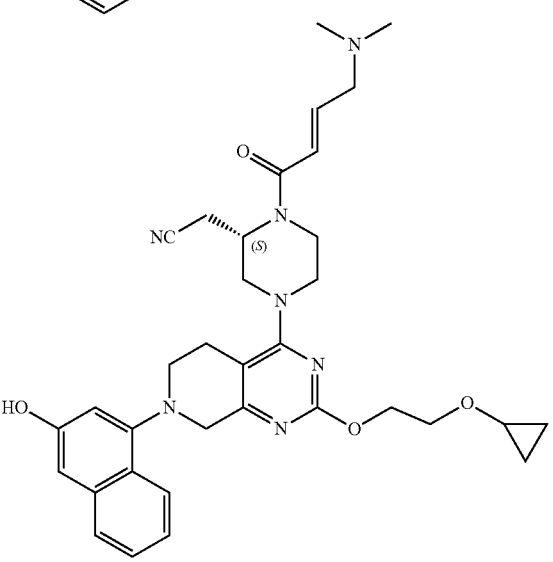
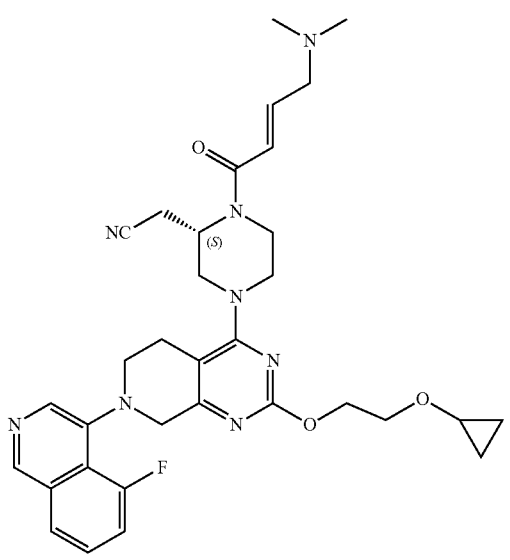

591
-continued
592
-continued
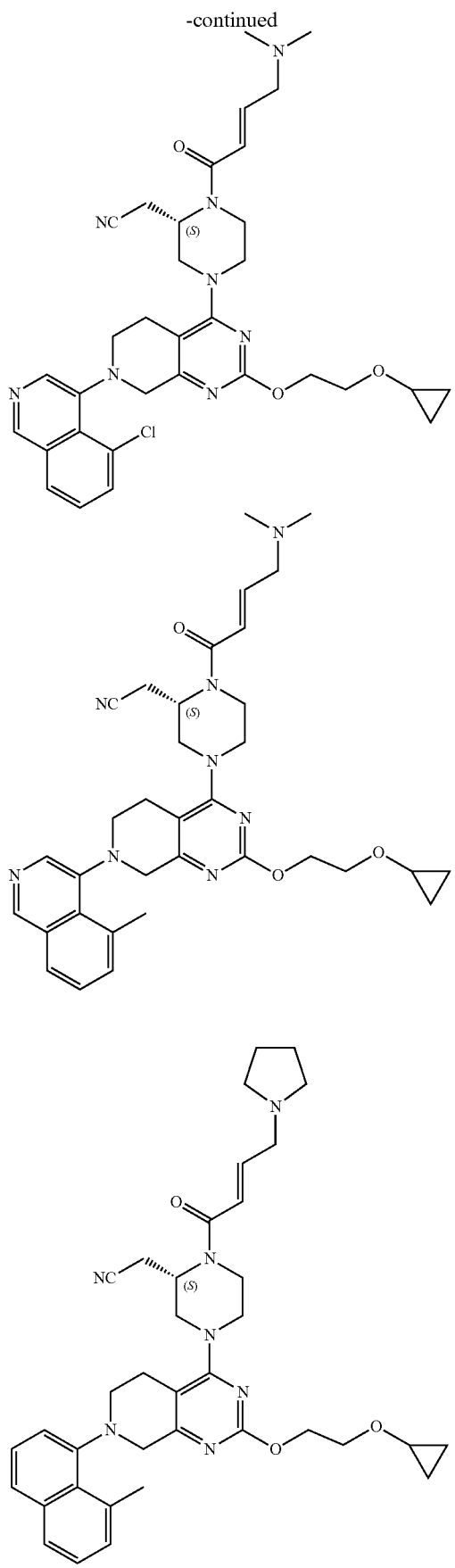
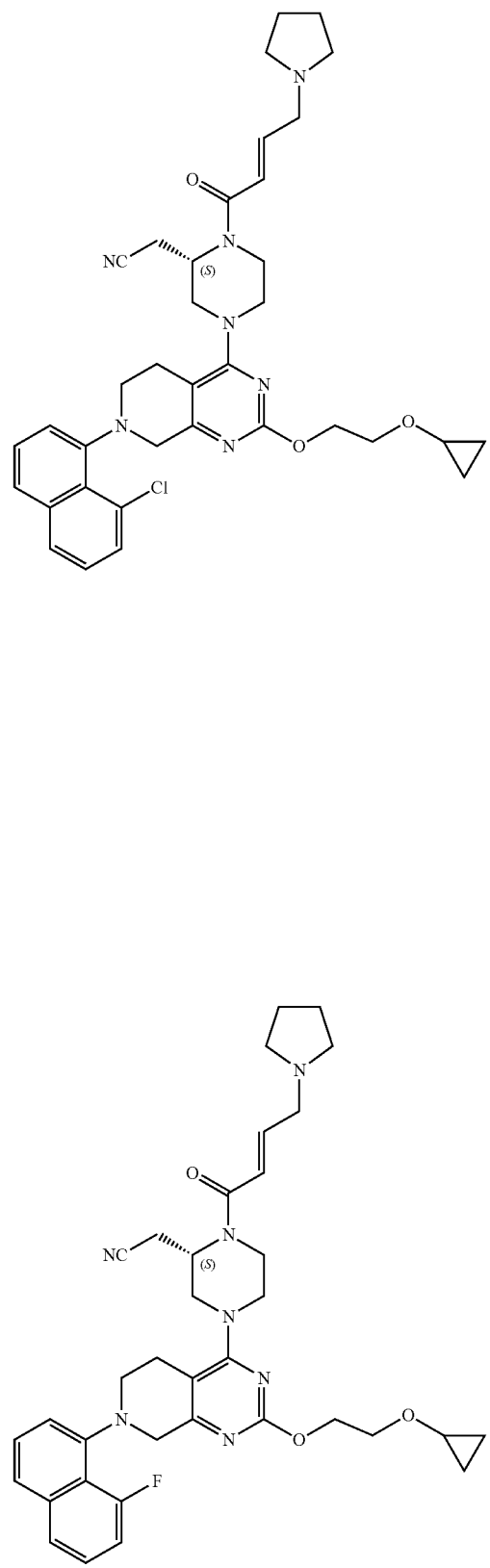

593
-continued
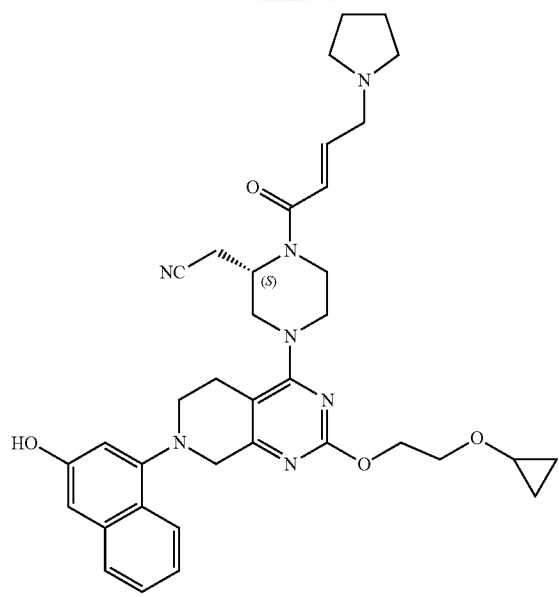
594
-continued
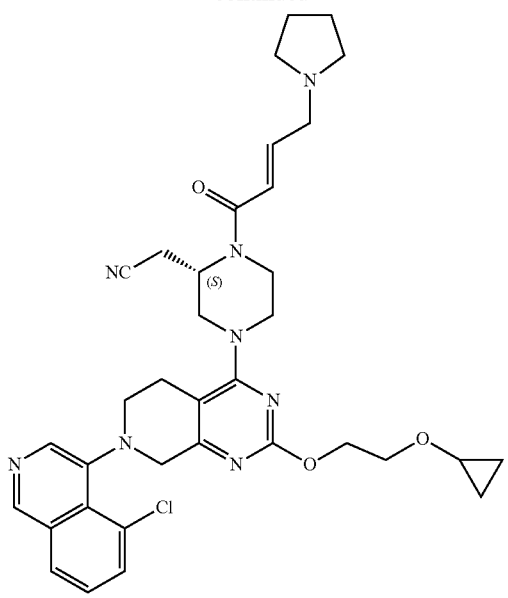
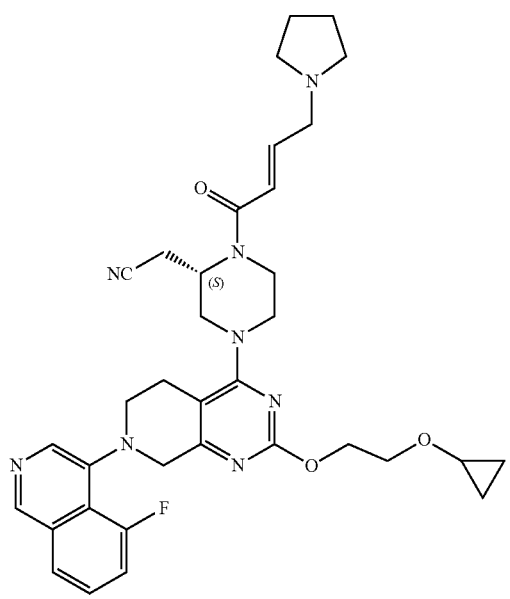
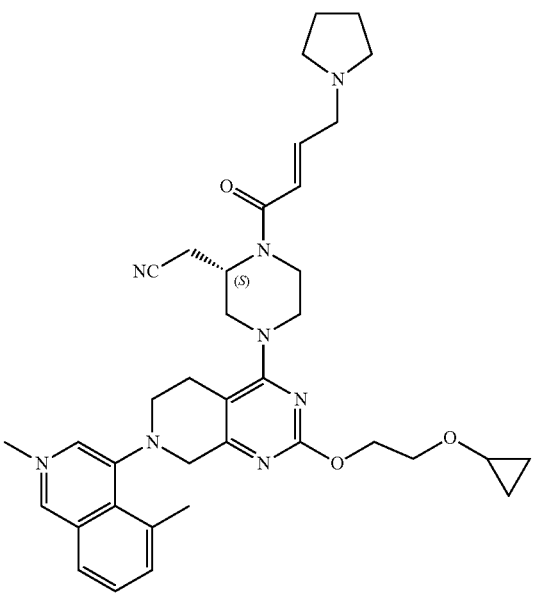

595
-continued
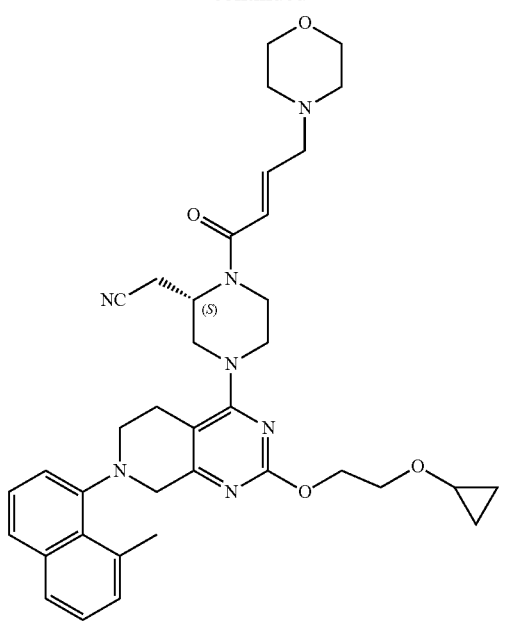
596
-continued
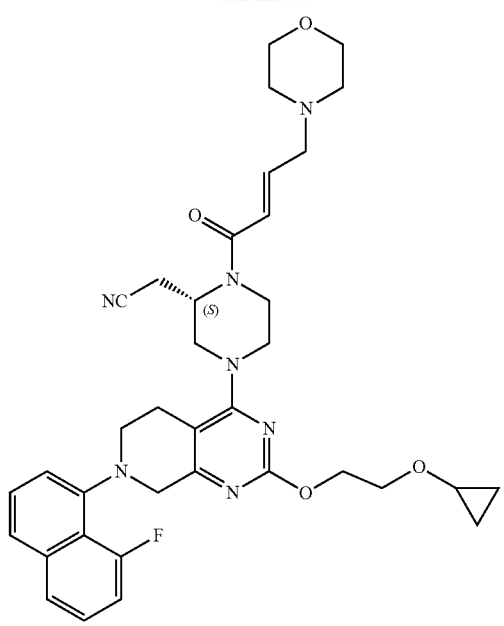
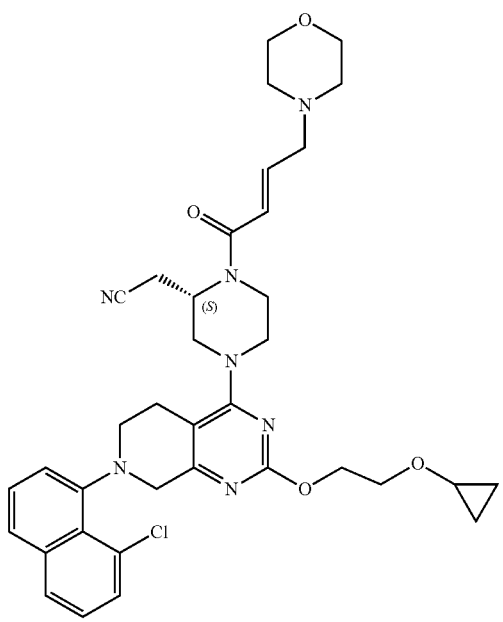
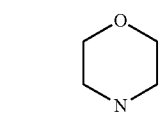

597
-continued
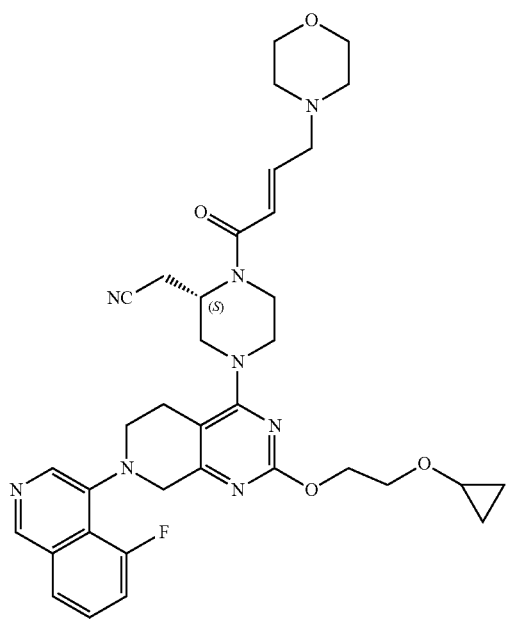
598
-continued
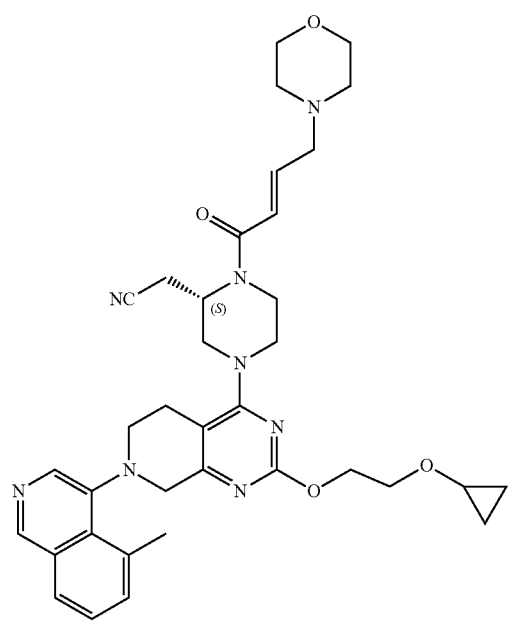

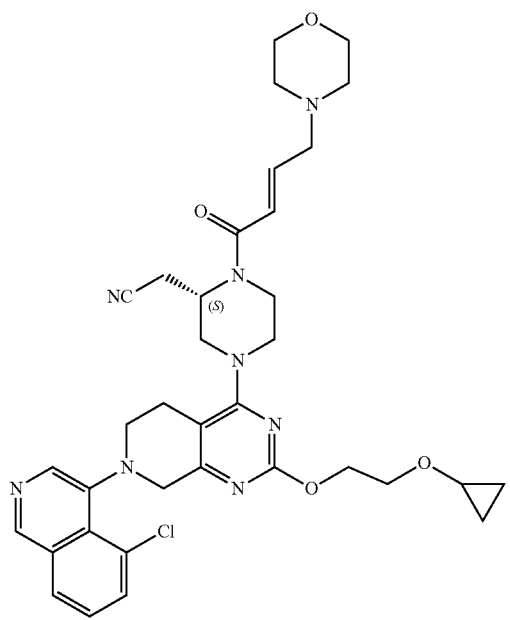
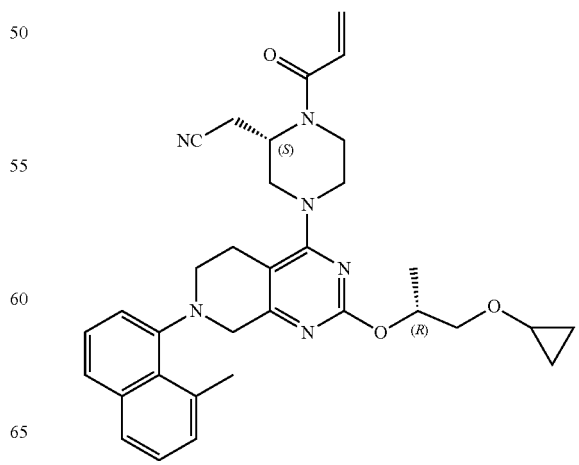

599
-continued
600
-continued
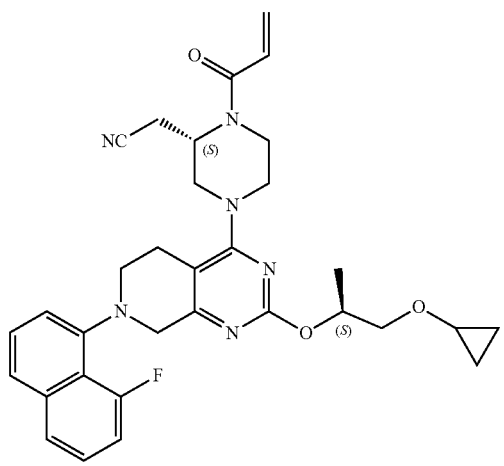
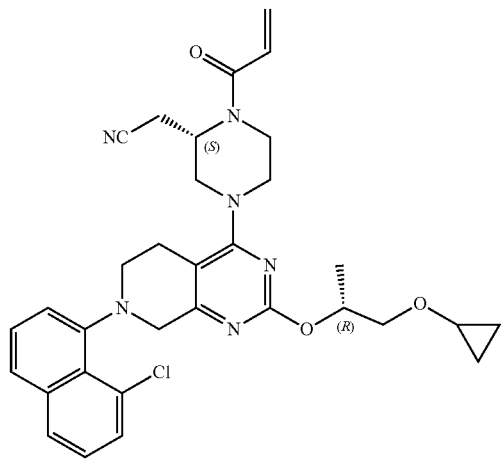
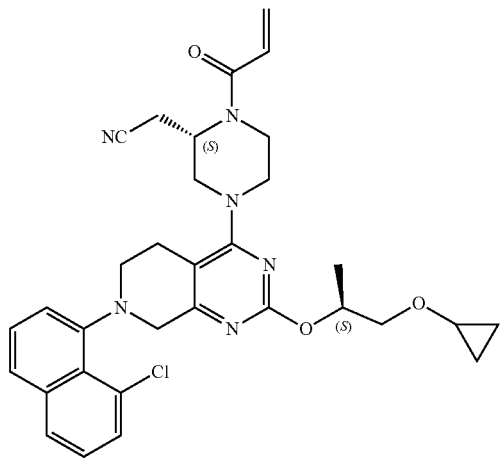
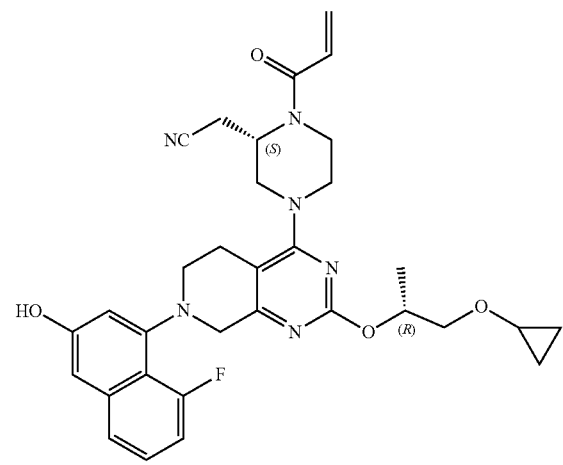

601
-continued
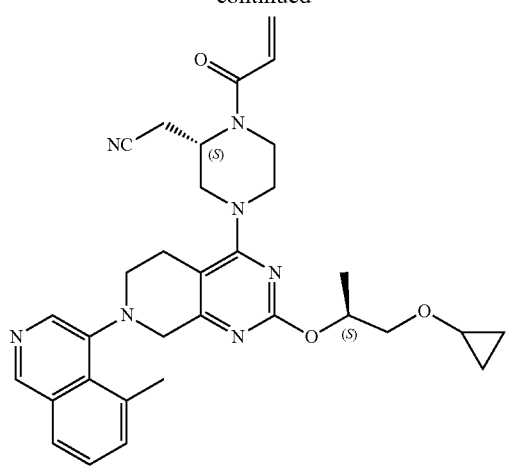
602
-continued
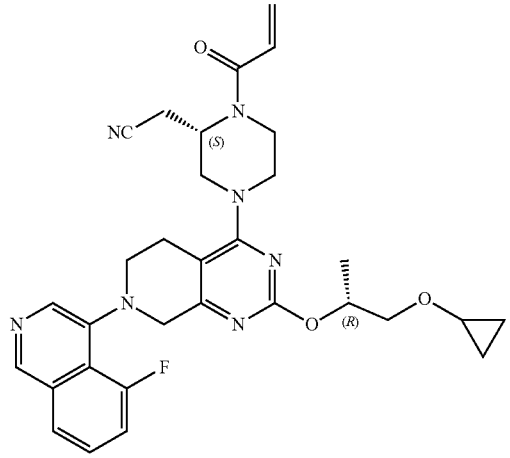
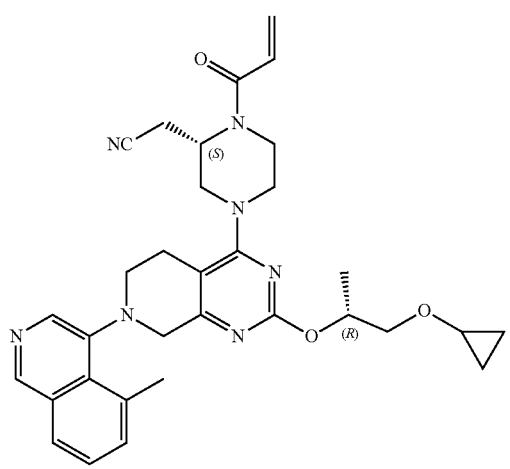
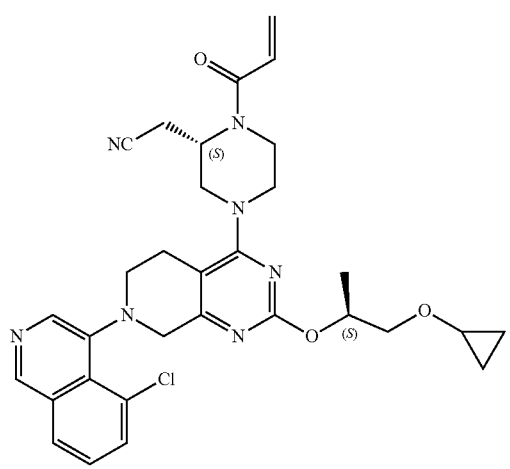
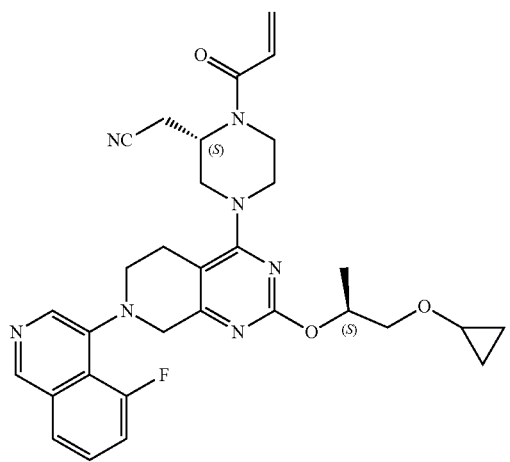
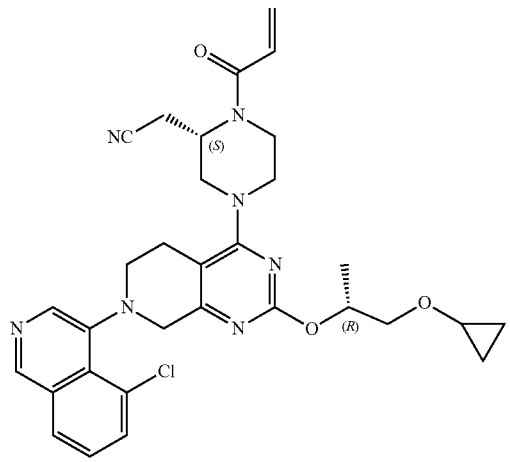

603
-continued
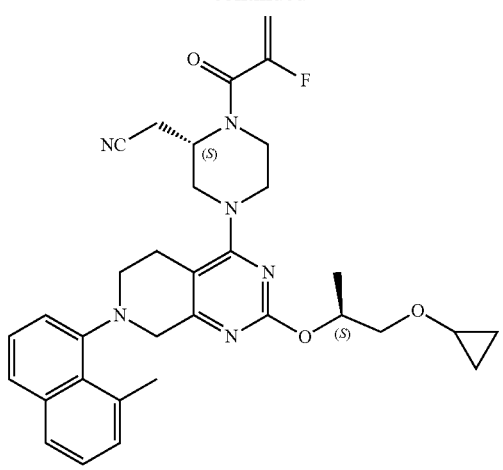
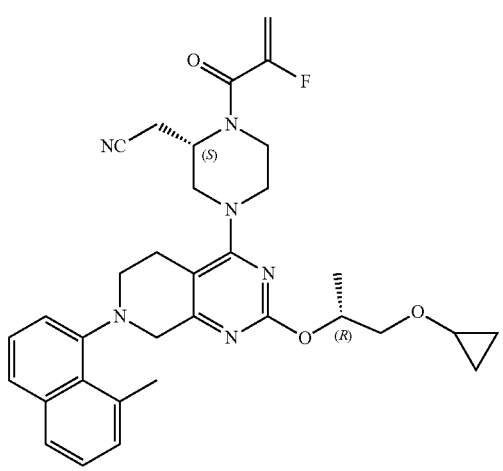
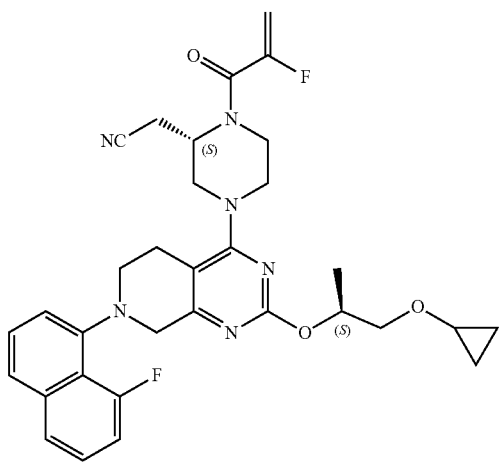
604
-continued
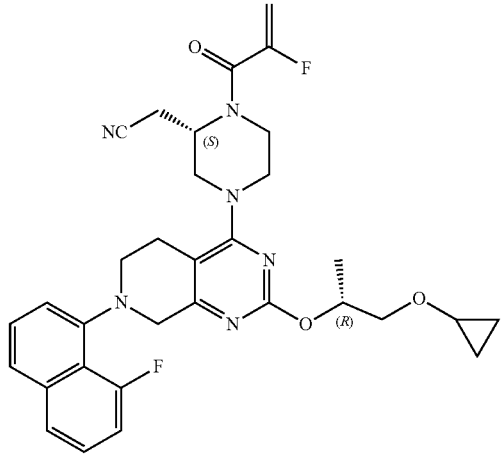
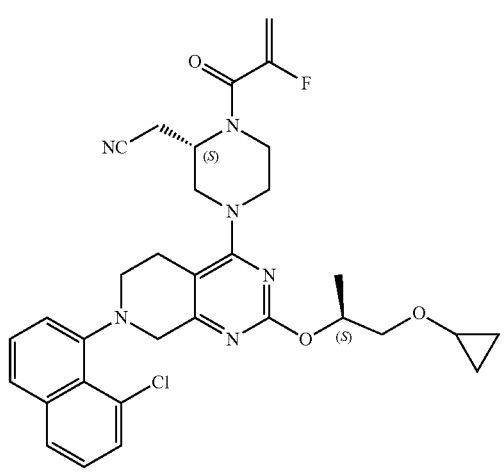
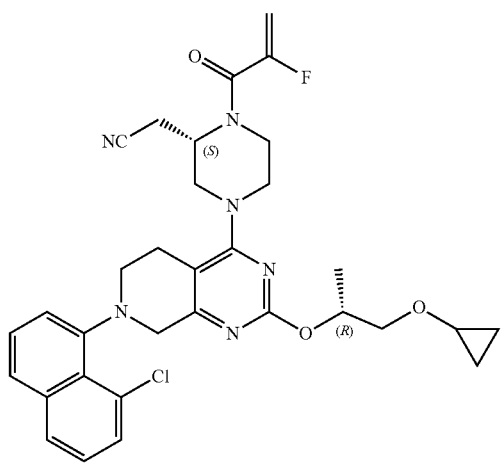

605
-continued
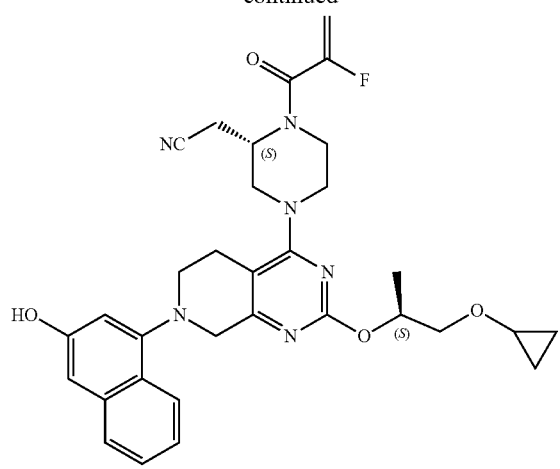
606
-continued
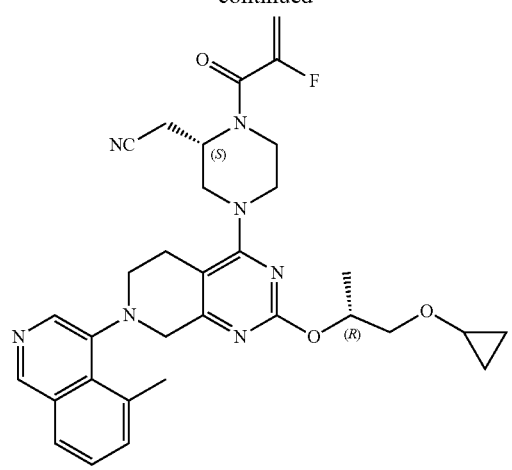
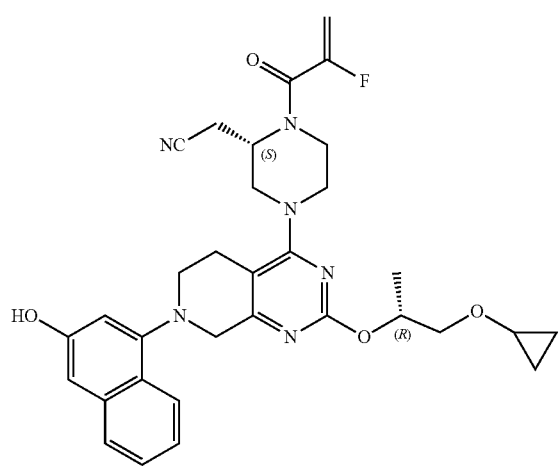
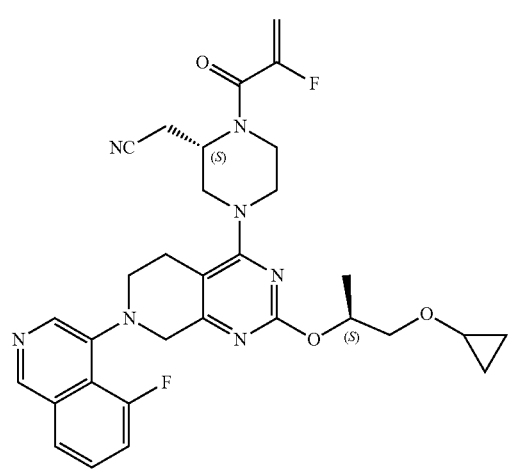
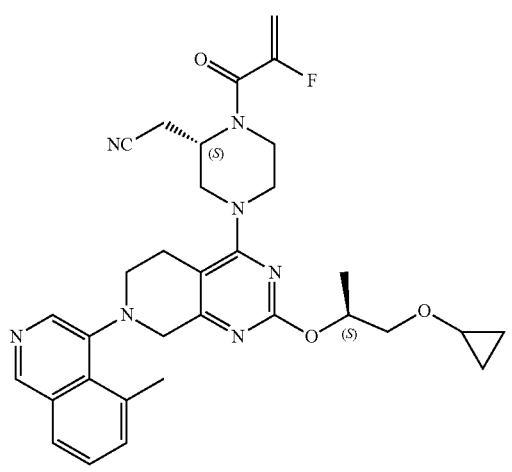
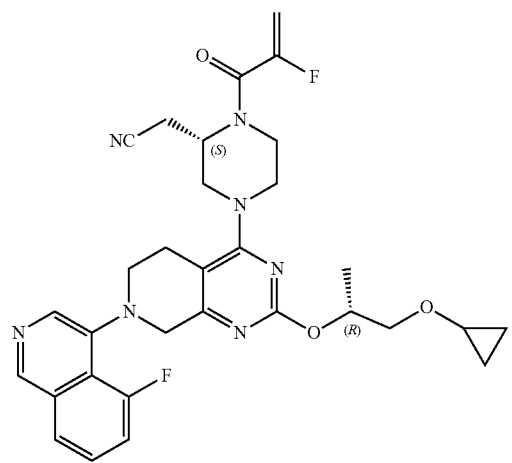

607
-continued

608
-continued

609
-continued
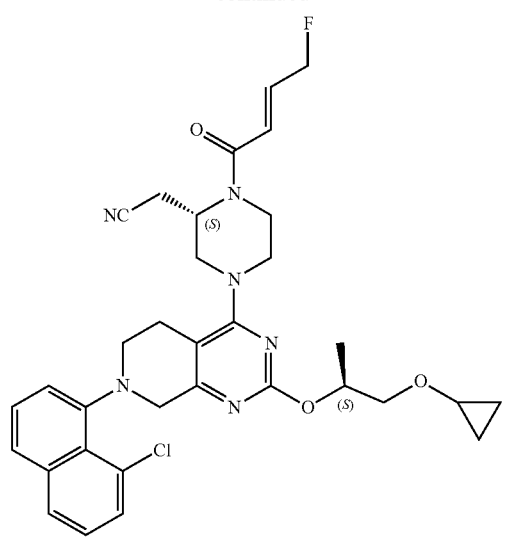
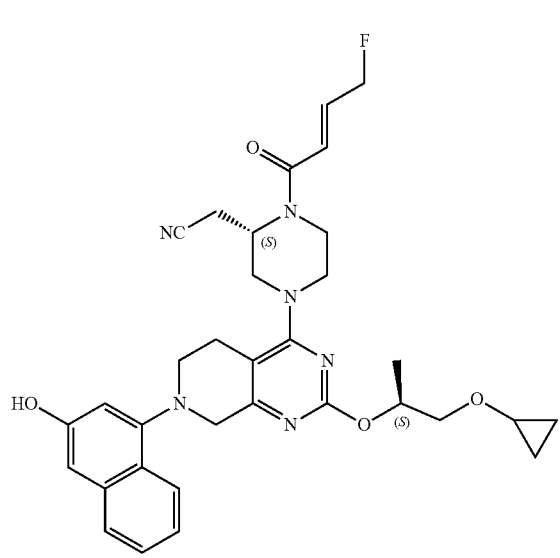
610
-continued
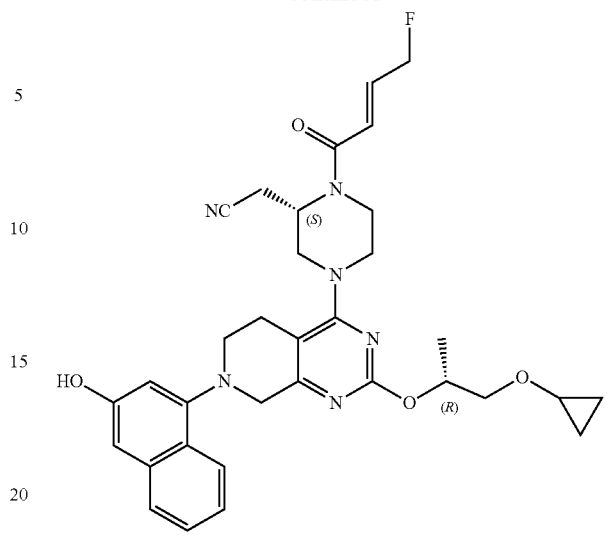
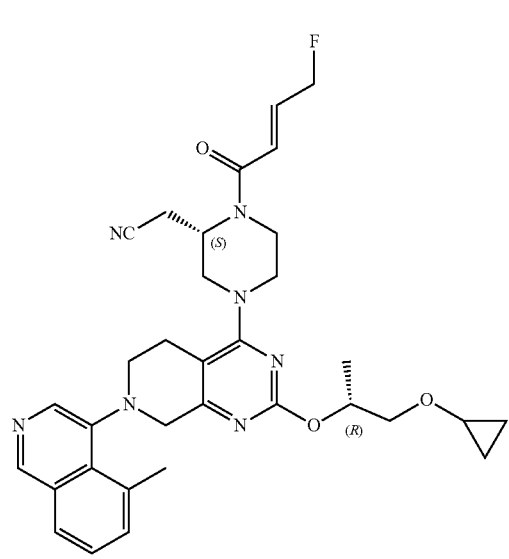

611
-continued
612
-continued
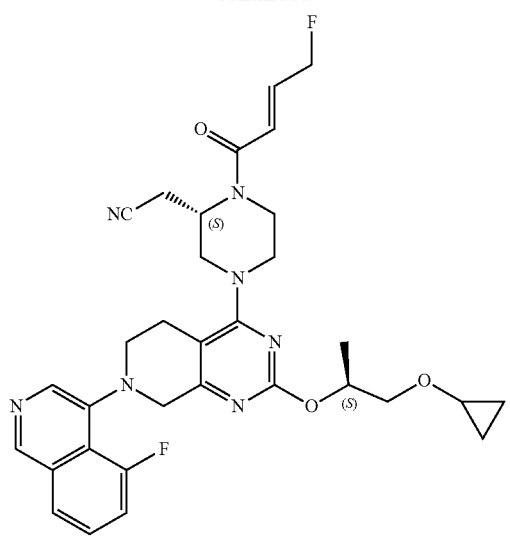
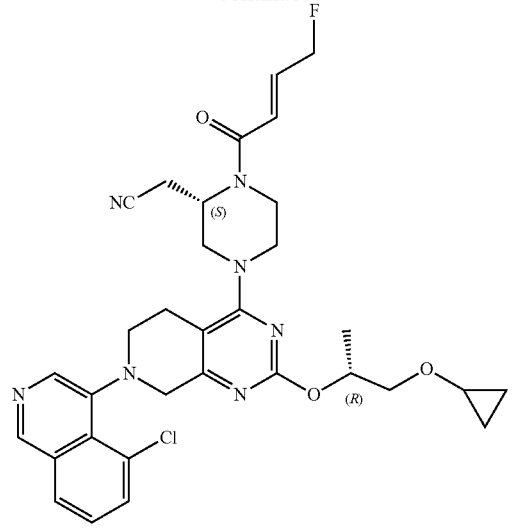
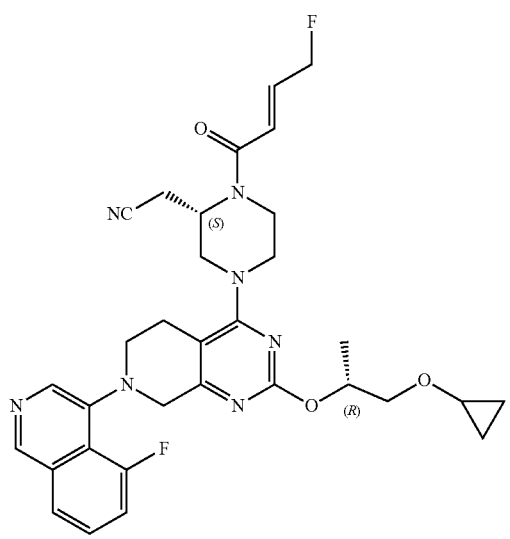
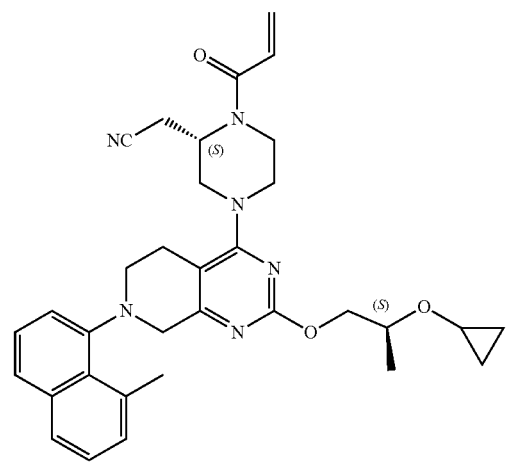
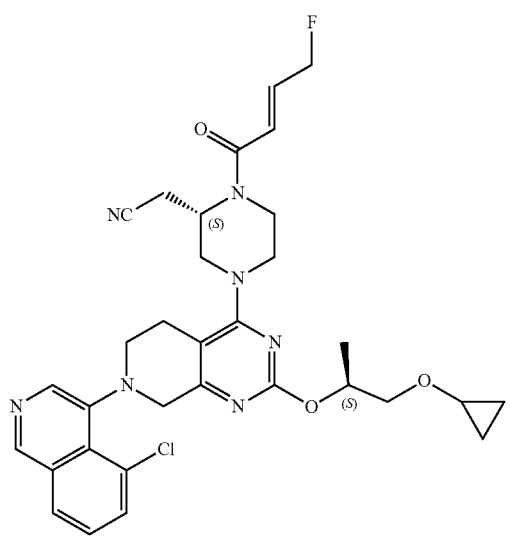
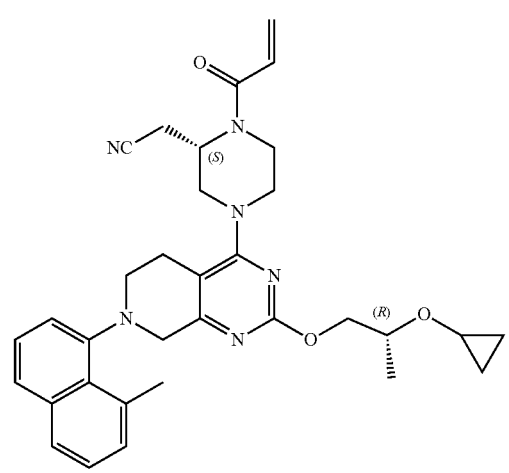

613
-continued
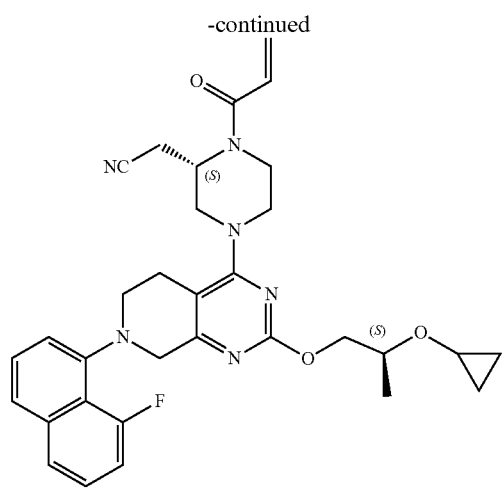
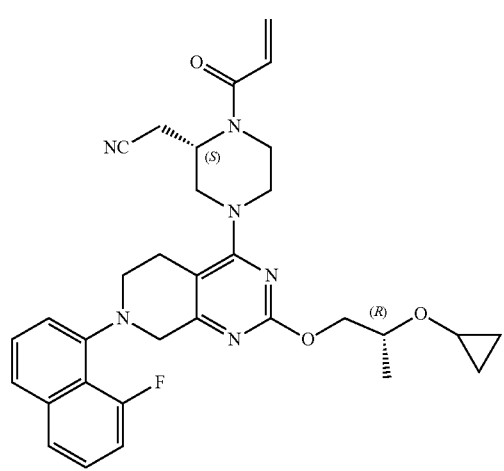
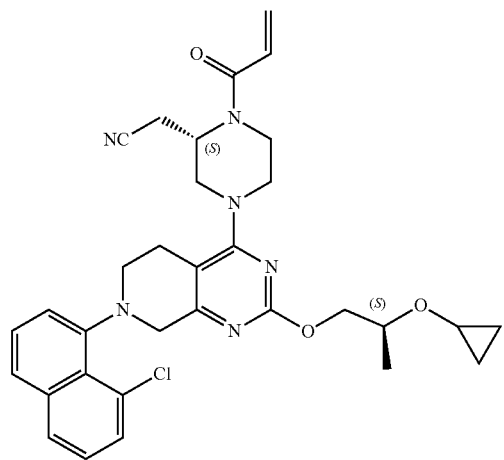
614
-continued
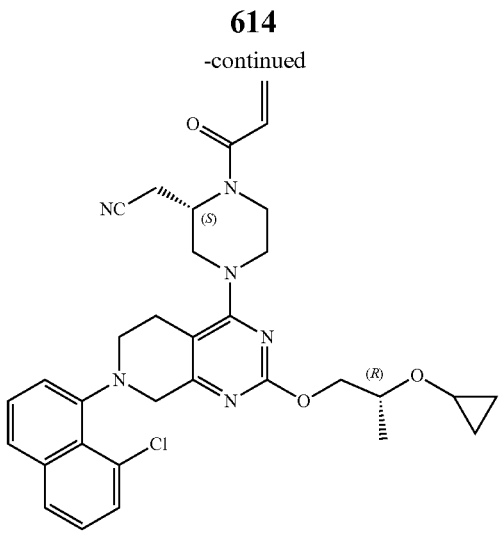
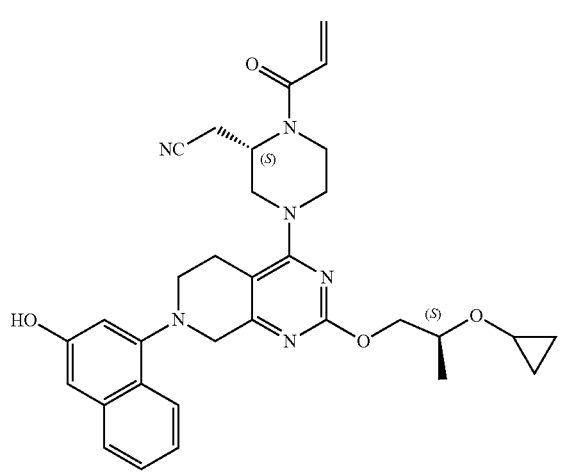
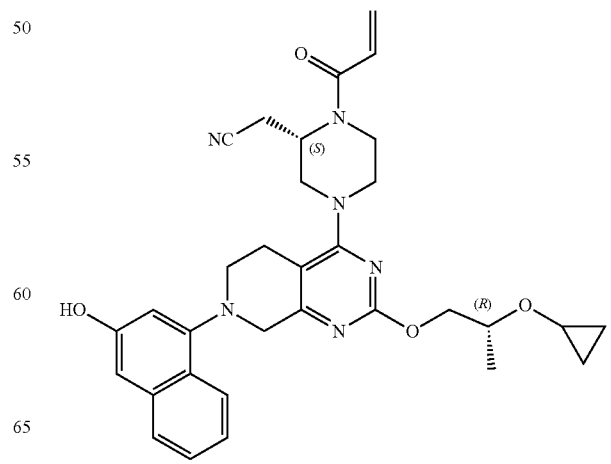

615
-continued
616
-continued
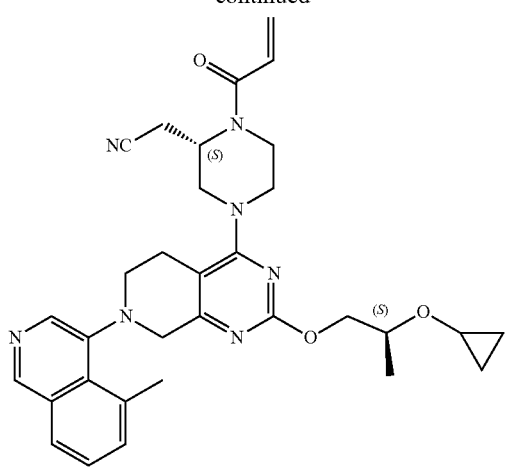
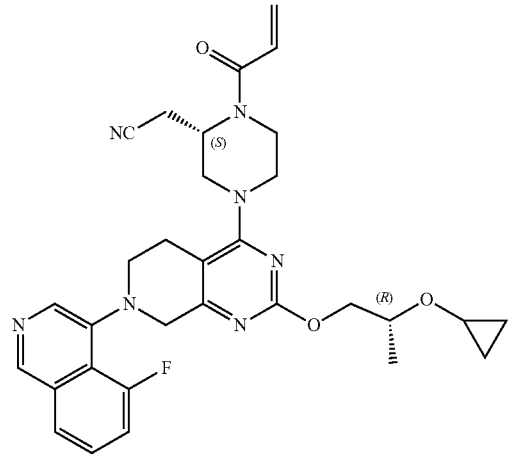
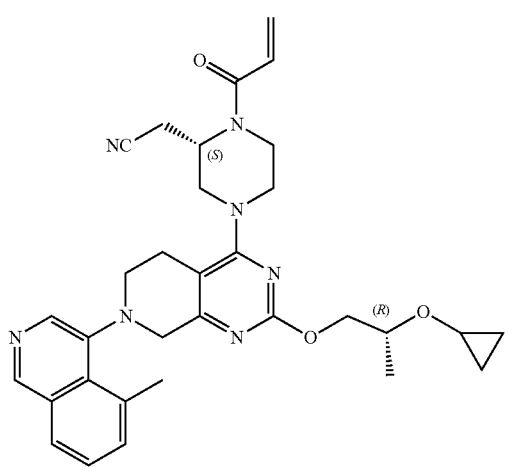
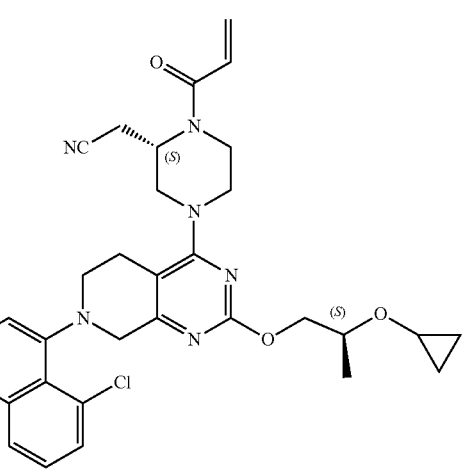
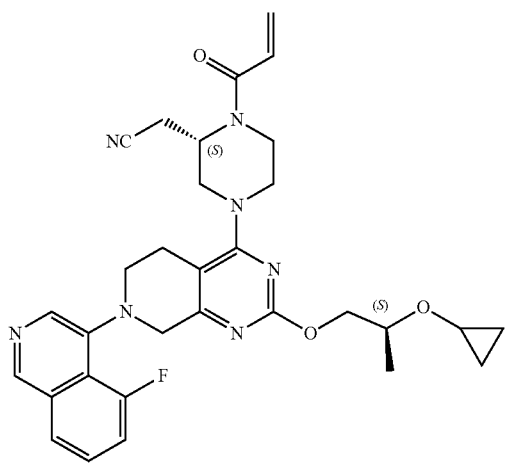
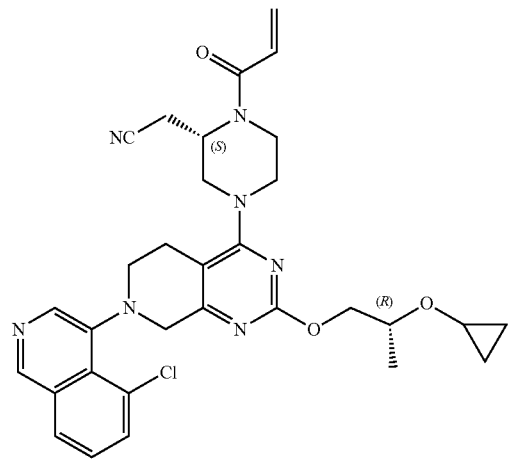

617
-continued
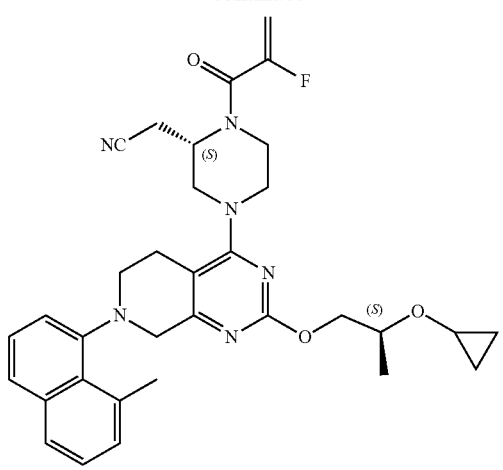
618
-continued
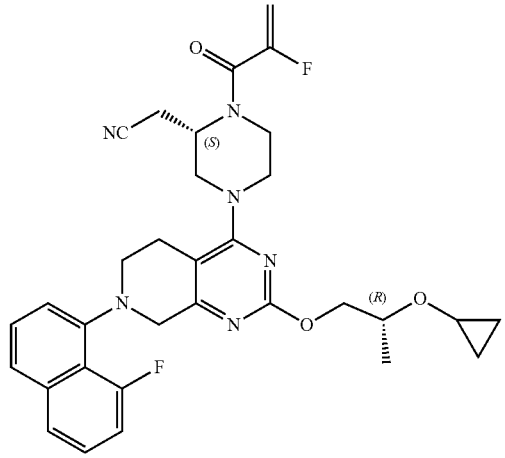
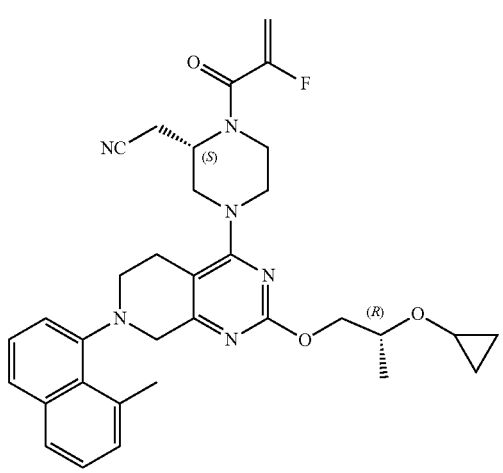
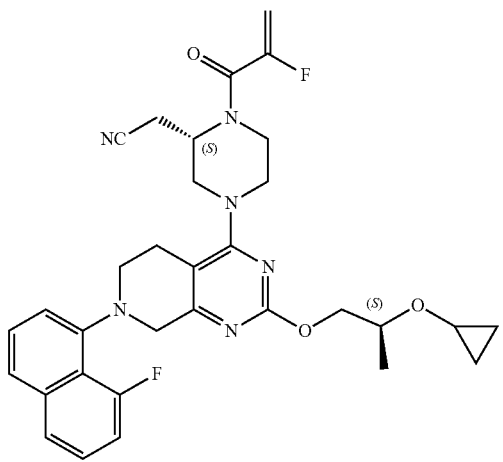
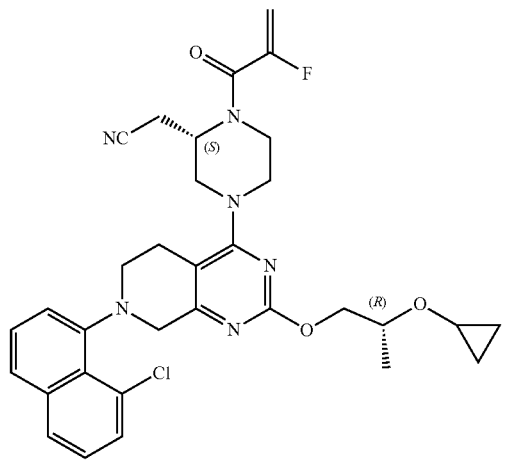

619
-continued
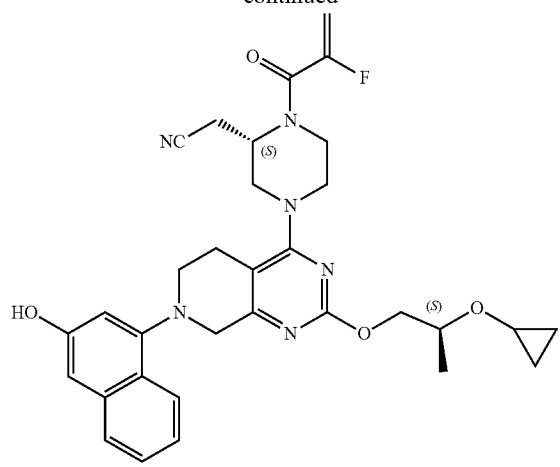
620
-continued
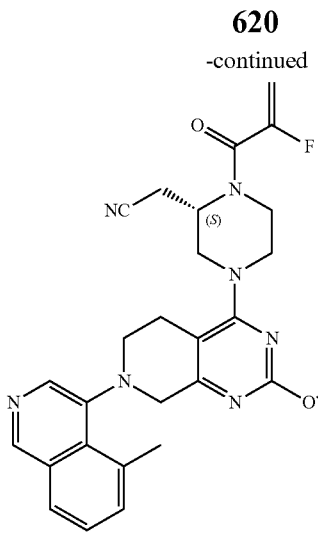
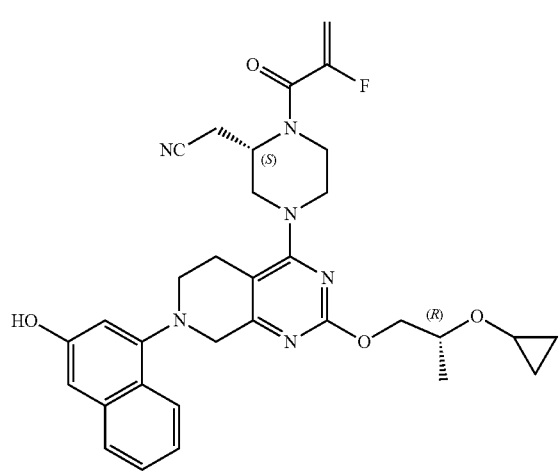
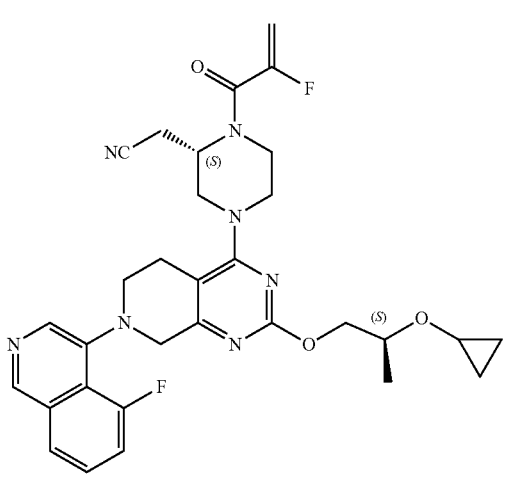
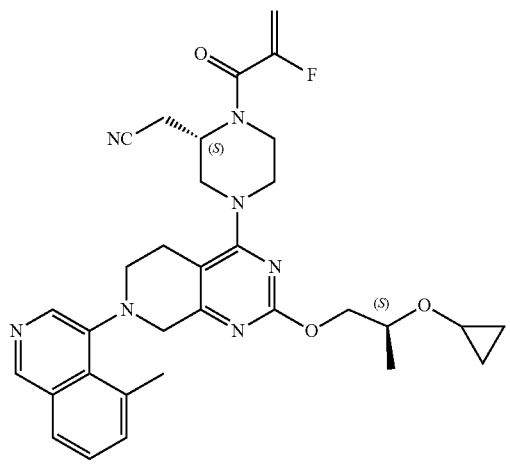
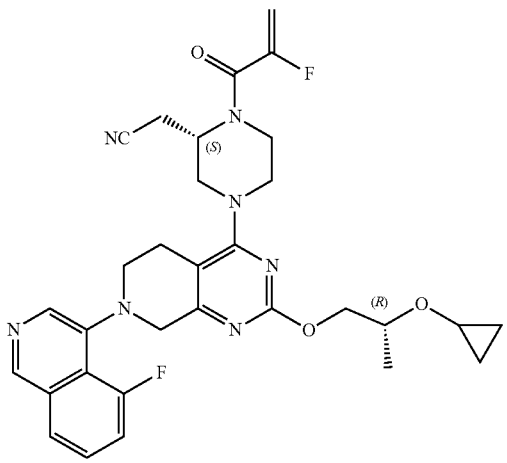

621
-continued
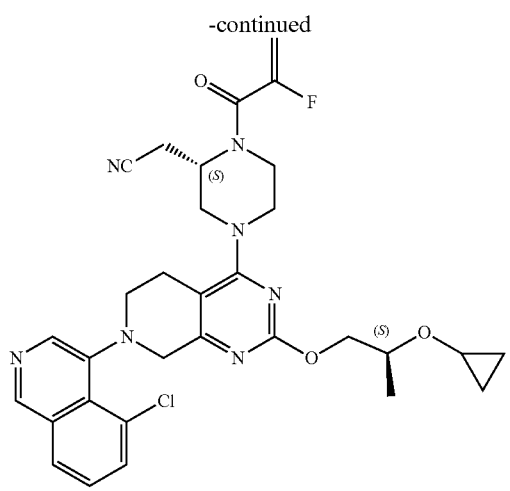
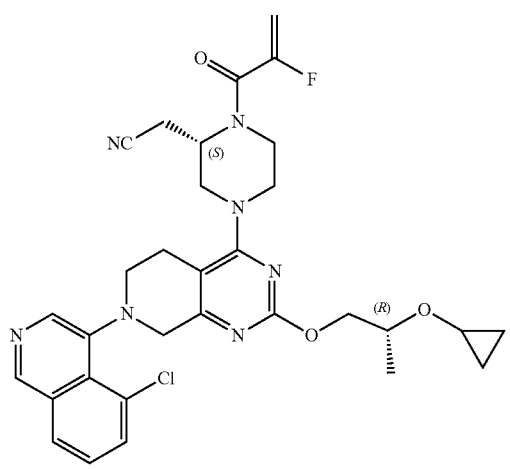
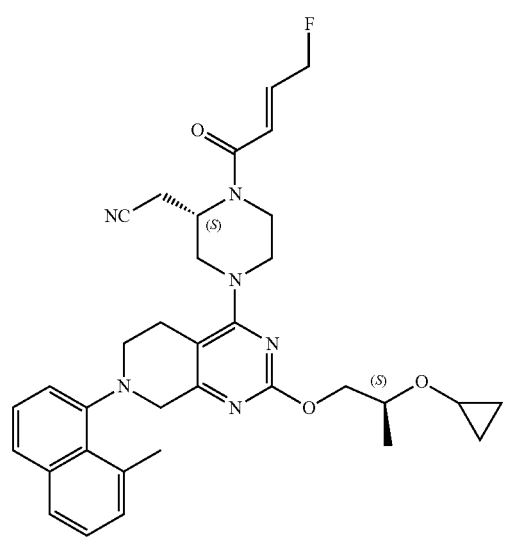
622
-continued
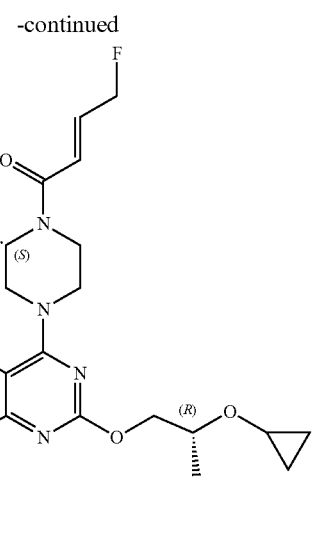
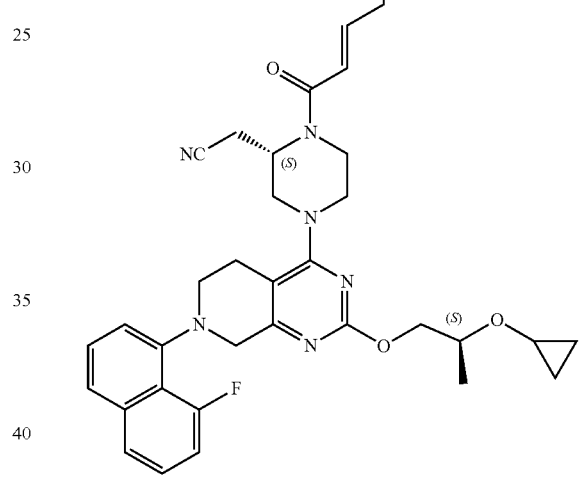
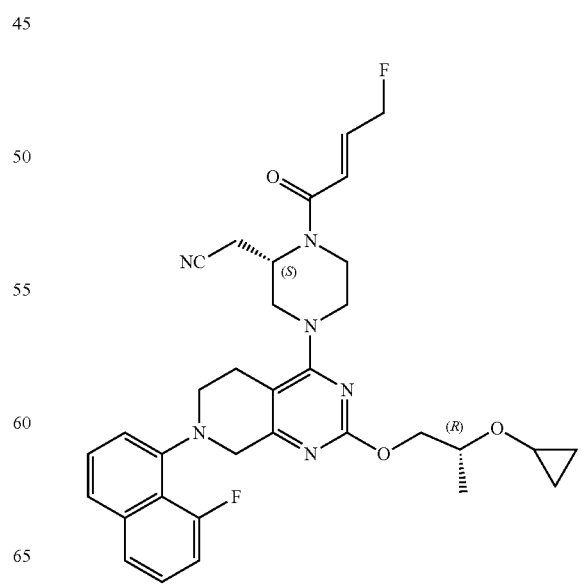

623
-continued
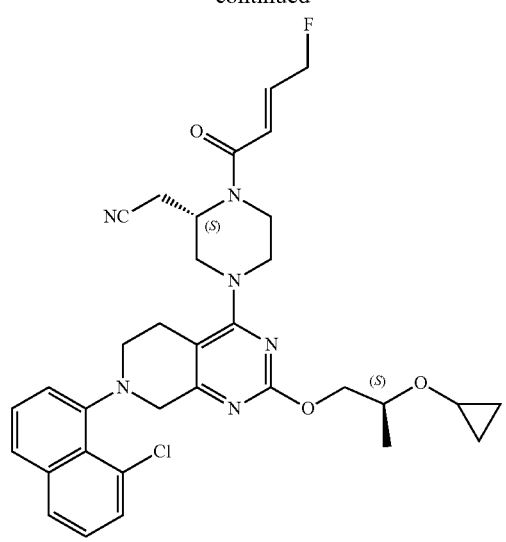
624
-continued
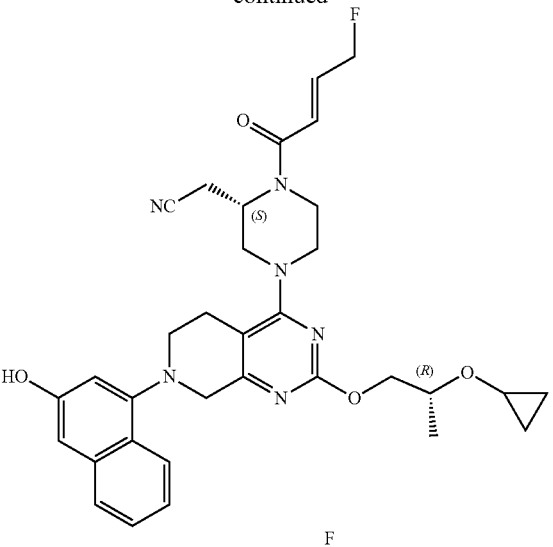
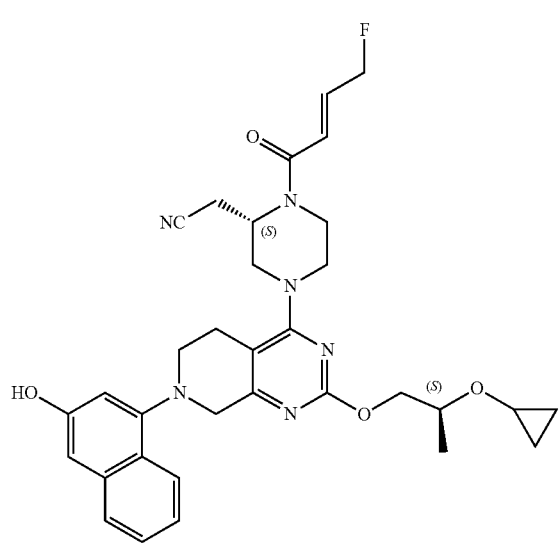
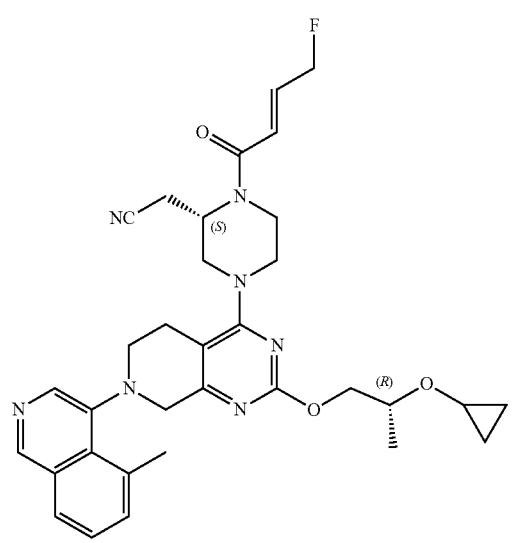

625
-continued
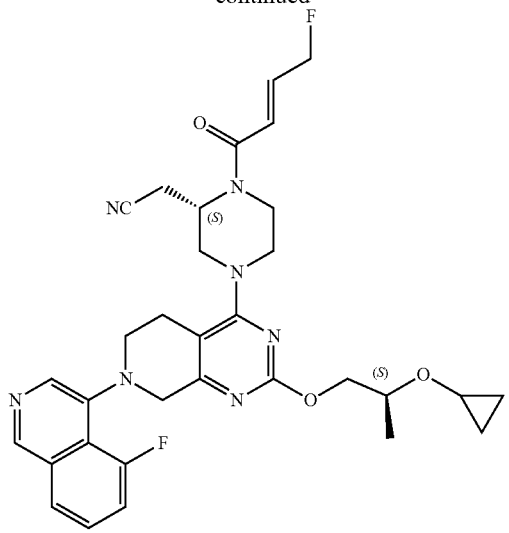
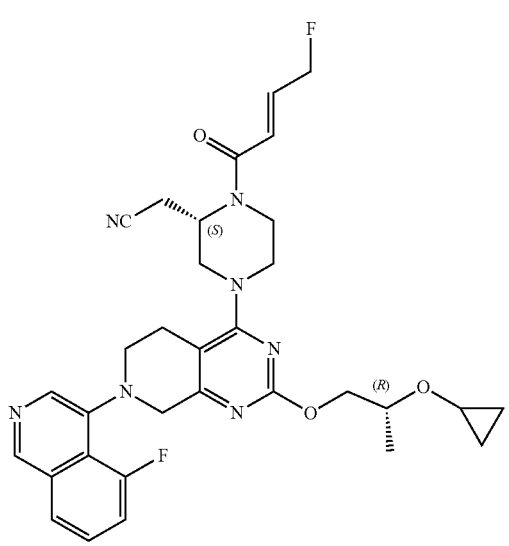
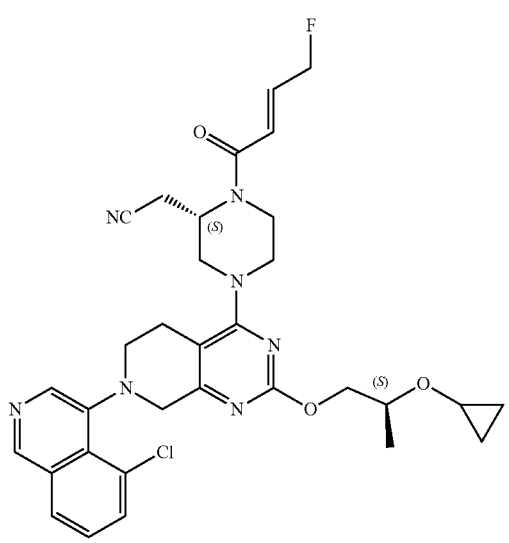
626
-continued
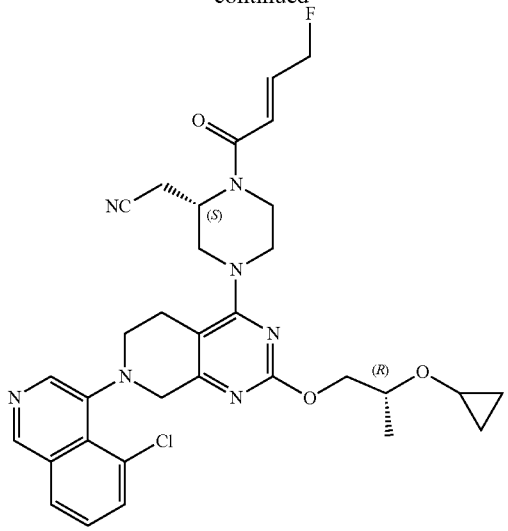
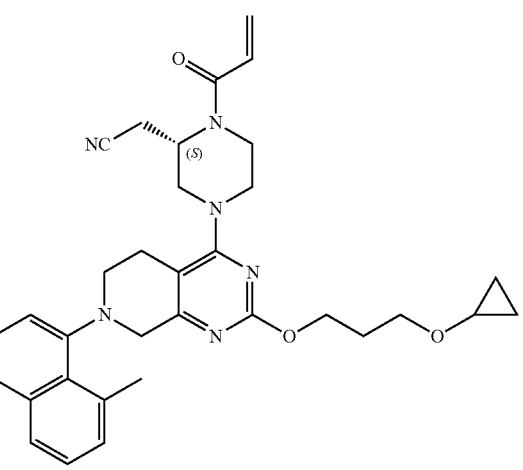
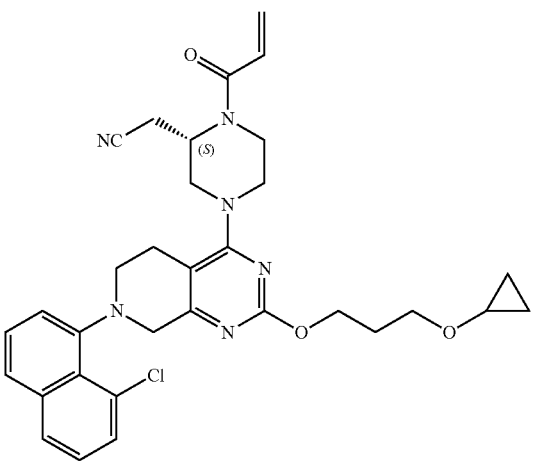

627
-continued
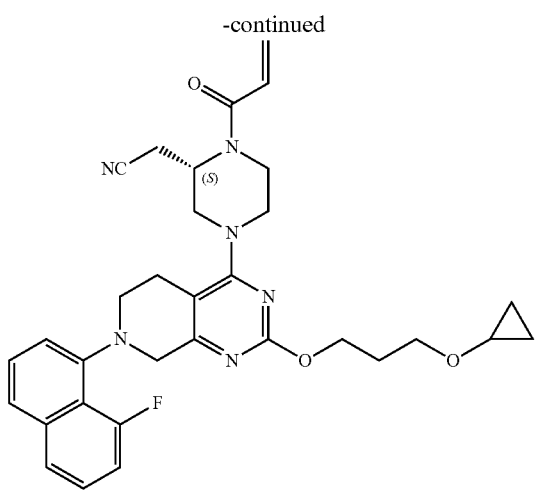
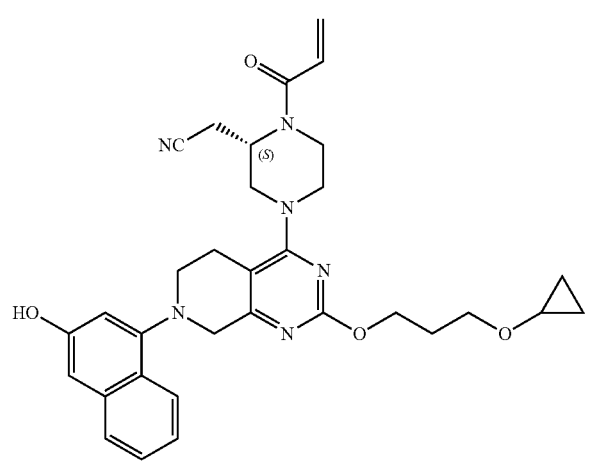
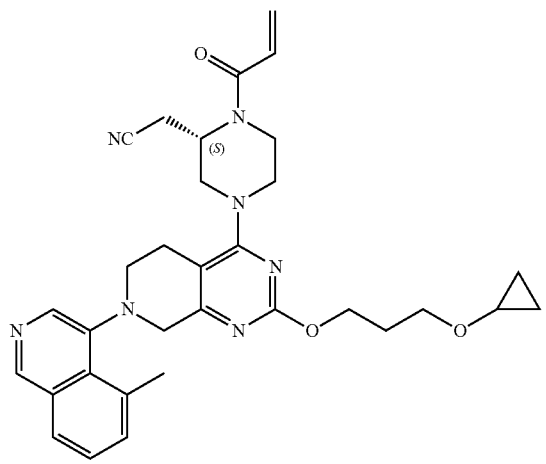
628
-continued
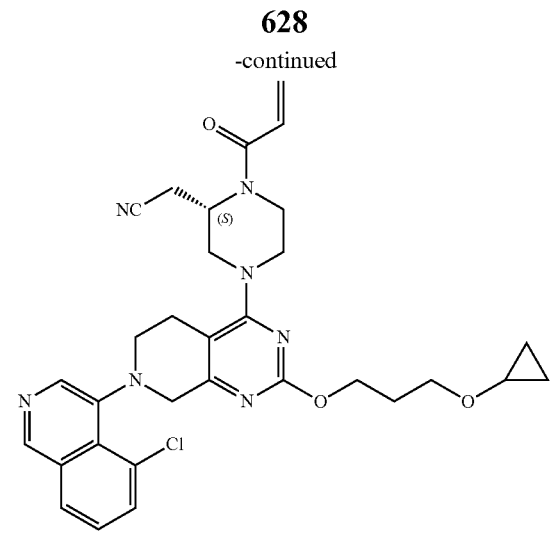
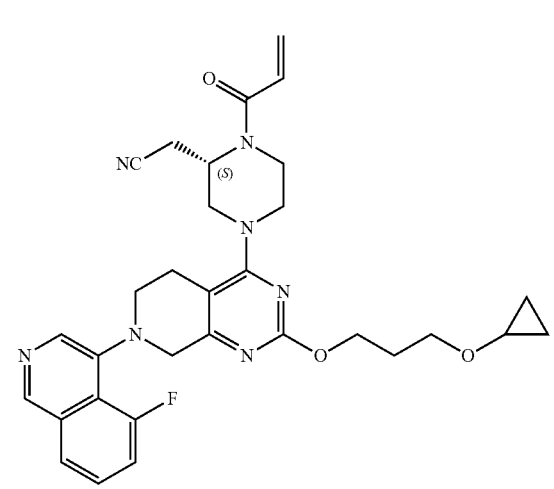
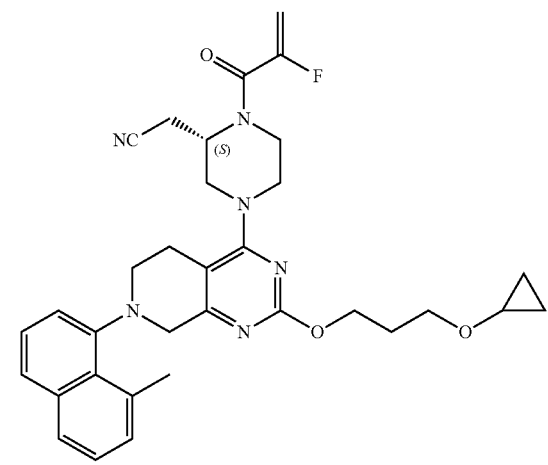

629
-continued
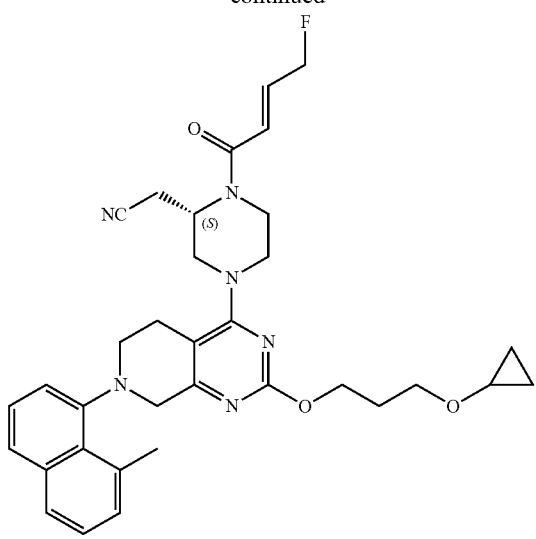
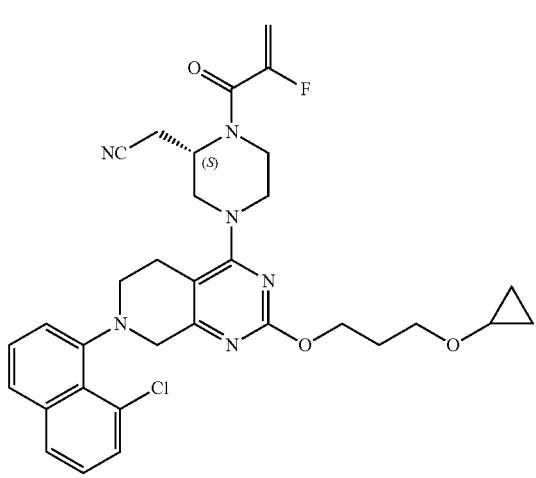
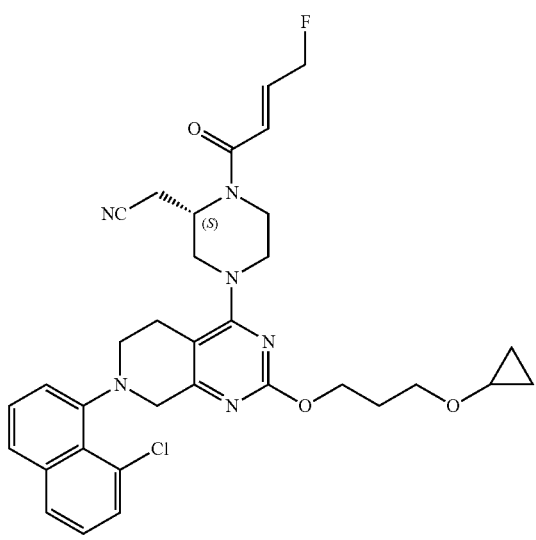
630
-continued
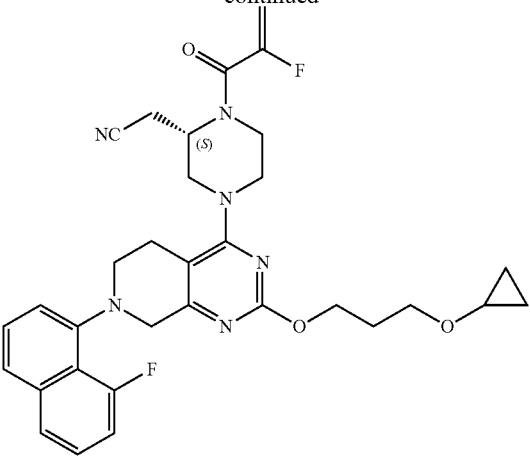
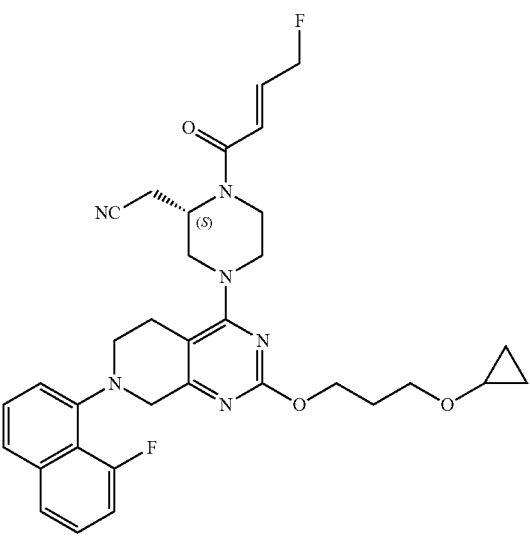
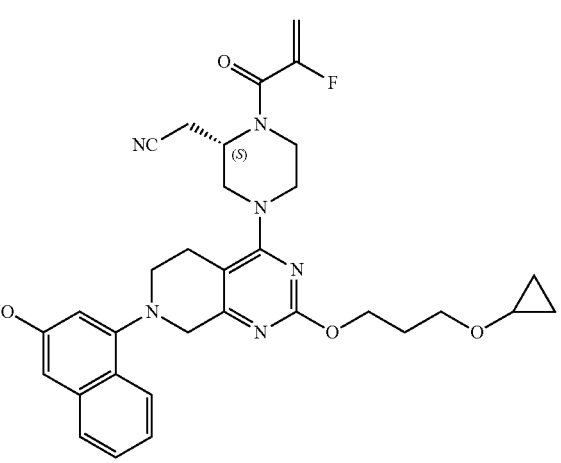

631
-continued
632
-continued
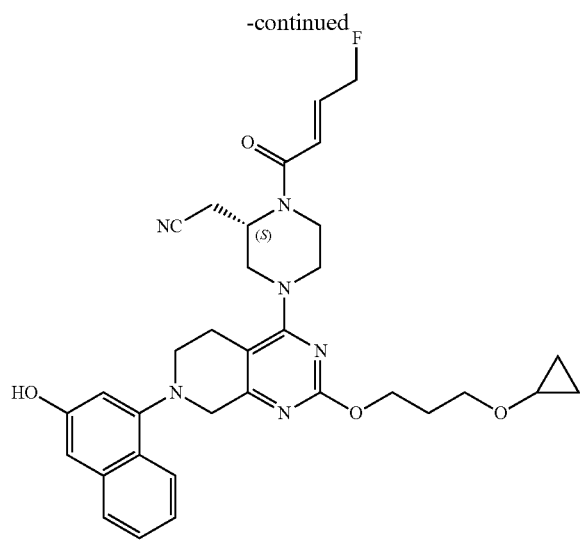
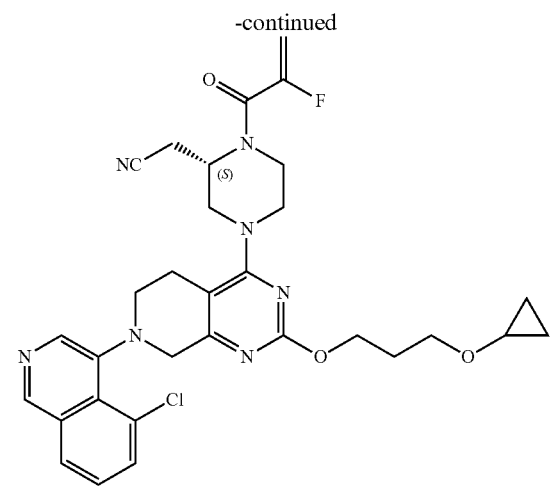
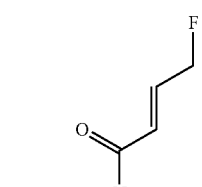
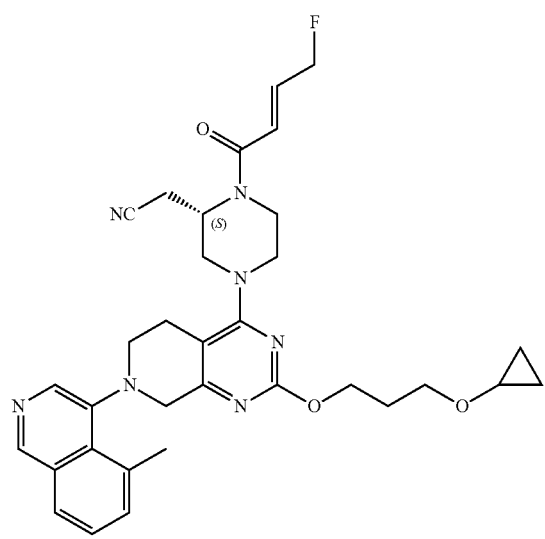
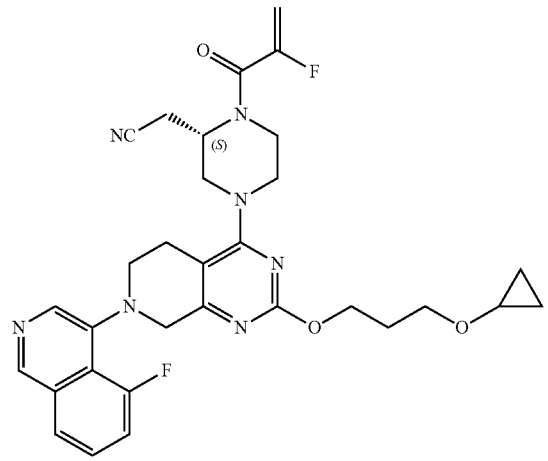

633
-continued
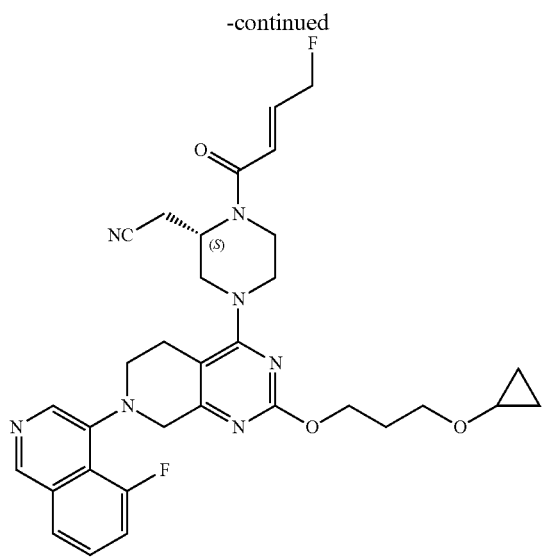
634
-continued
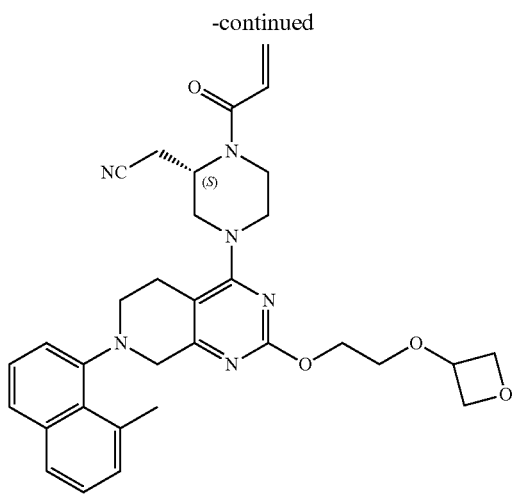
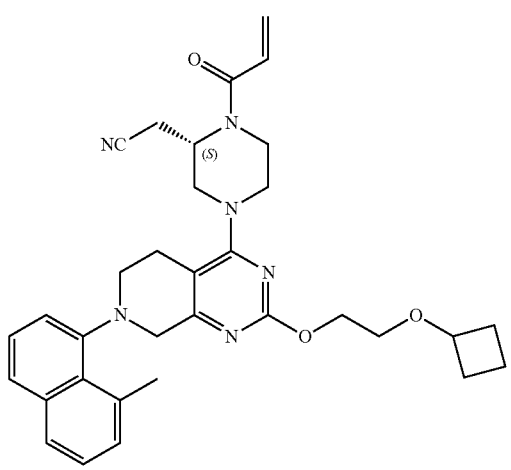
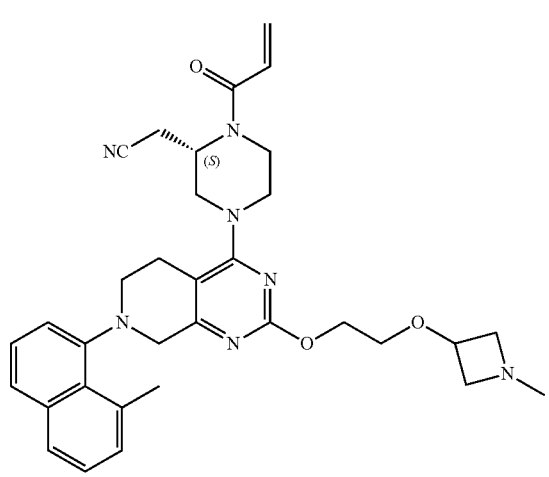
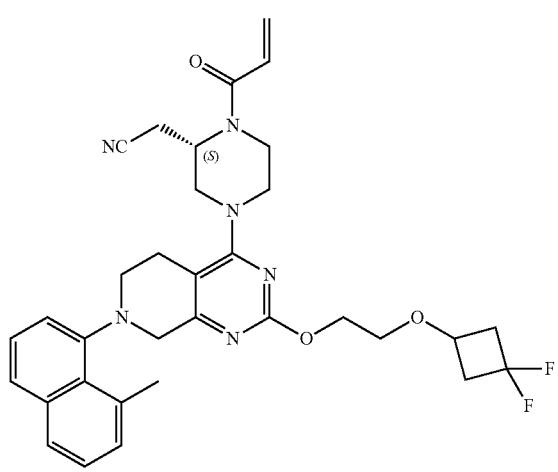
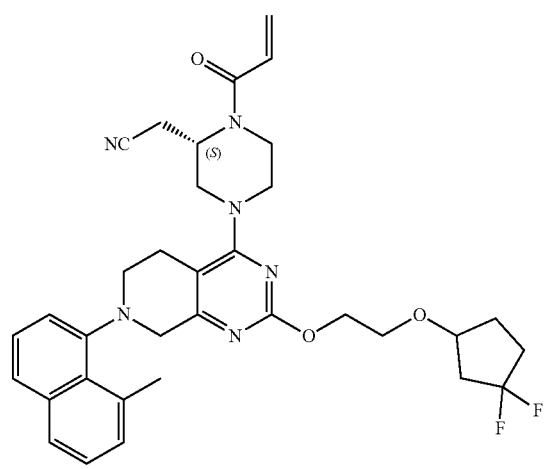

635
-continued
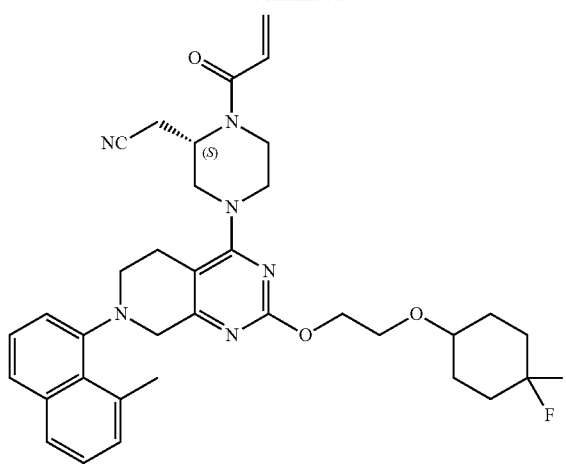
636
-continued
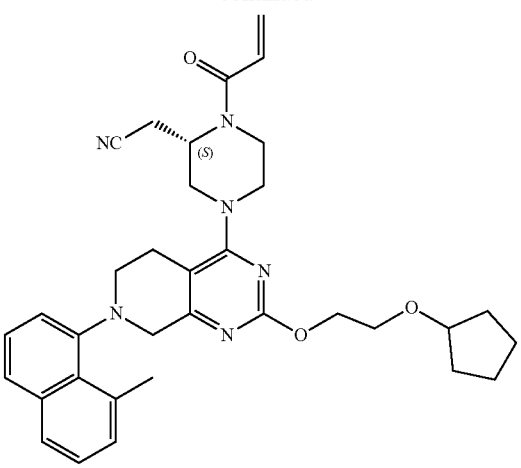
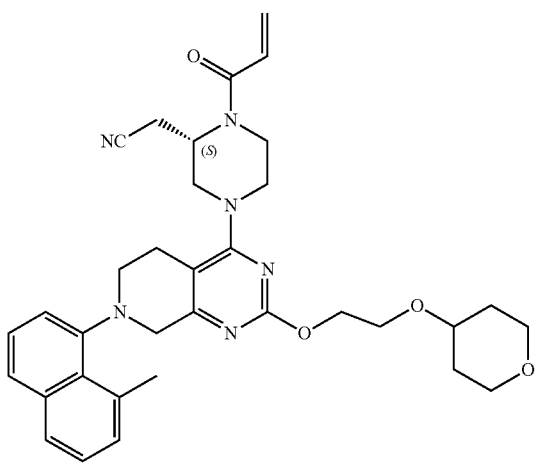
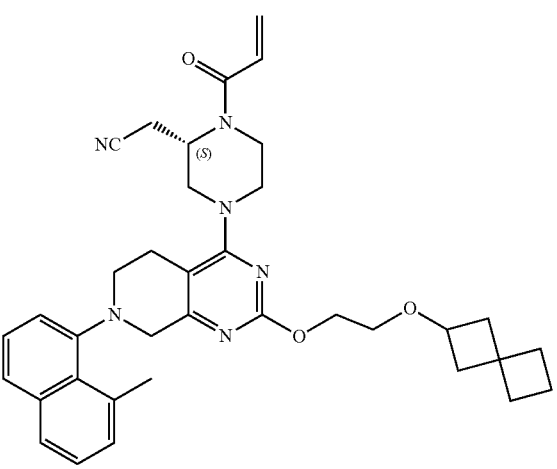

637
-continued
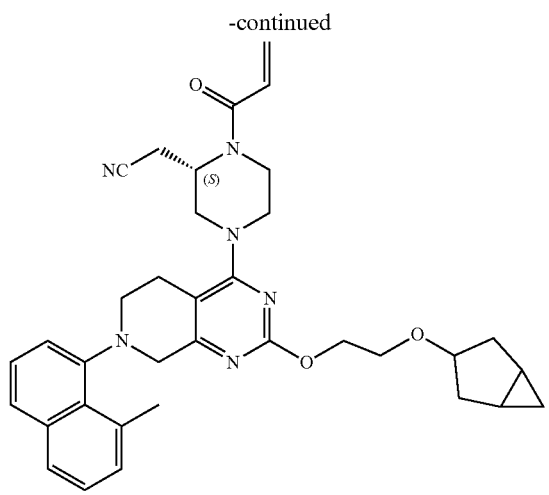
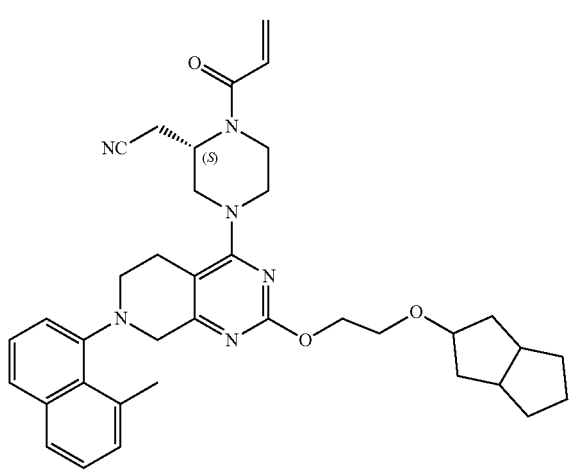
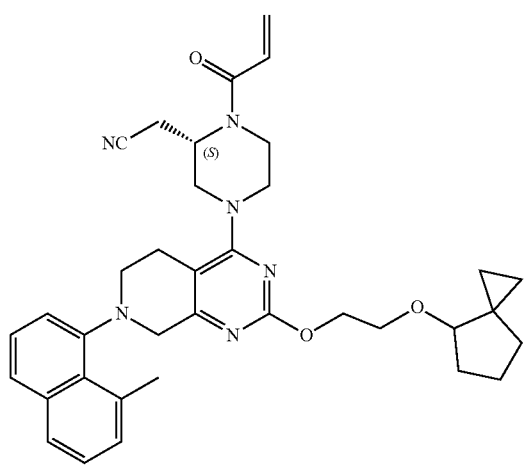
638
-continued
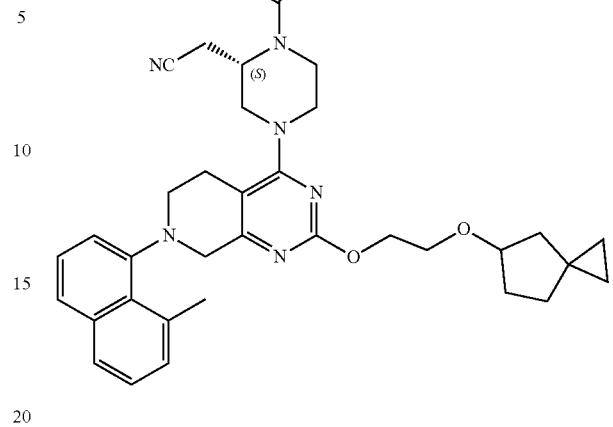
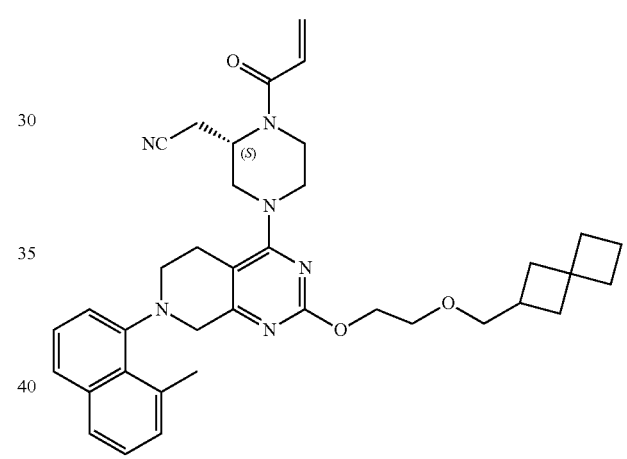
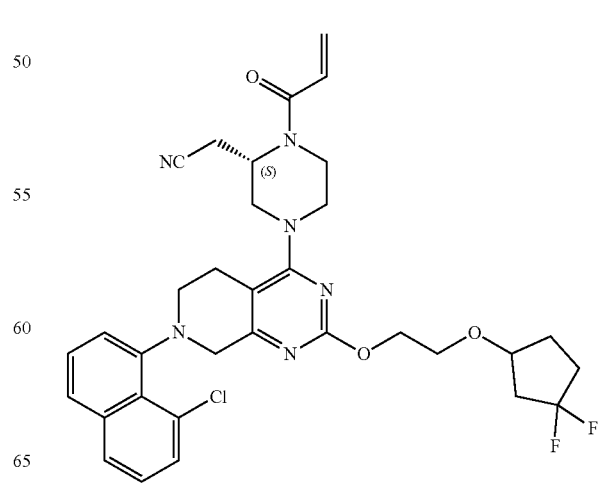

639
-continued
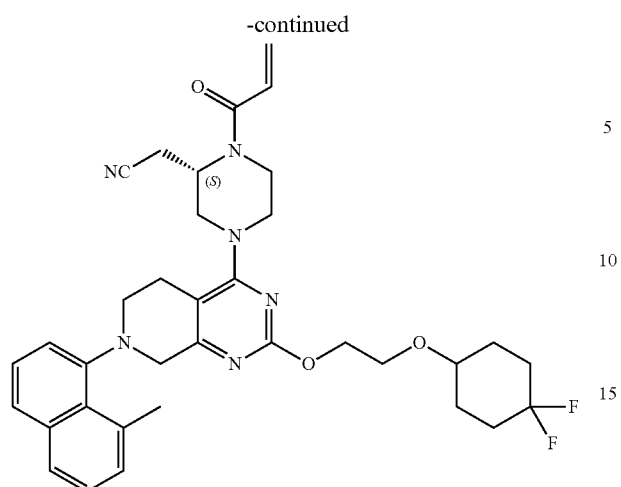
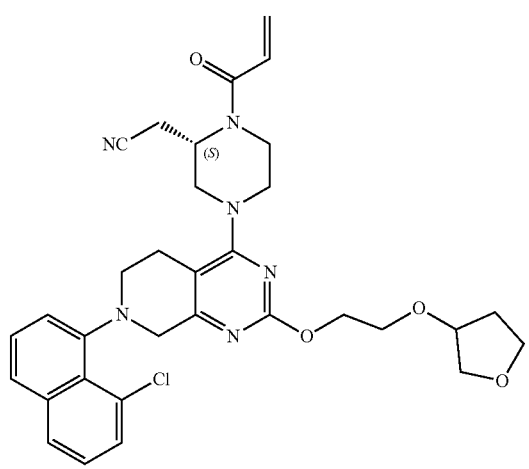
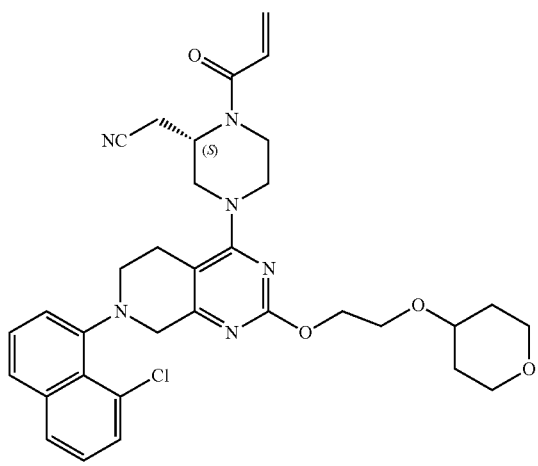
640
-continued
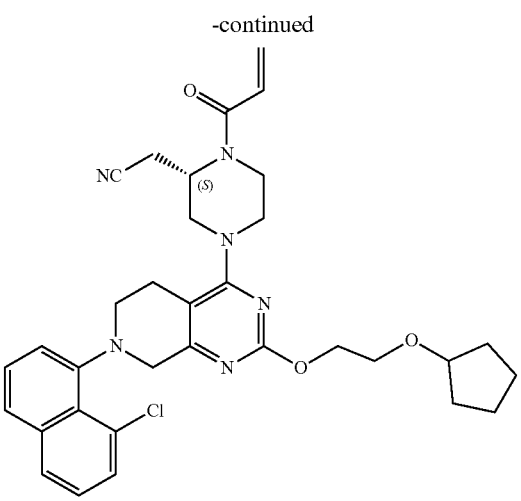
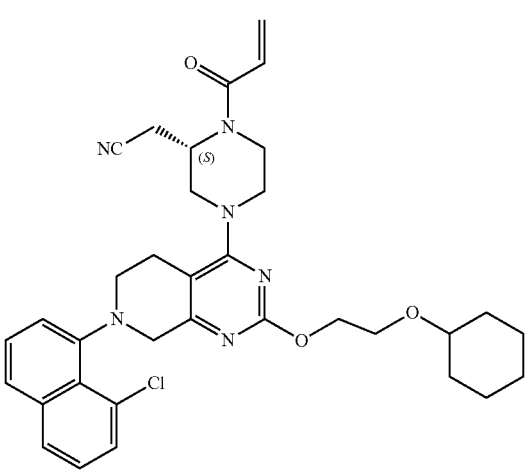
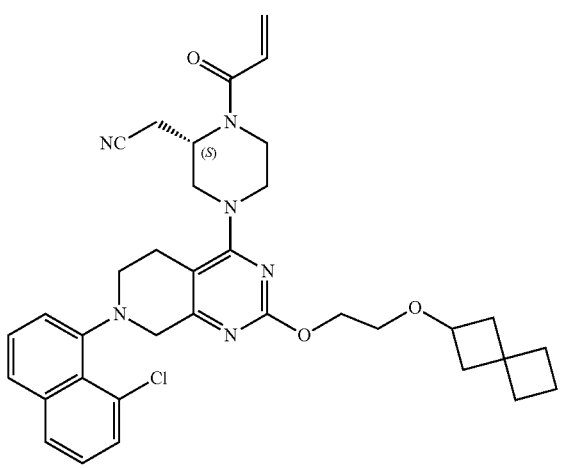

641
-continued
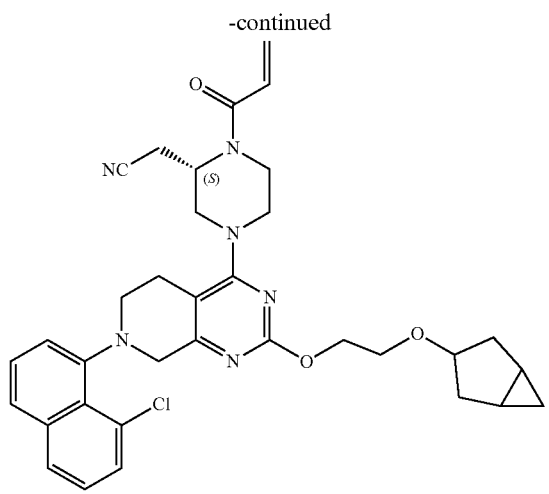
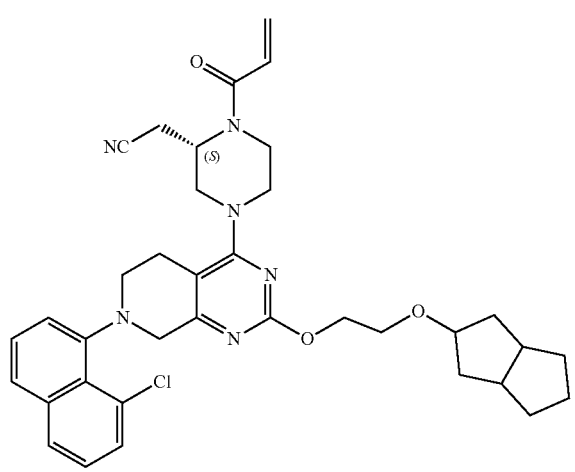
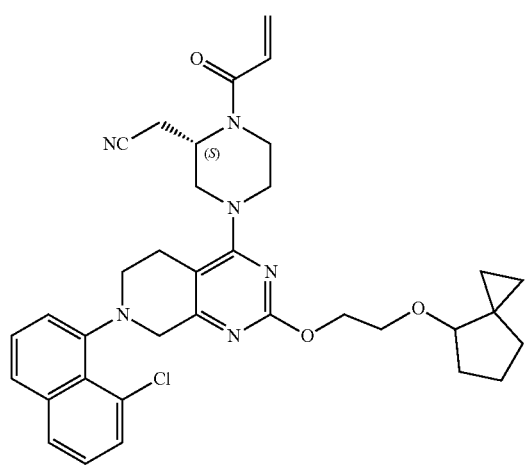
642
-continued
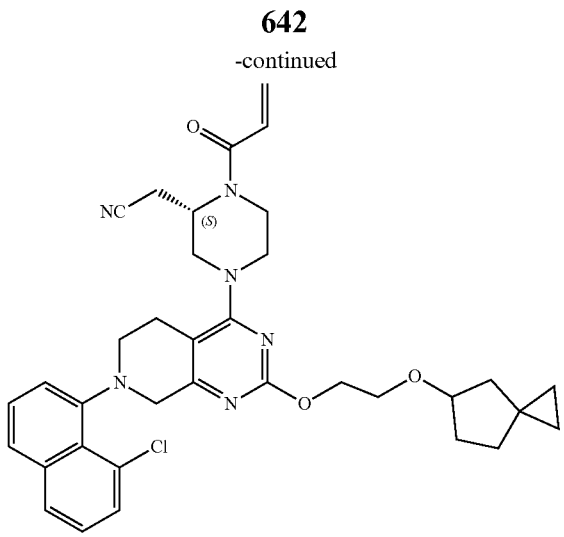
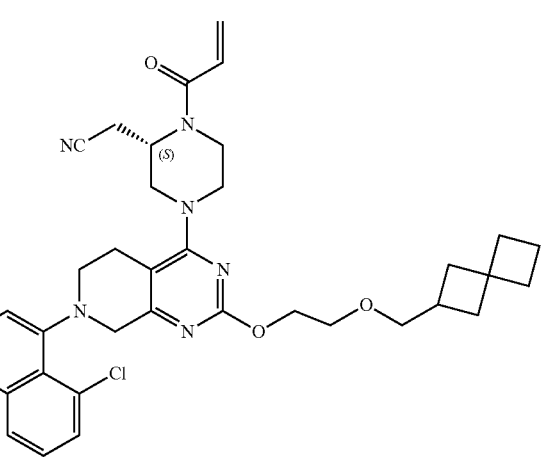
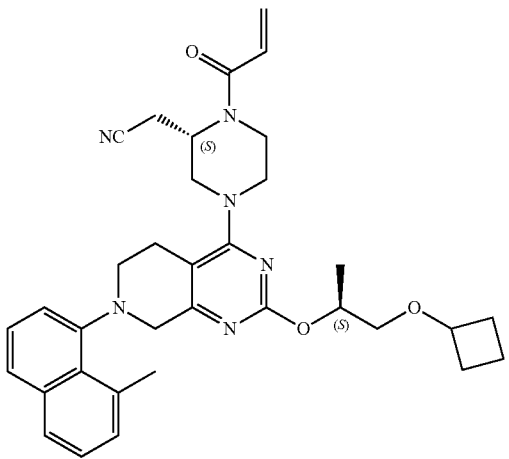

643
-continued
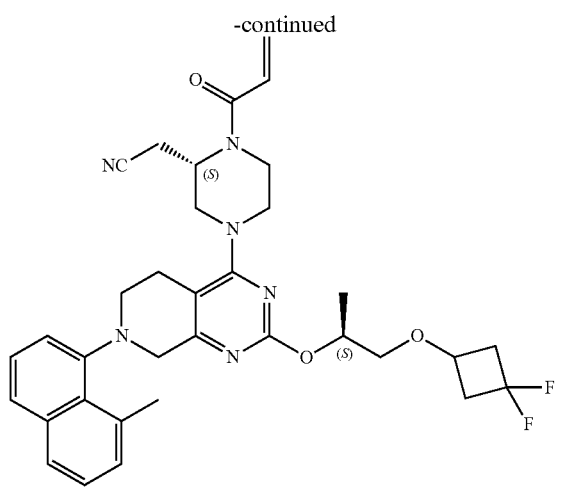
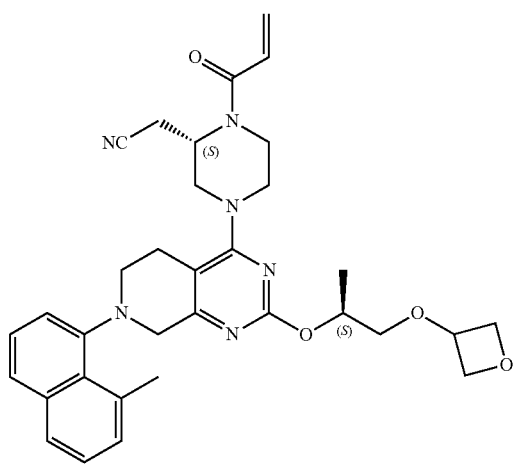
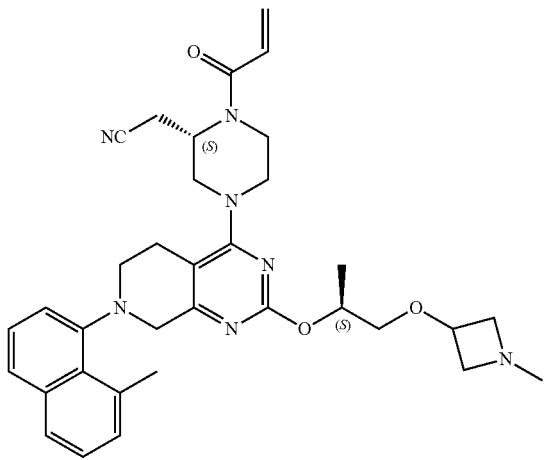
644
-continued
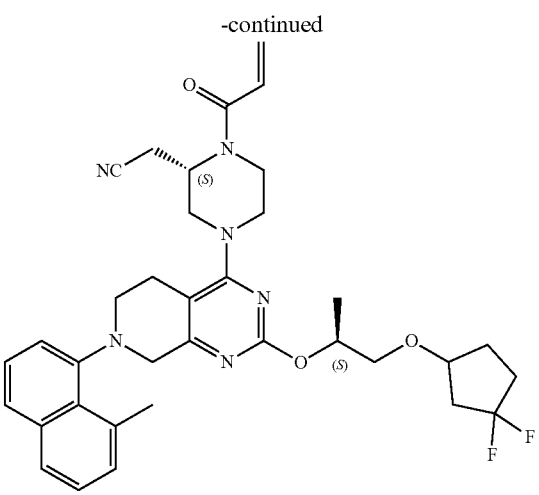
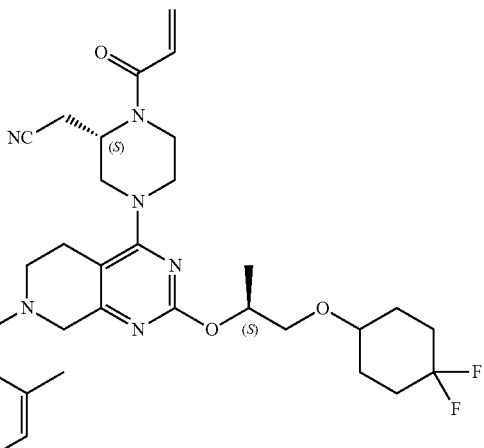
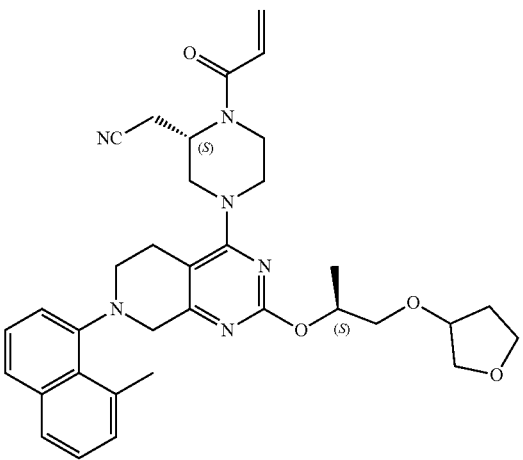

645
-continued
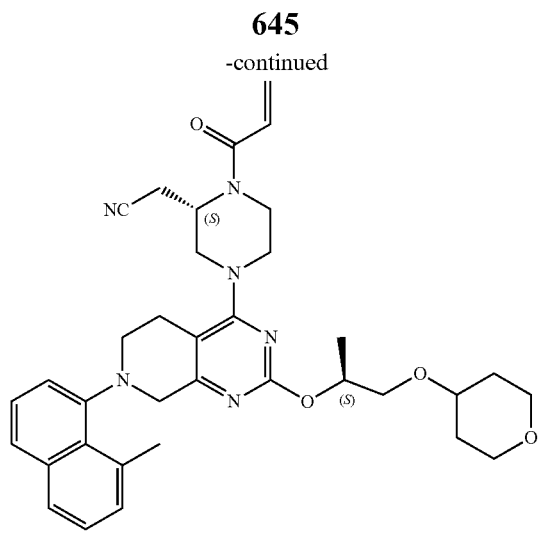
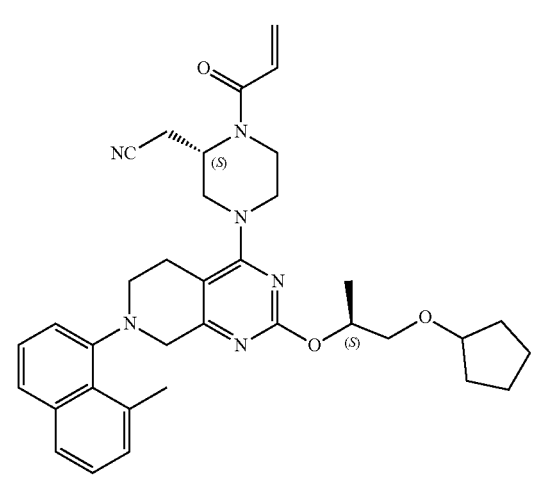
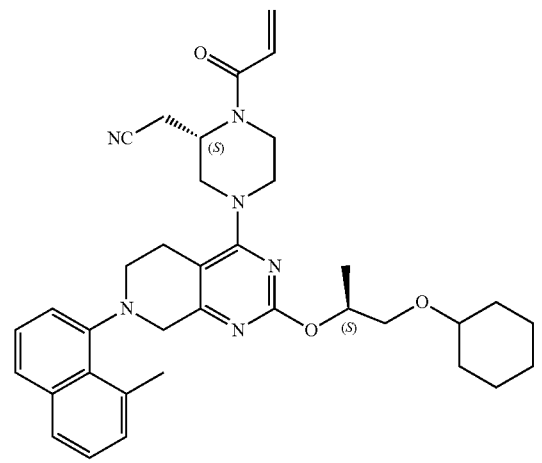
646
-continued
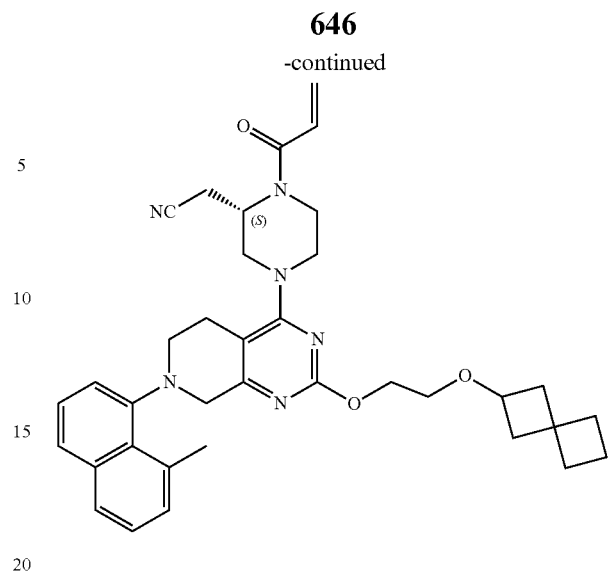
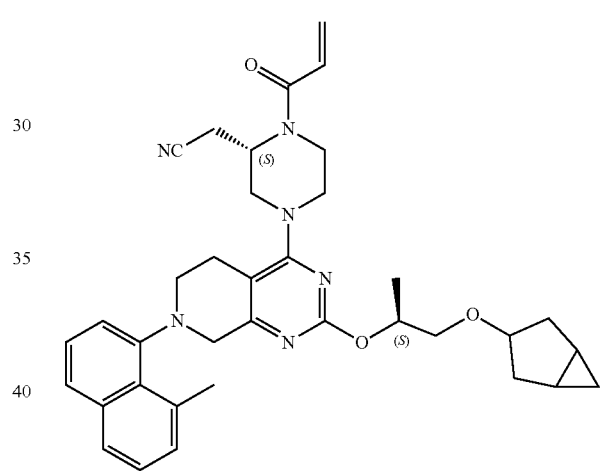
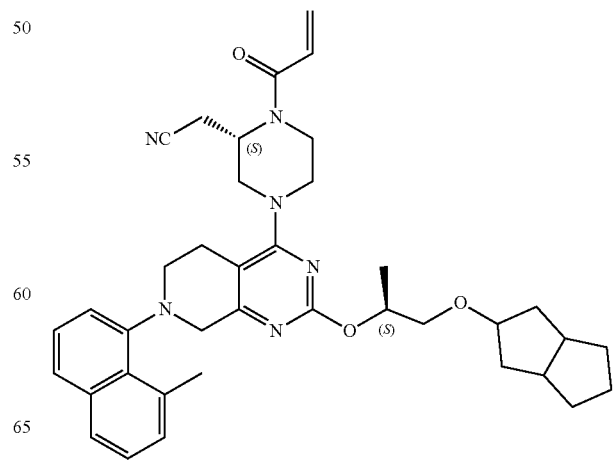

647
-continued
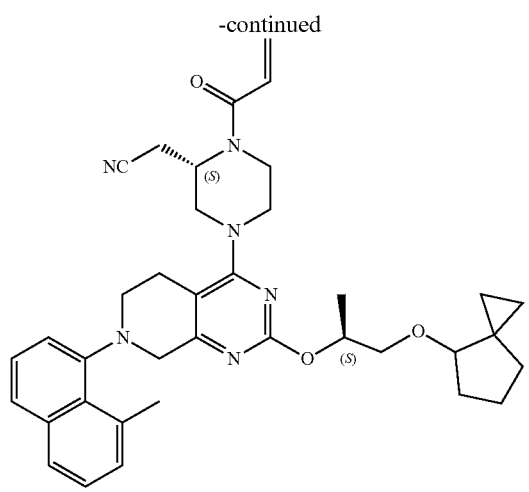
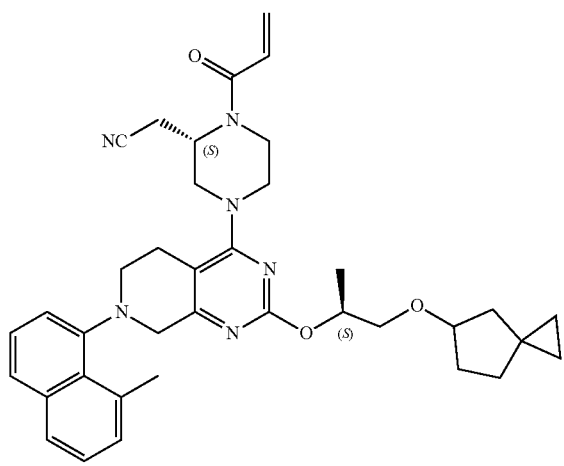
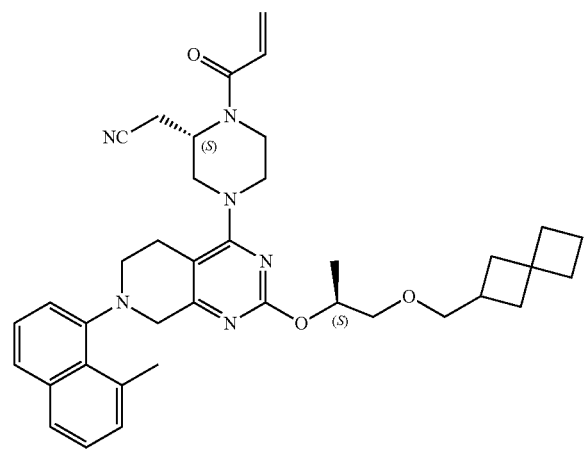
648
-continued
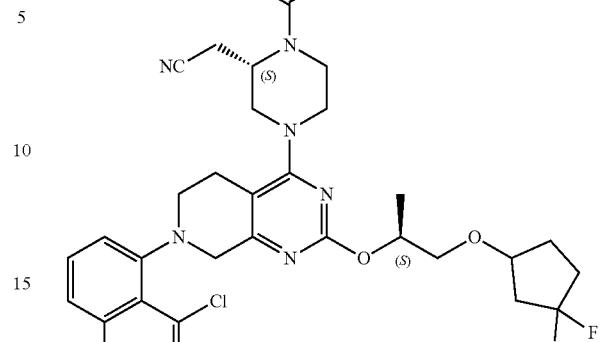
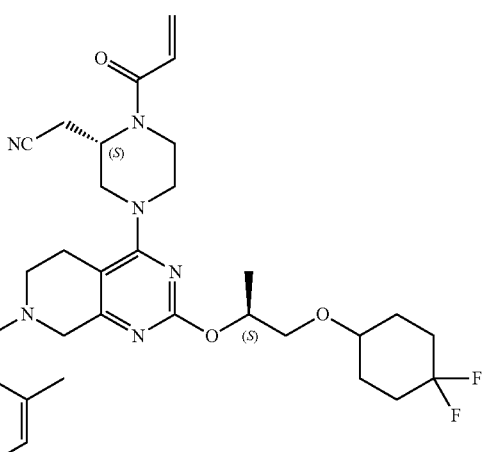
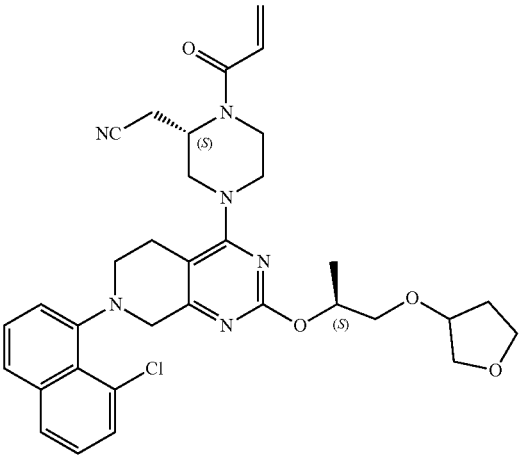

649
-continued
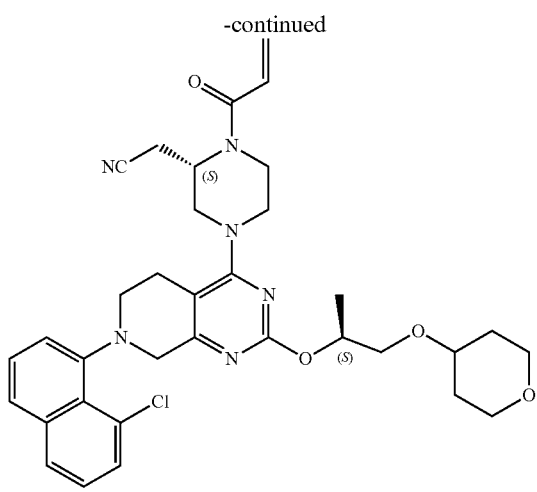
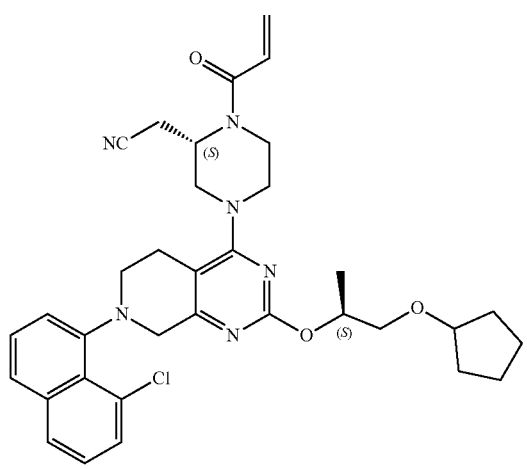
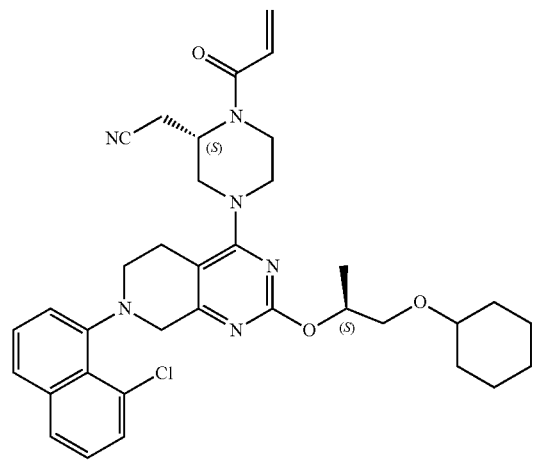
650
-continued
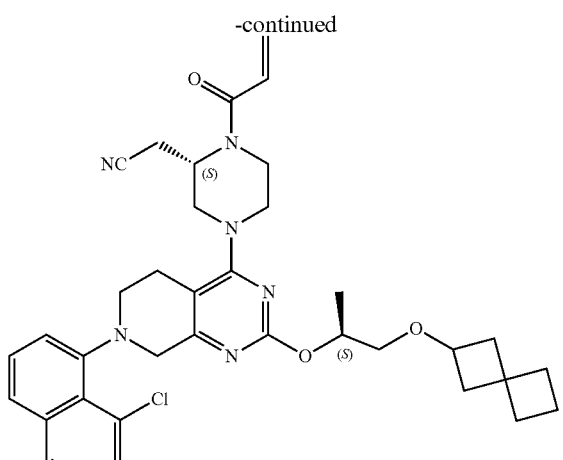
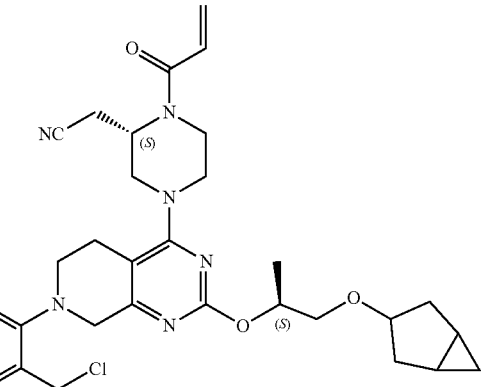
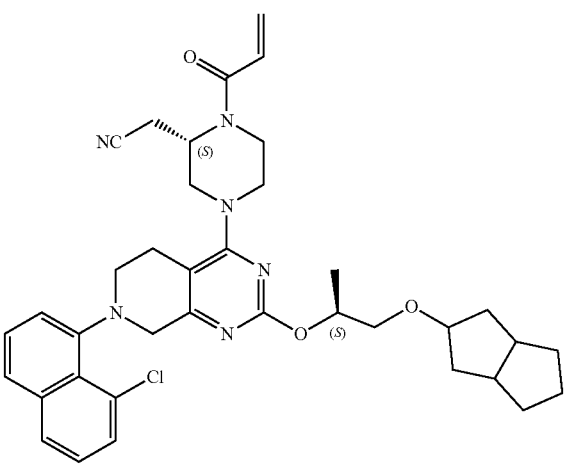

651
-continued
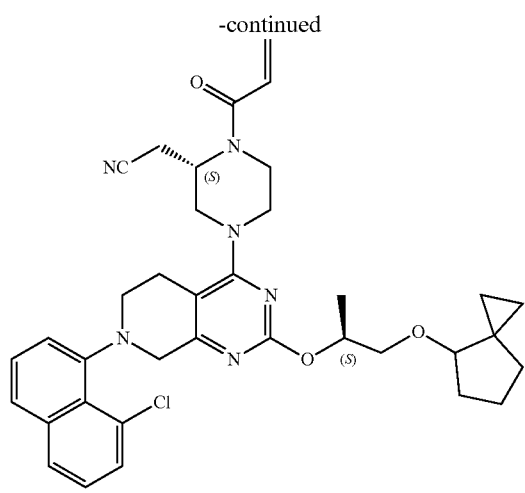
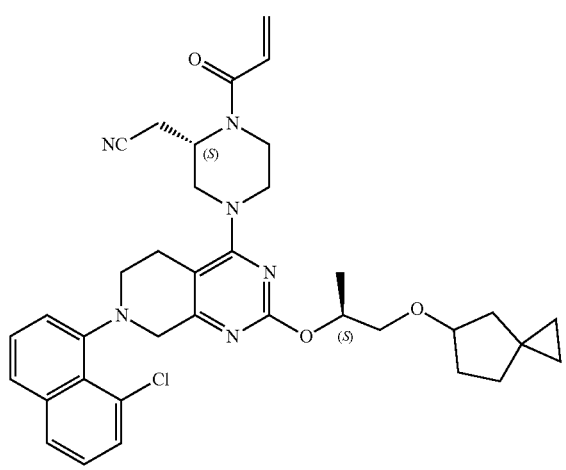
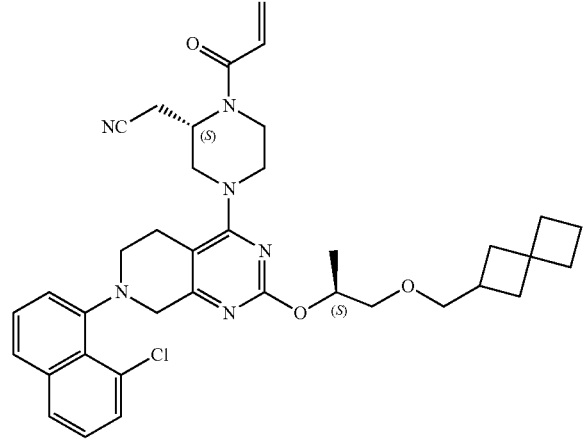
652
-continued
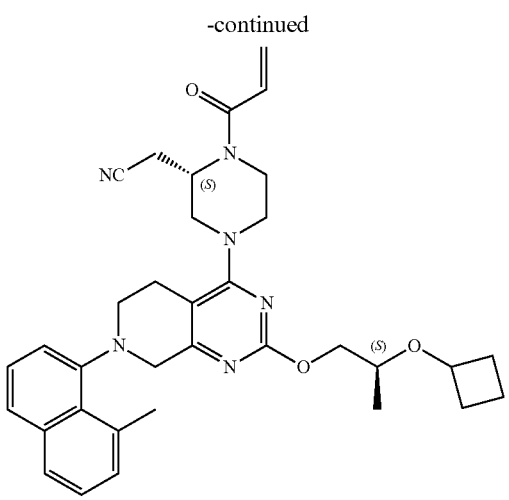
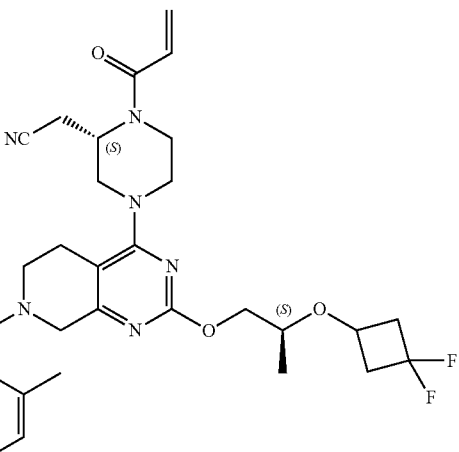
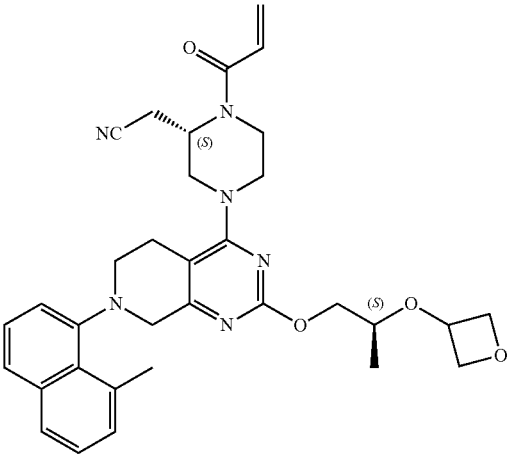

653
-continued
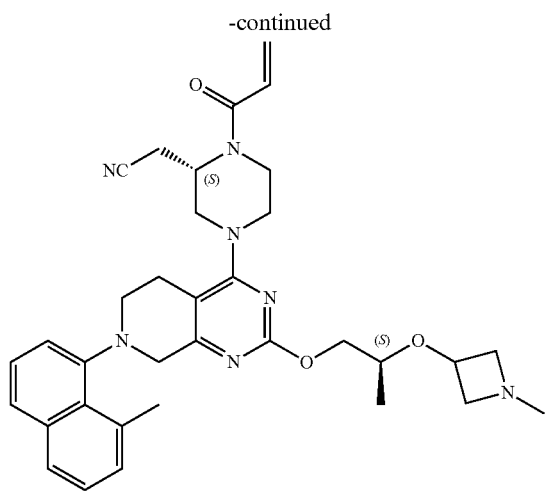
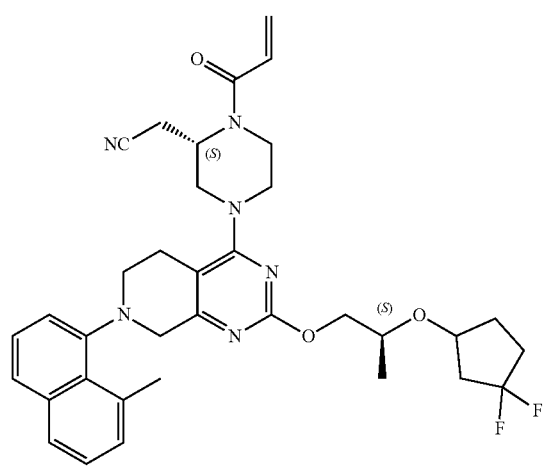
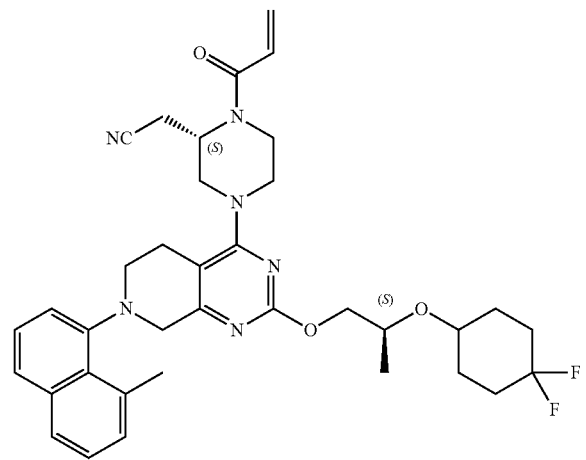
654
-continued
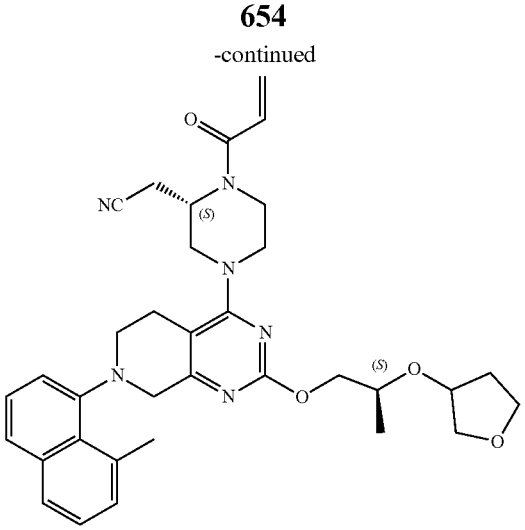
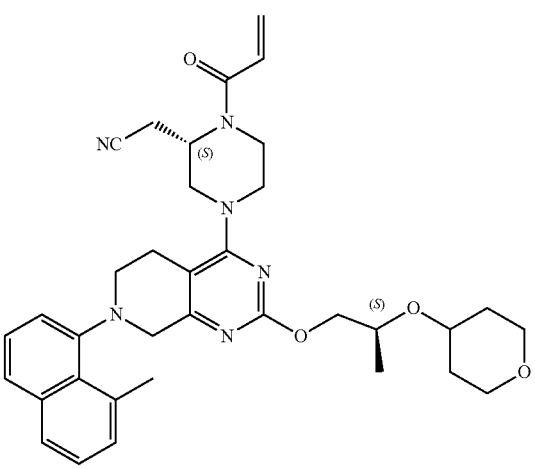
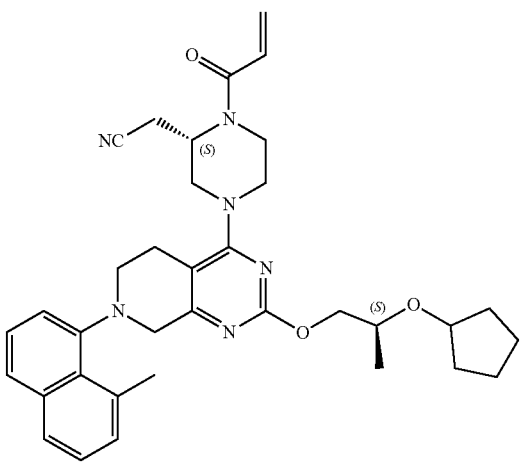

655
-continued
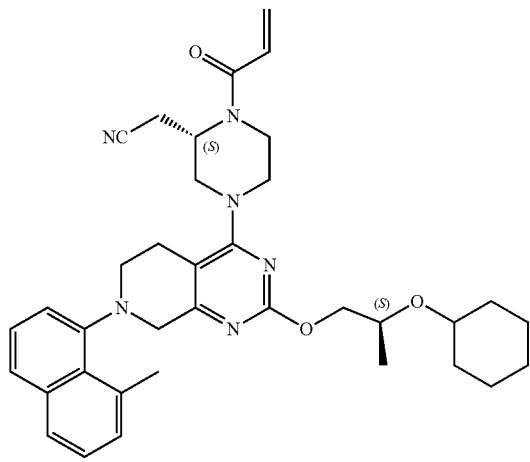
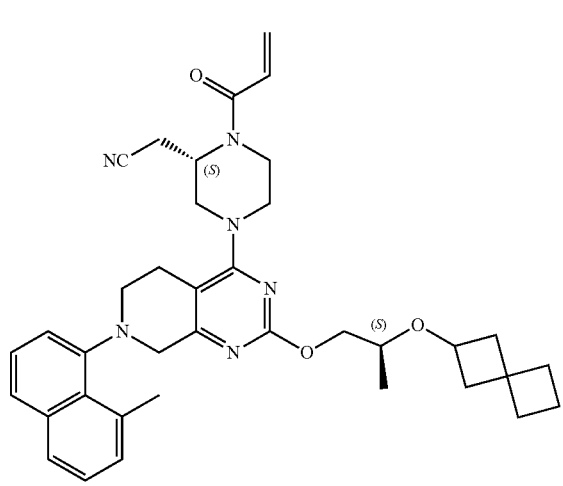
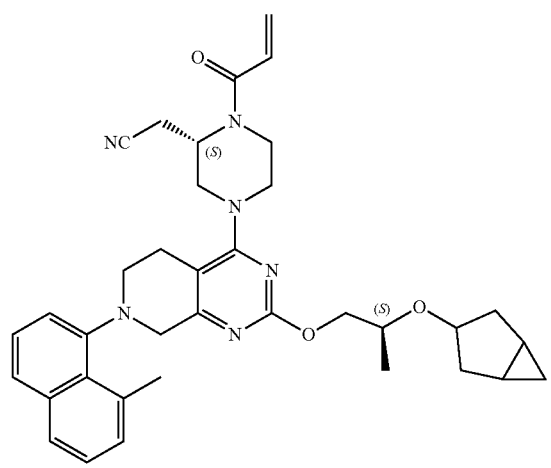
656
-continued
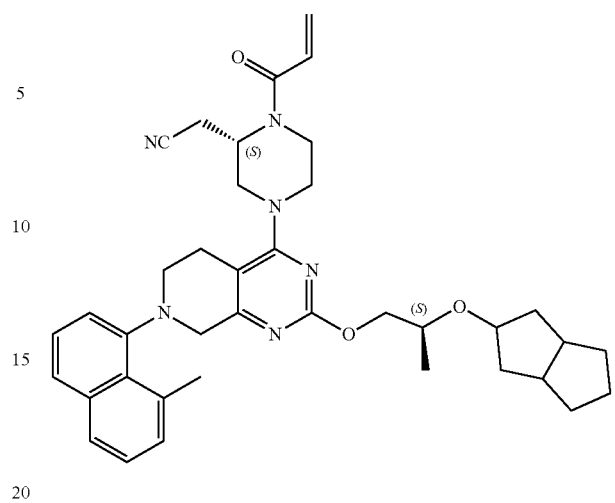
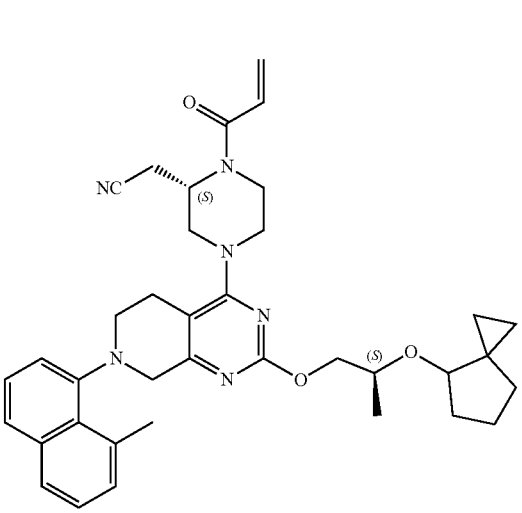
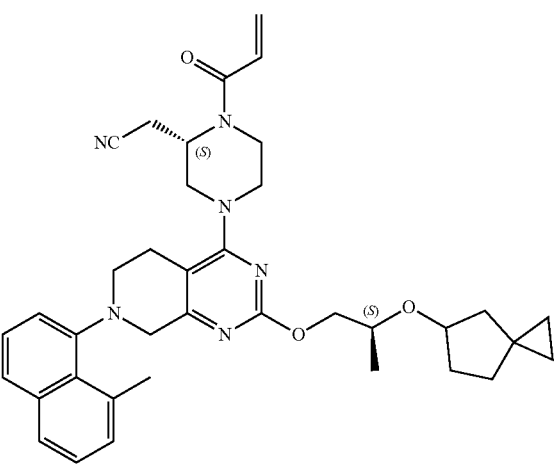

657
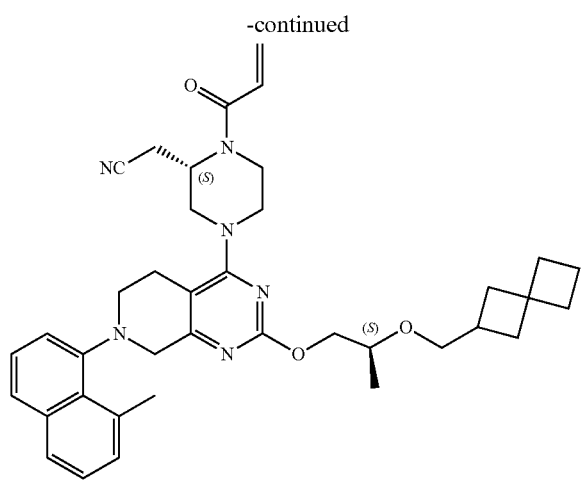
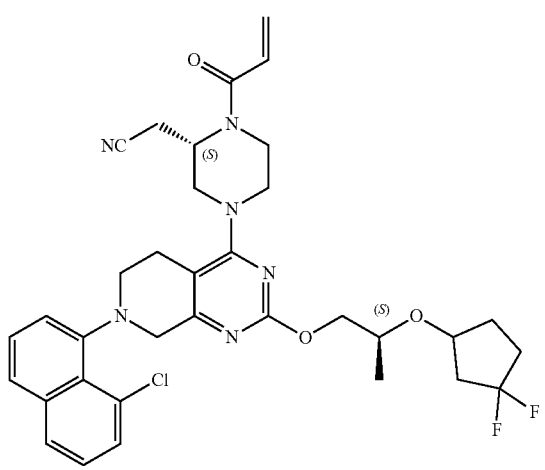
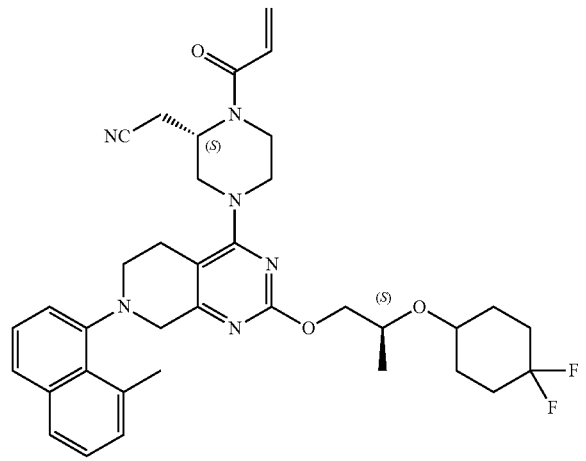
658
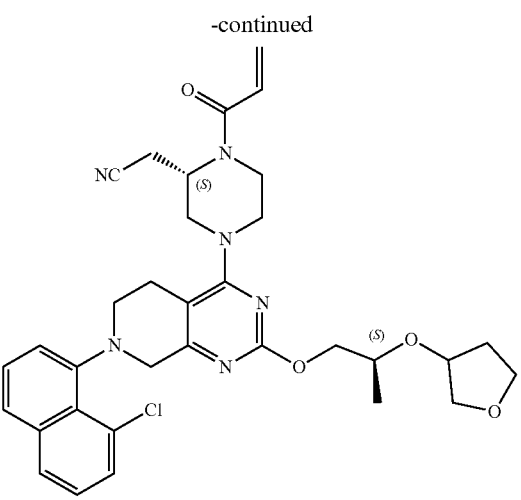
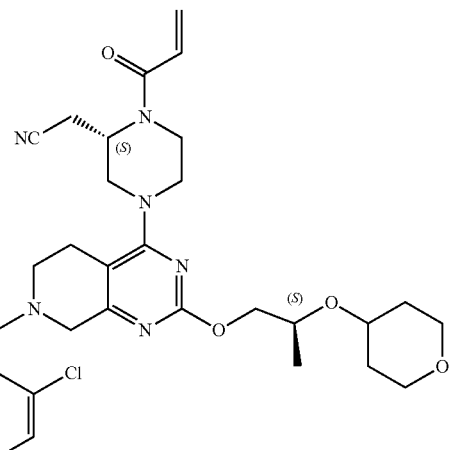
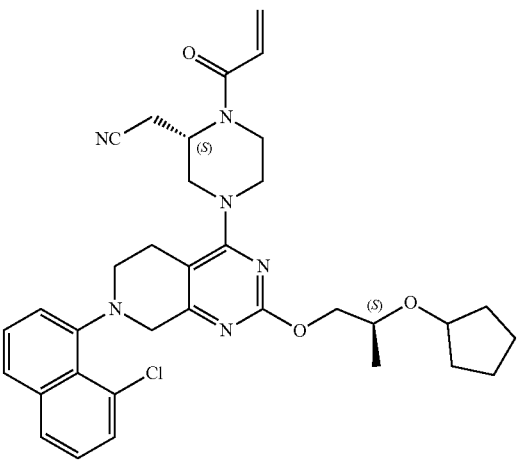

659
-continued
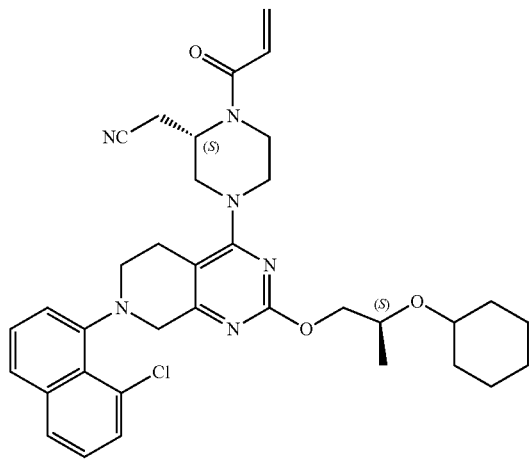
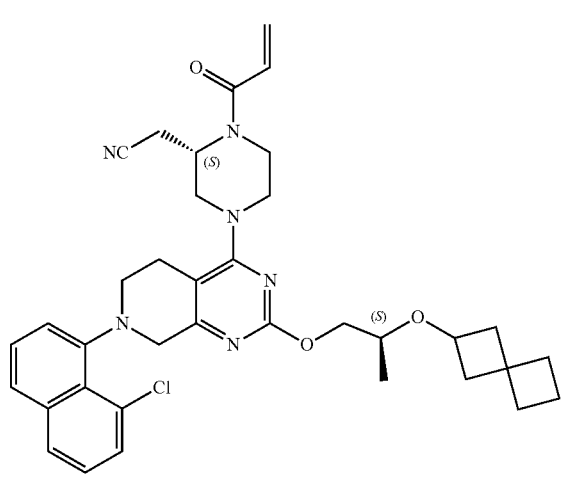
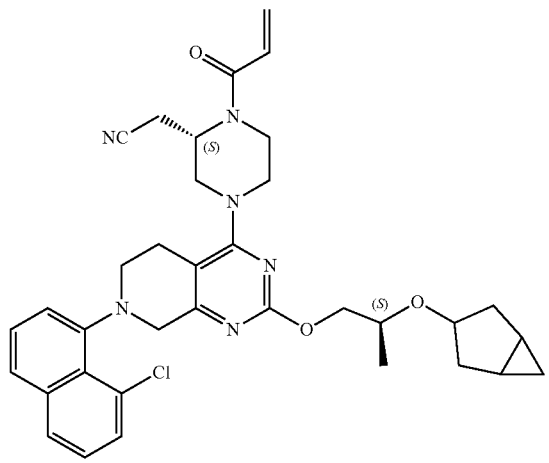
660
-continued
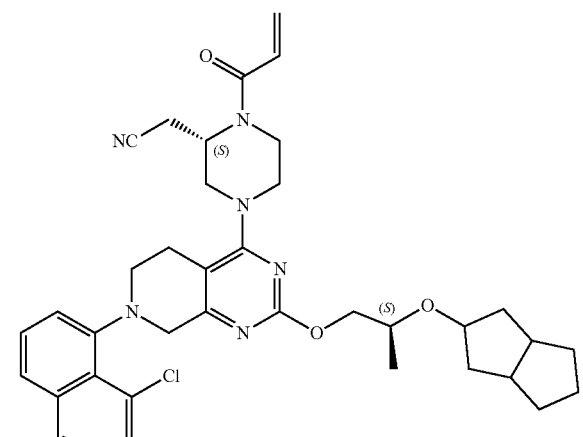
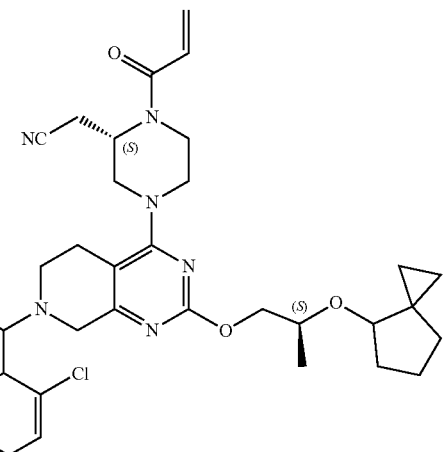
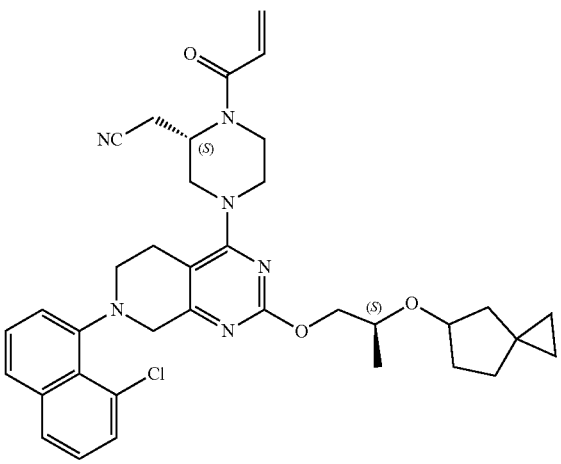

661
-continued
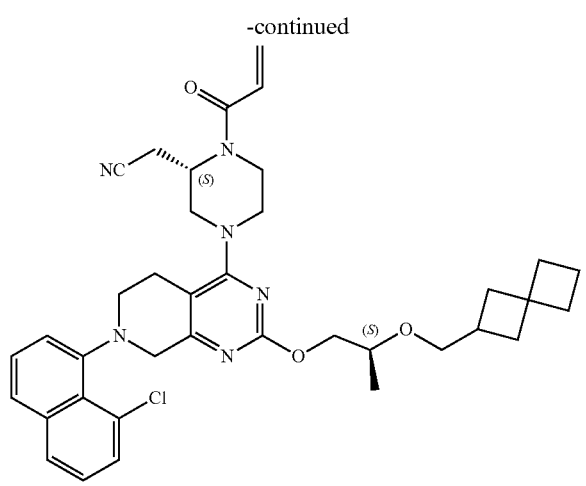
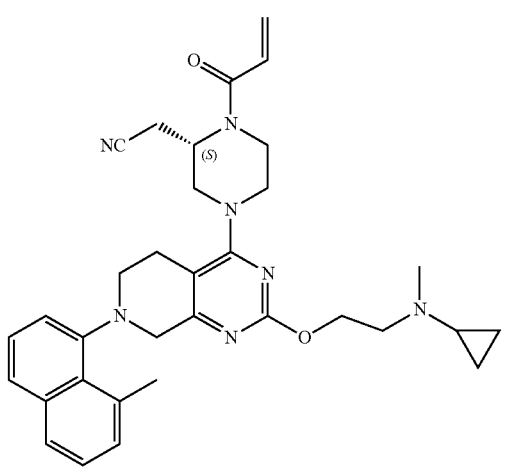
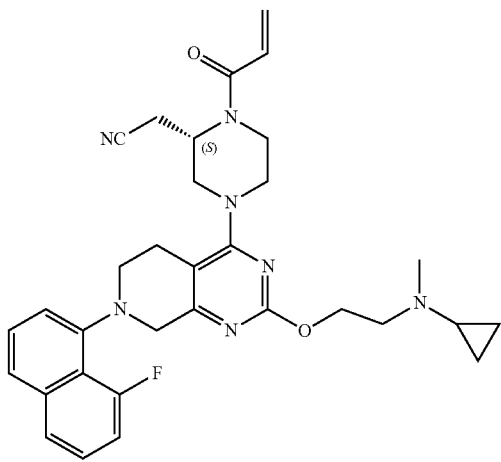
662
-continued
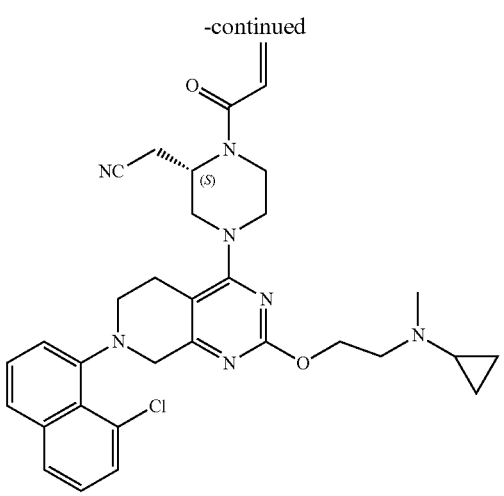
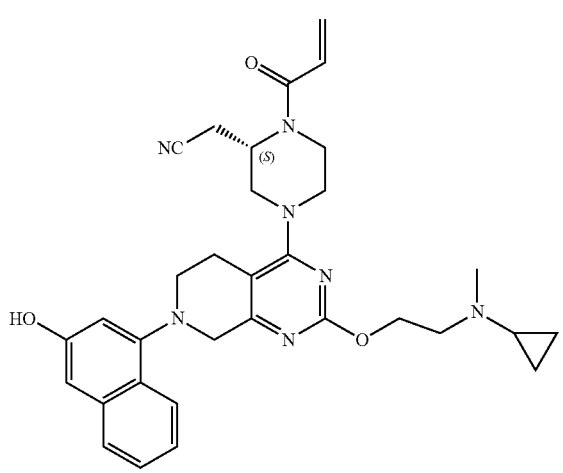
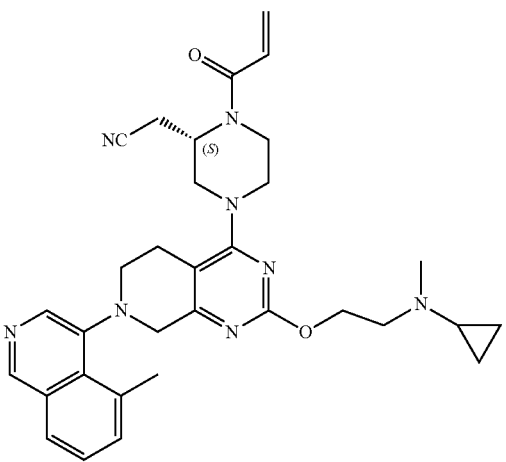

663
-continued
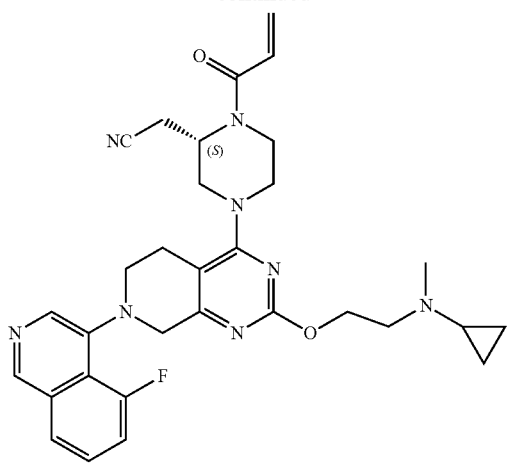
663
-continued
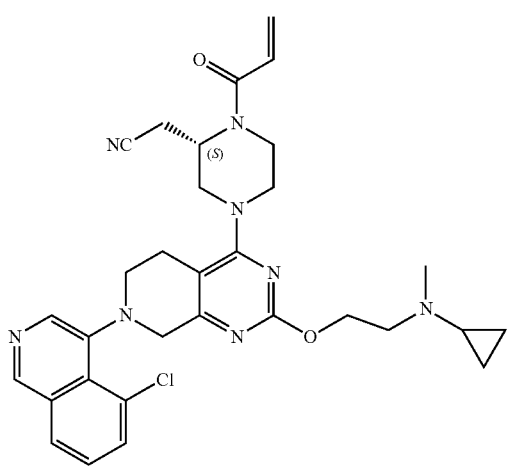
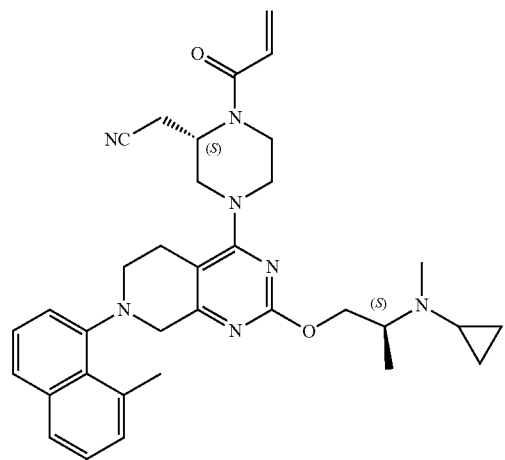
664
-continued
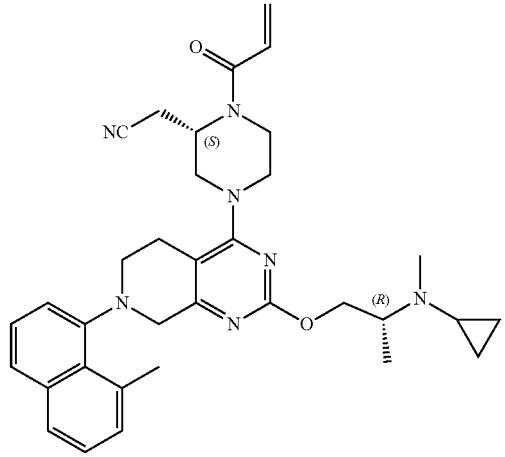
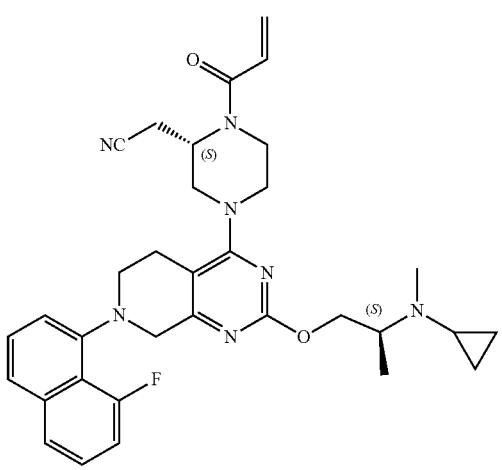
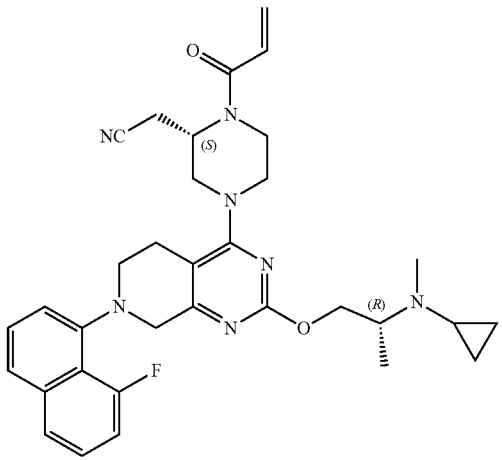

665
-continued
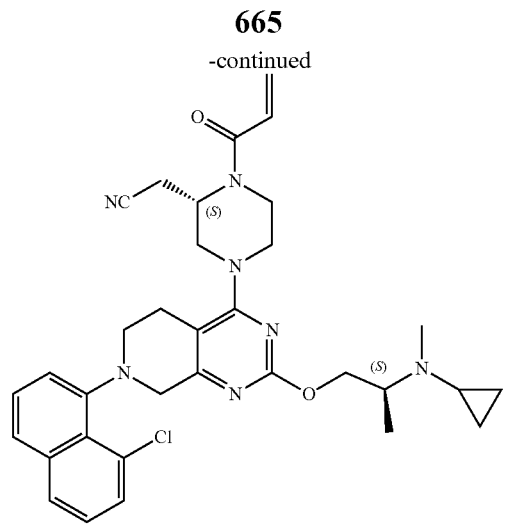
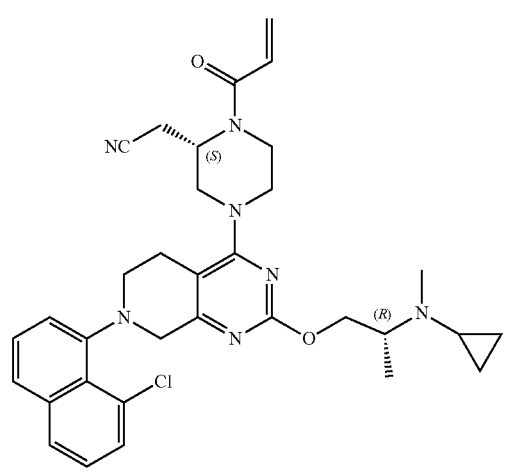
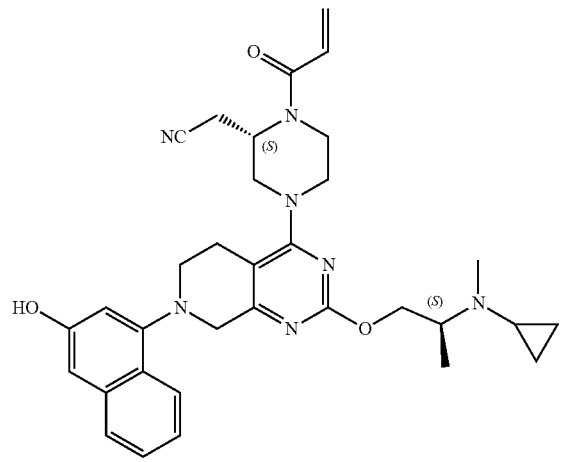
666
-continued
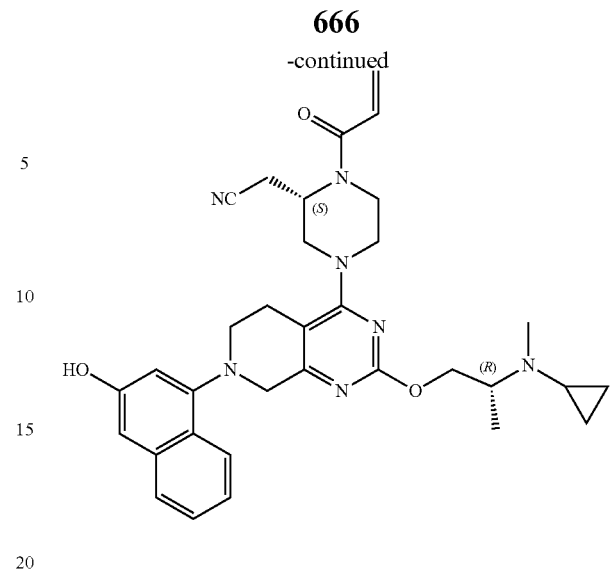
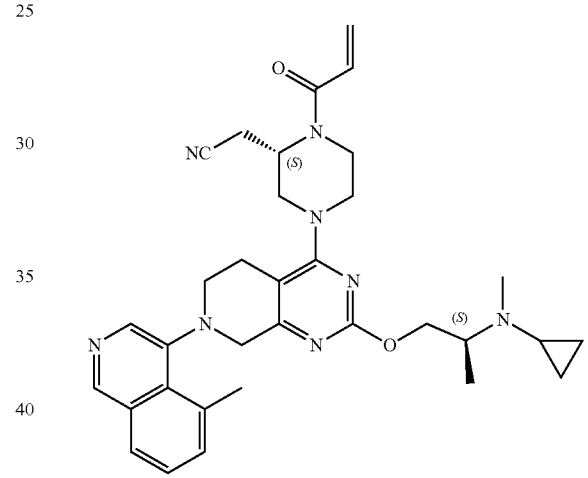
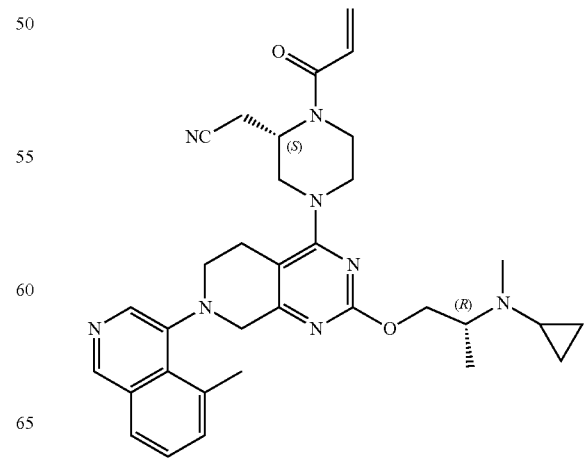

667
-continued
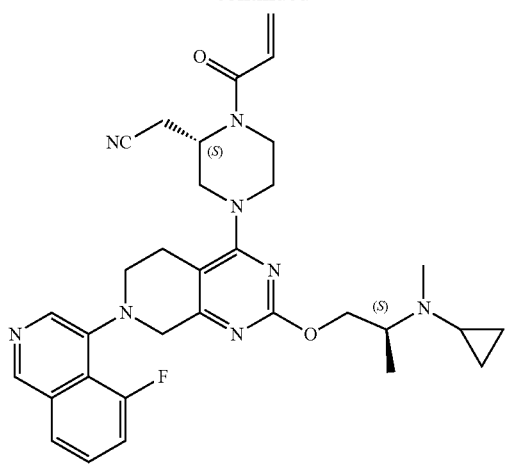
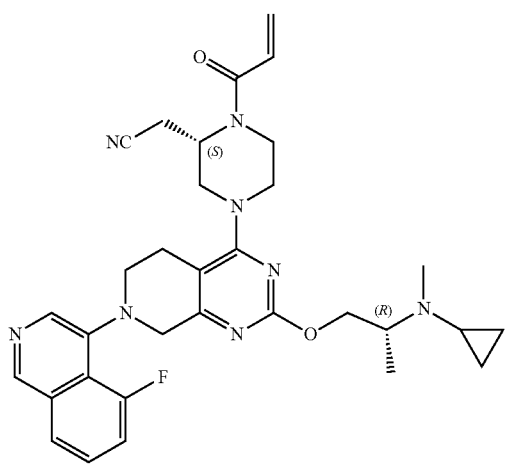
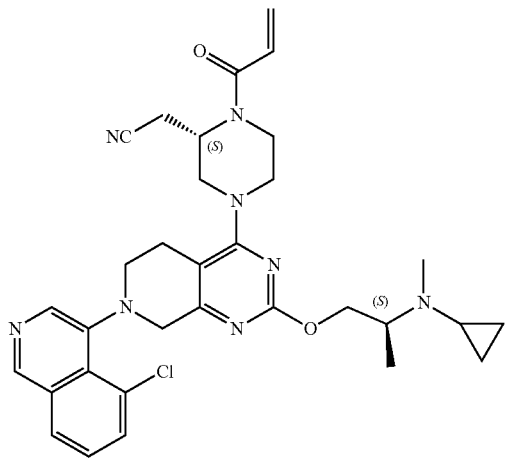
668
-continued
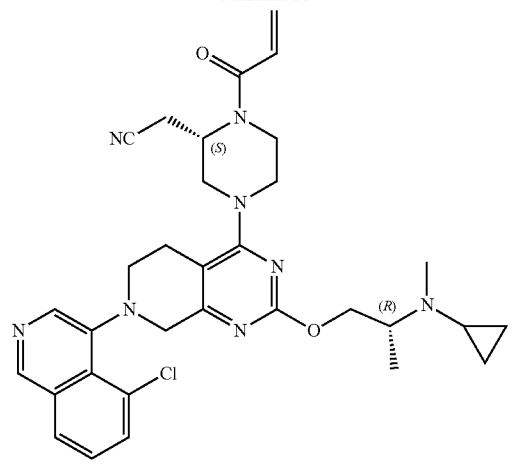
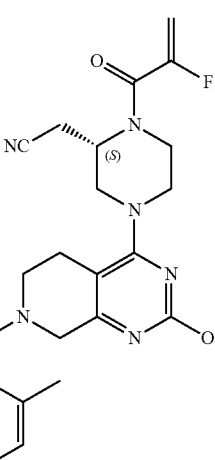
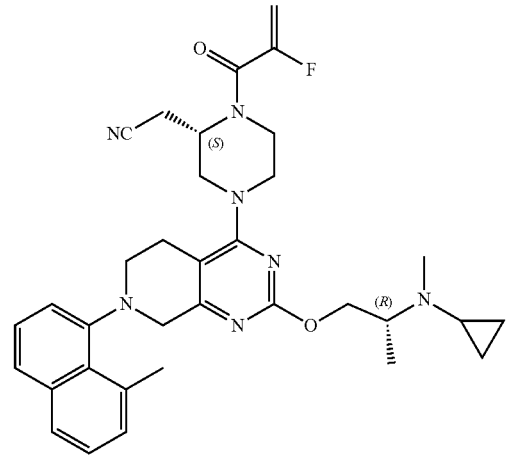

669
-continued
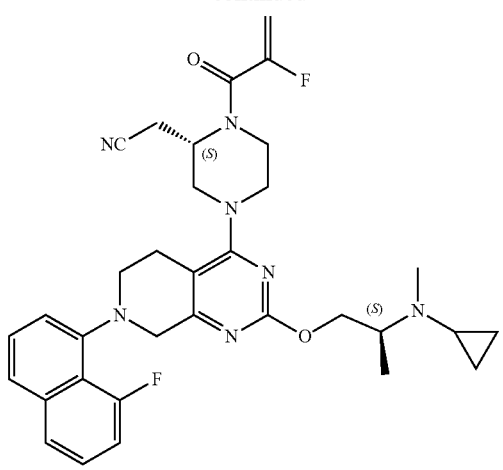
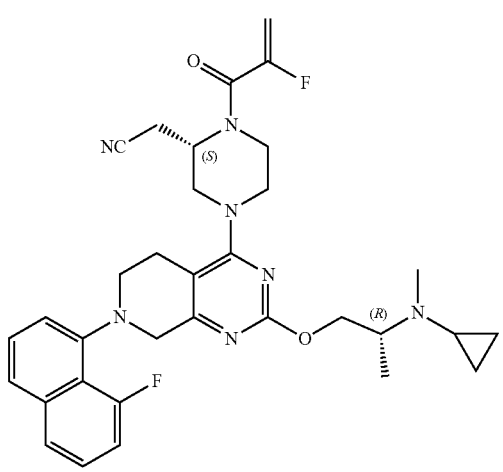
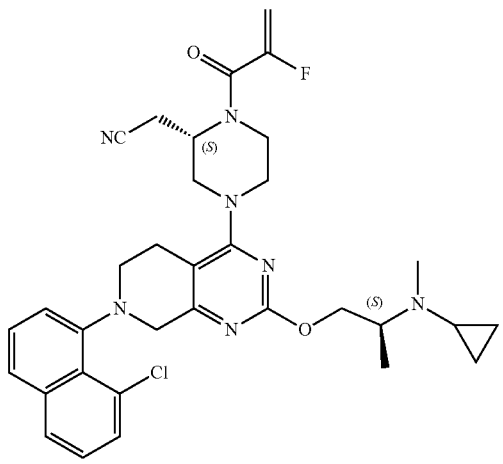
670
-continued
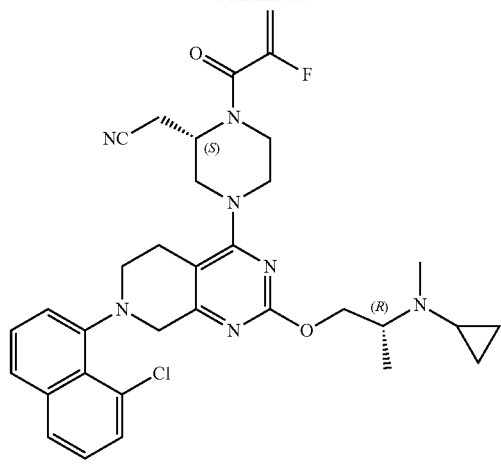
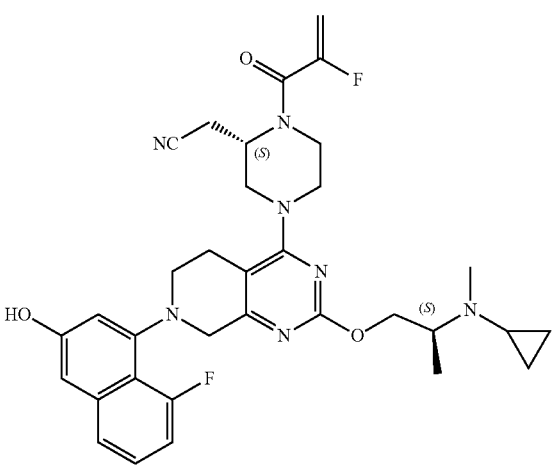
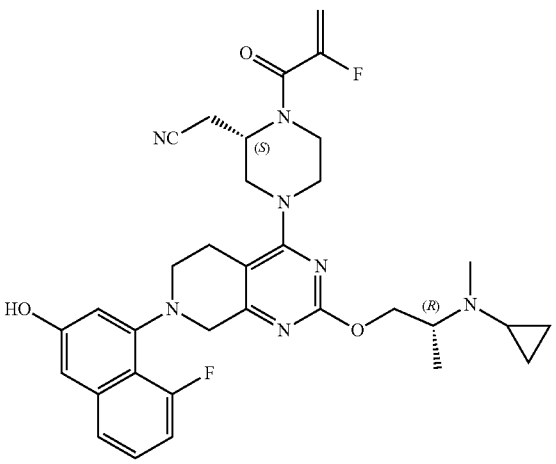

671
-continued
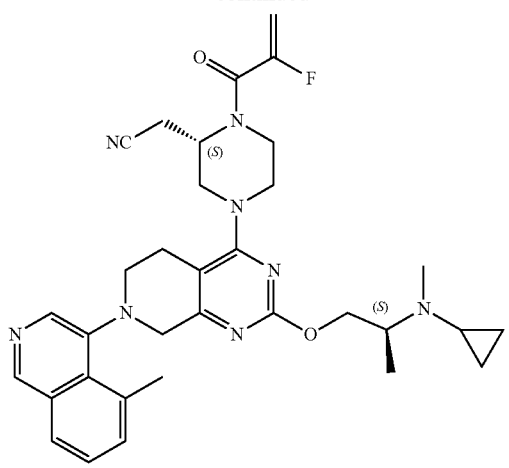
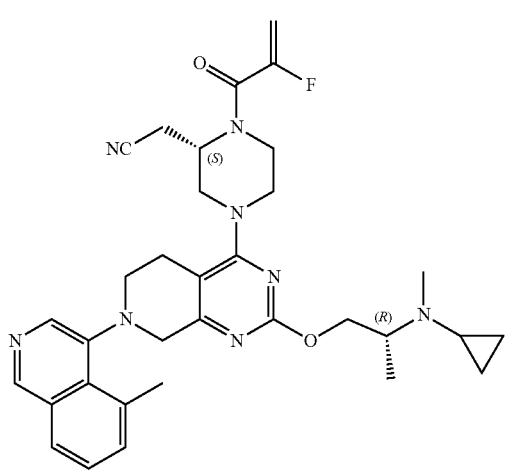
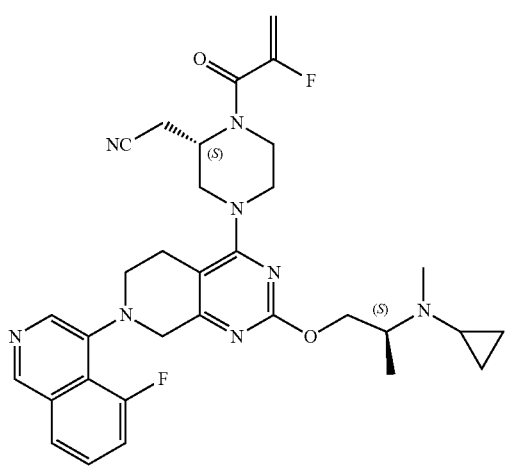
672
-continued
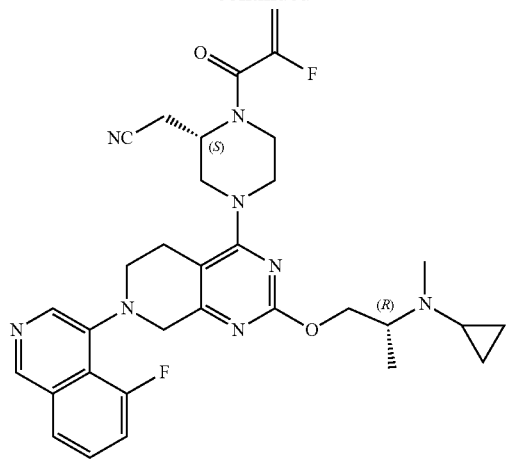
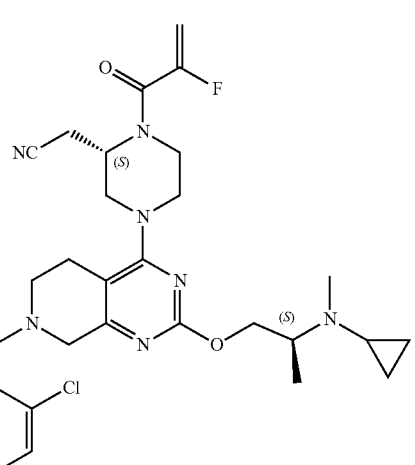
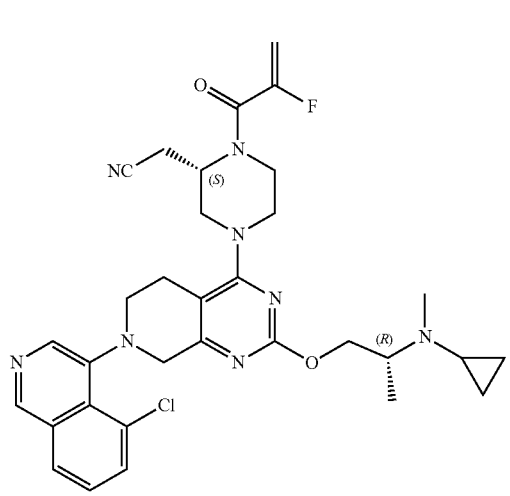

673
-continued
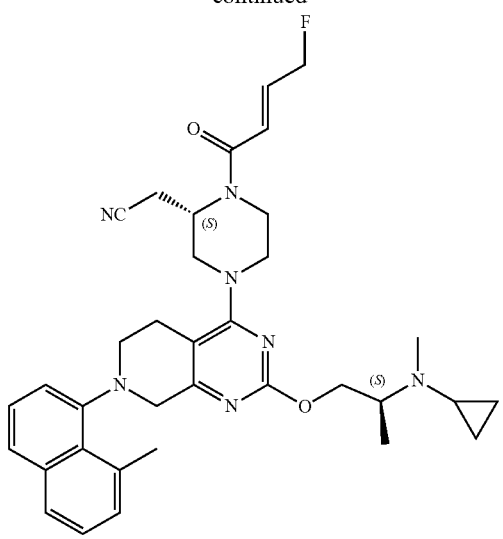
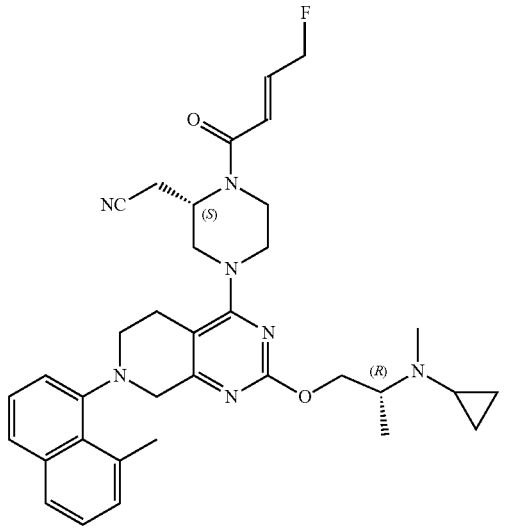
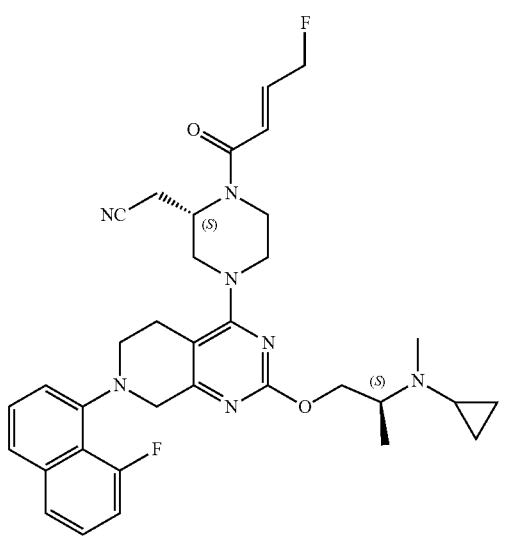
674
-continued
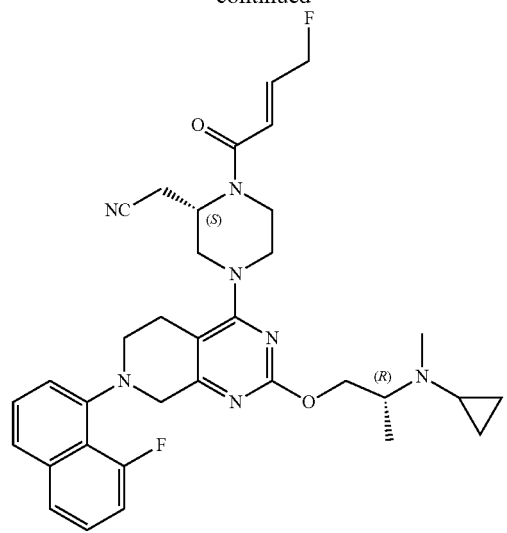
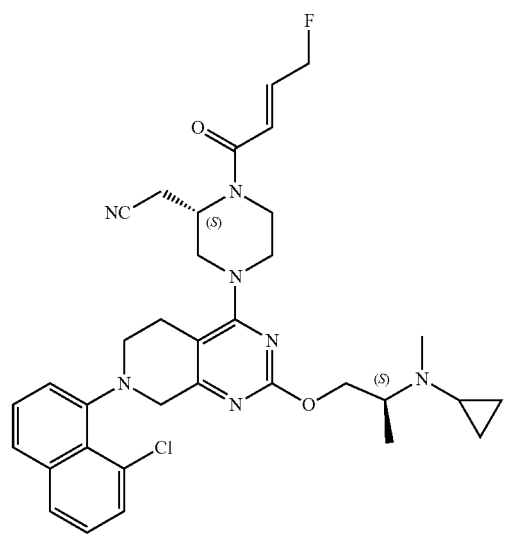
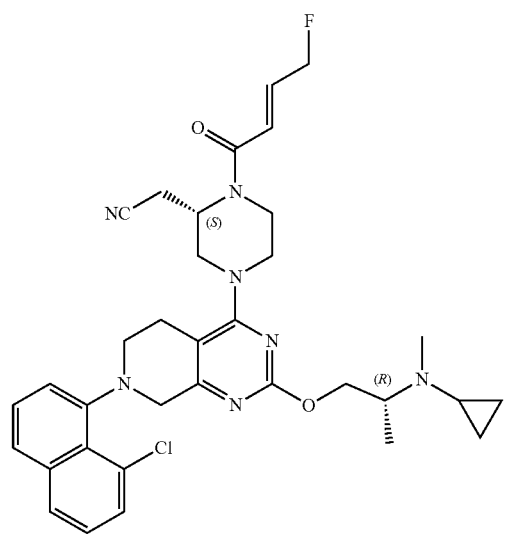

675
-continued
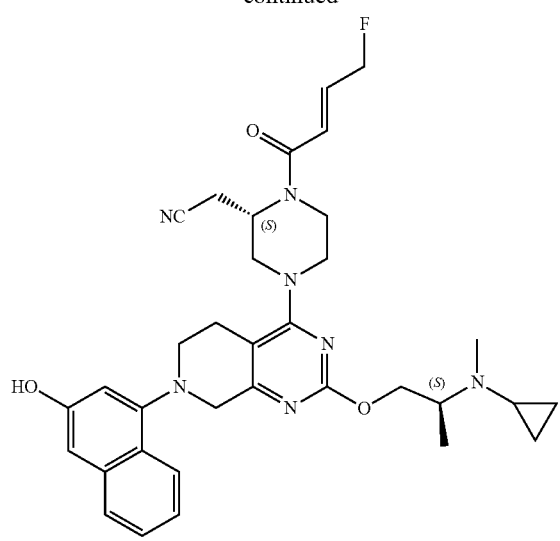
676
-continued
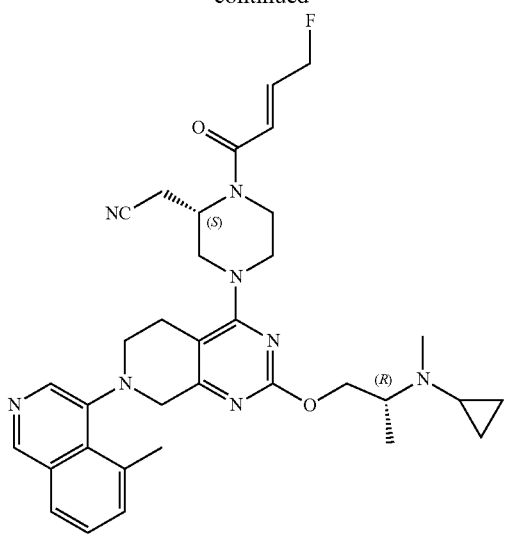
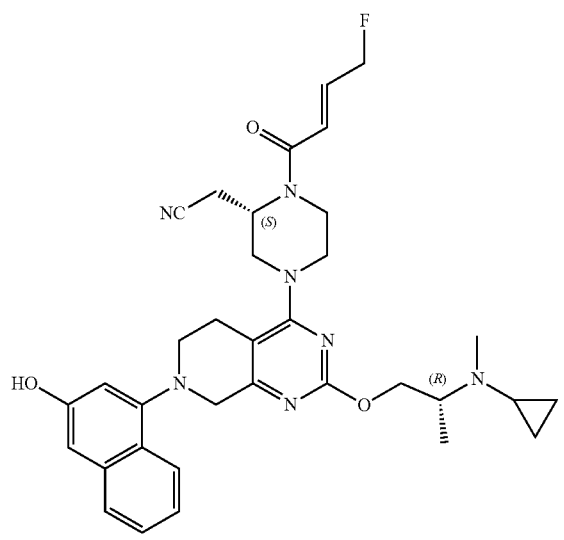
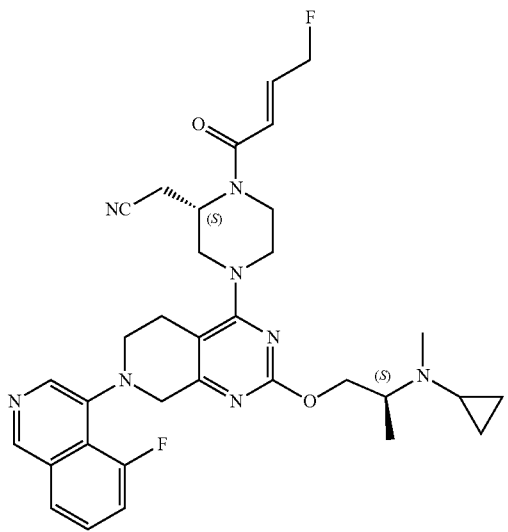
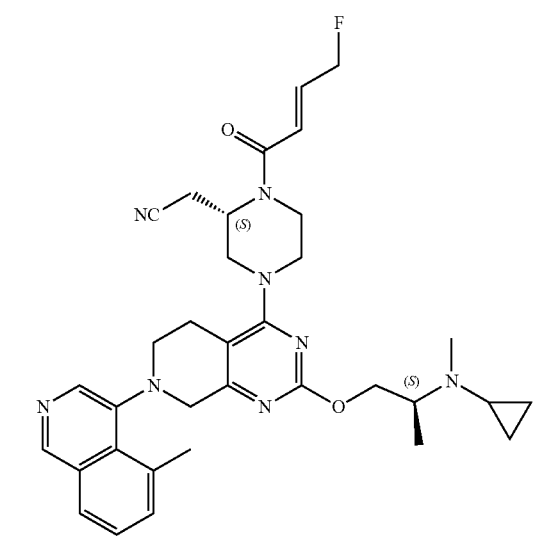

677
-continued
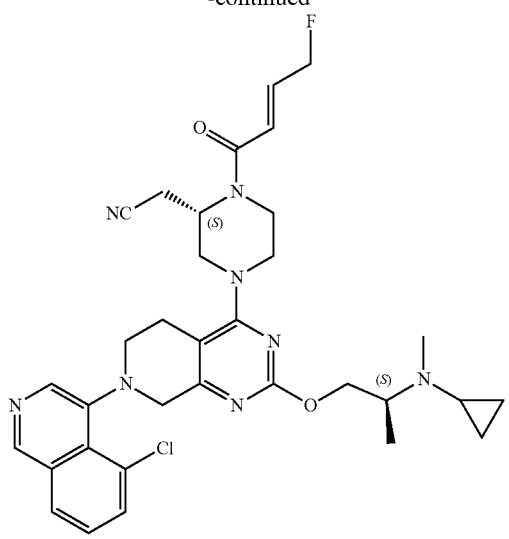
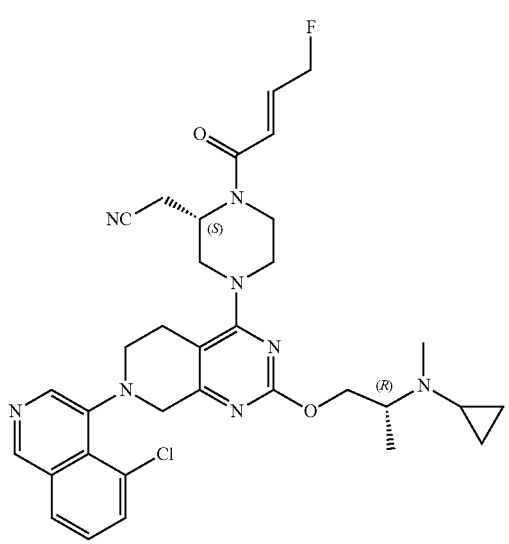
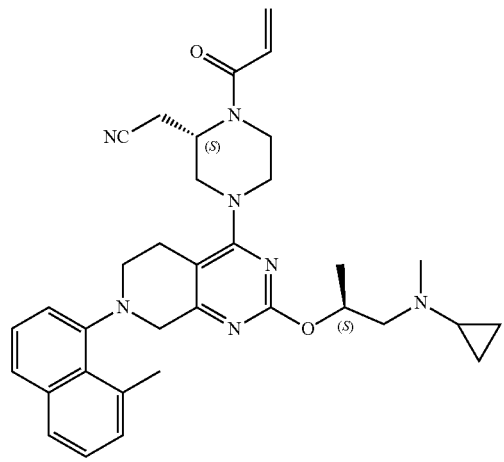
678
-continued
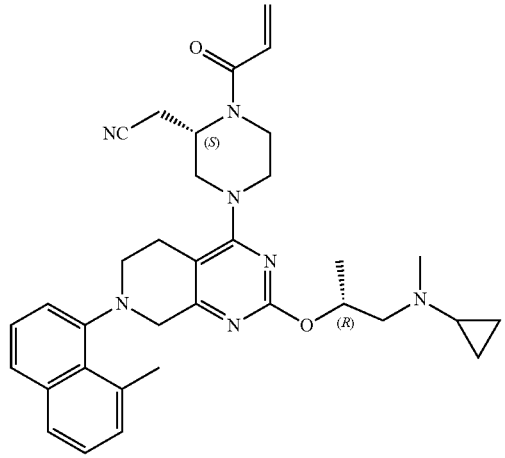
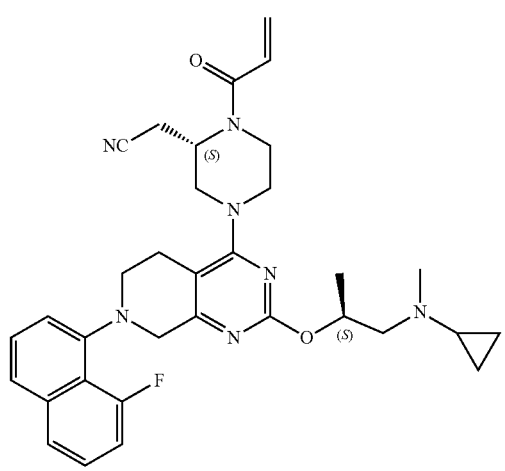
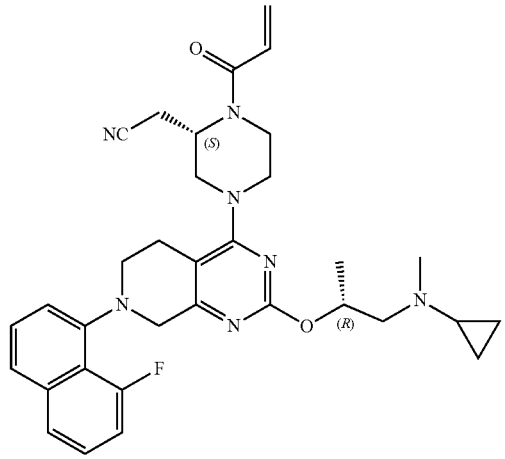

679
-continued
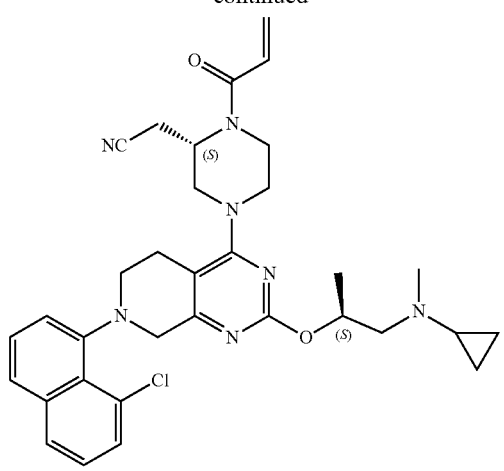
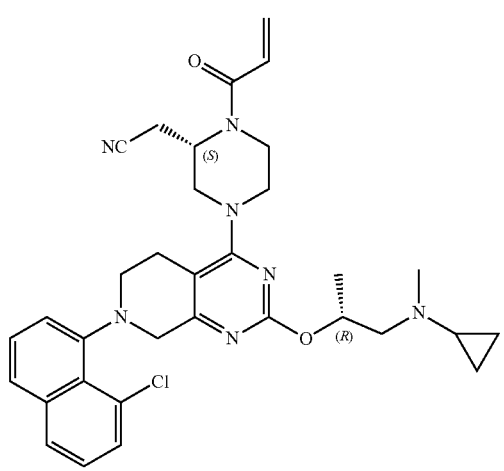
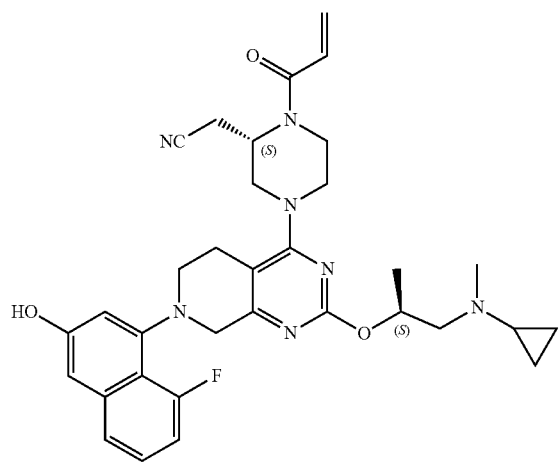
680
-continued
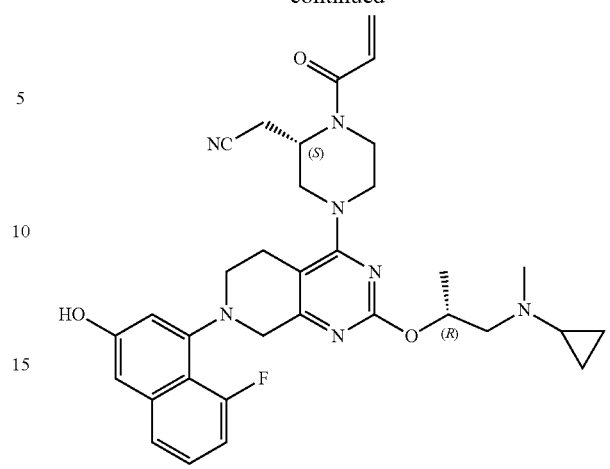
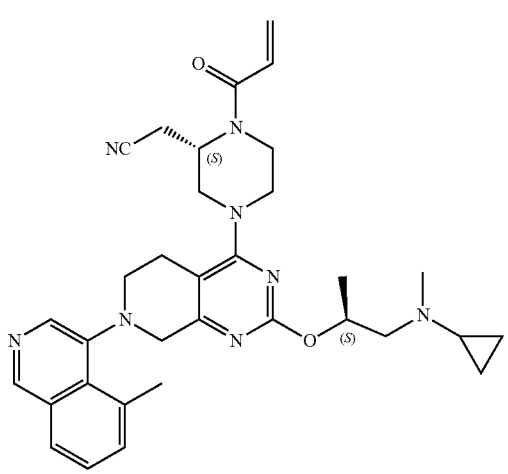
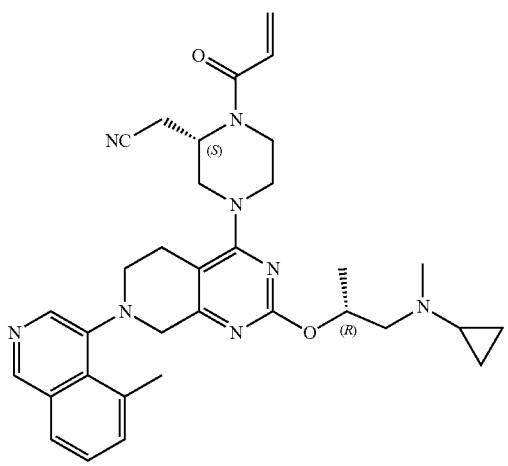

681
-continued
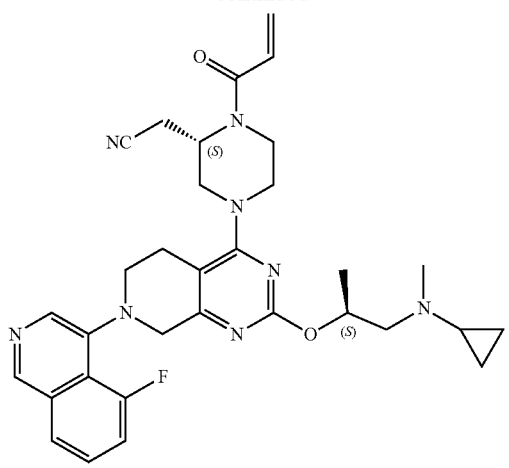
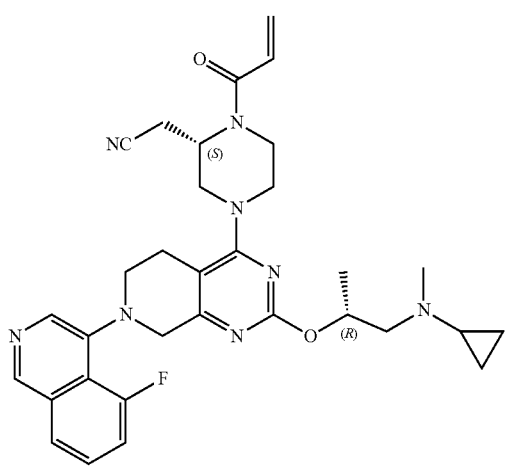
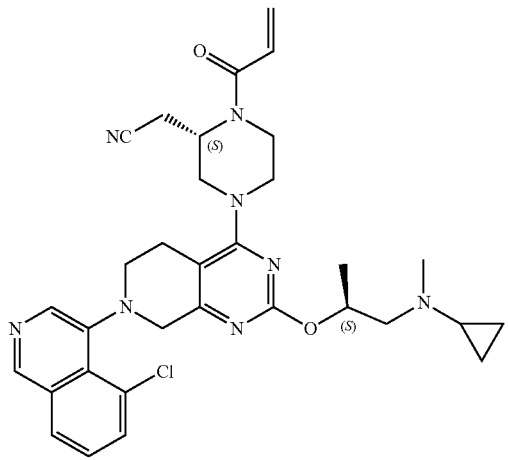
682
-continued
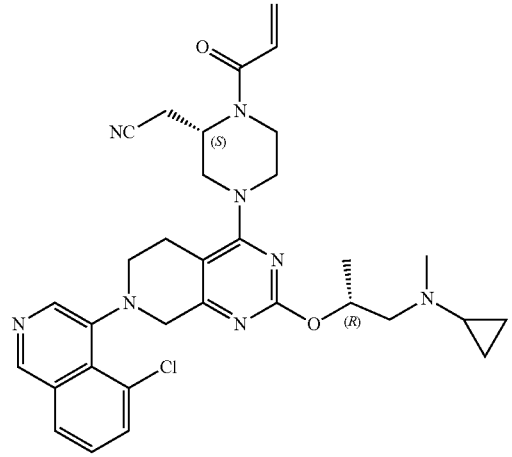
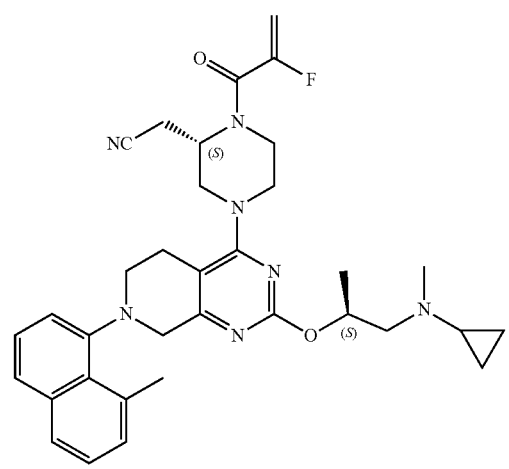
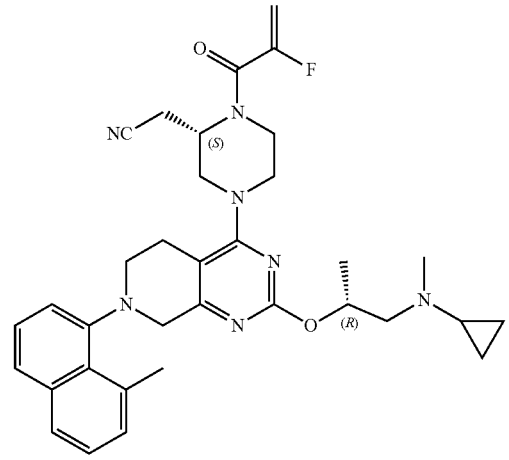

683
-continued
684
-continued
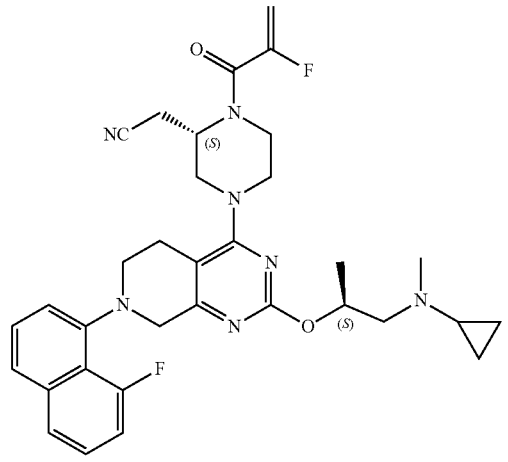
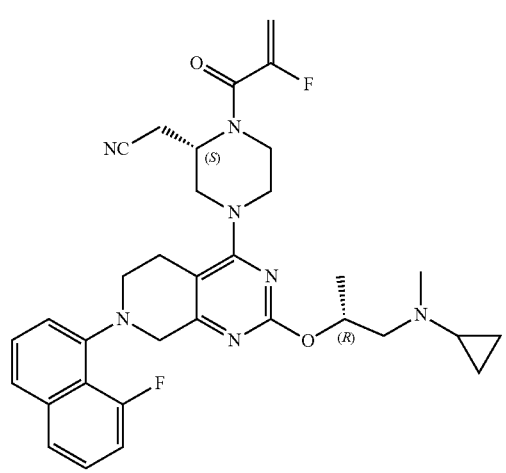
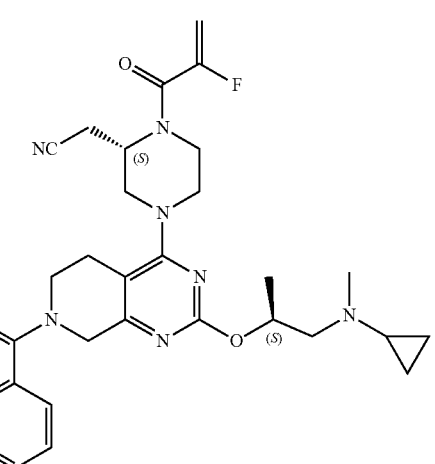
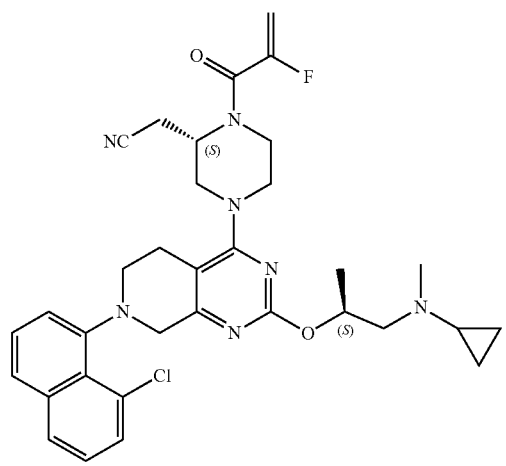
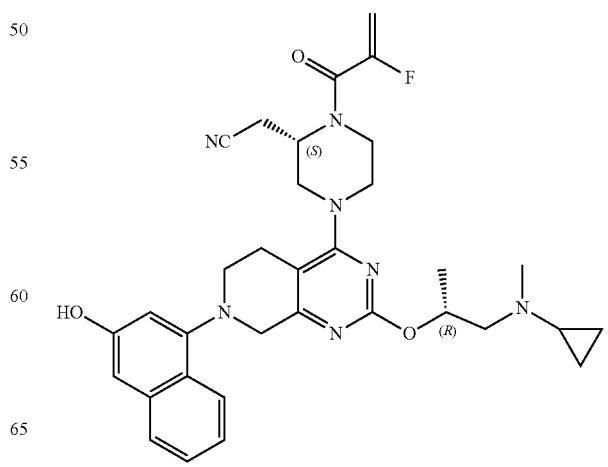

685
-continued
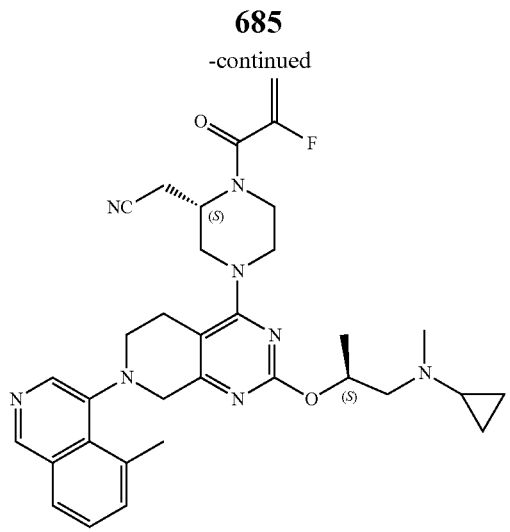
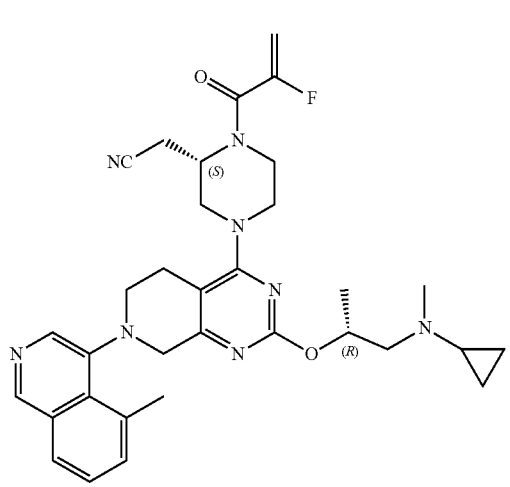
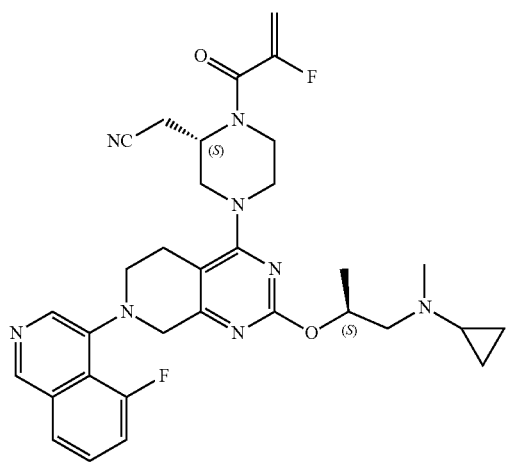
686
-continued
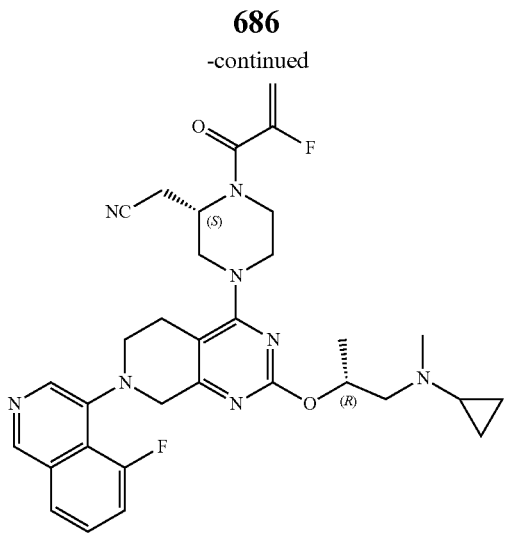
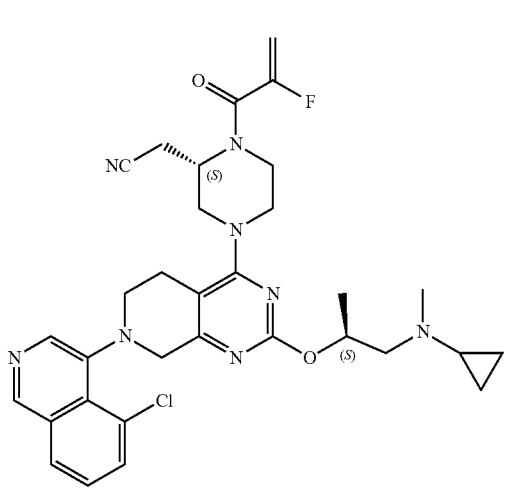
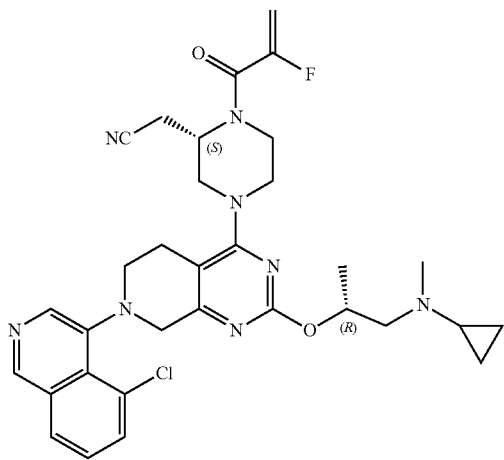

687
-continued
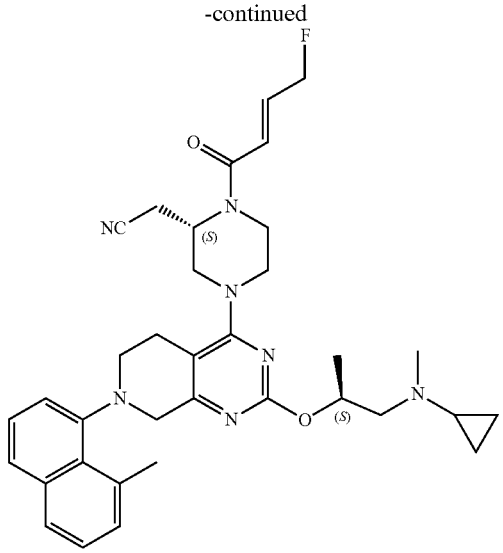
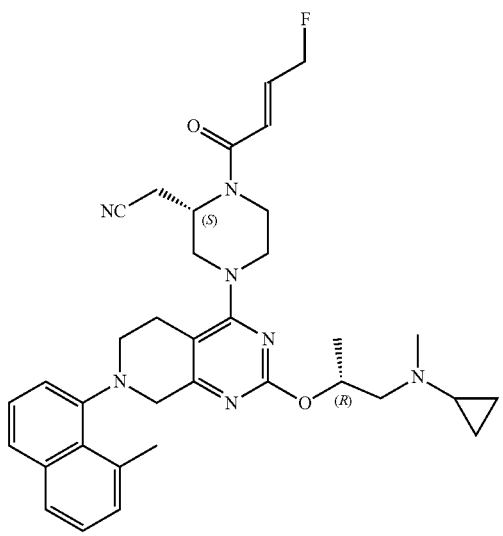
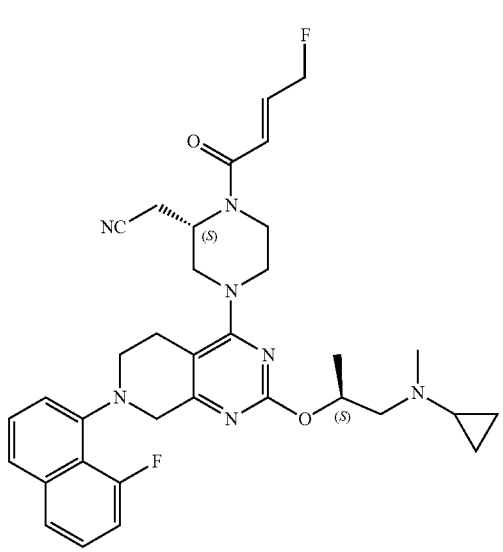
688
-continued
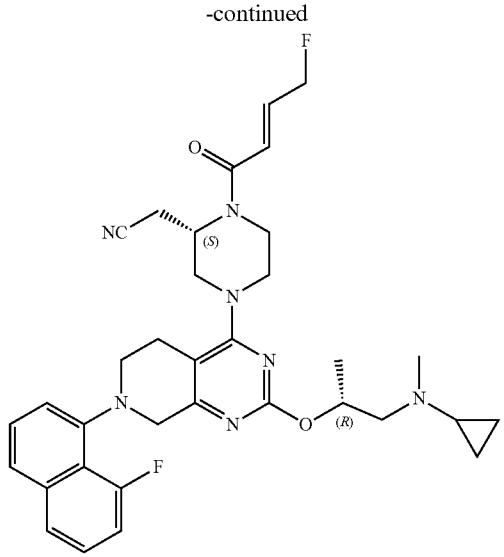
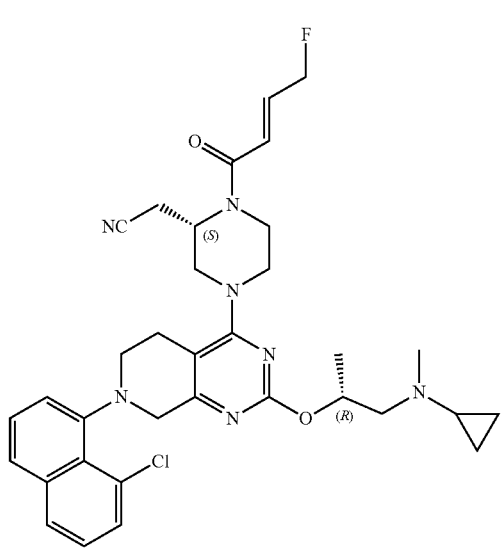
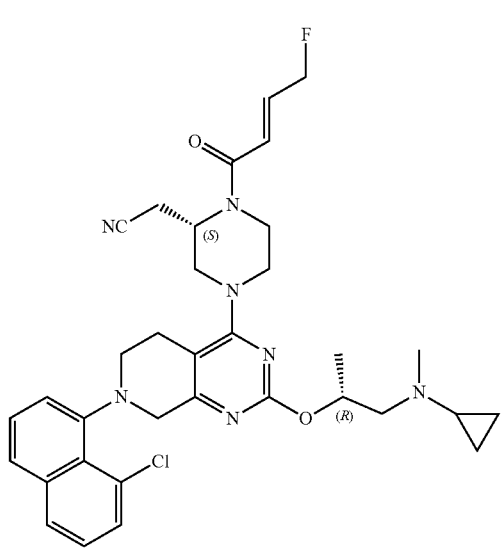

689
-continued
690
-continued
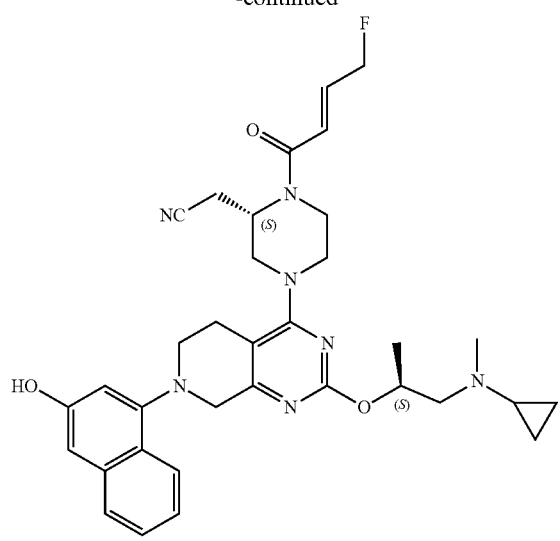
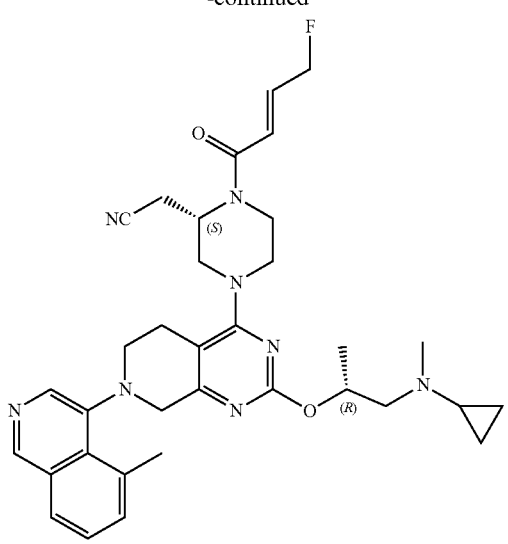

691
-continued
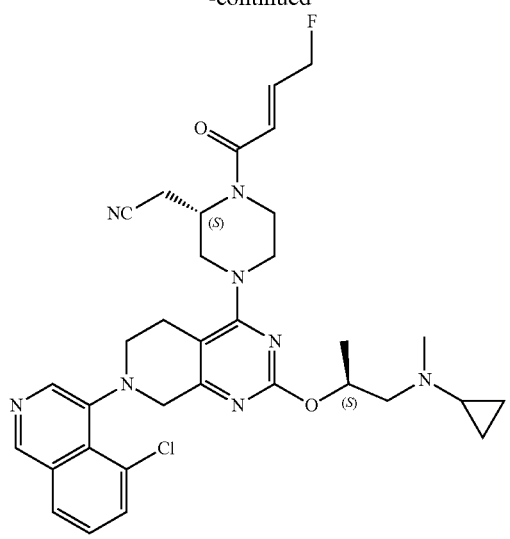
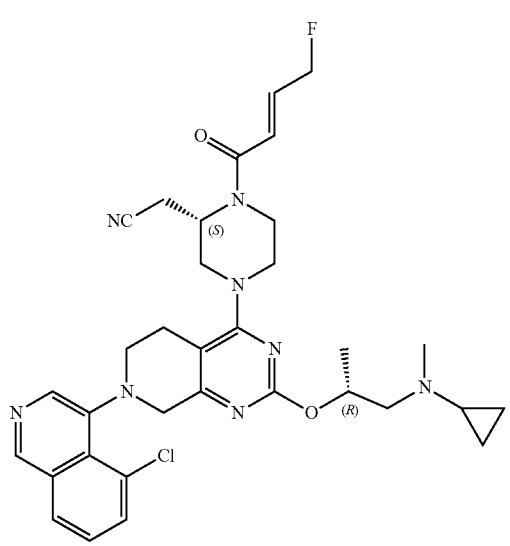
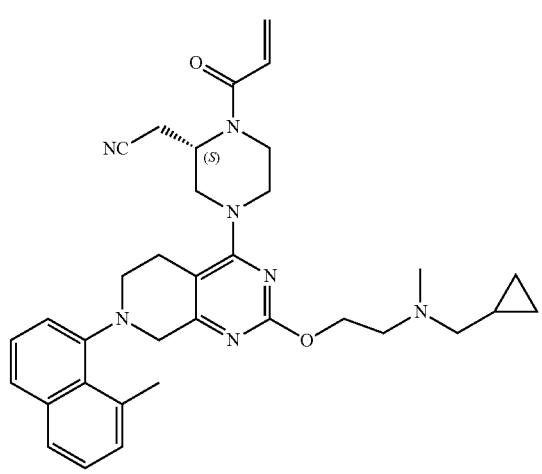
692
-continued
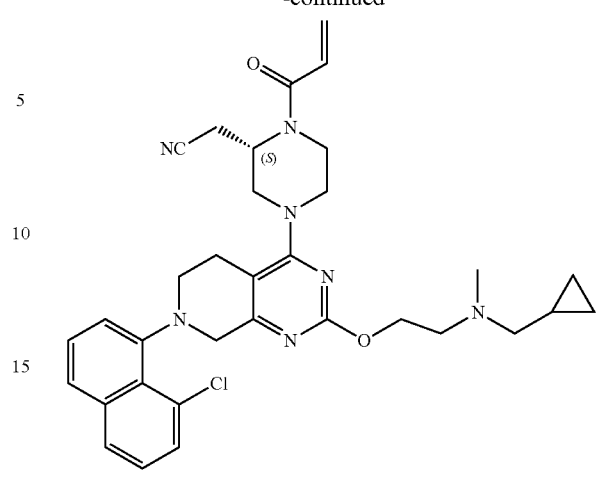
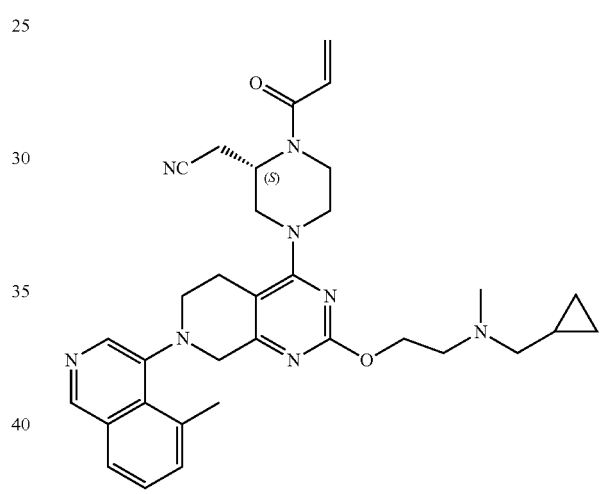
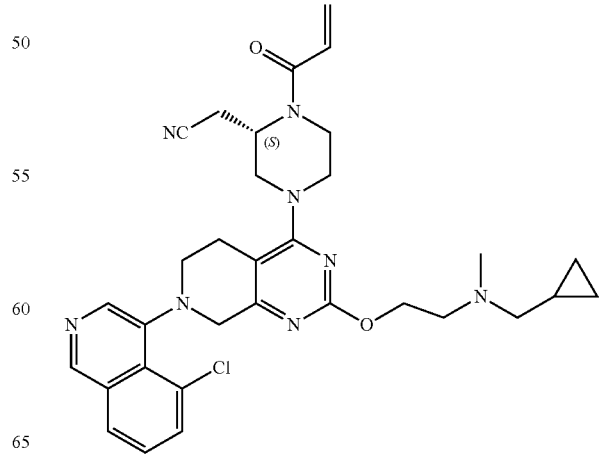

693
-continued
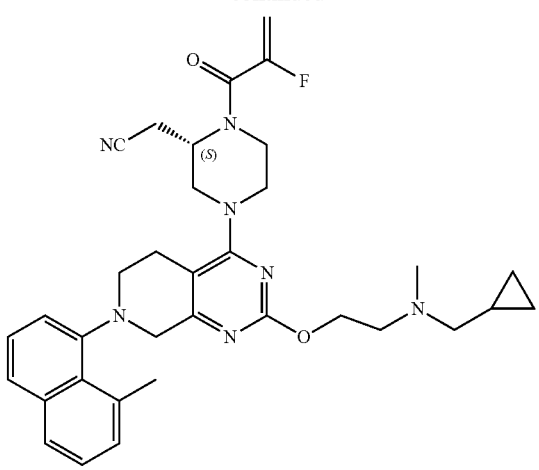
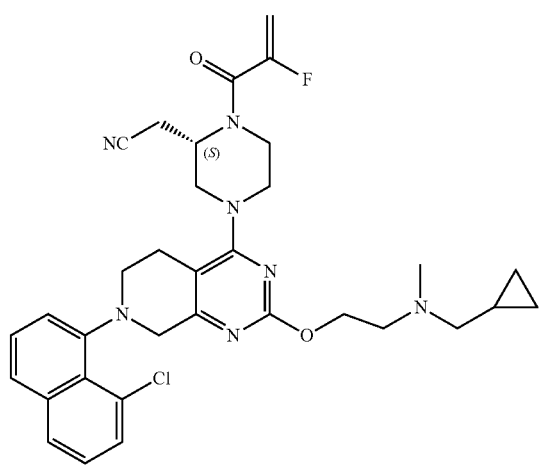
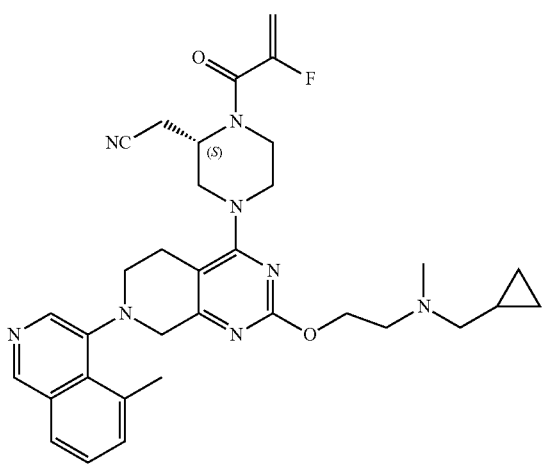
694
-continued
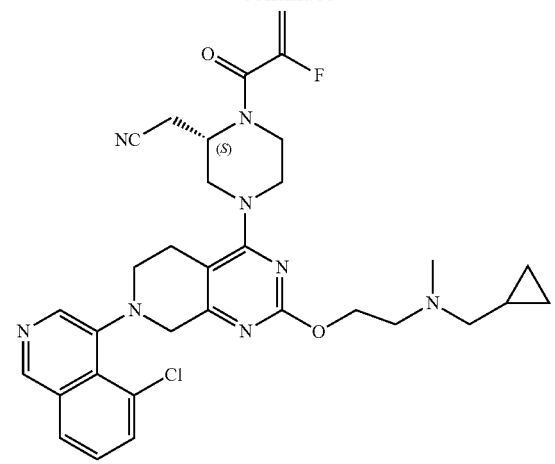
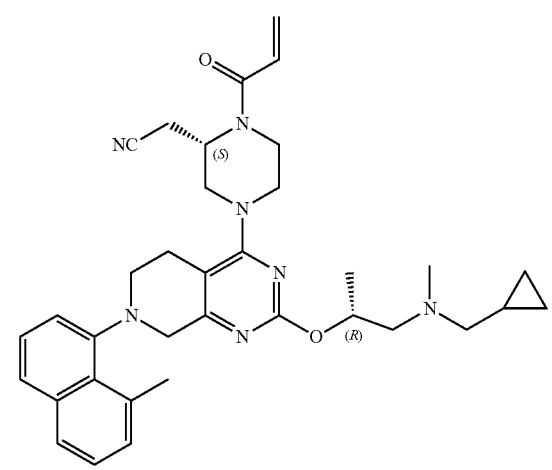
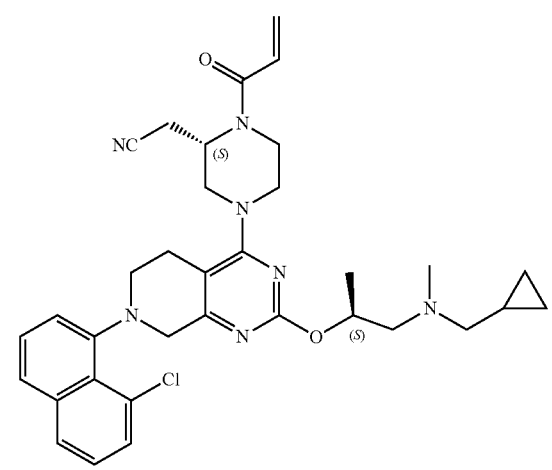

695
-continued
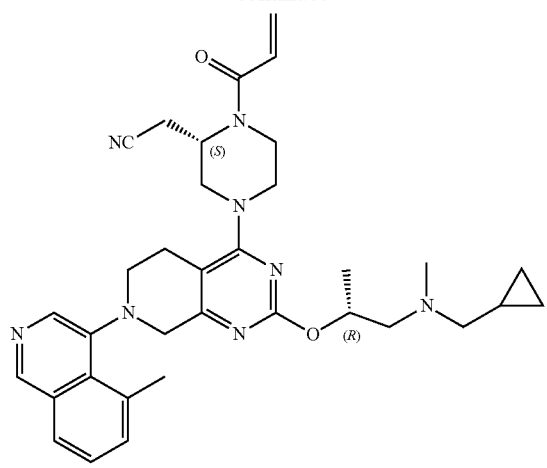
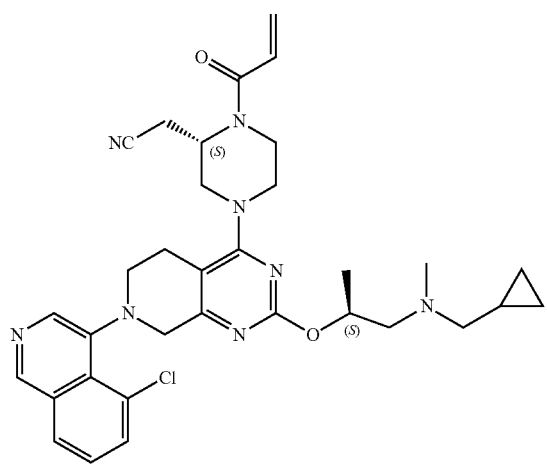
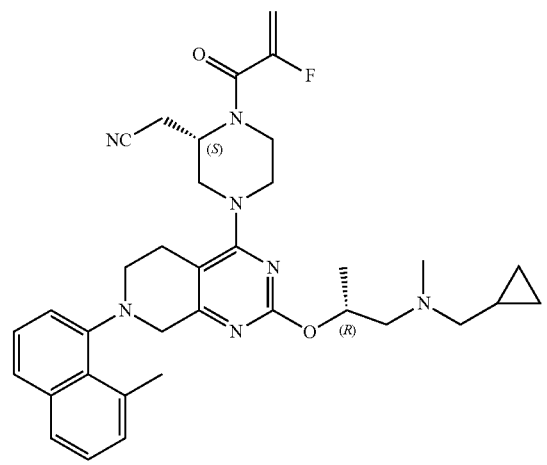
696
-continued
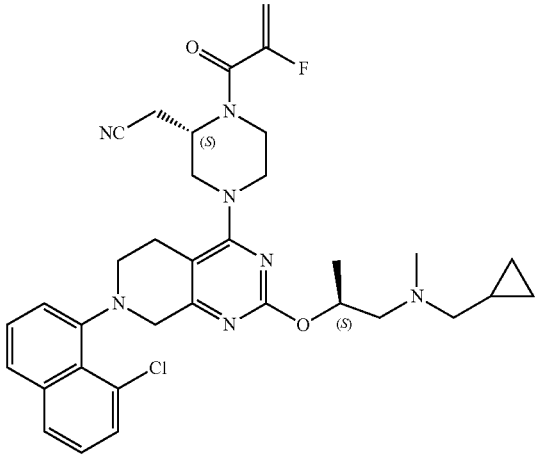
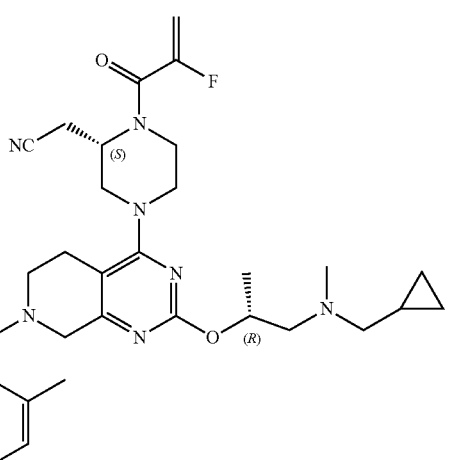
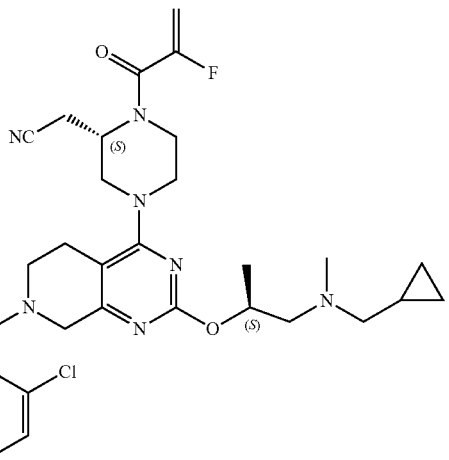

697
-continued
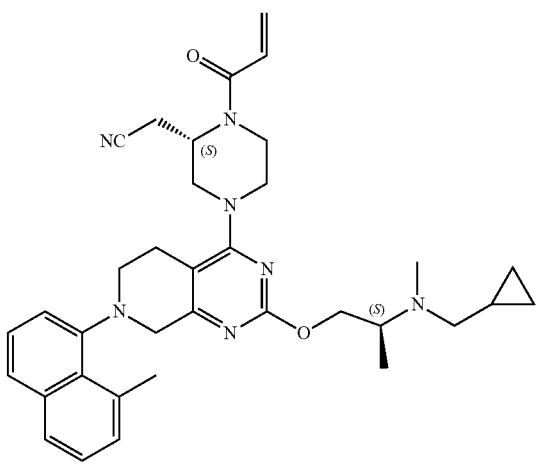
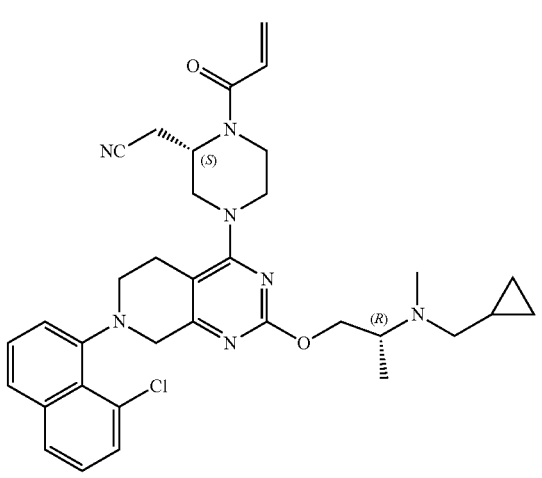
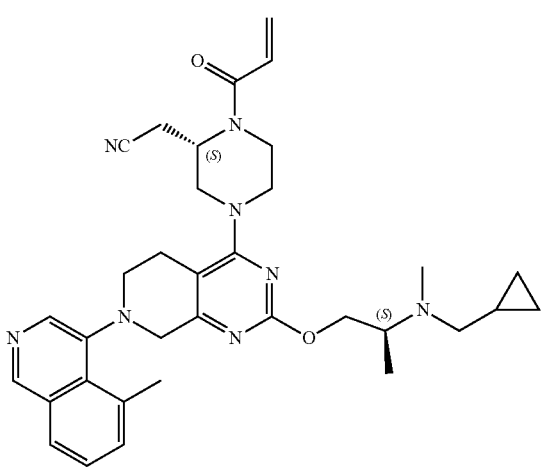
698
-continued
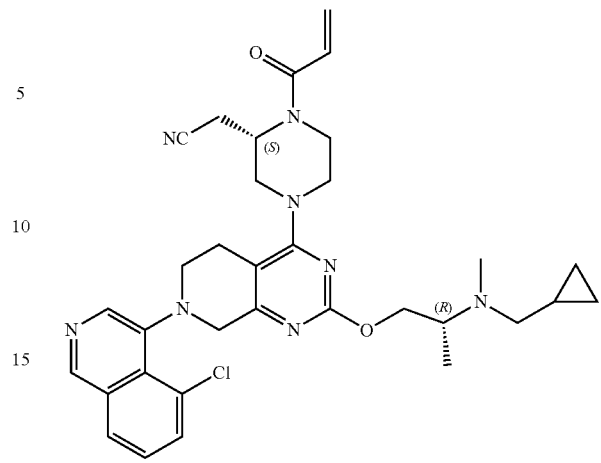

699
-continued
700
-continued
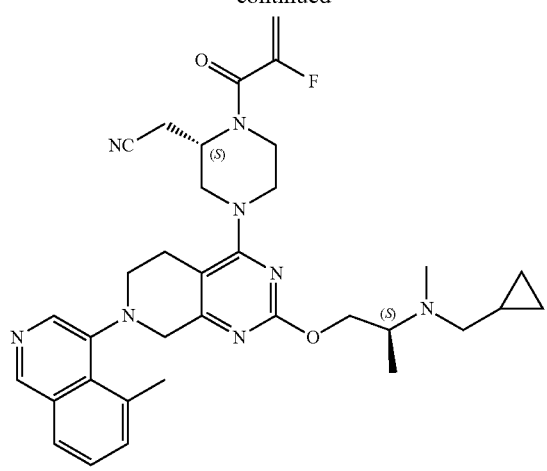
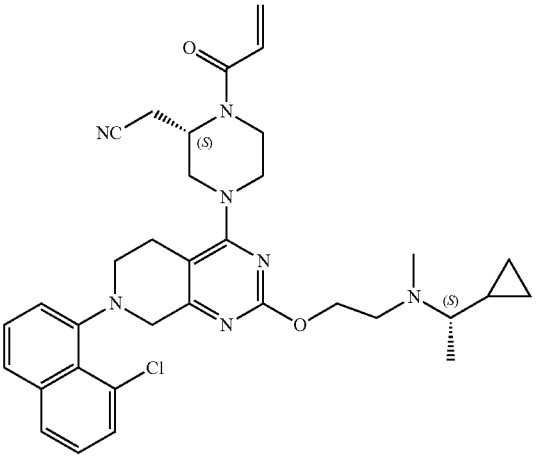
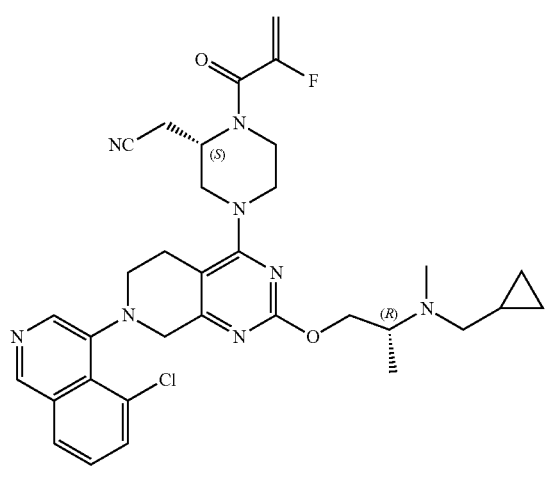
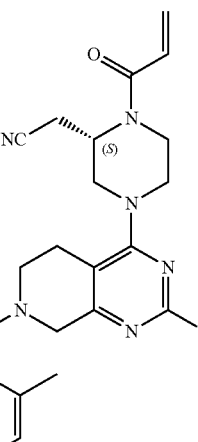
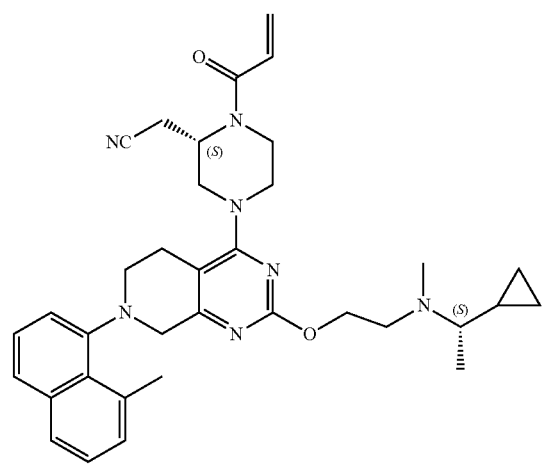
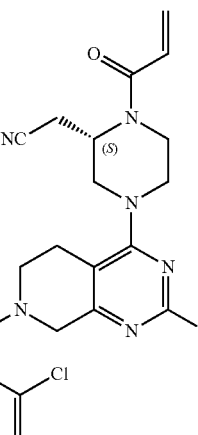

701
-continued
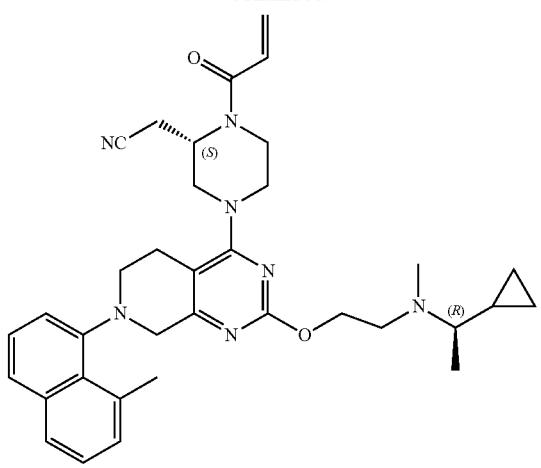
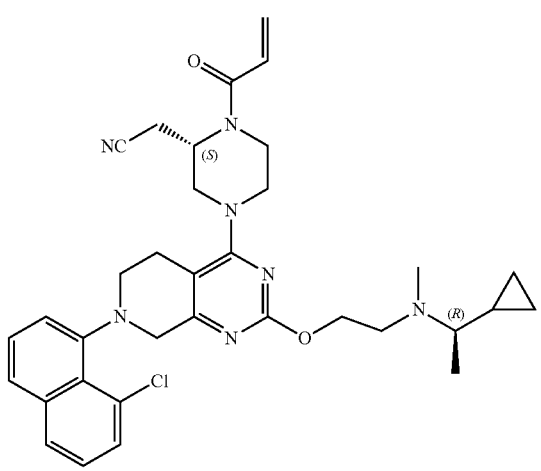
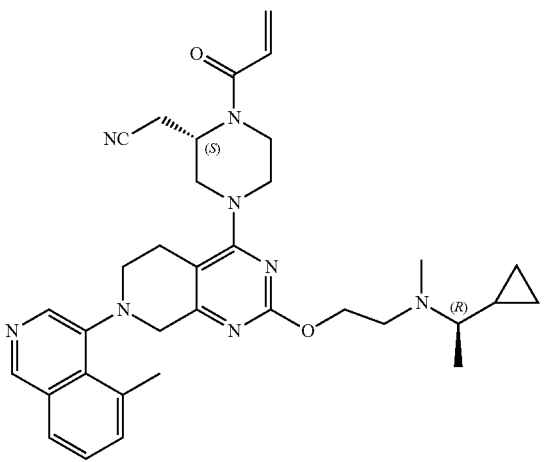
702
-continued
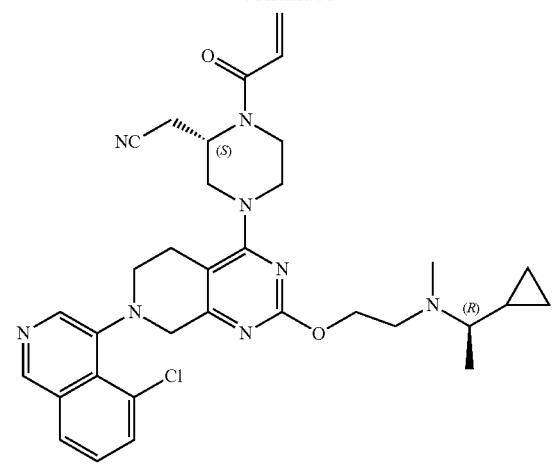
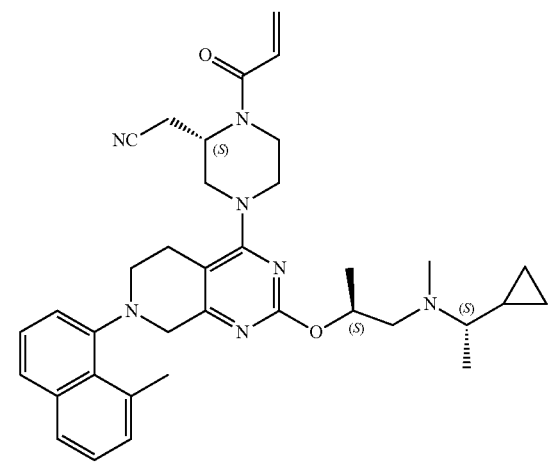
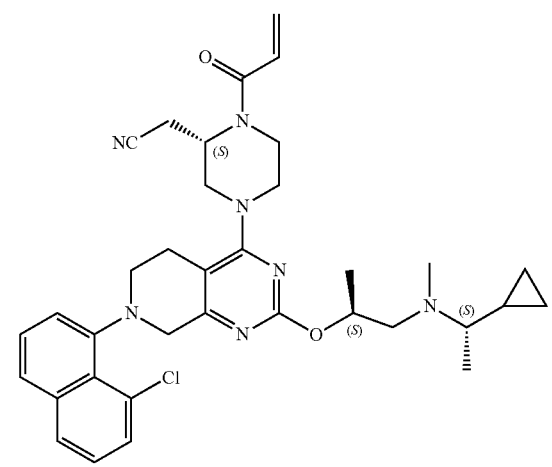

703
-continued
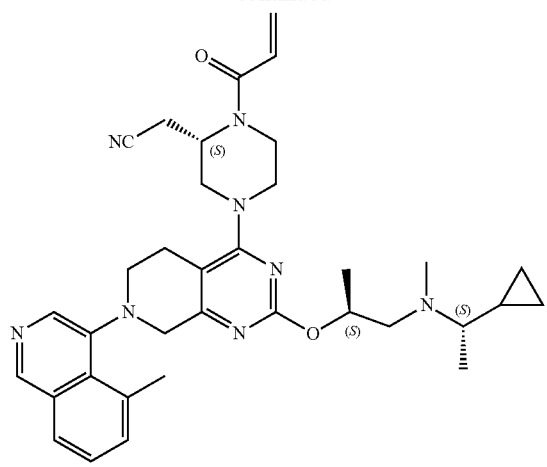
704
-continued
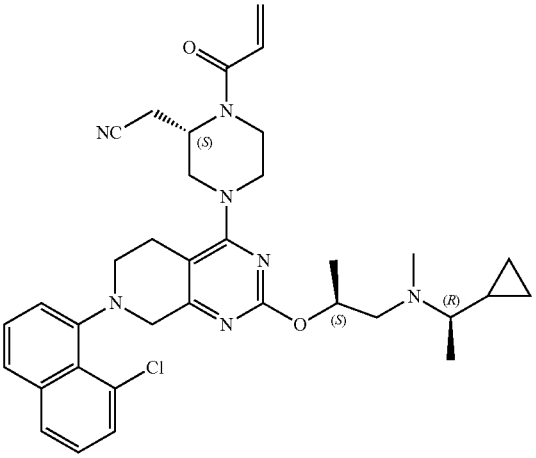
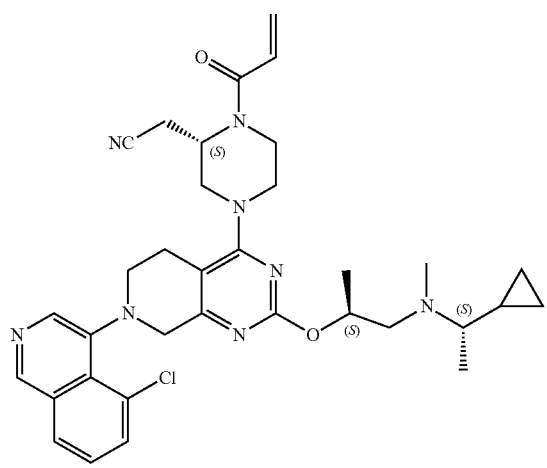
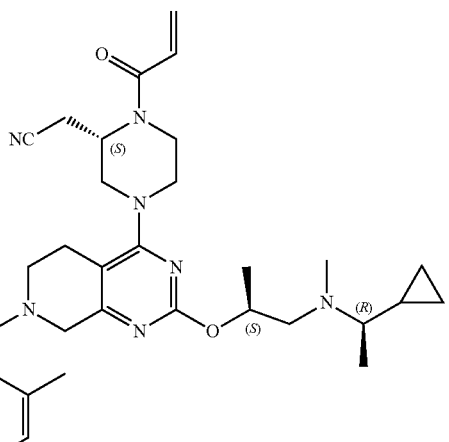
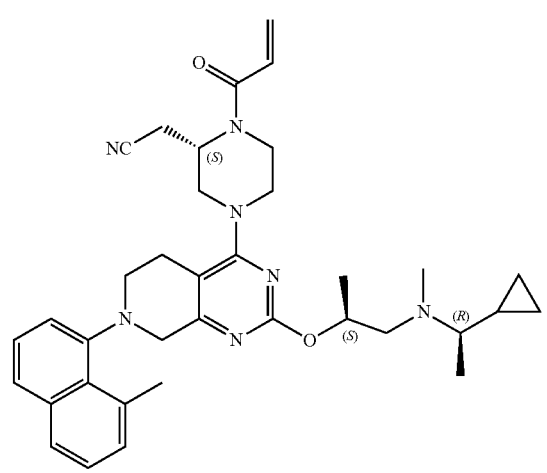
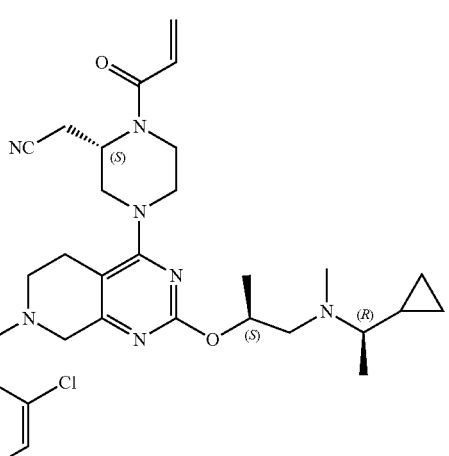

705
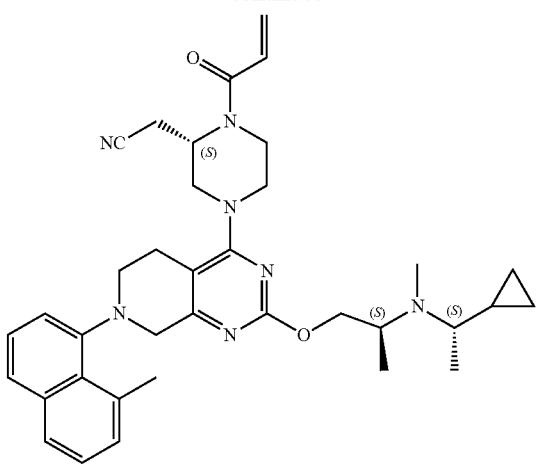
706
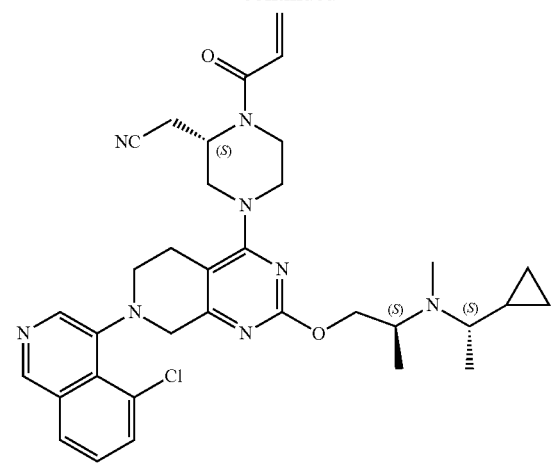
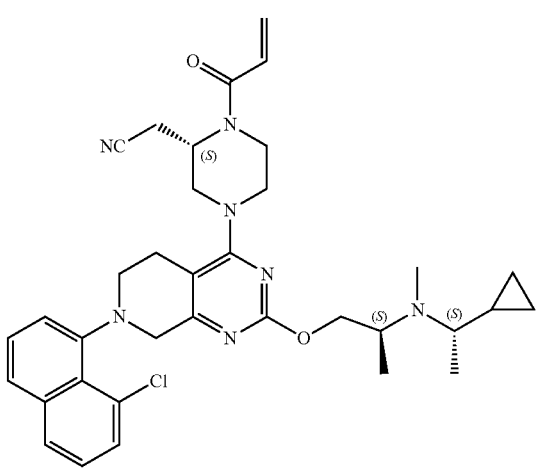
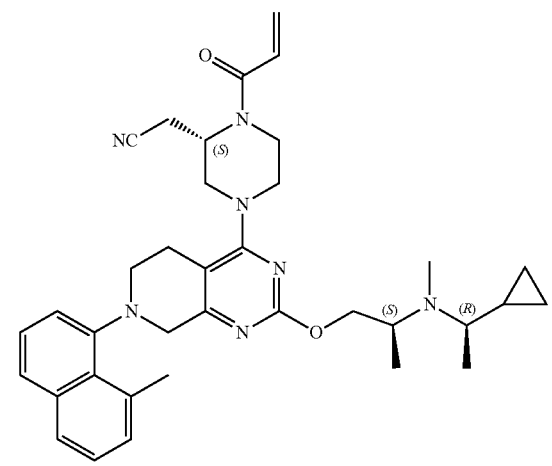
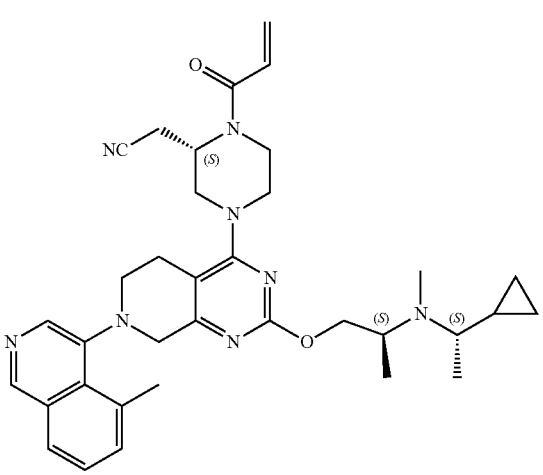
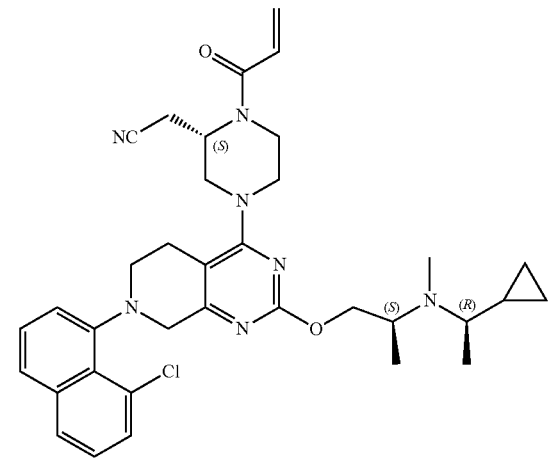

707
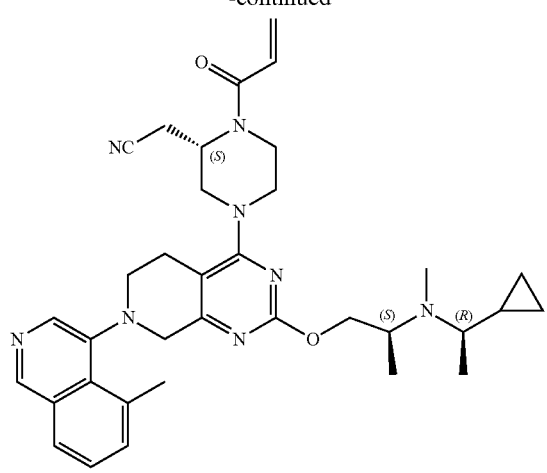
708
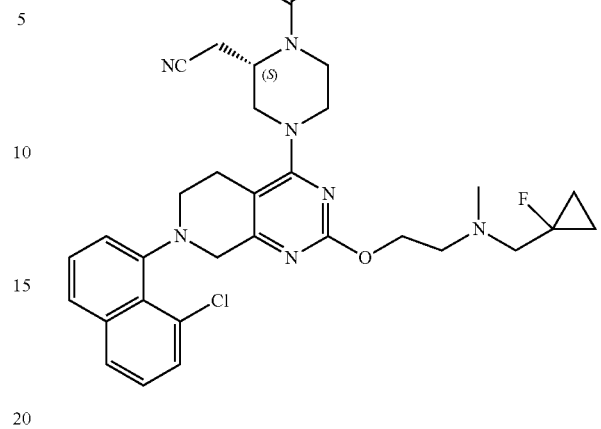
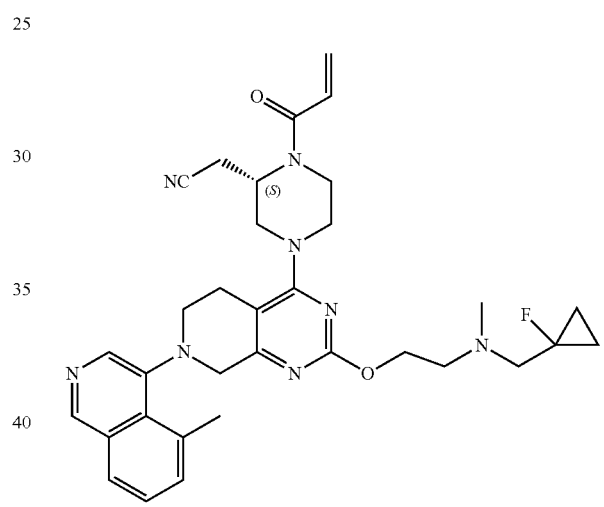
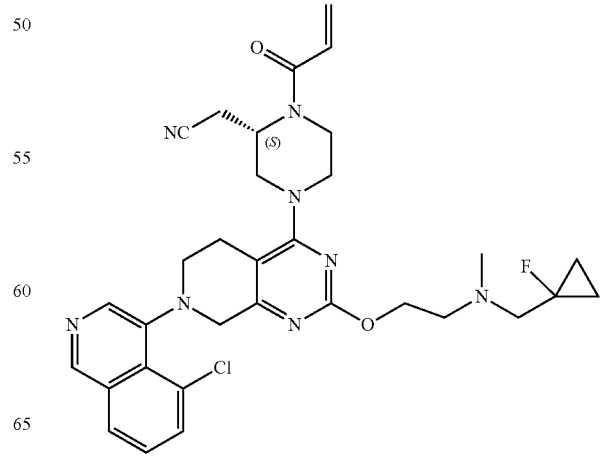

709
-continued
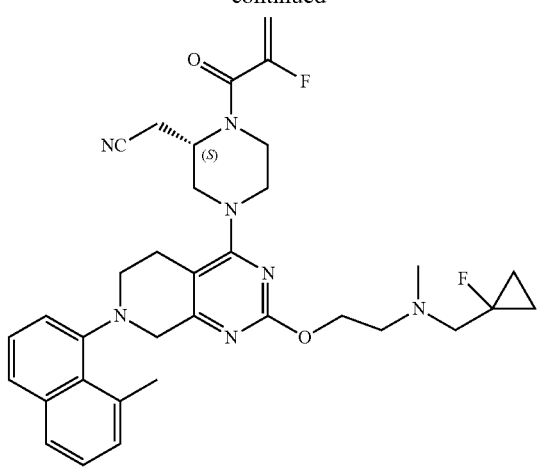
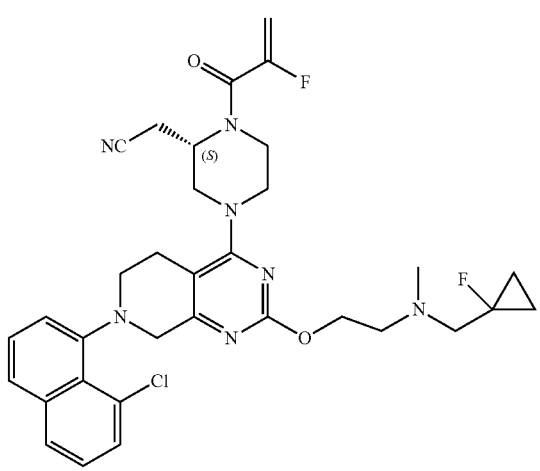
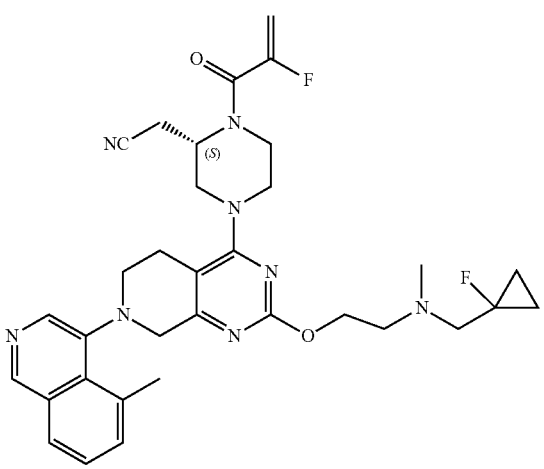
710
-continued
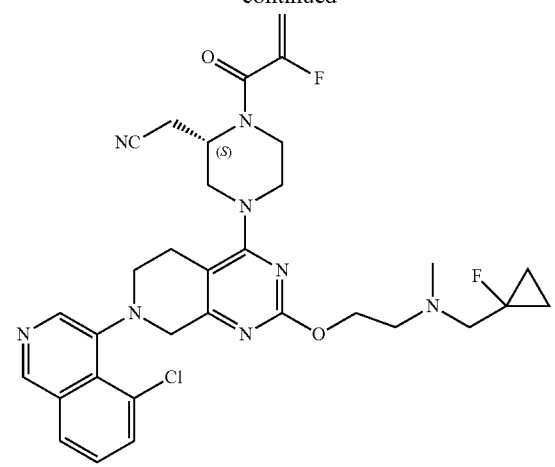
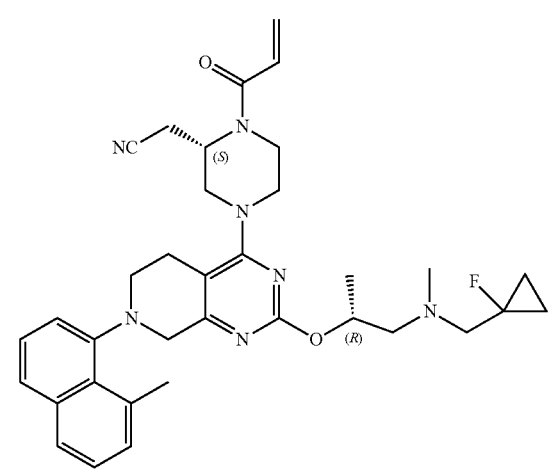
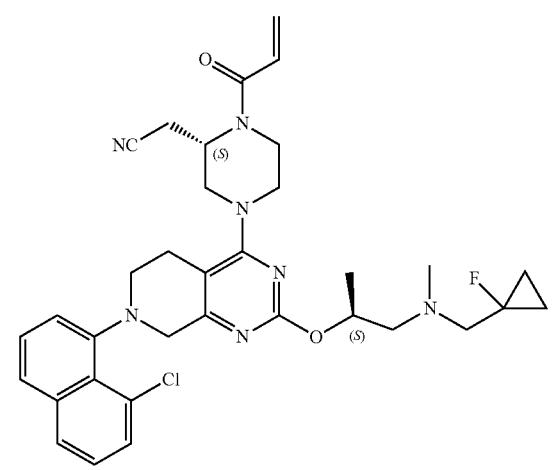

711
-continued
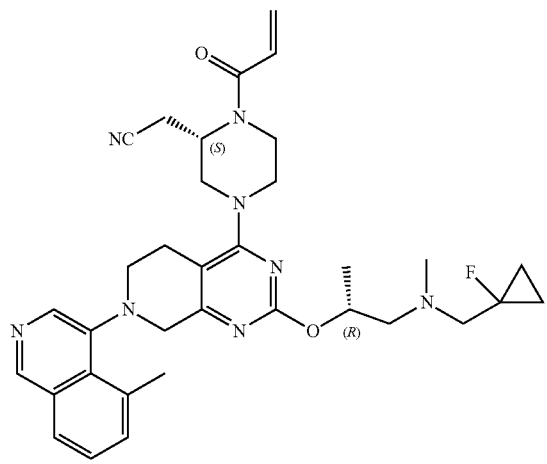
712
-continued
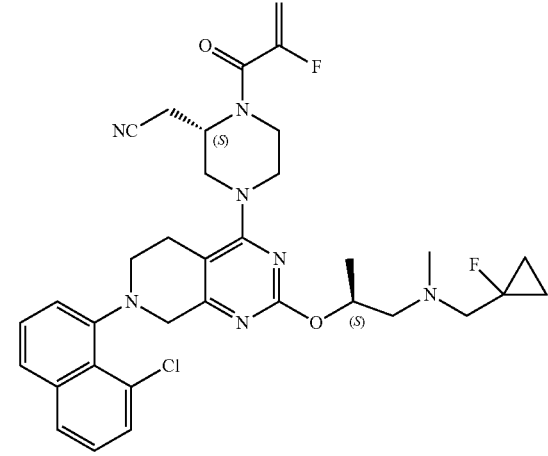
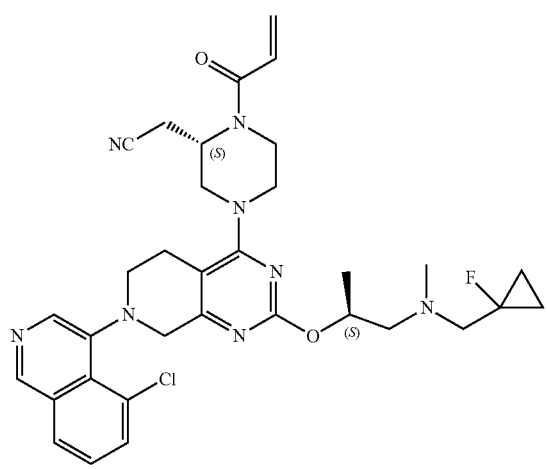
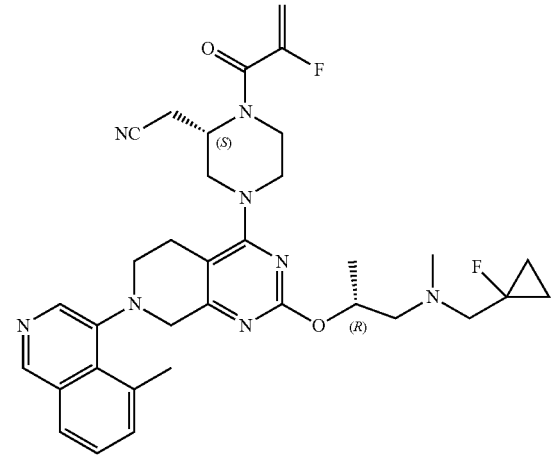
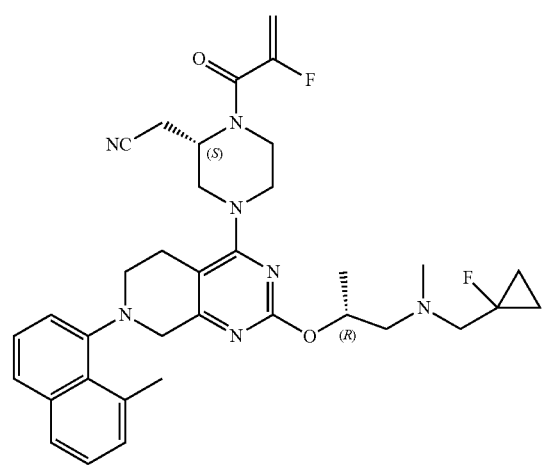
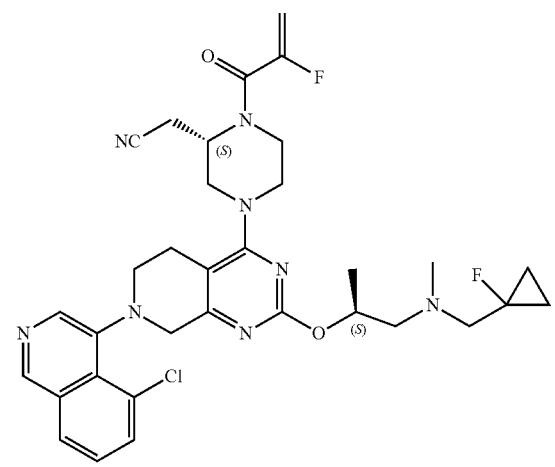

| 713 -continued | 714 -continued |
|---|---|
| 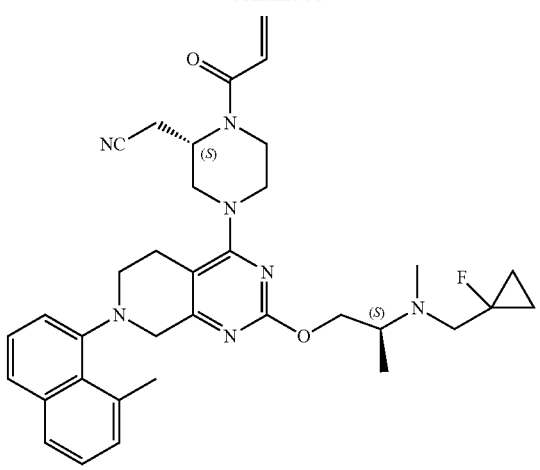 | 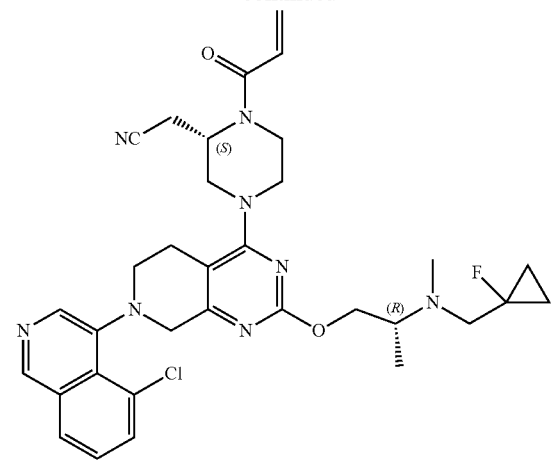 |
| 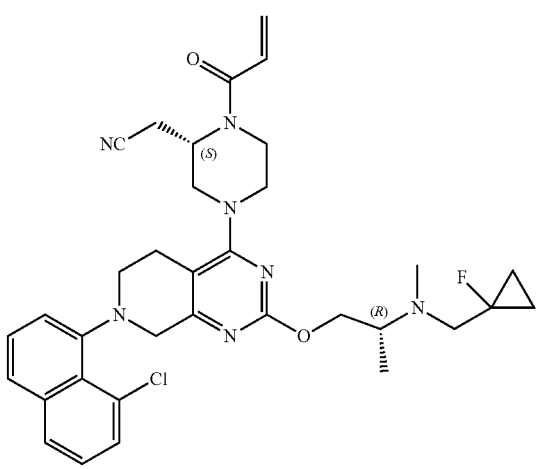 | 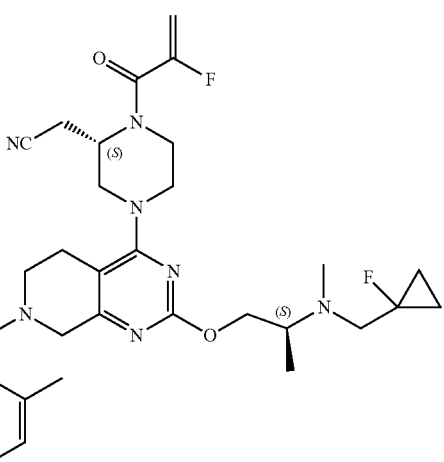 |
| 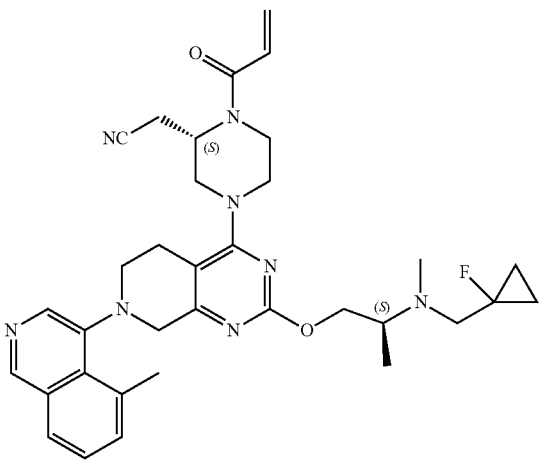 | 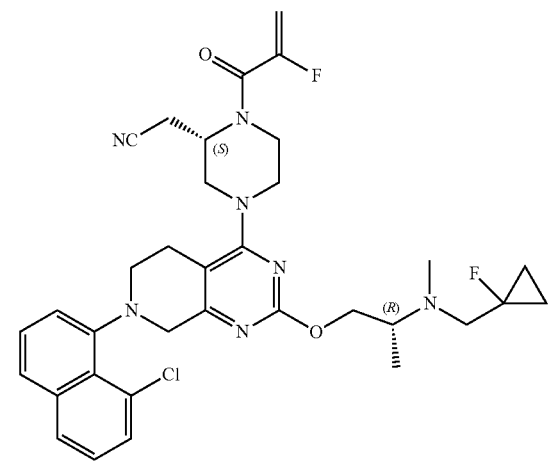 |

715
-continued
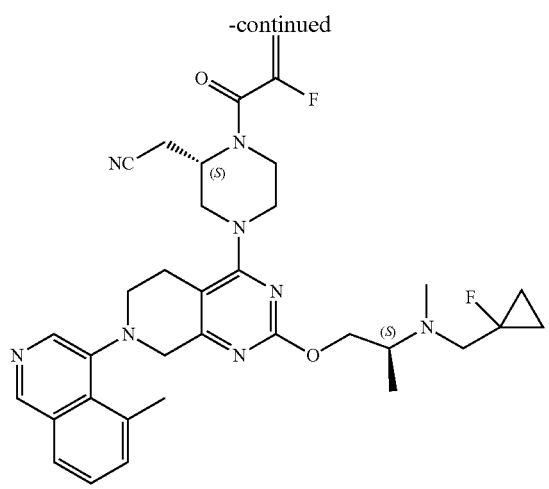
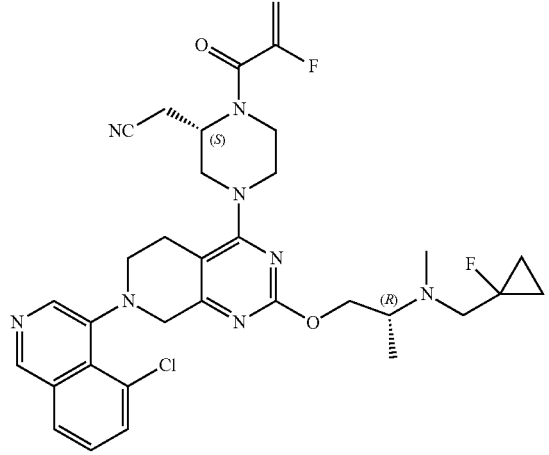
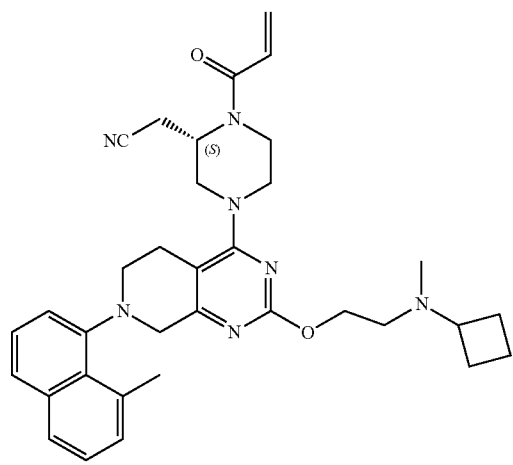
716
-continued
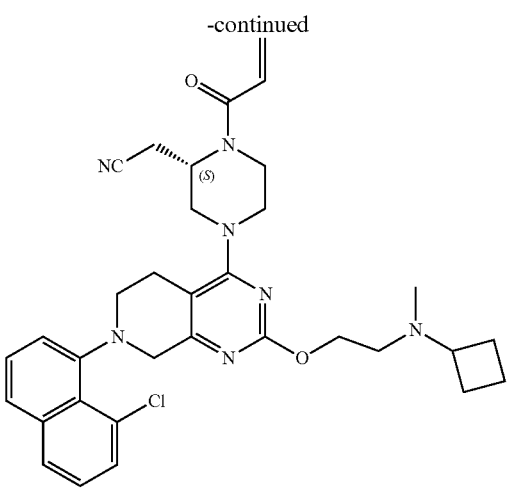
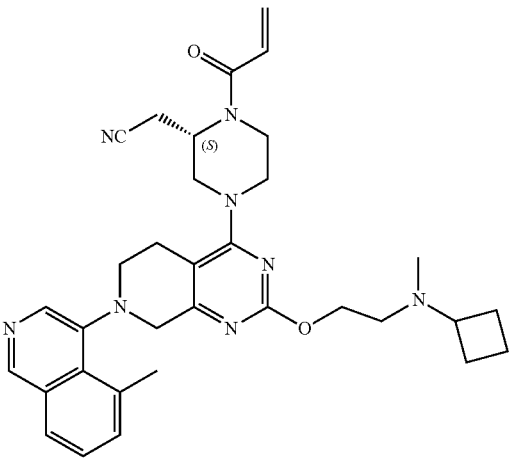
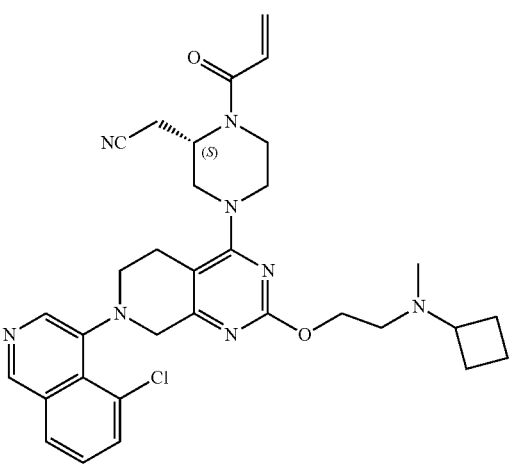

717
-continued
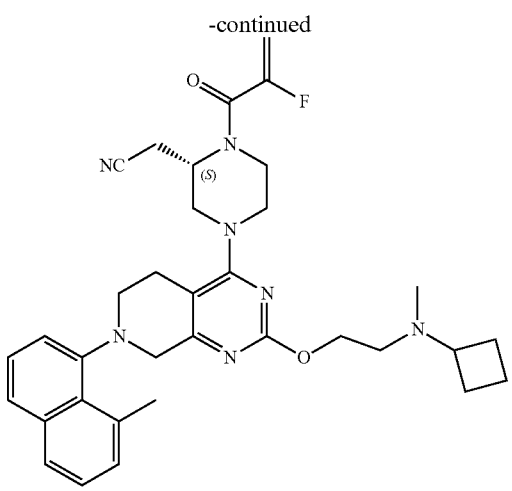
718
-continued
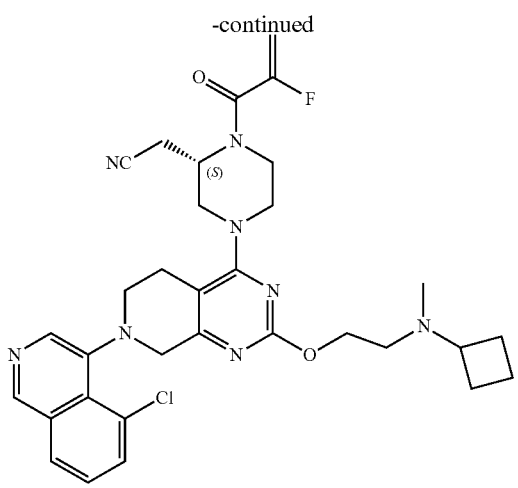
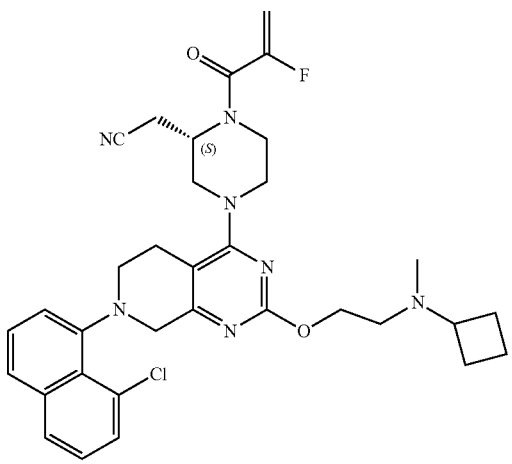
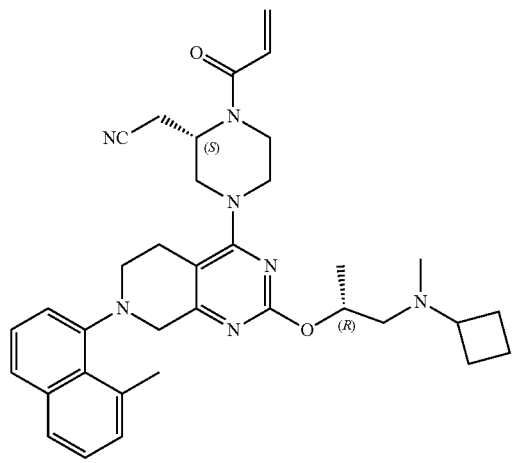
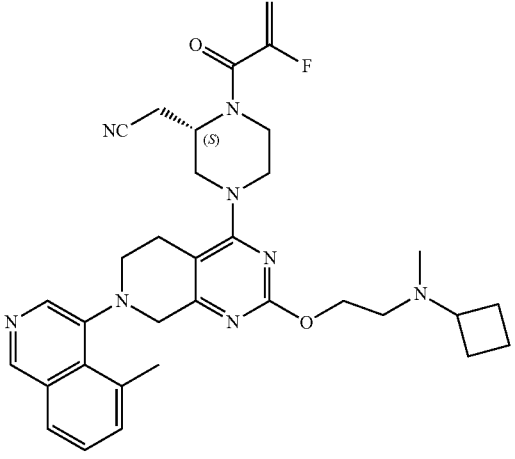
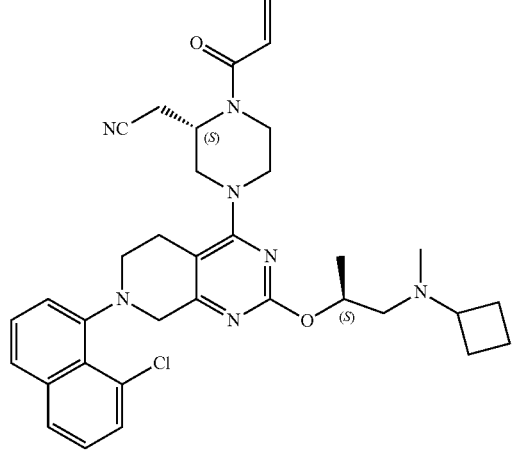

719
-continued
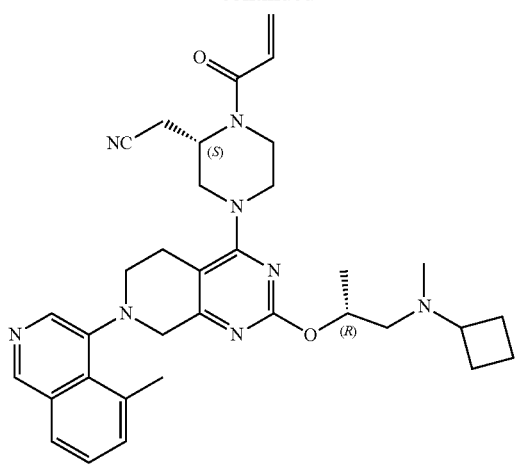
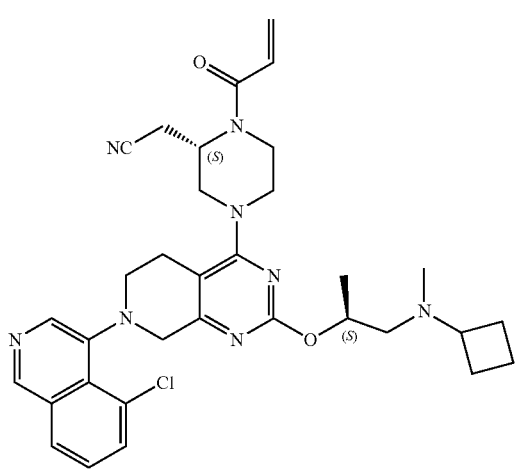
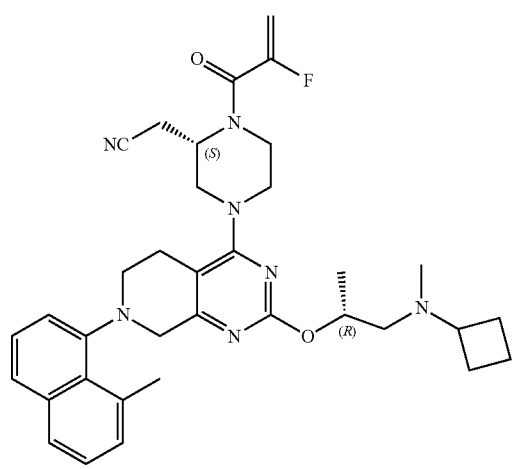
720
-continued
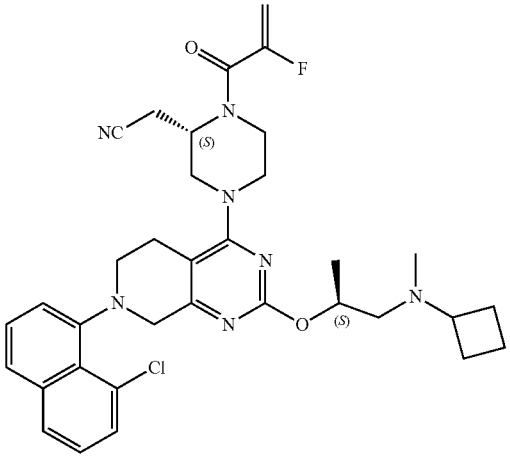
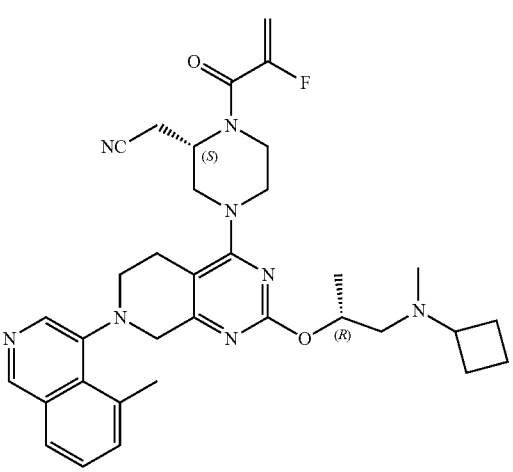
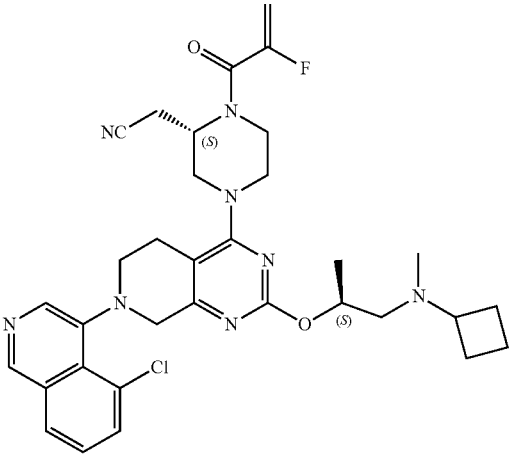

721
-continued
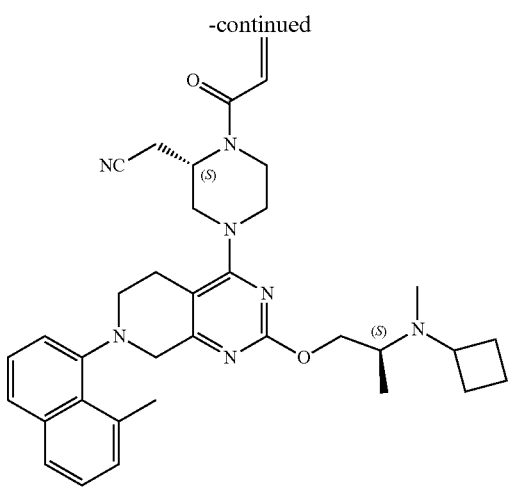
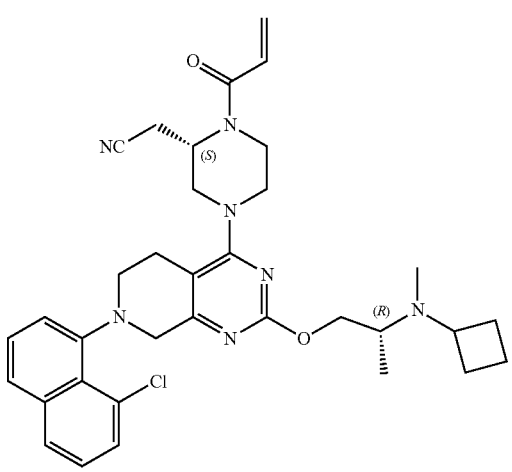
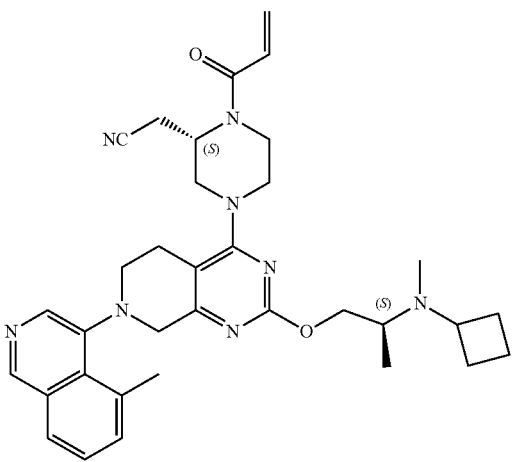
722
-continued
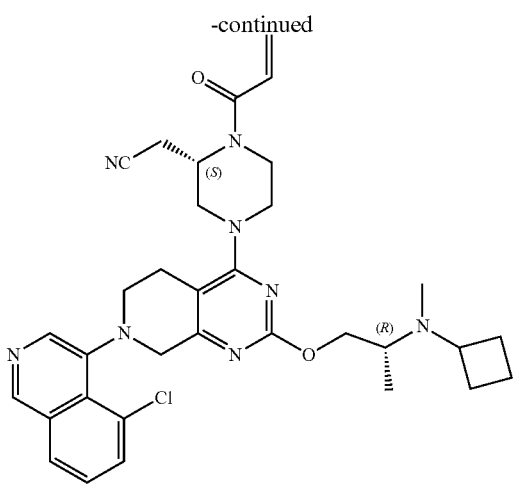
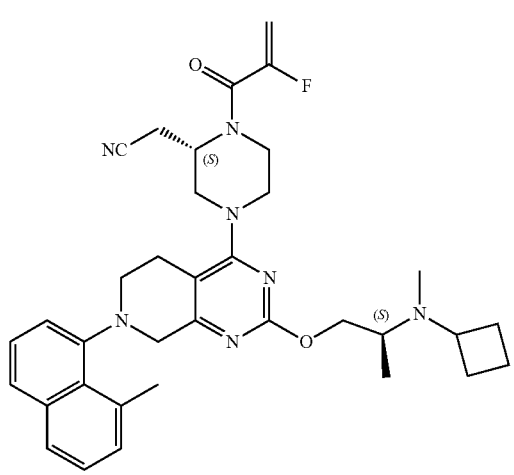
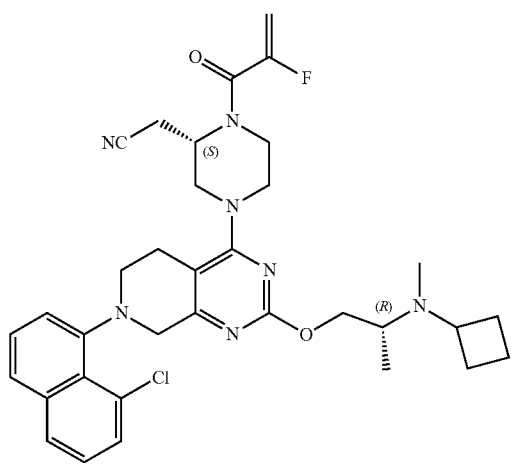

| 723 | 724 |
|---|---|
| 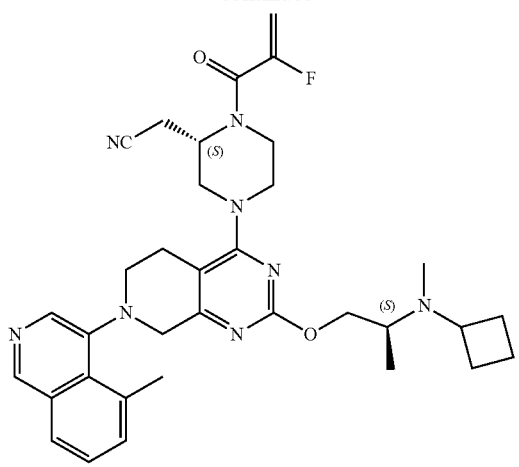 | 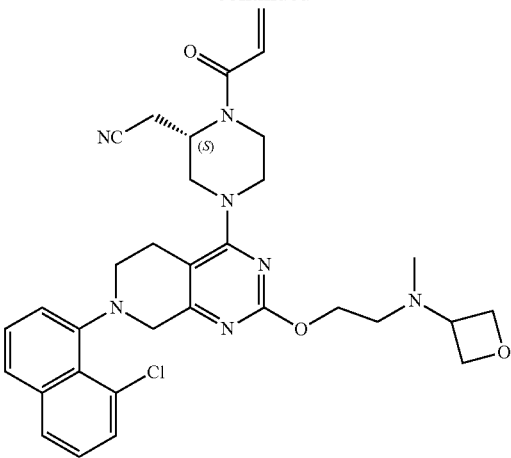 |
| 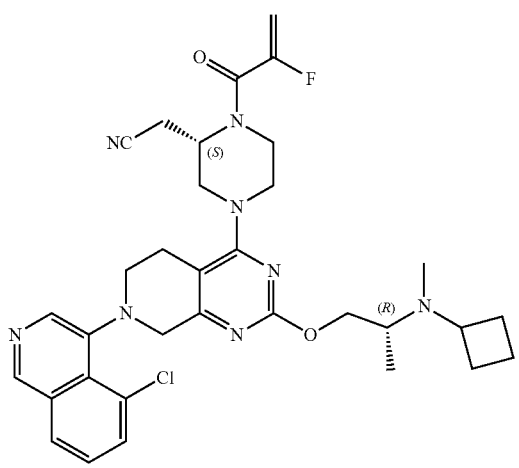 | 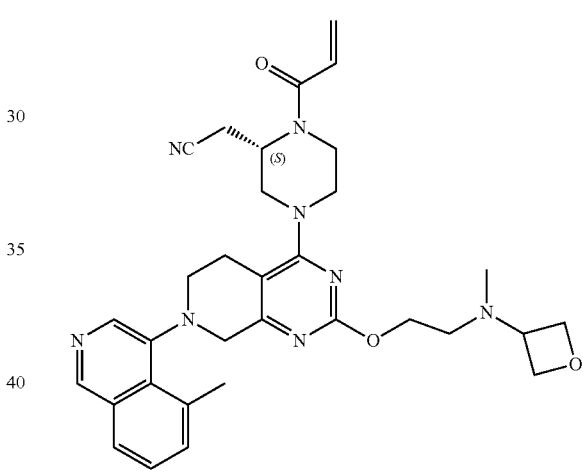 |
| 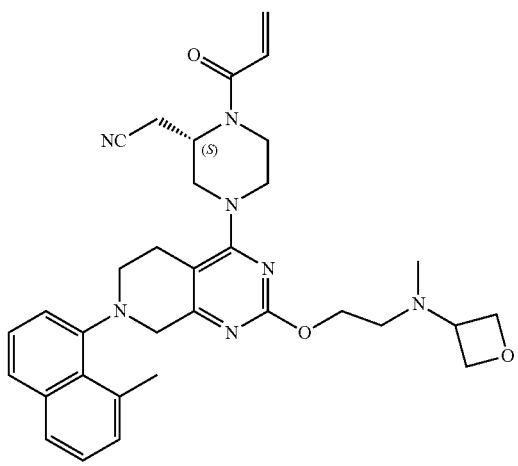 | 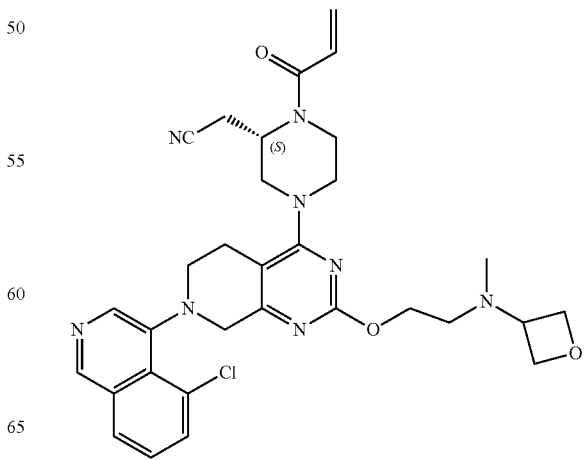 |

725
-continued
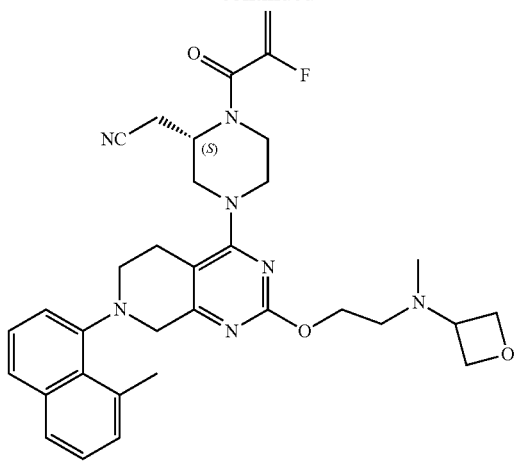
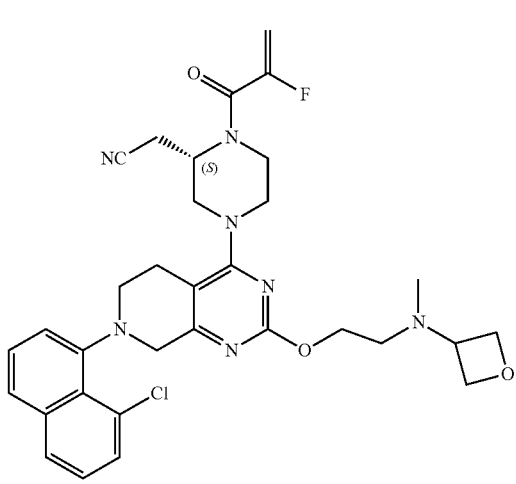
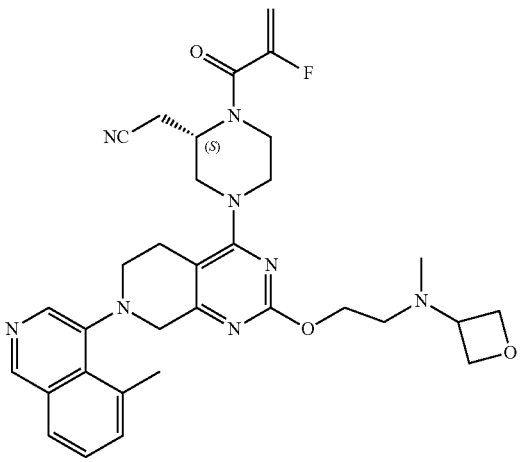
726
-continued
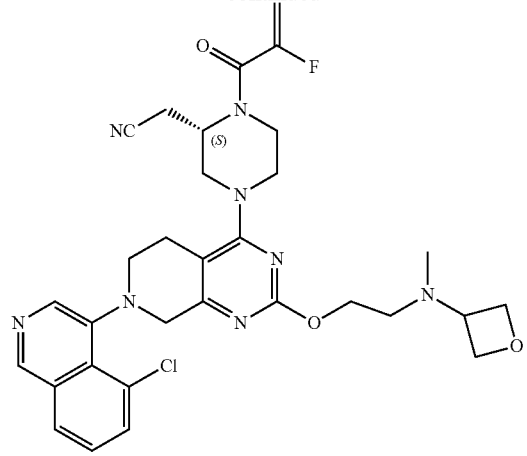
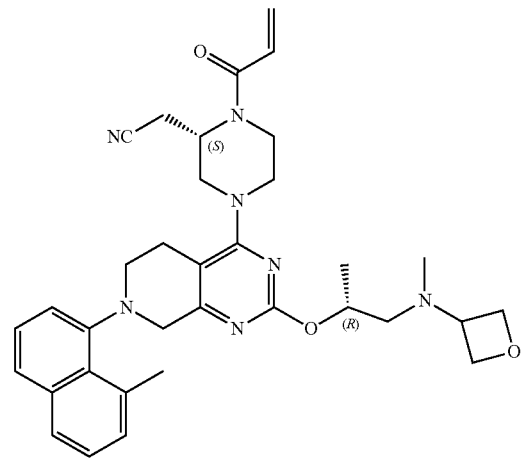
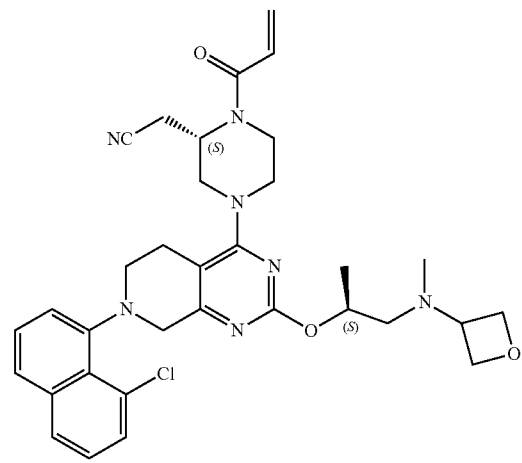

727
-continued
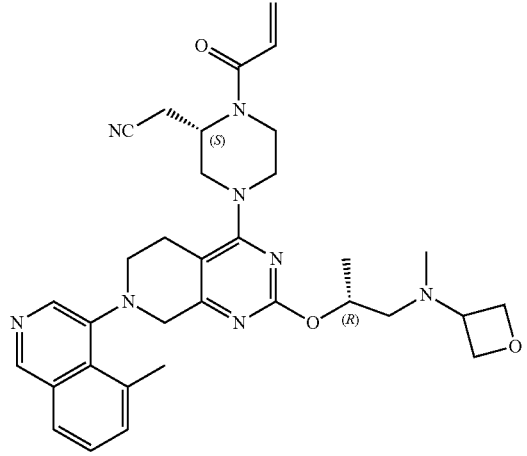
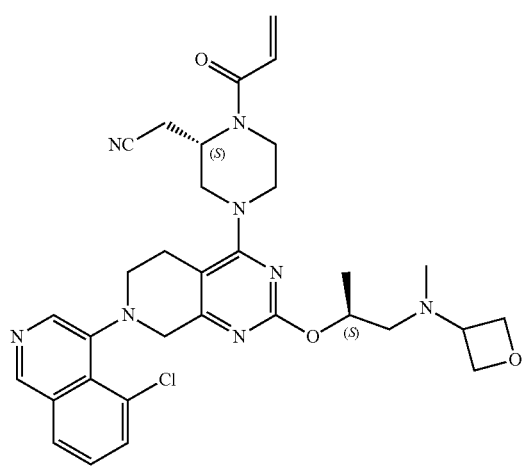
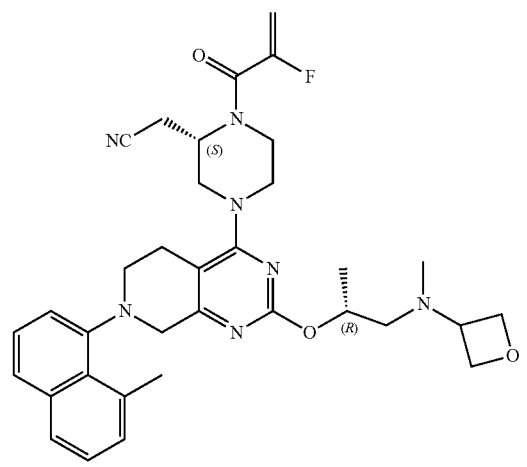
728
-continued
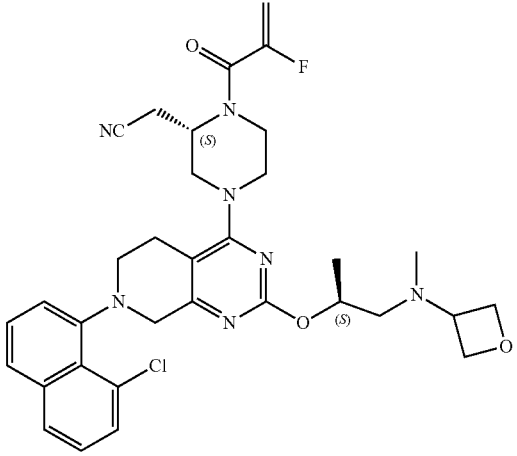
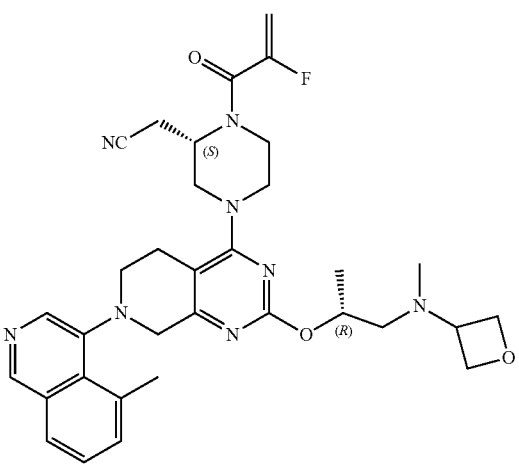
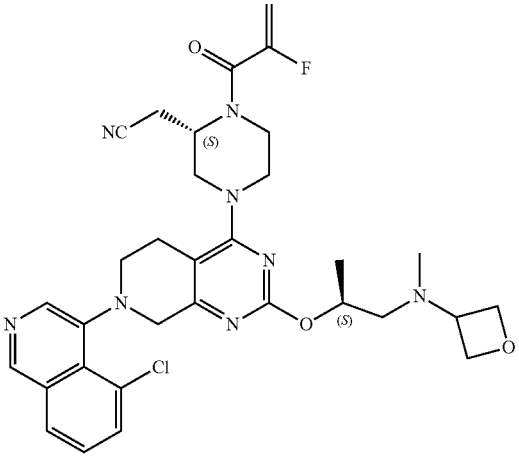

729
-continued
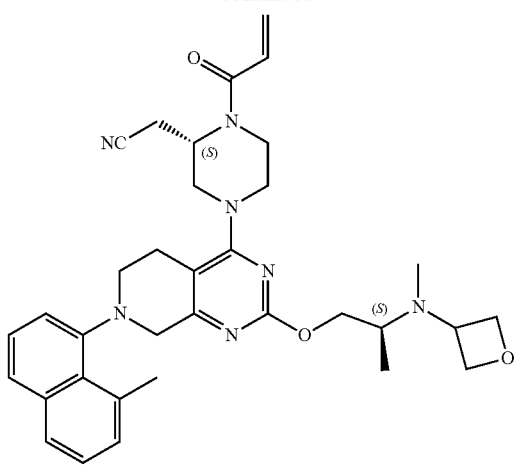
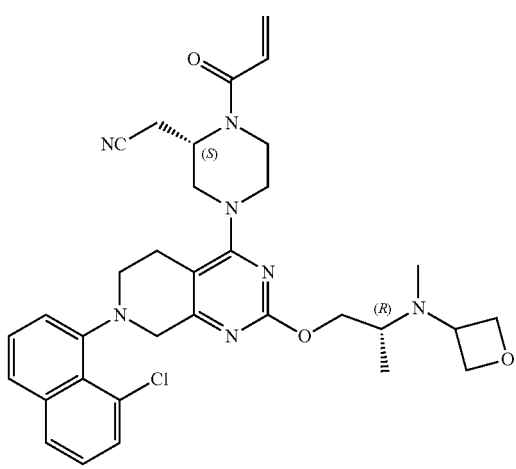
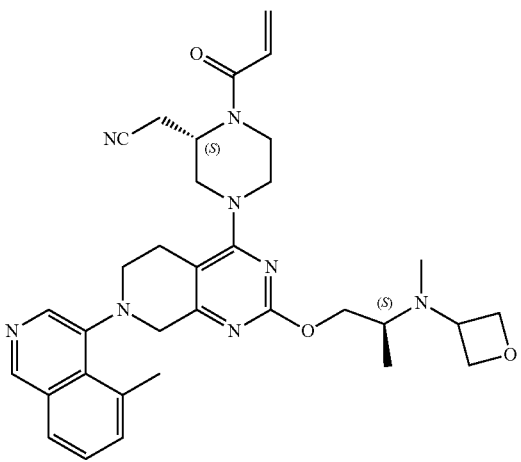
730
-continued
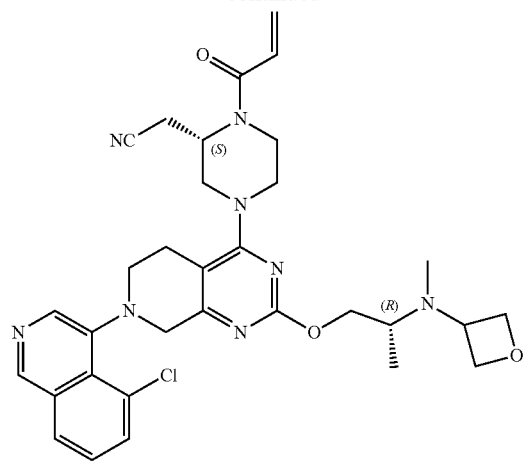

731
-continued
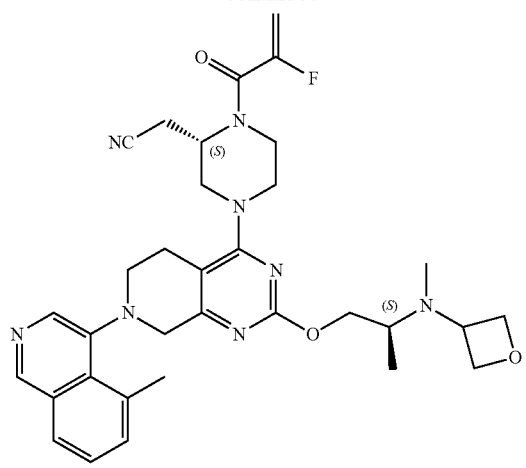
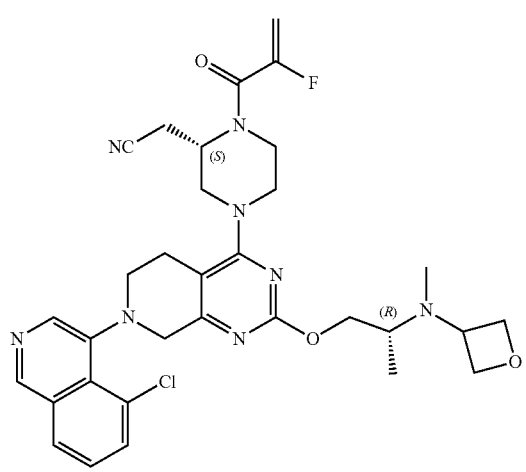
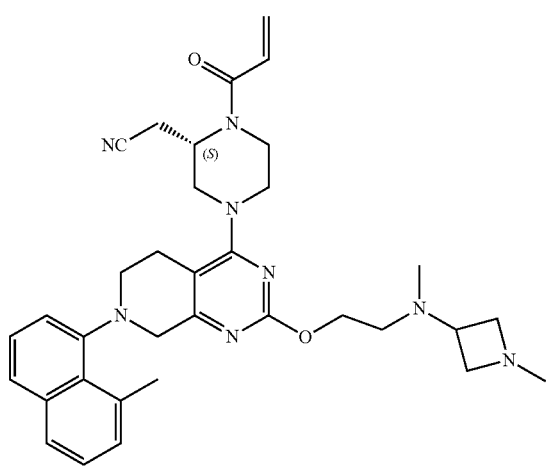
732
-continued
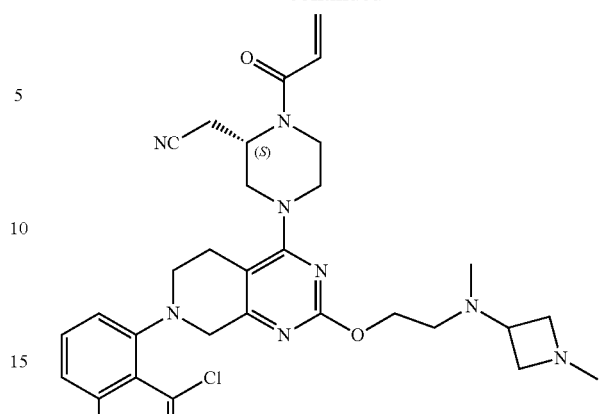
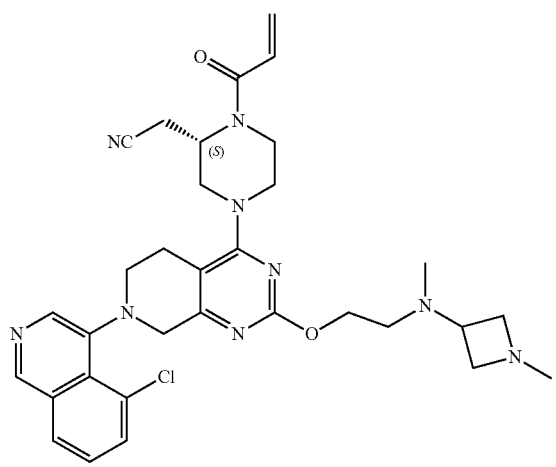

733
-continued
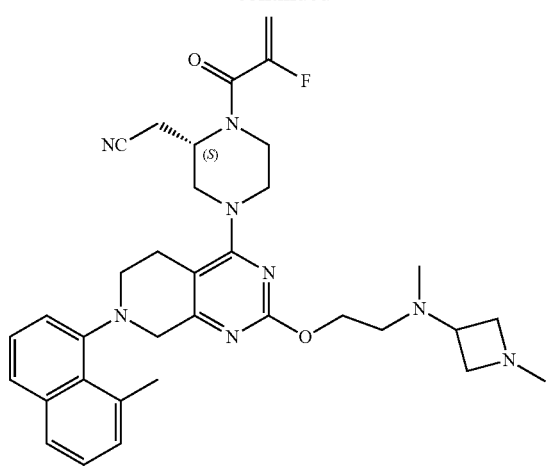
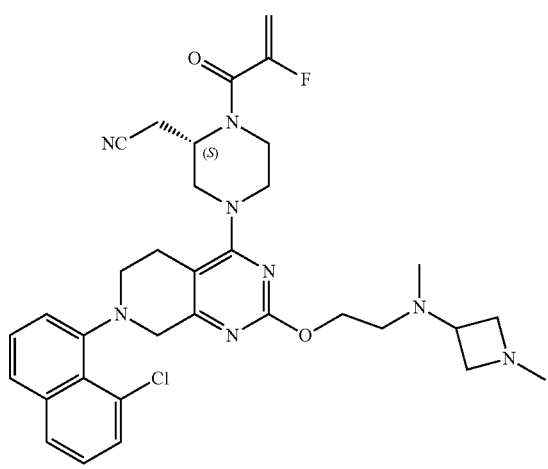
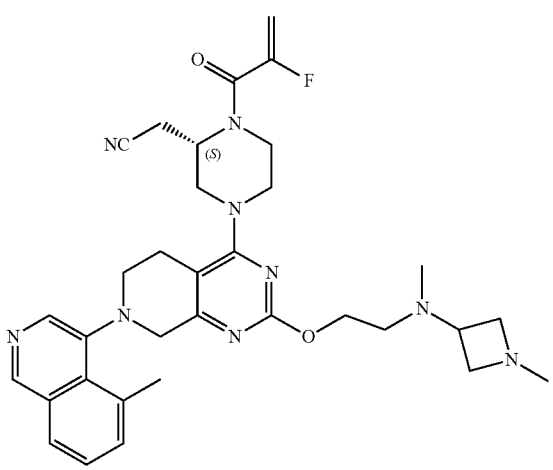
734
-continued
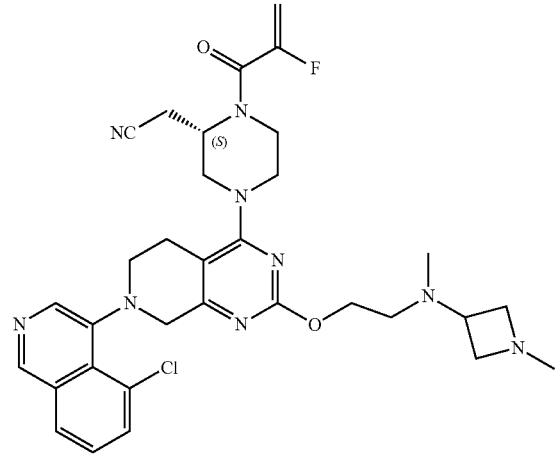
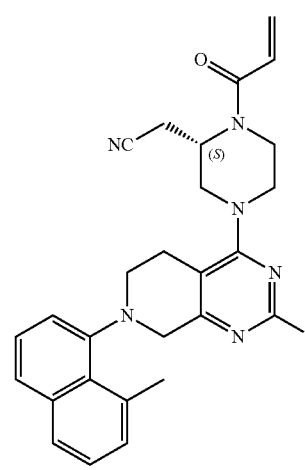
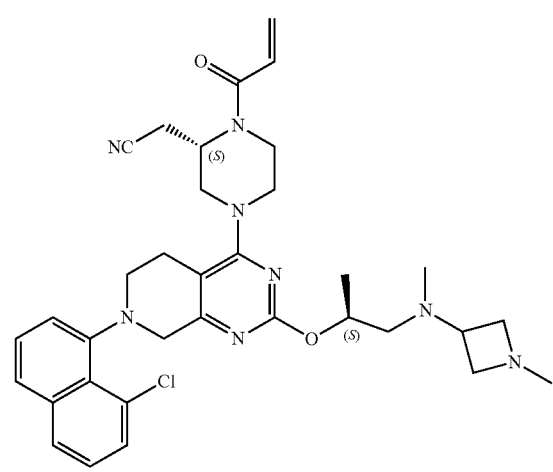

735
-continued
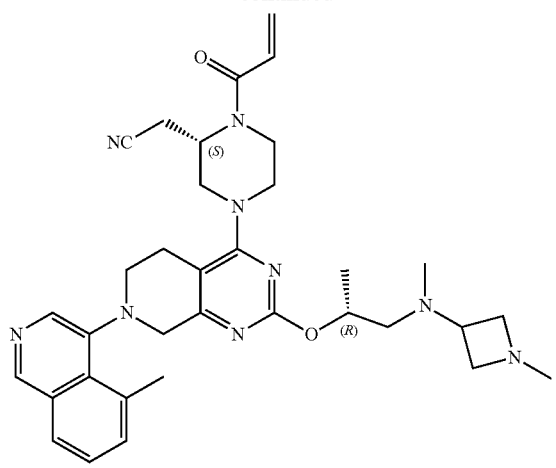
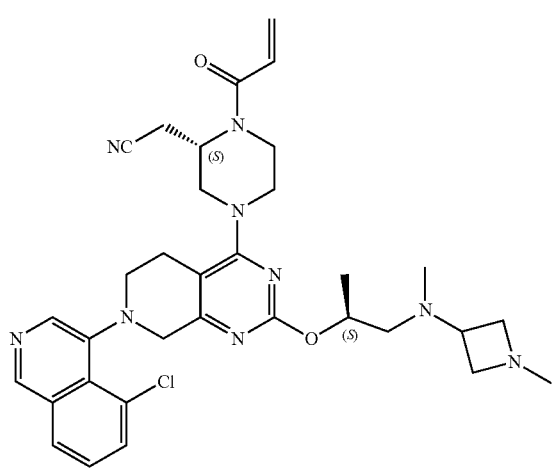
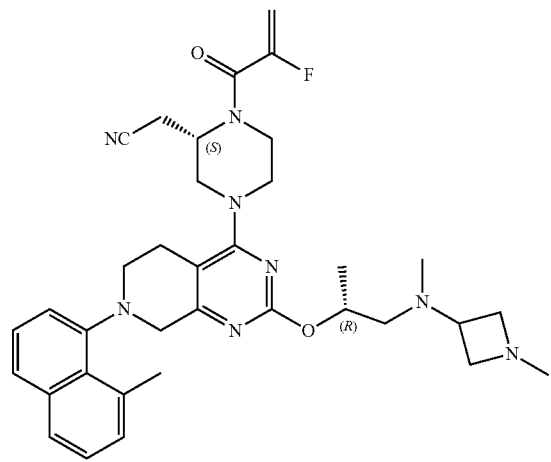
736
-continued
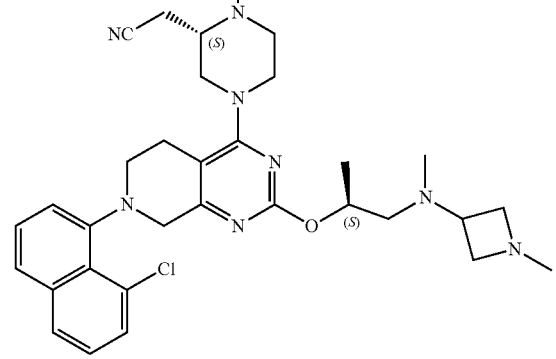
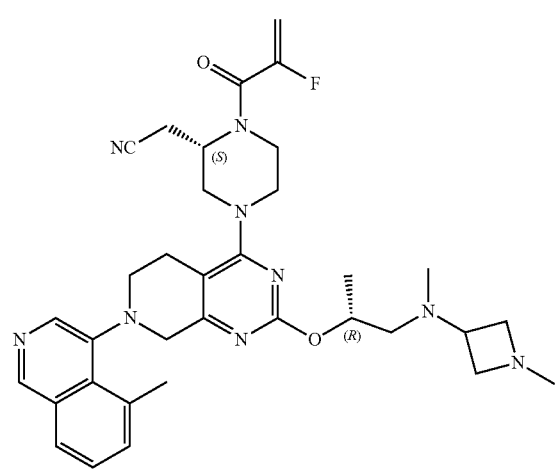
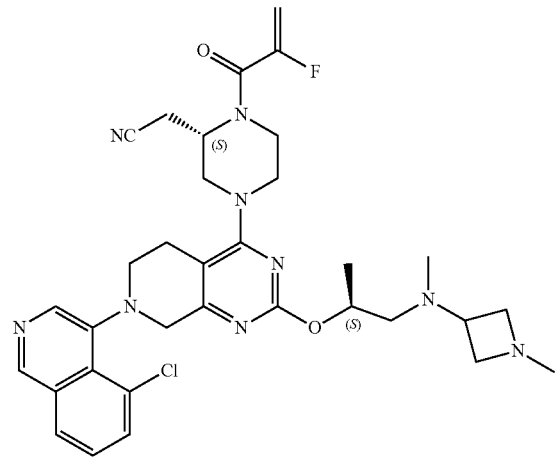

737
-continued
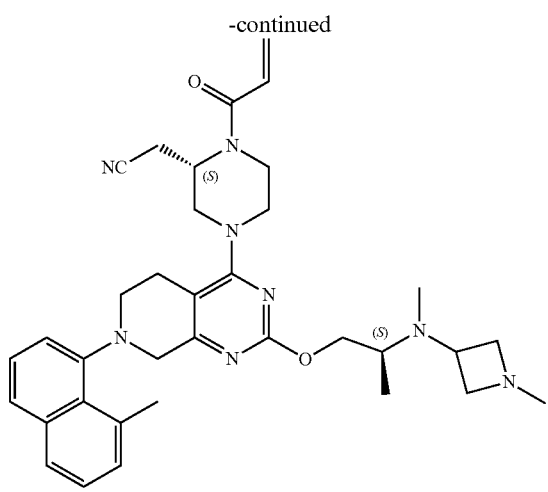
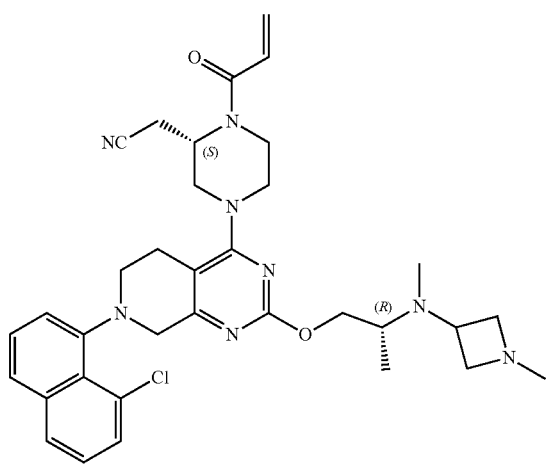
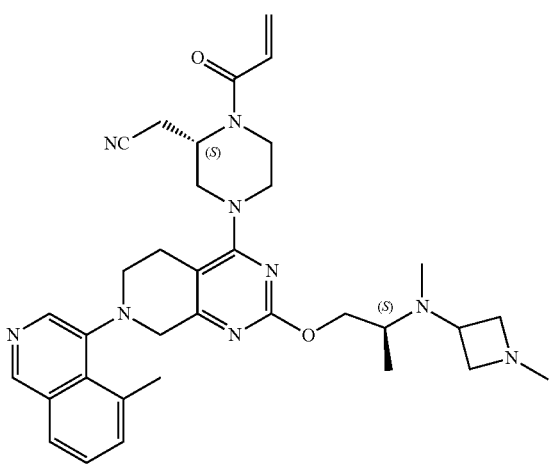
738
-continued
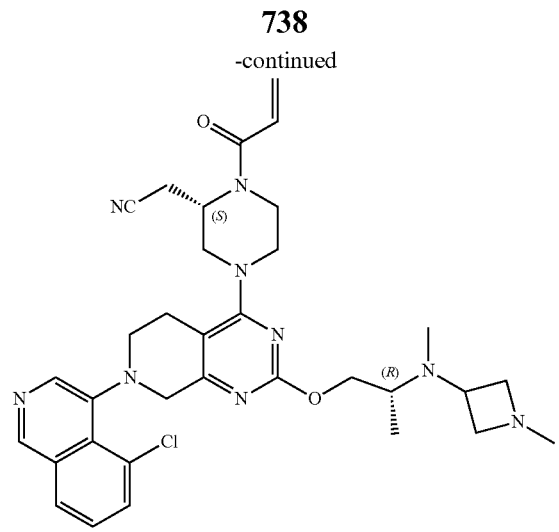
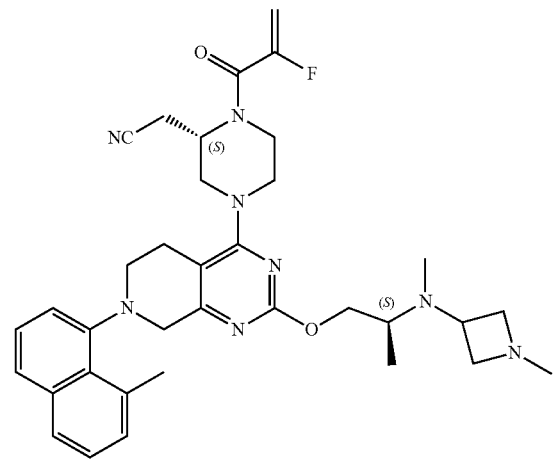
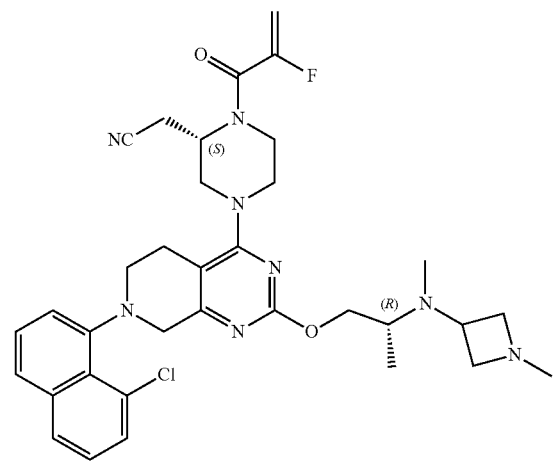

739 -continued
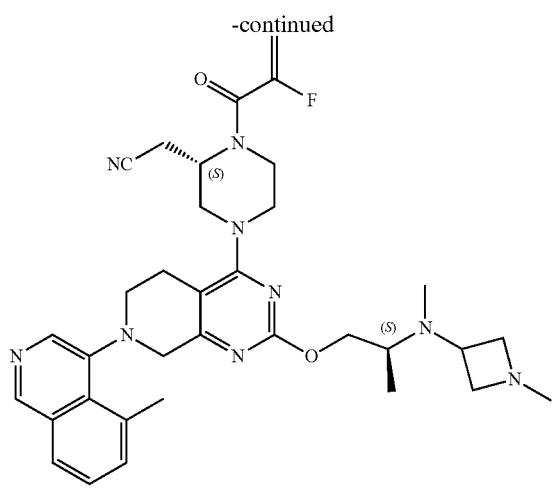
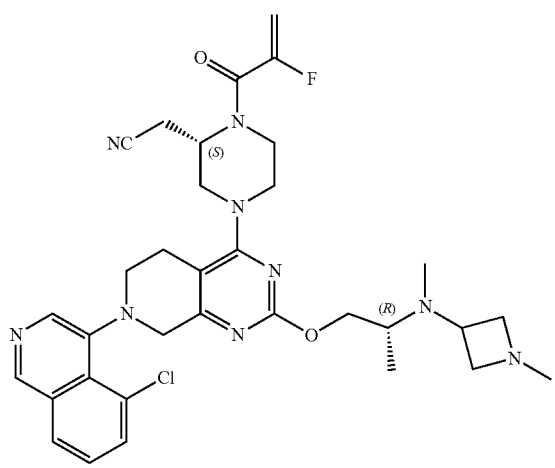
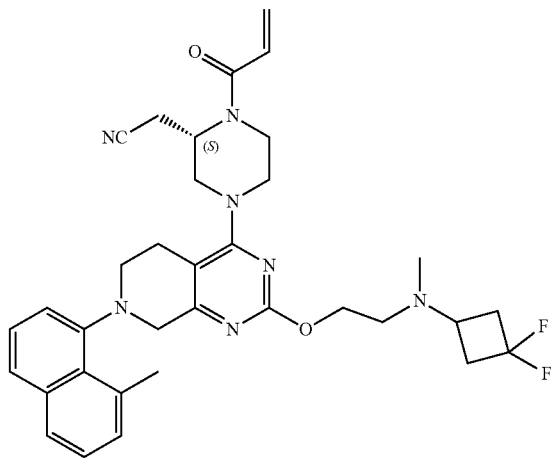
740 -continued
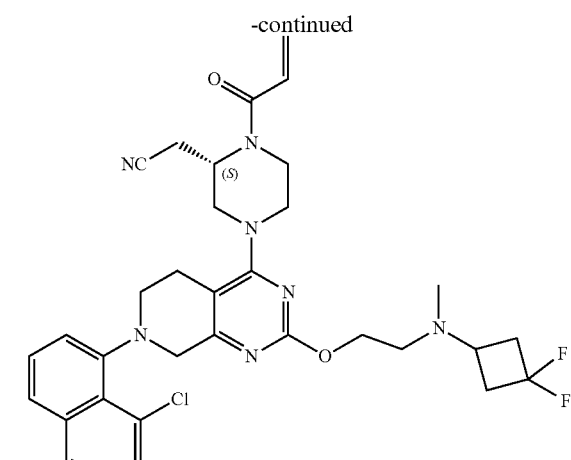
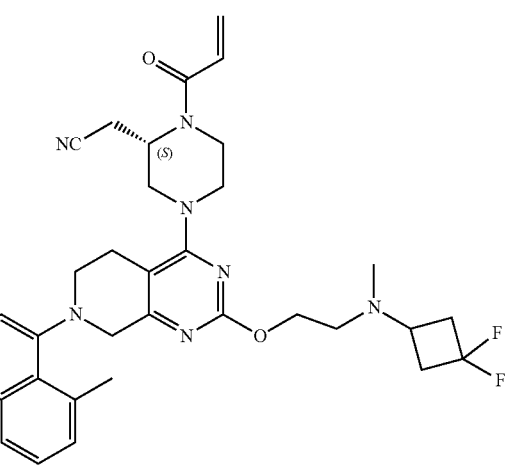
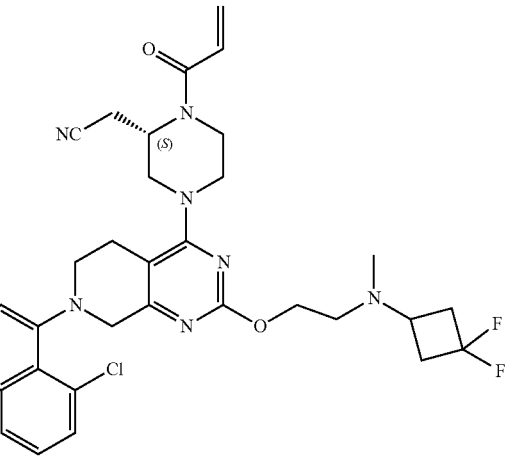

741
-continued
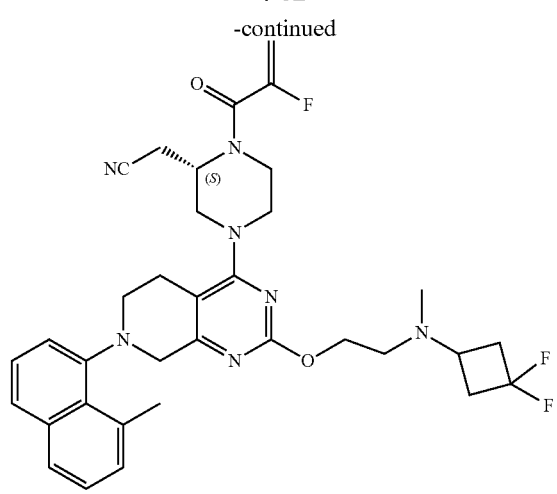
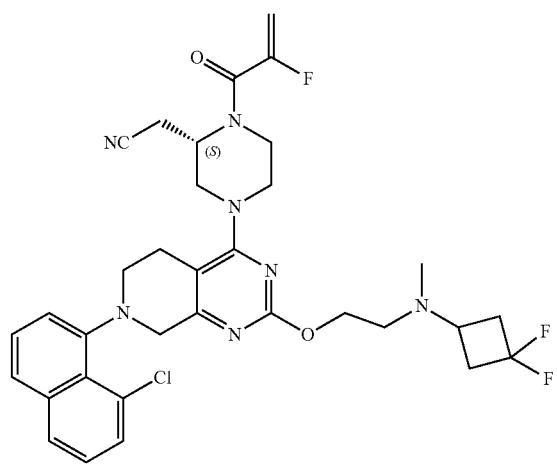
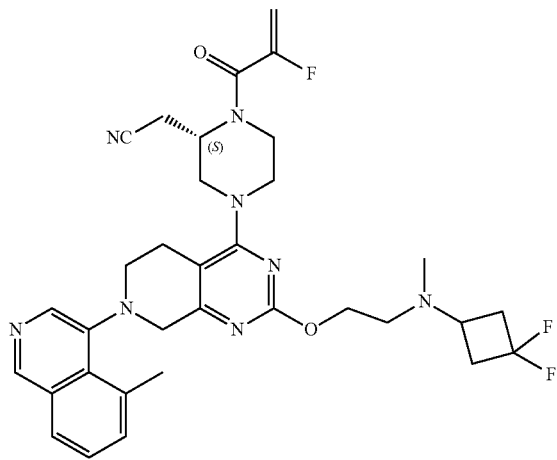
742
-continued
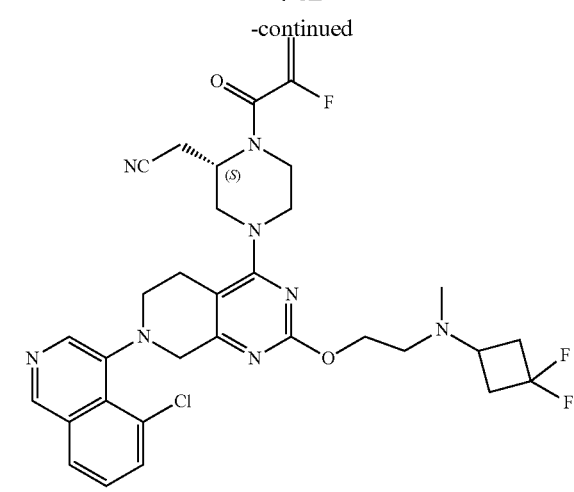
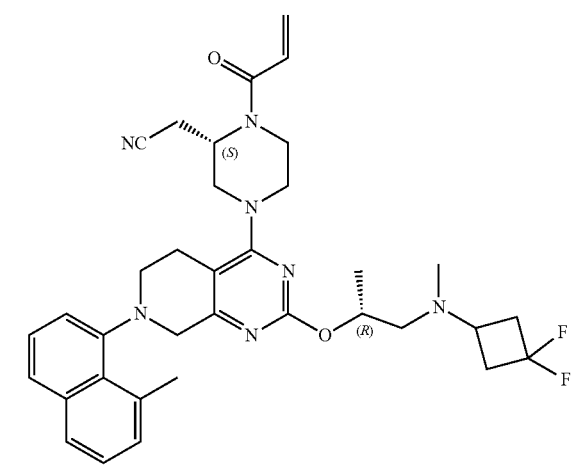
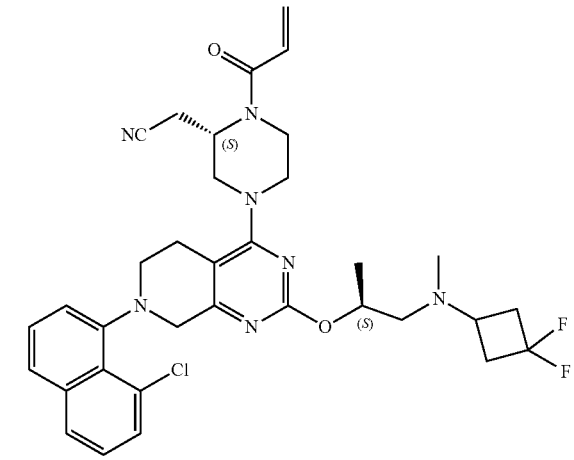

743
-continued

744
-continued

745
-continued
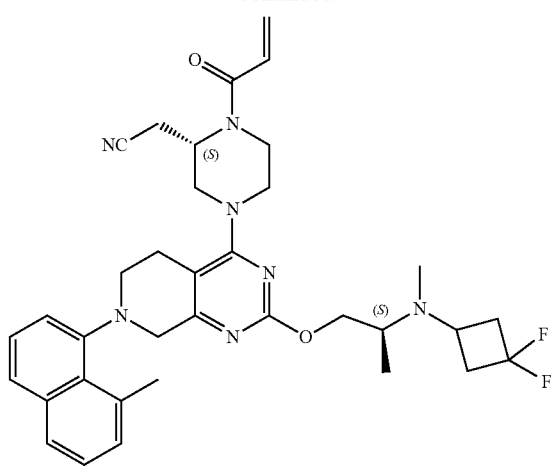
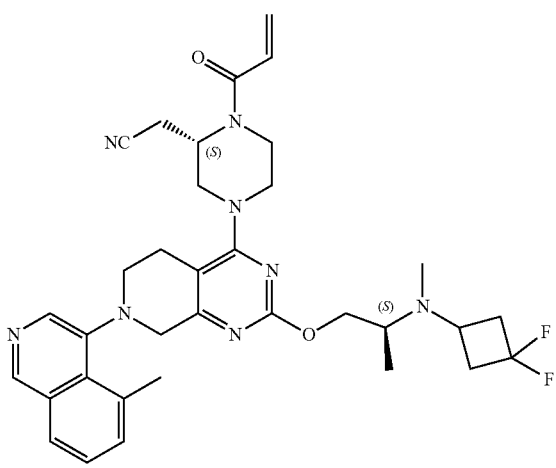
746
-continued
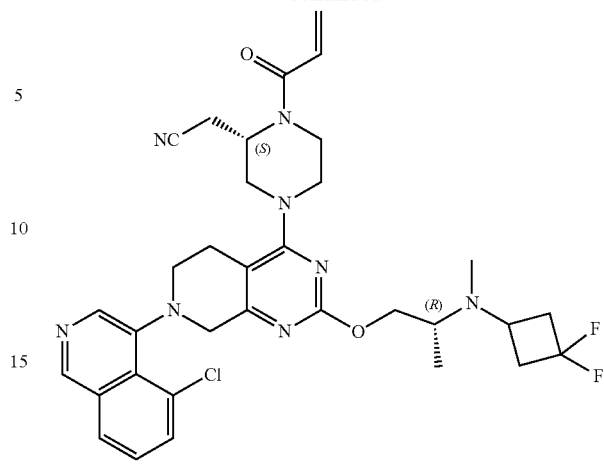
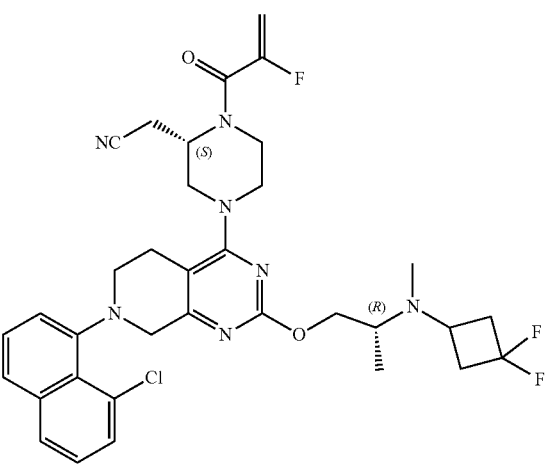

747
-continued
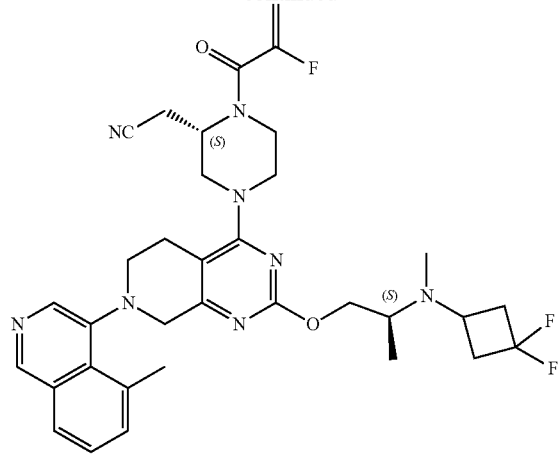
748
-continued
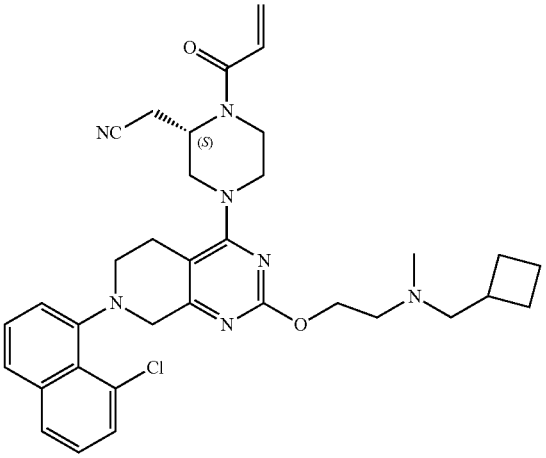
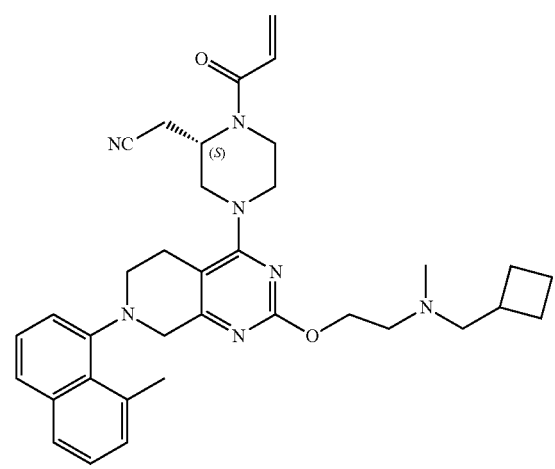
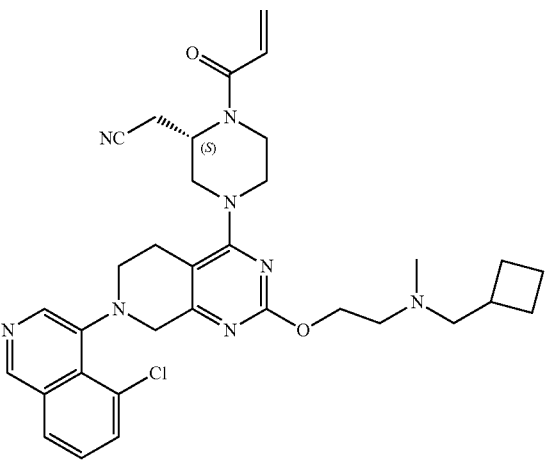

749                                           750
-continued                                    -continued
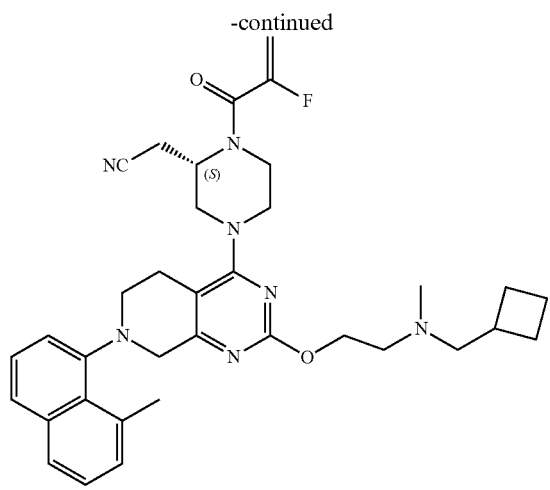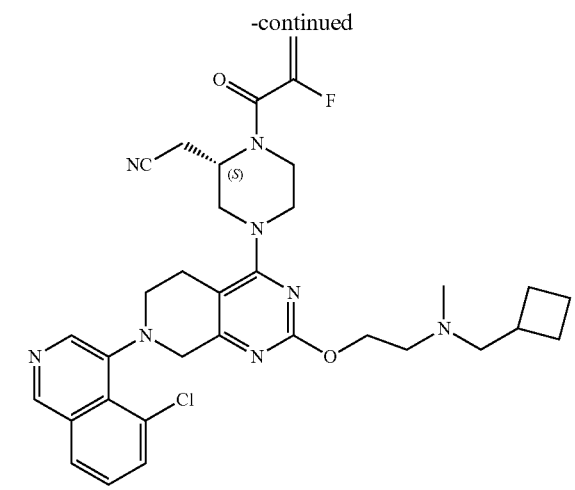
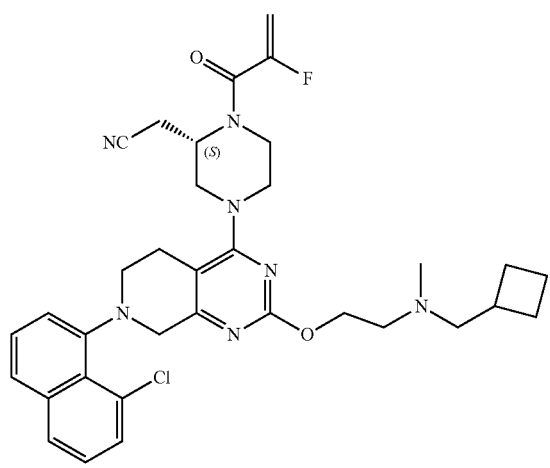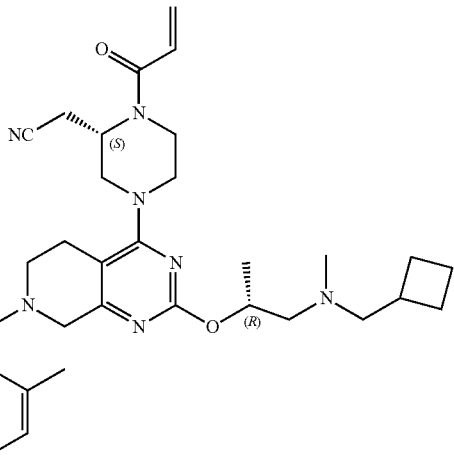
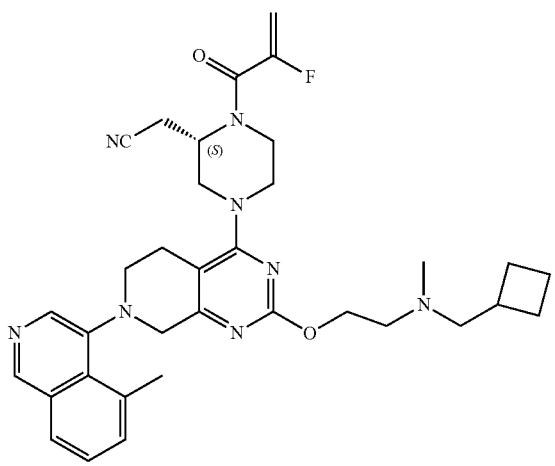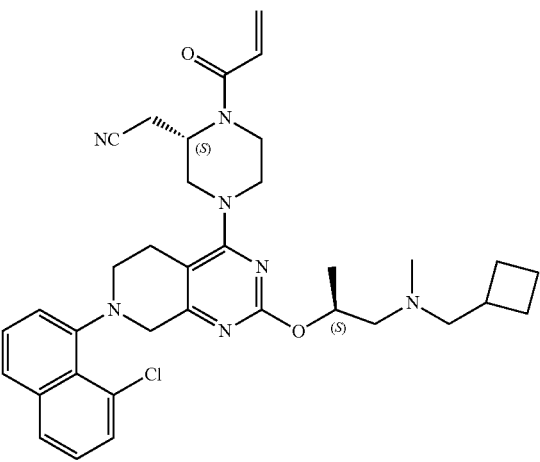

751
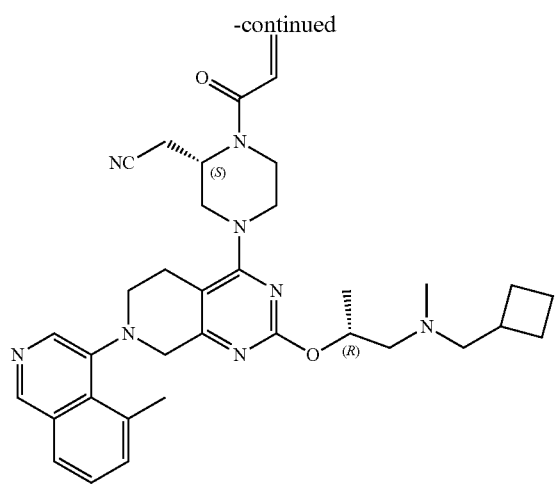
752
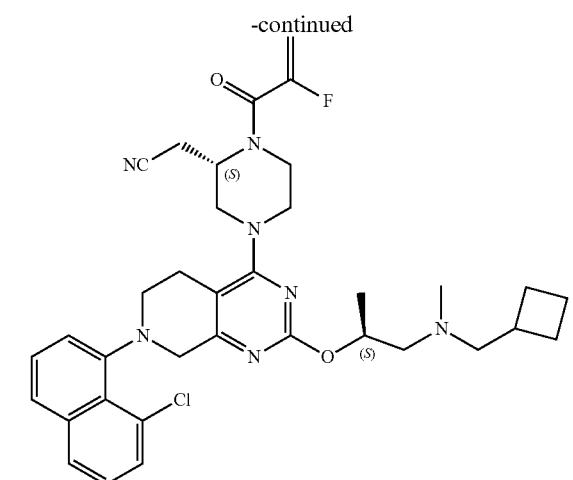
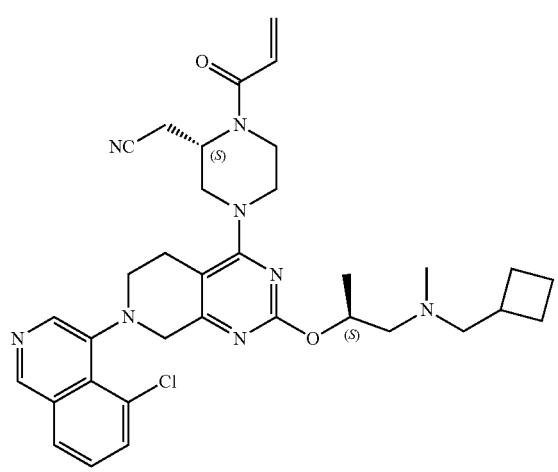
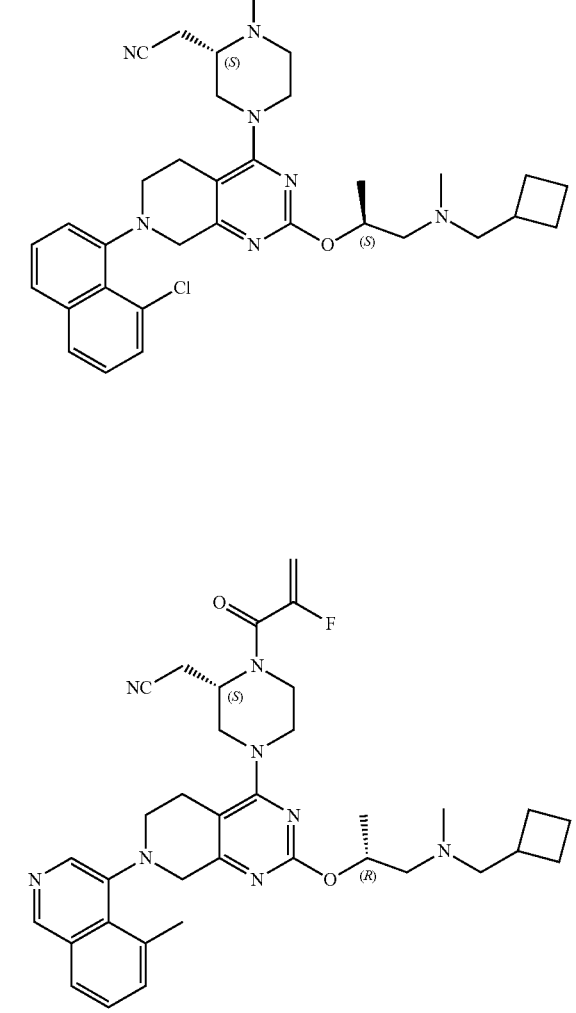
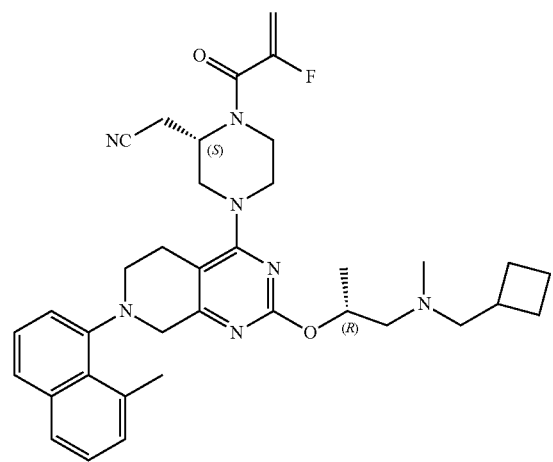
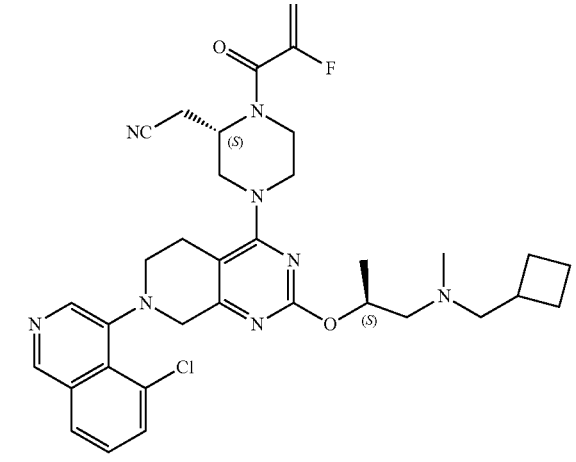

753
-continued
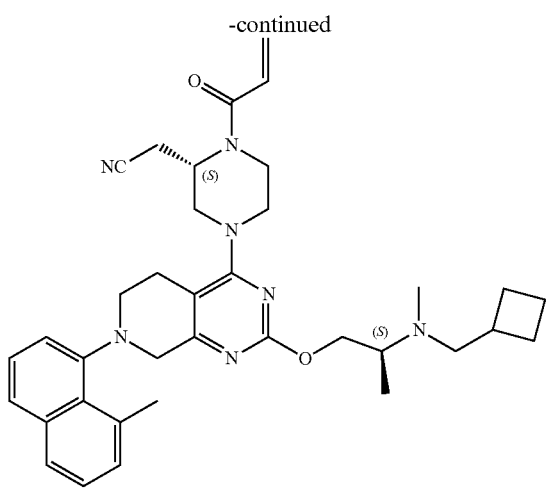
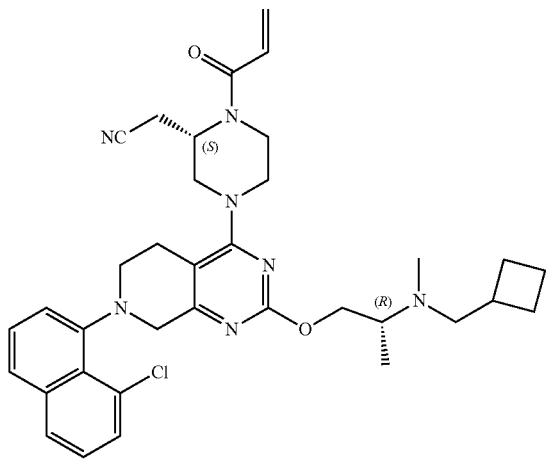
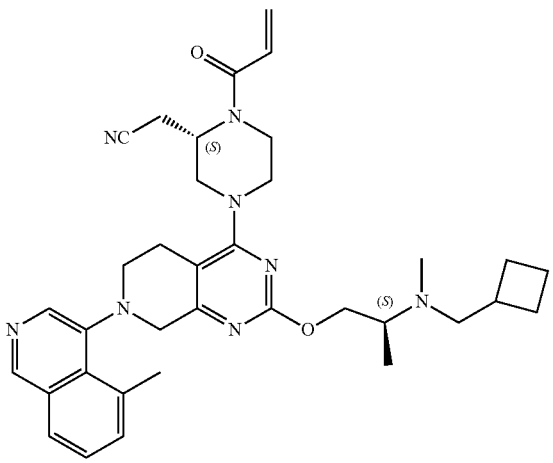
754
-continued
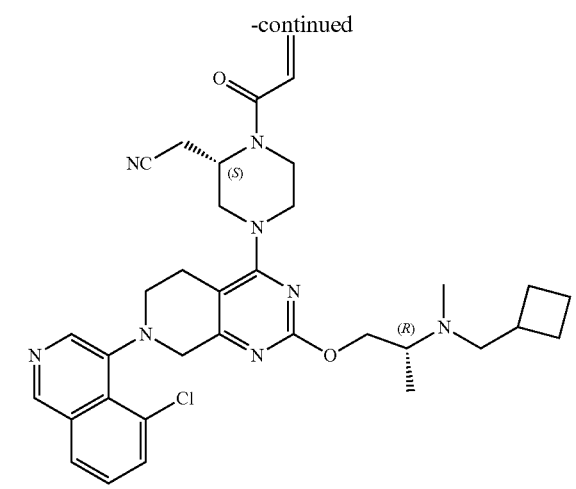
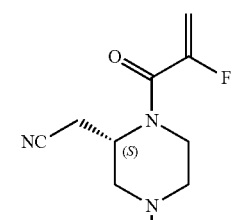
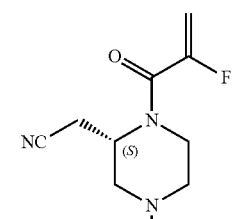
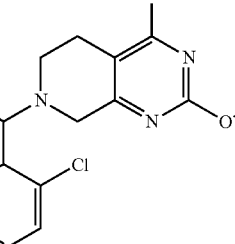

755
-continued
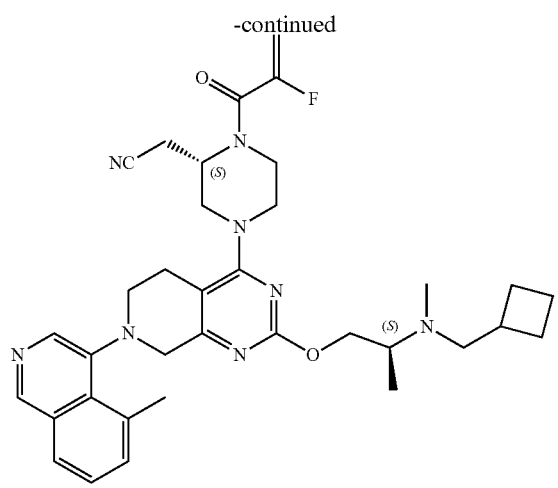
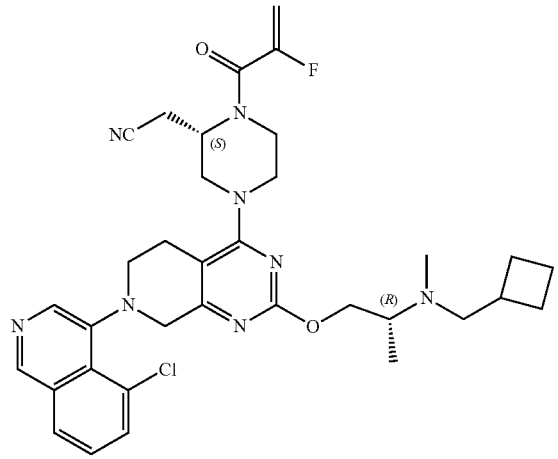
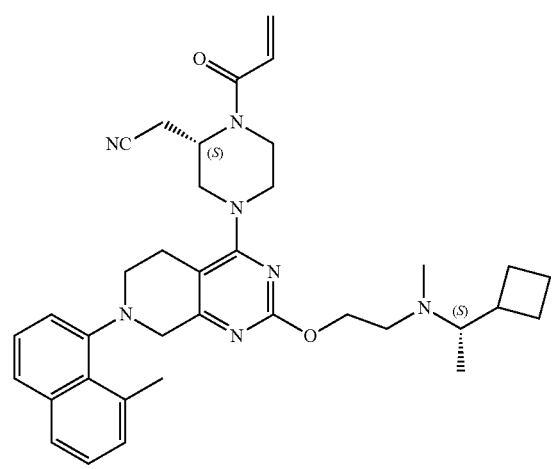
756
-continued
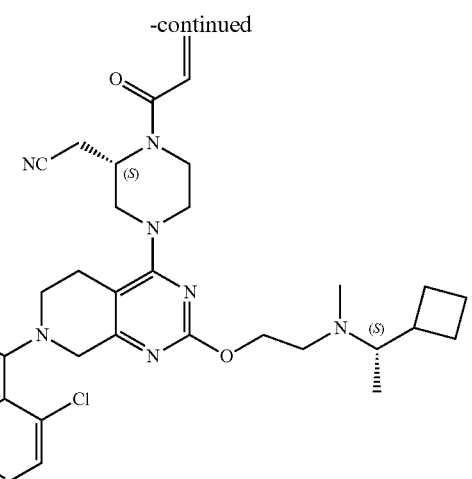
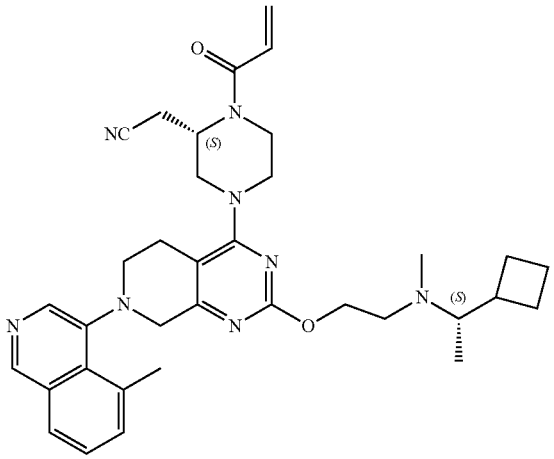
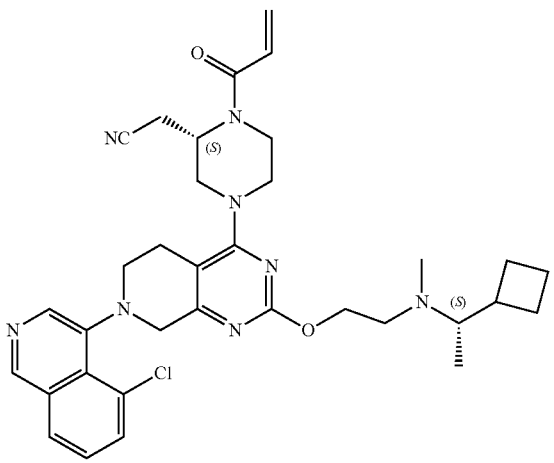

757
-continued
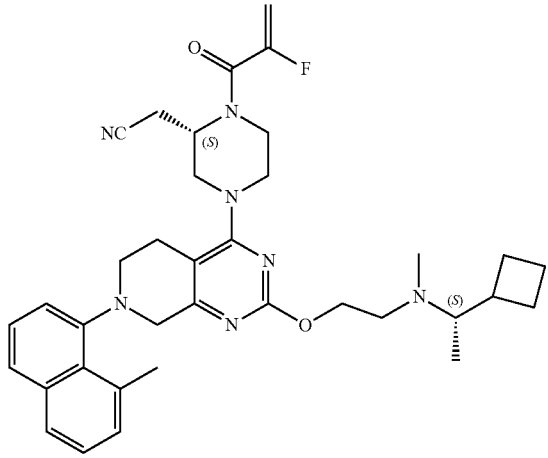
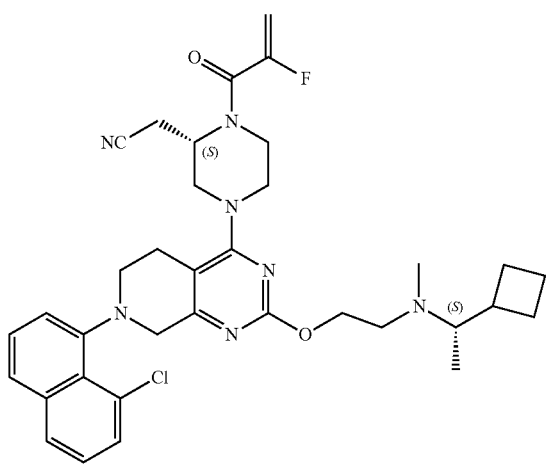
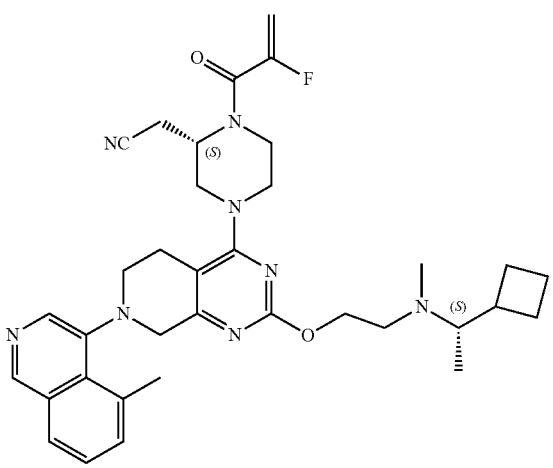
758
-continued
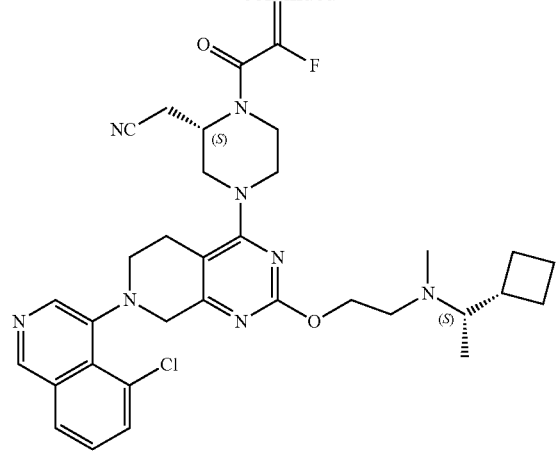
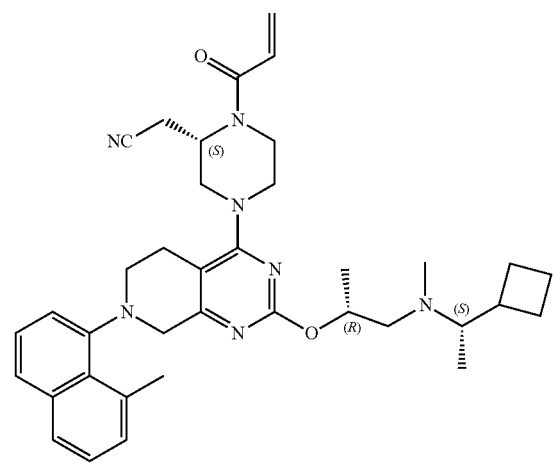
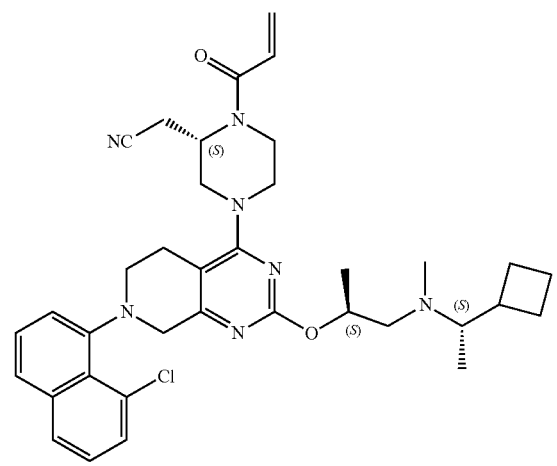

759
-continued
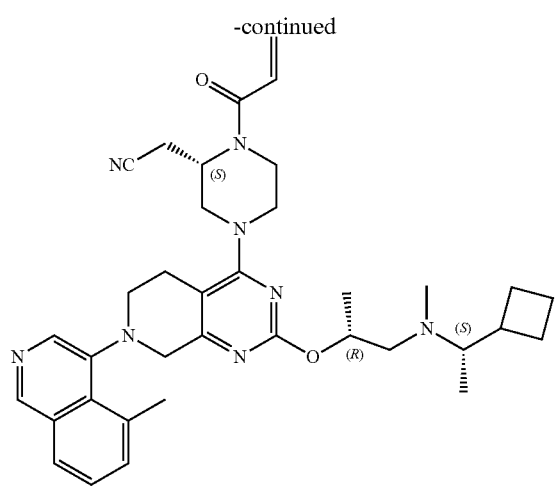
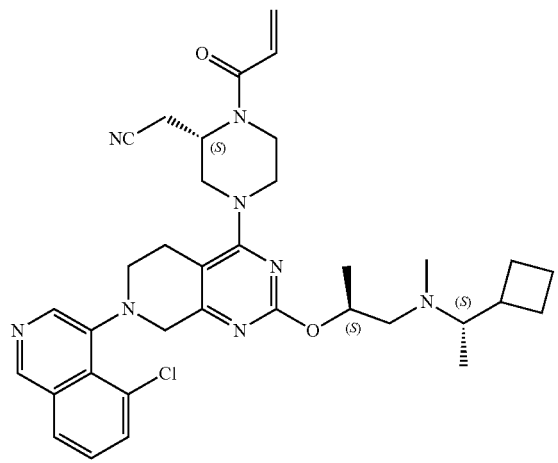
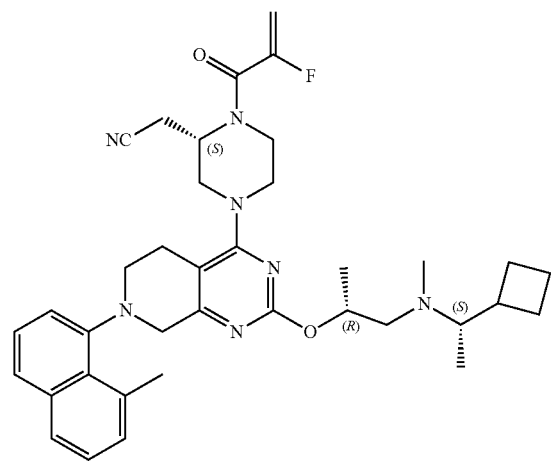
760
-continued
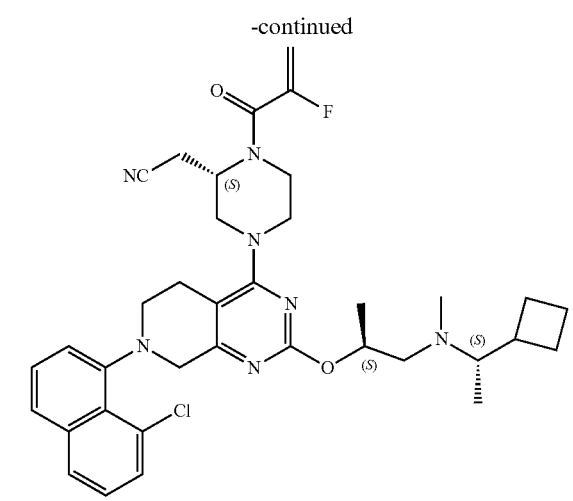
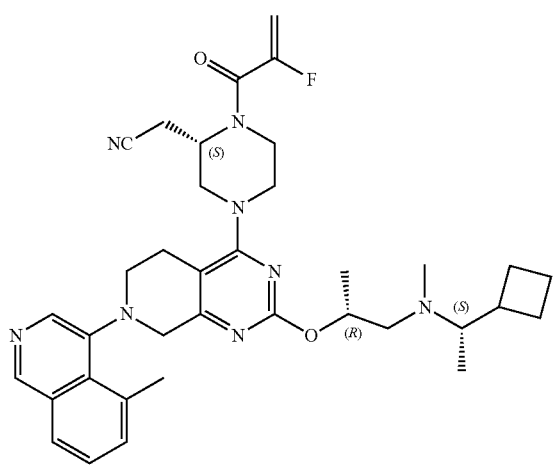
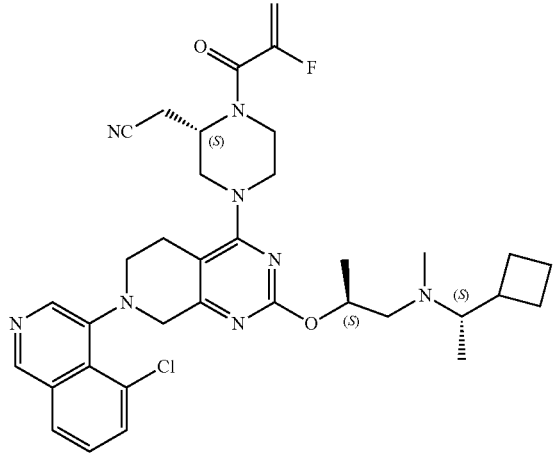

761
-continued
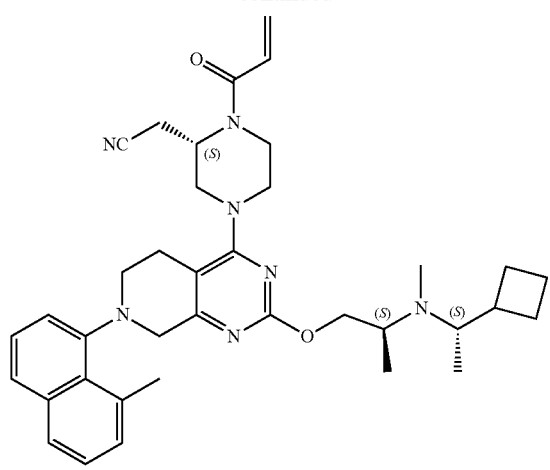
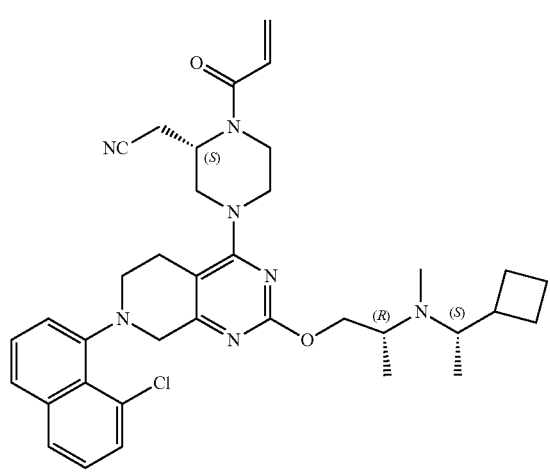
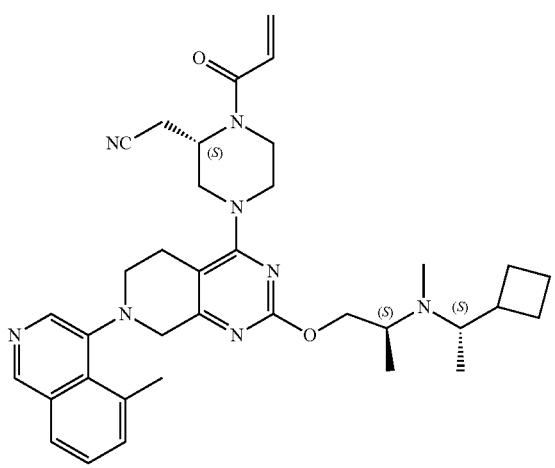
762
-continued
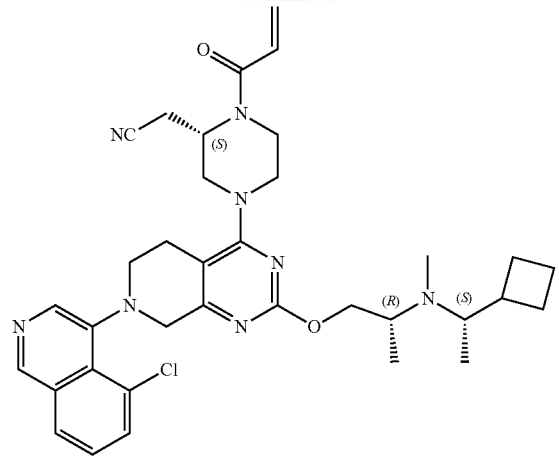
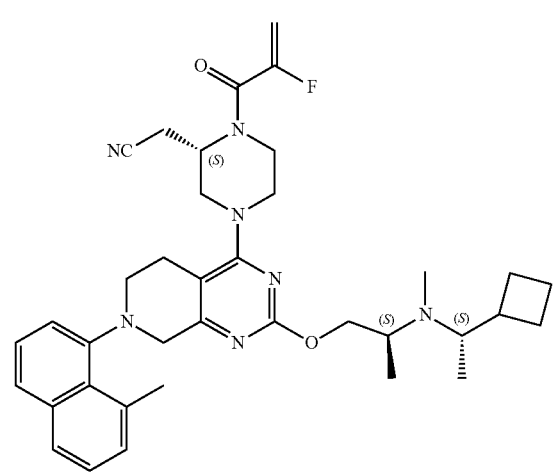
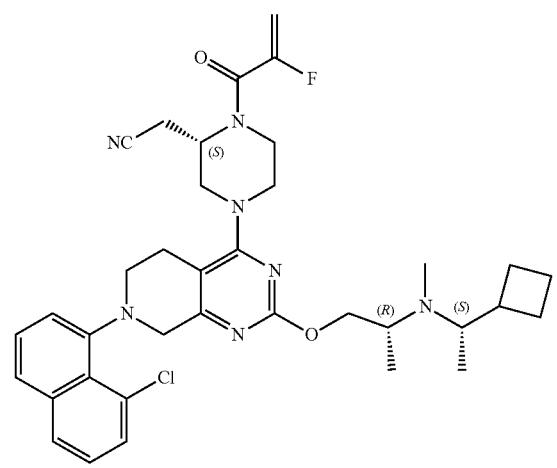

763
-continued
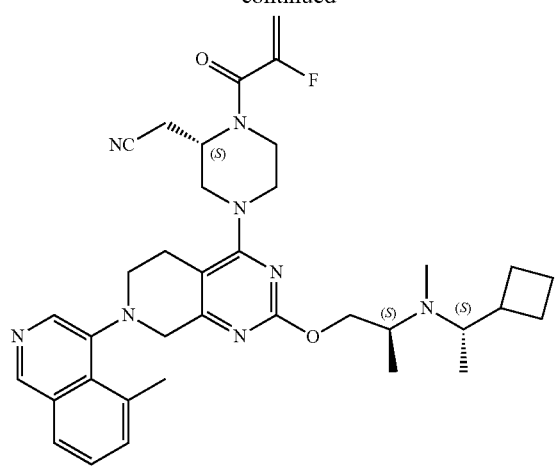
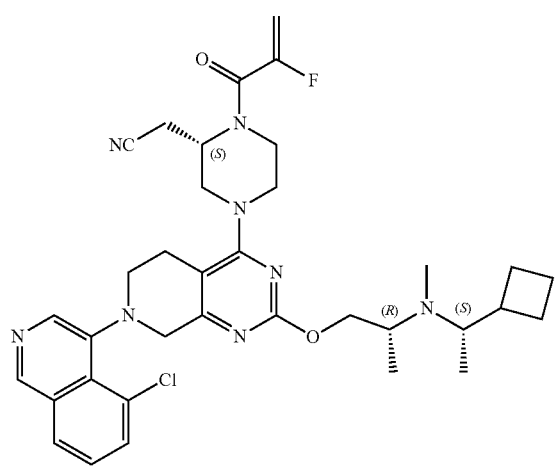
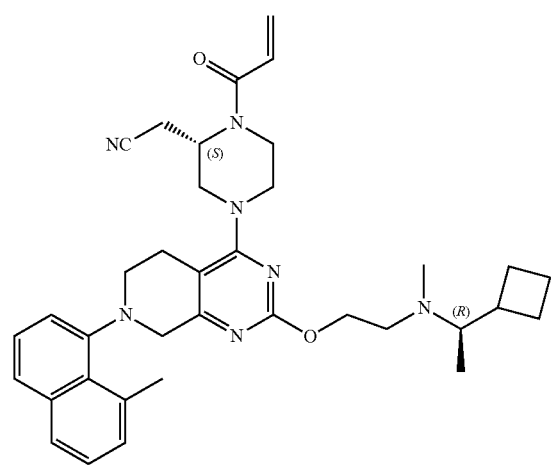
764
-continued
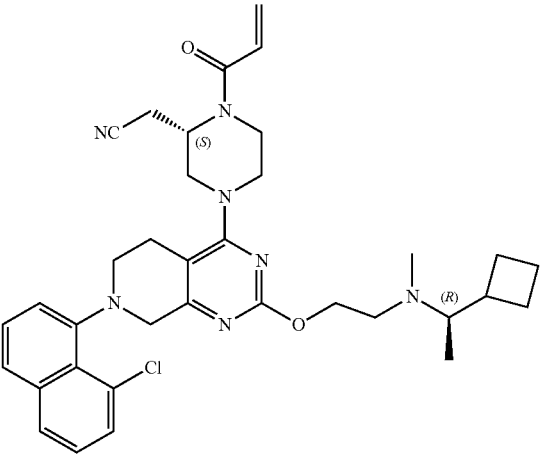
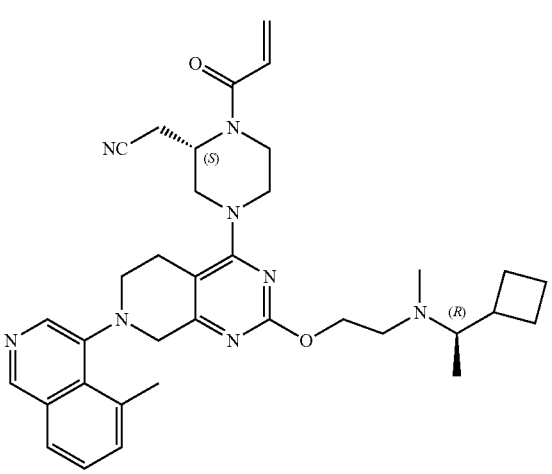
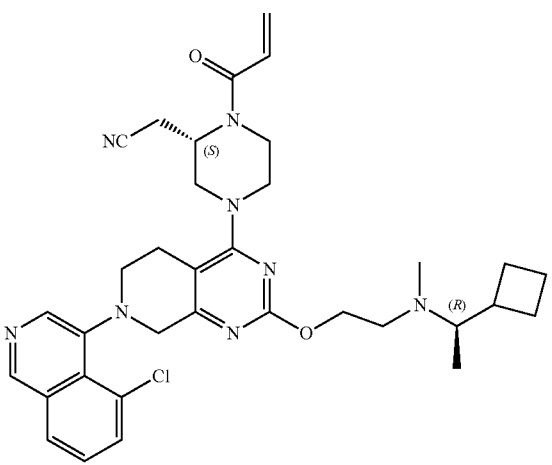

765
-continued
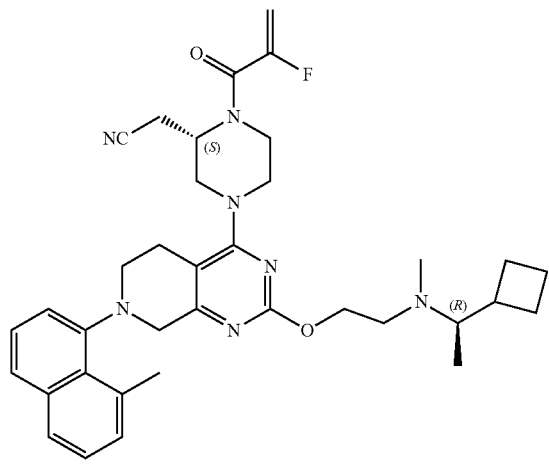
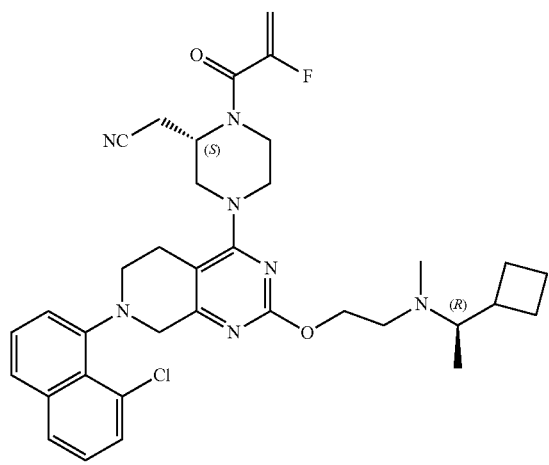
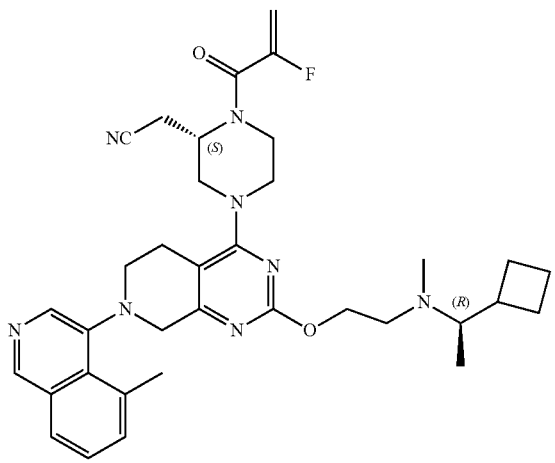
766
-continued
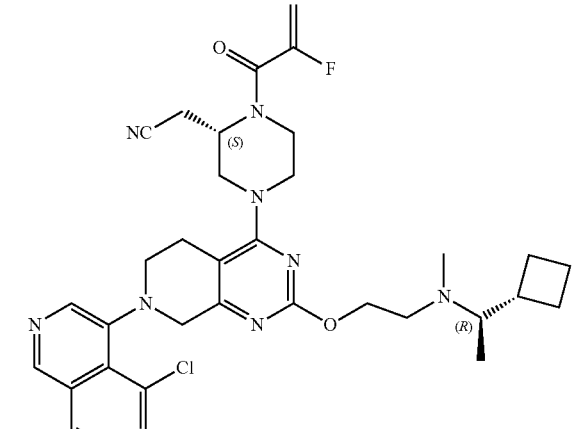
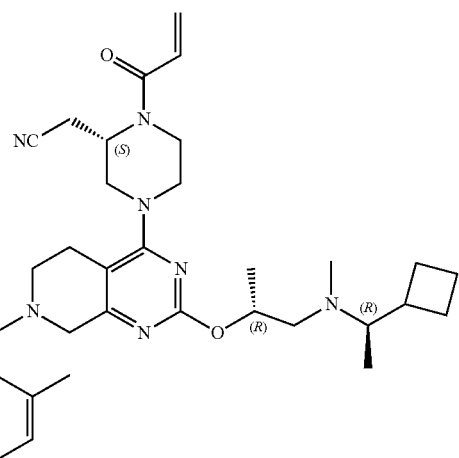
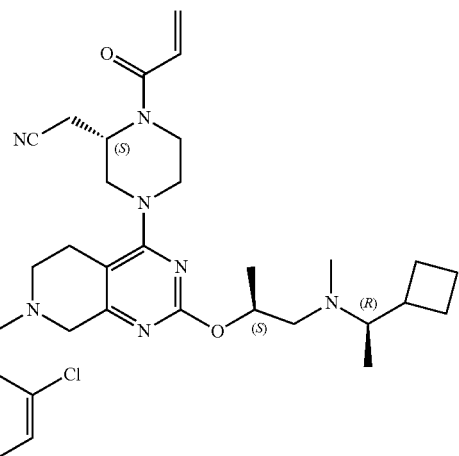

767
-continued
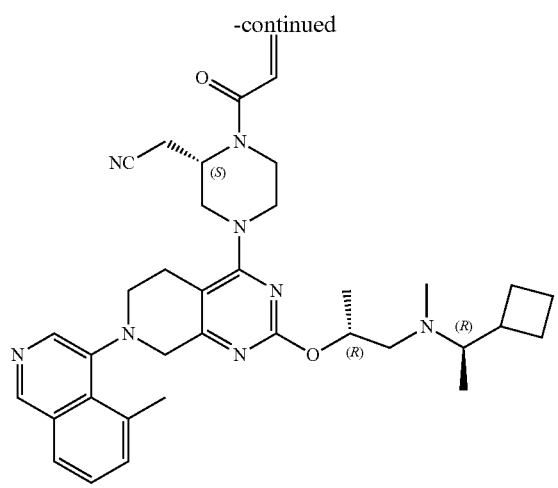
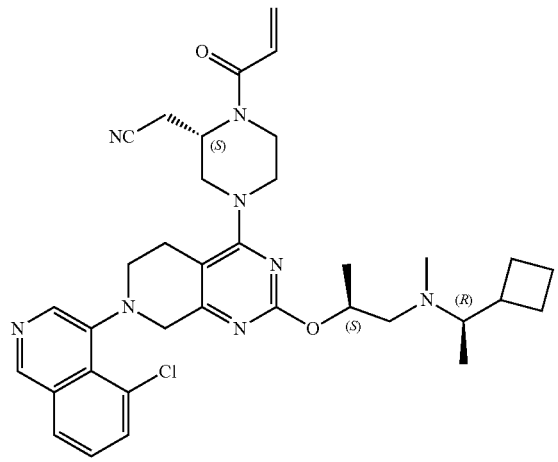
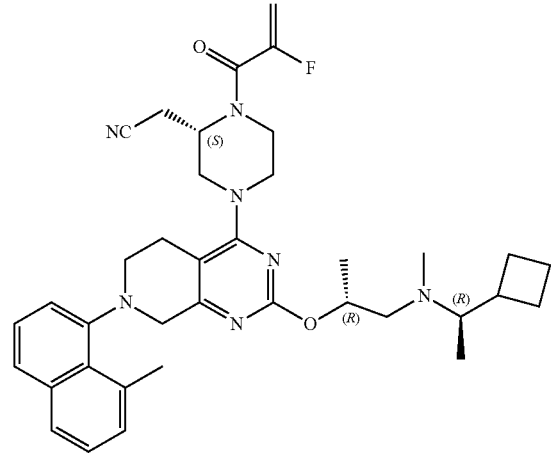
768
-continued
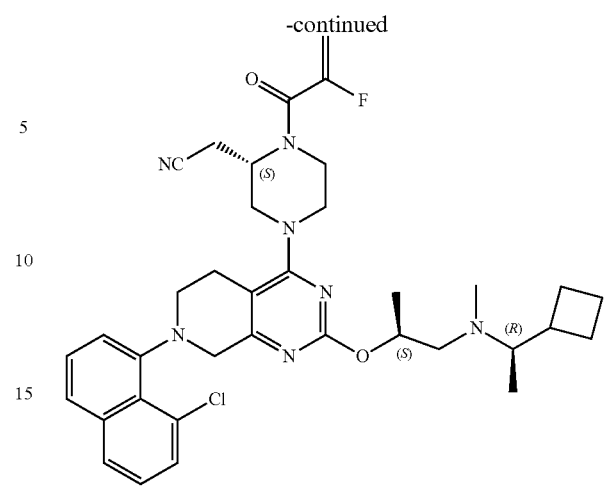
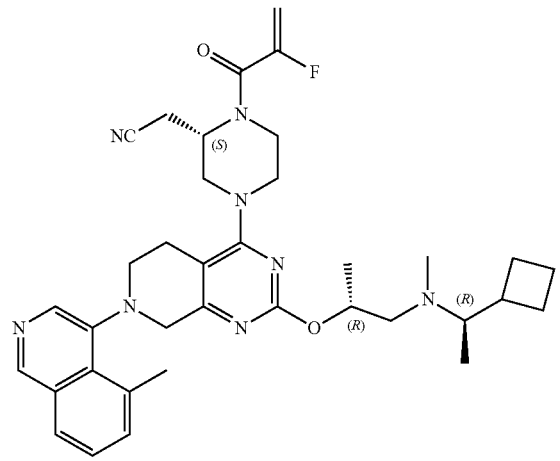
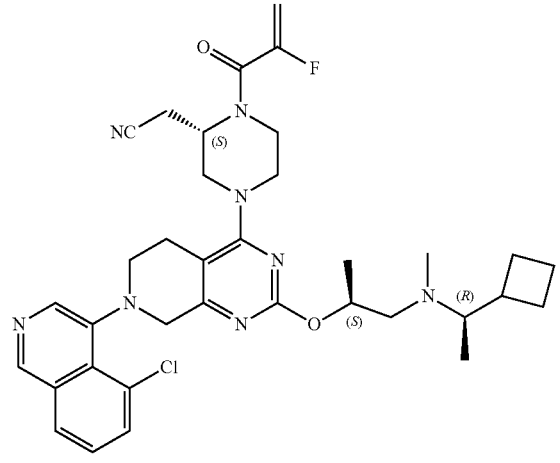

769
-continued
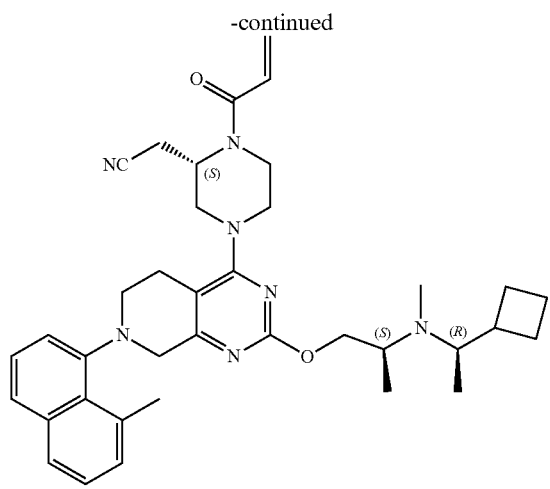
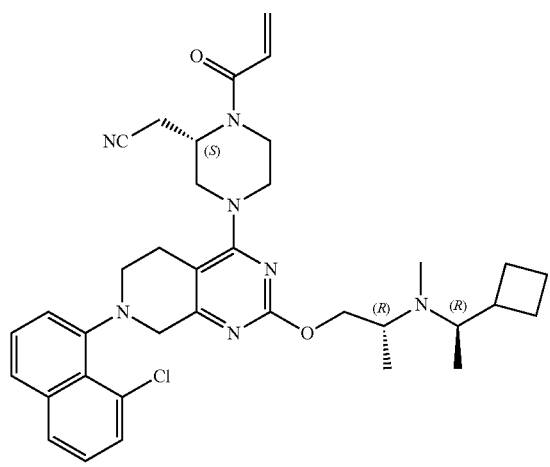
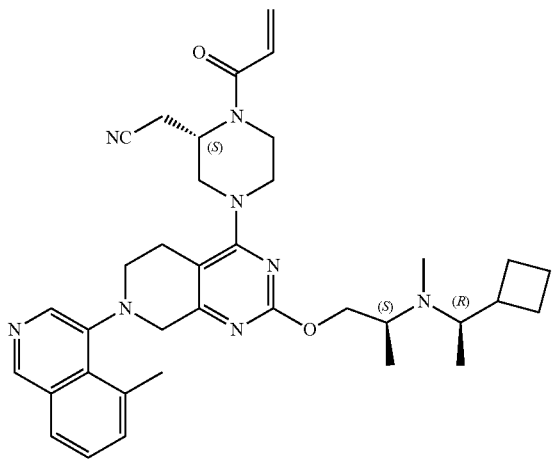
770
-continued
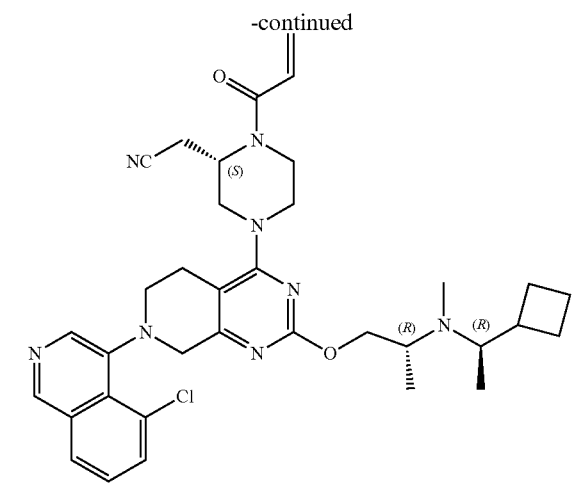
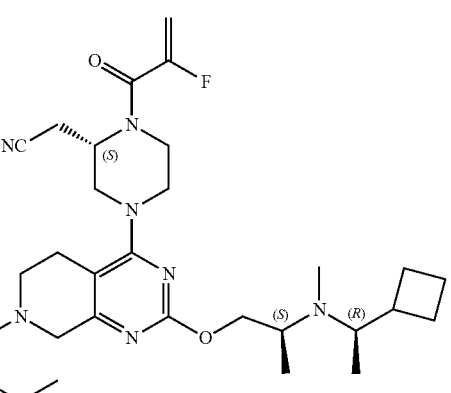
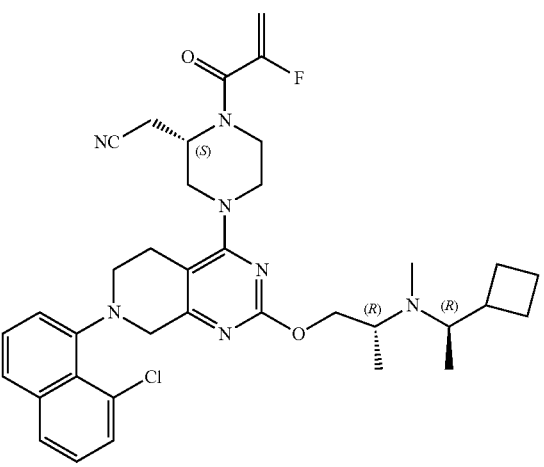

771
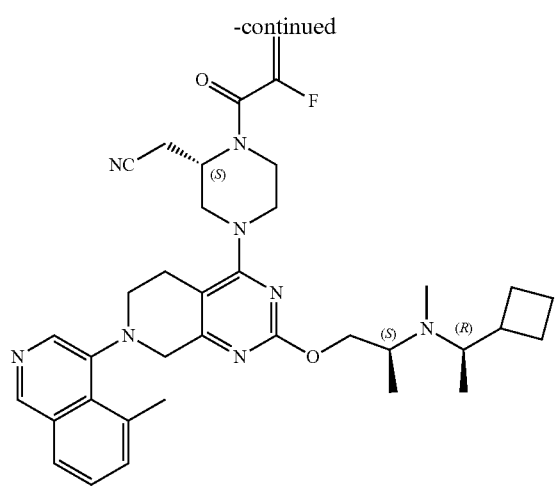
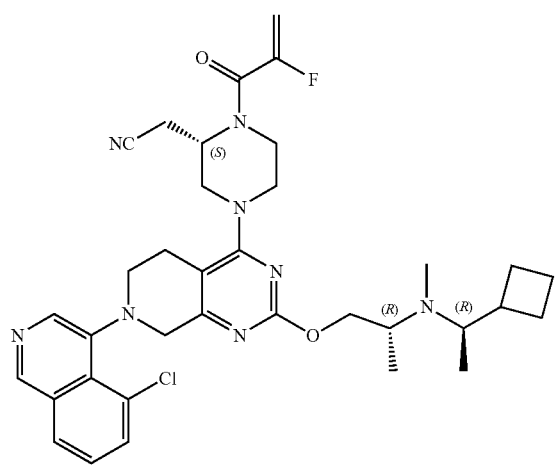
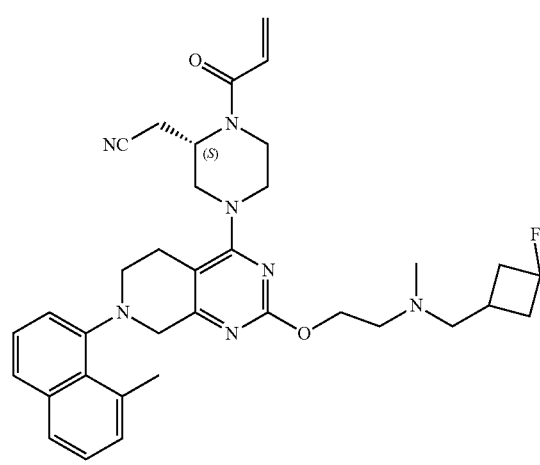
772
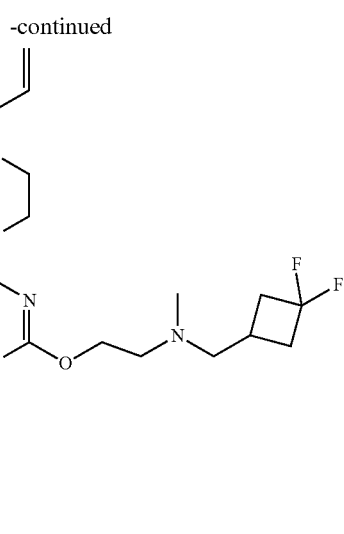
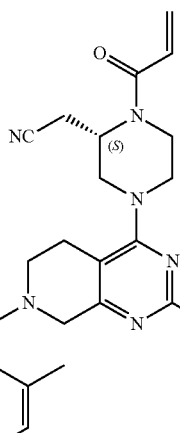
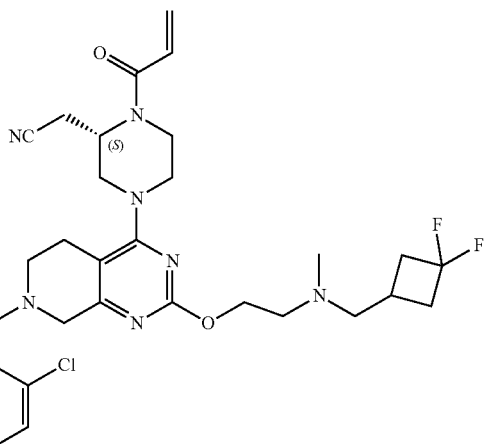

773
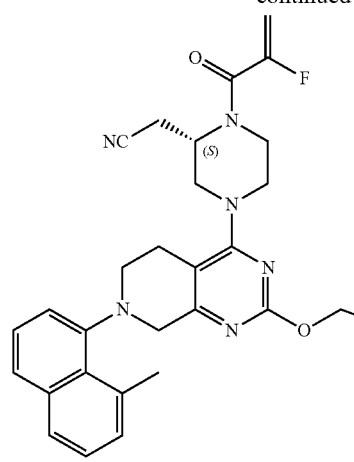
774
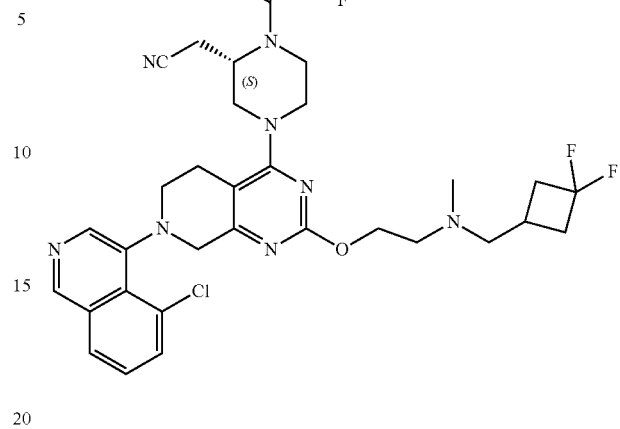
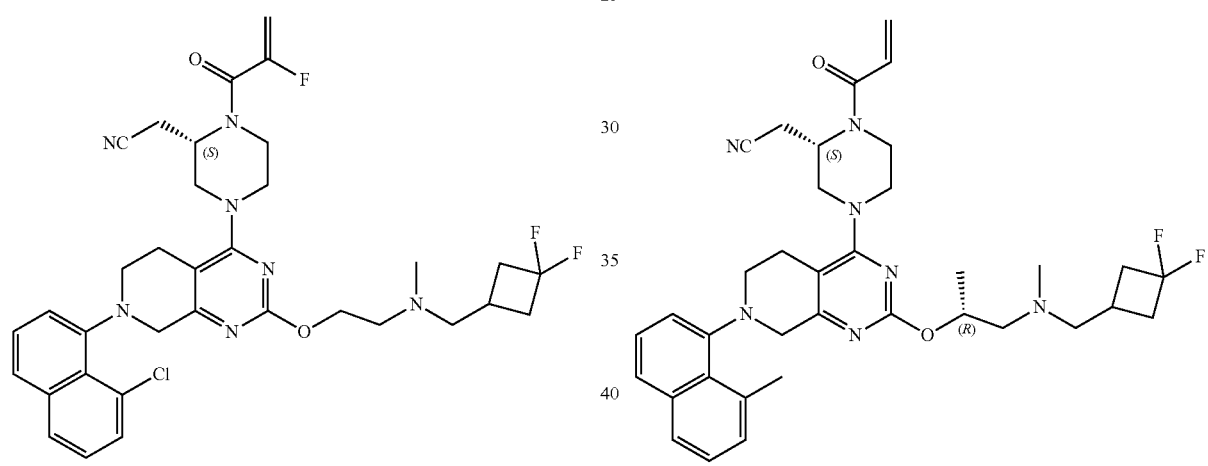
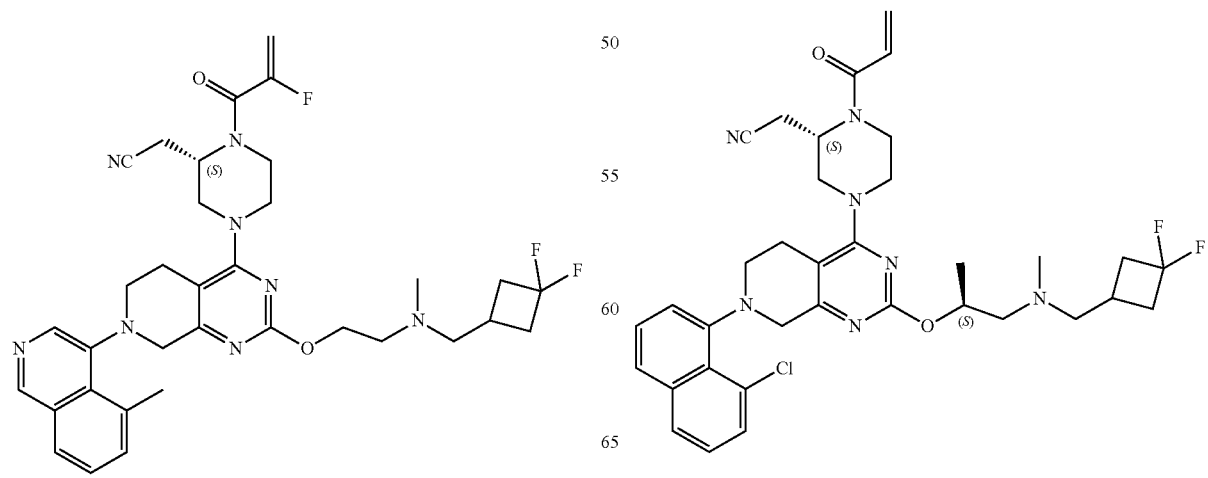

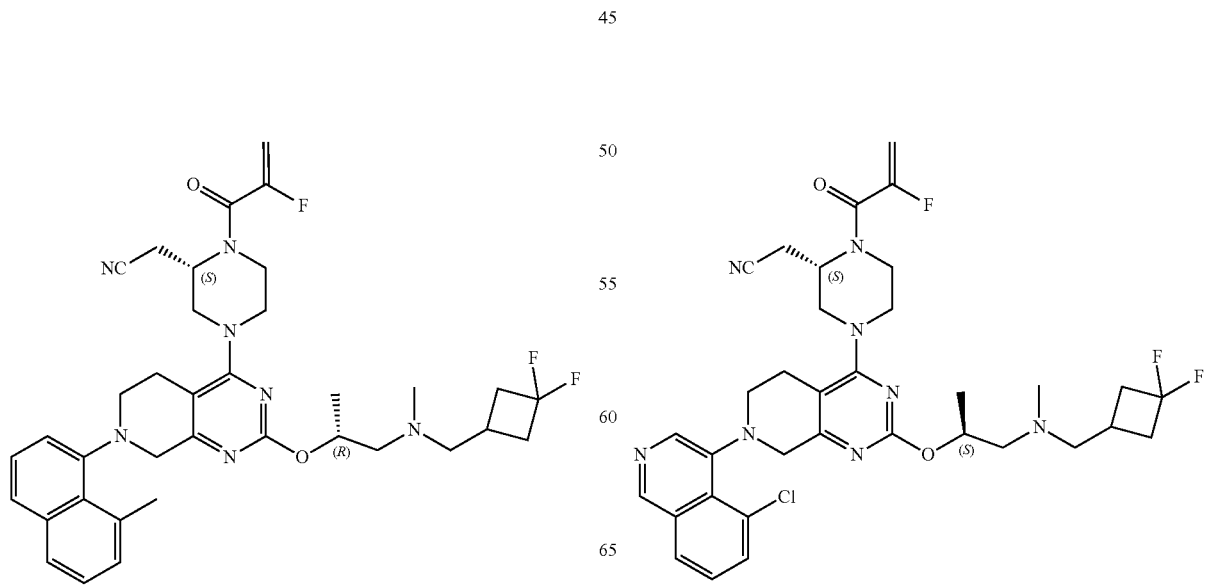

777
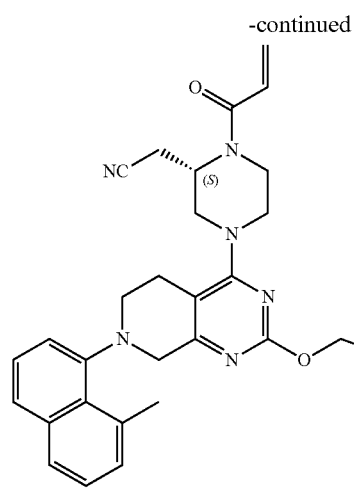
778
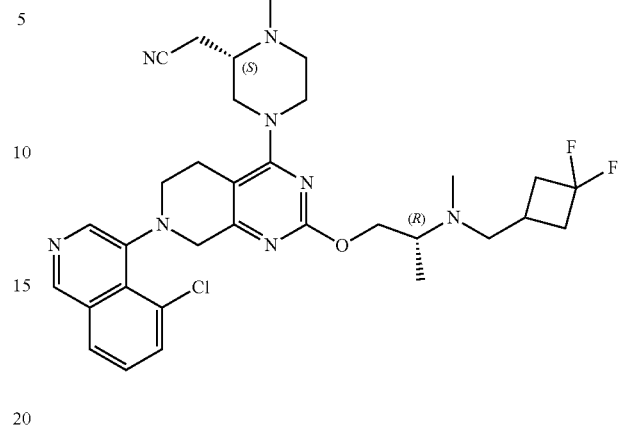
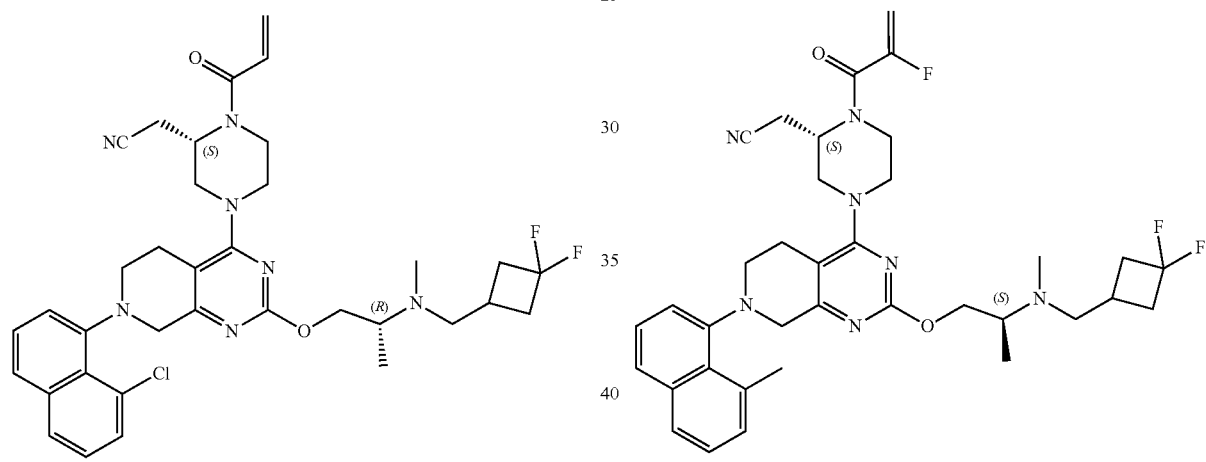

779
-continued
780
-continued
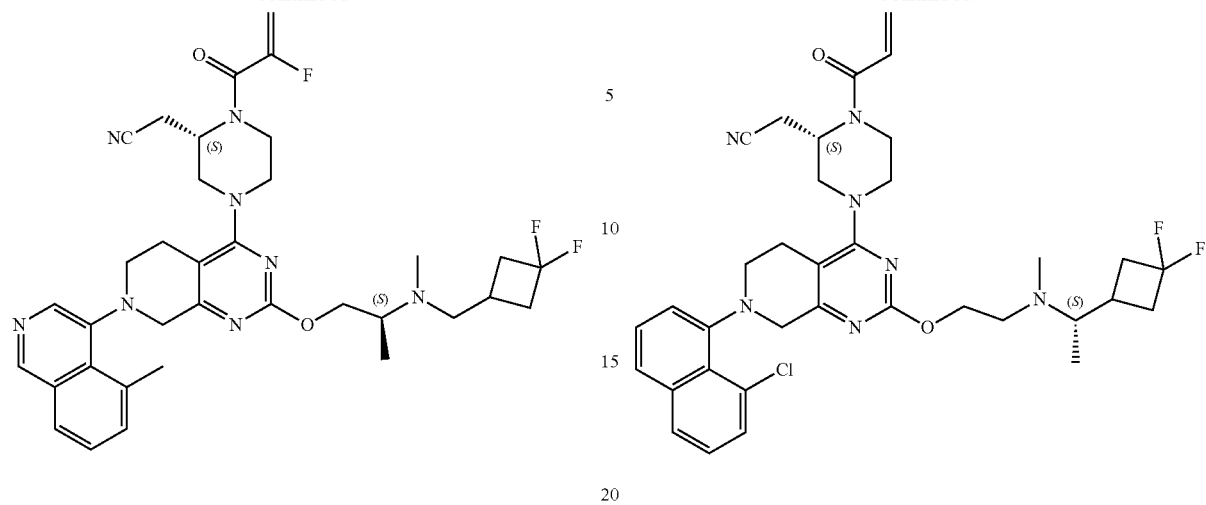

781
-continued
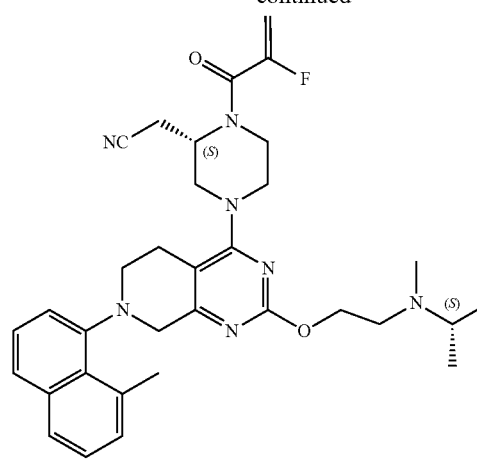
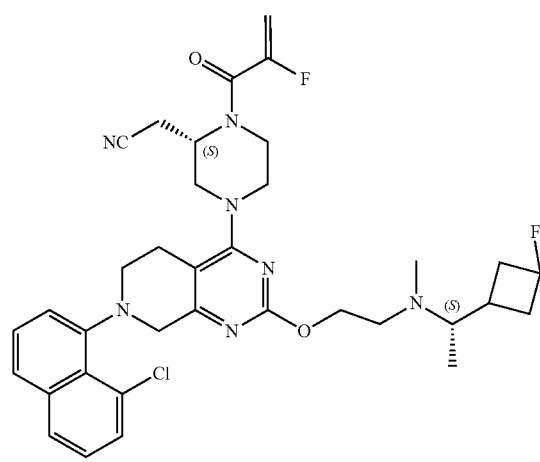
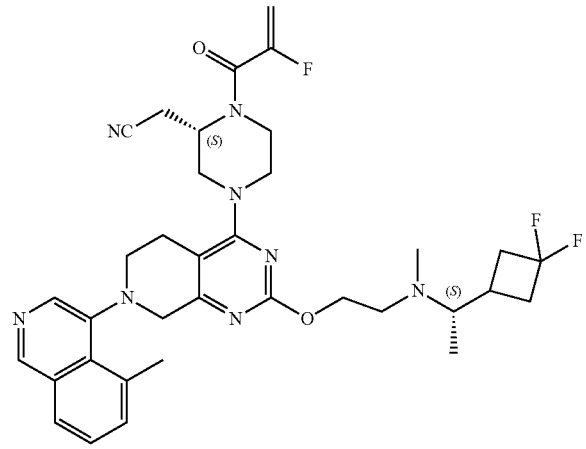
782
-continued
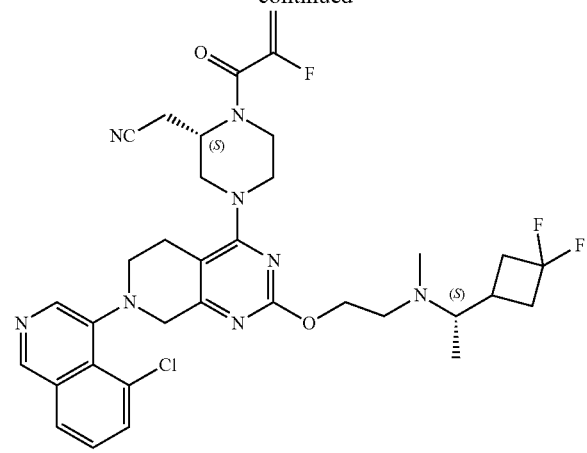
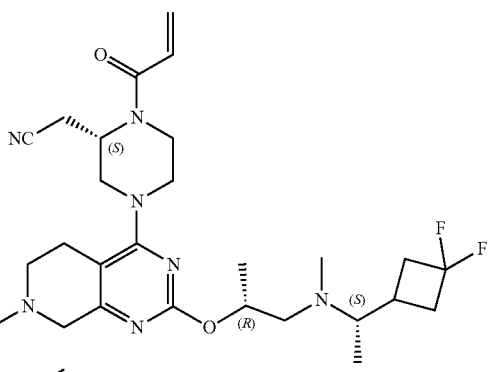
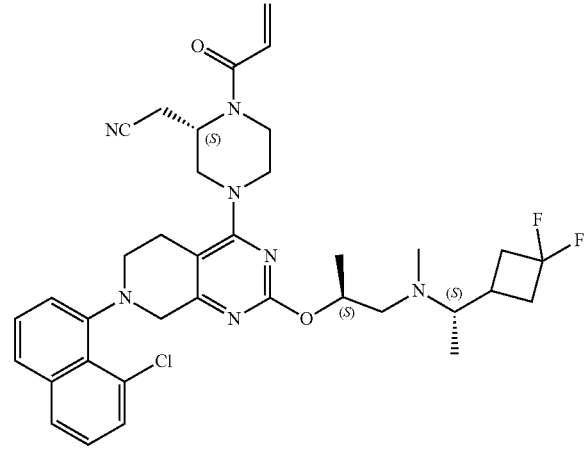

783
-continued
784
-continued
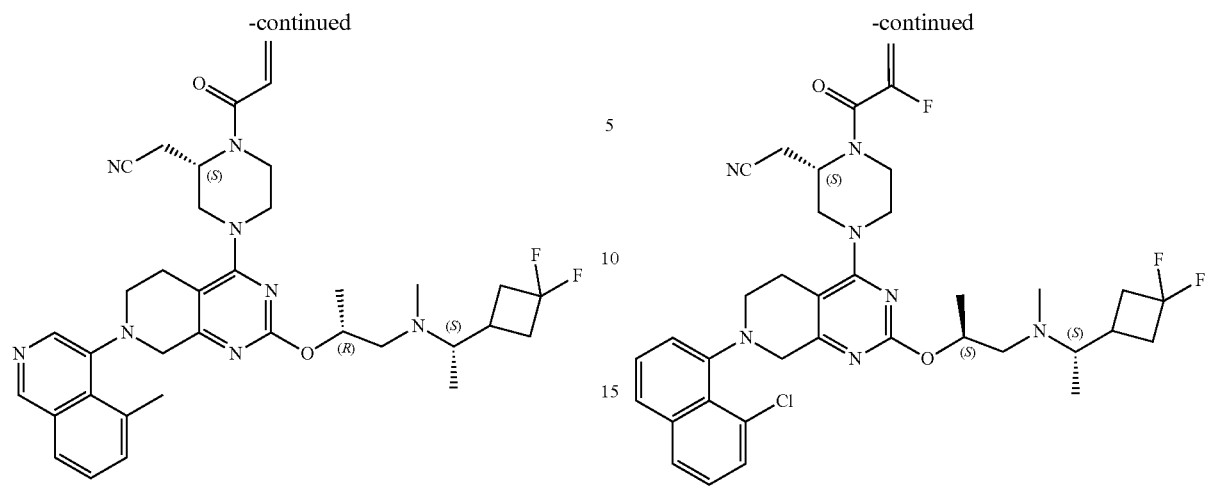
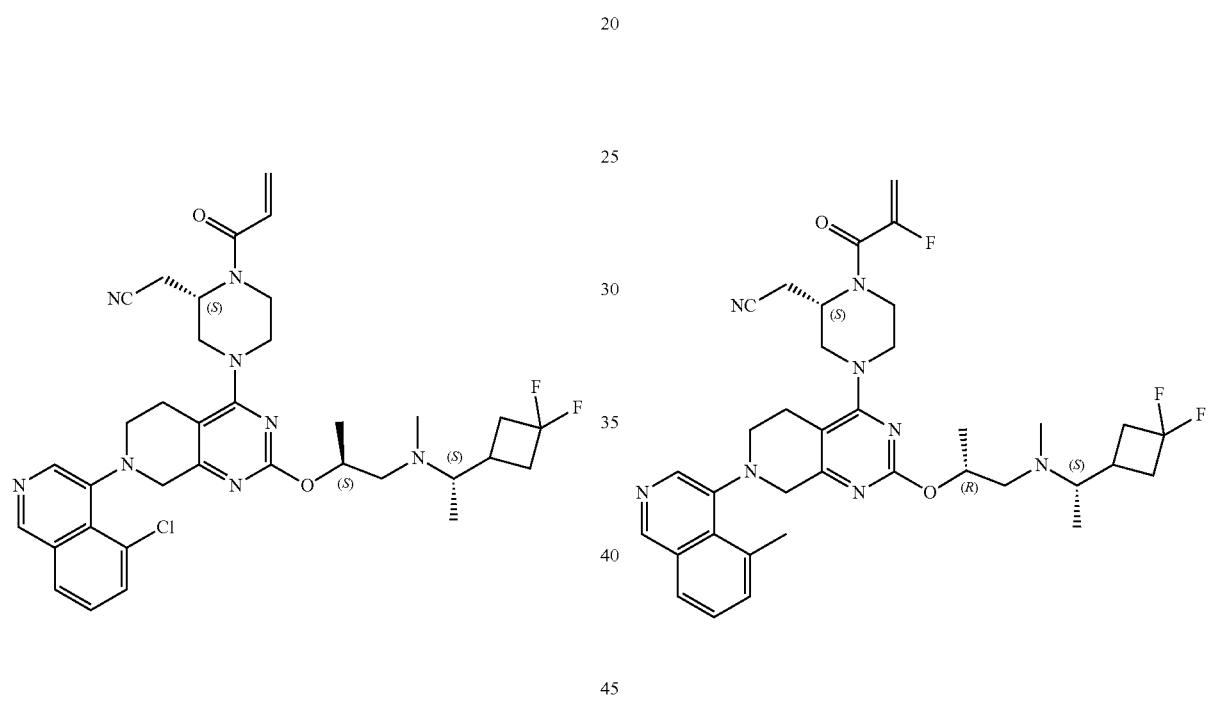
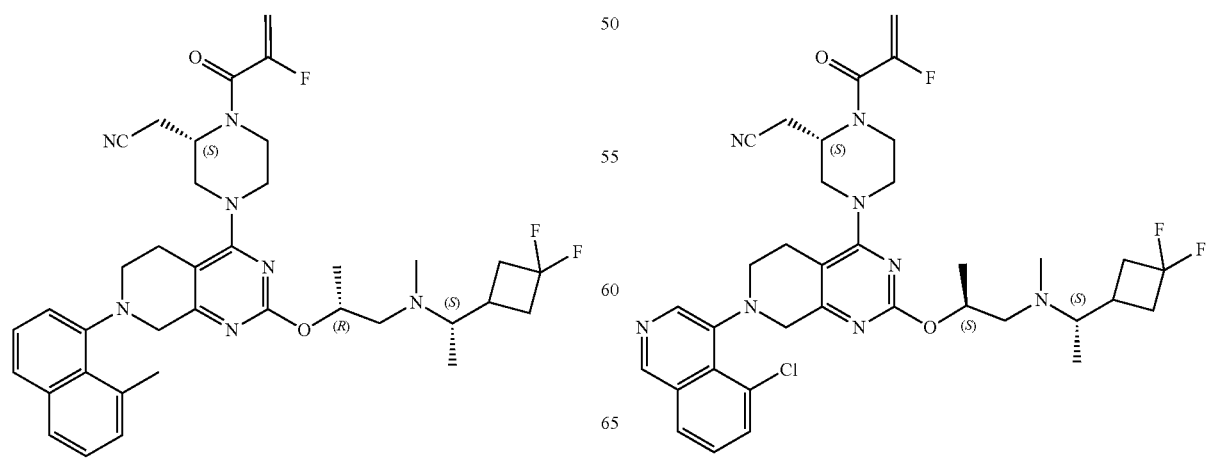

785
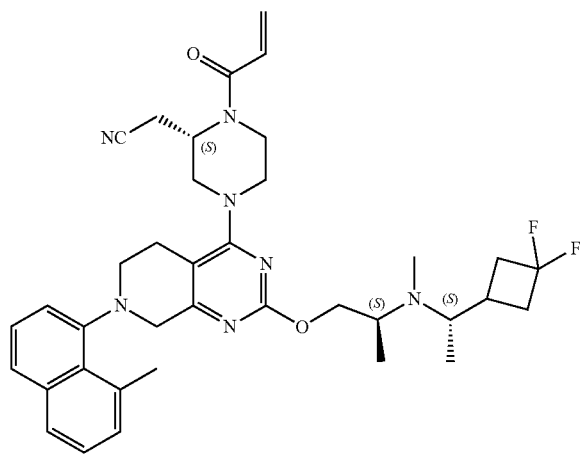
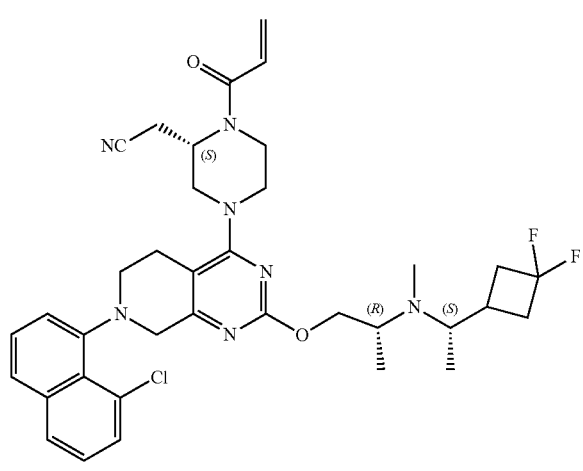
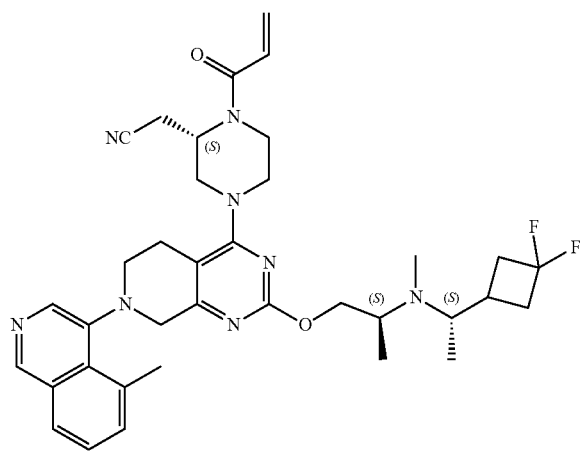
786
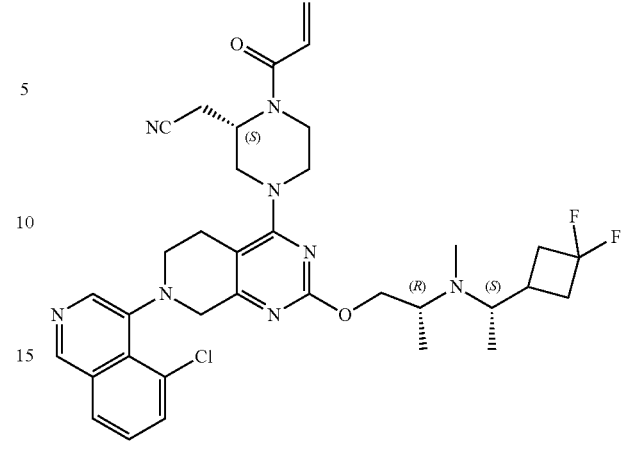
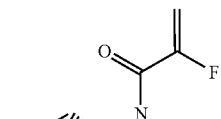
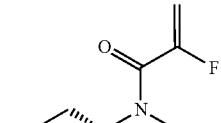

787
-continued
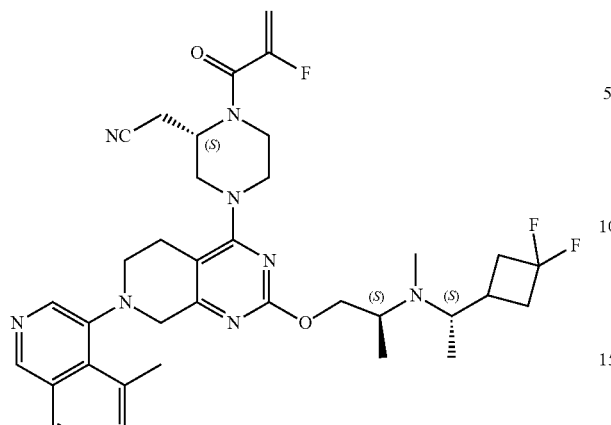
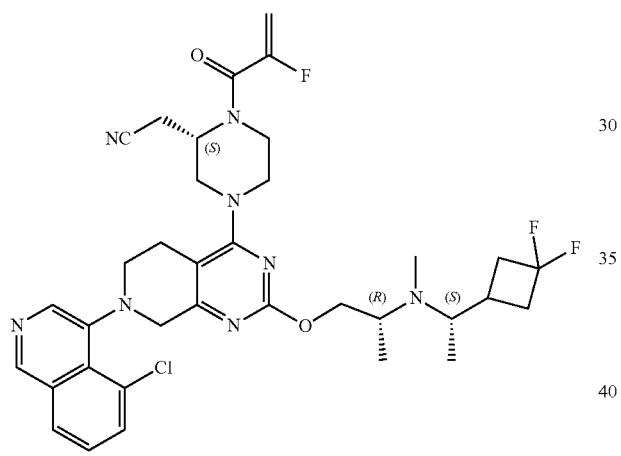
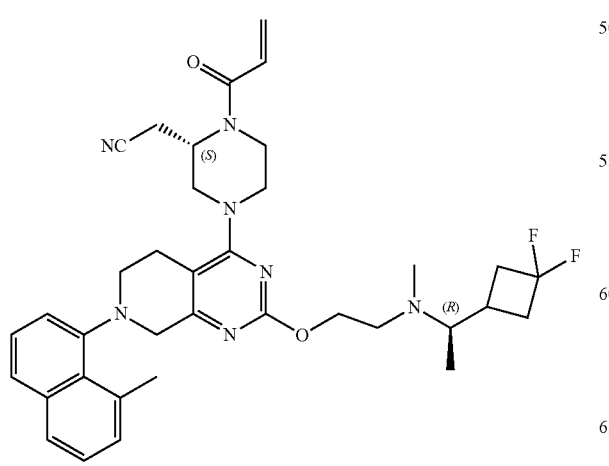
788
-continued
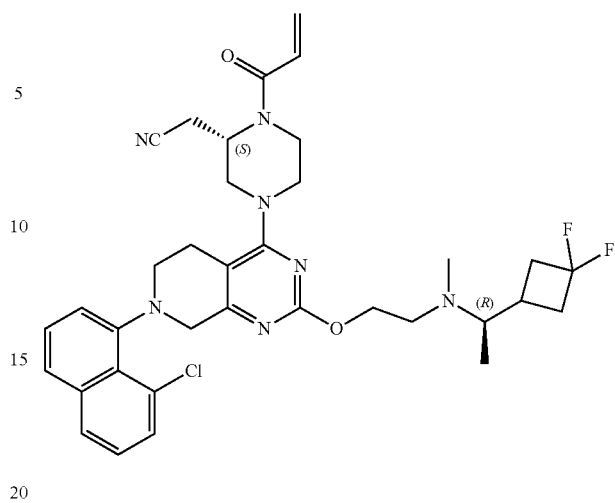
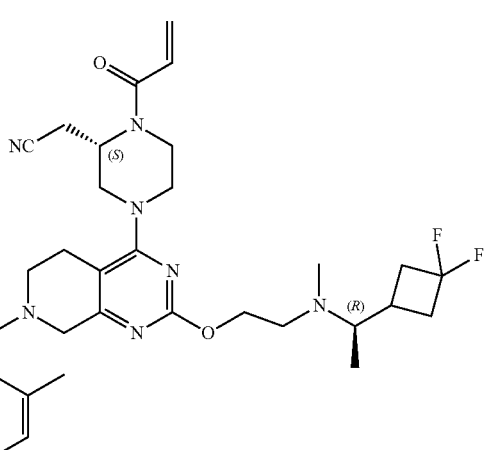
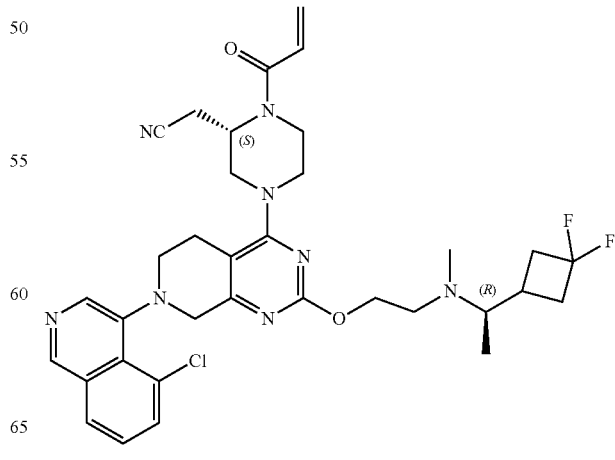

789
-continued
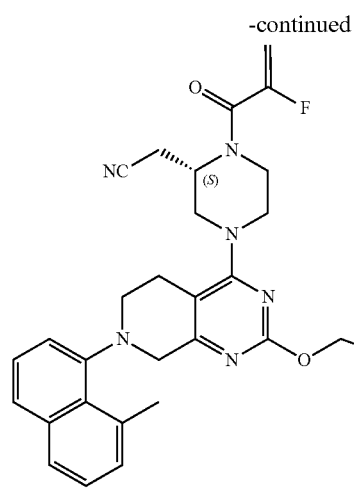
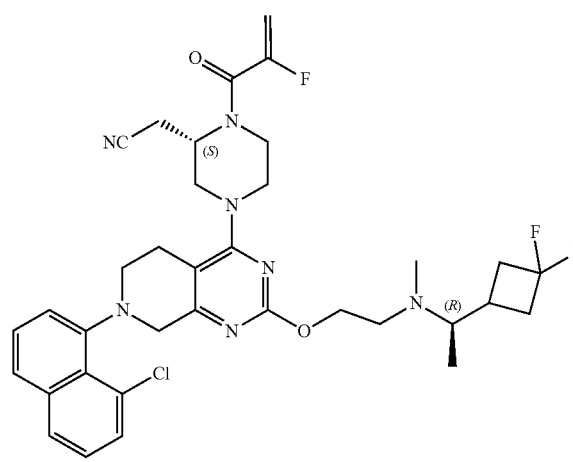
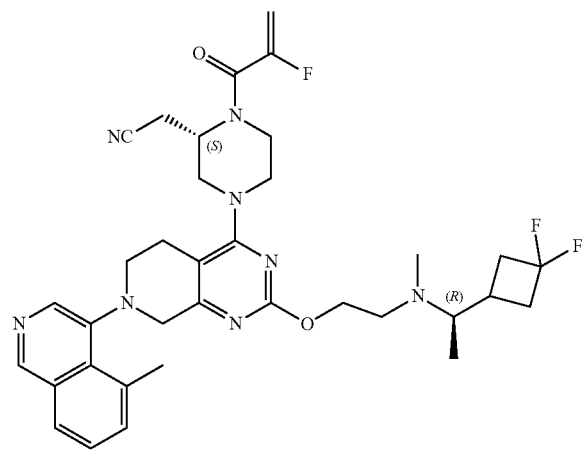
790
-continued
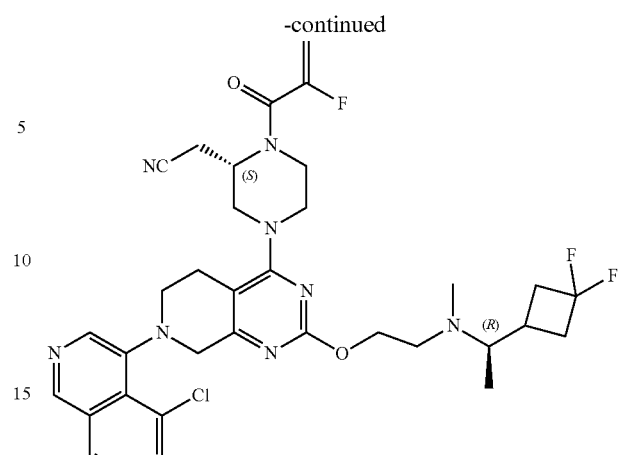
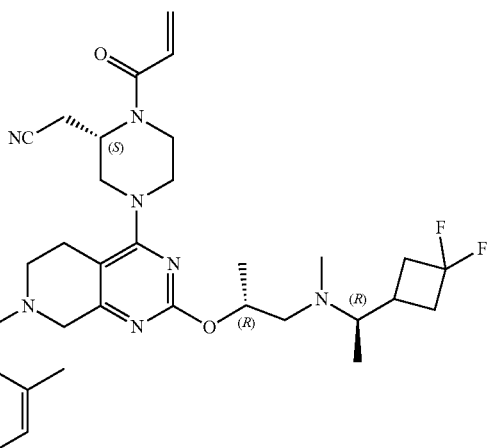
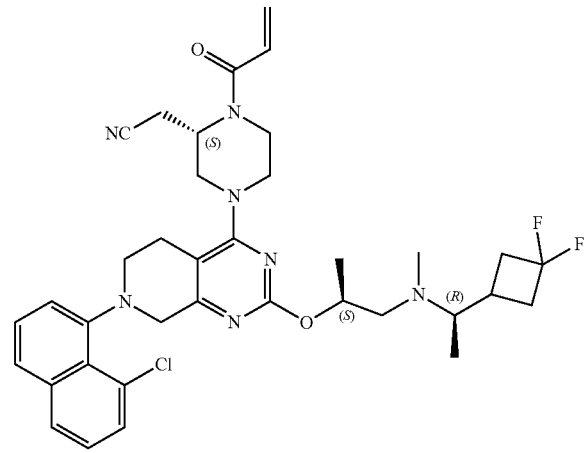

791
-continued
792
-continued
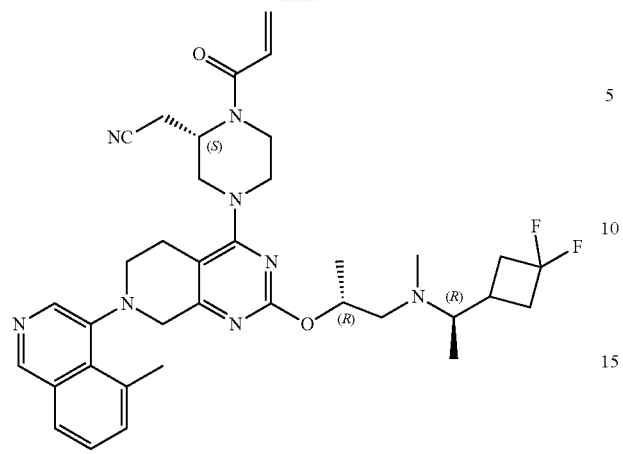
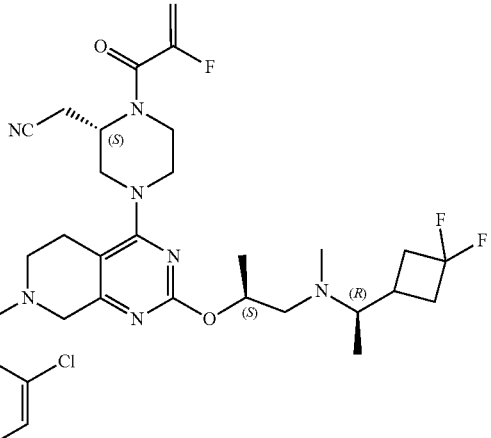
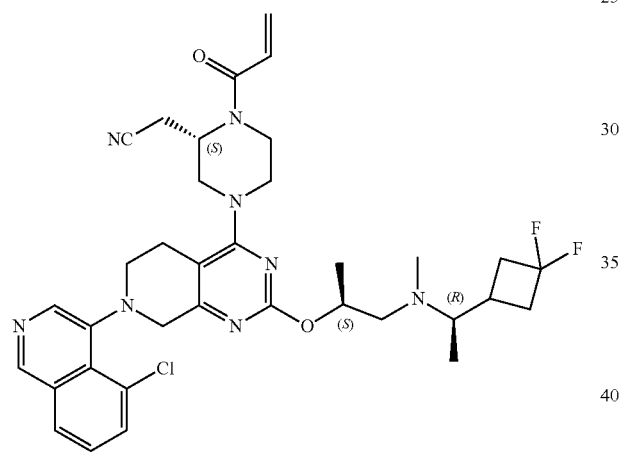
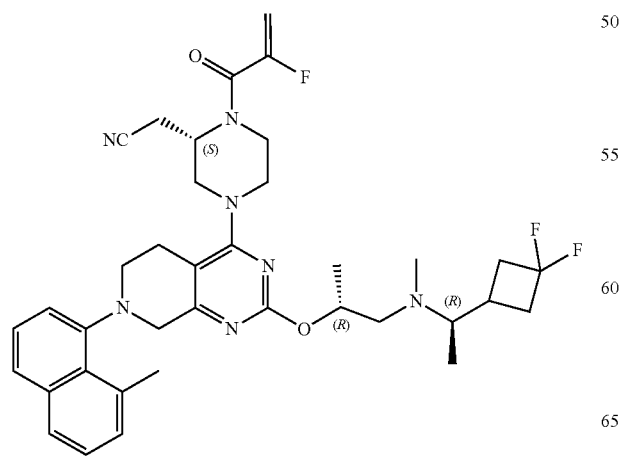

793
-continued
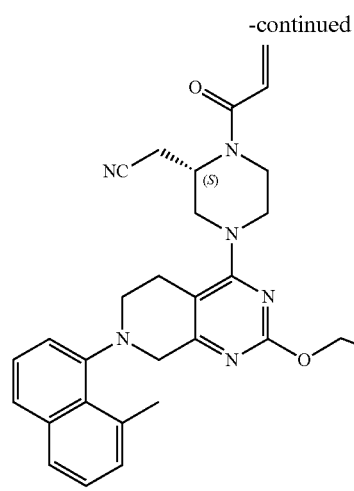
794
-continued
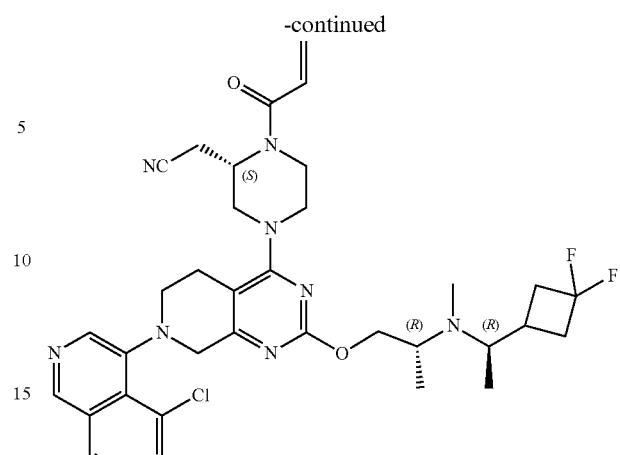
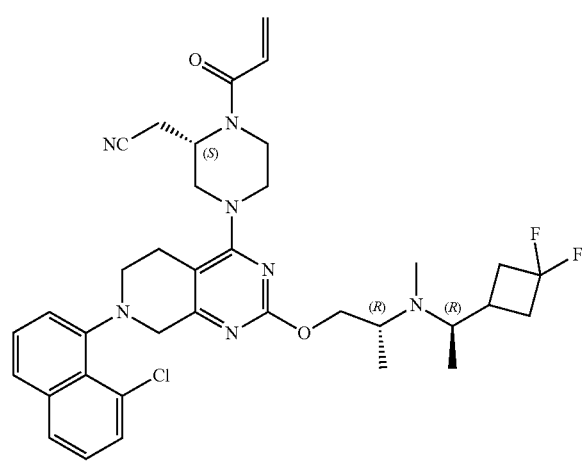
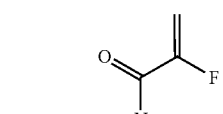
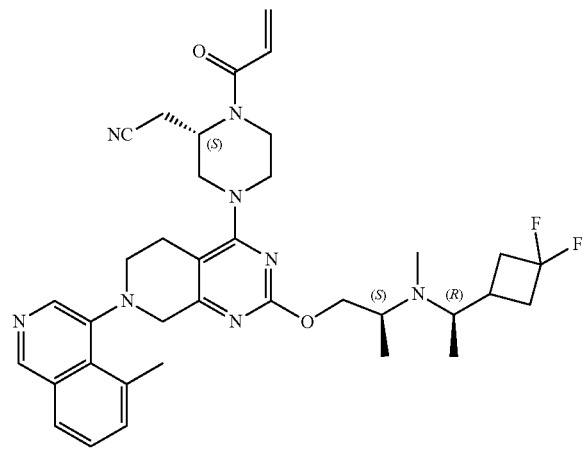
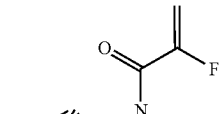

795
-continued
796
-continued
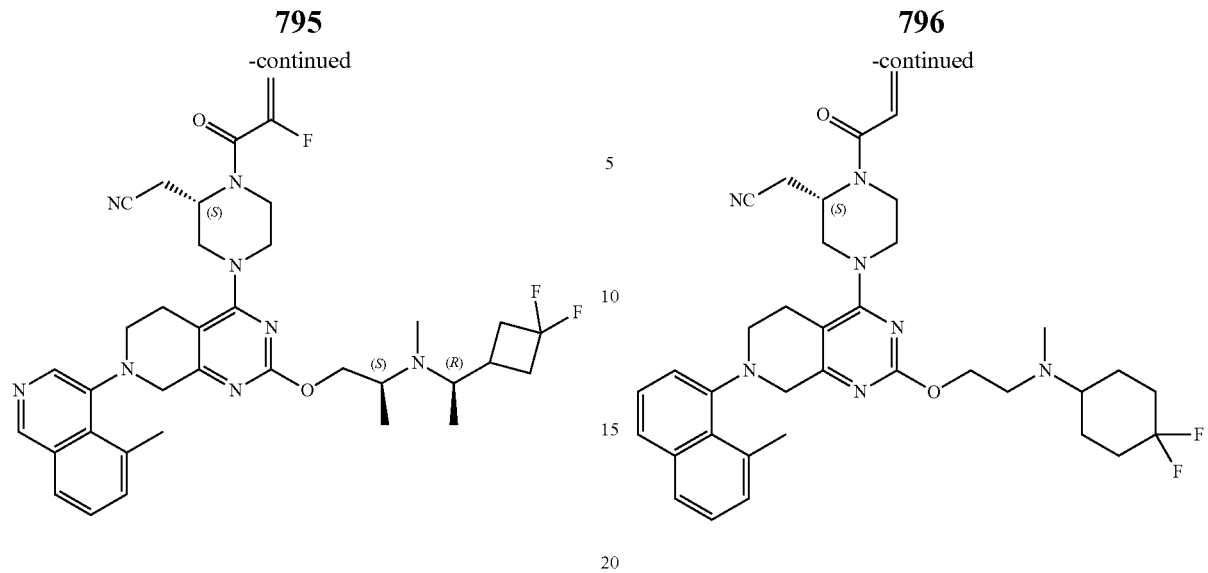
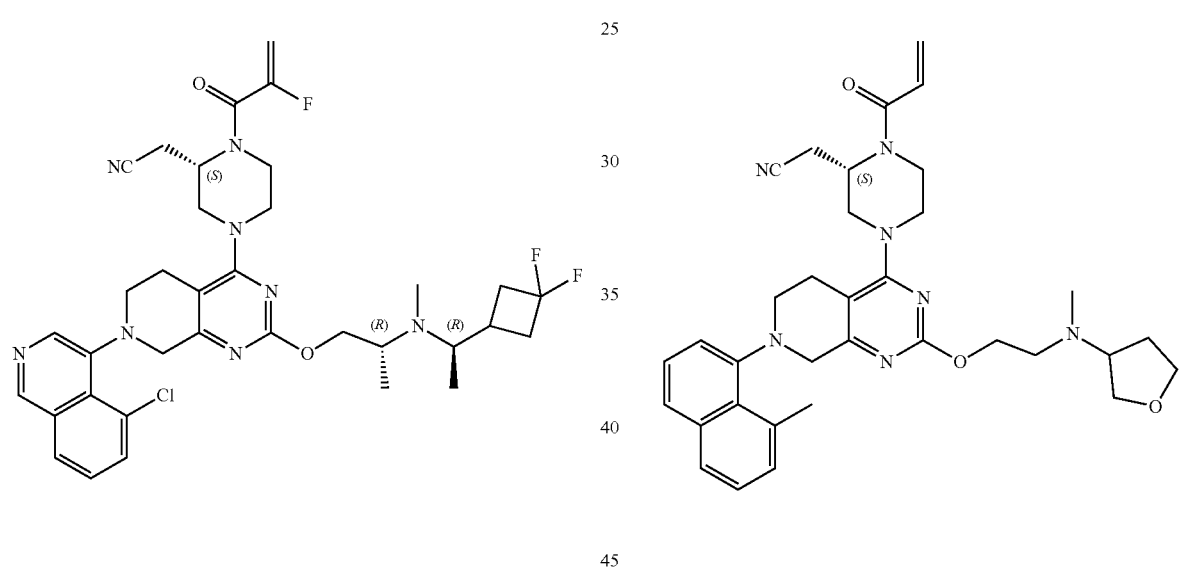
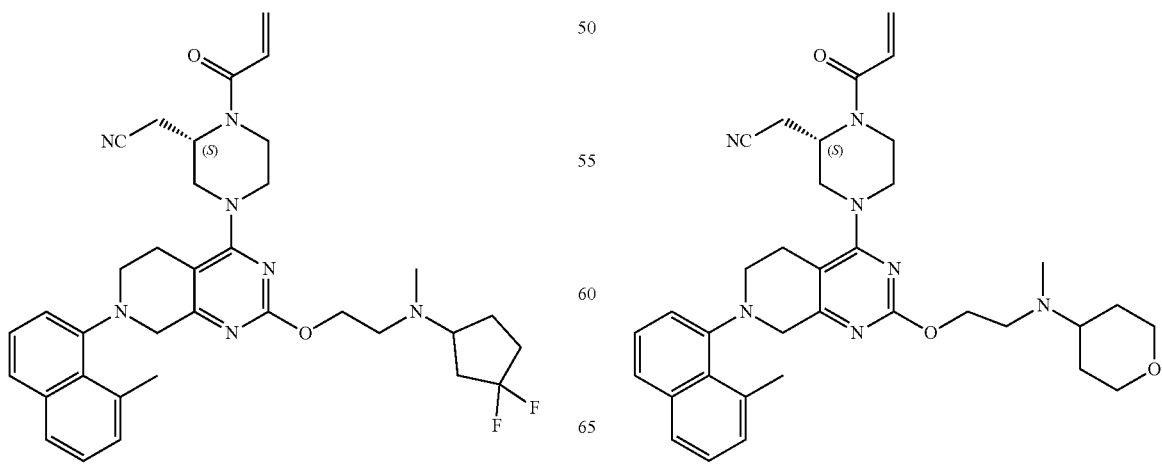

797
-continued
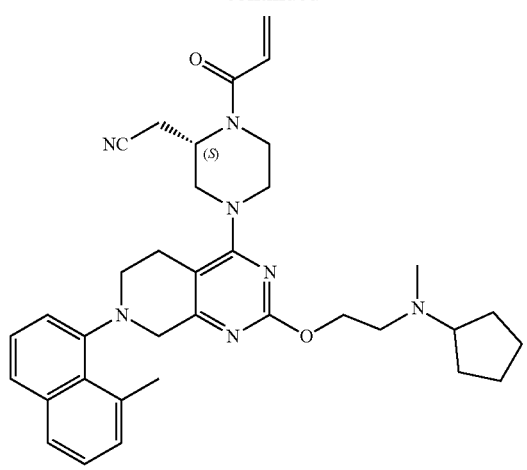
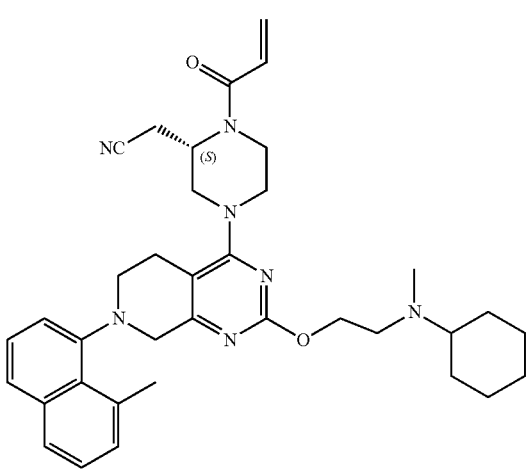
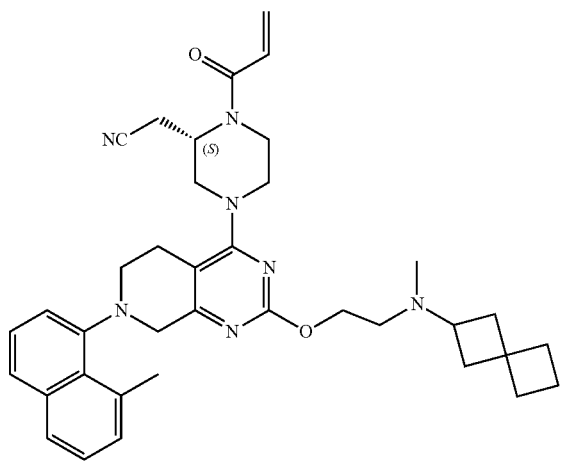
798
-continued
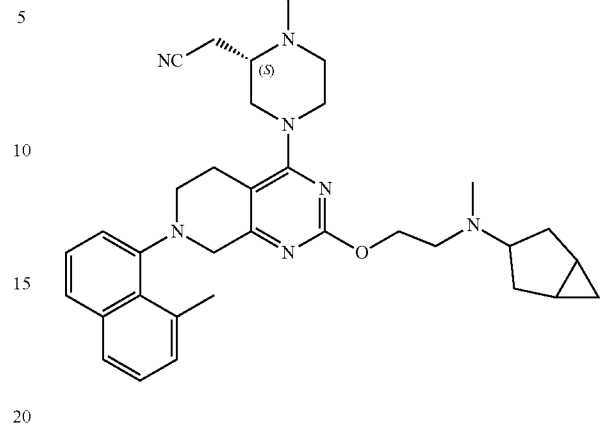
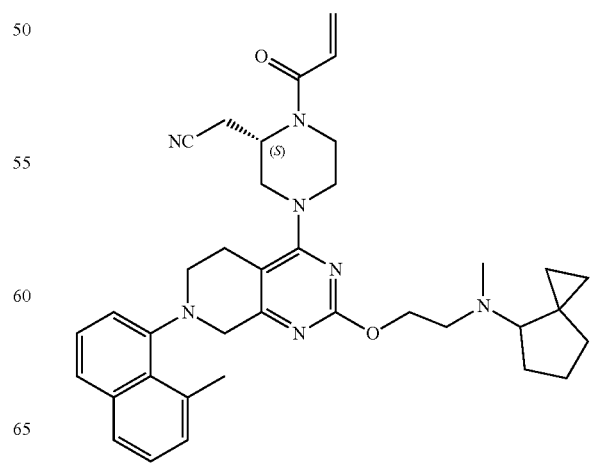

799
-continued
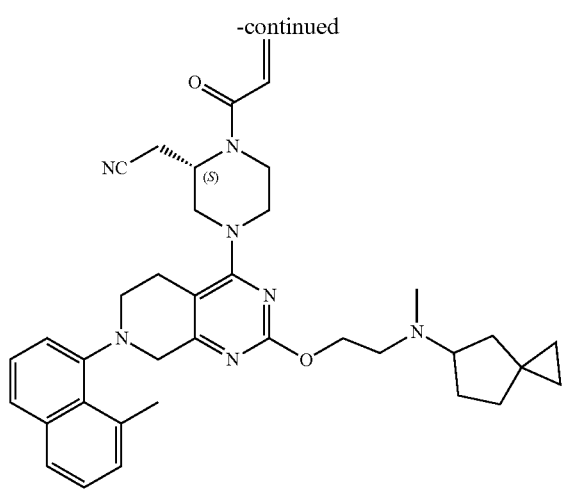
800
-continued
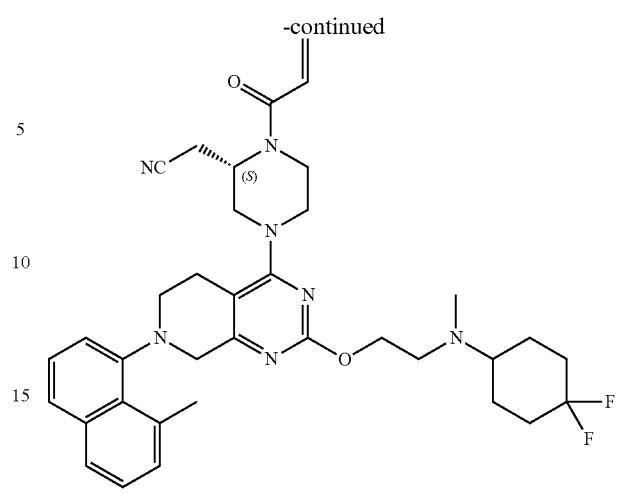
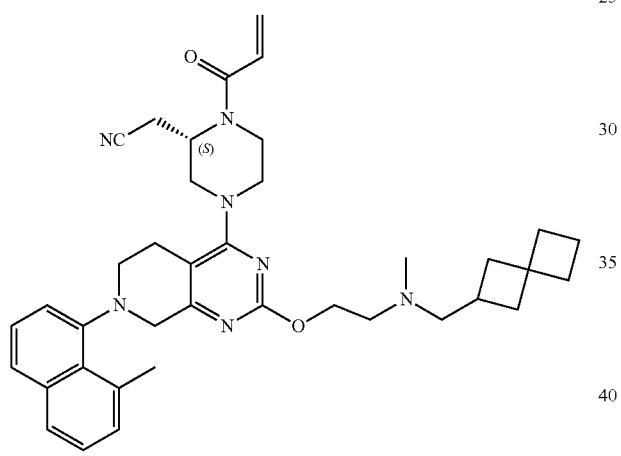
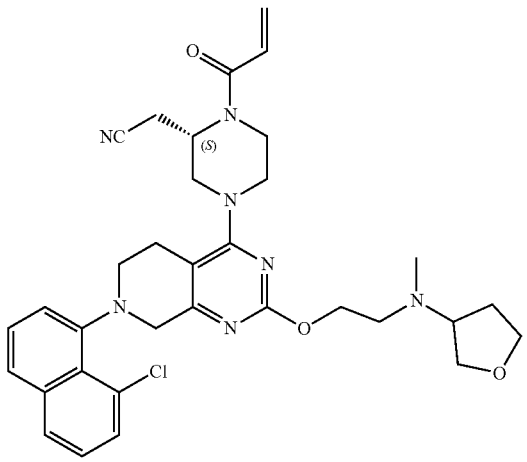
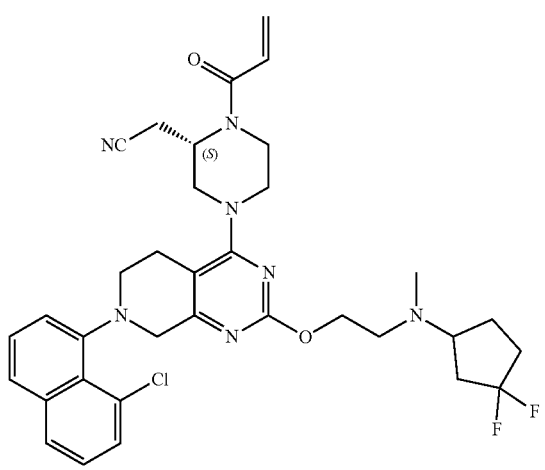
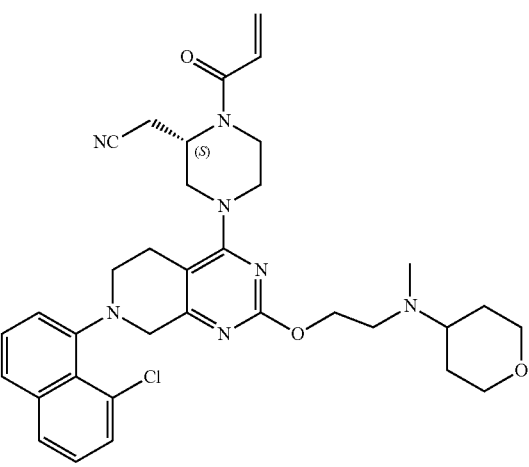

801
-continued
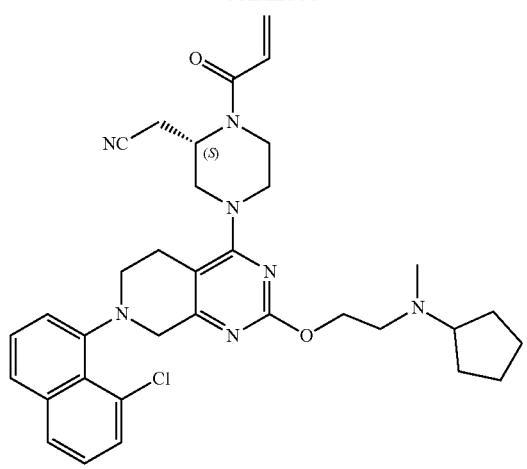
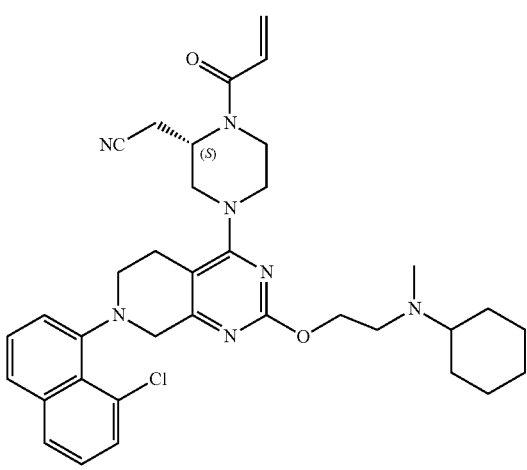
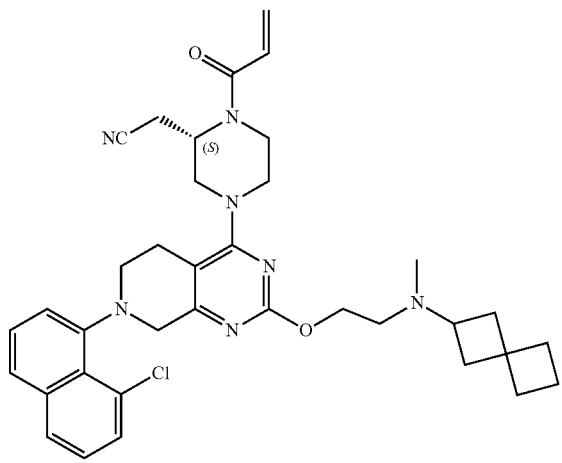
802
-continued
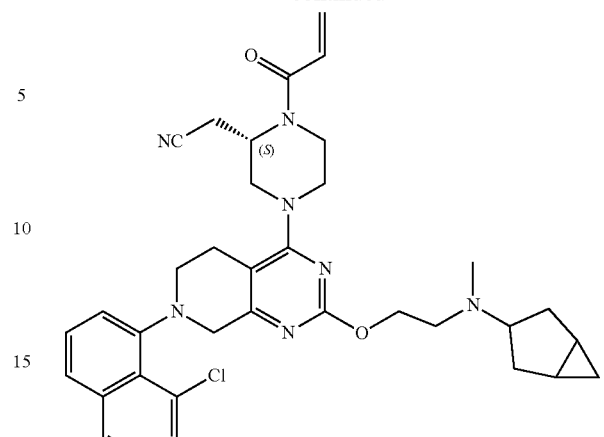
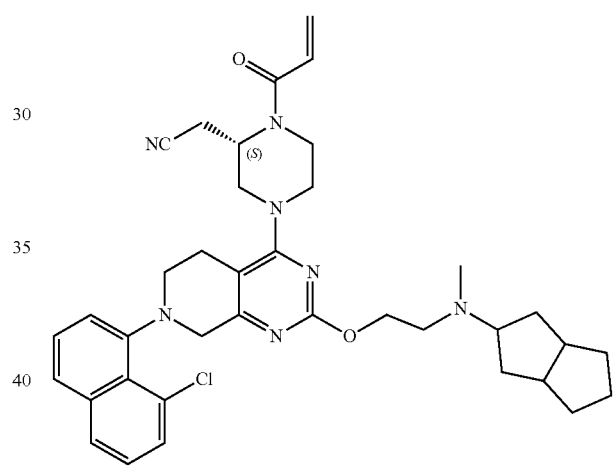
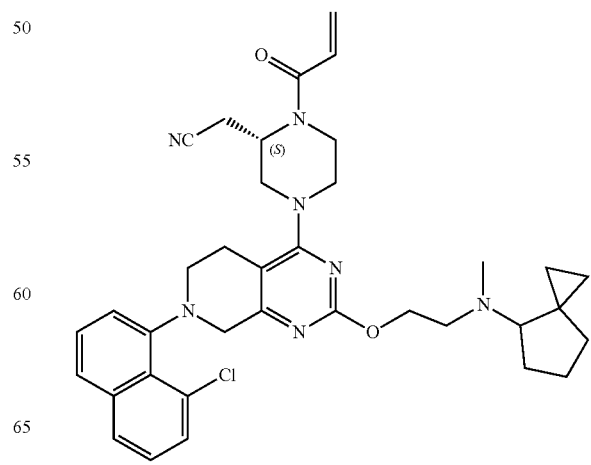

803
-continued
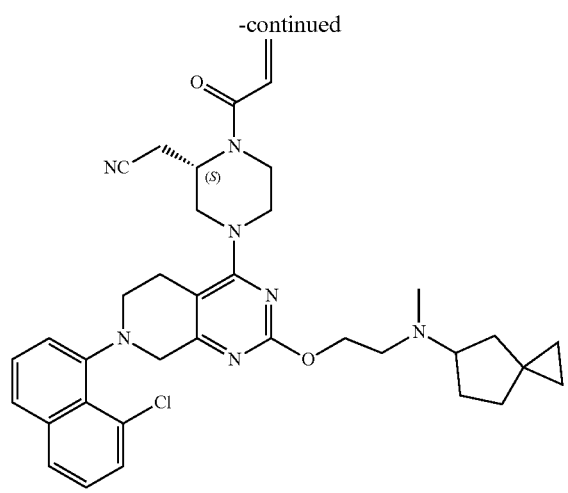
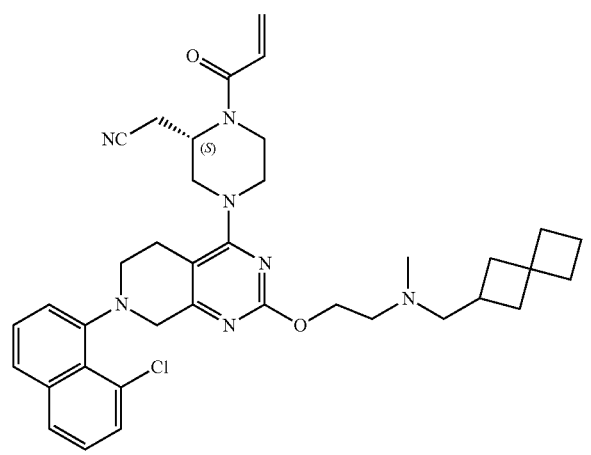
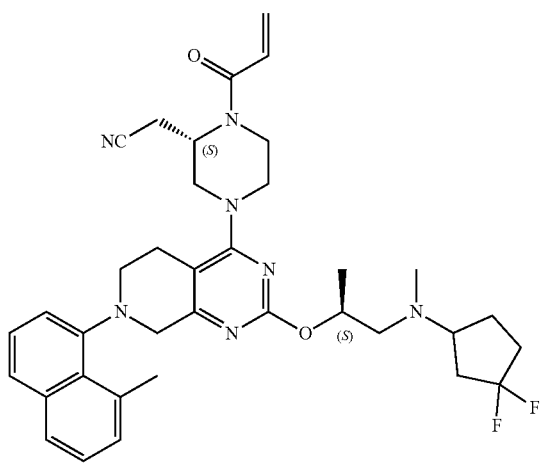
804
-continued
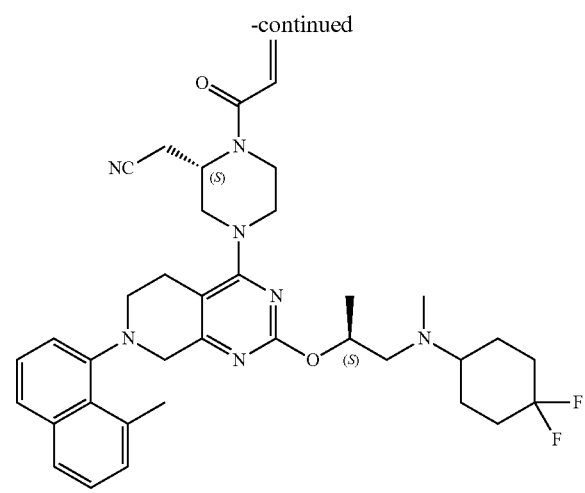
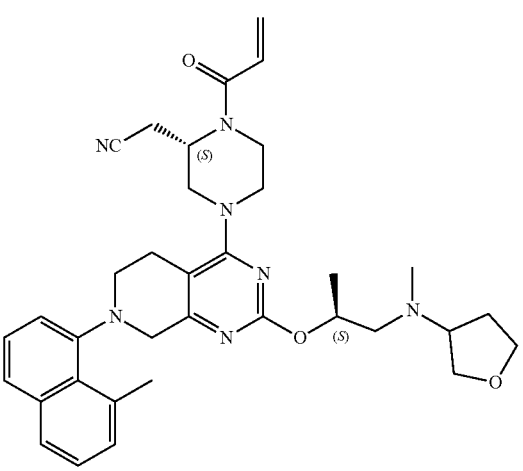
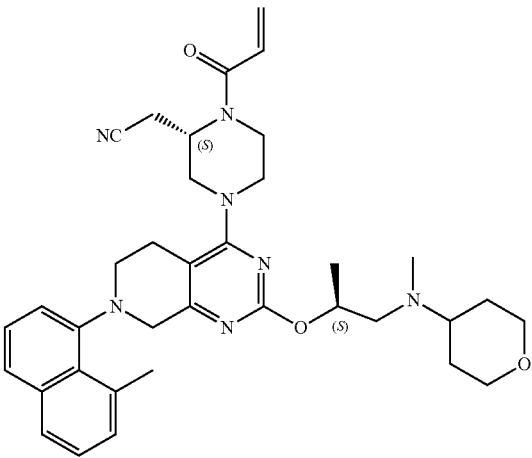

805
-continued
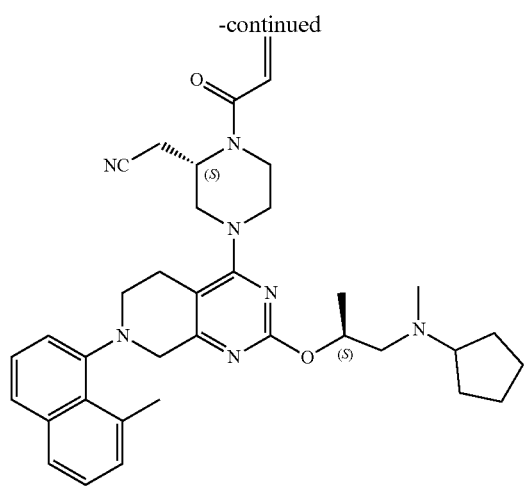
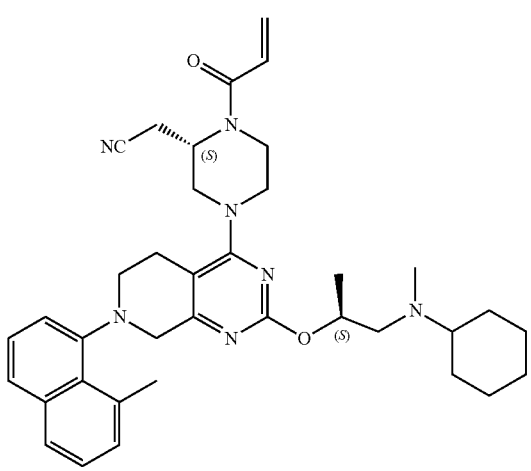
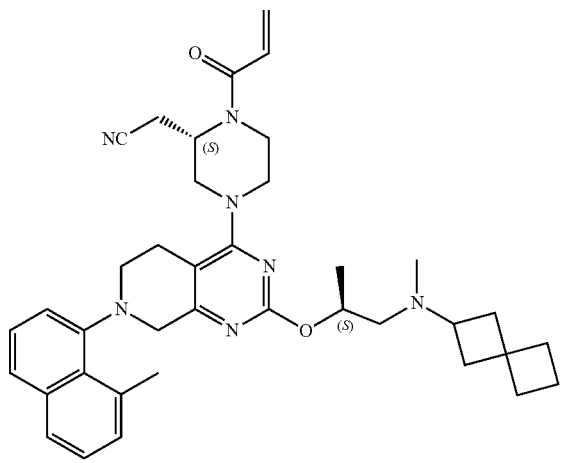
806
-continued
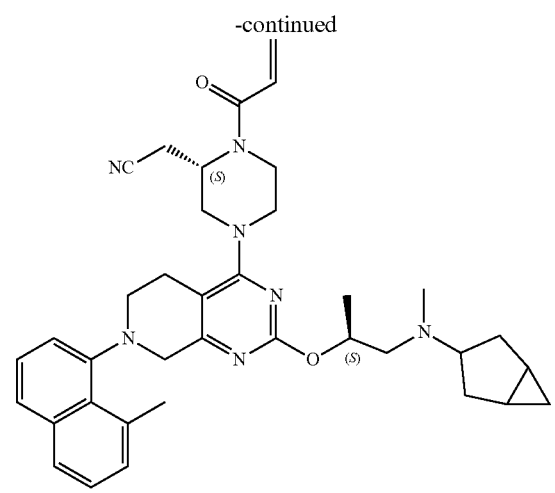
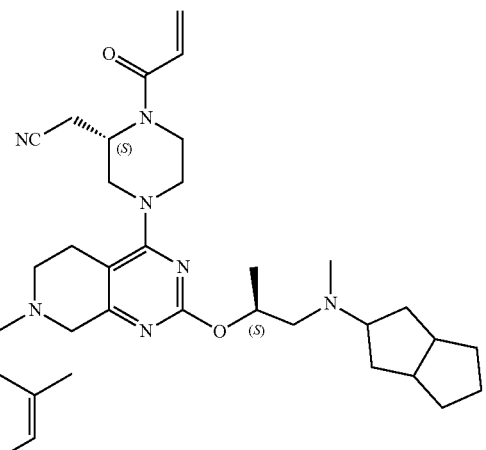
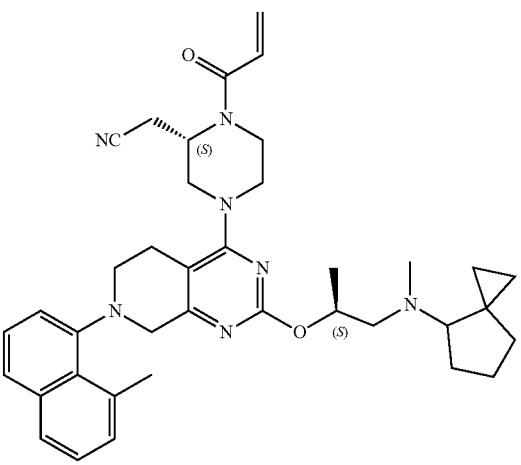

807
-continued
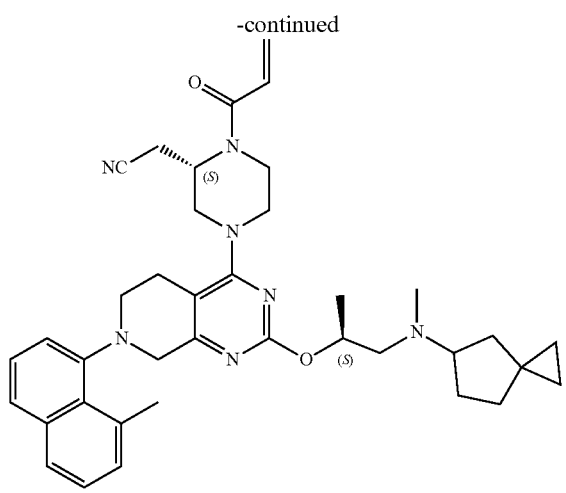
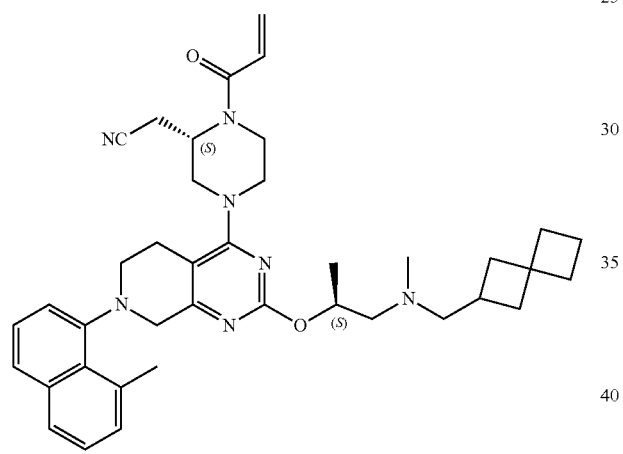
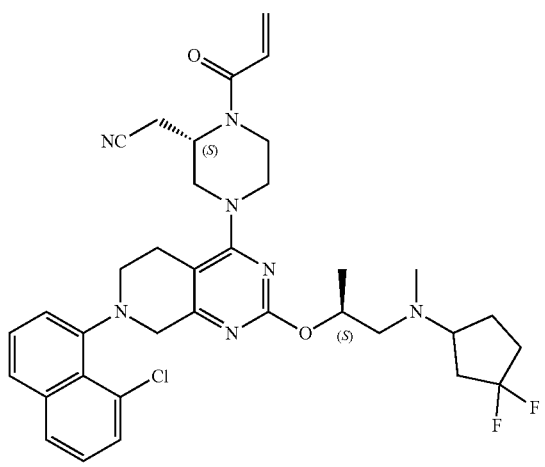
808
-continued
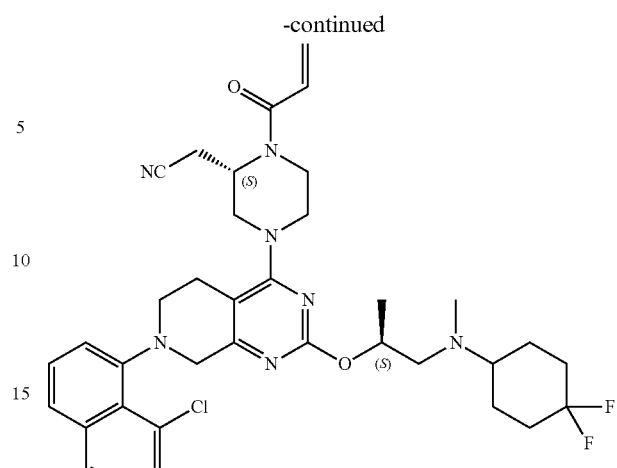
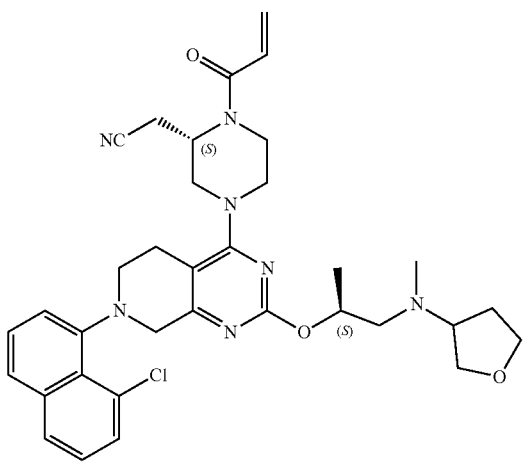
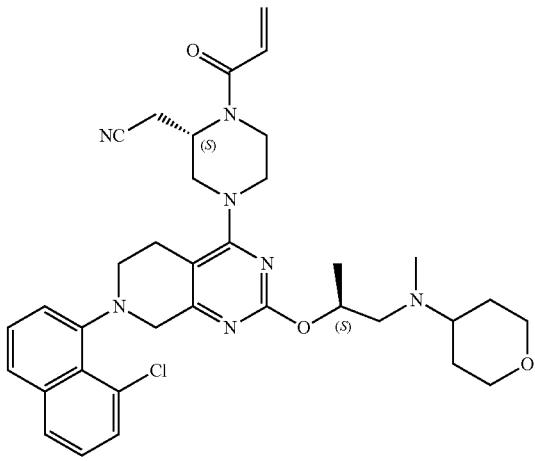

809
-continued
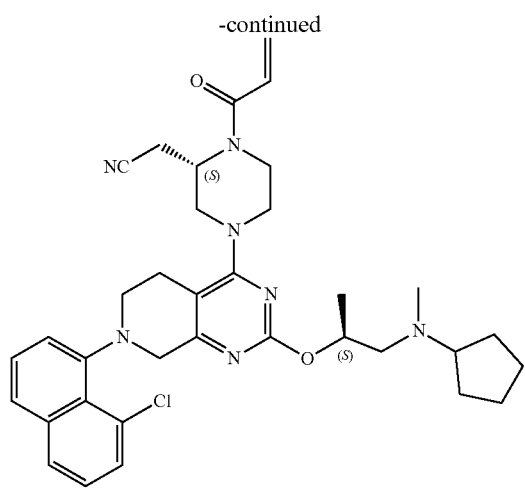
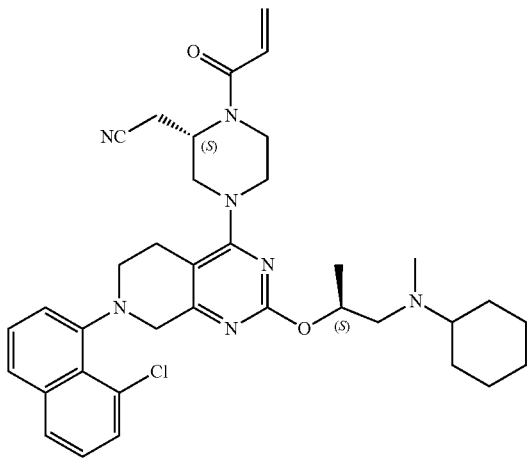
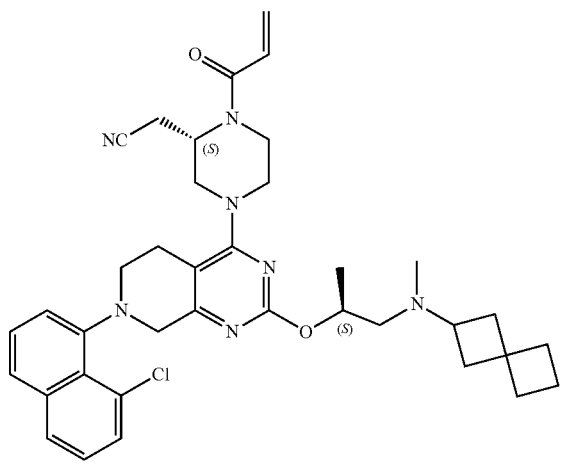
810
-continued
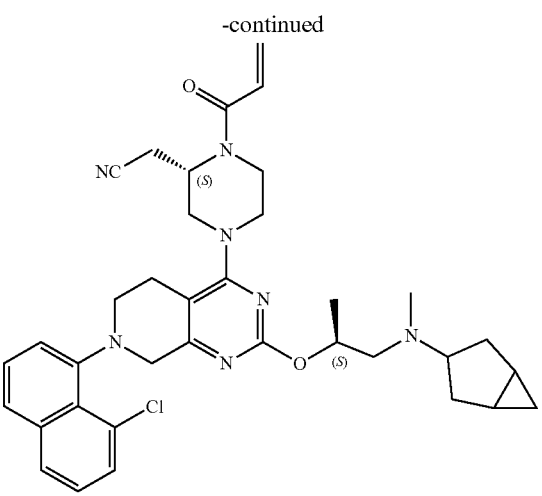
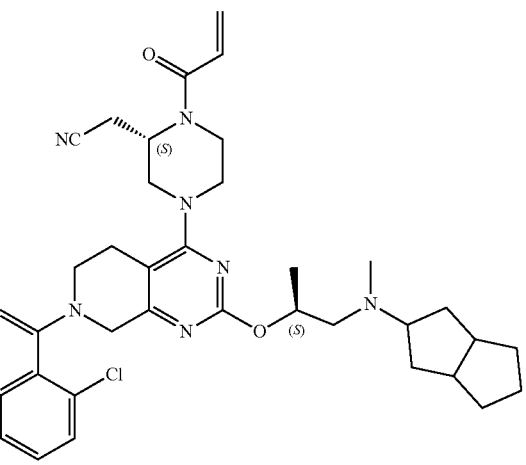
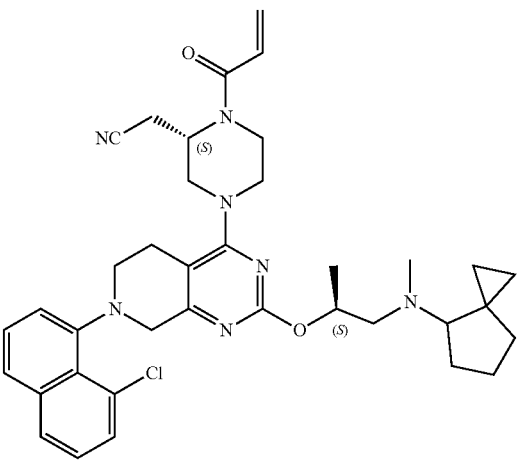

811
-continued
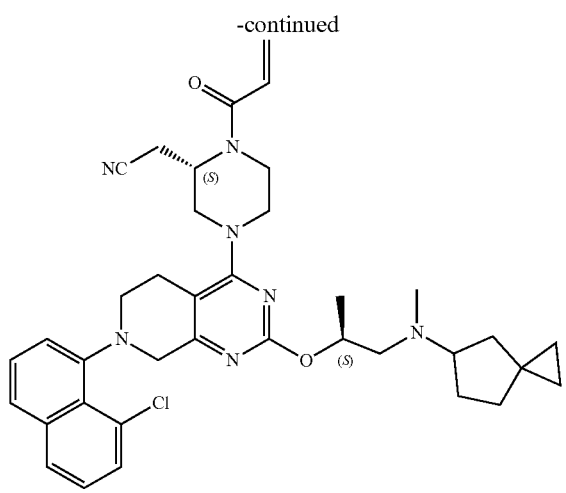
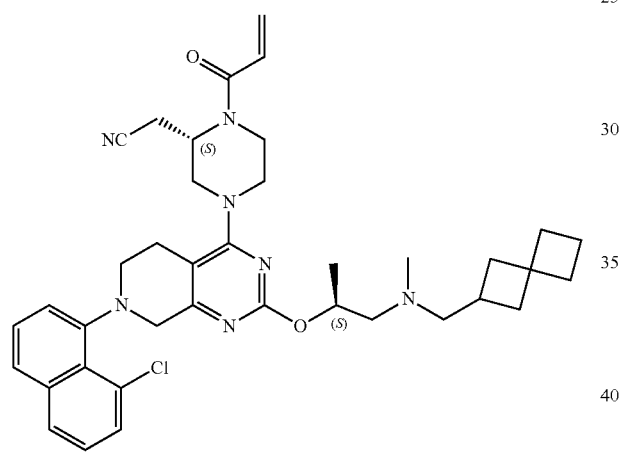
812
-continued
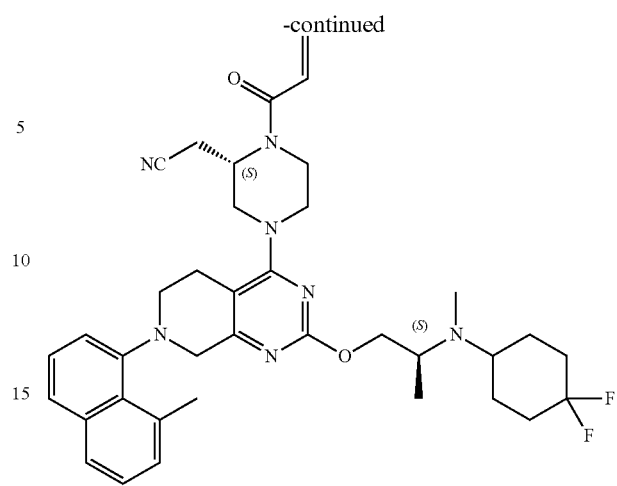
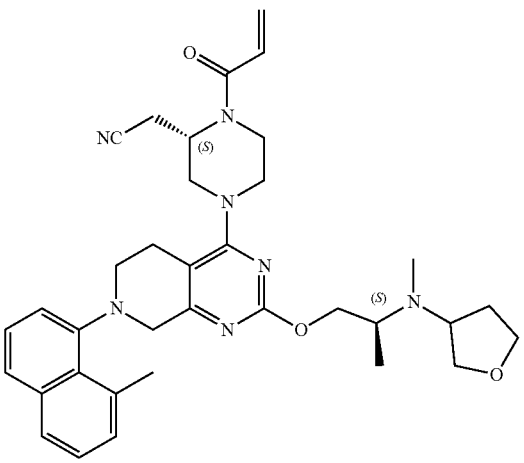

813
-continued
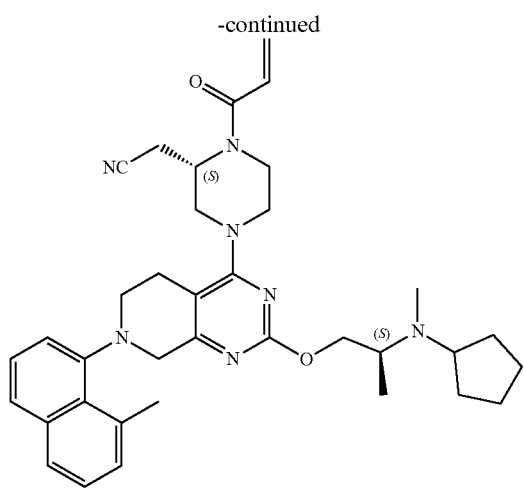
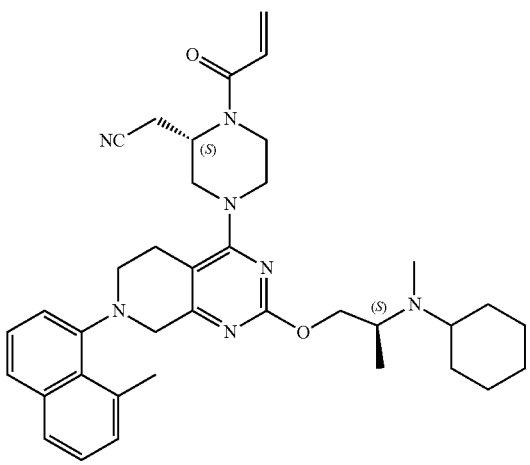
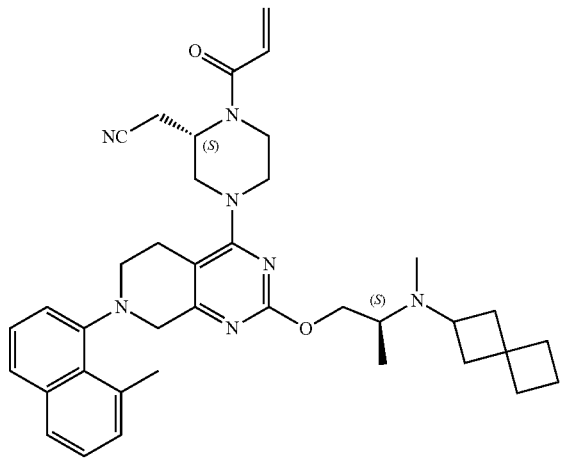
814
-continued
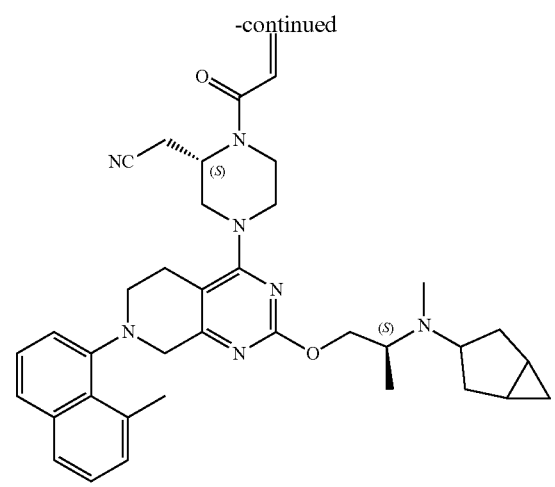
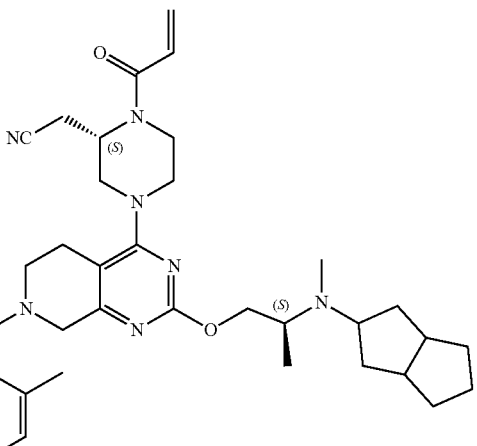
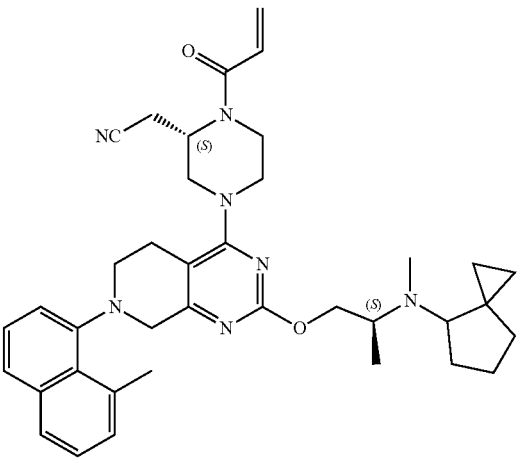

815
-continued
816
-continued
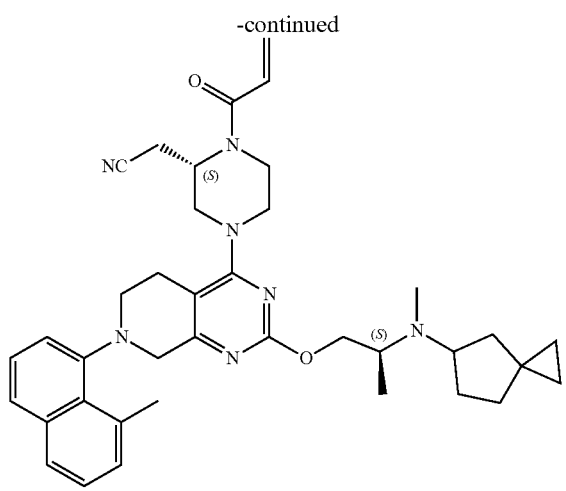
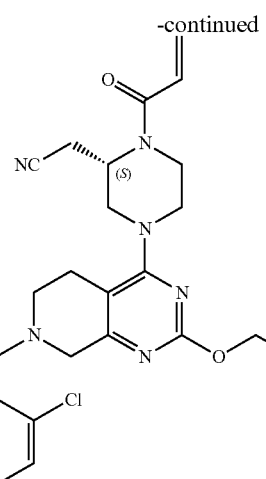
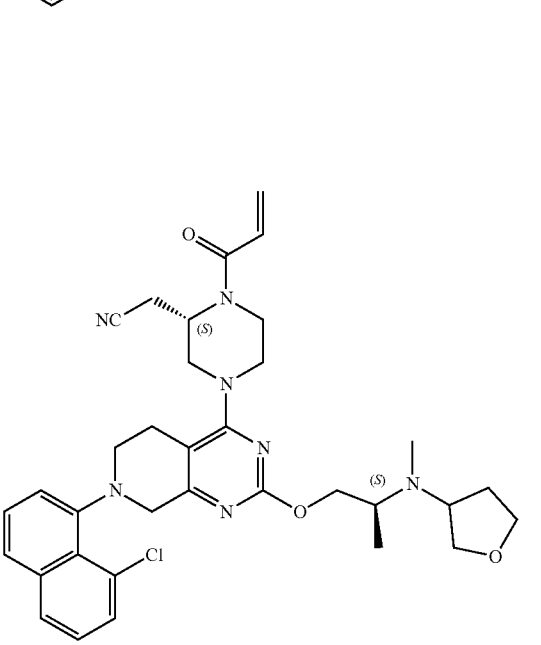
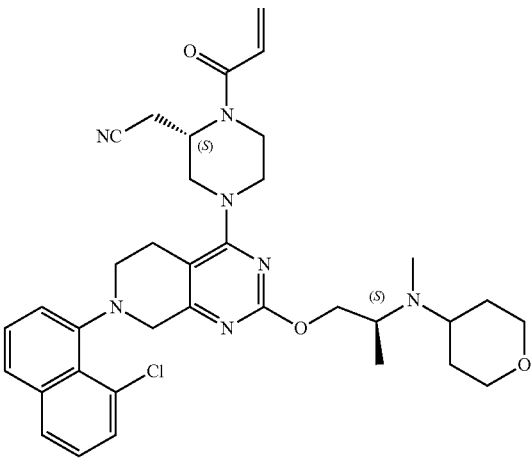

817
-continued
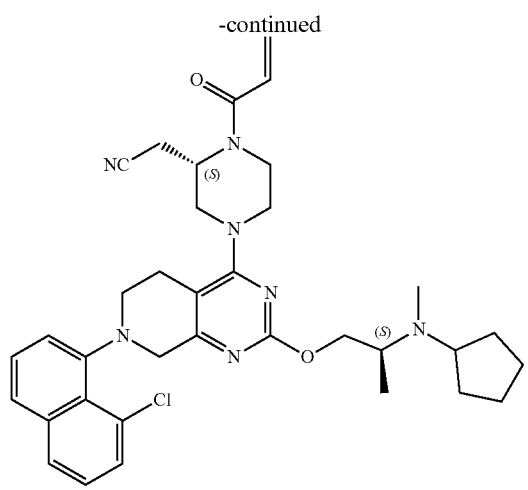
818
-continued
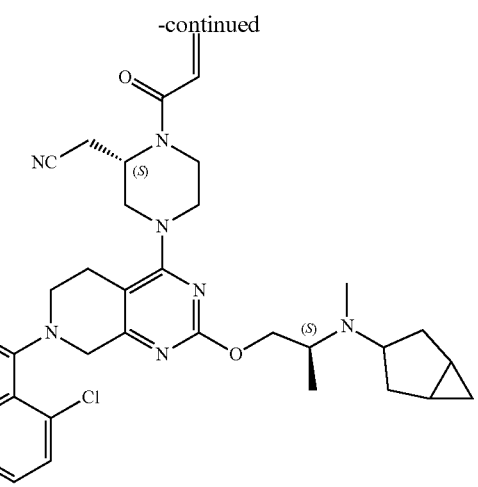
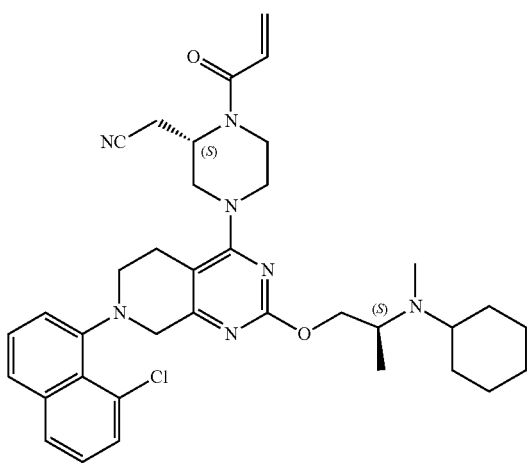
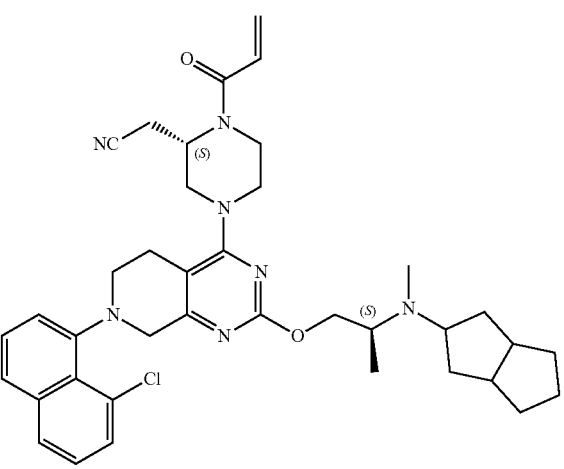
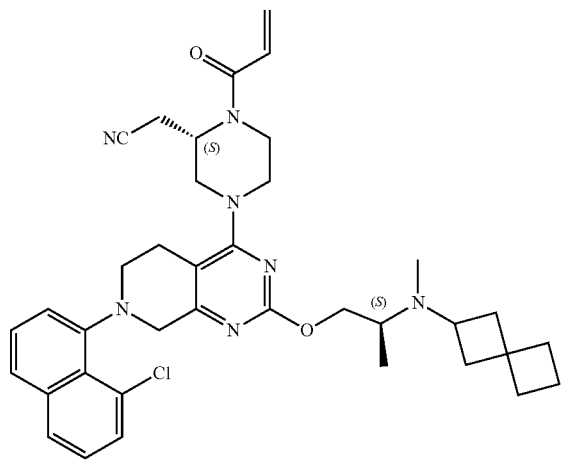
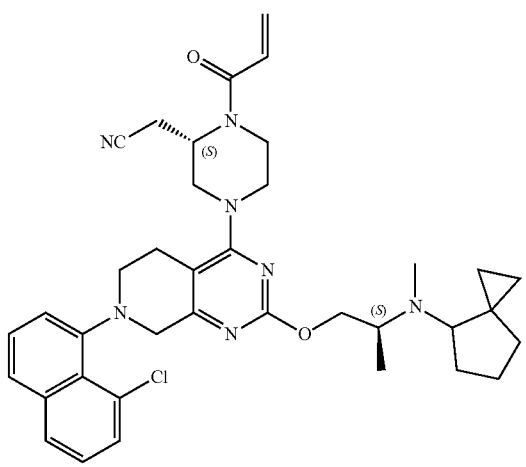

819
-continued
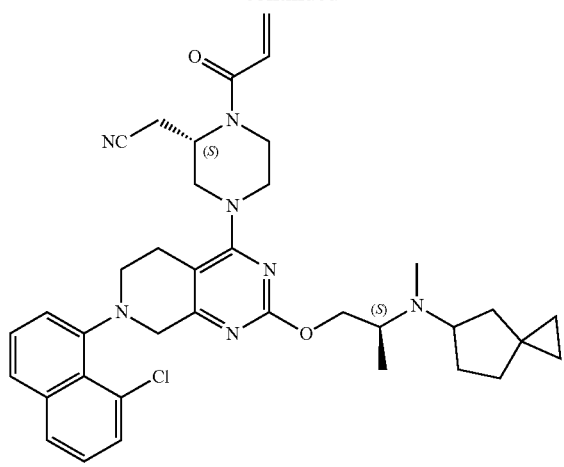
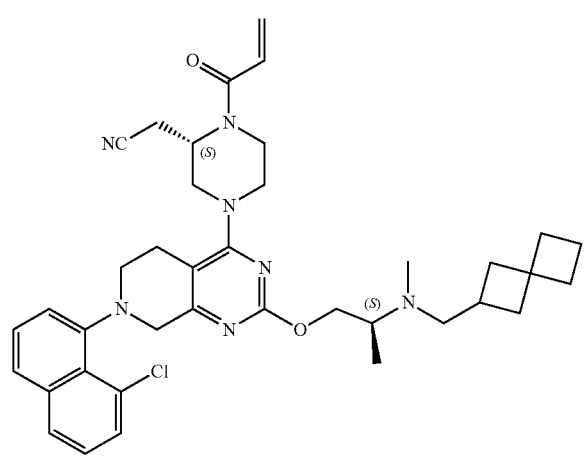
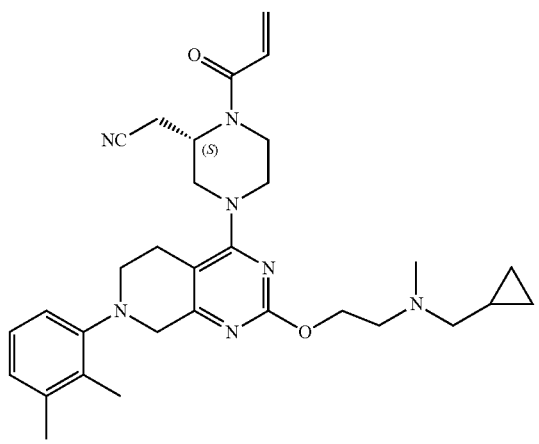
820
-continued
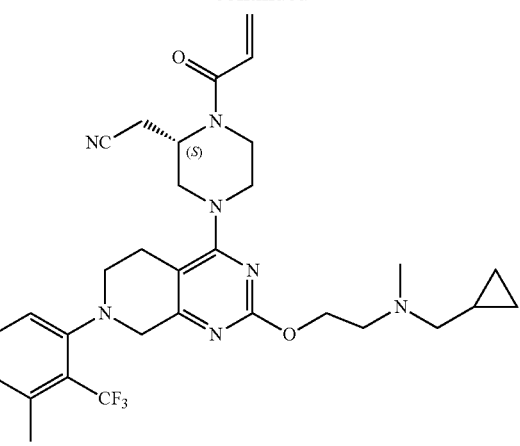
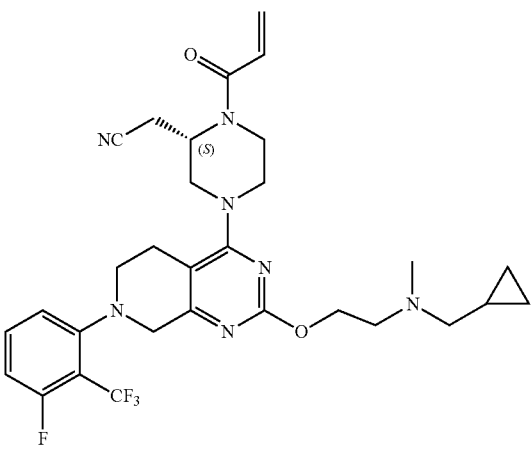
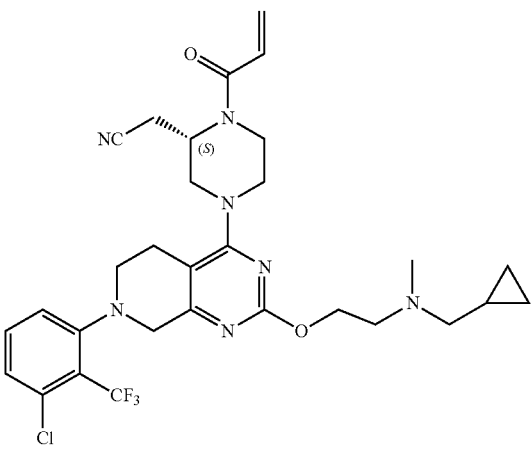

821
-continued
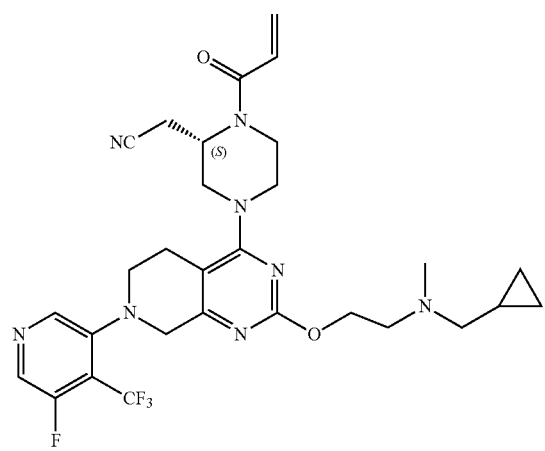
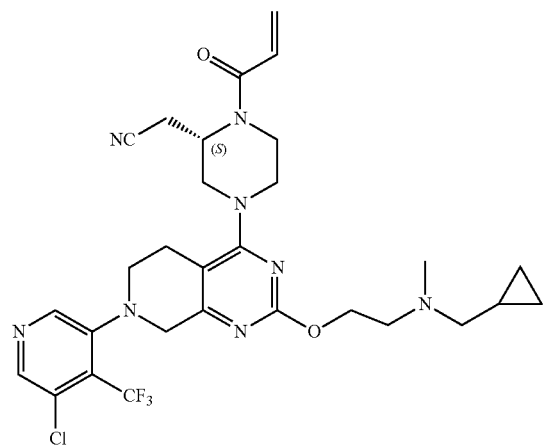
822
-continued
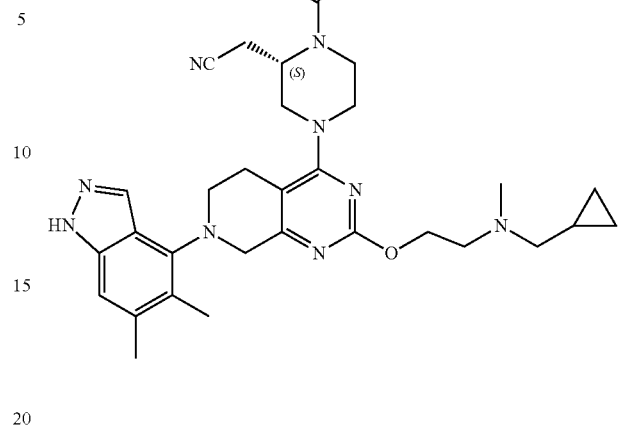
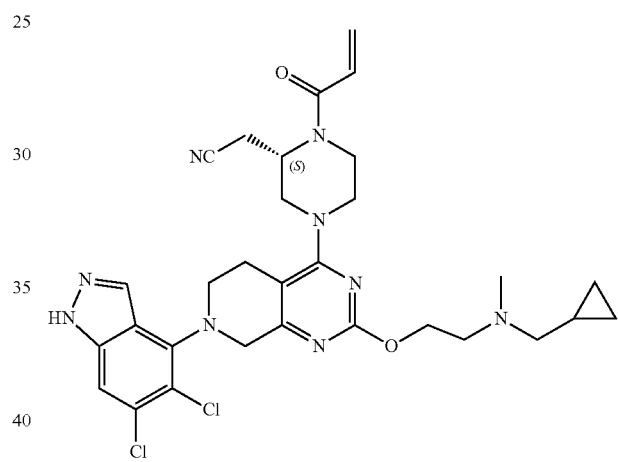
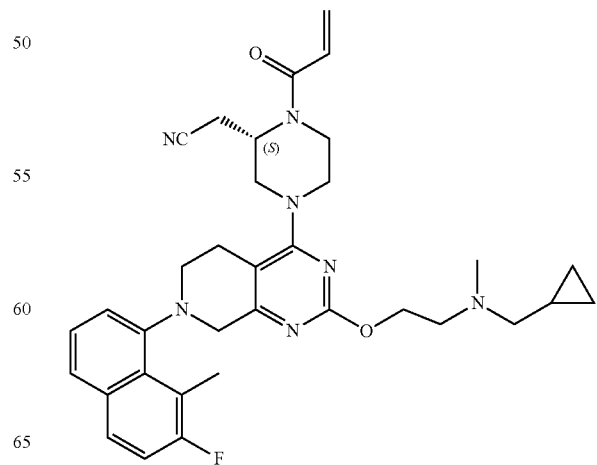

823
-continued
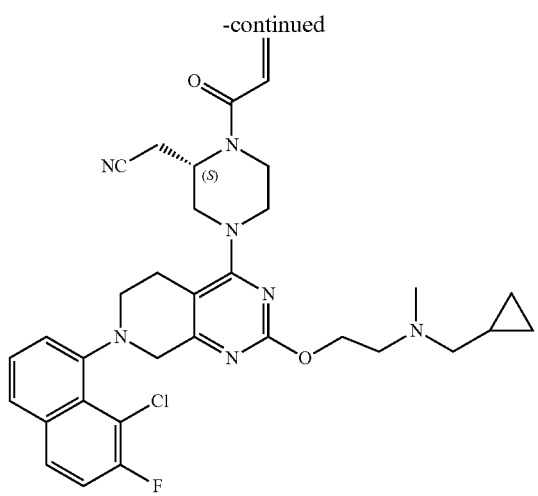
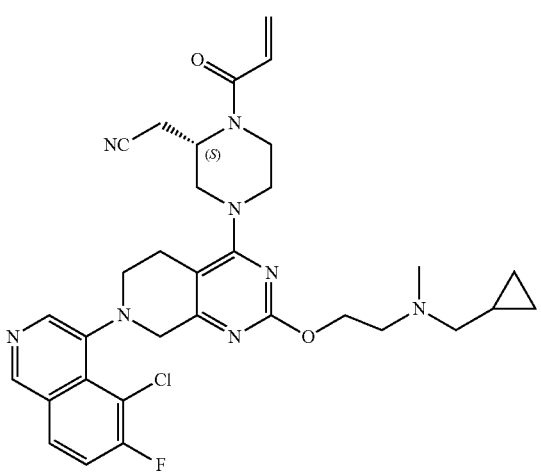
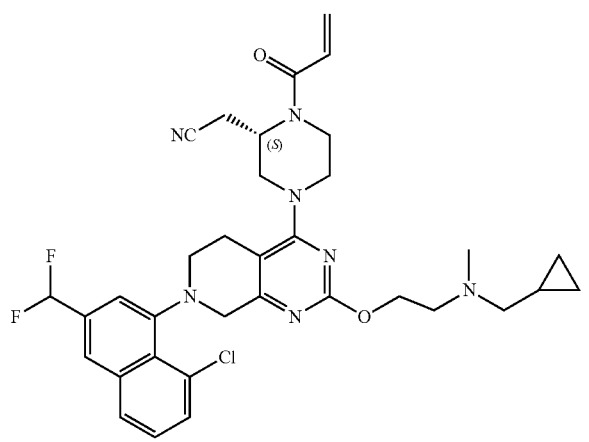
824
-continued
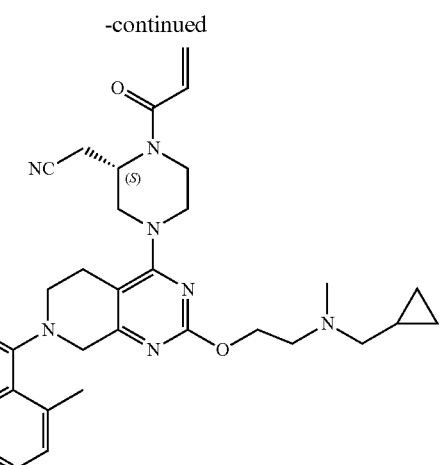
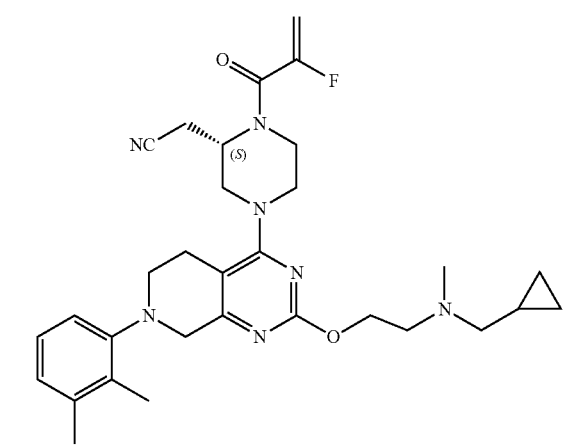
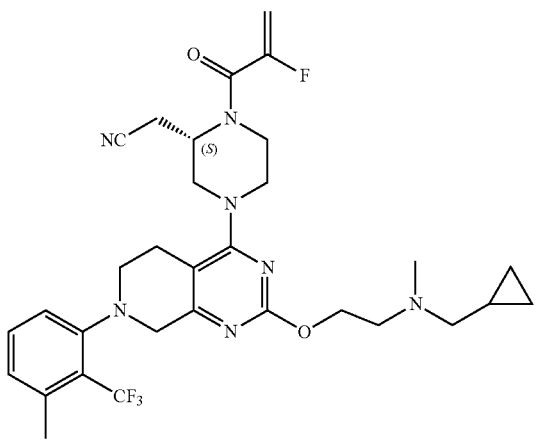

825
-continued
826
-continued
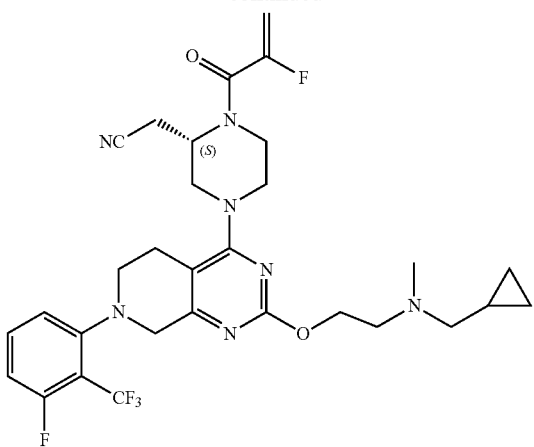
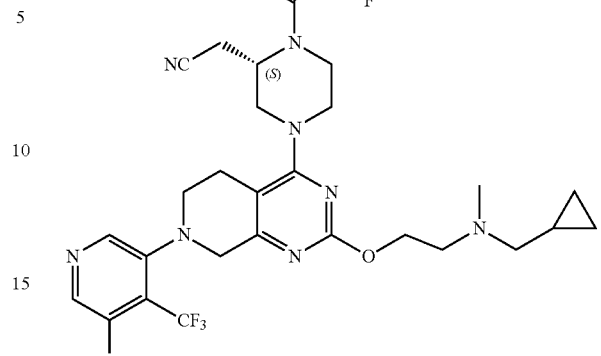
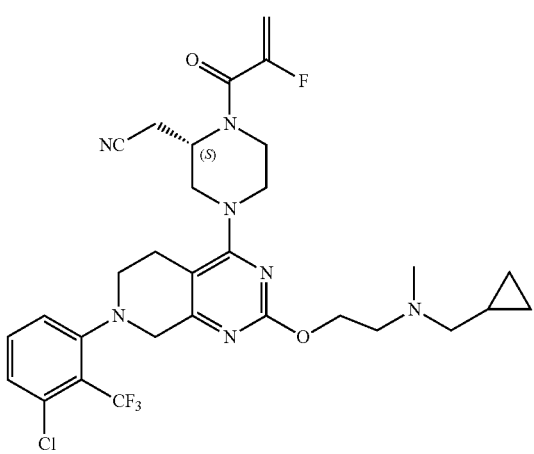
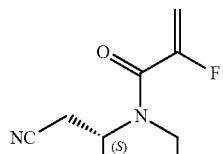
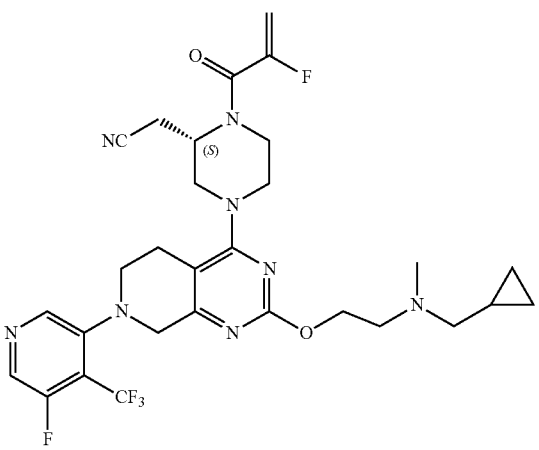
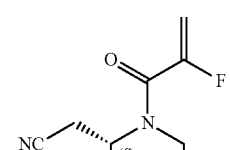

827
-continued
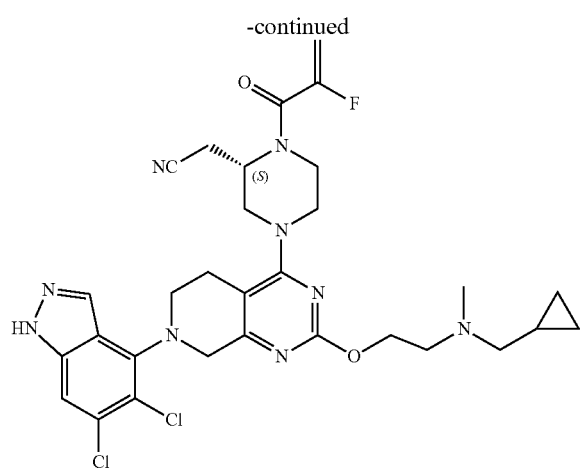
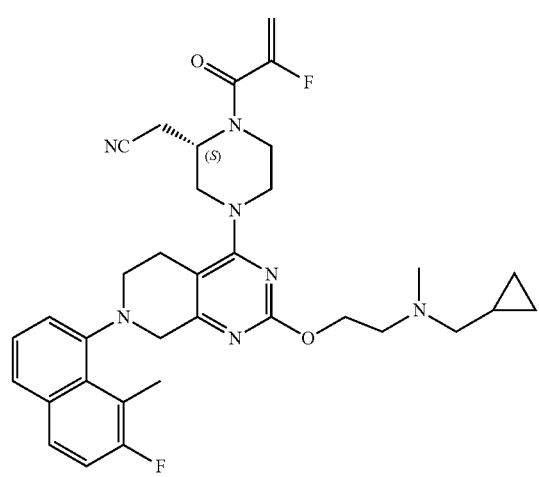
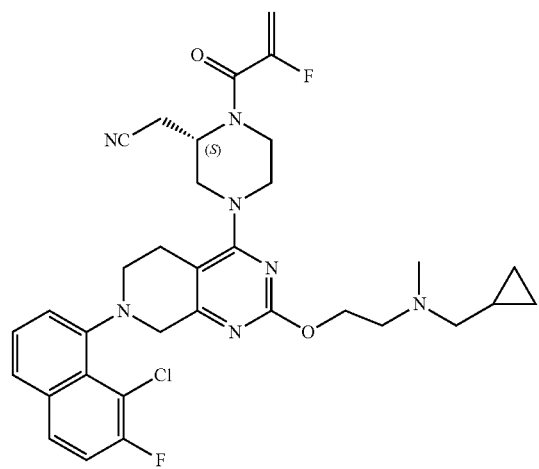
828
-continued
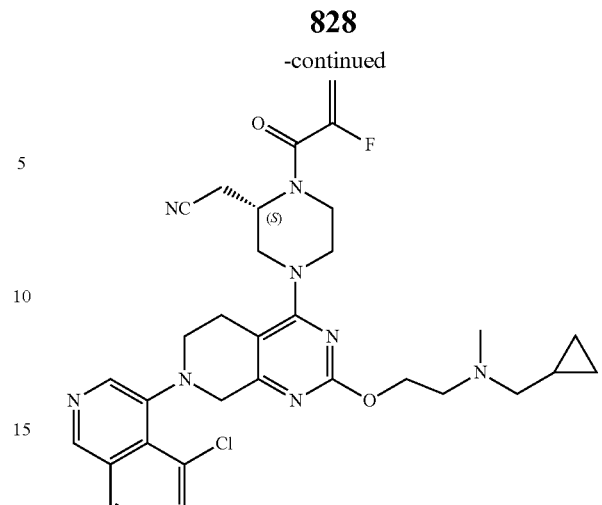
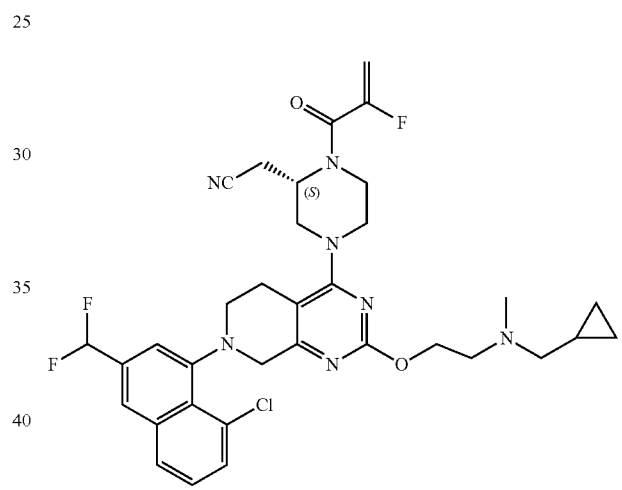
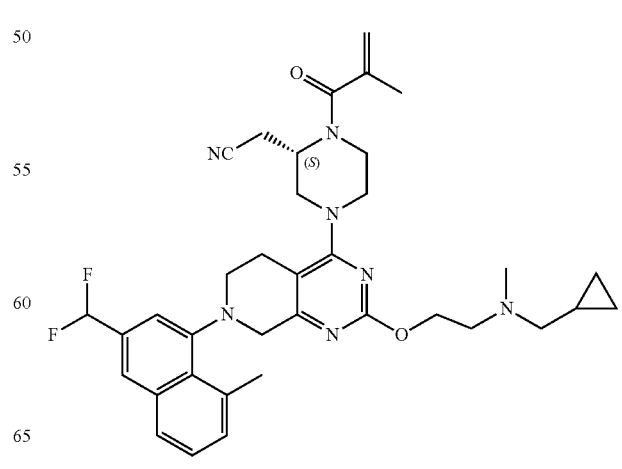

829
-continued
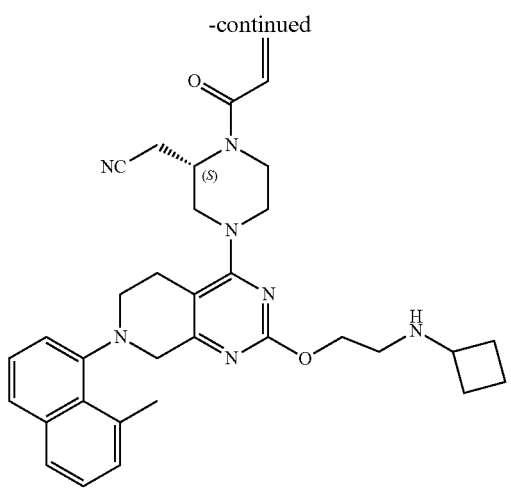
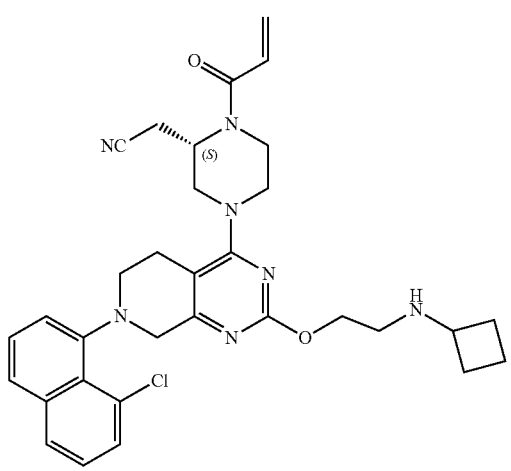
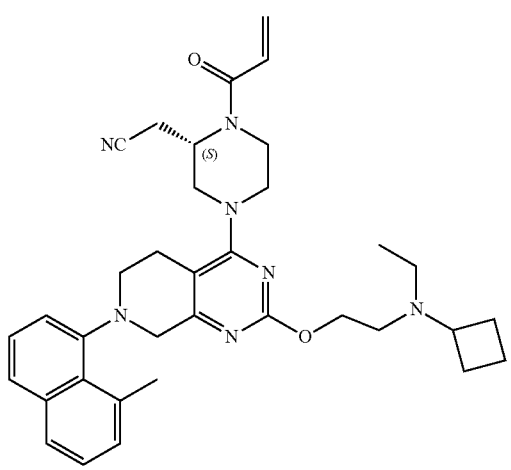
830
-continued
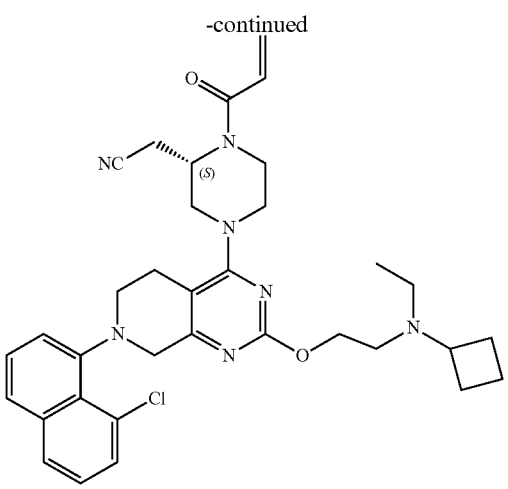
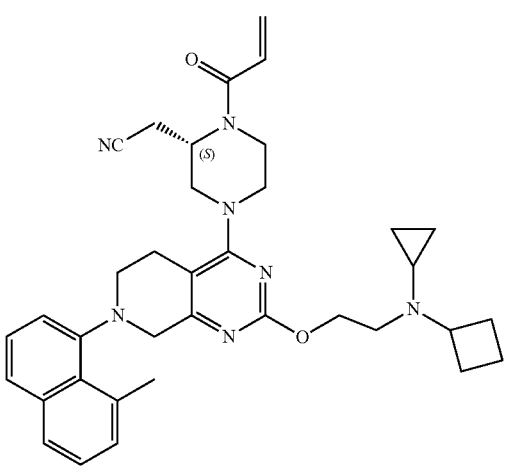
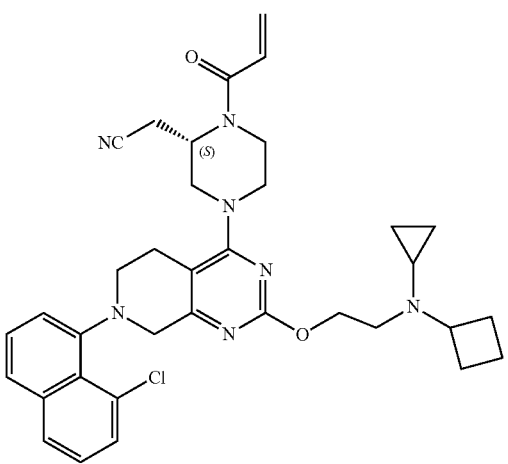

831
-continued
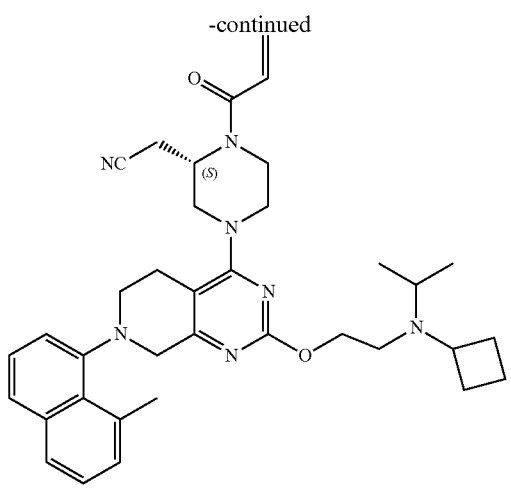
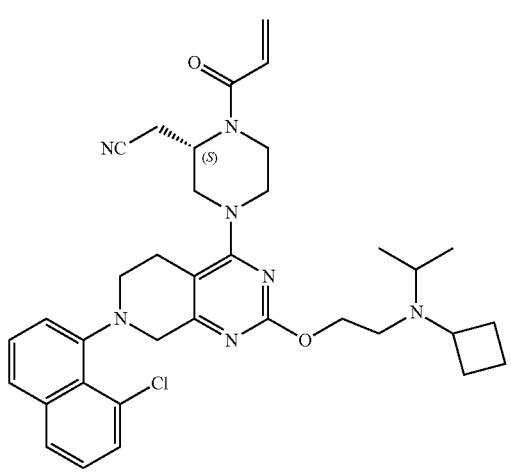
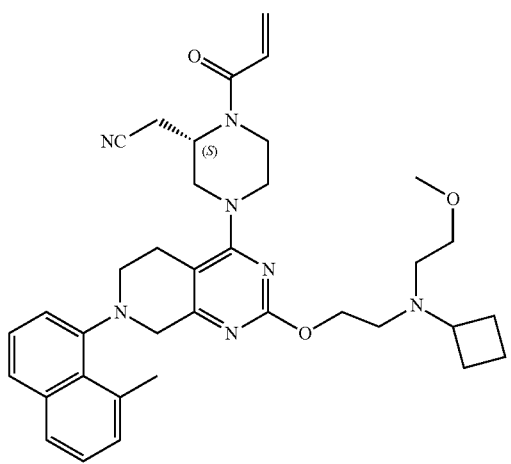
832
-continued
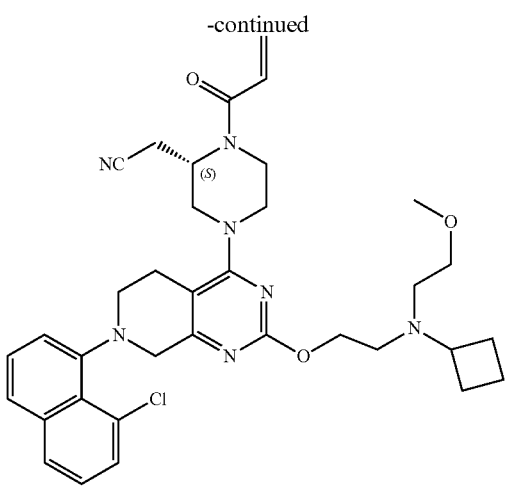
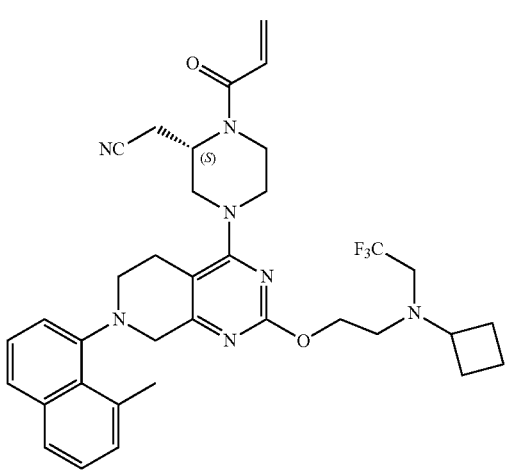
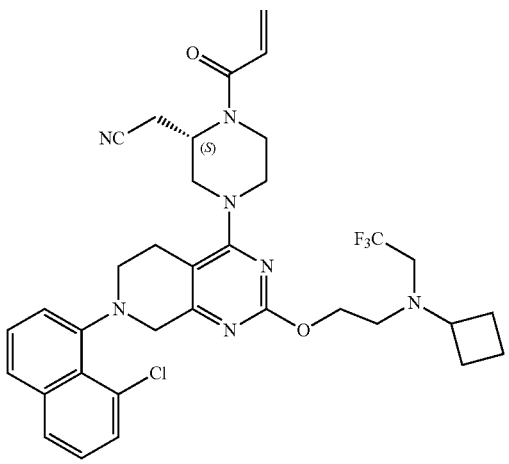

833
-continued
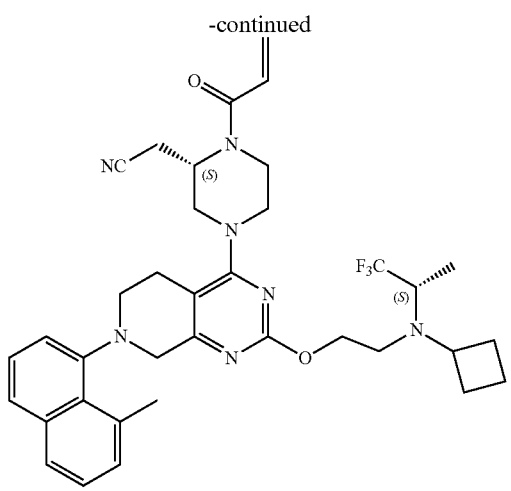
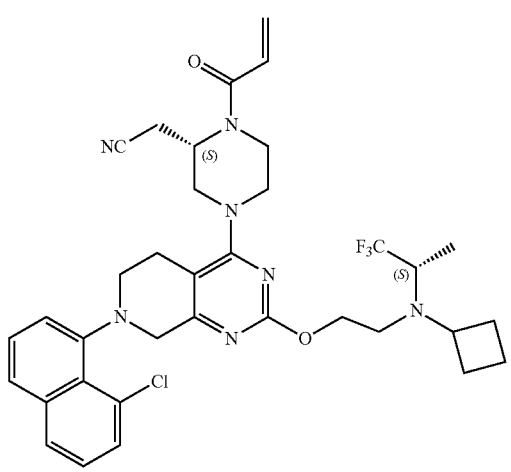
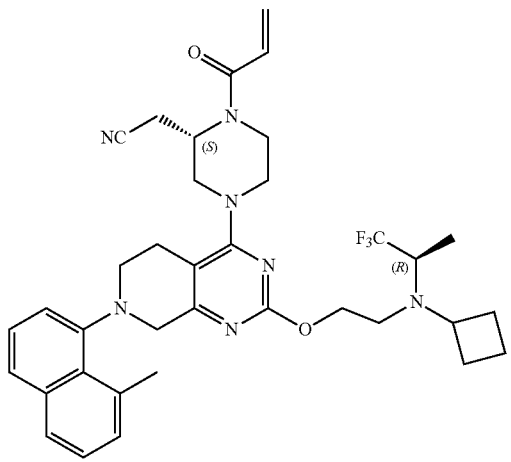
834
-continued
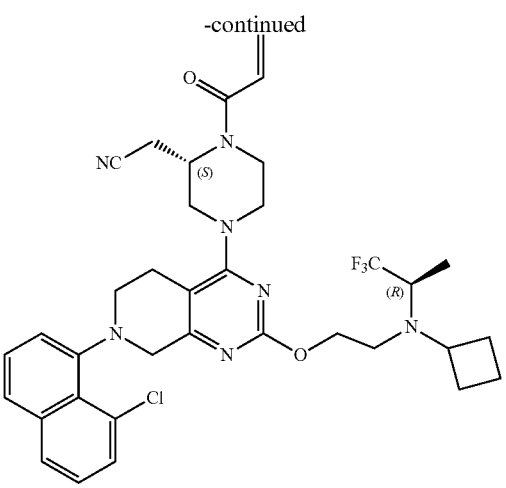
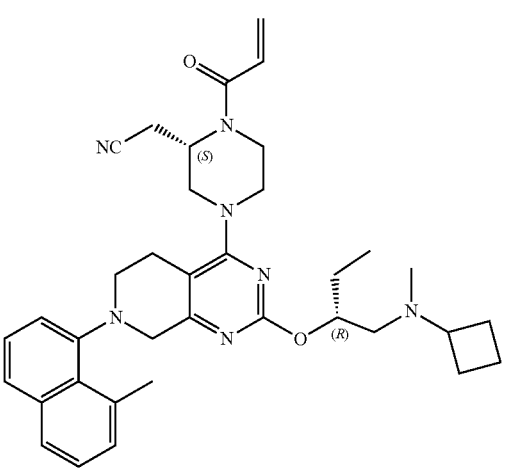
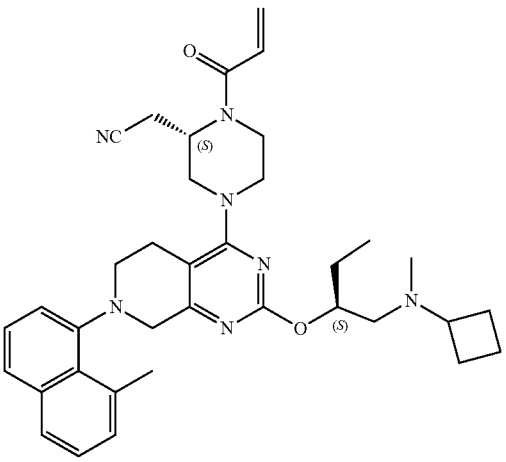

835
-continued
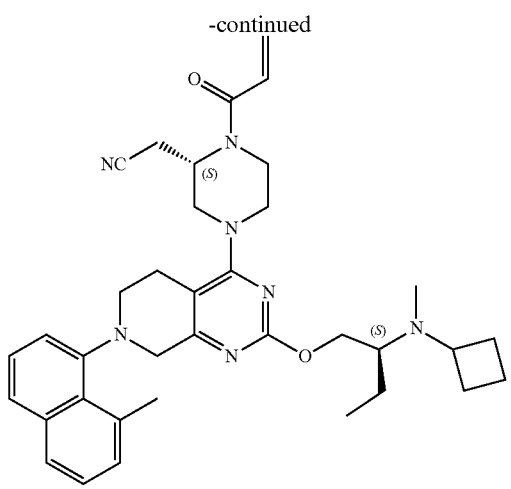
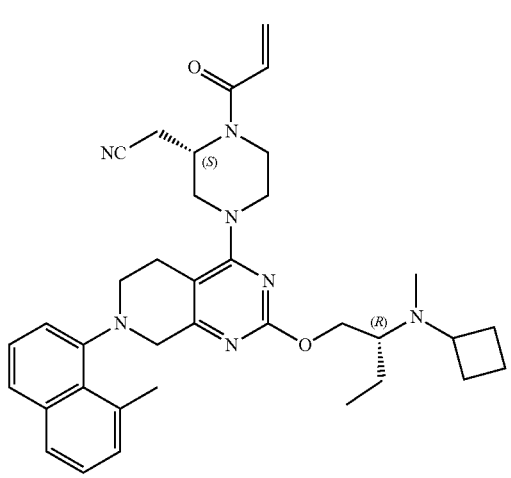
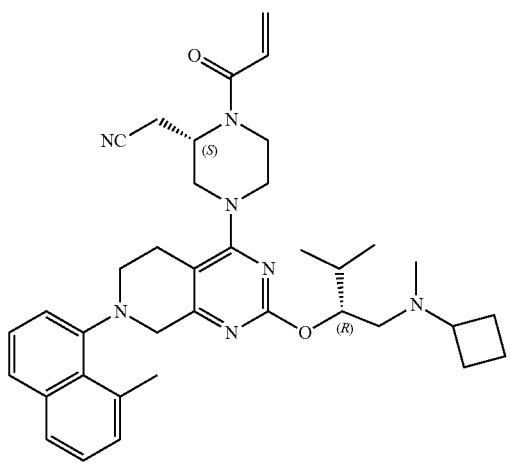
836
-continued
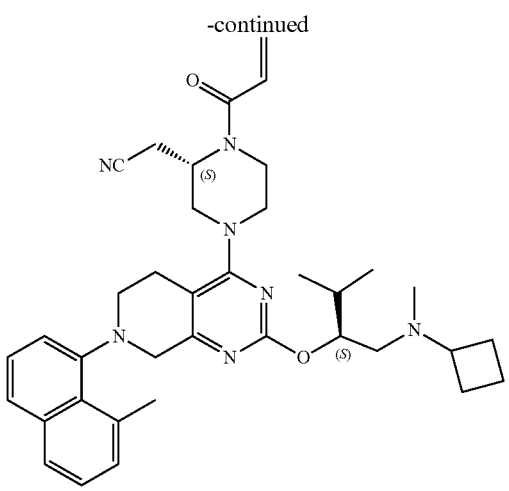
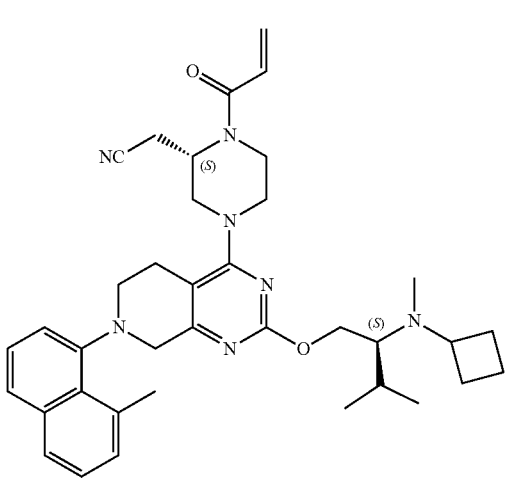
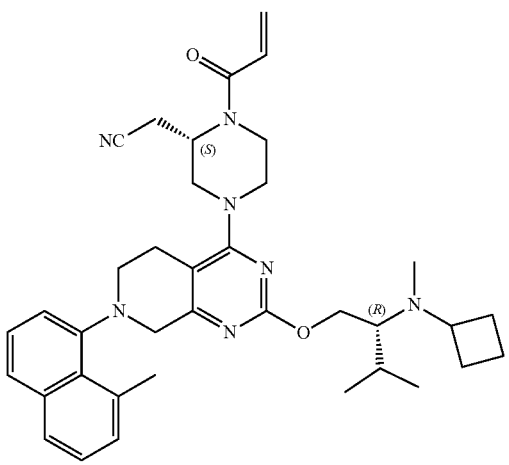

837
-continued
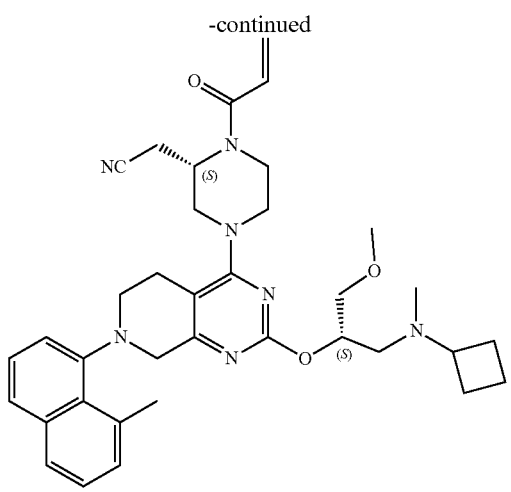
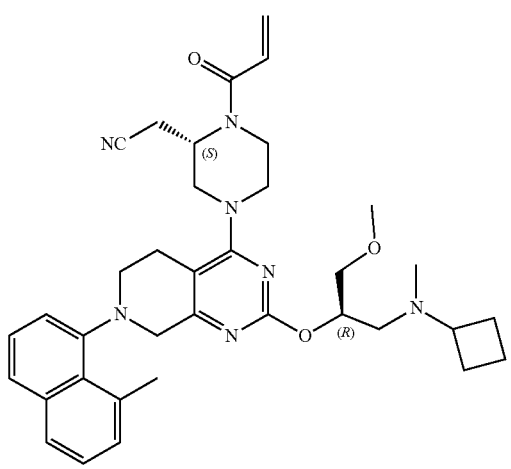
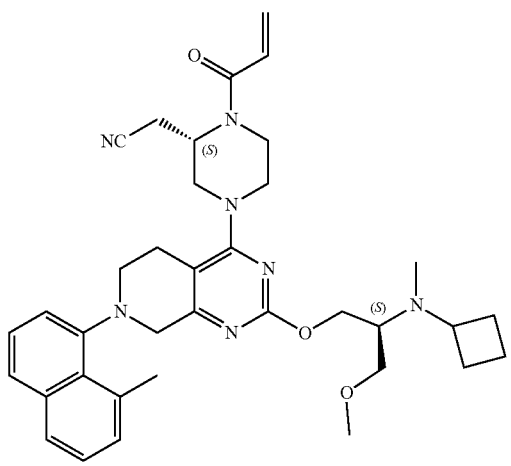
838
-continued
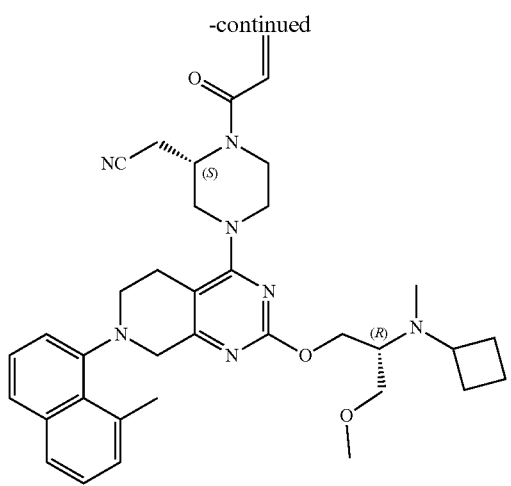
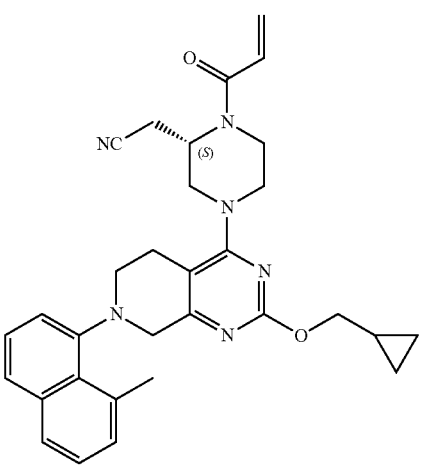
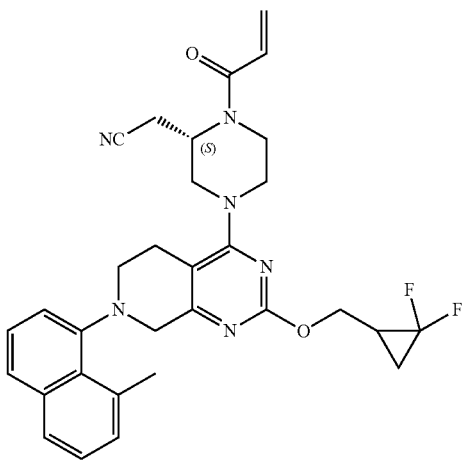

839
-continued
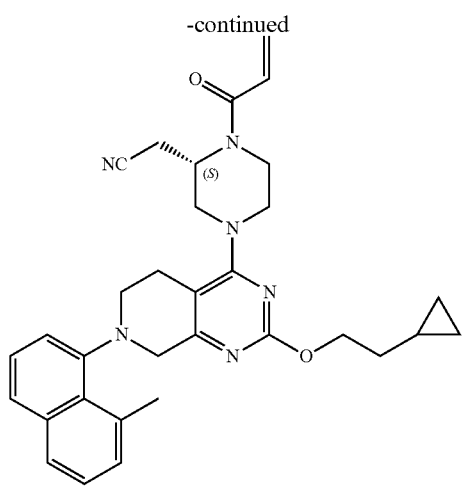
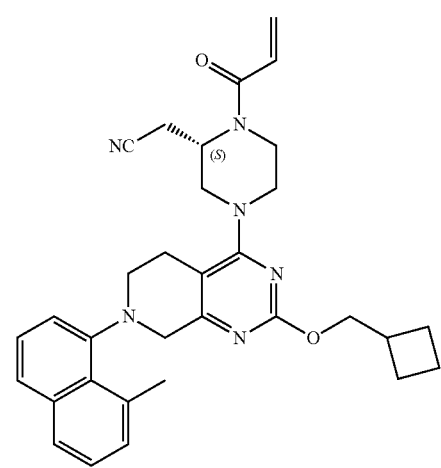
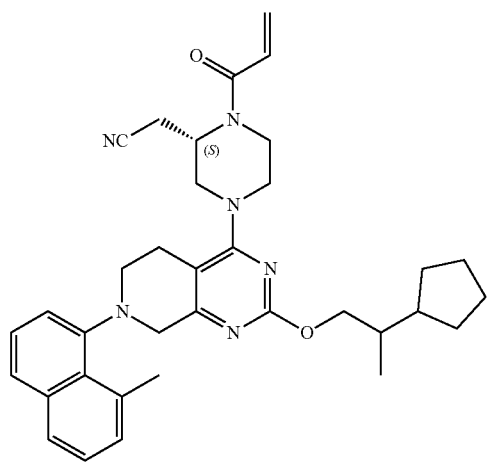
840
-continued
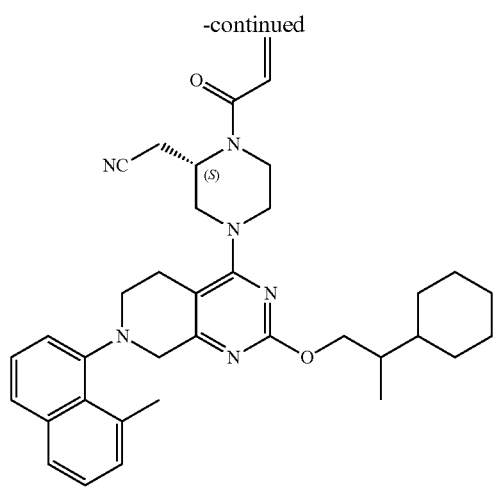
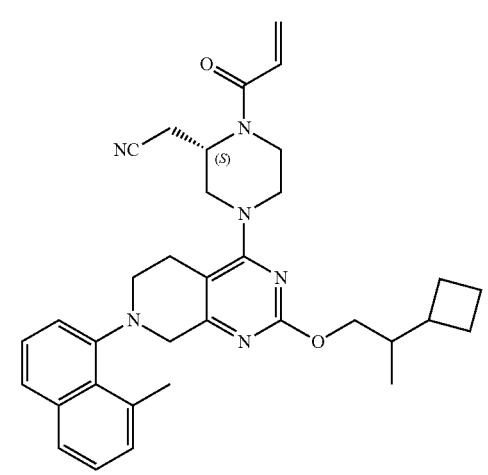
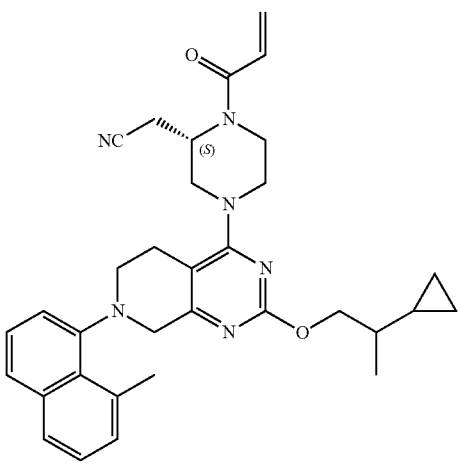

841
-continued
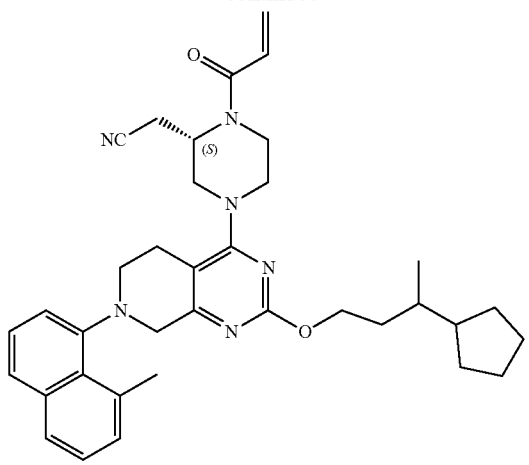
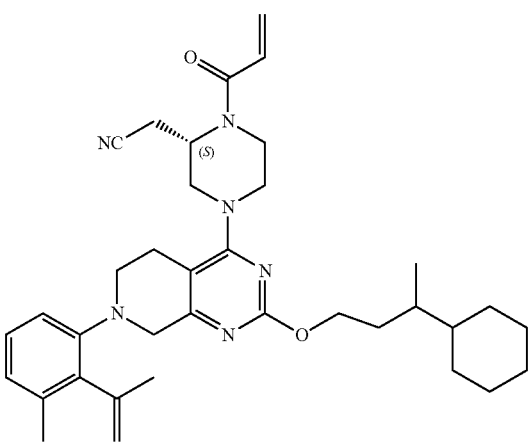
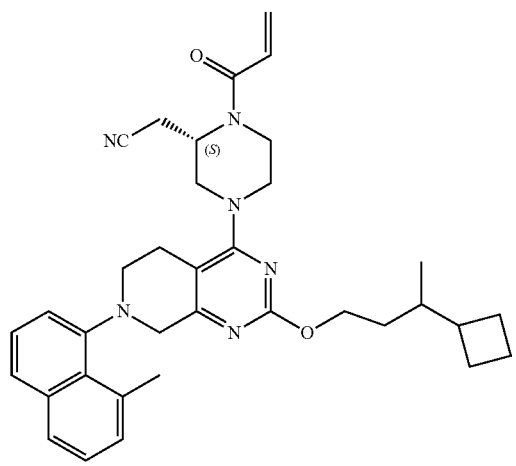
842
-continued
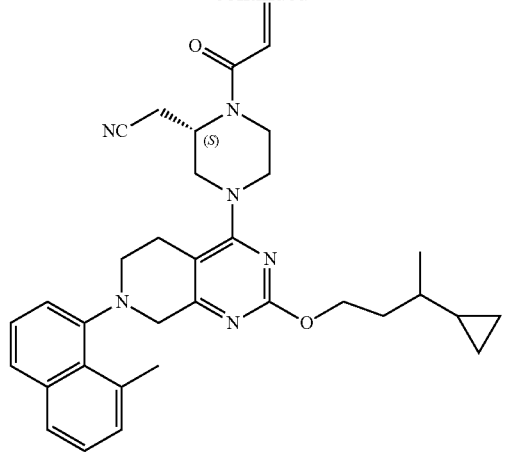
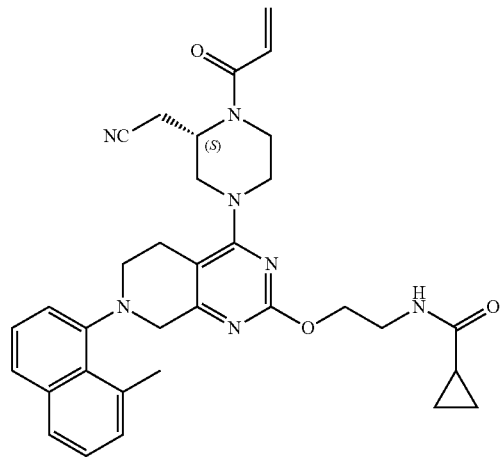
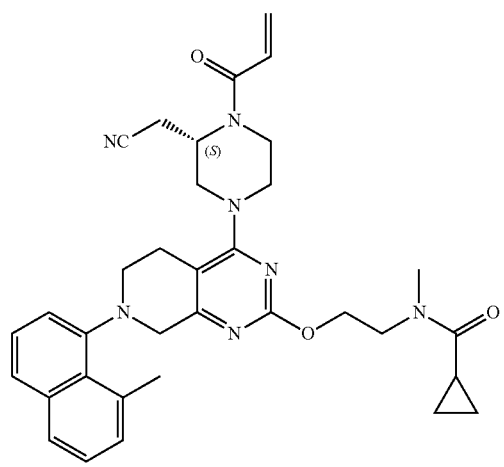

843
-continued
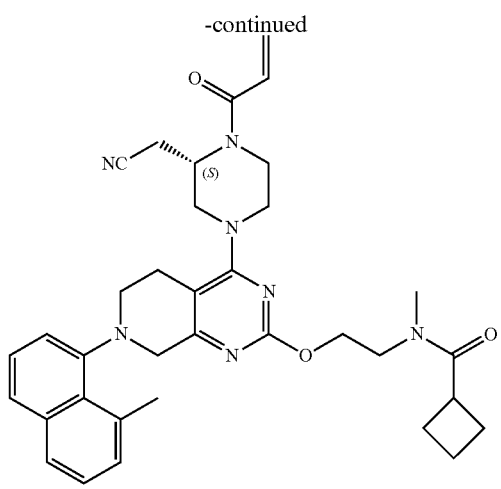
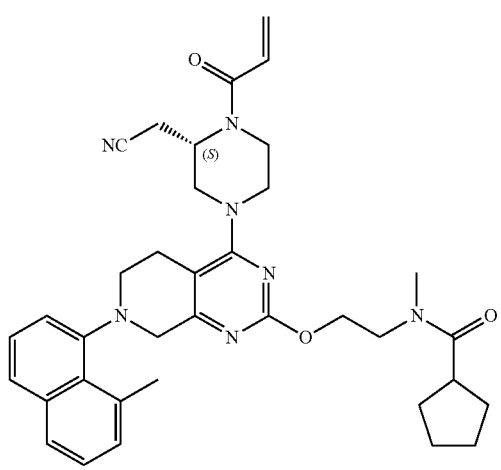
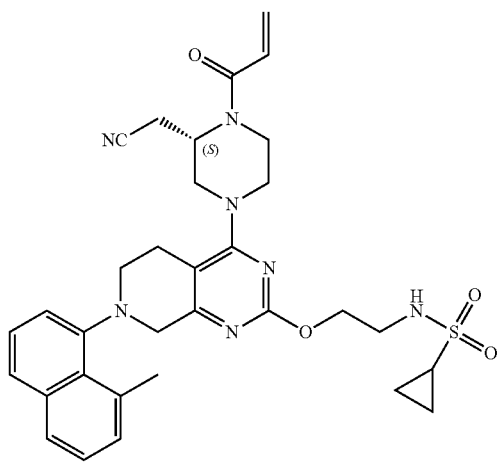
844
-continued
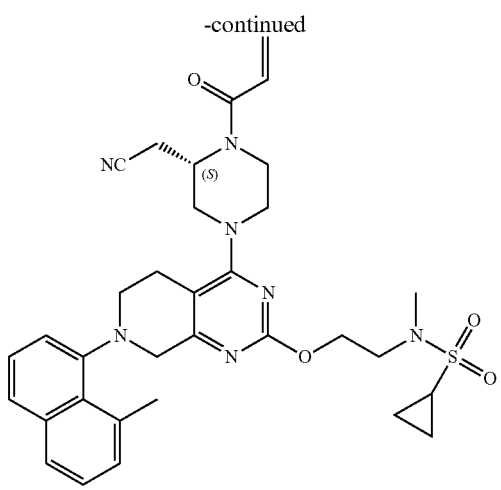
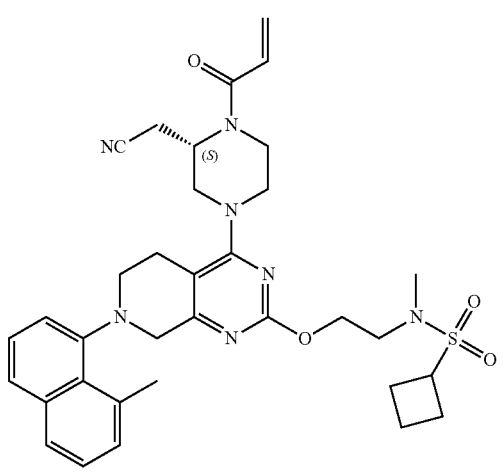
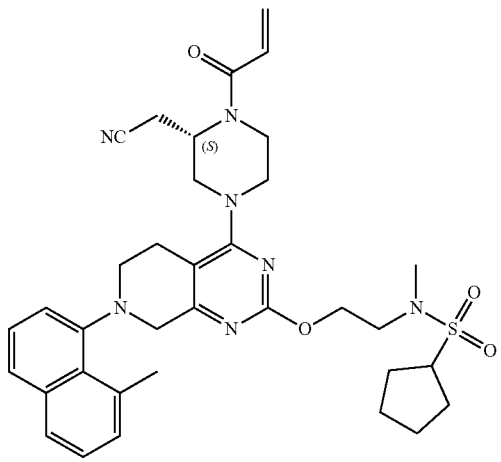

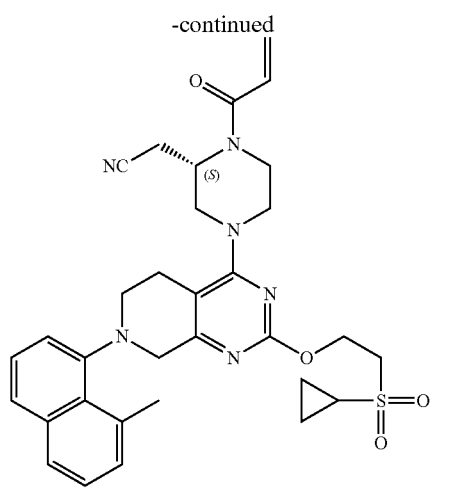
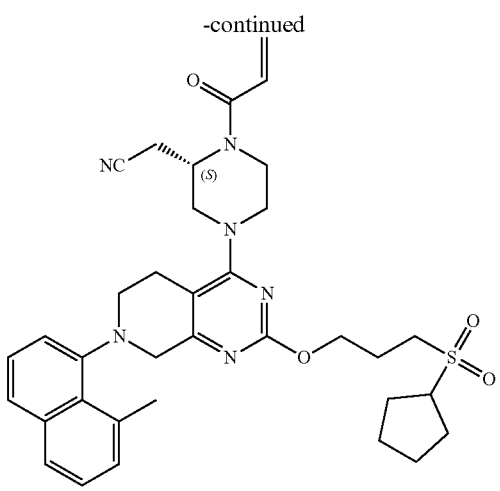
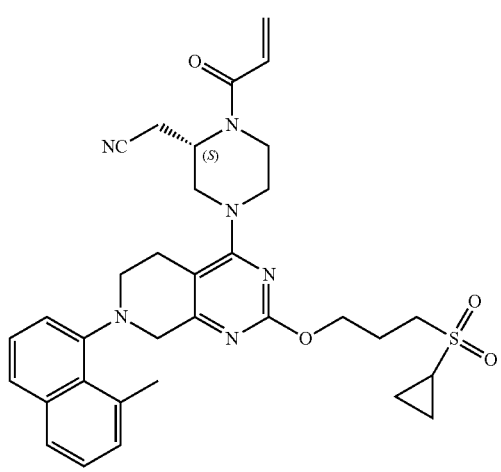
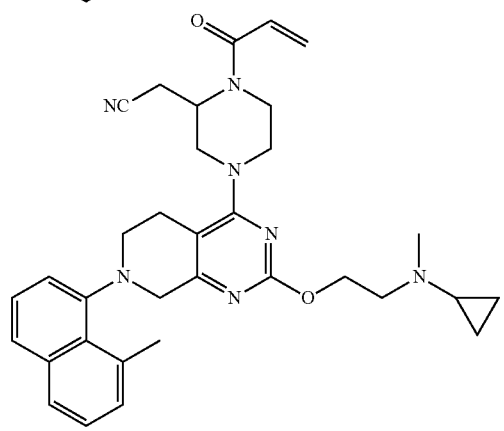
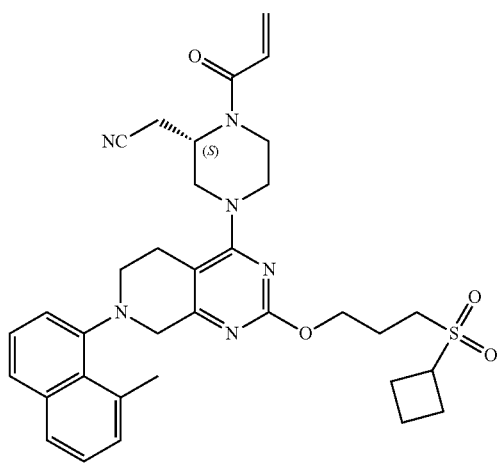
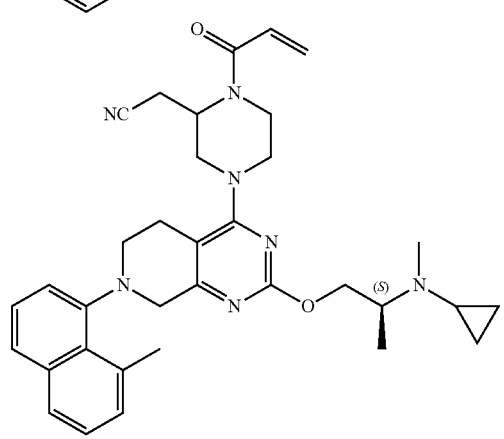
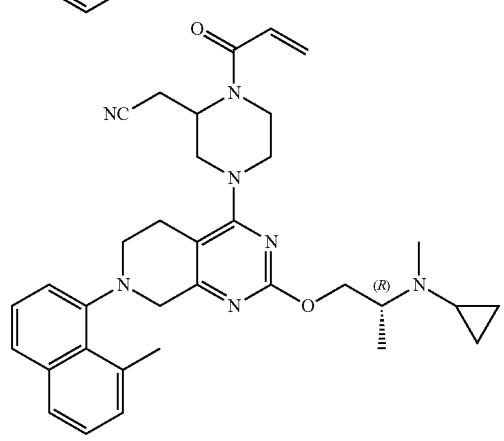

847
-continued
848
-continued
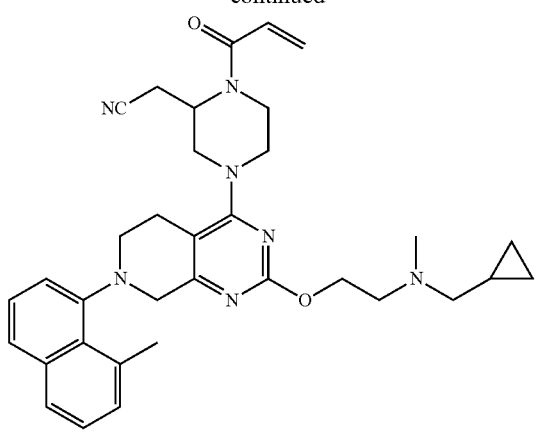
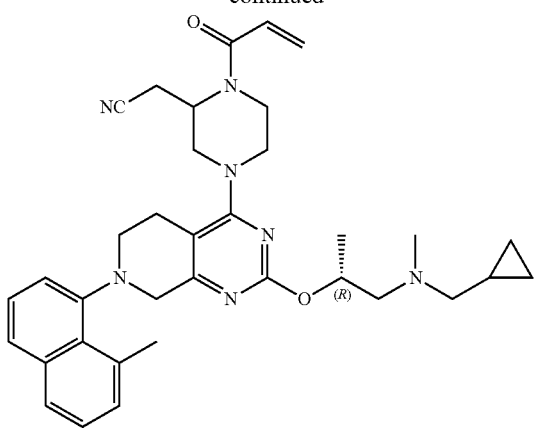

849
-continued
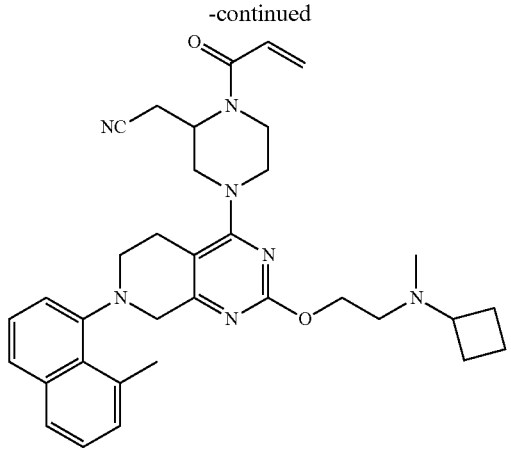
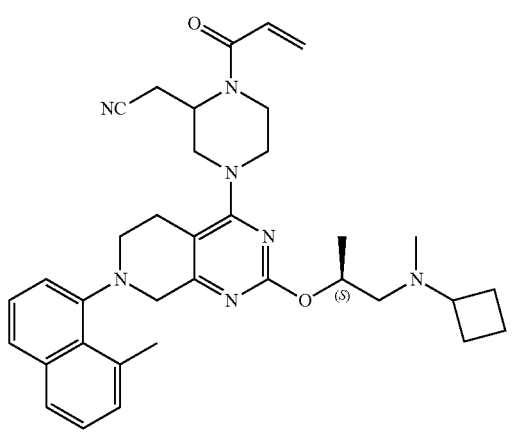
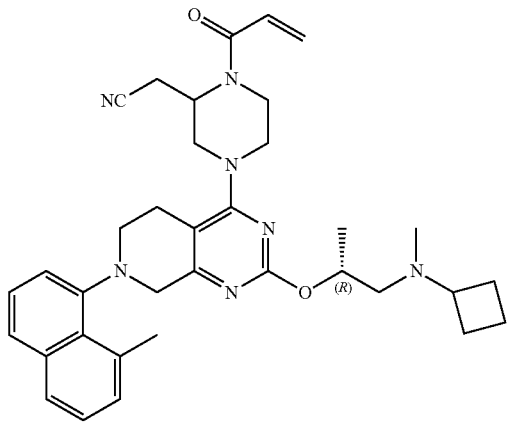
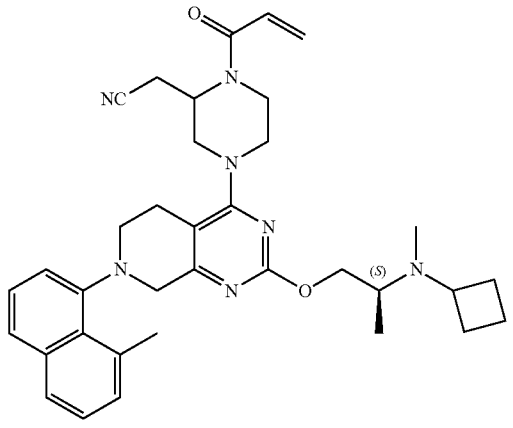
850
-continued
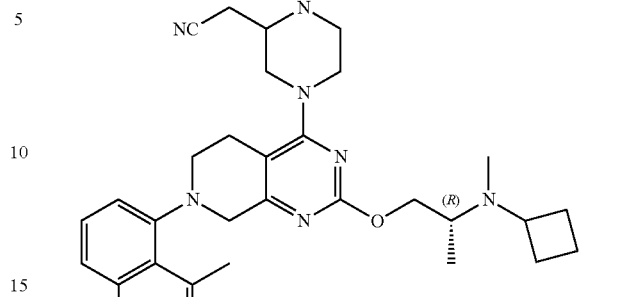
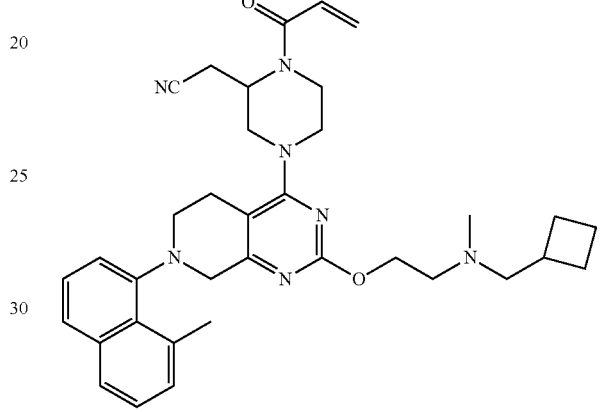
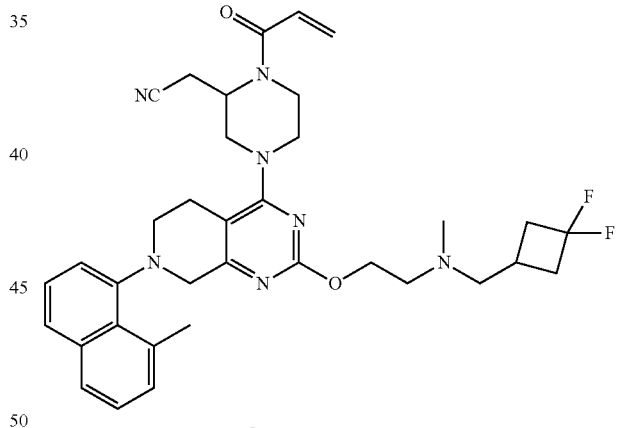
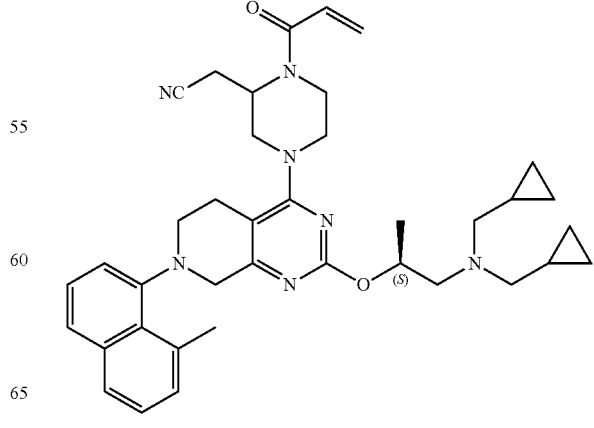

851
-continued
852
-continued
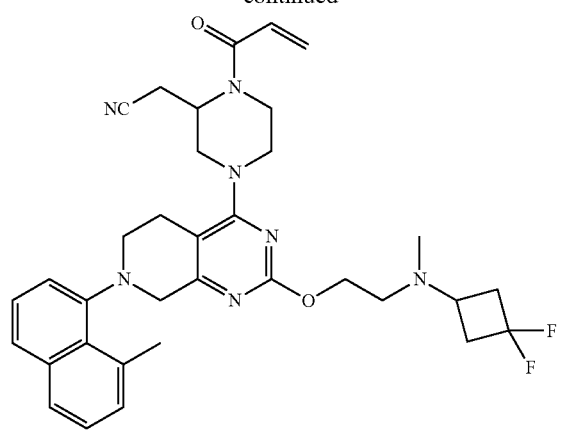
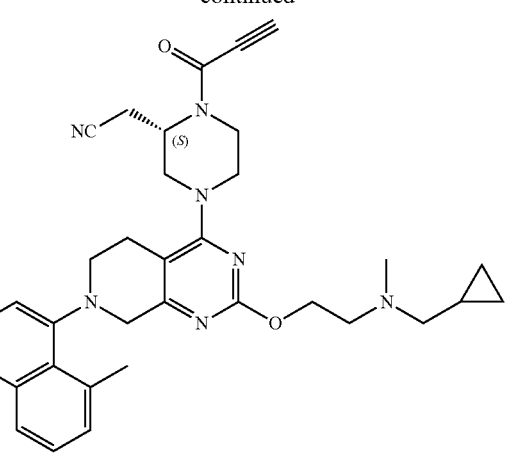
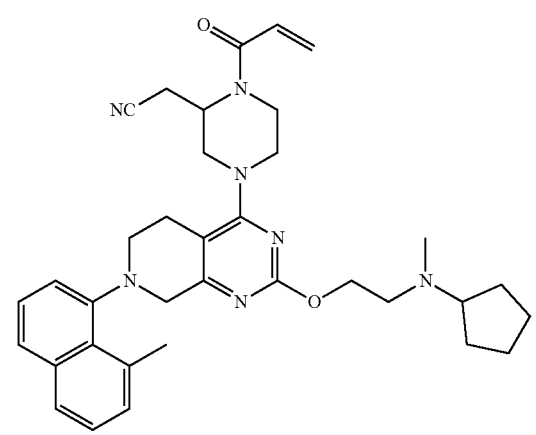
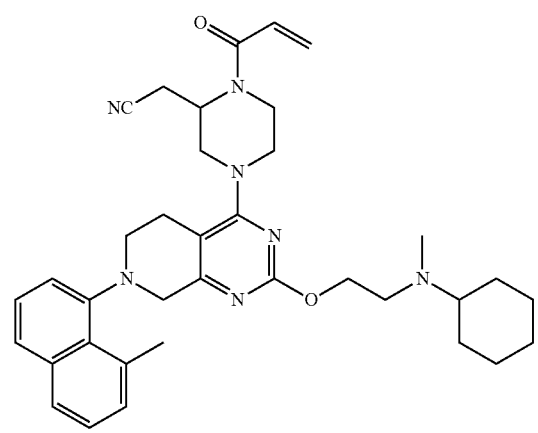
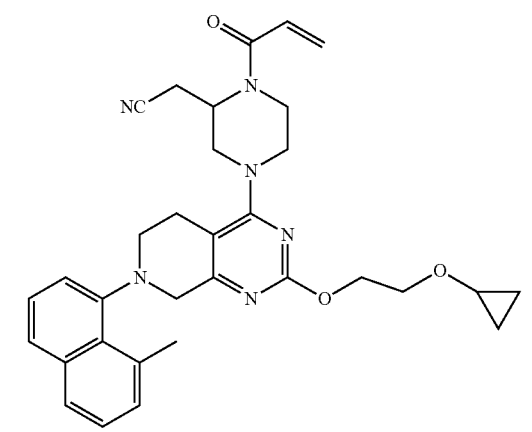

853
-continued
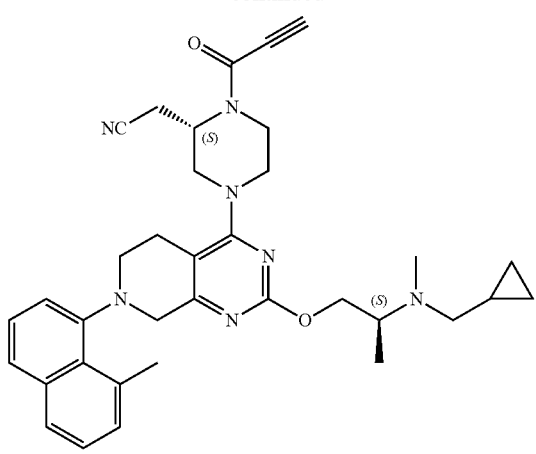
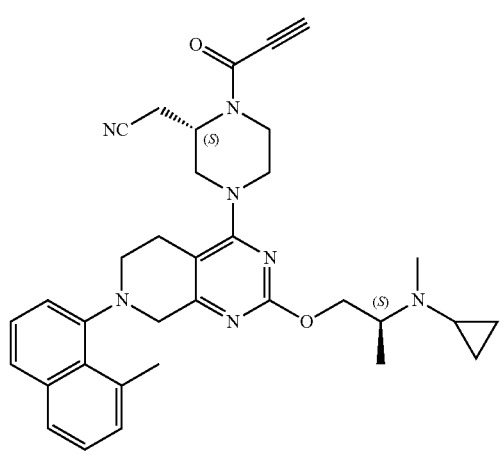
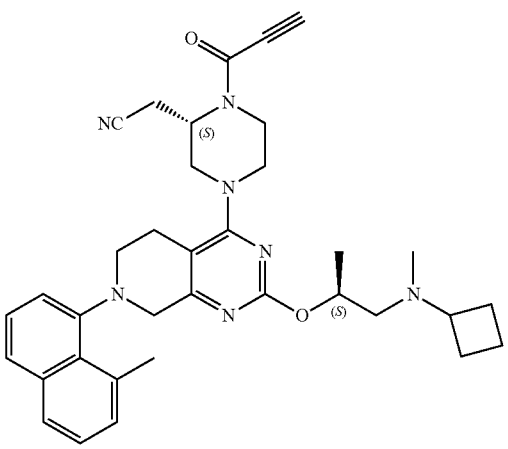
854
-continued
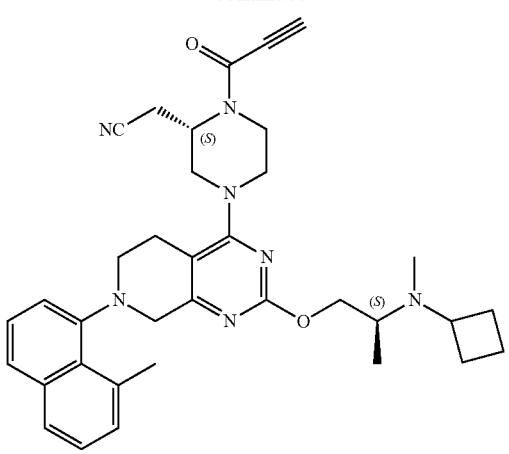
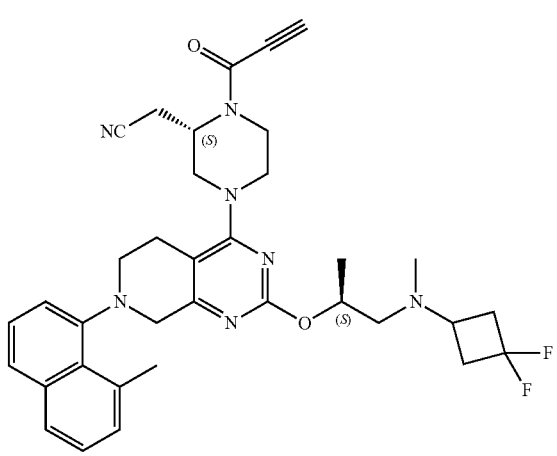
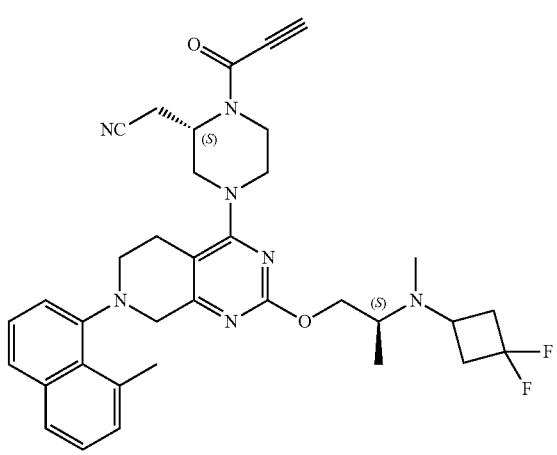

855
-continued
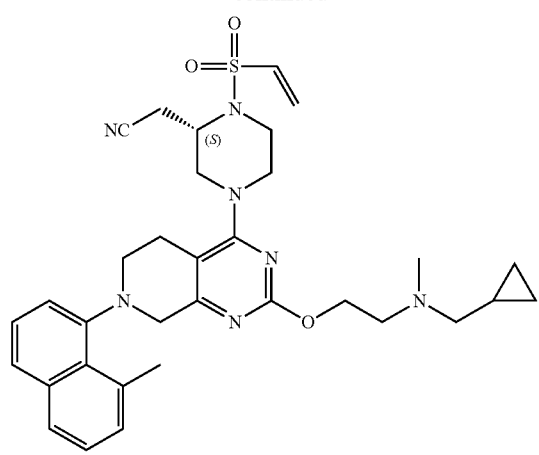
856
-continued
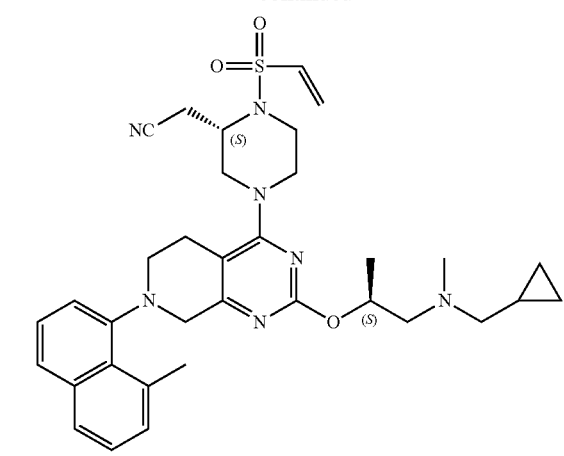
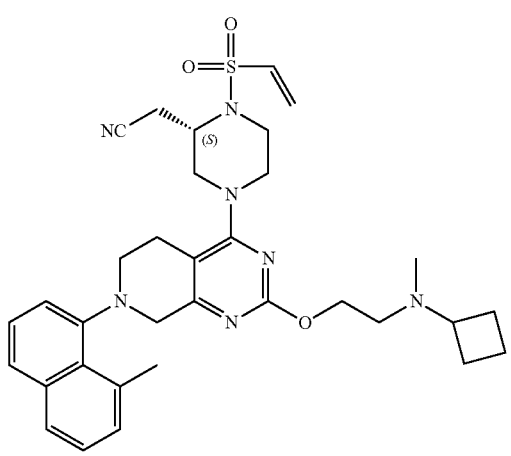
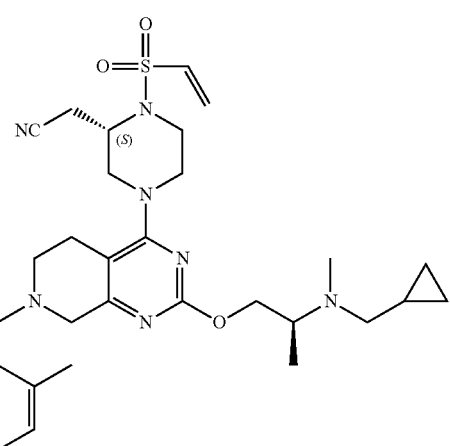
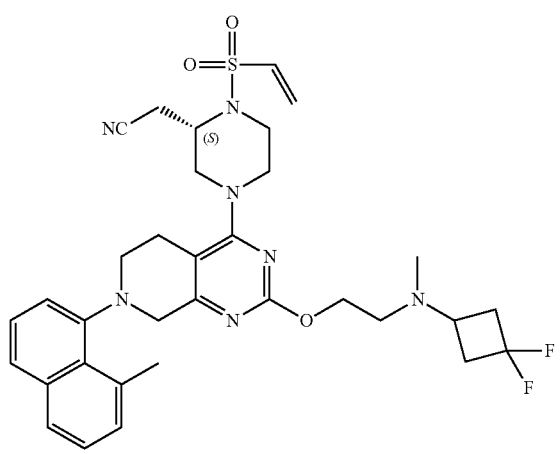
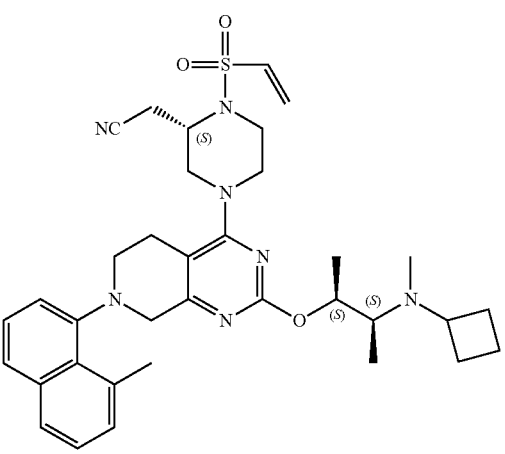

857
-continued
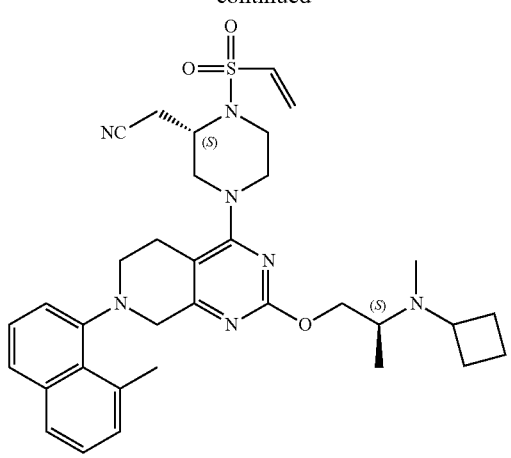
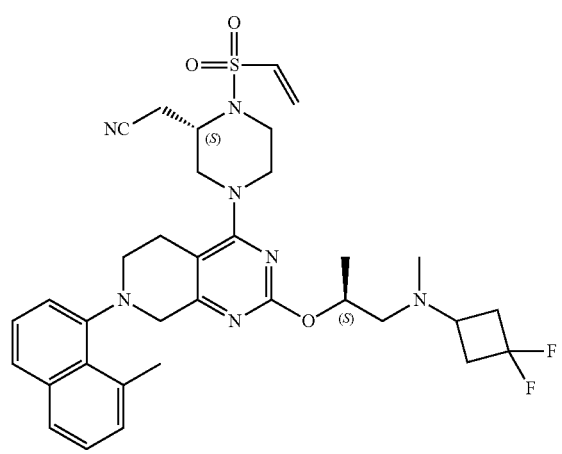
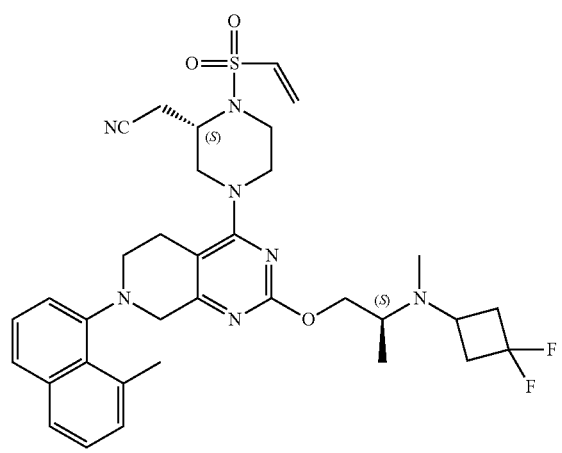
858
-continued
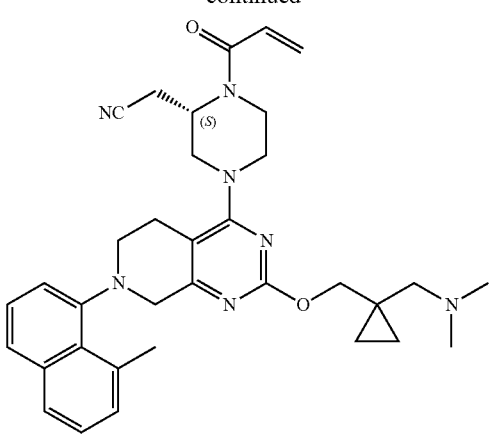
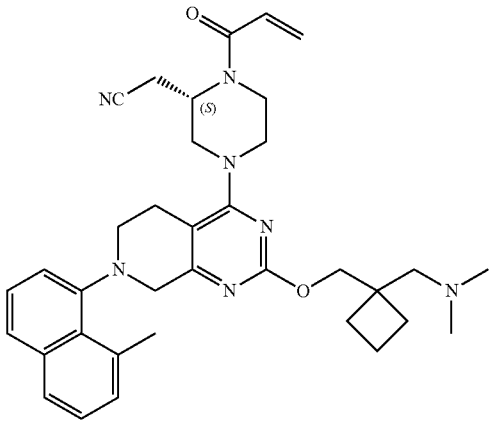
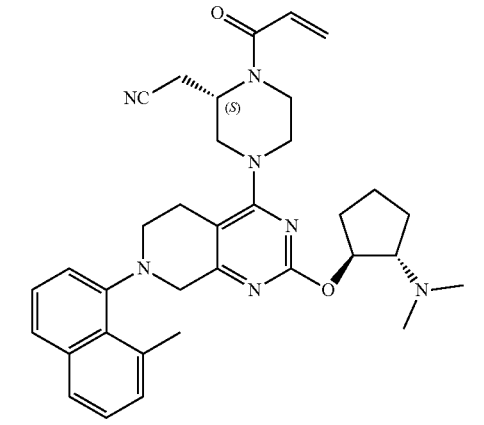
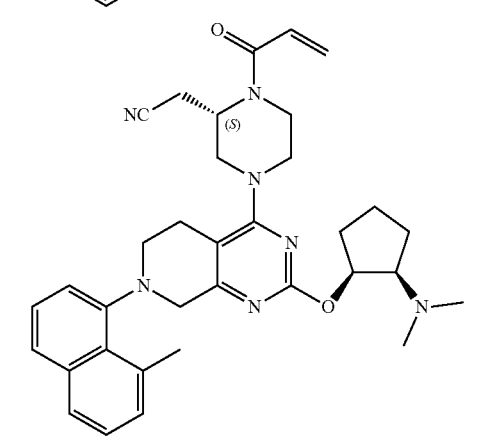

859
-continued

860
-continued

861 -continued
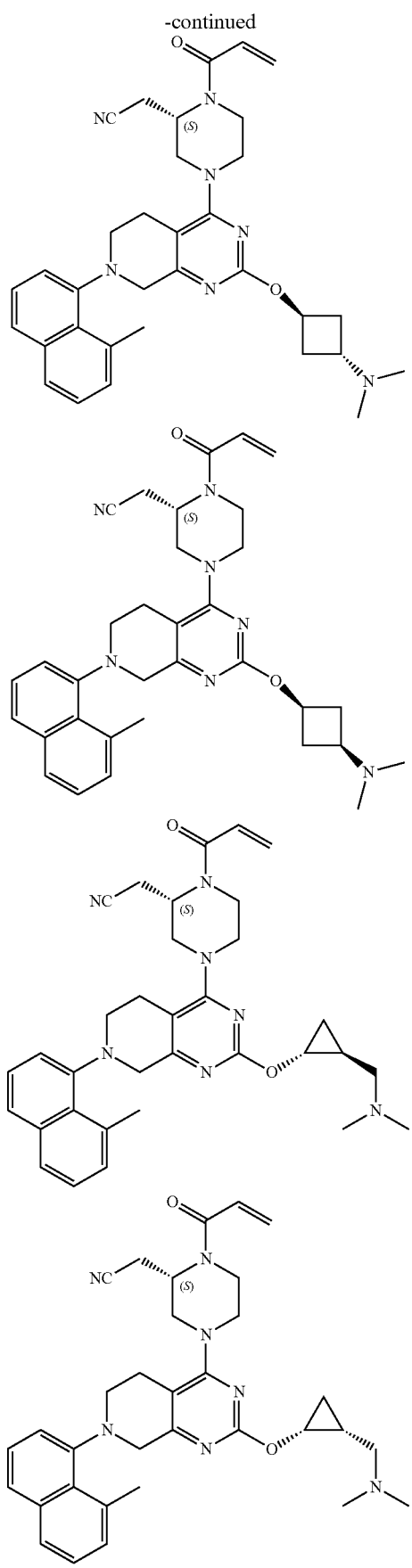
862 -continued
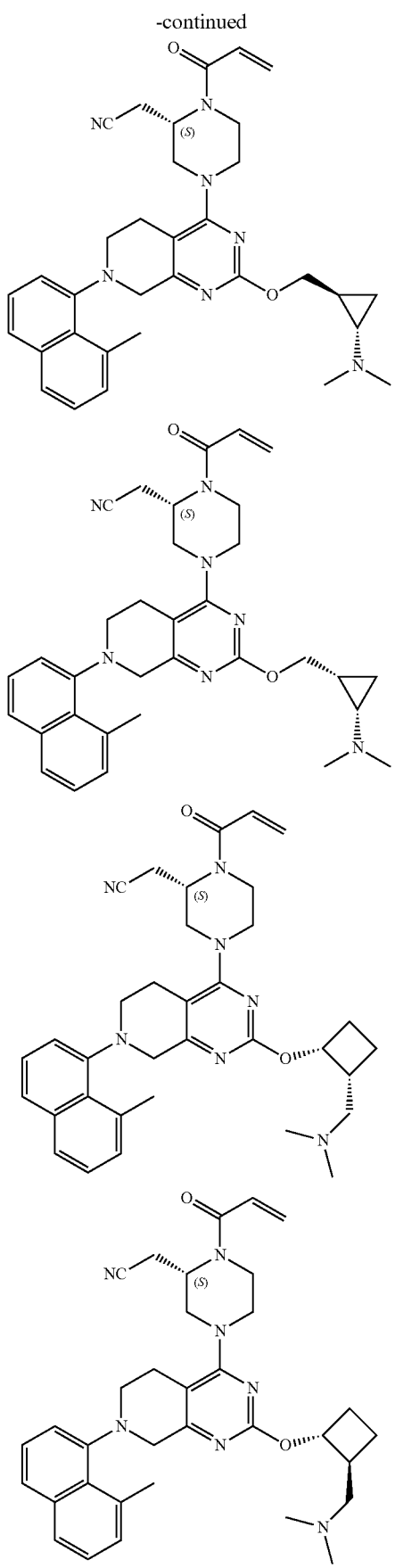

863
-continued
864
-continued
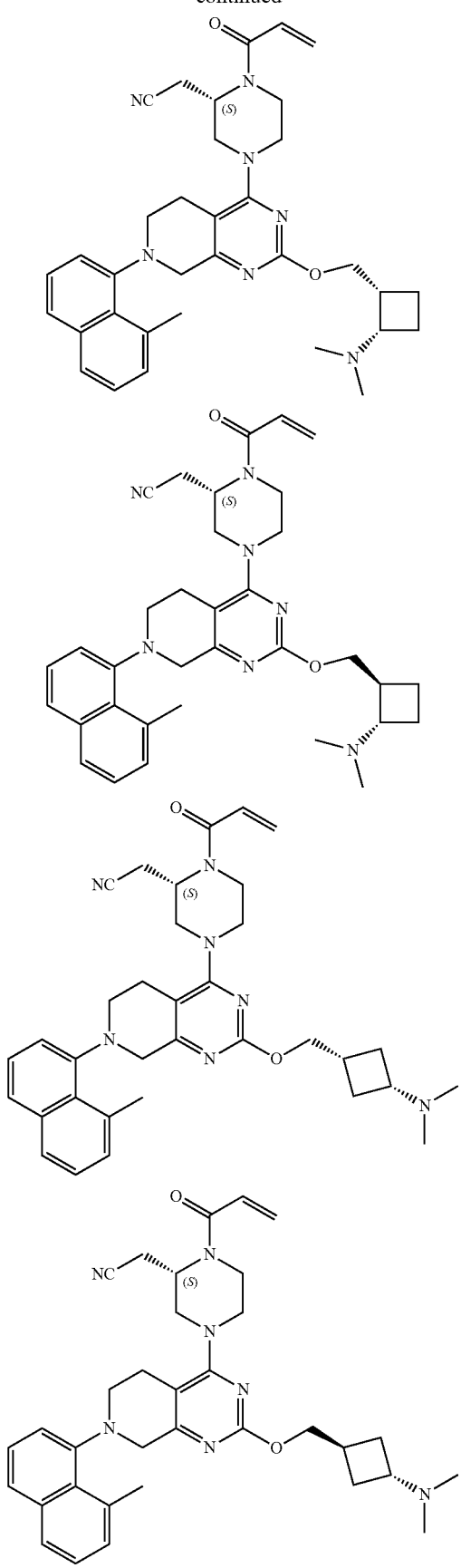
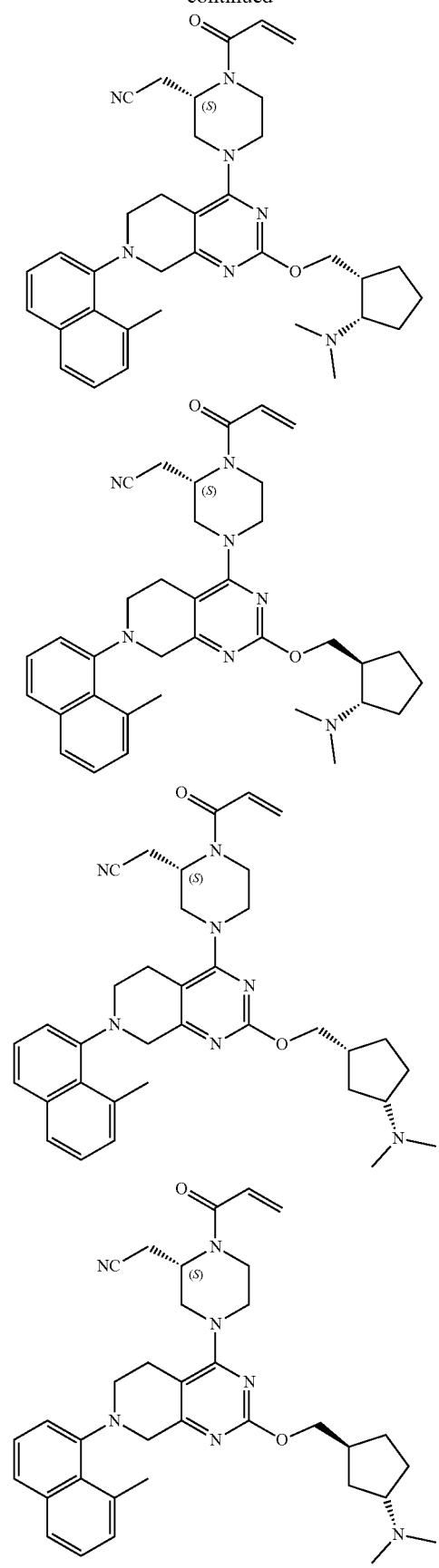

865
-continued
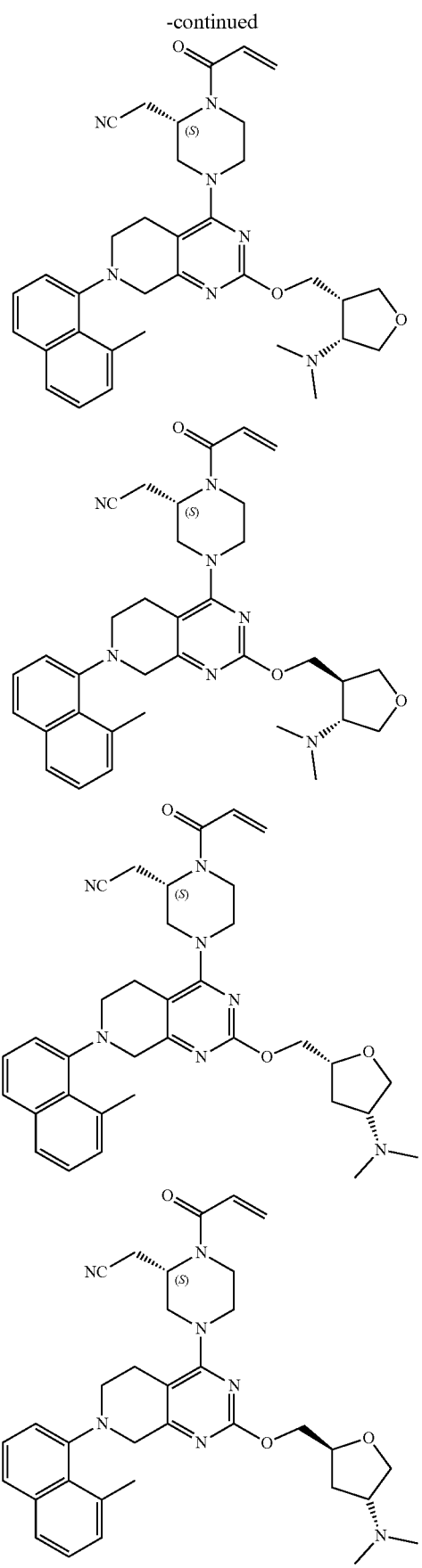
866
-continued
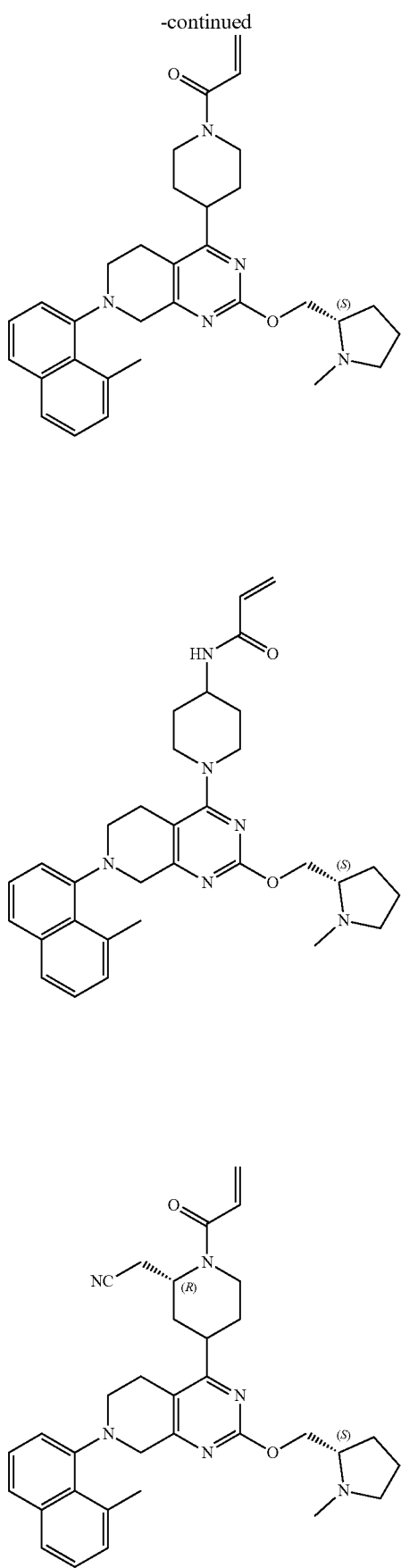

867
-continued
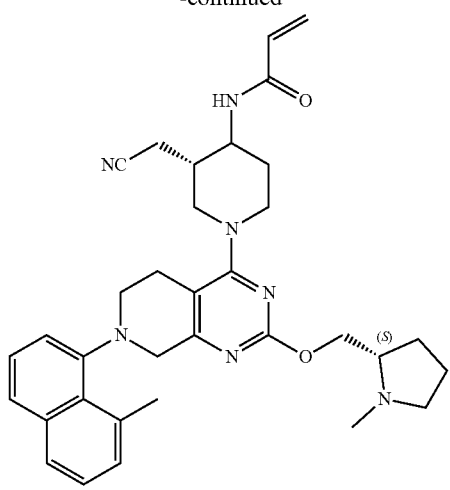
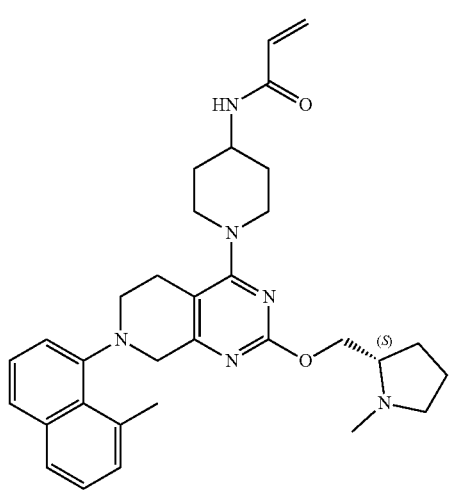
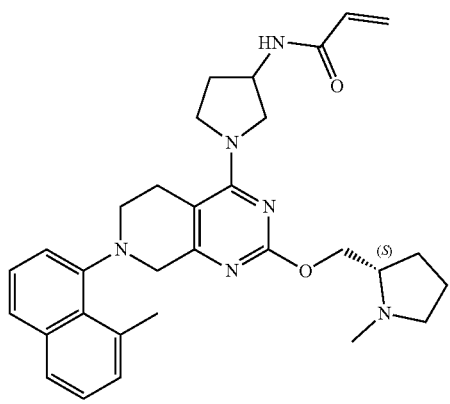
868
-continued
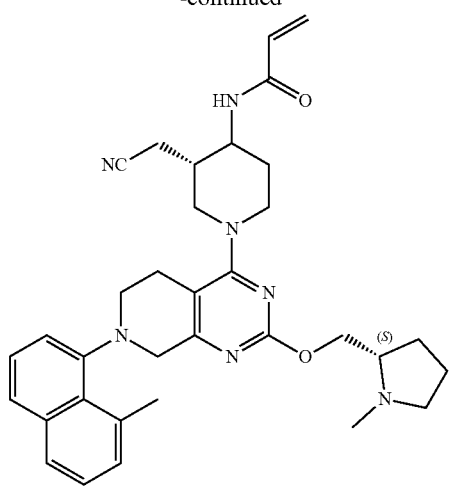
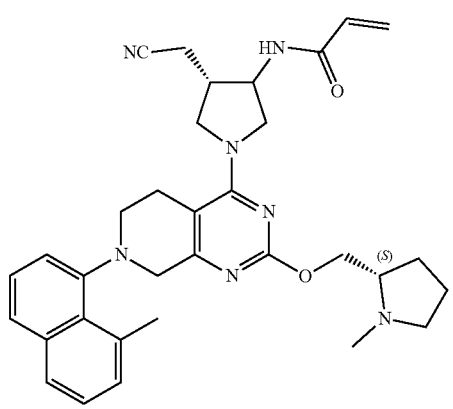
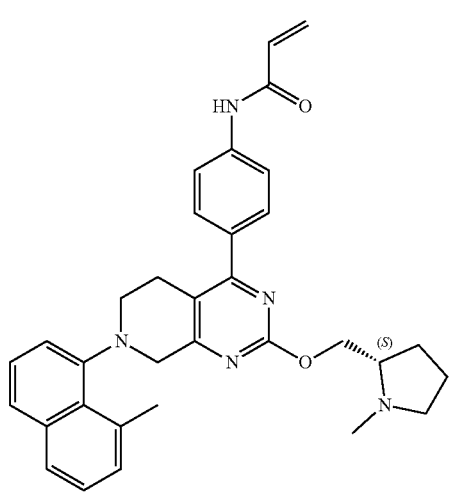

869
-continued
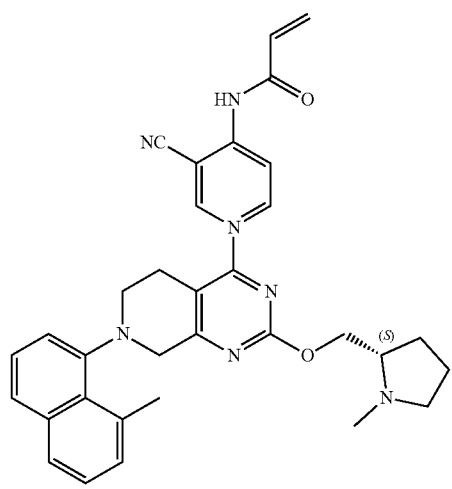
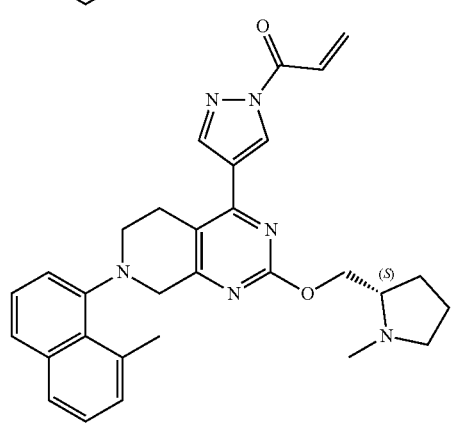
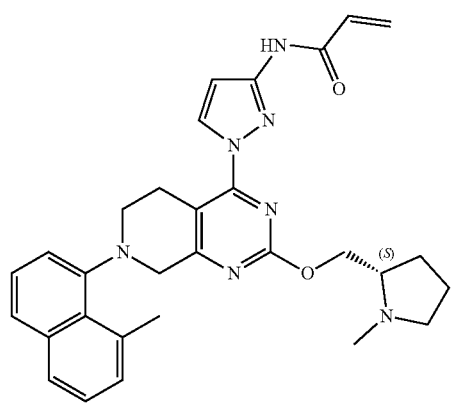
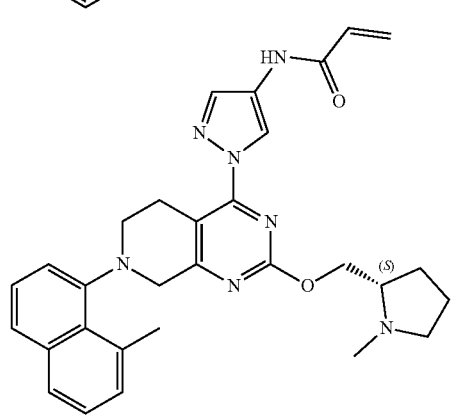
870
-continued
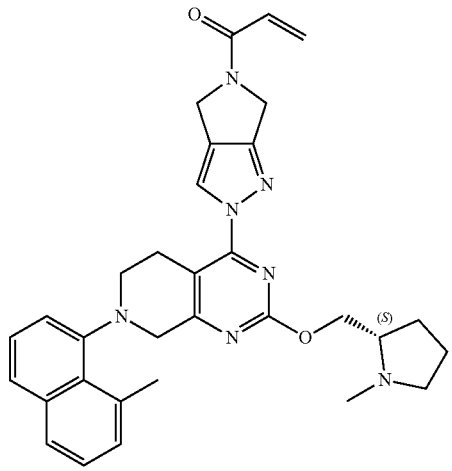
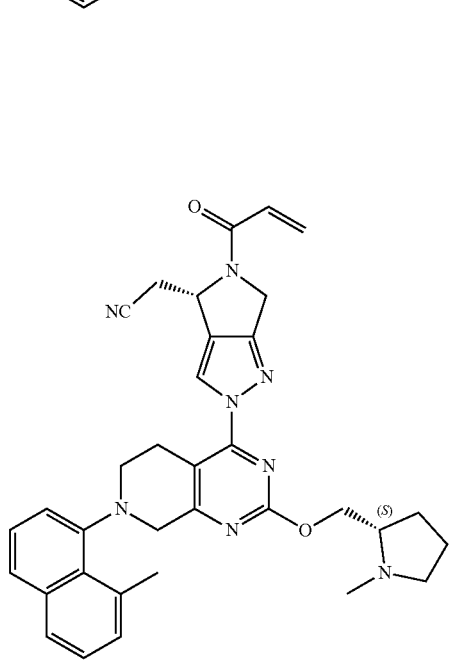
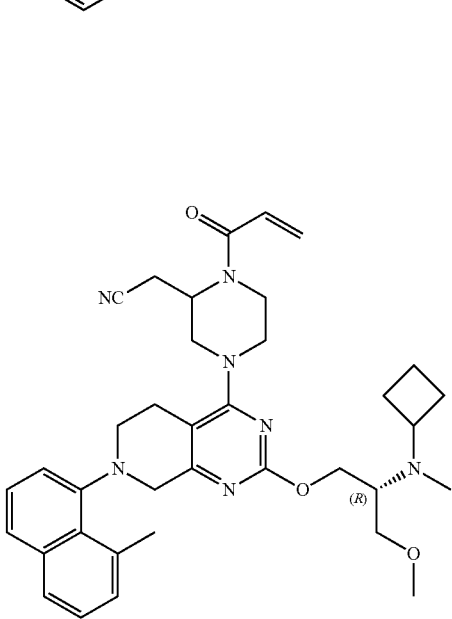

871
-continued
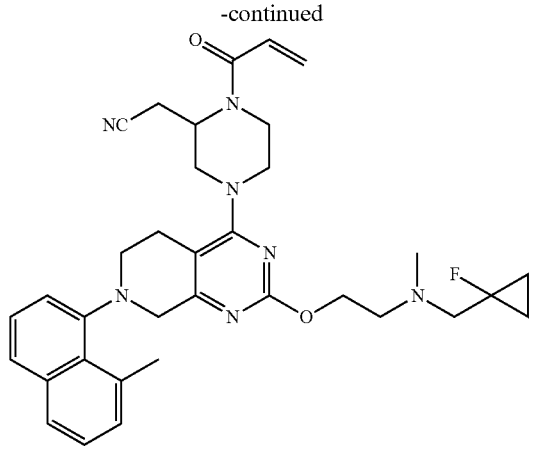
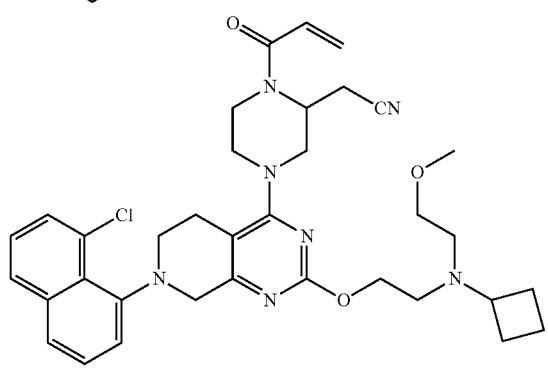
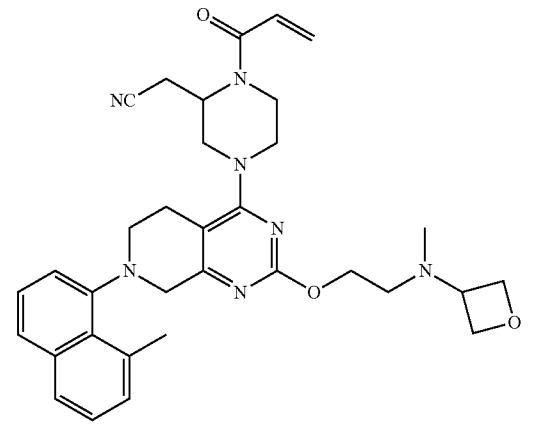
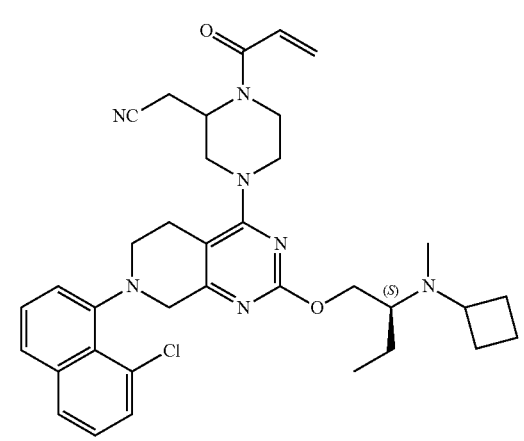
872
-continued
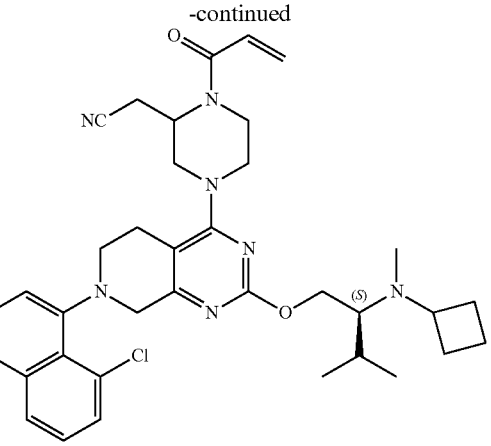
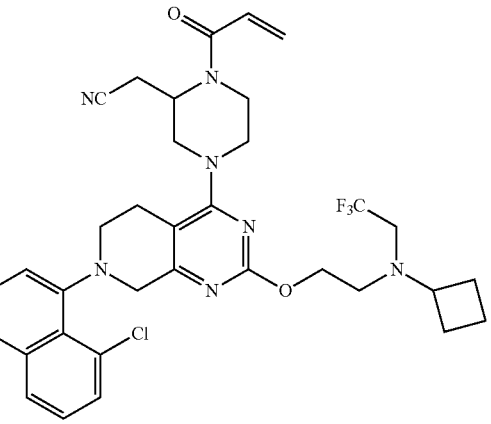
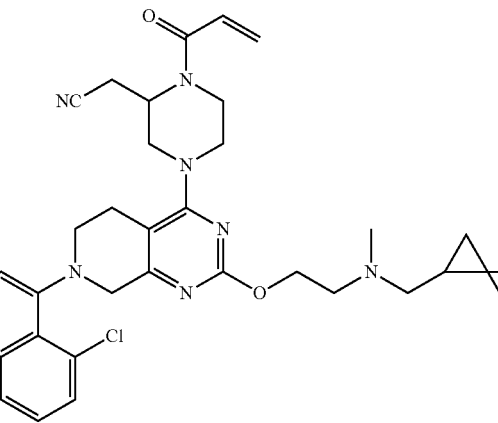
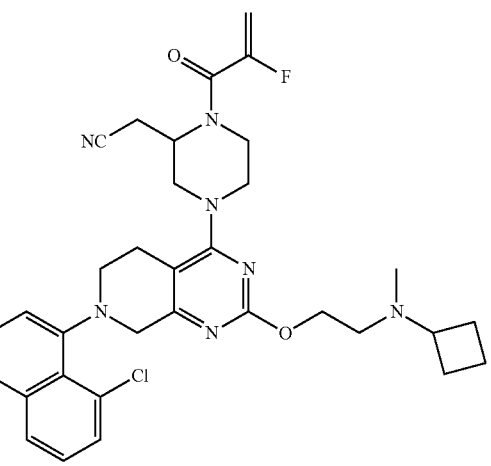

873
-continued
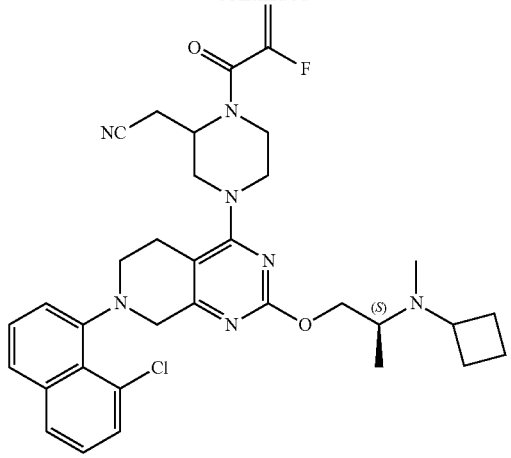
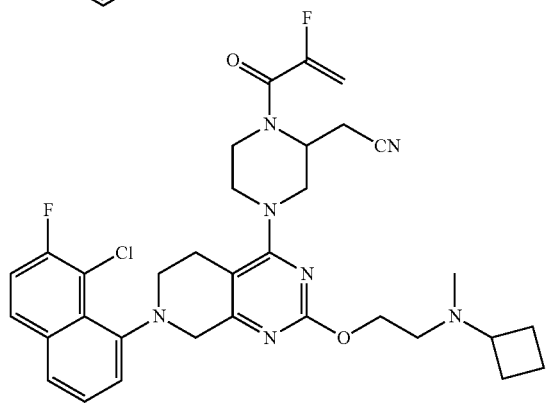
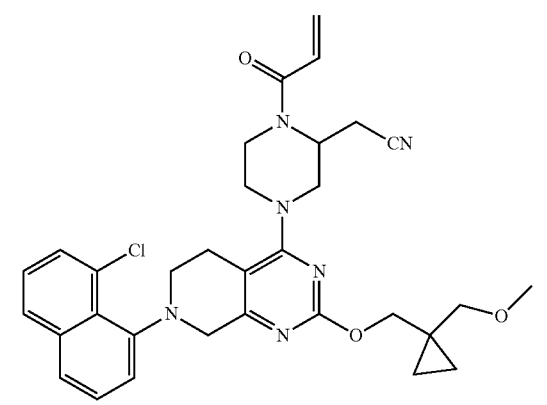
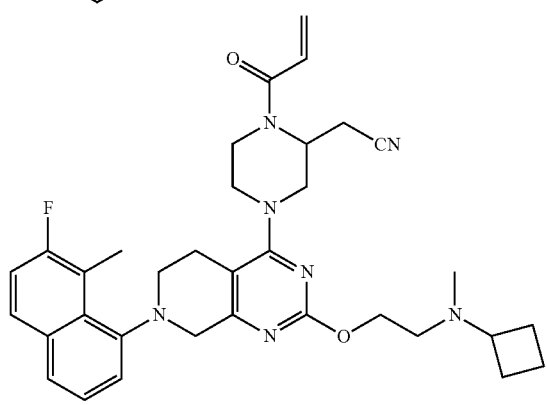
874
-continued
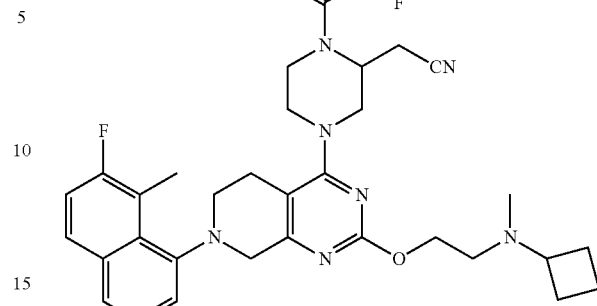
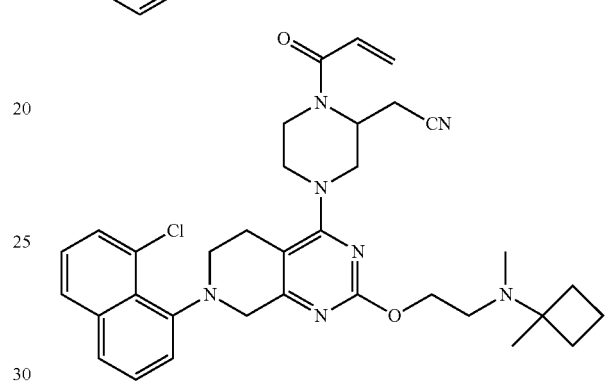
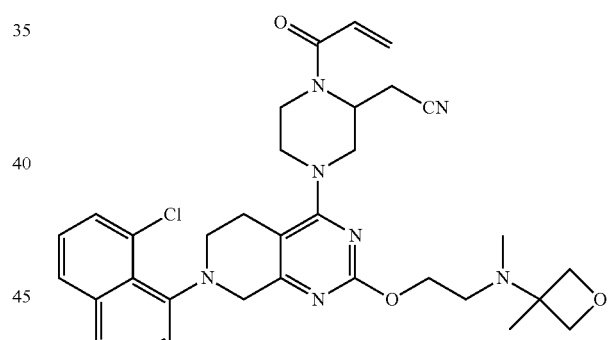
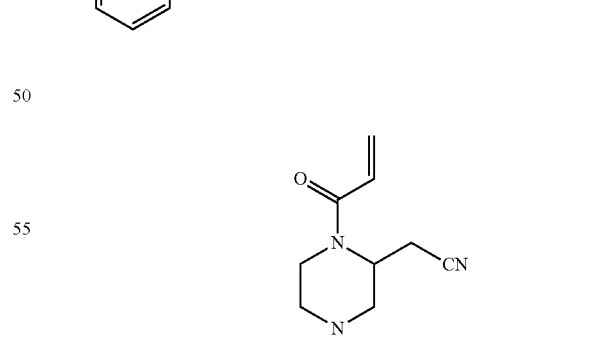
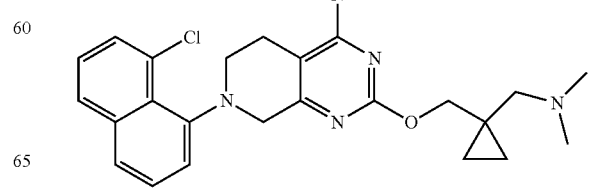

875
-continued
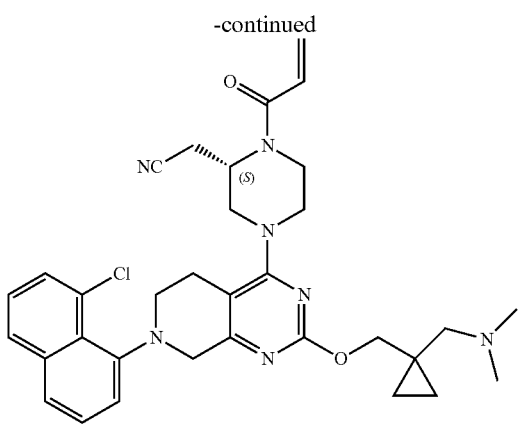
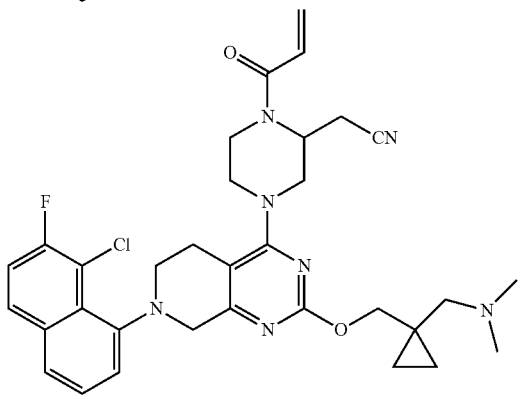
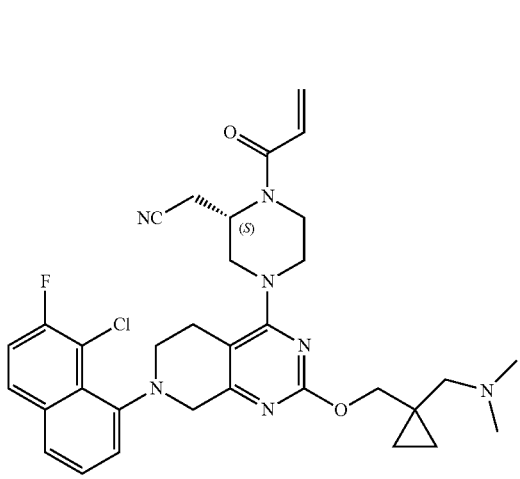
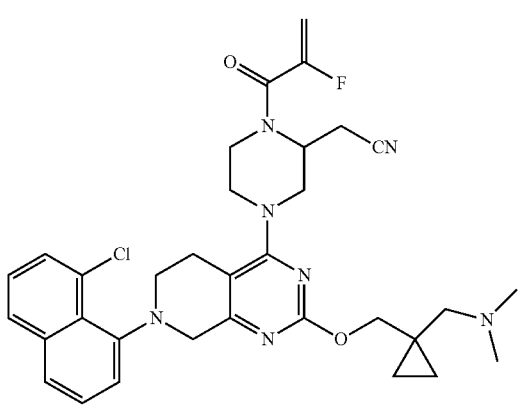
876
-continued
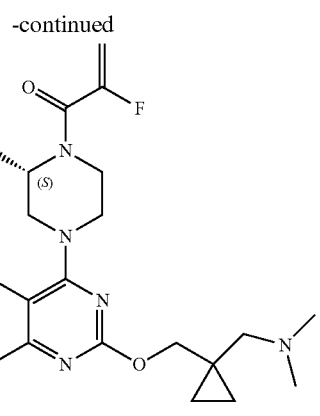
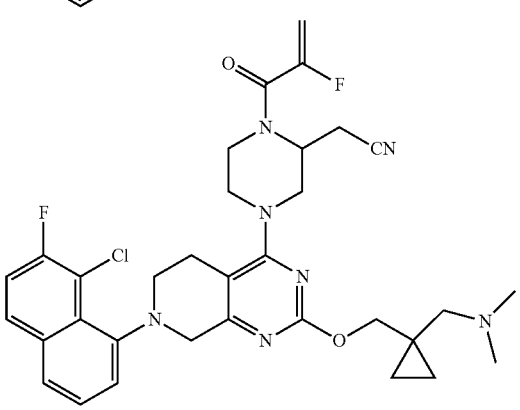
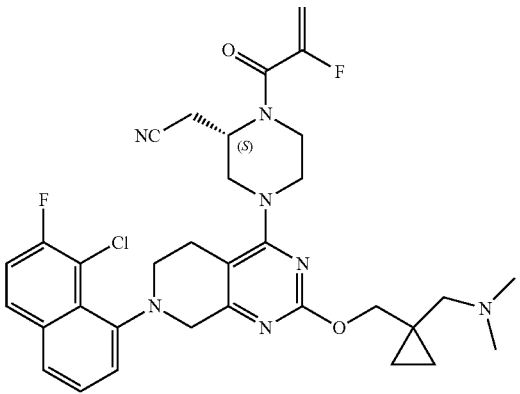
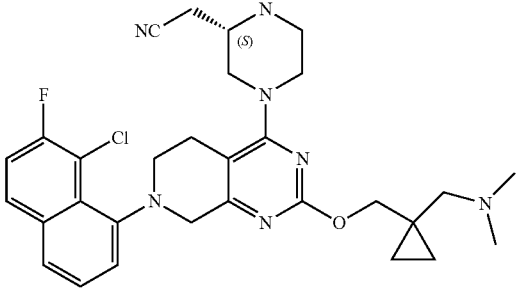

877
-continued
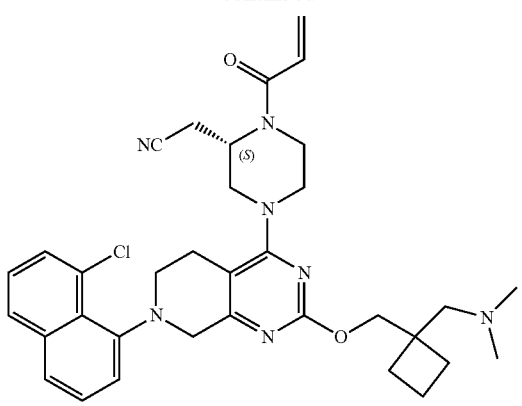
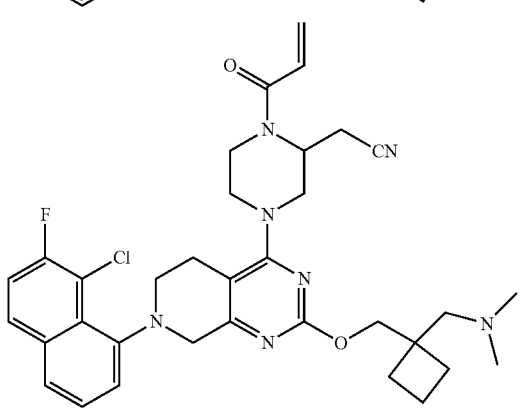
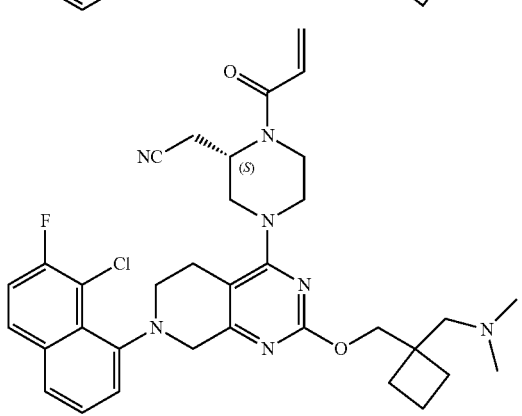
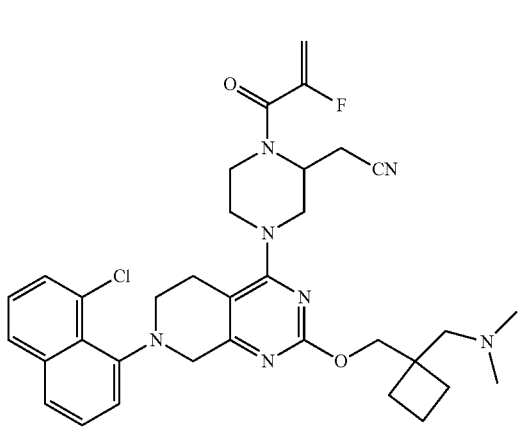
878
-continued
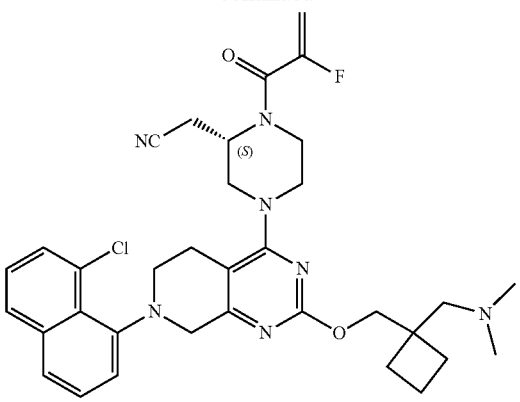
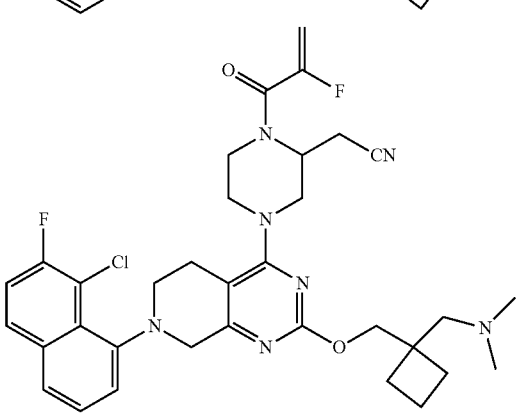
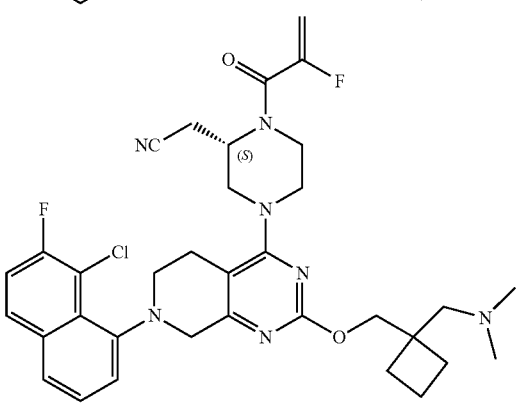
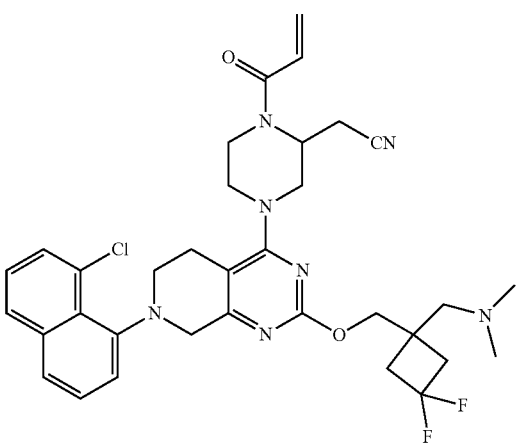

879
-continued
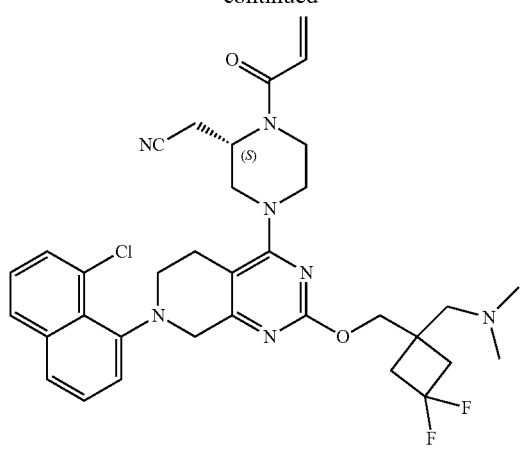
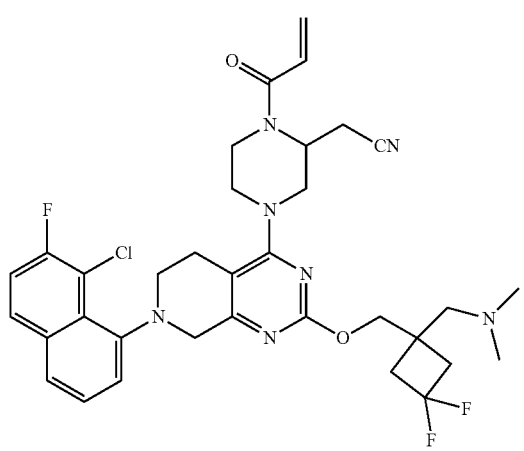
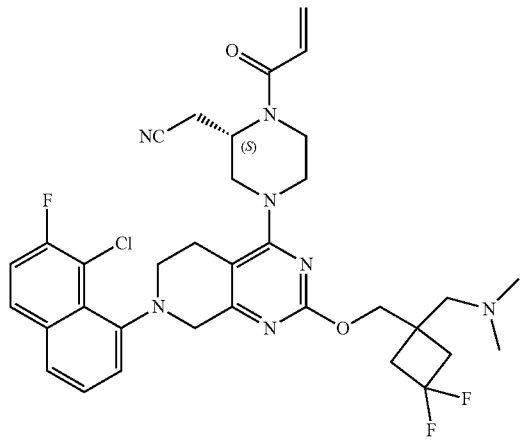
880
-continued
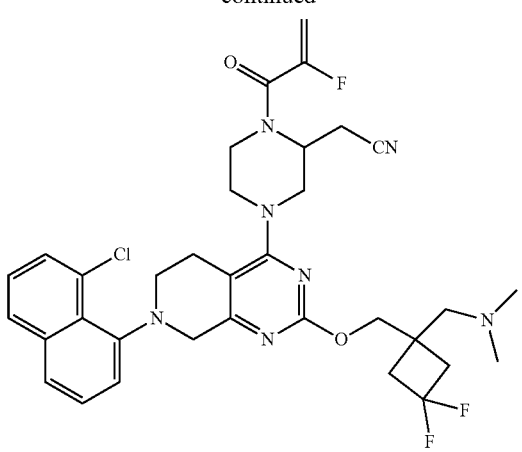
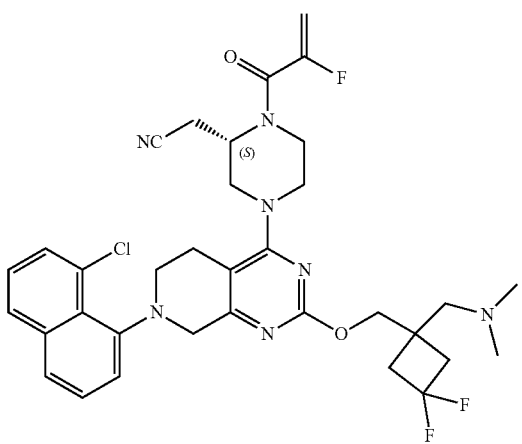
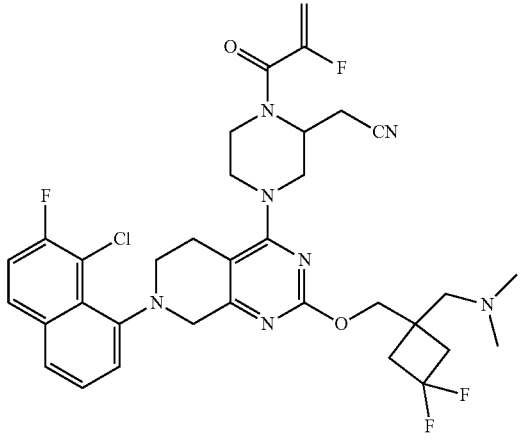

881
-continued
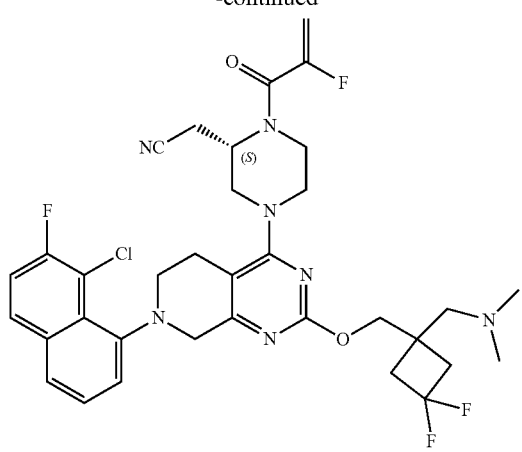
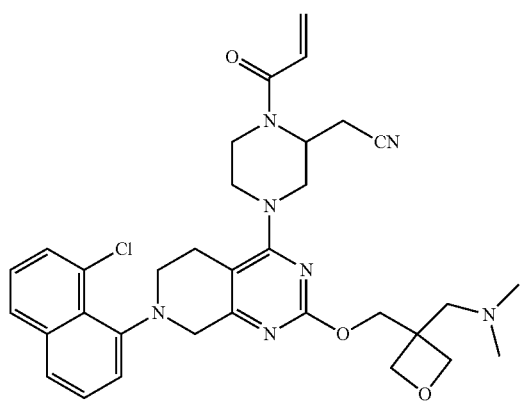
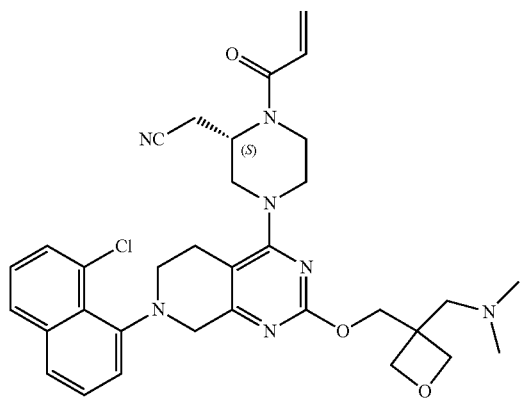
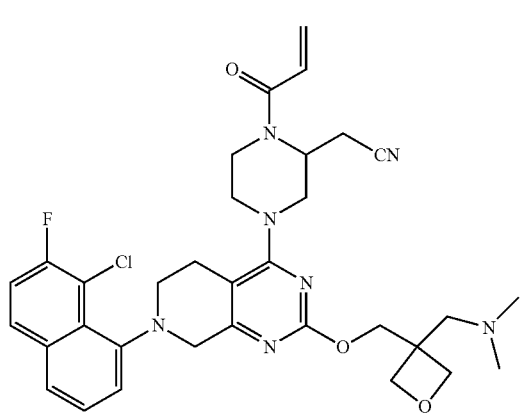
882
-continued
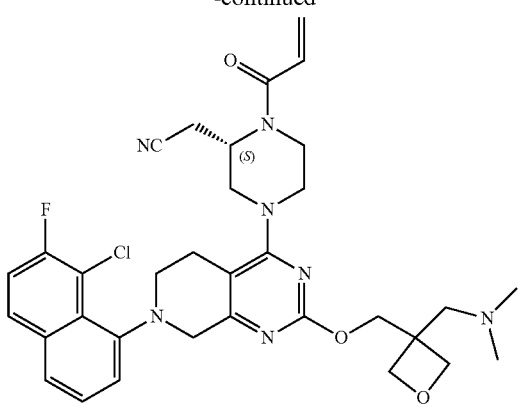
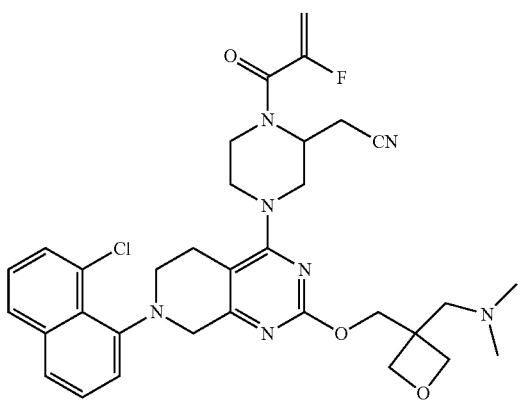
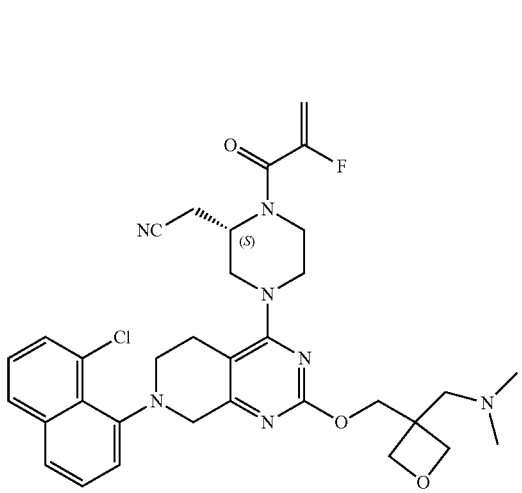
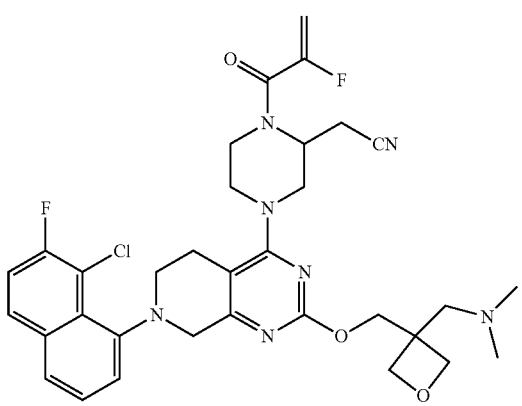

883
-continued
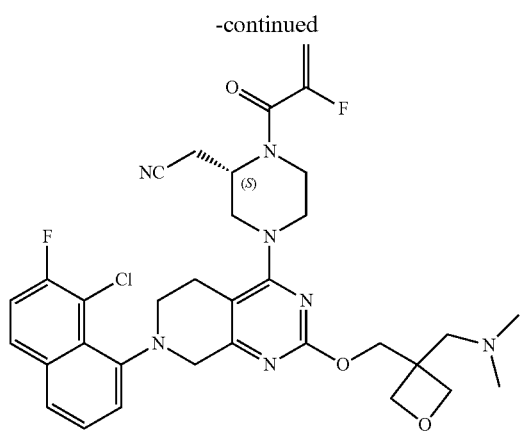
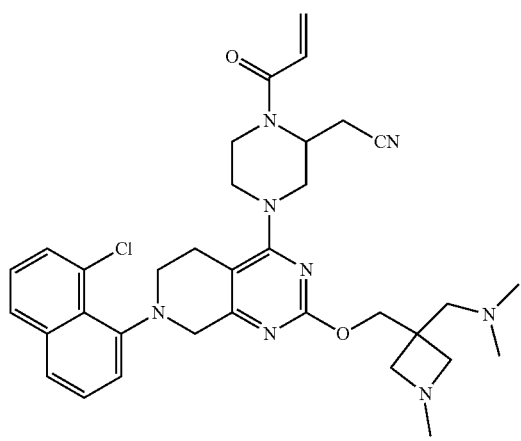
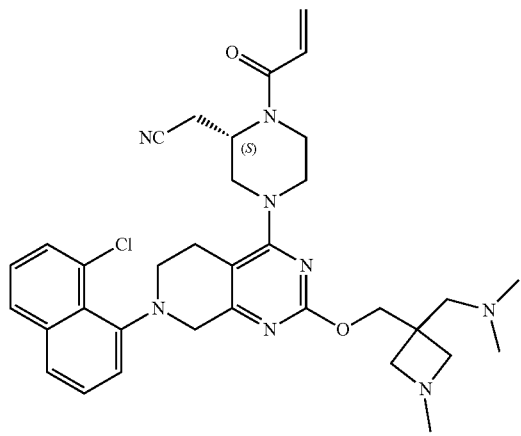
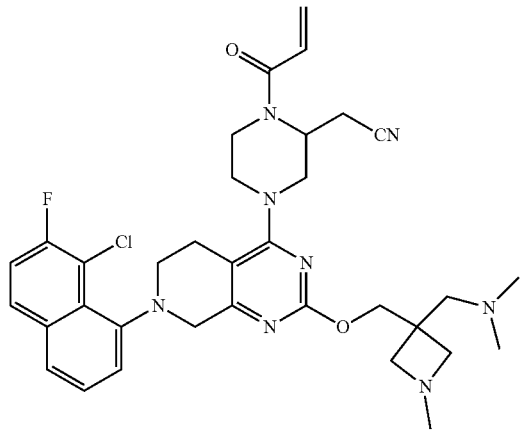
884
-continued
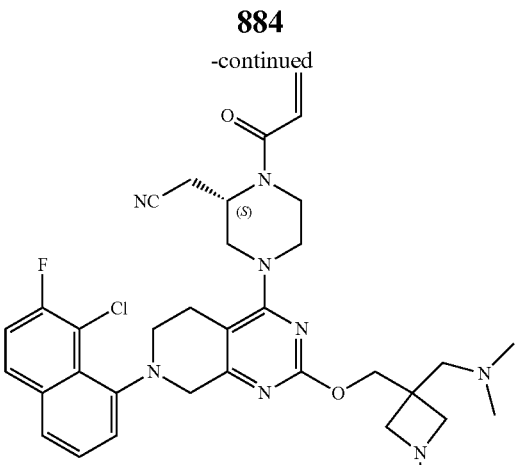
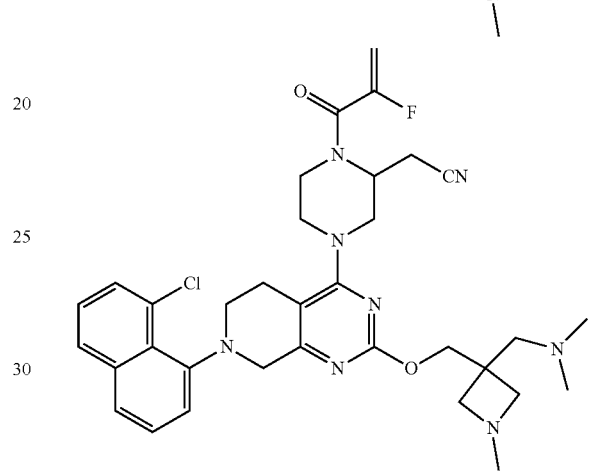
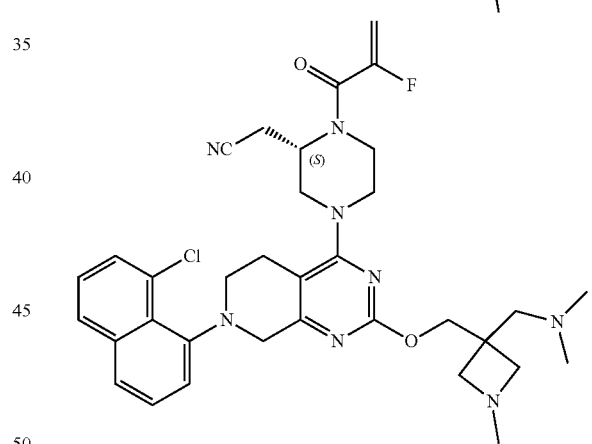
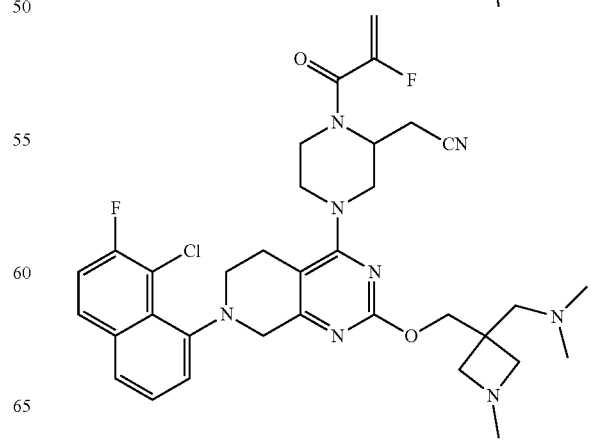

885
-continued
886
-continued
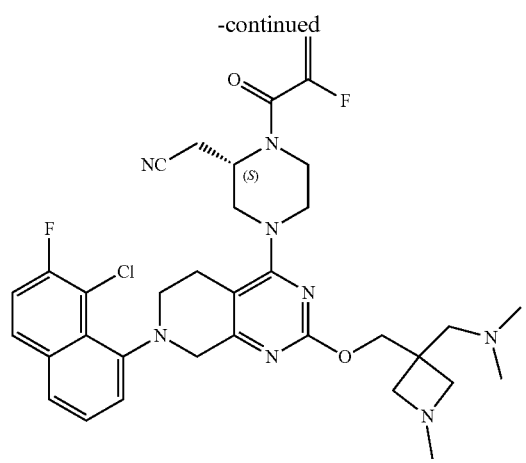
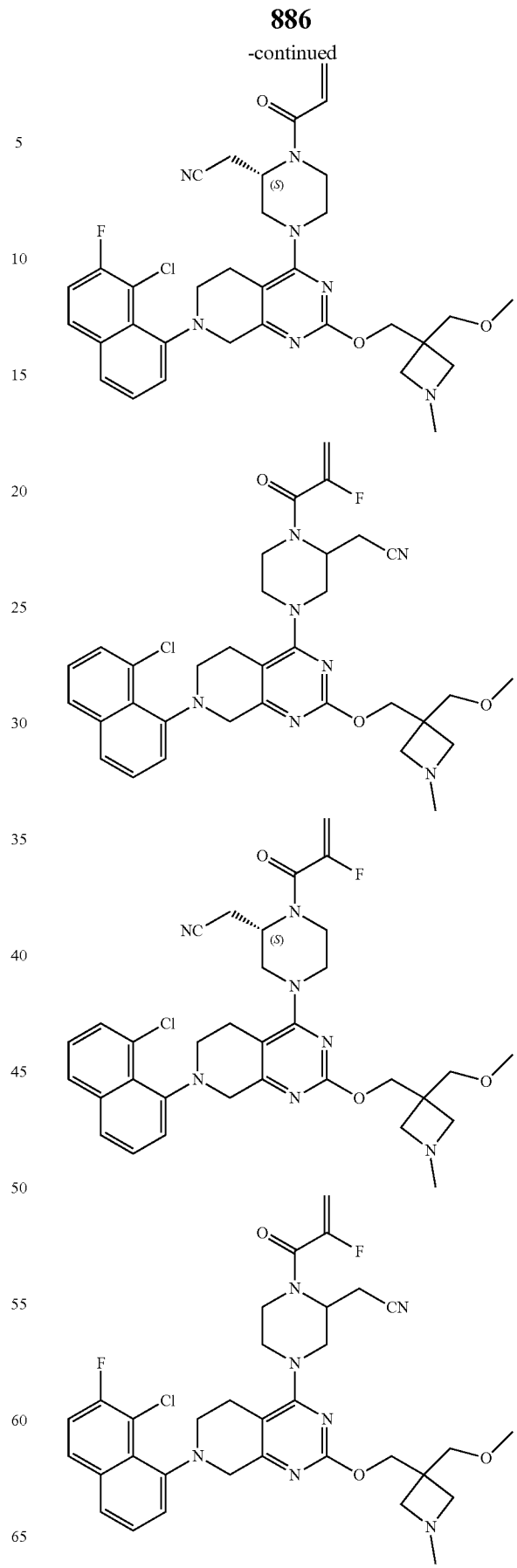

887
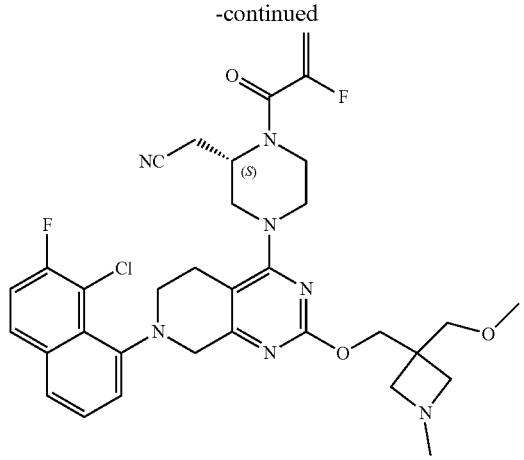
888
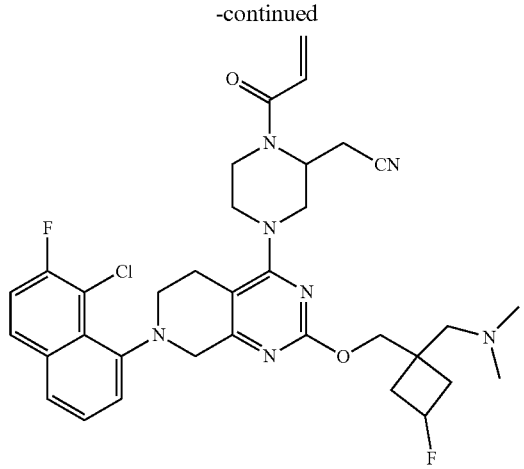
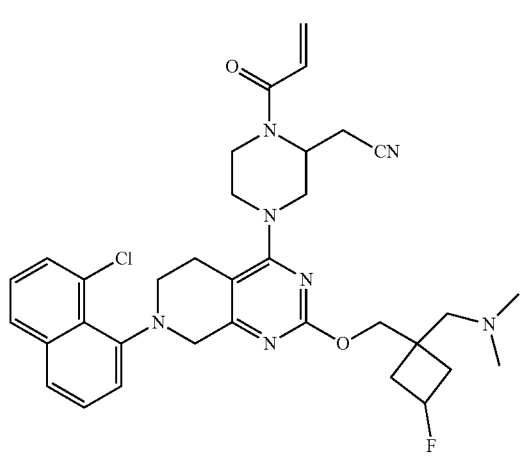
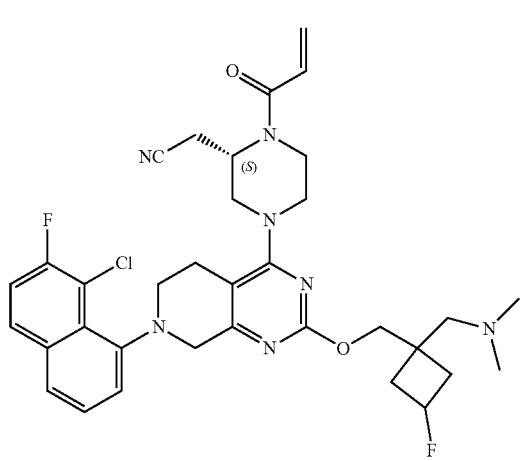
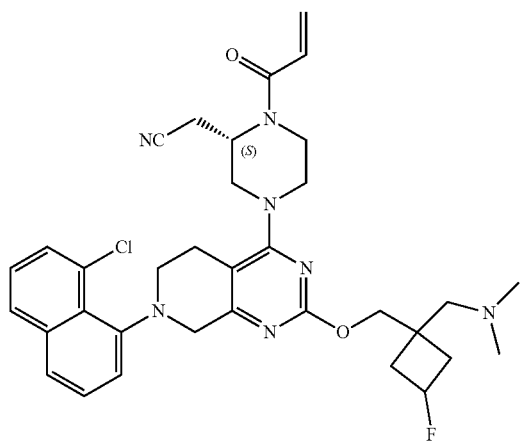
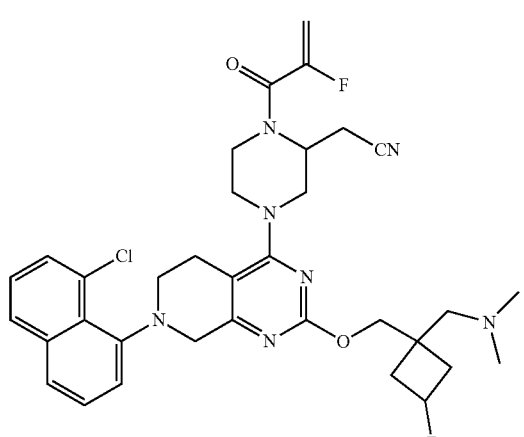

889
-continued
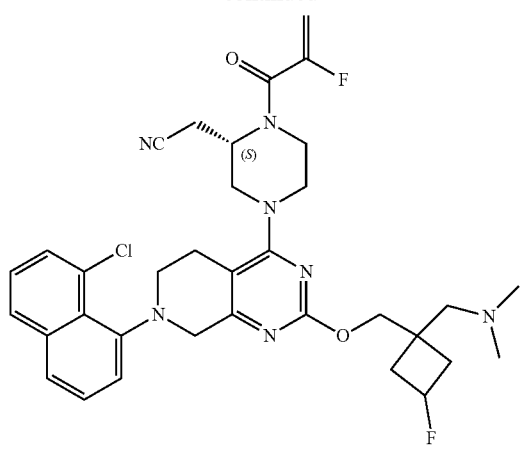
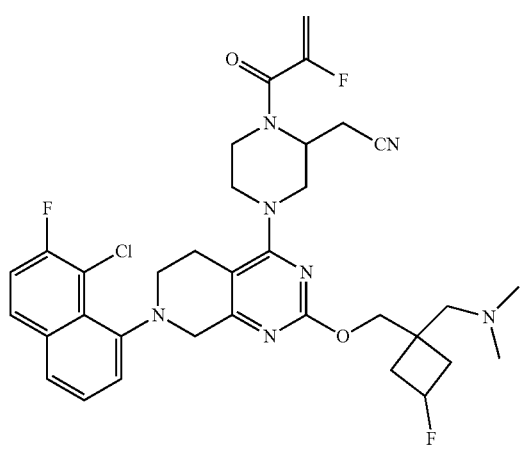
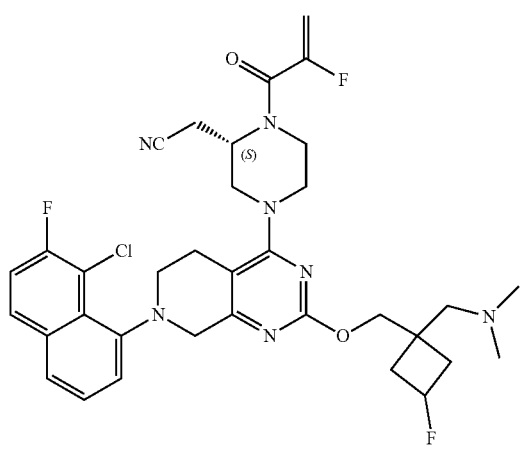
890
-continued

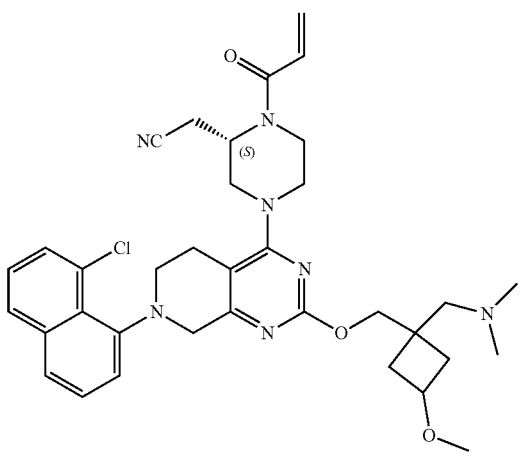
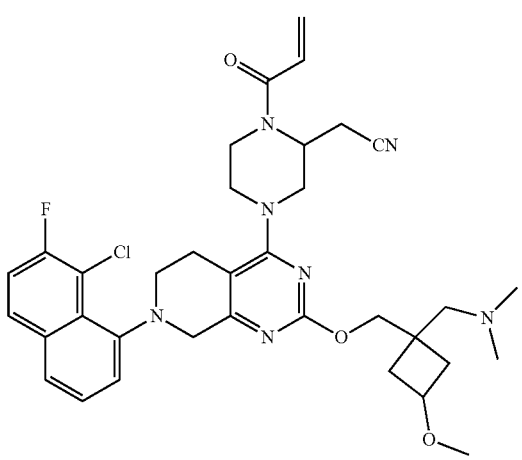

891
-continued
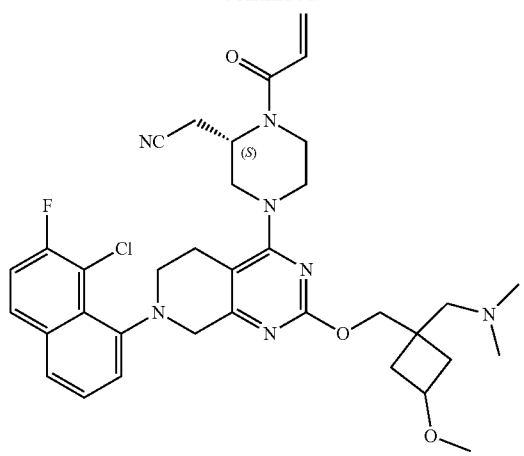
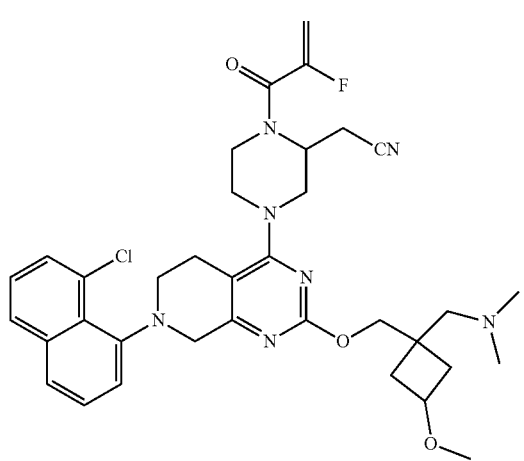
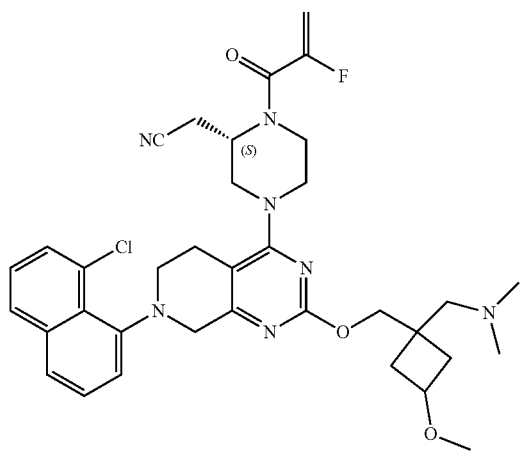
892
-continued
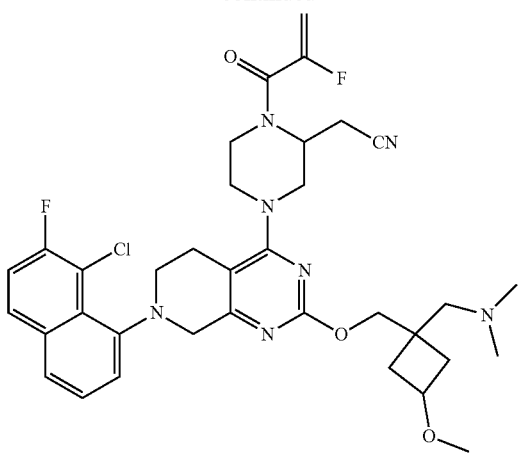
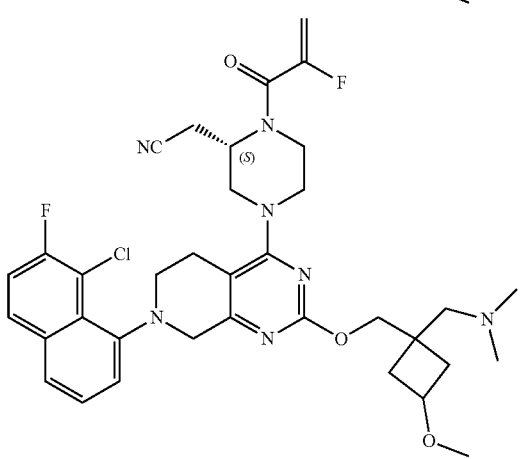
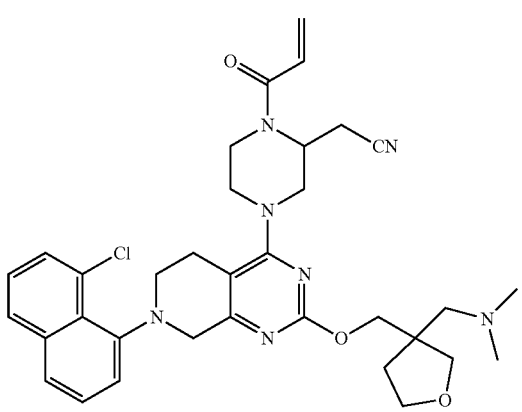
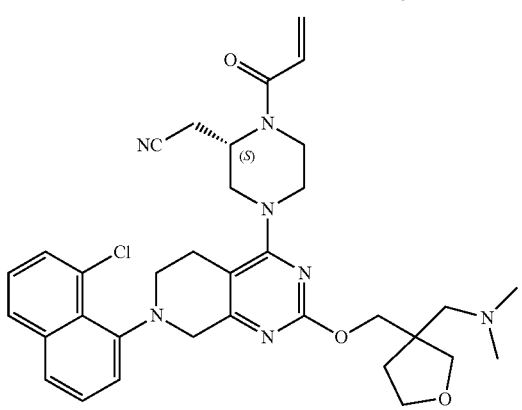

893
-continued
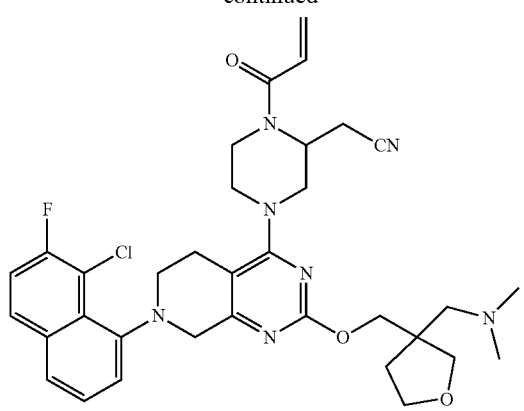
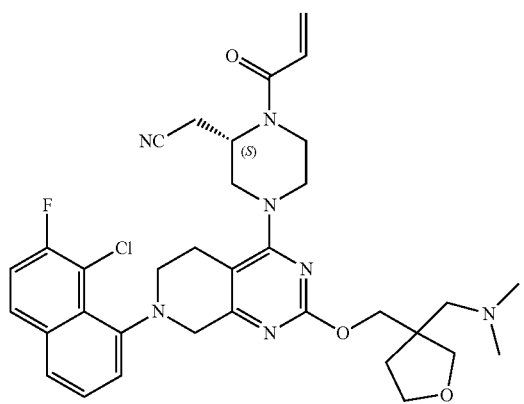
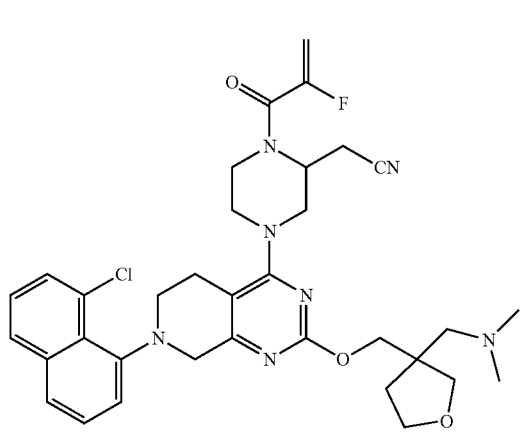
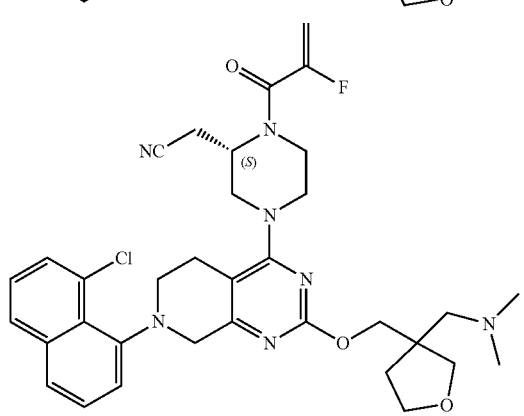
894
-continued
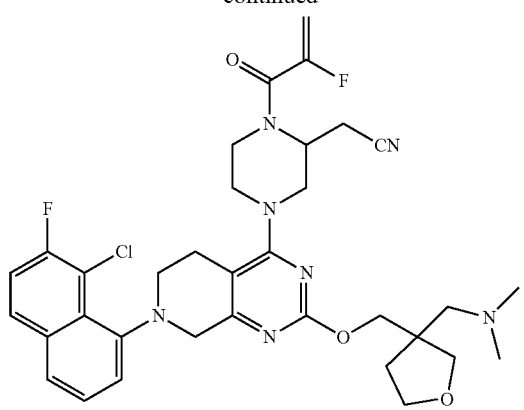
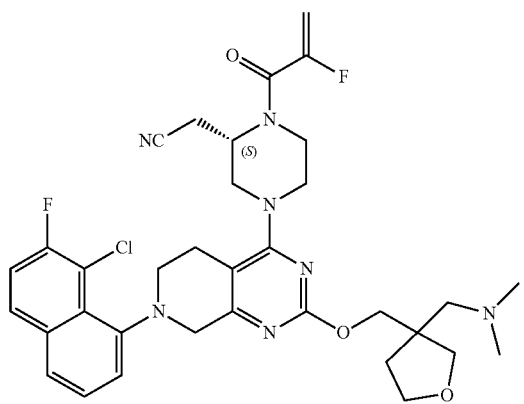
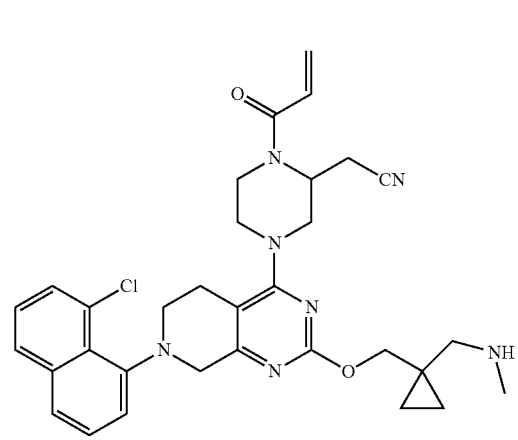
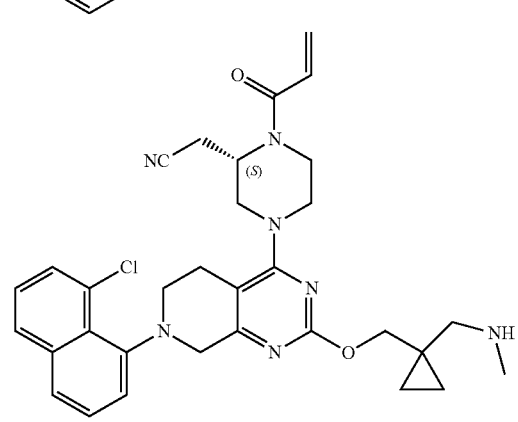

895
-continued
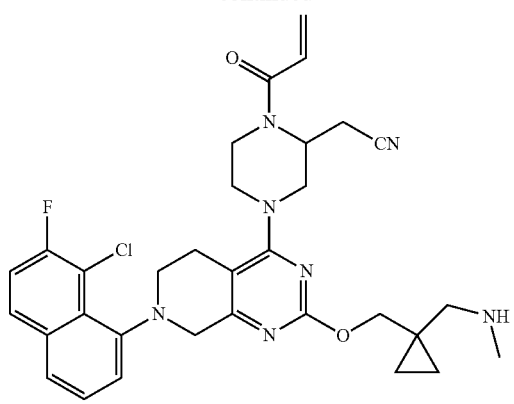
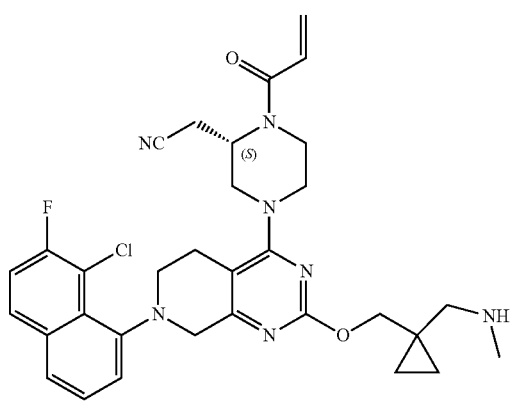
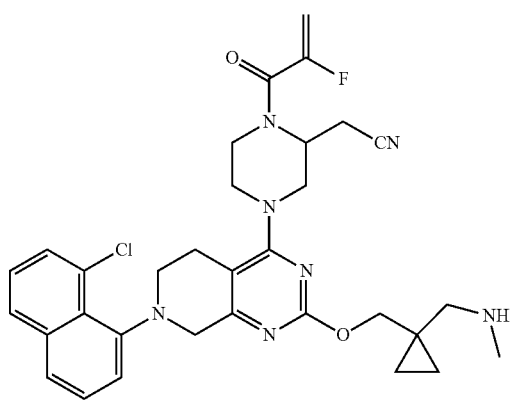
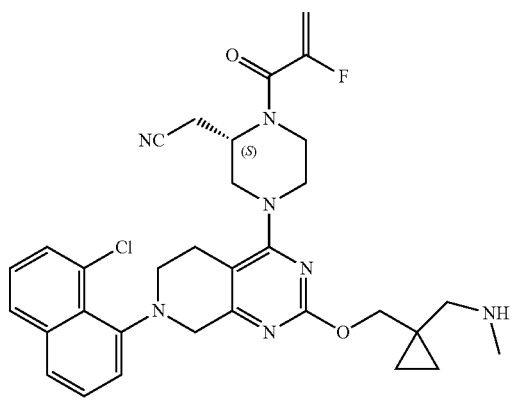
896
-continued
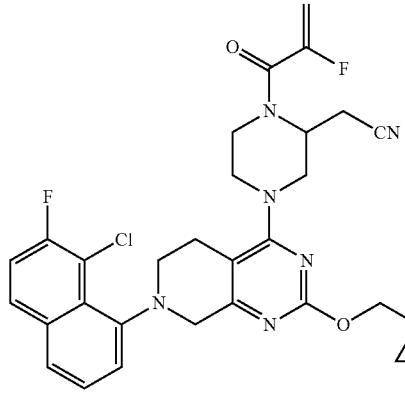
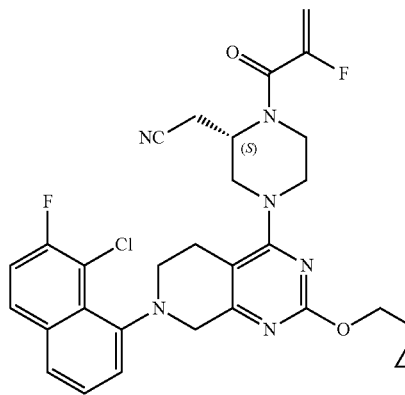
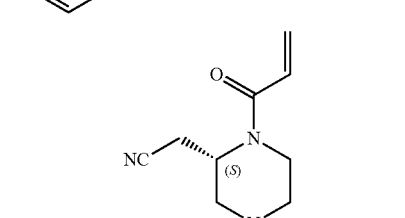
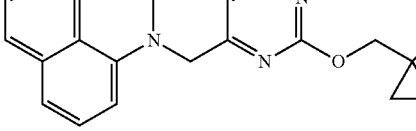

897
-continued
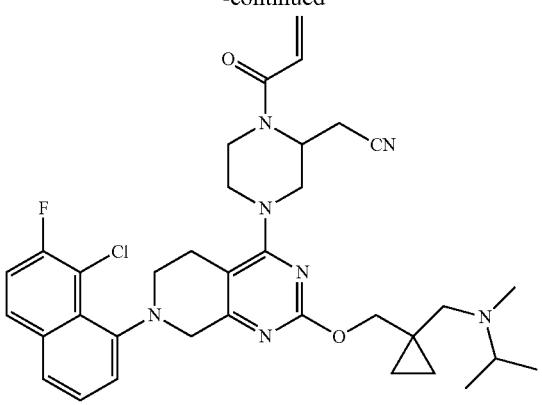
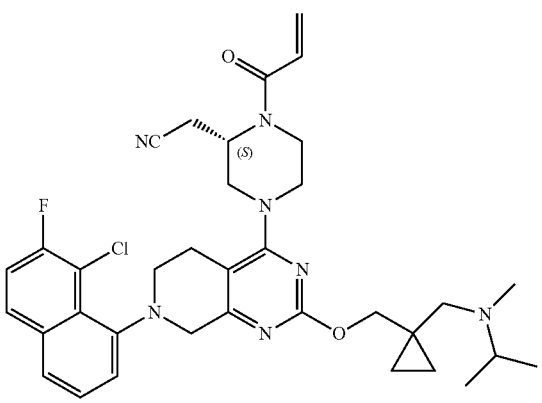
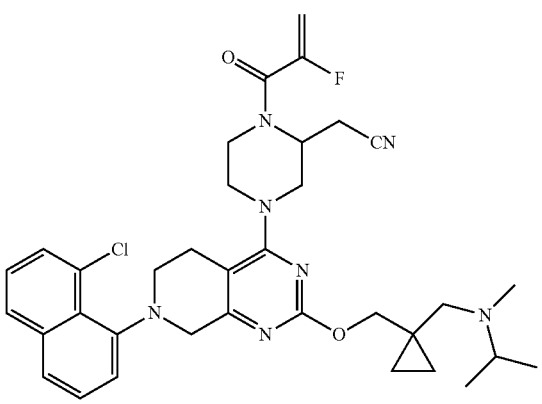
898
-continued
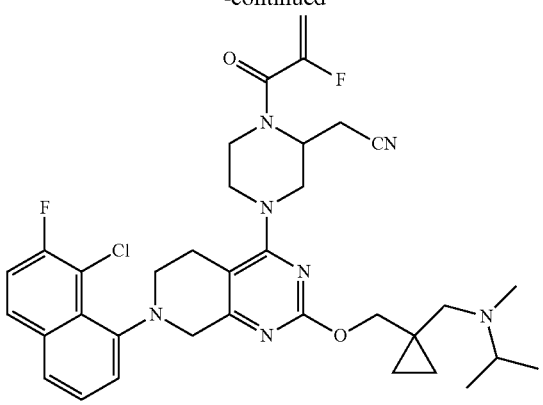
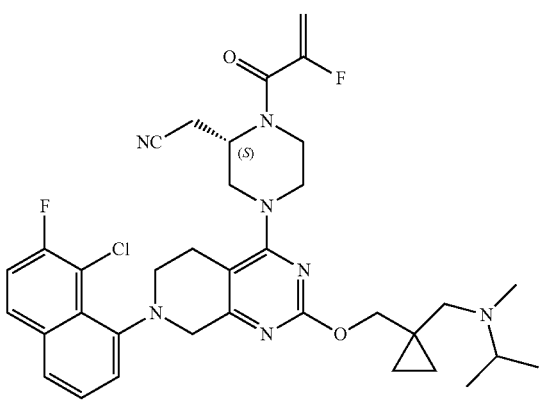
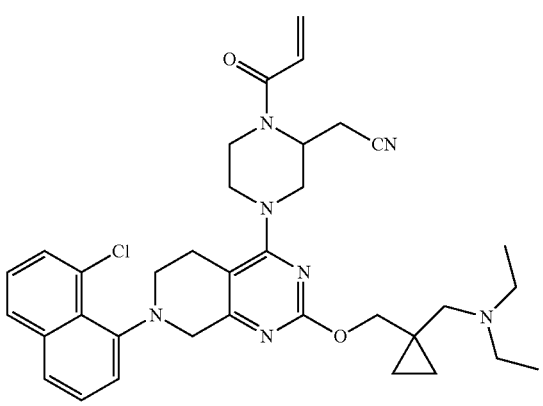
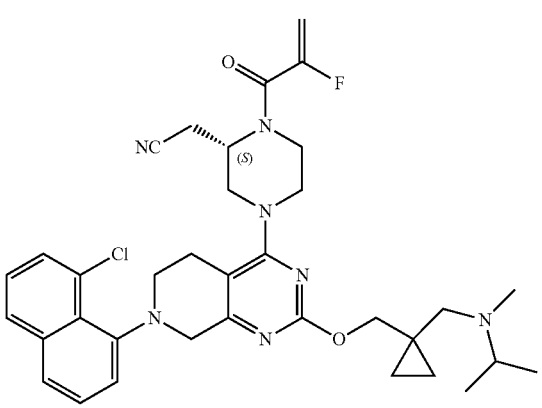
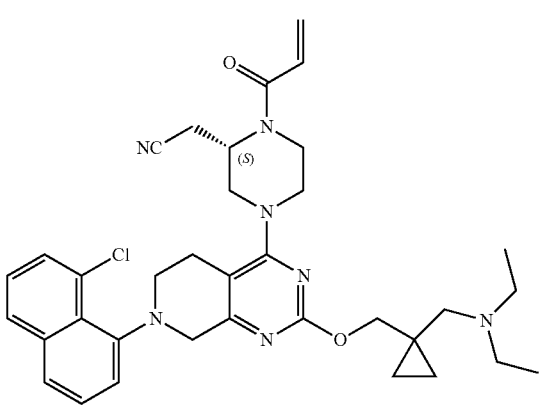

899
-continued
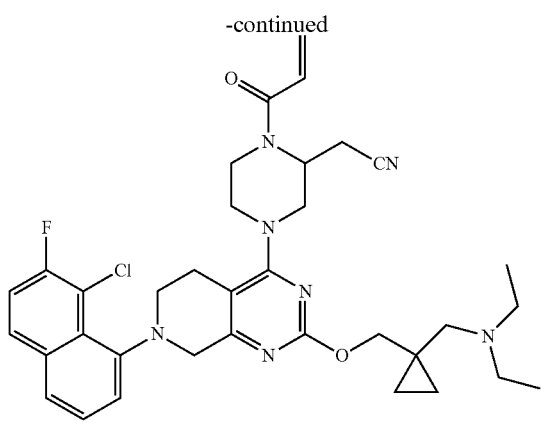
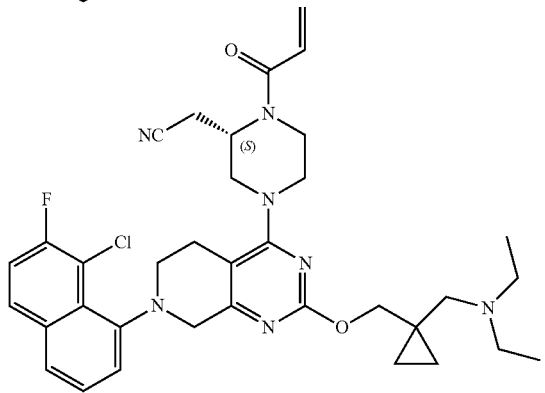
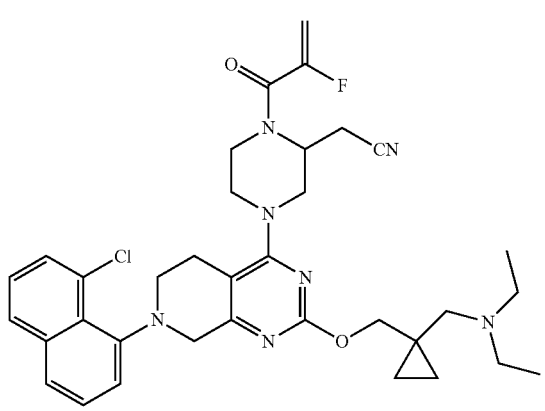
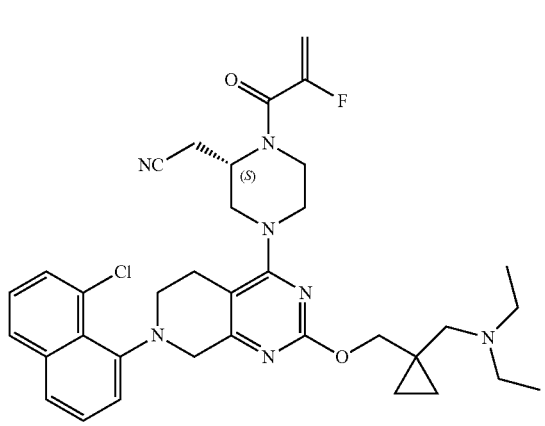
900
-continued
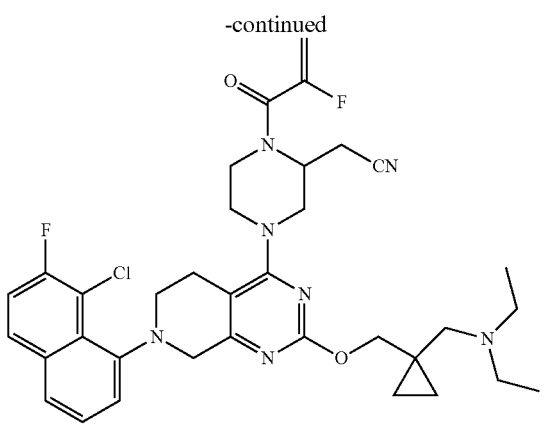
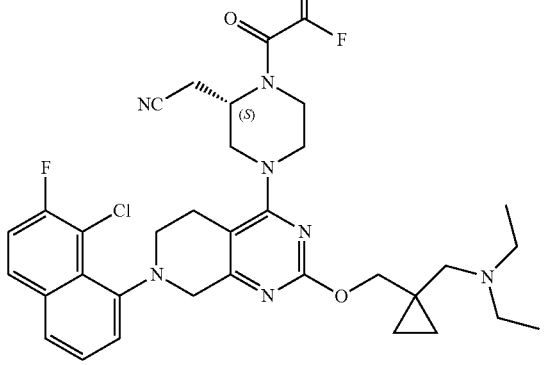
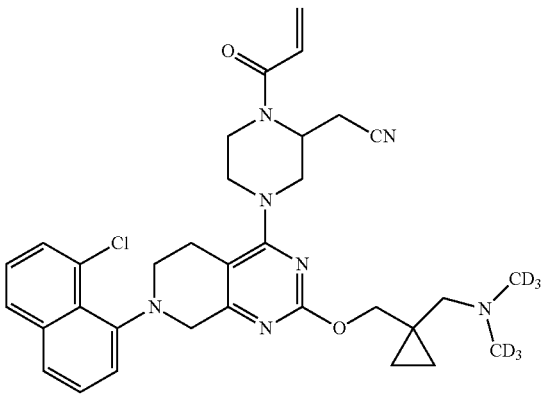
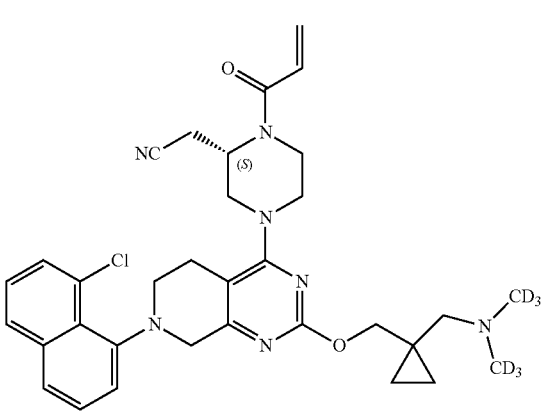

901
-continued
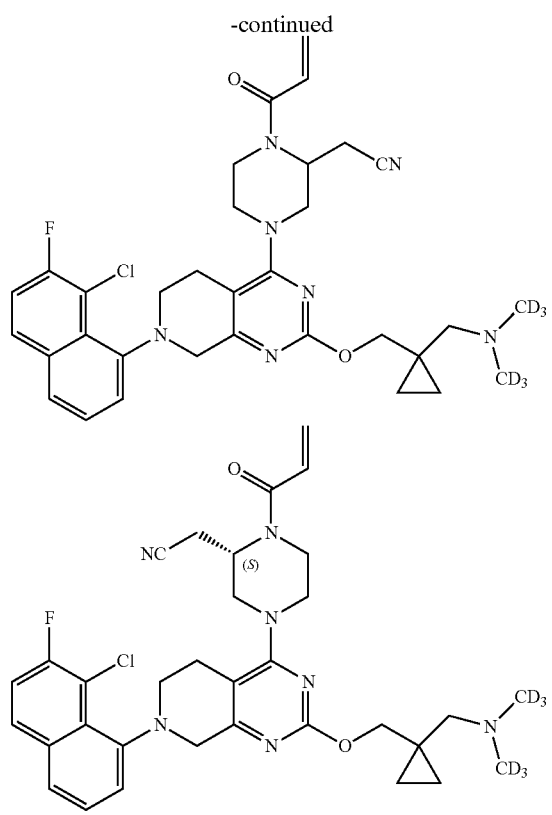
902
-continued
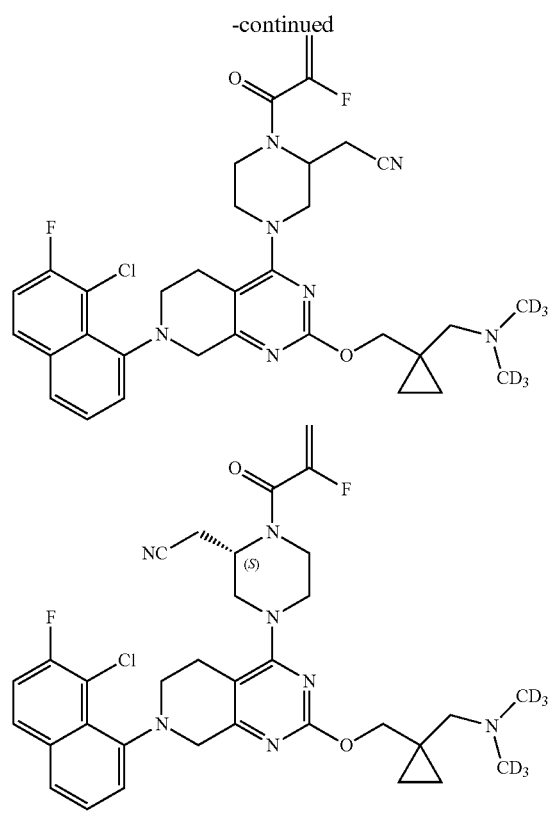
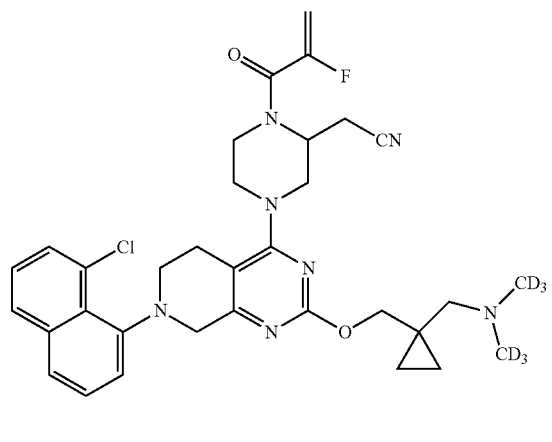
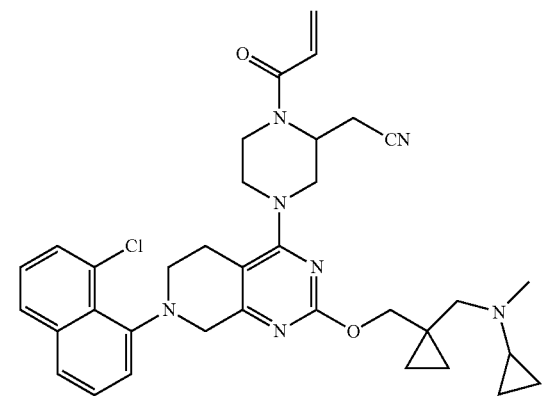
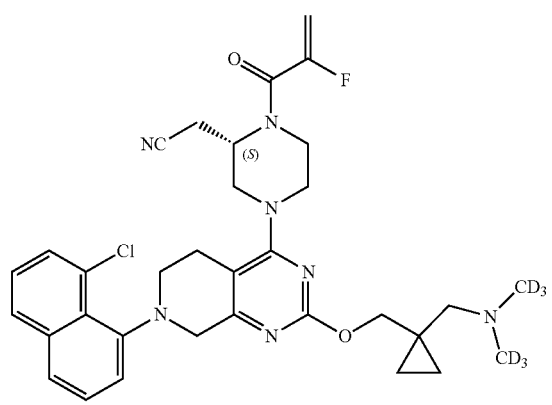
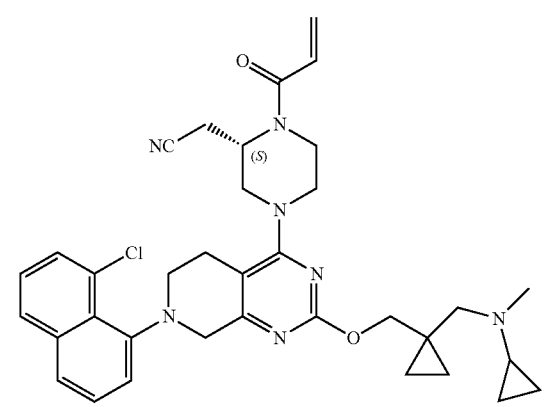

903
-continued
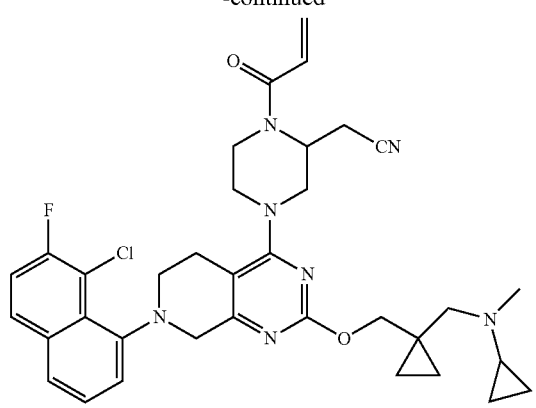
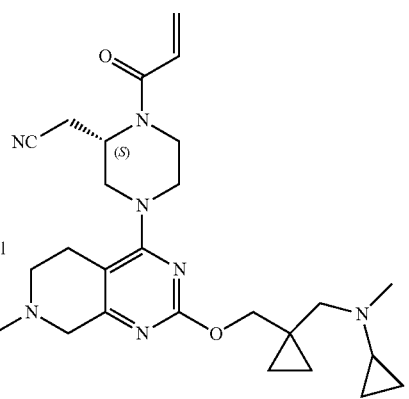
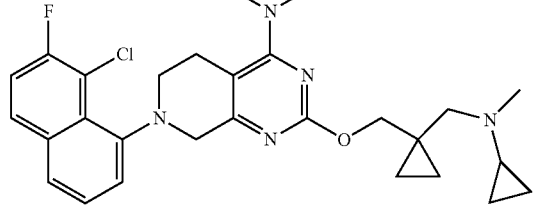
904
-continued
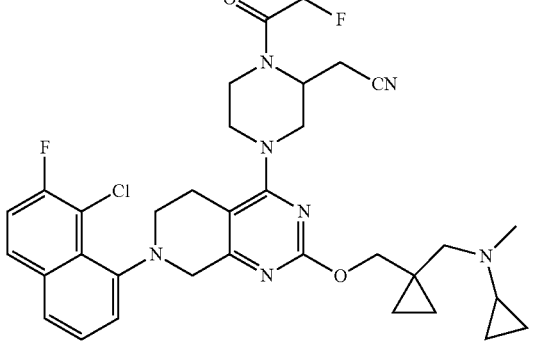
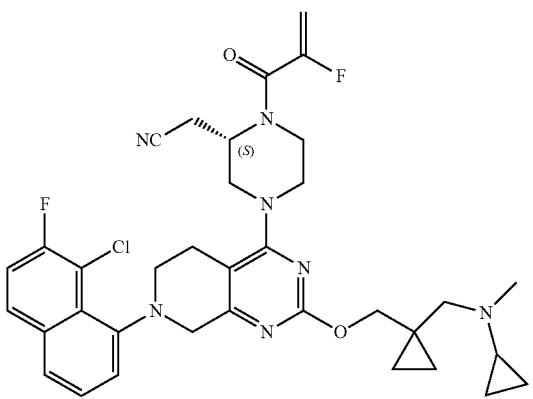
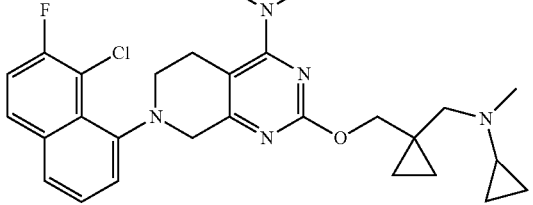
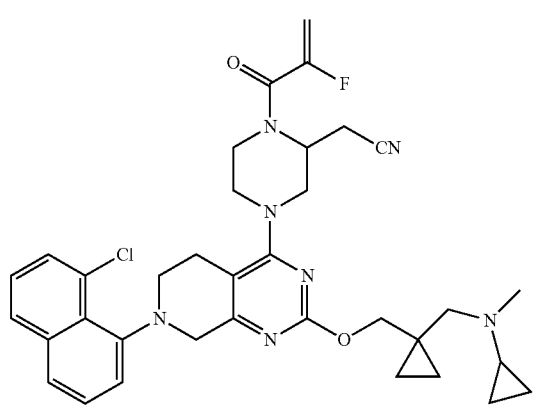
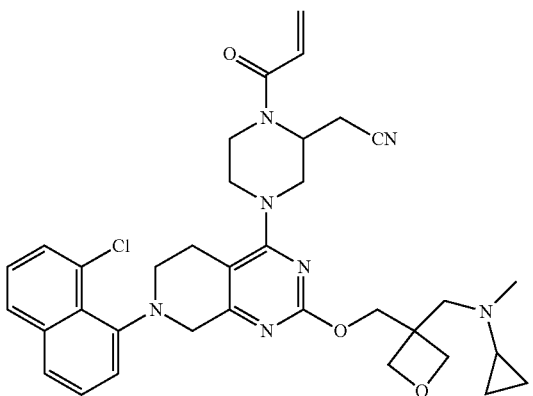
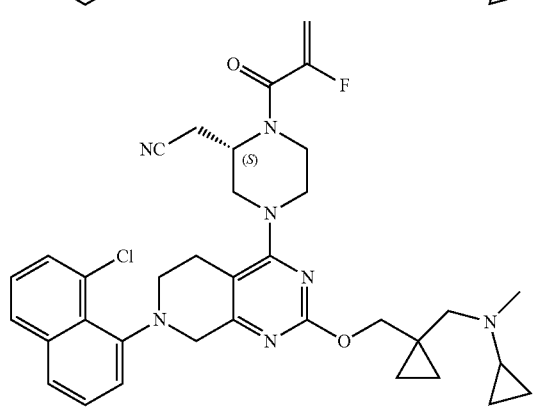
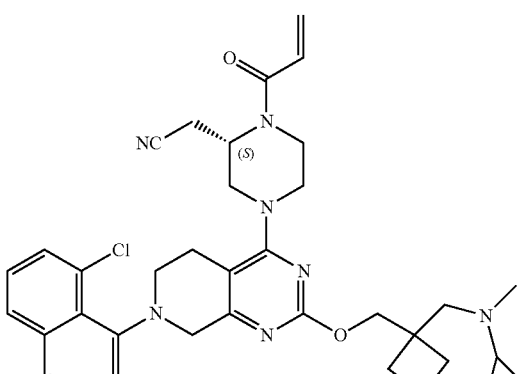

905
-continued
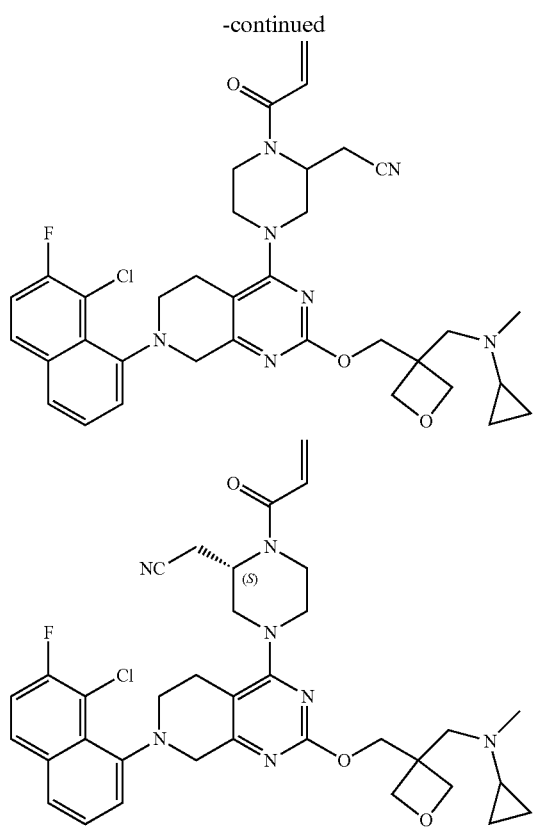
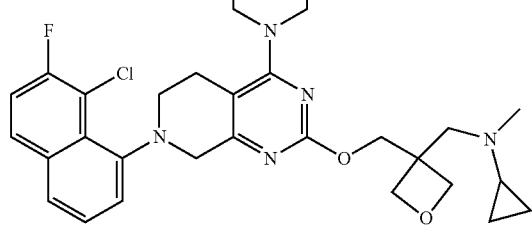
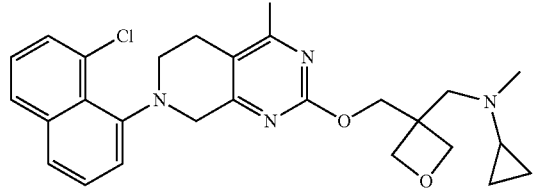
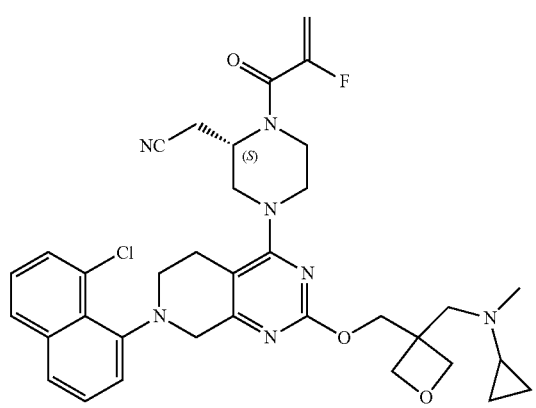
906
-continued
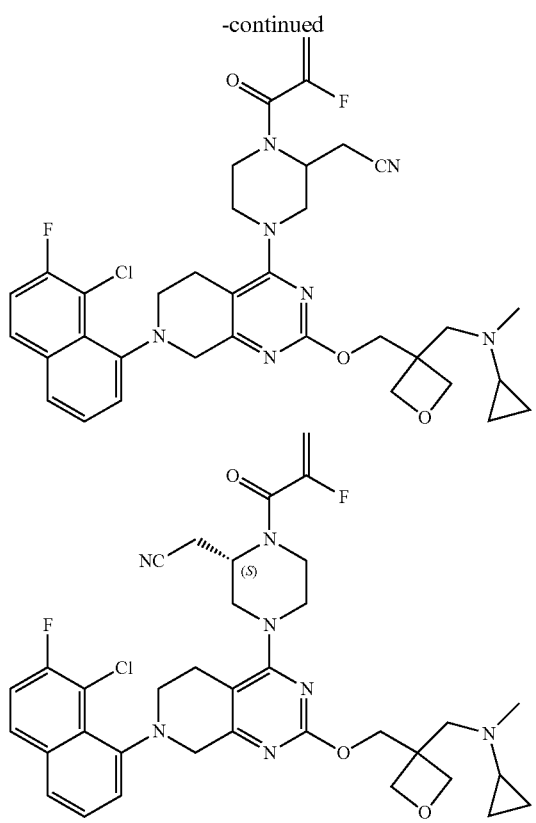
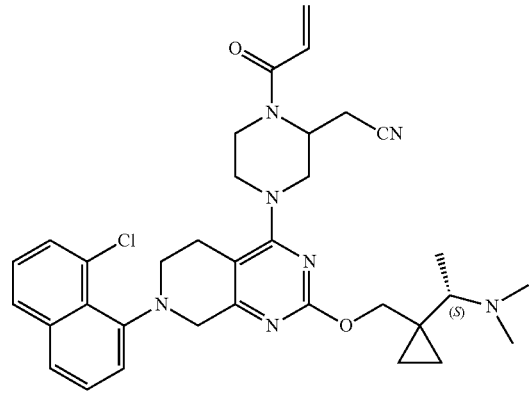
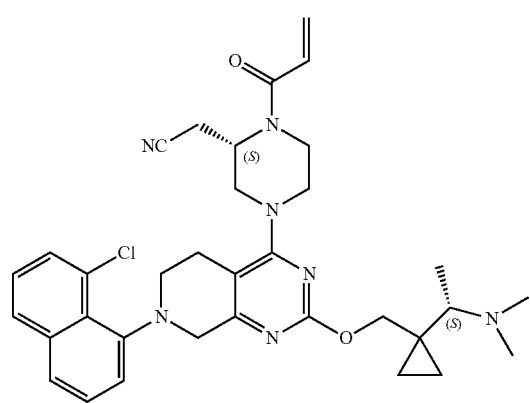

907
-continued
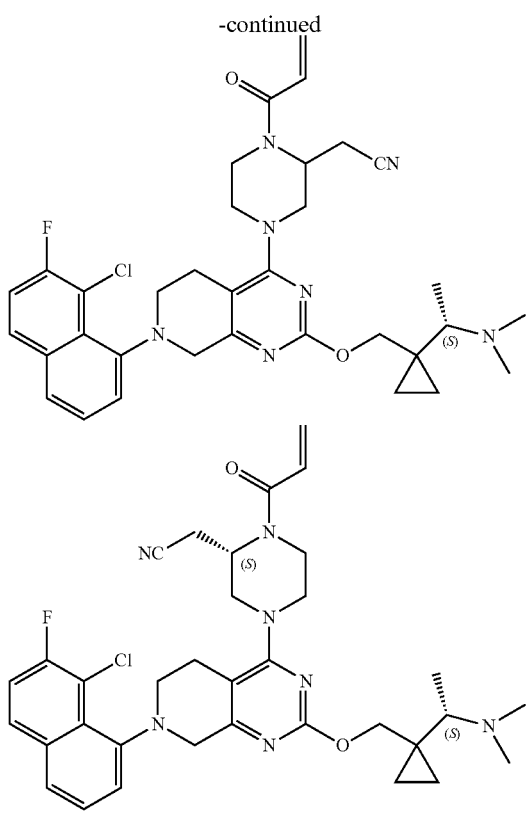
908
-continued
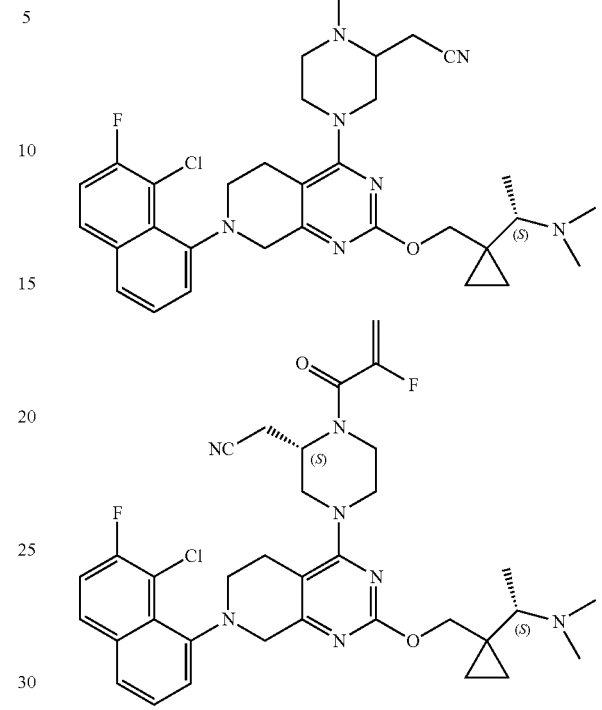
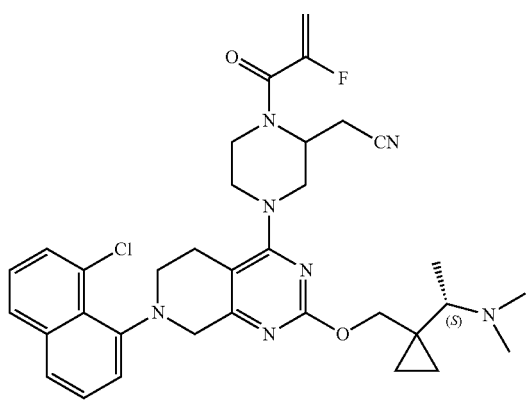
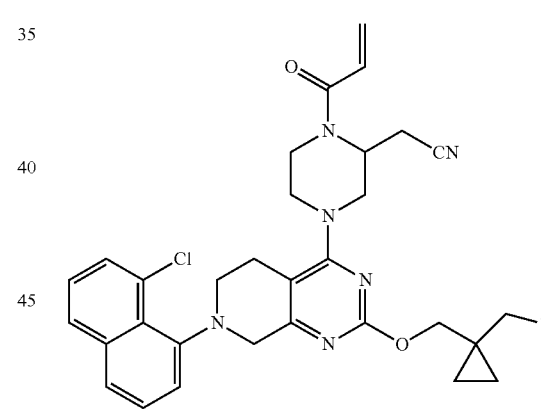
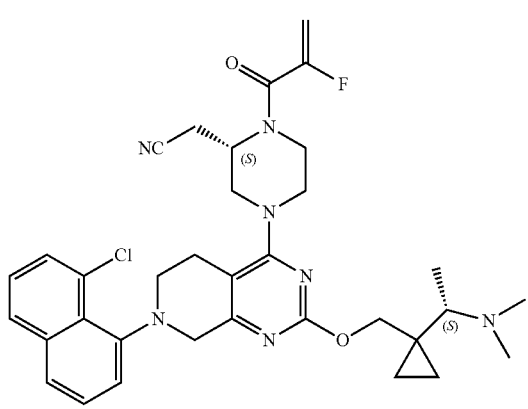
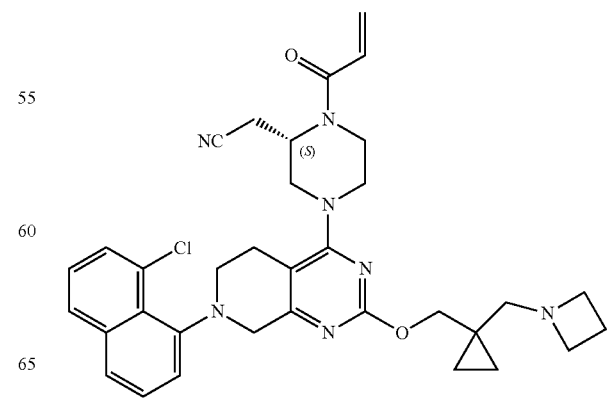

909
-continued
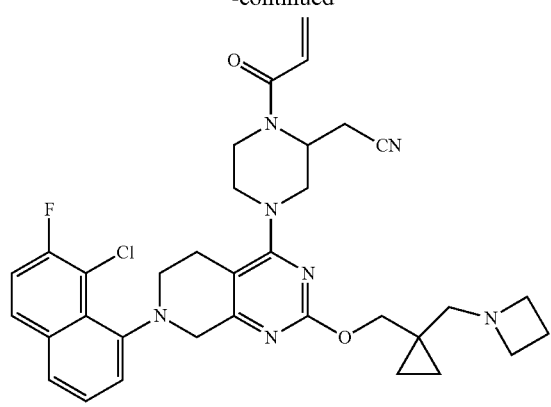
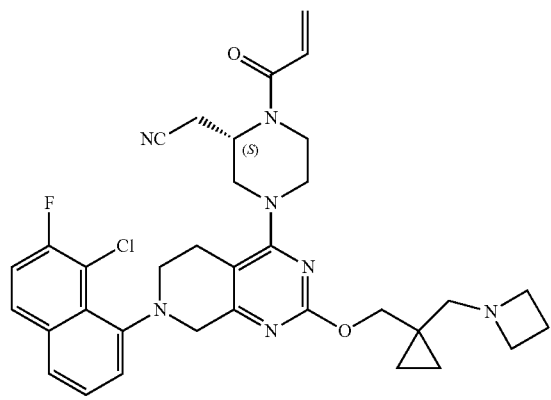
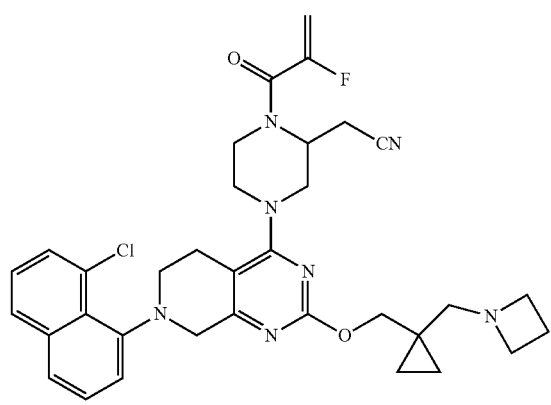
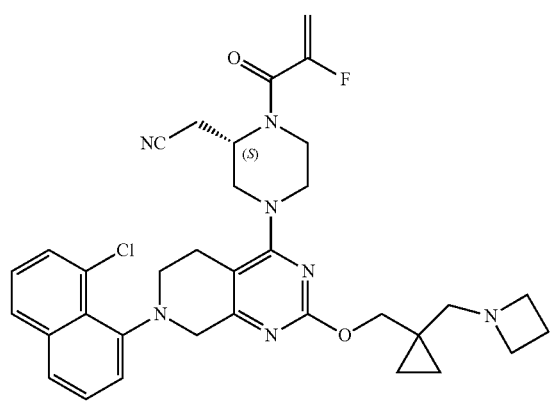
910
-continued
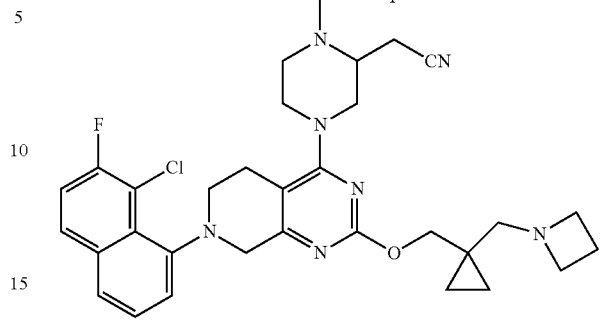
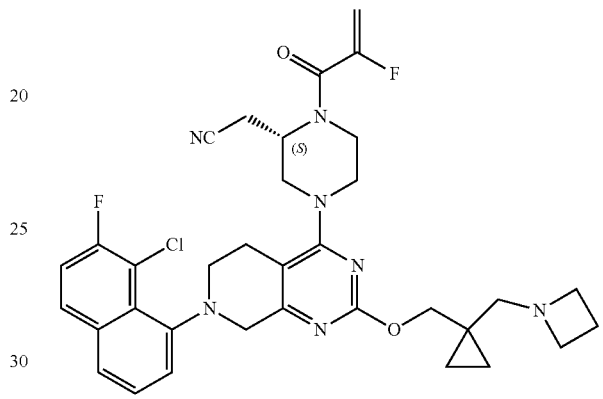
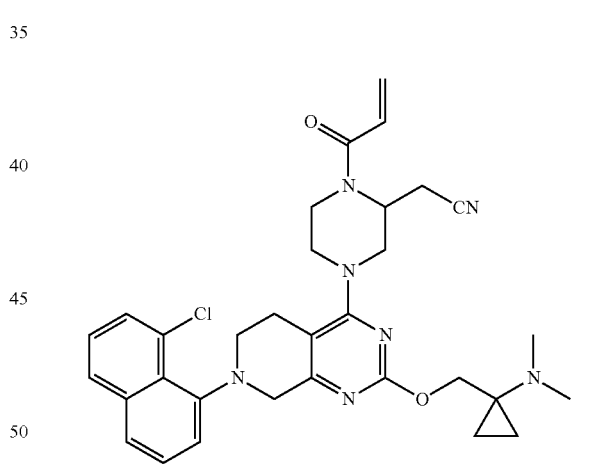
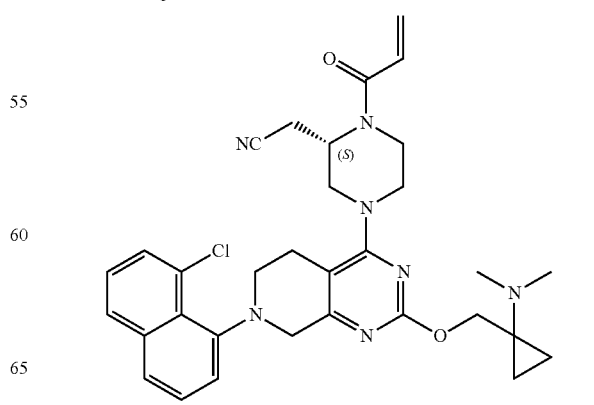

911
-continued
912
-continued
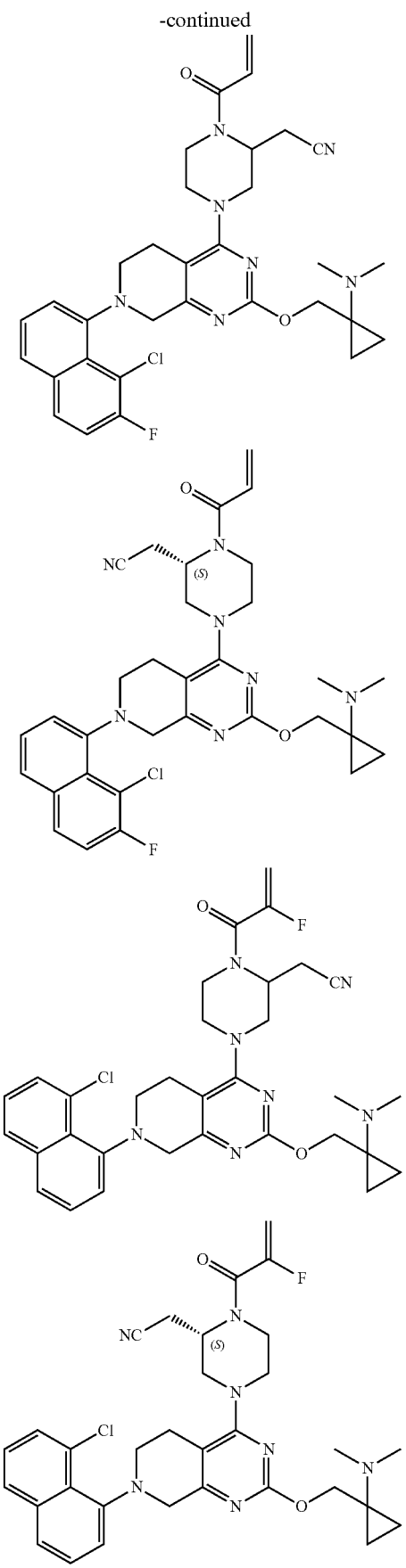
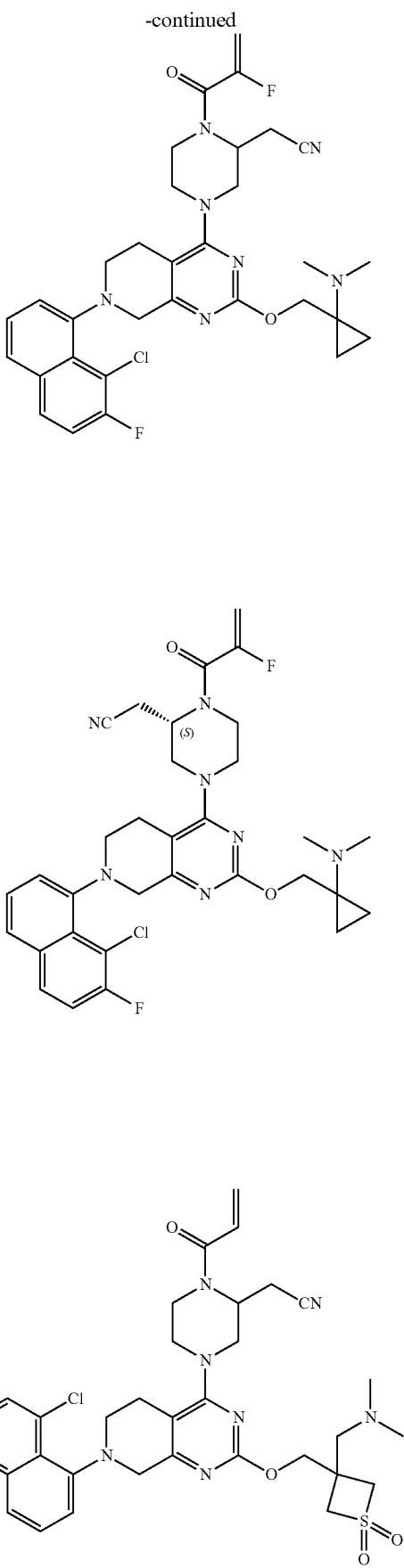

913
-continued
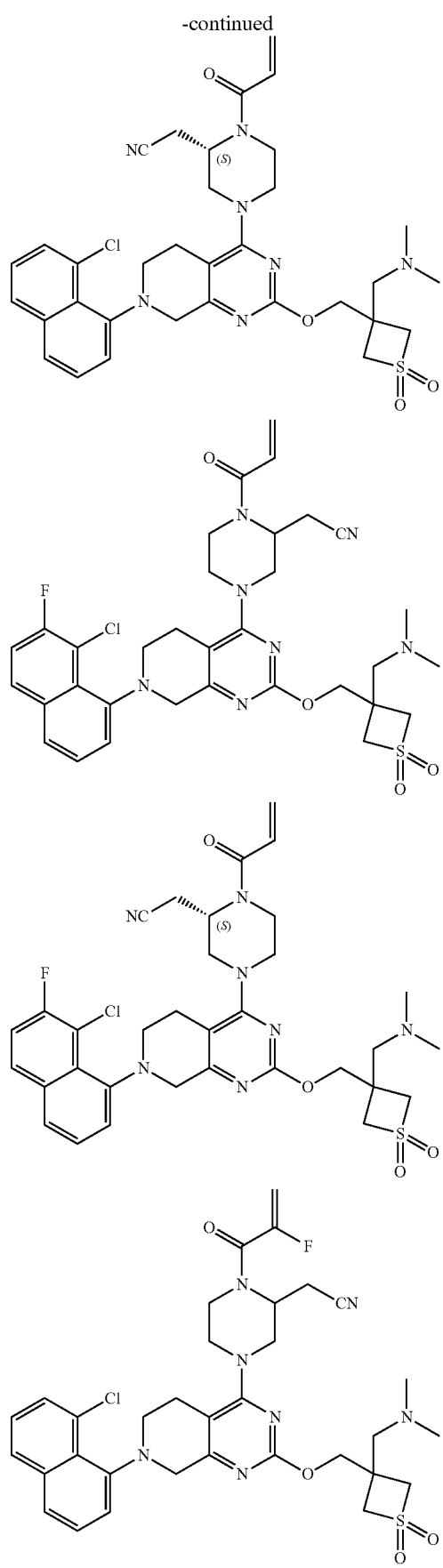
914
-continued
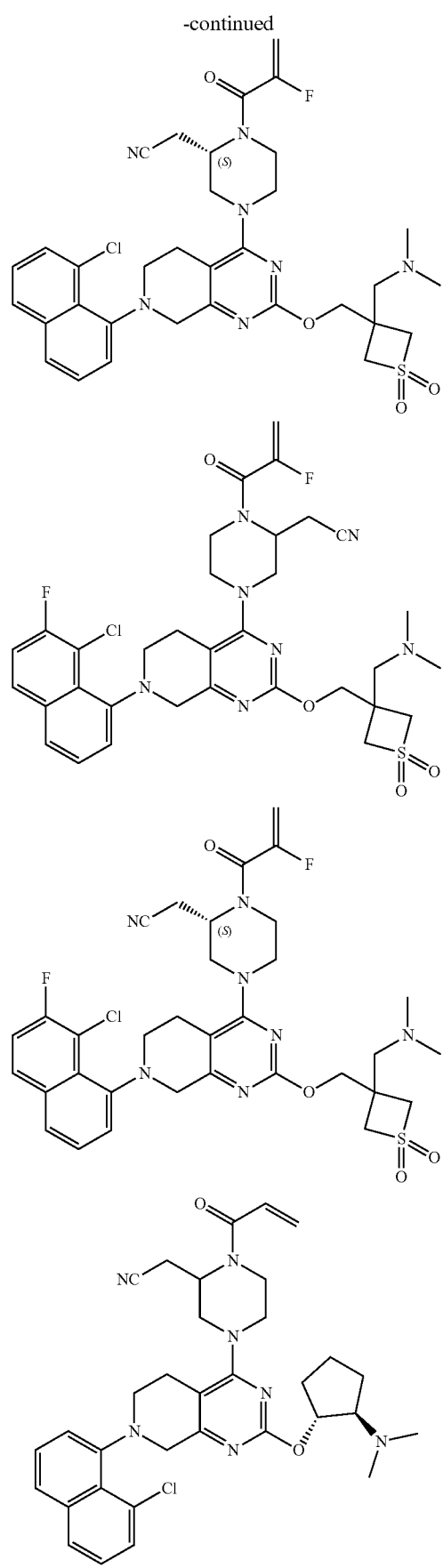

915
-continued
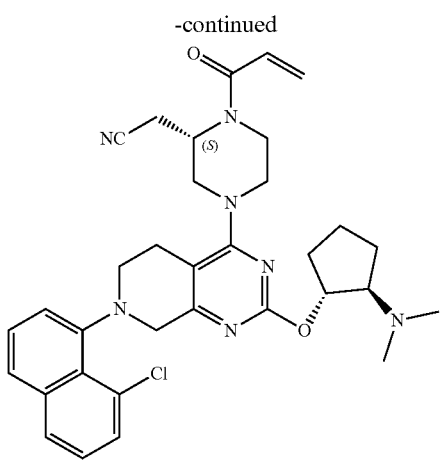
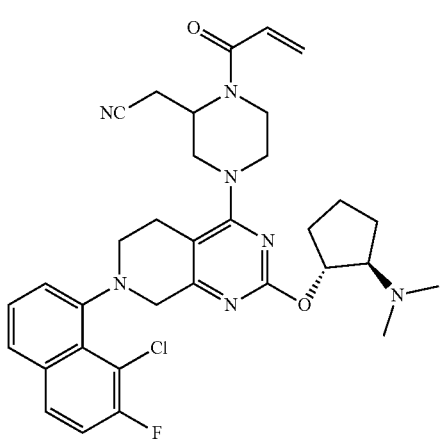
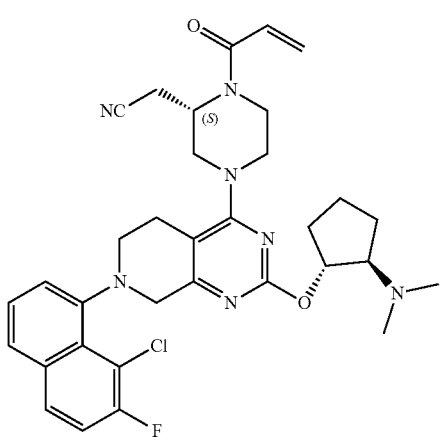
916
-continued
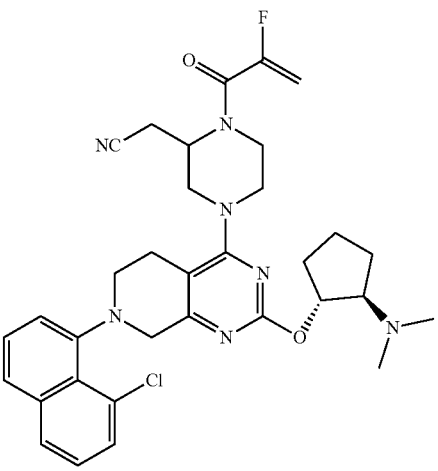
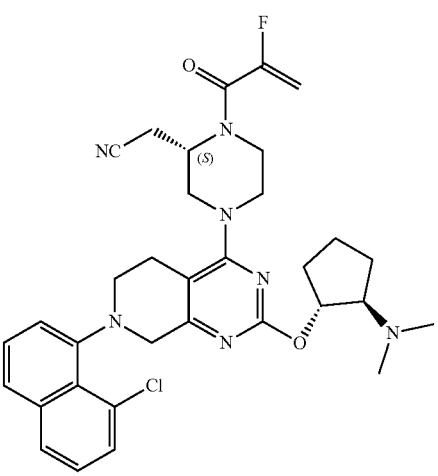

917
-continued
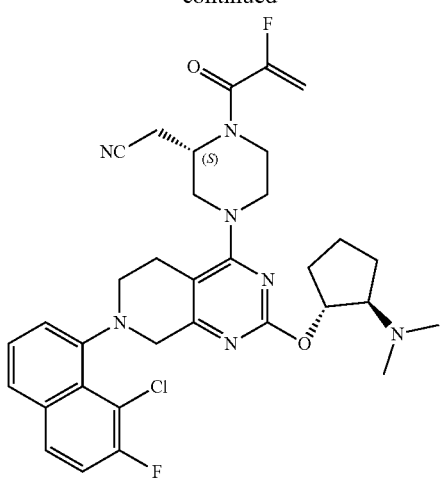
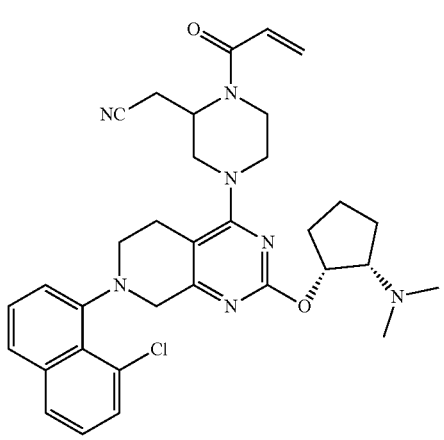
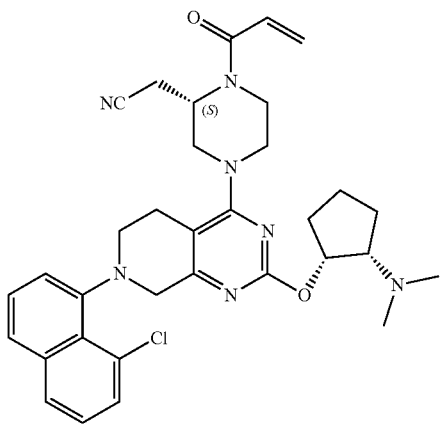
918
-continued
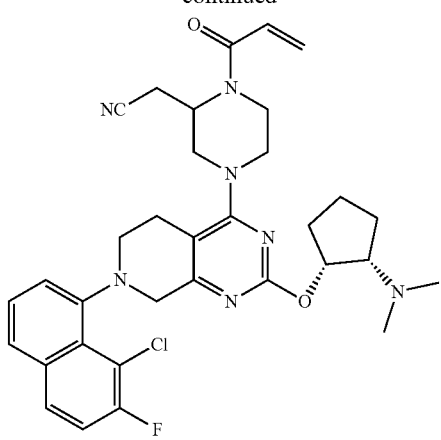
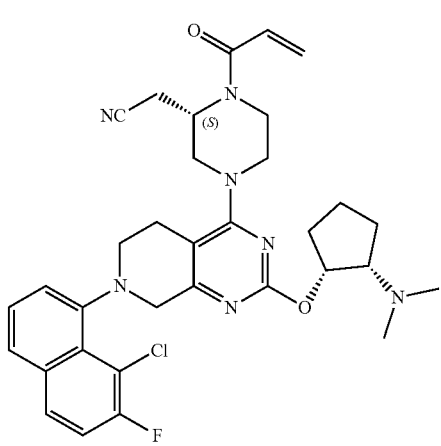
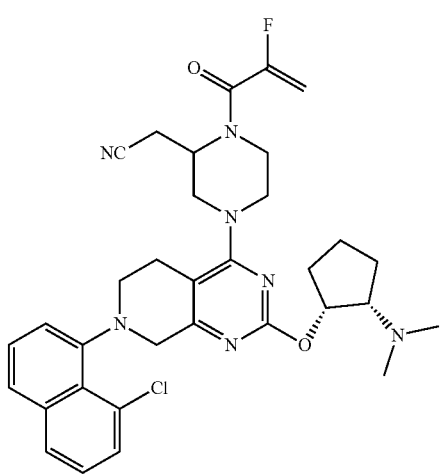

919
-continued
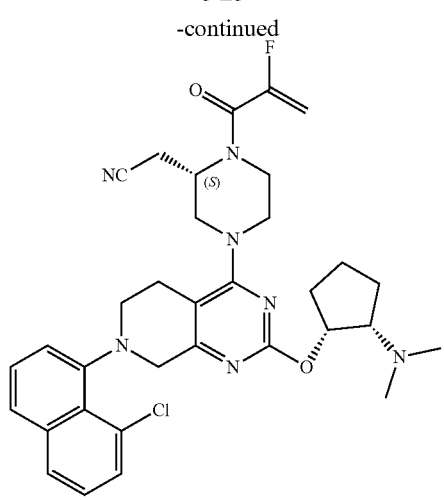
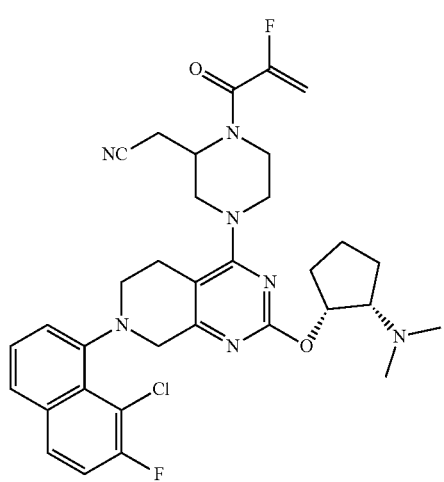
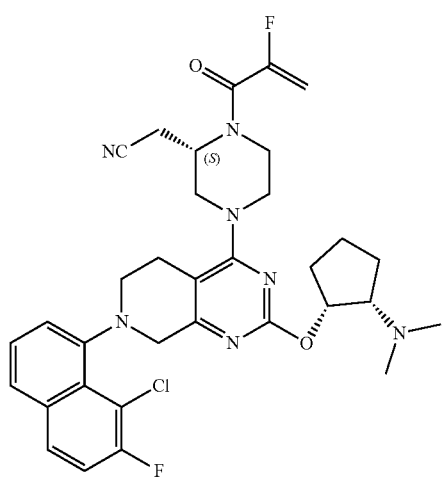
920
-continued
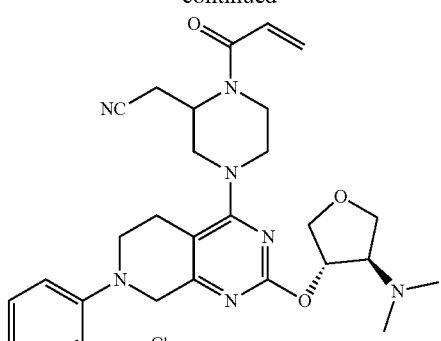
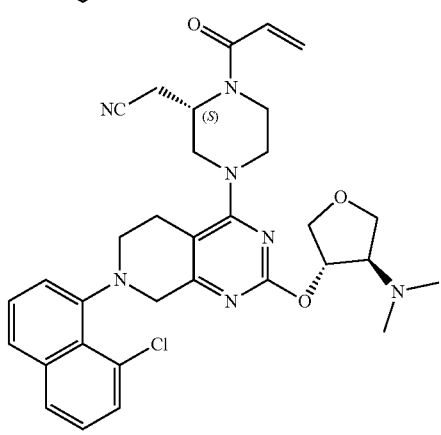
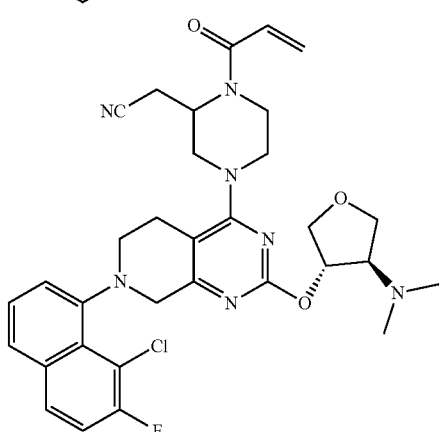

921
-continued
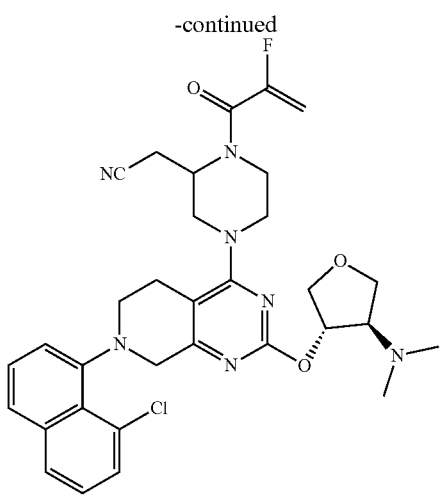
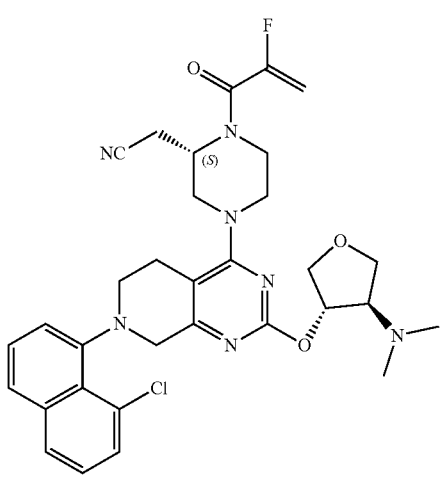
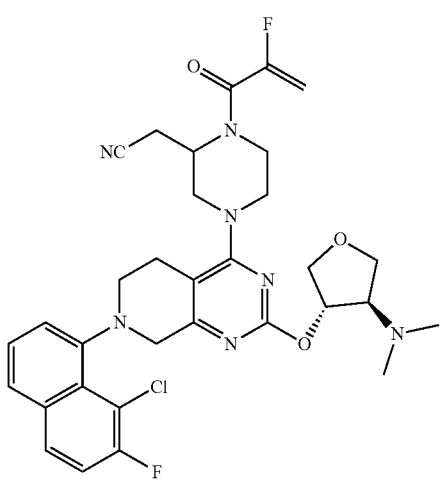
922
-continued
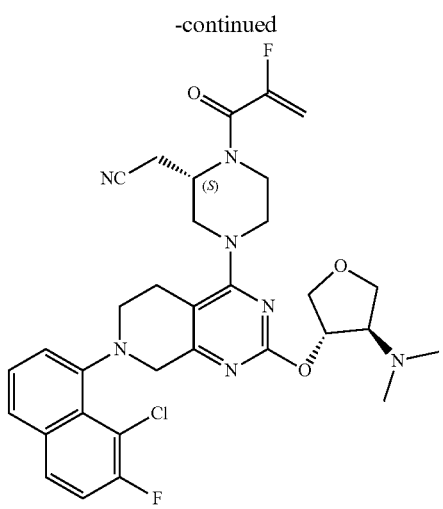
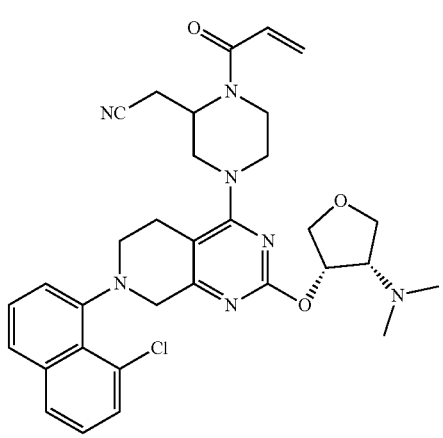
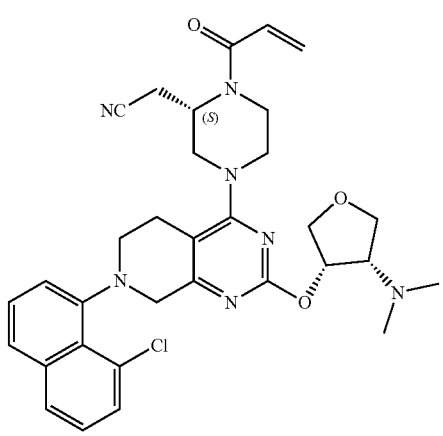

923
-continued
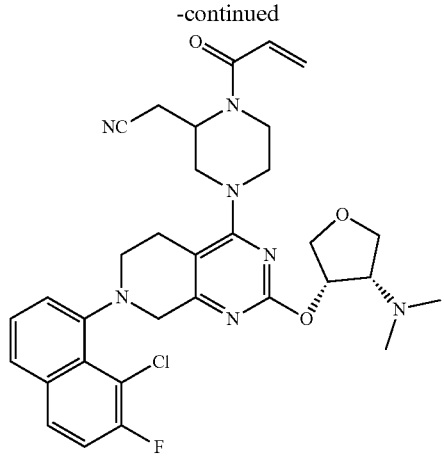
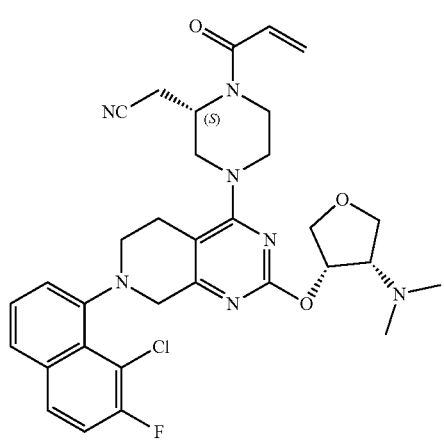
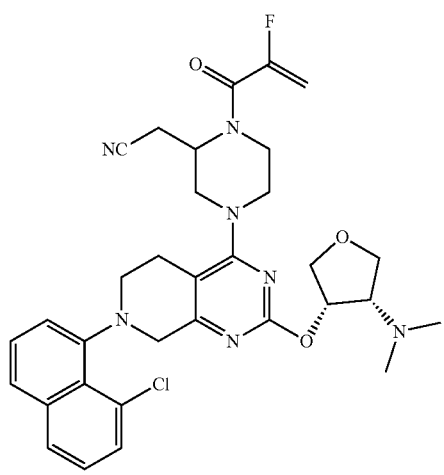
924
-continued
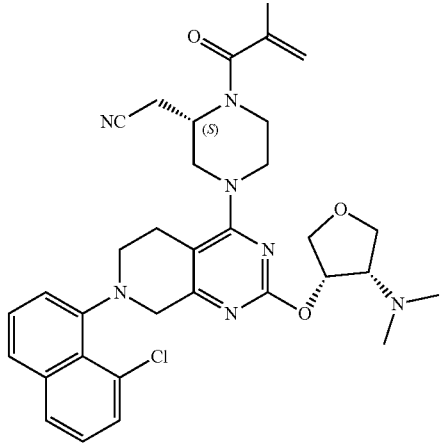
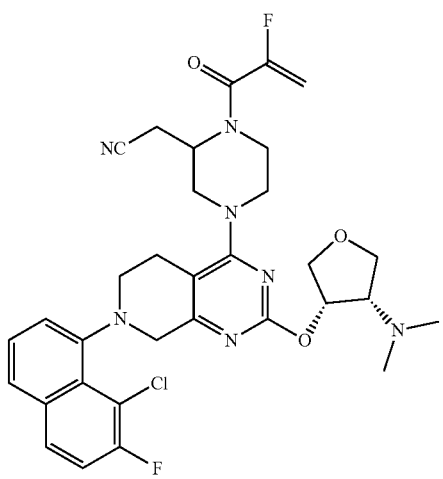
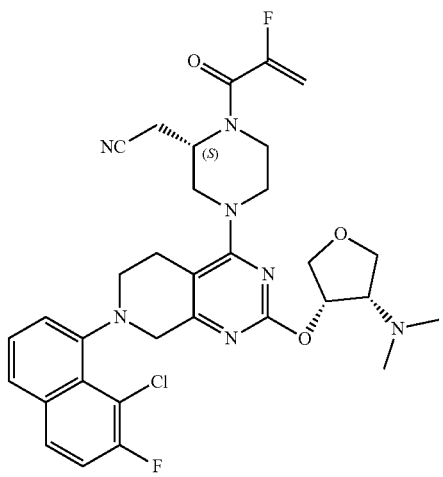

925 -continued 926 -continued
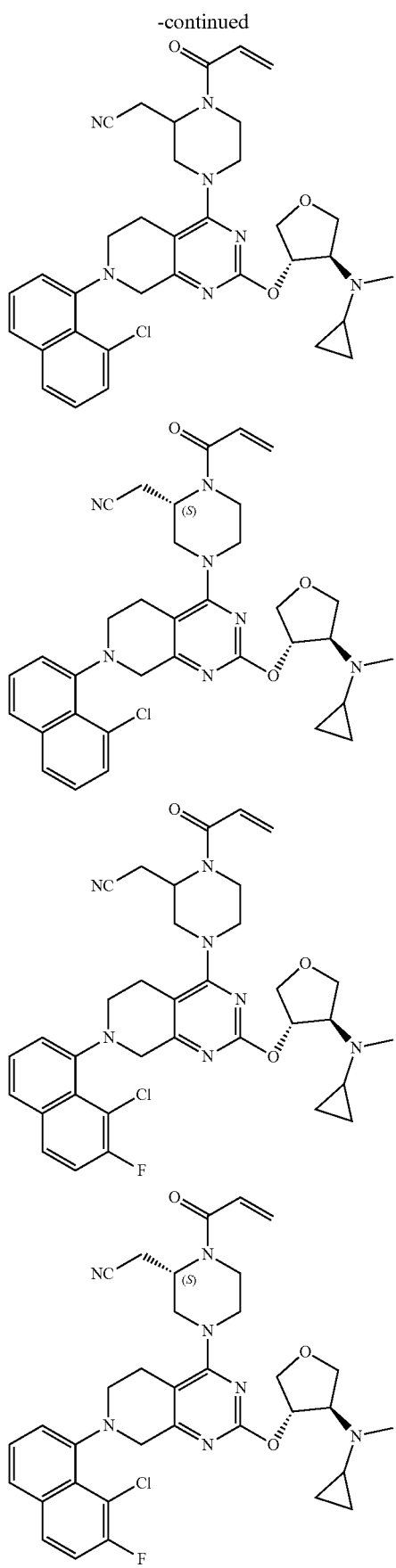

927
-continued
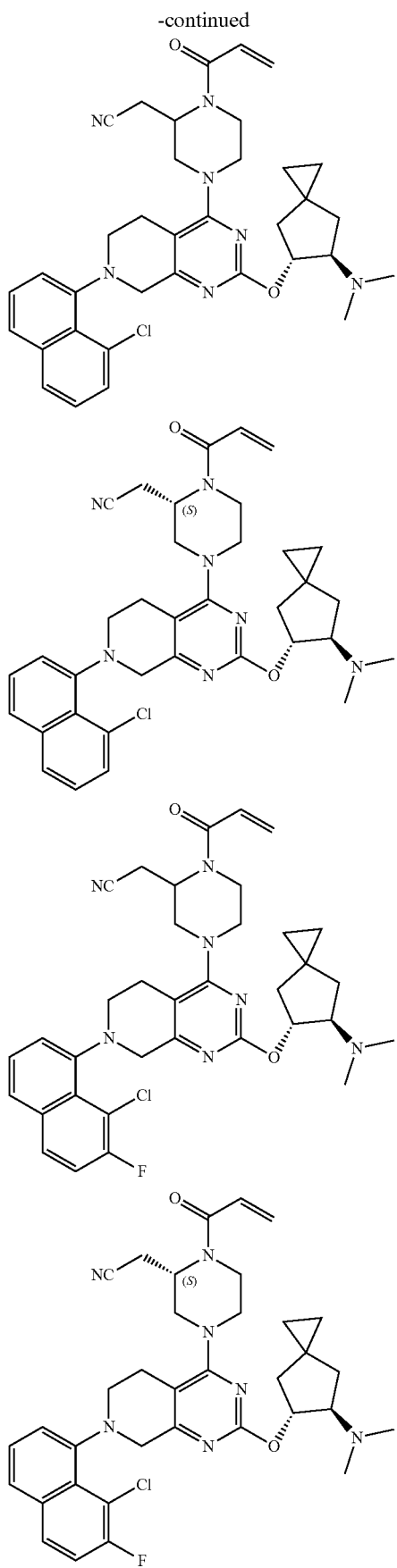
928
-continued
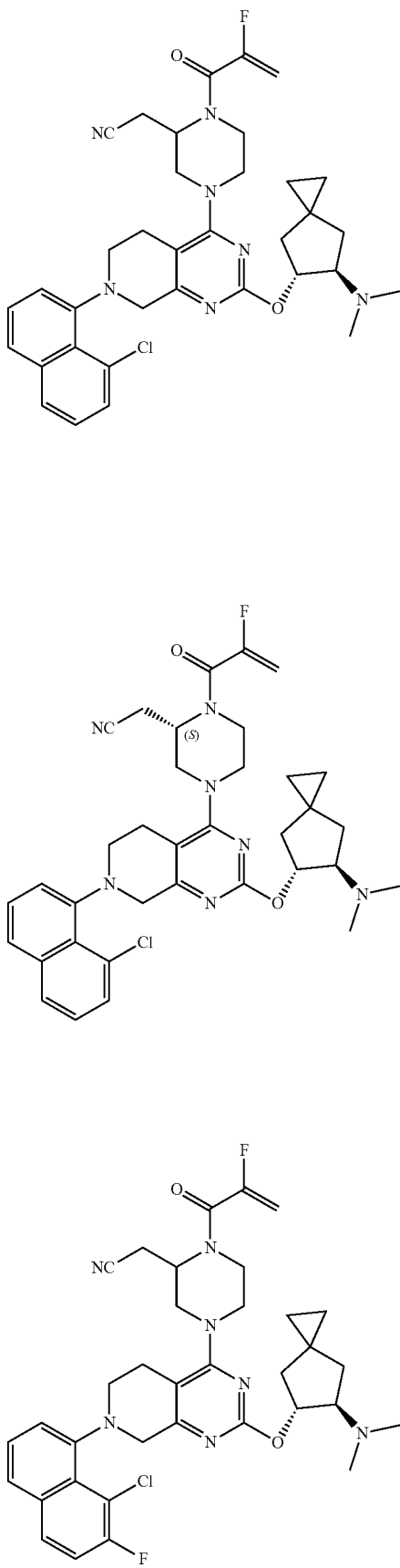

929
-continued
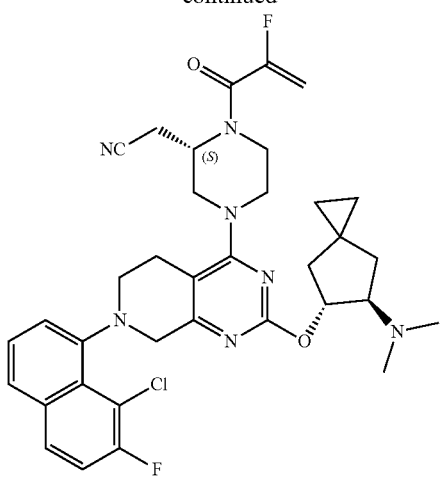
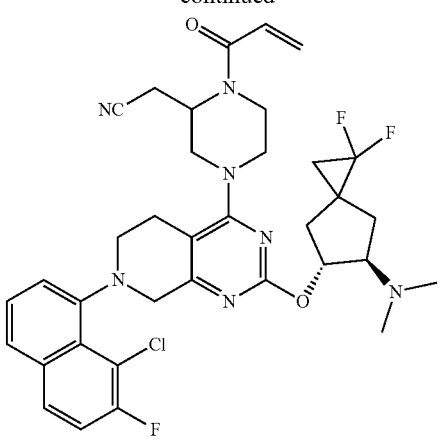
930
-continued
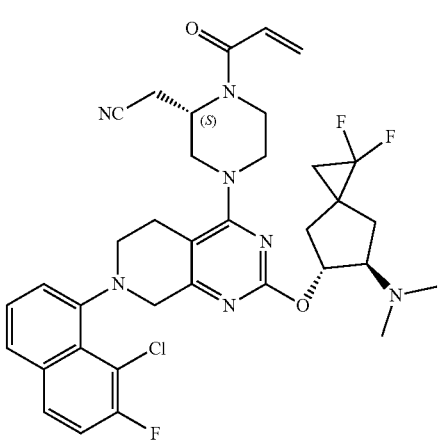
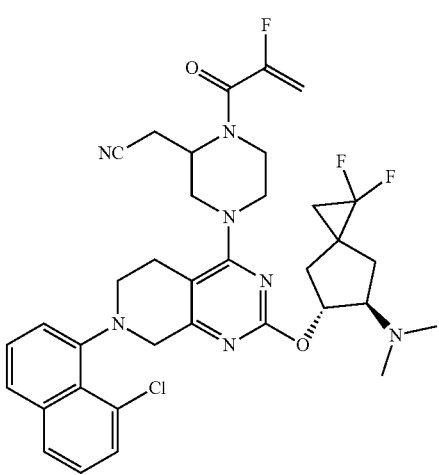

931
-continued
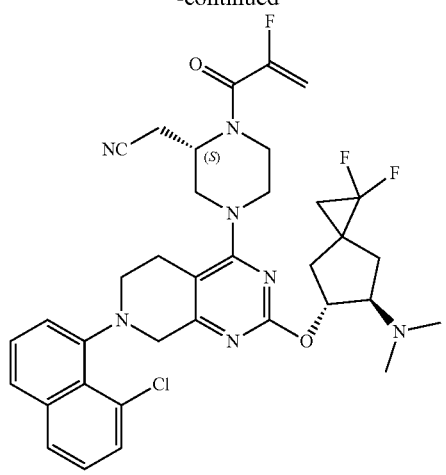
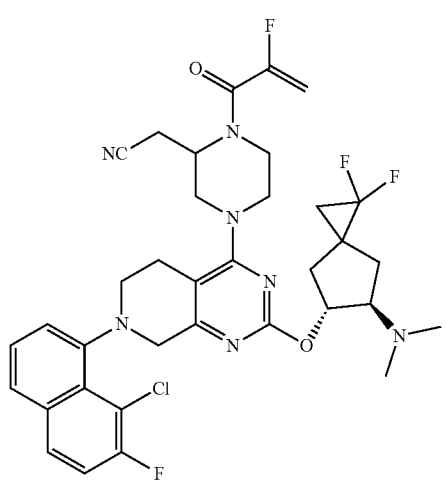
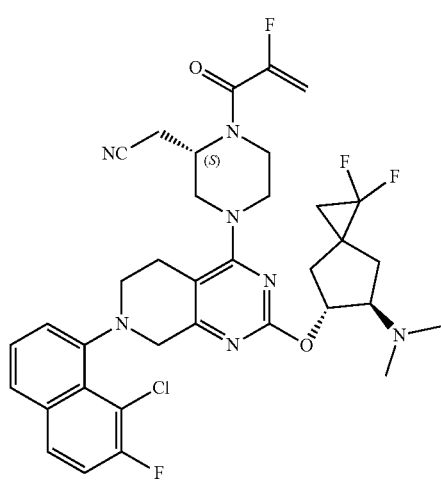
932
-continued
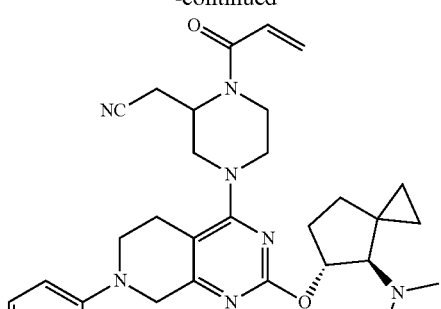
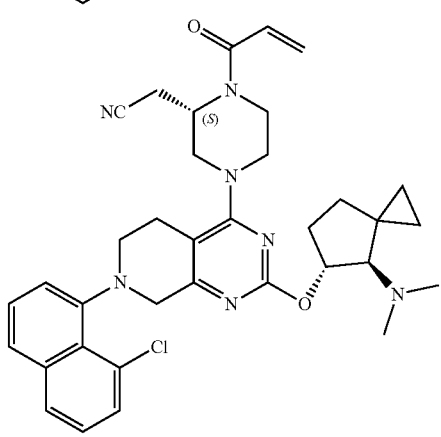
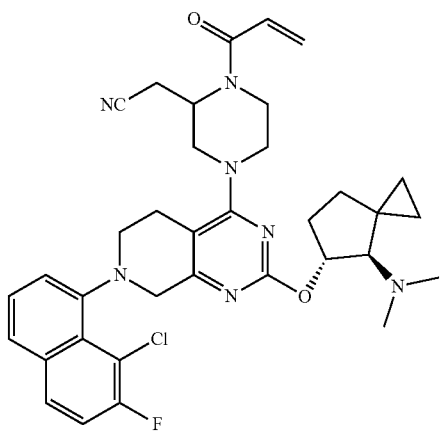
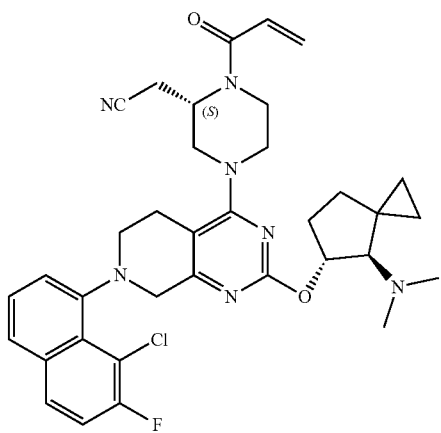

933
-continued
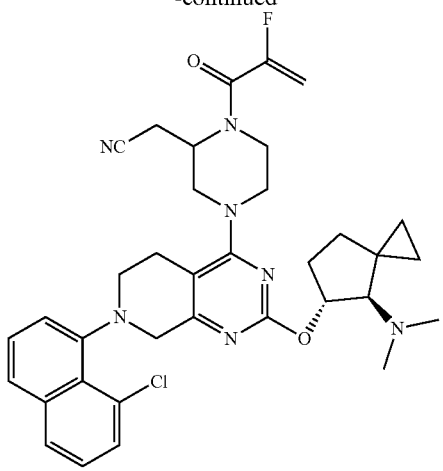
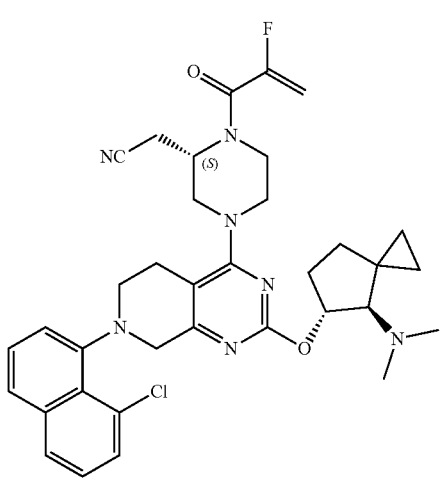
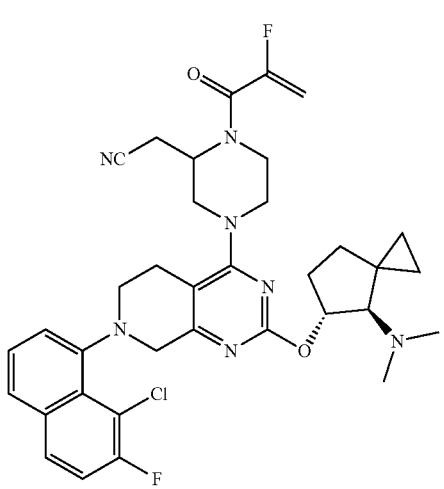
934
-continued
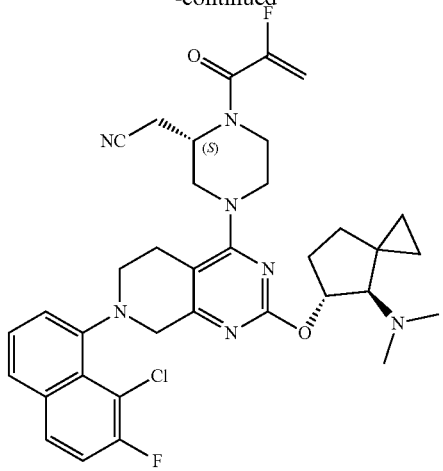
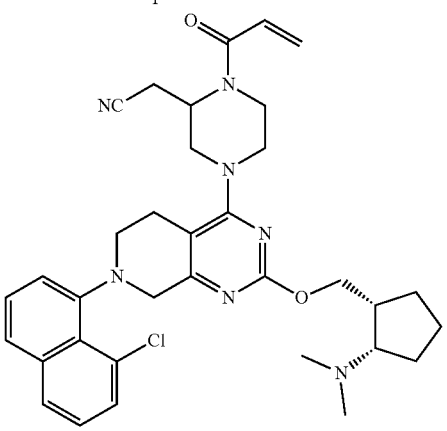
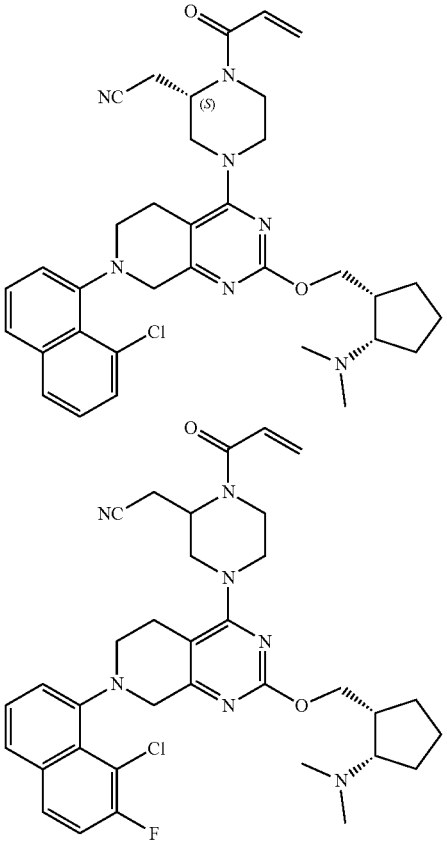

935
-continued
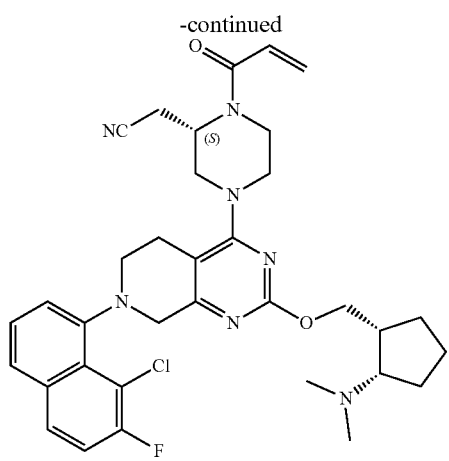
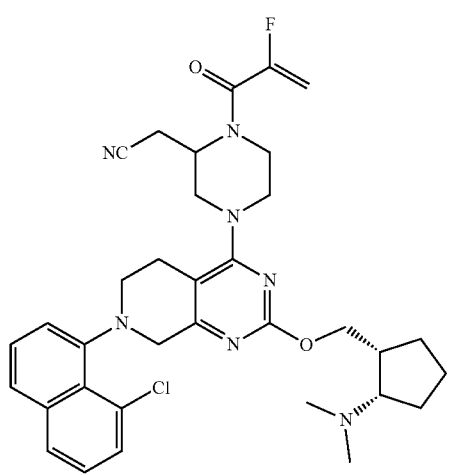
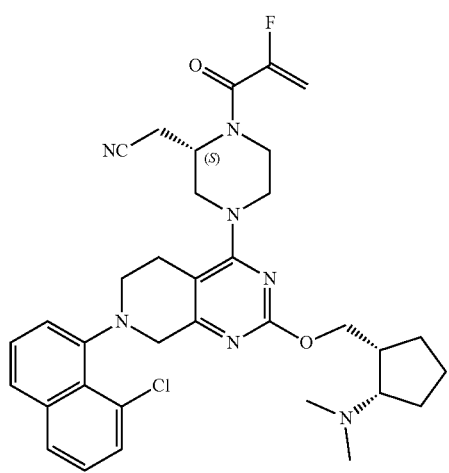
936
-continued
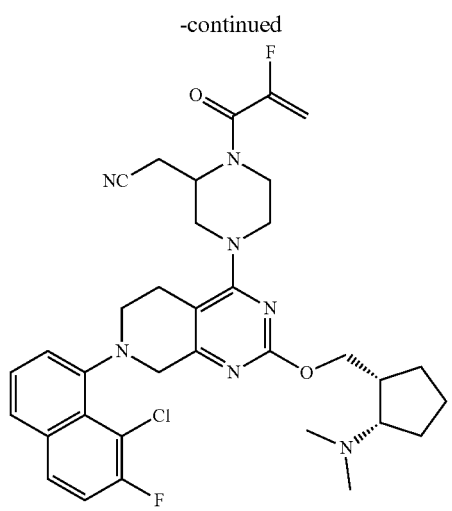
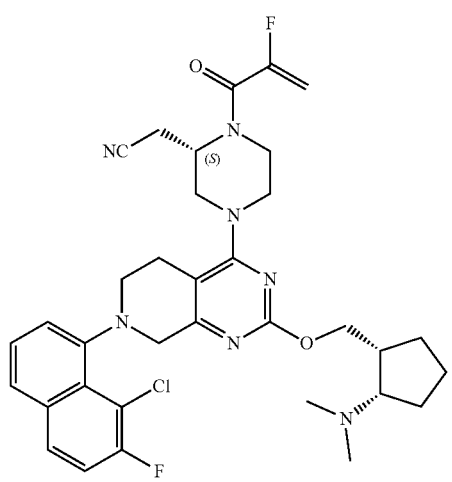
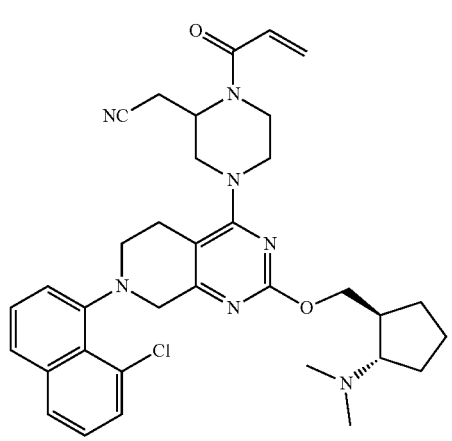

937
-continued

938
-continued

939
-continued
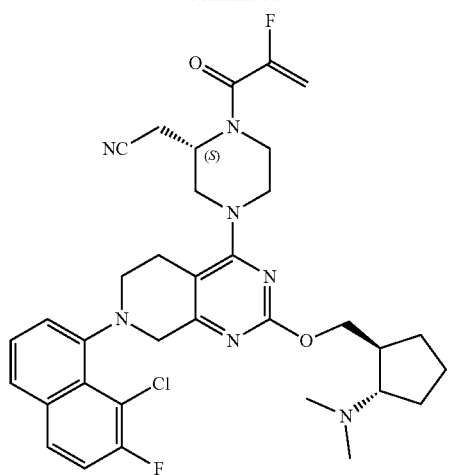
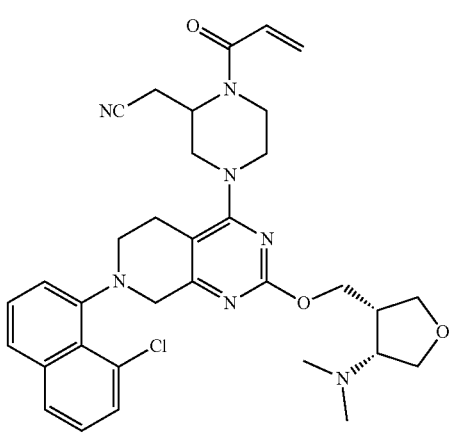
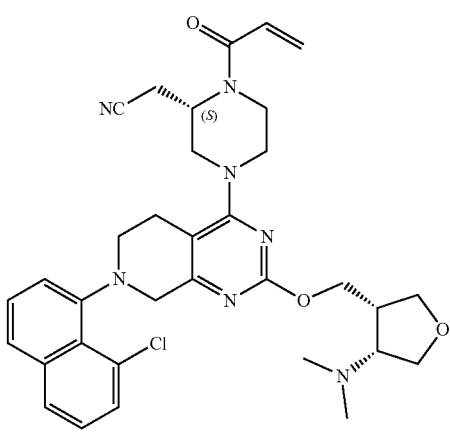
940
-continued
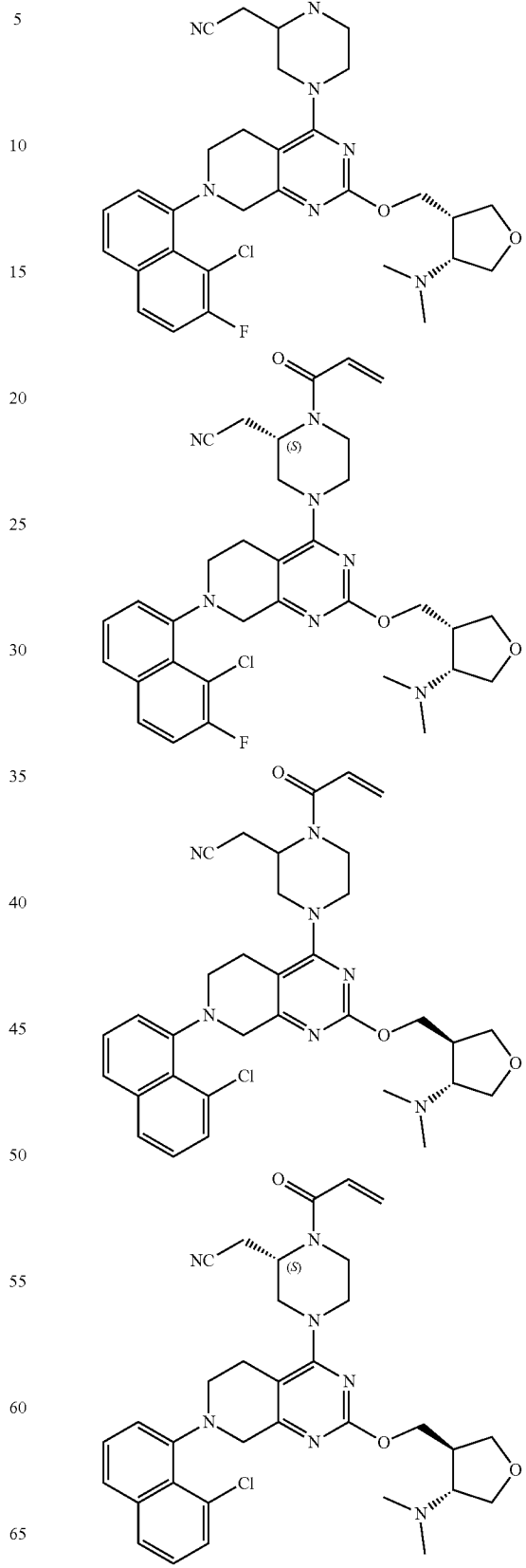

941
-continued
942
-continued
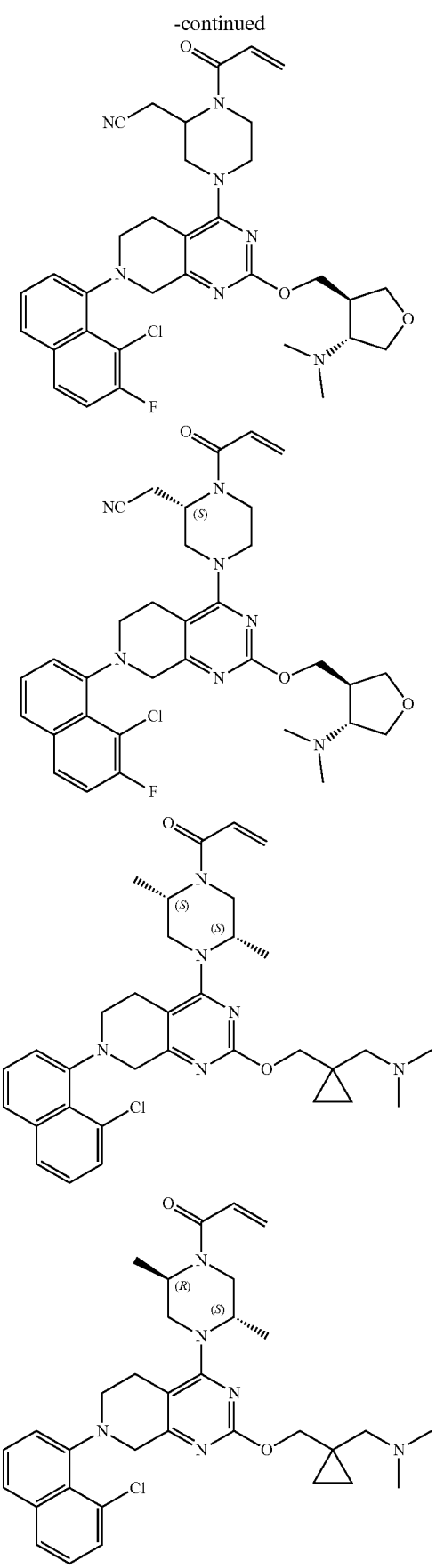
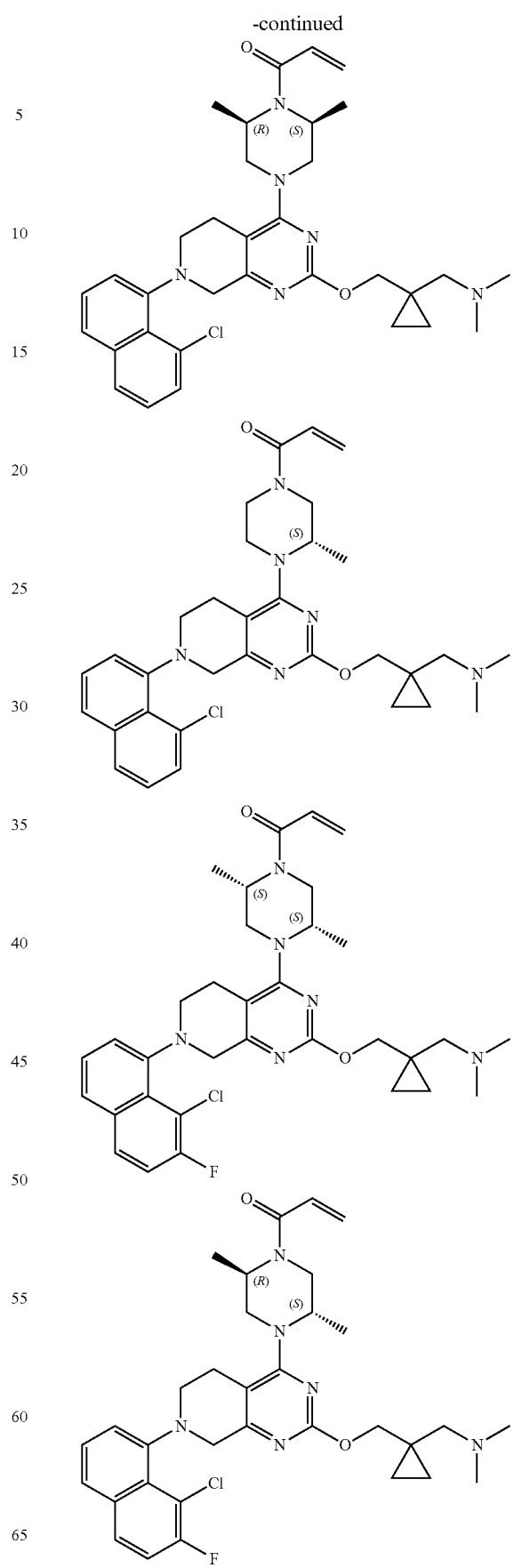

943
-continued
944
-continued
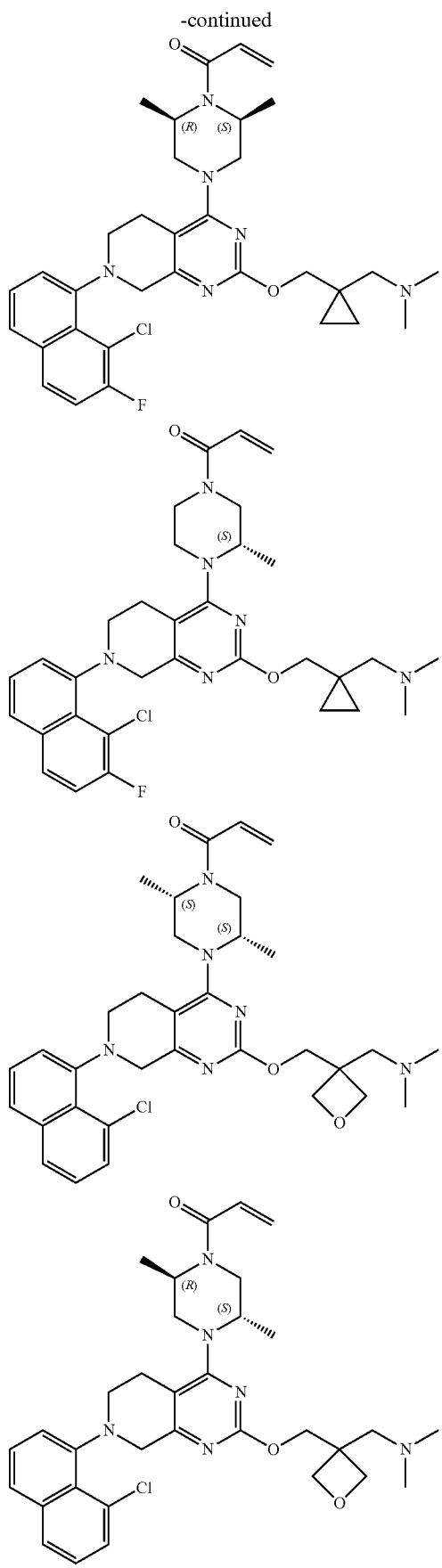
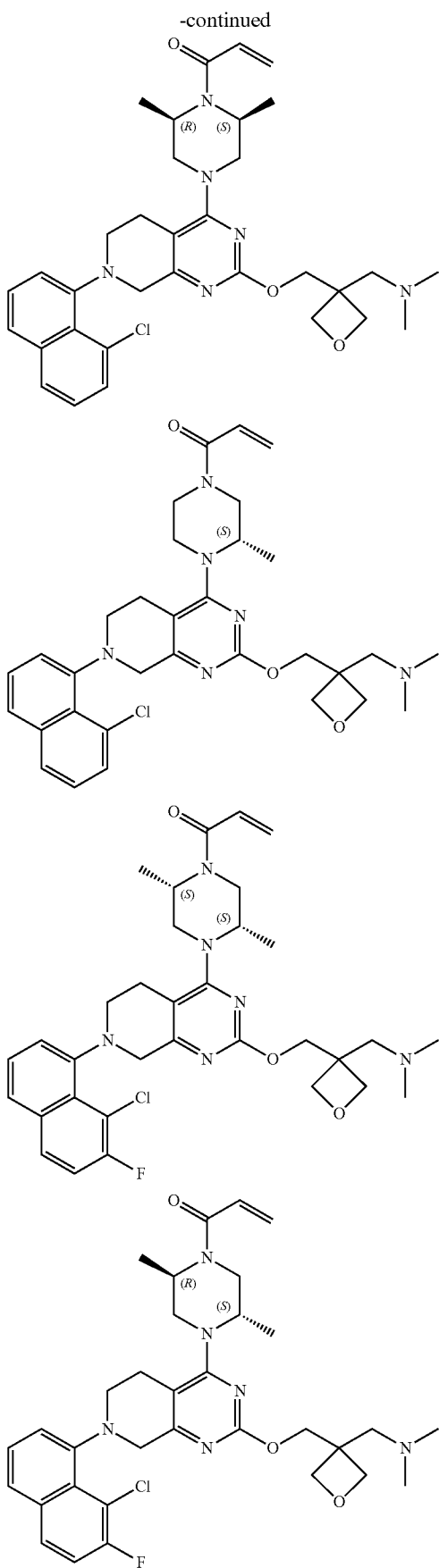

945
-continued
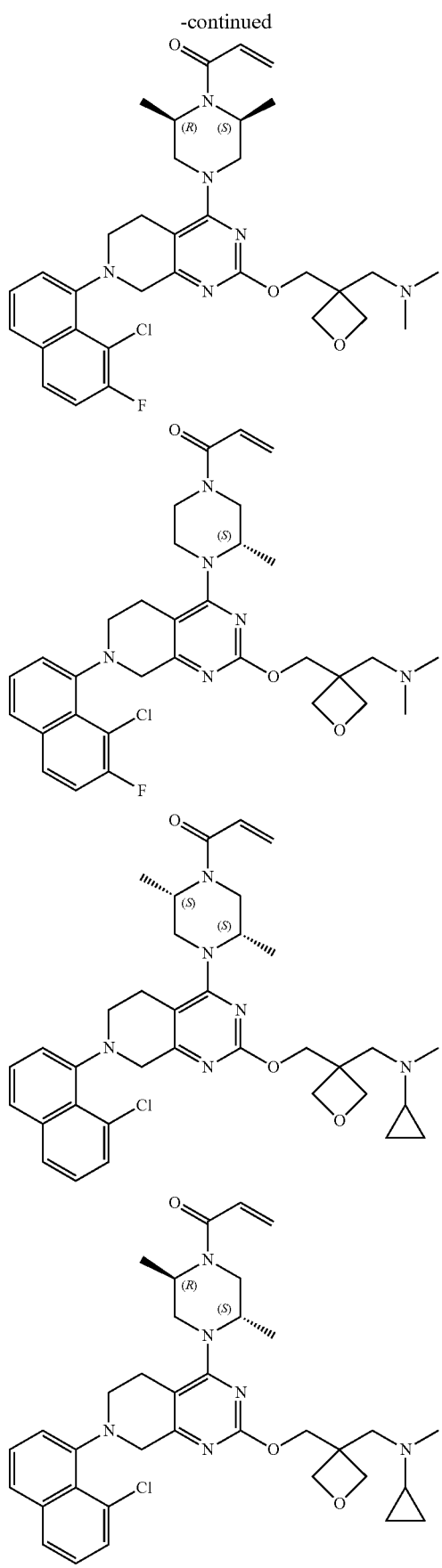
946
-continued
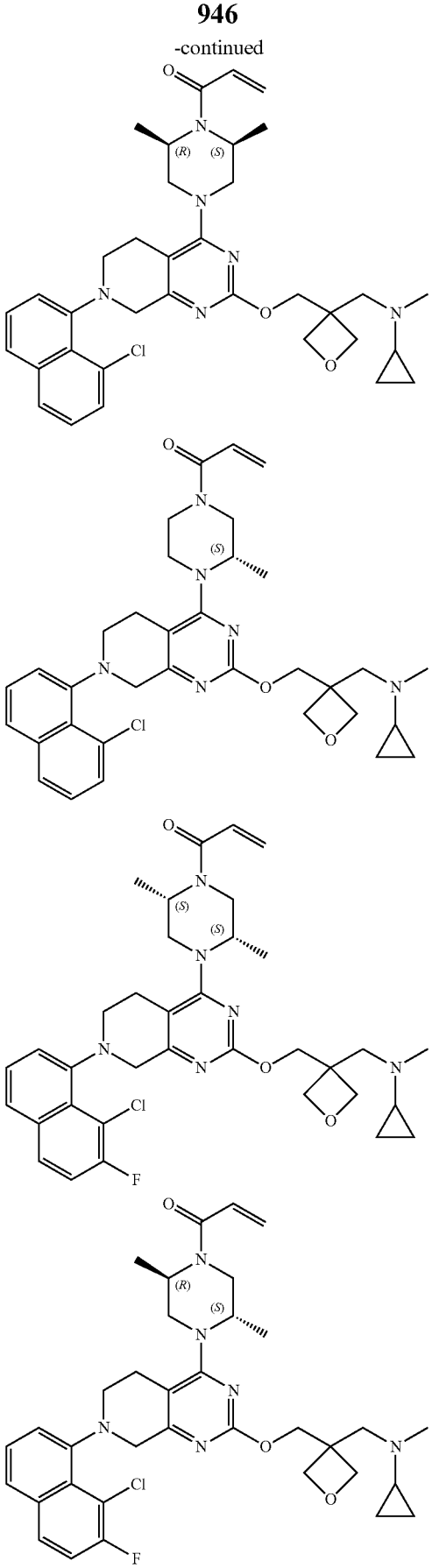

947
-continued
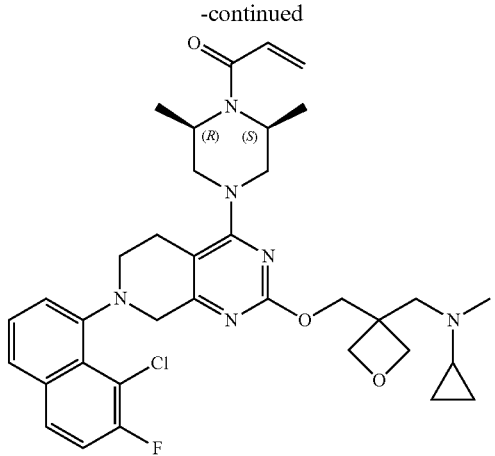
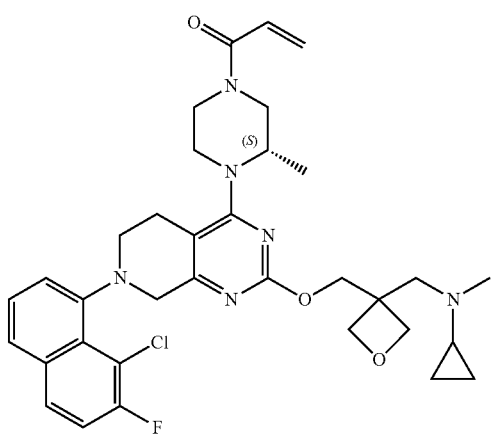
948
-continued
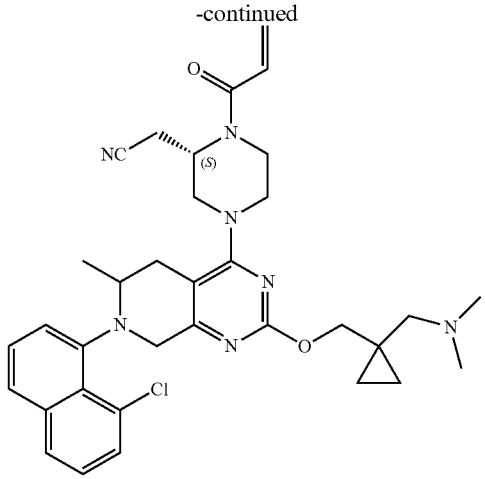
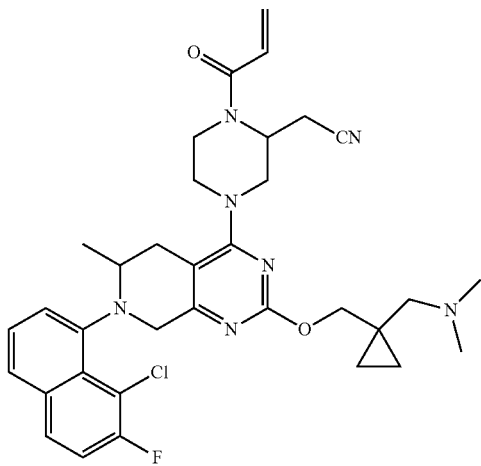
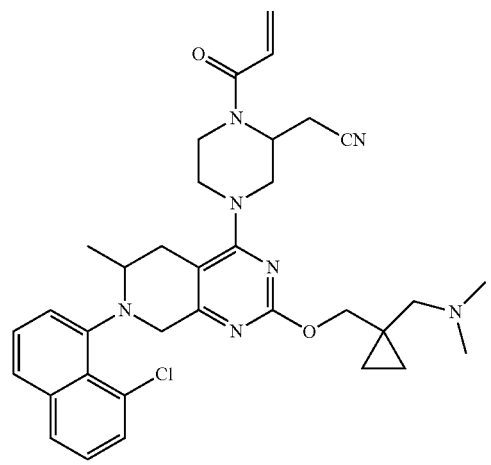
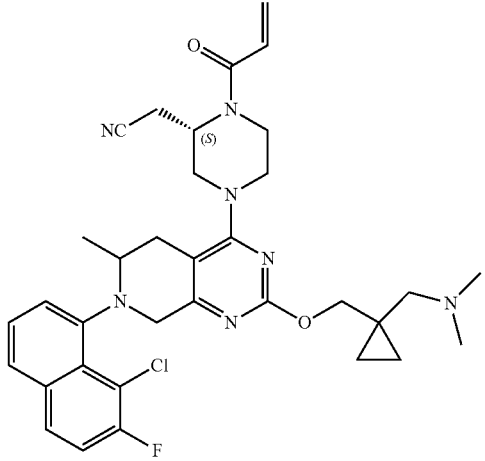

949
-continued
950
-continued
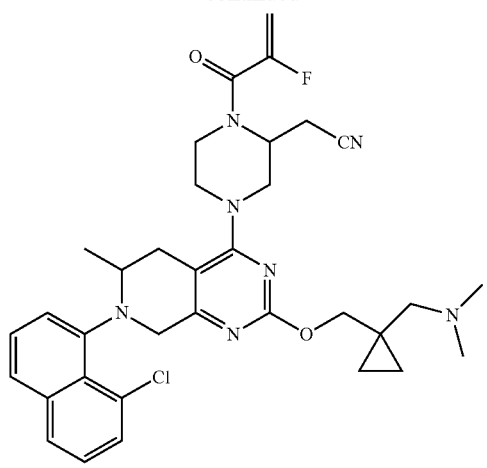
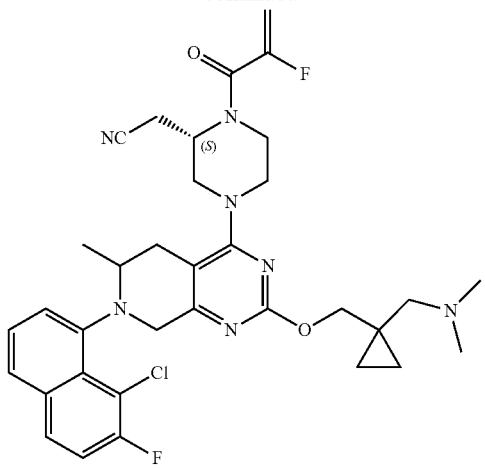
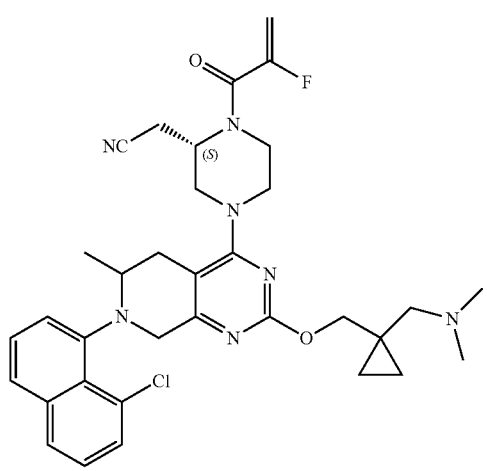
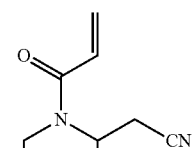
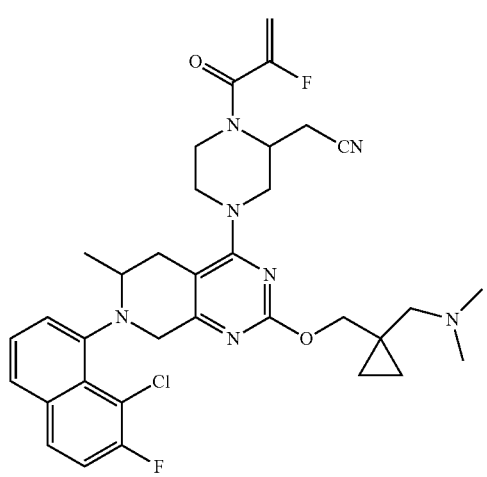
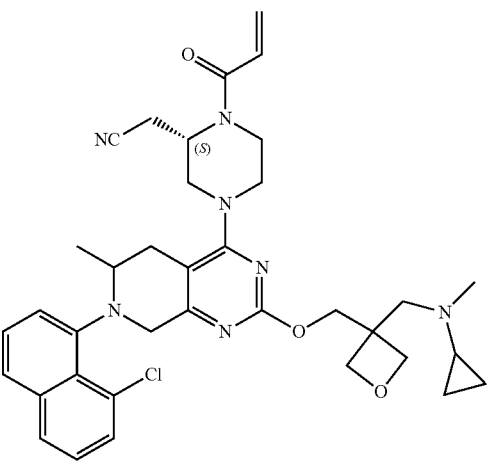

951
-continued
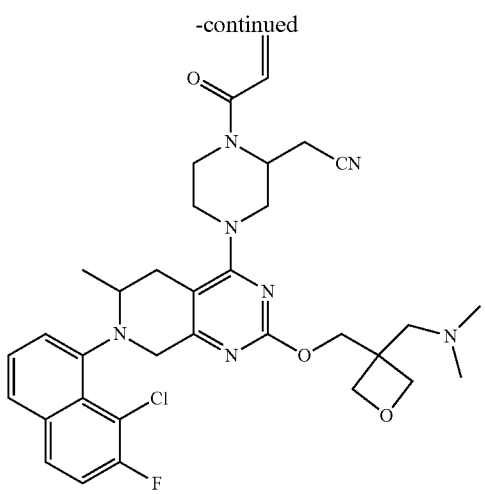
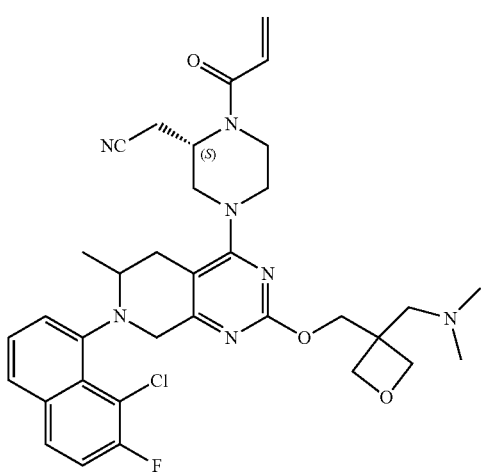
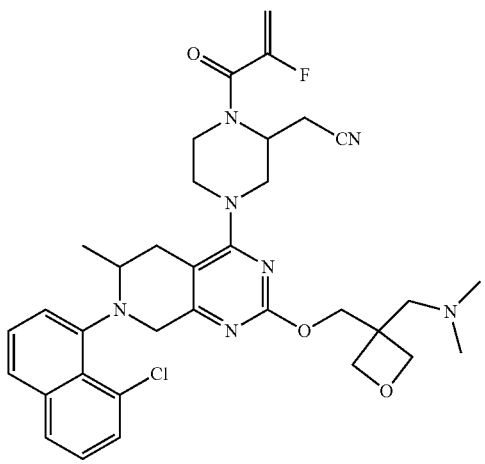
952
-continued
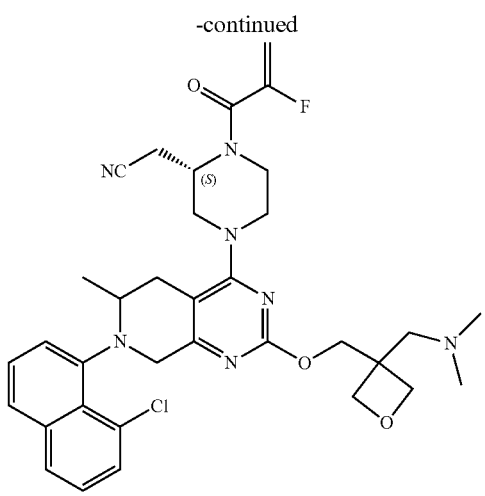
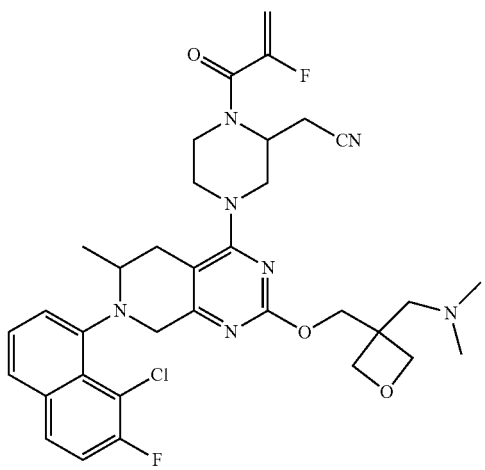
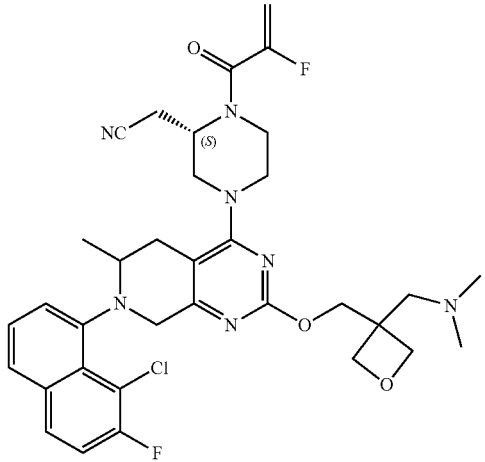

953
-continued
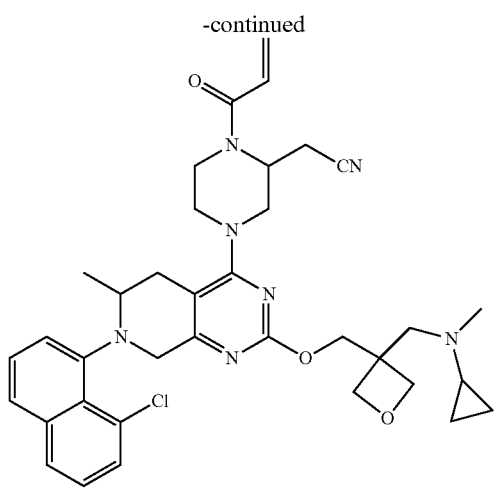
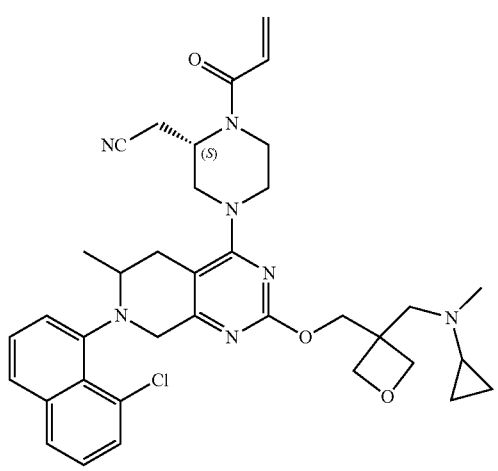
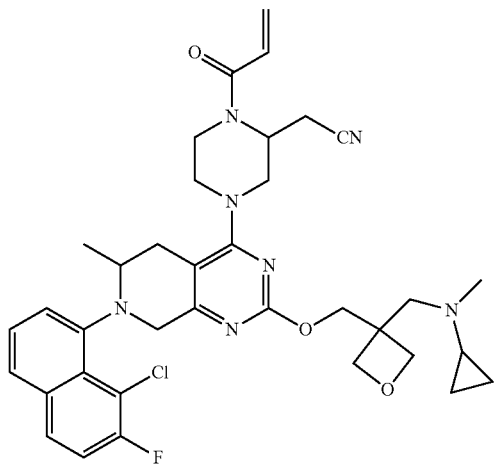
954
-continued
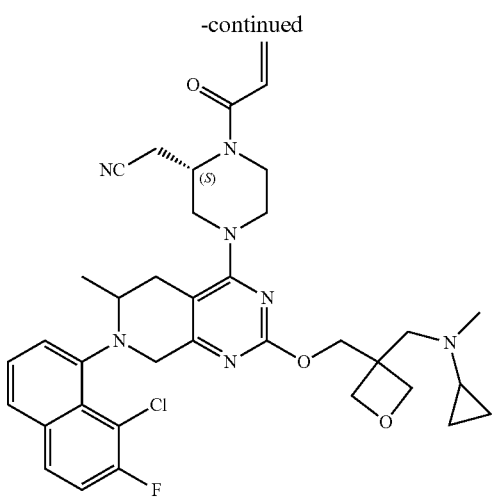
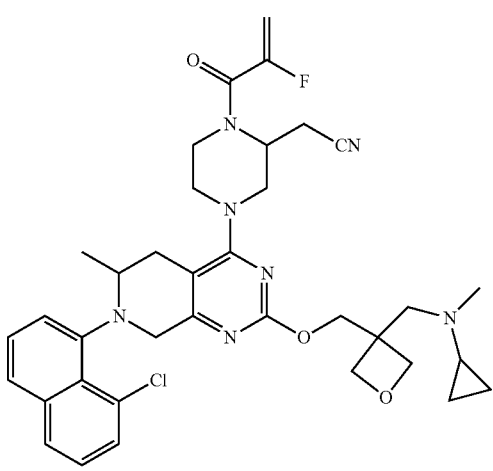
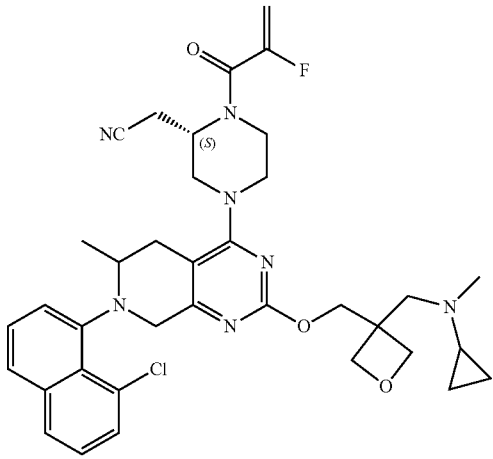

| 955 -continued | 956 -continued |
|---|---|
| 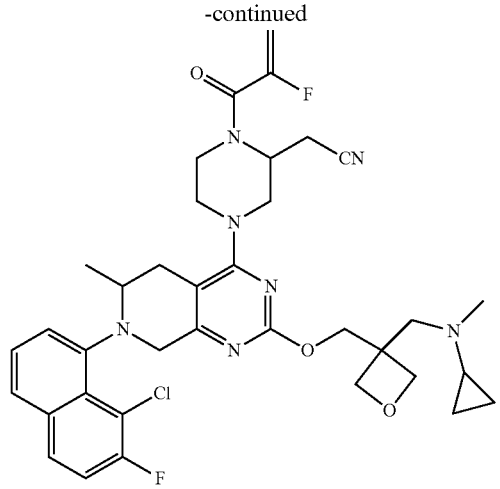 | 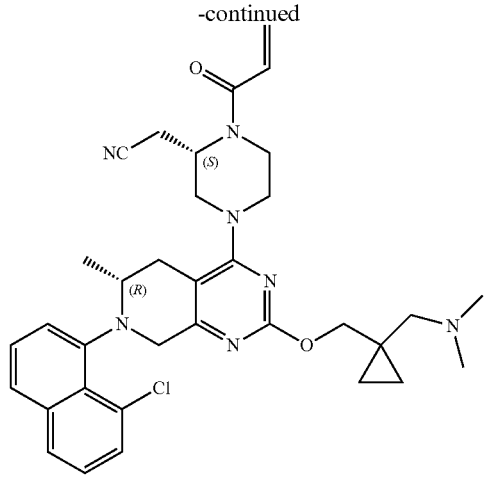 |
| 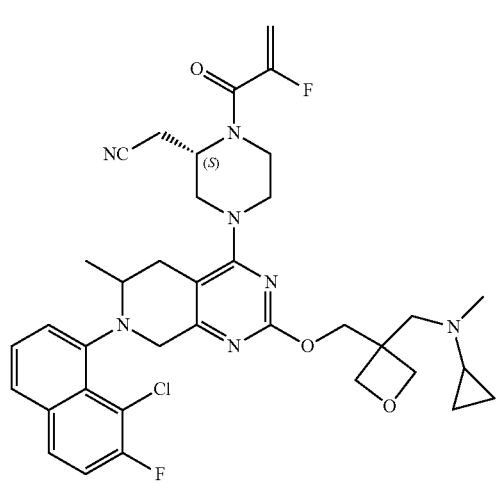 | 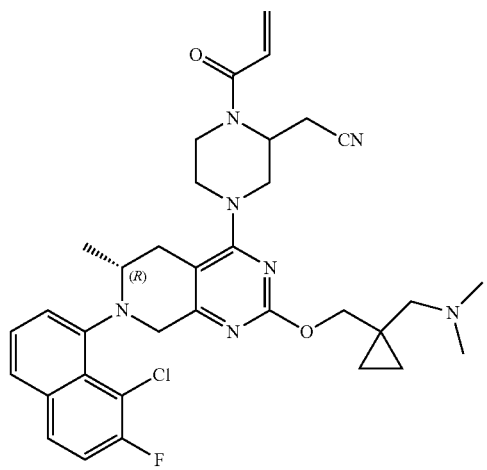 |
| 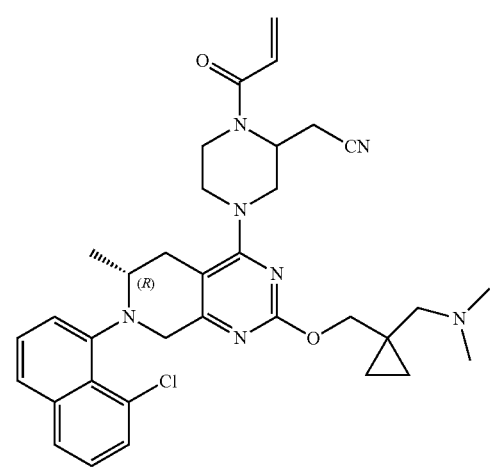 | 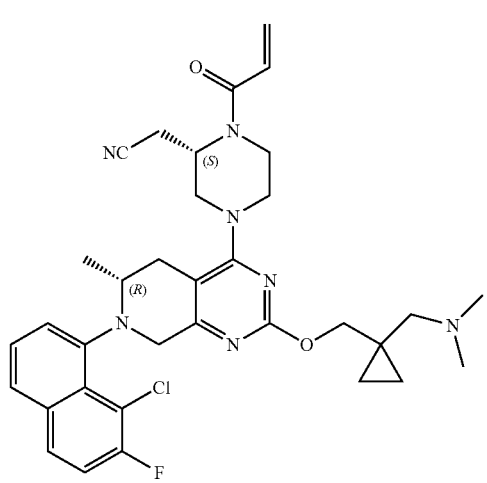 |

957
-continued
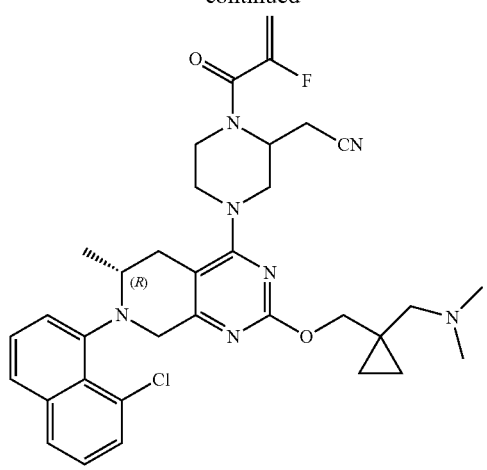
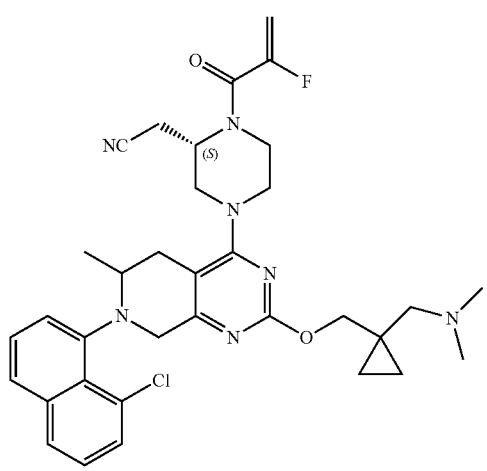
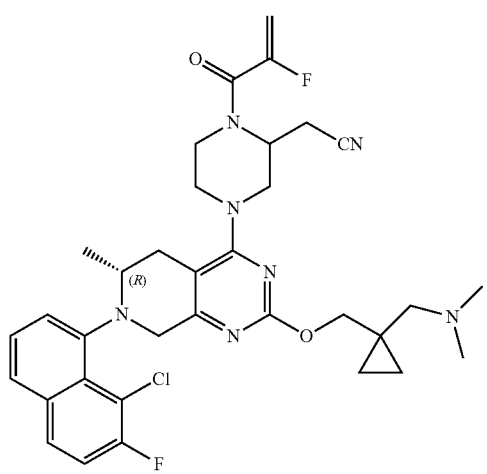
958
-continued
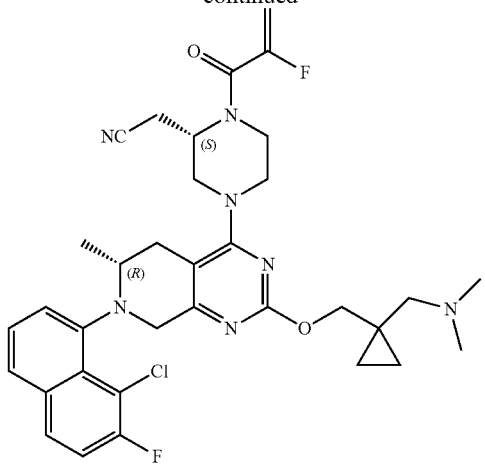
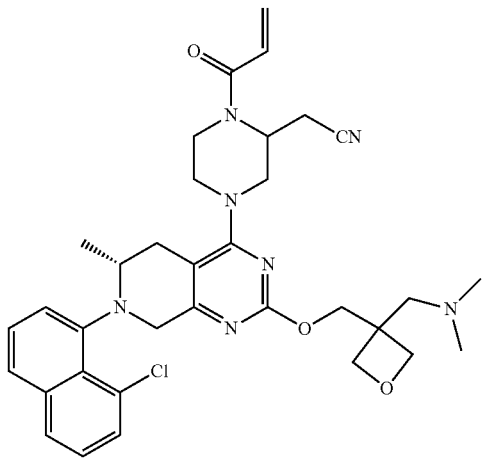
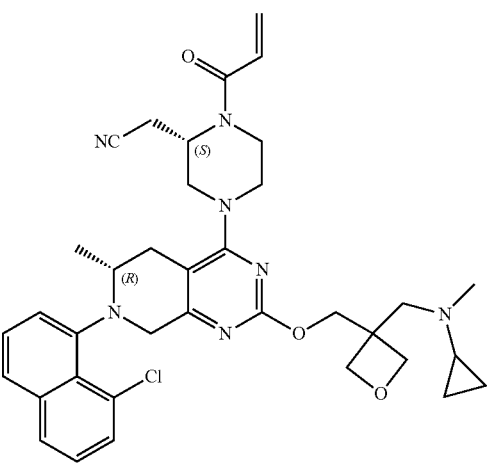

959
-continued
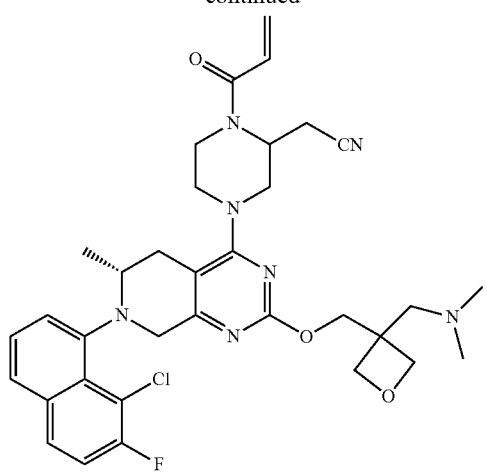
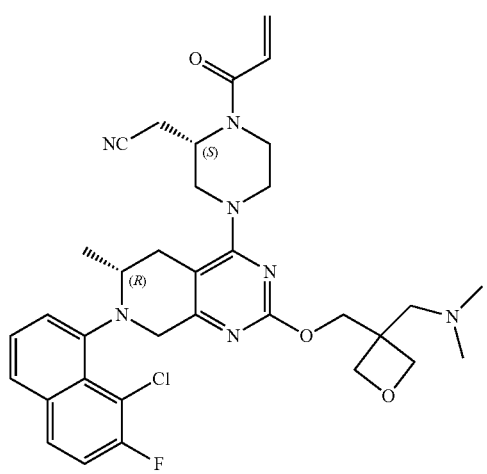
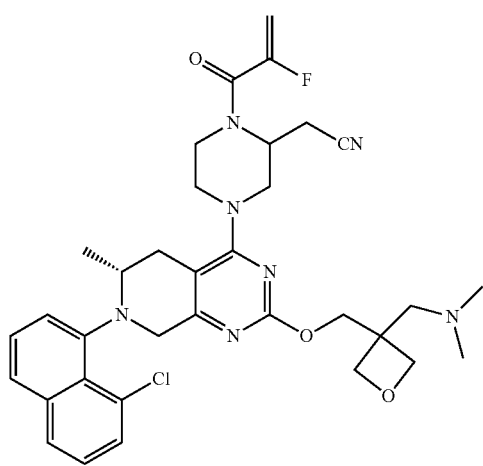
960
-continued
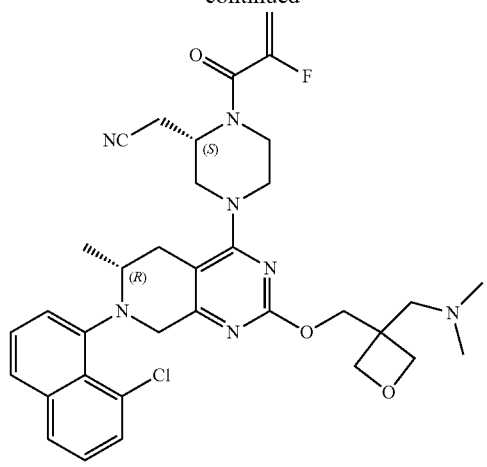
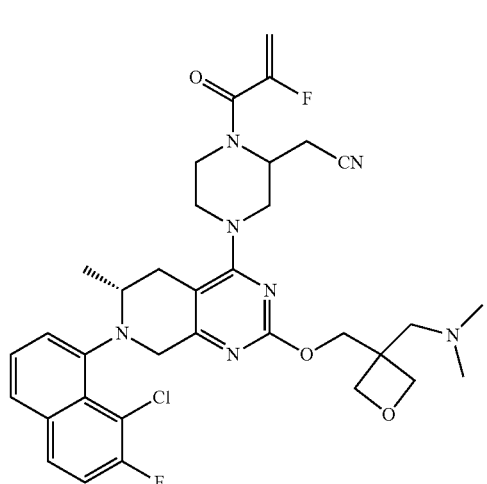
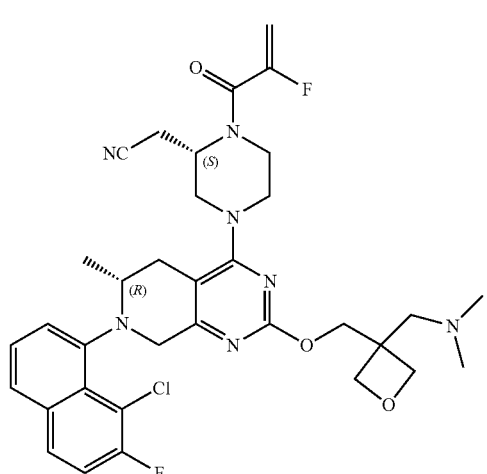

961
-continued
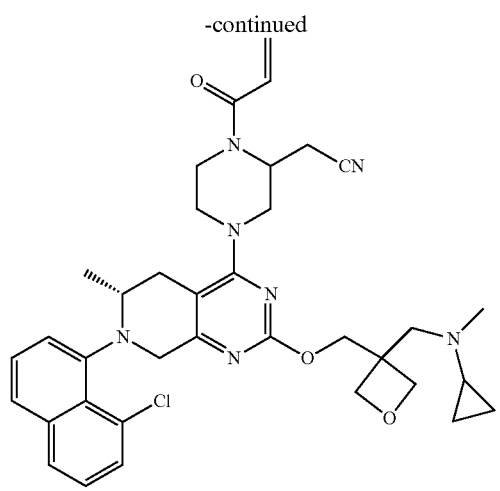
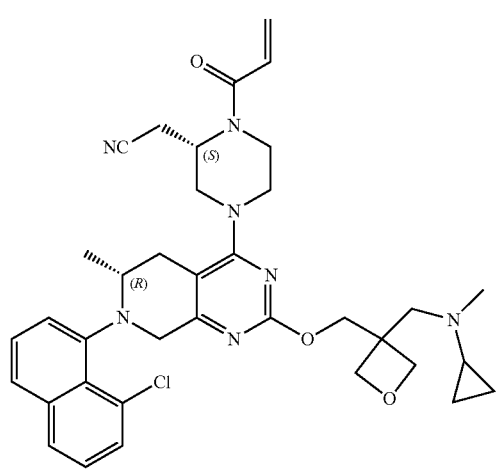
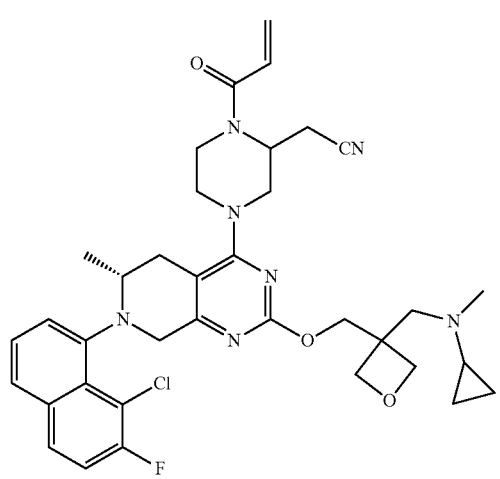
962
-continued
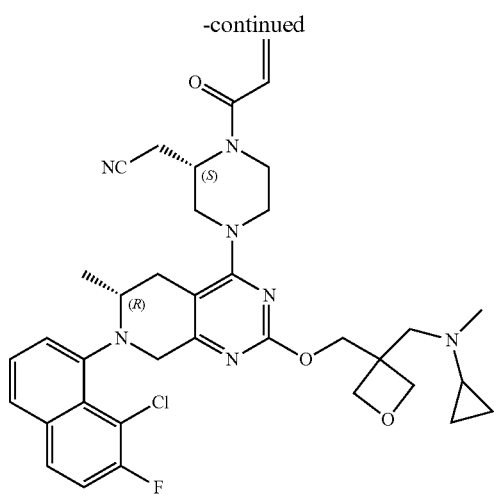
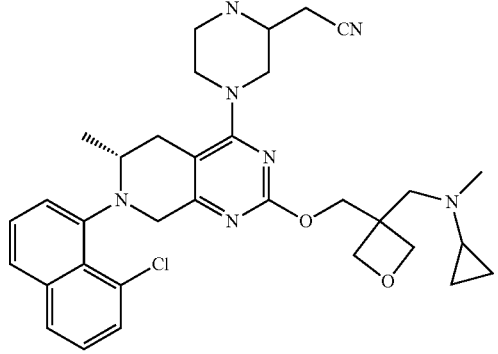
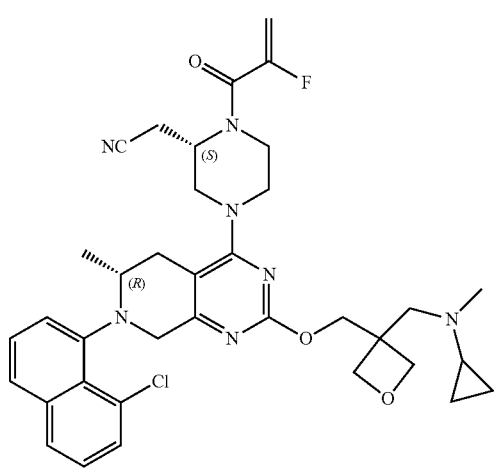

963
-continued
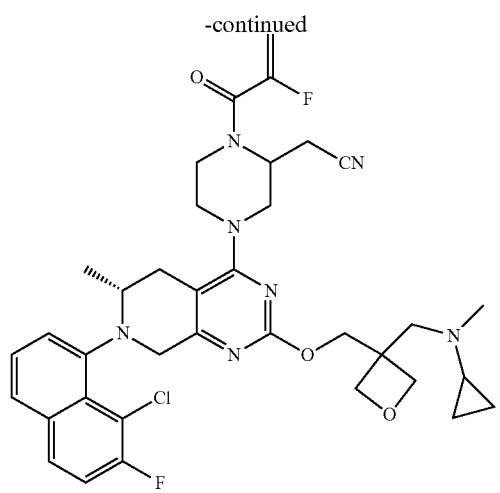
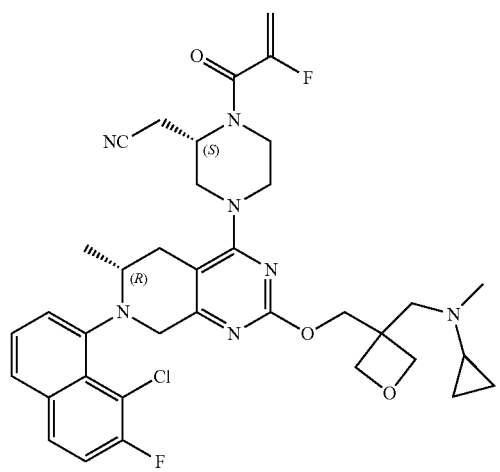
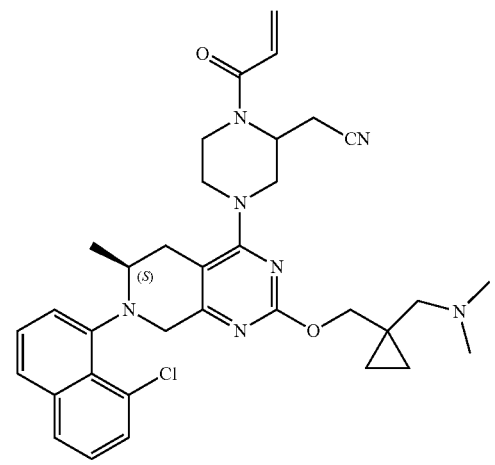
964
-continued
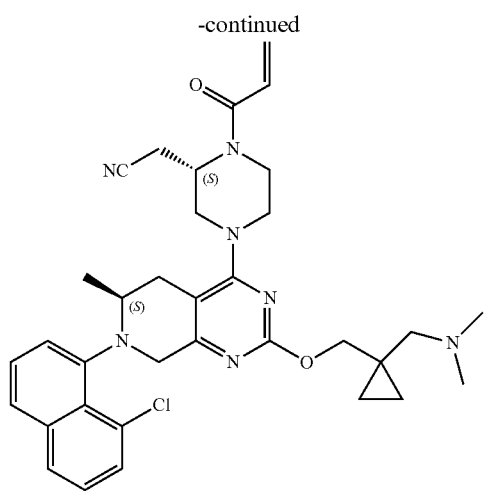
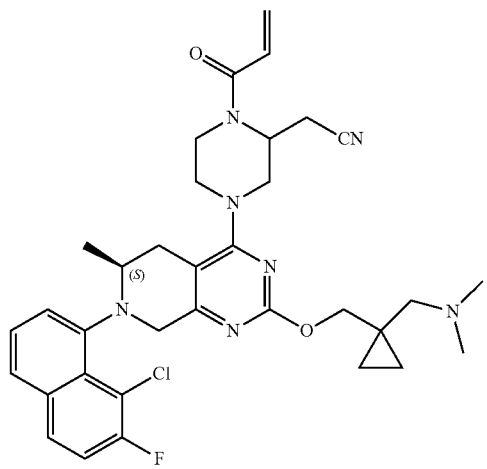
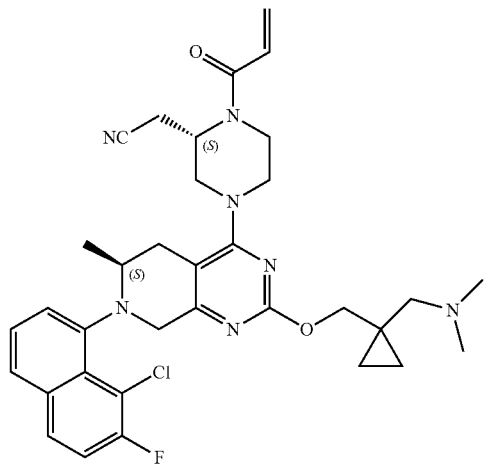

965
-continued
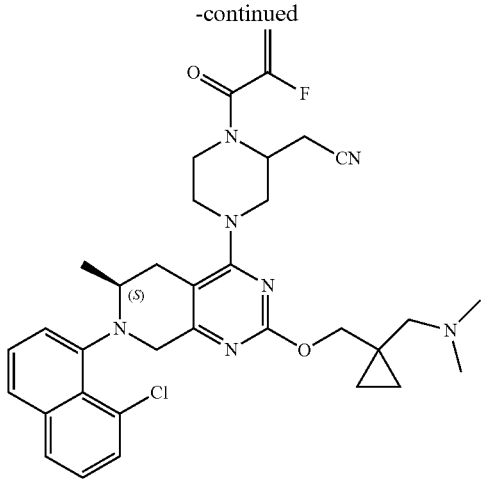
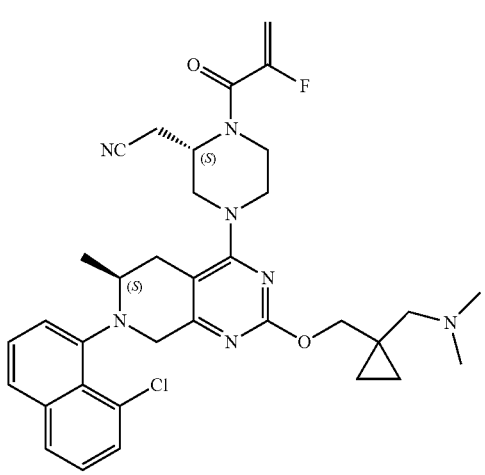
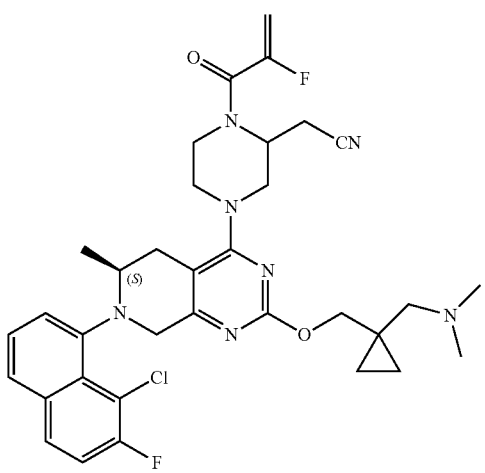
966
-continued
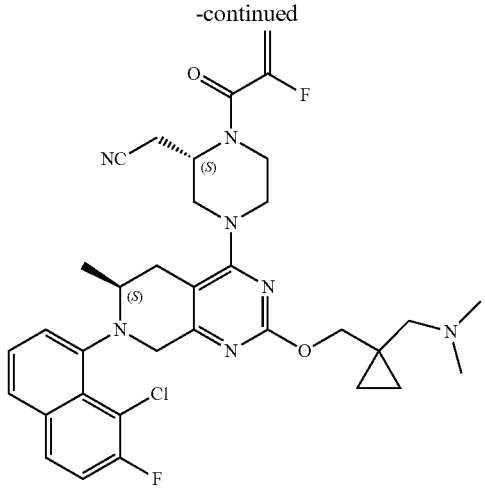
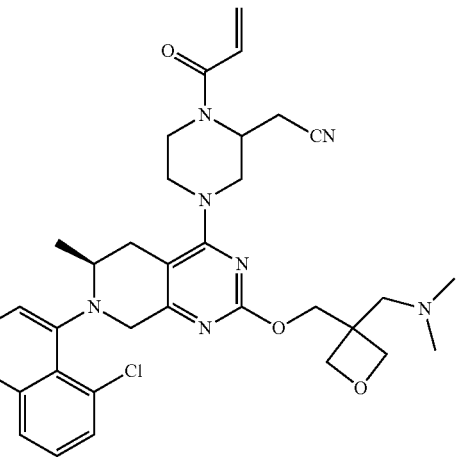
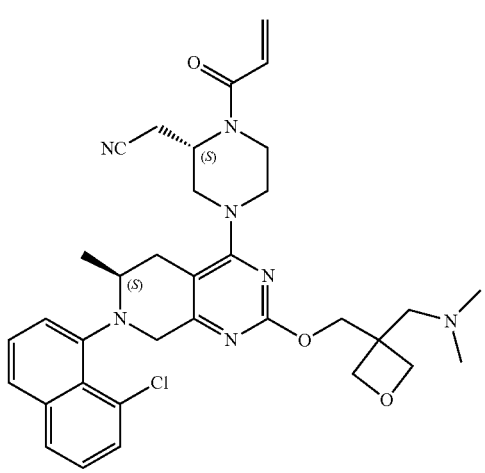

| 967 -continued | 968 -continued |
|---|---|
| 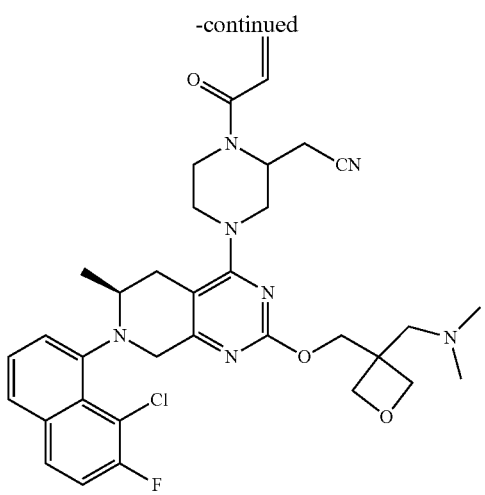 | 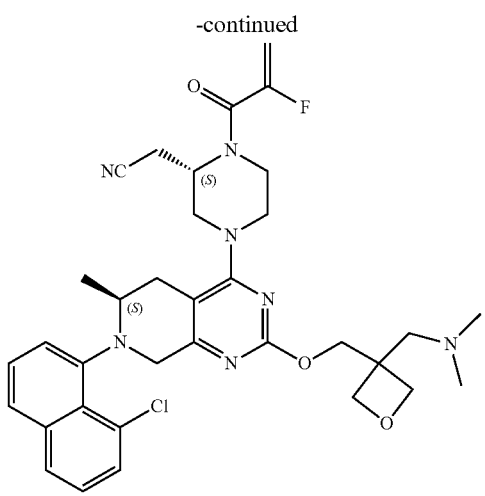 |
| 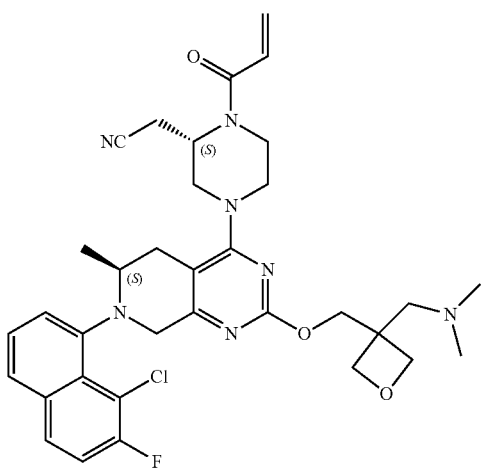 | 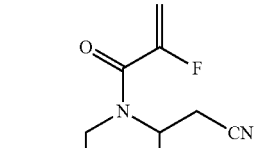 |
| 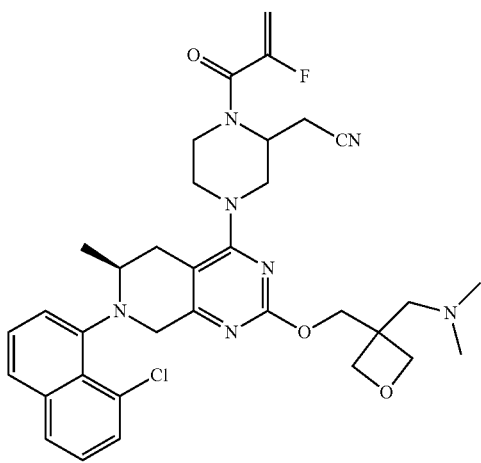 | 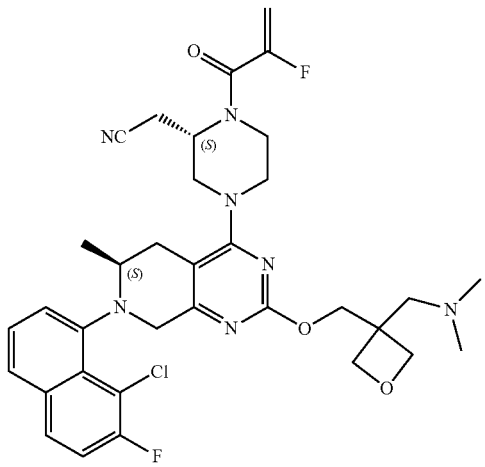 |

969
-continued
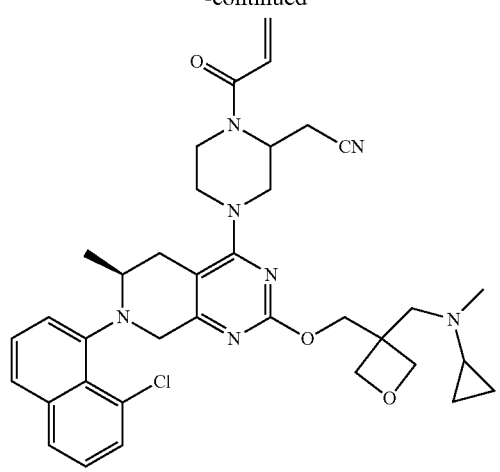
970
-continued
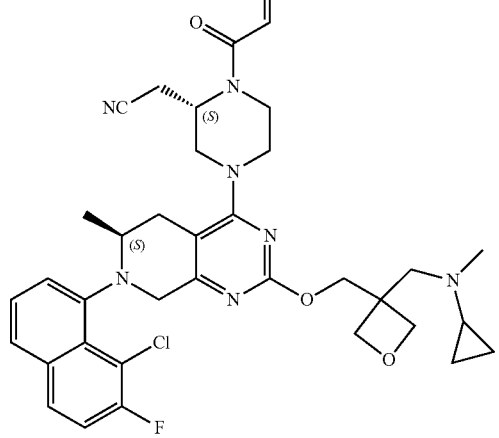
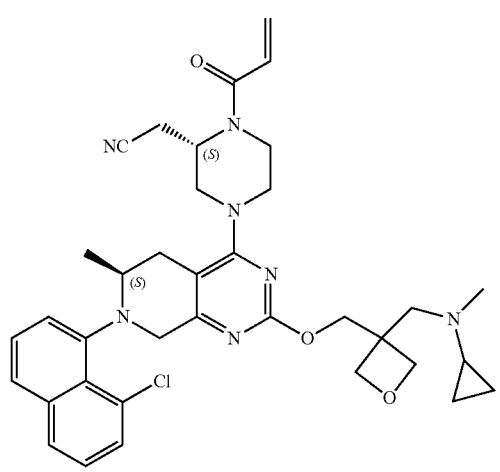
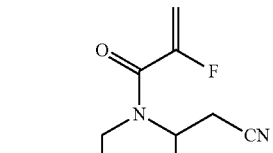
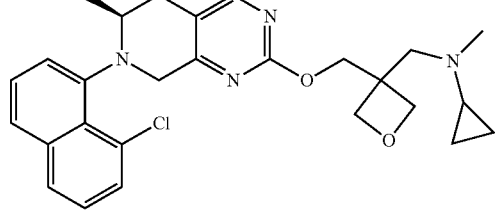
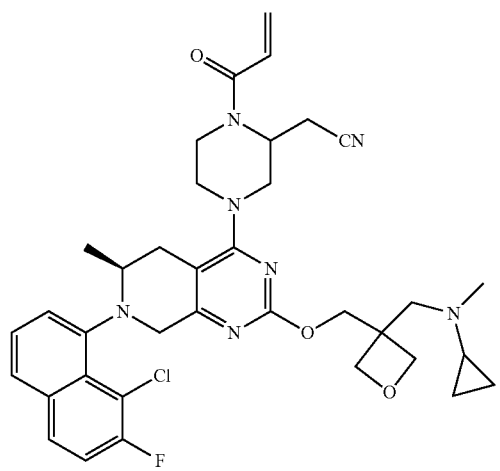
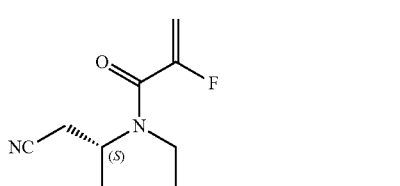
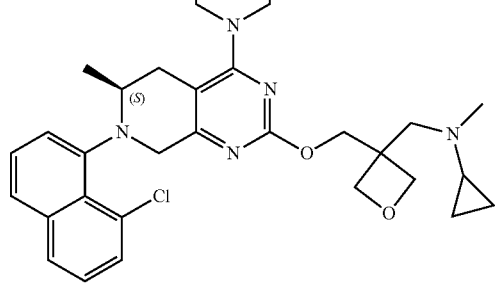

971
-continued
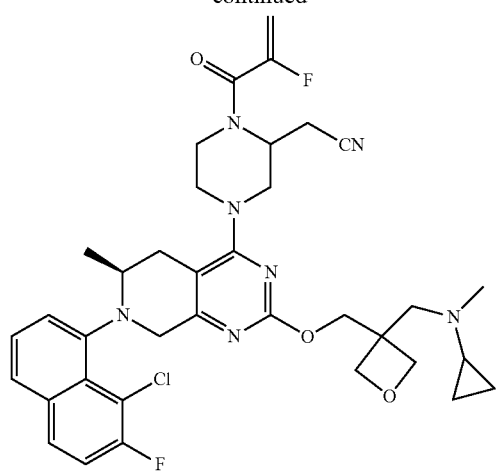
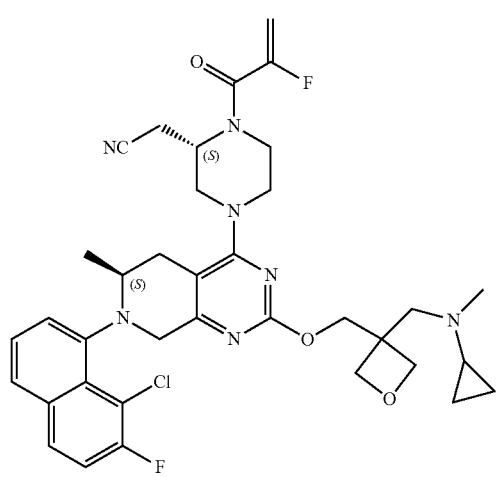
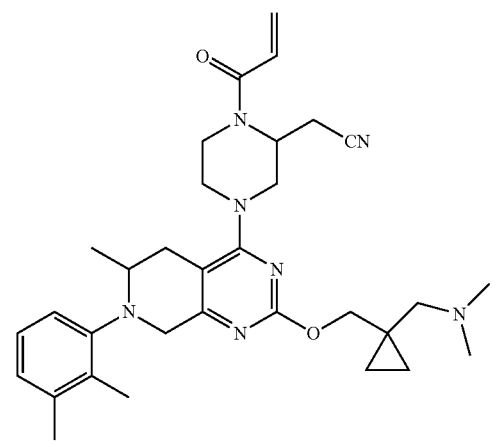
972
-continued
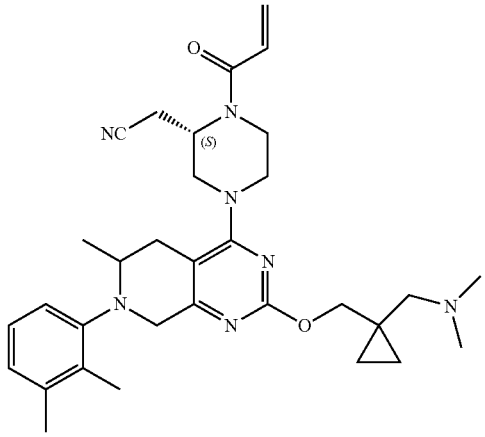
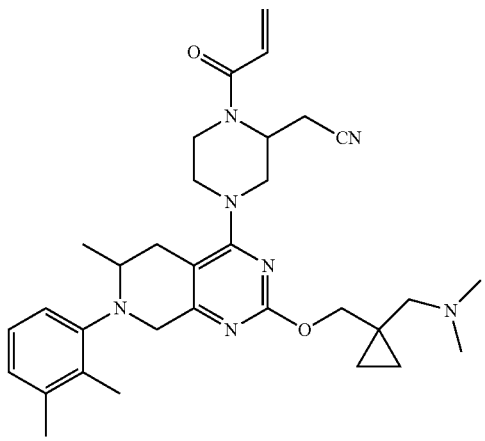
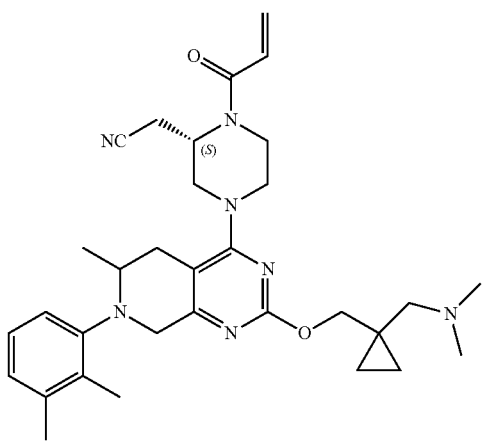

973
-continued
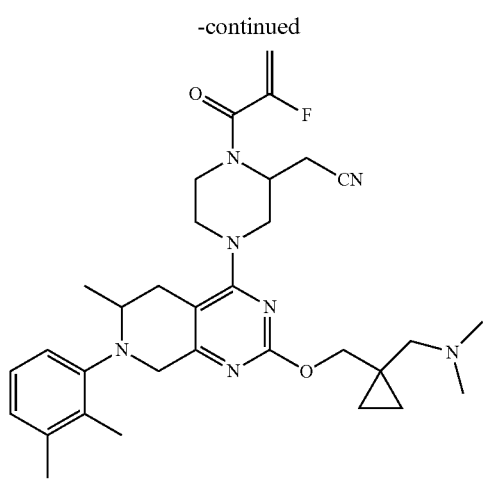
974
-continued
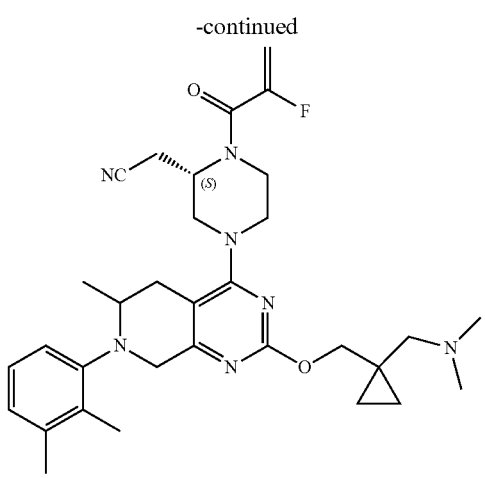
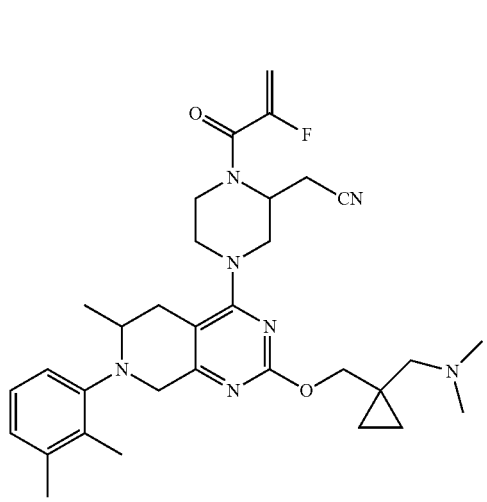

975
-continued
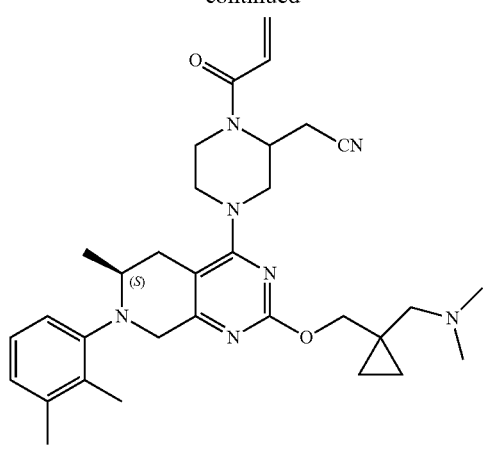
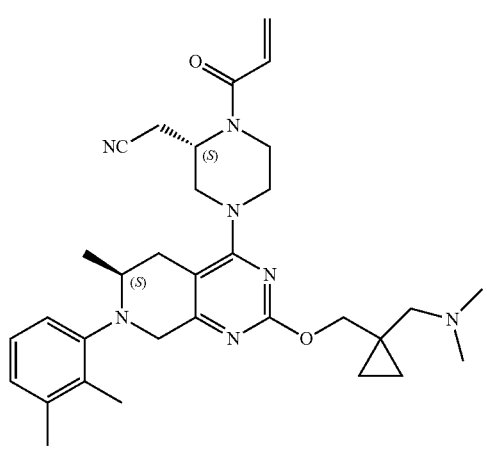
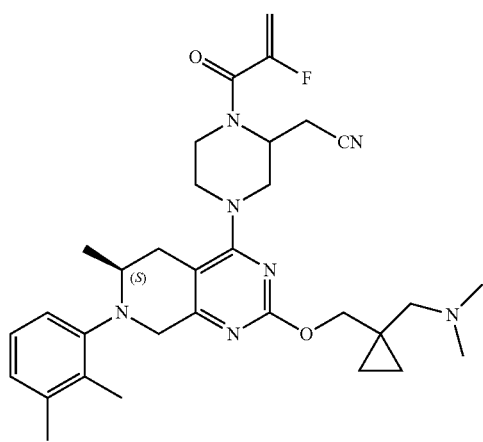
976
-continued
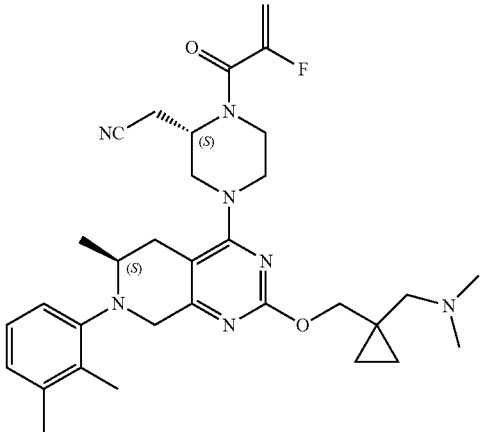
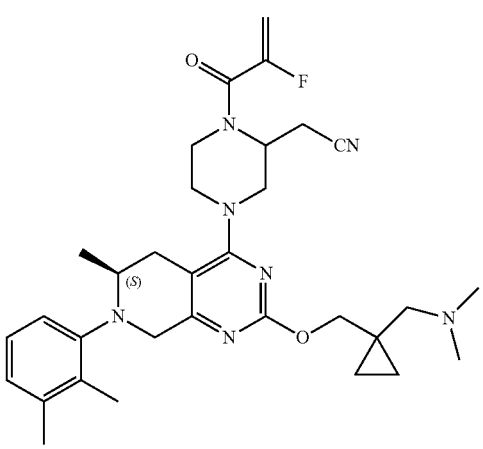
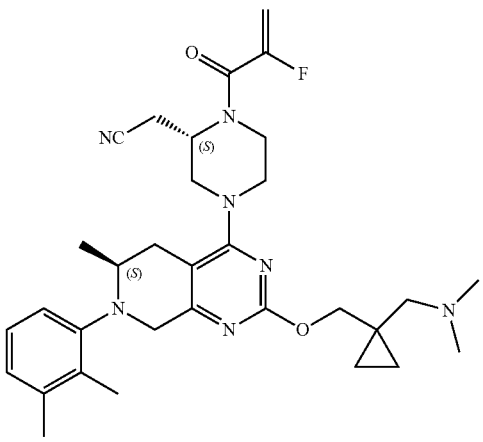

977
-continued
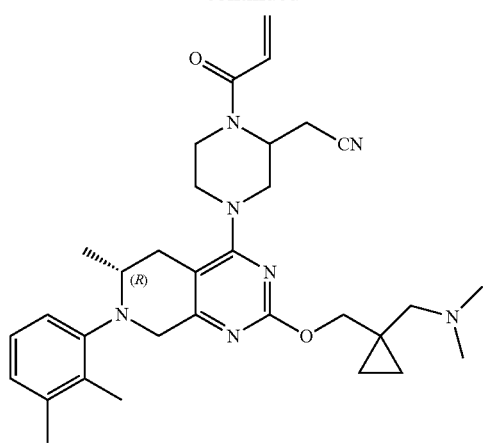
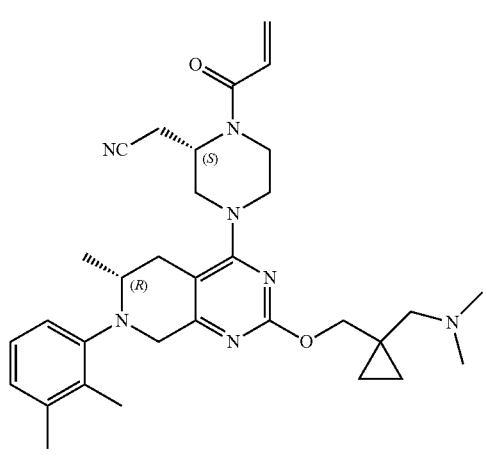
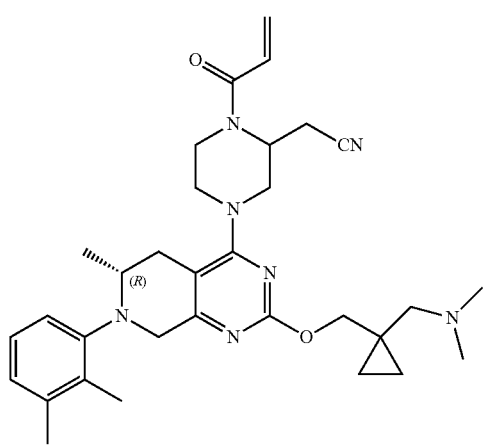
978
-continued
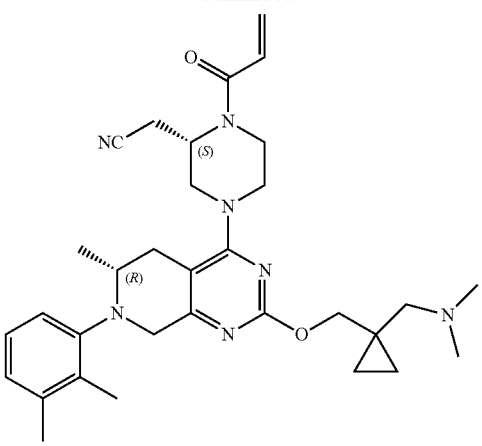
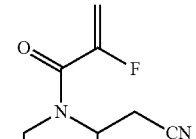
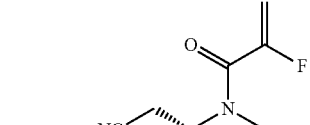
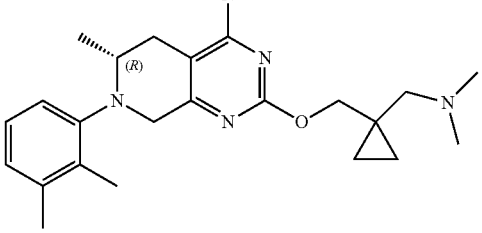

979
-continued
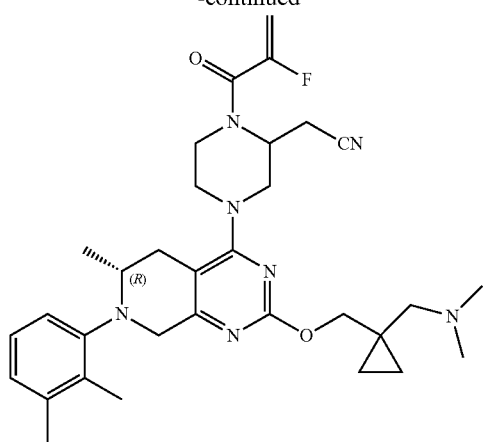
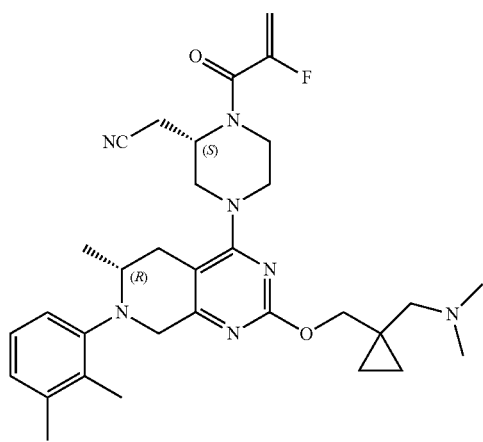
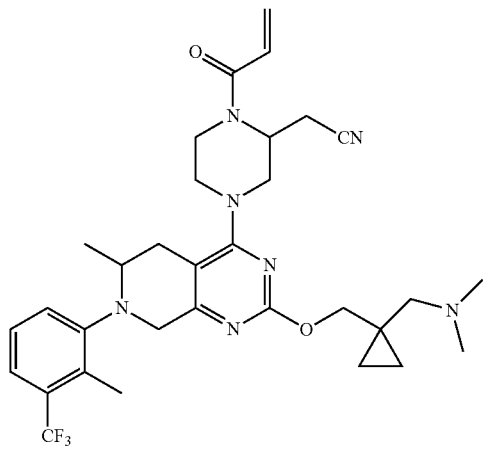
980
-continued
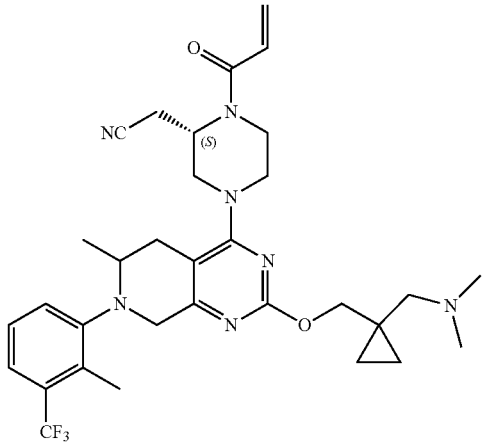
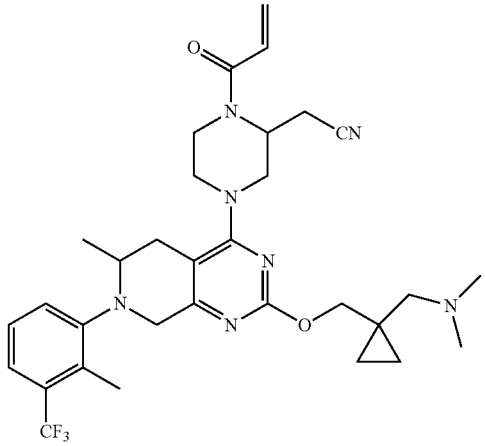
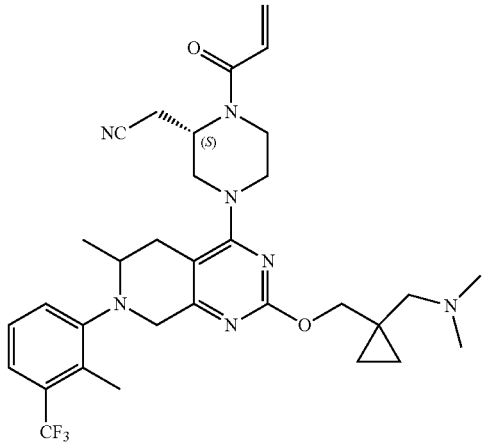

981
-continued
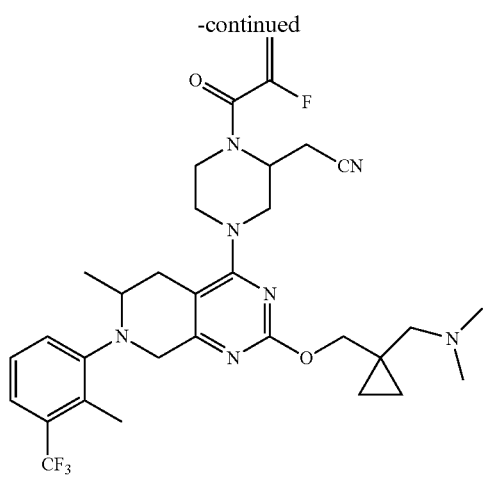
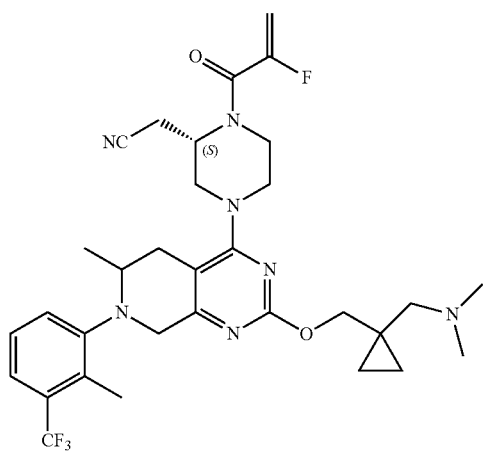
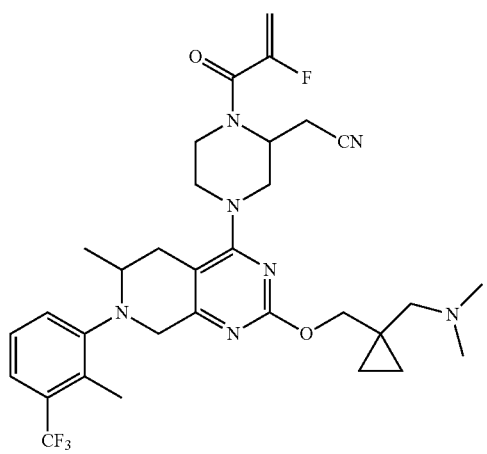
982
-continued
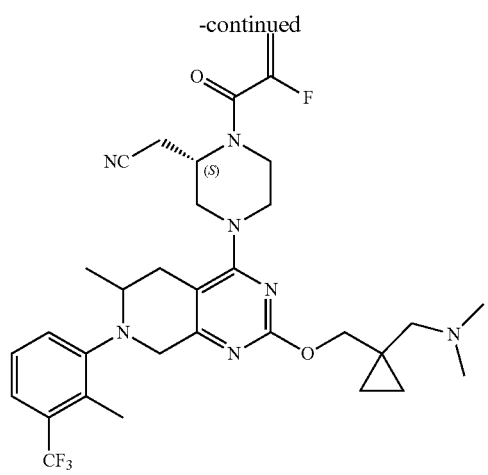
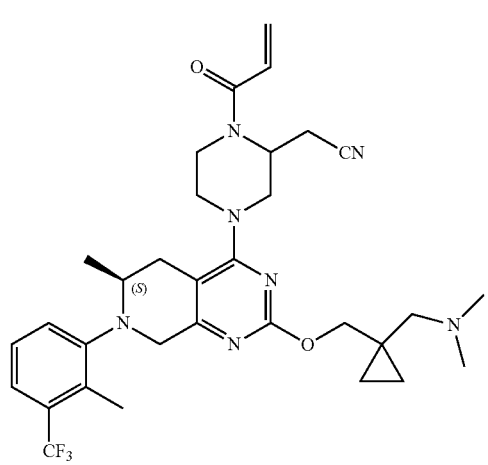
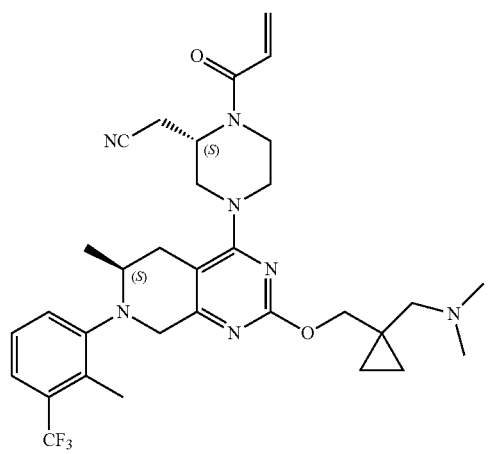

983
-continued
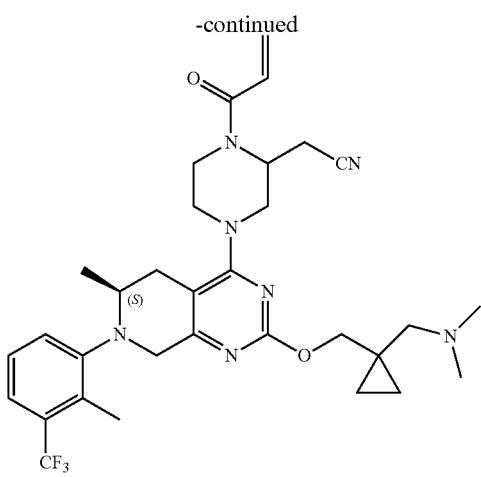
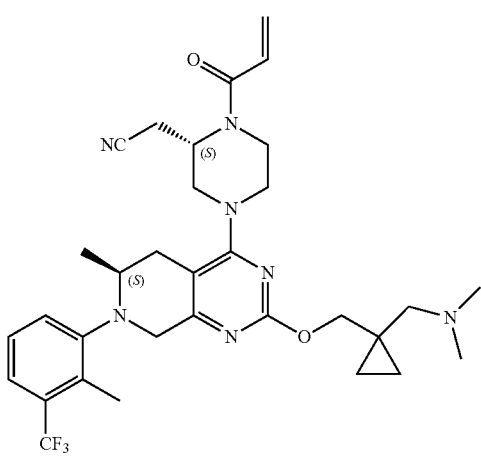
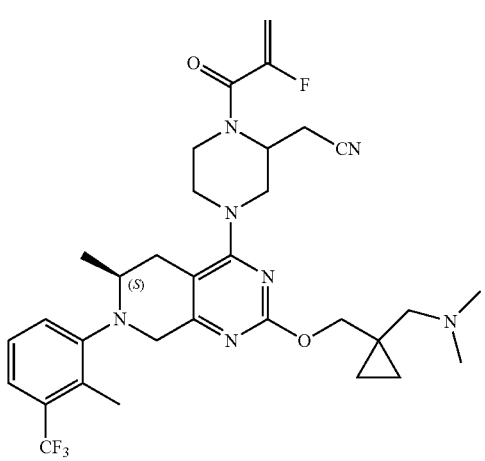
984
-continued
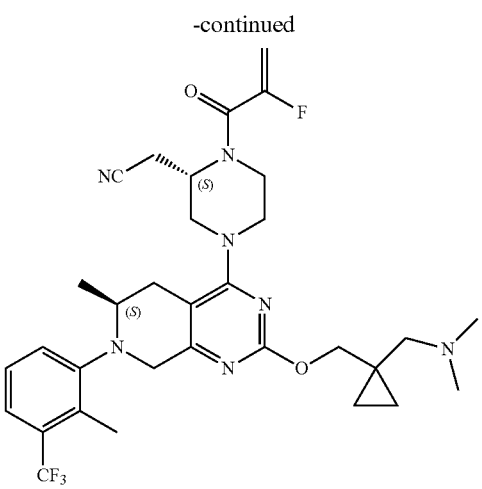
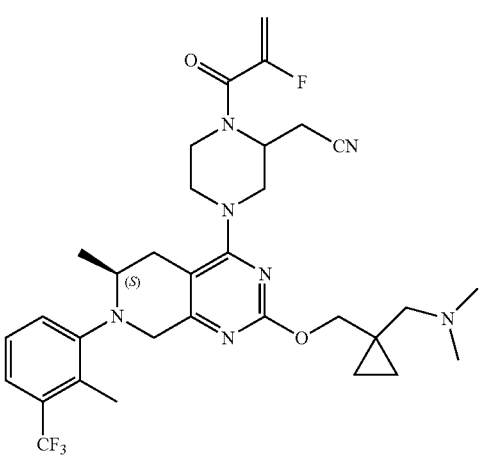
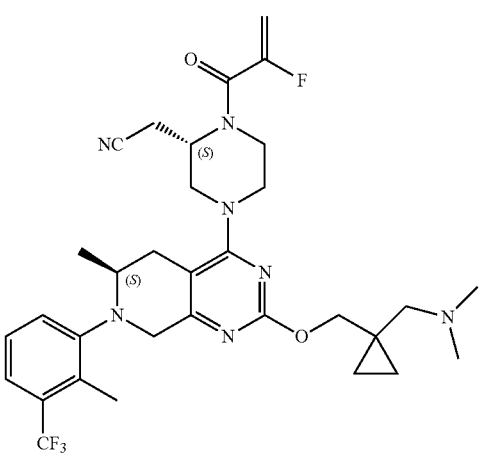

985
-continued
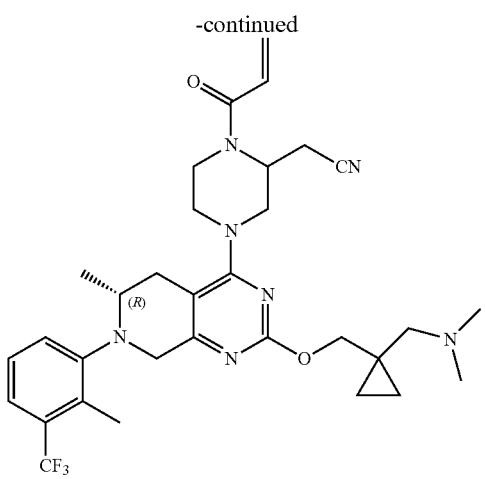
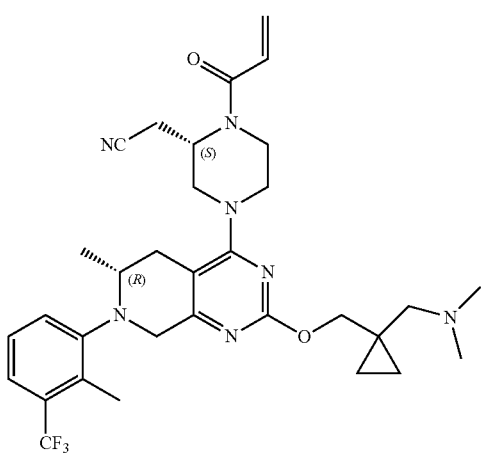
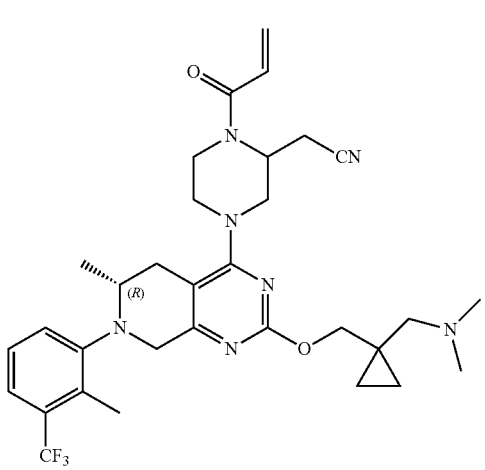
986
-continued
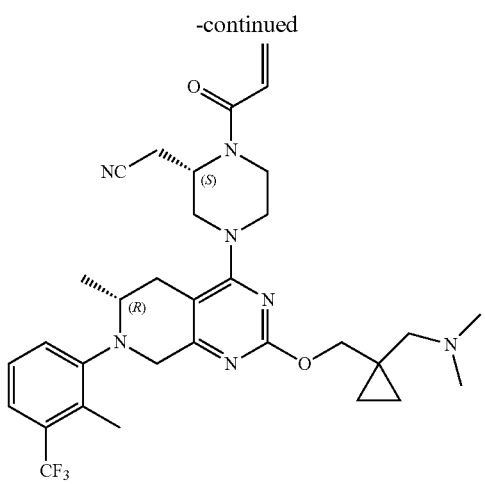
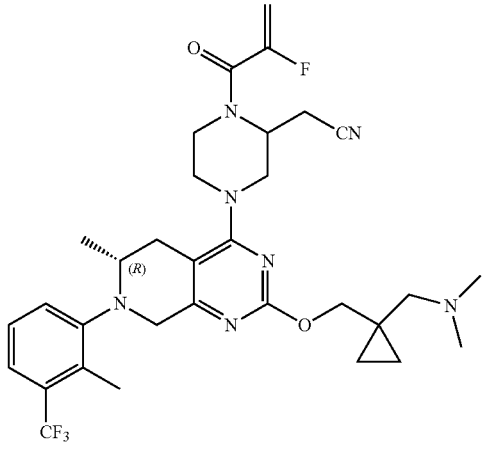
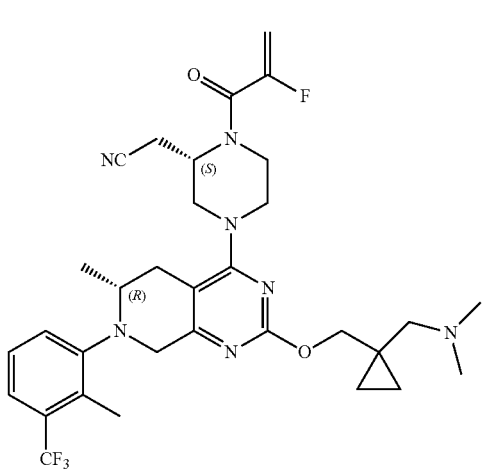

987
-continued
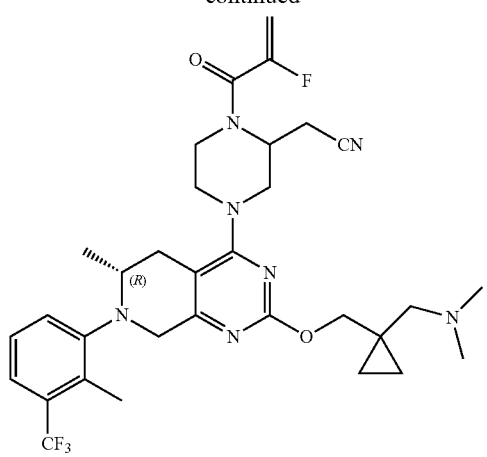
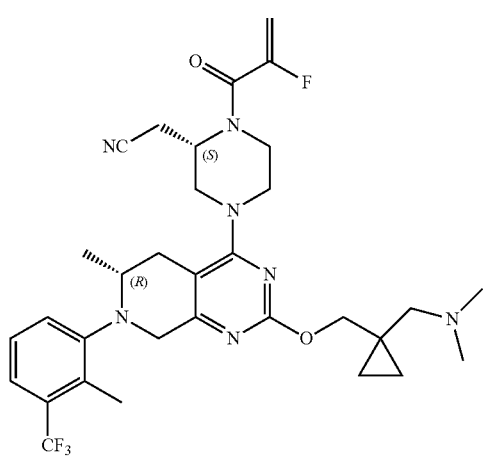
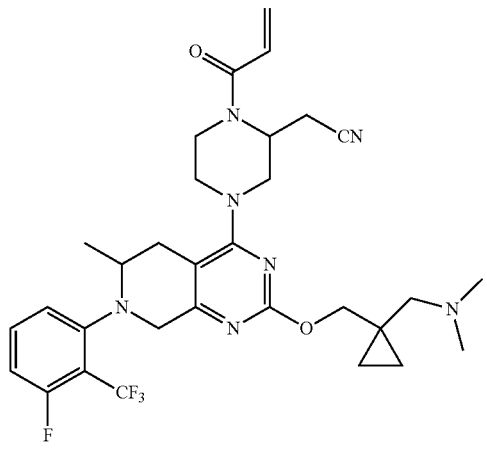
988
-continued
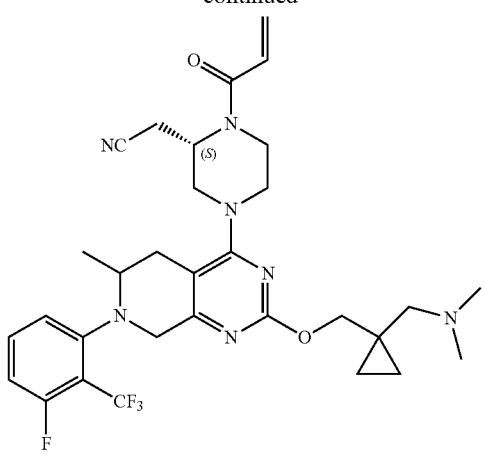
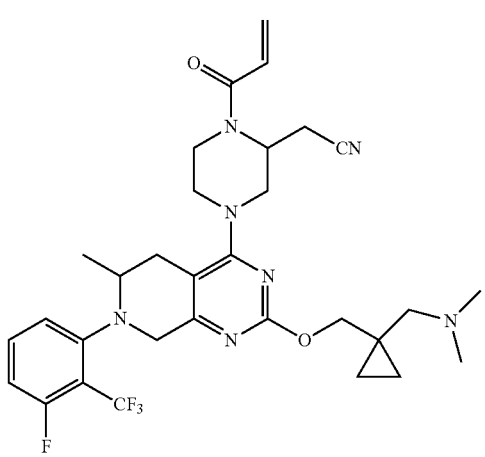
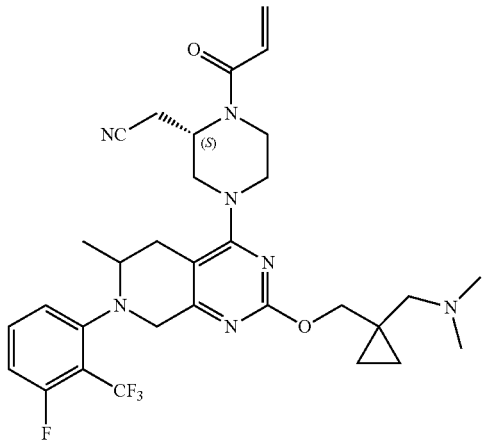

989
-continued
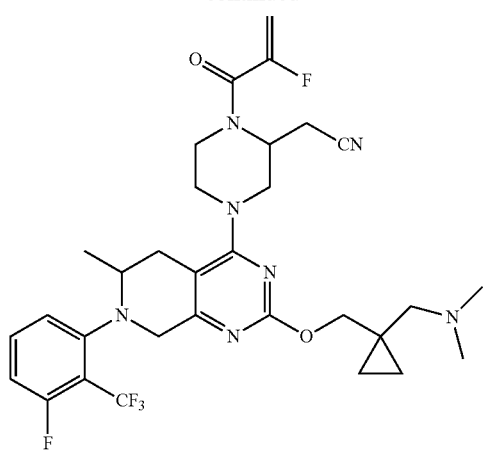
990
-continued
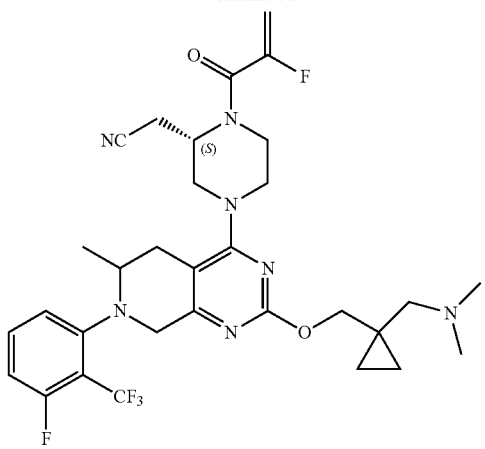
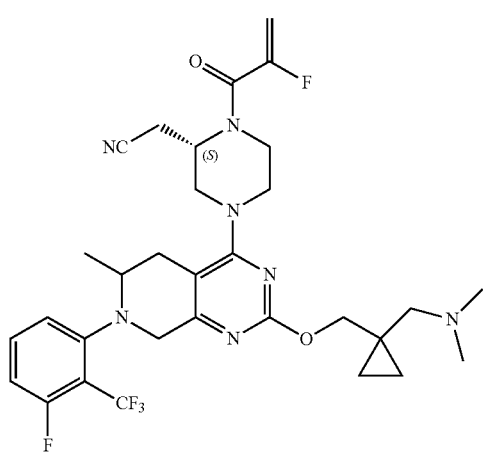
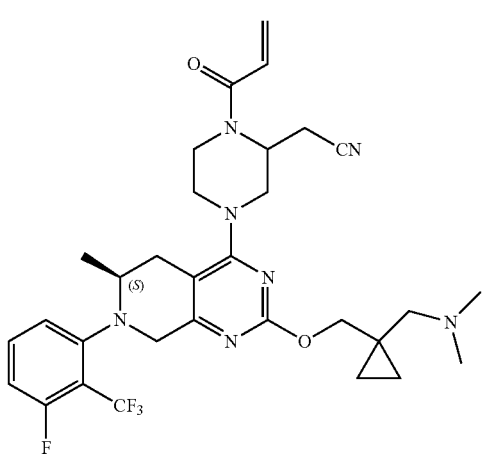
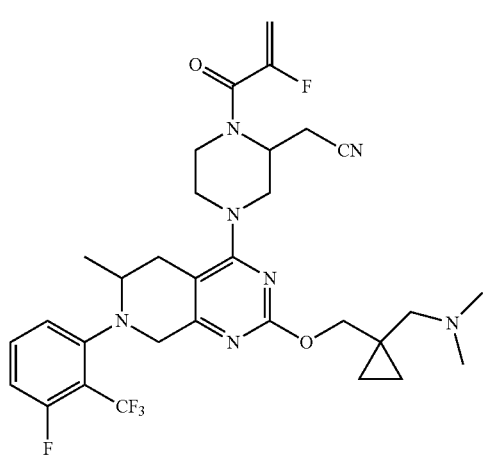
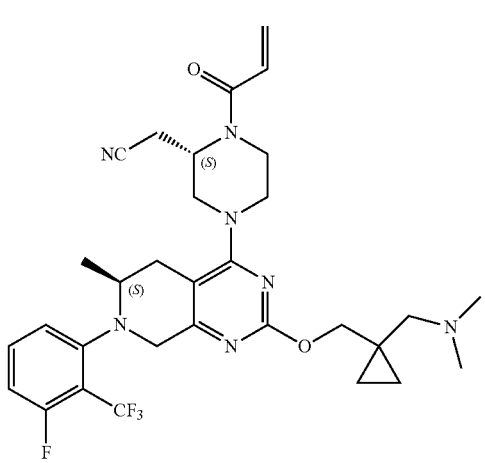

991
-continued
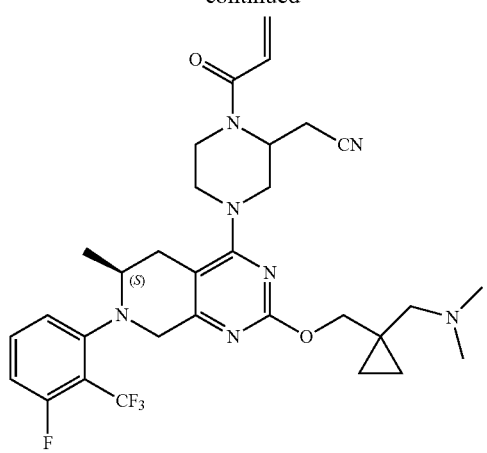
992
-continued
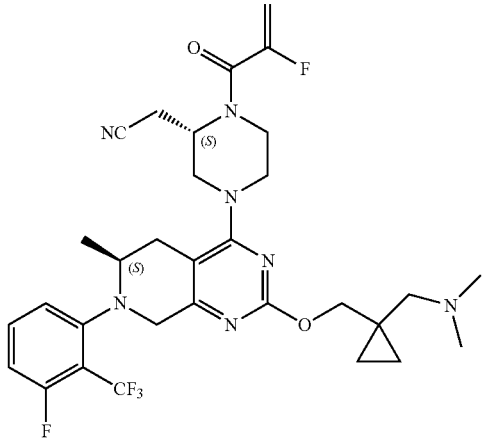
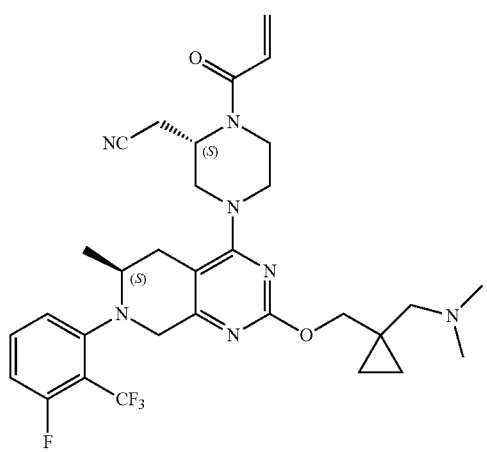
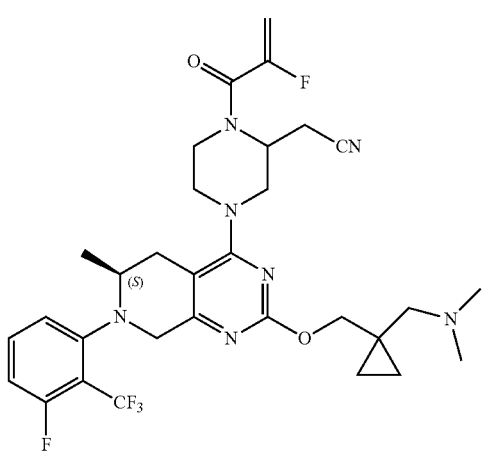
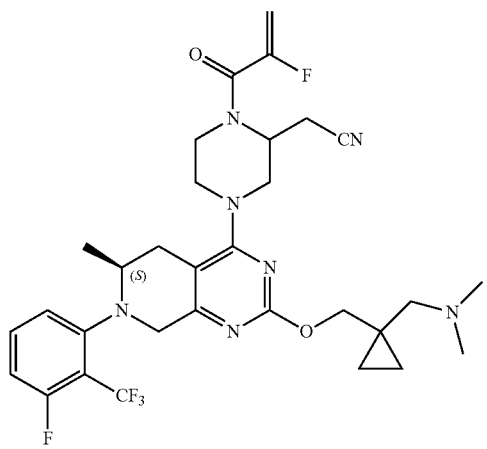
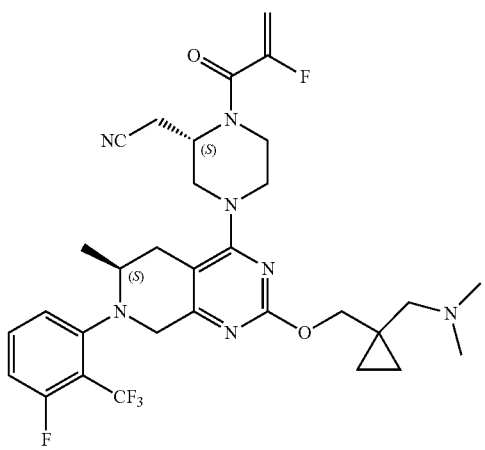

993
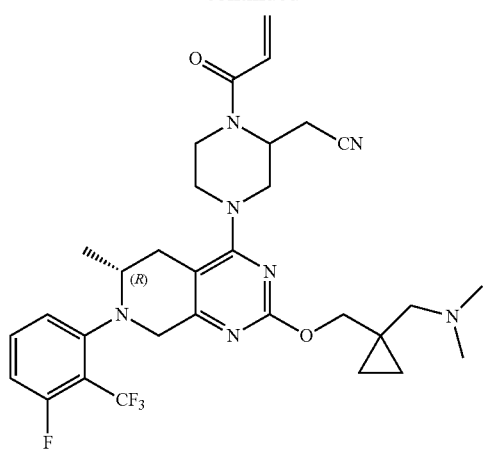
994
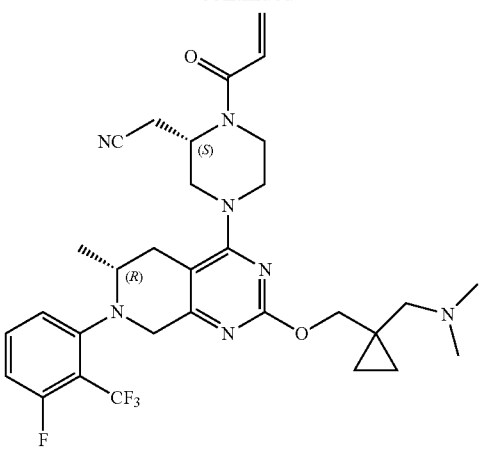
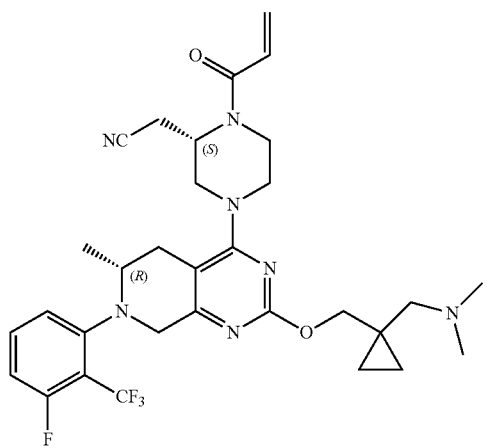
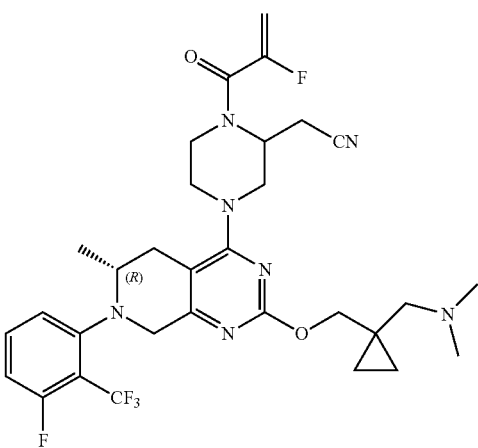
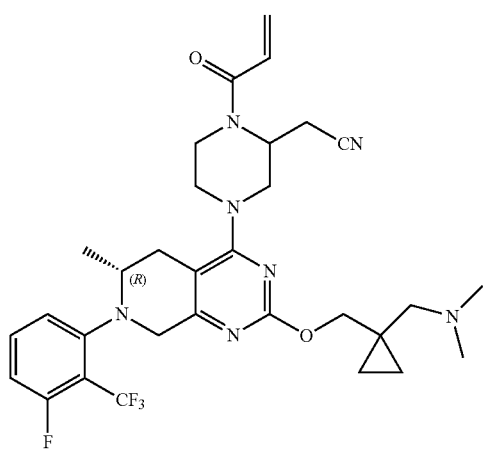
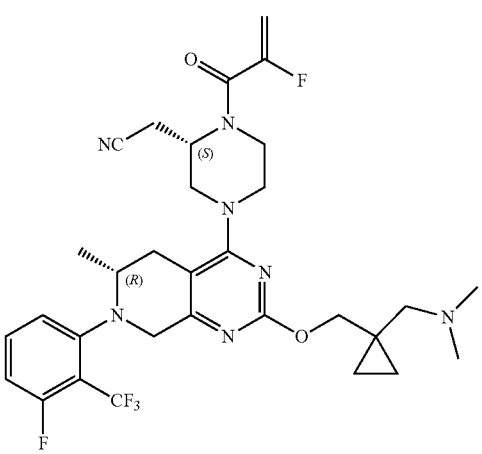

995
-continued
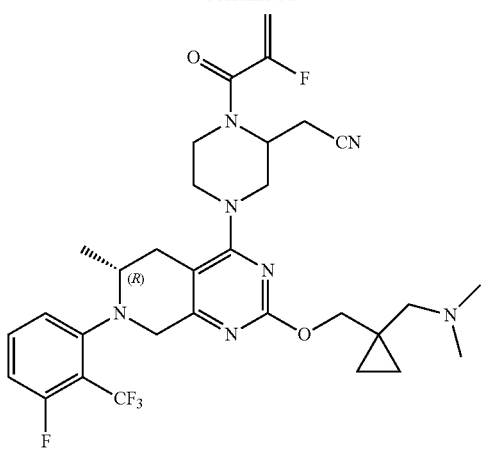
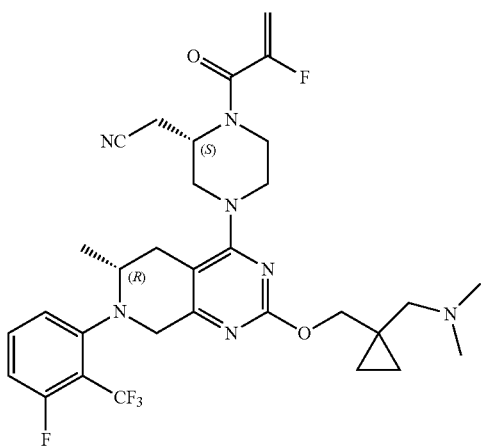
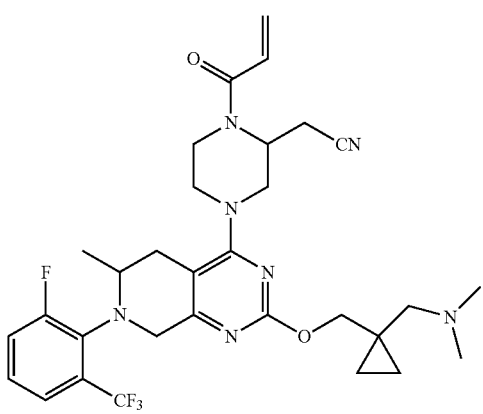
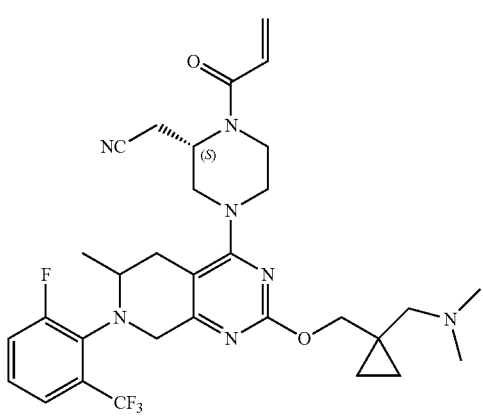
996
-continued
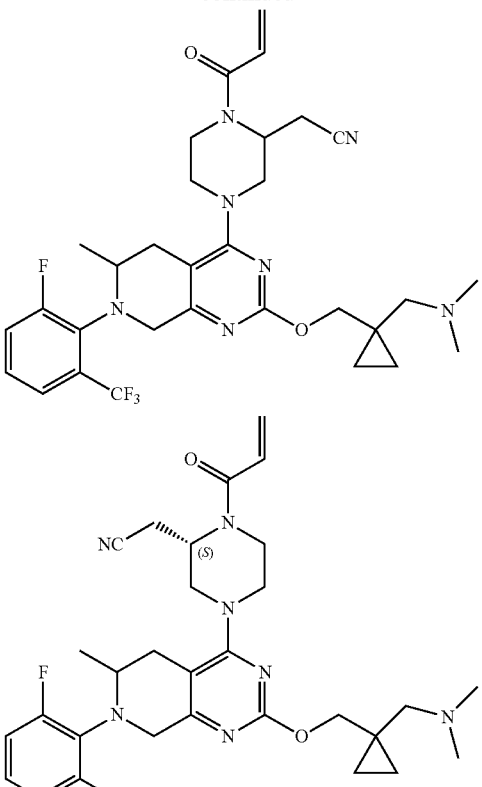
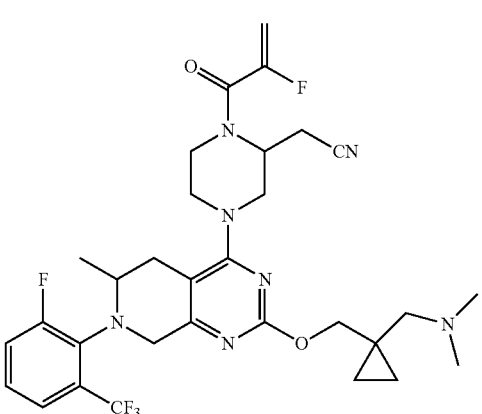
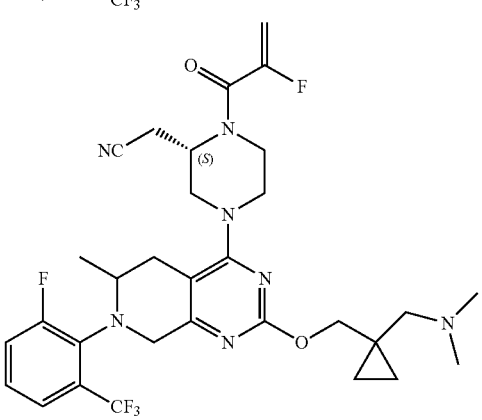

997
-continued
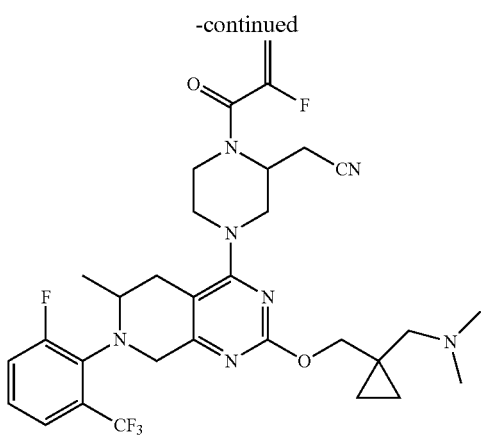
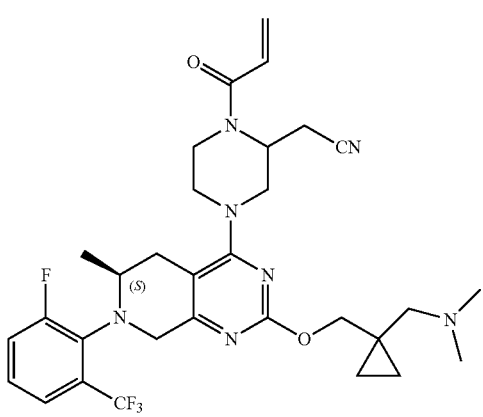
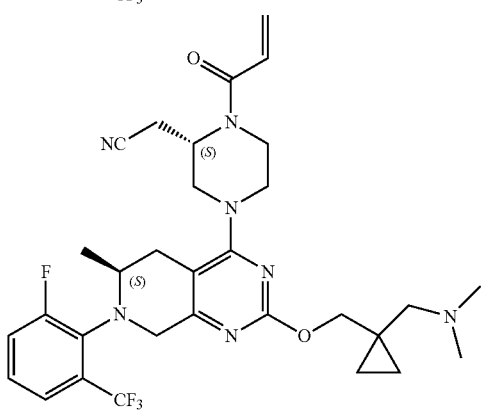
998
-continued
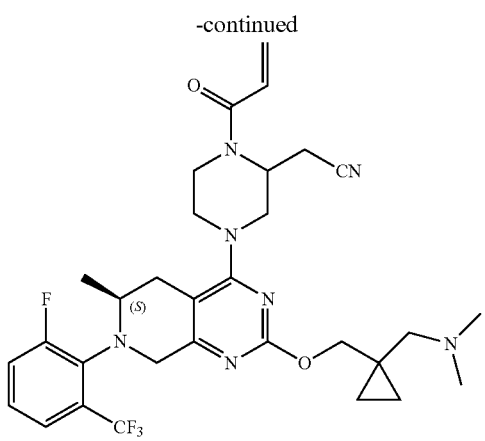
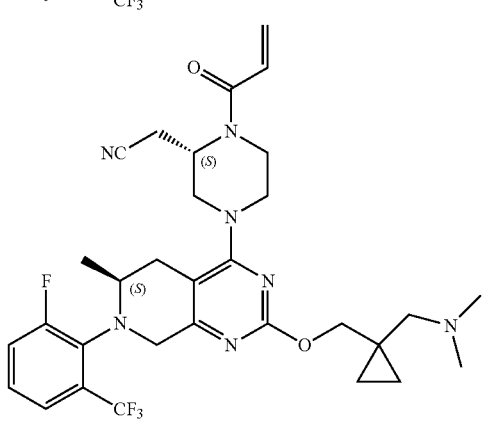
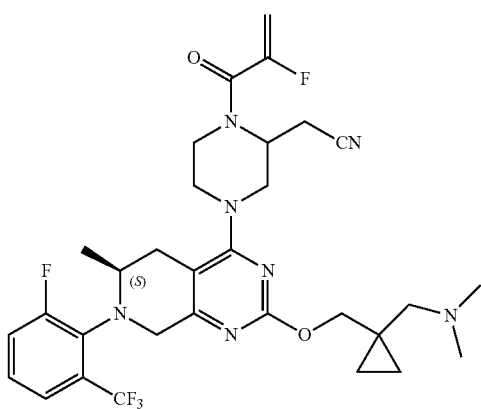
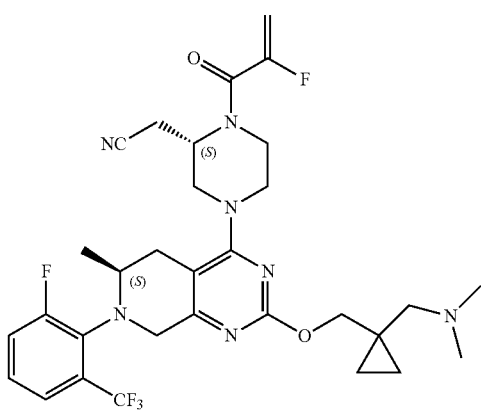

| 999 -continued | 1000 -continued |
|---|---|
| 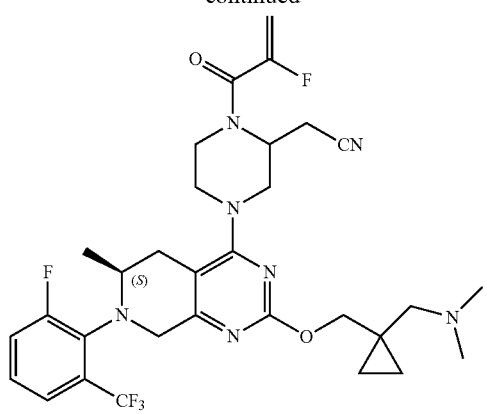 | 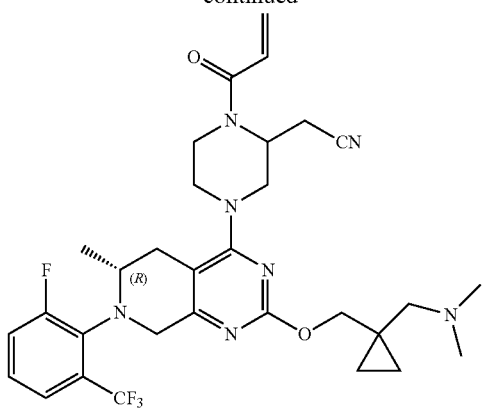 |
| 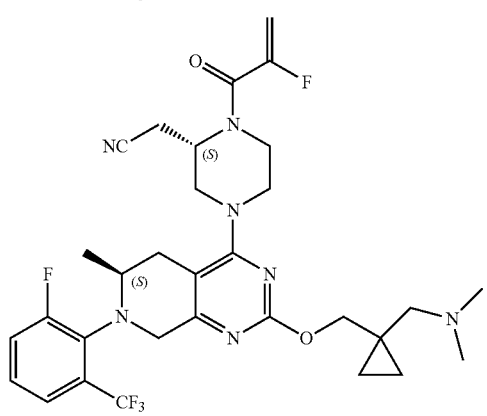 | 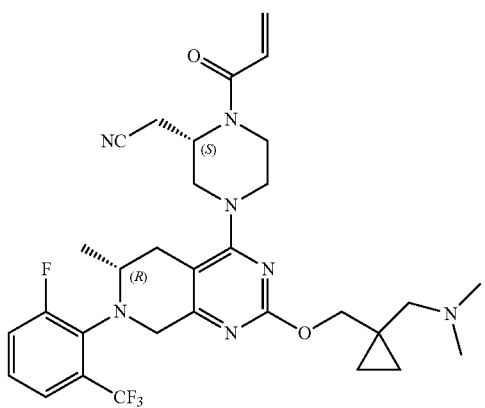 |
| 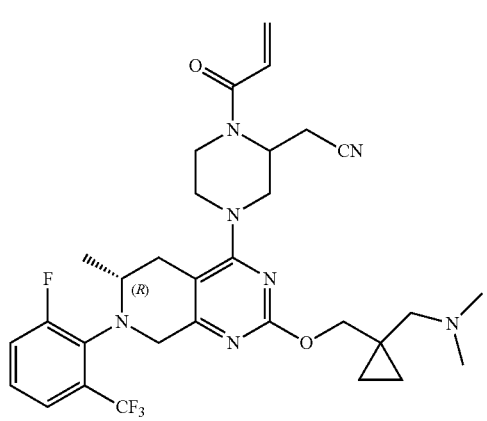 | 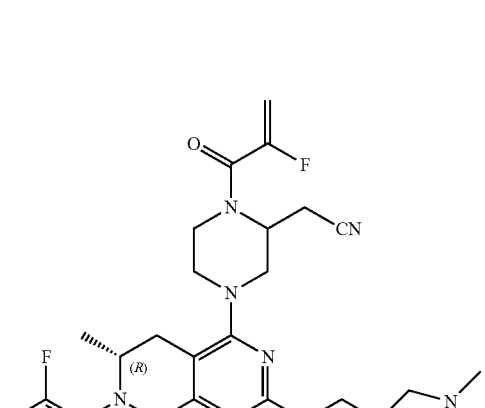 |
| 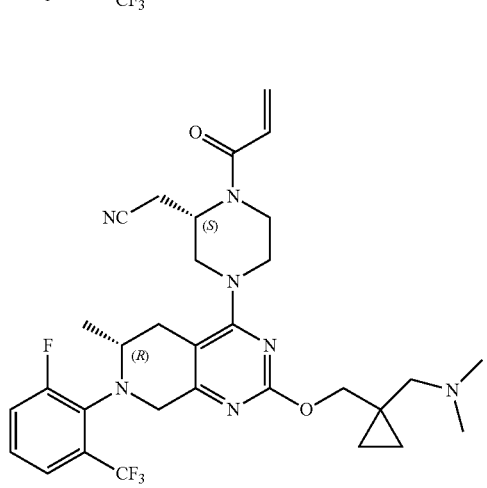 | 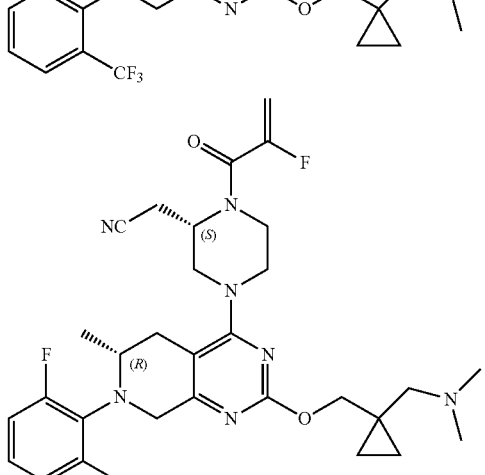 |

1001
-continued
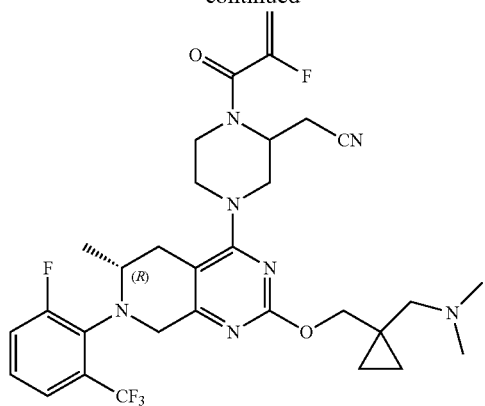
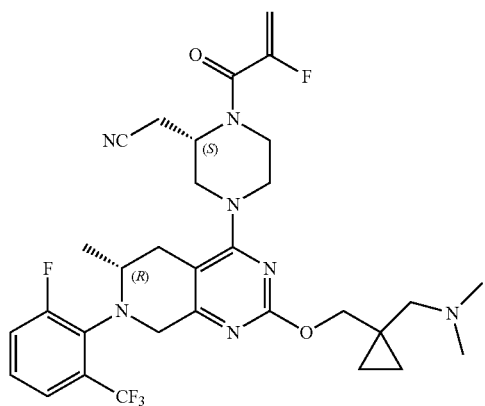
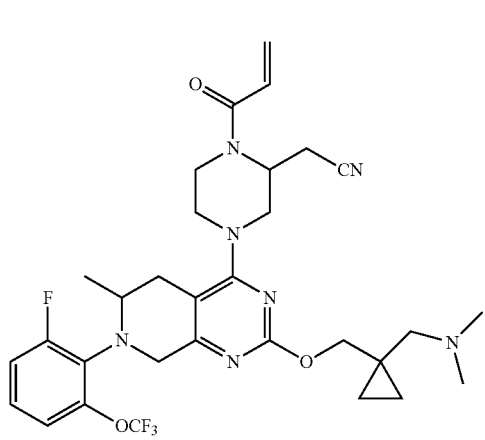
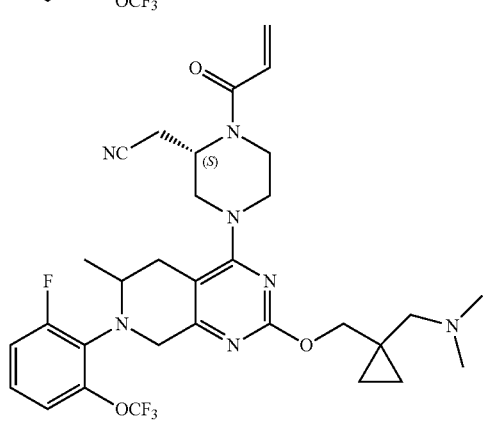
1002
-continued
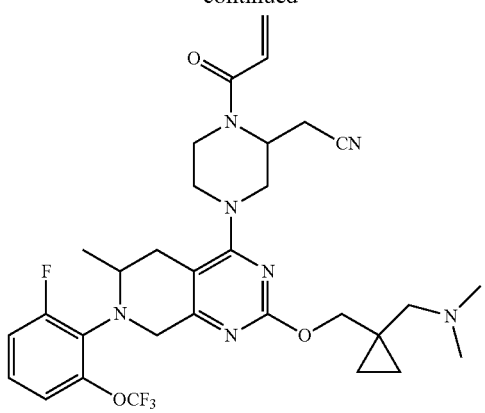
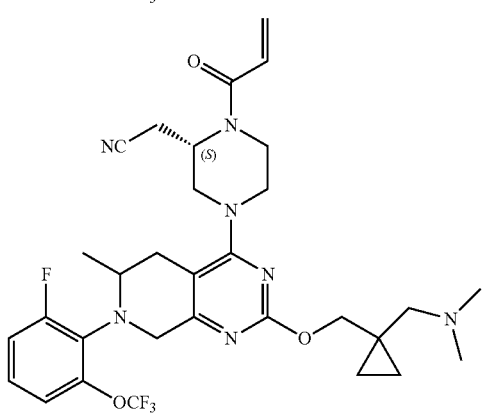
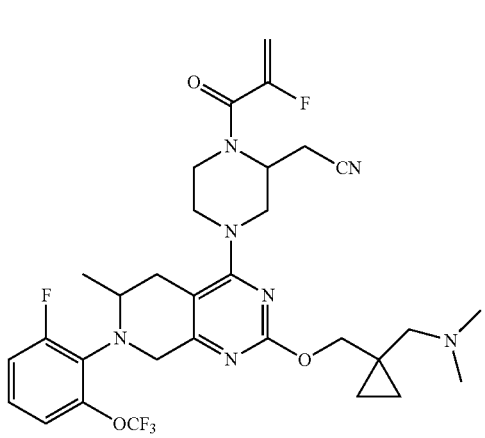
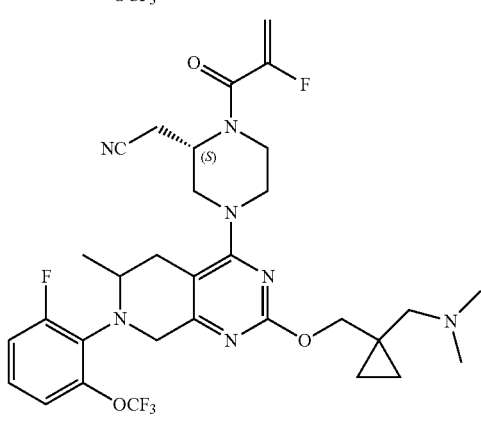

1003
-continued
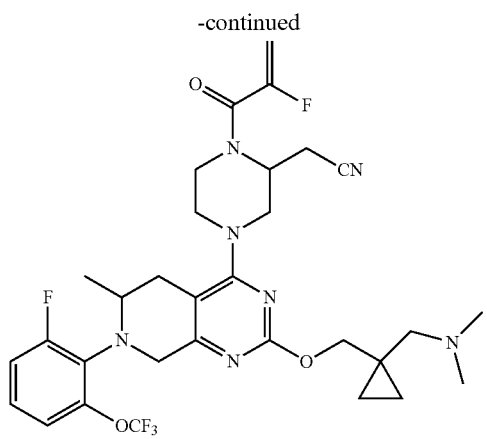
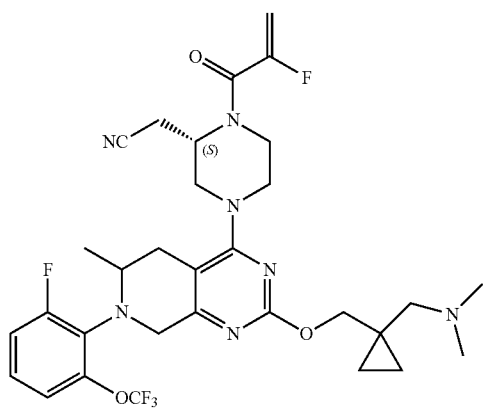
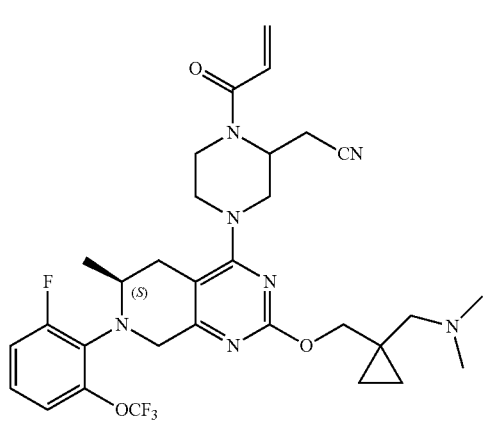
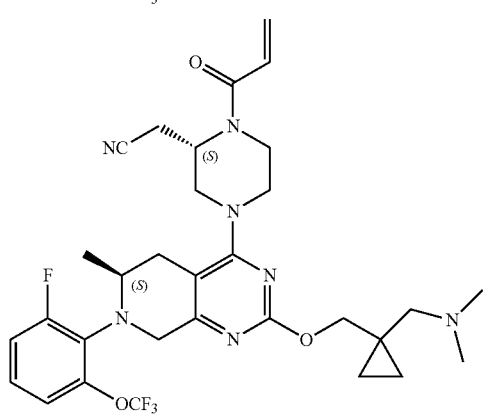
1004
-continued
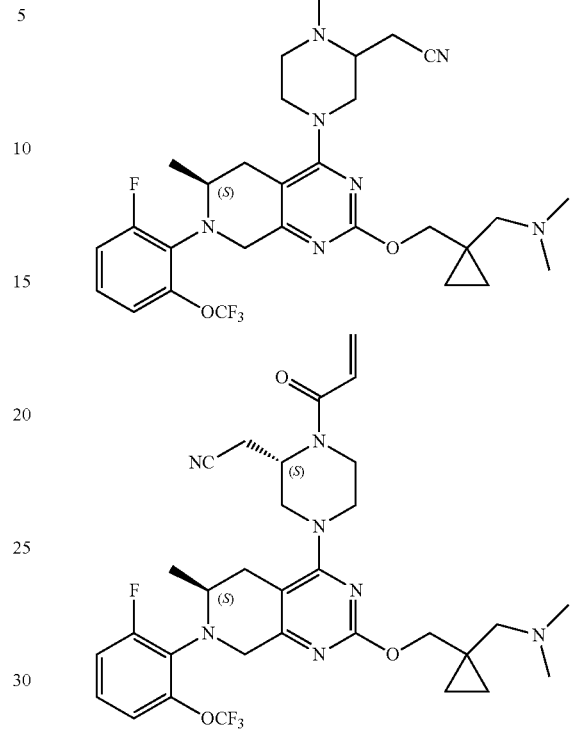
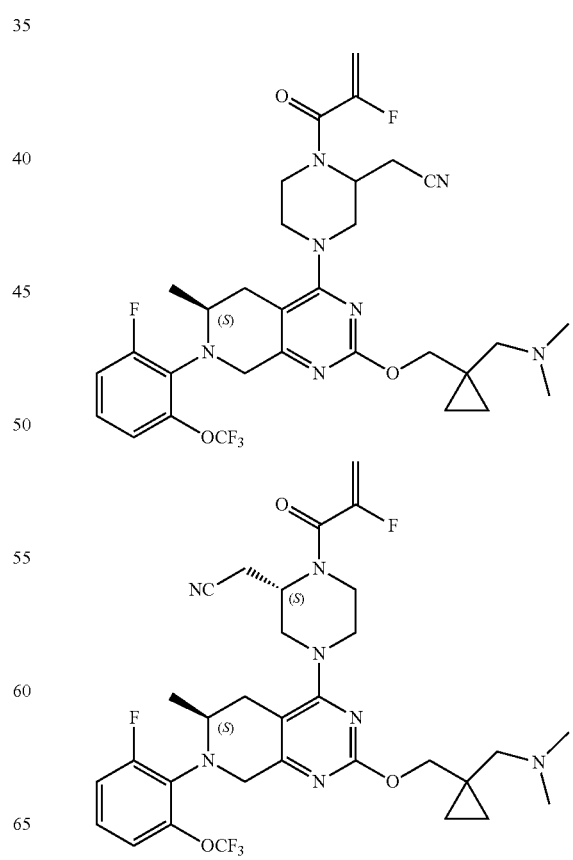

1005
-continued
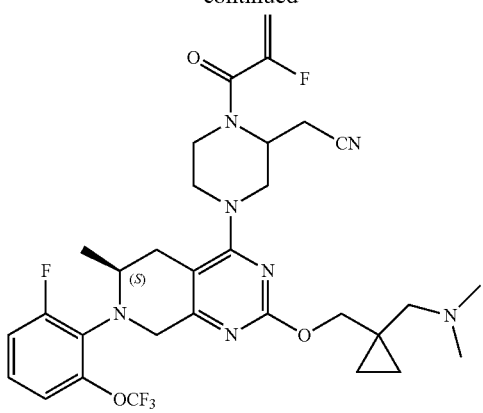
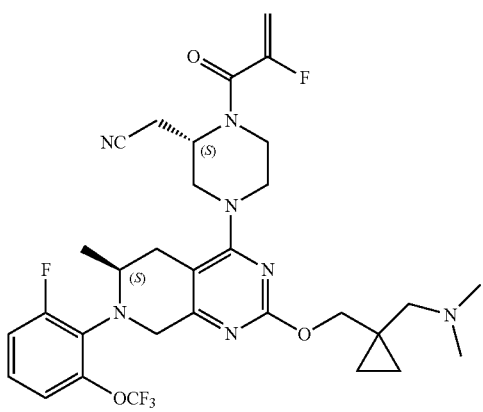
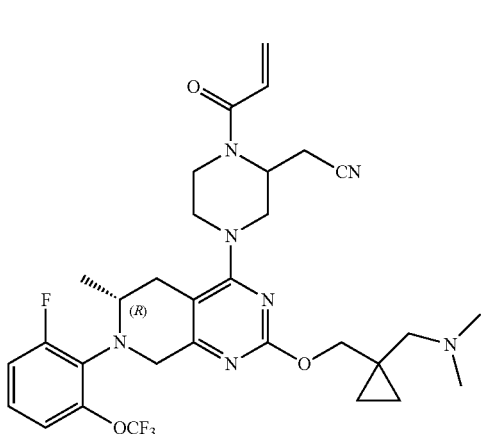
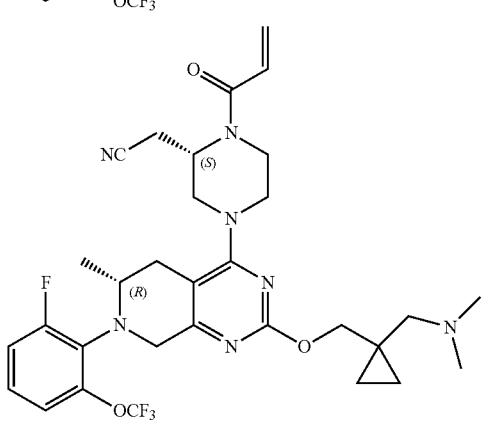
1006
-continued
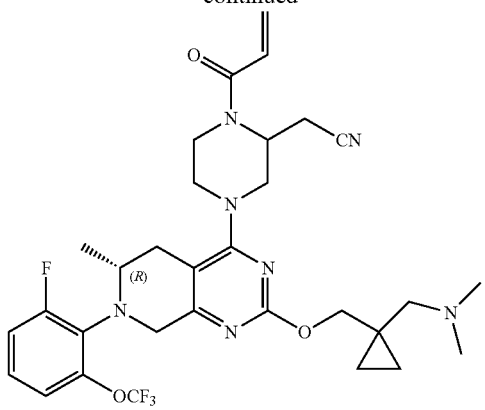
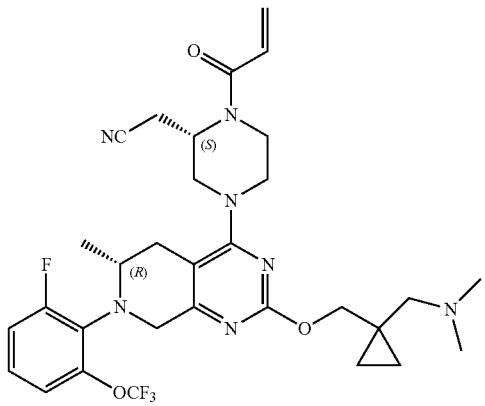
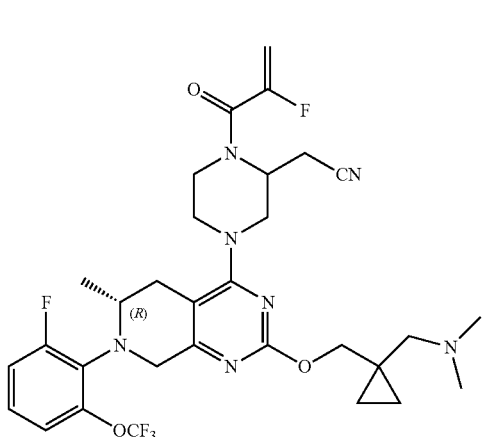
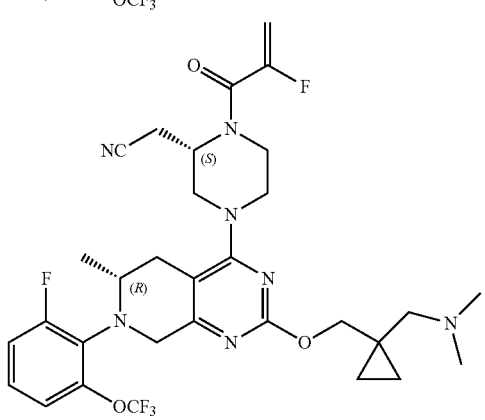

1007
-continued
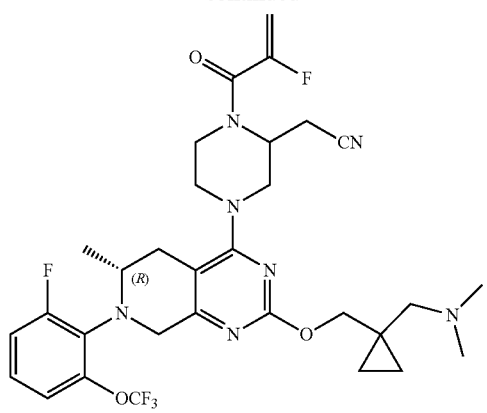
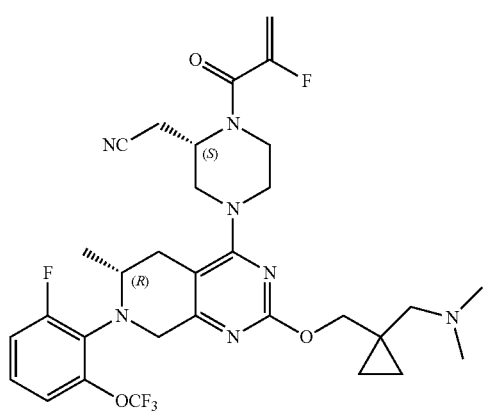
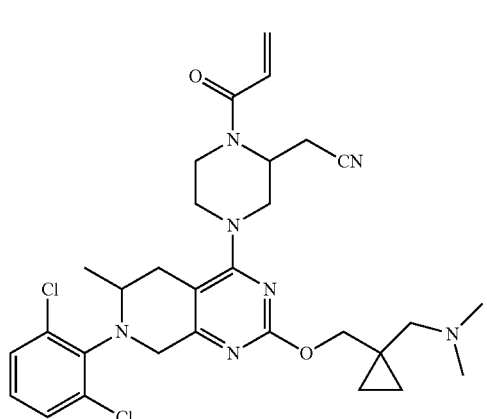
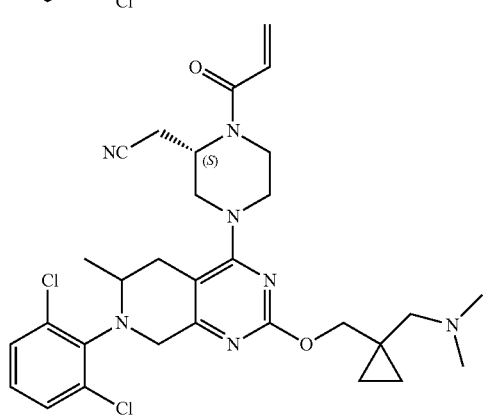
1008
-continued
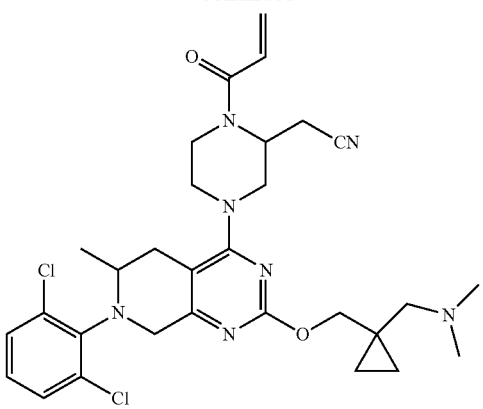
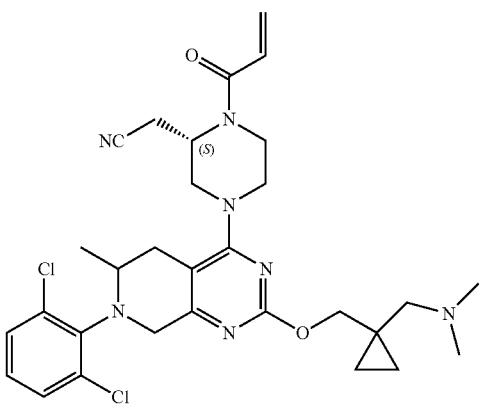
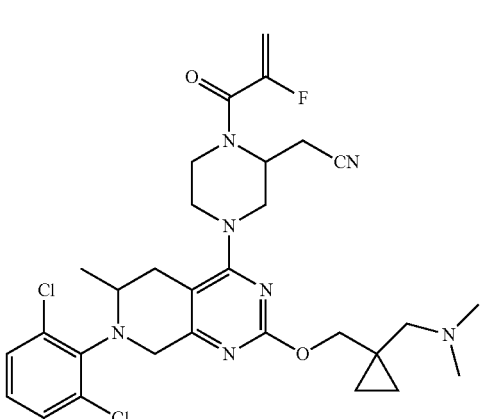
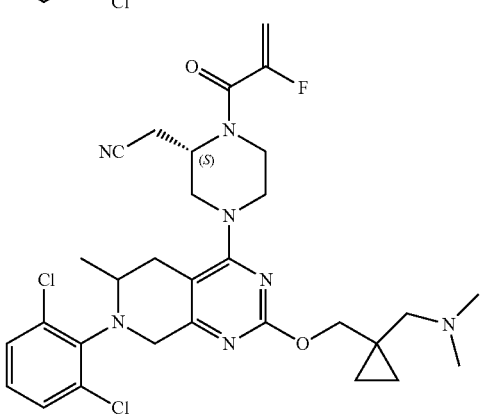

1009
-continued
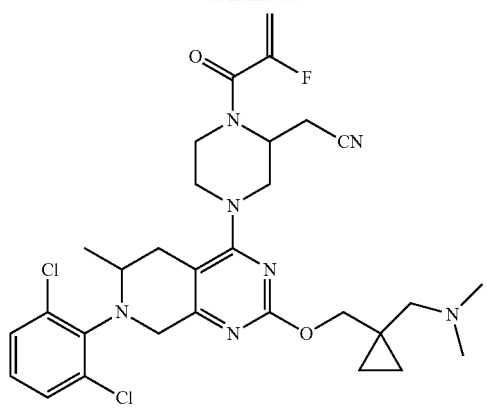
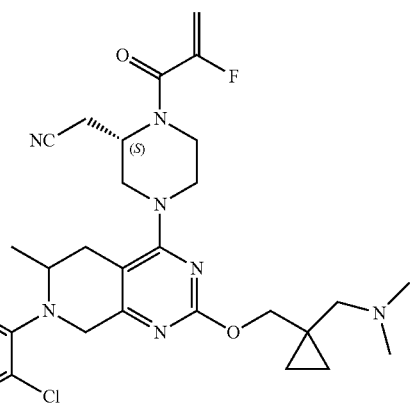
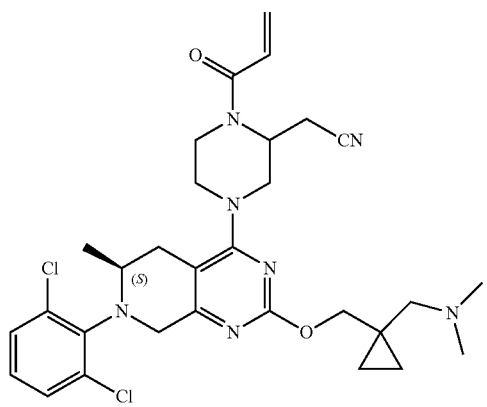
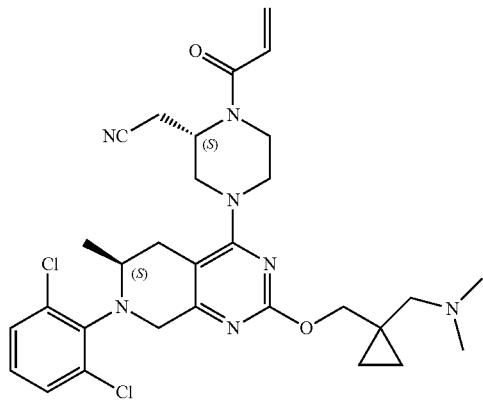
1010
-continued
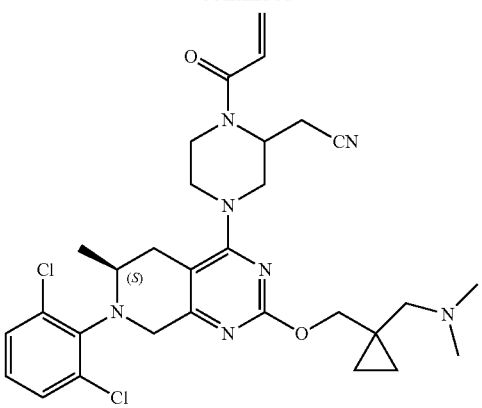
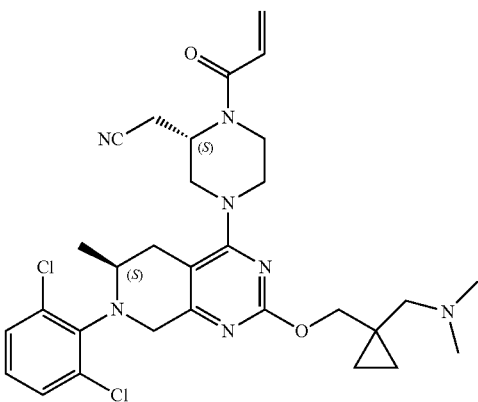
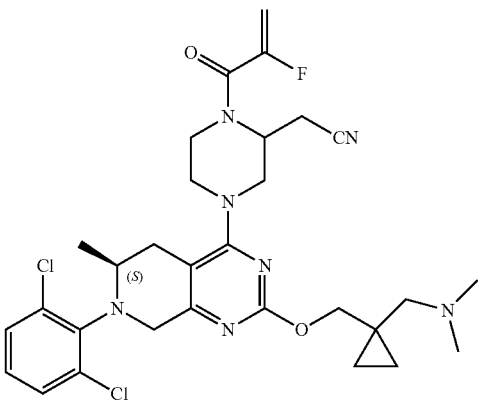
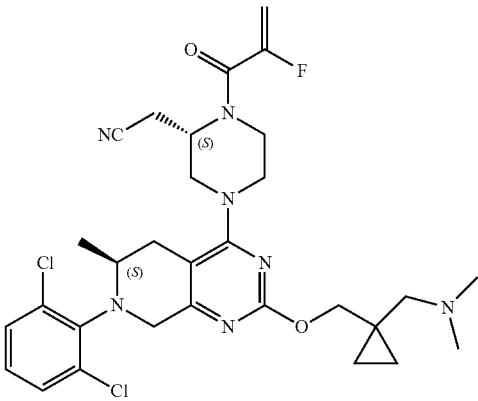

1011
-continued
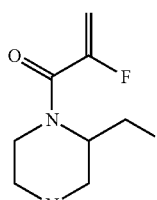
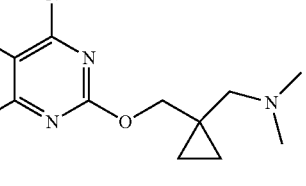
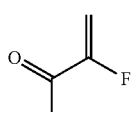
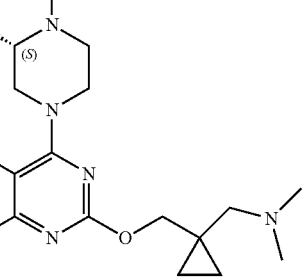
1012
-continued
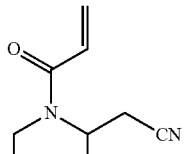
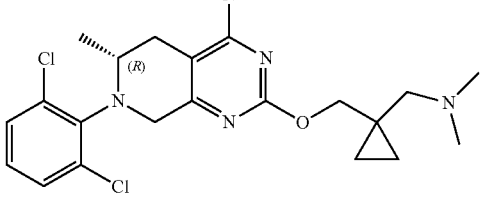
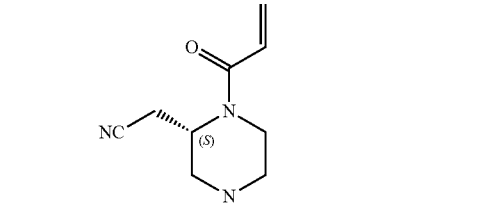
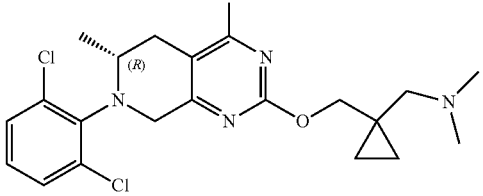
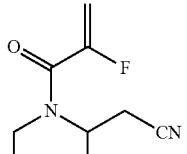
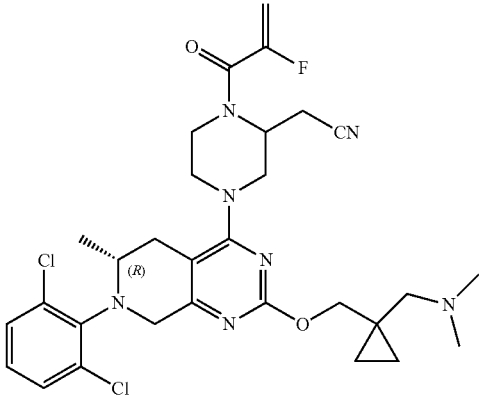
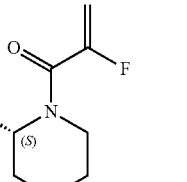
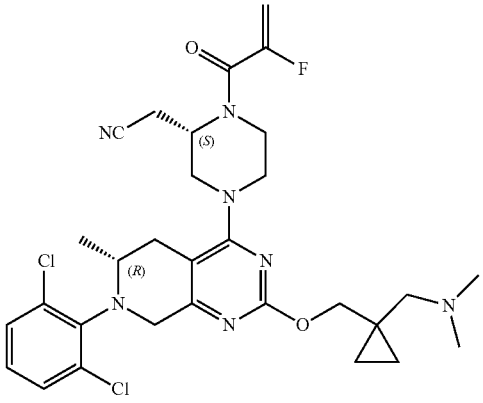

1013
-continued
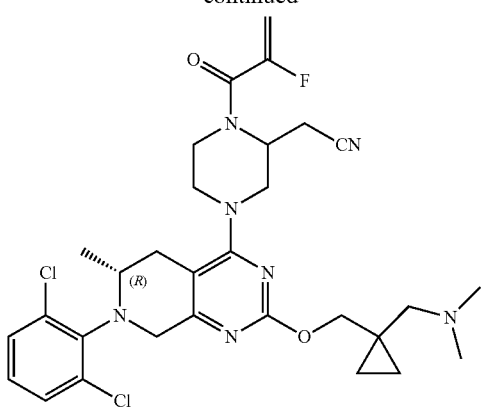
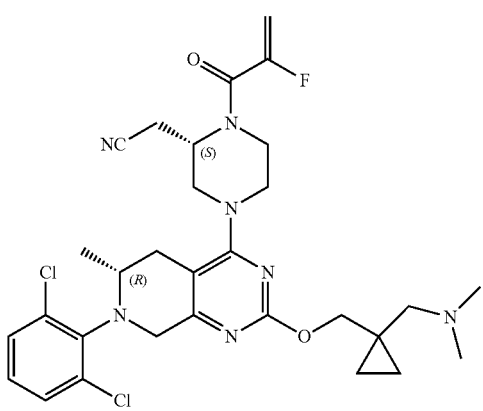
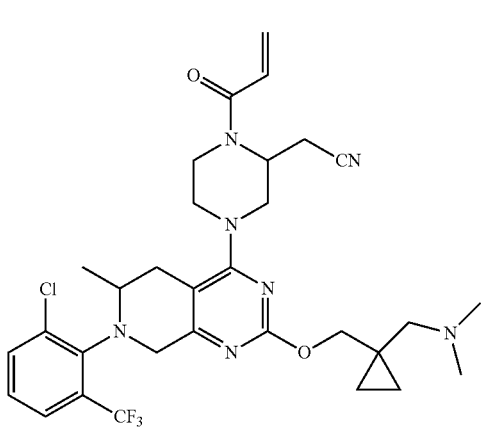
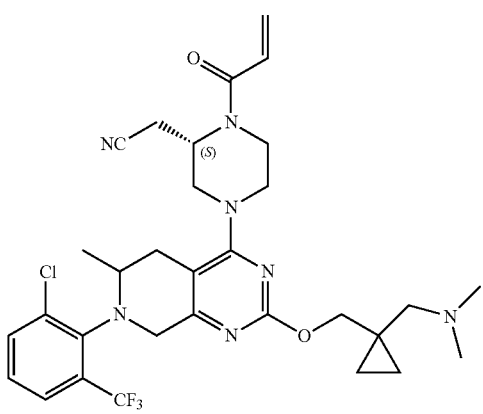
1014
-continued
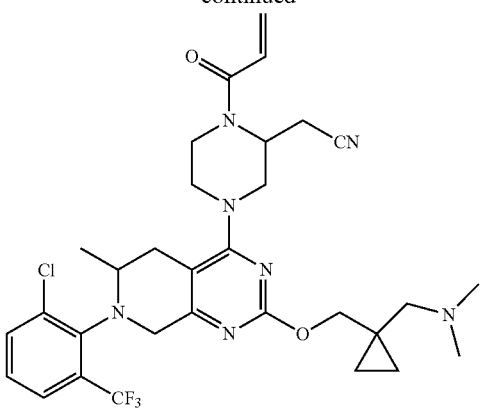
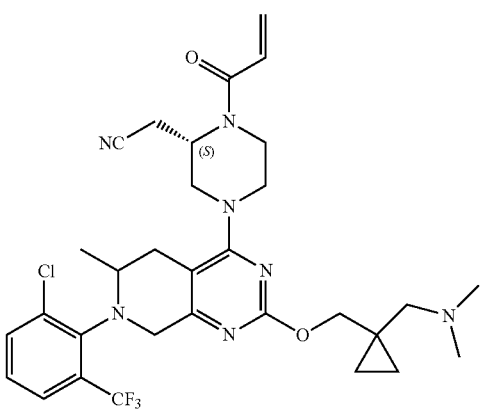
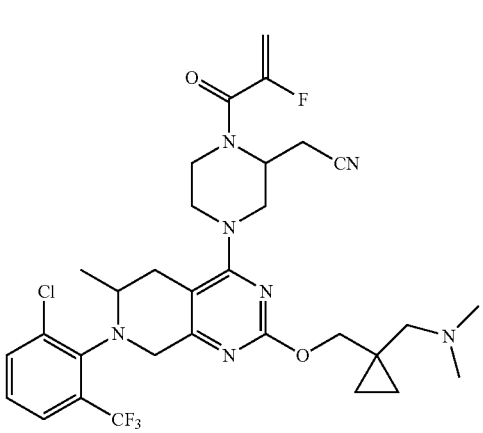
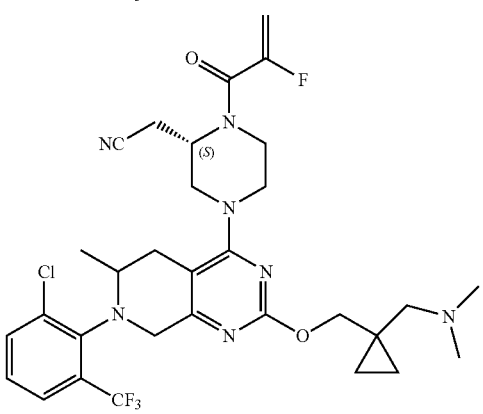

1015
-continued
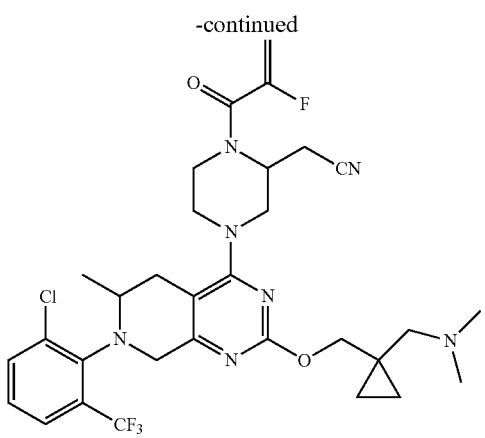
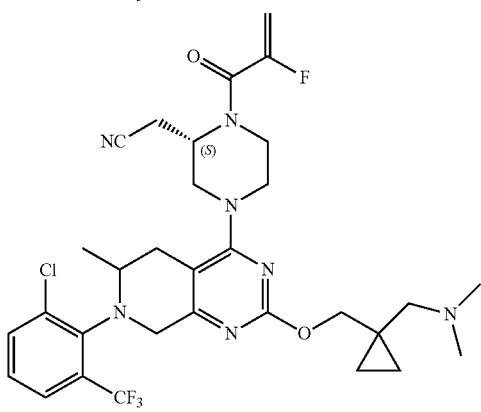
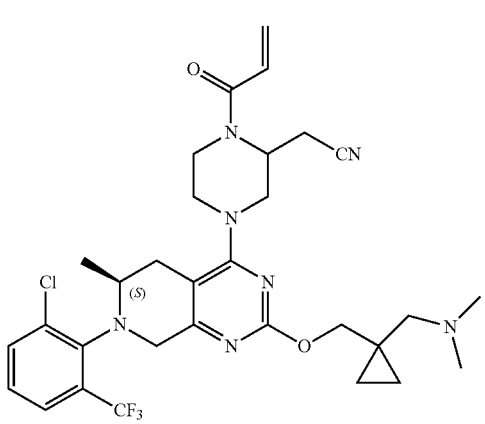
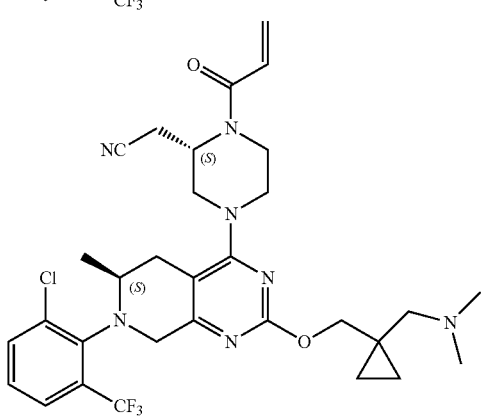
1016
-continued
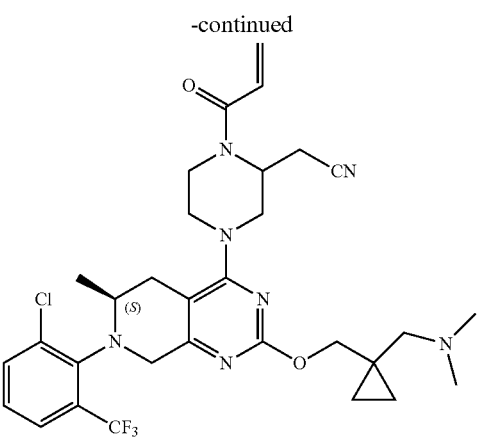
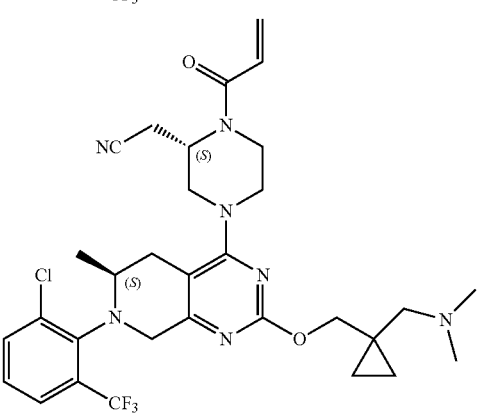
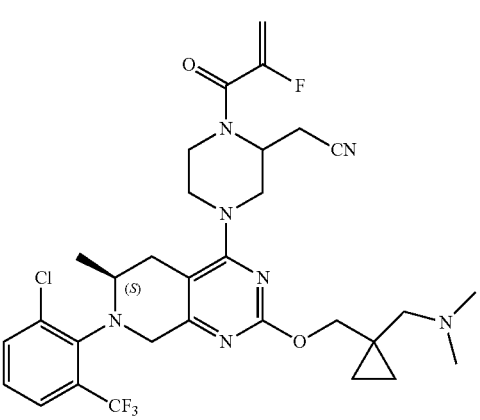
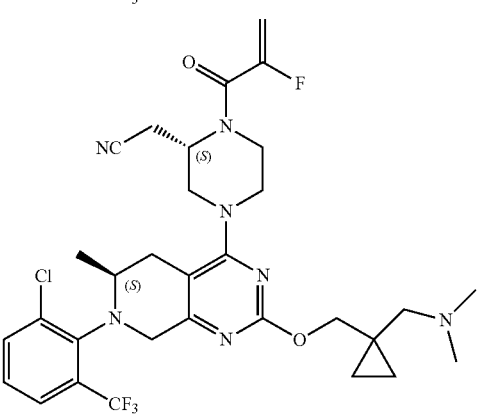

1017
-continued
1018
-continued
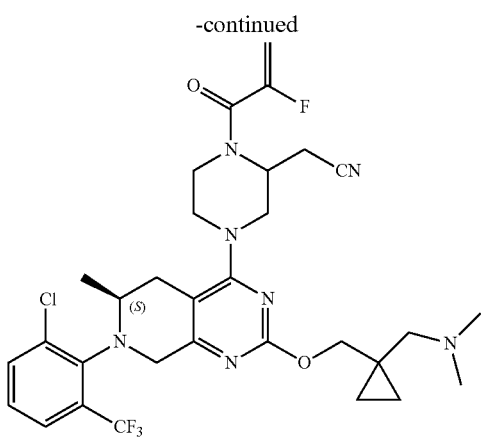
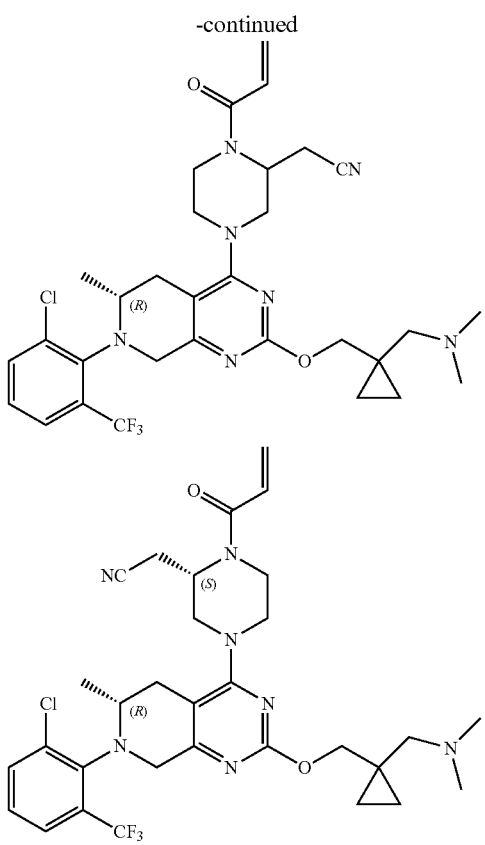
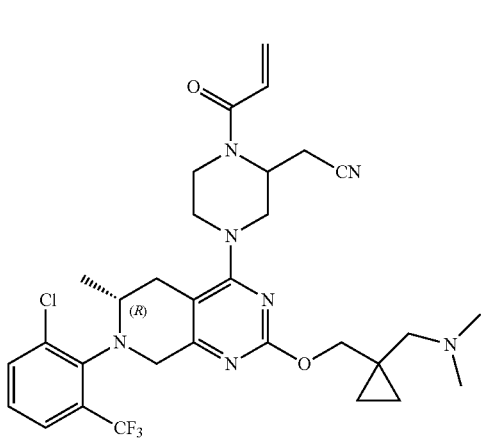
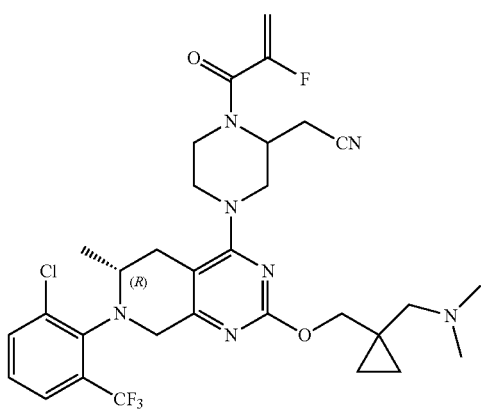
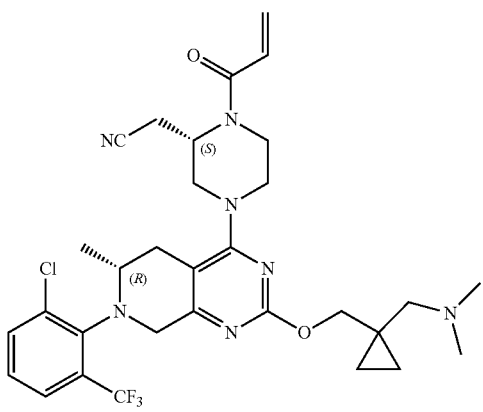
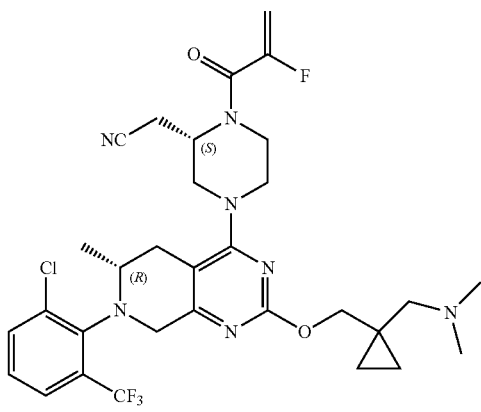

| 1019 | 1020 |
|---|---|
| -continued | -continued |
| 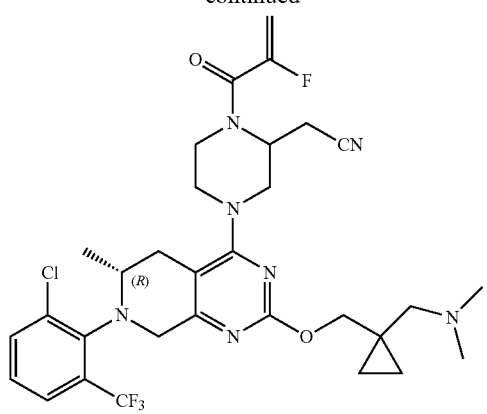 | 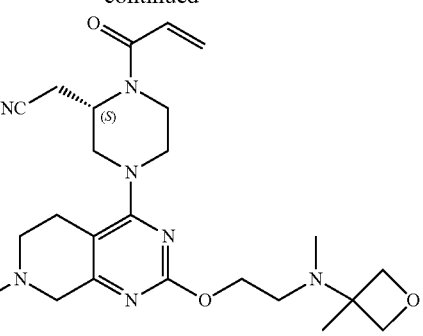 |
| 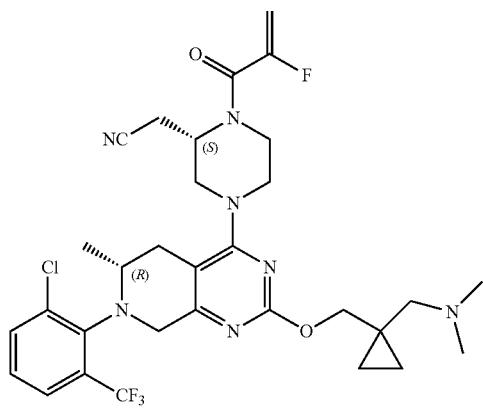 | 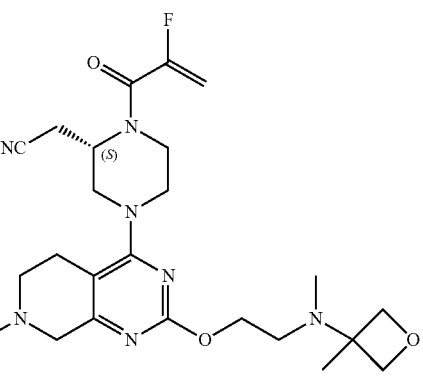 |
| 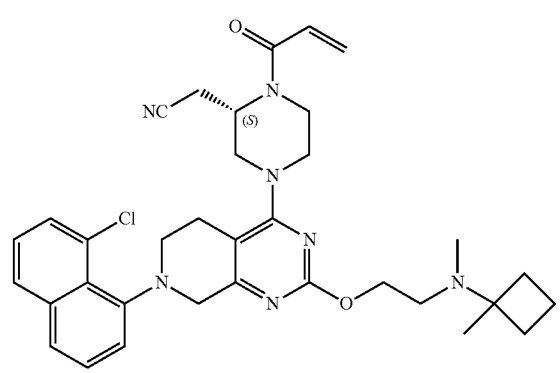 | 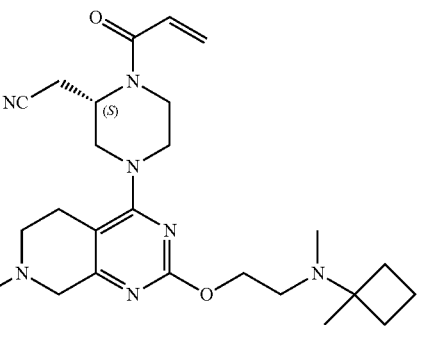 |
| 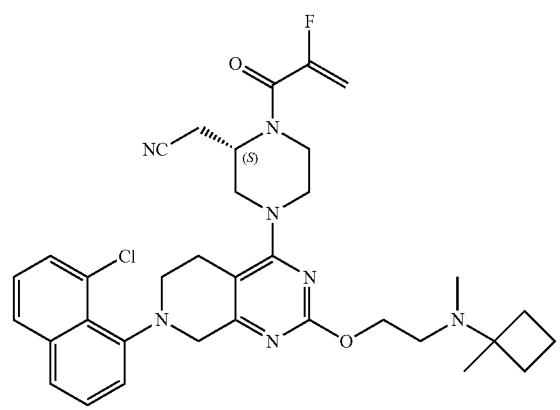 | 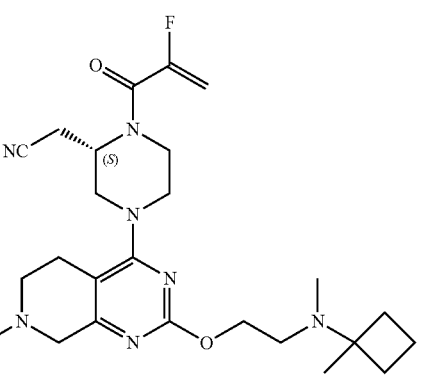 |

1021
-continued
1022
-continued
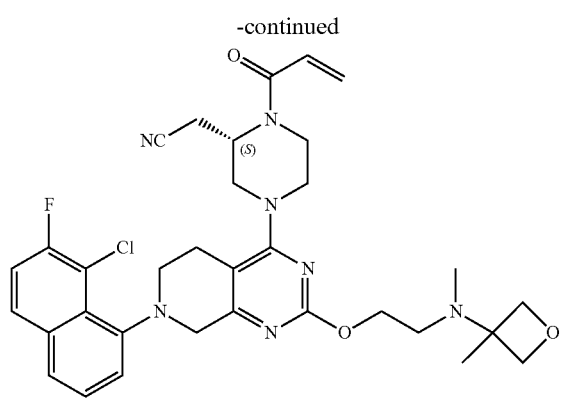
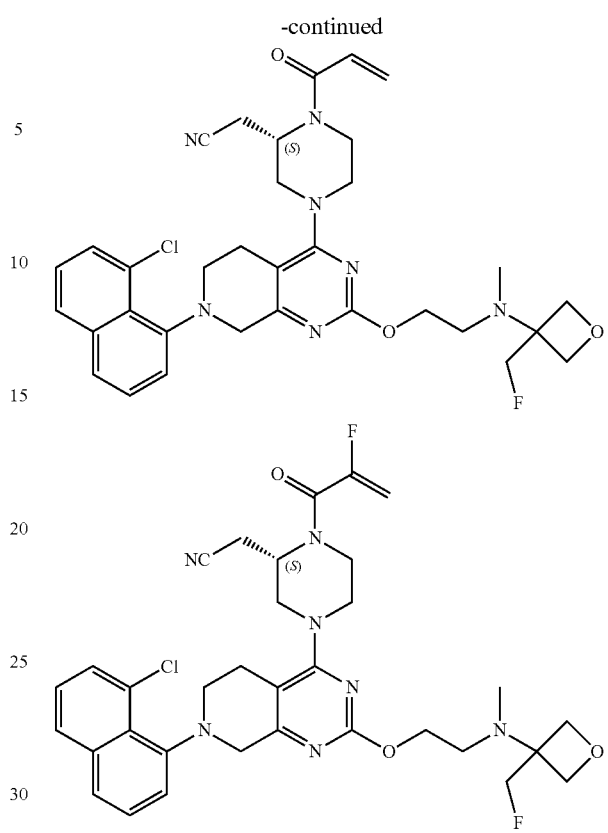
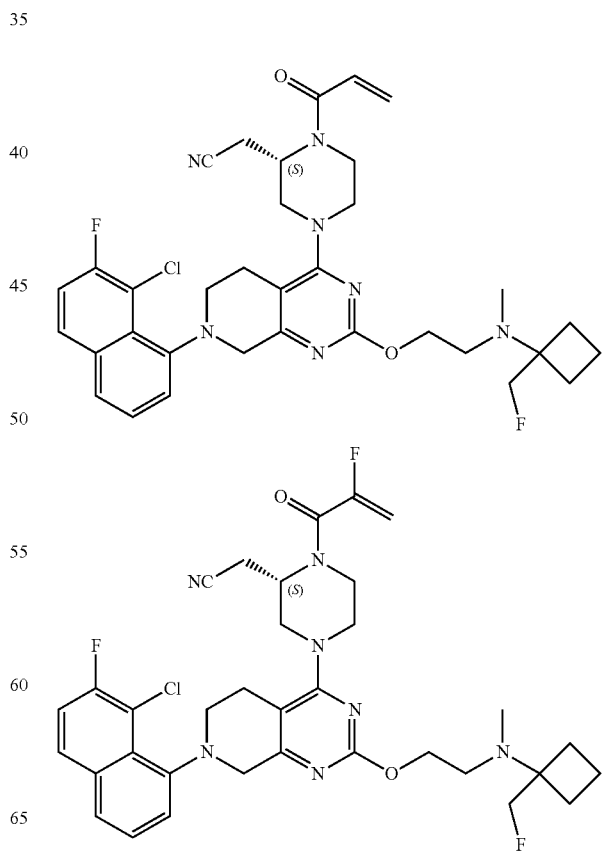

1023
-continued
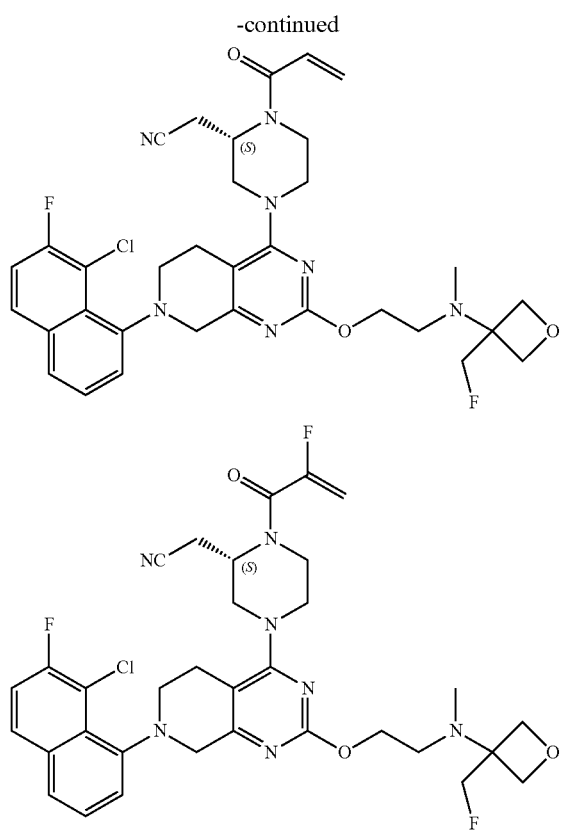
1024
-continued
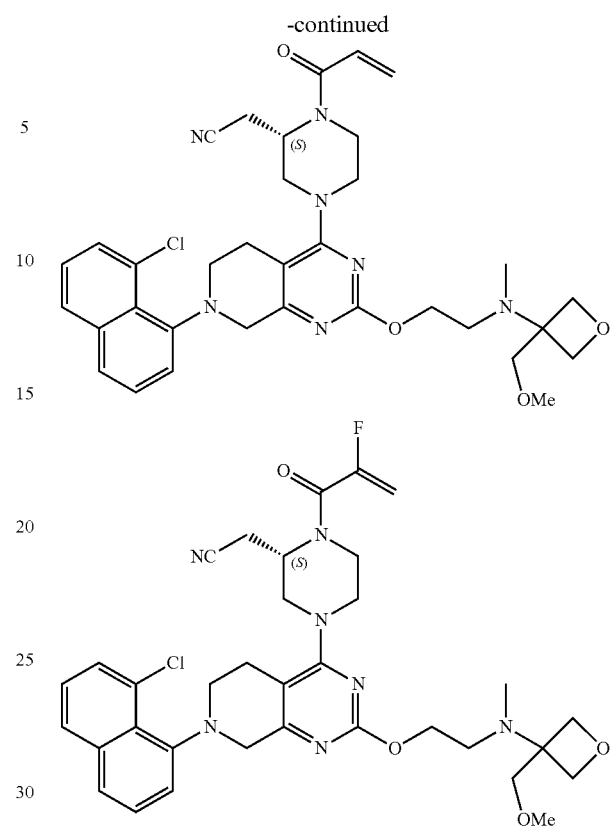
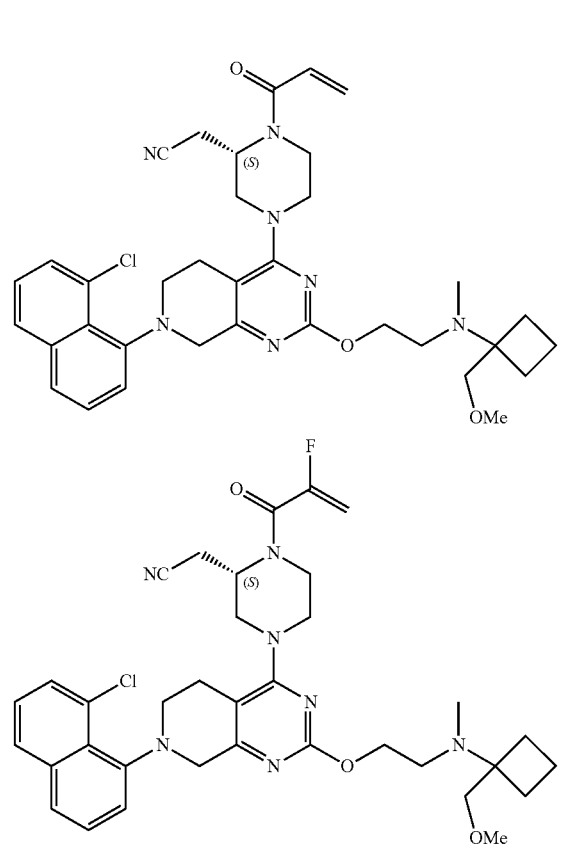

1025
-continued
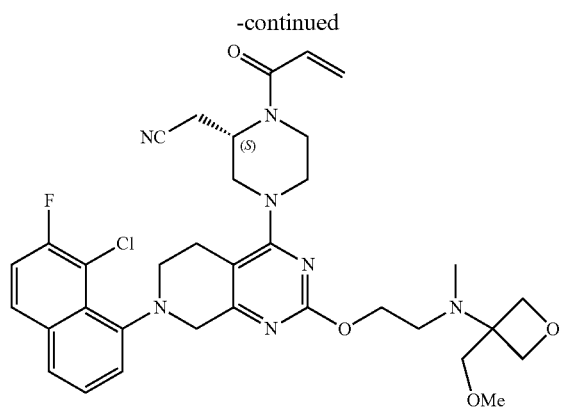
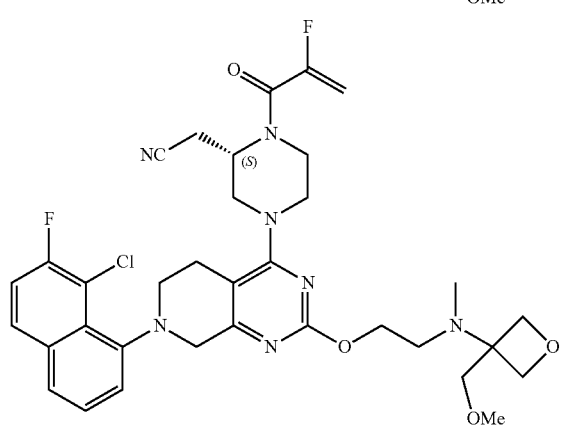
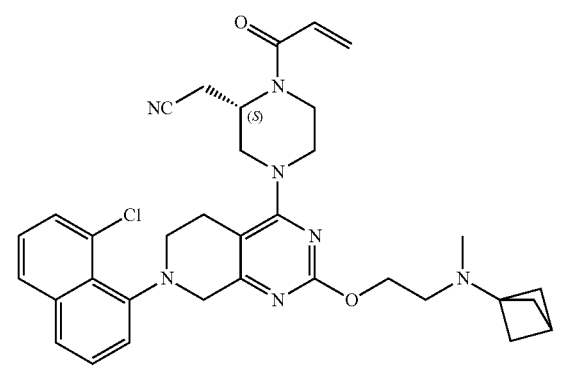
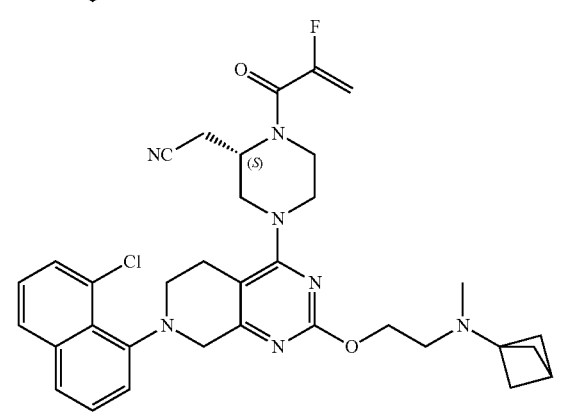
1026
-continued
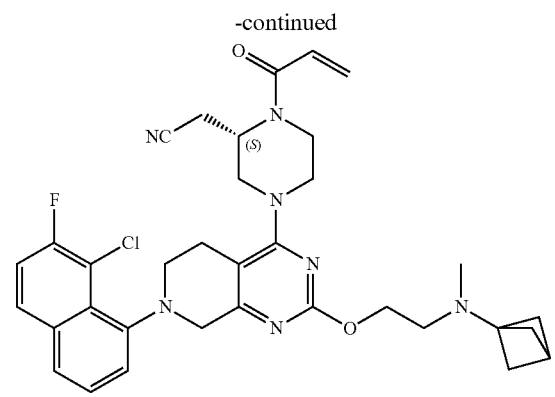
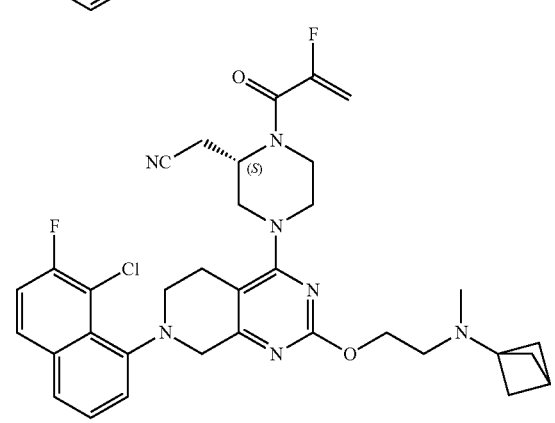
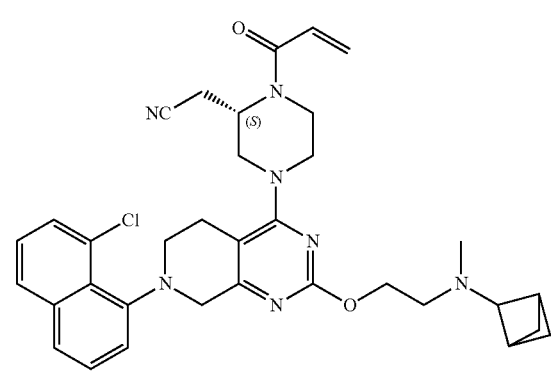
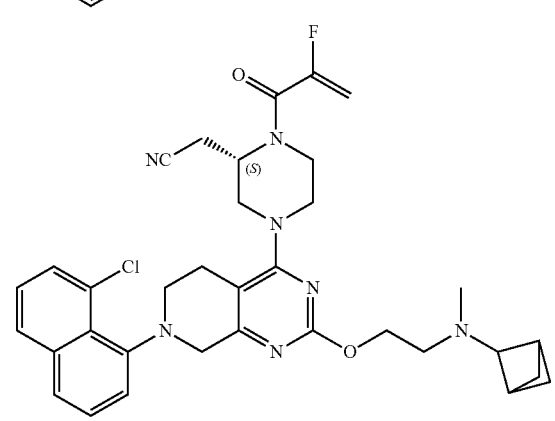

1027
-continued
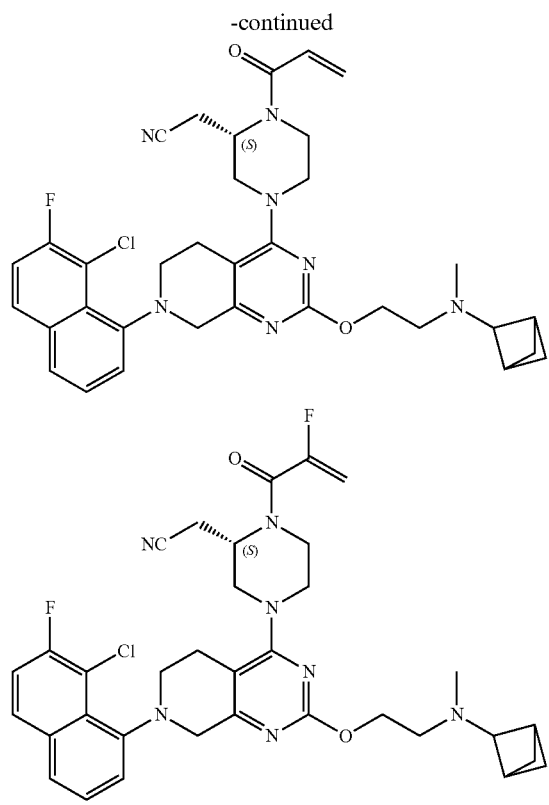
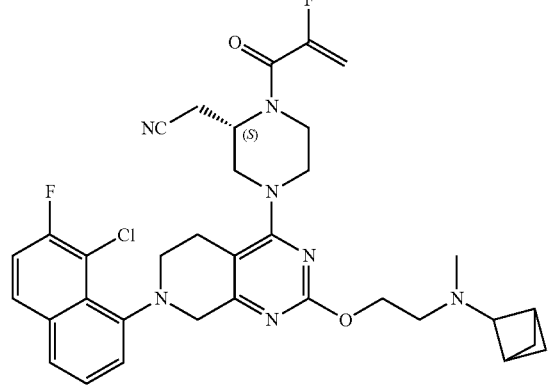
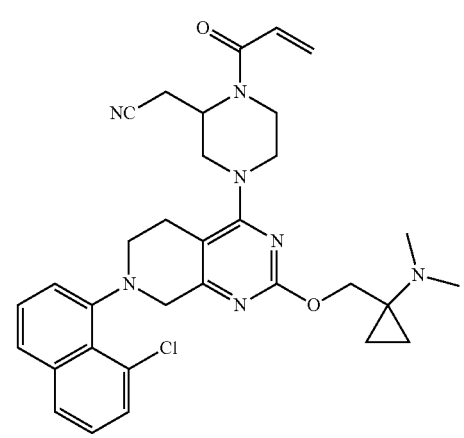
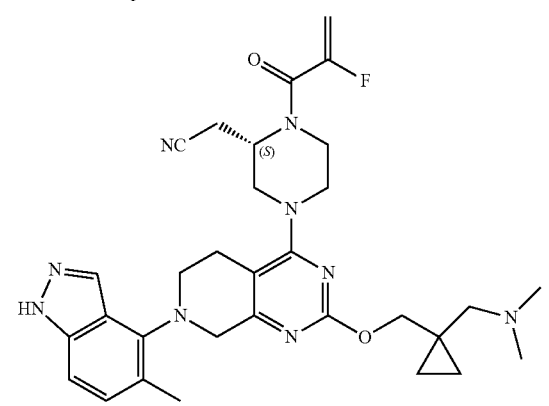
1028
-continued
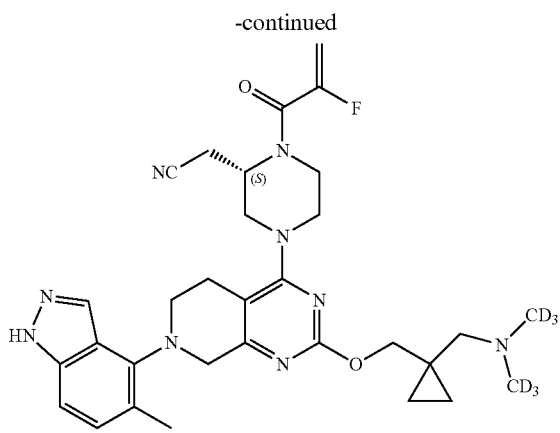
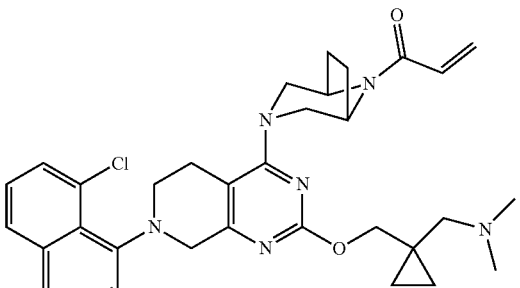
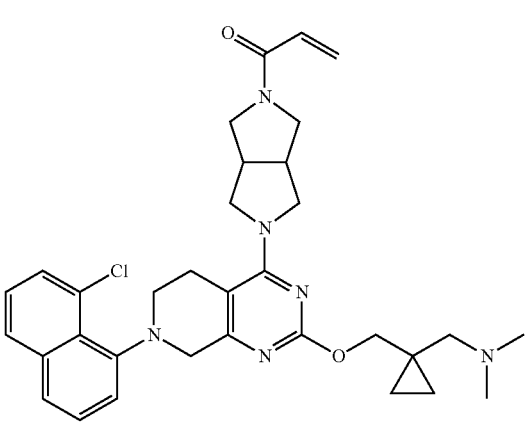
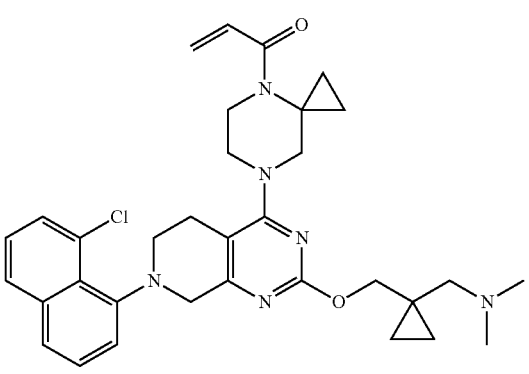

1029
-continued
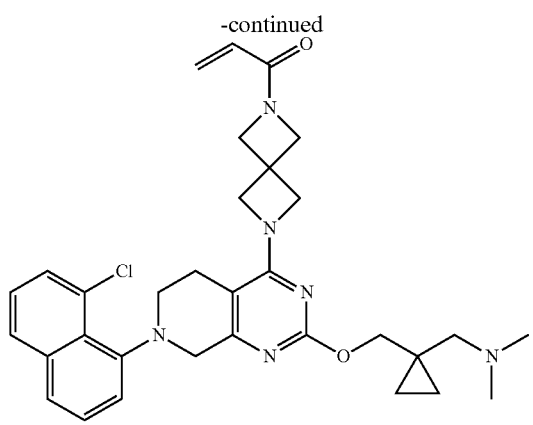
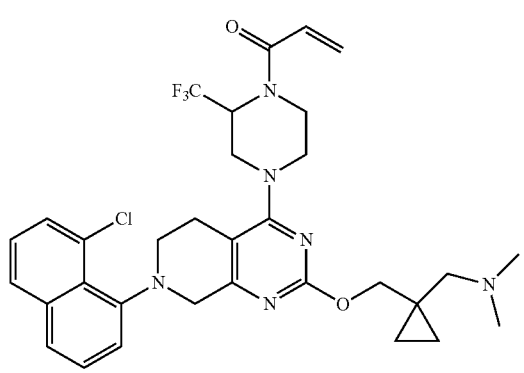
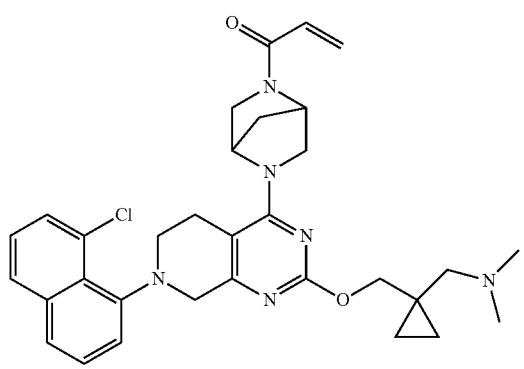
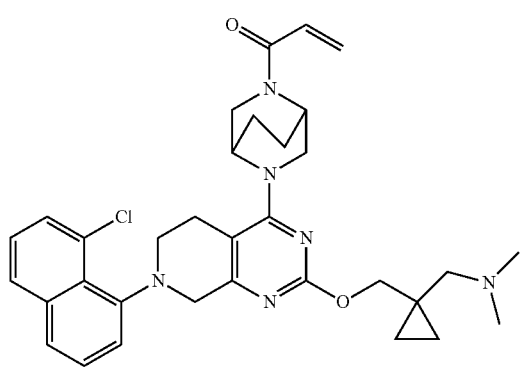
1030
-continued
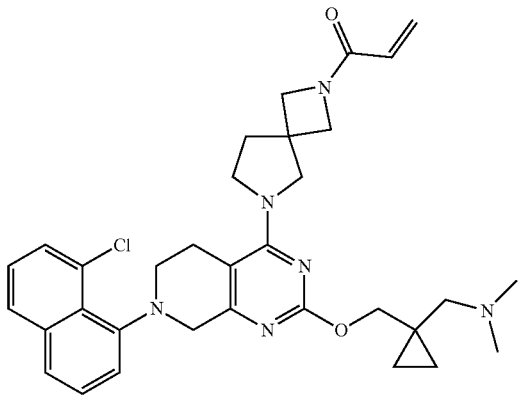
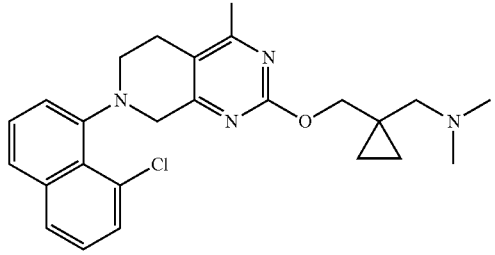
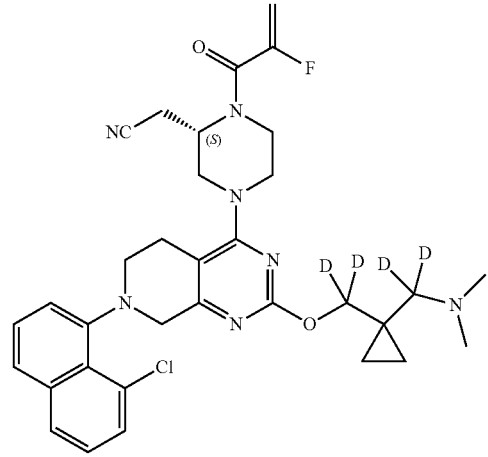

-continued
1031
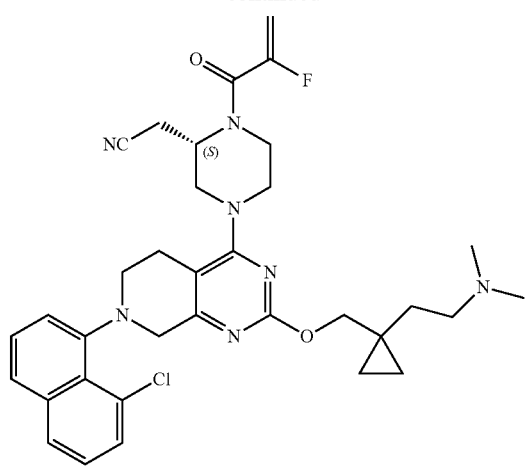
1032
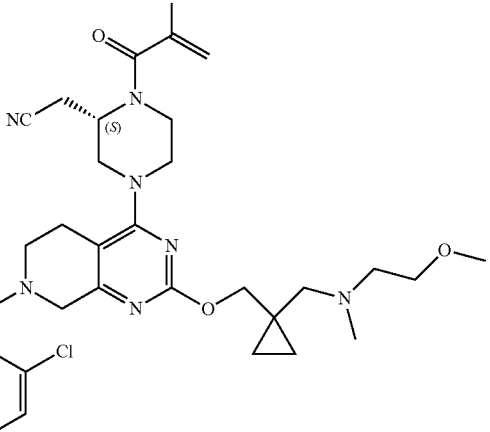
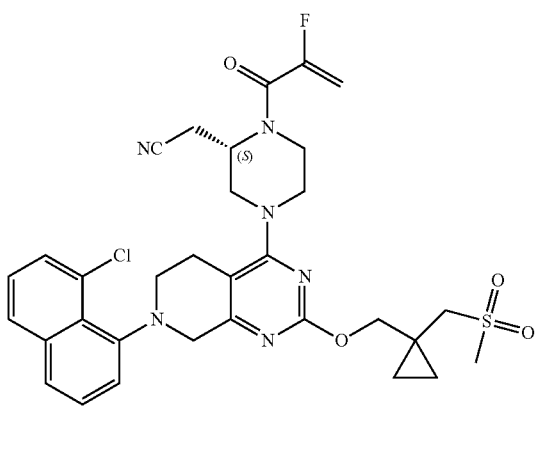
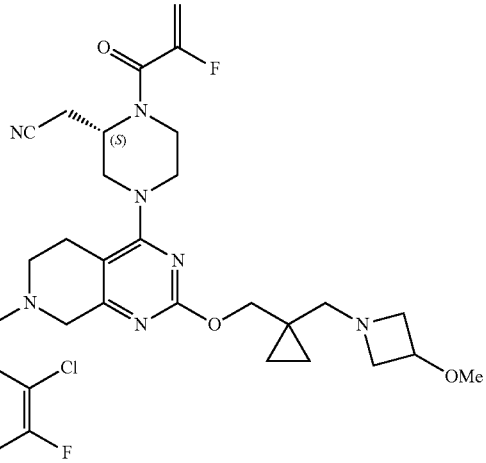
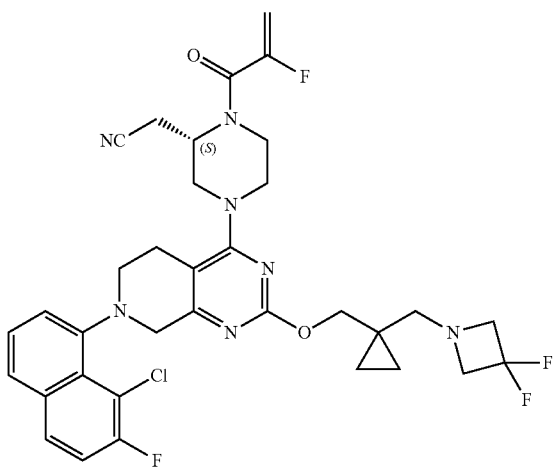
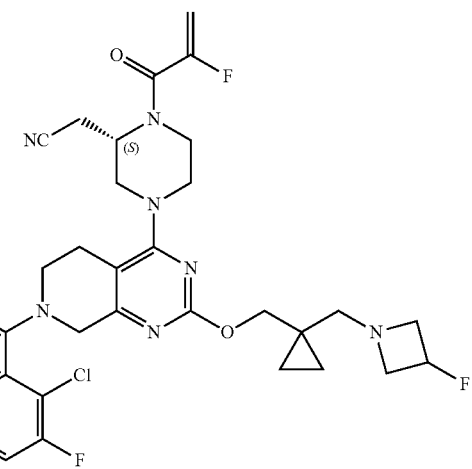

1033

-continued

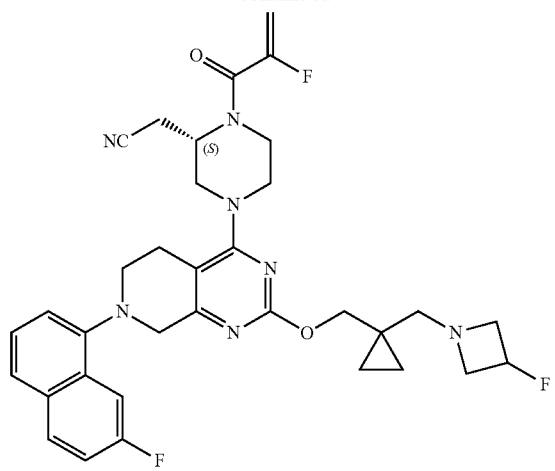

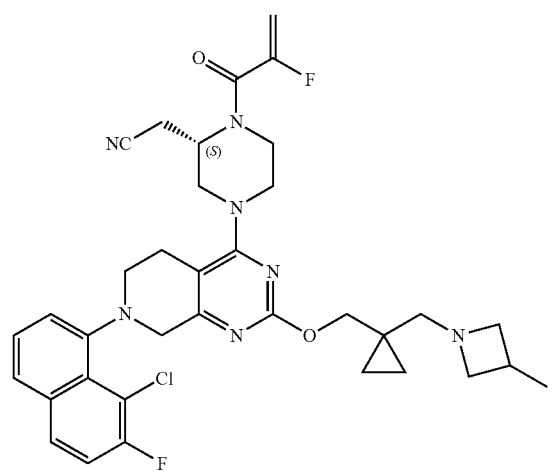

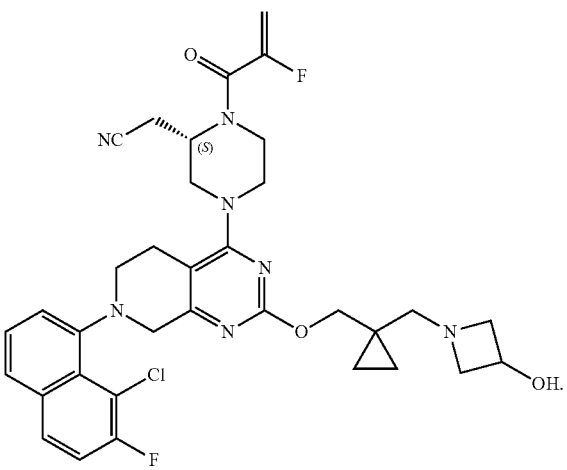

or a stereoisomer, tautomer, crystal form, pharmaceutically acceptable salt, hydrate, solvate or prodrug thereof.

4. A pharmaceutical composition comprises one or more of the compound, the stereoisomer, tautomer, crystal form, pharmaceutically acceptable salt, hydrate, solvate or prodrug thereof of claim 1; and a pharmaceutically acceptable carrier.

5. The compound, and the stereoisomer, tautomer, crystal form, pharmaceutically acceptable salt, hydrate, solvate or prodrug thereof of claim 2, wherein $R^4$ is

1034

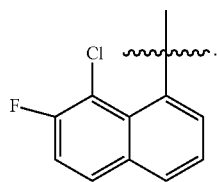 [SMILES: *c1cccc2ccc(F)c(Cl)c12]

6. The compound, and the stereoisomer, tautomer, crystal form, pharmaceutically acceptable salt, hydrate, solvate or prodrug thereof of claim 2, wherein the compound is selected from the group consisting of:

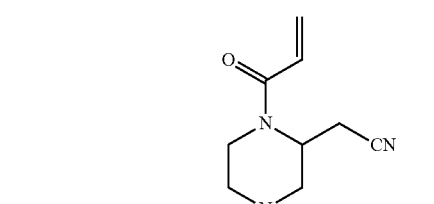

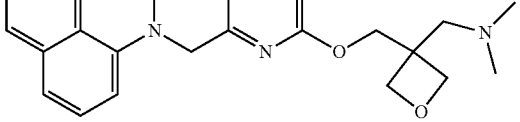

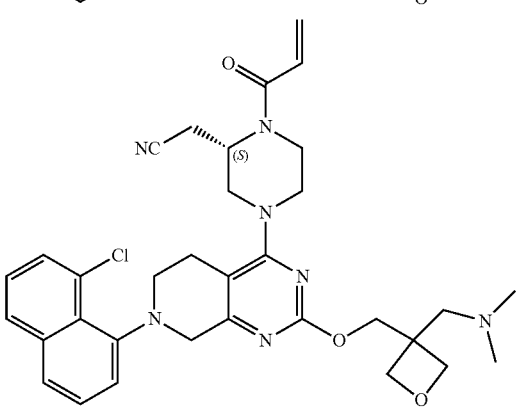

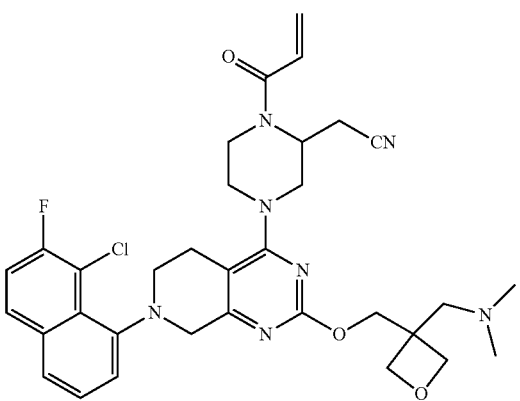

1035
-continued
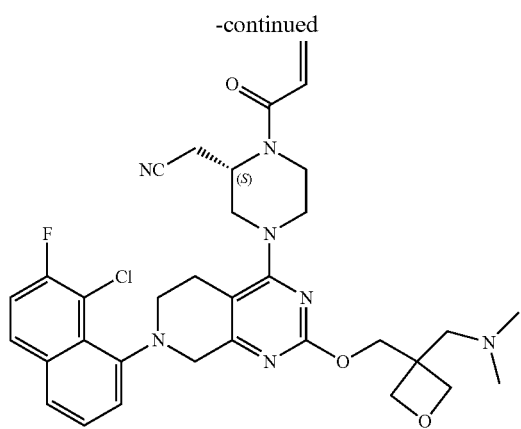
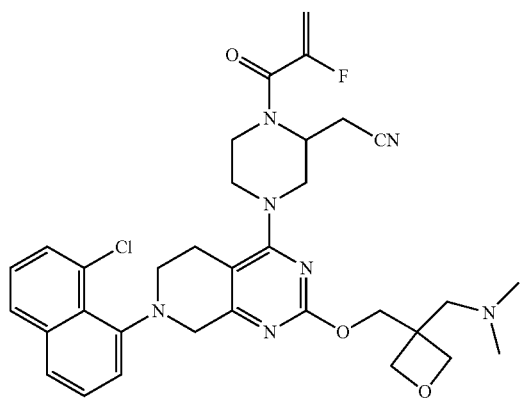
1036
-continued
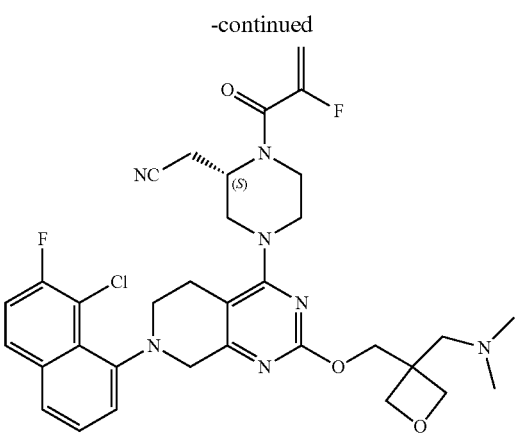
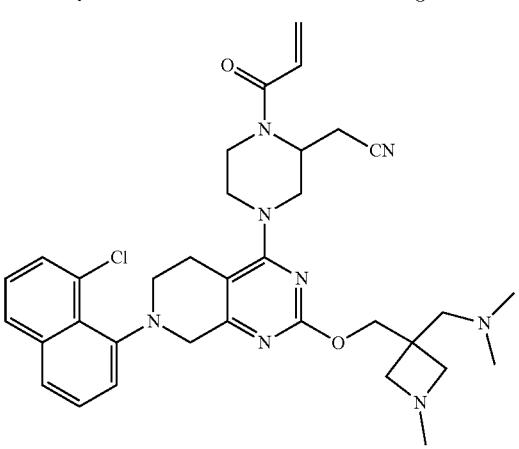
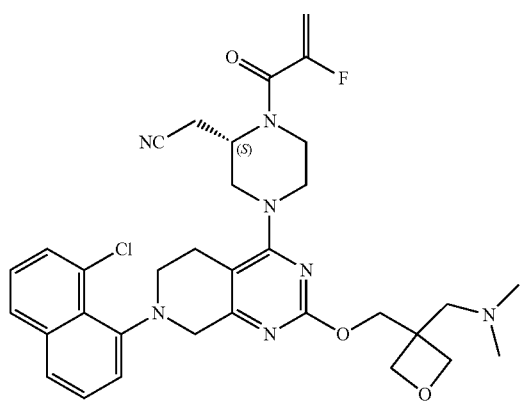
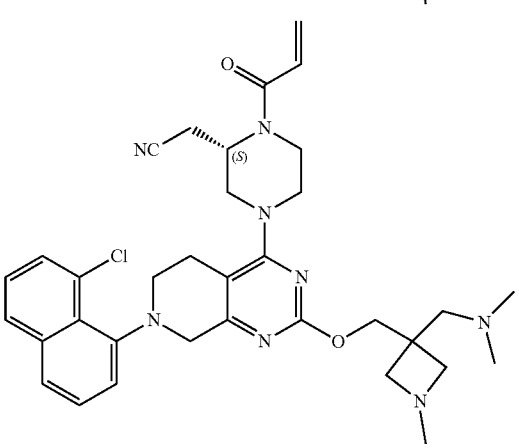
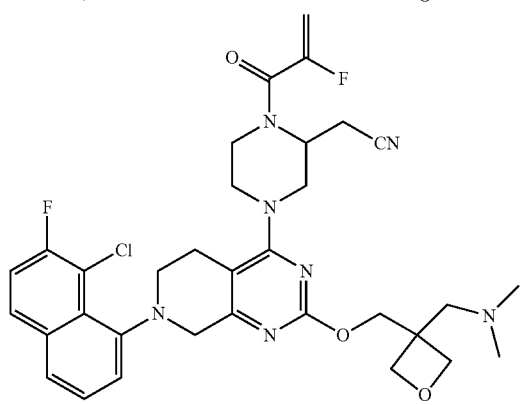
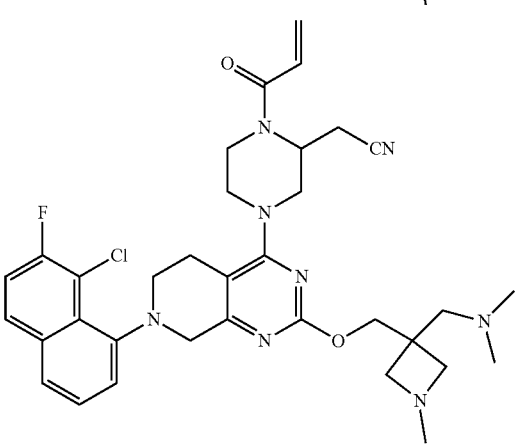

1037
-continued
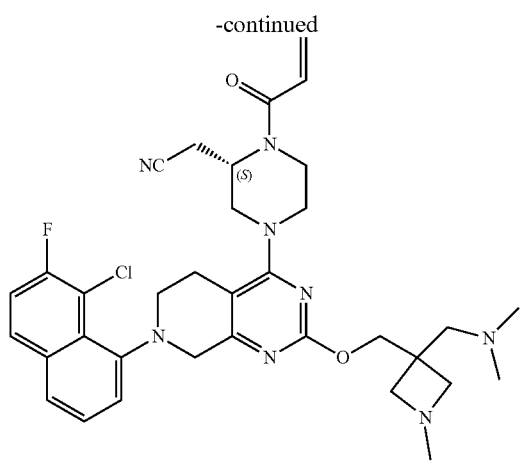
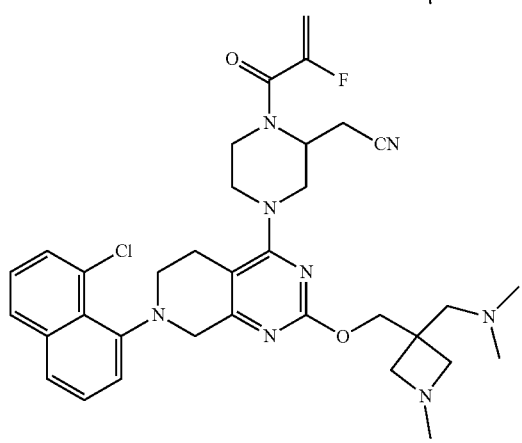
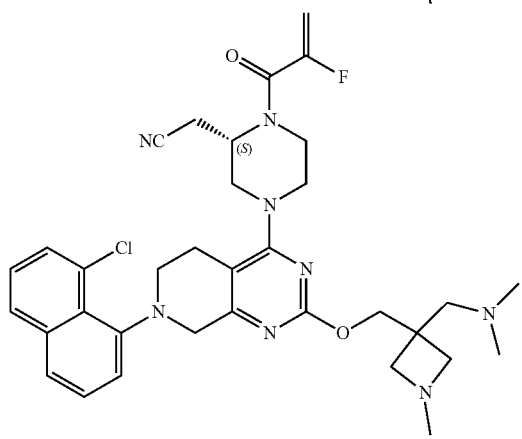
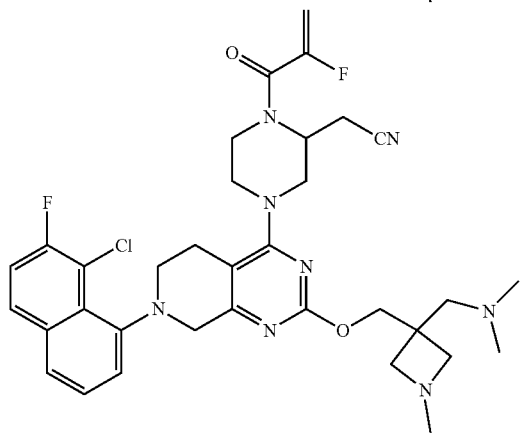
1038
-continued
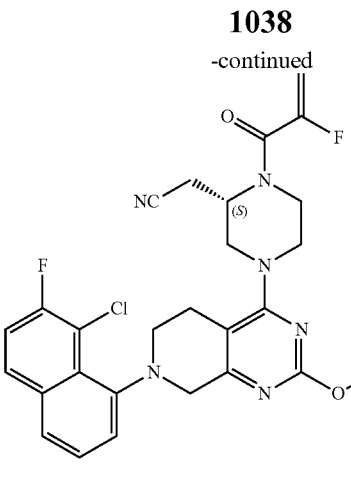
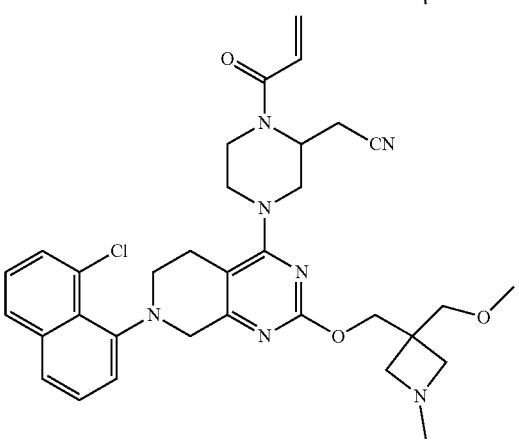
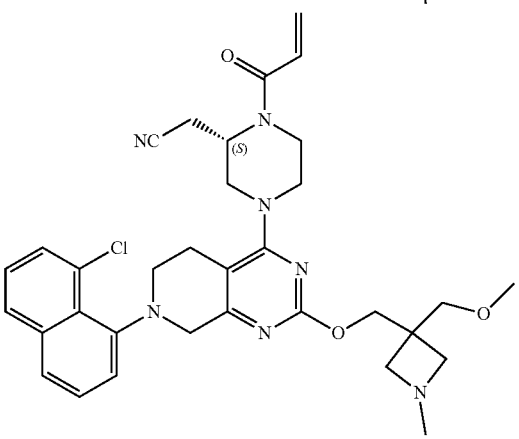
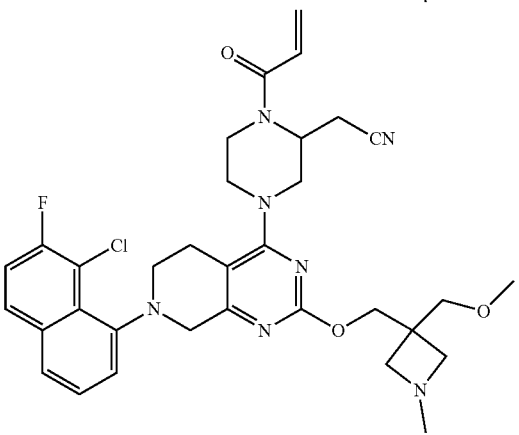

1039
-continued
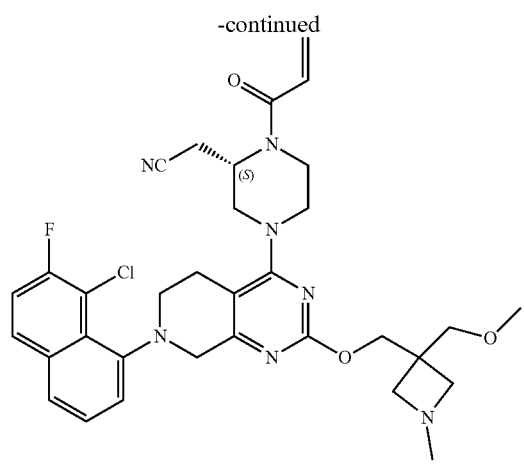
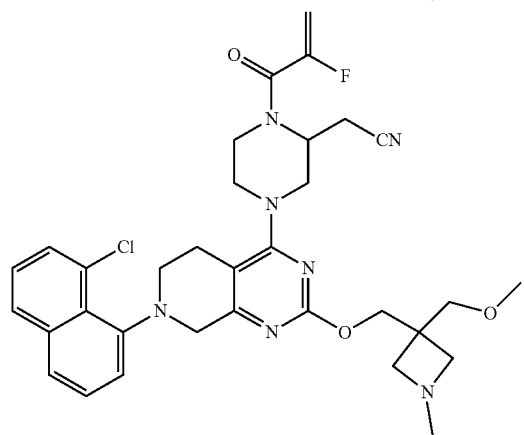
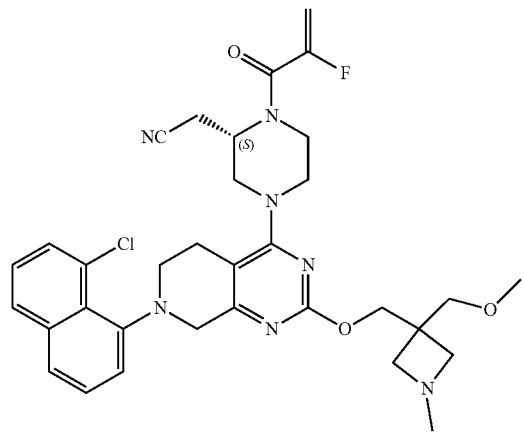
1040
-continued
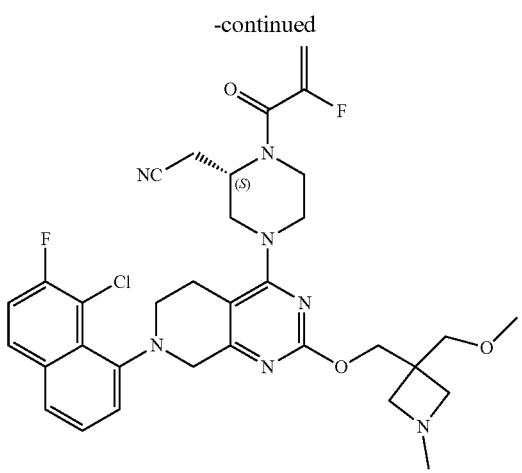
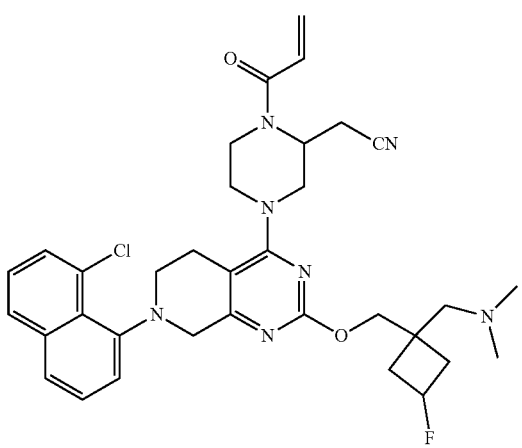
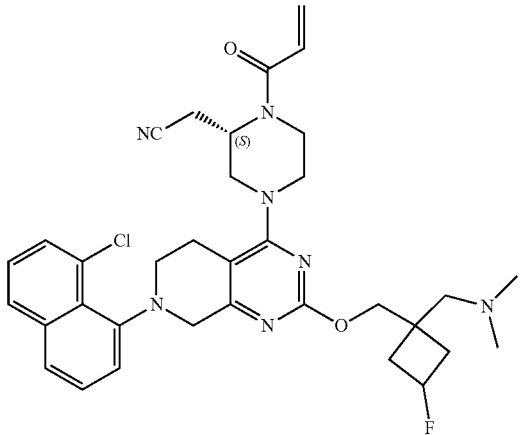

1041
-continued
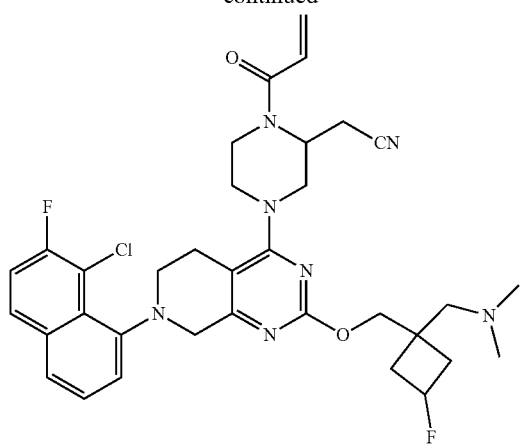
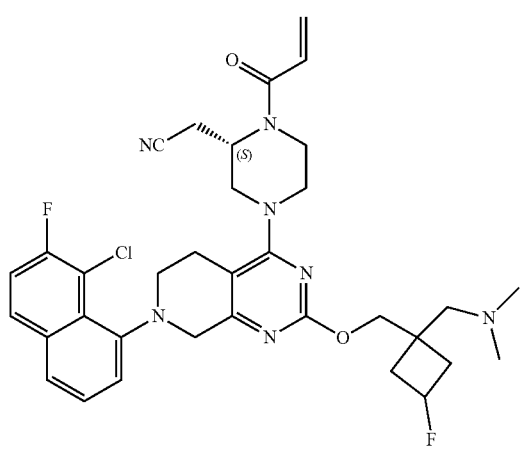
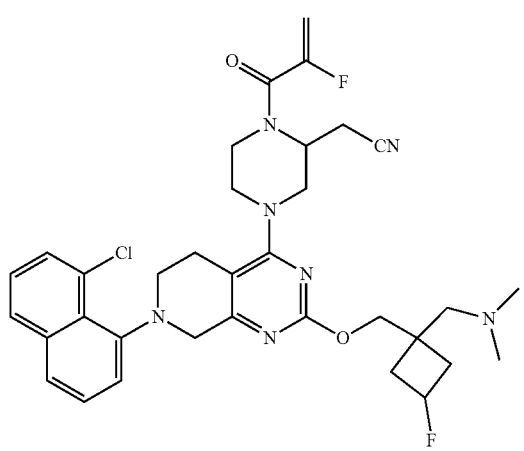
1042
-continued
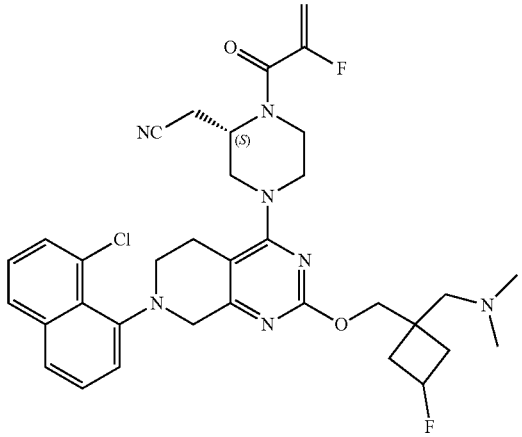
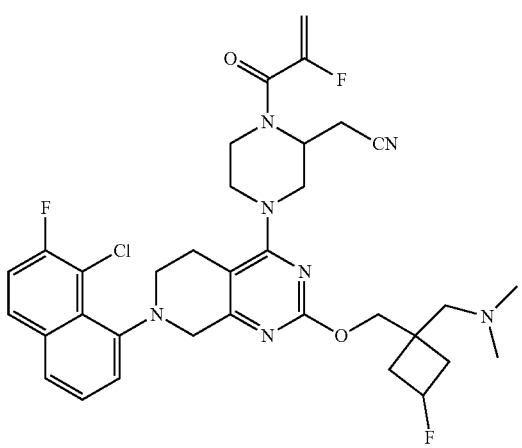
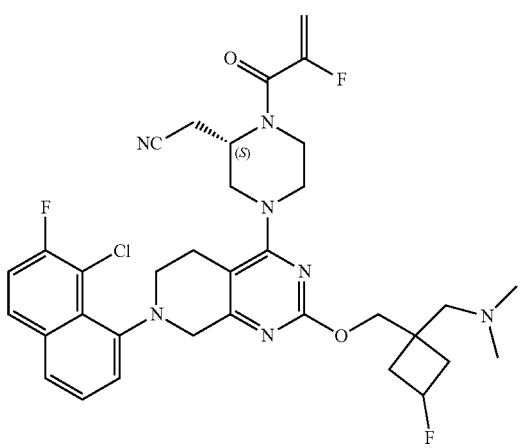

1043
-continued
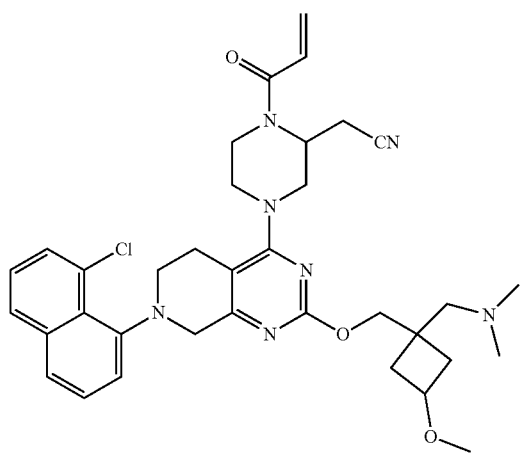
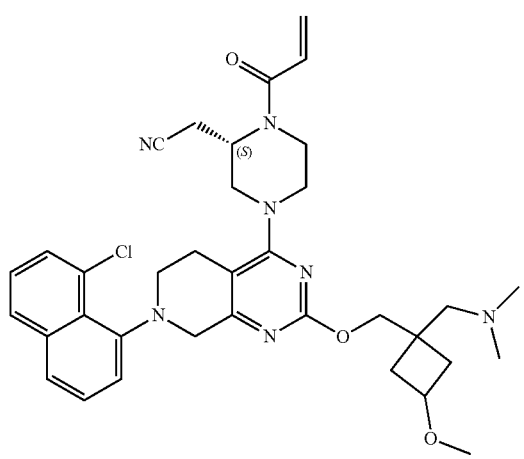
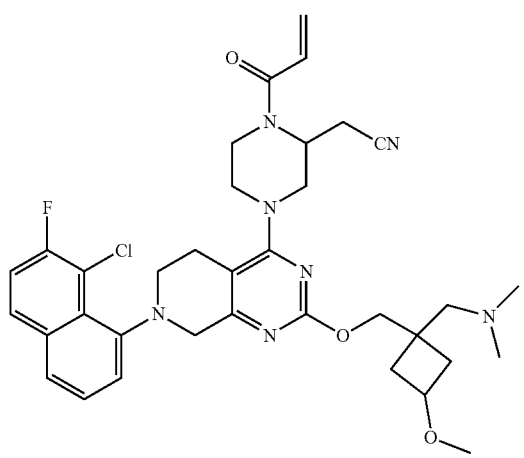
1044
-continued
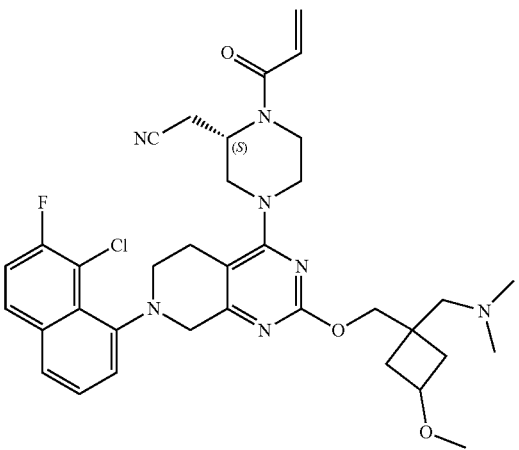
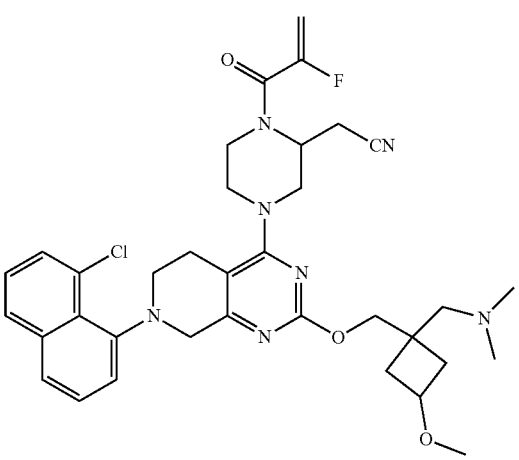
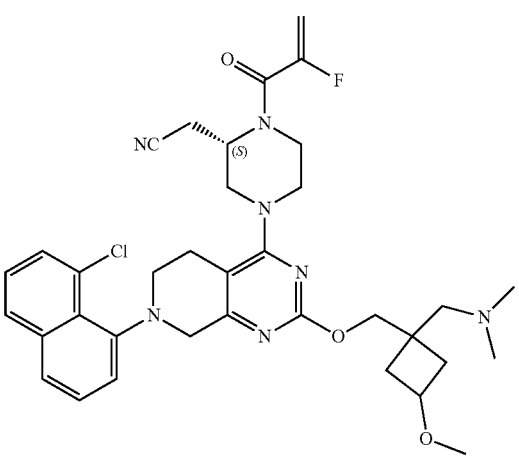

1045
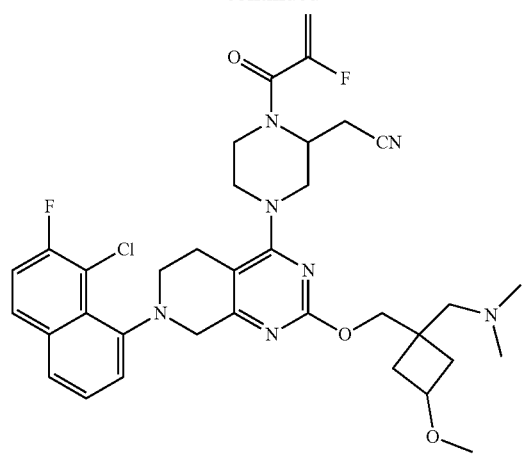
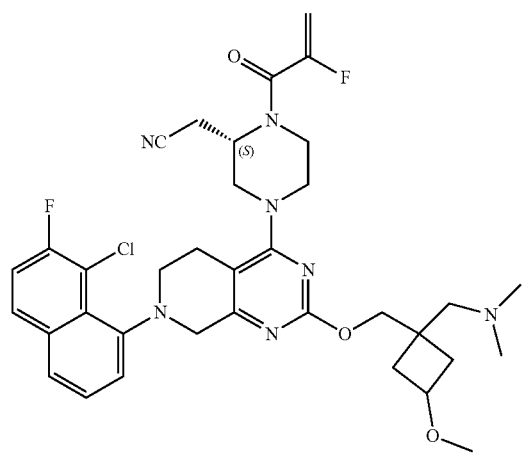
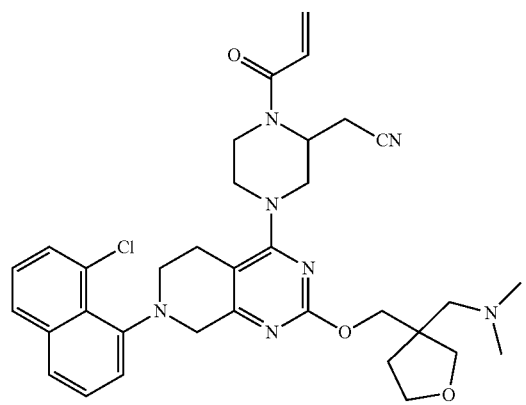
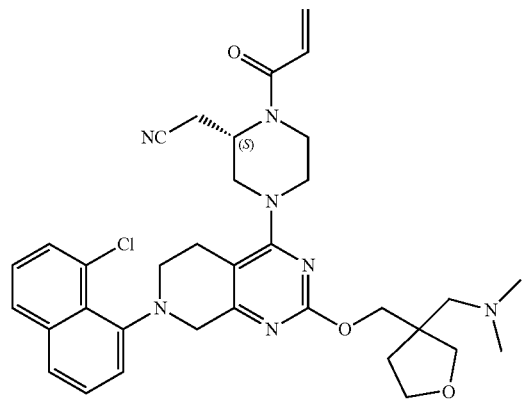
1046
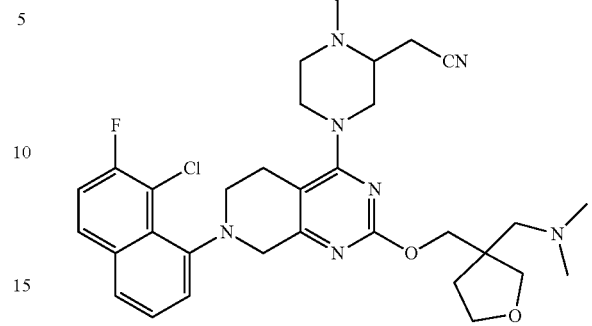
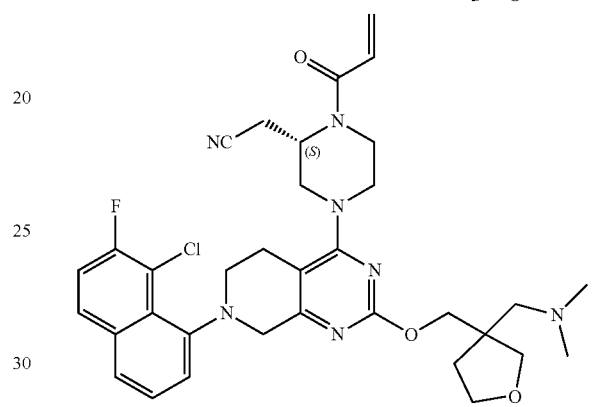
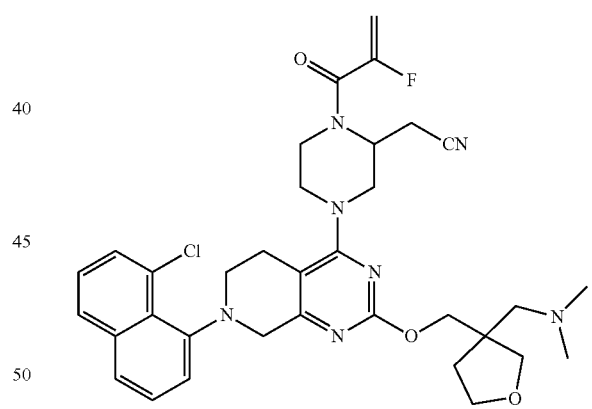
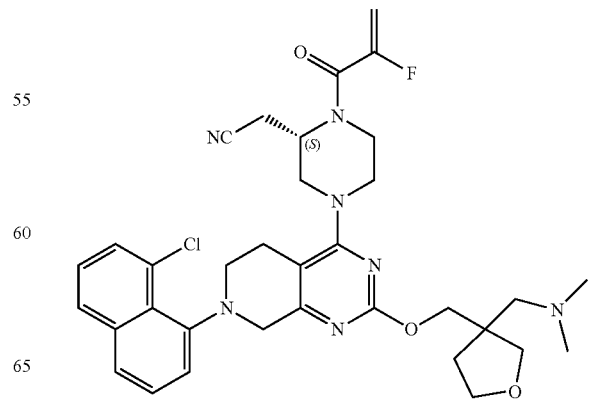

1047
-continued
1048
-continued
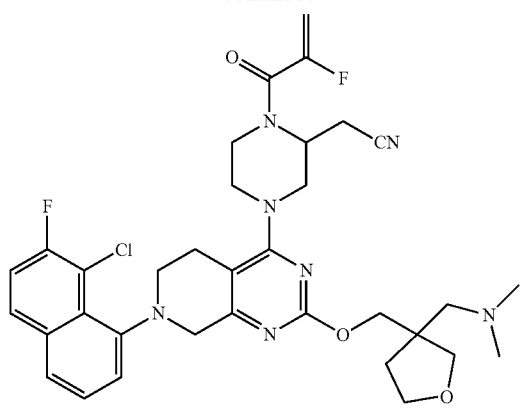
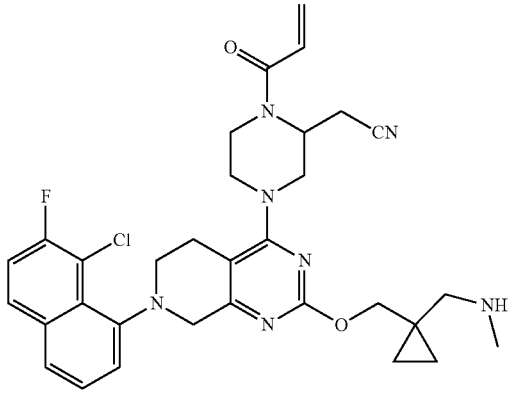
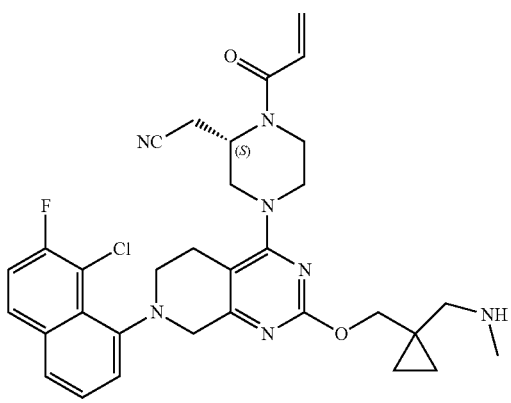
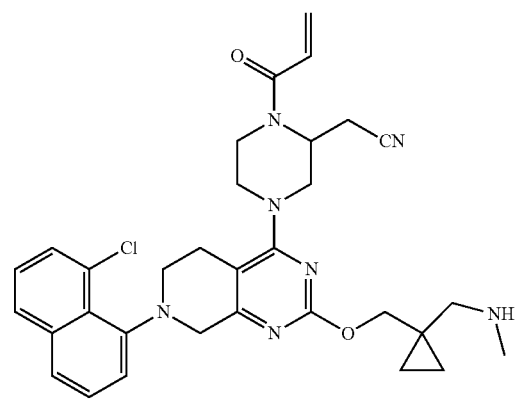
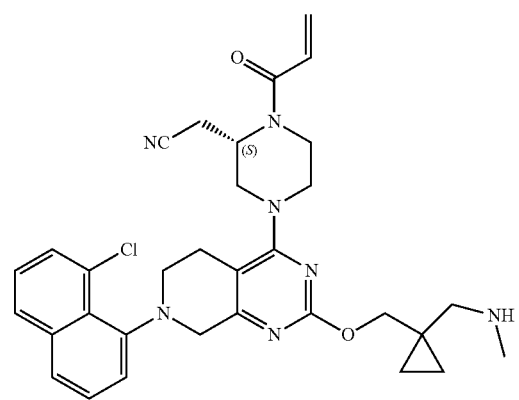

1049
-continued
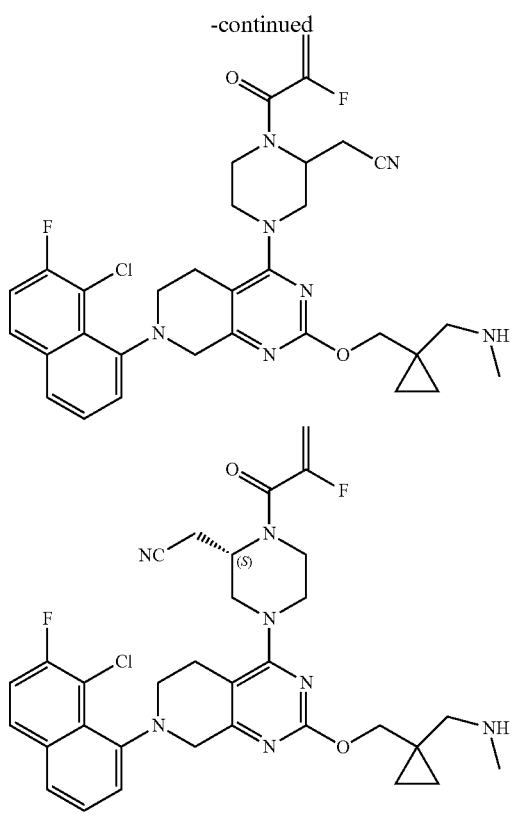
1050
-continued
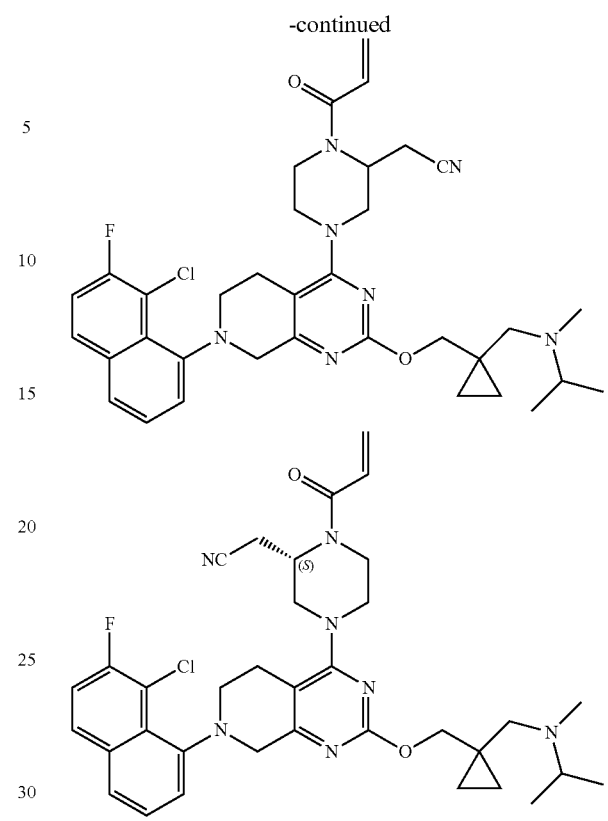
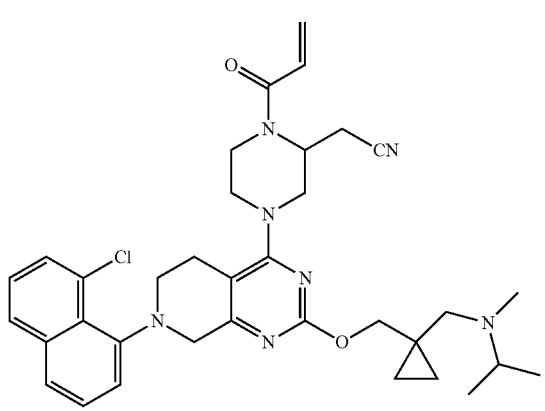
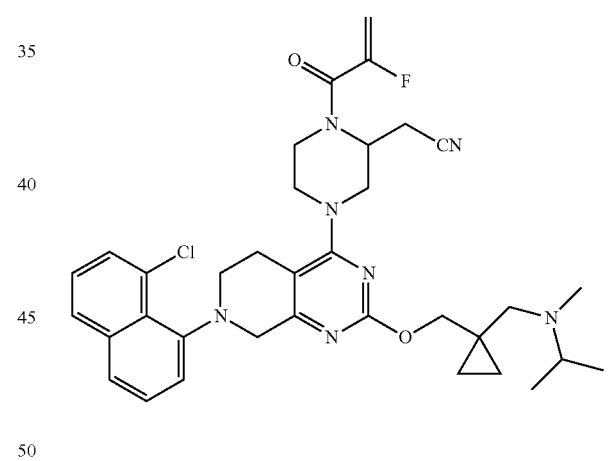
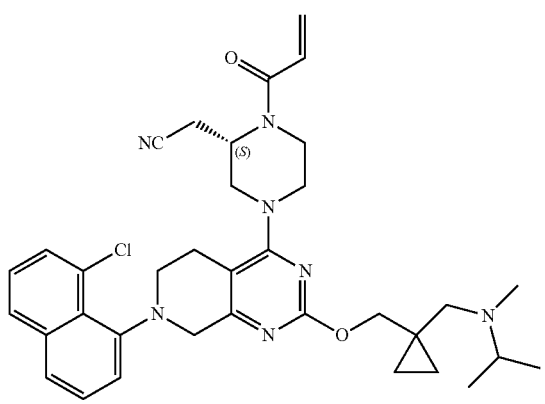
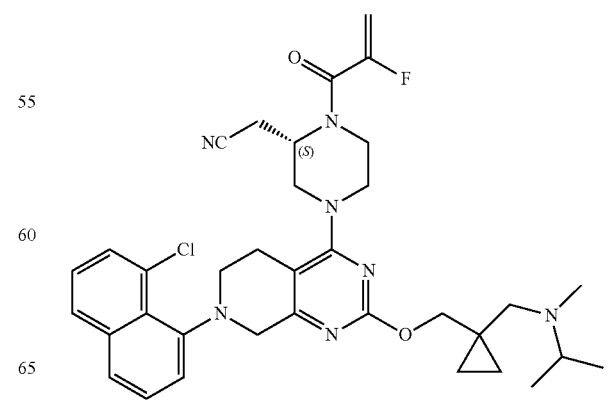

1051
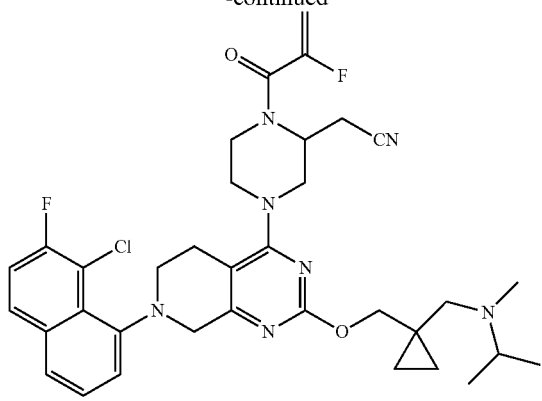
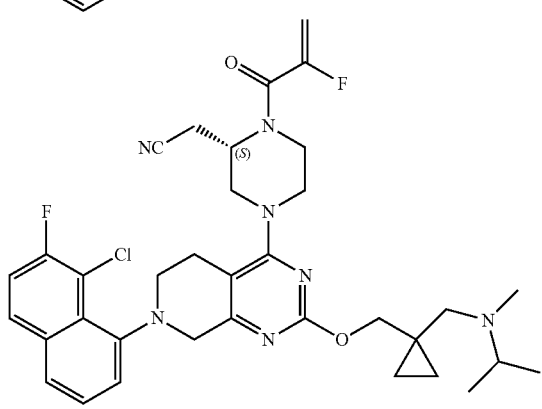
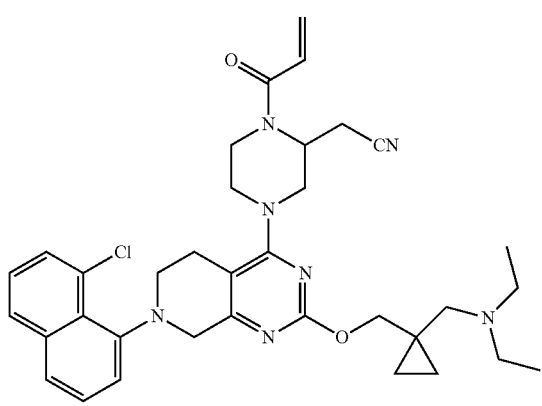
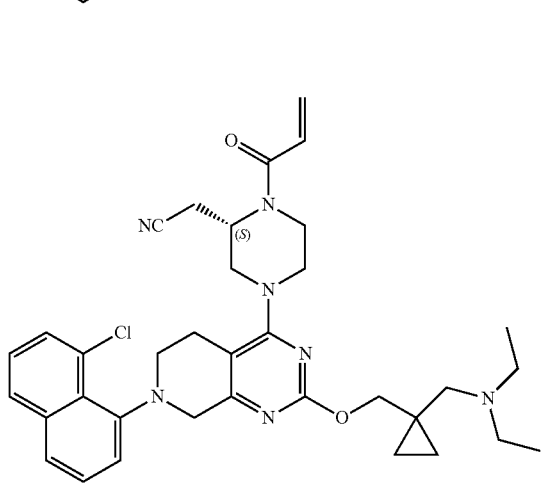
1052
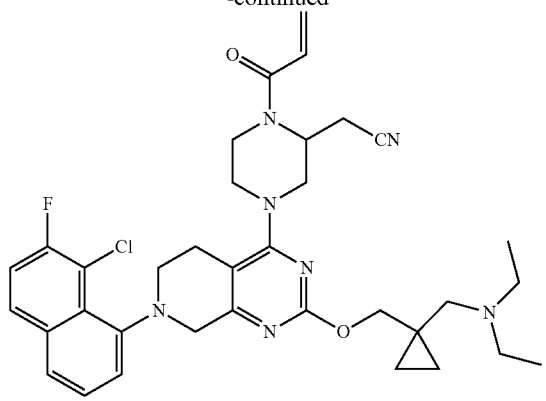
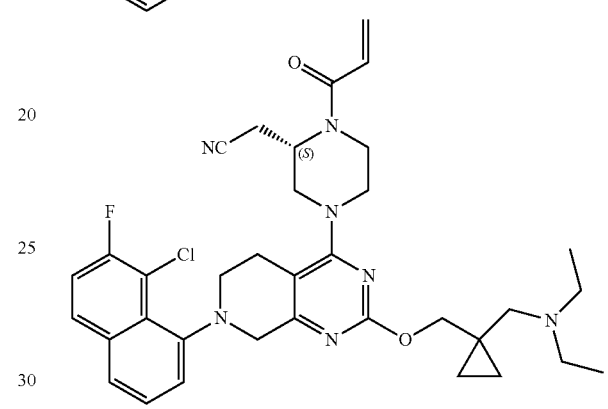
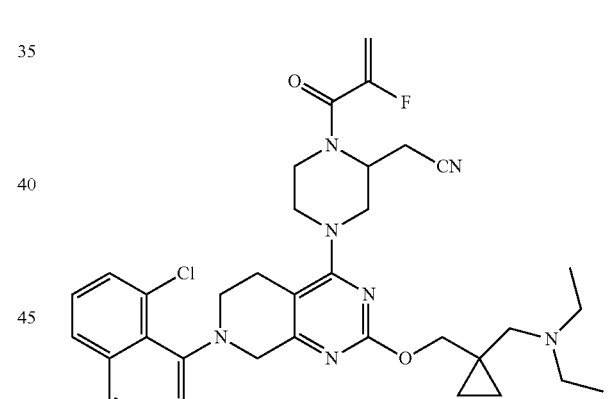
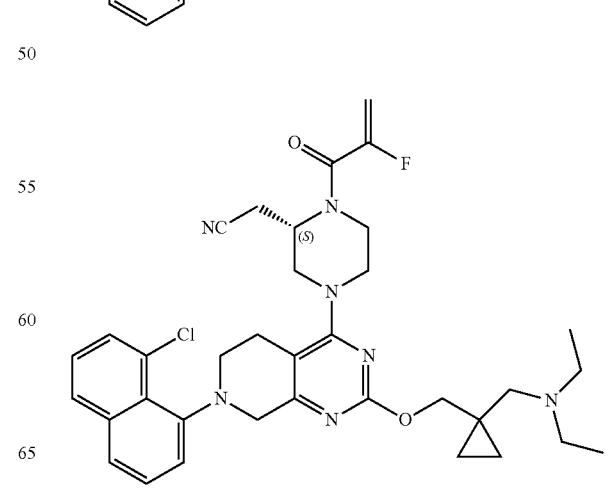

1053
-continued
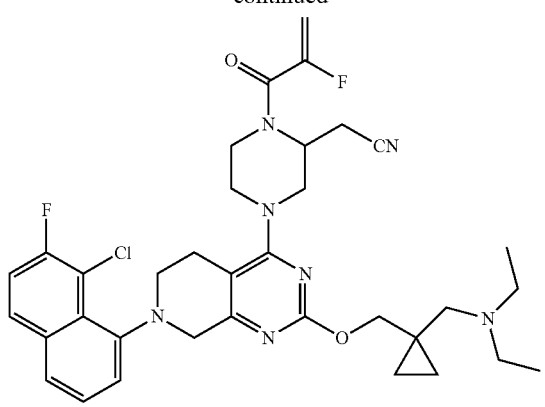
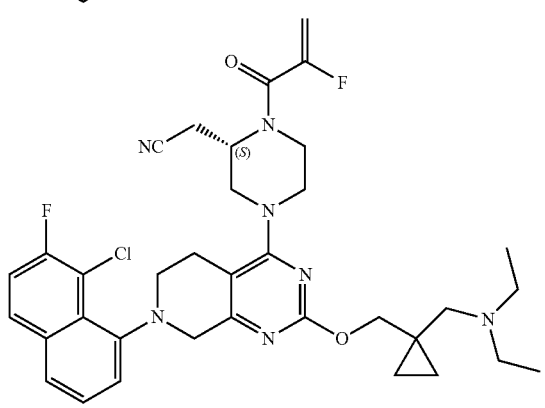
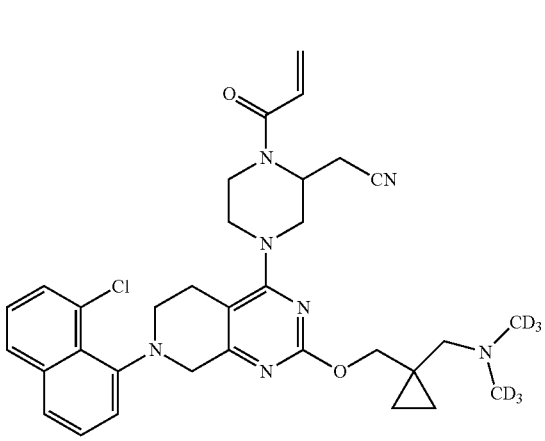
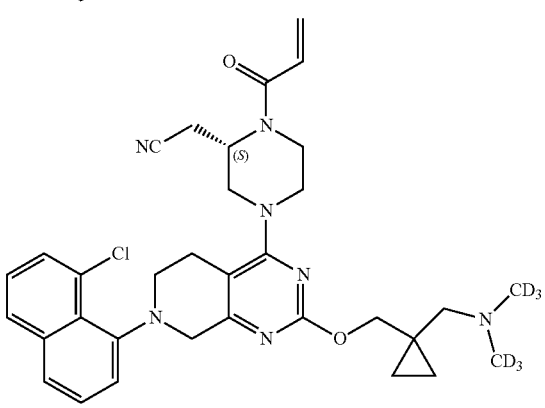
1054
-continued
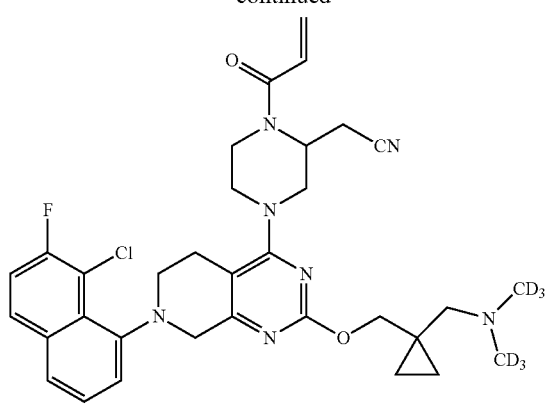
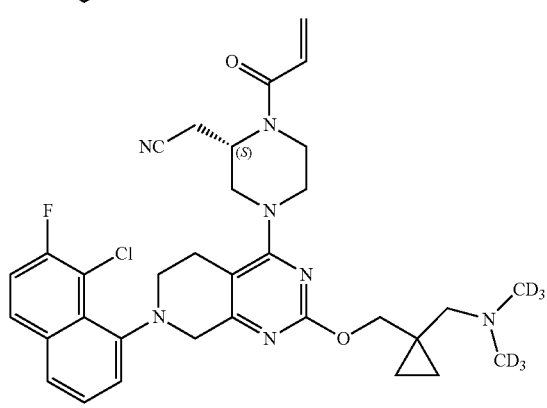
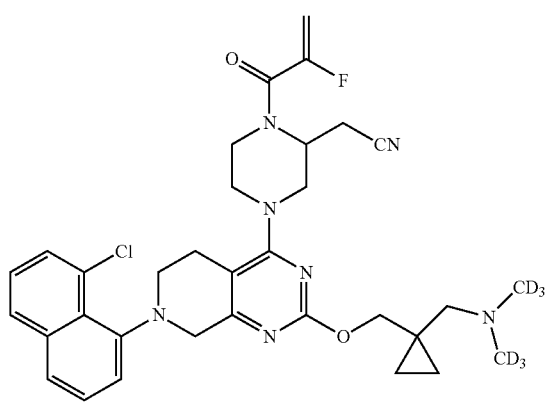
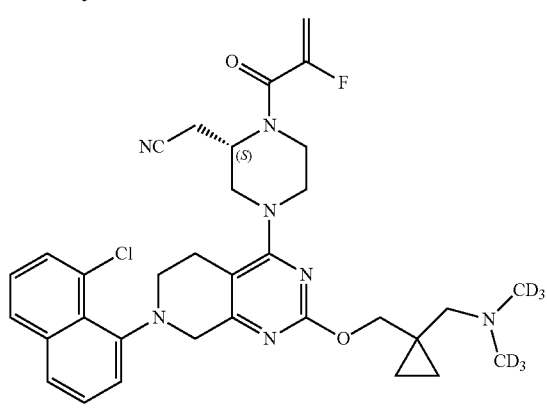

1055
-continued
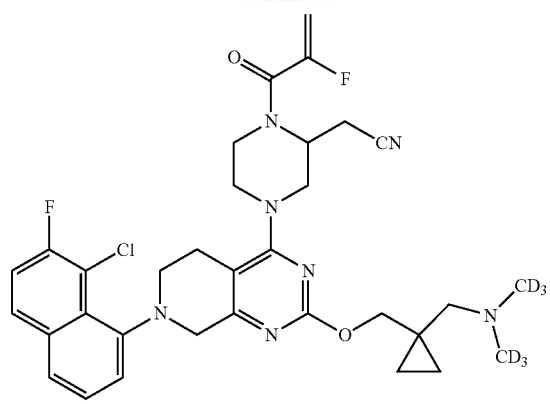
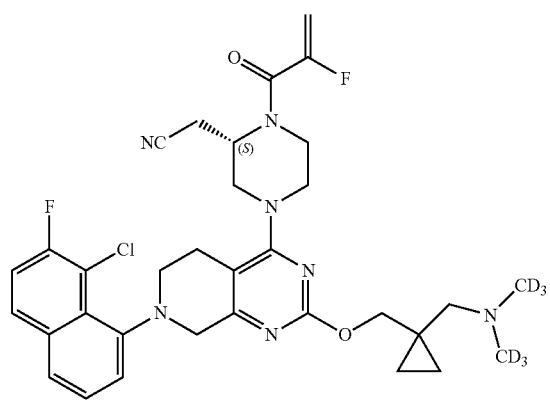
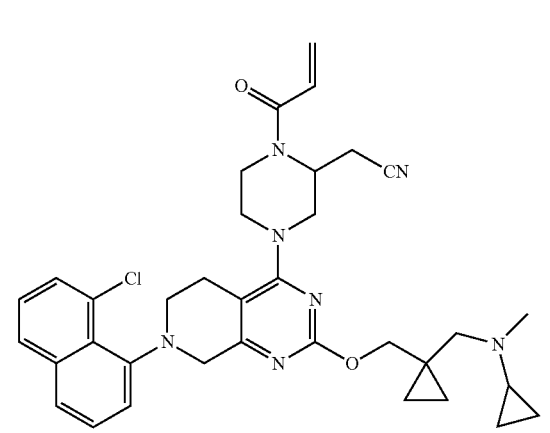
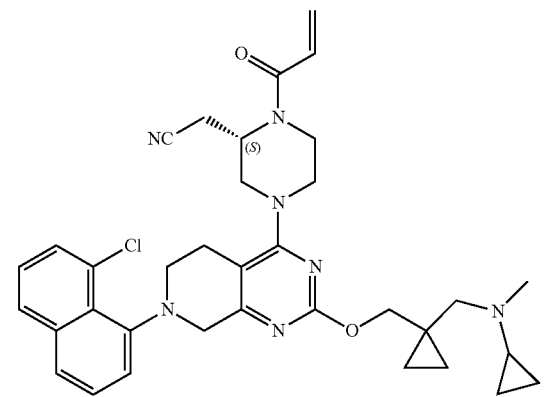
1056
-continued
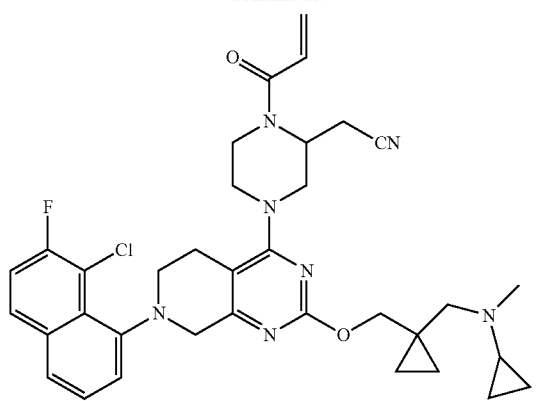
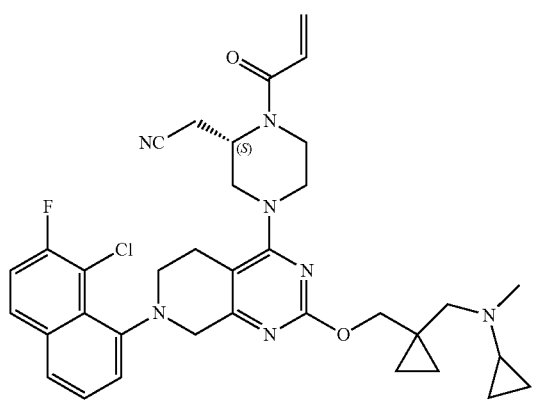
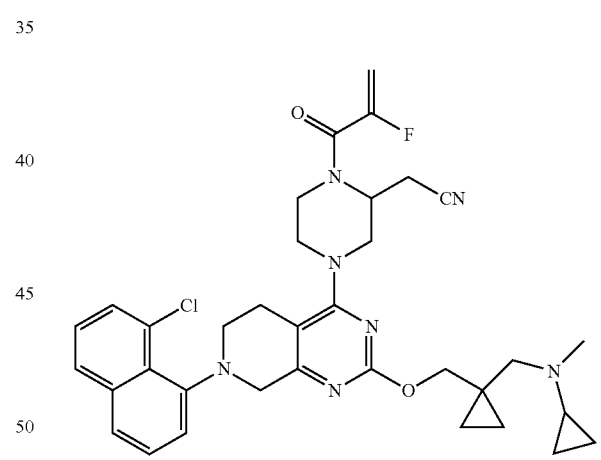
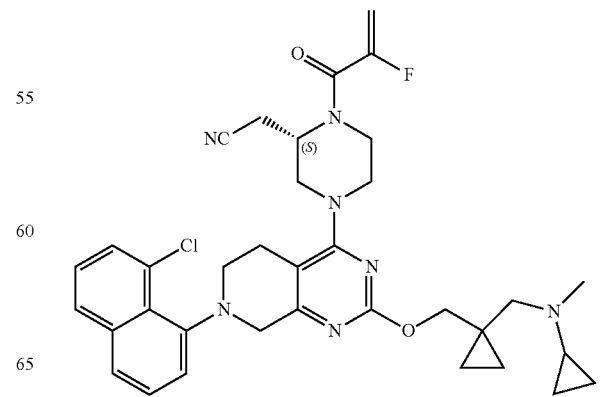

1057
-continued
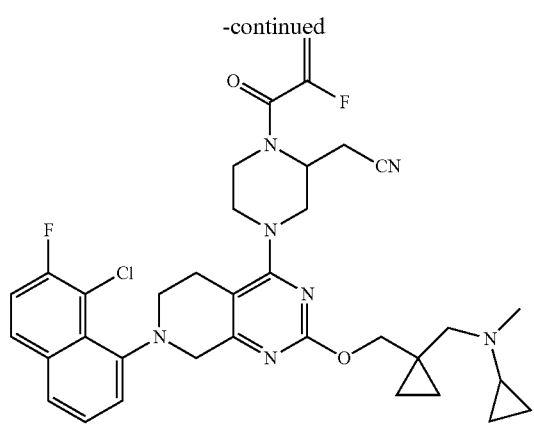
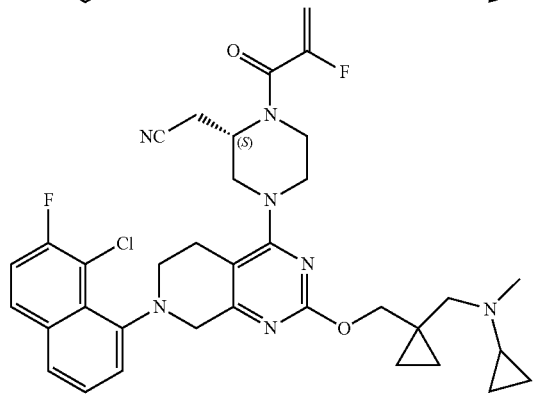
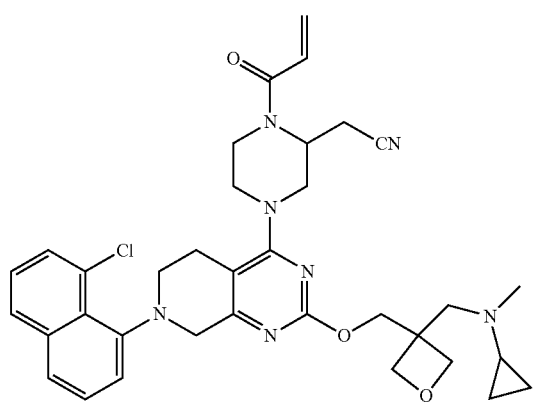
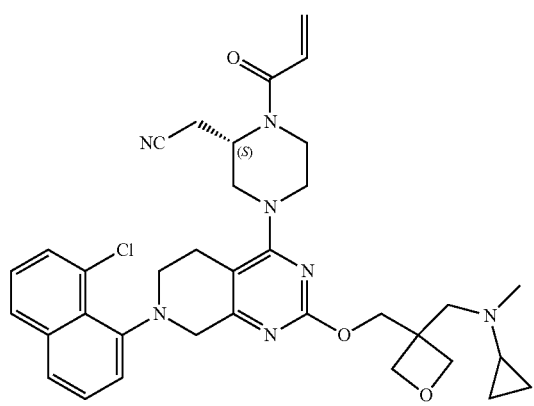
1058
-continued
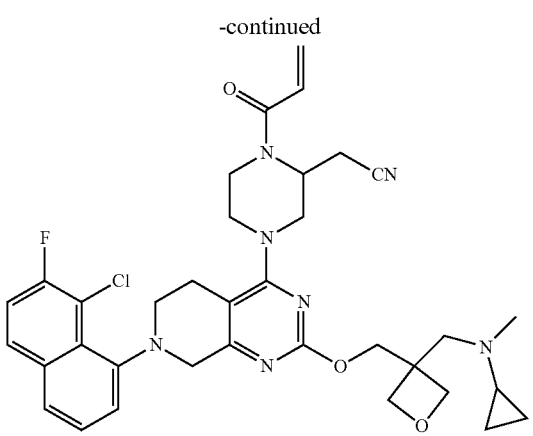
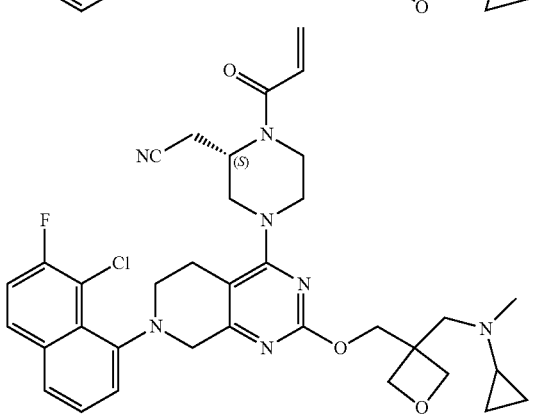
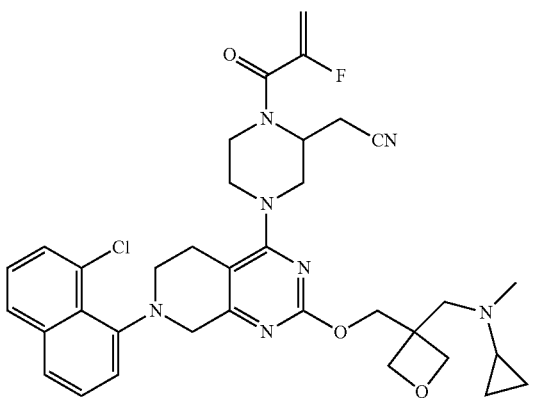
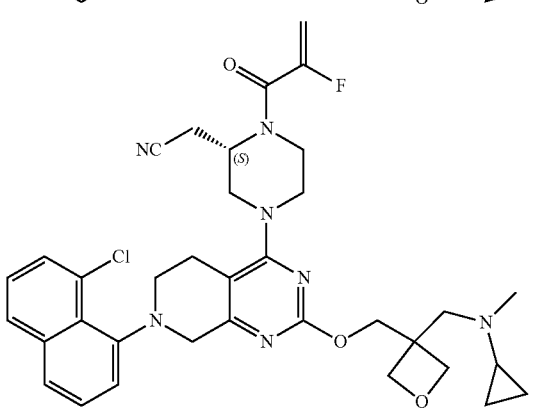

1059
-continued
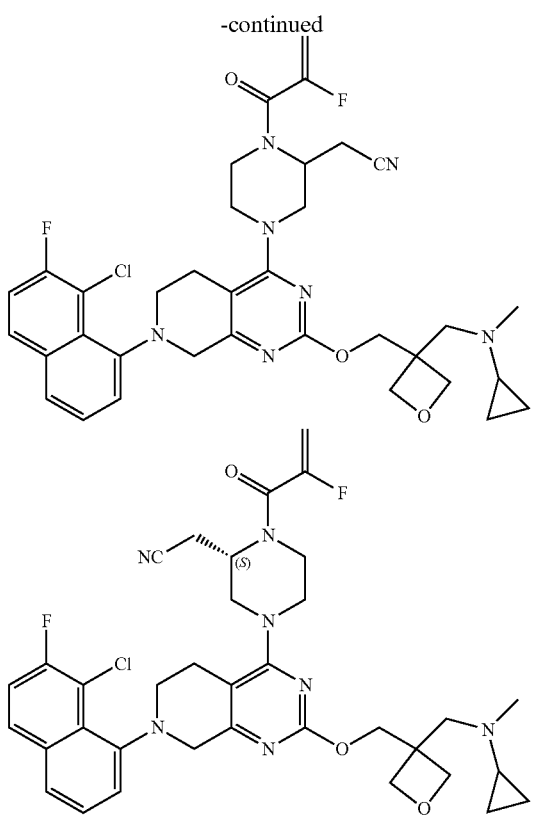
1060
-continued
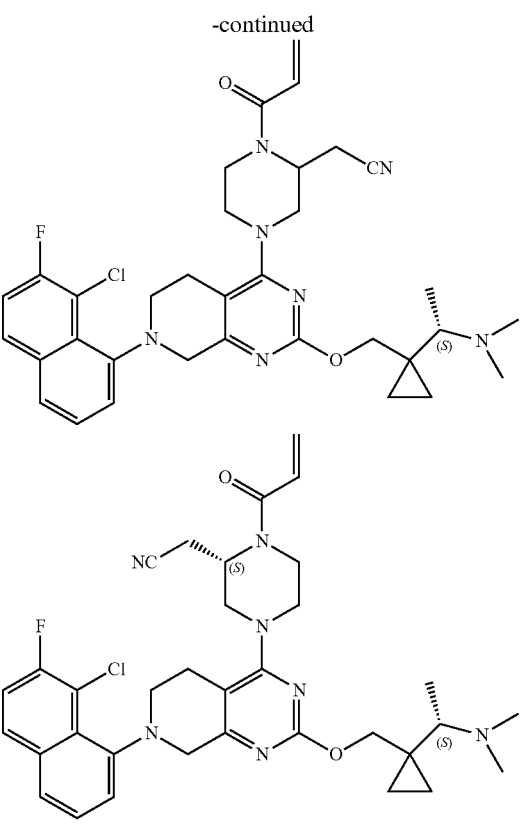
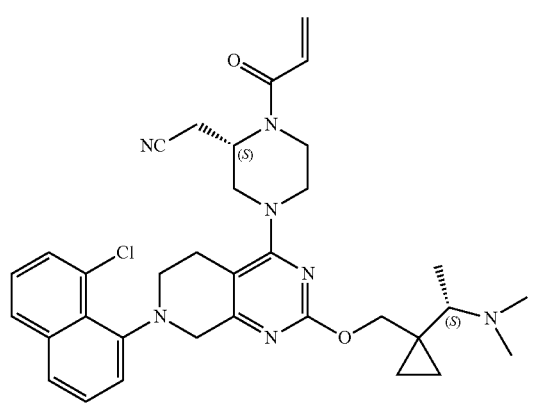

1061
-continued
1062
-continued
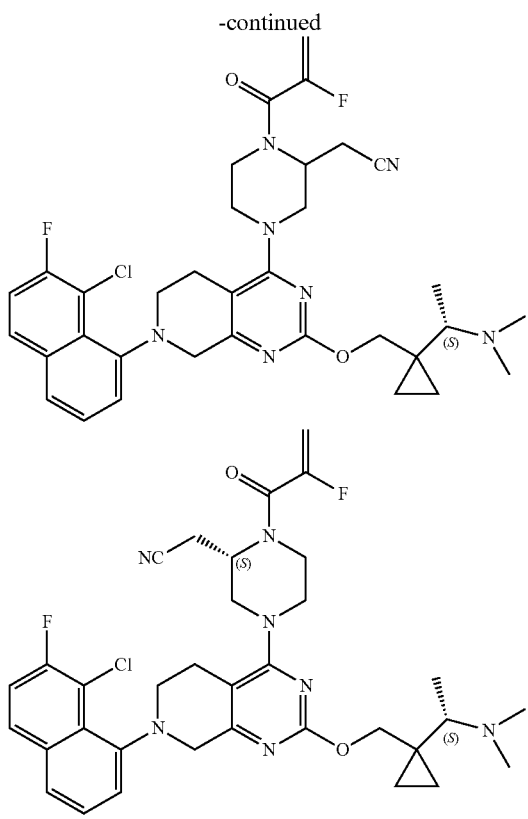
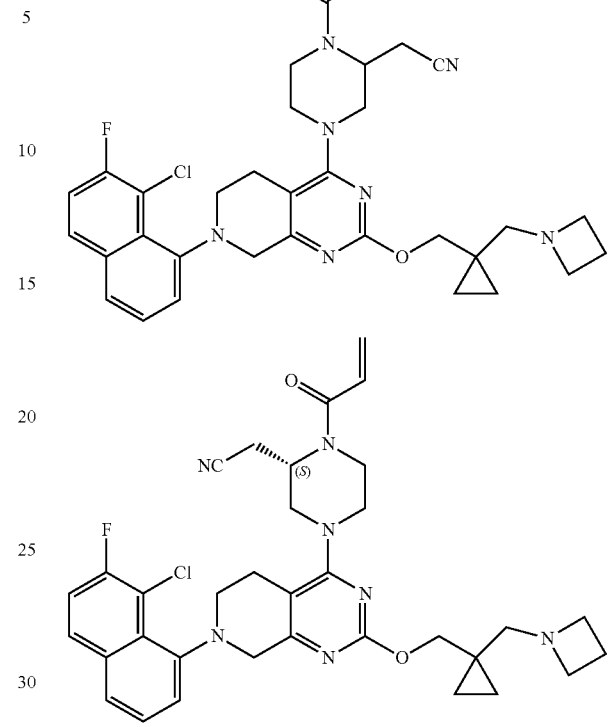
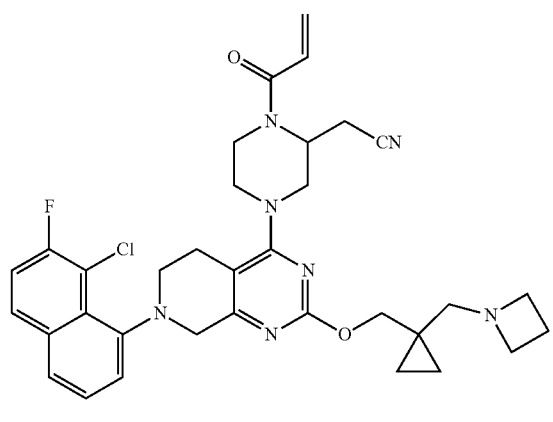
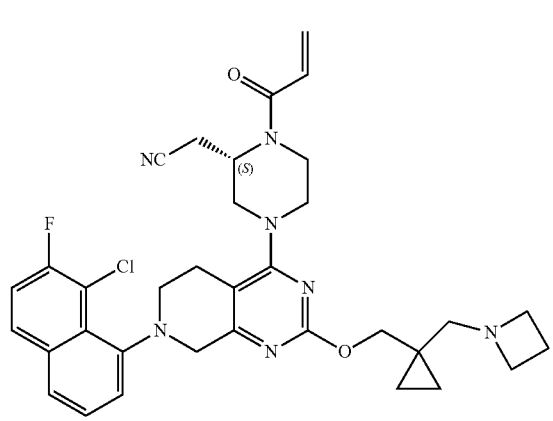

1063
-continued
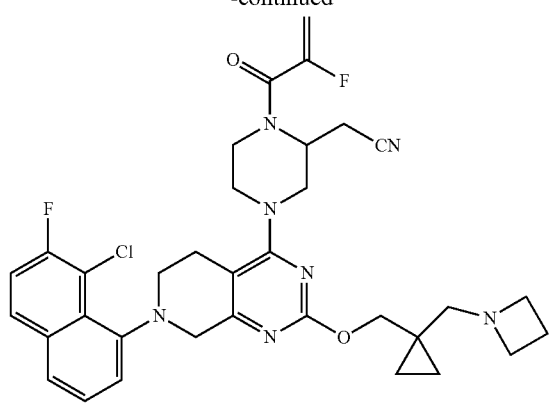
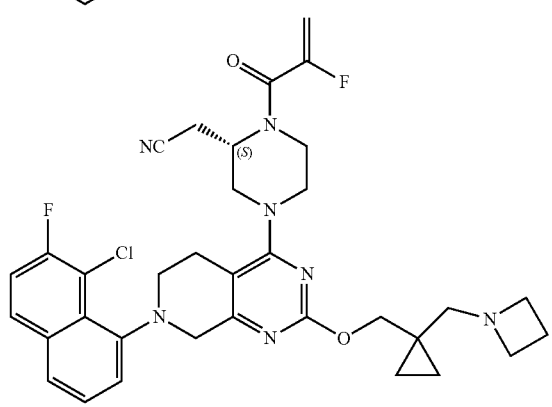
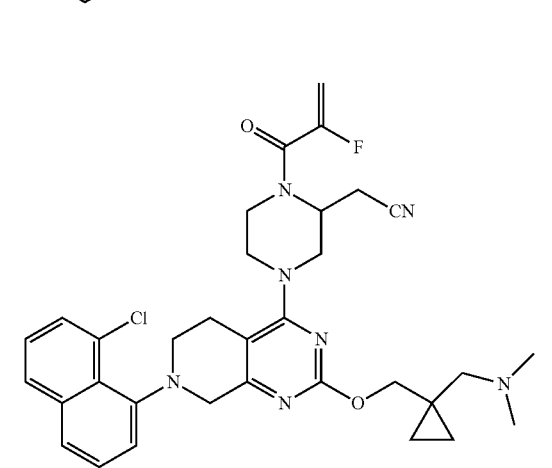
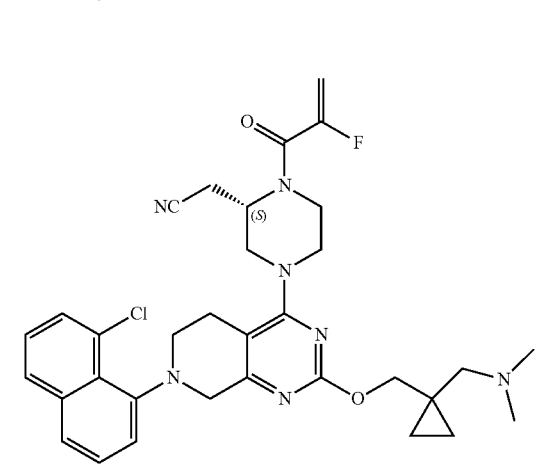
1064
-continued
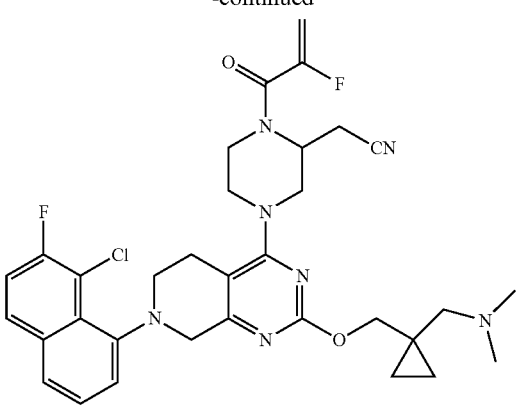
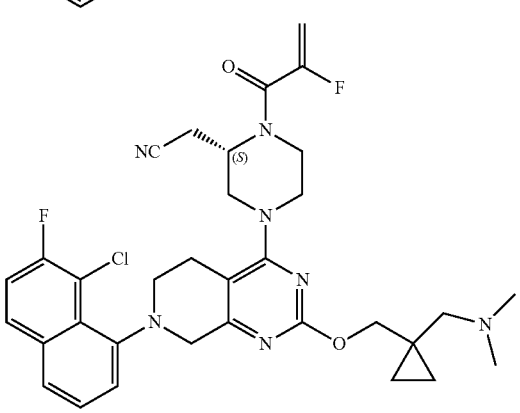
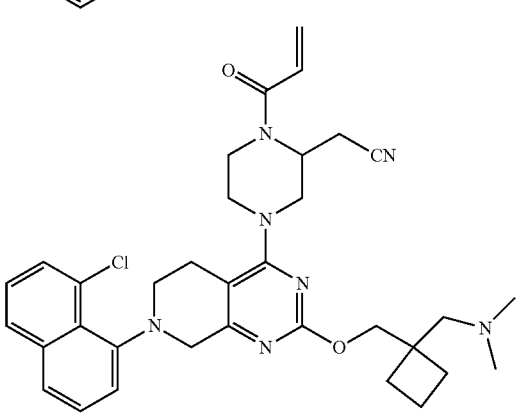
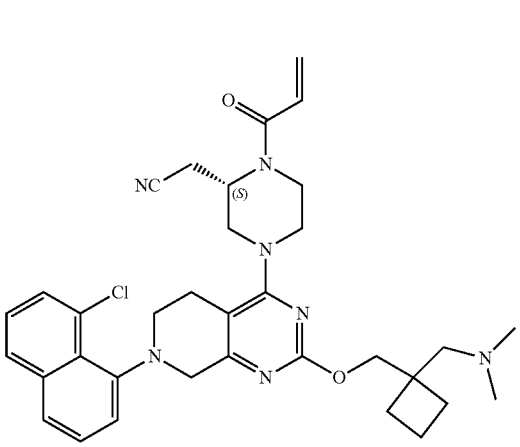

1065
-continued
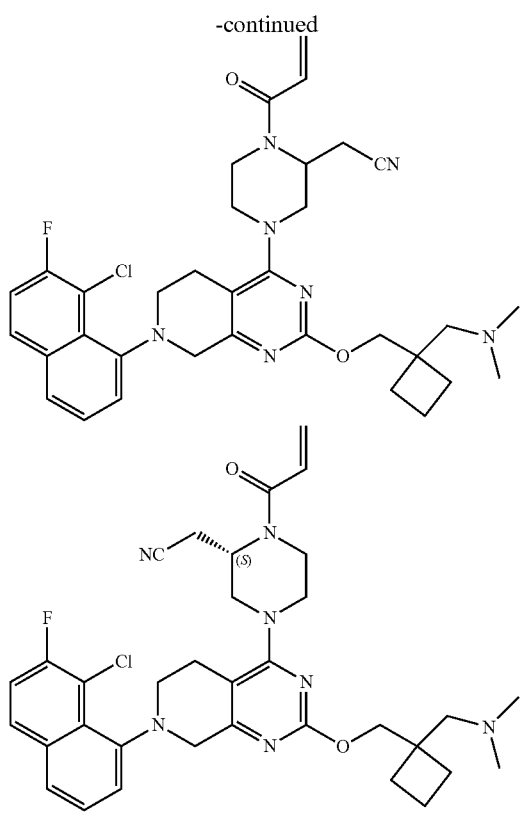
1066
-continued
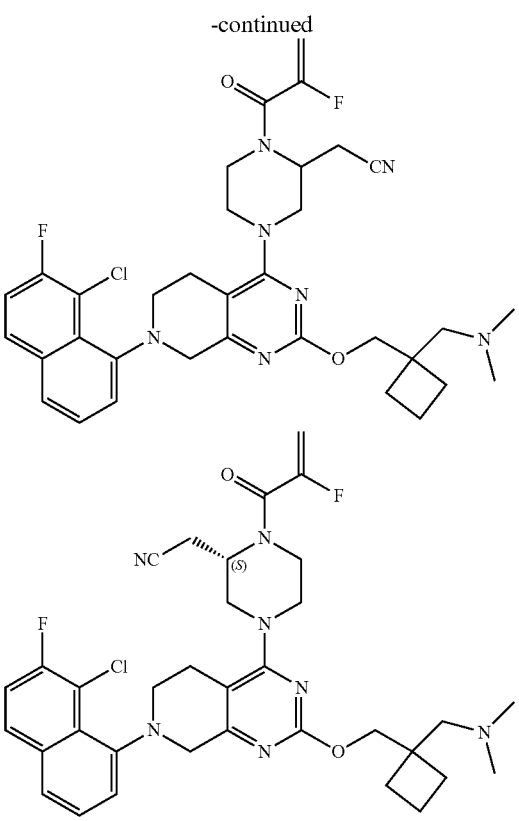

1067
-continued
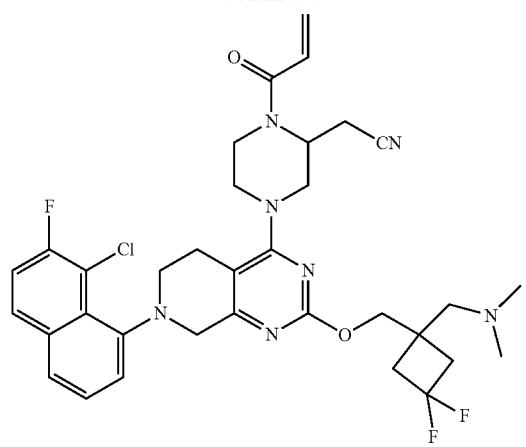
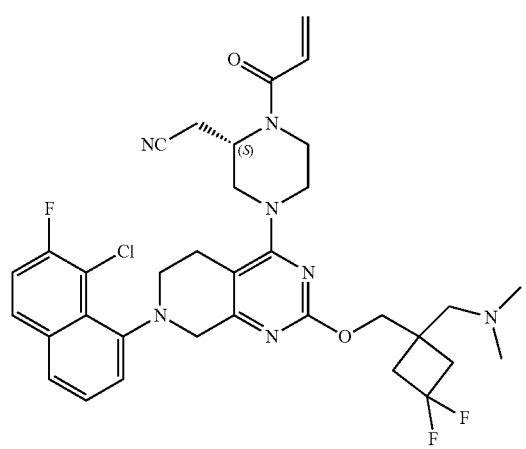
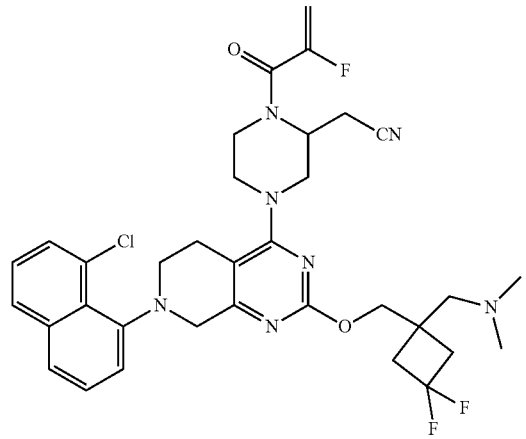
1068
-continued
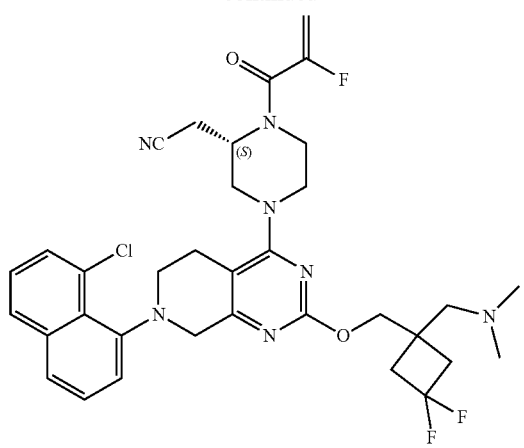
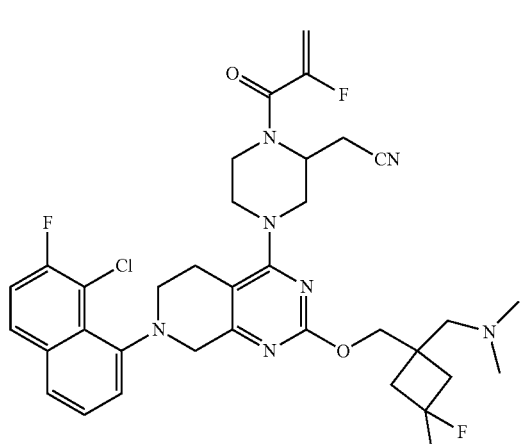
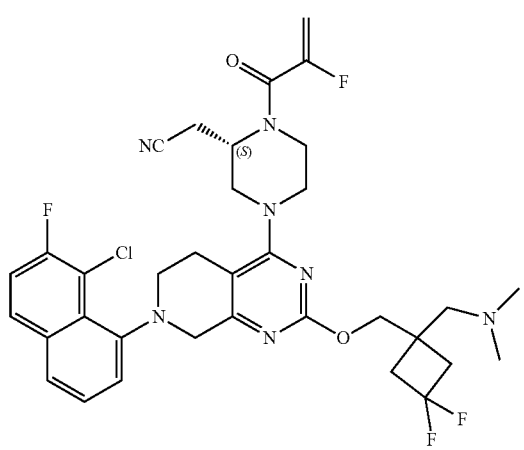

1069
-continued
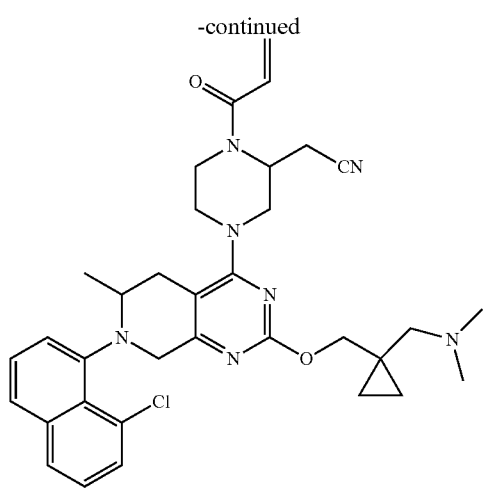
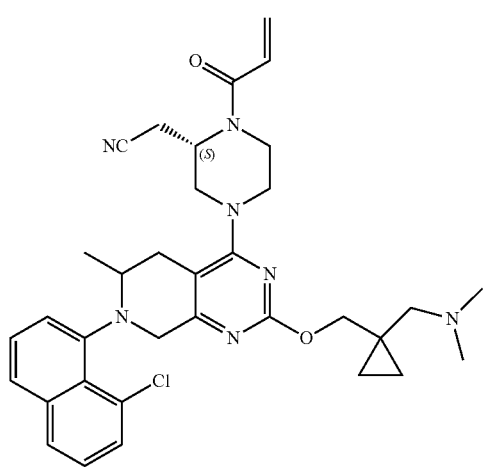
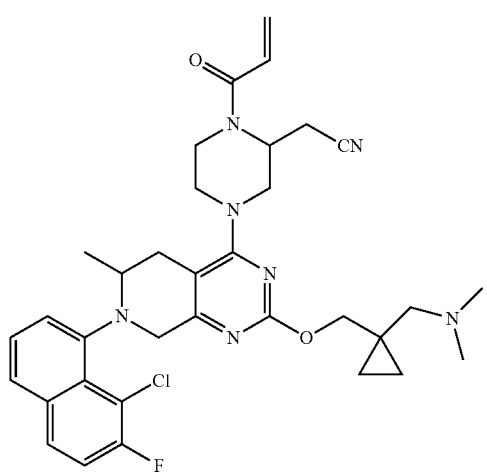
1070
-continued
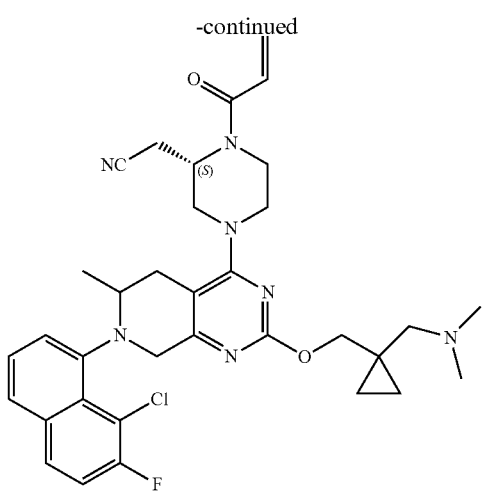
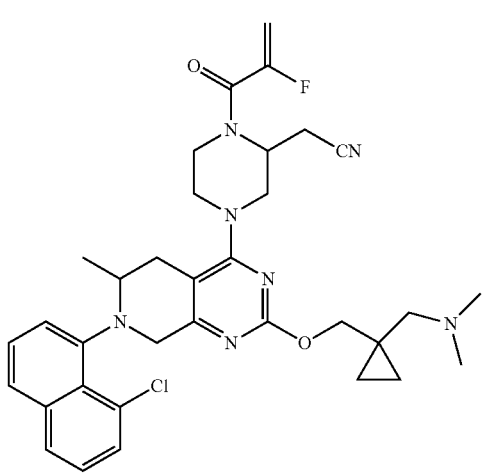
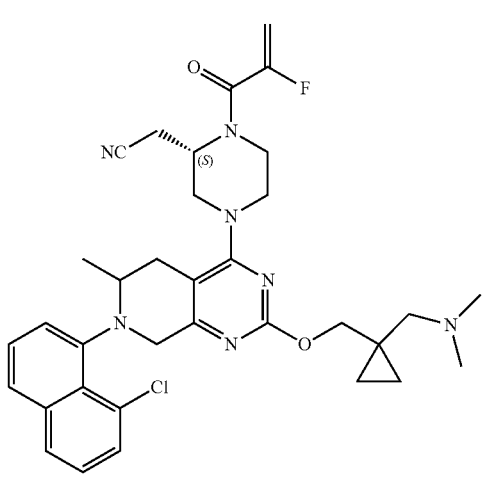

1071
-continued
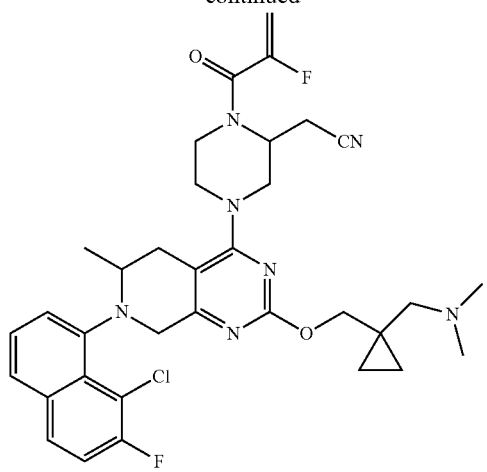
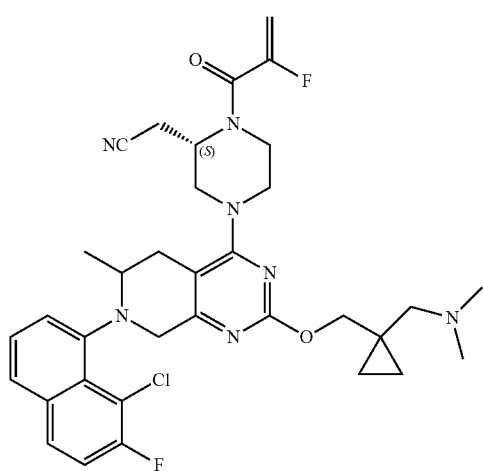
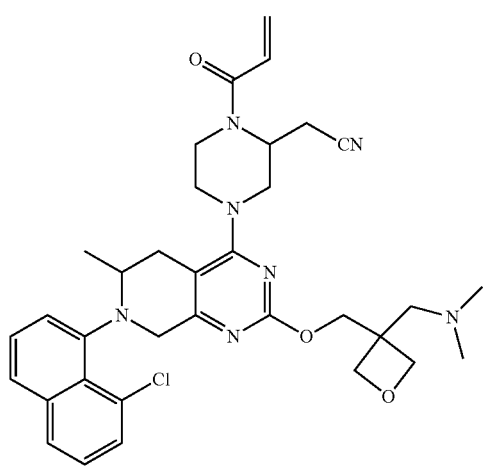
1072
-continued
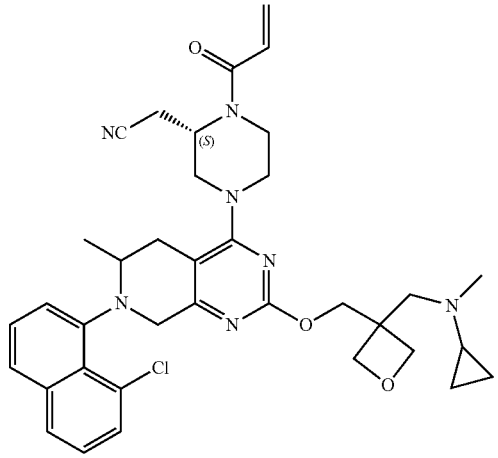
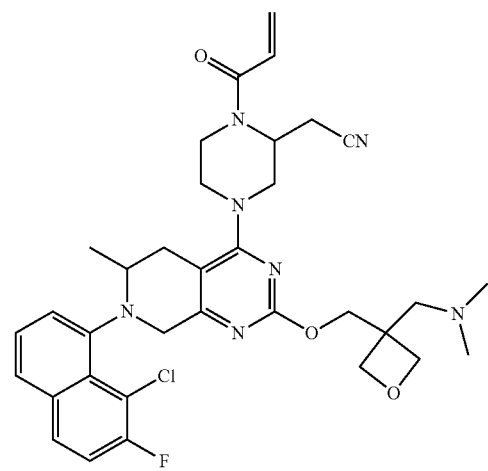
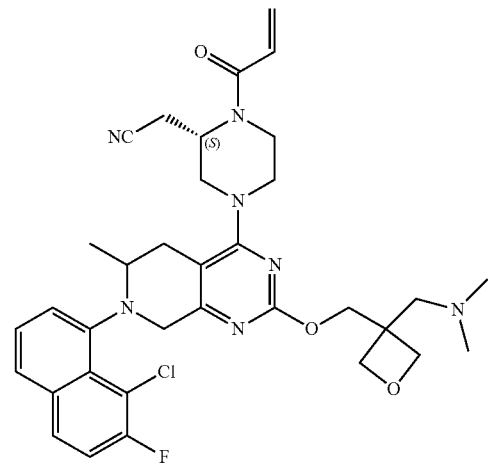

1073
-continued
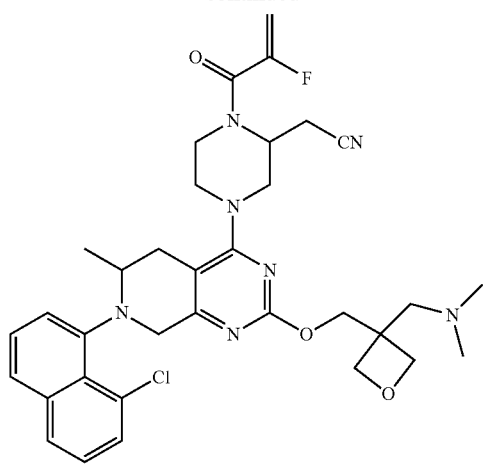
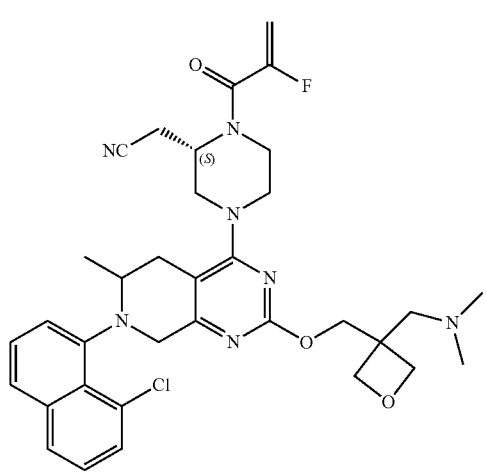
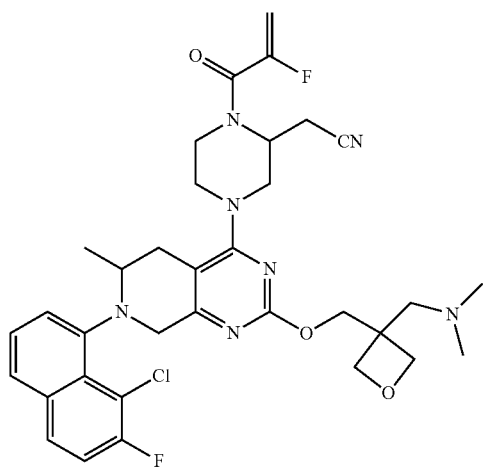
1074
-continued
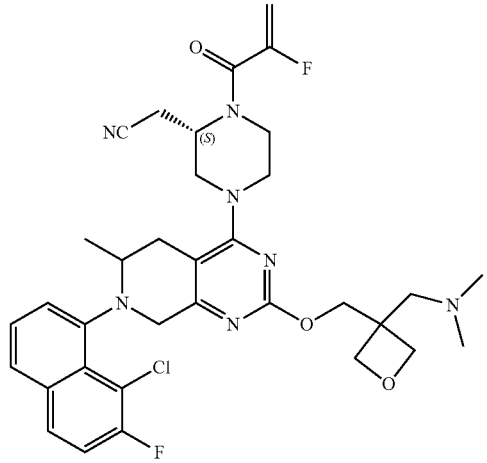
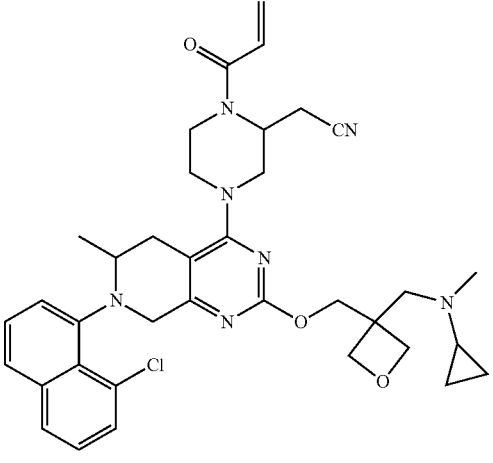
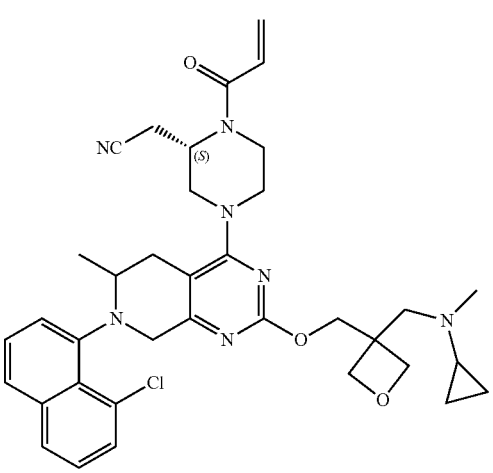

-continued
1075
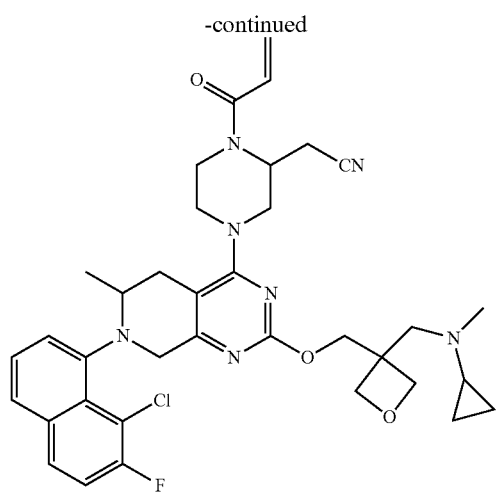
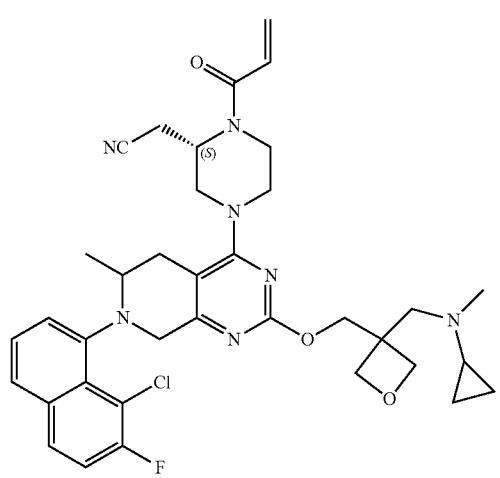
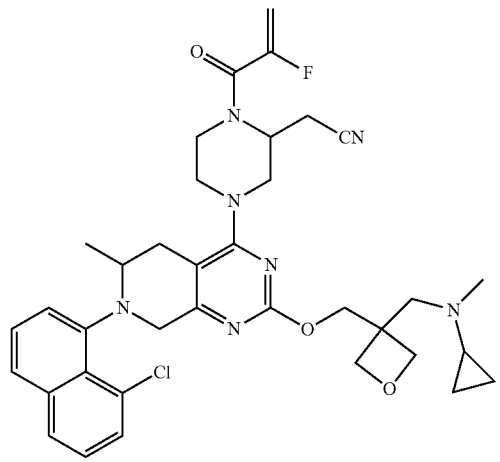
-continued
1076
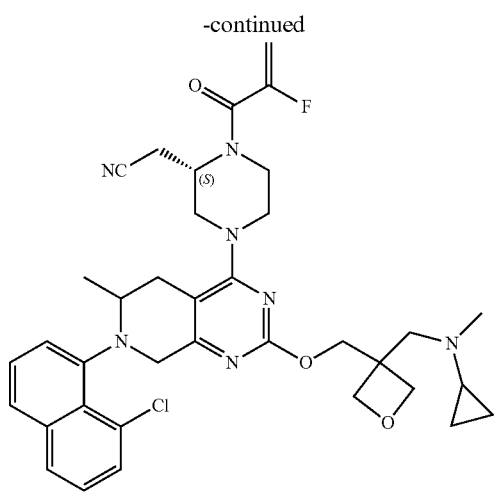
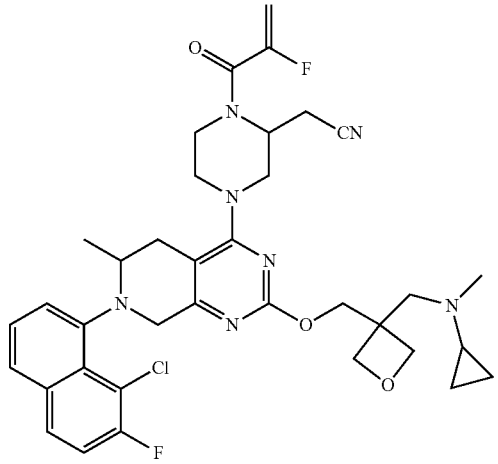
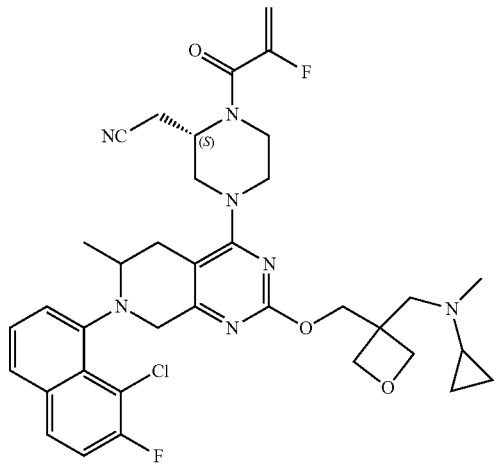

1077
-continued
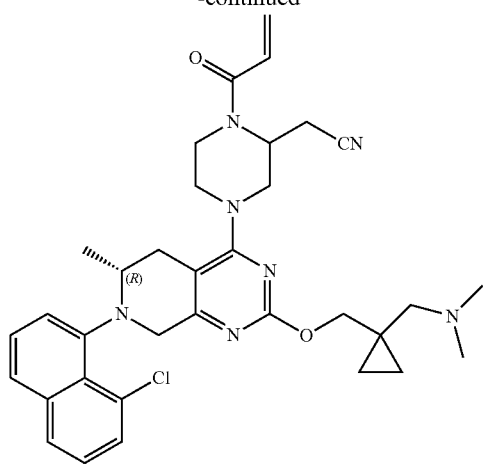
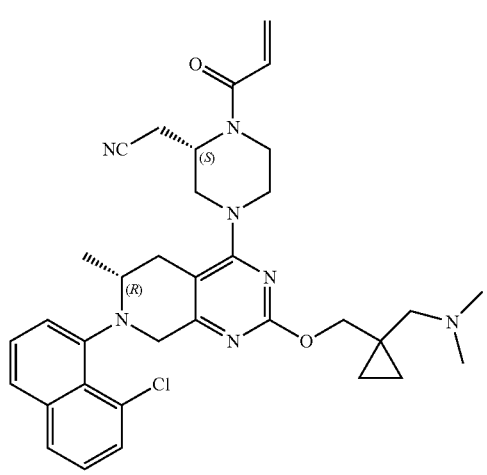
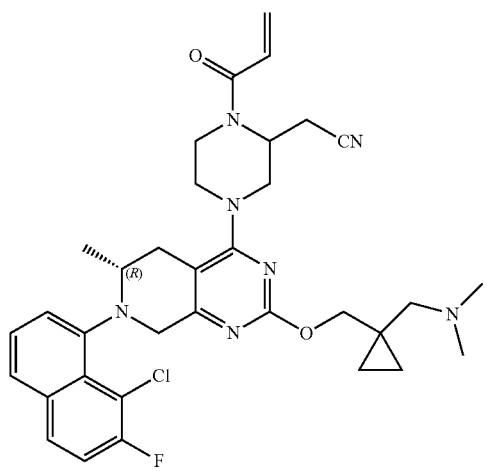
1078
-continued
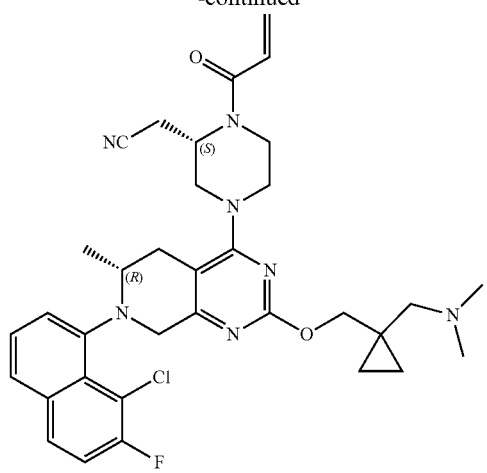
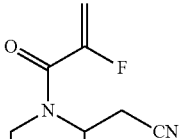
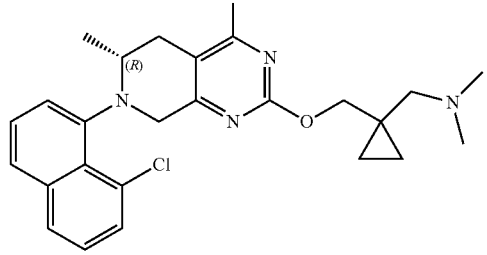
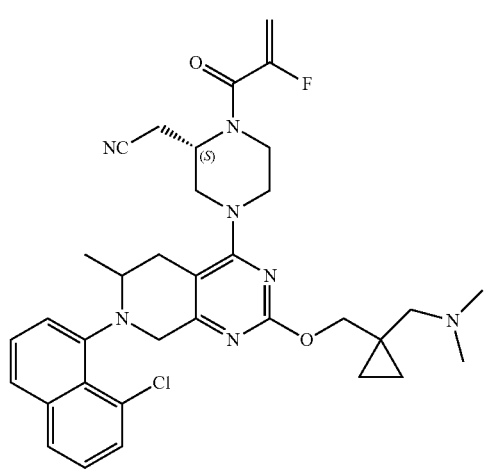

1079
-continued
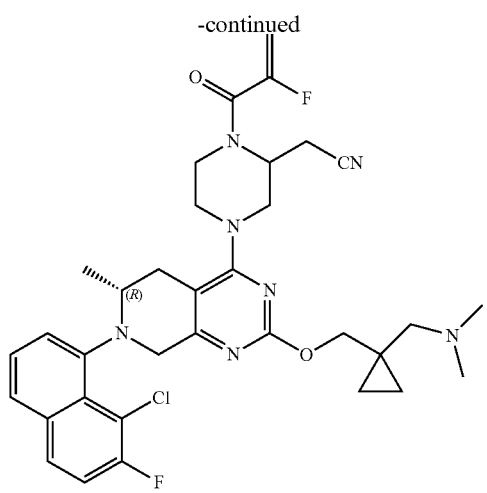
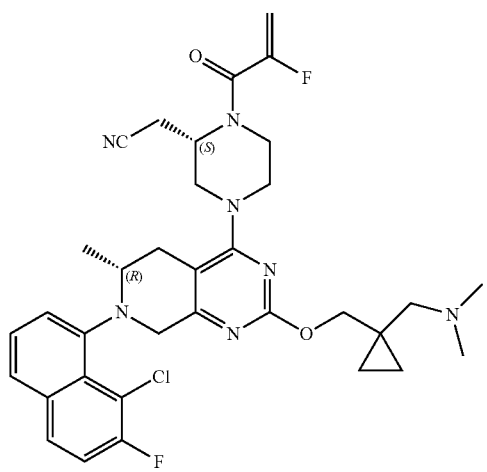
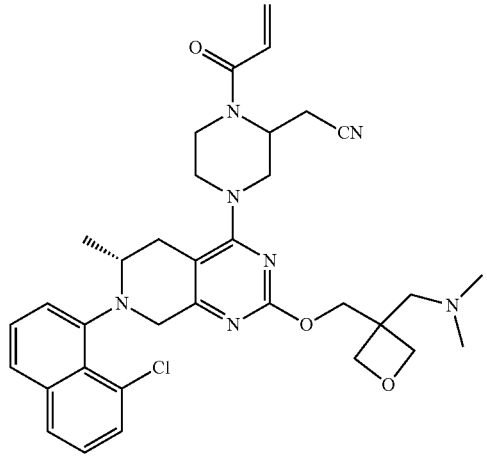
1080
-continued
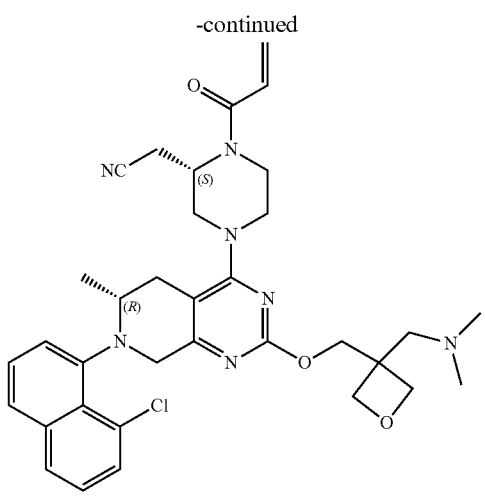
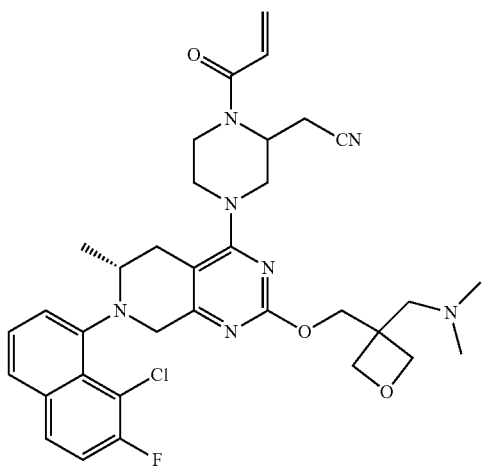
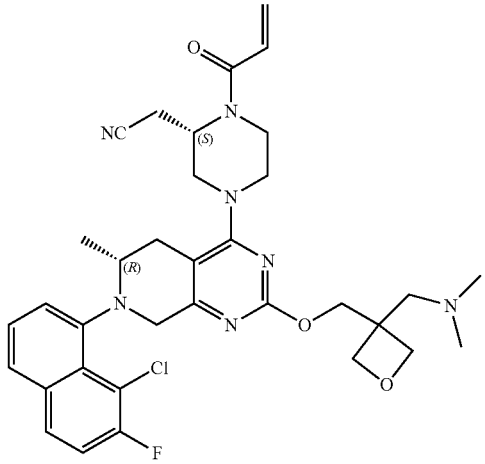

1081
-continued
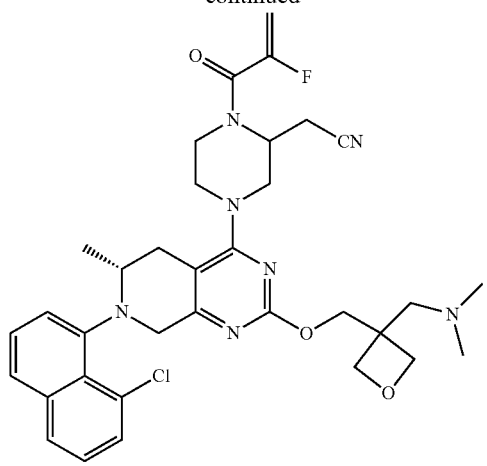
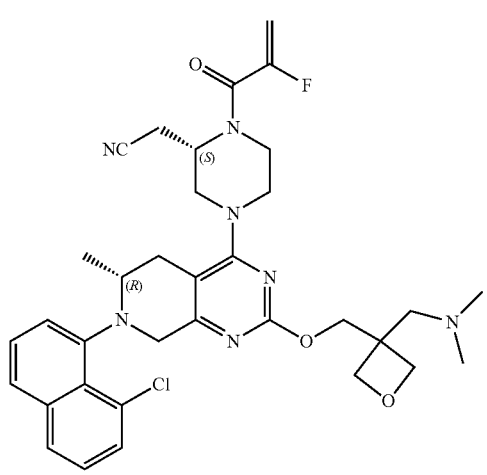
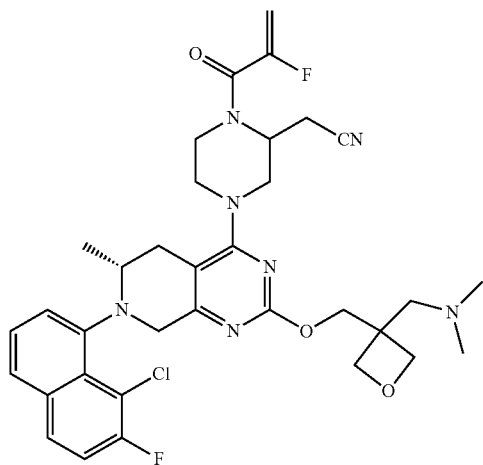
1082
-continued
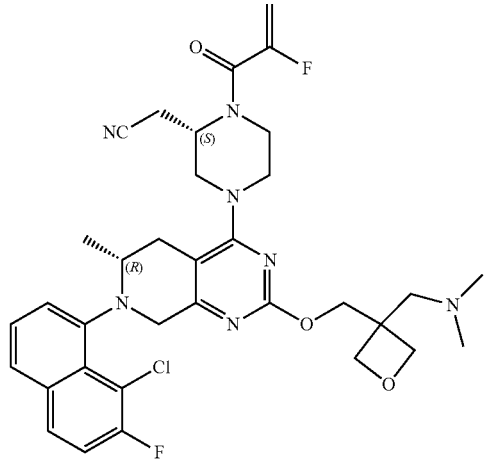
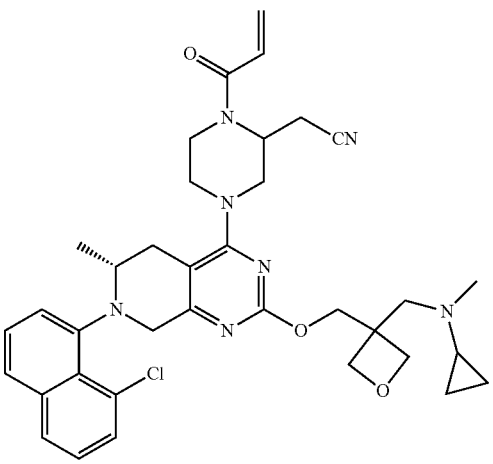
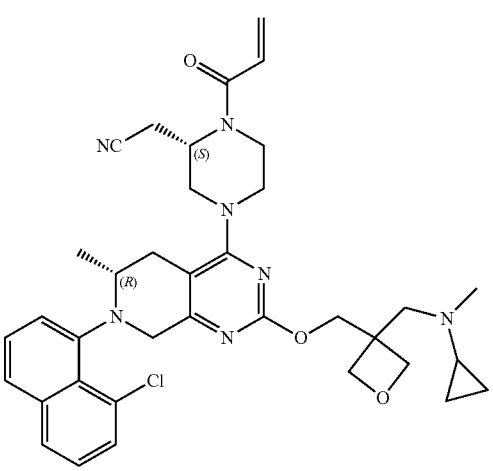

1083
-continued
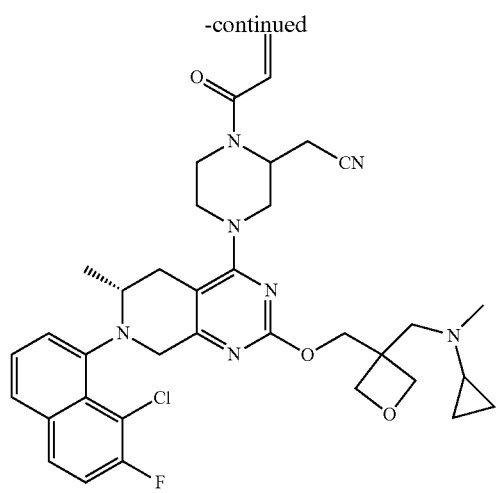
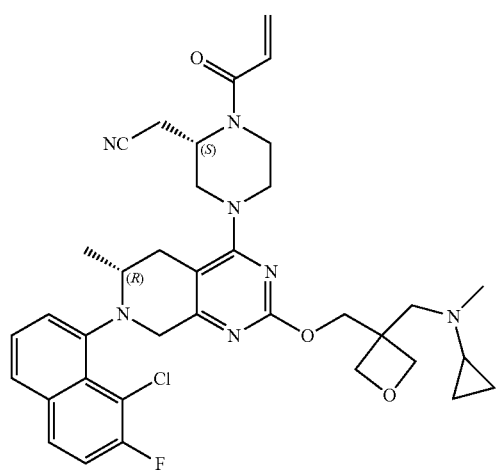
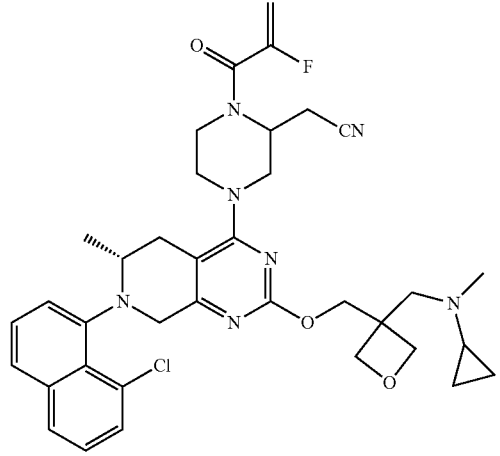
1084
-continued
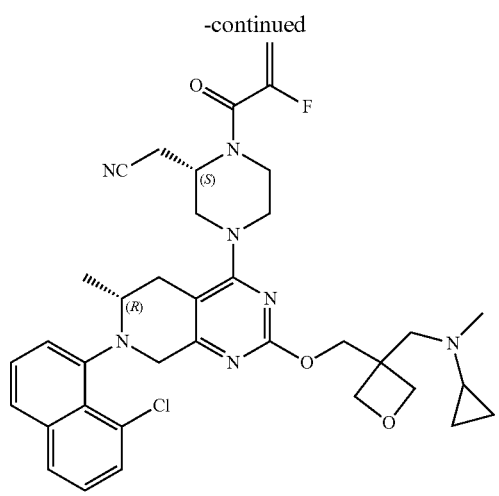
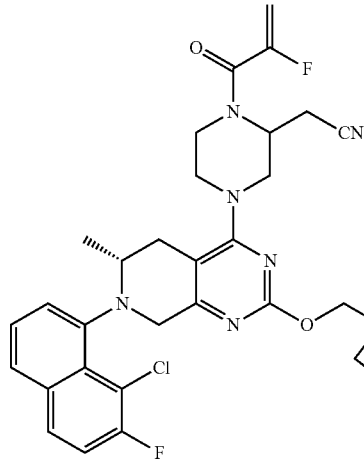
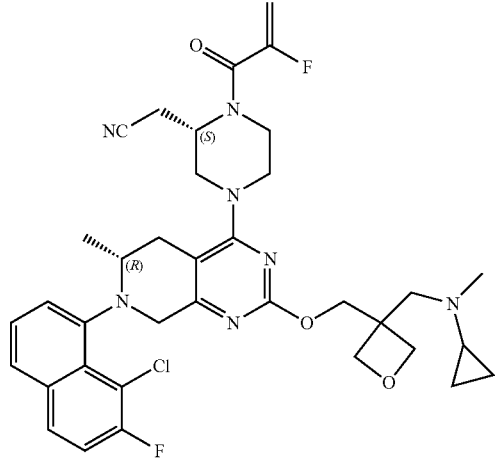

1085
-continued
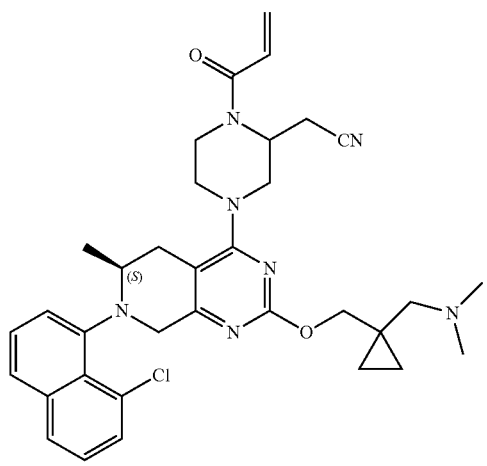
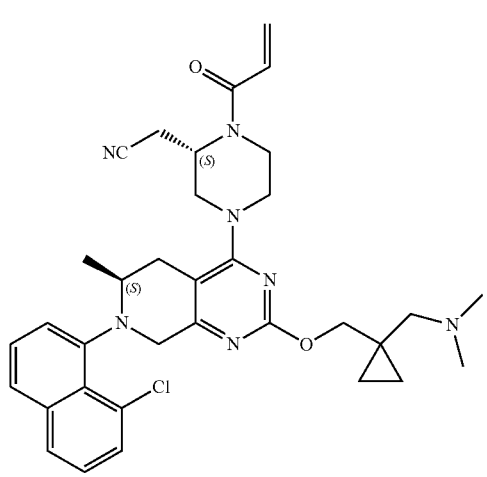
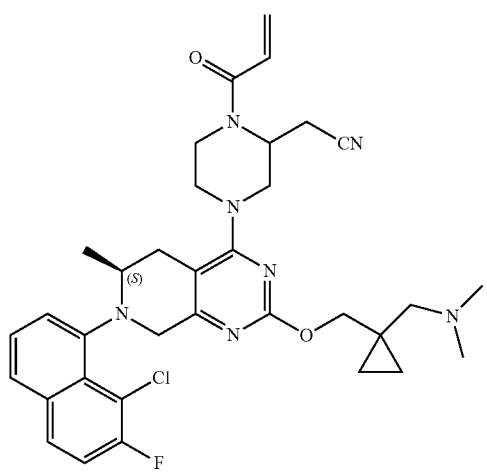
1086
-continued
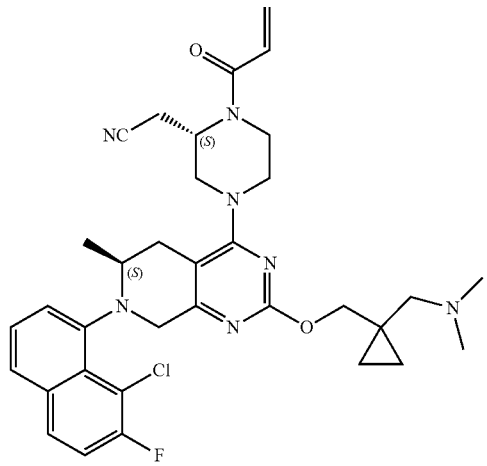
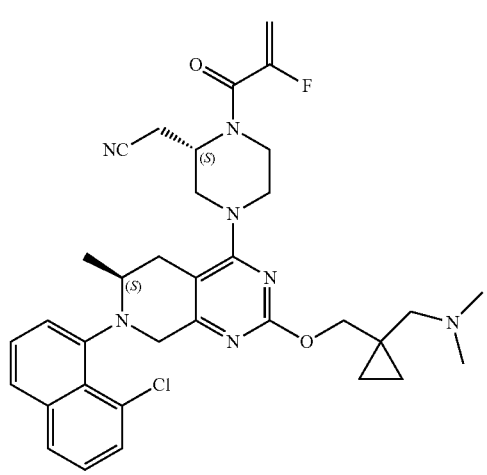

1087
-continued
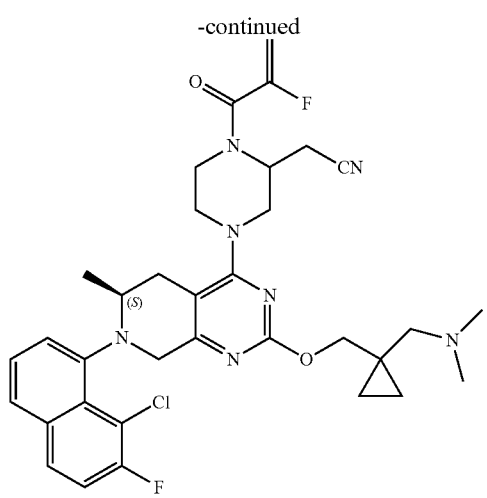
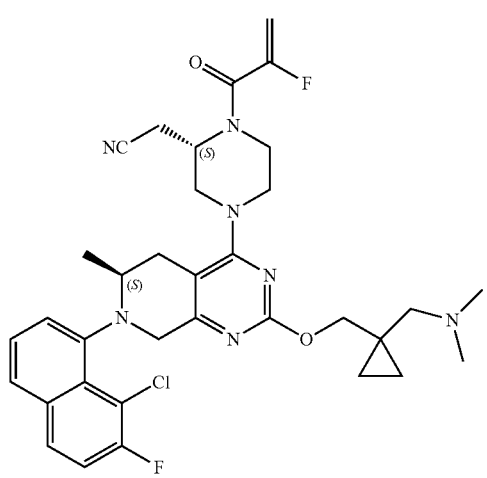
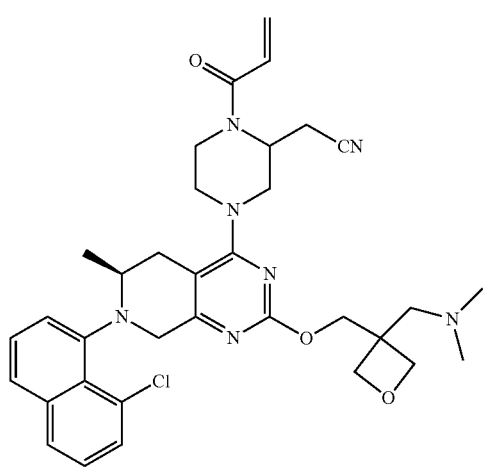
1088
-continued
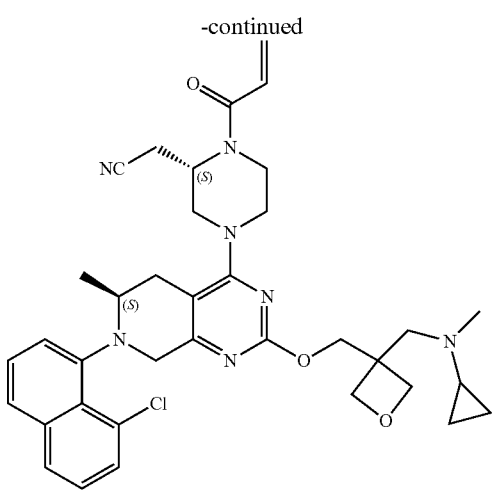
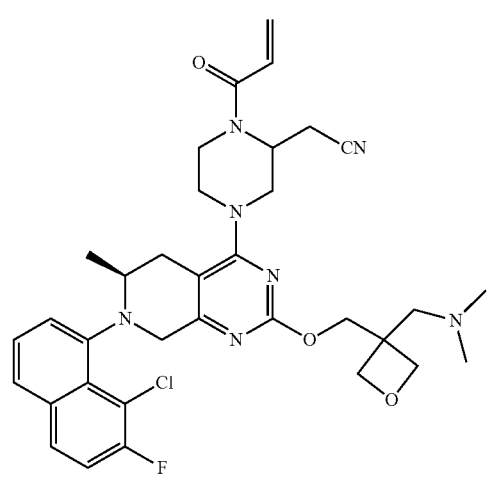
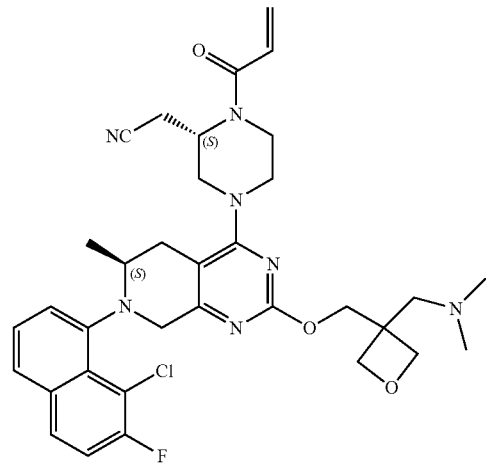

1089
-continued
1090
-continued
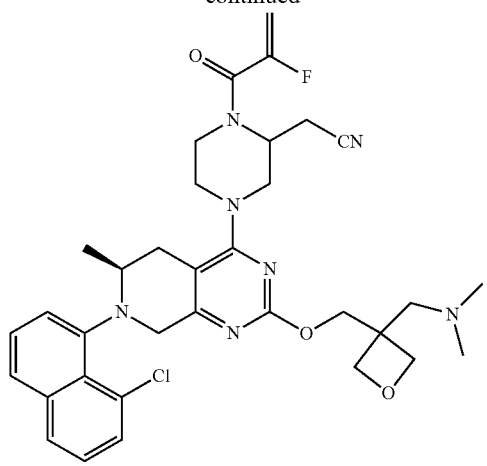
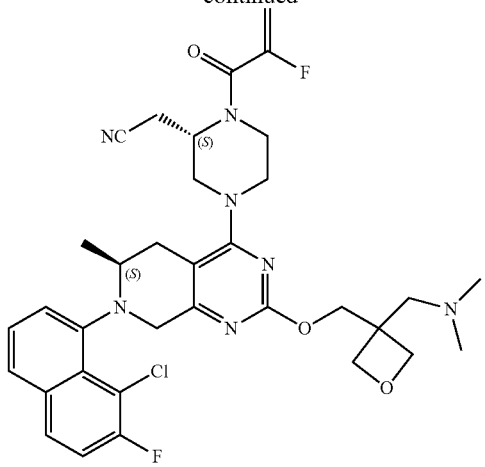
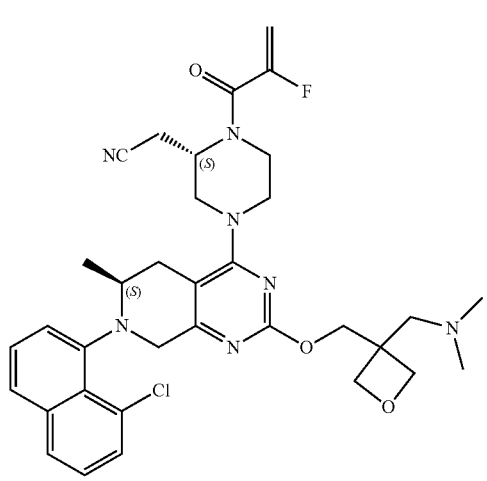
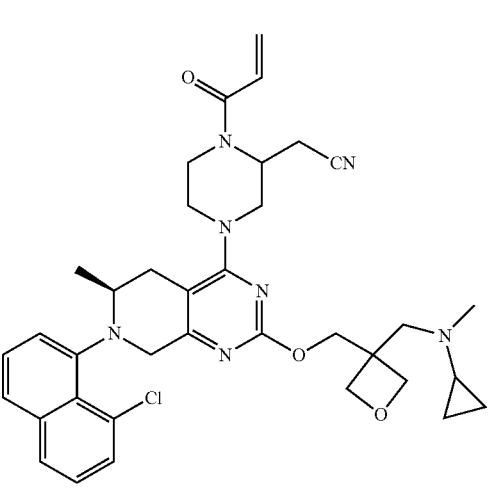
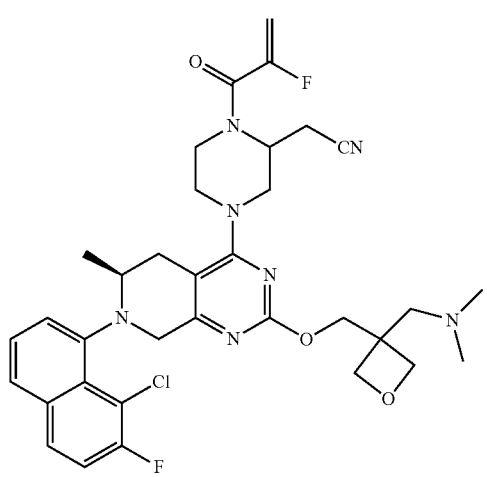
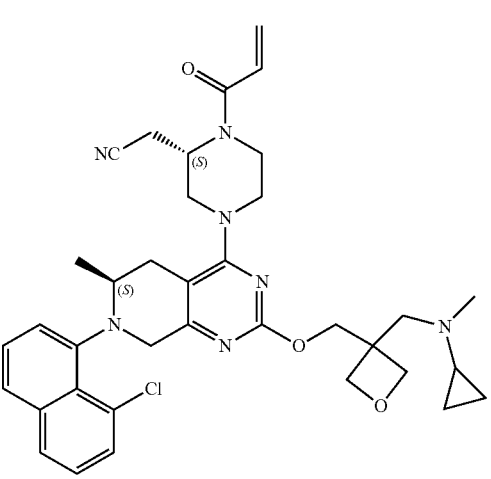

1091
-continued
1092
-continued
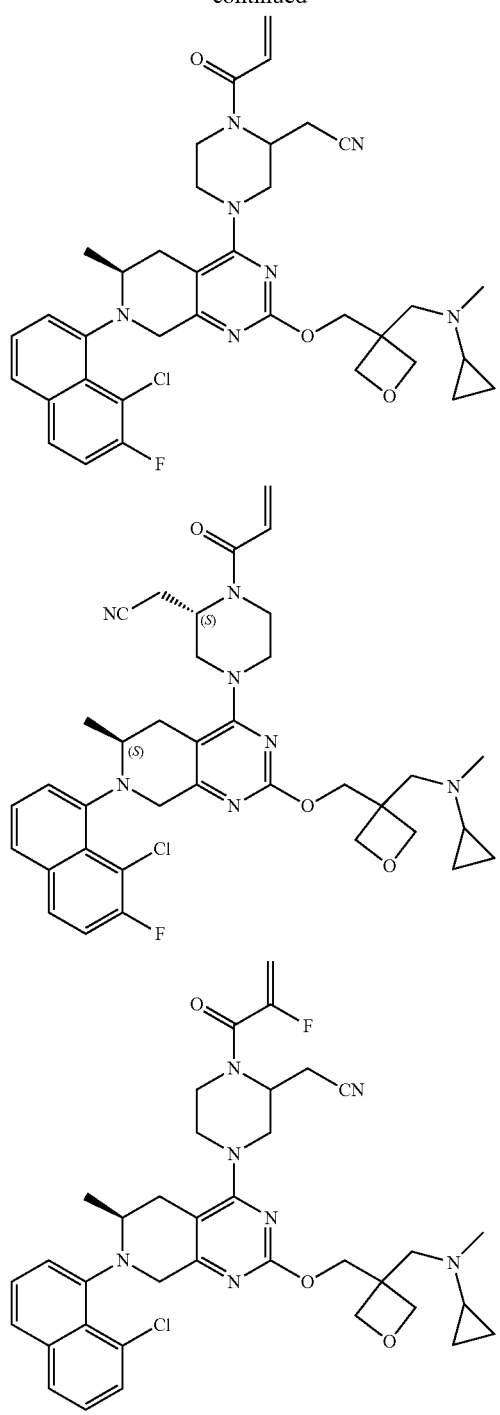
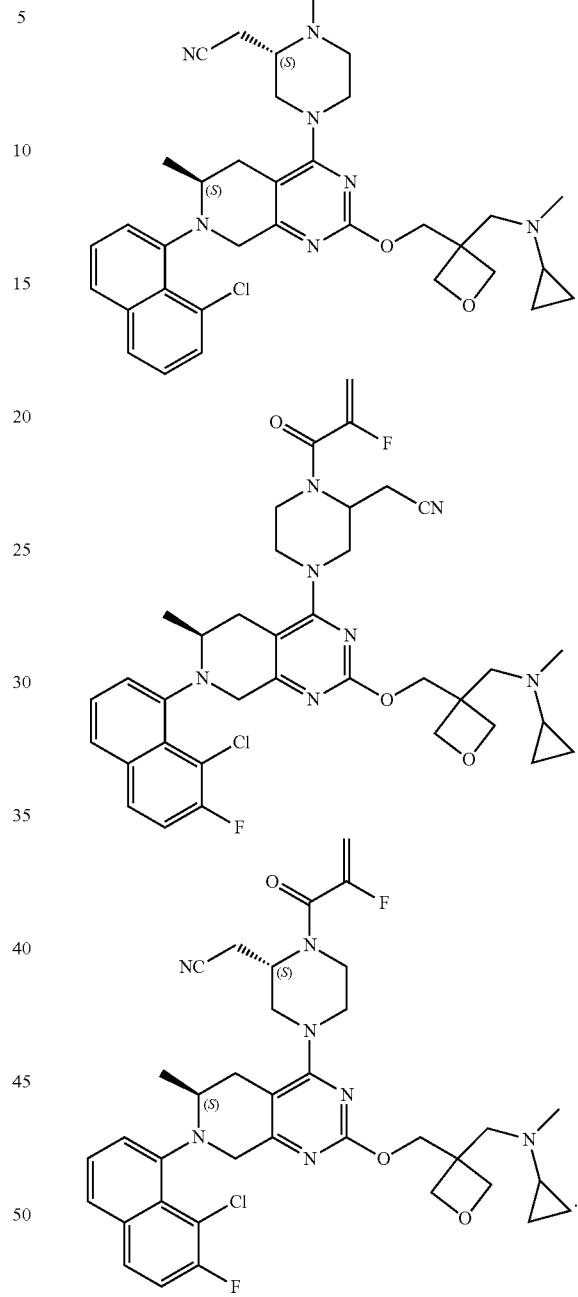
* * * * *